(12) United States Patent
Owada et al.

(10) Patent No.: US 8,318,796 B2
(45) Date of Patent: *Nov. 27, 2012

(54) HETEROCYCLIC COMPOUNDS AND THROMBOPOIETIN RECEPTOR ACTIVATORS

(75) Inventors: Shingo Owada, Funabashi (JP); Shunsuke Iwamoto, Funabashi (JP); Kazufumi Yanagihara, Funabashi (JP); Katsuaki Miyaji, Funabashi (JP); Takanori Nakamura, Minami-saitama-gun (JP); Norihisa Ishiwata, Minami-saitama-gun (JP); Yutaka Hirokawa, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 264 days.

This patent is subject to a terminal disclaimer.

(21) Appl. No.: 12/492,435

(22) Filed: Jun. 26, 2009

(65) Prior Publication Data

US 2011/0077290 A1    Mar. 31, 2011

Related U.S. Application Data

(60) Continuation of application No. 11/837,659, filed on Aug. 13, 2007, now Pat. No. 7,576,115, which is a division of application No. 11/294,609, filed on Dec. 6, 2005, now Pat. No. 7,351,841, which is a continuation-in-part of application No. PCT/JP2004/008165, filed on Jun. 4, 2004.

(30) Foreign Application Priority Data

| Jun. 6, 2003 | (JP) | 2003-161987 |
| Sep. 22, 2003 | (JP) | 2003-330627 |
| Dec. 3, 2003 | (JP) | 2003-404635 |
| Mar. 29, 2004 | (JP) | 2004-094931 |

(51) Int. Cl.
*A61K 31/38* (2006.01)
*C07D 333/12* (2006.01)

(52) U.S. Cl. ........ 514/445; 514/446; 549/62; 549/68
(58) Field of Classification Search ............ 514/445, 514/446; 549/62, 68
See application file for complete search history.

(56) References Cited

U.S. PATENT DOCUMENTS

| 5,965,491 | A | 10/1999 | Wu et al. | |
| 6,720,345 | B1 | 4/2004 | Luengo et al. | |
| 7,351,841 | B2 * | 4/2008 | Owada et al. | 549/62 |
| 7,576,115 | B2 | 8/2009 | Owada et al. | |
| 2004/0058990 | A1 | 3/2004 | Duffy et al. | |
| 2005/0282730 | A1 | 12/2005 | Miyaji et al. | |
| 2006/0069140 | A1 | 3/2006 | Miyaji et al. | |
| 2009/0023939 | A1 | 1/2009 | Tatsuta | |
| 2009/0118500 | A1 | 5/2009 | Miyaji et al. | |
| 2009/0131659 | A1 | 5/2009 | Miyaji et al. | |
| 2009/0131676 | A1 | 5/2009 | Miyaji et al. | |
| 2009/0198060 | A1 | 8/2009 | Miyaji et al. | |

FOREIGN PATENT DOCUMENTS

| EP | 0258 182 | 3/1988 |
| WO | 01/34585 | 5/2001 |
| WO | 02/49413 | 6/2002 |
| WO | 02/085343 | 10/2002 |
| WO | 2004/033433 | 4/2004 |

OTHER PUBLICATIONS

U.S. Appl. No. 11/721,252, filed Jun. 8, 2007, Miyaji, et al.
U.S. Appl. No. 12/082,834, filed May 7, 2008, Miyaji, et al.
U.S. Appl. No. 12/919,394, filed Aug. 25, 2010, Yanagihara, et al.
Mohareb, et al., CA 133:73973. 1988.
O'Mant, CA 69:27141, 1968.
Van den Oudenrijn, Thromobopoietin Receptor, retrieved Jan. 18, 2007 from Internet, http://mpr.nci.nih.gov/prow/guide/11586825g.htm>, Protein Review on the Web, p. 1-6.
Wood, Thrombopoietin, Sep. 10, 1998, New England Journal of Medicine, p. 746-754.
Caradonna et al., 1964, CAS:61:47837.
U.S. Appl. No. 13/503,560, filed Apr. 23, 2012, Shigeta, et al.
U.S. Appl. No. 12/492,435, filed Jun. 26, 2009, Owada, et al.

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

A compound represented by the formula (1):

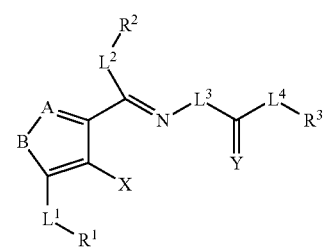

(1)

wherein A is a nitrogen atom or $CR^4$, B is an oxygen atom, a sulfur atom or $NR^9$ (provided that when A is a nitrogen atom, B is not NH), $R^1$ is a $C_{2-14}$ aryl group, $L^1$ is a bond, $CR^{10}R^{11}$, an oxygen atom, a sulfur atom or $NR^{12}$, X is $OR^{13}$, $SR^{13}$ or $NR^{14}NR^{15}$, $R^2$ is a hydrogen atom, a formyl group, a $C_{1-10}$ alkyl group or the like, $L^2$ is a bond or the like, $L^3$ is a bond, $CR^{17}R^{18}$, an oxygen atom, a sulfur atom or $NR^{19}$, $L^4$ is a bond, $CR^{20}R^{21}$, an oxygen atom, a sulfur atom or $NR^{22}$, Y is an oxygen atom, a sulfur atom or $NR^{23}$, and $R^3$ is a $C_{2-14}$ aryl group, a tautomer, prodrug or pharmaceutically acceptable salt of the compound or a solvate thereof.

36 Claims, 1 Drawing Sheet

HETEROCYCLIC COMPOUNDS AND THROMBOPOIETIN RECEPTOR ACTIVATORS

This application is continuation of Ser. No. 11/837,659 filed Aug. 13, 2007, now U.S. Pat. No. 7,576,115, which is a divisional of Ser. No. 11/294,609 filed Dec. 6, 2005, now U.S. Pat. No. 7,351,841, which is a continuation in part of PCT/JP2004/008165 filed on Jun. 4, 2004, and incorporated entirely herein by reference.

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 24).

1) Applications filed by Hokuriku Seiyaku Co., Ltd. relating to 1,4-benzodiazepine derivatives (patent documents 5 and 6)

2) International Laid-open Patent Applications filed by Shionogi & Co., Ltd. (patent documents 7-10)

3) International Laid-open Patent Applications filed by SmithKline Beecham Corp (patent documents 11-19)

4) Japanese Laid-open Patent Application filed by Torii Pharmaceutical Co., Ltd. (patent document 20)

5) International Laid-open Patent Application filed by Roche Diagnostics GMBH (patent document 21)

6) International Laid-open Patent Application filed by Yamanouchi Pharmaceutical Co., Ltd. (patent document 22 and 23)

7) Japanese Laid-open Patent Application filed by Japan Tabacco Inc. (Patent document 24)

Patent document 1 JP-A-10-72492
Patent document 2 WO96/40750
Patent document 3 WO96/40189
Patent document 4 WO98/25965
Patent document 5 JP-A-11-1477
Patent document 6 JP-A-11-152276
Patent document 7 WO01/07423
Patent document 8 WO01/53267
Patent document 9 WO02/059099
Patent document 10 WO02/059100
Patent document 11 WO00/35446
Patent document 12 WO00/66112
Patent document 13 WO01/34585
Patent document 14 WO01/17349
Patent document 15 WO01/39773
Patent document 16 WO01/21180
Patent document 17 WO01/89457
Patent document 18 WO02/49413
Patent document 19 WO02/085343
Patent document 20 JP-A-2001-97948
Patent document 21 WO99/11262
Patent document 22 WO02/062775
Patent document 23 WO03/062233
Patent document 24 JP-A-2003-238565
Non-patent document 1 Microvasc. Res., 1999: 58, p. 108-113
Non-patent document 2 Circ. Res., 1999: 84, p. 785-796
Non-patent document 3 Blood 2001:98, p. 71a-72a

DISCLOSURE OF THE INVENTION

Thrombopoietin and low molecular weight peptides having affinity for the thrombopoietin receptor are likely to be easily degraded in the gastrointestinal tract and are usually difficult to orally, administer. As to thrombopoietin itself, the appearance of anti thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to:
1. A compound represented by the formula (1)

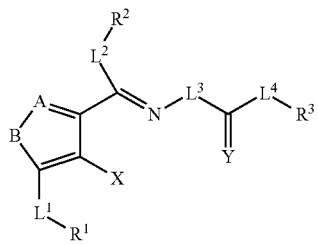

wherein A is a nitrogen atom or CR$^4$ (wherein R$^4$ is a hydrogen atom, a hydroxyl group (the hydroxyl group may be substituted with a C$_{2-6}$ alkenyl group or a C$_{2-6}$ alkynyl group), a thiol group (the thiol group may be substituted with a C$_{1-10}$ alkyl group, a C$_{2-6}$ alkenyl group, a C$_{2-6}$ alkynyl group or a C$_{1-10}$ alkylcarbonyl group), an amino group (the amino group may be substituted with one or two C$_{2-6}$ alkenyl groups or one or two C$_{2-6}$ alkynyl groups), a formyl group, a halogen atom, a nitro group, a cyano group, a C$_{1-10}$ alkyl group, a C$_{2-6}$ alkenyl group, a C$_{2-6}$ alkynyl group, a C$_{1-10}$ alkylcarbonyloxy group, a C$_{1-10}$ alkylcarbonylamino group, a mono- or di-C$_{1-10}$ alkylamino group, a C$_{1-10}$ alkoxy group (the C$_{1-10}$ alkyl group, the C$_{2-6}$ alkenyl group, the C$_{2-6}$ alkynyl group, the C$_{1-10}$ alkylcarbonyloxy group, the C$_{1-10}$ alkylcarbonylamino group, the mono- or di-C$_{1-10}$ alkylamino group and the C$_{1-10}$ alkoxy group may be optionally substituted with one or more substituents selected from the group consisting of: a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group (the C$_{2-14}$ aryl group and the C$_{2-14}$ aryloxy group may be substituted with one or more C$_{1-6}$ alkyl groups (the C$_{1-6}$ alkyl group may be substituted with one or more halogen atoms) or one or more halogen atoms)), a C$_{2-14}$ aryl group (the C$_{2-14}$ aryl group may be optionally substituted with one or more substituents selected from the group consisting of: a C$_{1-10}$ alkyl group (the C$_{1-10}$ alkyl group may be substituted with one or more halogen atoms), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group), a C$_{2-14}$ aryloxy group (the C$_{2-14}$ aryloxy group may be optionally substituted with one or more substituents selected from the group consisting of: a C$_{1-10}$ alkyl group (the C$_{1-10}$ alkyl group may be substituted with one or more halogen atoms), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group), SO$_2$R$^5$, SOR$^5$ or COR$^5$ (wherein R$^5$ is a hydroxyl group, a C$_{1-10}$ alkyl group, a C$_{2-6}$ alkenyl group, a C$_{2-6}$ alkynyl group, a C$_{1-10}$ alkoxy group (the C$_{1-10}$ alkyl group, the C$_{2-6}$ alkenyl group, the C$_{2-6}$ alkynyl group and the C$_{1-10}$ alkoxy group may be optionally substituted with one or more substituents selected from the group consisting of: a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-24}$ aryl group and a C$_{2-14}$ aryloxy group (the C$_{2-14}$ aryl group and the C$_{2-14}$ aryloxy group may be substituted with one or more C$_{1-6}$ alkyl groups (the C$_{1-6}$ alkyl group may be substituted with one or more halogen atoms) or one or more halogen atoms)), a C$_{2-14}$ aryl group (the C$_{2-14}$ aryl group may be optionally substituted with one or more substituents selected from the group consisting of: a C$_{1-10}$ alkyl group (the C$_{1-10}$ alkyl group may be substituted with one or more halogen atoms), a C$_{2-6}$ alkenyl group, a C$_{2-6}$ alkynyl group, a carboxyl group, nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group), a C$_{2-14}$ aryloxy group (the C$_{2-14}$ aryloxy group may be optionally substituted with one or more substituents selected from the group consisting of: a C$_{1-10}$ alkyl group (the C$_{1-10}$ alkyl group may be substituted with one or more halogen atoms), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group) or NR$^6$R$^7$ (wherein each of R$^6$ and R$^7$ is independently a hydrogen atom, a hydroxyl group, a formyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyloxy group, a C$_{1-10}$ alkoxycarbonyl group, a C$_{1-10}$ alkylcarbonyl group (the C$_{1-10}$ alkyl group, the C$_{2-6}$ alkenyl group, the C$_{2-6}$ alkynyl group, the C$_{1-10}$ alkoxy group, the C$_{1-10}$ alkylcarbonyloxy group, the C$_{1-10}$ alkoxycarbonyl group and the C$_{1-10}$ alkylcarbonyl group may be optionally substituted with one or more substituents selected from the group consisting of: a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group (the C$_{2-14}$ aryl group and the C$_{2-14}$ aryloxy group may be substituted with one or more C$_{1-6}$ alkyl groups (the C$_{1-6}$ alkyl group may be substituted with one or more halogen atoms) or one or more halogen atoms)) or a C$_{2-14}$ aryl group (the C$_{2-14}$ aryl group may be optionally substituted with one or more substituents selected from the group consisting of: a C$_{1-10}$ alkyl group (the C$_{1-10}$ alkyl group may be substituted with one or more halogen atoms), a C$_{2-6}$ alkenyl group, a C$_{2-6}$ alkynyl group, a carboxyl group, a nitro group, a cyano group, a halogen atom, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, an amino group, a mono- or di-C$_{1-10}$ alkylamino group, a hydroxyl group, a protected hydroxyl group, a C$_{2-14}$ aryl group and a C$_{2-14}$ aryloxy group), or R$^6$ and R$^7$ mean, together with each other, —(CH$_2$)$_{m1}$-E-(CH$_2$)$_{m2}$— (wherein E is an oxygen atom, a sulfur atom, CR$^{26}$R$^{27}$ (wherein each of R$^{26}$ and R$^{27}$ is independently a hydrogen atom, a C$_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), B is an oxygen atom, a sulfur atom or $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, $C_{2-6}$ alkynyl group, a carboxyl group, a nitro group, a cyano group, a halogen atom, a $C_{1-10}$ alkoxy group, a $C_{1-10}$ alkylcarbonyl group, a $C_{2-10}$ alkylcarbonyloxy group, a alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, protected hydroxyl group, a $C_{2-14}$ aryl group and a $C_{2-14}$ aryloxy group)) (provided that when A is a nitrogen atom, B is not NH), $R^1$ is a $C_{2-14}$ aryl group (the $C_{2-14}$ aryl group may be substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group and the $C_{1-10}$ alkoxycarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, protected hydroxyl group, a $C_{2-14}$ aryl group and a $C_{2-14}$ aryloxy group), a thiol group and an amino group (the thiol group and the amino group may be optionally substituted with one or two substituents selected from the group consisting of: a formyl group, a $C_{1-20}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{2-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more. $C_{1-6}$ alkyl groups (the $C_{1-6}$ alkyl group may be substituted with one or more halogen atoms) or one or more halogen atoms)))), $L^1$ is a bond, $CR^{10}R^{11}$ (wherein each of $R^{10}$ and $R^{11}$ is independently a hydrogen atom or a $C_{1-6}$ alkyl group (the $C_{1-6}$ alkyl group may be substituted with one or more halogen atoms)), an oxygen atom, a sulfur atom or $NR^{12}$ (wherein $R^{12}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), X is $OR^{13}$, $SR^{13}$ or $NR^{14}R^{15}$ (wherein $R^{13}$ is a hydrogen atom, a $C_{1-10}$ alkyl group, a $C_{2-6}$ alkenyl group, a $C_{2-6}$ alkynyl group or a $C_{2-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), and each of $R^{14}$ and $R^{15}$ is independently a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-24}$ aryl group and a $C_{2-14}$ aryloxy group)), $R^2$ is a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkoxycarbonyl group, a $C_{1-10}$ alkylcarbonyloxy group, (the $C_{1-10}$ alkyl group, the $C_{2-6}$ alkenyl group, the $C_{2-6}$ alkynyl group, the $C_{1-10}$ alkoxy group, the $C_{1-10}$ alkoxycarbonyl group, the $C_{1-10}$ alkylcarbonyloxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $L^2$ is a bond, $CR^{34}R^{35}$ (wherein each of $R^{34}$ and $R^{35}$ is independently a hydrogen atom or a $C_{1-6}$ alkyl group (the $C_{1-6}$ alkyl group may be substituted with one or more halogen atoms)), an oxygen atom, a sulfur atom or $NR^{16}$ (wherein $R^{16}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a alkylcarbonylamino group, an amino group, a mono- or alkylamino group, a hydroxyl group, a protected hydroxyl group, a $C_{2-14}$ aryl group and a $C_{2-14}$ aryloxy group)), $L^3$ is a bond, $CR^{17}R^{18}$ (wherein each of $R^{17}$ and $R^{18}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{3-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, $C_{2-14}$ aryl group and a $C_{2-14}$ aryloxy group)), an oxygen atom, a sulfur atom or $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-30}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino is group, an amino group, a mono- or di-$C_{1-10}$ alkylamino group, a hydroxyl group, a protected hydroxyl group, a $C_{2-14}$ aryl group and a $C_{2-14}$ aryloxy group)), $L^4$ is a bond, $CR^{20}R^{21}$ (wherein each of $R^{20}$ and $R^{21}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), an oxygen atom, a sulfur atom or $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), Y is an oxygen atom, a sulfur atom or $NR^{23}$ (wherein $R^{23}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and $R^3$ is a $C_{2-14}$ aryl group (the $C_{2-14}$ aryl group may be substituted with one or more substituents independently represented by —$W^1(CW^2W^3)_m W^4$ (wherein $W^1$ is $(CR^{24}R^{25})_n$ (wherein each of $R^{24}$ and $R^{25}$ is independently a hydrogen atom or a $C_{1-6}$ alkyl group, (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or and $W^4$ is a hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of: a carboxyl group, a nitro, group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a thiol group, a phosphonic acid group, a sulfonic acid group, a tetrazole group, a $C_{2-14}$ aryl group and a $C_{2-14}$ aryloxy group), $SO_2R^{28}$, $SOR^{28}$, $COR^{28}$ (wherein $R^{28}$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group, a $C_{2-14}$ aryloxy group (the $C_{2-14}$ aryl group and the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^{29}R^{30}$ (wherein each of $R^{29}$ and $R^{30}$ is independently a hydrogen atom, a hydroxyl group, a formyl group, a cyano group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^{29}$ and $R^{30}$, together with each other means —$(CH_2)_{m3}$-G-$(CH_2)_{m4}$— (wherein G is an oxygen atom, sulfur atom, a $CR^{31}R^{32}$ (wherein each of $R^{31}$ and $R^{32}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{33}$ (wherein $R^{33}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, $C_{1-10}$ alkoxycarbonyl group, a $C_{1-10}$ alkylcarbonylamino group, an amino group, a mono- or di-$CO_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m3 and m4 is independently an integer of from 0 to 5, provided that m3+m4 is 3, 4 or 5))), a tetrazole group, or a phosphonic acid group)), a tautomer, prodrug or pharmaceutically acceptable salt of the compound or a solvate thereof.

2. The compound according to 1, wherein A is a nitrogen atom, and B is a sulfur atom, a tautomer, prodrug or pharmaceutically acceptable salt of the compound or a solvate thereof.

3. The compound according to 1, wherein A is a nitrogen atom, and B is an oxygen atom, a tautomer, prodrug or pharmaceutically acceptable salt of the compound or a solvate thereof.

4. The compound according to 1, wherein A is a nitrogen atom, and B is NR$^9$ (wherein R$^9$ is a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ is alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl, group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, $C_{2-14}$ aryl group and a $C_{2-14}$ aryloxy group)), a tautomer, prodrug or pharmaceutically acceptable salt of the compound or a solvate thereof.

5. The compound according to 1, wherein A is CR$^4$ (wherein R$^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), SO$_2$R$^5$, SOR$^5$ or COR$^5$ (wherein R$^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-20}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-24}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-30}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-20}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is a oxygen atom, a tautomer, prodrug or pharmaceutically acceptable salt of the compound or a solvate thereof.

6. The compound according to 1, wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl is groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group; an amino group, a mono- or alkylamino group, a hydroxyl group, a protected hydroxyl group, a $C_{2-14}$ aryl group and a $C_{2-24}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is a sulfur atom, a tautomer, prodrug or pharmaceutically acceptable salt of the compound or a solvate thereof.

7. The compound according to 1, wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl, group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy is group, a $C_{1-10}$ alkylcarbonyl group, a $C_{1-10}$ alkylcarbonyloxy group, a $C_{1-10}$ alkoxycarbonyl group, a alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), a tautomer, prodrug or pharmaceutically acceptable salt of the compound or a solvate thereof.

8. The compound according to 1, wherein $L^1$ is a bond, a tautomer, prodrug or pharmaceutically acceptable salt of the compound or a solvate thereof.

9. The compound according to 2, wherein $L^1$ is a bond, a tautomer, prodrug or pharmaceutically acceptable salt of the compound or a solvate thereof.

10. The compound according to 3, wherein $L^1$ is a bond, a tautomer, prodrug or pharmaceutically acceptable salt of the compound or a solvate thereof.

11. The compound according to 4, wherein $L^1$ is a bond, a tautomer, prodrug or pharmaceutically acceptable salt of the compound or a solvate thereof.

12. The compound according to 5, wherein $L^1$ is a bond, a tautomer, prodrug or pharmaceutically acceptable salt of the compound or a solvate thereof.

13. The compound according to 6, wherein $L^1$ is a bond, a tautomer, prodrug or pharmaceutically acceptable salt of the compound or a solvate thereof.

14. The compound according to 7, wherein $L^1$ is a bond, a tautomer, prodrug or pharmaceutically acceptable salt of the compound or a solvate thereof.

15. The compound according to 1, wherein $L^2$ is a bond, a tautomer, prodrug or pharmaceutically acceptable salt of the compound or a solvate thereof.

16. The compound according to 2, wherein $L^2$ is a bond, a tautomer, prodrug or pharmaceutically acceptable salt of the compound or a solvate thereof.

17. The compound according to 3, wherein $L^2$ is a bond, a tautomer, prodrug or pharmaceutically acceptable salt of the compound or a solvate thereof.

18. The compound according to 4, wherein $L^2$ is a bond, a tautomer, prodrug or pharmaceutically acceptable salt of the compound or a solvate thereof.

19. The compound according to 5, wherein $L^2$ is a bond, tautomer, prodrug or pharmaceutically acceptable salt of is the compound or a solvate thereof.

20. The compound according to 6, wherein $L^2$ is a bond, tautomer, prodrug or pharmaceutically acceptable salt of the compound or a solvate thereof.

21. The compound according to 7, wherein $L^2$ is a bond, tautomer, prodrug or pharmaceutically acceptable salt of the compound or a solvate thereof.

22. The compound according to 8, wherein $L^2$ is a bond, a tautomer, prodrug or pharmaceutically acceptable salt of the compound or a solvate thereof.

23. The compound according to 9, wherein $L^2$ is a bond, a tautomer, prodrug or pharmaceutically acceptable salt of the compound or a solvate thereof.

24. The compound according to 10, wherein $L^2$ is a bond, a tautomer, prodrug or pharmaceutically acceptable salt of the compound or a solvate thereof.

25. The compound according to 11, wherein $L^2$ is a bond, a tautomer, prodrug or pharmaceutically acceptable salt of the compound or a solvate thereof.

26. The compound according to 12, wherein $L^2$ is a bond, a tautomer, prodrug or pharmaceutically acceptable salt of the compound or a solvate thereof.

27. The compound according to 13, wherein $L^2$ is a bond, a tautomer, prodrug or pharmaceutically acceptable salt of the compound or a solvate thereof.

28. The compound according to 14, wherein $L^2$ is a bond, a tautomer, prodrug or pharmaceutically acceptable salt of the compound or a solvate thereof.

29. The compound according to 1, 2, 3, 4, 5, 6, 7, 8, 9, 10, 11, 12, 13, 14, 15, 16, 17, 18, 19, 20, 21, 22, 23, 24, 25, 26, 27 or 28, wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-20}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), a tautomer, prodrug or pharmaceutically acceptable salt of the compound or a solvate thereof.

30. The compound according to 1, 2, 3, 4, 5, 6, 7, 8, 9, 10, 11, 12, 13, 14, 15, 16, 17, 18, 19, 20, 21, 22, 23, 24, 25, 26, 27 or 28, wherein $L^3$ is NH, a tautomer, prodrug or pharmaceutically acceptable salt of the compound or a solvate thereof.

31. The compound according to 29, wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), a tautomer, prodrug or pharmaceutically acceptable salt of the compound or a solvate thereof.

32. The compound according to 30, wherein $L^4$ is the same as defined in 31, a tautomer, prodrug or pharmaceutically acceptable salt of the compound or a solvate thereof.

33. The compound according to 29, wherein $L^4$ is NH, tautomer, prodrug or pharmaceutically acceptable salt of the compound or a solvate thereof.

34. The compound according to 30, wherein $L^4$ is NH, a tautomer, prodrug or pharmaceutically acceptable salt of the compound or a solvate thereof.

35. The compound according to 29, wherein $L^4$ is a bond, a tautomer, prodrug or pharmaceutically acceptable salt of the compound or a solvate thereof.

36. The compound according to 30, wherein $L^4$ is a bond, a tautomer, prodrug or pharmaceutically acceptable salt of the compound or a solvate thereof.

37. The compound according to 31, wherein Y is an oxygen atom, a tautomer, prodrug or pharmaceutically acceptable salt of the compound or a solvate thereof.

38. The compound according to 32, wherein Y is an oxygen atom, a tautomer, prodrug or pharmaceutically acceptable salt of the compound or a solvate thereof.

39. The compound according to 33, wherein Y is an oxygen atom, a tautomer, prodrug or pharmaceutically acceptable salt of the compound or a solvate thereof.

40. The compound according to 34, wherein Y is an oxygen atom, a tautomer, prodrug or pharmaceutically acceptable salt of the compound or a solvate thereof.

41. The compound according to 35, wherein Y is an oxygen atom, a tautomer, prodrug or pharmaceutically acceptable salt of the compound or a solvate thereof.

42. The compound according to 36, wherein Y is an oxygen atom, a tautomer, prodrug or pharmaceutically acceptable salt of the compound or a solvate thereof.

43. The compound according to 31, wherein Y is a sulfur atom, a tautomer, prodrug or pharmaceutically acceptable salt of the compound or a solvate thereof.

44. The compound according to 32, wherein Y is a sulfur atom, a tautomer, prodrug or pharmaceutically acceptable salt of the compound or a solvate thereof.

45. The compound according to 33, wherein Y is a sulfur atom, a tautomer, prodrug or pharmaceutically acceptable salt of the compound or a solvate thereof.

46. The compound according to 34, wherein Y is a sulfur atom, a tautomer, prodrug or pharmaceutically acceptable salt of the compound or a solvate thereof.

47. The compound according to 35, wherein Y is a sulfur atom, a tautomer, prodrug or pharmaceutically acceptable salt of the compound or a solvate thereof.

48. The compound according to 36, wherein Y is a sulfur atom, a tautomer, prodrug or pharmaceutically acceptable salt of the compound or a solvate thereof.

49. The compound according to 37, wherein X is a hydroxyl group, a tautomer, prodrug or pharmaceutically acceptable salt of the compound or a solvate thereof.

50. The compound according to 38, wherein X is a hydroxyl group, a tautomer, prodrug or pharmaceutically acceptable salt of the compound or a solvate thereof.

51. The compound according to 39, wherein X is a hydroxyl group, a tautomer, prodrug or pharmaceutically acceptable salt of the compound or a solvate thereof.

52. The compound according to 40, wherein X is a hydroxyl group, a tautomer, prodrug or pharmaceutically acceptable salt of the compound or a solvate thereof.

53. The compound according to 41, wherein X is a hydroxyl group, a tautomer, prodrug or pharmaceutically acceptable salt of the compound or a solvate thereof.

54. The compound according to 42, wherein X is a hydroxyl group, a tautomer, prodrug or pharmaceutically acceptable salt of the compound or a solvate thereof.

55. The compound according to 43, wherein X is a hydroxyl group, a tautomer, prodrug or pharmaceutically acceptable salt of the compound or a solvate thereof.

56. The compound according to 44, wherein X is a hydroxyl group, a tautomer, prodrug or pharmaceutically acceptable salt of the compound or a solvate thereof.

57. The compound according to 45, wherein X is a hydroxyl group, a tautomer, prodrug or pharmaceutically acceptable salt of the compound or a solvate thereof.

58. The compound according to 46, wherein X is a hydroxyl group, a tautomer, prodrug or pharmaceutically acceptable salt of the compound or a solvate thereof.

59. The compound according to 47, wherein X is a hydroxyl group, a tautomer, prodrug or pharmaceutically acceptable salt of the compound or a solvate thereof.

60. The compound according to 48, wherein X is a hydroxyl group, a tautomer, prodrug or pharmaceutically acceptable salt of the compound or a solvate thereof.

61. The compound according to 37, wherein $R^3$ is a $C_{2-14}$ aryl group (the $C_{2-14}$ aryl group is optionally substituted with one or more substituents selected from the group consisting of: a hydroxyl group, an amino group, a carboxyl group, a phosphonic acid group, a sulfonic acid group, a carbamido group, a sulfamido group, a tetrazole group and a $C_{1-10}$ alkoxycarbonyl group), a tautomer, prodrug or pharmaceutically acceptable salt of the compound or a solvate thereof.

62. The compound according to 38, wherein $R^3$ is the same as defined in 61, a tautomer, prodrug or pharmaceutically acceptable salt of the compound or a solvate thereof.

63. The compound according to 39, wherein $R^3$ is the same as defined in 61, a tautomer, prodrug or pharmaceutically acceptable salt of the compound or a solvate thereof.

64. The compound according to 40, wherein $R^3$ is the same as defined in 61, a tautomer, prodrug or pharmaceutically acceptable salt of the compound or a solvate thereof.

65. The compound according to 41, wherein $R^3$ is the same as defined in 61, a tautomer, prodrug or pharmaceutically acceptable salt of the compound or a solvate thereof.

66. The compound according to 42, wherein $R^3$ is the same as defined in 61, a tautomer, prodrug or pharmaceutically acceptable salt of the compound or a solvate thereof.

67. The compound according to 49, wherein $R^3$ is the same as defined in 61, a tautomer, prodrug or pharmaceutically acceptable salt of the compound or a solvate thereof.

68. The compound according to 50, wherein $R^3$ is the same as defined in 61, a tautomer, prodrug or pharmaceutically acceptable salt of the compound or a solvate thereof.

69. The compound according to 51, wherein $R^3$ is the same as defined in 61, a tautomer, prodrug or pharmaceutically acceptable salt of the compound or a solvate thereof.

70. The compound according to 52, wherein $R^3$ is the same as defined in 61, a tautomer, prodrug or pharmaceutically acceptable salt of the compound or a solvate thereof.

71. The compound according to 53, wherein $R^3$ is the same as defined in 61, a tautomer, prodrug or pharmaceutically acceptable salt of the compound or a solvate thereof.

72. The compound according to 54, wherein $R^3$ is the same as defined in 61, a tautomer, prodrug or pharmaceutically acceptable salt of the compound or a solvate thereof.

73. The compound according to 43, wherein $R^3$ is a $C_{2-14}$ aryl group (the $C_{2-14}$ aryl group is optionally substituted with one or more substituents selected from the group consisting of: a hydroxyl group, an amino group, a carboxyl group, a phosphonic acid group, a sulfonic acid group, a carbamido group, a sulfamido group, a tetrazole group and a $C_{1-10}$ alkoxycarbonyl group), a tautomer, prodrug or pharmaceutically acceptable salt of the compound or a solvate thereof.

74. The compound according to 44, wherein $R^3$ is the same as defined in 73, a tautomer, prodrug or pharmaceutically is acceptable salt of the compound or a solvate thereof.

75. The compound according to 45, wherein $R^3$ is the same as defined in 73, a tautomer, prodrug or pharmaceutically acceptable salt of the compound or a solvate thereof.

76. The compound according to 46, wherein $R^3$ is the same as defined in 73, a tautomer, prodrug or pharmaceutically acceptable salt of the compound or a solvate thereof.

77. The compound according to 47, wherein $R^3$ is the same as defined in 73, a tautomer, prodrug or pharmaceutically acceptable salt of the compound or a solvate thereof.

78. The compound according to 48, wherein $R^3$ is the same as defined in 73, a tautomer, prodrug or pharmaceutically acceptable salt of the compound or a solvate thereof.

79. The compound according to 55, wherein $R^3$ is the same as defined in 73, a tautomer, prodrug or pharmaceutically acceptable salt of the compound or a solvate thereof.

80. The compound according to 56, wherein $R^3$ is the same as defined in 73, a tautomer, prodrug or pharmaceutically acceptable salt of the compound or a solvate thereof.

81. The compound according to 57, wherein $R^3$ is the same as defined in 73, a tautomer, prodrug or pharmaceutically acceptable salt of the compound or a solvate thereof.

82. The compound according to 58, wherein $R^3$ is the same as defined in 73, a tautomer, prodrug or pharmaceutically acceptable salt of the compound or a solvate thereof.

83. The compound according to 59, wherein $R^3$ is the same as defined in 73, a tautomer, prodrug or pharmaceutically acceptable salt of the compound or a solvate thereof.

84. The compound according to 60, wherein $R^3$ is the same as defined in 73, a tautomer, prodrug or pharmaceutically acceptable salt of the compound or a solvate thereof.

85. The compound according to 37, wherein $R^3$ is a $C_{2-14}$ aryl group (the $C_{2-14}$ aryl group is optionally substituted with one or more substituents selected from the group consisting of: a $C_{1-10}$ alkoxy group, a $C_{1-10}$ alkylcarbonyl group, a $C_{1-10}$ alkylcarbonyloxy group, a $C_{1-10}$ alkylcarbonylamino group and a mono- or di-$C_{1-10}$ alkylamino group), a tautomer, prodrug or pharmaceutically acceptable salt of the compound or a solvate thereof.

86. The compound according to 38, wherein $R^3$ is the same as defined in 85, a tautomer, prodrug or pharmaceutically acceptable salt of the compound or a solvate thereof.

87. The compound according to 39, wherein $R^3$ is the same as defined in 85, a tautomer, prodrug or pharmaceutically acceptable salt of the compound or a solvate thereof.

88. The compound according to 40, wherein $R^3$ is, the same as defined in 85, a tautomer, prodrug or pharmaceutically acceptable salt of the compound or a solvate thereof.

89. The compound according to 41, wherein $R^3$ is the same as defined in 85, a tautomer, prodrug or pharmaceutically acceptable salt of the compound or a solvate thereof.

90. The compound according to 42, wherein $R^3$ is the same as defined in 85, a tautomer, prodrug or pharmaceutically acceptable salt of the compound or a solvate thereof.

91. The compound according to 49, wherein $R^3$ is the same as defined in 85, a tautomer, prodrug or pharmaceutically acceptable salt of the compound or a solvate thereof.

92. The compound according to 50, wherein $R^3$ is the same as defined in 85, a tautomer, prodrug or pharmaceutically acceptable salt of the compound or a solvate thereof.

93. The compound according to 51, wherein $R^3$ is the same as defined in 85, a tautomer, prodrug or pharmaceutically acceptable salt of the compound or a solvate thereof.

94. The compound according to 52, wherein $R^3$ is the same as defined in 85, a tautomer, prodrug or pharmaceutically acceptable salt of the compound or a solvate thereof.

95. The compound according to 53, wherein $R^3$ is the same as defined in 85, a tautomer, prodrug or pharmaceutically acceptable salt of the compound or a solvate thereof.

96. The compound according to 54, wherein $R^3$ is the same as defined in 85, a tautomer, prodrug or pharmaceutically acceptable salt of the compound or a solvate thereof.

97. The compound according to 43, wherein $R^3$ is a $C_{2-14}$ aryl group (the $C_{2-24}$ aryl group is optionally substituted with one or more substituents selected from the group consisting of: a $C_{1-10}$ alkoxy group, a $C_{1-10}$ alkylcarbonyl group, a $C_{1-10}$ alkylcarbonyloxy group, a $C_{1-10}$ alkylcarbonylamino group and a mono- or di-$C_{1-10}$ alkylamino group), a tautomer, prodrug or pharmaceutically acceptable salt of the compound or a solvate thereof.

98. The compound according to 44, wherein $R^3$ is the same as defined in 97, a tautomer, prodrug or pharmaceutically acceptable salt of the compound or a solvate thereof.

99. The compound according to 45, wherein $R^3$ is the same as defined in 97, a tautomer, prodrug or pharmaceutically acceptable salt of the compound or a solvate thereof.

100. The compound according to 46, wherein $R^3$ is the same as defined in 97, a tautomer, prodrug or pharmaceutically acceptable salt of the compound or a solvate thereof.

101. The compound according to 47, wherein $R^3$ is the same as defined in 97, a tautomer, prodrug or pharmaceutically acceptable salt of the compound or a solvate thereof.

102. The compound according to 48, wherein $R^3$ is the same as defined in 97, a tautomer, prodrug or pharmaceutically acceptable salt of the compound or a solvate thereof.
103. The compound according to 55, wherein $R^3$ is the same as defined in 97, a tautomer, prodrug or pharmaceutically acceptable salt of the compound or a solvate thereof.
104. The compound according to 56, wherein $R^3$ is the same as defined in 97, a tautomer, prodrug or pharmaceutically acceptable salt of the compound or a solvate thereof.
105. The compound according to 57, wherein $R^3$ is the same as defined in 97, a tautomer, prodrug or pharmaceutically acceptable salt of the compound or a solvate thereof.
106. The compound according to 58, wherein $R^3$ is the same as defined in 97, a tautomer, prodrug or pharmaceutically acceptable salt of the compound or a solvate thereof.
107. The compound according to 59, wherein $R^3$ is the same as defined in 97, a tautomer, prodrug or pharmaceutically acceptable salt of the compound or a solvate thereof.
108. The compound according to 60, wherein $R^3$ is the same as defined in 97, a tautomer, prodrug or pharmaceutically acceptable salt of the compound or a solvate thereof.
109. The compound according to 37, wherein $R^3$ is a $C_{2-14}$ aryl group (the $C_{2-14}$ aryl group is optionally substituted with one or more substituents selected from the group consisting of:
  a hydroxyl group, an amino group, a carboxyl group, a phosphonic acid group, a sulfonic acid group, carbamido group, a sulfamido group, a tetrazole group and a alkoxycarbonyl group
  and one or more substituents selected from the group consisting of:
  a nitro group, a cyano group, a halogen atom, a $C_{2-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), a tautomer, prodrug or pharmaceutically acceptable salt of the compound or a solvate thereof.
110. The compound according to 38, wherein $R^3$ is the same as defined in 109, a tautomer, prodrug or pharmaceutically acceptable salt of the compound or a solvate thereof.
111. The compound according to 39, wherein $R^3$ is the same as defined in 109, a tautomer, prodrug or pharmaceutically acceptable salt of the compound or a solvate thereof.
112. The compound according to 40, wherein $R^3$ is the same as defined in 109, a tautomer, prodrug or pharmaceutically acceptable salt of the compound or a solvate thereof.
113. The compound according to 41, wherein $R^3$ is the same as defined in 109, a tautomer, prodrug or pharmaceutically acceptable salt of the compound or a solvate thereof.
114. The compound according to 42, wherein $R^3$ is the same as defined in 109, a tautomer, prodrug or pharmaceutically acceptable salt of the compound or a solvate thereof.
115. The compound according to 49, wherein $R^3$ is the same as defined in 109, a tautomer, prodrug or pharmaceutically acceptable salt of the compound or a solvate thereof.
116. The compound according to 50, wherein $R^3$ is the same as defined in 109, a tautomer, prodrug or pharmaceutically acceptable salt of the compound or a solvate thereof.
117. The compound according to 51, wherein $R^3$ is the same as defined in 109, a tautomer, prodrug or pharmaceutically acceptable salt of the compound or a solvate thereof.
118. The compound according to 52, wherein $R^3$ is the same as defined in 109, a tautomer, prodrug or pharmaceutically acceptable salt of the compound or a solvate thereof.
119. The compound according to 53, wherein $R^3$ is the same as defined in 109, a tautomer, prodrug or pharmaceutically acceptable salt of the compound or a solvate thereof.
120. The compound according to 54, wherein $R^3$ is the same as defined in 109, a tautomer, prodrug or pharmaceutically acceptable salt of the compound or a solvate thereof.
121. The compound according to 43, wherein $R^3$ is a $C_{2-14}$ aryl group (the $C_{2-14}$ aryl group is optionally substituted with one or more substituents selected from the group consisting of:
  a hydroxyl group, an amino group, a carboxyl group, a phosphonic acid group, a sulfonic acid group, a carbamido group, a sulfamido group, a tetrazole group and a $C_{1-10}$ alkoxycarbonyl group
  and one or more substituents selected from the group consisting of:
  a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomer, prodrug or pharmaceutically acceptable salt of the compound or a solvate thereof.
122. The compound according to 44, wherein $R^3$ is the same as defined in 121, a tautomer, prodrug or pharmaceutically acceptable salt of the compound or a solvate thereof.
123. The compound according to 45, wherein $R^3$ is the same as defined in 121, a tautomer, prodrug or pharmaceutically acceptable salt of the compound or a solvate thereof.
124. The compound according to 46, wherein $R^3$ is the same as defined in 121, a tautomer, prodrug or pharmaceutically acceptable salt of the compound or a solvate thereof.
125. The compound according to 47, wherein $R^3$ is the same as defined in 121, a tautomer, prodrug or pharmaceutically acceptable salt of the compound or a solvate thereof.
126. The compound according to 48, wherein $R^3$ is the same as defined in 121, a tautomer, prodrug or pharmaceutically acceptable salt of the compound or a solvate thereof.
127. The compound according to 55, wherein $R^3$ is the same as defined in 121, a tautomer, prodrug or pharmaceutically acceptable salt of the compound or a solvate thereof.
128. The compound according to 56, wherein $R^3$ is the same as defined in 121, a tautomer, prodrug or pharmaceutically acceptable salt of the compound or a solvate thereof.
129. The compound according to 57, wherein $R^3$ is the same as defined in 121, a tautomer, prodrug or pharmaceutically acceptable salt of the compound or a solvate thereof.
130. The compound according to 58, wherein $R^3$ is the same as defined in 121, a tautomer, prodrug or pharmaceutically acceptable salt of the compound or a solvate thereof.
131. The compound according to 59, wherein $R^3$ is the same as defined in 121, a tautomer, prodrug or pharmaceutically acceptable salt of the compound or a solvate thereof.
132. The compound according to 60, wherein $R^3$ is the same as defined in 121, a tautomer, prodrug or pharmaceutically acceptable salt of the compound or a solvate thereof.
133. The thrombopoietin receptor activator according to 1.
134. The thrombopoietin receptor activator according to 2.
135. The thrombopoietin receptor activator according to 3.
136. The thrombopoietin receptor activator according to 4.
137. The thrombopoietin receptor activator according to 5.
138. The thrombopoietin receptor activator according to 6.
139. The thrombopoietin receptor activator according to 7.
140. The thrombopoietin receptor activator according to any one of 8 to 14.
141. The thrombopoietin receptor activator according to any one of 15 to 28.

142. The thrombopoietin receptor activator according to 29.
143. The thrombopoietin receptor activator according to 30.
144. The thrombopoietin receptor activator according to 31 or 32.
145. The thrombopoietin receptor activator according to 33 or 34.
146. The thrombopoietin receptor activator according to 35 or 36.
147. The thrombopoietin receptor activator according to any one of 37 to 42.
148. The thrombopoietin receptor activator according to any one of 43 to 48.
149. The thrombopoietin receptor activator according to any one of 49 to 54.
150. The thrombopoietin receptor activator according to any one of 55 to 60.
151. The thrombopoietin receptor activator according to any one of 61 to 72.
152. The thrombopoietin receptor activator according to any one of 73 to 84.
153. The thrombopoietin receptor activator according to any one of 85 to 96.
154. The thrombopoietin receptor activator according to any one of 97 to 108.
155. The thrombopoietin receptor activator according to any one of 109 to 120.
156. The thrombopoietin receptor activator according to any one of 121 to 132.
157. A preventive, therapeutic or improving agent for diseases against which activation of the thrombopoietin receptor is effective, which contains the thrombopoietin receptor activator according to any one of 133 to 156, a tautomer, prodrug or pharmaceutically acceptable salt of the activator or a solvate thereof, as an active ingredient.
158. A platelet increasing agent containing the thrombopoietin receptor activator according to any one of 133 to 156, a tautomer, prodrug or pharmaceutically acceptable salt of the activator or a solvate thereof, as an active ingredient.
159. Medicament containing the compound according to any one of 1 to 132, a tautomer, prodrug or pharmaceutically acceptable salt of the compound or a solvate thereof, as an active ingredient.

BEST MODE FOR CARRYING OUT THE INVENTION

Figure 1:
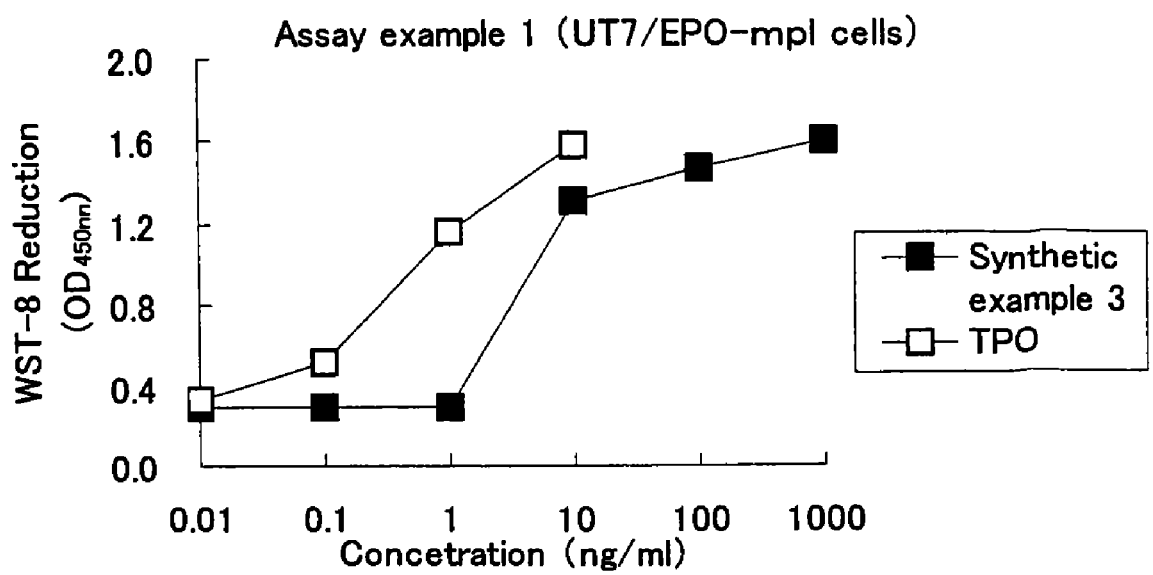
FIG. 1 shows the proliferation of UT7/EPO-mpl cells when stimulated by the compound of the present invention (Synthetic Example 3).

Now, the present invention will be described in detail.
In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Ac" denotes acetyl, "Naphthyl" denotes naphthyl, "Me" denotes methyl, "Et" denotes ethyl, "Pr" denotes propyl, and "Bu" denotes butyl.
First, the terms in the respective substituents $R^1$ to $R^{36}$ will be explained.
As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 2-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-s butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-6}$ alkenyl group may be linear, branched or a $C_{3-6}$ cycloalkenyl group, and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-14}$ aryl group may be a $C_{6-14}$ aryl group containing no hetero atoms as ring constituting atoms or a $C_{2-9}$ aromatic heterocyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered $C_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered $C_{5-9}$ fused heterocyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, 3-purinyl group, a 6-purinyl group, a 7-purinyl group, 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pterdinyl group, a 4-pterdinyl group, a 6-pterdinyl group, a 7-pterdinyl group or the like.

A $C_{2-14}$ aryloxy group may be a $C_{6-14}$ aryloxy group so containing no hetero atoms as ring constituting atoms or a $C_{2-9}$ aromatic heterocyclic oxy group, and a $C_{2-9}$ aromatic heterocyclic oxy group may be a 5 to 7-membered $C_{2-6}$ heteromonocyclic oxy group or 8 to 10-membered $C_{5-9}$ fused heterobicyclic oxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, a β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ heteromonocyclic oxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused heterocyclic oxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pterdinyloxy group, a 4-pterdinyloxy group, a 6-pterdinyloxy group, a 7-pterdinyloxy group or the like.

A $C_{1-6}$ alkylcarbonyl group may linear, branched or a $C_{3-6}$ cycloalkylcarbonyl group, and be methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

A $C_{1-10}$ alkylcarbonyl may be linear, branched or a $C_{3-10}$ cycloalkylcarbonyl group, and in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-10}$ alkoxy group may be linear, branched or a $C_{3-10}$ cycloalkoxy group, and methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-1-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-6}$ alkoxycarbonyl group may be linear, branched or a $C_{3-6}$ cycloalkoxycarbonyl group, and methoxycarbonyl, ethoxycarbonyl, n-propoxycarbonyl, i-propoxycarbonyl, c-propylcarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and in addition to those mentioned above, 1-methyl-1-ethyl-n-pentyloxycarbonyl, 1-heptyloxycarbonyl, 2-s heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonyloxy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-propylcarbonylamino, 1,2,2-trimethyl-c-propyl-carbonylamino, 1,2,3-trimethyl-c-propyl carbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A $C_{1-10}$ dialkylamino group may be symmetric or asymmetric. A symmetric $C_{1-10}$ dialkylamino group may be linear, branched or a $C_{3-10}$ cycloalkylamino group, and dimethylamino, diethylamino, di-n-propylamino, di-i-propylamino, di-c-propylamino, di-n-butylamino, di-i-butylamino, di-s-butylamino, di-t-butylamino, d-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2- methyl-c-propyl)amino, di-(2-ethyl-3-methyl-c-propyl) amino, di-(1-methyl-1-ethyl-n-pentyl)amino, di-(1-heptyl) amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl) amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric $C_{1-10}$ dialkylamino group may be linear, branched or a $C_{3-10}$ cycloalkylamino group, and (methyl, ethyl)amino, (methyl, n-propyl)amino, (methyl, i-propyl) amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl) amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl) amino, (ethyl, c-pentyl)amino, (ethyl, n-hexyl)amino, (ethyl, hexyl)amino, (n-propyl, i-propyl)amino, (n-propyl, c-propyl) amino, (n-propyl, n-butyl)amino, (n-propyl, butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl) amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, butyl)amino, (c-propyl, i-butyl)amino, (c-propyl, s-butyl) amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl) amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, pentyl)amino, (s-butyl, c-pentyl) amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl) amino, (n-pentyl, n-hexyl)amino, (n-pentyl, c-hexyl)amino, (c-pentyl, n-hexyl)amino, (c-pentyl, c-hexyl)amino, (n-hexyl, c-hexyl)amino, (methyl, n-heptyl)amino, (methyl, n-octyl)amino, (methyl, n-nonanyl)amino, (methyl, n-decyl) amino, (methyl, n-heptyl)amino, (ethyl, n-octyl)amino, (ethyl, n-nonanyl)amino, (ethyl, n-decyl)amino or the like may be mentioned.

The protecting group in a protected hydroxyl group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, p-AOM: p-anisyloxymethyl and the like, preferably benzyloxymethyl or the like), a $C_{1-4}$ alkylaminomethyl group (such as dimethylaminomethyl), a substituted acetamidomethyl group (such as Acm: acetamidomethyl, Tacm: trimethylacetamidemethyl and the like), a substituted thiomethyl group (such as MTM: methylthiomethyl, PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl and the like), an arylcarbonyl group (such as benzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl, and the like), an arylaminocarbonyl group (such as phenylcarbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

Specific preferred examples of the substituent $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a $C_{1-10}$ alkyl group, a halogen atom, a $C_{1-10}$ alkyl group substituted with one or more halogen atoms, a nitro group, an amino group, an amino group substituted with one or two $C_{1-10}$ alkyl groups, an amino group substituted with a $C_{1-10}$ alkylcarbonyl group, a thiol group substituted with a $C_{1-10}$ alkyl group, a thiol group substituted with a $C_{1-10}$ alkylcarbonyl group, hydroxyl group, a $C_{1-6}$ alkoxy group, a $C_{1-10}$ alkoxy group substituted with one or more halogen atoms, a $C_{1-10}$ alkylcarbonyloxy group, a $C_{1-10}$ alkoxycarbonyl group and a $C_{1-10}$ alkylcarbonyl group.

Particularly preferred examples of the substituent $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl: group, a 7-isoquinolyl group and a 8-isoquinolyl group) optionally substituted with one or more of the following substituents.

Substituents: a methyl group, a t-butyl group, a trifluoromethyl group, a trifluoromethoxy group, a bromine atom, a chlorine atom, a fluorine atom, a methoxy group, a methylamino group, a dimethylamino group, a t-butyloxy group and a t-butylamino group.

Still further preferred specific examples of the substituent are a 3-methyl-phenyl group, a 4-methyl-phenyl group, a 3,4-dimethyl-phenyl group, a 3-t-butyl-phenyl group, a 4-t-butyl-phenyl group, a 3-trifluoromethyl-phenyl group, a 4-trifluoromethyl-phenyl group, a 4-trifluoromethoxy-phenyl group, a 4-bromo-phenyl group, a 3,4-ditrifluoromethyl-phenyl group, a 3-chloro-phenyl group, a 4-chloro-phenyl group, a 3-fluoro-phenyl group, a 4-fluoro-phenyl group, a 3,4-dichloro-phenyl group, 3,4-difluoro-phenyl group, a 4-methoxy-phenyl group, a 4-methylamino-phenyl group, a 4-methyl-2-thienyl group, a 5-methyl-2-thienyl group, a 4,5-dimethyl-2-thienyl group, a 4-t-butyl-2-thienyl group, a 5-t-butyl-2-thienyl group, a 4-trifluoromethyl-2-thienyl group, a 5-trifluoromethyl-2-thienyl group, a 4,5-ditrifluoromethyl-2-thienyl group, a 4-chloro-2-thienyl group, a 5-chloro-2-thienyl group, a 4-fluoro-2-thienyl group, a 5-fluoro-2-thienyl group, a 4,5-dichloro-2-thienyl group, 4,5-ditrifluoromethyl-2-thienyl group, a 5-methoxy-2-thienyl group, a 5-methylamino-2-thienyl group, a 4-methyl-2-furyl group, a 5-methyl-2-furyl group, a 4,5-dimethyl-2-furyl group, a 4-t-butyl-2-furyl group, a 5-t-butyl-2-furyl group, a 4-trifluoromethyl-2-furyl group, a 5-trifluoromethyl-2-furyl group, a 4,5-ditrifluoromethyl-2-furyl group, a 4-chloro-2-furyl group, a 5-chloro-2-furyl group, a 4-fluoro-2-furyl group, a 5-fluoro-2-furyl group, a 4,5-dichloro-2-furyl group, a 5-methoxy-2-furyl group, a 5-methylamino-2-furyl group, a 6-chloro-3-pyridazinyl group, a 6-methyl-3-pyridazinyl group, a 6-methoxy-3-pyridazinyl group, a 6-chloro-3-pyridazinyl group, a 6-methylpyridazinyl group, a 6-methoxy-3-pyridazinyl group, a 6-t-butoxy-3-pyridazinyl group, a 5,6-dimethyl-3-pyridazinyl group, a 5,6-dichloro-3-pyridazinyl group, a 6-t-butyl-3-pyridazinyl group, a 5-chloro-2-pyridyl group, a 5-s trifluoromethyl-2-pyridyl group, a 5-methyl-2-pyridyl group, a 4,5-dimethyl-2-pyridyl group, a 5,6-dimethyl-2-pyridyl group, a 5-t-butyl-2-pyridyl group, a 4,5-dichloro-2-pyridyl group, a 5,6-dichloro-2-pyridyl group and the like.

Specific preferable examples of $L^1$ are a bond, $CH_2$, a oxygen atom, a sulfur atom, NH, N-Me, N—CHO, CHMe, $CMe_2$, N—$CH_2$Ph and the like, and particularly preferable examples are a bond, $CH_2$, an oxygen atom, a sulfur atom, NH, NMe and the like.

Specific preferable examples of the substituent $R^2$ are a hydrogen atom, a methyl group, an ethyl group, a n-propyl group, an i-propyl group, a t-butyl group, and a phenyl group (the methyl group, the ethyl group, the n-propyl group, the i-propyl group, the t-butyl group and the phenyl group may be optionally substituted with an amino group, a monomethylamino group, a dimethylamino group, a monoethylamino group, a diethylamino group, a methoxy group, an ethoxy group, a methoxycarbonyl group, an ethoxycarbonyl group, a methylcarbonyloxy group, an ethylcarbonyloxy group, a methylcarbonylamino group or an ethylcarbonylamino group and the like), and particularly preferable examples are a hydrogen atom, a methyl group, an ethyl group, a n-propyl group, an i-propyl group, a t-butyl group, a phenyl group and the like.

Specific preferable examples of $L^2$ are a bond, $CH_2$, oxygen atom, a sulfur atom, NH, N-Me, N—CHO, CHMe, $CMe_2$, N—$CH_2$Ph and the like, and particularly preferable examples are a bond, $CH_2$, an oxygen atom, a sulfur atom, NH, NMe and the like.

Specific preferable examples of $L^3$ are a bond, $CH_2$, an oxygen atom, a sulfur atom, NH, NH—OH, N-Me, N—CHO, CHMe, $CMe_2$, N—$CH_2$PH and the like, and particularly preferred examples are a bond, $CH_2$, an oxygen atom, a sulfur atom, NH, NMe and the like.

Specific preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a hydroxyl group, an amino group, a carboxyl group, a phosphonic acid group, a sulfonic acid group, a carbamido group, a hydroxycarbamido group, a cyanocarbamido group, a sulfamido group, a hydroxysulfamido group, a cyanosulfamido group, a tetrazole group, —$CH_2CO_2H$, —$OCH_2CO_2H$, —$NHCH_2CO_2H$, —$CH_2CH_2CO_2H$, an alkoxycarbonyl group and the following heterocyclic groups substituted with a hydroxyl group.

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group and a 1,2-thiazole group.

Still further, specific preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more substituents optionally selected from substituent set A and with one or more substituents optionally selected from substituent set B.

Substituent set A: a hydroxyl group, an amino group, a carboxyl group, a phosphonic acid group, a sulfonic acid, a carbamido group, a hydroxycarbamido group, a cyanocarbamido group, a sulfamido group, hydroxysulfamido group, a cyanosulfamido group, a tetrazole group, —$CH_2CO_2H$, —$OCH_2CO_2H$, —$NHCH_2CO_2H$, —$CH_2CH_2CO_2H$ and an alkoxycarbonyl group.

Substituent set B: an amino group, a nitro group, a cyano group, a halogen atom, a $C_{1-10}$ alkyl group substituted with one or more fluorines, a sulfamido group substituted with one or more $C_{1-10}$ alkyl groups, carbamido group substituted with one or more $C_{1-10}$ alkyl groups and a $C_{1-10}$ alkylcarbonylamino group.

Specific particularly preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinoyl group and a 8-quinolyl group) and isoquinolyl groups (a 1-isoquinolyl group, 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a hydroxyl group, an amino group, a carboxyl group, a phosphonic acid group, a sulfonic acid group, a carbamido group, a sulfamido group, a tetrazole group, —$CH_2CO_2H$, —$OCH_2CO_2H$, —$NHCH_2CO_2H$ and —$CH_2CH_2CO_2H$.

Still further, specific particularly preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more substituents optionally selected from substituent set A and with one or more substituents optionally selected from substituent set B.

Substituent set A: a hydroxyl group, an amino group, a carboxyl group, a phosphonic acid group, a sulfonic acid group, a carbamido group, a sulfamido group, a tetrazole group, —$CH_2CO_2H$, —$OCH_2CO_2H$, —$NHCH_2CO_2H$ and —$CH_2CH_2CO_2H$.

Substituent set B: an amino group, a nitro group, cyano group, a halogen atom, a $C_{1-10}$ alkyl group substituted with one or more fluorine atoms, a sulfamido group substituted with one or more $C_{1-10}$ alkyl groups, carbamido group substituted with one or more $C_{1-10}$ alkyl groups and a $C_{1-10}$ alkylcarbonylamino group.

Specific preferable examples of $L^4$ are a bond, $CH_2$, an oxygen atom, a sulfur atom, NH, N-Me, N—CHO, CHMe, $CMe_2$, N—$CH_2Ph$ and the like, and particularly preferred examples are a single bond, $CH_2$, an oxygen atom, a sulfur atom, NH, NMe and the like.

Specific preferable examples of X are OH, SH, $NH_2$, OMe, SMe, NHMe, NHEt, NH—CHO, NH—$CH_2Ph$, $OCH_2Ph$, $SCH_2Ph$, OC(=O)$CH_3$, SC(=O)$CH_3$, NC(=O)$CH_3$ and the like, and particularly preferred examples are OH, SH, $NH_2$ and the like Specific preferable examples of Y are an oxygen atom, a sulfur atom, NH, N—OH, N—CHO, N-Me, N—$CH_2Ph$, N-OMe, N—$OCH_2Ph$ an the like, and particularly preferred examples are an oxygen atom, a sulfur atom, NH, N—OH and the like.

Favorable compounds as the thrombopoietin receptor activator, the preventive, therapeutic or improving agent for diseases against which activation of the thrombopoietin receptor is effective and the platelet increasing agent of the present invention are as follows.

1) Compounds represented by the formula (1) wherein A is a nitrogen atom, and B is a sulfur atom, tautomers, prodrugs or pharmaceutically acceptable salts of the compounds or solvates thereof.

2) Compounds represented by the formula (1) wherein A is a nitrogen atom, and B is an oxygen atom, tautomers, prodrugs or pharmaceutically acceptable salts of the compounds or solvates thereof.

3) Compounds represented by the formula (1) wherein A is a nitrogen atom, and B is $NR^9$ (wherein $R^9$ is a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), tautomers, prodrugs or pharmaceutically acceptable salts of the compounds or solvates thereof.

4) Compounds represented by the formula (1) wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, protected hydroxyl group, a $C_{2-14}$ aryl group and a $C_{2-14}$ aryloxy group (the $C_{2-14}$ aryl group and the $C_{2-14}$ aryloxy group may be, substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, $—(CH_2)_{m1}E-(CH_2)_{m2}—$ (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is a oxygen atom, tautomers, prodrugs or pharmaceutically acceptable salts of the compounds or solvates thereof.

5) Compounds represented by the formula (1) wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, to a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-20}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{2-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, —$(CH_2)_{m1}$-E-$(CH_2)_{m2}$— (wherein E is an oxygen atom, sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-20}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is a sulfur atom, tautomers, prodrugs or pharmaceutically acceptable salts of the compounds or solvates thereof.

6) Compounds represented by the formula (1) wherein. A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen, atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy is group), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected is hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), tautomers, prodrugs or pharmaceutically acceptable salts of the compounds or solvates thereof.

7) Compounds represented by the formula (1) according to 4), 5) or 6) wherein A is $CR^{37}$ (wherein $R^{37}$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxy group, the $C_{1-10}$ alkylcarbonylamino group and the mono- or di-$C_{1-10}$ alkylamino group may be substituted with one or more substituents selected from the group consisting of: a halogen atom, a carboxyl group, a nitro group and a cyano group), $SO_2R^{38}$, $SOR^{38}$ or $COR^{38}$ (wherein $R^{38}$ is a hydroxyl group, a $C_{1-10}$ alkyl group, a $C_{2-6}$ alkenyl group; a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be substituted with one or more substituents selected from the group consisting of: a halogen atom, a carboxyl group, a nitro group and a cyano group), a $C_{2-14}$ aryl group or a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), tautomers, prodrugs or pharmaceutically acceptable salts of the compounds or solvates thereof. The terms in the respective substituents $R^{37}$ and $R^{38}$ are the same as those in the respective substituents $R^1$ to $R^{36}$.

8) Compounds represented by the formula (1) according to 3) or 6) wherein B is $NR^{39}$ (wherein $R^{39}$ is a hydrogen atom, a hydroxyl group, a formyl group, a $C_{1-10}$ alkyl group, a $C_{2-6}$ alkenyl group, a $C_{2-6}$ alkynyl group, a $C_{1-20}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be substituted with one or more substituents selected from the group consisting of: a carboxyl group, a halogen atom, a nitro group and a cyano group), a $C_{2-14}$ aryl group or a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms), a $C_{2-6}$ alkenyl group, a $C_{2-6}$ alkynyl group, a carboxyl group, a nitro group, a cyano group and a halogen atom)), tautomers prodrugs or pharmaceutically acceptable salts of the compounds or solvates thereof. The terms in the substituent $R^{39}$ are the same as those in the respective substituents $R^1$ to $R^{36}$.

9) Compounds represented by the formula (1) according to 1), 2), 3), 4), 5), 6), 7) or 8) wherein $L^1$ is a bond, tautomers prodrugs or pharmaceutically acceptable salts of the compounds or solvates thereof.

10) Compounds represented by the formula (1) according to 1), 2), 3), 4), 5), 6), 7), 8) or 9) wherein $L^2$ is a bond, tautomers, prodrugs or pharmaceutically acceptable salts of the compounds or solvates thereof.

11) Compounds represented by the formula (1) according to 1), 2), 3), 4), 5), 6), 7), 8), 9) or 10) wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), tautomers, prodrugs or pharmaceutically acceptable salts of the compounds or solvates thereof.

12) The compounds according to 1), 2), 3), 4), 5), 6), 7), 8), 9) or 10) wherein $L^3$ is NH, tautomers, prodrugs or pharmaceutically acceptable salts of the compounds or solvates thereof.

13) The compounds according to 1), 2), 3), 4), 5), 6), 7), 8), 9) or 10) wherein $L^3$ is $CH_2$, tautomers, prodrugs or pharmaceutically acceptable salts of the compounds or solvates thereof.

14) The compounds according to 11), 12) or 13) wherein $L^4$ is a bond, tautomers, prodrugs or pharmaceutically acceptable salts of the compounds or solvates thereof.

15) The compounds according to 11), 12) or 13) wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), tautomers, prodrugs or pharmaceutically acceptable salts of the compounds or solvates thereof.

16) The compounds according to 11), 12) or 13) wherein $L^4$ is NH, tautomers, prodrugs or pharmaceutically acceptable salts of the compounds or solvates thereof.

17) The compounds according to 11), 12) or 13) wherein $L^4$ is $CH_2$, tautomers, prodrugs or pharmaceutically acceptable salts of the compounds or solvates thereof.

18) The compounds according to 14), 15), 16) or 17) wherein $R^2$ is a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group and the $C_{1-10}$ alkoxycarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcabonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{1-12}$ aryl group or a $C_{2-14}$ aryloxy group (the $C_{2-14}$ aryl group and $C_{2-14}$ aryloxy group may be substituted with one or more $C_{1-6}$ alkyl groups (the $C_{1-6}$ alkyl group may be substituted with one or more halogen atoms) or one or more halogen atoms), tautomers, prodrugs or pharmaceutically acceptable salts of the compounds or solvates thereof.

19) The compounds according to 14), 15), 16) or 17) wherein $R^2$ is a hydrogen atom, a $C_{1-10}$ alkyl group, a $C_{2-6}$ alkenyl group, a $C_{2-6}$ alkynyl group, a $C_{1-3}$ alkoxy group (the $C_{1-10}$ alkyl group, the $C_{2-6}$ alkenyl group, the $C_{2-6}$ alkynyl group and the $C_{1-3}$ alkoxy group may be optionally substituted with one or more substituents selected from the group consisting of: a carboxyl group, a nitro group, a cyano group, a halogen atom, a $C_{1-10}$ alkoxy group, a alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a phenyl group and a phenyloxy group (the phenyl group and the phenyloxy group may be substituted with one or more $C_{1-6}$ alkyl groups (the $C_{1-6}$ alkyl group may be substituted with one or more halogen atoms) or one or more halogen atoms)), a phenyl group or a phenyloxy group (the phenyl group and the phenyloxy group may be substituted with one or more $C_{1-6}$ alkyl groups (the $C_{1-6}$ alkyl group may be substituted with one or more halogen atoms) or one or more halogen atoms), tautomers, prodrugs or pharmaceutically acceptable salts of the compounds or solvates thereof.

20) The compounds according to 14), 15), 16) or 17) wherein. $R^2$ is a hydrogen atom, a $C_{1-10}$ alkyl group, a $C_{2-6}$ alkenyl group or a $C_{2-6}$ alkynyl group (the $C_{1-10}$ alkyl group, the $C_{2-6}$ alkenyl group and the $C_{2-6}$ alkynyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group and a protected hydroxyl group), tautomers, prodrugs or pharmaceutically acceptable salts of the compounds or solvates thereof.

21) The compounds according to 14), 15), 16) or 17) wherein $R^2$ is a hydrogen atom or a $C_{1-6}$ alkyl group (the $C_{2-6}$ alkyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group and a protected hydroxyl group), tautomers, prodrugs or pharmaceutically acceptable salts of the compounds or solvates thereof.

22) The compounds according to 14), 15), 16) or 17) wherein $R^2$ is a hydrogen atom or a $C_{1-3}$ alkyl group (the $C_{1-3}$ alkyl group may be optionally substituted with one or more substituents selected from the group consisting of: a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group and a protected hydroxyl group), tautomers, prodrugs or pharmaceutically acceptable salts of the compounds or solvates thereof.

23) The compounds according to 18), 19), 20), 21) or 22) wherein $R^1$ is a $C_{2-14}$ aryl group (the $C_{2-14}$ aryl group may be optionally substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkoxycarbonyl group, a $C_{1-10}$ alkylcarbonyloxy group (the $C_{1-10}$ alkyl group, the $C_{2-6}$ alkenyl group, the $C_{2-6}$ alkynyl group, $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group, a $C_{2-14}$ aryloxy group (the $C_{2-14}$ aryl group and the $C_{2-14}$ aryloxy group may be substituted with one or more substituents selected from the group consisting of: a $C_{1-6}$ alkyl group (the $C_{1-6}$ is alkyl group may be substituted with one or more halogen atoms) or one or more halogen atoms), a thiol group and an amino group (the thiol group and the amino group may be optionally substituted with one or more substituents selected from the group consisting of: a formyl group, a $C_{1-10}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)))), tautomers, prodrugs or pharmaceutically acceptable salts of the compounds or solvates thereof.

24) The compounds according to 18), 19), 20), 21) or 22) wherein $R^1$ is a phenyl group, a thienyl group, a furyl group, a pyridazinyl group, a pyridyl group, quinolyl group or an isoquinolyl group (the phenyl group, the thienyl group, the furyl group, the pyridazinyl group, the pyridyl group, the quinolyl group and the isoquinolyl group may be optionally substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkoxycarbonyl group, a $C_{1-10}$ alkylcarbonyloxy group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group and the $C_{1-10}$ alkoxycarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a thiol group and an amino (the thiol group and the amino group may be optionally substituted with one or more substituents selected from the group consisting of: a formyl group, a $C_{1-10}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-20}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)))), tautomers, prodrugs or pharmaceutically acceptable salts of the compounds or solvates thereof.

25) The compounds according to 18), 19), 20), 21) or 22) wherein $R^1$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group may be optionally substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, $C_{1-10}$ alkylcarbonyl group, a $C_{1-10}$ alkoxycarbonyl group, a $C_{1-10}$ alkylcarbonyloxy group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkoxycarbonyl group and the $C_{1-10}$ alkylcarbonyloxy group may be optionally substituted with one or more substituents selected from the group consisting of: a halogen atom, a carboxyl group, a nitro group and a cyano group), a $C_{2-14}$ aryl group, a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms), a thiol group and an amino group (the thiol group and the amino group may be optionally substituted with one or more substituents selected from the group consisting of: a formyl group, a $C_{1-10}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a halogen atom, a carboxyl group, a nitro group, a cyano group, a hydroxyl group and a protected hydroxyl group))), tautomers, prodrugs or pharmaceutically acceptable salts of the compounds or solvates thereof.

26) The compounds according to 18), 19), 20), 21) or 22) wherein $R^1$ is a phenyl group (the phenyl group may be optionally substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkoxycarbonyl group, a $C_{1-10}$ alkylcarbonyloxy group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkoxycarbonyl group and the $C_{1-10}$ alkylcarbonyloxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a thiol group and an amino group (the thiol group and the amino group may be optionally substituted with one or more substituents selected from the group consisting of: a formyl group, a $C_{1-10}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)))), tautomers, prodrugs or pharmaceutically acceptable salts of the compounds or solvates thereof.

27) The compounds according to 18), 19), 20), 21) or 22) wherein $R^1$ is a phenyl group (the phenyl group may be optionally substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkoxycarbonyl group, a $C_{1-10}$ alkylcarbonyloxy group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkoxycarbonyl group and the $C_{1-10}$ alkylcarbonyloxy group may be optionally substituted with one or more substituents selected from the group consisting of: a halogen atom, a carboxyl group, a nitro group and a cyano group), a $C_{2-14}$ aryl group, a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms), a thiol group and an amino group (the thiol group and the amino group may be optionally substituted with one or more substituents selected from the group consisting of: a formyl group, a $C_{1-10}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a halogen atom, a carboxyl group, a nitro group, a cyano group, a hydroxyl group and a protected hydroxyl group))), tautomers, prodrugs or pharmaceutically acceptable salts of the compounds or solvates thereof.

28) The compounds according to 23), 24), 25), 26) or 27) wherein Y is an oxygen atom, tautomers, prodrugs or pharmaceutically acceptable salts of the compounds or solvates thereof.

29) The compounds according to 23), 24), 25), 26) or 27) wherein Y is a sulfur atom, tautomers, prodrugs or pharmaceutically acceptable salts of the compounds or solvates thereof.

30) The compounds according to 28) or 29) wherein X is a hydroxyl group, tautomers, prodrugs or pharmaceutically acceptable salts of the compounds or solvates thereof.

31) The compounds according to 28), 29) or 30) wherein $R^3$ is a $C_{2-14}$ aryl group (the $C_{2-14}$ aryl group may be optionally substituted with one or more substituents selected from the group consisting of: a hydroxyl group, an amino group, a carboxyl group, a phosphonic acid group, a sulfonic acid group, a carbamido group, a sulfamido group, a hydroxycarbamido group, a hydroxysulfamido group, a tetrazole group, a nitro group, a cyano group, a halogen atom, a $C_{1-10}$ alkyl group substituted with one or more fluorine atoms, a sulfamido group substituted with one or more $C_{1-10}$ alkyl groups, a carbamido group substituted with one or more $C_{1-10}$ alkyl groups, a $C_{1-10}$ alkoxycarbonyl group, a $C_{1-10}$ alkoxy group, a $C_{1-10}$ alkyl group, a $C_{1-10}$ alkylcarbonyl group, a $C_{1-10}$ alkylcarbonyloxy group, a $C_{1-10}$ alkylcarbonylamino group and a mono- or di-$C_{1-10}$ alkylamino group (the $C_{1-10}$ alkoxycarbonyl group, the $C_{1-10}$ alkoxy group, the $C_{1-10}$ alkyl group, the $C_{1-10}$ alkylcarbonyl group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of: a hydroxyl group, an amino group, a mono- or di-$C_{1-10}$ alkylamino group, a carboxyl group, a nitro group, a cyano group and a halogen atom)), tautomers, prodrugs or pharmaceutically acceptable salts of the compounds or solvates thereof.

32) The compounds according to 28), 29) or 30) wherein $R^3$ is a phenyl group, a thienyl, a furyl group, a pyridazinyl group, a pyridyl group, a quinolyl group or an isoquinolyl group (the phenyl group, the thienyl, the furyl group, the pyridazinyl group, the pyridyl group, the quinolyl group and the isoquinolyl group may be optionally substituted with one or more substituents selected from the group consisting of: a hydroxyl group, an amino group, a carboxyl group, a phosphonic acid group, a sulfonic acid group, a carbamido group, a sulfamido group, a hydroxycarbamido group, a hydroxysulfamido group, a tetrazole group, a nitro group, a cyano group, a halogen atom, a $C_{1-10}$ alkyl group substituted with one or more fluorine atoms, a sulfamido group substituted with one or more $C_{1-10}$ alkyl groups, a carbamido group substituted with one or more $C_{1-10}$ alkyl groups, a $C_{1-10}$ alkoxycarbonyl group, a $C_{1-10}$ alkoxy group, a $C_{1-10}$ alkyl group, a $C_{1-10}$ alkylcarbonyl group, a $C_{1-10}$ alkylcarbonyloxy group, a $C_{1-10}$ alkylcarbonylamino group and a mono- or di-$C_{1-10}$ alkylamino group (the $C_{1-10}$ alkoxycarbonyl group, the $C_{1-10}$ alkoxy group, the $C_{1-10}$ alkyl group, the $C_{1-10}$ alkylcarbonyl group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of: a hydroxyl group, an amino group, a mono- or di-$C_{1-10}$ alkylamino group, a carboxyl group, a nitro group, a cyano group and a halogen atom)), tautomers, prodrugs or pharmaceutically acceptable salts of the compounds or solvates thereof.

33) The compounds according to 28), 29) or 30) wherein $R^3$ is a phenyl group (the phenyl group may be optionally substituted with one or more substituents selected from the group consisting of: a hydroxyl group, an amino group, a carboxyl group, a phosphonic acid group, a sulfonic acid group, a carbamido group, a sulfamido group, a hydroxycarbamido group, hydroxysulfamido group, a tetrazole group, a nitro group, a cyano group, a halogen atom, a $C_{2-10}$ alkyl group substituted with one or more fluorine atoms, a sulfamido group substituted with one or more $C_{1-10}$ alkyl groups, a carbamido group substituted with one or more $C_{1-10}$ alkyl groups, a $C_{1-10}$ alkoxycarbonyl group, a $C_{1-10}$ alkoxy group, a $C_{1-10}$ alkyl group, a $C_{1-10}$ alkylcarbonyl group, a $C_{1-10}$ alkylcarbonyloxy group, $C_{1-10}$ alkylcarbonylamino group and a mono- or di-$C_{1-10}$ alkylamino group (the $C_{1-10}$ alkoxycarbonyl group, the $C_{1-10}$ alkoxy group, the $C_{1-10}$ alkyl group, the $C_{1-10}$ alkylcarbonyl group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of: a hydroxyl group, an amino group, a mono- or di-$C_{1-10}$ alkylamino group, a carboxyl group, a nitro group, a cyano group and a halogen atom)), tautomers, prodrugs or pharmaceutically acceptable salts of the compounds or solvates thereof.

34) The compounds according to 28), 29) or 30) wherein $R^3$ is a phenyl group, a thienyl, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of: a carboxyl group, a phosphonic acid group, a sulfonic acid group, a carbamido group, a sulfamido group, a hydroxycarbamido group, a hydroxysulfamido group, a tetrazole group, a nitro group, a cyano group, a halogen atom, a $C_{1-10}$ alkyl group substituted with one or more fluorine atoms, a sulfamido group substituted with one or more $C_{1-10}$ alkyl groups, a carbamido group substituted with one or more $C_{1-10}$ alkyl groups and a $C_{1-10}$ alkylcarbonylamino group), tautomers, prodrugs or pharmaceutically acceptable salts of the compounds or solvates thereof.

35) The compounds according to 28), 29) or 30) wherein $R^3$ is a phenyl group (the phenyl group is optionally substituted with a carboxyl group, a phosphonic acid group, a sulfonic acid group, a carbamido group, a sulfamido group, a hydroxycarbamido group, a hydroxysulfamido group or a tetrazole group), tautomers, prodrugs or pharmaceutically acceptable salts of the compounds or solvates thereof.

36) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with a carboxyl group, a phosphonic acid group, a sulfonic acid group or a tetrazole group), tautomers, prodrugs or pharmaceutically acceptable salts of the compounds or solvates thereof.

37) The compounds according to 28), 29) or 30) wherein $R^3$ is a phenyl group (the phenyl group is optionally substituted with a carboxyl group, a phosphonic acid group, a sulfonic acid group or a tetrazole group), tautomers, prodrugs or pharmaceutically acceptable salts of the compounds or solvates thereof.

38) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with a carboxyl group), tautomers, prodrugs or pharmaceutically acceptable salts of the compounds or solvates thereof.

39) The compounds according to 28), 29) or 30) wherein $R^3$ is a phenyl group substituted with a carboxyl group, tautomers, prodrugs or pharmaceutically acceptable salts of the compounds or solvates thereof.

40) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with a sulfonic acid group), tautomers, prodrugs or pharmaceutically acceptable salts of the compounds or solvates thereof.

41) The compounds according to 28), 29) or 30) wherein $R^3$ is a phenyl group substituted with a sulfonic acid group, tautomers, prodrugs or pharmaceutically acceptable salts of the compounds or solvates thereof.

42) The compounds according to 28), 29) or 30) wherein $R^3$ is a phenyl group, a pyridyl group, a thienyl group, a furyl group, a pyridazinyl group, a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group, a 1,2-thiazole group, a quinolyl group or an isoquinolyl group (the phenyl group, the pyridyl group, the thienyl group, the furyl group, the pyridazinyl group, the 1,3,4-oxadiazole group, the 1,3,4-thiadiazole group, the 1,2,4-oxadiazole group, the 1,2,4-thiadiazole group, the 1,2,5-oxadiazole group, the 1,2,5-thiadiazole group, the 1,2-oxazole group, the 1,2-thiazole group, the quinolyl group and the isoquinolyl group are optionally substituted with one or more hydroxyl groups), tautomers, prodrugs or pharmaceutically acceptable salts of the compounds or solvates thereof.

43) The compounds according to 28), 29) or 30) wherein $R^3$ is a phenyl group, a pyridyl group, a thienyl group, a furyl group, a pyridazinyl group, a quinolyl group or an isoquinolyl group (the phenyl group, the pyridyl group, the thienyl group, the furyl group, the pyridazinyl group, the quinolyl group and the isoquinolyl group are optionally substituted with an azole group optionally substituted with one or more hydroxyl groups (the azole group is a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group or a 1,2-thiazole group)), tautomers, prodrugs or pharmaceutically acceptable salts of the compounds or solvates thereof.

44) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more —CH$_2$CO$_2$H groups), tautomers, prodrugs or pharmaceutically acceptable salts of the compounds or solvates thereof.

45) The compounds according to 28), 29) or 30) wherein $R^3$ is a phenyl group substituted with one or more —CH$_2$CO$_2$H groups, tautomers, prodrugs or pharmaceutically acceptable salts of the compounds or solvates thereof.

46) The compounds according to 28), 29) or 30) wherein $R^3$ is a phenyl group, a thienyl group, a furyl group, a pyridazinyl group, a pyridyl group, a quinolyl group or an isoquinolyl group, (the phenyl group, the thienyl group, the furyl group, the pyridazinyl group, the pyridyl group, the quinolyl group and the isoquinolyl group are substituted with one or more —OCH$_2$CO$_2$H groups), tautomers, prodrugs or pharmaceutically acceptable salts of the compounds or solvates thereof.

47) The compounds according to 28), 29) or 30) wherein $R^3$ is a phenyl group substituted with one or more —OCH$_2$CO$_2$H groups, tautomers, prodrugs or pharmaceutically acceptable salts of the compounds or solvates thereof.

48) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with one or more —NHCH$_2$CO$_2$H groups), tautomers, prodrugs or pharmaceutically acceptable salts of the compounds or solvates thereof.

49) The compounds according to 28), 29) or 30) wherein $R^3$ is a phenyl group substituted with one or more —NHCH$_2$CO$_2$H groups, tautomers, prodrugs or pharmaceutically acceptable salts of the compounds or solvates thereof.

50) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with one or more —CH$_2$CH$_2$CO$_2$H groups), tautomers, prodrugs or pharmaceutically acceptable salts of the compounds or solvates thereof.

51) The compounds according to 28), 29) or 30) wherein $R^3$ is a phenyl group substituted with one or more —CH$_2$CH$_2$CO$_2$H groups, tautomers, prodrugs or pharmaceutically acceptable salts of the compounds or solvates thereof.

52) The compounds according to 28), 29) or 30) wherein $R^3$ is a phenyl group (the phenyl group is optionally substituted with one or more substituents optionally selected from the group consisting of:

a carboxyl group, a phosphonic acid group, a sulfonic acid group, a carbamido group, a sulfamido group, a hydroxycarbamido group, a hydroxysulfamido group and a tetrazole group and a substituent optionally selected from the group consisting of:

a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

53) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with one or more substituents selected from the group consisting of:

a carboxyl group, a phosphonic acid group, a sulfonic acid group and a tetrazole group and one or more substituents optionally selected from the group consisting of:

a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

54) The compounds according to 28), 29) or 30) wherein $R^3$ is a phenyl group (the phenyl group is optionally substituted with one or more substituents selected from the group consisting of:

a carboxyl group, a phosphonic acid group, a sulfonic acid group and a tetrazole group and one or more substituents optionally selected from the group consisting of:

a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

55) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with a carboxyl group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

56) The compounds according to 28), 29) or 30) wherein $R^3$ is a phenyl group substituted with a carboxyl group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group, tautomers, prodrugs or pharmaceutically acceptable salts of the compounds or solvates thereof.

57) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with a sulfonic acid group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

58) The compounds according to 28), 29) or 30) wherein $R^3$ is a phenyl group substituted with a sulfonic acid group and a substituent optionally selected from a nitro group, a cyano group, a halogen atom, a $C_{1-10}$ alkyl group substituted with one or more fluorine atoms, sulfamido group substituted with one or two $C_{1-10}$ alkyl groups, a carbamido group substituted with one or two $C_{1-10}$ alkyl groups and a $C_{1-10}$ alkylcarbonylamino group, tautomers, prodrugs or pharmaceutically acceptable salts of the compounds or solvates thereof.

59) The compounds according to 28), 29) or 30) wherein $R^3$ is a phenyl group, a pyridyl group, a thienyl group, a furyl group, a pyridazinyl group, a quinolyl group or an isoquinolyl group (the phenyl group, the pyridyl group, the thienyl group, the furyl group, the pyridazinyl group, the quinolyl group and the isoquinolyl group are optionally substituted with one or more hydroxyl groups and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

60) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are optionally substituted with a —$CH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

61) The compounds according to 28), 29) or 30) wherein $R^3$ is a phenyl group substituted with a —$CH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, carbamido group substituted with one or two $C_{1-10}$ alkyl groups and a $C_{1-10}$ alkylcarbonylamino group, tautomers, prodrugs or pharmaceutically acceptable salts of the compounds or solvates thereof.

62) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with a —$OCH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

63) The compounds according to 28), 29) or 30) wherein $R^3$ is a phenyl group substituted with a —$OCH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group, tautomers, prodrugs or pharmaceutically acceptable salts of the compounds or solvates thereof.

64) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with a —$NHCH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

65) The compounds according to 28), 29) or 30) wherein $R^3$ is a phenyl group substituted with a —$NHCH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group, tautomers, prodrugs or pharmaceutically acceptable salts of the compounds or solvates thereof.

66) The compounds according to 28), 29) or 30) wherein $R^3$ is a phenyl group, a thienyl group, a furyl group, a pyridazinyl group, a pyridyl group, a quinolyl group or an isoquinolyl group (the phenyl group, the thienyl group, the furyl group, the pyridazinyl group, the pyridyl group, the quinolyl group and the isoquinolyl group are substituted with a —$CH_2CH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers, prodrugs or pharmaceutically acceptable salts of the compounds or solvates thereof.

67) The compounds according to 28), 29) or 30) wherein $R^3$ is a phenyl group substituted with a —$CH_2CH_2CO_2H$ group and a substituent optionally selected from a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group, tautomers, prodrugs or pharmaceutically acceptable salts of the compounds or solvates thereof.

68) The compounds wherein A, B, $R^1$, $L^1$, $R^2$, $L^2$, $L^3$, $L^4$, $R^3$ and X are any of the following combinations in Table 1, tautomers, prodrugs or pharmaceutically acceptable salts of the compounds or solvates thereof.

The symbols in Table 1 denote the flowing substituents.

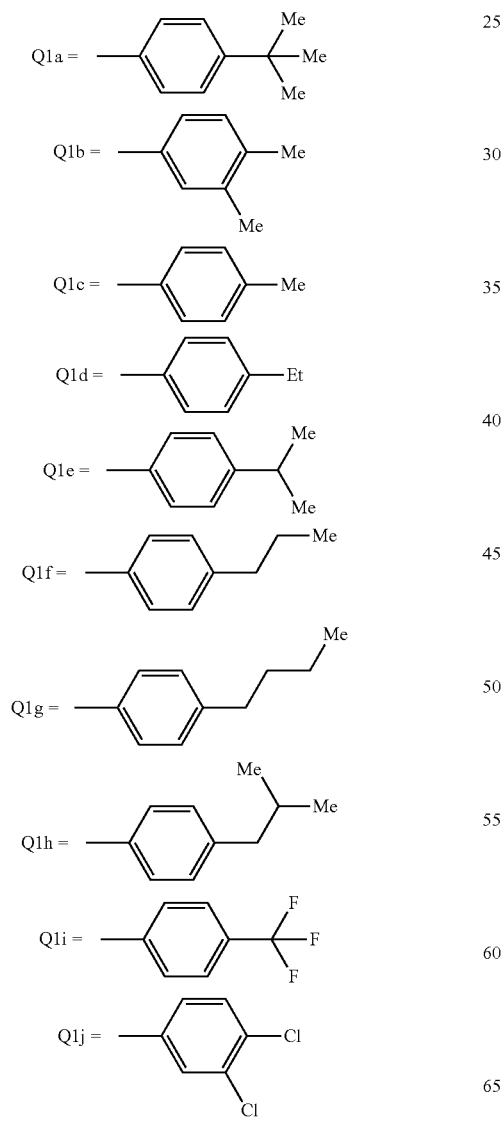

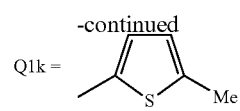
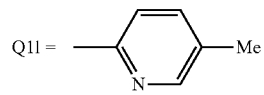
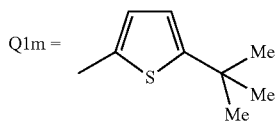
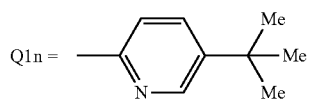
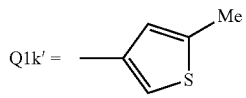
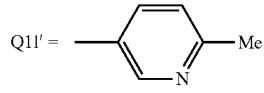
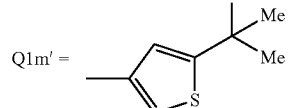
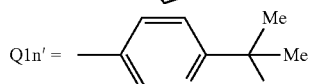
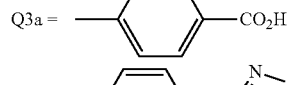
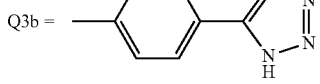
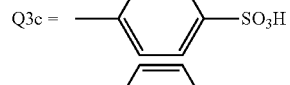
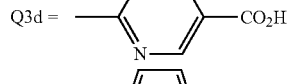
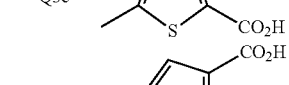
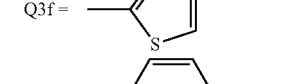
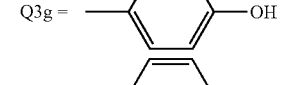
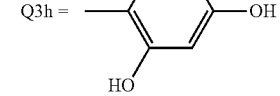

TABLE 1

| No | A | B | R¹ | L¹ | R² | L² | L³ | Y | L⁴ | R³ | X |
|---|---|---|---|---|---|---|---|---|---|---|---|
| 1 | N | NMe | Q1a | a bond | Me | a bond | NH | S | NH | Q3a | OH |
| 2 | N | NMe | Q1a | a bond | Me | a bond | NH | S | NH | Q3b | OH |
| 3 | N | NMe | Q1a | a bond | Me | a bond | NH | S | NH | Q3c | OH |
| 4 | N | NMe | Q1a | a bond | Me | a bond | NH | S | a bond | Q3a | OH |
| 5 | N | NMe | Q1a | a bond | Me | a bond | NH | S | a bond | Q3b | OH |
| 6 | N | NMe | Q1a | a bond | Me | a bond | NH | S | a bond | Q3c | OH |
| 7 | N | NMe | Q1a | a bond | Me | a bond | NH | O | NH | Q3a | OH |
| 8 | N | NMe | Q1a | a bond | Me | a bond | NH | O | NH | Q3b | OH |
| 9 | N | NMe | Q1a | a bond | Me | a bond | NH | O | NH | Q3c | OH |
| 10 | N | NMe | Q1a | a bond | Me | a bond | NH | O | a bond | Q3a | OH |
| 11 | N | NMe | Q1a | a bond | Me | a bond | NH | O | a bond | Q3b | OH |
| 12 | N | NMe | Q1a | a bond | Me | a bond | NH | O | a bond | Q3c | OH |
| 13 | N | NMe | Q1a | a bond | H | a bond | NH | S | NH | Q3a | OH |
| 14 | N | NMe | Q1a | a bond | H | a bond | NH | S | NH | Q3b | OH |
| 15 | N | NMe | Q1a | a bond | H | a bond | NH | S | NH | Q3c | OH |
| 16 | N | NMe | Q1a | a bond | H | a bond | NH | S | a bond | Q3a | OH |
| 17 | N | NMe | Q1a | a bond | H | a bond | NH | S | a bond | Q3b | OH |
| 18 | N | NMe | Q1a | a bond | H | a bond | NH | S | a bond | Q3c | OH |
| 19 | N | NMe | Q1a | a bond | H | a bond | NH | O | NH | Q3a | OH |
| 20 | N | NMe | Q1a | a bond | H | a bond | NH | O | NH | Q3b | OH |
| 21 | N | NMe | Q1a | a bond | H | a bond | NH | O | NH | Q3c | OH |
| 22 | N | NMe | Q1a | a bond | H | a bond | NH | O | a bond | Q3a | OH |
| 23 | N | NMe | Q1a | a bond | H | a bond | NH | O | a bond | Q3b | OH |
| 24 | N | NMe | Q1a | a bond | H | a bond | NH | O | a bond | Q3c | OH |
| 25 | N | NMe | Q1b | a bond | Me | a bond | NH | S | NH | Q3a | OH |
| 26 | N | NMe | Q1b | a bond | Me | a bond | NH | S | NH | Q3b | OH |
| 27 | N | NMe | Q1b | a bond | Me | a bond | NH | S | NH | Q3c | OH |
| 28 | N | NMe | Q1b | a bond | Me | a bond | NH | S | a bond | Q3a | OH |
| 29 | N | NMe | Q1b | a bond | Me | a bond | NH | S | a bond | Q3b | OH |
| 30 | N | NMe | Q1b | a bond | Me | a bond | NH | S | a bond | Q3c | OH |
| 31 | N | NMe | Q1b | a bond | Me | a bond | NH | O | NH | Q3a | OH |
| 32 | N | NMe | Q1b | a bond | Me | a bond | NH | O | NH | Q3b | OH |
| 33 | N | NMe | Q1b | a bond | Me | a bond | NH | O | NH | Q3c | OH |
| 34 | N | NMe | Q1b | a bond | Me | a bond | NH | O | a bond | Q3a | OH |
| 35 | N | NMe | Q1b | a bond | Me | a bond | NH | O | a bond | Q3b | OH |
| 36 | N | NMe | Q1b | a bond | Me | a bond | NH | O | a bond | Q3c | OH |
| 37 | N | NMe | Q1b | a bond | H | a bond | NH | S | NH | Q3a | OH |
| 38 | N | NMe | Q1b | a bond | H | a bond | NH | S | NH | Q3b | OH |
| 39 | N | NMe | Q1b | a bond | H | a bond | NH | S | NH | Q3c | OH |
| 40 | N | NMe | Q1b | a bond | H | a bond | NH | S | a bond | Q3a | OH |
| 41 | N | NMe | Q1b | a bond | H | a bond | NH | S | a bond | Q3b | OH |
| 42 | N | NMe | Q1b | a bond | H | a bond | NH | S | a bond | Q3c | OH |
| 43 | N | NMe | Q1b | a bond | H | a bond | NH | O | NH | Q3a | OH |
| 44 | N | NMe | Q1b | a bond | H | a bond | NH | O | NH | Q3b | OH |
| 45 | N | NMe | Q1b | a bond | H | a bond | NH | O | NH | Q3c | OH |
| 46 | N | NMe | Q1b | a bond | H | a bond | NH | O | a bond | Q3a | OH |
| 47 | N | NMe | Q1b | a bond | H | a bond | NH | O | a bond | Q3b | OH |
| 48 | N | NMe | Q1b | a bond | H | a bond | NH | O | a bond | Q3c | OH |
| 49 | N | NMe | Q1c | a bond | Me | a bond | NH | S | NH | Q3a | OH |
| 50 | N | NMe | Q1c | a bond | Me | a bond | NH | S | NH | Q3b | OH |
| 51 | N | NMe | Q1c | a bond | Me | a bond | NH | S | NH | Q3c | OH |
| 52 | N | NMe | Q1c | a bond | Me | a bond | NH | S | a bond | Q3a | OH |
| 53 | N | NMe | Q1c | a bond | Me | a bond | NH | S | a bond | Q3b | OH |
| 54 | N | NMe | Q1c | a bond | Me | a bond | NH | S | a bond | Q3c | OH |
| 55 | N | NMe | Q1c | a bond | Me | a bond | NH | O | NH | Q3a | OH |
| 56 | N | NMe | Q1c | a bond | Me | a bond | NH | O | NH | Q3b | OH |
| 57 | N | NMe | Q1c | a bond | Me | a bond | NH | O | NH | Q3c | OH |
| 58 | N | NMe | Q1c | a bond | Me | a bond | NH | O | a bond | Q3a | OH |
| 59 | N | NMe | Q1c | a bond | Me | a bond | NH | O | a bond | Q3b | OH |
| 60 | N | NMe | Q1c | a bond | Me | a bond | NH | O | a bond | Q3c | OH |
| 61 | N | NMe | Q1c | a bond | H | a bond | NH | S | NH | Q3a | OH |
| 62 | N | NMe | Q1c | a bond | H | a bond | NH | S | NH | Q3b | OH |
| 63 | N | NMe | Q1c | a bond | H | a bond | NH | S | NH | Q3c | OH |
| 64 | N | NMe | Q1c | a bond | H | a bond | NH | S | a bond | Q3a | OH |
| 65 | N | NMe | Q1c | a bond | H | a bond | NH | S | a bond | Q3b | OH |
| 66 | N | NMe | Q1c | a bond | H | a bond | NH | S | a bond | Q3c | OH |
| 67 | N | NMe | Q1c | a bond | H | a bond | NH | O | NH | Q3a | OH |
| 68 | N | NMe | Q1c | a bond | H | a bond | NH | O | NH | Q3b | OH |
| 69 | N | NMe | Q1c | a bond | H | a bond | NH | O | NH | Q3c | OH |
| 70 | N | NMe | Q1c | a bond | H | a bond | NH | O | a bond | Q3a | OH |
| 71 | N | NMe | Q1c | a bond | H | a bond | NH | O | a bond | Q3b | OH |
| 72 | N | NMe | Q1c | a bond | H | a bond | NH | O | a bond | Q3c | OH |
| 73 | N | NMe | Q1d | a bond | Me | a bond | NH | S | NH | Q3a | OH |
| 74 | N | NMe | Q1d | a bond | Me | a bond | NH | S | NH | Q3b | OH |
| 75 | N | NMe | Q1d | a bond | Me | a bond | NH | S | NH | Q3c | OH |
| 76 | N | NMe | Q1d | a bond | Me | a bond | NH | S | a bond | Q3a | OH |
| 77 | N | NMe | Q1d | a bond | Me | a bond | NH | S | a bond | Q3b | OH |
| 78 | N | NMe | Q1d | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 79 | N | NMe | Q1d | a bond | Me | a bond | NH | O | NH | Q3a | OH |
| 80 | N | NMe | Q1d | a bond | Me | a bond | NH | O | NH | Q3b | OH |
| 81 | N | NMe | Q1d | a bond | Me | a bond | NH | O | NH | Q3c | OH |
| 82 | N | NMe | Q1d | a bond | Me | a bond | NH | O | a bond | Q3a | OH |
| 83 | N | NMe | Q1d | a bond | Me | a bond | NH | O | a bond | Q3b | OH |
| 84 | N | NMe | Q1d | a bond | Me | a bond | NH | O | a bond | Q3c | OH |
| 85 | N | NMe | Q1d | a bond | H | a bond | NH | S | NH | Q3a | OH |
| 86 | N | NMe | Q1d | a bond | H | a bond | NH | S | NH | Q3b | OH |
| 87 | N | NMe | Q1d | a bond | H | a bond | NH | S | NH | Q3c | OH |
| 88 | N | NMe | Q1d | a bond | H | a bond | NH | S | a bond | Q3a | OH |
| 89 | N | NMe | Q1d | a bond | H | a bond | NH | S | a bond | Q3b | OH |
| 90 | N | NMe | Q1d | a bond | H | a bond | NH | S | a bond | Q3c | OH |
| 91 | N | NMe | Q1d | a bond | H | a bond | NH | O | NH | Q3a | OH |
| 92 | N | NMe | Q1d | a bond | H | a bond | NH | O | NH | Q3b | OH |
| 93 | N | NMe | Q1d | a bond | H | a bond | NH | O | NH | Q3c | OH |
| 94 | N | NMe | Q1d | a bond | H | a bond | NH | O | a bond | Q3a | OH |
| 95 | N | NMe | Q1d | a bond | H | a bond | NH | O | a bond | Q3b | OH |
| 96 | N | NMe | Q1d | a bond | H | a bond | NH | O | a bond | Q3c | OH |
| 97 | N | NMe | Q1e | a bond | Me | a bond | NH | S | NH | Q3a | OH |
| 98 | N | NMe | Q1e | a bond | Me | a bond | NH | S | NH | Q3b | OH |
| 99 | N | NMe | Q1e | a bond | Me | a bond | NH | S | NH | Q3c | OH |
| 100 | N | NMe | Q1e | a bond | Me | a bond | NH | S | a bond | Q3a | OH |
| 101 | N | NMe | Q1e | a bond | Me | a bond | NH | S | a bond | Q3b | OH |
| 102 | N | NMe | Q1e | a bond | Me | a bond | NH | S | a bond | Q3c | OH |
| 103 | N | NMe | Q1e | a bond | Me | a bond | NH | O | NH | Q3a | OH |
| 104 | N | NMe | Q1e | a bond | Me | a bond | NH | O | NH | Q3b | OH |
| 105 | N | NMe | Q1e | a bond | Me | a bond | NH | O | NH | Q3c | OH |
| 106 | N | NMe | Q1e | a bond | Me | a bond | NH | O | a bond | Q3a | OH |
| 107 | N | NMe | Q1e | a bond | Me | a bond | NH | O | a bond | Q3b | OH |
| 108 | N | NMe | Q1e | a bond | Me | a bond | NH | O | a bond | Q3c | OH |
| 109 | N | NMe | Q1e | a bond | H | a bond | NH | S | NH | Q3a | OH |
| 110 | N | NMe | Q1e | a bond | H | a bond | NH | S | NH | Q3b | OH |
| 111 | N | NMe | Q1e | a bond | H | a bond | NH | S | NH | Q3c | OH |
| 112 | N | NMe | Q1e | a bond | H | a bond | NH | S | a bond | Q3a | OH |
| 113 | N | NMe | Q1e | a bond | H | a bond | NH | S | a bond | Q3b | OH |
| 114 | N | NMe | Q1e | a bond | H | a bond | NH | S | a bond | Q3c | OH |
| 115 | N | NMe | Q1e | a bond | H | a bond | NH | O | NH | Q3a | OH |
| 116 | N | NMe | Q1e | a bond | H | a bond | NH | O | NH | Q3b | OH |
| 117 | N | NMe | Q1e | a bond | H | a bond | NH | O | NH | Q3c | OH |
| 118 | N | NMe | Q1e | a bond | H | a bond | NH | O | a bond | Q3a | OH |
| 119 | N | NMe | Q1e | a bond | H | a bond | NH | O | a bond | Q3b | OH |
| 120 | N | NMe | Q1e | a bond | H | a bond | NH | O | a bond | Q3c | OH |
| 121 | N | NMe | Q1f | a bond | Me | a bond | NH | S | NH | Q3a | OH |
| 122 | N | NMe | Q1f | a bond | Me | a bond | NH | S | NH | Q3b | OH |
| 123 | N | NMe | Q1f | a bond | Me | a bond | NH | S | NH | Q3c | OH |
| 124 | N | NMe | Q1f | a bond | Me | a bond | NH | S | a bond | Q3a | OH |
| 125 | N | NMe | Q1f | a bond | Me | a bond | NH | S | a bond | Q3b | OH |
| 126 | N | NMe | Q1f | a bond | Me | a bond | NH | S | a bond | Q3c | OH |
| 127 | N | NMe | Q1f | a bond | Me | a bond | NH | O | NH | Q3a | OH |
| 128 | N | NMe | Q1f | a bond | Me | a bond | NH | O | NH | Q3b | OH |
| 129 | N | NMe | Q1f | a bond | Me | a bond | NH | O | NH | Q3c | OH |
| 130 | N | NMe | Q1f | a bond | Me | a bond | NH | O | a bond | Q3a | OH |
| 131 | N | NMe | Q1f | a bond | Me | a bond | NH | O | a bond | Q3b | OH |
| 132 | N | NMe | Q1f | a bond | Me | a bond | NH | O | a bond | Q3c | OH |
| 133 | N | NMe | Q1f | a bond | H | a bond | NH | S | NH | Q3a | OH |
| 134 | N | NMe | Q1f | a bond | H | a bond | NH | S | NH | Q3b | OH |
| 135 | N | NMe | Q1f | a bond | H | a bond | NH | S | NH | Q3c | OH |
| 136 | N | NMe | Q1f | a bond | H | a bond | NH | S | a bond | Q3a | OH |
| 137 | N | NMe | Q1f | a bond | H | a bond | NH | S | a bond | Q3b | OH |
| 138 | N | NMe | Q1f | a bond | H | a bond | NH | S | a bond | Q3c | OH |
| 139 | N | NMe | Q1f | a bond | H | a bond | NH | O | NH | Q3a | OH |
| 140 | N | NMe | Q1f | a bond | H | a bond | NH | O | NH | Q3b | OH |
| 141 | N | NMe | Q1f | a bond | H | a bond | NH | O | NH | Q3c | OH |
| 142 | N | NMe | Q1f | a bond | H | a bond | NH | O | a bond | Q3a | OH |
| 143 | N | NMe | Q1f | a bond | H | a bond | NH | O | a bond | Q3b | OH |
| 144 | N | NMe | Q1f | a bond | H | a bond | NH | O | a bond | Q3c | OH |
| 145 | N | NMe | Q1g | a bond | Me | a bond | NH | S | NH | Q3a | OH |
| 146 | N | NMe | Q1g | a bond | Me | a bond | NH | S | NH | Q3b | OH |
| 147 | N | NMe | Q1g | a bond | Me | a bond | NH | S | NH | Q3c | OH |
| 148 | N | NMe | Q1g | a bond | Me | a bond | NH | S | a bond | Q3a | OH |
| 149 | N | NMe | Q1g | a bond | Me | a bond | NH | S | a bond | Q3b | OH |
| 150 | N | NMe | Q1g | a bond | Me | a bond | NH | S | a bond | Q3c | OH |
| 151 | N | NMe | Q1g | a bond | Me | a bond | NH | O | NH | Q3a | OH |
| 152 | N | NMe | Q1g | a bond | Me | a bond | NH | O | NH | Q3b | OH |
| 153 | N | NMe | Q1g | a bond | Me | a bond | NH | O | NH | Q3c | OH |
| 154 | N | NMe | Q1g | a bond | Me | a bond | NH | O | a bond | Q3a | OH |
| 155 | N | NMe | Q1g | a bond | Me | a bond | NH | O | a bond | Q3b | OH |
| 156 | N | NMe | Q1g | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 157 | N | NMe | Q1g | a bond | H | a bond | NH | S | NH | Q3a | OH |
| 158 | N | NMe | Q1g | a bond | H | a bond | NH | S | NH | Q3b | OH |
| 159 | N | NMe | Q1g | a bond | H | a bond | NH | S | NH | Q3c | OH |
| 160 | N | NMe | Q1g | a bond | H | a bond | NH | S | a bond | Q3a | OH |
| 161 | N | NMe | Q1g | a bond | H | a bond | NH | S | a bond | Q3b | OH |
| 162 | N | NMe | Q1g | a bond | H | a bond | NH | S | a bond | Q3c | OH |
| 163 | N | NMe | Q1g | a bond | H | a bond | NH | O | NH | Q3a | OH |
| 164 | N | NMe | Q1g | a bond | H | a bond | NH | O | NH | Q3b | OH |
| 165 | N | NMe | Q1g | a bond | H | a bond | NH | O | NH | Q3c | OH |
| 166 | N | NMe | Q1g | a bond | H | a bond | NH | O | a bond | Q3a | OH |
| 167 | N | NMe | Q1g | a bond | H | a bond | NH | O | a bond | Q3b | OH |
| 168 | N | NMe | Q1g | a bond | H | a bond | NH | O | a bond | Q3c | OH |
| 169 | N | NMe | Q1h | a bond | Me | a bond | NH | S | NH | Q3a | OH |
| 170 | N | NMe | Q1h | a bond | Me | a bond | NH | S | NH | Q3b | OH |
| 171 | N | NMe | Q1h | a bond | Me | a bond | NH | S | NH | Q3c | OH |
| 172 | N | NMe | Q1h | a bond | Me | a bond | NH | S | a bond | Q3a | OH |
| 173 | N | NMe | Q1h | a bond | Me | a bond | NH | S | a bond | Q3b | OH |
| 174 | N | NMe | Q1h | a bond | Me | a bond | NH | S | a bond | Q3c | OH |
| 175 | N | NMe | Q1h | a bond | Me | a bond | NH | O | NH | Q3a | OH |
| 176 | N | NMe | Q1h | a bond | Me | a bond | NH | O | NH | Q3b | OH |
| 177 | N | NMe | Q1h | a bond | Me | a bond | NH | O | NH | Q3c | OH |
| 178 | N | NMe | Q1h | a bond | Me | a bond | NH | O | a bond | Q3a | OH |
| 179 | N | NMe | Q1h | a bond | Me | a bond | NH | O | a bond | Q3b | OH |
| 180 | N | NMe | Q1h | a bond | Me | a bond | NH | O | a bond | Q3c | OH |
| 181 | N | NMe | Q1h | a bond | H | a bond | NH | S | NH | Q3a | OH |
| 182 | N | NMe | Q1h | a bond | H | a bond | NH | S | NH | Q3b | OH |
| 183 | N | NMe | Q1h | a bond | H | a bond | NH | S | NH | Q3c | OH |
| 184 | N | NMe | Q1h | a bond | H | a bond | NH | S | a bond | Q3a | OH |
| 185 | N | NMe | Q1h | a bond | H | a bond | NH | S | a bond | Q3b | OH |
| 186 | N | NMe | Q1h | a bond | H | a bond | NH | S | a bond | Q3c | OH |
| 187 | N | NMe | Q1h | a bond | H | a bond | NH | O | NH | Q3a | OH |
| 188 | N | NMe | Q1h | a bond | H | a bond | NH | O | NH | Q3b | OH |
| 189 | N | NMe | Q1h | a bond | H | a bond | NH | O | NH | Q3c | OH |
| 190 | N | NMe | Q1h | a bond | H | a bond | NH | O | a bond | Q3a | OH |
| 191 | N | NMe | Q1h | a bond | H | a bond | NH | O | a bond | Q3b | OH |
| 192 | N | NMe | Q1h | a bond | H | a bond | NH | O | a bond | Q3c | OH |
| 193 | N | NMe | Q1i | a bond | Me | a bond | NH | S | NH | Q3a | OH |
| 194 | N | NMe | Q1i | a bond | Me | a bond | NH | S | NH | Q3b | OH |
| 195 | N | NMe | Q1i | a bond | Me | a bond | NH | S | NH | Q3c | OH |
| 196 | N | NMe | Q1i | a bond | Me | a bond | NH | S | a bond | Q3a | OH |
| 197 | N | NMe | Q1i | a bond | Me | a bond | NH | S | a bond | Q3b | OH |
| 198 | N | NMe | Q1i | a bond | Me | a bond | NH | S | a bond | Q3c | OH |
| 199 | N | NMe | Q1i | a bond | Me | a bond | NH | O | NH | Q3a | OH |
| 200 | N | NMe | Q1i | a bond | Me | a bond | NH | O | NH | Q3b | OH |
| 201 | N | NMe | Q1i | a bond | Me | a bond | NH | O | NH | Q3c | OH |
| 202 | N | NMe | Q1i | a bond | Me | a bond | NH | O | a bond | Q3a | OH |
| 203 | N | NMe | Q1i | a bond | Me | a bond | NH | O | a bond | Q3b | OH |
| 204 | N | NMe | Q1i | a bond | Me | a bond | NH | O | a bond | Q3c | OH |
| 205 | N | NMe | Q1i | a bond | H | a bond | NH | S | NH | Q3a | OH |
| 206 | N | NMe | Q1i | a bond | H | a bond | NH | S | NH | Q3b | OH |
| 207 | N | NMe | Q1i | a bond | H | a bond | NH | S | NH | Q3c | OH |
| 208 | N | NMe | Q1i | a bond | H | a bond | NH | S | a bond | Q3a | OH |
| 209 | N | NMe | Q1i | a bond | H | a bond | NH | S | a bond | Q3b | OH |
| 210 | N | NMe | Q1i | a bond | H | a bond | NH | S | a bond | Q3c | OH |
| 211 | N | NMe | Q1i | a bond | H | a bond | NH | O | NH | Q3a | OH |
| 212 | N | NMe | Q1i | a bond | H | a bond | NH | O | NH | Q3b | OH |
| 213 | N | NMe | Q1i | a bond | H | a bond | NH | O | NH | Q3c | OH |
| 214 | N | NMe | Q1i | a bond | H | a bond | NH | O | a bond | Q3a | OH |
| 215 | N | NMe | Q1i | a bond | H | a bond | NH | O | a bond | Q3b | OH |
| 216 | N | NMe | Q1i | a bond | H | a bond | NH | O | a bond | Q3c | OH |
| 217 | N | NMe | Q1j | a bond | Me | a bond | NH | S | NH | Q3a | OH |
| 218 | N | NMe | Q1j | a bond | Me | a bond | NH | S | NH | Q3b | OH |
| 219 | N | NMe | Q1j | a bond | Me | a bond | NH | S | NH | Q3c | OH |
| 220 | N | NMe | Q1j | a bond | Me | a bond | NH | S | a bond | Q3a | OH |
| 221 | N | NMe | Q1j | a bond | Me | a bond | NH | S | a bond | Q3b | OH |
| 222 | N | NMe | Q1j | a bond | Me | a bond | NH | S | a bond | Q3c | OH |
| 223 | N | NMe | Q1j | a bond | Me | a bond | NH | O | NH | Q3a | OH |
| 224 | N | NMe | Q1j | a bond | Me | a bond | NH | O | NH | Q3b | OH |
| 225 | N | NMe | Q1j | a bond | Me | a bond | NH | O | NH | Q3c | OH |
| 226 | N | NMe | Q1j | a bond | Me | a bond | NH | O | a bond | Q3a | OH |
| 227 | N | NMe | Q1j | a bond | Me | a bond | NH | O | a bond | Q3b | OH |
| 228 | N | NMe | Q1j | a bond | Me | a bond | NH | O | a bond | Q3c | OH |
| 229 | N | NMe | Q1j | a bond | H | a bond | NH | S | NH | Q3a | OH |
| 230 | N | NMe | Q1j | a bond | H | a bond | NH | S | NH | Q3b | OH |
| 231 | N | NMe | Q1j | a bond | H | a bond | NH | S | NH | Q3c | OH |
| 232 | N | NMe | Q1j | a bond | H | a bond | NH | S | a bond | Q3a | OH |
| 233 | N | NMe | Q1j | a bond | H | a bond | NH | S | a bond | Q3b | OH |
| 234 | N | NMe | Q1j | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 235 | N | NMe | Q1j | a bond | H | a bond | NH | O | NH | Q3a | OH |
| 236 | N | NMe | Q1j | a bond | H | a bond | NH | O | NH | Q3b | OH |
| 237 | N | NMe | Q1j | a bond | H | a bond | NH | O | NH | Q3c | OH |
| 238 | N | NMe | Q1j | a bond | H | a bond | NH | O | a bond | Q3a | OH |
| 239 | N | NMe | Q1j | a bond | H | a bond | NH | O | a bond | Q3b | OH |
| 240 | N | NMe | Q1j | a bond | H | a bond | NH | O | a bond | Q3c | OH |
| 241 | N | NEt | Q1a | a bond | Me | a bond | NH | S | NH | Q3a | OH |
| 242 | N | NEt | Q1a | a bond | Me | a bond | NH | S | NH | Q3b | OH |
| 243 | N | NEt | Q1a | a bond | Me | a bond | NH | S | NH | Q3c | OH |
| 244 | N | NEt | Q1a | a bond | Me | a bond | NH | S | a bond | Q3a | OH |
| 245 | N | NEt | Q1a | a bond | Me | a bond | NH | S | a bond | Q3b | OH |
| 246 | N | NEt | Q1a | a bond | Me | a bond | NH | S | a bond | Q3c | OH |
| 247 | N | NEt | Q1a | a bond | Me | a bond | NH | O | NH | Q3a | OH |
| 248 | N | NEt | Q1a | a bond | Me | a bond | NH | O | NH | Q3b | OH |
| 249 | N | NEt | Q1a | a bond | Me | a bond | NH | O | NH | Q3c | OH |
| 250 | N | NEt | Q1a | a bond | Me | a bond | NH | O | a bond | Q3a | OH |
| 251 | N | NEt | Q1a | a bond | Me | a bond | NH | O | a bond | Q3b | OH |
| 252 | N | NEt | Q1a | a bond | Me | a bond | NH | O | a bond | Q3c | OH |
| 253 | N | NEt | Q1a | a bond | H | a bond | NH | S | NH | Q3a | OH |
| 254 | N | NEt | Q1a | a bond | H | a bond | NH | S | NH | Q3b | OH |
| 255 | N | NEt | Q1a | a bond | H | a bond | NH | S | NH | Q3c | OH |
| 256 | N | NEt | Q1a | a bond | H | a bond | NH | S | a bond | Q3a | OH |
| 257 | N | NEt | Q1a | a bond | H | a bond | NH | S | a bond | Q3b | OH |
| 258 | N | NEt | Q1a | a bond | H | a bond | NH | S | a bond | Q3c | OH |
| 259 | N | NEt | Q1a | a bond | H | a bond | NH | O | NH | Q3a | OH |
| 260 | N | NEt | Q1a | a bond | H | a bond | NH | O | NH | Q3b | OH |
| 261 | N | NEt | Q1a | a bond | H | a bond | NH | O | NH | Q3c | OH |
| 262 | N | NEt | Q1a | a bond | H | a bond | NH | O | a bond | Q3a | OH |
| 263 | N | NEt | Q1a | a bond | H | a bond | NH | O | a bond | Q3b | OH |
| 264 | N | NEt | Q1a | a bond | H | a bond | NH | O | a bond | Q3c | OH |
| 265 | N | NEt | Q1b | a bond | Me | a bond | NH | S | NH | Q3a | OH |
| 266 | N | NEt | Q1b | a bond | Me | a bond | NH | S | NH | Q3b | OH |
| 267 | N | NEt | Q1b | a bond | Me | a bond | NH | S | NH | Q3c | OH |
| 268 | N | NEt | Q1b | a bond | Me | a bond | NH | S | a bond | Q3a | OH |
| 269 | N | NEt | Q1b | a bond | Me | a bond | NH | S | a bond | Q3b | OH |
| 270 | N | NEt | Q1b | a bond | Me | a bond | NH | S | a bond | Q3c | OH |
| 271 | N | NEt | Q1b | a bond | Me | a bond | NH | O | NH | Q3a | OH |
| 272 | N | NEt | Q1b | a bond | Me | a bond | NH | O | NH | Q3b | OH |
| 273 | N | NEt | Q1b | a bond | Me | a bond | NH | O | NH | Q3c | OH |
| 274 | N | NEt | Q1b | a bond | Me | a bond | NH | O | a bond | Q3a | OH |
| 275 | N | NEt | Q1b | a bond | Me | a bond | NH | O | a bond | Q3b | OH |
| 276 | N | NEt | Q1b | a bond | Me | a bond | NH | O | a bond | Q3c | OH |
| 277 | N | NEt | Q1b | a bond | H | a bond | NH | S | NH | Q3a | OH |
| 278 | N | NEt | Q1b | a bond | H | a bond | NH | S | NH | Q3b | OH |
| 279 | N | NEt | Q1b | a bond | H | a bond | NH | S | NH | Q3c | OH |
| 280 | N | NEt | Q1b | a bond | H | a bond | NH | S | a bond | Q3a | OH |
| 281 | N | NEt | Q1b | a bond | H | a bond | NH | S | a bond | Q3b | OH |
| 282 | N | NEt | Q1b | a bond | H | a bond | NH | S | a bond | Q3c | OH |
| 283 | N | NEt | Q1b | a bond | H | a bond | NH | O | NH | Q3a | OH |
| 284 | N | NEt | Q1b | a bond | H | a bond | NH | O | NH | Q3b | OH |
| 285 | N | NEt | Q1b | a bond | H | a bond | NH | O | NH | Q3c | OH |
| 286 | N | NEt | Q1b | a bond | H | a bond | NH | O | a bond | Q3a | OH |
| 287 | N | NEt | Q1b | a bond | H | a bond | NH | O | a bond | Q3b | OH |
| 288 | N | NEt | Q1b | a bond | H | a bond | NH | O | a bond | Q3c | OH |
| 289 | N | NEt | Q1c | a bond | Me | a bond | NH | S | NH | Q3a | OH |
| 290 | N | NEt | Q1c | a bond | Me | a bond | NH | S | NH | Q3b | OH |
| 291 | N | NEt | Q1c | a bond | Me | a bond | NH | S | NH | Q3c | OH |
| 292 | N | NEt | Q1c | a bond | Me | a bond | NH | S | a bond | Q3a | OH |
| 293 | N | NEt | Q1c | a bond | Me | a bond | NH | S | a bond | Q3b | OH |
| 294 | N | NEt | Q1c | a bond | Me | a bond | NH | S | a bond | Q3c | OH |
| 295 | N | NEt | Q1c | a bond | Me | a bond | NH | O | NH | Q3a | OH |
| 296 | N | NEt | Q1c | a bond | Me | a bond | NH | O | NH | Q3b | OH |
| 297 | N | NEt | Q1c | a bond | Me | a bond | NH | O | NH | Q3c | OH |
| 298 | N | NEt | Q1c | a bond | Me | a bond | NH | O | a bond | Q3a | OH |
| 299 | N | NEt | Q1c | a bond | Me | a bond | NH | O | a bond | Q3b | OH |
| 300 | N | NEt | Q1c | a bond | Me | a bond | NH | O | a bond | Q3c | OH |
| 301 | N | NEt | Q1c | a bond | H | a bond | NH | S | NH | Q3a | OH |
| 302 | N | NEt | Q1c | a bond | H | a bond | NH | S | NH | Q3b | OH |
| 303 | N | NEt | Q1c | a bond | H | a bond | NH | S | NH | Q3c | OH |
| 304 | N | NEt | Q1c | a bond | H | a bond | NH | S | a bond | Q3a | OH |
| 305 | N | NEt | Q1c | a bond | H | a bond | NH | S | a bond | Q3b | OH |
| 306 | N | NEt | Q1c | a bond | H | a bond | NH | S | a bond | Q3c | OH |
| 307 | N | NEt | Q1c | a bond | H | a bond | NH | O | NH | Q3a | OH |
| 308 | N | NEt | Q1c | a bond | H | a bond | NH | O | NH | Q3b | OH |
| 309 | N | NEt | Q1c | a bond | H | a bond | NH | O | NH | Q3c | OH |
| 310 | N | NEt | Q1c | a bond | H | a bond | NH | O | a bond | Q3a | OH |
| 311 | N | NEt | Q1c | a bond | H | a bond | NH | O | a bond | Q3b | OH |
| 312 | N | NEt | Q1c | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 313 | N | NEt | Q1d | a bond | Me | a bond | NH | S | NH | Q3a | OH |
| 314 | N | NEt | Q1d | a bond | Me | a bond | NH | S | NH | Q3b | OH |
| 315 | N | NEt | Q1d | a bond | Me | a bond | NH | S | NH | Q3c | OH |
| 316 | N | NEt | Q1d | a bond | Me | a bond | NH | S | a bond | Q3a | OH |
| 317 | N | NEt | Q1d | a bond | Me | a bond | NH | S | a bond | Q3b | OH |
| 318 | N | NEt | Q1d | a bond | Me | a bond | NH | S | a bond | Q3c | OH |
| 319 | N | NEt | Q1d | a bond | Me | a bond | NH | O | NH | Q3a | OH |
| 320 | N | NEt | Q1d | a bond | Me | a bond | NH | O | NH | Q3b | OH |
| 321 | N | NEt | Q1d | a bond | Me | a bond | NH | O | NH | Q3c | OH |
| 322 | N | NEt | Q1d | a bond | Me | a bond | NH | O | a bond | Q3a | OH |
| 323 | N | NEt | Q1d | a bond | Me | a bond | NH | O | a bond | Q3b | OH |
| 324 | N | NEt | Q1d | a bond | Me | a bond | NH | O | a bond | Q3c | OH |
| 325 | N | NEt | Q1d | a bond | H | a bond | NH | S | NH | Q3a | OH |
| 326 | N | NEt | Q1d | a bond | H | a bond | NH | S | NH | Q3b | OH |
| 327 | N | NEt | Q1d | a bond | H | a bond | NH | S | NH | Q3c | OH |
| 328 | N | NEt | Q1d | a bond | H | a bond | NH | S | a bond | Q3a | OH |
| 329 | N | NEt | Q1d | a bond | H | a bond | NH | S | a bond | Q3b | OH |
| 330 | N | NEt | Q1d | a bond | H | a bond | NH | S | a bond | Q3c | OH |
| 331 | N | NEt | Q1d | a bond | H | a bond | NH | O | NH | Q3a | OH |
| 332 | N | NEt | Q1d | a bond | H | a bond | NH | O | NH | Q3b | OH |
| 333 | N | NEt | Q1d | a bond | H | a bond | NH | O | NH | Q3c | OH |
| 334 | N | NEt | Q1d | a bond | H | a bond | NH | O | a bond | Q3a | OH |
| 335 | N | NEt | Q1d | a bond | H | a bond | NH | O | a bond | Q3b | OH |
| 336 | N | NEt | Q1d | a bond | H | a bond | NH | O | a bond | Q3c | OH |
| 337 | N | NEt | Q1e | a bond | Me | a bond | NH | S | NH | Q3a | OH |
| 338 | N | NEt | Q1e | a bond | Me | a bond | NH | S | NH | Q3b | OH |
| 339 | N | NEt | Q1e | a bond | Me | a bond | NH | S | NH | Q3c | OH |
| 340 | N | NEt | Q1e | a bond | Me | a bond | NH | S | a bond | Q3a | OH |
| 341 | N | NEt | Q1e | a bond | Me | a bond | NH | S | a bond | Q3b | OH |
| 342 | N | NEt | Q1e | a bond | Me | a bond | NH | S | a bond | Q3c | OH |
| 343 | N | NEt | Q1e | a bond | Me | a bond | NH | O | NH | Q3a | OH |
| 344 | N | NEt | Q1e | a bond | Me | a bond | NH | O | NH | Q3b | OH |
| 345 | N | NEt | Q1e | a bond | Me | a bond | NH | O | NH | Q3c | OH |
| 346 | N | NEt | Q1e | a bond | Me | a bond | NH | O | a bond | Q3a | OH |
| 347 | N | NEt | Q1e | a bond | Me | a bond | NH | O | a bond | Q3b | OH |
| 348 | N | NEt | Q1e | a bond | Me | a bond | NH | O | a bond | Q3c | OH |
| 349 | N | NEt | Q1e | a bond | H | a bond | NH | S | NH | Q3a | OH |
| 350 | N | NEt | Q1e | a bond | H | a bond | NH | S | NH | Q3b | OH |
| 351 | N | NEt | Q1e | a bond | H | a bond | NH | S | NH | Q3c | OH |
| 352 | N | NEt | Q1e | a bond | H | a bond | NH | S | a bond | Q3a | OH |
| 353 | N | NEt | Q1e | a bond | H | a bond | NH | S | a bond | Q3b | OH |
| 354 | N | NEt | Q1e | a bond | H | a bond | NH | S | a bond | Q3c | OH |
| 355 | N | NEt | Q1e | a bond | H | a bond | NH | O | NH | Q3a | OH |
| 356 | N | NEt | Q1e | a bond | H | a bond | NH | O | NH | Q3b | OH |
| 357 | N | NEt | Q1e | a bond | H | a bond | NH | O | NH | Q3c | OH |
| 358 | N | NEt | Q1e | a bond | H | a bond | NH | O | a bond | Q3a | OH |
| 359 | N | NEt | Q1e | a bond | H | a bond | NH | O | a bond | Q3b | OH |
| 360 | N | NEt | Q1e | a bond | H | a bond | NH | O | a bond | Q3c | OH |
| 361 | N | NEt | Q1f | a bond | Me | a bond | NH | S | NH | Q3a | OH |
| 362 | N | NEt | Q1f | a bond | Me | a bond | NH | S | NH | Q3b | OH |
| 363 | N | NEt | Q1f | a bond | Me | a bond | NH | S | NH | Q3c | OH |
| 364 | N | NEt | Q1f | a bond | Me | a bond | NH | S | a bond | Q3a | OH |
| 365 | N | NEt | Q1f | a bond | Me | a bond | NH | S | a bond | Q3b | OH |
| 366 | N | NEt | Q1f | a bond | Me | a bond | NH | S | a bond | Q3c | OH |
| 367 | N | NEt | Q1f | a bond | Me | a bond | NH | O | NH | Q3a | OH |
| 368 | N | NEt | Q1f | a bond | Me | a bond | NH | O | NH | Q3b | OH |
| 369 | N | NEt | Q1f | a bond | Me | a bond | NH | O | NH | Q3c | OH |
| 370 | N | NEt | Q1f | a bond | Me | a bond | NH | O | a bond | Q3a | OH |
| 371 | N | NEt | Q1f | a bond | Me | a bond | NH | O | a bond | Q3b | OH |
| 372 | N | NEt | Q1f | a bond | Me | a bond | NH | O | a bond | Q3c | OH |
| 373 | N | NEt | Q1f | a bond | H | a bond | NH | S | NH | Q3a | OH |
| 374 | N | NEt | Q1f | a bond | H | a bond | NH | S | NH | Q3b | OH |
| 375 | N | NEt | Q1f | a bond | H | a bond | NH | S | NH | Q3c | OH |
| 376 | N | NEt | Q1f | a bond | H | a bond | NH | S | a bond | Q3a | OH |
| 377 | N | NEt | Q1f | a bond | H | a bond | NH | S | a bond | Q3b | OH |
| 378 | N | NEt | Q1f | a bond | H | a bond | NH | S | a bond | Q3c | OH |
| 379 | N | NEt | Q1f | a bond | H | a bond | NH | O | NH | Q3a | OH |
| 380 | N | NEt | Q1f | a bond | H | a bond | NH | O | NH | Q3b | OH |
| 381 | N | NEt | Q1f | a bond | H | a bond | NH | O | NH | Q3c | OH |
| 382 | N | NEt | Q1f | a bond | H | a bond | NH | O | a bond | Q3a | OH |
| 383 | N | NEt | Q1f | a bond | H | a bond | NH | O | a bond | Q3b | OH |
| 384 | N | NEt | Q1f | a bond | H | a bond | NH | O | a bond | Q3c | OH |
| 385 | N | NEt | Q1g | a bond | Me | a bond | NH | S | NH | Q3a | OH |
| 386 | N | NEt | Q1g | a bond | Me | a bond | NH | S | NH | Q3b | OH |
| 387 | N | NEt | Q1g | a bond | Me | a bond | NH | S | NH | Q3c | OH |
| 388 | N | NEt | Q1g | a bond | Me | a bond | NH | S | a bond | Q3a | OH |
| 389 | N | NEt | Q1g | a bond | Me | a bond | NH | S | a bond | Q3b | OH |
| 390 | N | NEt | Q1g | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 391 | N | NEt | Q1g | a bond | Me | a bond | NH | O | NH | Q3a | OH |
| 392 | N | NEt | Q1g | a bond | Me | a bond | NH | O | NH | Q3b | OH |
| 393 | N | NEt | Q1g | a bond | Me | a bond | NH | O | NH | Q3c | OH |
| 394 | N | NEt | Q1g | a bond | Me | a bond | NH | O | a bond | Q3a | OH |
| 395 | N | NEt | Q1g | a bond | Me | a bond | NH | O | a bond | Q3b | OH |
| 396 | N | NEt | Q1g | a bond | Me | a bond | NH | O | a bond | Q3c | OH |
| 397 | N | NEt | Q1g | a bond | H | a bond | NH | S | NH | Q3a | OH |
| 398 | N | NEt | Q1g | a bond | H | a bond | NH | S | NH | Q3b | OH |
| 399 | N | NEt | Q1g | a bond | H | a bond | NH | S | NH | Q3c | OH |
| 400 | N | NEt | Q1g | a bond | H | a bond | NH | S | a bond | Q3a | OH |
| 401 | N | NEt | Q1g | a bond | H | a bond | NH | S | a bond | Q3b | OH |
| 402 | N | NEt | Q1g | a bond | H | a bond | NH | S | a bond | Q3c | OH |
| 403 | N | NEt | Q1g | a bond | H | a bond | NH | O | NH | Q3a | OH |
| 404 | N | NEt | Q1g | a bond | H | a bond | NH | O | NH | Q3b | OH |
| 405 | N | NEt | Q1g | a bond | H | a bond | NH | O | NH | Q3c | OH |
| 406 | N | NEt | Q1g | a bond | H | a bond | NH | O | a bond | Q3a | OH |
| 407 | N | NEt | Q1g | a bond | H | a bond | NH | O | a bond | Q3b | OH |
| 408 | N | NEt | Q1g | a bond | H | a bond | NH | O | a bond | Q3c | OH |
| 409 | N | NEt | Q1h | a bond | Me | a bond | NH | S | NH | Q3a | OH |
| 410 | N | NEt | Q1h | a bond | Me | a bond | NH | S | NH | Q3b | OH |
| 411 | N | NEt | Q1h | a bond | Me | a bond | NH | S | NH | Q3c | OH |
| 412 | N | NEt | Q1h | a bond | Me | a bond | NH | S | a bond | Q3a | OH |
| 413 | N | NEt | Q1h | a bond | Me | a bond | NH | S | a bond | Q3b | OH |
| 414 | N | NEt | Q1h | a bond | Me | a bond | NH | S | a bond | Q3c | OH |
| 415 | N | NEt | Q1h | a bond | Me | a bond | NH | O | NH | Q3a | OH |
| 416 | N | NEt | Q1h | a bond | Me | a bond | NH | O | NH | Q3b | OH |
| 417 | N | NEt | Q1h | a bond | Me | a bond | NH | O | NH | Q3c | OH |
| 418 | N | NEt | Q1h | a bond | Me | a bond | NH | O | a bond | Q3a | OH |
| 419 | N | NEt | Q1h | a bond | Me | a bond | NH | O | a bond | Q3b | OH |
| 420 | N | NEt | Q1h | a bond | Me | a bond | NH | O | a bond | Q3c | OH |
| 421 | N | NEt | Q1h | a bond | H | a bond | NH | S | NH | Q3a | OH |
| 422 | N | NEt | Q1h | a bond | H | a bond | NH | S | NH | Q3b | OH |
| 423 | N | NEt | Q1h | a bond | H | a bond | NH | S | NH | Q3c | OH |
| 424 | N | NEt | Q1h | a bond | H | a bond | NH | S | a bond | Q3a | OH |
| 425 | N | NEt | Q1h | a bond | H | a bond | NH | S | a bond | Q3b | OH |
| 426 | N | NEt | Q1h | a bond | H | a bond | NH | S | a bond | Q3c | OH |
| 427 | N | NEt | Q1h | a bond | H | a bond | NH | O | NH | Q3a | OH |
| 428 | N | NEt | Q1h | a bond | H | a bond | NH | O | NH | Q3b | OH |
| 429 | N | NEt | Q1h | a bond | H | a bond | NH | O | NH | Q3c | OH |
| 430 | N | NEt | Q1h | a bond | H | a bond | NH | O | a bond | Q3a | OH |
| 431 | N | NEt | Q1h | a bond | H | a bond | NH | O | a bond | Q3b | OH |
| 432 | N | NEt | Q1h | a bond | H | a bond | NH | O | a bond | Q3c | OH |
| 433 | N | NEt | Q1i | a bond | Me | a bond | NH | S | NH | Q3a | OH |
| 434 | N | NEt | Q1i | a bond | Me | a bond | NH | S | NH | Q3b | OH |
| 435 | N | NEt | Q1i | a bond | Me | a bond | NH | S | NH | Q3c | OH |
| 436 | N | NEt | Q1i | a bond | Me | a bond | NH | S | a bond | Q3a | OH |
| 437 | N | NEt | Q1i | a bond | Me | a bond | NH | S | a bond | Q3b | OH |
| 438 | N | NEt | Q1i | a bond | Me | a bond | NH | S | a bond | Q3c | OH |
| 439 | N | NEt | Q1i | a bond | Me | a bond | NH | O | NH | Q3a | OH |
| 440 | N | NEt | Q1i | a bond | Me | a bond | NH | O | NH | Q3b | OH |
| 441 | N | NEt | Q1i | a bond | Me | a bond | NH | O | NH | Q3c | OH |
| 442 | N | NEt | Q1i | a bond | Me | a bond | NH | O | a bond | Q3a | OH |
| 443 | N | NEt | Q1i | a bond | Me | a bond | NH | O | a bond | Q3b | OH |
| 444 | N | NEt | Q1i | a bond | Me | a bond | NH | O | a bond | Q3c | OH |
| 445 | N | NEt | Q1i | a bond | H | a bond | NH | S | NH | Q3a | OH |
| 446 | N | NEt | Q1i | a bond | H | a bond | NH | S | NH | Q3b | OH |
| 447 | N | NEt | Q1i | a bond | H | a bond | NH | S | NH | Q3c | OH |
| 448 | N | NEt | Q1i | a bond | H | a bond | NH | S | a bond | Q3a | OH |
| 449 | N | NEt | Q1i | a bond | H | a bond | NH | S | a bond | Q3b | OH |
| 450 | N | NEt | Q1i | a bond | H | a bond | NH | S | a bond | Q3c | OH |
| 451 | N | NEt | Q1i | a bond | H | a bond | NH | O | NH | Q3a | OH |
| 452 | N | NEt | Q1i | a bond | H | a bond | NH | O | NH | Q3b | OH |
| 453 | N | NEt | Q1i | a bond | H | a bond | NH | O | NH | Q3c | OH |
| 454 | N | NEt | Q1i | a bond | H | a bond | NH | O | a bond | Q3a | OH |
| 455 | N | NEt | Q1i | a bond | H | a bond | NH | O | a bond | Q3b | OH |
| 456 | N | NEt | Q1i | a bond | H | a bond | NH | O | a bond | Q3c | OH |
| 457 | N | NEt | Q1j | a bond | Me | a bond | NH | S | NH | Q3a | OH |
| 458 | N | NEt | Q1j | a bond | Me | a bond | NH | S | NH | Q3b | OH |
| 459 | N | NEt | Q1j | a bond | Me | a bond | NH | S | NH | Q3c | OH |
| 460 | N | NEt | Q1j | a bond | Me | a bond | NH | S | a bond | Q3a | OH |
| 461 | N | NEt | Q1j | a bond | Me | a bond | NH | S | a bond | Q3b | OH |
| 462 | N | NEt | Q1j | a bond | Me | a bond | NH | S | a bond | Q3c | OH |
| 463 | N | NEt | Q1j | a bond | Me | a bond | NH | O | NH | Q3a | OH |
| 464 | N | NEt | Q1j | a bond | Me | a bond | NH | O | NH | Q3b | OH |
| 465 | N | NEt | Q1j | a bond | Me | a bond | NH | O | NH | Q3c | OH |
| 466 | N | NEt | Q1j | a bond | Me | a bond | NH | O | a bond | Q3a | OH |
| 467 | N | NEt | Q1j | a bond | Me | a bond | NH | O | a bond | Q3b | OH |
| 468 | N | NEt | Q1j | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 469 | N | NEt | Q1j | a bond | H | a bond | NH | S | NH | Q3a | OH |
| 470 | N | NEt | Q1j | a bond | H | a bond | NH | S | NH | Q3b | OH |
| 471 | N | NEt | Q1j | a bond | H | a bond | NH | S | NH | Q3c | OH |
| 472 | N | NEt | Q1j | a bond | H | a bond | NH | S | a bond | Q3a | OH |
| 473 | N | NEt | Q1j | a bond | H | a bond | NH | S | a bond | Q3b | OH |
| 474 | N | NEt | Q1j | a bond | H | a bond | NH | S | a bond | Q3c | OH |
| 475 | N | NEt | Q1j | a bond | H | a bond | NH | O | NH | Q3a | OH |
| 476 | N | NEt | Q1j | a bond | H | a bond | NH | O | NH | Q3b | OH |
| 477 | N | NEt | Q1j | a bond | H | a bond | NH | O | NH | Q3c | OH |
| 478 | N | NEt | Q1j | a bond | H | a bond | NH | O | a bond | Q3a | OH |
| 479 | N | NEt | Q1j | a bond | H | a bond | NH | O | a bond | Q3b | OH |
| 480 | N | NEt | Q1j | a bond | H | a bond | NH | O | a bond | Q3c | OH |
| 481 | N | S | Q1a | a bond | Me | a bond | NH | S | NH | Q3a | OH |
| 482 | N | S | Q1a | a bond | Me | a bond | NH | S | NH | Q3b | OH |
| 483 | N | S | Q1a | a bond | Me | a bond | NH | S | NH | Q3c | OH |
| 484 | N | S | Q1a | a bond | Me | a bond | NH | S | a bond | Q3a | OH |
| 485 | N | S | Q1a | a bond | Me | a bond | NH | S | a bond | Q3b | OH |
| 486 | N | S | Q1a | a bond | Me | a bond | NH | S | a bond | Q3c | OH |
| 487 | N | S | Q1a | a bond | Me | a bond | NH | O | NH | Q3a | OH |
| 488 | N | S | Q1a | a bond | Me | a bond | NH | O | NH | Q3b | OH |
| 489 | N | S | Q1a | a bond | Me | a bond | NH | O | NH | Q3c | OH |
| 490 | N | S | Q1a | a bond | Me | a bond | NH | O | a bond | Q3a | OH |
| 491 | N | S | Q1a | a bond | Me | a bond | NH | O | a bond | Q3b | OH |
| 492 | N | S | Q1a | a bond | Me | a bond | NH | O | a bond | Q3c | OH |
| 493 | N | S | Q1a | a bond | H | a bond | NH | S | NH | Q3a | OH |
| 494 | N | S | Q1a | a bond | H | a bond | NH | S | NH | Q3b | OH |
| 495 | N | S | Q1a | a bond | H | a bond | NH | S | NH | Q3c | OH |
| 496 | N | S | Q1a | a bond | H | a bond | NH | S | a bond | Q3a | OH |
| 497 | N | S | Q1a | a bond | H | a bond | NH | S | a bond | Q3b | OH |
| 498 | N | S | Q1a | a bond | H | a bond | NH | S | a bond | Q3c | OH |
| 499 | N | S | Q1a | a bond | H | a bond | NH | O | NH | Q3a | OH |
| 500 | N | S | Q1a | a bond | H | a bond | NH | O | NH | Q3b | OH |
| 501 | N | S | Q1a | a bond | H | a bond | NH | O | NH | Q3c | OH |
| 502 | N | S | Q1a | a bond | H | a bond | NH | O | a bond | Q3a | OH |
| 503 | N | S | Q1a | a bond | H | a bond | NH | O | a bond | Q3b | OH |
| 504 | N | S | Q1a | a bond | H | a bond | NH | O | a bond | Q3c | OH |
| 505 | N | S | Q1b | a bond | Me | a bond | NH | S | NH | Q3a | OH |
| 506 | N | S | Q1b | a bond | Me | a bond | NH | S | NH | Q3b | OH |
| 507 | N | S | Q1b | a bond | Me | a bond | NH | S | NH | Q3c | OH |
| 508 | N | S | Q1b | a bond | Me | a bond | NH | S | a bond | Q3a | OH |
| 509 | N | S | Q1b | a bond | Me | a bond | NH | S | a bond | Q3b | OH |
| 510 | N | S | Q1b | a bond | Me | a bond | NH | S | a bond | Q3c | OH |
| 511 | N | S | Q1b | a bond | Me | a bond | NH | O | NH | Q3a | OH |
| 512 | N | S | Q1b | a bond | Me | a bond | NH | O | NH | Q3b | OH |
| 513 | N | S | Q1b | a bond | Me | a bond | NH | O | NH | Q3c | OH |
| 514 | N | S | Q1b | a bond | Me | a bond | NH | O | a bond | Q3a | OH |
| 515 | N | S | Q1b | a bond | Me | a bond | NH | O | a bond | Q3b | OH |
| 516 | N | S | Q1b | a bond | Me | a bond | NH | O | a bond | Q3c | OH |
| 517 | N | S | Q1b | a bond | H | a bond | NH | S | NH | Q3a | OH |
| 518 | N | S | Q1b | a bond | H | a bond | NH | S | NH | Q3b | OH |
| 519 | N | S | Q1b | a bond | H | a bond | NH | S | NH | Q3c | OH |
| 520 | N | S | Q1b | a bond | H | a bond | NH | S | a bond | Q3a | OH |
| 521 | N | S | Q1b | a bond | H | a bond | NH | S | a bond | Q3b | OH |
| 522 | N | S | Q1b | a bond | H | a bond | NH | S | a bond | Q3c | OH |
| 523 | N | S | Q1b | a bond | H | a bond | NH | O | NH | Q3a | OH |
| 524 | N | S | Q1b | a bond | H | a bond | NH | O | NH | Q3b | OH |
| 525 | N | S | Q1b | a bond | H | a bond | NH | O | NH | Q3c | OH |
| 526 | N | S | Q1b | a bond | H | a bond | NH | O | a bond | Q3a | OH |
| 527 | N | S | Q1b | a bond | H | a bond | NH | O | a bond | Q3b | OH |
| 528 | N | S | Q1b | a bond | H | a bond | NH | O | a bond | Q3c | OH |
| 529 | N | S | Q1c | a bond | Me | a bond | NH | S | NH | Q3a | OH |
| 530 | N | S | Q1c | a bond | Me | a bond | NH | S | NH | Q3b | OH |
| 531 | N | S | Q1c | a bond | Me | a bond | NH | S | NH | Q3c | OH |
| 532 | N | S | Q1c | a bond | Me | a bond | NH | S | a bond | Q3a | OH |
| 533 | N | S | Q1c | a bond | Me | a bond | NH | S | a bond | Q3b | OH |
| 534 | N | S | Q1c | a bond | Me | a bond | NH | S | a bond | Q3c | OH |
| 535 | N | S | Q1c | a bond | Me | a bond | NH | O | NH | Q3a | OH |
| 536 | N | S | Q1c | a bond | Me | a bond | NH | O | NH | Q3b | OH |
| 537 | N | S | Q1c | a bond | Me | a bond | NH | O | NH | Q3c | OH |
| 538 | N | S | Q1c | a bond | Me | a bond | NH | O | a bond | Q3a | OH |
| 539 | N | S | Q1c | a bond | Me | a bond | NH | O | a bond | Q3b | OH |
| 540 | N | S | Q1c | a bond | Me | a bond | NH | O | a bond | Q3c | OH |
| 541 | N | S | Q1c | a bond | H | a bond | NH | S | NH | Q3a | OH |
| 542 | N | S | Q1c | a bond | H | a bond | NH | S | NH | Q3b | OH |
| 543 | N | S | Q1c | a bond | H | a bond | NH | S | NH | Q3c | OH |
| 544 | N | S | Q1c | a bond | H | a bond | NH | S | a bond | Q3a | OH |
| 545 | N | S | Q1c | a bond | H | a bond | NH | S | a bond | Q3b | OH |
| 546 | N | S | Q1c | a bond | H | a bond | NH | S | a bond | Q3c | OH |

TABLE 1-continued

| No | A | B | R$^1$ | L$^1$ | R$^2$ | L$^2$ | L$^3$ | Y | L$^4$ | R$^3$ | X |
|---|---|---|---|---|---|---|---|---|---|---|---|
| 547 | N | S | Q1c | a bond | H | a bond | NH | O | NH | Q3a | OH |
| 548 | N | S | Q1c | a bond | H | a bond | NH | O | NH | Q3b | OH |
| 549 | N | S | Q1c | a bond | H | a bond | NH | O | NH | Q3c | OH |
| 550 | N | S | Q1c | a bond | H | a bond | NH | O | a bond | Q3a | OH |
| 551 | N | S | Q1c | a bond | H | a bond | NH | O | a bond | Q3b | OH |
| 552 | N | S | Q1c | a bond | H | a bond | NH | O | a bond | Q3c | OH |
| 553 | N | S | Q1d | a bond | Me | a bond | NH | S | NH | Q3a | OH |
| 554 | N | S | Q1d | a bond | Me | a bond | NH | S | NH | Q3b | OH |
| 555 | N | S | Q1d | a bond | Me | a bond | NH | S | NH | Q3c | OH |
| 556 | N | S | Q1d | a bond | Me | a bond | NH | S | a bond | Q3a | OH |
| 557 | N | S | Q1d | a bond | Me | a bond | NH | S | a bond | Q3b | OH |
| 558 | N | S | Q1d | a bond | Me | a bond | NH | S | a bond | Q3c | OH |
| 559 | N | S | Q1d | a bond | Me | a bond | NH | O | NH | Q3a | OH |
| 560 | N | S | Q1d | a bond | Me | a bond | NH | O | NH | Q3b | OH |
| 561 | N | S | Q1d | a bond | Me | a bond | NH | O | NH | Q3c | OH |
| 562 | N | S | Q1d | a bond | Me | a bond | NH | O | a bond | Q3a | OH |
| 563 | N | S | Q1d | a bond | Me | a bond | NH | O | a bond | Q3b | OH |
| 564 | N | S | Q1d | a bond | Me | a bond | NH | O | a bond | Q3c | OH |
| 565 | N | S | Q1d | a bond | H | a bond | NH | S | NH | Q3a | OH |
| 566 | N | S | Q1d | a bond | H | a bond | NH | S | NH | Q3b | OH |
| 567 | N | S | Q1d | a bond | H | a bond | NH | S | NH | Q3c | OH |
| 568 | N | S | Q1d | a bond | H | a bond | NH | S | a bond | Q3a | OH |
| 569 | N | S | Q1d | a bond | H | a bond | NH | S | a bond | Q3b | OH |
| 570 | N | S | Q1d | a bond | H | a bond | NH | S | a bond | Q3c | OH |
| 571 | N | S | Q1d | a bond | H | a bond | NH | O | NH | Q3a | OH |
| 572 | N | S | Q1d | a bond | H | a bond | NH | O | NH | Q3b | OH |
| 573 | N | S | Q1d | a bond | H | a bond | NH | O | NH | Q3c | OH |
| 574 | N | S | Q1d | a bond | H | a bond | NH | O | a bond | Q3a | OH |
| 575 | N | S | Q1d | a bond | H | a bond | NH | O | a bond | Q3b | OH |
| 576 | N | S | Q1d | a bond | H | a bond | NH | O | a bond | Q3c | OH |
| 577 | N | S | Q1e | a bond | Me | a bond | NH | S | NH | Q3a | OH |
| 578 | N | S | Q1e | a bond | Me | a bond | NH | S | NH | Q3b | OH |
| 579 | N | S | Q1e | a bond | Me | a bond | NH | S | NH | Q3c | OH |
| 580 | N | S | Q1e | a bond | Me | a bond | NH | S | a bond | Q3a | OH |
| 581 | N | S | Q1e | a bond | Me | a bond | NH | S | a bond | Q3b | OH |
| 582 | N | S | Q1e | a bond | Me | a bond | NH | S | a bond | Q3c | OH |
| 583 | N | S | Q1e | a bond | Me | a bond | NH | O | NH | Q3a | OH |
| 584 | N | S | Q1e | a bond | Me | a bond | NH | O | NH | Q3b | OH |
| 585 | N | S | Q1e | a bond | Me | a bond | NH | O | NH | Q3c | OH |
| 586 | N | S | Q1e | a bond | Me | a bond | NH | O | a bond | Q3a | OH |
| 587 | N | S | Q1e | a bond | Me | a bond | NH | O | a bond | Q3b | OH |
| 588 | N | S | Q1e | a bond | Me | a bond | NH | O | a bond | Q3c | OH |
| 589 | N | S | Q1e | a bond | H | a bond | NH | S | NH | Q3a | OH |
| 590 | N | S | Q1e | a bond | H | a bond | NH | S | NH | Q3b | OH |
| 591 | N | S | Q1e | a bond | H | a bond | NH | S | NH | Q3c | OH |
| 592 | N | S | Q1e | a bond | H | a bond | NH | S | a bond | Q3a | OH |
| 593 | N | S | Q1e | a bond | H | a bond | NH | S | a bond | Q3b | OH |
| 594 | N | S | Q1e | a bond | H | a bond | NH | S | a bond | Q3c | OH |
| 595 | N | S | Q1e | a bond | H | a bond | NH | O | NH | Q3a | OH |
| 596 | N | S | Q1e | a bond | H | a bond | NH | O | NH | Q3b | OH |
| 597 | N | S | Q1e | a bond | H | a bond | NH | O | NH | Q3c | OH |
| 598 | N | S | Q1e | a bond | H | a bond | NH | O | a bond | Q3a | OH |
| 599 | N | S | Q1e | a bond | H | a bond | NH | O | a bond | Q3b | OH |
| 600 | N | S | Q1e | a bond | H | a bond | NH | O | a bond | Q3c | OH |
| 601 | N | S | Q1f | a bond | Me | a bond | NH | S | NH | Q3a | OH |
| 602 | N | S | Q1f | a bond | Me | a bond | NH | S | NH | Q3b | OH |
| 603 | N | S | Q1f | a bond | Me | a bond | NH | S | NH | Q3c | OH |
| 604 | N | S | Q1f | a bond | Me | a bond | NH | S | a bond | Q3a | OH |
| 605 | N | S | Q1f | a bond | Me | a bond | NH | S | a bond | Q3b | OH |
| 606 | N | S | Q1f | a bond | Me | a bond | NH | S | a bond | Q3c | OH |
| 607 | N | S | Q1f | a bond | Me | a bond | NH | O | NH | Q3a | OH |
| 608 | N | S | Q1f | a bond | Me | a bond | NH | O | NH | Q3b | OH |
| 609 | N | S | Q1f | a bond | Me | a bond | NH | O | NH | Q3c | OH |
| 610 | N | S | Q1f | a bond | Me | a bond | NH | O | a bond | Q3a | OH |
| 611 | N | S | Q1f | a bond | Me | a bond | NH | O | a bond | Q3b | OH |
| 612 | N | S | Q1f | a bond | Me | a bond | NH | O | a bond | Q3c | OH |
| 613 | N | S | Q1f | a bond | H | a bond | NH | S | NH | Q3a | OH |
| 614 | N | S | Q1f | a bond | H | a bond | NH | S | NH | Q3b | OH |
| 615 | N | S | Q1f | a bond | H | a bond | NH | S | NH | Q3c | OH |
| 616 | N | S | Q1f | a bond | H | a bond | NH | S | a bond | Q3a | OH |
| 617 | N | S | Q1f | a bond | H | a bond | NH | S | a bond | Q3b | OH |
| 618 | N | S | Q1f | a bond | H | a bond | NH | S | a bond | Q3c | OH |
| 619 | N | S | Q1f | a bond | H | a bond | NH | O | NH | Q3a | OH |
| 620 | N | S | Q1f | a bond | H | a bond | NH | O | NH | Q3b | OH |
| 621 | N | S | Q1f | a bond | H | a bond | NH | O | NH | Q3c | OH |
| 622 | N | S | Q1f | a bond | H | a bond | NH | O | a bond | Q3a | OH |
| 623 | N | S | Q1f | a bond | H | a bond | NH | O | a bond | Q3b | OH |
| 624 | N | S | Q1f | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 625 | N | S | Q1g | a bond | Me | a bond | NH | S | NH | Q3a | OH |
| 626 | N | S | Q1g | a bond | Me | a bond | NH | S | NH | Q3b | OH |
| 627 | N | S | Q1g | a bond | Me | a bond | NH | S | NH | Q3c | OH |
| 628 | N | S | Q1g | a bond | Me | a bond | NH | S | a bond | Q3a | OH |
| 629 | N | S | Q1g | a bond | Me | a bond | NH | S | a bond | Q3b | OH |
| 630 | N | S | Q1g | a bond | Me | a bond | NH | S | a bond | Q3c | OH |
| 631 | N | S | Q1g | a bond | Me | a bond | NH | O | NH | Q3a | OH |
| 632 | N | S | Q1g | a bond | Me | a bond | NH | O | NH | Q3b | OH |
| 633 | N | S | Q1g | a bond | Me | a bond | NH | O | NH | Q3c | OH |
| 634 | N | S | Q1g | a bond | Me | a bond | NH | O | a bond | Q3a | OH |
| 635 | N | S | Q1g | a bond | Me | a bond | NH | O | a bond | Q3b | OH |
| 636 | N | S | Q1g | a bond | Me | a bond | NH | O | a bond | Q3c | OH |
| 637 | N | S | Q1g | a bond | H | a bond | NH | S | NH | Q3a | OH |
| 638 | N | S | Q1g | a bond | H | a bond | NH | S | NH | Q3b | OH |
| 639 | N | S | Q1g | a bond | H | a bond | NH | S | NH | Q3c | OH |
| 640 | N | S | Q1g | a bond | H | a bond | NH | S | a bond | Q3a | OH |
| 641 | N | S | Q1g | a bond | H | a bond | NH | S | a bond | Q3b | OH |
| 642 | N | S | Q1g | a bond | H | a bond | NH | S | a bond | Q3c | OH |
| 643 | N | S | Q1g | a bond | H | a bond | NH | O | NH | Q3a | OH |
| 644 | N | S | Q1g | a bond | H | a bond | NH | O | NH | Q3b | OH |
| 645 | N | S | Q1g | a bond | H | a bond | NH | O | NH | Q3c | OH |
| 646 | N | S | Q1g | a bond | H | a bond | NH | O | a bond | Q3a | OH |
| 647 | N | S | Q1g | a bond | H | a bond | NH | O | a bond | Q3b | OH |
| 648 | N | S | Q1g | a bond | H | a bond | NH | O | a bond | Q3c | OH |
| 649 | N | S | Q1h | a bond | Me | a bond | NH | S | NH | Q3a | OH |
| 650 | N | S | Q1h | a bond | Me | a bond | NH | S | NH | Q3b | OH |
| 651 | N | S | Q1h | a bond | Me | a bond | NH | S | NH | Q3c | OH |
| 652 | N | S | Q1h | a bond | Me | a bond | NH | S | a bond | Q3a | OH |
| 653 | N | S | Q1h | a bond | Me | a bond | NH | S | a bond | Q3b | OH |
| 654 | N | S | Q1h | a bond | Me | a bond | NH | S | a bond | Q3c | OH |
| 655 | N | S | Q1h | a bond | Me | a bond | NH | O | NH | Q3a | OH |
| 656 | N | S | Q1h | a bond | Me | a bond | NH | O | NH | Q3b | OH |
| 657 | N | S | Q1h | a bond | Me | a bond | NH | O | NH | Q3c | OH |
| 658 | N | S | Q1h | a bond | Me | a bond | NH | O | a bond | Q3a | OH |
| 659 | N | S | Q1h | a bond | Me | a bond | NH | O | a bond | Q3b | OH |
| 660 | N | S | Q1h | a bond | Me | a bond | NH | O | a bond | Q3c | OH |
| 661 | N | S | Q1h | a bond | H | a bond | NH | S | NH | Q3a | OH |
| 662 | N | S | Q1h | a bond | H | a bond | NH | S | NH | Q3b | OH |
| 663 | N | S | Q1h | a bond | H | a bond | NH | S | NH | Q3c | OH |
| 664 | N | S | Q1h | a bond | H | a bond | NH | S | a bond | Q3a | OH |
| 665 | N | S | Q1h | a bond | H | a bond | NH | S | a bond | Q3b | OH |
| 666 | N | S | Q1h | a bond | H | a bond | NH | S | a bond | Q3c | OH |
| 667 | N | S | Q1h | a bond | H | a bond | NH | O | NH | Q3a | OH |
| 668 | N | S | Q1h | a bond | H | a bond | NH | O | NH | Q3b | OH |
| 669 | N | S | Q1h | a bond | H | a bond | NH | O | NH | Q3c | OH |
| 670 | N | S | Q1h | a bond | H | a bond | NH | O | a bond | Q3a | OH |
| 671 | N | S | Q1h | a bond | H | a bond | NH | O | a bond | Q3b | OH |
| 672 | N | S | Q1h | a bond | H | a bond | NH | O | a bond | Q3c | OH |
| 673 | N | S | Q1i | a bond | Me | a bond | NH | S | NH | Q3a | OH |
| 674 | N | S | Q1i | a bond | Me | a bond | NH | S | NH | Q3b | OH |
| 675 | N | S | Q1i | a bond | Me | a bond | NH | S | NH | Q3c | OH |
| 676 | N | S | Q1i | a bond | Me | a bond | NH | S | a bond | Q3a | OH |
| 677 | N | S | Q1i | a bond | Me | a bond | NH | S | a bond | Q3b | OH |
| 678 | N | S | Q1i | a bond | Me | a bond | NH | S | a bond | Q3c | OH |
| 679 | N | S | Q1i | a bond | Me | a bond | NH | O | NH | Q3a | OH |
| 680 | N | S | Q1i | a bond | Me | a bond | NH | O | NH | Q3b | OH |
| 681 | N | S | Q1i | a bond | Me | a bond | NH | O | NH | Q3c | OH |
| 682 | N | S | Q1i | a bond | Me | a bond | NH | O | a bond | Q3a | OH |
| 683 | N | S | Q1i | a bond | Me | a bond | NH | O | a bond | Q3b | OH |
| 684 | N | S | Q1i | a bond | Me | a bond | NH | O | a bond | Q3c | OH |
| 685 | N | S | Q1i | a bond | H | a bond | NH | S | NH | Q3a | OH |
| 686 | N | S | Q1i | a bond | H | a bond | NH | S | NH | Q3b | OH |
| 687 | N | S | Q1i | a bond | H | a bond | NH | S | NH | Q3c | OH |
| 688 | N | S | Q1i | a bond | H | a bond | NH | S | a bond | Q3a | OH |
| 689 | N | S | Q1i | a bond | H | a bond | NH | S | a bond | Q3b | OH |
| 690 | N | S | Q1i | a bond | H | a bond | NH | S | a bond | Q3c | OH |
| 691 | N | S | Q1i | a bond | H | a bond | NH | O | NH | Q3a | OH |
| 692 | N | S | Q1i | a bond | H | a bond | NH | O | NH | Q3b | OH |
| 693 | N | S | Q1i | a bond | H | a bond | NH | O | NH | Q3c | OH |
| 694 | N | S | Q1i | a bond | H | a bond | NH | O | a bond | Q3a | OH |
| 695 | N | S | Q1i | a bond | H | a bond | NH | O | a bond | Q3b | OH |
| 696 | N | S | Q1i | a bond | H | a bond | NH | O | a bond | Q3c | OH |
| 697 | N | S | Q1j | a bond | Me | a bond | NH | S | NH | Q3a | OH |
| 698 | N | S | Q1j | a bond | Me | a bond | NH | S | NH | Q3b | OH |
| 699 | N | S | Q1j | a bond | Me | a bond | NH | S | NH | Q3c | OH |
| 700 | N | S | Q1j | a bond | Me | a bond | NH | S | a bond | Q3a | OH |
| 701 | N | S | Q1j | a bond | Me | a bond | NH | S | a bond | Q3b | OH |
| 702 | N | S | Q1j | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 703 | N | S | Q1j | a bond | Me | a bond | NH | O | NH | Q3a | OH |
| 704 | N | S | Q1j | a bond | Me | a bond | NH | O | NH | Q3b | OH |
| 705 | N | S | Q1j | a bond | Me | a bond | NH | O | NH | Q3c | OH |
| 706 | N | S | Q1j | a bond | Me | a bond | NH | O | a bond | Q3a | OH |
| 707 | N | S | Q1j | a bond | Me | a bond | NH | O | a bond | Q3b | OH |
| 708 | N | S | Q1j | a bond | Me | a bond | NH | O | a bond | Q3c | OH |
| 709 | N | S | Q1j | a bond | H | a bond | NH | S | NH | Q3a | OH |
| 710 | N | S | Q1j | a bond | H | a bond | NH | S | NH | Q3b | OH |
| 711 | N | S | Q1j | a bond | H | a bond | NH | S | NH | Q3c | OH |
| 712 | N | S | Q1j | a bond | H | a bond | NH | S | a bond | Q3a | OH |
| 713 | N | S | Q1j | a bond | H | a bond | NH | S | a bond | Q3b | OH |
| 714 | N | S | Q1j | a bond | H | a bond | NH | S | a bond | Q3c | OH |
| 715 | N | S | Q1j | a bond | H | a bond | NH | O | NH | Q3a | OH |
| 716 | N | S | Q1j | a bond | H | a bond | NH | O | NH | Q3b | OH |
| 717 | N | S | Q1j | a bond | H | a bond | NH | O | NH | Q3c | OH |
| 718 | N | S | Q1j | a bond | H | a bond | NH | O | a bond | Q3a | OH |
| 719 | N | S | Q1j | a bond | H | a bond | NH | O | a bond | Q3b | OH |
| 720 | N | S | Q1j | a bond | H | a bond | NH | O | a bond | Q3c | OH |
| 721 | N | O | Q1a | a bond | Me | a bond | NH | S | NH | Q3a | OH |
| 722 | N | O | Q1a | a bond | Me | a bond | NH | S | NH | Q3b | OH |
| 723 | N | O | Q1a | a bond | Me | a bond | NH | S | NH | Q3c | OH |
| 724 | N | O | Q1a | a bond | Me | a bond | NH | S | a bond | Q3a | OH |
| 725 | N | O | Q1a | a bond | Me | a bond | NH | S | a bond | Q3b | OH |
| 726 | N | O | Q1a | a bond | Me | a bond | NH | S | a bond | Q3c | OH |
| 727 | N | O | Q1a | a bond | Me | a bond | NH | O | NH | Q3a | OH |
| 728 | N | O | Q1a | a bond | Me | a bond | NH | O | NH | Q3b | OH |
| 729 | N | O | Q1a | a bond | Me | a bond | NH | O | NH | Q3c | OH |
| 730 | N | O | Q1a | a bond | Me | a bond | NH | O | a bond | Q3a | OH |
| 731 | N | O | Q1a | a bond | Me | a bond | NH | O | a bond | Q3b | OH |
| 732 | N | O | Q1a | a bond | Me | a bond | NH | O | a bond | Q3c | OH |
| 733 | N | O | Q1a | a bond | H | a bond | NH | S | NH | Q3a | OH |
| 734 | N | O | Q1a | a bond | H | a bond | NH | S | NH | Q3b | OH |
| 735 | N | O | Q1a | a bond | H | a bond | NH | S | NH | Q3c | OH |
| 736 | N | O | Q1a | a bond | H | a bond | NH | S | a bond | Q3a | OH |
| 737 | N | O | Q1a | a bond | H | a bond | NH | S | a bond | Q3b | OH |
| 738 | N | O | Q1a | a bond | H | a bond | NH | S | a bond | Q3c | OH |
| 739 | N | O | Q1a | a bond | H | a bond | NH | O | NH | Q3a | OH |
| 740 | N | O | Q1a | a bond | H | a bond | NH | O | NH | Q3b | OH |
| 741 | N | O | Q1a | a bond | H | a bond | NH | O | NH | Q3c | OH |
| 742 | N | O | Q1a | a bond | H | a bond | NH | O | a bond | Q3a | OH |
| 743 | N | O | Q1a | a bond | H | a bond | NH | O | a bond | Q3b | OH |
| 744 | N | O | Q1a | a bond | H | a bond | NH | O | a bond | Q3c | OH |
| 745 | N | O | Q1b | a bond | Me | a bond | NH | S | NH | Q3a | OH |
| 746 | N | O | Q1b | a bond | Me | a bond | NH | S | NH | Q3b | OH |
| 747 | N | O | Q1b | a bond | Me | a bond | NH | S | NH | Q3c | OH |
| 748 | N | O | Q1b | a bond | Me | a bond | NH | S | a bond | Q3a | OH |
| 749 | N | O | Q1b | a bond | Me | a bond | NH | S | a bond | Q3b | OH |
| 750 | N | O | Q1b | a bond | Me | a bond | NH | S | a bond | Q3c | OH |
| 751 | N | O | Q1b | a bond | Me | a bond | NH | O | NH | Q3a | OH |
| 752 | N | O | Q1b | a bond | Me | a bond | NH | O | NH | Q3b | OH |
| 753 | N | O | Q1b | a bond | Me | a bond | NH | O | NH | Q3c | OH |
| 754 | N | O | Q1b | a bond | Me | a bond | NH | O | a bond | Q3a | OH |
| 755 | N | O | Q1b | a bond | Me | a bond | NH | O | a bond | Q3b | OH |
| 756 | N | O | Q1b | a bond | Me | a bond | NH | O | a bond | Q3c | OH |
| 757 | N | O | Q1b | a bond | H | a bond | NH | S | NH | Q3a | OH |
| 758 | N | O | Q1b | a bond | H | a bond | NH | S | NH | Q3b | OH |
| 759 | N | O | Q1b | a bond | H | a bond | NH | S | NH | Q3c | OH |
| 760 | N | O | Q1b | a bond | H | a bond | NH | S | a bond | Q3a | OH |
| 761 | N | O | Q1b | a bond | H | a bond | NH | S | a bond | Q3b | OH |
| 762 | N | O | Q1b | a bond | H | a bond | NH | S | a bond | Q3c | OH |
| 763 | N | O | Q1b | a bond | H | a bond | NH | O | NH | Q3a | OH |
| 764 | N | O | Q1b | a bond | H | a bond | NH | O | NH | Q3b | OH |
| 765 | N | O | Q1b | a bond | H | a bond | NH | O | NH | Q3c | OH |
| 766 | N | O | Q1b | a bond | H | a bond | NH | O | a bond | Q3a | OH |
| 767 | N | O | Q1b | a bond | H | a bond | NH | O | a bond | Q3b | OH |
| 768 | N | O | Q1b | a bond | H | a bond | NH | O | a bond | Q3c | OH |
| 769 | N | O | Q1c | a bond | Me | a bond | NH | S | NH | Q3a | OH |
| 770 | N | O | Q1c | a bond | Me | a bond | NH | S | NH | Q3b | OH |
| 771 | N | O | Q1c | a bond | Me | a bond | NH | S | NH | Q3c | OH |
| 772 | N | O | Q1c | a bond | Me | a bond | NH | S | a bond | Q3a | OH |
| 773 | N | O | Q1c | a bond | Me | a bond | NH | S | a bond | Q3b | OH |
| 774 | N | O | Q1c | a bond | Me | a bond | NH | S | a bond | Q3c | OH |
| 775 | N | O | Q1c | a bond | Me | a bond | NH | O | NH | Q3a | OH |
| 776 | N | O | Q1c | a bond | Me | a bond | NH | O | NH | Q3b | OH |
| 777 | N | O | Q1c | a bond | Me | a bond | NH | O | NH | Q3c | OH |
| 778 | N | O | Q1c | a bond | Me | a bond | NH | O | a bond | Q3a | OH |
| 779 | N | O | Q1c | a bond | Me | a bond | NH | O | a bond | Q3b | OH |
| 780 | N | O | Q1c | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 781 | N | O | Q1c | a bond | H | a bond | NH | S | NH | Q3a | OH |
| 782 | N | O | Q1c | a bond | H | a bond | NH | S | NH | Q3b | OH |
| 783 | N | O | Q1c | a bond | H | a bond | NH | S | NH | Q3c | OH |
| 784 | N | O | Q1c | a bond | H | a bond | NH | S | a bond | Q3a | OH |
| 785 | N | O | Q1c | a bond | H | a bond | NH | S | a bond | Q3b | OH |
| 786 | N | O | Q1c | a bond | H | a bond | NH | S | a bond | Q3c | OH |
| 787 | N | O | Q1c | a bond | H | a bond | NH | O | NH | Q3a | OH |
| 788 | N | O | Q1c | a bond | H | a bond | NH | O | NH | Q3b | OH |
| 789 | N | O | Q1c | a bond | H | a bond | NH | O | NH | Q3c | OH |
| 790 | N | O | Q1c | a bond | H | a bond | NH | O | a bond | Q3a | OH |
| 791 | N | O | Q1c | a bond | H | a bond | NH | O | a bond | Q3b | OH |
| 792 | N | O | Q1c | a bond | H | a bond | NH | O | a bond | Q3c | OH |
| 793 | N | O | Q1d | a bond | Me | a bond | NH | S | NH | Q3a | OH |
| 794 | N | O | Q1d | a bond | Me | a bond | NH | S | NH | Q3b | OH |
| 795 | N | O | Q1d | a bond | Me | a bond | NH | S | NH | Q3c | OH |
| 796 | N | O | Q1d | a bond | Me | a bond | NH | S | a bond | Q3a | OH |
| 797 | N | O | Q1d | a bond | Me | a bond | NH | S | a bond | Q3b | OH |
| 798 | N | O | Q1d | a bond | Me | a bond | NH | S | a bond | Q3c | OH |
| 799 | N | O | Q1d | a bond | Me | a bond | NH | O | NH | Q3a | OH |
| 800 | N | O | Q1d | a bond | Me | a bond | NH | O | NH | Q3b | OH |
| 801 | N | O | Q1d | a bond | Me | a bond | NH | O | NH | Q3c | OH |
| 802 | N | O | Q1d | a bond | Me | a bond | NH | O | a bond | Q3a | OH |
| 803 | N | O | Q1d | a bond | Me | a bond | NH | O | a bond | Q3b | OH |
| 804 | N | O | Q1d | a bond | Me | a bond | NH | O | a bond | Q3c | OH |
| 805 | N | O | Q1d | a bond | H | a bond | NH | S | NH | Q3a | OH |
| 806 | N | O | Q1d | a bond | H | a bond | NH | S | NH | Q3b | OH |
| 807 | N | O | Q1d | a bond | H | a bond | NH | S | NH | Q3c | OH |
| 808 | N | O | Q1d | a bond | H | a bond | NH | S | a bond | Q3a | OH |
| 809 | N | O | Q1d | a bond | H | a bond | NH | S | a bond | Q3b | OH |
| 810 | N | O | Q1d | a bond | H | a bond | NH | S | a bond | Q3c | OH |
| 811 | N | O | Q1d | a bond | H | a bond | NH | O | NH | Q3a | OH |
| 812 | N | O | Q1d | a bond | H | a bond | NH | O | NH | Q3b | OH |
| 813 | N | O | Q1d | a bond | H | a bond | NH | O | NH | Q3c | OH |
| 814 | N | O | Q1d | a bond | H | a bond | NH | O | a bond | Q3a | OH |
| 815 | N | O | Q1d | a bond | H | a bond | NH | O | a bond | Q3b | OH |
| 816 | N | O | Q1d | a bond | H | a bond | NH | O | a bond | Q3c | OH |
| 817 | N | O | Q1e | a bond | Me | a bond | NH | S | NH | Q3a | OH |
| 818 | N | O | Q1e | a bond | Me | a bond | NH | S | NH | Q3b | OH |
| 819 | N | O | Q1e | a bond | Me | a bond | NH | S | NH | Q3c | OH |
| 820 | N | O | Q1e | a bond | Me | a bond | NH | S | a bond | Q3a | OH |
| 821 | N | O | Q1e | a bond | Me | a bond | NH | S | a bond | Q3b | OH |
| 822 | N | O | Q1e | a bond | Me | a bond | NH | S | a bond | Q3c | OH |
| 823 | N | O | Q1e | a bond | Me | a bond | NH | O | NH | Q3a | OH |
| 824 | N | O | Q1e | a bond | Me | a bond | NH | O | NH | Q3b | OH |
| 825 | N | O | Q1e | a bond | Me | a bond | NH | O | NH | Q3c | OH |
| 826 | N | O | Q1e | a bond | Me | a bond | NH | O | a bond | Q3a | OH |
| 827 | N | O | Q1e | a bond | Me | a bond | NH | O | a bond | Q3b | OH |
| 828 | N | O | Q1e | a bond | Me | a bond | NH | O | a bond | Q3c | OH |
| 829 | N | O | Q1e | a bond | H | a bond | NH | S | NH | Q3a | OH |
| 830 | N | O | Q1e | a bond | H | a bond | NH | S | NH | Q3b | OH |
| 831 | N | O | Q1e | a bond | H | a bond | NH | S | NH | Q3c | OH |
| 832 | N | O | Q1e | a bond | H | a bond | NH | S | a bond | Q3a | OH |
| 833 | N | O | Q1e | a bond | H | a bond | NH | S | a bond | Q3b | OH |
| 834 | N | O | Q1e | a bond | H | a bond | NH | S | a bond | Q3c | OH |
| 835 | N | O | Q1e | a bond | H | a bond | NH | O | NH | Q3a | OH |
| 836 | N | O | Q1e | a bond | H | a bond | NH | O | NH | Q3b | OH |
| 837 | N | O | Q1e | a bond | H | a bond | NH | O | NH | Q3c | OH |
| 838 | N | O | Q1e | a bond | H | a bond | NH | O | a bond | Q3a | OH |
| 839 | N | O | Q1e | a bond | H | a bond | NH | O | a bond | Q3b | OH |
| 840 | N | O | Q1e | a bond | H | a bond | NH | O | a bond | Q3c | OH |
| 841 | N | O | Q1f | a bond | Me | a bond | NH | S | NH | Q3a | OH |
| 842 | N | O | Q1f | a bond | Me | a bond | NH | S | NH | Q3b | OH |
| 843 | N | O | Q1f | a bond | Me | a bond | NH | S | NH | Q3c | OH |
| 844 | N | O | Q1f | a bond | Me | a bond | NH | S | a bond | Q3a | OH |
| 845 | N | O | Q1f | a bond | Me | a bond | NH | S | a bond | Q3b | OH |
| 846 | N | O | Q1f | a bond | Me | a bond | NH | S | a bond | Q3c | OH |
| 847 | N | O | Q1f | a bond | Me | a bond | NH | O | NH | Q3a | OH |
| 848 | N | O | Q1f | a bond | Me | a bond | NH | O | NH | Q3b | OH |
| 849 | N | O | Q1f | a bond | Me | a bond | NH | O | NH | Q3c | OH |
| 850 | N | O | Q1f | a bond | Me | a bond | NH | O | a bond | Q3a | OH |
| 851 | N | O | Q1f | a bond | Me | a bond | NH | O | a bond | Q3b | OH |
| 852 | N | O | Q1f | a bond | Me | a bond | NH | O | a bond | Q3c | OH |
| 853 | N | O | Q1f | a bond | H | a bond | NH | S | NH | Q3a | OH |
| 854 | N | O | Q1f | a bond | H | a bond | NH | S | NH | Q3b | OH |
| 855 | N | O | Q1f | a bond | H | a bond | NH | S | NH | Q3c | OH |
| 856 | N | O | Q1f | a bond | H | a bond | NH | S | a bond | Q3a | OH |
| 857 | N | O | Q1f | a bond | H | a bond | NH | S | a bond | Q3b | OH |
| 858 | N | O | Q1f | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 859 | N | O | Q1f | a bond | H | a bond | NH | O | NH | Q3a | OH |
| 860 | N | O | Q1f | a bond | H | a bond | NH | O | NH | Q3b | OH |
| 861 | N | O | Q1f | a bond | H | a bond | NH | O | NH | Q3c | OH |
| 862 | N | O | Q1f | a bond | H | a bond | NH | O | a bond | Q3a | OH |
| 863 | N | O | Q1f | a bond | H | a bond | NH | O | a bond | Q3b | OH |
| 864 | N | O | Q1f | a bond | H | a bond | NH | O | a bond | Q3c | OH |
| 865 | N | O | Q1g | a bond | Me | a bond | NH | S | NH | Q3a | OH |
| 866 | N | O | Q1g | a bond | Me | a bond | NH | S | NH | Q3b | OH |
| 867 | N | O | Q1g | a bond | Me | a bond | NH | S | NH | Q3c | OH |
| 868 | N | O | Q1g | a bond | Me | a bond | NH | S | a bond | Q3a | OH |
| 869 | N | O | Q1g | a bond | Me | a bond | NH | S | a bond | Q3b | OH |
| 870 | N | O | Q1g | a bond | Me | a bond | NH | S | a bond | Q3c | OH |
| 871 | N | O | Q1g | a bond | Me | a bond | NH | O | NH | Q3a | OH |
| 872 | N | O | Q1g | a bond | Me | a bond | NH | O | NH | Q3b | OH |
| 873 | N | O | Q1g | a bond | Me | a bond | NH | O | NH | Q3c | OH |
| 874 | N | O | Q1g | a bond | Me | a bond | NH | O | a bond | Q3a | OH |
| 875 | N | O | Q1g | a bond | Me | a bond | NH | O | a bond | Q3b | OH |
| 876 | N | O | Q1g | a bond | Me | a bond | NH | O | a bond | Q3c | OH |
| 877 | N | O | Q1g | a bond | H | a bond | NH | S | NH | Q3a | OH |
| 878 | N | O | Q1g | a bond | H | a bond | NH | S | NH | Q3b | OH |
| 879 | N | O | Q1g | a bond | H | a bond | NH | S | NH | Q3c | OH |
| 880 | N | O | Q1g | a bond | H | a bond | NH | S | a bond | Q3a | OH |
| 881 | N | O | Q1g | a bond | H | a bond | NH | S | a bond | Q3b | OH |
| 882 | N | O | Q1g | a bond | H | a bond | NH | S | a bond | Q3c | OH |
| 883 | N | O | Q1g | a bond | H | a bond | NH | O | NH | Q3a | OH |
| 884 | N | O | Q1g | a bond | H | a bond | NH | O | NH | Q3b | OH |
| 885 | N | O | Q1g | a bond | H | a bond | NH | O | NH | Q3c | OH |
| 886 | N | O | Q1g | a bond | H | a bond | NH | O | a bond | Q3a | OH |
| 887 | N | O | Q1g | a bond | H | a bond | NH | O | a bond | Q3b | OH |
| 888 | N | O | Q1g | a bond | H | a bond | NH | O | a bond | Q3c | OH |
| 889 | N | O | Q1h | a bond | Me | a bond | NH | S | NH | Q3a | OH |
| 890 | N | O | Q1h | a bond | Me | a bond | NH | S | NH | Q3b | OH |
| 891 | N | O | Q1h | a bond | Me | a bond | NH | S | NH | Q3c | OH |
| 892 | N | O | Q1h | a bond | Me | a bond | NH | S | a bond | Q3a | OH |
| 893 | N | O | Q1h | a bond | Me | a bond | NH | S | a bond | Q3b | OH |
| 894 | N | O | Q1h | a bond | Me | a bond | NH | S | a bond | Q3c | OH |
| 895 | N | O | Q1h | a bond | Me | a bond | NH | O | NH | Q3a | OH |
| 896 | N | O | Q1h | a bond | Me | a bond | NH | O | NH | Q3b | OH |
| 897 | N | O | Q1h | a bond | Me | a bond | NH | O | NH | Q3c | OH |
| 898 | N | O | Q1h | a bond | Me | a bond | NH | O | a bond | Q3a | OH |
| 899 | N | O | Q1h | a bond | Me | a bond | NH | O | a bond | Q3b | OH |
| 900 | N | O | Q1h | a bond | Me | a bond | NH | O | a bond | Q3c | OH |
| 901 | N | O | Q1h | a bond | H | a bond | NH | S | NH | Q3a | OH |
| 902 | N | O | Q1h | a bond | H | a bond | NH | S | NH | Q3b | OH |
| 903 | N | O | Q1h | a bond | H | a bond | NH | S | NH | Q3c | OH |
| 904 | N | O | Q1h | a bond | H | a bond | NH | S | a bond | Q3a | OH |
| 905 | N | O | Q1h | a bond | H | a bond | NH | S | a bond | Q3b | OH |
| 906 | N | O | Q1h | a bond | H | a bond | NH | S | a bond | Q3c | OH |
| 907 | N | O | Q1h | a bond | H | a bond | NH | O | NH | Q3a | OH |
| 908 | N | O | Q1h | a bond | H | a bond | NH | O | NH | Q3b | OH |
| 909 | N | O | Q1h | a bond | H | a bond | NH | O | NH | Q3c | OH |
| 910 | N | O | Q1h | a bond | H | a bond | NH | O | a bond | Q3a | OH |
| 911 | N | O | Q1h | a bond | H | a bond | NH | O | a bond | Q3b | OH |
| 912 | N | O | Q1h | a bond | H | a bond | NH | O | a bond | Q3c | OH |
| 913 | N | O | Q1i | a bond | Me | a bond | NH | S | NH | Q3a | OH |
| 914 | N | O | Q1i | a bond | Me | a bond | NH | S | NH | Q3b | OH |
| 915 | N | O | Q1i | a bond | Me | a bond | NH | S | NH | Q3c | OH |
| 916 | N | O | Q1i | a bond | Me | a bond | NH | S | a bond | Q3a | OH |
| 917 | N | O | Q1i | a bond | Me | a bond | NH | S | a bond | Q3b | OH |
| 918 | N | O | Q1i | a bond | Me | a bond | NH | S | a bond | Q3c | OH |
| 919 | N | O | Q1i | a bond | Me | a bond | NH | O | NH | Q3a | OH |
| 920 | N | O | Q1i | a bond | Me | a bond | NH | O | NH | Q3b | OH |
| 921 | N | O | Q1i | a bond | Me | a bond | NH | O | NH | Q3c | OH |
| 922 | N | O | Q1i | a bond | Me | a bond | NH | O | a bond | Q3a | OH |
| 923 | N | O | Q1i | a bond | Me | a bond | NH | O | a bond | Q3b | OH |
| 924 | N | O | Q1i | a bond | Me | a bond | NH | O | a bond | Q3c | OH |
| 925 | N | O | Q1i | a bond | H | a bond | NH | S | NH | Q3a | OH |
| 926 | N | O | Q1i | a bond | H | a bond | NH | S | NH | Q3b | OH |
| 927 | N | O | Q1i | a bond | H | a bond | NH | S | NH | Q3c | OH |
| 928 | N | O | Q1i | a bond | H | a bond | NH | S | a bond | Q3a | OH |
| 929 | N | O | Q1i | a bond | H | a bond | NH | S | a bond | Q3b | OH |
| 930 | N | O | Q1i | a bond | H | a bond | NH | S | a bond | Q3c | OH |
| 931 | N | O | Q1i | a bond | H | a bond | NH | O | NH | Q3a | OH |
| 932 | N | O | Q1i | a bond | H | a bond | NH | O | NH | Q3b | OH |
| 933 | N | O | Q1i | a bond | H | a bond | NH | O | NH | Q3c | OH |
| 934 | N | O | Q1i | a bond | H | a bond | NH | O | a bond | Q3a | OH |
| 935 | N | O | Q1i | a bond | H | a bond | NH | O | a bond | Q3b | OH |
| 936 | N | O | Q1i | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 937 | N | O | Q1j | a bond | Me | a bond | NH | S | NH | Q3a | OH |
| 938 | N | O | Q1j | a bond | Me | a bond | NH | S | NH | Q3b | OH |
| 939 | N | O | Q1j | a bond | Me | a bond | NH | S | NH | Q3c | OH |
| 940 | N | O | Q1j | a bond | Me | a bond | NH | S | a bond | Q3a | OH |
| 941 | N | O | Q1j | a bond | Me | a bond | NH | S | a bond | Q3b | OH |
| 942 | N | O | Q1j | a bond | Me | a bond | NH | S | a bond | Q3c | OH |
| 943 | N | O | Q1j | a bond | Me | a bond | NH | O | NH | Q3a | OH |
| 944 | N | O | Q1j | a bond | Me | a bond | NH | O | NH | Q3b | OH |
| 945 | N | O | Q1j | a bond | Me | a bond | NH | O | NH | Q3c | OH |
| 946 | N | O | Q1j | a bond | Me | a bond | NH | O | a bond | Q3a | OH |
| 947 | N | O | Q1j | a bond | Me | a bond | NH | O | a bond | Q3b | OH |
| 948 | N | O | Q1j | a bond | Me | a bond | NH | O | a bond | Q3c | OH |
| 949 | N | O | Q1j | a bond | H | a bond | NH | S | NH | Q3a | OH |
| 950 | N | O | Q1j | a bond | H | a bond | NH | S | NH | Q3b | OH |
| 951 | N | O | Q1j | a bond | H | a bond | NH | S | NH | Q3c | OH |
| 952 | N | O | Q1j | a bond | H | a bond | NH | S | a bond | Q3a | OH |
| 953 | N | O | Q1j | a bond | H | a bond | NH | S | a bond | Q3b | OH |
| 954 | N | O | Q1j | a bond | H | a bond | NH | S | a bond | Q3c | OH |
| 955 | N | O | Q1j | a bond | H | a bond | NH | O | NH | Q3a | OH |
| 956 | N | O | Q1j | a bond | H | a bond | NH | O | NH | Q3b | OH |
| 957 | N | O | Q1j | a bond | H | a bond | NH | O | NH | Q3c | OH |
| 958 | N | O | Q1j | a bond | H | a bond | NH | O | a bond | Q3a | OH |
| 959 | N | O | Q1j | a bond | H | a bond | NH | O | a bond | Q3b | OH |
| 960 | N | O | Q1j | a bond | H | a bond | NH | O | a bond | Q3c | OH |
| 961 | CH | NMe | Q1a | a bond | Me | a bond | NH | S | NH | Q3a | OH |
| 962 | CH | NMe | Q1a | a bond | Me | a bond | NH | S | NH | Q3b | OH |
| 963 | CH | NMe | Q1a | a bond | Me | a bond | NH | S | NH | Q3c | OH |
| 964 | CH | NMe | Q1a | a bond | Me | a bond | NH | S | a bond | Q3a | OH |
| 965 | CH | NMe | Q1a | a bond | Me | a bond | NH | S | a bond | Q3b | OH |
| 966 | CH | NMe | Q1a | a bond | Me | a bond | NH | S | a bond | Q3c | OH |
| 967 | CH | NMe | Q1a | a bond | Me | a bond | NH | O | NH | Q3a | OH |
| 968 | CH | NMe | Q1a | a bond | Me | a bond | NH | O | NH | Q3b | OH |
| 969 | CH | NMe | Q1a | a bond | Me | a bond | NH | O | NH | Q3c | OH |
| 970 | CH | NMe | Q1a | a bond | Me | a bond | NH | O | a bond | Q3a | OH |
| 971 | CH | NMe | Q1a | a bond | Me | a bond | NH | O | a bond | Q3b | OH |
| 972 | CH | NMe | Q1a | a bond | Me | a bond | NH | O | a bond | Q3c | OH |
| 973 | CH | NMe | Q1a | a bond | H | a bond | NH | S | NH | Q3a | OH |
| 974 | CH | NMe | Q1a | a bond | H | a bond | NH | S | NH | Q3b | OH |
| 975 | CH | NMe | Q1a | a bond | H | a bond | NH | S | NH | Q3c | OH |
| 976 | CH | NMe | Q1a | a bond | H | a bond | NH | S | a bond | Q3a | OH |
| 977 | CH | NMe | Q1a | a bond | H | a bond | NH | S | a bond | Q3b | OH |
| 978 | CH | NMe | Q1a | a bond | H | a bond | NH | S | a bond | Q3c | OH |
| 979 | CH | NMe | Q1a | a bond | H | a bond | NH | O | NH | Q3a | OH |
| 980 | CH | NMe | Q1a | a bond | H | a bond | NH | O | NH | Q3b | OH |
| 981 | CH | NMe | Q1a | a bond | H | a bond | NH | O | NH | Q3c | OH |
| 982 | CH | NMe | Q1a | a bond | H | a bond | NH | O | a bond | Q3a | OH |
| 983 | CH | NMe | Q1a | a bond | H | a bond | NH | O | a bond | Q3b | OH |
| 984 | CH | NMe | Q1a | a bond | H | a bond | NH | O | a bond | Q3c | OH |
| 985 | CH | NMe | Q1b | a bond | Me | a bond | NH | S | NH | Q3a | OH |
| 986 | CH | NMe | Q1b | a bond | Me | a bond | NH | S | NH | Q3b | OH |
| 987 | CH | NMe | Q1b | a bond | Me | a bond | NH | S | NH | Q3c | OH |
| 988 | CH | NMe | Q1b | a bond | Me | a bond | NH | S | a bond | Q3a | OH |
| 989 | CH | NMe | Q1b | a bond | Me | a bond | NH | S | a bond | Q3b | OH |
| 990 | CH | NMe | Q1b | a bond | Me | a bond | NH | S | a bond | Q3c | OH |
| 991 | CH | NMe | Q1b | a bond | Me | a bond | NH | O | NH | Q3a | OH |
| 992 | CH | NMe | Q1b | a bond | Me | a bond | NH | O | NH | Q3b | OH |
| 993 | CH | NMe | Q1b | a bond | Me | a bond | NH | O | NH | Q3c | OH |
| 994 | CH | NMe | Q1b | a bond | Me | a bond | NH | O | a bond | Q3a | OH |
| 995 | CH | NMe | Q1b | a bond | Me | a bond | NH | O | a bond | Q3b | OH |
| 996 | CH | NMe | Q1b | a bond | Me | a bond | NH | O | a bond | Q3c | OH |
| 997 | CH | NMe | Q1b | a bond | H | a bond | NH | S | NH | Q3a | OH |
| 998 | CH | NMe | Q1b | a bond | H | a bond | NH | S | NH | Q3b | OH |
| 999 | CH | NMe | Q1b | a bond | H | a bond | NH | S | NH | Q3c | OH |
| 1000 | CH | NMe | Q1b | a bond | H | a bond | NH | S | a bond | Q3a | OH |
| 1001 | CH | NMe | Q1b | a bond | H | a bond | NH | S | a bond | Q3b | OH |
| 1002 | CH | NMe | Q1b | a bond | H | a bond | NH | S | a bond | Q3c | OH |
| 1003 | CH | NMe | Q1b | a bond | H | a bond | NH | O | NH | Q3a | OH |
| 1004 | CH | NMe | Q1b | a bond | H | a bond | NH | O | NH | Q3b | OH |
| 1005 | CH | NMe | Q1b | a bond | H | a bond | NH | O | NH | Q3c | OH |
| 1006 | CH | NMe | Q1b | a bond | H | a bond | NH | O | a bond | Q3a | OH |
| 1007 | CH | NMe | Q1b | a bond | H | a bond | NH | O | a bond | Q3b | OH |
| 1008 | CH | NMe | Q1b | a bond | H | a bond | NH | O | a bond | Q3c | OH |
| 1009 | CH | NMe | Q1c | a bond | Me | a bond | NH | S | NH | Q3a | OH |
| 1010 | CH | NMe | Q1c | a bond | Me | a bond | NH | S | NH | Q3b | OH |
| 1011 | CH | NMe | Q1c | a bond | Me | a bond | NH | S | NH | Q3c | OH |
| 1012 | CH | NMe | Q1c | a bond | Me | a bond | NH | S | a bond | Q3a | OH |
| 1013 | CH | NMe | Q1c | a bond | Me | a bond | NH | S | a bond | Q3b | OH |
| 1014 | CH | NMe | Q1c | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1015 | CH | NMe | Q1c | a bond | Me | a bond | NH | O | NH | Q3a | OH |
| 1016 | CH | NMe | Q1c | a bond | Me | a bond | NH | O | NH | Q3b | OH |
| 1017 | CH | NMe | Q1c | a bond | Me | a bond | NH | O | NH | Q3c | OH |
| 1018 | CH | NMe | Q1c | a bond | Me | a bond | NH | O | a bond | Q3a | OH |
| 1019 | CH | NMe | Q1c | a bond | Me | a bond | NH | O | a bond | Q3b | OH |
| 1020 | CH | NMe | Q1c | a bond | Me | a bond | NH | O | a bond | Q3c | OH |
| 1021 | CH | NMe | Q1c | a bond | H | a bond | NH | S | NH | Q3a | OH |
| 1022 | CH | NMe | Q1c | a bond | H | a bond | NH | S | NH | Q3b | OH |
| 1023 | CH | NMe | Q1c | a bond | H | a bond | NH | S | NH | Q3c | OH |
| 1024 | CH | NMe | Q1c | a bond | H | a bond | NH | S | a bond | Q3a | OH |
| 1025 | CH | NMe | Q1c | a bond | H | a bond | NH | S | a bond | Q3b | OH |
| 1026 | CH | NMe | Q1c | a bond | H | a bond | NH | S | a bond | Q3c | OH |
| 1027 | CH | NMe | Q1c | a bond | H | a bond | NH | O | NH | Q3a | OH |
| 1028 | CH | NMe | Q1c | a bond | H | a bond | NH | O | NH | Q3b | OH |
| 1029 | CH | NMe | Q1c | a bond | H | a bond | NH | O | NH | Q3c | OH |
| 1030 | CH | NMe | Q1c | a bond | H | a bond | NH | O | a bond | Q3a | OH |
| 1031 | CH | NMe | Q1c | a bond | H | a bond | NH | O | a bond | Q3b | OH |
| 1032 | CH | NMe | Q1c | a bond | H | a bond | NH | O | a bond | Q3c | OH |
| 1033 | CH | NMe | Q1d | a bond | Me | a bond | NH | S | NH | Q3a | OH |
| 1034 | CH | NMe | Q1d | a bond | Me | a bond | NH | S | NH | Q3b | OH |
| 1035 | CH | NMe | Q1d | a bond | Me | a bond | NH | S | NH | Q3c | OH |
| 1036 | CH | NMe | Q1d | a bond | Me | a bond | NH | S | a bond | Q3a | OH |
| 1037 | CH | NMe | Q1d | a bond | Me | a bond | NH | S | a bond | Q3b | OH |
| 1038 | CH | NMe | Q1d | a bond | Me | a bond | NH | S | a bond | Q3c | OH |
| 1039 | CH | NMe | Q1d | a bond | Me | a bond | NH | O | NH | Q3a | OH |
| 1040 | CH | NMe | Q1d | a bond | Me | a bond | NH | O | NH | Q3b | OH |
| 1041 | CH | NMe | Q1d | a bond | Me | a bond | NH | O | NH | Q3c | OH |
| 1042 | CH | NMe | Q1d | a bond | Me | a bond | NH | O | a bond | Q3a | OH |
| 1043 | CH | NMe | Q1d | a bond | Me | a bond | NH | O | a bond | Q3b | OH |
| 1044 | CH | NMe | Q1d | a bond | Me | a bond | NH | O | a bond | Q3c | OH |
| 1045 | CH | NMe | Q1d | a bond | H | a bond | NH | S | NH | Q3a | OH |
| 1046 | CH | NMe | Q1d | a bond | H | a bond | NH | S | NH | Q3b | OH |
| 1047 | CH | NMe | Q1d | a bond | H | a bond | NH | S | NH | Q3c | OH |
| 1048 | CH | NMe | Q1d | a bond | H | a bond | NH | S | a bond | Q3a | OH |
| 1049 | CH | NMe | Q1d | a bond | H | a bond | NH | S | a bond | Q3b | OH |
| 1050 | CH | NMe | Q1d | a bond | H | a bond | NH | S | a bond | Q3c | OH |
| 1051 | CH | NMe | Q1d | a bond | H | a bond | NH | O | NH | Q3a | OH |
| 1052 | CH | NMe | Q1d | a bond | H | a bond | NH | O | NH | Q3b | OH |
| 1053 | CH | NMe | Q1d | a bond | H | a bond | NH | O | NH | Q3c | OH |
| 1054 | CH | NMe | Q1d | a bond | H | a bond | NH | O | a bond | Q3a | OH |
| 1055 | CH | NMe | Q1d | a bond | H | a bond | NH | O | a bond | Q3b | OH |
| 1056 | CH | NMe | Q1d | a bond | H | a bond | NH | O | a bond | Q3c | OH |
| 1057 | CH | NMe | Q1e | a bond | Me | a bond | NH | S | NH | Q3a | OH |
| 1058 | CH | NMe | Q1e | a bond | Me | a bond | NH | S | NH | Q3b | OH |
| 1059 | CH | NMe | Q1e | a bond | Me | a bond | NH | S | NH | Q3c | OH |
| 1060 | CH | NMe | Q1e | a bond | Me | a bond | NH | S | a bond | Q3a | OH |
| 1061 | CH | NMe | Q1e | a bond | Me | a bond | NH | S | a bond | Q3b | OH |
| 1062 | CH | NMe | Q1e | a bond | Me | a bond | NH | S | a bond | Q3c | OH |
| 1063 | CH | NMe | Q1e | a bond | Me | a bond | NH | O | NH | Q3a | OH |
| 1064 | CH | NMe | Q1e | a bond | Me | a bond | NH | O | NH | Q3b | OH |
| 1065 | CH | NMe | Q1e | a bond | Me | a bond | NH | O | NH | Q3c | OH |
| 1066 | CH | NMe | Q1e | a bond | Me | a bond | NH | O | a bond | Q3a | OH |
| 1067 | CH | NMe | Q1e | a bond | Me | a bond | NH | O | a bond | Q3b | OH |
| 1068 | CH | NMe | Q1e | a bond | Me | a bond | NH | O | a bond | Q3c | OH |
| 1069 | CH | NMe | Q1e | a bond | H | a bond | NH | S | NH | Q3a | OH |
| 1070 | CH | NMe | Q1e | a bond | H | a bond | NH | S | NH | Q3b | OH |
| 1071 | CH | NMe | Q1e | a bond | H | a bond | NH | S | NH | Q3c | OH |
| 1072 | CH | NMe | Q1e | a bond | H | a bond | NH | S | a bond | Q3a | OH |
| 1073 | CH | NMe | Q1e | a bond | H | a bond | NH | S | a bond | Q3b | OH |
| 1074 | CH | NMe | Q1e | a bond | H | a bond | NH | S | a bond | Q3c | OH |
| 1075 | CH | NMe | Q1e | a bond | H | a bond | NH | O | NH | Q3a | OH |
| 1076 | CH | NMe | Q1e | a bond | H | a bond | NH | O | NH | Q3b | OH |
| 1077 | CH | NMe | Q1e | a bond | H | a bond | NH | O | NH | Q3c | OH |
| 1078 | CH | NMe | Q1e | a bond | H | a bond | NH | O | a bond | Q3a | OH |
| 1079 | CH | NMe | Q1e | a bond | H | a bond | NH | O | a bond | Q3b | OH |
| 1080 | CH | NMe | Q1e | a bond | H | a bond | NH | O | a bond | Q3c | OH |
| 1081 | CH | NMe | Q1f | a bond | Me | a bond | NH | S | NH | Q3a | OH |
| 1082 | CH | NMe | Q1f | a bond | Me | a bond | NH | S | NH | Q3b | OH |
| 1083 | CH | NMe | Q1f | a bond | Me | a bond | NH | S | NH | Q3c | OH |
| 1084 | CH | NMe | Q1f | a bond | Me | a bond | NH | S | a bond | Q3a | OH |
| 1085 | CH | NMe | Q1f | a bond | Me | a bond | NH | S | a bond | Q3b | OH |
| 1086 | CH | NMe | Q1f | a bond | Me | a bond | NH | S | a bond | Q3c | OH |
| 1087 | CH | NMe | Q1f | a bond | Me | a bond | NH | O | NH | Q3a | OH |
| 1088 | CH | NMe | Q1f | a bond | Me | a bond | NH | O | NH | Q3b | OH |
| 1089 | CH | NMe | Q1f | a bond | Me | a bond | NH | O | NH | Q3c | OH |
| 1090 | CH | NMe | Q1f | a bond | Me | a bond | NH | O | a bond | Q3a | OH |
| 1091 | CH | NMe | Q1f | a bond | Me | a bond | NH | O | a bond | Q3b | OH |
| 1092 | CH | NMe | Q1f | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1093 | CH | NMe | Q1f | a bond | H | a bond | NH | S | NH | Q3a | OH |
| 1094 | CH | NMe | Q1f | a bond | H | a bond | NH | S | NH | Q3b | OH |
| 1095 | CH | NMe | Q1f | a bond | H | a bond | NH | S | NH | Q3c | OH |
| 1096 | CH | NMe | Q1f | a bond | H | a bond | NH | S | a bond | Q3a | OH |
| 1097 | CH | NMe | Q1f | a bond | H | a bond | NH | S | a bond | Q3b | OH |
| 1098 | CH | NMe | Q1f | a bond | H | a bond | NH | S | a bond | Q3c | OH |
| 1099 | CH | NMe | Q1f | a bond | H | a bond | NH | O | NH | Q3a | OH |
| 1100 | CH | NMe | Q1f | a bond | H | a bond | NH | O | NH | Q3b | OH |
| 1101 | CH | NMe | Q1f | a bond | H | a bond | NH | O | NH | Q3c | OH |
| 1102 | CH | NMe | Q1f | a bond | H | a bond | NH | O | a bond | Q3a | OH |
| 1103 | CH | NMe | Q1f | a bond | H | a bond | NH | O | a bond | Q3b | OH |
| 1104 | CH | NMe | Q1f | a bond | H | a bond | NH | O | a bond | Q3c | OH |
| 1105 | CH | NMe | Q1g | a bond | Me | a bond | NH | S | NH | Q3a | OH |
| 1106 | CH | NMe | Q1g | a bond | Me | a bond | NH | S | NH | Q3b | OH |
| 1107 | CH | NMe | Q1g | a bond | Me | a bond | NH | S | NH | Q3c | OH |
| 1108 | CH | NMe | Q1g | a bond | Me | a bond | NH | S | a bond | Q3a | OH |
| 1109 | CH | NMe | Q1g | a bond | Me | a bond | NH | S | a bond | Q3b | OH |
| 1110 | CH | NMe | Q1g | a bond | Me | a bond | NH | S | a bond | Q3c | OH |
| 1111 | CH | NMe | Q1g | a bond | Me | a bond | NH | O | NH | Q3a | OH |
| 1112 | CH | NMe | Q1g | a bond | Me | a bond | NH | O | NH | Q3b | OH |
| 1113 | CH | NMe | Q1g | a bond | Me | a bond | NH | O | NH | Q3c | OH |
| 1114 | CH | NMe | Q1g | a bond | Me | a bond | NH | O | a bond | Q3a | OH |
| 1115 | CH | NMe | Q1g | a bond | Me | a bond | NH | O | a bond | Q3b | OH |
| 1116 | CH | NMe | Q1g | a bond | Me | a bond | NH | O | a bond | Q3c | OH |
| 1117 | CH | NMe | Q1g | a bond | H | a bond | NH | S | NH | Q3a | OH |
| 1118 | CH | NMe | Q1g | a bond | H | a bond | NH | S | NH | Q3b | OH |
| 1119 | CH | NMe | Q1g | a bond | H | a bond | NH | S | NH | Q3c | OH |
| 1120 | CH | NMe | Q1g | a bond | H | a bond | NH | S | a bond | Q3a | OH |
| 1121 | CH | NMe | Q1g | a bond | H | a bond | NH | S | a bond | Q3b | OH |
| 1122 | CH | NMe | Q1g | a bond | H | a bond | NH | S | a bond | Q3c | OH |
| 1123 | CH | NMe | Q1g | a bond | H | a bond | NH | O | NH | Q3a | OH |
| 1124 | CH | NMe | Q1g | a bond | H | a bond | NH | O | NH | Q3b | OH |
| 1125 | CH | NMe | Q1g | a bond | H | a bond | NH | O | NH | Q3c | OH |
| 1126 | CH | NMe | Q1g | a bond | H | a bond | NH | O | a bond | Q3a | OH |
| 1127 | CH | NMe | Q1g | a bond | H | a bond | NH | O | a bond | Q3b | OH |
| 1128 | CH | NMe | Q1g | a bond | H | a bond | NH | O | a bond | Q3c | OH |
| 1129 | CH | NMe | Q1h | a bond | Me | a bond | NH | S | NH | Q3a | OH |
| 1130 | CH | NMe | Q1h | a bond | Me | a bond | NH | S | NH | Q3b | OH |
| 1131 | CH | NMe | Q1h | a bond | Me | a bond | NH | S | NH | Q3c | OH |
| 1132 | CH | NMe | Q1h | a bond | Me | a bond | NH | S | a bond | Q3a | OH |
| 1133 | CH | NMe | Q1h | a bond | Me | a bond | NH | S | a bond | Q3b | OH |
| 1134 | CH | NMe | Q1h | a bond | Me | a bond | NH | S | a bond | Q3c | OH |
| 1135 | CH | NMe | Q1h | a bond | Me | a bond | NH | O | NH | Q3a | OH |
| 1136 | CH | NMe | Q1h | a bond | Me | a bond | NH | O | NH | Q3b | OH |
| 1137 | CH | NMe | Q1h | a bond | Me | a bond | NH | O | NH | Q3c | OH |
| 1138 | CH | NMe | Q1h | a bond | Me | a bond | NH | O | a bond | Q3a | OH |
| 1139 | CH | NMe | Q1h | a bond | Me | a bond | NH | O | a bond | Q3b | OH |
| 1140 | CH | NMe | Q1h | a bond | Me | a bond | NH | O | a bond | Q3c | OH |
| 1141 | CH | NMe | Q1h | a bond | H | a bond | NH | S | NH | Q3a | OH |
| 1142 | CH | NMe | Q1h | a bond | H | a bond | NH | S | NH | Q3b | OH |
| 1143 | CH | NMe | Q1h | a bond | H | a bond | NH | S | NH | Q3c | OH |
| 1144 | CH | NMe | Q1h | a bond | H | a bond | NH | S | a bond | Q3a | OH |
| 1145 | CH | NMe | Q1h | a bond | H | a bond | NH | S | a bond | Q3b | OH |
| 1146 | CH | NMe | Q1h | a bond | H | a bond | NH | S | a bond | Q3c | OH |
| 1147 | CH | NMe | Q1h | a bond | H | a bond | NH | O | NH | Q3a | OH |
| 1148 | CH | NMe | Q1h | a bond | H | a bond | NH | O | NH | Q3b | OH |
| 1149 | CH | NMe | Q1h | a bond | H | a bond | NH | O | NH | Q3c | OH |
| 1150 | CH | NMe | Q1h | a bond | H | a bond | NH | O | a bond | Q3a | OH |
| 1151 | CH | NMe | Q1h | a bond | H | a bond | NH | O | a bond | Q3b | OH |
| 1152 | CH | NMe | Q1h | a bond | H | a bond | NH | O | a bond | Q3c | OH |
| 1153 | CH | NMe | Q1i | a bond | Me | a bond | NH | S | NH | Q3a | OH |
| 1154 | CH | NMe | Q1i | a bond | Me | a bond | NH | S | NH | Q3b | OH |
| 1155 | CH | NMe | Q1i | a bond | Me | a bond | NH | S | NH | Q3c | OH |
| 1156 | CH | NMe | Q1i | a bond | Me | a bond | NH | S | a bond | Q3a | OH |
| 1157 | CH | NMe | Q1i | a bond | Me | a bond | NH | S | a bond | Q3b | OH |
| 1158 | CH | NMe | Q1i | a bond | Me | a bond | NH | S | a bond | Q3c | OH |
| 1159 | CH | NMe | Q1i | a bond | Me | a bond | NH | O | NH | Q3a | OH |
| 1160 | CH | NMe | Q1i | a bond | Me | a bond | NH | O | NH | Q3b | OH |
| 1161 | CH | NMe | Q1i | a bond | Me | a bond | NH | O | NH | Q3c | OH |
| 1162 | CH | NMe | Q1i | a bond | Me | a bond | NH | O | a bond | Q3a | OH |
| 1163 | CH | NMe | Q1i | a bond | Me | a bond | NH | O | a bond | Q3b | OH |
| 1164 | CH | NMe | Q1i | a bond | Me | a bond | NH | O | a bond | Q3c | OH |
| 1165 | CH | NMe | Q1i | a bond | H | a bond | NH | S | NH | Q3a | OH |
| 1166 | CH | NMe | Q1i | a bond | H | a bond | NH | S | NH | Q3b | OH |
| 1167 | CH | NMe | Q1i | a bond | H | a bond | NH | S | NH | Q3c | OH |
| 1168 | CH | NMe | Q1i | a bond | H | a bond | NH | S | a bond | Q3a | OH |
| 1169 | CH | NMe | Q1i | a bond | H | a bond | NH | S | a bond | Q3b | OH |
| 1170 | CH | NMe | Q1i | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1171 | CH | NMe | Q1i | a bond | H | a bond | NH | O | NH | Q3a | OH |
| 1172 | CH | NMe | Q1i | a bond | H | a bond | NH | O | NH | Q3b | OH |
| 1173 | CH | NMe | Q1i | a bond | H | a bond | NH | O | NH | Q3c | OH |
| 1174 | CH | NMe | Q1i | a bond | H | a bond | NH | O | a bond | Q3a | OH |
| 1175 | CH | NMe | Q1i | a bond | H | a bond | NH | O | a bond | Q3b | OH |
| 1176 | CH | NMe | Q1i | a bond | H | a bond | NH | O | a bond | Q3c | OH |
| 1177 | CH | NMe | Q1j | a bond | Me | a bond | NH | S | NH | Q3a | OH |
| 1178 | CH | NMe | Q1j | a bond | Me | a bond | NH | S | NH | Q3b | OH |
| 1179 | CH | NMe | Q1j | a bond | Me | a bond | NH | S | NH | Q3c | OH |
| 1180 | CH | NMe | Q1j | a bond | Me | a bond | NH | S | a bond | Q3a | OH |
| 1181 | CH | NMe | Q1j | a bond | Me | a bond | NH | S | a bond | Q3b | OH |
| 1182 | CH | NMe | Q1j | a bond | Me | a bond | NH | S | a bond | Q3c | OH |
| 1183 | CH | NMe | Q1j | a bond | Me | a bond | NH | O | NH | Q3a | OH |
| 1184 | CH | NMe | Q1j | a bond | Me | a bond | NH | O | NH | Q3b | OH |
| 1185 | CH | NMe | Q1j | a bond | Me | a bond | NH | O | NH | Q3c | OH |
| 1186 | CH | NMe | Q1j | a bond | Me | a bond | NH | O | a bond | Q3a | OH |
| 1187 | CH | NMe | Q1j | a bond | Me | a bond | NH | O | a bond | Q3b | OH |
| 1188 | CH | NMe | Q1j | a bond | Me | a bond | NH | O | a bond | Q3c | OH |
| 1189 | CH | NMe | Q1j | a bond | H | a bond | NH | S | NH | Q3a | OH |
| 1190 | CH | NMe | Q1j | a bond | H | a bond | NH | S | NH | Q3b | OH |
| 1191 | CH | NMe | Q1j | a bond | H | a bond | NH | S | NH | Q3c | OH |
| 1192 | CH | NMe | Q1j | a bond | H | a bond | NH | S | a bond | Q3a | OH |
| 1193 | CH | NMe | Q1j | a bond | H | a bond | NH | S | a bond | Q3b | OH |
| 1194 | CH | NMe | Q1j | a bond | H | a bond | NH | S | a bond | Q3c | OH |
| 1195 | CH | NMe | Q1j | a bond | H | a bond | NH | O | NH | Q3a | OH |
| 1196 | CH | NMe | Q1j | a bond | H | a bond | NH | O | NH | Q3b | OH |
| 1197 | CH | NMe | Q1j | a bond | H | a bond | NH | O | NH | Q3c | OH |
| 1198 | CH | NMe | Q1j | a bond | H | a bond | NH | O | a bond | Q3a | OH |
| 1199 | CH | NMe | Q1j | a bond | H | a bond | NH | O | a bond | Q3b | OH |
| 1200 | CH | NMe | Q1j | a bond | H | a bond | NH | O | a bond | Q3c | OH |
| 1201 | CH | NEt | Q1a | a bond | Me | a bond | NH | S | NH | Q3a | OH |
| 1202 | CH | NEt | Q1a | a bond | Me | a bond | NH | S | NH | Q3b | OH |
| 1203 | CH | NEt | Q1a | a bond | Me | a bond | NH | S | NH | Q3c | OH |
| 1204 | CH | NEt | Q1a | a bond | Me | a bond | NH | S | a bond | Q3a | OH |
| 1205 | CH | NEt | Q1a | a bond | Me | a bond | NH | S | a bond | Q3b | OH |
| 1206 | CH | NEt | Q1a | a bond | Me | a bond | NH | S | a bond | Q3c | OH |
| 1207 | CH | NEt | Q1a | a bond | Me | a bond | NH | O | NH | Q3a | OH |
| 1208 | CH | NEt | Q1a | a bond | Me | a bond | NH | O | NH | Q3b | OH |
| 1209 | CH | NEt | Q1a | a bond | Me | a bond | NH | O | NH | Q3c | OH |
| 1210 | CH | NEt | Q1a | a bond | Me | a bond | NH | O | a bond | Q3a | OH |
| 1211 | CH | NEt | Q1a | a bond | Me | a bond | NH | O | a bond | Q3b | OH |
| 1212 | CH | NEt | Q1a | a bond | Me | a bond | NH | O | a bond | Q3c | OH |
| 1213 | CH | NEt | Q1a | a bond | H | a bond | NH | S | NH | Q3a | OH |
| 1214 | CH | NEt | Q1a | a bond | H | a bond | NH | S | NH | Q3b | OH |
| 1215 | CH | NEt | Q1a | a bond | H | a bond | NH | S | NH | Q3c | OH |
| 1216 | CH | NEt | Q1a | a bond | H | a bond | NH | S | a bond | Q3a | OH |
| 1217 | CH | NEt | Q1a | a bond | H | a bond | NH | S | a bond | Q3b | OH |
| 1218 | CH | NEt | Q1a | a bond | H | a bond | NH | S | a bond | Q3c | OH |
| 1219 | CH | NEt | Q1a | a bond | H | a bond | NH | O | NH | Q3a | OH |
| 1220 | CH | NEt | Q1a | a bond | H | a bond | NH | O | NH | Q3b | OH |
| 1221 | CH | NEt | Q1a | a bond | H | a bond | NH | O | NH | Q3c | OH |
| 1222 | CH | NEt | Q1a | a bond | H | a bond | NH | O | a bond | Q3a | OH |
| 1223 | CH | NEt | Q1a | a bond | H | a bond | NH | O | a bond | Q3b | OH |
| 1224 | CH | NEt | Q1a | a bond | H | a bond | NH | O | a bond | Q3c | OH |
| 1225 | CH | NEt | Q1b | a bond | Me | a bond | NH | S | NH | Q3a | OH |
| 1226 | CH | NEt | Q1b | a bond | Me | a bond | NH | S | NH | Q3b | OH |
| 1227 | CH | NEt | Q1b | a bond | Me | a bond | NH | S | NH | Q3c | OH |
| 1228 | CH | NEt | Q1b | a bond | Me | a bond | NH | S | a bond | Q3a | OH |
| 1229 | CH | NEt | Q1b | a bond | Me | a bond | NH | S | a bond | Q3b | OH |
| 1230 | CH | NEt | Q1b | a bond | Me | a bond | NH | S | a bond | Q3c | OH |
| 1231 | CH | NEt | Q1b | a bond | Me | a bond | NH | O | NH | Q3a | OH |
| 1232 | CH | NEt | Q1b | a bond | Me | a bond | NH | O | NH | Q3b | OH |
| 1233 | CH | NEt | Q1b | a bond | Me | a bond | NH | O | NH | Q3c | OH |
| 1234 | CH | NEt | Q1b | a bond | Me | a bond | NH | O | a bond | Q3a | OH |
| 1235 | CH | NEt | Q1b | a bond | Me | a bond | NH | O | a bond | Q3b | OH |
| 1236 | CH | NEt | Q1b | a bond | Me | a bond | NH | O | a bond | Q3c | OH |
| 1237 | CH | NEt | Q1b | a bond | H | a bond | NH | S | NH | Q3a | OH |
| 1238 | CH | NEt | Q1b | a bond | H | a bond | NH | S | NH | Q3b | OH |
| 1239 | CH | NEt | Q1b | a bond | H | a bond | NH | S | NH | Q3c | OH |
| 1240 | CH | NEt | Q1b | a bond | H | a bond | NH | S | a bond | Q3a | OH |
| 1241 | CH | NEt | Q1b | a bond | H | a bond | NH | S | a bond | Q3b | OH |
| 1242 | CH | NEt | Q1b | a bond | H | a bond | NH | S | a bond | Q3c | OH |
| 1243 | CH | NEt | Q1b | a bond | H | a bond | NH | O | NH | Q3a | OH |
| 1244 | CH | NEt | Q1b | a bond | H | a bond | NH | O | NH | Q3b | OH |
| 1245 | CH | NEt | Q1b | a bond | H | a bond | NH | O | NH | Q3c | OH |
| 1246 | CH | NEt | Q1b | a bond | H | a bond | NH | O | a bond | Q3a | OH |
| 1247 | CH | NEt | Q1b | a bond | H | a bond | NH | O | a bond | Q3b | OH |
| 1248 | CH | NEt | Q1b | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1249 | CH | NEt | Q1c | a bond | Me | a bond | NH | S | NH | Q3a | OH |
| 1250 | CH | NEt | Q1c | a bond | Me | a bond | NH | S | NH | Q3b | OH |
| 1251 | CH | NEt | Q1c | a bond | Me | a bond | NH | S | NH | Q3c | OH |
| 1252 | CH | NEt | Q1c | a bond | Me | a bond | NH | S | a bond | Q3a | OH |
| 1253 | CH | NEt | Q1c | a bond | Me | a bond | NH | S | a bond | Q3b | OH |
| 1254 | CH | NEt | Q1c | a bond | Me | a bond | NH | S | a bond | Q3c | OH |
| 1255 | CH | NEt | Q1c | a bond | Me | a bond | NH | O | NH | Q3a | OH |
| 1256 | CH | NEt | Q1c | a bond | Me | a bond | NH | O | NH | Q3b | OH |
| 1257 | CH | NEt | Q1c | a bond | Me | a bond | NH | O | NH | Q3c | OH |
| 1258 | CH | NEt | Q1c | a bond | Me | a bond | NH | O | a bond | Q3a | OH |
| 1259 | CH | NEt | Q1c | a bond | Me | a bond | NH | O | a bond | Q3b | OH |
| 1260 | CH | NEt | Q1c | a bond | Me | a bond | NH | O | a bond | Q3c | OH |
| 1261 | CH | NEt | Q1c | a bond | H | a bond | NH | S | NH | Q3a | OH |
| 1262 | CH | NEt | Q1c | a bond | H | a bond | NH | S | NH | Q3b | OH |
| 1263 | CH | NEt | Q1c | a bond | H | a bond | NH | S | NH | Q3c | OH |
| 1264 | CH | NEt | Q1c | a bond | H | a bond | NH | S | a bond | Q3a | OH |
| 1265 | CH | NEt | Q1c | a bond | H | a bond | NH | S | a bond | Q3b | OH |
| 1266 | CH | NEt | Q1c | a bond | H | a bond | NH | S | a bond | Q3c | OH |
| 1267 | CH | NEt | Q1c | a bond | H | a bond | NH | O | NH | Q3a | OH |
| 1268 | CH | NEt | Q1c | a bond | H | a bond | NH | O | NH | Q3b | OH |
| 1269 | CH | NEt | Q1c | a bond | H | a bond | NH | O | NH | Q3c | OH |
| 1270 | CH | NEt | Q1c | a bond | H | a bond | NH | O | a bond | Q3a | OH |
| 1271 | CH | NEt | Q1c | a bond | H | a bond | NH | O | a bond | Q3b | OH |
| 1272 | CH | NEt | Q1c | a bond | H | a bond | NH | O | a bond | Q3c | OH |
| 1273 | CH | NEt | Q1d | a bond | Me | a bond | NH | S | NH | Q3a | OH |
| 1274 | CH | NEt | Q1d | a bond | Me | a bond | NH | S | NH | Q3b | OH |
| 1275 | CH | NEt | Q1d | a bond | Me | a bond | NH | S | NH | Q3c | OH |
| 1276 | CH | NEt | Q1d | a bond | Me | a bond | NH | S | a bond | Q3a | OH |
| 1277 | CH | NEt | Q1d | a bond | Me | a bond | NH | S | a bond | Q3b | OH |
| 1278 | CH | NEt | Q1d | a bond | Me | a bond | NH | S | a bond | Q3c | OH |
| 1279 | CH | NEt | Q1d | a bond | Me | a bond | NH | O | NH | Q3a | OH |
| 1280 | CH | NEt | Q1d | a bond | Me | a bond | NH | O | NH | Q3b | OH |
| 1281 | CH | NEt | Q1d | a bond | Me | a bond | NH | O | NH | Q3c | OH |
| 1282 | CH | NEt | Q1d | a bond | Me | a bond | NH | O | a bond | Q3a | OH |
| 1283 | CH | NEt | Q1d | a bond | Me | a bond | NH | O | a bond | Q3b | OH |
| 1284 | CH | NEt | Q1d | a bond | Me | a bond | NH | O | a bond | Q3c | OH |
| 1285 | CH | NEt | Q1d | a bond | H | a bond | NH | S | NH | Q3a | OH |
| 1286 | CH | NEt | Q1d | a bond | H | a bond | NH | S | NH | Q3b | OH |
| 1287 | CH | NEt | Q1d | a bond | H | a bond | NH | S | NH | Q3c | OH |
| 1288 | CH | NEt | Q1d | a bond | H | a bond | NH | S | a bond | Q3a | OH |
| 1289 | CH | NEt | Q1d | a bond | H | a bond | NH | S | a bond | Q3b | OH |
| 1290 | CH | NEt | Q1d | a bond | H | a bond | NH | S | a bond | Q3c | OH |
| 1291 | CH | NEt | Q1d | a bond | H | a bond | NH | O | NH | Q3a | OH |
| 1292 | CH | NEt | Q1d | a bond | H | a bond | NH | O | NH | Q3b | OH |
| 1293 | CH | NEt | Q1d | a bond | H | a bond | NH | O | NH | Q3c | OH |
| 1294 | CH | NEt | Q1d | a bond | H | a bond | NH | O | a bond | Q3a | OH |
| 1295 | CH | NEt | Q1d | a bond | H | a bond | NH | O | a bond | Q3b | OH |
| 1296 | CH | NEt | Q1d | a bond | H | a bond | NH | O | a bond | Q3c | OH |
| 1297 | CH | NEt | Q1e | a bond | Me | a bond | NH | S | NH | Q3a | OH |
| 1298 | CH | NEt | Q1e | a bond | Me | a bond | NH | S | NH | Q3b | OH |
| 1299 | CH | NEt | Q1e | a bond | Me | a bond | NH | S | NH | Q3c | OH |
| 1300 | CH | NEt | Q1e | a bond | Me | a bond | NH | S | a bond | Q3a | OH |
| 1301 | CH | NEt | Q1e | a bond | Me | a bond | NH | S | a bond | Q3b | OH |
| 1302 | CH | NEt | Q1e | a bond | Me | a bond | NH | S | a bond | Q3c | OH |
| 1303 | CH | NEt | Q1e | a bond | Me | a bond | NH | O | NH | Q3a | OH |
| 1304 | CH | NEt | Q1e | a bond | Me | a bond | NH | O | NH | Q3b | OH |
| 1305 | CH | NEt | Q1e | a bond | Me | a bond | NH | O | NH | Q3c | OH |
| 1306 | CH | NEt | Q1e | a bond | Me | a bond | NH | O | a bond | Q3a | OH |
| 1307 | CH | NEt | Q1e | a bond | Me | a bond | NH | O | a bond | Q3b | OH |
| 1308 | CH | NEt | Q1e | a bond | Me | a bond | NH | O | a bond | Q3c | OH |
| 1309 | CH | NEt | Q1e | a bond | H | a bond | NH | S | NH | Q3a | OH |
| 1310 | CH | NEt | Q1e | a bond | H | a bond | NH | S | NH | Q3b | OH |
| 1311 | CH | NEt | Q1e | a bond | H | a bond | NH | S | NH | Q3c | OH |
| 1312 | CH | NEt | Q1e | a bond | H | a bond | NH | S | a bond | Q3a | OH |
| 1313 | CH | NEt | Q1e | a bond | H | a bond | NH | S | a bond | Q3b | OH |
| 1314 | CH | NEt | Q1e | a bond | H | a bond | NH | S | a bond | Q3c | OH |
| 1315 | CH | NEt | Q1e | a bond | H | a bond | NH | O | NH | Q3a | OH |
| 1316 | CH | NEt | Q1e | a bond | H | a bond | NH | O | NH | Q3b | OH |
| 1317 | CH | NEt | Q1e | a bond | H | a bond | NH | O | NH | Q3c | OH |
| 1318 | CH | NEt | Q1e | a bond | H | a bond | NH | O | a bond | Q3a | OH |
| 1319 | CH | NEt | Q1e | a bond | H | a bond | NH | O | a bond | Q3b | OH |
| 1320 | CH | NEt | Q1e | a bond | H | a bond | NH | O | a bond | Q3c | OH |
| 1321 | CH | NEt | Q1f | a bond | Me | a bond | NH | S | NH | Q3a | OH |
| 1322 | CH | NEt | Q1f | a bond | Me | a bond | NH | S | NH | Q3b | OH |
| 1323 | CH | NEt | Q1f | a bond | Me | a bond | NH | S | NH | Q3c | OH |
| 1324 | CH | NEt | Q1f | a bond | Me | a bond | NH | S | a bond | Q3a | OH |
| 1325 | CH | NEt | Q1f | a bond | Me | a bond | NH | S | a bond | Q3b | OH |
| 1326 | CH | NEt | Q1f | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1327 | CH | NEt | Q1f | a bond | Me | a bond | NH | O | NH | Q3a | OH |
| 1328 | CH | NEt | Q1f | a bond | Me | a bond | NH | O | NH | Q3b | OH |
| 1329 | CH | NEt | Q1f | a bond | Me | a bond | NH | O | NH | Q3c | OH |
| 1330 | CH | NEt | Q1f | a bond | Me | a bond | NH | O | a bond | Q3a | OH |
| 1331 | CH | NEt | Q1f | a bond | Me | a bond | NH | O | a bond | Q3b | OH |
| 1332 | CH | NEt | Q1f | a bond | Me | a bond | NH | O | a bond | Q3c | OH |
| 1333 | CH | NEt | Q1f | a bond | H | a bond | NH | S | NH | Q3a | OH |
| 1334 | CH | NEt | Q1f | a bond | H | a bond | NH | S | NH | Q3b | OH |
| 1335 | CH | NEt | Q1f | a bond | H | a bond | NH | S | NH | Q3c | OH |
| 1336 | CH | NEt | Q1f | a bond | H | a bond | NH | S | a bond | Q3a | OH |
| 1337 | CH | NEt | Q1f | a bond | H | a bond | NH | S | a bond | Q3b | OH |
| 1338 | CH | NEt | Q1f | a bond | H | a bond | NH | S | a bond | Q3c | OH |
| 1339 | CH | NEt | Q1f | a bond | H | a bond | NH | O | NH | Q3a | OH |
| 1340 | CH | NEt | Q1f | a bond | H | a bond | NH | O | NH | Q3b | OH |
| 1341 | CH | NEt | Q1f | a bond | H | a bond | NH | O | NH | Q3c | OH |
| 1342 | CH | NEt | Q1f | a bond | H | a bond | NH | O | a bond | Q3a | OH |
| 1343 | CH | NEt | Q1f | a bond | H | a bond | NH | O | a bond | Q3b | OH |
| 1344 | CH | NEt | Q1f | a bond | H | a bond | NH | O | a bond | Q3c | OH |
| 1345 | CH | NEt | Q1g | a bond | Me | a bond | NH | S | NH | Q3a | OH |
| 1346 | CH | NEt | Q1g | a bond | Me | a bond | NH | S | NH | Q3b | OH |
| 1347 | CH | NEt | Q1g | a bond | Me | a bond | NH | S | NH | Q3c | OH |
| 1348 | CH | NEt | Q1g | a bond | Me | a bond | NH | S | a bond | Q3a | OH |
| 1349 | CH | NEt | Q1g | a bond | Me | a bond | NH | S | a bond | Q3b | OH |
| 1350 | CH | NEt | Q1g | a bond | Me | a bond | NH | S | a bond | Q3c | OH |
| 1351 | CH | NEt | Q1g | a bond | Me | a bond | NH | O | NH | Q3a | OH |
| 1352 | CH | NEt | Q1g | a bond | Me | a bond | NH | O | NH | Q3b | OH |
| 1353 | CH | NEt | Q1g | a bond | Me | a bond | NH | O | NH | Q3c | OH |
| 1354 | CH | NEt | Q1g | a bond | Me | a bond | NH | O | a bond | Q3a | OH |
| 1355 | CH | NEt | Q1g | a bond | Me | a bond | NH | O | a bond | Q3b | OH |
| 1356 | CH | NEt | Q1g | a bond | Me | a bond | NH | O | a bond | Q3c | OH |
| 1357 | CH | NEt | Q1g | a bond | H | a bond | NH | S | NH | Q3a | OH |
| 1358 | CH | NEt | Q1g | a bond | H | a bond | NH | S | NH | Q3b | OH |
| 1359 | CH | NEt | Q1g | a bond | H | a bond | NH | S | NH | Q3c | OH |
| 1360 | CH | NEt | Q1g | a bond | H | a bond | NH | S | a bond | Q3a | OH |
| 1361 | CH | NEt | Q1g | a bond | H | a bond | NH | S | a bond | Q3b | OH |
| 1362 | CH | NEt | Q1g | a bond | H | a bond | NH | S | a bond | Q3c | OH |
| 1363 | CH | NEt | Q1g | a bond | H | a bond | NH | O | NH | Q3a | OH |
| 1364 | CH | NEt | Q1g | a bond | H | a bond | NH | O | NH | Q3b | OH |
| 1365 | CH | NEt | Q1g | a bond | H | a bond | NH | O | NH | Q3c | OH |
| 1366 | CH | NEt | Q1g | a bond | H | a bond | NH | O | a bond | Q3a | OH |
| 1367 | CH | NEt | Q1g | a bond | H | a bond | NH | O | a bond | Q3b | OH |
| 1368 | CH | NEt | Q1g | a bond | H | a bond | NH | O | a bond | Q3c | OH |
| 1369 | CH | NEt | Q1h | a bond | Me | a bond | NH | S | NH | Q3a | OH |
| 1370 | CH | NEt | Q1h | a bond | Me | a bond | NH | S | NH | Q3b | OH |
| 1371 | CH | NEt | Q1h | a bond | Me | a bond | NH | S | NH | Q3c | OH |
| 1372 | CH | NEt | Q1h | a bond | Me | a bond | NH | S | a bond | Q3a | OH |
| 1373 | CH | NEt | Q1h | a bond | Me | a bond | NH | S | a bond | Q3b | OH |
| 1374 | CH | NEt | Q1h | a bond | Me | a bond | NH | S | a bond | Q3c | OH |
| 1375 | CH | NEt | Q1h | a bond | Me | a bond | NH | O | NH | Q3a | OH |
| 1376 | CH | NEt | Q1h | a bond | Me | a bond | NH | O | NH | Q3b | OH |
| 1377 | CH | NEt | Q1h | a bond | Me | a bond | NH | O | NH | Q3c | OH |
| 1378 | CH | NEt | Q1h | a bond | Me | a bond | NH | O | a bond | Q3a | OH |
| 1379 | CH | NEt | Q1h | a bond | Me | a bond | NH | O | a bond | Q3b | OH |
| 1380 | CH | NEt | Q1h | a bond | Me | a bond | NH | O | a bond | Q3c | OH |
| 1381 | CH | NEt | Q1h | a bond | H | a bond | NH | S | NH | Q3a | OH |
| 1382 | CH | NEt | Q1h | a bond | H | a bond | NH | S | NH | Q3b | OH |
| 1383 | CH | NEt | Q1h | a bond | H | a bond | NH | S | NH | Q3c | OH |
| 1384 | CH | NEt | Q1h | a bond | H | a bond | NH | S | a bond | Q3a | OH |
| 1385 | CH | NEt | Q1h | a bond | H | a bond | NH | S | a bond | Q3b | OH |
| 1386 | CH | NEt | Q1h | a bond | H | a bond | NH | S | a bond | Q3c | OH |
| 1387 | CH | NEt | Q1h | a bond | H | a bond | NH | O | NH | Q3a | OH |
| 1388 | CH | NEt | Q1h | a bond | H | a bond | NH | O | NH | Q3b | OH |
| 1389 | CH | NEt | Q1h | a bond | H | a bond | NH | O | NH | Q3c | OH |
| 1390 | CH | NEt | Q1h | a bond | H | a bond | NH | O | a bond | Q3a | OH |
| 1391 | CH | NEt | Q1h | a bond | H | a bond | NH | O | a bond | Q3b | OH |
| 1392 | CH | NEt | Q1h | a bond | H | a bond | NH | O | a bond | Q3c | OH |
| 1393 | CH | NEt | Q1i | a bond | Me | a bond | NH | S | NH | Q3a | OH |
| 1394 | CH | NEt | Q1i | a bond | Me | a bond | NH | S | NH | Q3b | OH |
| 1395 | CH | NEt | Q1i | a bond | Me | a bond | NH | S | NH | Q3c | OH |
| 1396 | CH | NEt | Q1i | a bond | Me | a bond | NH | S | a bond | Q3a | OH |
| 1397 | CH | NEt | Q1i | a bond | Me | a bond | NH | S | a bond | Q3b | OH |
| 1398 | CH | NEt | Q1i | a bond | Me | a bond | NH | S | a bond | Q3c | OH |
| 1399 | CH | NEt | Q1i | a bond | Me | a bond | NH | O | NH | Q3a | OH |
| 1400 | CH | NEt | Q1i | a bond | Me | a bond | NH | O | NH | Q3b | OH |
| 1401 | CH | NEt | Q1i | a bond | Me | a bond | NH | O | NH | Q3c | OH |
| 1402 | CH | NEt | Q1i | a bond | Me | a bond | NH | O | a bond | Q3a | OH |
| 1403 | CH | NEt | Q1i | a bond | Me | a bond | NH | O | a bond | Q3b | OH |
| 1404 | CH | NEt | Q1i | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1405 | CH | NEt | Q1i | a bond | H | a bond | NH | S | NH | Q3a | OH |
| 1406 | CH | NEt | Q1i | a bond | H | a bond | NH | S | NH | Q3b | OH |
| 1407 | CH | NEt | Q1i | a bond | H | a bond | NH | S | NH | Q3c | OH |
| 1408 | CH | NEt | Q1i | a bond | H | a bond | NH | S | a bond | Q3a | OH |
| 1409 | CH | NEt | Q1i | a bond | H | a bond | NH | S | a bond | Q3b | OH |
| 1410 | CH | NEt | Q1i | a bond | H | a bond | NH | S | a bond | Q3c | OH |
| 1411 | CH | NEt | Q1i | a bond | H | a bond | NH | O | NH | Q3a | OH |
| 1412 | CH | NEt | Q1i | a bond | H | a bond | NH | O | NH | Q3b | OH |
| 1413 | CH | NEt | Q1i | a bond | H | a bond | NH | O | NH | Q3c | OH |
| 1414 | CH | NEt | Q1i | a bond | H | a bond | NH | O | a bond | Q3a | OH |
| 1415 | CH | NEt | Q1i | a bond | H | a bond | NH | O | a bond | Q3b | OH |
| 1416 | CH | NEt | Q1i | a bond | H | a bond | NH | O | a bond | Q3c | OH |
| 1417 | CH | NEt | Q1j | a bond | Me | a bond | NH | S | NH | Q3a | OH |
| 1418 | CH | NEt | Q1j | a bond | Me | a bond | NH | S | NH | Q3b | OH |
| 1419 | CH | NEt | Q1j | a bond | Me | a bond | NH | S | NH | Q3c | OH |
| 1420 | CH | NEt | Q1j | a bond | Me | a bond | NH | S | a bond | Q3a | OH |
| 1421 | CH | NEt | Q1j | a bond | Me | a bond | NH | S | a bond | Q3b | OH |
| 1422 | CH | NEt | Q1j | a bond | Me | a bond | NH | S | a bond | Q3c | OH |
| 1423 | CH | NEt | Q1j | a bond | Me | a bond | NH | O | NH | Q3a | OH |
| 1424 | CH | NEt | Q1j | a bond | Me | a bond | NH | O | NH | Q3b | OH |
| 1425 | CH | NEt | Q1j | a bond | Me | a bond | NH | O | NH | Q3c | OH |
| 1426 | CH | NEt | Q1j | a bond | Me | a bond | NH | O | a bond | Q3a | OH |
| 1427 | CH | NEt | Q1j | a bond | Me | a bond | NH | O | a bond | Q3b | OH |
| 1428 | CH | NEt | Q1j | a bond | Me | a bond | NH | O | a bond | Q3c | OH |
| 1429 | CH | NEt | Q1j | a bond | H | a bond | NH | S | NH | Q3a | OH |
| 1430 | CH | NEt | Q1j | a bond | H | a bond | NH | S | NH | Q3b | OH |
| 1431 | CH | NEt | Q1j | a bond | H | a bond | NH | S | NH | Q3c | OH |
| 1432 | CH | NEt | Q1j | a bond | H | a bond | NH | S | a bond | Q3a | OH |
| 1433 | CH | NEt | Q1j | a bond | H | a bond | NH | S | a bond | Q3b | OH |
| 1434 | CH | NEt | Q1j | a bond | H | a bond | NH | S | a bond | Q3c | OH |
| 1435 | CH | NEt | Q1j | a bond | H | a bond | NH | O | NH | Q3a | OH |
| 1436 | CH | NEt | Q1j | a bond | H | a bond | NH | O | NH | Q3b | OH |
| 1437 | CH | NEt | Q1j | a bond | H | a bond | NH | O | NH | Q3c | OH |
| 1438 | CH | NEt | Q1j | a bond | H | a bond | NH | O | a bond | Q3a | OH |
| 1439 | CH | NEt | Q1j | a bond | H | a bond | NH | O | a bond | Q3b | OH |
| 1440 | CH | NEt | Q1j | a bond | H | a bond | NH | O | a bond | Q3c | OH |
| 1441 | CH | S | Q1a | a bond | Me | a bond | NH | S | NH | Q3a | OH |
| 1442 | CH | S | Q1a | a bond | Me | a bond | NH | S | NH | Q3b | OH |
| 1443 | CH | S | Q1a | a bond | Me | a bond | NH | S | NH | Q3c | OH |
| 1444 | CH | S | Q1a | a bond | Me | a bond | NH | S | a bond | Q3a | OH |
| 1445 | CH | S | Q1a | a bond | Me | a bond | NH | S | a bond | Q3b | OH |
| 1446 | CH | S | Q1a | a bond | Me | a bond | NH | S | a bond | Q3c | OH |
| 1447 | CH | S | Q1a | a bond | Me | a bond | NH | O | NH | Q3a | OH |
| 1448 | CH | S | Q1a | a bond | Me | a bond | NH | O | NH | Q3b | OH |
| 1449 | CH | S | Q1a | a bond | Me | a bond | NH | O | NH | Q3c | OH |
| 1450 | CH | S | Q1a | a bond | Me | a bond | NH | O | a bond | Q3a | OH |
| 1451 | CH | S | Q1a | a bond | Me | a bond | NH | O | a bond | Q3b | OH |
| 1452 | CH | S | Q1a | a bond | Me | a bond | NH | O | a bond | Q3c | OH |
| 1453 | CH | S | Q1a | a bond | H | a bond | NH | S | NH | Q3a | OH |
| 1454 | CH | S | Q1a | a bond | H | a bond | NH | S | NH | Q3b | OH |
| 1455 | CH | S | Q1a | a bond | H | a bond | NH | S | NH | Q3c | OH |
| 1456 | CH | S | Q1a | a bond | H | a bond | NH | S | a bond | Q3a | OH |
| 1457 | CH | S | Q1a | a bond | H | a bond | NH | S | a bond | Q3b | OH |
| 1458 | CH | S | Q1a | a bond | H | a bond | NH | S | a bond | Q3c | OH |
| 1459 | CH | S | Q1a | a bond | H | a bond | NH | O | NH | Q3a | OH |
| 1460 | CH | S | Q1a | a bond | H | a bond | NH | O | NH | Q3b | OH |
| 1461 | CH | S | Q1a | a bond | H | a bond | NH | O | NH | Q3c | OH |
| 1462 | CH | S | Q1a | a bond | H | a bond | NH | O | a bond | Q3a | OH |
| 1463 | CH | S | Q1a | a bond | H | a bond | NH | O | a bond | Q3b | OH |
| 1464 | CH | S | Q1a | a bond | H | a bond | NH | O | a bond | Q3c | OH |
| 1465 | CH | S | Q1b | a bond | Me | a bond | NH | S | NH | Q3a | OH |
| 1466 | CH | S | Q1b | a bond | Me | a bond | NH | S | NH | Q3b | OH |
| 1467 | CH | S | Q1b | a bond | Me | a bond | NH | S | NH | Q3c | OH |
| 1468 | CH | S | Q1b | a bond | Me | a bond | NH | S | a bond | Q3a | OH |
| 1469 | CH | S | Q1b | a bond | Me | a bond | NH | S | a bond | Q3b | OH |
| 1470 | CH | S | Q1b | a bond | Me | a bond | NH | S | a bond | Q3c | OH |
| 1471 | CH | S | Q1b | a bond | Me | a bond | NH | O | NH | Q3a | OH |
| 1472 | CH | S | Q1b | a bond | Me | a bond | NH | O | NH | Q3b | OH |
| 1473 | CH | S | Q1b | a bond | Me | a bond | NH | O | NH | Q3c | OH |
| 1474 | CH | S | Q1b | a bond | Me | a bond | NH | O | a bond | Q3a | OH |
| 1475 | CH | S | Q1b | a bond | Me | a bond | NH | O | a bond | Q3b | OH |
| 1476 | CH | S | Q1b | a bond | Me | a bond | NH | O | a bond | Q3c | OH |
| 1477 | CH | S | Q1b | a bond | H | a bond | NH | S | NH | Q3a | OH |
| 1478 | CH | S | Q1b | a bond | H | a bond | NH | S | NH | Q3b | OH |
| 1479 | CH | S | Q1b | a bond | H | a bond | NH | S | NH | Q3c | OH |
| 1480 | CH | S | Q1b | a bond | H | a bond | NH | S | a bond | Q3a | OH |
| 1481 | CH | S | Q1b | a bond | H | a bond | NH | S | a bond | Q3b | OH |
| 1482 | CH | S | Q1b | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1483 | CH | S | Q1b | a bond | H | a bond | NH | O | NH | Q3a | OH |
| 1484 | CH | S | Q1b | a bond | H | a bond | NH | O | NH | Q3b | OH |
| 1485 | CH | S | Q1b | a bond | H | a bond | NH | O | NH | Q3c | OH |
| 1486 | CH | S | Q1b | a bond | H | a bond | NH | O | a bond | Q3a | OH |
| 1487 | CH | S | Q1b | a bond | H | a bond | NH | O | a bond | Q3b | OH |
| 1488 | CH | S | Q1b | a bond | H | a bond | NH | O | a bond | Q3c | OH |
| 1489 | CH | S | Q1c | a bond | Me | a bond | NH | S | NH | Q3a | OH |
| 1490 | CH | S | Q1c | a bond | Me | a bond | NH | S | NH | Q3b | OH |
| 1491 | CH | S | Q1c | a bond | Me | a bond | NH | S | NH | Q3c | OH |
| 1492 | CH | S | Q1c | a bond | Me | a bond | NH | S | a bond | Q3a | OH |
| 1493 | CH | S | Q1c | a bond | Me | a bond | NH | S | a bond | Q3b | OH |
| 1494 | CH | S | Q1c | a bond | Me | a bond | NH | S | a bond | Q3c | OH |
| 1495 | CH | S | Q1c | a bond | Me | a bond | NH | O | NH | Q3a | OH |
| 1496 | CH | S | Q1c | a bond | Me | a bond | NH | O | NH | Q3b | OH |
| 1497 | CH | S | Q1c | a bond | Me | a bond | NH | O | NH | Q3c | OH |
| 1498 | CH | S | Q1c | a bond | Me | a bond | NH | O | a bond | Q3a | OH |
| 1499 | CH | S | Q1c | a bond | Me | a bond | NH | O | a bond | Q3b | OH |
| 1500 | CH | S | Q1c | a bond | Me | a bond | NH | O | a bond | Q3c | OH |
| 1501 | CH | S | Q1c | a bond | H | a bond | NH | S | NH | Q3a | OH |
| 1502 | CH | S | Q1c | a bond | H | a bond | NH | S | NH | Q3b | OH |
| 1503 | CH | S | Q1c | a bond | H | a bond | NH | S | NH | Q3c | OH |
| 1504 | CH | S | Q1c | a bond | H | a bond | NH | S | a bond | Q3a | OH |
| 1505 | CH | S | Q1c | a bond | H | a bond | NH | S | a bond | Q3b | OH |
| 1506 | CH | S | Q1c | a bond | H | a bond | NH | S | a bond | Q3c | OH |
| 1507 | CH | S | Q1c | a bond | H | a bond | NH | O | NH | Q3a | OH |
| 1508 | CH | S | Q1c | a bond | H | a bond | NH | O | NH | Q3b | OH |
| 1509 | CH | S | Q1c | a bond | H | a bond | NH | O | NH | Q3c | OH |
| 1510 | CH | S | Q1c | a bond | H | a bond | NH | O | a bond | Q3a | OH |
| 1511 | CH | S | Q1c | a bond | H | a bond | NH | O | a bond | Q3b | OH |
| 1512 | CH | S | Q1c | a bond | H | a bond | NH | O | a bond | Q3c | OH |
| 1513 | CH | S | Q1d | a bond | Me | a bond | NH | S | NH | Q3a | OH |
| 1514 | CH | S | Q1d | a bond | Me | a bond | NH | S | NH | Q3b | OH |
| 1515 | CH | S | Q1d | a bond | Me | a bond | NH | S | NH | Q3c | OH |
| 1516 | CH | S | Q1d | a bond | Me | a bond | NH | S | a bond | Q3a | OH |
| 1517 | CH | S | Q1d | a bond | Me | a bond | NH | S | a bond | Q3b | OH |
| 1518 | CH | S | Q1d | a bond | Me | a bond | NH | S | a bond | Q3c | OH |
| 1519 | CH | S | Q1d | a bond | Me | a bond | NH | O | NH | Q3a | OH |
| 1520 | CH | S | Q1d | a bond | Me | a bond | NH | O | NH | Q3b | OH |
| 1521 | CH | S | Q1d | a bond | Me | a bond | NH | O | NH | Q3c | OH |
| 1522 | CH | S | Q1d | a bond | Me | a bond | NH | O | a bond | Q3a | OH |
| 1523 | CH | S | Q1d | a bond | Me | a bond | NH | O | a bond | Q3b | OH |
| 1524 | CH | S | Q1d | a bond | Me | a bond | NH | O | a bond | Q3c | OH |
| 1525 | CH | S | Q1d | a bond | H | a bond | NH | S | NH | Q3a | OH |
| 1526 | CH | S | Q1d | a bond | H | a bond | NH | S | NH | Q3b | OH |
| 1527 | CH | S | Q1d | a bond | H | a bond | NH | S | NH | Q3c | OH |
| 1528 | CH | S | Q1d | a bond | H | a bond | NH | S | a bond | Q3a | OH |
| 1529 | CH | S | Q1d | a bond | H | a bond | NH | S | a bond | Q3b | OH |
| 1530 | CH | S | Q1d | a bond | H | a bond | NH | S | a bond | Q3c | OH |
| 1531 | CH | S | Q1d | a bond | H | a bond | NH | O | NH | Q3a | OH |
| 1532 | CH | S | Q1d | a bond | H | a bond | NH | O | NH | Q3b | OH |
| 1533 | CH | S | Q1d | a bond | H | a bond | NH | O | NH | Q3c | OH |
| 1534 | CH | S | Q1d | a bond | H | a bond | NH | O | a bond | Q3a | OH |
| 1535 | CH | S | Q1d | a bond | H | a bond | NH | O | a bond | Q3b | OH |
| 1536 | CH | S | Q1d | a bond | H | a bond | NH | O | a bond | Q3c | OH |
| 1537 | CH | S | Q1e | a bond | Me | a bond | NH | S | NH | Q3a | OH |
| 1538 | CH | S | Q1e | a bond | Me | a bond | NH | S | NH | Q3b | OH |
| 1539 | CH | S | Q1e | a bond | Me | a bond | NH | S | NH | Q3c | OH |
| 1540 | CH | S | Q1e | a bond | Me | a bond | NH | S | a bond | Q3a | OH |
| 1541 | CH | S | Q1e | a bond | Me | a bond | NH | S | a bond | Q3b | OH |
| 1542 | CH | S | Q1e | a bond | Me | a bond | NH | S | a bond | Q3c | OH |
| 1543 | CH | S | Q1e | a bond | Me | a bond | NH | O | NH | Q3a | OH |
| 1544 | CH | S | Q1e | a bond | Me | a bond | NH | O | NH | Q3b | OH |
| 1545 | CH | S | Q1e | a bond | Me | a bond | NH | O | NH | Q3c | OH |
| 1546 | CH | S | Q1e | a bond | Me | a bond | NH | O | a bond | Q3a | OH |
| 1547 | CH | S | Q1e | a bond | Me | a bond | NH | O | a bond | Q3b | OH |
| 1548 | CH | S | Q1e | a bond | Me | a bond | NH | O | a bond | Q3c | OH |
| 1549 | CH | S | Q1e | a bond | H | a bond | NH | S | NH | Q3a | OH |
| 1550 | CH | S | Q1e | a bond | H | a bond | NH | S | NH | Q3b | OH |
| 1551 | CH | S | Q1e | a bond | H | a bond | NH | S | NH | Q3c | OH |
| 1552 | CH | S | Q1e | a bond | H | a bond | NH | S | a bond | Q3a | OH |
| 1553 | CH | S | Q1e | a bond | H | a bond | NH | S | a bond | Q3b | OH |
| 1554 | CH | S | Q1e | a bond | H | a bond | NH | S | a bond | Q3c | OH |
| 1555 | CH | S | Q1e | a bond | H | a bond | NH | O | NH | Q3a | OH |
| 1556 | CH | S | Q1e | a bond | H | a bond | NH | O | NH | Q3b | OH |
| 1557 | CH | S | Q1e | a bond | H | a bond | NH | O | NH | Q3c | OH |
| 1558 | CH | S | Q1e | a bond | H | a bond | NH | O | a bond | Q3a | OH |
| 1559 | CH | S | Q1e | a bond | H | a bond | NH | O | a bond | Q3b | OH |
| 1560 | CH | S | Q1e | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1561 | CH | S | Q1f | a bond | Me | a bond | NH | S | NH | Q3a | OH |
| 1562 | CH | S | Q1f | a bond | Me | a bond | NH | S | NH | Q3b | OH |
| 1563 | CH | S | Q1f | a bond | Me | a bond | NH | S | NH | Q3c | OH |
| 1564 | CH | S | Q1f | a bond | Me | a bond | NH | S | a bond | Q3a | OH |
| 1565 | CH | S | Q1f | a bond | Me | a bond | NH | S | a bond | Q3b | OH |
| 1566 | CH | S | Q1f | a bond | Me | a bond | NH | S | a bond | Q3c | OH |
| 1567 | CH | S | Q1f | a bond | Me | a bond | NH | O | NH | Q3a | OH |
| 1568 | CH | S | Q1f | a bond | Me | a bond | NH | O | NH | Q3b | OH |
| 1569 | CH | S | Q1f | a bond | Me | a bond | NH | O | NH | Q3c | OH |
| 1570 | CH | S | Q1f | a bond | Me | a bond | NH | O | a bond | Q3a | OH |
| 1571 | CH | S | Q1f | a bond | Me | a bond | NH | O | a bond | Q3b | OH |
| 1572 | CH | S | Q1f | a bond | Me | a bond | NH | O | a bond | Q3c | OH |
| 1573 | CH | S | Q1f | a bond | H | a bond | NH | S | NH | Q3a | OH |
| 1574 | CH | S | Q1f | a bond | H | a bond | NH | S | NH | Q3b | OH |
| 1575 | CH | S | Q1f | a bond | H | a bond | NH | S | NH | Q3c | OH |
| 1576 | CH | S | Q1f | a bond | H | a bond | NH | S | a bond | Q3a | OH |
| 1577 | CH | S | Q1f | a bond | H | a bond | NH | S | a bond | Q3b | OH |
| 1578 | CH | S | Q1f | a bond | H | a bond | NH | S | a bond | Q3c | OH |
| 1579 | CH | S | Q1f | a bond | H | a bond | NH | O | NH | Q3a | OH |
| 1580 | CH | S | Q1f | a bond | H | a bond | NH | O | NH | Q3b | OH |
| 1581 | CH | S | Q1f | a bond | H | a bond | NH | O | NH | Q3c | OH |
| 1582 | CH | S | Q1f | a bond | H | a bond | NH | O | a bond | Q3a | OH |
| 1583 | CH | S | Q1f | a bond | H | a bond | NH | O | a bond | Q3b | OH |
| 1584 | CH | S | Q1f | a bond | H | a bond | NH | O | a bond | Q3c | OH |
| 1585 | CH | S | Q1g | a bond | Me | a bond | NH | S | NH | Q3a | OH |
| 1586 | CH | S | Q1g | a bond | Me | a bond | NH | S | NH | Q3b | OH |
| 1587 | CH | S | Q1g | a bond | Me | a bond | NH | S | NH | Q3c | OH |
| 1588 | CH | S | Q1g | a bond | Me | a bond | NH | S | a bond | Q3a | OH |
| 1589 | CH | S | Q1g | a bond | Me | a bond | NH | S | a bond | Q3b | OH |
| 1590 | CH | S | Q1g | a bond | Me | a bond | NH | S | a bond | Q3c | OH |
| 1591 | CH | S | Q1g | a bond | Me | a bond | NH | O | NH | Q3a | OH |
| 1592 | CH | S | Q1g | a bond | Me | a bond | NH | O | NH | Q3b | OH |
| 1593 | CH | S | Q1g | a bond | Me | a bond | NH | O | NH | Q3c | OH |
| 1594 | CH | S | Q1g | a bond | Me | a bond | NH | O | a bond | Q3a | OH |
| 1595 | CH | S | Q1g | a bond | Me | a bond | NH | O | a bond | Q3b | OH |
| 1596 | CH | S | Q1g | a bond | Me | a bond | NH | O | a bond | Q3c | OH |
| 1597 | CH | S | Q1g | a bond | H | a bond | NH | S | NH | Q3a | OH |
| 1598 | CH | S | Q1g | a bond | H | a bond | NH | S | NH | Q3b | OH |
| 1599 | CH | S | Q1g | a bond | H | a bond | NH | S | NH | Q3c | OH |
| 1600 | CH | S | Q1g | a bond | H | a bond | NH | S | a bond | Q3a | OH |
| 1601 | CH | S | Q1g | a bond | H | a bond | NH | S | a bond | Q3b | OH |
| 1602 | CH | S | Q1g | a bond | H | a bond | NH | S | a bond | Q3c | OH |
| 1603 | CH | S | Q1g | a bond | H | a bond | NH | O | NH | Q3a | OH |
| 1604 | CH | S | Q1g | a bond | H | a bond | NH | O | NH | Q3b | OH |
| 1605 | CH | S | Q1g | a bond | H | a bond | NH | O | NH | Q3c | OH |
| 1606 | CH | S | Q1g | a bond | H | a bond | NH | O | a bond | Q3a | OH |
| 1607 | CH | S | Q1g | a bond | H | a bond | NH | O | a bond | Q3b | OH |
| 1608 | CH | S | Q1g | a bond | H | a bond | NH | O | a bond | Q3c | OH |
| 1609 | CH | S | Q1h | a bond | Me | a bond | NH | S | NH | Q3a | OH |
| 1610 | CH | S | Q1h | a bond | Me | a bond | NH | S | NH | Q3b | OH |
| 1611 | CH | S | Q1h | a bond | Me | a bond | NH | S | NH | Q3c | OH |
| 1612 | CH | S | Q1h | a bond | Me | a bond | NH | S | a bond | Q3a | OH |
| 1613 | CH | S | Q1h | a bond | Me | a bond | NH | S | a bond | Q3b | OH |
| 1614 | CH | S | Q1h | a bond | Me | a bond | NH | S | a bond | Q3c | OH |
| 1615 | CH | S | Q1h | a bond | Me | a bond | NH | O | NH | Q3a | OH |
| 1616 | CH | S | Q1h | a bond | Me | a bond | NH | O | NH | Q3b | OH |
| 1617 | CH | S | Q1h | a bond | Me | a bond | NH | O | NH | Q3c | OH |
| 1618 | CH | S | Q1h | a bond | Me | a bond | NH | O | a bond | Q3a | OH |
| 1619 | CH | S | Q1h | a bond | Me | a bond | NH | O | a bond | Q3b | OH |
| 1620 | CH | S | Q1h | a bond | Me | a bond | NH | O | a bond | Q3c | OH |
| 1621 | CH | S | Q1h | a bond | H | a bond | NH | S | NH | Q3a | OH |
| 1622 | CH | S | Q1h | a bond | H | a bond | NH | S | NH | Q3b | OH |
| 1623 | CH | S | Q1h | a bond | H | a bond | NH | S | NH | Q3c | OH |
| 1624 | CH | S | Q1h | a bond | H | a bond | NH | S | a bond | Q3a | OH |
| 1625 | CH | S | Q1h | a bond | H | a bond | NH | S | a bond | Q3b | OH |
| 1626 | CH | S | Q1h | a bond | H | a bond | NH | S | a bond | Q3c | OH |
| 1627 | CH | S | Q1h | a bond | H | a bond | NH | O | NH | Q3a | OH |
| 1628 | CH | S | Q1h | a bond | H | a bond | NH | O | NH | Q3b | OH |
| 1629 | CH | S | Q1h | a bond | H | a bond | NH | O | NH | Q3c | OH |
| 1630 | CH | S | Q1h | a bond | H | a bond | NH | O | a bond | Q3a | OH |
| 1631 | CH | S | Q1h | a bond | H | a bond | NH | O | a bond | Q3b | OH |
| 1632 | CH | S | Q1h | a bond | H | a bond | NH | O | a bond | Q3c | OH |
| 1633 | CH | S | Q1i | a bond | Me | a bond | NH | S | NH | Q3a | OH |
| 1634 | CH | S | Q1i | a bond | Me | a bond | NH | S | NH | Q3b | OH |
| 1635 | CH | S | Q1i | a bond | Me | a bond | NH | S | NH | Q3c | OH |
| 1636 | CH | S | Q1i | a bond | Me | a bond | NH | S | a bond | Q3a | OH |
| 1637 | CH | S | Q1i | a bond | Me | a bond | NH | S | a bond | Q3b | OH |
| 1638 | CH | S | Q1i | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1639 | CH | S | Q1i | a bond | Me | a bond | NH | O | NH | Q3a | OH |
| 1640 | CH | S | Q1i | a bond | Me | a bond | NH | O | NH | Q3b | OH |
| 1641 | CH | S | Q1i | a bond | Me | a bond | NH | O | NH | Q3c | OH |
| 1642 | CH | S | Q1i | a bond | Me | a bond | NH | O | a bond | Q3a | OH |
| 1643 | CH | S | Q1i | a bond | Me | a bond | NH | O | a bond | Q3b | OH |
| 1644 | CH | S | Q1i | a bond | Me | a bond | NH | O | a bond | Q3c | OH |
| 1645 | CH | S | Q1i | a bond | H | a bond | NH | S | NH | Q3a | OH |
| 1646 | CH | S | Q1i | a bond | H | a bond | NH | S | NH | Q3b | OH |
| 1647 | CH | S | Q1i | a bond | H | a bond | NH | S | NH | Q3c | OH |
| 1648 | CH | S | Q1i | a bond | H | a bond | NH | S | a bond | Q3a | OH |
| 1649 | CH | S | Q1i | a bond | H | a bond | NH | S | a bond | Q3b | OH |
| 1650 | CH | S | Q1i | a bond | H | a bond | NH | S | a bond | Q3c | OH |
| 1651 | CH | S | Q1i | a bond | H | a bond | NH | O | NH | Q3a | OH |
| 1652 | CH | S | Q1i | a bond | H | a bond | NH | O | NH | Q3b | OH |
| 1653 | CH | S | Q1i | a bond | H | a bond | NH | O | NH | Q3c | OH |
| 1654 | CH | S | Q1i | a bond | H | a bond | NH | O | a bond | Q3a | OH |
| 1655 | CH | S | Q1i | a bond | H | a bond | NH | O | a bond | Q3b | OH |
| 1656 | CH | S | Q1i | a bond | H | a bond | NH | O | a bond | Q3c | OH |
| 1657 | CH | S | Q1j | a bond | Me | a bond | NH | S | NH | Q3a | OH |
| 1658 | CH | S | Q1j | a bond | Me | a bond | NH | S | NH | Q3b | OH |
| 1659 | CH | S | Q1j | a bond | Me | a bond | NH | S | NH | Q3c | OH |
| 1660 | CH | S | Q1j | a bond | Me | a bond | NH | S | a bond | Q3a | OH |
| 1661 | CH | S | Q1j | a bond | Me | a bond | NH | S | a bond | Q3b | OH |
| 1662 | CH | S | Q1j | a bond | Me | a bond | NH | S | a bond | Q3c | OH |
| 1663 | CH | S | Q1j | a bond | Me | a bond | NH | O | NH | Q3a | OH |
| 1664 | CH | S | Q1j | a bond | Me | a bond | NH | O | NH | Q3b | OH |
| 1665 | CH | S | Q1j | a bond | Me | a bond | NH | O | NH | Q3c | OH |
| 1666 | CH | S | Q1j | a bond | Me | a bond | NH | O | a bond | Q3a | OH |
| 1667 | CH | S | Q1j | a bond | Me | a bond | NH | O | a bond | Q3b | OH |
| 1668 | CH | S | Q1j | a bond | Me | a bond | NH | O | a bond | Q3c | OH |
| 1669 | CH | S | Q1j | a bond | H | a bond | NH | S | NH | Q3a | OH |
| 1670 | CH | S | Q1j | a bond | H | a bond | NH | S | NH | Q3b | OH |
| 1671 | CH | S | Q1j | a bond | H | a bond | NH | S | NH | Q3c | OH |
| 1672 | CH | S | Q1j | a bond | H | a bond | NH | S | a bond | Q3a | OH |
| 1673 | CH | S | Q1j | a bond | H | a bond | NH | S | a bond | Q3b | OH |
| 1674 | CH | S | Q1j | a bond | H | a bond | NH | S | a bond | Q3c | OH |
| 1675 | CH | S | Q1j | a bond | H | a bond | NH | O | NH | Q3a | OH |
| 1676 | CH | S | Q1j | a bond | H | a bond | NH | O | NH | Q3b | OH |
| 1677 | CH | S | Q1j | a bond | H | a bond | NH | O | NH | Q3c | OH |
| 1678 | CH | S | Q1j | a bond | H | a bond | NH | O | a bond | Q3a | OH |
| 1679 | CH | S | Q1j | a bond | H | a bond | NH | O | a bond | Q3b | OH |
| 1680 | CH | S | Q1j | a bond | H | a bond | NH | O | a bond | Q3c | OH |
| 1681 | CH | O | Q1a | a bond | Me | a bond | NH | S | NH | Q3a | OH |
| 1682 | CH | O | Q1a | a bond | Me | a bond | NH | S | NH | Q3b | OH |
| 1683 | CH | O | Q1a | a bond | Me | a bond | NH | S | NH | Q3c | OH |
| 1684 | CH | O | Q1a | a bond | Me | a bond | NH | S | a bond | Q3a | OH |
| 1685 | CH | O | Q1a | a bond | Me | a bond | NH | S | a bond | Q3b | OH |
| 1686 | CH | O | Q1a | a bond | Me | a bond | NH | S | a bond | Q3c | OH |
| 1687 | CH | O | Q1a | a bond | Me | a bond | NH | O | NH | Q3a | OH |
| 1688 | CH | O | Q1a | a bond | Me | a bond | NH | O | NH | Q3b | OH |
| 1689 | CH | O | Q1a | a bond | Me | a bond | NH | O | NH | Q3c | OH |
| 1690 | CH | O | Q1a | a bond | Me | a bond | NH | O | a bond | Q3a | OH |
| 1691 | CH | O | Q1a | a bond | Me | a bond | NH | O | a bond | Q3b | OH |
| 1692 | CH | O | Q1a | a bond | Me | a bond | NH | O | a bond | Q3c | OH |
| 1693 | CH | O | Q1a | a bond | H | a bond | NH | S | NH | Q3a | OH |
| 1694 | CH | O | Q1a | a bond | H | a bond | NH | S | NH | Q3b | OH |
| 1695 | CH | O | Q1a | a bond | H | a bond | NH | S | NH | Q3c | OH |
| 1696 | CH | O | Q1a | a bond | H | a bond | NH | S | a bond | Q3a | OH |
| 1697 | CH | O | Q1a | a bond | H | a bond | NH | S | a bond | Q3b | OH |
| 1698 | CH | O | Q1a | a bond | H | a bond | NH | S | a bond | Q3c | OH |
| 1699 | CH | O | Q1a | a bond | H | a bond | NH | O | NH | Q3a | OH |
| 1700 | CH | O | Q1a | a bond | H | a bond | NH | O | NH | Q3b | OH |
| 1701 | CH | O | Q1a | a bond | H | a bond | NH | O | NH | Q3c | OH |
| 1702 | CH | O | Q1a | a bond | H | a bond | NH | O | a bond | Q3a | OH |
| 1703 | CH | O | Q1a | a bond | H | a bond | NH | O | a bond | Q3b | OH |
| 1704 | CH | O | Q1a | a bond | H | a bond | NH | O | a bond | Q3c | OH |
| 1705 | CH | O | Q1b | a bond | Me | a bond | NH | S | NH | Q3a | OH |
| 1706 | CH | O | Q1b | a bond | Me | a bond | NH | S | NH | Q3b | OH |
| 1707 | CH | O | Q1b | a bond | Me | a bond | NH | S | NH | Q3c | OH |
| 1708 | CH | O | Q1b | a bond | Me | a bond | NH | S | a bond | Q3a | OH |
| 1709 | CH | O | Q1b | a bond | Me | a bond | NH | S | a bond | Q3b | OH |
| 1710 | CH | O | Q1b | a bond | Me | a bond | NH | S | a bond | Q3c | OH |
| 1711 | CH | O | Q1b | a bond | Me | a bond | NH | O | NH | Q3a | OH |
| 1712 | CH | O | Q1b | a bond | Me | a bond | NH | O | NH | Q3b | OH |
| 1713 | CH | O | Q1b | a bond | Me | a bond | NH | O | NH | Q3c | OH |
| 1714 | CH | O | Q1b | a bond | Me | a bond | NH | O | a bond | Q3a | OH |
| 1715 | CH | O | Q1b | a bond | Me | a bond | NH | O | a bond | Q3b | OH |
| 1716 | CH | O | Q1b | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1717 | CH | O | Q1b | a bond | H | a bond | NH | S | NH | Q3a | OH |
| 1718 | CH | O | Q1b | a bond | H | a bond | NH | S | NH | Q3b | OH |
| 1719 | CH | O | Q1b | a bond | H | a bond | NH | S | NH | Q3c | OH |
| 1720 | CH | O | Q1b | a bond | H | a bond | NH | S | a bond | Q3a | OH |
| 1721 | CH | O | Q1b | a bond | H | a bond | NH | S | a bond | Q3b | OH |
| 1722 | CH | O | Q1b | a bond | H | a bond | NH | S | a bond | Q3c | OH |
| 1723 | CH | O | Q1b | a bond | H | a bond | NH | O | NH | Q3a | OH |
| 1724 | CH | O | Q1b | a bond | H | a bond | NH | O | NH | Q3b | OH |
| 1725 | CH | O | Q1b | a bond | H | a bond | NH | O | NH | Q3c | OH |
| 1726 | CH | O | Q1b | a bond | H | a bond | NH | O | a bond | Q3a | OH |
| 1727 | CH | O | Q1b | a bond | H | a bond | NH | O | a bond | Q3b | OH |
| 1728 | CH | O | Q1b | a bond | H | a bond | NH | O | a bond | Q3c | OH |
| 1729 | CH | O | Q1c | a bond | Me | a bond | NH | S | NH | Q3a | OH |
| 1730 | CH | O | Q1c | a bond | Me | a bond | NH | S | NH | Q3b | OH |
| 1731 | CH | O | Q1c | a bond | Me | a bond | NH | S | NH | Q3c | OH |
| 1732 | CH | O | Q1c | a bond | Me | a bond | NH | S | a bond | Q3a | OH |
| 1733 | CH | O | Q1c | a bond | Me | a bond | NH | S | a bond | Q3b | OH |
| 1734 | CH | O | Q1c | a bond | Me | a bond | NH | S | a bond | Q3c | OH |
| 1735 | CH | O | Q1c | a bond | Me | a bond | NH | O | NH | Q3a | OH |
| 1736 | CH | O | Q1c | a bond | Me | a bond | NH | O | NH | Q3b | OH |
| 1737 | CH | O | Q1c | a bond | Me | a bond | NH | O | NH | Q3c | OH |
| 1738 | CH | O | Q1c | a bond | Me | a bond | NH | O | a bond | Q3a | OH |
| 1739 | CH | O | Q1c | a bond | Me | a bond | NH | O | a bond | Q3b | OH |
| 1740 | CH | O | Q1c | a bond | Me | a bond | NH | O | a bond | Q3c | OH |
| 1741 | CH | O | Q1c | a bond | H | a bond | NH | S | NH | Q3a | OH |
| 1742 | CH | O | Q1c | a bond | H | a bond | NH | S | NH | Q3b | OH |
| 1743 | CH | O | Q1c | a bond | H | a bond | NH | S | NH | Q3c | OH |
| 1744 | CH | O | Q1c | a bond | H | a bond | NH | S | a bond | Q3a | OH |
| 1745 | CH | O | Q1c | a bond | H | a bond | NH | S | a bond | Q3b | OH |
| 1746 | CH | O | Q1c | a bond | H | a bond | NH | S | a bond | Q3c | OH |
| 1747 | CH | O | Q1c | a bond | H | a bond | NH | O | NH | Q3a | OH |
| 1748 | CH | O | Q1c | a bond | H | a bond | NH | O | NH | Q3b | OH |
| 1749 | CH | O | Q1c | a bond | H | a bond | NH | O | NH | Q3c | OH |
| 1750 | CH | O | Q1c | a bond | H | a bond | NH | O | a bond | Q3a | OH |
| 1751 | CH | O | Q1c | a bond | H | a bond | NH | O | a bond | Q3b | OH |
| 1752 | CH | O | Q1c | a bond | H | a bond | NH | O | a bond | Q3c | OH |
| 1753 | CH | O | Q1d | a bond | Me | a bond | NH | S | NH | Q3a | OH |
| 1754 | CH | O | Q1d | a bond | Me | a bond | NH | S | NH | Q3b | OH |
| 1755 | CH | O | Q1d | a bond | Me | a bond | NH | S | NH | Q3c | OH |
| 1756 | CH | O | Q1d | a bond | Me | a bond | NH | S | a bond | Q3a | OH |
| 1757 | CH | O | Q1d | a bond | Me | a bond | NH | S | a bond | Q3b | OH |
| 1758 | CH | O | Q1d | a bond | Me | a bond | NH | S | a bond | Q3c | OH |
| 1759 | CH | O | Q1d | a bond | Me | a bond | NH | O | NH | Q3a | OH |
| 1760 | CH | O | Q1d | a bond | Me | a bond | NH | O | NH | Q3b | OH |
| 1761 | CH | O | Q1d | a bond | Me | a bond | NH | O | NH | Q3c | OH |
| 1762 | CH | O | Q1d | a bond | Me | a bond | NH | O | a bond | Q3a | OH |
| 1763 | CH | O | Q1d | a bond | Me | a bond | NH | O | a bond | Q3b | OH |
| 1764 | CH | O | Q1d | a bond | Me | a bond | NH | O | a bond | Q3c | OH |
| 1765 | CH | O | Q1d | a bond | H | a bond | NH | S | NH | Q3a | OH |
| 1766 | CH | O | Q1d | a bond | H | a bond | NH | S | NH | Q3b | OH |
| 1767 | CH | O | Q1d | a bond | H | a bond | NH | S | NH | Q3c | OH |
| 1768 | CH | O | Q1d | a bond | H | a bond | NH | S | a bond | Q3a | OH |
| 1769 | CH | O | Q1d | a bond | H | a bond | NH | S | a bond | Q3b | OH |
| 1770 | CH | O | Q1d | a bond | H | a bond | NH | S | a bond | Q3c | OH |
| 1771 | CH | O | Q1d | a bond | H | a bond | NH | O | NH | Q3a | OH |
| 1772 | CH | O | Q1d | a bond | H | a bond | NH | O | NH | Q3b | OH |
| 1773 | CH | O | Q1d | a bond | H | a bond | NH | O | NH | Q3c | OH |
| 1774 | CH | O | Q1d | a bond | H | a bond | NH | O | a bond | Q3a | OH |
| 1775 | CH | O | Q1d | a bond | H | a bond | NH | O | a bond | Q3b | OH |
| 1776 | CH | O | Q1d | a bond | H | a bond | NH | O | a bond | Q3c | OH |
| 1777 | CH | O | Q1e | a bond | Me | a bond | NH | S | NH | Q3a | OH |
| 1778 | CH | O | Q1e | a bond | Me | a bond | NH | S | NH | Q3b | OH |
| 1779 | CH | O | Q1e | a bond | Me | a bond | NH | S | NH | Q3c | OH |
| 1780 | CH | O | Q1e | a bond | Me | a bond | NH | S | a bond | Q3a | OH |
| 1781 | CH | O | Q1e | a bond | Me | a bond | NH | S | a bond | Q3b | OH |
| 1782 | CH | O | Q1e | a bond | Me | a bond | NH | S | a bond | Q3c | OH |
| 1783 | CH | O | Q1e | a bond | Me | a bond | NH | O | NH | Q3a | OH |
| 1784 | CH | O | Q1e | a bond | Me | a bond | NH | O | NH | Q3b | OH |
| 1785 | CH | O | Q1e | a bond | Me | a bond | NH | O | NH | Q3c | OH |
| 1786 | CH | O | Q1e | a bond | Me | a bond | NH | O | a bond | Q3a | OH |
| 1787 | CH | O | Q1e | a bond | Me | a bond | NH | O | a bond | Q3b | OH |
| 1788 | CH | O | Q1e | a bond | Me | a bond | NH | O | a bond | Q3c | OH |
| 1789 | CH | O | Q1e | a bond | H | a bond | NH | S | NH | Q3a | OH |
| 1790 | CH | O | Q1e | a bond | H | a bond | NH | S | NH | Q3b | OH |
| 1791 | CH | O | Q1e | a bond | H | a bond | NH | S | NH | Q3c | OH |
| 1792 | CH | O | Q1e | a bond | H | a bond | NH | S | a bond | Q3a | OH |
| 1793 | CH | O | Q1e | a bond | H | a bond | NH | S | a bond | Q3b | OH |
| 1794 | CH | O | Q1e | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1795 | CH | O | Q1e | a bond | H | a bond | NH | O | NH | Q3a | OH |
| 1796 | CH | O | Q1e | a bond | H | a bond | NH | O | NH | Q3b | OH |
| 1797 | CH | O | Q1e | a bond | H | a bond | NH | O | NH | Q3c | OH |
| 1798 | CH | O | Q1e | a bond | H | a bond | NH | O | a bond | Q3a | OH |
| 1799 | CH | O | Q1e | a bond | H | a bond | NH | O | a bond | Q3b | OH |
| 1800 | CH | O | Q1e | a bond | H | a bond | NH | O | a bond | Q3c | OH |
| 1801 | CH | O | Q1f | a bond | Me | a bond | NH | S | NH | Q3a | OH |
| 1802 | CH | O | Q1f | a bond | Me | a bond | NH | S | NH | Q3b | OH |
| 1803 | CH | O | Q1f | a bond | Me | a bond | NH | S | NH | Q3c | OH |
| 1804 | CH | O | Q1f | a bond | Me | a bond | NH | S | a bond | Q3a | OH |
| 1805 | CH | O | Q1f | a bond | Me | a bond | NH | S | a bond | Q3b | OH |
| 1806 | CH | O | Q1f | a bond | Me | a bond | NH | S | a bond | Q3c | OH |
| 1807 | CH | O | Q1f | a bond | Me | a bond | NH | O | NH | Q3a | OH |
| 1808 | CH | O | Q1f | a bond | Me | a bond | NH | O | NH | Q3b | OH |
| 1809 | CH | O | Q1f | a bond | Me | a bond | NH | O | NH | Q3c | OH |
| 1810 | CH | O | Q1f | a bond | Me | a bond | NH | O | a bond | Q3a | OH |
| 1811 | CH | O | Q1f | a bond | Me | a bond | NH | O | a bond | Q3b | OH |
| 1812 | CH | O | Q1f | a bond | Me | a bond | NH | O | a bond | Q3c | OH |
| 1813 | CH | O | Q1f | a bond | H | a bond | NH | S | NH | Q3a | OH |
| 1814 | CH | O | Q1f | a bond | H | a bond | NH | S | NH | Q3b | OH |
| 1815 | CH | O | Q1f | a bond | H | a bond | NH | S | NH | Q3c | OH |
| 1816 | CH | O | Q1f | a bond | H | a bond | NH | S | a bond | Q3a | OH |
| 1817 | CH | O | Q1f | a bond | H | a bond | NH | S | a bond | Q3b | OH |
| 1818 | CH | O | Q1f | a bond | H | a bond | NH | S | a bond | Q3c | OH |
| 1819 | CH | O | Q1f | a bond | H | a bond | NH | O | NH | Q3a | OH |
| 1820 | CH | O | Q1f | a bond | H | a bond | NH | O | NH | Q3b | OH |
| 1821 | CH | O | Q1f | a bond | H | a bond | NH | O | NH | Q3c | OH |
| 1822 | CH | O | Q1f | a bond | H | a bond | NH | O | a bond | Q3a | OH |
| 1823 | CH | O | Q1f | a bond | H | a bond | NH | O | a bond | Q3b | OH |
| 1824 | CH | O | Q1f | a bond | H | a bond | NH | O | a bond | Q3c | OH |
| 1825 | CH | O | Q1g | a bond | Me | a bond | NH | S | NH | Q3a | OH |
| 1826 | CH | O | Q1g | a bond | Me | a bond | NH | S | NH | Q3b | OH |
| 1827 | CH | O | Q1g | a bond | Me | a bond | NH | S | NH | Q3c | OH |
| 1828 | CH | O | Q1g | a bond | Me | a bond | NH | S | a bond | Q3a | OH |
| 1829 | CH | O | Q1g | a bond | Me | a bond | NH | S | a bond | Q3b | OH |
| 1830 | CH | O | Q1g | a bond | Me | a bond | NH | S | a bond | Q3c | OH |
| 1831 | CH | O | Q1g | a bond | Me | a bond | NH | O | NH | Q3a | OH |
| 1832 | CH | O | Q1g | a bond | Me | a bond | NH | O | NH | Q3b | OH |
| 1833 | CH | O | Q1g | a bond | Me | a bond | NH | O | NH | Q3c | OH |
| 1834 | CH | O | Q1g | a bond | Me | a bond | NH | O | a bond | Q3a | OH |
| 1835 | CH | O | Q1g | a bond | Me | a bond | NH | O | a bond | Q3b | OH |
| 1836 | CH | O | Q1g | a bond | Me | a bond | NH | O | a bond | Q3c | OH |
| 1837 | CH | O | Q1g | a bond | H | a bond | NH | S | NH | Q3a | OH |
| 1838 | CH | O | Q1g | a bond | H | a bond | NH | S | NH | Q3b | OH |
| 1839 | CH | O | Q1g | a bond | H | a bond | NH | S | NH | Q3c | OH |
| 1840 | CH | O | Q1g | a bond | H | a bond | NH | S | a bond | Q3a | OH |
| 1841 | CH | O | Q1g | a bond | H | a bond | NH | S | a bond | Q3b | OH |
| 1842 | CH | O | Q1g | a bond | H | a bond | NH | S | a bond | Q3c | OH |
| 1843 | CH | O | Q1g | a bond | H | a bond | NH | O | NH | Q3a | OH |
| 1844 | CH | O | Q1g | a bond | H | a bond | NH | O | NH | Q3b | OH |
| 1845 | CH | O | Q1g | a bond | H | a bond | NH | O | NH | Q3c | OH |
| 1846 | CH | O | Q1g | a bond | H | a bond | NH | O | a bond | Q3a | OH |
| 1847 | CH | O | Q1g | a bond | H | a bond | NH | O | a bond | Q3b | OH |
| 1848 | CH | O | Q1g | a bond | H | a bond | NH | O | a bond | Q3c | OH |
| 1849 | CH | O | Q1h | a bond | Me | a bond | NH | S | NH | Q3a | OH |
| 1850 | CH | O | Q1h | a bond | Me | a bond | NH | S | NH | Q3b | OH |
| 1851 | CH | O | Q1h | a bond | Me | a bond | NH | S | NH | Q3c | OH |
| 1852 | CH | O | Q1h | a bond | Me | a bond | NH | S | a bond | Q3a | OH |
| 1853 | CH | O | Q1h | a bond | Me | a bond | NH | S | a bond | Q3b | OH |
| 1854 | CH | O | Q1h | a bond | Me | a bond | NH | S | a bond | Q3c | OH |
| 1855 | CH | O | Q1h | a bond | Me | a bond | NH | O | NH | Q3a | OH |
| 1856 | CH | O | Q1h | a bond | Me | a bond | NH | O | NH | Q3b | OH |
| 1857 | CH | O | Q1h | a bond | Me | a bond | NH | O | NH | Q3c | OH |
| 1858 | CH | O | Q1h | a bond | Me | a bond | NH | O | a bond | Q3a | OH |
| 1859 | CH | O | Q1h | a bond | Me | a bond | NH | O | a bond | Q3b | OH |
| 1860 | CH | O | Q1h | a bond | Me | a bond | NH | O | a bond | Q3c | OH |
| 1861 | CH | O | Q1h | a bond | H | a bond | NH | S | NH | Q3a | OH |
| 1862 | CH | O | Q1h | a bond | H | a bond | NH | S | NH | Q3b | OH |
| 1863 | CH | O | Q1h | a bond | H | a bond | NH | S | NH | Q3c | OH |
| 1864 | CH | O | Q1h | a bond | H | a bond | NH | S | a bond | Q3a | OH |
| 1865 | CH | O | Q1h | a bond | H | a bond | NH | S | a bond | Q3b | OH |
| 1866 | CH | O | Q1h | a bond | H | a bond | NH | S | a bond | Q3c | OH |
| 1867 | CH | O | Q1h | a bond | H | a bond | NH | O | NH | Q3a | OH |
| 1868 | CH | O | Q1h | a bond | H | a bond | NH | O | NH | Q3b | OH |
| 1869 | CH | O | Q1h | a bond | H | a bond | NH | O | NH | Q3c | OH |
| 1870 | CH | O | Q1h | a bond | H | a bond | NH | O | a bond | Q3a | OH |
| 1871 | CH | O | Q1h | a bond | H | a bond | NH | O | a bond | Q3b | OH |
| 1872 | CH | O | Q1h | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1873 | CH | O | Q1i | a bond | Me | a bond | NH | S | NH | Q3a | OH |
| 1874 | CH | O | Q1i | a bond | Me | a bond | NH | S | NH | Q3b | OH |
| 1875 | CH | O | Q1i | a bond | Me | a bond | NH | S | NH | Q3c | OH |
| 1876 | CH | O | Q1i | a bond | Me | a bond | NH | S | a bond | Q3a | OH |
| 1877 | CH | O | Q1i | a bond | Me | a bond | NH | S | a bond | Q3b | OH |
| 1878 | CH | O | Q1i | a bond | Me | a bond | NH | S | a bond | Q3c | OH |
| 1879 | CH | O | Q1i | a bond | Me | a bond | NH | O | NH | Q3a | OH |
| 1880 | CH | O | Q1i | a bond | Me | a bond | NH | O | NH | Q3b | OH |
| 1881 | CH | O | Q1i | a bond | Me | a bond | NH | O | NH | Q3c | OH |
| 1882 | CH | O | Q1i | a bond | Me | a bond | NH | O | a bond | Q3a | OH |
| 1883 | CH | O | Q1i | a bond | Me | a bond | NH | O | a bond | Q3b | OH |
| 1884 | CH | O | Q1i | a bond | Me | a bond | NH | O | a bond | Q3c | OH |
| 1885 | CH | O | Q1i | a bond | H | a bond | NH | S | NH | Q3a | OH |
| 1886 | CH | O | Q1i | a bond | H | a bond | NH | S | NH | Q3b | OH |
| 1887 | CH | O | Q1i | a bond | H | a bond | NH | S | NH | Q3c | OH |
| 1888 | CH | O | Q1i | a bond | H | a bond | NH | S | a bond | Q3a | OH |
| 1889 | CH | O | Q1i | a bond | H | a bond | NH | S | a bond | Q3b | OH |
| 1890 | CH | O | Q1i | a bond | H | a bond | NH | S | a bond | Q3c | OH |
| 1891 | CH | O | Q1i | a bond | H | a bond | NH | O | NH | Q3a | OH |
| 1892 | CH | O | Q1i | a bond | H | a bond | NH | O | NH | Q3b | OH |
| 1893 | CH | O | Q1i | a bond | H | a bond | NH | O | NH | Q3c | OH |
| 1894 | CH | O | Q1i | a bond | H | a bond | NH | O | a bond | Q3a | OH |
| 1895 | CH | O | Q1i | a bond | H | a bond | NH | O | a bond | Q3b | OH |
| 1896 | CH | O | Q1i | a bond | H | a bond | NH | O | a bond | Q3c | OH |
| 1897 | CH | O | Q1j | a bond | Me | a bond | NH | S | NH | Q3a | OH |
| 1898 | CH | O | Q1j | a bond | Me | a bond | NH | S | NH | Q3b | OH |
| 1899 | CH | O | Q1j | a bond | Me | a bond | NH | S | NH | Q3c | OH |
| 1900 | CH | O | Q1j | a bond | Me | a bond | NH | S | a bond | Q3a | OH |
| 1901 | CH | O | Q1j | a bond | Me | a bond | NH | S | a bond | Q3b | OH |
| 1902 | CH | O | Q1j | a bond | Me | a bond | NH | S | a bond | Q3c | OH |
| 1903 | CH | O | Q1j | a bond | Me | a bond | NH | O | NH | Q3a | OH |
| 1904 | CH | O | Q1j | a bond | Me | a bond | NH | O | NH | Q3b | OH |
| 1905 | CH | O | Q1j | a bond | Me | a bond | NH | O | NH | Q3c | OH |
| 1906 | CH | O | Q1j | a bond | Me | a bond | NH | O | a bond | Q3a | OH |
| 1907 | CH | O | Q1j | a bond | Me | a bond | NH | O | a bond | Q3b | OH |
| 1908 | CH | O | Q1j | a bond | Me | a bond | NH | O | a bond | Q3c | OH |
| 1909 | CH | O | Q1j | a bond | H | a bond | NH | S | NH | Q3a | OH |
| 1910 | CH | O | Q1j | a bond | H | a bond | NH | S | NH | Q3b | OH |
| 1911 | CH | O | Q1j | a bond | H | a bond | NH | S | NH | Q3c | OH |
| 1912 | CH | O | Q1j | a bond | H | a bond | NH | S | a bond | Q3a | OH |
| 1913 | CH | O | Q1j | a bond | H | a bond | NH | S | a bond | Q3b | OH |
| 1914 | CH | O | Q1j | a bond | H | a bond | NH | S | a bond | Q3c | OH |
| 1915 | CH | O | Q1j | a bond | H | a bond | NH | O | NH | Q3a | OH |
| 1916 | CH | O | Q1j | a bond | H | a bond | NH | O | NH | Q3b | OH |
| 1917 | CH | O | Q1j | a bond | H | a bond | NH | O | NH | Q3c | OH |
| 1918 | CH | O | Q1j | a bond | H | a bond | NH | O | a bond | Q3a | OH |
| 1919 | CH | O | Q1j | a bond | H | a bond | NH | O | a bond | Q3b | OH |
| 1920 | CH | O | Q1j | a bond | H | a bond | NH | O | a bond | Q3c | OH |
| 1921 | CMe | NMe | Q1a | a bond | Me | a bond | NH | S | NH | Q3a | OH |
| 1922 | CMe | NMe | Q1a | a bond | Me | a bond | NH | S | NH | Q3b | OH |
| 1923 | CMe | NMe | Q1a | a bond | Me | a bond | NH | S | NH | Q3c | OH |
| 1924 | CMe | NMe | Q1a | a bond | Me | a bond | NH | S | a bond | Q3a | OH |
| 1925 | CMe | NMe | Q1a | a bond | Me | a bond | NH | S | a bond | Q3b | OH |
| 1926 | CMe | NMe | Q1a | a bond | Me | a bond | NH | S | a bond | Q3c | OH |
| 1927 | CMe | NMe | Q1a | a bond | Me | a bond | NH | O | NH | Q3a | OH |
| 1928 | CMe | NMe | Q1a | a bond | Me | a bond | NH | O | NH | Q3b | OH |
| 1929 | CMe | NMe | Q1a | a bond | Me | a bond | NH | O | NH | Q3c | OH |
| 1930 | CMe | NMe | Q1a | a bond | Me | a bond | NH | O | a bond | Q3a | OH |
| 1931 | CMe | NMe | Q1a | a bond | Me | a bond | NH | O | a bond | Q3b | OH |
| 1932 | CMe | NMe | Q1a | a bond | Me | a bond | NH | O | a bond | Q3c | OH |
| 1933 | CMe | NMe | Q1a | a bond | H | a bond | NH | S | NH | Q3a | OH |
| 1934 | CMe | NMe | Q1a | a bond | H | a bond | NH | S | NH | Q3b | OH |
| 1935 | CMe | NMe | Q1a | a bond | H | a bond | NH | S | NH | Q3c | OH |
| 1936 | CMe | NMe | Q1a | a bond | H | a bond | NH | S | a bond | Q3a | OH |
| 1937 | CMe | NMe | Q1a | a bond | H | a bond | NH | S | a bond | Q3b | OH |
| 1938 | CMe | NMe | Q1a | a bond | H | a bond | NH | S | a bond | Q3c | OH |
| 1939 | CMe | NMe | Q1a | a bond | H | a bond | NH | O | NH | Q3a | OH |
| 1940 | CMe | NMe | Q1a | a bond | H | a bond | NH | O | NH | Q3b | OH |
| 1941 | CMe | NMe | Q1a | a bond | H | a bond | NH | O | NH | Q3c | OH |
| 1942 | CMe | NMe | Q1a | a bond | H | a bond | NH | O | a bond | Q3a | OH |
| 1943 | CMe | NMe | Q1a | a bond | H | a bond | NH | O | a bond | Q3b | OH |
| 1944 | CMe | NMe | Q1a | a bond | H | a bond | NH | O | a bond | Q3c | OH |
| 1945 | CMe | NMe | Q1b | a bond | Me | a bond | NH | S | NH | Q3a | OH |
| 1946 | CMe | NMe | Q1b | a bond | Me | a bond | NH | S | NH | Q3b | OH |
| 1947 | CMe | NMe | Q1b | a bond | Me | a bond | NH | S | NH | Q3c | OH |
| 1948 | CMe | NMe | Q1b | a bond | Me | a bond | NH | S | a bond | Q3a | OH |
| 1949 | CMe | NMe | Q1b | a bond | Me | a bond | NH | S | a bond | Q3b | OH |
| 1950 | CMe | NMe | Q1b | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 1951 | CMe | NMe | Q1b | a bond | Me | a bond | NH | O | NH | Q3a | OH |
| 1952 | CMe | NMe | Q1b | a bond | Me | a bond | NH | O | NH | Q3b | OH |
| 1953 | CMe | NMe | Q1b | a bond | Me | a bond | NH | O | NH | Q3c | OH |
| 1954 | CMe | NMe | Q1b | a bond | Me | a bond | NH | O | a bond | Q3a | OH |
| 1955 | CMe | NMe | Q1b | a bond | Me | a bond | NH | O | a bond | Q3b | OH |
| 1956 | CMe | NMe | Q1b | a bond | Me | a bond | NH | O | a bond | Q3c | OH |
| 1957 | CMe | NMe | Q1b | a bond | H | a bond | NH | S | NH | Q3a | OH |
| 1958 | CMe | NMe | Q1b | a bond | H | a bond | NH | S | NH | Q3b | OH |
| 1959 | CMe | NMe | Q1b | a bond | H | a bond | NH | S | NH | Q3c | OH |
| 1960 | CMe | NMe | Q1b | a bond | H | a bond | NH | S | a bond | Q3a | OH |
| 1961 | CMe | NMe | Q1b | a bond | H | a bond | NH | S | a bond | Q3b | OH |
| 1962 | CMe | NMe | Q1b | a bond | H | a bond | NH | S | a bond | Q3c | OH |
| 1963 | CMe | NMe | Q1b | a bond | H | a bond | NH | O | NH | Q3a | OH |
| 1964 | CMe | NMe | Q1b | a bond | H | a bond | NH | O | NH | Q3b | OH |
| 1965 | CMe | NMe | Q1b | a bond | H | a bond | NH | O | NH | Q3c | OH |
| 1966 | CMe | NMe | Q1b | a bond | H | a bond | NH | O | a bond | Q3a | OH |
| 1967 | CMe | NMe | Q1b | a bond | H | a bond | NH | O | a bond | Q3b | OH |
| 1968 | CMe | NMe | Q1b | a bond | H | a bond | NH | O | a bond | Q3c | OH |
| 1969 | CMe | NMe | Q1c | a bond | Me | a bond | NH | S | NH | Q3a | OH |
| 1970 | CMe | NMe | Q1c | a bond | Me | a bond | NH | S | NH | Q3b | OH |
| 1971 | CMe | NMe | Q1c | a bond | Me | a bond | NH | S | NH | Q3c | OH |
| 1972 | CMe | NMe | Q1c | a bond | Me | a bond | NH | S | a bond | Q3a | OH |
| 1973 | CMe | NMe | Q1c | a bond | Me | a bond | NH | S | a bond | Q3b | OH |
| 1974 | CMe | NMe | Q1c | a bond | Me | a bond | NH | S | a bond | Q3c | OH |
| 1975 | CMe | NMe | Q1c | a bond | Me | a bond | NH | O | NH | Q3a | OH |
| 1976 | CMe | NMe | Q1c | a bond | Me | a bond | NH | O | NH | Q3b | OH |
| 1977 | CMe | NMe | Q1c | a bond | Me | a bond | NH | O | NH | Q3c | OH |
| 1978 | CMe | NMe | Q1c | a bond | Me | a bond | NH | O | a bond | Q3a | OH |
| 1979 | CMe | NMe | Q1c | a bond | Me | a bond | NH | O | a bond | Q3b | OH |
| 1980 | CMe | NMe | Q1c | a bond | Me | a bond | NH | O | a bond | Q3c | OH |
| 1981 | CMe | NMe | Q1c | a bond | H | a bond | NH | S | NH | Q3a | OH |
| 1982 | CMe | NMe | Q1c | a bond | H | a bond | NH | S | NH | Q3b | OH |
| 1983 | CMe | NMe | Q1c | a bond | H | a bond | NH | S | NH | Q3c | OH |
| 1984 | CMe | NMe | Q1c | a bond | H | a bond | NH | S | a bond | Q3a | OH |
| 1985 | CMe | NMe | Q1c | a bond | H | a bond | NH | S | a bond | Q3b | OH |
| 1986 | CMe | NMe | Q1c | a bond | H | a bond | NH | S | a bond | Q3c | OH |
| 1987 | CMe | NMe | Q1c | a bond | H | a bond | NH | O | NH | Q3a | OH |
| 1988 | CMe | NMe | Q1c | a bond | H | a bond | NH | O | NH | Q3b | OH |
| 1989 | CMe | NMe | Q1c | a bond | H | a bond | NH | O | NH | Q3c | OH |
| 1990 | CMe | NMe | Q1c | a bond | H | a bond | NH | O | a bond | Q3a | OH |
| 1991 | CMe | NMe | Q1c | a bond | H | a bond | NH | O | a bond | Q3b | OH |
| 1992 | CMe | NMe | Q1c | a bond | H | a bond | NH | O | a bond | Q3c | OH |
| 1993 | CMe | NMe | Q1d | a bond | Me | a bond | NH | S | NH | Q3a | OH |
| 1994 | CMe | NMe | Q1d | a bond | Me | a bond | NH | S | NH | Q3b | OH |
| 1995 | CMe | NMe | Q1d | a bond | Me | a bond | NH | S | NH | Q3c | OH |
| 1996 | CMe | NMe | Q1d | a bond | Me | a bond | NH | S | a bond | Q3a | OH |
| 1997 | CMe | NMe | Q1d | a bond | Me | a bond | NH | S | a bond | Q3b | OH |
| 1998 | CMe | NMe | Q1d | a bond | Me | a bond | NH | S | a bond | Q3c | OH |
| 1999 | CMe | NMe | Q1d | a bond | Me | a bond | NH | O | NH | Q3a | OH |
| 2000 | CMe | NMe | Q1d | a bond | Me | a bond | NH | O | NH | Q3b | OH |
| 2001 | CMe | NMe | Q1d | a bond | Me | a bond | NH | O | NH | Q3c | OH |
| 2002 | CMe | NMe | Q1d | a bond | Me | a bond | NH | O | a bond | Q3a | OH |
| 2003 | CMe | NMe | Q1d | a bond | Me | a bond | NH | O | a bond | Q3b | OH |
| 2004 | CMe | NMe | Q1d | a bond | Me | a bond | NH | O | a bond | Q3c | OH |
| 2005 | CMe | NMe | Q1d | a bond | H | a bond | NH | S | NH | Q3a | OH |
| 2006 | CMe | NMe | Q1d | a bond | H | a bond | NH | S | NH | Q3b | OH |
| 2007 | CMe | NMe | Q1d | a bond | H | a bond | NH | S | NH | Q3c | OH |
| 2008 | CMe | NMe | Q1d | a bond | H | a bond | NH | S | a bond | Q3a | OH |
| 2009 | CMe | NMe | Q1d | a bond | H | a bond | NH | S | a bond | Q3b | OH |
| 2010 | CMe | NMe | Q1d | a bond | H | a bond | NH | S | a bond | Q3c | OH |
| 2011 | CMe | NMe | Q1d | a bond | H | a bond | NH | O | NH | Q3a | OH |
| 2012 | CMe | NMe | Q1d | a bond | H | a bond | NH | O | NH | Q3b | OH |
| 2013 | CMe | NMe | Q1d | a bond | H | a bond | NH | O | NH | Q3c | OH |
| 2014 | CMe | NMe | Q1d | a bond | H | a bond | NH | O | a bond | Q3a | OH |
| 2015 | CMe | NMe | Q1d | a bond | H | a bond | NH | O | a bond | Q3b | OH |
| 2016 | CMe | NMe | Q1d | a bond | H | a bond | NH | O | a bond | Q3c | OH |
| 2017 | CMe | NMe | Q1e | a bond | Me | a bond | NH | S | NH | Q3a | OH |
| 2018 | CMe | NMe | Q1e | a bond | Me | a bond | NH | S | NH | Q3b | OH |
| 2019 | CMe | NMe | Q1e | a bond | Me | a bond | NH | S | NH | Q3c | OH |
| 2020 | CMe | NMe | Q1e | a bond | Me | a bond | NH | S | a bond | Q3a | OH |
| 2021 | CMe | NMe | Q1e | a bond | Me | a bond | NH | S | a bond | Q3b | OH |
| 2022 | CMe | NMe | Q1e | a bond | Me | a bond | NH | S | a bond | Q3c | OH |
| 2023 | CMe | NMe | Q1e | a bond | Me | a bond | NH | O | NH | Q3a | OH |
| 2024 | CMe | NMe | Q1e | a bond | Me | a bond | NH | O | NH | Q3b | OH |
| 2025 | CMe | NMe | Q1e | a bond | Me | a bond | NH | O | NH | Q3c | OH |
| 2026 | CMe | NMe | Q1e | a bond | Me | a bond | NH | O | a bond | Q3a | OH |
| 2027 | CMe | NMe | Q1e | a bond | Me | a bond | NH | O | a bond | Q3b | OH |
| 2028 | CMe | NMe | Q1e | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2029 | CMe | NMe | Q1e | a bond | H | a bond | NH | S | NH | Q3a | OH |
| 2030 | CMe | NMe | Q1e | a bond | H | a bond | NH | S | NH | Q3b | OH |
| 2031 | CMe | NMe | Q1e | a bond | H | a bond | NH | S | NH | Q3c | OH |
| 2032 | CMe | NMe | Q1e | a bond | H | a bond | NH | S | a bond | Q3a | OH |
| 2033 | CMe | NMe | Q1e | a bond | H | a bond | NH | S | a bond | Q3b | OH |
| 2034 | CMe | NMe | Q1e | a bond | H | a bond | NH | S | a bond | Q3c | OH |
| 2035 | CMe | NMe | Q1e | a bond | H | a bond | NH | O | NH | Q3a | OH |
| 2036 | CMe | NMe | Q1e | a bond | H | a bond | NH | O | NH | Q3b | OH |
| 2037 | CMe | NMe | Q1e | a bond | H | a bond | NH | O | NH | Q3c | OH |
| 2038 | CMe | NMe | Q1e | a bond | H | a bond | NH | O | a bond | Q3a | OH |
| 2039 | CMe | NMe | Q1e | a bond | H | a bond | NH | O | a bond | Q3b | OH |
| 2040 | CMe | NMe | Q1e | a bond | H | a bond | NH | O | a bond | Q3c | OH |
| 2041 | CMe | NMe | Q1f | a bond | Me | a bond | NH | S | NH | Q3a | OH |
| 2042 | CMe | NMe | Q1f | a bond | Me | a bond | NH | S | NH | Q3b | OH |
| 2043 | CMe | NMe | Q1f | a bond | Me | a bond | NH | S | NH | Q3c | OH |
| 2044 | CMe | NMe | Q1f | a bond | Me | a bond | NH | S | a bond | Q3a | OH |
| 2045 | CMe | NMe | Q1f | a bond | Me | a bond | NH | S | a bond | Q3b | OH |
| 2046 | CMe | NMe | Q1f | a bond | Me | a bond | NH | S | a bond | Q3c | OH |
| 2047 | CMe | NMe | Q1f | a bond | Me | a bond | NH | O | NH | Q3a | OH |
| 2048 | CMe | NMe | Q1f | a bond | Me | a bond | NH | O | NH | Q3b | OH |
| 2049 | CMe | NMe | Q1f | a bond | Me | a bond | NH | O | NH | Q3c | OH |
| 2050 | CMe | NMe | Q1f | a bond | Me | a bond | NH | O | a bond | Q3a | OH |
| 2051 | CMe | NMe | Q1f | a bond | Me | a bond | NH | O | a bond | Q3b | OH |
| 2052 | CMe | NMe | Q1f | a bond | Me | a bond | NH | O | a bond | Q3c | OH |
| 2053 | CMe | NMe | Q1f | a bond | H | a bond | NH | S | NH | Q3a | OH |
| 2054 | CMe | NMe | Q1f | a bond | H | a bond | NH | S | NH | Q3b | OH |
| 2055 | CMe | NMe | Q1f | a bond | H | a bond | NH | S | NH | Q3c | OH |
| 2056 | CMe | NMe | Q1f | a bond | H | a bond | NH | S | a bond | Q3a | OH |
| 2057 | CMe | NMe | Q1f | a bond | H | a bond | NH | S | a bond | Q3b | OH |
| 2058 | CMe | NMe | Q1f | a bond | H | a bond | NH | S | a bond | Q3c | OH |
| 2059 | CMe | NMe | Q1f | a bond | H | a bond | NH | O | NH | Q3a | OH |
| 2060 | CMe | NMe | Q1f | a bond | H | a bond | NH | O | NH | Q3b | OH |
| 2061 | CMe | NMe | Q1f | a bond | H | a bond | NH | O | NH | Q3c | OH |
| 2062 | CMe | NMe | Q1f | a bond | H | a bond | NH | O | a bond | Q3a | OH |
| 2063 | CMe | NMe | Q1f | a bond | H | a bond | NH | O | a bond | Q3b | OH |
| 2064 | CMe | NMe | Q1f | a bond | H | a bond | NH | O | a bond | Q3c | OH |
| 2065 | CMe | NMe | Q1g | a bond | Me | a bond | NH | S | NH | Q3a | OH |
| 2066 | CMe | NMe | Q1g | a bond | Me | a bond | NH | S | NH | Q3b | OH |
| 2067 | CMe | NMe | Q1g | a bond | Me | a bond | NH | S | NH | Q3c | OH |
| 2068 | CMe | NMe | Q1g | a bond | Me | a bond | NH | S | a bond | Q3a | OH |
| 2069 | CMe | NMe | Q1g | a bond | Me | a bond | NH | S | a bond | Q3b | OH |
| 2070 | CMe | NMe | Q1g | a bond | Me | a bond | NH | S | a bond | Q3c | OH |
| 2071 | CMe | NMe | Q1g | a bond | Me | a bond | NH | O | NH | Q3a | OH |
| 2072 | CMe | NMe | Q1g | a bond | Me | a bond | NH | O | NH | Q3b | OH |
| 2073 | CMe | NMe | Q1g | a bond | Me | a bond | NH | O | NH | Q3c | OH |
| 2074 | CMe | NMe | Q1g | a bond | Me | a bond | NH | O | a bond | Q3a | OH |
| 2075 | CMe | NMe | Q1g | a bond | Me | a bond | NH | O | a bond | Q3b | OH |
| 2076 | CMe | NMe | Q1g | a bond | Me | a bond | NH | O | a bond | Q3c | OH |
| 2077 | CMe | NMe | Q1g | a bond | H | a bond | NH | S | NH | Q3a | OH |
| 2078 | CMe | NMe | Q1g | a bond | H | a bond | NH | S | NH | Q3b | OH |
| 2079 | CMe | NMe | Q1g | a bond | H | a bond | NH | S | NH | Q3c | OH |
| 2080 | CMe | NMe | Q1g | a bond | H | a bond | NH | S | a bond | Q3a | OH |
| 2081 | CMe | NMe | Q1g | a bond | H | a bond | NH | S | a bond | Q3b | OH |
| 2082 | CMe | NMe | Q1g | a bond | H | a bond | NH | S | a bond | Q3c | OH |
| 2083 | CMe | NMe | Q1g | a bond | H | a bond | NH | O | NH | Q3a | OH |
| 2084 | CMe | NMe | Q1g | a bond | H | a bond | NH | O | NH | Q3b | OH |
| 2085 | CMe | NMe | Q1g | a bond | H | a bond | NH | O | NH | Q3c | OH |
| 2086 | CMe | NMe | Q1g | a bond | H | a bond | NH | O | a bond | Q3a | OH |
| 2087 | CMe | NMe | Q1g | a bond | H | a bond | NH | O | a bond | Q3b | OH |
| 2088 | CMe | NMe | Q1g | a bond | H | a bond | NH | O | a bond | Q3c | OH |
| 2089 | CMe | NMe | Q1h | a bond | Me | a bond | NH | S | NH | Q3a | OH |
| 2090 | CMe | NMe | Q1h | a bond | Me | a bond | NH | S | NH | Q3b | OH |
| 2091 | CMe | NMe | Q1h | a bond | Me | a bond | NH | S | NH | Q3c | OH |
| 2092 | CMe | NMe | Q1h | a bond | Me | a bond | NH | S | a bond | Q3a | OH |
| 2093 | CMe | NMe | Q1h | a bond | Me | a bond | NH | S | a bond | Q3b | OH |
| 2094 | CMe | NMe | Q1h | a bond | Me | a bond | NH | S | a bond | Q3c | OH |
| 2095 | CMe | NMe | Q1h | a bond | Me | a bond | NH | O | NH | Q3a | OH |
| 2096 | CMe | NMe | Q1h | a bond | Me | a bond | NH | O | NH | Q3b | OH |
| 2097 | CMe | NMe | Q1h | a bond | Me | a bond | NH | O | NH | Q3c | OH |
| 2098 | CMe | NMe | Q1h | a bond | Me | a bond | NH | O | a bond | Q3a | OH |
| 2099 | CMe | NMe | Q1h | a bond | Me | a bond | NH | O | a bond | Q3b | OH |
| 2100 | CMe | NMe | Q1h | a bond | Me | a bond | NH | O | a bond | Q3c | OH |
| 2101 | CMe | NMe | Q1h | a bond | H | a bond | NH | S | NH | Q3a | OH |
| 2102 | CMe | NMe | Q1h | a bond | H | a bond | NH | S | NH | Q3b | OH |
| 2103 | CMe | NMe | Q1h | a bond | H | a bond | NH | S | NH | Q3c | OH |
| 2104 | CMe | NMe | Q1h | a bond | H | a bond | NH | S | a bond | Q3a | OH |
| 2105 | CMe | NMe | Q1h | a bond | H | a bond | NH | S | a bond | Q3b | OH |
| 2106 | CMe | NMe | Q1h | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2107 | CMe | NMe | Q1h | a bond | H | a bond | NH | O | NH | Q3a | OH |
| 2108 | CMe | NMe | Q1h | a bond | H | a bond | NH | O | NH | Q3b | OH |
| 2109 | CMe | NMe | Q1h | a bond | H | a bond | NH | O | NH | Q3c | OH |
| 2110 | CMe | NMe | Q1h | a bond | H | a bond | NH | O | a bond | Q3a | OH |
| 2111 | CMe | NMe | Q1h | a bond | H | a bond | NH | O | a bond | Q3b | OH |
| 2112 | CMe | NMe | Q1h | a bond | H | a bond | NH | O | a bond | Q3c | OH |
| 2113 | CMe | NMe | Q1i | a bond | Me | a bond | NH | S | NH | Q3a | OH |
| 2114 | CMe | NMe | Q1i | a bond | Me | a bond | NH | S | NH | Q3b | OH |
| 2115 | CMe | NMe | Q1i | a bond | Me | a bond | NH | S | NH | Q3c | OH |
| 2116 | CMe | NMe | Q1i | a bond | Me | a bond | NH | S | a bond | Q3a | OH |
| 2117 | CMe | NMe | Q1i | a bond | Me | a bond | NH | S | a bond | Q3b | OH |
| 2118 | CMe | NMe | Q1i | a bond | Me | a bond | NH | S | a bond | Q3c | OH |
| 2119 | CMe | NMe | Q1i | a bond | Me | a bond | NH | O | NH | Q3a | OH |
| 2120 | CMe | NMe | Q1i | a bond | Me | a bond | NH | O | NH | Q3b | OH |
| 2121 | CMe | NMe | Q1i | a bond | Me | a bond | NH | O | NH | Q3c | OH |
| 2122 | CMe | NMe | Q1i | a bond | Me | a bond | NH | O | a bond | Q3a | OH |
| 2123 | CMe | NMe | Q1i | a bond | Me | a bond | NH | O | a bond | Q3b | OH |
| 2124 | CMe | NMe | Q1i | a bond | Me | a bond | NH | O | a bond | Q3c | OH |
| 2125 | CMe | NMe | Q1i | a bond | H | a bond | NH | S | NH | Q3a | OH |
| 2126 | CMe | NMe | Q1i | a bond | H | a bond | NH | S | NH | Q3b | OH |
| 2127 | CMe | NMe | Q1i | a bond | H | a bond | NH | S | NH | Q3c | OH |
| 2128 | CMe | NMe | Q1i | a bond | H | a bond | NH | S | a bond | Q3a | OH |
| 2129 | CMe | NMe | Q1i | a bond | H | a bond | NH | S | a bond | Q3b | OH |
| 2130 | CMe | NMe | Q1i | a bond | H | a bond | NH | S | a bond | Q3c | OH |
| 2131 | CMe | NMe | Q1i | a bond | H | a bond | NH | O | NH | Q3a | OH |
| 2132 | CMe | NMe | Q1i | a bond | H | a bond | NH | O | NH | Q3b | OH |
| 2133 | CMe | NMe | Q1i | a bond | H | a bond | NH | O | NH | Q3c | OH |
| 2134 | CMe | NMe | Q1i | a bond | H | a bond | NH | O | a bond | Q3a | OH |
| 2135 | CMe | NMe | Q1i | a bond | H | a bond | NH | O | a bond | Q3b | OH |
| 2136 | CMe | NMe | Q1i | a bond | H | a bond | NH | O | a bond | Q3c | OH |
| 2137 | CMe | NMe | Q1j | a bond | Me | a bond | NH | S | NH | Q3a | OH |
| 2138 | CMe | NMe | Q1j | a bond | Me | a bond | NH | S | NH | Q3b | OH |
| 2139 | CMe | NMe | Q1j | a bond | Me | a bond | NH | S | NH | Q3c | OH |
| 2140 | CMe | NMe | Q1j | a bond | Me | a bond | NH | S | a bond | Q3a | OH |
| 2141 | CMe | NMe | Q1j | a bond | Me | a bond | NH | S | a bond | Q3b | OH |
| 2142 | CMe | NMe | Q1j | a bond | Me | a bond | NH | S | a bond | Q3c | OH |
| 2143 | CMe | NMe | Q1j | a bond | Me | a bond | NH | O | NH | Q3a | OH |
| 2144 | CMe | NMe | Q1j | a bond | Me | a bond | NH | O | NH | Q3b | OH |
| 2145 | CMe | NMe | Q1j | a bond | Me | a bond | NH | O | NH | Q3c | OH |
| 2146 | CMe | NMe | Q1j | a bond | Me | a bond | NH | O | a bond | Q3a | OH |
| 2147 | CMe | NMe | Q1j | a bond | Me | a bond | NH | O | a bond | Q3b | OH |
| 2148 | CMe | NMe | Q1j | a bond | Me | a bond | NH | O | a bond | Q3c | OH |
| 2149 | CMe | NMe | Q1j | a bond | H | a bond | NH | S | NH | Q3a | OH |
| 2150 | CMe | NMe | Q1j | a bond | H | a bond | NH | S | NH | Q3b | OH |
| 2151 | CMe | NMe | Q1j | a bond | H | a bond | NH | S | NH | Q3c | OH |
| 2152 | CMe | NMe | Q1j | a bond | H | a bond | NH | S | a bond | Q3a | OH |
| 2153 | CMe | NMe | Q1j | a bond | H | a bond | NH | S | a bond | Q3b | OH |
| 2154 | CMe | NMe | Q1j | a bond | H | a bond | NH | S | a bond | Q3c | OH |
| 2155 | CMe | NMe | Q1j | a bond | H | a bond | NH | O | NH | Q3a | OH |
| 2156 | CMe | NMe | Q1j | a bond | H | a bond | NH | O | NH | Q3b | OH |
| 2157 | CMe | NMe | Q1j | a bond | H | a bond | NH | O | NH | Q3c | OH |
| 2158 | CMe | NMe | Q1j | a bond | H | a bond | NH | O | a bond | Q3a | OH |
| 2159 | CMe | NMe | Q1j | a bond | H | a bond | NH | O | a bond | Q3b | OH |
| 2160 | CMe | NMe | Q1j | a bond | H | a bond | NH | O | a bond | Q3c | OH |
| 2161 | CMe | NEt | Q1a | a bond | Me | a bond | NH | S | NH | Q3a | OH |
| 2162 | CMe | NEt | Q1a | a bond | Me | a bond | NH | S | NH | Q3b | OH |
| 2163 | CMe | NEt | Q1a | a bond | Me | a bond | NH | S | NH | Q3c | OH |
| 2164 | CMe | NEt | Q1a | a bond | Me | a bond | NH | S | a bond | Q3a | OH |
| 2165 | CMe | NEt | Q1a | a bond | Me | a bond | NH | S | a bond | Q3b | OH |
| 2166 | CMe | NEt | Q1a | a bond | Me | a bond | NH | S | a bond | Q3c | OH |
| 2167 | CMe | NEt | Q1a | a bond | Me | a bond | NH | O | NH | Q3a | OH |
| 2168 | CMe | NEt | Q1a | a bond | Me | a bond | NH | O | NH | Q3b | OH |
| 2169 | CMe | NEt | Q1a | a bond | Me | a bond | NH | O | NH | Q3c | OH |
| 2170 | CMe | NEt | Q1a | a bond | Me | a bond | NH | O | a bond | Q3a | OH |
| 2171 | CMe | NEt | Q1a | a bond | Me | a bond | NH | O | a bond | Q3b | OH |
| 2172 | CMe | NEt | Q1a | a bond | Me | a bond | NH | O | a bond | Q3c | OH |
| 2173 | CMe | NEt | Q1a | a bond | H | a bond | NH | S | NH | Q3a | OH |
| 2174 | CMe | NEt | Q1a | a bond | H | a bond | NH | S | NH | Q3b | OH |
| 2175 | CMe | NEt | Q1a | a bond | H | a bond | NH | S | NH | Q3c | OH |
| 2176 | CMe | NEt | Q1a | a bond | H | a bond | NH | S | a bond | Q3a | OH |
| 2177 | CMe | NEt | Q1a | a bond | H | a bond | NH | S | a bond | Q3b | OH |
| 2178 | CMe | NEt | Q1a | a bond | H | a bond | NH | S | a bond | Q3c | OH |
| 2179 | CMe | NEt | Q1a | a bond | H | a bond | NH | O | NH | Q3a | OH |
| 2180 | CMe | NEt | Q1a | a bond | H | a bond | NH | O | NH | Q3b | OH |
| 2181 | CMe | NEt | Q1a | a bond | H | a bond | NH | O | NH | Q3c | OH |
| 2182 | CMe | NEt | Q1a | a bond | H | a bond | NH | O | a bond | Q3a | OH |
| 2183 | CMe | NEt | Q1a | a bond | H | a bond | NH | O | a bond | Q3b | OH |
| 2184 | CMe | NEt | Q1a | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2185 | CMe | NEt | Q1b | a bond | Me | a bond | NH | S | NH | Q3a | OH |
| 2186 | CMe | NEt | Q1b | a bond | Me | a bond | NH | S | NH | Q3b | OH |
| 2187 | CMe | NEt | Q1b | a bond | Me | a bond | NH | S | NH | Q3c | OH |
| 2188 | CMe | NEt | Q1b | a bond | Me | a bond | NH | S | a bond | Q3a | OH |
| 2189 | CMe | NEt | Q1b | a bond | Me | a bond | NH | S | a bond | Q3b | OH |
| 2190 | CMe | NEt | Q1b | a bond | Me | a bond | NH | S | a bond | Q3c | OH |
| 2191 | CMe | NEt | Q1b | a bond | Me | a bond | NH | O | NH | Q3a | OH |
| 2192 | CMe | NEt | Q1b | a bond | Me | a bond | NH | O | NH | Q3b | OH |
| 2193 | CMe | NEt | Q1b | a bond | Me | a bond | NH | O | NH | Q3c | OH |
| 2194 | CMe | NEt | Q1b | a bond | Me | a bond | NH | O | a bond | Q3a | OH |
| 2195 | CMe | NEt | Q1b | a bond | Me | a bond | NH | O | a bond | Q3b | OH |
| 2196 | CMe | NEt | Q1b | a bond | Me | a bond | NH | O | a bond | Q3c | OH |
| 2197 | CMe | NEt | Q1b | a bond | H | a bond | NH | S | NH | Q3a | OH |
| 2198 | CMe | NEt | Q1b | a bond | H | a bond | NH | S | NH | Q3b | OH |
| 2199 | CMe | NEt | Q1b | a bond | H | a bond | NH | S | NH | Q3c | OH |
| 2200 | CMe | NEt | Q1b | a bond | H | a bond | NH | S | a bond | Q3a | OH |
| 2201 | CMe | NEt | Q1b | a bond | H | a bond | NH | S | a bond | Q3b | OH |
| 2202 | CMe | NEt | Q1b | a bond | H | a bond | NH | S | a bond | Q3c | OH |
| 2203 | CMe | NEt | Q1b | a bond | H | a bond | NH | O | NH | Q3a | OH |
| 2204 | CMe | NEt | Q1b | a bond | H | a bond | NH | O | NH | Q3b | OH |
| 2205 | CMe | NEt | Q1b | a bond | H | a bond | NH | O | NH | Q3c | OH |
| 2206 | CMe | NEt | Q1b | a bond | H | a bond | NH | O | a bond | Q3a | OH |
| 2207 | CMe | NEt | Q1b | a bond | H | a bond | NH | O | a bond | Q3b | OH |
| 2208 | CMe | NEt | Q1b | a bond | H | a bond | NH | O | a bond | Q3c | OH |
| 2209 | CMe | NEt | Q1c | a bond | Me | a bond | NH | S | NH | Q3a | OH |
| 2210 | CMe | NEt | Q1c | a bond | Me | a bond | NH | S | NH | Q3b | OH |
| 2211 | CMe | NEt | Q1c | a bond | Me | a bond | NH | S | NH | Q3c | OH |
| 2212 | CMe | NEt | Q1c | a bond | Me | a bond | NH | S | a bond | Q3a | OH |
| 2213 | CMe | NEt | Q1c | a bond | Me | a bond | NH | S | a bond | Q3b | OH |
| 2214 | CMe | NEt | Q1c | a bond | Me | a bond | NH | S | a bond | Q3c | OH |
| 2215 | CMe | NEt | Q1c | a bond | Me | a bond | NH | O | NH | Q3a | OH |
| 2216 | CMe | NEt | Q1c | a bond | Me | a bond | NH | O | NH | Q3b | OH |
| 2217 | CMe | NEt | Q1c | a bond | Me | a bond | NH | O | NH | Q3c | OH |
| 2218 | CMe | NEt | Q1c | a bond | Me | a bond | NH | O | a bond | Q3a | OH |
| 2219 | CMe | NEt | Q1c | a bond | Me | a bond | NH | O | a bond | Q3b | OH |
| 2220 | CMe | NEt | Q1c | a bond | Me | a bond | NH | O | a bond | Q3c | OH |
| 2221 | CMe | NEt | Q1c | a bond | H | a bond | NH | S | NH | Q3a | OH |
| 2222 | CMe | NEt | Q1c | a bond | H | a bond | NH | S | NH | Q3b | OH |
| 2223 | CMe | NEt | Q1c | a bond | H | a bond | NH | S | NH | Q3c | OH |
| 2224 | CMe | NEt | Q1c | a bond | H | a bond | NH | S | a bond | Q3a | OH |
| 2225 | CMe | NEt | Q1c | a bond | H | a bond | NH | S | a bond | Q3b | OH |
| 2226 | CMe | NEt | Q1c | a bond | H | a bond | NH | S | a bond | Q3c | OH |
| 2227 | CMe | NEt | Q1c | a bond | H | a bond | NH | O | NH | Q3a | OH |
| 2228 | CMe | NEt | Q1c | a bond | H | a bond | NH | O | NH | Q3b | OH |
| 2229 | CMe | NEt | Q1c | a bond | H | a bond | NH | O | NH | Q3c | OH |
| 2230 | CMe | NEt | Q1c | a bond | H | a bond | NH | O | a bond | Q3a | OH |
| 2231 | CMe | NEt | Q1c | a bond | H | a bond | NH | O | a bond | Q3b | OH |
| 2232 | CMe | NEt | Q1c | a bond | H | a bond | NH | O | a bond | Q3c | OH |
| 2233 | CMe | NEt | Q1d | a bond | Me | a bond | NH | S | NH | Q3a | OH |
| 2234 | CMe | NEt | Q1d | a bond | Me | a bond | NH | S | NH | Q3b | OH |
| 2235 | CMe | NEt | Q1d | a bond | Me | a bond | NH | S | NH | Q3c | OH |
| 2236 | CMe | NEt | Q1d | a bond | Me | a bond | NH | S | a bond | Q3a | OH |
| 2237 | CMe | NEt | Q1d | a bond | Me | a bond | NH | S | a bond | Q3b | OH |
| 2238 | CMe | NEt | Q1d | a bond | Me | a bond | NH | S | a bond | Q3c | OH |
| 2239 | CMe | NEt | Q1d | a bond | Me | a bond | NH | O | NH | Q3a | OH |
| 2240 | CMe | NEt | Q1d | a bond | Me | a bond | NH | O | NH | Q3b | OH |
| 2241 | CMe | NEt | Q1d | a bond | Me | a bond | NH | O | NH | Q3c | OH |
| 2242 | CMe | NEt | Q1d | a bond | Me | a bond | NH | O | a bond | Q3a | OH |
| 2243 | CMe | NEt | Q1d | a bond | Me | a bond | NH | O | a bond | Q3b | OH |
| 2244 | CMe | NEt | Q1d | a bond | Me | a bond | NH | O | a bond | Q3c | OH |
| 2245 | CMe | NEt | Q1d | a bond | H | a bond | NH | S | NH | Q3a | OH |
| 2246 | CMe | NEt | Q1d | a bond | H | a bond | NH | S | NH | Q3b | OH |
| 2247 | CMe | NEt | Q1d | a bond | H | a bond | NH | S | NH | Q3c | OH |
| 2248 | CMe | NEt | Q1d | a bond | H | a bond | NH | S | a bond | Q3a | OH |
| 2249 | CMe | NEt | Q1d | a bond | H | a bond | NH | S | a bond | Q3b | OH |
| 2250 | CMe | NEt | Q1d | a bond | H | a bond | NH | S | a bond | Q3c | OH |
| 2251 | CMe | NEt | Q1d | a bond | H | a bond | NH | O | NH | Q3a | OH |
| 2252 | CMe | NEt | Q1d | a bond | H | a bond | NH | O | NH | Q3b | OH |
| 2253 | CMe | NEt | Q1d | a bond | H | a bond | NH | O | NH | Q3c | OH |
| 2254 | CMe | NEt | Q1d | a bond | H | a bond | NH | O | a bond | Q3a | OH |
| 2255 | CMe | NEt | Q1d | a bond | H | a bond | NH | O | a bond | Q3b | OH |
| 2256 | CMe | NEt | Q1d | a bond | H | a bond | NH | O | a bond | Q3c | OH |
| 2257 | CMe | NEt | Q1e | a bond | Me | a bond | NH | S | NH | Q3a | OH |
| 2258 | CMe | NEt | Q1e | a bond | Me | a bond | NH | S | NH | Q3b | OH |
| 2259 | CMe | NEt | Q1e | a bond | Me | a bond | NH | S | NH | Q3c | OH |
| 2260 | CMe | NEt | Q1e | a bond | Me | a bond | NH | S | a bond | Q3a | OH |
| 2261 | CMe | NEt | Q1e | a bond | Me | a bond | NH | S | a bond | Q3b | OH |
| 2262 | CMe | NEt | Q1e | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2263 | CMe | NEt | Q1e | a bond | Me | a bond | NH | O | NH | Q3a | OH |
| 2264 | CMe | NEt | Q1e | a bond | Me | a bond | NH | O | NH | Q3b | OH |
| 2265 | CMe | NEt | Q1e | a bond | Me | a bond | NH | O | NH | Q3c | OH |
| 2266 | CMe | NEt | Q1e | a bond | Me | a bond | NH | O | a bond | Q3a | OH |
| 2267 | CMe | NEt | Q1e | a bond | Me | a bond | NH | O | a bond | Q3b | OH |
| 2268 | CMe | NEt | Q1e | a bond | Me | a bond | NH | O | a bond | Q3c | OH |
| 2269 | CMe | NEt | Q1e | a bond | H | a bond | NH | S | NH | Q3a | OH |
| 2270 | CMe | NEt | Q1e | a bond | H | a bond | NH | S | NH | Q3b | OH |
| 2271 | CMe | NEt | Q1e | a bond | H | a bond | NH | S | NH | Q3c | OH |
| 2272 | CMe | NEt | Q1e | a bond | H | a bond | NH | S | a bond | Q3a | OH |
| 2273 | CMe | NEt | Q1e | a bond | H | a bond | NH | S | a bond | Q3b | OH |
| 2274 | CMe | NEt | Q1e | a bond | H | a bond | NH | S | a bond | Q3c | OH |
| 2275 | CMe | NEt | Q1e | a bond | H | a bond | NH | O | NH | Q3a | OH |
| 2276 | CMe | NEt | Q1e | a bond | H | a bond | NH | O | NH | Q3b | OH |
| 2277 | CMe | NEt | Q1e | a bond | H | a bond | NH | O | NH | Q3c | OH |
| 2278 | CMe | NEt | Q1e | a bond | H | a bond | NH | O | a bond | Q3a | OH |
| 2279 | CMe | NEt | Q1e | a bond | H | a bond | NH | O | a bond | Q3b | OH |
| 2280 | CMe | NEt | Q1e | a bond | H | a bond | NH | O | a bond | Q3c | OH |
| 2281 | CMe | NEt | Q1f | a bond | Me | a bond | NH | S | NH | Q3a | OH |
| 2282 | CMe | NEt | Q1f | a bond | Me | a bond | NH | S | NH | Q3b | OH |
| 2283 | CMe | NEt | Q1f | a bond | Me | a bond | NH | S | NH | Q3c | OH |
| 2284 | CMe | NEt | Q1f | a bond | Me | a bond | NH | S | a bond | Q3a | OH |
| 2285 | CMe | NEt | Q1f | a bond | Me | a bond | NH | S | a bond | Q3b | OH |
| 2286 | CMe | NEt | Q1f | a bond | Me | a bond | NH | S | a bond | Q3c | OH |
| 2287 | CMe | NEt | Q1f | a bond | Me | a bond | NH | O | NH | Q3a | OH |
| 2288 | CMe | NEt | Q1f | a bond | Me | a bond | NH | O | NH | Q3b | OH |
| 2289 | CMe | NEt | Q1f | a bond | Me | a bond | NH | O | NH | Q3c | OH |
| 2290 | CMe | NEt | Q1f | a bond | Me | a bond | NH | O | a bond | Q3a | OH |
| 2291 | CMe | NEt | Q1f | a bond | Me | a bond | NH | O | a bond | Q3b | OH |
| 2292 | CMe | NEt | Q1f | a bond | Me | a bond | NH | O | a bond | Q3c | OH |
| 2293 | CMe | NEt | Q1f | a bond | H | a bond | NH | S | NH | Q3a | OH |
| 2294 | CMe | NEt | Q1f | a bond | H | a bond | NH | S | NH | Q3b | OH |
| 2295 | CMe | NEt | Q1f | a bond | H | a bond | NH | S | NH | Q3c | OH |
| 2296 | CMe | NEt | Q1f | a bond | H | a bond | NH | S | a bond | Q3a | OH |
| 2297 | CMe | NEt | Q1f | a bond | H | a bond | NH | S | a bond | Q3b | OH |
| 2298 | CMe | NEt | Q1f | a bond | H | a bond | NH | S | a bond | Q3c | OH |
| 2299 | CMe | NEt | Q1f | a bond | H | a bond | NH | O | NH | Q3a | OH |
| 2300 | CMe | NEt | Q1f | a bond | H | a bond | NH | O | NH | Q3b | OH |
| 2301 | CMe | NEt | Q1f | a bond | H | a bond | NH | O | NH | Q3c | OH |
| 2302 | CMe | NEt | Q1f | a bond | H | a bond | NH | O | a bond | Q3a | OH |
| 2303 | CMe | NEt | Q1f | a bond | H | a bond | NH | O | a bond | Q3b | OH |
| 2304 | CMe | NEt | Q1f | a bond | H | a bond | NH | O | a bond | Q3c | OH |
| 2305 | CMe | NEt | Q1g | a bond | Me | a bond | NH | S | NH | Q3a | OH |
| 2306 | CMe | NEt | Q1g | a bond | Me | a bond | NH | S | NH | Q3b | OH |
| 2307 | CMe | NEt | Q1g | a bond | Me | a bond | NH | S | NH | Q3c | OH |
| 2308 | CMe | NEt | Q1g | a bond | Me | a bond | NH | S | a bond | Q3a | OH |
| 2309 | CMe | NEt | Q1g | a bond | Me | a bond | NH | S | a bond | Q3b | OH |
| 2310 | CMe | NEt | Q1g | a bond | Me | a bond | NH | S | a bond | Q3c | OH |
| 2311 | CMe | NEt | Q1g | a bond | Me | a bond | NH | O | NH | Q3a | OH |
| 2312 | CMe | NEt | Q1g | a bond | Me | a bond | NH | O | NH | Q3b | OH |
| 2313 | CMe | NEt | Q1g | a bond | Me | a bond | NH | O | NH | Q3c | OH |
| 2314 | CMe | NEt | Q1g | a bond | Me | a bond | NH | O | a bond | Q3a | OH |
| 2315 | CMe | NEt | Q1g | a bond | Me | a bond | NH | O | a bond | Q3b | OH |
| 2316 | CMe | NEt | Q1g | a bond | Me | a bond | NH | O | a bond | Q3c | OH |
| 2317 | CMe | NEt | Q1g | a bond | H | a bond | NH | S | NH | Q3a | OH |
| 2318 | CMe | NEt | Q1g | a bond | H | a bond | NH | S | NH | Q3b | OH |
| 2319 | CMe | NEt | Q1g | a bond | H | a bond | NH | S | NH | Q3c | OH |
| 2320 | CMe | NEt | Q1g | a bond | H | a bond | NH | S | a bond | Q3a | OH |
| 2321 | CMe | NEt | Q1g | a bond | H | a bond | NH | S | a bond | Q3b | OH |
| 2322 | CMe | NEt | Q1g | a bond | H | a bond | NH | S | a bond | Q3c | OH |
| 2323 | CMe | NEt | Q1g | a bond | H | a bond | NH | O | NH | Q3a | OH |
| 2324 | CMe | NEt | Q1g | a bond | H | a bond | NH | O | NH | Q3b | OH |
| 2325 | CMe | NEt | Q1g | a bond | H | a bond | NH | O | NH | Q3c | OH |
| 2326 | CMe | NEt | Q1g | a bond | H | a bond | NH | O | a bond | Q3a | OH |
| 2327 | CMe | NEt | Q1g | a bond | H | a bond | NH | O | a bond | Q3b | OH |
| 2328 | CMe | NEt | Q1g | a bond | H | a bond | NH | O | a bond | Q3c | OH |
| 2329 | CMe | NEt | Q1h | a bond | Me | a bond | NH | S | NH | Q3a | OH |
| 2330 | CMe | NEt | Q1h | a bond | Me | a bond | NH | S | NH | Q3b | OH |
| 2331 | CMe | NEt | Q1h | a bond | Me | a bond | NH | S | NH | Q3c | OH |
| 2332 | CMe | NEt | Q1h | a bond | Me | a bond | NH | S | a bond | Q3a | OH |
| 2333 | CMe | NEt | Q1h | a bond | Me | a bond | NH | S | a bond | Q3b | OH |
| 2334 | CMe | NEt | Q1h | a bond | Me | a bond | NH | S | a bond | Q3c | OH |
| 2335 | CMe | NEt | Q1h | a bond | Me | a bond | NH | O | NH | Q3a | OH |
| 2336 | CMe | NEt | Q1h | a bond | Me | a bond | NH | O | NH | Q3b | OH |
| 2337 | CMe | NEt | Q1h | a bond | Me | a bond | NH | O | NH | Q3c | OH |
| 2338 | CMe | NEt | Q1h | a bond | Me | a bond | NH | O | a bond | Q3a | OH |
| 2339 | CMe | NEt | Q1h | a bond | Me | a bond | NH | O | a bond | Q3b | OH |
| 2340 | CMe | NEt | Q1h | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2341 | CMe | NEt | Q1h | a bond | H | a bond | NH | S | NH | Q3a | OH |
| 2342 | CMe | NEt | Q1h | a bond | H | a bond | NH | S | NH | Q3b | OH |
| 2343 | CMe | NEt | Q1h | a bond | H | a bond | NH | S | NH | Q3c | OH |
| 2344 | CMe | NEt | Q1h | a bond | H | a bond | NH | S | a bond | Q3a | OH |
| 2345 | CMe | NEt | Q1h | a bond | H | a bond | NH | S | a bond | Q3b | OH |
| 2346 | CMe | NEt | Q1h | a bond | H | a bond | NH | S | a bond | Q3c | OH |
| 2347 | CMe | NEt | Q1h | a bond | H | a bond | NH | O | NH | Q3a | OH |
| 2348 | CMe | NEt | Q1h | a bond | H | a bond | NH | O | NH | Q3b | OH |
| 2349 | CMe | NEt | Q1h | a bond | H | a bond | NH | O | NH | Q3c | OH |
| 2350 | CMe | NEt | Q1h | a bond | H | a bond | NH | O | a bond | Q3a | OH |
| 2351 | CMe | NEt | Q1h | a bond | H | a bond | NH | O | a bond | Q3b | OH |
| 2352 | CMe | NEt | Q1h | a bond | H | a bond | NH | O | a bond | Q3c | OH |
| 2353 | CMe | NEt | Q1i | a bond | Me | a bond | NH | S | NH | Q3a | OH |
| 2354 | CMe | NEt | Q1i | a bond | Me | a bond | NH | S | NH | Q3b | OH |
| 2355 | CMe | NEt | Q1i | a bond | Me | a bond | NH | S | NH | Q3c | OH |
| 2356 | CMe | NEt | Q1i | a bond | Me | a bond | NH | S | a bond | Q3a | OH |
| 2357 | CMe | NEt | Q1i | a bond | Me | a bond | NH | S | a bond | Q3b | OH |
| 2358 | CMe | NEt | Q1i | a bond | Me | a bond | NH | S | a bond | Q3c | OH |
| 2359 | CMe | NEt | Q1i | a bond | Me | a bond | NH | O | NH | Q3a | OH |
| 2360 | CMe | NEt | Q1i | a bond | Me | a bond | NH | O | NH | Q3b | OH |
| 2361 | CMe | NEt | Q1i | a bond | Me | a bond | NH | O | NH | Q3c | OH |
| 2362 | CMe | NEt | Q1i | a bond | Me | a bond | NH | O | a bond | Q3a | OH |
| 2363 | CMe | NEt | Q1i | a bond | Me | a bond | NH | O | a bond | Q3b | OH |
| 2364 | CMe | NEt | Q1i | a bond | Me | a bond | NH | O | a bond | Q3c | OH |
| 2365 | CMe | NEt | Q1i | a bond | H | a bond | NH | S | NH | Q3a | OH |
| 2366 | CMe | NEt | Q1i | a bond | H | a bond | NH | S | NH | Q3b | OH |
| 2367 | CMe | NEt | Q1i | a bond | H | a bond | NH | S | NH | Q3c | OH |
| 2368 | CMe | NEt | Q1i | a bond | H | a bond | NH | S | a bond | Q3a | OH |
| 2369 | CMe | NEt | Q1i | a bond | H | a bond | NH | S | a bond | Q3b | OH |
| 2370 | CMe | NEt | Q1i | a bond | H | a bond | NH | S | a bond | Q3c | OH |
| 2371 | CMe | NEt | Q1i | a bond | H | a bond | NH | O | NH | Q3a | OH |
| 2372 | CMe | NEt | Q1i | a bond | H | a bond | NH | O | NH | Q3b | OH |
| 2373 | CMe | NEt | Q1i | a bond | H | a bond | NH | O | NH | Q3c | OH |
| 2374 | CMe | NEt | Q1i | a bond | H | a bond | NH | O | a bond | Q3a | OH |
| 2375 | CMe | NEt | Q1i | a bond | H | a bond | NH | O | a bond | Q3b | OH |
| 2376 | CMe | NEt | Q1i | a bond | H | a bond | NH | O | a bond | Q3c | OH |
| 2377 | CMe | NEt | Q1j | a bond | Me | a bond | NH | S | NH | Q3a | OH |
| 2378 | CMe | NEt | Q1j | a bond | Me | a bond | NH | S | NH | Q3b | OH |
| 2379 | CMe | NEt | Q1j | a bond | Me | a bond | NH | S | NH | Q3c | OH |
| 2380 | CMe | NEt | Q1j | a bond | Me | a bond | NH | S | a bond | Q3a | OH |
| 2381 | CMe | NEt | Q1j | a bond | Me | a bond | NH | S | a bond | Q3b | OH |
| 2382 | CMe | NEt | Q1j | a bond | Me | a bond | NH | S | a bond | Q3c | OH |
| 2383 | CMe | NEt | Q1j | a bond | Me | a bond | NH | O | NH | Q3a | OH |
| 2384 | CMe | NEt | Q1j | a bond | Me | a bond | NH | O | NH | Q3b | OH |
| 2385 | CMe | NEt | Q1j | a bond | Me | a bond | NH | O | NH | Q3c | OH |
| 2386 | CMe | NEt | Q1j | a bond | Me | a bond | NH | O | a bond | Q3a | OH |
| 2387 | CMe | NEt | Q1j | a bond | Me | a bond | NH | O | a bond | Q3b | OH |
| 2388 | CMe | NEt | Q1j | a bond | Me | a bond | NH | O | a bond | Q3c | OH |
| 2389 | CMe | NEt | Q1j | a bond | H | a bond | NH | S | NH | Q3a | OH |
| 2390 | CMe | NEt | Q1j | a bond | H | a bond | NH | S | NH | Q3b | OH |
| 2391 | CMe | NEt | Q1j | a bond | H | a bond | NH | S | NH | Q3c | OH |
| 2392 | CMe | NEt | Q1j | a bond | H | a bond | NH | S | a bond | Q3a | OH |
| 2393 | CMe | NEt | Q1j | a bond | H | a bond | NH | S | a bond | Q3b | OH |
| 2394 | CMe | NEt | Q1j | a bond | H | a bond | NH | S | a bond | Q3c | OH |
| 2395 | CMe | NEt | Q1j | a bond | H | a bond | NH | O | NH | Q3a | OH |
| 2396 | CMe | NEt | Q1j | a bond | H | a bond | NH | O | NH | Q3b | OH |
| 2397 | CMe | NEt | Q1j | a bond | H | a bond | NH | O | NH | Q3c | OH |
| 2398 | CMe | NEt | Q1j | a bond | H | a bond | NH | O | a bond | Q3a | OH |
| 2399 | CMe | NEt | Q1j | a bond | H | a bond | NH | O | a bond | Q3b | OH |
| 2400 | CMe | NEt | Q1j | a bond | H | a bond | NH | O | a bond | Q3c | OH |
| 2401 | CMe | S | Q1a | a bond | Me | a bond | NH | S | NH | Q3a | OH |
| 2402 | CMe | S | Q1a | a bond | Me | a bond | NH | S | NH | Q3b | OH |
| 2403 | CMe | S | Q1a | a bond | Me | a bond | NH | S | NH | Q3c | OH |
| 2404 | CMe | S | Q1a | a bond | Me | a bond | NH | S | a bond | Q3a | OH |
| 2405 | CMe | S | Q1a | a bond | Me | a bond | NH | S | a bond | Q3b | OH |
| 2406 | CMe | S | Q1a | a bond | Me | a bond | NH | S | a bond | Q3c | OH |
| 2407 | CMe | S | Q1a | a bond | Me | a bond | NH | O | NH | Q3a | OH |
| 2408 | CMe | S | Q1a | a bond | Me | a bond | NH | O | NH | Q3b | OH |
| 2409 | CMe | S | Q1a | a bond | Me | a bond | NH | O | NH | Q3c | OH |
| 2410 | CMe | S | Q1a | a bond | Me | a bond | NH | O | a bond | Q3a | OH |
| 2411 | CMe | S | Q1a | a bond | Me | a bond | NH | O | a bond | Q3b | OH |
| 2412 | CMe | S | Q1a | a bond | Me | a bond | NH | O | a bond | Q3c | OH |
| 2413 | CMe | S | Q1a | a bond | H | a bond | NH | S | NH | Q3a | OH |
| 2414 | CMe | S | Q1a | a bond | H | a bond | NH | S | NH | Q3b | OH |
| 2415 | CMe | S | Q1a | a bond | H | a bond | NH | S | NH | Q3c | OH |
| 2416 | CMe | S | Q1a | a bond | H | a bond | NH | S | a bond | Q3a | OH |
| 2417 | CMe | S | Q1a | a bond | H | a bond | NH | S | a bond | Q3b | OH |
| 2418 | CMe | S | Q1a | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2419 | CMe | S | Q1a | a bond | H | a bond | NH | O | NH | Q3a | OH |
| 2420 | CMe | S | Q1a | a bond | H | a bond | NH | O | NH | Q3b | OH |
| 2421 | CMe | S | Q1a | a bond | H | a bond | NH | O | NH | Q3c | OH |
| 2422 | CMe | S | Q1a | a bond | H | a bond | NH | O | a bond | Q3a | OH |
| 2423 | CMe | S | Q1a | a bond | H | a bond | NH | O | a bond | Q3b | OH |
| 2424 | CMe | S | Q1a | a bond | H | a bond | NH | O | a bond | Q3c | OH |
| 2425 | CMe | S | Q1b | a bond | Me | a bond | NH | S | NH | Q3a | OH |
| 2426 | CMe | S | Q1b | a bond | Me | a bond | NH | S | NH | Q3b | OH |
| 2427 | CMe | S | Q1b | a bond | Me | a bond | NH | S | NH | Q3c | OH |
| 2428 | CMe | S | Q1b | a bond | Me | a bond | NH | S | a bond | Q3a | OH |
| 2429 | CMe | S | Q1b | a bond | Me | a bond | NH | S | a bond | Q3b | OH |
| 2430 | CMe | S | Q1b | a bond | Me | a bond | NH | S | a bond | Q3c | OH |
| 2431 | CMe | S | Q1b | a bond | Me | a bond | NH | O | NH | Q3a | OH |
| 2432 | CMe | S | Q1b | a bond | Me | a bond | NH | O | NH | Q3b | OH |
| 2433 | CMe | S | Q1b | a bond | Me | a bond | NH | O | NH | Q3c | OH |
| 2434 | CMe | S | Q1b | a bond | Me | a bond | NH | O | a bond | Q3a | OH |
| 2435 | CMe | S | Q1b | a bond | Me | a bond | NH | O | a bond | Q3b | OH |
| 2436 | CMe | S | Q1b | a bond | Me | a bond | NH | O | a bond | Q3c | OH |
| 2437 | CMe | S | Q1b | a bond | H | a bond | NH | S | NH | Q3a | OH |
| 2438 | CMe | S | Q1b | a bond | H | a bond | NH | S | NH | Q3b | OH |
| 2439 | CMe | S | Q1b | a bond | H | a bond | NH | S | NH | Q3c | OH |
| 2440 | CMe | S | Q1b | a bond | H | a bond | NH | S | a bond | Q3a | OH |
| 2441 | CMe | S | Q1b | a bond | H | a bond | NH | S | a bond | Q3b | OH |
| 2442 | CMe | S | Q1b | a bond | H | a bond | NH | S | a bond | Q3c | OH |
| 2443 | CMe | S | Q1b | a bond | H | a bond | NH | O | NH | Q3a | OH |
| 2444 | CMe | S | Q1b | a bond | H | a bond | NH | O | NH | Q3b | OH |
| 2445 | CMe | S | Q1b | a bond | H | a bond | NH | O | NH | Q3c | OH |
| 2446 | CMe | S | Q1b | a bond | H | a bond | NH | O | a bond | Q3a | OH |
| 2447 | CMe | S | Q1b | a bond | H | a bond | NH | O | a bond | Q3b | OH |
| 2448 | CMe | S | Q1b | a bond | H | a bond | NH | O | a bond | Q3c | OH |
| 2449 | CMe | S | Q1c | a bond | Me | a bond | NH | S | NH | Q3a | OH |
| 2450 | CMe | S | Q1c | a bond | Me | a bond | NH | S | NH | Q3b | OH |
| 2451 | CMe | S | Q1c | a bond | Me | a bond | NH | S | NH | Q3c | OH |
| 2452 | CMe | S | Q1c | a bond | Me | a bond | NH | S | a bond | Q3a | OH |
| 2453 | CMe | S | Q1c | a bond | Me | a bond | NH | S | a bond | Q3b | OH |
| 2454 | CMe | S | Q1c | a bond | Me | a bond | NH | S | a bond | Q3c | OH |
| 2455 | CMe | S | Q1c | a bond | Me | a bond | NH | O | NH | Q3a | OH |
| 2456 | CMe | S | Q1c | a bond | Me | a bond | NH | O | NH | Q3b | OH |
| 2457 | CMe | S | Q1c | a bond | Me | a bond | NH | O | NH | Q3c | OH |
| 2458 | CMe | S | Q1c | a bond | Me | a bond | NH | O | a bond | Q3a | OH |
| 2459 | CMe | S | Q1c | a bond | Me | a bond | NH | O | a bond | Q3b | OH |
| 2460 | CMe | S | Q1c | a bond | Me | a bond | NH | O | a bond | Q3c | OH |
| 2461 | CMe | S | Q1c | a bond | H | a bond | NH | S | NH | Q3a | OH |
| 2462 | CMe | S | Q1c | a bond | H | a bond | NH | S | NH | Q3b | OH |
| 2463 | CMe | S | Q1c | a bond | H | a bond | NH | S | NH | Q3c | OH |
| 2464 | CMe | S | Q1c | a bond | H | a bond | NH | S | a bond | Q3a | OH |
| 2465 | CMe | S | Q1c | a bond | H | a bond | NH | S | a bond | Q3b | OH |
| 2466 | CMe | S | Q1c | a bond | H | a bond | NH | S | a bond | Q3c | OH |
| 2467 | CMe | S | Q1c | a bond | H | a bond | NH | O | NH | Q3a | OH |
| 2468 | CMe | S | Q1c | a bond | H | a bond | NH | O | NH | Q3b | OH |
| 2469 | CMe | S | Q1c | a bond | H | a bond | NH | O | NH | Q3c | OH |
| 2470 | CMe | S | Q1c | a bond | H | a bond | NH | O | a bond | Q3a | OH |
| 2471 | CMe | S | Q1c | a bond | H | a bond | NH | O | a bond | Q3b | OH |
| 2472 | CMe | S | Q1c | a bond | H | a bond | NH | O | a bond | Q3c | OH |
| 2473 | CMe | S | Q1d | a bond | Me | a bond | NH | S | NH | Q3a | OH |
| 2474 | CMe | S | Q1d | a bond | Me | a bond | NH | S | NH | Q3b | OH |
| 2475 | CMe | S | Q1d | a bond | Me | a bond | NH | S | NH | Q3c | OH |
| 2476 | CMe | S | Q1d | a bond | Me | a bond | NH | S | a bond | Q3a | OH |
| 2477 | CMe | S | Q1d | a bond | Me | a bond | NH | S | a bond | Q3b | OH |
| 2478 | CMe | S | Q1d | a bond | Me | a bond | NH | S | a bond | Q3c | OH |
| 2479 | CMe | S | Q1d | a bond | Me | a bond | NH | O | NH | Q3a | OH |
| 2480 | CMe | S | Q1d | a bond | Me | a bond | NH | O | NH | Q3b | OH |
| 2481 | CMe | S | Q1d | a bond | Me | a bond | NH | O | NH | Q3c | OH |
| 2482 | CMe | S | Q1d | a bond | Me | a bond | NH | O | a bond | Q3a | OH |
| 2483 | CMe | S | Q1d | a bond | Me | a bond | NH | O | a bond | Q3b | OH |
| 2484 | CMe | S | Q1d | a bond | Me | a bond | NH | O | a bond | Q3c | OH |
| 2485 | CMe | S | Q1d | a bond | H | a bond | NH | S | NH | Q3a | OH |
| 2486 | CMe | S | Q1d | a bond | H | a bond | NH | S | NH | Q3b | OH |
| 2487 | CMe | S | Q1d | a bond | H | a bond | NH | S | NH | Q3c | OH |
| 2488 | CMe | S | Q1d | a bond | H | a bond | NH | S | a bond | Q3a | OH |
| 2489 | CMe | S | Q1d | a bond | H | a bond | NH | S | a bond | Q3b | OH |
| 2490 | CMe | S | Q1d | a bond | H | a bond | NH | S | a bond | Q3c | OH |
| 2491 | CMe | S | Q1d | a bond | H | a bond | NH | O | NH | Q3a | OH |
| 2492 | CMe | S | Q1d | a bond | H | a bond | NH | O | NH | Q3b | OH |
| 2493 | CMe | S | Q1d | a bond | H | a bond | NH | O | NH | Q3c | OH |
| 2494 | CMe | S | Q1d | a bond | H | a bond | NH | O | a bond | Q3a | OH |
| 2495 | CMe | S | Q1d | a bond | H | a bond | NH | O | a bond | Q3b | OH |
| 2496 | CMe | S | Q1d | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2497 | CMe | S | Q1e | a bond | Me | a bond | NH | S | NH | Q3a | OH |
| 2498 | CMe | S | Q1e | a bond | Me | a bond | NH | S | NH | Q3b | OH |
| 2499 | CMe | S | Q1e | a bond | Me | a bond | NH | S | NH | Q3c | OH |
| 2500 | CMe | S | Q1e | a bond | Me | a bond | NH | S | a bond | Q3a | OH |
| 2501 | CMe | S | Q1e | a bond | Me | a bond | NH | S | a bond | Q3b | OH |
| 2502 | CMe | S | Q1e | a bond | Me | a bond | NH | S | a bond | Q3c | OH |
| 2503 | CMe | S | Q1e | a bond | Me | a bond | NH | O | NH | Q3a | OH |
| 2504 | CMe | S | Q1e | a bond | Me | a bond | NH | O | NH | Q3b | OH |
| 2505 | CMe | S | Q1e | a bond | Me | a bond | NH | O | NH | Q3c | OH |
| 2506 | CMe | S | Q1e | a bond | Me | a bond | NH | O | a bond | Q3a | OH |
| 2507 | CMe | S | Q1e | a bond | Me | a bond | NH | O | a bond | Q3b | OH |
| 2508 | CMe | S | Q1e | a bond | Me | a bond | NH | O | a bond | Q3c | OH |
| 2509 | CMe | S | Q1e | a bond | H | a bond | NH | S | NH | Q3a | OH |
| 2510 | CMe | S | Q1e | a bond | H | a bond | NH | S | NH | Q3b | OH |
| 2511 | CMe | S | Q1e | a bond | H | a bond | NH | S | NH | Q3c | OH |
| 2512 | CMe | S | Q1e | a bond | H | a bond | NH | S | a bond | Q3a | OH |
| 2513 | CMe | S | Q1e | a bond | H | a bond | NH | S | a bond | Q3b | OH |
| 2514 | CMe | S | Q1e | a bond | H | a bond | NH | S | a bond | Q3c | OH |
| 2515 | CMe | S | Q1e | a bond | H | a bond | NH | O | NH | Q3a | OH |
| 2516 | CMe | S | Q1e | a bond | H | a bond | NH | O | NH | Q3b | OH |
| 2517 | CMe | S | Q1e | a bond | H | a bond | NH | O | NH | Q3c | OH |
| 2518 | CMe | S | Q1e | a bond | H | a bond | NH | O | a bond | Q3a | OH |
| 2519 | CMe | S | Q1e | a bond | H | a bond | NH | O | a bond | Q3b | OH |
| 2520 | CMe | S | Q1e | a bond | H | a bond | NH | O | a bond | Q3c | OH |
| 2521 | CMe | S | Q1f | a bond | Me | a bond | NH | S | NH | Q3a | OH |
| 2522 | CMe | S | Q1f | a bond | Me | a bond | NH | S | NH | Q3b | OH |
| 2523 | CMe | S | Q1f | a bond | Me | a bond | NH | S | NH | Q3c | OH |
| 2524 | CMe | S | Q1f | a bond | Me | a bond | NH | S | a bond | Q3a | OH |
| 2525 | CMe | S | Q1f | a bond | Me | a bond | NH | S | a bond | Q3b | OH |
| 2526 | CMe | S | Q1f | a bond | Me | a bond | NH | S | a bond | Q3c | OH |
| 2527 | CMe | S | Q1f | a bond | Me | a bond | NH | O | NH | Q3a | OH |
| 2528 | CMe | S | Q1f | a bond | Me | a bond | NH | O | NH | Q3b | OH |
| 2529 | CMe | S | Q1f | a bond | Me | a bond | NH | O | NH | Q3c | OH |
| 2530 | CMe | S | Q1f | a bond | Me | a bond | NH | O | a bond | Q3a | OH |
| 2531 | CMe | S | Q1f | a bond | Me | a bond | NH | O | a bond | Q3b | OH |
| 2532 | CMe | S | Q1f | a bond | Me | a bond | NH | O | a bond | Q3c | OH |
| 2533 | CMe | S | Q1f | a bond | H | a bond | NH | S | NH | Q3a | OH |
| 2534 | CMe | S | Q1f | a bond | H | a bond | NH | S | NH | Q3b | OH |
| 2535 | CMe | S | Q1f | a bond | H | a bond | NH | S | NH | Q3c | OH |
| 2536 | CMe | S | Q1f | a bond | H | a bond | NH | S | a bond | Q3a | OH |
| 2537 | CMe | S | Q1f | a bond | H | a bond | NH | S | a bond | Q3b | OH |
| 2538 | CMe | S | Q1f | a bond | H | a bond | NH | S | a bond | Q3c | OH |
| 2539 | CMe | S | Q1f | a bond | H | a bond | NH | O | NH | Q3a | OH |
| 2540 | CMe | S | Q1f | a bond | H | a bond | NH | O | NH | Q3b | OH |
| 2541 | CMe | S | Q1f | a bond | H | a bond | NH | O | NH | Q3c | OH |
| 2542 | CMe | S | Q1f | a bond | H | a bond | NH | O | a bond | Q3a | OH |
| 2543 | CMe | S | Q1f | a bond | H | a bond | NH | O | a bond | Q3b | OH |
| 2544 | CMe | S | Q1f | a bond | H | a bond | NH | O | a bond | Q3c | OH |
| 2545 | CMe | S | Q1g | a bond | Me | a bond | NH | S | NH | Q3a | OH |
| 2546 | CMe | S | Q1g | a bond | Me | a bond | NH | S | NH | Q3b | OH |
| 2547 | CMe | S | Q1g | a bond | Me | a bond | NH | S | NH | Q3c | OH |
| 2548 | CMe | S | Q1g | a bond | Me | a bond | NH | S | a bond | Q3a | OH |
| 2549 | CMe | S | Q1g | a bond | Me | a bond | NH | S | a bond | Q3b | OH |
| 2550 | CMe | S | Q1g | a bond | Me | a bond | NH | S | a bond | Q3c | OH |
| 2551 | CMe | S | Q1g | a bond | Me | a bond | NH | O | NH | Q3a | OH |
| 2552 | CMe | S | Q1g | a bond | Me | a bond | NH | O | NH | Q3b | OH |
| 2553 | CMe | S | Q1g | a bond | Me | a bond | NH | O | NH | Q3c | OH |
| 2554 | CMe | S | Q1g | a bond | Me | a bond | NH | O | a bond | Q3a | OH |
| 2555 | CMe | S | Q1g | a bond | Me | a bond | NH | O | a bond | Q3b | OH |
| 2556 | CMe | S | Q1g | a bond | Me | a bond | NH | O | a bond | Q3c | OH |
| 2557 | CMe | S | Q1g | a bond | H | a bond | NH | S | NH | Q3a | OH |
| 2558 | CMe | S | Q1g | a bond | H | a bond | NH | S | NH | Q3b | OH |
| 2559 | CMe | S | Q1g | a bond | H | a bond | NH | S | NH | Q3c | OH |
| 2560 | CMe | S | Q1g | a bond | H | a bond | NH | S | a bond | Q3a | OH |
| 2561 | CMe | S | Q1g | a bond | H | a bond | NH | S | a bond | Q3b | OH |
| 2562 | CMe | S | Q1g | a bond | H | a bond | NH | S | a bond | Q3c | OH |
| 2563 | CMe | S | Q1g | a bond | H | a bond | NH | O | NH | Q3a | OH |
| 2564 | CMe | S | Q1g | a bond | H | a bond | NH | O | NH | Q3b | OH |
| 2565 | CMe | S | Q1g | a bond | H | a bond | NH | O | NH | Q3c | OH |
| 2566 | CMe | S | Q1g | a bond | H | a bond | NH | O | a bond | Q3a | OH |
| 2567 | CMe | S | Q1g | a bond | H | a bond | NH | O | a bond | Q3b | OH |
| 2568 | CMe | S | Q1g | a bond | H | a bond | NH | O | a bond | Q3c | OH |
| 2569 | CMe | S | Q1h | a bond | Me | a bond | NH | S | NH | Q3a | OH |
| 2570 | CMe | S | Q1h | a bond | Me | a bond | NH | S | NH | Q3b | OH |
| 2571 | CMe | S | Q1h | a bond | Me | a bond | NH | S | NH | Q3c | OH |
| 2572 | CMe | S | Q1h | a bond | Me | a bond | NH | S | a bond | Q3a | OH |
| 2573 | CMe | S | Q1h | a bond | Me | a bond | NH | S | a bond | Q3b | OH |
| 2574 | CMe | S | Q1h | a bond | Me | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2575 | CMe | S | Q1h | a bond | Me | a bond | NH | O | NH | Q3a | OH |
| 2576 | CMe | S | Q1h | a bond | Me | a bond | NH | O | NH | Q3b | OH |
| 2577 | CMe | S | Q1h | a bond | Me | a bond | NH | O | NH | Q3c | OH |
| 2578 | CMe | S | Q1h | a bond | Me | a bond | NH | O | a bond | Q3a | OH |
| 2579 | CMe | S | Q1h | a bond | Me | a bond | NH | O | a bond | Q3b | OH |
| 2580 | CMe | S | Q1h | a bond | Me | a bond | NH | O | a bond | Q3c | OH |
| 2581 | CMe | S | Q1h | a bond | H | a bond | NH | S | NH | Q3a | OH |
| 2582 | CMe | S | Q1h | a bond | H | a bond | NH | S | NH | Q3b | OH |
| 2583 | CMe | S | Q1h | a bond | H | a bond | NH | S | NH | Q3c | OH |
| 2584 | CMe | S | Q1h | a bond | H | a bond | NH | S | a bond | Q3a | OH |
| 2585 | CMe | S | Q1h | a bond | H | a bond | NH | S | a bond | Q3b | OH |
| 2586 | CMe | S | Q1h | a bond | H | a bond | NH | S | a bond | Q3c | OH |
| 2587 | CMe | S | Q1h | a bond | H | a bond | NH | O | NH | Q3a | OH |
| 2588 | CMe | S | Q1h | a bond | H | a bond | NH | O | NH | Q3b | OH |
| 2589 | CMe | S | Q1h | a bond | H | a bond | NH | O | NH | Q3c | OH |
| 2590 | CMe | S | Q1h | a bond | H | a bond | NH | O | a bond | Q3a | OH |
| 2591 | CMe | S | Q1h | a bond | H | a bond | NH | O | a bond | Q3b | OH |
| 2592 | CMe | S | Q1h | a bond | H | a bond | NH | O | a bond | Q3c | OH |
| 2593 | CMe | S | Q1i | a bond | Me | a bond | NH | S | NH | Q3a | OH |
| 2594 | CMe | S | Q1i | a bond | Me | a bond | NH | S | NH | Q3b | OH |
| 2595 | CMe | S | Q1i | a bond | Me | a bond | NH | S | NH | Q3c | OH |
| 2596 | CMe | S | Q1i | a bond | Me | a bond | NH | S | a bond | Q3a | OH |
| 2597 | CMe | S | Q1i | a bond | Me | a bond | NH | S | a bond | Q3b | OH |
| 2598 | CMe | S | Q1i | a bond | Me | a bond | NH | S | a bond | Q3c | OH |
| 2599 | CMe | S | Q1i | a bond | Me | a bond | NH | O | NH | Q3a | OH |
| 2600 | CMe | S | Q1i | a bond | Me | a bond | NH | O | NH | Q3b | OH |
| 2601 | CMe | S | Q1i | a bond | Me | a bond | NH | O | NH | Q3c | OH |
| 2602 | CMe | S | Q1i | a bond | Me | a bond | NH | O | a bond | Q3a | OH |
| 2603 | CMe | S | Q1i | a bond | Me | a bond | NH | O | a bond | Q3b | OH |
| 2604 | CMe | S | Q1i | a bond | Me | a bond | NH | O | a bond | Q3c | OH |
| 2605 | CMe | S | Q1i | a bond | H | a bond | NH | S | NH | Q3a | OH |
| 2606 | CMe | S | Q1i | a bond | H | a bond | NH | S | NH | Q3b | OH |
| 2607 | CMe | S | Q1i | a bond | H | a bond | NH | S | NH | Q3c | OH |
| 2608 | CMe | S | Q1i | a bond | H | a bond | NH | S | a bond | Q3a | OH |
| 2609 | CMe | S | Q1i | a bond | H | a bond | NH | S | a bond | Q3b | OH |
| 2610 | CMe | S | Q1i | a bond | H | a bond | NH | S | a bond | Q3c | OH |
| 2611 | CMe | S | Q1i | a bond | H | a bond | NH | O | NH | Q3a | OH |
| 2612 | CMe | S | Q1i | a bond | H | a bond | NH | O | NH | Q3b | OH |
| 2613 | CMe | S | Q1i | a bond | H | a bond | NH | O | NH | Q3c | OH |
| 2614 | CMe | S | Q1i | a bond | H | a bond | NH | O | a bond | Q3a | OH |
| 2615 | CMe | S | Q1i | a bond | H | a bond | NH | O | a bond | Q3b | OH |
| 2616 | CMe | S | Q1i | a bond | H | a bond | NH | O | a bond | Q3c | OH |
| 2617 | CMe | S | Q1j | a bond | Me | a bond | NH | S | NH | Q3a | OH |
| 2618 | CMe | S | Q1j | a bond | Me | a bond | NH | S | NH | Q3b | OH |
| 2619 | CMe | S | Q1j | a bond | Me | a bond | NH | S | NH | Q3c | OH |
| 2620 | CMe | S | Q1j | a bond | Me | a bond | NH | S | a bond | Q3a | OH |
| 2621 | CMe | S | Q1j | a bond | Me | a bond | NH | S | a bond | Q3b | OH |
| 2622 | CMe | S | Q1j | a bond | Me | a bond | NH | S | a bond | Q3c | OH |
| 2623 | CMe | S | Q1j | a bond | Me | a bond | NH | O | NH | Q3a | OH |
| 2624 | CMe | S | Q1j | a bond | Me | a bond | NH | O | NH | Q3b | OH |
| 2625 | CMe | S | Q1j | a bond | Me | a bond | NH | O | NH | Q3c | OH |
| 2626 | CMe | S | Q1j | a bond | Me | a bond | NH | O | a bond | Q3a | OH |
| 2627 | CMe | S | Q1j | a bond | Me | a bond | NH | O | a bond | Q3b | OH |
| 2628 | CMe | S | Q1j | a bond | Me | a bond | NH | O | a bond | Q3c | OH |
| 2629 | CMe | S | Q1j | a bond | H | a bond | NH | S | NH | Q3a | OH |
| 2630 | CMe | S | Q1j | a bond | H | a bond | NH | S | NH | Q3b | OH |
| 2631 | CMe | S | Q1j | a bond | H | a bond | NH | S | NH | Q3c | OH |
| 2632 | CMe | S | Q1j | a bond | H | a bond | NH | S | a bond | Q3a | OH |
| 2633 | CMe | S | Q1j | a bond | H | a bond | NH | S | a bond | Q3b | OH |
| 2634 | CMe | S | Q1j | a bond | H | a bond | NH | S | a bond | Q3c | OH |
| 2635 | CMe | S | Q1j | a bond | H | a bond | NH | O | NH | Q3a | OH |
| 2636 | CMe | S | Q1j | a bond | H | a bond | NH | O | NH | Q3b | OH |
| 2637 | CMe | S | Q1j | a bond | H | a bond | NH | O | NH | Q3c | OH |
| 2638 | CMe | S | Q1j | a bond | H | a bond | NH | O | a bond | Q3a | OH |
| 2639 | CMe | S | Q1j | a bond | H | a bond | NH | O | a bond | Q3b | OH |
| 2640 | CMe | S | Q1j | a bond | H | a bond | NH | O | a bond | Q3c | OH |
| 2641 | CMe | O | Q1a | a bond | Me | a bond | NH | S | NH | Q3a | OH |
| 2642 | CMe | O | Q1a | a bond | Me | a bond | NH | S | NH | Q3b | OH |
| 2643 | CMe | O | Q1a | a bond | Me | a bond | NH | S | NH | Q3c | OH |
| 2644 | CMe | O | Q1a | a bond | Me | a bond | NH | S | a bond | Q3a | OH |
| 2645 | CMe | O | Q1a | a bond | Me | a bond | NH | S | a bond | Q3b | OH |
| 2646 | CMe | O | Q1a | a bond | Me | a bond | NH | S | a bond | Q3c | OH |
| 2647 | CMe | O | Q1a | a bond | Me | a bond | NH | O | NH | Q3a | OH |
| 2648 | CMe | O | Q1a | a bond | Me | a bond | NH | O | NH | Q3b | OH |
| 2649 | CMe | O | Q1a | a bond | Me | a bond | NH | O | NH | Q3c | OH |
| 2650 | CMe | O | Q1a | a bond | Me | a bond | NH | O | a bond | Q3a | OH |
| 2651 | CMe | O | Q1a | a bond | Me | a bond | NH | O | a bond | Q3b | OH |
| 2652 | CMe | O | Q1a | a bond | Me | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2653 | CMe | O | Q1a | a bond | H | a bond | NH | S | NH | Q3a | OH |
| 2654 | CMe | O | Q1a | a bond | H | a bond | NH | S | NH | Q3b | OH |
| 2655 | CMe | O | Q1a | a bond | H | a bond | NH | S | NH | Q3c | OH |
| 2656 | CMe | O | Q1a | a bond | H | a bond | NH | S | a bond | Q3a | OH |
| 2657 | CMe | O | Q1a | a bond | H | a bond | NH | S | a bond | Q3b | OH |
| 2658 | CMe | O | Q1a | a bond | H | a bond | NH | S | a bond | Q3c | OH |
| 2659 | CMe | O | Q1a | a bond | H | a bond | NH | O | NH | Q3a | OH |
| 2660 | CMe | O | Q1a | a bond | H | a bond | NH | O | NH | Q3b | OH |
| 2661 | CMe | O | Q1a | a bond | H | a bond | NH | O | NH | Q3c | OH |
| 2662 | CMe | O | Q1a | a bond | H | a bond | NH | O | a bond | Q3a | OH |
| 2663 | CMe | O | Q1a | a bond | H | a bond | NH | O | a bond | Q3b | OH |
| 2664 | CMe | O | Q1a | a bond | H | a bond | NH | O | a bond | Q3c | OH |
| 2665 | CMe | O | Q1b | a bond | Me | a bond | NH | S | NH | Q3a | OH |
| 2666 | CMe | O | Q1b | a bond | Me | a bond | NH | S | NH | Q3b | OH |
| 2667 | CMe | O | Q1b | a bond | Me | a bond | NH | S | NH | Q3c | OH |
| 2668 | CMe | O | Q1b | a bond | Me | a bond | NH | S | a bond | Q3a | OH |
| 2669 | CMe | O | Q1b | a bond | Me | a bond | NH | S | a bond | Q3b | OH |
| 2670 | CMe | O | Q1b | a bond | Me | a bond | NH | S | a bond | Q3c | OH |
| 2671 | CMe | O | Q1b | a bond | Me | a bond | NH | O | NH | Q3a | OH |
| 2672 | CMe | O | Q1b | a bond | Me | a bond | NH | O | NH | Q3b | OH |
| 2673 | CMe | O | Q1b | a bond | Me | a bond | NH | O | NH | Q3c | OH |
| 2674 | CMe | O | Q1b | a bond | Me | a bond | NH | O | a bond | Q3a | OH |
| 2675 | CMe | O | Q1b | a bond | Me | a bond | NH | O | a bond | Q3b | OH |
| 2676 | CMe | O | Q1b | a bond | Me | a bond | NH | O | a bond | Q3c | OH |
| 2677 | CMe | O | Q1b | a bond | H | a bond | NH | S | NH | Q3a | OH |
| 2678 | CMe | O | Q1b | a bond | H | a bond | NH | S | NH | Q3b | OH |
| 2679 | CMe | O | Q1b | a bond | H | a bond | NH | S | NH | Q3c | OH |
| 2680 | CMe | O | Q1b | a bond | H | a bond | NH | S | a bond | Q3a | OH |
| 2681 | CMe | O | Q1b | a bond | H | a bond | NH | S | a bond | Q3b | OH |
| 2682 | CMe | O | Q1b | a bond | H | a bond | NH | S | a bond | Q3c | OH |
| 2683 | CMe | O | Q1b | a bond | H | a bond | NH | O | NH | Q3a | OH |
| 2684 | CMe | O | Q1b | a bond | H | a bond | NH | O | NH | Q3b | OH |
| 2685 | CMe | O | Q1b | a bond | H | a bond | NH | O | NH | Q3c | OH |
| 2686 | CMe | O | Q1b | a bond | H | a bond | NH | O | a bond | Q3a | OH |
| 2687 | CMe | O | Q1b | a bond | H | a bond | NH | O | a bond | Q3b | OH |
| 2688 | CMe | O | Q1b | a bond | H | a bond | NH | O | a bond | Q3c | OH |
| 2689 | CMe | O | Q1c | a bond | Me | a bond | NH | S | NH | Q3a | OH |
| 2690 | CMe | O | Q1c | a bond | Me | a bond | NH | S | NH | Q3b | OH |
| 2691 | CMe | O | Q1c | a bond | Me | a bond | NH | S | NH | Q3c | OH |
| 2692 | CMe | O | Q1c | a bond | Me | a bond | NH | S | a bond | Q3a | OH |
| 2693 | CMe | O | Q1c | a bond | Me | a bond | NH | S | a bond | Q3b | OH |
| 2694 | CMe | O | Q1c | a bond | Me | a bond | NH | S | a bond | Q3c | OH |
| 2695 | CMe | O | Q1c | a bond | Me | a bond | NH | O | NH | Q3a | OH |
| 2696 | CMe | O | Q1c | a bond | Me | a bond | NH | O | NH | Q3b | OH |
| 2697 | CMe | O | Q1c | a bond | Me | a bond | NH | O | NH | Q3c | OH |
| 2698 | CMe | O | Q1c | a bond | Me | a bond | NH | O | a bond | Q3a | OH |
| 2699 | CMe | O | Q1c | a bond | Me | a bond | NH | O | a bond | Q3b | OH |
| 2700 | CMe | O | Q1c | a bond | Me | a bond | NH | O | a bond | Q3c | OH |
| 2701 | CMe | O | Q1c | a bond | H | a bond | NH | S | NH | Q3a | OH |
| 2702 | CMe | O | Q1c | a bond | H | a bond | NH | S | NH | Q3b | OH |
| 2703 | CMe | O | Q1c | a bond | H | a bond | NH | S | NH | Q3c | OH |
| 2704 | CMe | O | Q1c | a bond | H | a bond | NH | S | a bond | Q3a | OH |
| 2705 | CMe | O | Q1c | a bond | H | a bond | NH | S | a bond | Q3b | OH |
| 2706 | CMe | O | Q1c | a bond | H | a bond | NH | S | a bond | Q3c | OH |
| 2707 | CMe | O | Q1c | a bond | H | a bond | NH | O | NH | Q3a | OH |
| 2708 | CMe | O | Q1c | a bond | H | a bond | NH | O | NH | Q3b | OH |
| 2709 | CMe | O | Q1c | a bond | H | a bond | NH | O | NH | Q3c | OH |
| 2710 | CMe | O | Q1c | a bond | H | a bond | NH | O | a bond | Q3a | OH |
| 2711 | CMe | O | Q1c | a bond | H | a bond | NH | O | a bond | Q3b | OH |
| 2712 | CMe | O | Q1c | a bond | H | a bond | NH | O | a bond | Q3c | OH |
| 2713 | CMe | O | Q1d | a bond | Me | a bond | NH | S | NH | Q3a | OH |
| 2714 | CMe | O | Q1d | a bond | Me | a bond | NH | S | NH | Q3b | OH |
| 2715 | CMe | O | Q1d | a bond | Me | a bond | NH | S | NH | Q3c | OH |
| 2716 | CMe | O | Q1d | a bond | Me | a bond | NH | S | a bond | Q3a | OH |
| 2717 | CMe | O | Q1d | a bond | Me | a bond | NH | S | a bond | Q3b | OH |
| 2718 | CMe | O | Q1d | a bond | Me | a bond | NH | S | a bond | Q3c | OH |
| 2719 | CMe | O | Q1d | a bond | Me | a bond | NH | O | NH | Q3a | OH |
| 2720 | CMe | O | Q1d | a bond | Me | a bond | NH | O | NH | Q3b | OH |
| 2721 | CMe | O | Q1d | a bond | Me | a bond | NH | O | NH | Q3c | OH |
| 2722 | CMe | O | Q1d | a bond | Me | a bond | NH | O | a bond | Q3a | OH |
| 2723 | CMe | O | Q1d | a bond | Me | a bond | NH | O | a bond | Q3b | OH |
| 2724 | CMe | O | Q1d | a bond | Me | a bond | NH | O | a bond | Q3c | OH |
| 2725 | CMe | O | Q1d | a bond | H | a bond | NH | S | NH | Q3a | OH |
| 2726 | CMe | O | Q1d | a bond | H | a bond | NH | S | NH | Q3b | OH |
| 2727 | CMe | O | Q1d | a bond | H | a bond | NH | S | NH | Q3c | OH |
| 2728 | CMe | O | Q1d | a bond | H | a bond | NH | S | a bond | Q3a | OH |
| 2729 | CMe | O | Q1d | a bond | H | a bond | NH | S | a bond | Q3b | OH |
| 2730 | CMe | O | Q1d | a bond | H | a bond | NH | S | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2731 | CMe | O | Q1d | a bond | H | a bond | NH | O | NH | Q3a | OH |
| 2732 | CMe | O | Q1d | a bond | H | a bond | NH | O | NH | Q3b | OH |
| 2733 | CMe | O | Q1d | a bond | H | a bond | NH | O | NH | Q3c | OH |
| 2734 | CMe | O | Q1d | a bond | H | a bond | NH | O | a bond | Q3a | OH |
| 2735 | CMe | O | Q1d | a bond | H | a bond | NH | O | a bond | Q3b | OH |
| 2736 | CMe | O | Q1d | a bond | H | a bond | NH | O | a bond | Q3c | OH |
| 2737 | CMe | O | Q1e | a bond | Me | a bond | NH | S | NH | Q3a | OH |
| 2738 | CMe | O | Q1e | a bond | Me | a bond | NH | S | NH | Q3b | OH |
| 2739 | CMe | O | Q1e | a bond | Me | a bond | NH | S | NH | Q3c | OH |
| 2740 | CMe | O | Q1e | a bond | Me | a bond | NH | S | a bond | Q3a | OH |
| 2741 | CMe | O | Q1e | a bond | Me | a bond | NH | S | a bond | Q3b | OH |
| 2742 | CMe | O | Q1e | a bond | Me | a bond | NH | S | a bond | Q3c | OH |
| 2743 | CMe | O | Q1e | a bond | Me | a bond | NH | O | NH | Q3a | OH |
| 2744 | CMe | O | Q1e | a bond | Me | a bond | NH | O | NH | Q3b | OH |
| 2745 | CMe | O | Q1e | a bond | Me | a bond | NH | O | NH | Q3c | OH |
| 2746 | CMe | O | Q1e | a bond | Me | a bond | NH | O | a bond | Q3a | OH |
| 2747 | CMe | O | Q1e | a bond | Me | a bond | NH | O | a bond | Q3b | OH |
| 2748 | CMe | O | Q1e | a bond | Me | a bond | NH | O | a bond | Q3c | OH |
| 2749 | CMe | O | Q1e | a bond | H | a bond | NH | S | NH | Q3a | OH |
| 2750 | CMe | O | Q1e | a bond | H | a bond | NH | S | NH | Q3b | OH |
| 2751 | CMe | O | Q1e | a bond | H | a bond | NH | S | NH | Q3c | OH |
| 2752 | CMe | O | Q1e | a bond | H | a bond | NH | S | a bond | Q3a | OH |
| 2753 | CMe | O | Q1e | a bond | H | a bond | NH | S | a bond | Q3b | OH |
| 2754 | CMe | O | Q1e | a bond | H | a bond | NH | S | a bond | Q3c | OH |
| 2755 | CMe | O | Q1e | a bond | H | a bond | NH | O | NH | Q3a | OH |
| 2756 | CMe | O | Q1e | a bond | H | a bond | NH | O | NH | Q3b | OH |
| 2757 | CMe | O | Q1e | a bond | H | a bond | NH | O | NH | Q3c | OH |
| 2758 | CMe | O | Q1e | a bond | H | a bond | NH | O | a bond | Q3a | OH |
| 2759 | CMe | O | Q1e | a bond | H | a bond | NH | O | a bond | Q3b | OH |
| 2760 | CMe | O | Q1e | a bond | H | a bond | NH | O | a bond | Q3c | OH |
| 2761 | CMe | O | Q1f | a bond | Me | a bond | NH | S | NH | Q3a | OH |
| 2762 | CMe | O | Q1f | a bond | Me | a bond | NH | S | NH | Q3b | OH |
| 2763 | CMe | O | Q1f | a bond | Me | a bond | NH | S | NH | Q3c | OH |
| 2764 | CMe | O | Q1f | a bond | Me | a bond | NH | S | a bond | Q3a | OH |
| 2765 | CMe | O | Q1f | a bond | Me | a bond | NH | S | a bond | Q3b | OH |
| 2766 | CMe | O | Q1f | a bond | Me | a bond | NH | S | a bond | Q3c | OH |
| 2767 | CMe | O | Q1f | a bond | Me | a bond | NH | O | NH | Q3a | OH |
| 2768 | CMe | O | Q1f | a bond | Me | a bond | NH | O | NH | Q3b | OH |
| 2769 | CMe | O | Q1f | a bond | Me | a bond | NH | O | NH | Q3c | OH |
| 2770 | CMe | O | Q1f | a bond | Me | a bond | NH | O | a bond | Q3a | OH |
| 2771 | CMe | O | Q1f | a bond | Me | a bond | NH | O | a bond | Q3b | OH |
| 2772 | CMe | O | Q1f | a bond | Me | a bond | NH | O | a bond | Q3c | OH |
| 2773 | CMe | O | Q1f | a bond | H | a bond | NH | S | NH | Q3a | OH |
| 2774 | CMe | O | Q1f | a bond | H | a bond | NH | S | NH | Q3b | OH |
| 2775 | CMe | O | Q1f | a bond | H | a bond | NH | S | NH | Q3c | OH |
| 2776 | CMe | O | Q1f | a bond | H | a bond | NH | S | a bond | Q3a | OH |
| 2777 | CMe | O | Q1f | a bond | H | a bond | NH | S | a bond | Q3b | OH |
| 2778 | CMe | O | Q1f | a bond | H | a bond | NH | S | a bond | Q3c | OH |
| 2779 | CMe | O | Q1f | a bond | H | a bond | NH | O | NH | Q3a | OH |
| 2780 | CMe | O | Q1f | a bond | H | a bond | NH | O | NH | Q3b | OH |
| 2781 | CMe | O | Q1f | a bond | H | a bond | NH | O | NH | Q3c | OH |
| 2782 | CMe | O | Q1f | a bond | H | a bond | NH | O | a bond | Q3a | OH |
| 2783 | CMe | O | Q1f | a bond | H | a bond | NH | O | a bond | Q3b | OH |
| 2784 | CMe | O | Q1f | a bond | H | a bond | NH | O | a bond | Q3c | OH |
| 2785 | CMe | O | Q1g | a bond | Me | a bond | NH | S | NH | Q3a | OH |
| 2786 | CMe | O | Q1g | a bond | Me | a bond | NH | S | NH | Q3b | OH |
| 2787 | CMe | O | Q1g | a bond | Me | a bond | NH | S | NH | Q3c | OH |
| 2788 | CMe | O | Q1g | a bond | Me | a bond | NH | S | a bond | Q3a | OH |
| 2789 | CMe | O | Q1g | a bond | Me | a bond | NH | S | a bond | Q3b | OH |
| 2790 | CMe | O | Q1g | a bond | Me | a bond | NH | S | a bond | Q3c | OH |
| 2791 | CMe | O | Q1g | a bond | Me | a bond | NH | O | NH | Q3a | OH |
| 2792 | CMe | O | Q1g | a bond | Me | a bond | NH | O | NH | Q3b | OH |
| 2793 | CMe | O | Q1g | a bond | Me | a bond | NH | O | NH | Q3c | OH |
| 2794 | CMe | O | Q1g | a bond | Me | a bond | NH | O | a bond | Q3a | OH |
| 2795 | CMe | O | Q1g | a bond | Me | a bond | NH | O | a bond | Q3b | OH |
| 2796 | CMe | O | Q1g | a bond | Me | a bond | NH | O | a bond | Q3c | OH |
| 2797 | CMe | O | Q1g | a bond | H | a bond | NH | S | NH | Q3a | OH |
| 2798 | CMe | O | Q1g | a bond | H | a bond | NH | S | NH | Q3b | OH |
| 2799 | CMe | O | Q1g | a bond | H | a bond | NH | S | NH | Q3c | OH |
| 2800 | CMe | O | Q1g | a bond | H | a bond | NH | S | a bond | Q3a | OH |
| 2801 | CMe | O | Q1g | a bond | H | a bond | NH | S | a bond | Q3b | OH |
| 2802 | CMe | O | Q1g | a bond | H | a bond | NH | S | a bond | Q3c | OH |
| 2803 | CMe | O | Q1g | a bond | H | a bond | NH | O | NH | Q3a | OH |
| 2804 | CMe | O | Q1g | a bond | H | a bond | NH | O | NH | Q3b | OH |
| 2805 | CMe | O | Q1g | a bond | H | a bond | NH | O | NH | Q3c | OH |
| 2806 | CMe | O | Q1g | a bond | H | a bond | NH | O | a bond | Q3a | OH |
| 2807 | CMe | O | Q1g | a bond | H | a bond | NH | O | a bond | Q3b | OH |
| 2808 | CMe | O | Q1g | a bond | H | a bond | NH | O | a bond | Q3c | OH |

TABLE 1-continued

| No | A | B | R¹ | L¹ | R² | L² | L³ | Y | L⁴ | R³ | X |
|---|---|---|---|---|---|---|---|---|---|---|---|
| 2809 | CMe | O | Q1h | a bond | Me | a bond | NH | S | NH | Q3a | OH |
| 2810 | CMe | O | Q1h | a bond | Me | a bond | NH | S | NH | Q3b | OH |
| 2811 | CMe | O | Q1h | a bond | Me | a bond | NH | S | NH | Q3c | OH |
| 2812 | CMe | O | Q1h | a bond | Me | a bond | NH | S | a bond | Q3a | OH |
| 2813 | CMe | O | Q1h | a bond | Me | a bond | NH | S | a bond | Q3b | OH |
| 2814 | CMe | O | Q1h | a bond | Me | a bond | NH | S | a bond | Q3c | OH |
| 2815 | CMe | O | Q1h | a bond | Me | a bond | NH | O | NH | Q3a | OH |
| 2816 | CMe | O | Q1h | a bond | Me | a bond | NH | O | NH | Q3b | OH |
| 2817 | CMe | O | Q1h | a bond | Me | a bond | NH | O | NH | Q3c | OH |
| 2818 | CMe | O | Q1h | a bond | Me | a bond | NH | O | a bond | Q3a | OH |
| 2819 | CMe | O | Q1h | a bond | Me | a bond | NH | O | a bond | Q3b | OH |
| 2820 | CMe | O | Q1h | a bond | Me | a bond | NH | O | a bond | Q3c | OH |
| 2821 | CMe | O | Q1h | a bond | H | a bond | NH | S | NH | Q3a | OH |
| 2822 | CMe | O | Q1h | a bond | H | a bond | NH | S | NH | Q3b | OH |
| 2823 | CMe | O | Q1h | a bond | H | a bond | NH | S | NH | Q3c | OH |
| 2824 | CMe | O | Q1h | a bond | H | a bond | NH | S | a bond | Q3a | OH |
| 2825 | CMe | O | Q1h | a bond | H | a bond | NH | S | a bond | Q3b | OH |
| 2826 | CMe | O | Q1h | a bond | H | a bond | NH | S | a bond | Q3c | OH |
| 2827 | CMe | O | Q1h | a bond | H | a bond | NH | O | NH | Q3a | OH |
| 2828 | CMe | O | Q1h | a bond | H | a bond | NH | O | NH | Q3b | OH |
| 2829 | CMe | O | Q1h | a bond | H | a bond | NH | O | NH | Q3c | OH |
| 2830 | CMe | O | Q1h | a bond | H | a bond | NH | O | a bond | Q3a | OH |
| 2831 | CMe | O | Q1h | a bond | H | a bond | NH | O | a bond | Q3b | OH |
| 2832 | CMe | O | Q1h | a bond | H | a bond | NH | O | a bond | Q3c | OH |
| 2833 | CMe | O | Q1i | a bond | Me | a bond | NH | S | NH | Q3a | OH |
| 2834 | CMe | O | Q1i | a bond | Me | a bond | NH | S | NH | Q3b | OH |
| 2835 | CMe | O | Q1i | a bond | Me | a bond | NH | S | NH | Q3c | OH |
| 2836 | CMe | O | Q1i | a bond | Me | a bond | NH | S | a bond | Q3a | OH |
| 2837 | CMe | O | Q1i | a bond | Me | a bond | NH | S | a bond | Q3b | OH |
| 2838 | CMe | O | Q1i | a bond | Me | a bond | NH | S | a bond | Q3c | OH |
| 2839 | CMe | O | Q1i | a bond | Me | a bond | NH | O | NH | Q3a | OH |
| 2840 | CMe | O | Q1i | a bond | Me | a bond | NH | O | NH | Q3b | OH |
| 2841 | CMe | O | Q1i | a bond | Me | a bond | NH | O | NH | Q3c | OH |
| 2842 | CMe | O | Q1i | a bond | Me | a bond | NH | O | a bond | Q3a | OH |
| 2843 | CMe | O | Q1i | a bond | Me | a bond | NH | O | a bond | Q3b | OH |
| 2844 | CMe | O | Q1i | a bond | Me | a bond | NH | O | a bond | Q3c | OH |
| 2845 | CMe | O | Q1i | a bond | H | a bond | NH | S | NH | Q3a | OH |
| 2846 | CMe | O | Q1i | a bond | H | a bond | NH | S | NH | Q3b | OH |
| 2847 | CMe | O | Q1i | a bond | H | a bond | NH | S | NH | Q3c | OH |
| 2848 | CMe | O | Q1i | a bond | H | a bond | NH | S | a bond | Q3a | OH |
| 2849 | CMe | O | Q1i | a bond | H | a bond | NH | S | a bond | Q3b | OH |
| 2850 | CMe | O | Q1i | a bond | H | a bond | NH | S | a bond | Q3c | OH |
| 2851 | CMe | O | Q1i | a bond | H | a bond | NH | O | NH | Q3a | OH |
| 2852 | CMe | O | Q1i | a bond | H | a bond | NH | O | NH | Q3b | OH |
| 2853 | CMe | O | Q1i | a bond | H | a bond | NH | O | NH | Q3c | OH |
| 2854 | CMe | O | Q1i | a bond | H | a bond | NH | O | a bond | Q3a | OH |
| 2855 | CMe | O | Q1i | a bond | H | a bond | NH | O | a bond | Q3b | OH |
| 2856 | CMe | O | Q1i | a bond | H | a bond | NH | O | a bond | Q3c | OH |
| 2857 | CMe | O | Q1j | a bond | Me | a bond | NH | S | NH | Q3a | OH |
| 2858 | CMe | O | Q1j | a bond | Me | a bond | NH | S | NH | Q3b | OH |
| 2859 | CMe | O | Q1j | a bond | Me | a bond | NH | S | NH | Q3c | OH |
| 2860 | CMe | O | Q1j | a bond | Me | a bond | NH | S | a bond | Q3a | OH |
| 2861 | CMe | O | Q1j | a bond | Me | a bond | NH | S | a bond | Q3b | OH |
| 2862 | CMe | O | Q1j | a bond | Me | a bond | NH | S | a bond | Q3c | OH |
| 2863 | CMe | O | Q1j | a bond | Me | a bond | NH | O | NH | Q3a | OH |
| 2864 | CMe | O | Q1j | a bond | Me | a bond | NH | O | NH | Q3b | OH |
| 2865 | CMe | O | Q1j | a bond | Me | a bond | NH | O | NH | Q3c | OH |
| 2866 | CMe | O | Q1j | a bond | Me | a bond | NH | O | a bond | Q3a | OH |
| 2867 | CMe | O | Q1j | a bond | Me | a bond | NH | O | a bond | Q3b | OH |
| 2868 | CMe | O | Q1j | a bond | Me | a bond | NH | O | a bond | Q3c | OH |
| 2869 | CMe | O | Q1j | a bond | H | a bond | NH | S | NH | Q3a | OH |
| 2870 | CMe | O | Q1j | a bond | H | a bond | NH | S | NH | Q3b | OH |
| 2871 | CMe | O | Q1j | a bond | H | a bond | NH | S | NH | Q3c | OH |
| 2872 | CMe | O | Q1j | a bond | H | a bond | NH | S | a bond | Q3a | OH |
| 2873 | CMe | O | Q1j | a bond | H | a bond | NH | S | a bond | Q3b | OH |
| 2874 | CMe | O | Q1j | a bond | H | a bond | NH | S | a bond | Q3c | OH |
| 2875 | CMe | O | Q1j | a bond | H | a bond | NH | O | NH | Q3a | OH |
| 2876 | CMe | O | Q1j | a bond | H | a bond | NH | O | NH | Q3b | OH |
| 2877 | CMe | O | Q1j | a bond | H | a bond | NH | O | NH | Q3c | OH |
| 2878 | CMe | O | Q1j | a bond | H | a bond | NH | O | a bond | Q3a | OH |
| 2879 | CMe | O | Q1j | a bond | H | a bond | NH | O | a bond | Q3b | OH |
| 2880 | CMe | O | Q1j | a bond | H | a bond | NH | O | a bond | Q3c | OH |
| 2881 | N | NMe | Q1k | a bond | Me | a bond | NH | O | a bond | Q3d | OH |
| 2882 | N | NMe | Q1k | a bond | Me | a bond | NH | O | a bond | Q3e | OH |
| 2883 | N | NMe | Q1k | a bond | Me | a bond | NH | O | a bond | Q3f | OH |
| 2884 | N | NMe | Q1k | a bond | Me | a bond | NH | O | NH | Q3a | OH |
| 2885 | N | NMe | Q1k | a bond | Me | a bond | NH | O | NH | Q3a | OH |
| 2886 | N | NMe | Q1k | a bond | Me | a bond | NH | O | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 2887 | N | NMe | Q1k | a bond | Me | a bond | NH | O | NH | Q3e | OH |
| 2888 | N | NMe | Q1k | a bond | Me | a bond | NH | O | NH | Q3f | OH |
| 2889 | N | NMe | Q1k | a bond | Me | a bond | NH | S | a bond | Q3a | OH |
| 2890 | N | NMe | Q1k | a bond | Me | a bond | NH | S | a bond | Q3d | OH |
| 2891 | N | NMe | Q1k | a bond | Me | a bond | NH | S | a bond | Q3e | OH |
| 2892 | N | NMe | Q1k | a bond | Me | a bond | NH | S | a bond | Q3f | OH |
| 2893 | N | NMe | Q1k | a bond | Me | a bond | NH | S | NH | Q3a | OH |
| 2894 | N | NMe | Q1k | a bond | Me | a bond | NH | S | NH | Q3d | OH |
| 2895 | N | NMe | Q1k | a bond | Me | a bond | NH | S | NH | Q3e | OH |
| 2896 | N | NMe | Q1k | a bond | Me | a bond | NH | S | NH | Q3f | OH |
| 2897 | N | NMe | Q1l | a bond | Me | a bond | NH | O | a bond | Q3a | OH |
| 2898 | N | NMe | Q1l | a bond | Me | a bond | NH | O | a bond | Q3d | OH |
| 2899 | N | NMe | Q1l | a bond | Me | a bond | NH | O | a bond | Q3e | OH |
| 2900 | N | NMe | Q1l | a bond | Me | a bond | NH | O | a bond | Q3f | OH |
| 2901 | N | NMe | Q1l | a bond | Me | a bond | NH | O | NH | Q3a | OH |
| 2902 | N | NMe | Q1l | a bond | Me | a bond | NH | O | NH | Q3d | OH |
| 2903 | N | NMe | Q1l | a bond | Me | a bond | NH | O | NH | Q3e | OH |
| 2904 | N | NMe | Q1l | a bond | Me | a bond | NH | O | NH | Q3f | OH |
| 2905 | N | NMe | Q1l | a bond | Me | a bond | NH | S | a bond | Q3a | OH |
| 2906 | N | NMe | Q1l | a bond | Me | a bond | NH | S | a bond | Q3d | OH |
| 2907 | N | NMe | Q1l | a bond | Me | a bond | NH | S | a bond | Q3e | OH |
| 2908 | N | NMe | Q1l | a bond | Me | a bond | NH | S | a bond | Q3f | OH |
| 2909 | N | NMe | Q1l | a bond | Me | a bond | NH | S | NH | Q3a | OH |
| 2910 | N | NMe | Q1l | a bond | Me | a bond | NH | S | NH | Q3d | OH |
| 2911 | N | NMe | Q1l | a bond | Me | a bond | NH | S | NH | Q3e | OH |
| 2912 | N | NMe | Q1l | a bond | Me | a bond | NH | S | NH | Q3f | OH |
| 2913 | N | NMe | Q1m | a bond | Me | a bond | NH | O | a bond | Q3a | OH |
| 2914 | N | NMe | Q1m | a bond | Me | a bond | NH | O | a bond | Q3d | OH |
| 2915 | N | NMe | Q1m | a bond | Me | a bond | NH | O | a bond | Q3e | OH |
| 2916 | N | NMe | Q1m | a bond | Me | a bond | NH | O | a bond | Q3f | OH |
| 2917 | N | NMe | Q1m | a bond | Me | a bond | NH | O | NH | Q3a | OH |
| 2918 | N | NMe | Q1m | a bond | Me | a bond | NH | O | NH | Q3d | OH |
| 2919 | N | NMe | Q1m | a bond | Me | a bond | NH | O | NH | Q3e | OH |
| 2920 | N | NMe | Q1m | a bond | Me | a bond | NH | O | NH | Q3f | OH |
| 2921 | N | NMe | Q1m | a bond | Me | a bond | NH | S | a bond | Q3a | OH |
| 2922 | N | NMe | Q1m | a bond | Me | a bond | NH | S | a bond | Q3d | OH |
| 2923 | N | NMe | Q1m | a bond | Me | a bond | NH | S | a bond | Q3e | OH |
| 2924 | N | NMe | Q1m | a bond | Me | a bond | NH | S | a bond | Q3f | OH |
| 2925 | N | NMe | Q1m | a bond | Me | a bond | NH | S | NH | Q3a | OH |
| 2926 | N | NMe | Q1m | a bond | Me | a bond | NH | S | NH | Q3d | OH |
| 2927 | N | NMe | Q1m | a bond | Me | a bond | NH | S | NH | Q3e | OH |
| 2928 | N | NMe | Q1m | a bond | Me | a bond | NH | S | NH | Q3f | OH |
| 2929 | N | NMe | Q1n | a bond | Me | a bond | NH | O | a bond | Q3a | OH |
| 2930 | N | NMe | Q1n | a bond | Me | a bond | NH | O | a bond | Q3d | OH |
| 2931 | N | NMe | Q1n | a bond | Me | a bond | NH | O | a bond | Q3e | OH |
| 2932 | N | NMe | Q1n | a bond | Me | a bond | NH | O | a bond | Q3f | OH |
| 2933 | N | NMe | Q1n | a bond | Me | a bond | NH | O | NH | Q3a | OH |
| 2934 | N | NMe | Q1n | a bond | Me | a bond | NH | O | NH | Q3d | OH |
| 2935 | N | NMe | Q1n | a bond | Me | a bond | NH | O | NH | Q3e | OH |
| 2936 | N | NMe | Q1n | a bond | Me | a bond | NH | O | NH | Q3f | OH |
| 2937 | N | NMe | Q1n | a bond | Me | a bond | NH | S | a bond | Q3a | OH |
| 2938 | N | NMe | Q1n | a bond | Me | a bond | NH | S | a bond | Q3d | OH |
| 2939 | N | NMe | Q1n | a bond | Me | a bond | NH | S | a bond | Q3e | OH |
| 2940 | N | NMe | Q1n | a bond | Me | a bond | NH | S | a bond | Q3f | OH |
| 2941 | N | NMe | Q1n | a bond | Me | a bond | NH | S | NH | Q3a | OH |
| 2942 | N | NMe | Q1n | a bond | Me | a bond | NH | S | NH | Q3d | OH |
| 2943 | N | NMe | Q1n | a bond | Me | a bond | NH | S | NH | Q3e | OH |
| 2944 | N | NMe | Q1n | a bond | Me | a bond | NH | S | NH | Q3f | OH |
| 2945 | N | NEt | Q1k | a bond | Me | a bond | NH | O | a bond | Q3a | OH |
| 2946 | N | NEt | Q1k | a bond | Me | a bond | NH | O | a bond | Q3d | OH |
| 2947 | N | NEt | Q1k | a bond | Me | a bond | NH | O | a bond | Q3e | OH |
| 2948 | N | NEt | Q1k | a bond | Me | a bond | NH | O | a bond | Q3f | OH |
| 2949 | N | NEt | Q1k | a bond | Me | a bond | NH | O | NH | Q3a | OH |
| 2950 | N | NEt | Q1k | a bond | Me | a bond | NH | O | NH | Q3d | OH |
| 2951 | N | NEt | Q1k | a bond | Me | a bond | NH | O | NH | Q3e | OH |
| 2952 | N | NEt | Q1k | a bond | Me | a bond | NH | O | NH | Q3f | OH |
| 2953 | N | NEt | Q1k | a bond | Me | a bond | NH | S | a bond | Q3a | OH |
| 2954 | N | NEt | Q1k | a bond | Me | a bond | NH | S | a bond | Q3d | OH |
| 2955 | N | NEt | Q1k | a bond | Me | a bond | NH | S | a bond | Q3e | OH |
| 2956 | N | NEt | Q1k | a bond | Me | a bond | NH | S | a bond | Q3f | OH |
| 2957 | N | NEt | Q1k | a bond | Me | a bond | NH | S | NH | Q3a | OH |
| 2958 | N | NEt | Q1k | a bond | Me | a bond | NH | S | NH | Q3d | OH |
| 2959 | N | NEt | Q1k | a bond | Me | a bond | NH | S | NH | Q3e | OH |
| 2960 | N | NEt | Q1k | a bond | Me | a bond | NH | S | NH | Q3f | OH |
| 2961 | N | NEt | Q1l | a bond | Me | a bond | NH | O | a bond | Q3a | OH |
| 2962 | N | NEt | Q1l | a bond | Me | a bond | NH | O | a bond | Q3d | OH |
| 2963 | N | NEt | Q1l | a bond | Me | a bond | NH | O | a bond | Q3e | OH |
| 2964 | N | NEt | Q1l | a bond | Me | a bond | NH | O | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 2965 | N | NEt | Q1l | a bond | Me | a bond | NH | O | NH | Q3a | OH |
| 2966 | N | NEt | Q1l | a bond | Me | a bond | NH | O | NH | Q3d | OH |
| 2967 | N | NEt | Q1l | a bond | Me | a bond | NH | O | NH | Q3e | OH |
| 2968 | N | NEt | Q1l | a bond | Me | a bond | NH | O | NH | Q3f | OH |
| 2969 | N | NEt | Q1l | a bond | Me | a bond | NH | S | a bond | Q3a | OH |
| 2970 | N | NEt | Q1l | a bond | Me | a bond | NH | S | a bond | Q3d | OH |
| 2971 | N | NEt | Q1l | a bond | Me | a bond | NH | S | a bond | Q3e | OH |
| 2972 | N | NEt | Q1l | a bond | Me | a bond | NH | S | a bond | Q3f | OH |
| 2973 | N | NEt | Q1l | a bond | Me | a bond | NH | S | NH | Q3a | OH |
| 2974 | N | NEt | Q1l | a bond | Me | a bond | NH | S | NH | Q3d | OH |
| 2975 | N | NEt | Q1l | a bond | Me | a bond | NH | S | NH | Q3e | OH |
| 2976 | N | NEt | Q1l | a bond | Me | a bond | NH | S | NH | Q3f | OH |
| 2977 | N | NEt | Q1m | a bond | Me | a bond | NH | O | a bond | Q3a | OH |
| 2978 | N | NEt | Q1m | a bond | Me | a bond | NH | O | a bond | Q3d | OH |
| 2979 | N | NEt | Q1m | a bond | Me | a bond | NH | O | a bond | Q3e | OH |
| 2980 | N | NEt | Q1m | a bond | Me | a bond | NH | O | a bond | Q3f | OH |
| 2981 | N | NEt | Q1m | a bond | Me | a bond | NH | O | NH | Q3a | OH |
| 2982 | N | NEt | Q1m | a bond | Me | a bond | NH | O | NH | Q3d | OH |
| 2983 | N | NEt | Q1m | a bond | Me | a bond | NH | O | NH | Q3e | OH |
| 2984 | N | NEt | Q1m | a bond | Me | a bond | NH | O | NH | Q3f | OH |
| 2985 | N | NEt | Q1m | a bond | Me | a bond | NH | S | a bond | Q3a | OH |
| 2986 | N | NEt | Q1m | a bond | Me | a bond | NH | S | a bond | Q3d | OH |
| 2987 | N | NEt | Q1m | a bond | Me | a bond | NH | S | a bond | Q3e | OH |
| 2988 | N | NEt | Q1m | a bond | Me | a bond | NH | S | a bond | Q3f | OH |
| 2989 | N | NEt | Q1m | a bond | Me | a bond | NH | S | NH | Q3a | OH |
| 2990 | N | NEt | Q1m | a bond | Me | a bond | NH | S | NH | Q3d | OH |
| 2991 | N | NEt | Q1m | a bond | Me | a bond | NH | S | NH | Q3e | OH |
| 2992 | N | NEt | Q1m | a bond | Me | a bond | NH | S | NH | Q3f | OH |
| 2993 | N | NEt | Q1n | a bond | Me | a bond | NH | O | a bond | Q3a | OH |
| 2994 | N | NEt | Q1n | a bond | Me | a bond | NH | O | a bond | Q3d | OH |
| 2995 | N | NEt | Q1n | a bond | Me | a bond | NH | O | a bond | Q3e | OH |
| 2996 | N | NEt | Q1n | a bond | Me | a bond | NH | O | a bond | Q3f | OH |
| 2997 | N | NEt | Q1n | a bond | Me | a bond | NH | O | NH | Q3a | OH |
| 2998 | N | NEt | Q1n | a bond | Me | a bond | NH | O | NH | Q3d | OH |
| 2999 | N | NEt | Q1n | a bond | Me | a bond | NH | O | NH | Q3e | OH |
| 3000 | N | NEt | Q1n | a bond | Me | a bond | NH | O | NH | Q3f | OH |
| 3001 | N | NEt | Q1n | a bond | Me | a bond | NH | S | a bond | Q3a | OH |
| 3002 | N | NEt | Q1n | a bond | Me | a bond | NH | S | a bond | Q3d | OH |
| 3003 | N | NEt | Q1n | a bond | Me | a bond | NH | S | a bond | Q3e | OH |
| 3004 | N | NEt | Q1n | a bond | Me | a bond | NH | S | a bond | Q3f | OH |
| 3005 | N | NEt | Q1n | a bond | Me | a bond | NH | S | NH | Q3a | OH |
| 3006 | N | NEt | Q1n | a bond | Me | a bond | NH | S | NH | Q3d | OH |
| 3007 | N | NEt | Q1n | a bond | Me | a bond | NH | S | NH | Q3e | OH |
| 3008 | N | NEt | Q1n | a bond | Me | a bond | NH | S | NH | Q3f | OH |
| 3009 | N | S | Q1k | a bond | Me | a bond | NH | O | a bond | Q3a | OH |
| 3010 | N | S | Q1k | a bond | Me | a bond | NH | O | a bond | Q3d | OH |
| 3011 | N | S | Q1k | a bond | Me | a bond | NH | O | a bond | Q3e | OH |
| 3012 | N | S | Q1k | a bond | Me | a bond | NH | O | a bond | Q3f | OH |
| 3013 | N | S | Q1k | a bond | Me | a bond | NH | O | NH | Q3a | OH |
| 3014 | N | S | Q1k | a bond | Me | a bond | NH | O | NH | Q3d | OH |
| 3015 | N | S | Q1k | a bond | Me | a bond | NH | O | NH | Q3e | OH |
| 3016 | N | S | Q1k | a bond | Me | a bond | NH | O | NH | Q3f | OH |
| 3017 | N | S | Q1k | a bond | Me | a bond | NH | S | a bond | Q3a | OH |
| 3018 | N | S | Q1k | a bond | Me | a bond | NH | S | a bond | Q3d | OH |
| 3019 | N | S | Q1k | a bond | Me | a bond | NH | S | a bond | Q3e | OH |
| 3020 | N | S | Q1k | a bond | Me | a bond | NH | S | a bond | Q3f | OH |
| 3021 | N | S | Q1k | a bond | Me | a bond | NH | S | NH | Q3a | OH |
| 3022 | N | S | Q1k | a bond | Me | a bond | NH | S | NH | Q3d | OH |
| 3023 | N | S | Q1k | a bond | Me | a bond | NH | S | NH | Q3e | OH |
| 3024 | N | S | Q1k | a bond | Me | a bond | NH | S | NH | Q3f | OH |
| 3025 | N | S | Q1l | a bond | Me | a bond | NH | O | a bond | Q3a | OH |
| 3026 | N | S | Q1l | a bond | Me | a bond | NH | O | a bond | Q3d | OH |
| 3027 | N | S | Q1l | a bond | Me | a bond | NH | O | a bond | Q3e | OH |
| 3028 | N | S | Q1l | a bond | Me | a bond | NH | O | a bond | Q3f | OH |
| 3029 | N | S | Q1l | a bond | Me | a bond | NH | O | NH | Q3a | OH |
| 3030 | N | S | Q1l | a bond | Me | a bond | NH | O | NH | Q3d | OH |
| 3031 | N | S | Q1l | a bond | Me | a bond | NH | O | NH | Q3e | OH |
| 3032 | N | S | Q1l | a bond | Me | a bond | NH | O | NH | Q3f | OH |
| 3033 | N | S | Q1l | a bond | Me | a bond | NH | S | a bond | Q3a | OH |
| 3034 | N | S | Q1l | a bond | Me | a bond | NH | S | a bond | Q3d | OH |
| 3035 | N | S | Q1l | a bond | Me | a bond | NH | S | a bond | Q3e | OH |
| 3036 | N | S | Q1l | a bond | Me | a bond | NH | S | a bond | Q3f | OH |
| 3037 | N | S | Q1l | a bond | Me | a bond | NH | S | NH | Q3a | OH |
| 3038 | N | S | Q1l | a bond | Me | a bond | NH | S | NH | Q3d | OH |
| 3039 | N | S | Q1l | a bond | Me | a bond | NH | S | NH | Q3e | OH |
| 3040 | N | S | Q1l | a bond | Me | a bond | NH | S | NH | Q3f | OH |
| 3041 | N | S | Q1m | a bond | Me | a bond | NH | O | a bond | Q3a | OH |
| 3042 | N | S | Q1m | a bond | Me | a bond | NH | O | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3043 | N | S | Q1m | a bond | Me | a bond | NH | O | a bond | Q3e | OH |
| 3044 | N | S | Q1m | a bond | Me | a bond | NH | O | a bond | Q3f | OH |
| 3045 | N | S | Q1m | a bond | Me | a bond | NH | O | NH | Q3a | OH |
| 3046 | N | S | Q1m | a bond | Me | a bond | NH | O | NH | Q3d | OH |
| 3047 | N | S | Q1m | a bond | Me | a bond | NH | O | NH | Q3e | OH |
| 3048 | N | S | Q1m | a bond | Me | a bond | NH | O | NH | Q3f | OH |
| 3049 | N | S | Q1m | a bond | Me | a bond | NH | S | a bond | Q3a | OH |
| 3050 | N | S | Q1m | a bond | Me | a bond | NH | S | a bond | Q3d | OH |
| 3051 | N | S | Q1m | a bond | Me | a bond | NH | S | a bond | Q3e | OH |
| 3052 | N | S | Q1m | a bond | Me | a bond | NH | S | a bond | Q3f | OH |
| 3053 | N | S | Q1m | a bond | Me | a bond | NH | S | NH | Q3a | OH |
| 3054 | N | S | Q1m | a bond | Me | a bond | NH | S | NH | Q3d | OH |
| 3055 | N | S | Q1m | a bond | Me | a bond | NH | S | NH | Q3e | OH |
| 3056 | N | S | Q1m | a bond | Me | a bond | NH | S | NH | Q3f | OH |
| 3057 | N | S | Q1n | a bond | Me | a bond | NH | O | a bond | Q3a | OH |
| 3058 | N | S | Q1n | a bond | Me | a bond | NH | O | a bond | Q3d | OH |
| 3059 | N | S | Q1n | a bond | Me | a bond | NH | O | a bond | Q3e | OH |
| 3060 | N | S | Q1n | a bond | Me | a bond | NH | O | a bond | Q3f | OH |
| 3061 | N | S | Q1n | a bond | Me | a bond | NH | O | NH | Q3a | OH |
| 3062 | N | S | Q1n | a bond | Me | a bond | NH | O | NH | Q3d | OH |
| 3063 | N | S | Q1n | a bond | Me | a bond | NH | O | NH | Q3e | OH |
| 3064 | N | S | Q1n | a bond | Me | a bond | NH | O | NH | Q3f | OH |
| 3065 | N | S | Q1n | a bond | Me | a bond | NH | S | a bond | Q3a | OH |
| 3066 | N | S | Q1n | a bond | Me | a bond | NH | S | a bond | Q3d | OH |
| 3067 | N | S | Q1n | a bond | Me | a bond | NH | S | a bond | Q3e | OH |
| 3068 | N | S | Q1n | a bond | Me | a bond | NH | S | a bond | Q3f | OH |
| 3069 | N | S | Q1n | a bond | Me | a bond | NH | S | NH | Q3a | OH |
| 3070 | N | S | Q1n | a bond | Me | a bond | NH | S | NH | Q3d | OH |
| 3071 | N | S | Q1n | a bond | Me | a bond | NH | S | NH | Q3e | OH |
| 3072 | N | S | Q1n | a bond | Me | a bond | NH | S | NH | Q3f | OH |
| 3073 | N | O | Q1k | a bond | Me | a bond | NH | O | a bond | Q3a | OH |
| 3074 | N | O | Q1k | a bond | Me | a bond | NH | O | a bond | Q3d | OH |
| 3075 | N | O | Q1k | a bond | Me | a bond | NH | O | a bond | Q3e | OH |
| 3076 | N | O | Q1k | a bond | Me | a bond | NH | O | a bond | Q3f | OH |
| 3077 | N | O | Q1k | a bond | Me | a bond | NH | O | NH | Q3a | OH |
| 3078 | N | O | Q1k | a bond | Me | a bond | NH | O | NH | Q3d | OH |
| 3079 | N | O | Q1k | a bond | Me | a bond | NH | O | NH | Q3e | OH |
| 3080 | N | O | Q1k | a bond | Me | a bond | NH | O | NH | Q3f | OH |
| 3081 | N | O | Q1k | a bond | Me | a bond | NH | S | a bond | Q3a | OH |
| 3082 | N | O | Q1k | a bond | Me | a bond | NH | S | a bond | Q3d | OH |
| 3083 | N | O | Q1k | a bond | Me | a bond | NH | S | a bond | Q3e | OH |
| 3084 | N | O | Q1k | a bond | Me | a bond | NH | S | a bond | Q3f | OH |
| 3085 | N | O | Q1k | a bond | Me | a bond | NH | S | NH | Q3a | OH |
| 3086 | N | O | Q1k | a bond | Me | a bond | NH | S | NH | Q3d | OH |
| 3087 | N | O | Q1k | a bond | Me | a bond | NH | S | NH | Q3e | OH |
| 3088 | N | O | Q1k | a bond | Me | a bond | NH | S | NH | Q3f | OH |
| 3089 | N | O | Q1l | a bond | Me | a bond | NH | O | a bond | Q3a | OH |
| 3090 | N | O | Q1l | a bond | Me | a bond | NH | O | a bond | Q3d | OH |
| 3091 | N | O | Q1l | a bond | Me | a bond | NH | O | a bond | Q3e | OH |
| 3092 | N | O | Q1l | a bond | Me | a bond | NH | O | a bond | Q3f | OH |
| 3093 | N | O | Q1l | a bond | Me | a bond | NH | O | NH | Q3a | OH |
| 3094 | N | O | Q1l | a bond | Me | a bond | NH | O | NH | Q3d | OH |
| 3095 | N | O | Q1l | a bond | Me | a bond | NH | O | NH | Q3e | OH |
| 3096 | N | O | Q1l | a bond | Me | a bond | NH | O | NH | Q3f | OH |
| 3097 | N | O | Q1l | a bond | Me | a bond | NH | S | a bond | Q3a | OH |
| 3098 | N | O | Q1l | a bond | Me | a bond | NH | S | a bond | Q3d | OH |
| 3099 | N | O | Q1l | a bond | Me | a bond | NH | S | a bond | Q3e | OH |
| 3100 | N | O | Q1l | a bond | Me | a bond | NH | S | a bond | Q3f | OH |
| 3101 | N | O | Q1l | a bond | Me | a bond | NH | S | NH | Q3a | OH |
| 3102 | N | O | Q1l | a bond | Me | a bond | NH | S | NH | Q3d | OH |
| 3103 | N | O | Q1l | a bond | Me | a bond | NH | S | NH | Q3e | OH |
| 3104 | N | O | Q1l | a bond | Me | a bond | NH | S | NH | Q3f | OH |
| 3105 | N | O | Q1m | a bond | Me | a bond | NH | O | a bond | Q3a | OH |
| 3106 | N | O | Q1m | a bond | Me | a bond | NH | O | a bond | Q3d | OH |
| 3107 | N | O | Q1m | a bond | Me | a bond | NH | O | a bond | Q3e | OH |
| 3108 | N | O | Q1m | a bond | Me | a bond | NH | O | a bond | Q3f | OH |
| 3109 | N | O | Q1m | a bond | Me | a bond | NH | O | NH | Q3a | OH |
| 3110 | N | O | Q1m | a bond | Me | a bond | NH | O | NH | Q3d | OH |
| 3111 | N | O | Q1m | a bond | Me | a bond | NH | O | NH | Q3e | OH |
| 3112 | N | O | Q1m | a bond | Me | a bond | NH | O | NH | Q3f | OH |
| 3113 | N | O | Q1m | a bond | Me | a bond | NH | S | a bond | Q3a | OH |
| 3114 | N | O | Q1m | a bond | Me | a bond | NH | S | a bond | Q3d | OH |
| 3115 | N | O | Q1m | a bond | Me | a bond | NH | S | a bond | Q3e | OH |
| 3116 | N | O | Q1m | a bond | Me | a bond | NH | S | a bond | Q3f | OH |
| 3117 | N | O | Q1m | a bond | Me | a bond | NH | S | NH | Q3a | OH |
| 3118 | N | O | Q1m | a bond | Me | a bond | NH | S | NH | Q3d | OH |
| 3119 | N | O | Q1m | a bond | Me | a bond | NH | S | NH | Q3e | OH |
| 3120 | N | O | Q1m | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3121 | N | O | Q1n | a bond | Me | a bond | NH | O | a bond | Q3a | OH |
| 3122 | N | O | Q1n | a bond | Me | a bond | NH | O | a bond | Q3d | OH |
| 3123 | N | O | Q1n | a bond | Me | a bond | NH | O | a bond | Q3e | OH |
| 3124 | N | O | Q1n | a bond | Me | a bond | NH | O | a bond | Q3f | OH |
| 3125 | N | O | Q1n | a bond | Me | a bond | NH | O | NH | Q3a | OH |
| 3126 | N | O | Q1n | a bond | Me | a bond | NH | O | NH | Q3d | OH |
| 3127 | N | O | Q1n | a bond | Me | a bond | NH | O | NH | Q3e | OH |
| 3128 | N | O | Q1n | a bond | Me | a bond | NH | O | NH | Q3f | OH |
| 3129 | N | O | Q1n | a bond | Me | a bond | NH | S | a bond | Q3a | OH |
| 3130 | N | O | Q1n | a bond | Me | a bond | NH | S | a bond | Q3d | OH |
| 3131 | N | O | Q1n | a bond | Me | a bond | NH | S | a bond | Q3e | OH |
| 3132 | N | O | Q1n | a bond | Me | a bond | NH | S | a bond | Q3f | OH |
| 3133 | N | O | Q1n | a bond | Me | a bond | NH | S | NH | Q3a | OH |
| 3134 | N | O | Q1n | a bond | Me | a bond | NH | S | NH | Q3d | OH |
| 3135 | N | O | Q1n | a bond | Me | a bond | NH | S | NH | Q3e | OH |
| 3136 | N | O | Q1n | a bond | Me | a bond | NH | S | NH | Q3f | OH |
| 3137 | CH | NMe | Q1k | a bond | Me | a bond | NH | O | a bond | Q3a | OH |
| 3138 | CH | NMe | Q1k | a bond | Me | a bond | NH | O | a bond | Q3d | OH |
| 3139 | CH | NMe | Q1k | a bond | Me | a bond | NH | O | a bond | Q3e | OH |
| 3140 | CH | NMe | Q1k | a bond | Me | a bond | NH | O | a bond | Q3f | OH |
| 3141 | CH | NMe | Q1k | a bond | Me | a bond | NH | O | NH | Q3a | OH |
| 3142 | CH | NMe | Q1k | a bond | Me | a bond | NH | O | NH | Q3d | OH |
| 3143 | CH | NMe | Q1k | a bond | Me | a bond | NH | O | NH | Q3e | OH |
| 3144 | CH | NMe | Q1k | a bond | Me | a bond | NH | O | NH | Q3f | OH |
| 3145 | CH | NMe | Q1k | a bond | Me | a bond | NH | S | a bond | Q3a | OH |
| 3146 | CH | NMe | Q1k | a bond | Me | a bond | NH | S | a bond | Q3d | OH |
| 3147 | CH | NMe | Q1k | a bond | Me | a bond | NH | S | a bond | Q3e | OH |
| 3148 | CH | NMe | Q1k | a bond | Me | a bond | NH | S | a bond | Q3f | OH |
| 3149 | CH | NMe | Q1k | a bond | Me | a bond | NH | S | NH | Q3a | OH |
| 3150 | CH | NMe | Q1k | a bond | Me | a bond | NH | S | NH | Q3d | OH |
| 3151 | CH | NMe | Q1k | a bond | Me | a bond | NH | S | NH | Q3e | OH |
| 3152 | CH | NMe | Q1k | a bond | Me | a bond | NH | S | NH | Q3f | OH |
| 3153 | CH | NMe | Q1l | a bond | Me | a bond | NH | O | a bond | Q3a | OH |
| 3154 | CH | NMe | Q1l | a bond | Me | a bond | NH | O | a bond | Q3d | OH |
| 3155 | CH | NMe | Q1l | a bond | Me | a bond | NH | O | a bond | Q3e | OH |
| 3156 | CH | NMe | Q1l | a bond | Me | a bond | NH | O | a bond | Q3f | OH |
| 3157 | CH | NMe | Q1l | a bond | Me | a bond | NH | O | NH | Q3a | OH |
| 3158 | CH | NMe | Q1l | a bond | Me | a bond | NH | O | NH | Q3d | OH |
| 3159 | CH | NMe | Q1l | a bond | Me | a bond | NH | O | NH | Q3e | OH |
| 3160 | CH | NMe | Q1l | a bond | Me | a bond | NH | O | NH | Q3f | OH |
| 3161 | CH | NMe | Q1l | a bond | Me | a bond | NH | S | a bond | Q3a | OH |
| 3162 | CH | NMe | Q1l | a bond | Me | a bond | NH | S | a bond | Q3d | OH |
| 3163 | CH | NMe | Q1l | a bond | Me | a bond | NH | S | a bond | Q3e | OH |
| 3164 | CH | NMe | Q1l | a bond | Me | a bond | NH | S | a bond | Q3f | OH |
| 3165 | CH | NMe | Q1l | a bond | Me | a bond | NH | S | NH | Q3a | OH |
| 3166 | CH | NMe | Q1l | a bond | Me | a bond | NH | S | NH | Q3d | OH |
| 3167 | CH | NMe | Q1l | a bond | Me | a bond | NH | S | NH | Q3e | OH |
| 3168 | CH | NMe | Q1l | a bond | Me | a bond | NH | S | NH | Q3f | OH |
| 3169 | CH | NMe | Q1m | a bond | Me | a bond | NH | O | a bond | Q3a | OH |
| 3170 | CH | NMe | Q1m | a bond | Me | a bond | NH | O | a bond | Q3d | OH |
| 3171 | CH | NMe | Q1m | a bond | Me | a bond | NH | O | a bond | Q3e | OH |
| 3172 | CH | NMe | Q1m | a bond | Me | a bond | NH | O | a bond | Q3f | OH |
| 3173 | CH | NMe | Q1m | a bond | Me | a bond | NH | O | NH | Q3a | OH |
| 3174 | CH | NMe | Q1m | a bond | Me | a bond | NH | O | NH | Q3d | OH |
| 3175 | CH | NMe | Q1m | a bond | Me | a bond | NH | O | NH | Q3e | OH |
| 3176 | CH | NMe | Q1m | a bond | Me | a bond | NH | O | NH | Q3f | OH |
| 3177 | CH | NMe | Q1m | a bond | Me | a bond | NH | S | a bond | Q3a | OH |
| 3178 | CH | NMe | Q1m | a bond | Me | a bond | NH | S | a bond | Q3d | OH |
| 3179 | CH | NMe | Q1m | a bond | Me | a bond | NH | S | a bond | Q3e | OH |
| 3180 | CH | NMe | Q1m | a bond | Me | a bond | NH | S | a bond | Q3f | OH |
| 3181 | CH | NMe | Q1m | a bond | Me | a bond | NH | S | NH | Q3a | OH |
| 3182 | CH | NMe | Q1m | a bond | Me | a bond | NH | S | NH | Q3d | OH |
| 3183 | CH | NMe | Q1m | a bond | Me | a bond | NH | S | NH | Q3e | OH |
| 3184 | CH | NMe | Q1m | a bond | Me | a bond | NH | S | NH | Q3f | OH |
| 3185 | CH | NMe | Q1n | a bond | Me | a bond | NH | O | a bond | Q3a | OH |
| 3186 | CH | NMe | Q1n | a bond | Me | a bond | NH | O | a bond | Q3d | OH |
| 3187 | CH | NMe | Q1n | a bond | Me | a bond | NH | O | a bond | Q3e | OH |
| 3188 | CH | NMe | Q1n | a bond | Me | a bond | NH | O | a bond | Q3f | OH |
| 3189 | CH | NMe | Q1n | a bond | Me | a bond | NH | O | NH | Q3a | OH |
| 3190 | CH | NMe | Q1n | a bond | Me | a bond | NH | O | NH | Q3d | OH |
| 3191 | CH | NMe | Q1n | a bond | Me | a bond | NH | O | NH | Q3e | OH |
| 3192 | CH | NMe | Q1n | a bond | Me | a bond | NH | O | NH | Q3f | OH |
| 3193 | CH | NMe | Q1n | a bond | Me | a bond | NH | S | a bond | Q3a | OH |
| 3194 | CH | NMe | Q1n | a bond | Me | a bond | NH | S | a bond | Q3d | OH |
| 3195 | CH | NMe | Q1n | a bond | Me | a bond | NH | S | a bond | Q3e | OH |
| 3196 | CH | NMe | Q1n | a bond | Me | a bond | NH | S | a bond | Q3f | OH |
| 3197 | CH | NMe | Q1n | a bond | Me | a bond | NH | S | NH | Q3a | OH |
| 3198 | CH | NMe | Q1n | a bond | Me | a bond | NH | S | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3199 | CH | NMe | Q1n | a bond | Me | a bond | NH | S | NH | Q3e | OH |
| 3200 | CH | NMe | Q1n | a bond | Me | a bond | NH | S | NH | Q3f | OH |
| 3201 | CH | NEt | Q1k | a bond | Me | a bond | NH | O | a bond | Q3a | OH |
| 3202 | CH | NEt | Q1k | a bond | Me | a bond | NH | O | a bond | Q3d | OH |
| 3203 | CH | NEt | Q1k | a bond | Me | a bond | NH | O | a bond | Q3e | OH |
| 3204 | CH | NEt | Q1k | a bond | Me | a bond | NH | O | a bond | Q3f | OH |
| 3205 | CH | NEt | Q1k | a bond | Me | a bond | NH | O | NH | Q3a | OH |
| 3206 | CH | NEt | Q1k | a bond | Me | a bond | NH | O | NH | Q3d | OH |
| 3207 | CH | NEt | Q1k | a bond | Me | a bond | NH | O | NH | Q3e | OH |
| 3208 | CH | NEt | Q1k | a bond | Me | a bond | NH | O | NH | Q3f | OH |
| 3209 | CH | NEt | Q1k | a bond | Me | a bond | NH | S | a bond | Q3a | OH |
| 3210 | CH | NEt | Q1k | a bond | Me | a bond | NH | S | a bond | Q3d | OH |
| 3211 | CH | NEt | Q1k | a bond | Me | a bond | NH | S | a bond | Q3e | OH |
| 3212 | CH | NEt | Q1k | a bond | Me | a bond | NH | S | a bond | Q3f | OH |
| 3213 | CH | NEt | Q1k | a bond | Me | a bond | NH | S | NH | Q3a | OH |
| 3214 | CH | NEt | Q1k | a bond | Me | a bond | NH | S | NH | Q3d | OH |
| 3215 | CH | NEt | Q1k | a bond | Me | a bond | NH | S | NH | Q3e | OH |
| 3216 | CH | NEt | Q1k | a bond | Me | a bond | NH | S | NH | Q3f | OH |
| 3217 | CH | NEt | Q1l | a bond | Me | a bond | NH | O | a bond | Q3a | OH |
| 3218 | CH | NEt | Q1l | a bond | Me | a bond | NH | O | a bond | Q3d | OH |
| 3219 | CH | NEt | Q1l | a bond | Me | a bond | NH | O | a bond | Q3e | OH |
| 3220 | CH | NEt | Q1l | a bond | Me | a bond | NH | O | a bond | Q3f | OH |
| 3221 | CH | NEt | Q1l | a bond | Me | a bond | NH | O | NH | Q3a | OH |
| 3222 | CH | NEt | Q1l | a bond | Me | a bond | NH | O | NH | Q3d | OH |
| 3223 | CH | NEt | Q1l | a bond | Me | a bond | NH | O | NH | Q3e | OH |
| 3224 | CH | NEt | Q1l | a bond | Me | a bond | NH | O | NH | Q3f | OH |
| 3225 | CH | NEt | Q1l | a bond | Me | a bond | NH | S | a bond | Q3a | OH |
| 3226 | CH | NEt | Q1l | a bond | Me | a bond | NH | S | a bond | Q3d | OH |
| 3227 | CH | NEt | Q1l | a bond | Me | a bond | NH | S | a bond | Q3e | OH |
| 3228 | CH | NEt | Q1l | a bond | Me | a bond | NH | S | a bond | Q3f | OH |
| 3229 | CH | NEt | Q1l | a bond | Me | a bond | NH | S | NH | Q3a | OH |
| 3230 | CH | NEt | Q1l | a bond | Me | a bond | NH | S | NH | Q3d | OH |
| 3231 | CH | NEt | Q1l | a bond | Me | a bond | NH | S | NH | Q3e | OH |
| 3232 | CH | NEt | Q1l | a bond | Me | a bond | NH | S | NH | Q3f | OH |
| 3233 | CH | NEt | Q1m | a bond | Me | a bond | NH | O | a bond | Q3a | OH |
| 3234 | CH | NEt | Q1m | a bond | Me | a bond | NH | O | a bond | Q3d | OH |
| 3235 | CH | NEt | Q1m | a bond | Me | a bond | NH | O | a bond | Q3e | OH |
| 3236 | CH | NEt | Q1m | a bond | Me | a bond | NH | O | a bond | Q3f | OH |
| 3237 | CH | NEt | Q1m | a bond | Me | a bond | NH | O | NH | Q3a | OH |
| 3238 | CH | NEt | Q1m | a bond | Me | a bond | NH | O | NH | Q3d | OH |
| 3239 | CH | NEt | Q1m | a bond | Me | a bond | NH | O | NH | Q3e | OH |
| 3240 | CH | NEt | Q1m | a bond | Me | a bond | NH | O | NH | Q3f | OH |
| 3241 | CH | NEt | Q1m | a bond | Me | a bond | NH | S | a bond | Q3a | OH |
| 3242 | CH | NEt | Q1m | a bond | Me | a bond | NH | S | a bond | Q3d | OH |
| 3243 | CH | NEt | Q1m | a bond | Me | a bond | NH | S | a bond | Q3e | OH |
| 3244 | CH | NEt | Q1m | a bond | Me | a bond | NH | S | a bond | Q3f | OH |
| 3245 | CH | NEt | Q1m | a bond | Me | a bond | NH | S | NH | Q3a | OH |
| 3246 | CH | NEt | Q1m | a bond | Me | a bond | NH | S | NH | Q3d | OH |
| 3247 | CH | NEt | Q1m | a bond | Me | a bond | NH | S | NH | Q3e | OH |
| 3248 | CH | NEt | Q1m | a bond | Me | a bond | NH | S | NH | Q3f | OH |
| 3249 | CH | NEt | Q1n | a bond | Me | a bond | NH | O | a bond | Q3a | OH |
| 3250 | CH | NEt | Q1n | a bond | Me | a bond | NH | O | a bond | Q3d | OH |
| 3251 | CH | NEt | Q1n | a bond | Me | a bond | NH | O | a bond | Q3e | OH |
| 3252 | CH | NEt | Q1n | a bond | Me | a bond | NH | O | a bond | Q3f | OH |
| 3253 | CH | NEt | Q1n | a bond | Me | a bond | NH | O | NH | Q3a | OH |
| 3254 | CH | NEt | Q1n | a bond | Me | a bond | NH | O | NH | Q3d | OH |
| 3255 | CH | NEt | Q1n | a bond | Me | a bond | NH | O | NH | Q3e | OH |
| 3256 | CH | NEt | Q1n | a bond | Me | a bond | NH | O | NH | Q3f | OH |
| 3257 | CH | NEt | Q1n | a bond | Me | a bond | NH | S | a bond | Q3a | OH |
| 3258 | CH | NEt | Q1n | a bond | Me | a bond | NH | S | a bond | Q3d | OH |
| 3259 | CH | NEt | Q1n | a bond | Me | a bond | NH | S | a bond | Q3e | OH |
| 3260 | CH | NEt | Q1n | a bond | Me | a bond | NH | S | a bond | Q3f | OH |
| 3261 | CH | NEt | Q1n | a bond | Me | a bond | NH | S | NH | Q3a | OH |
| 3262 | CH | NEt | Q1n | a bond | Me | a bond | NH | S | NH | Q3d | OH |
| 3263 | CH | NEt | Q1n | a bond | Me | a bond | NH | S | NH | Q3e | OH |
| 3264 | CH | NEt | Q1n | a bond | Me | a bond | NH | S | NH | Q3f | OH |
| 3265 | CH | S | Q1k | a bond | Me | a bond | NH | O | a bond | Q3a | OH |
| 3266 | CH | S | Q1k | a bond | Me | a bond | NH | O | a bond | Q3d | OH |
| 3267 | CH | S | Q1k | a bond | Me | a bond | NH | O | a bond | Q3e | OH |
| 3268 | CH | S | Q1k | a bond | Me | a bond | NH | O | a bond | Q3f | OH |
| 3269 | CH | S | Q1k | a bond | Me | a bond | NH | O | NH | Q3a | OH |
| 3270 | CH | S | Q1k | a bond | Me | a bond | NH | O | NH | Q3d | OH |
| 3271 | CH | S | Q1k | a bond | Me | a bond | NH | O | NH | Q3e | OH |
| 3272 | CH | S | Q1k | a bond | Me | a bond | NH | O | NH | Q3f | OH |
| 3273 | CH | S | Q1k | a bond | Me | a bond | NH | S | a bond | Q3a | OH |
| 3274 | CH | S | Q1k | a bond | Me | a bond | NH | S | a bond | Q3d | OH |
| 3275 | CH | S | Q1k | a bond | Me | a bond | NH | S | a bond | Q3e | OH |
| 3276 | CH | S | Q1k | a bond | Me | a bond | NH | S | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3277 | CH | S | Q1k | a bond | Me | a bond | NH | S | NH | Q3a | OH |
| 3278 | CH | S | Q1k | a bond | Me | a bond | NH | S | NH | Q3d | OH |
| 3279 | CH | S | Q1k | a bond | Me | a bond | NH | S | NH | Q3e | OH |
| 3280 | CH | S | Q1k | a bond | Me | a bond | NH | S | NH | Q3f | OH |
| 3281 | CH | S | Q1l | a bond | Me | a bond | NH | O | a bond | Q3a | OH |
| 3282 | CH | S | Q1l | a bond | Me | a bond | NH | O | a bond | Q3d | OH |
| 3283 | CH | S | Q1l | a bond | Me | a bond | NH | O | a bond | Q3e | OH |
| 3284 | CH | S | Q1l | a bond | Me | a bond | NH | O | a bond | Q3f | OH |
| 3285 | CH | S | Q1l | a bond | Me | a bond | NH | O | NH | Q3a | OH |
| 3286 | CH | S | Q1l | a bond | Me | a bond | NH | O | NH | Q3d | OH |
| 3287 | CH | S | Q1l | a bond | Me | a bond | NH | O | NH | Q3e | OH |
| 3288 | CH | S | Q1l | a bond | Me | a bond | NH | O | NH | Q3f | OH |
| 3289 | CH | S | Q1l | a bond | Me | a bond | NH | S | a bond | Q3a | OH |
| 3290 | CH | S | Q1l | a bond | Me | a bond | NH | S | a bond | Q3d | OH |
| 3291 | CH | S | Q1l | a bond | Me | a bond | NH | S | a bond | Q3e | OH |
| 3292 | CH | S | Q1l | a bond | Me | a bond | NH | S | a bond | Q3f | OH |
| 3293 | CH | S | Q1l | a bond | Me | a bond | NH | S | NH | Q3a | OH |
| 3294 | CH | S | Q1l | a bond | Me | a bond | NH | S | NH | Q3d | OH |
| 3295 | CH | S | Q1l | a bond | Me | a bond | NH | S | NH | Q3e | OH |
| 3296 | CH | S | Q1l | a bond | Me | a bond | NH | S | NH | Q3f | OH |
| 3297 | CH | S | Q1m | a bond | Me | a bond | NH | O | a bond | Q3a | OH |
| 3298 | CH | S | Q1m | a bond | Me | a bond | NH | O | a bond | Q3d | OH |
| 3299 | CH | S | Q1m | a bond | Me | a bond | NH | O | a bond | Q3e | OH |
| 3300 | CH | S | Q1m | a bond | Me | a bond | NH | O | a bond | Q3f | OH |
| 3301 | CH | S | Q1m | a bond | Me | a bond | NH | O | NH | Q3a | OH |
| 3302 | CH | S | Q1m | a bond | Me | a bond | NH | O | NH | Q3d | OH |
| 3303 | CH | S | Q1m | a bond | Me | a bond | NH | O | NH | Q3e | OH |
| 3304 | CH | S | Q1m | a bond | Me | a bond | NH | O | NH | Q3f | OH |
| 3305 | CH | S | Q1m | a bond | Me | a bond | NH | S | a bond | Q3a | OH |
| 3306 | CH | S | Q1m | a bond | Me | a bond | NH | S | a bond | Q3d | OH |
| 3307 | CH | S | Q1m | a bond | Me | a bond | NH | S | a bond | Q3e | OH |
| 3308 | CH | S | Q1m | a bond | Me | a bond | NH | S | a bond | Q3f | OH |
| 3309 | CH | S | Q1m | a bond | Me | a bond | NH | S | NH | Q3a | OH |
| 3310 | CH | S | Q1m | a bond | Me | a bond | NH | S | NH | Q3d | OH |
| 3311 | CH | S | Q1m | a bond | Me | a bond | NH | S | NH | Q3e | OH |
| 3312 | CH | S | Q1m | a bond | Me | a bond | NH | S | NH | Q3f | OH |
| 3313 | CH | S | Q1n | a bond | Me | a bond | NH | O | a bond | Q3a | OH |
| 3314 | CH | S | Q1n | a bond | Me | a bond | NH | O | a bond | Q3d | OH |
| 3315 | CH | S | Q1n | a bond | Me | a bond | NH | O | a bond | Q3e | OH |
| 3316 | CH | S | Q1n | a bond | Me | a bond | NH | O | a bond | Q3f | OH |
| 3317 | CH | S | Q1n | a bond | Me | a bond | NH | O | NH | Q3a | OH |
| 3318 | CH | S | Q1n | a bond | Me | a bond | NH | O | NH | Q3d | OH |
| 3319 | CH | S | Q1n | a bond | Me | a bond | NH | O | NH | Q3e | OH |
| 3320 | CH | S | Q1n | a bond | Me | a bond | NH | O | NH | Q3f | OH |
| 3321 | CH | S | Q1n | a bond | Me | a bond | NH | S | a bond | Q3a | OH |
| 3322 | CH | S | Q1n | a bond | Me | a bond | NH | S | a bond | Q3d | OH |
| 3323 | CH | S | Q1n | a bond | Me | a bond | NH | S | a bond | Q3e | OH |
| 3324 | CH | S | Q1n | a bond | Me | a bond | NH | S | a bond | Q3f | OH |
| 3325 | CH | S | Q1n | a bond | Me | a bond | NH | S | NH | Q3a | OH |
| 3326 | CH | S | Q1n | a bond | Me | a bond | NH | S | NH | Q3d | OH |
| 3327 | CH | S | Q1n | a bond | Me | a bond | NH | S | NH | Q3e | OH |
| 3328 | CH | S | Q1n | a bond | Me | a bond | NH | S | NH | Q3f | OH |
| 3329 | CH | O | Q1k | a bond | Me | a bond | NH | O | a bond | Q3a | OH |
| 3330 | CH | O | Q1k | a bond | Me | a bond | NH | O | a bond | Q3d | OH |
| 3331 | CH | O | Q1k | a bond | Me | a bond | NH | O | a bond | Q3e | OH |
| 3332 | CH | O | Q1k | a bond | Me | a bond | NH | O | a bond | Q3f | OH |
| 3333 | CH | O | Q1k | a bond | Me | a bond | NH | O | NH | Q3a | OH |
| 3334 | CH | O | Q1k | a bond | Me | a bond | NH | O | NH | Q3d | OH |
| 3335 | CH | O | Q1k | a bond | Me | a bond | NH | O | NH | Q3e | OH |
| 3336 | CH | O | Q1k | a bond | Me | a bond | NH | O | NH | Q3f | OH |
| 3337 | CH | O | Q1k | a bond | Me | a bond | NH | S | a bond | Q3a | OH |
| 3338 | CH | O | Q1k | a bond | Me | a bond | NH | S | a bond | Q3d | OH |
| 3339 | CH | O | Q1k | a bond | Me | a bond | NH | S | a bond | Q3e | OH |
| 3340 | CH | O | Q1k | a bond | Me | a bond | NH | S | a bond | Q3f | OH |
| 3341 | CH | O | Q1k | a bond | Me | a bond | NH | S | NH | Q3a | OH |
| 3342 | CH | O | Q1k | a bond | Me | a bond | NH | S | NH | Q3d | OH |
| 3343 | CH | O | Q1k | a bond | Me | a bond | NH | S | NH | Q3e | OH |
| 3344 | CH | O | Q1k | a bond | Me | a bond | NH | S | NH | Q3f | OH |
| 3345 | CH | O | Q1l | a bond | Me | a bond | NH | O | a bond | Q3a | OH |
| 3346 | CH | O | Q1l | a bond | Me | a bond | NH | O | a bond | Q3d | OH |
| 3347 | CH | O | Q1l | a bond | Me | a bond | NH | O | a bond | Q3e | OH |
| 3348 | CH | O | Q1l | a bond | Me | a bond | NH | O | a bond | Q3f | OH |
| 3349 | CH | O | Q1l | a bond | Me | a bond | NH | O | NH | Q3a | OH |
| 3350 | CH | O | Q1l | a bond | Me | a bond | NH | O | NH | Q3d | OH |
| 3351 | CH | O | Q1l | a bond | Me | a bond | NH | O | NH | Q3e | OH |
| 3352 | CH | O | Q1l | a bond | Me | a bond | NH | O | NH | Q3f | OH |
| 3353 | CH | O | Q1l | a bond | Me | a bond | NH | S | a bond | Q3a | OH |
| 3354 | CH | O | Q1l | a bond | Me | a bond | NH | S | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3355 | CH | O | Q1l | a bond | Me | a bond | NH | S | a bond | Q3e | OH |
| 3356 | CH | O | Q1l | a bond | Me | a bond | NH | S | a bond | Q3f | OH |
| 3357 | CH | O | Q1l | a bond | Me | a bond | NH | S | NH | Q3a | OH |
| 3358 | CH | O | Q1l | a bond | Me | a bond | NH | S | NH | Q3d | OH |
| 3359 | CH | O | Q1l | a bond | Me | a bond | NH | S | NH | Q3e | OH |
| 3360 | CH | O | Q1l | a bond | Me | a bond | NH | S | NH | Q3f | OH |
| 3361 | CH | O | Q1m | a bond | Me | a bond | NH | O | a bond | Q3a | OH |
| 3362 | CH | O | Q1m | a bond | Me | a bond | NH | O | a bond | Q3d | OH |
| 3363 | CH | O | Q1m | a bond | Me | a bond | NH | O | a bond | Q3e | OH |
| 3364 | CH | O | Q1m | a bond | Me | a bond | NH | O | a bond | Q3f | OH |
| 3365 | CH | O | Q1m | a bond | Me | a bond | NH | O | NH | Q3a | OH |
| 3366 | CH | O | Q1m | a bond | Me | a bond | NH | O | NH | Q3d | OH |
| 3367 | CH | O | Q1m | a bond | Me | a bond | NH | O | NH | Q3e | OH |
| 3368 | CH | O | Q1m | a bond | Me | a bond | NH | O | NH | Q3f | OH |
| 3369 | CH | O | Q1m | a bond | Me | a bond | NH | S | a bond | Q3a | OH |
| 3370 | CH | O | Q1m | a bond | Me | a bond | NH | S | a bond | Q3d | OH |
| 3371 | CH | O | Q1m | a bond | Me | a bond | NH | S | a bond | Q3e | OH |
| 3372 | CH | O | Q1m | a bond | Me | a bond | NH | S | a bond | Q3f | OH |
| 3373 | CH | O | Q1m | a bond | Me | a bond | NH | S | NH | Q3a | OH |
| 3374 | CH | O | Q1m | a bond | Me | a bond | NH | S | NH | Q3d | OH |
| 3375 | CH | O | Q1m | a bond | Me | a bond | NH | S | NH | Q3e | OH |
| 3376 | CH | O | Q1m | a bond | Me | a bond | NH | S | NH | Q3f | OH |
| 3377 | CH | O | Q1n | a bond | Me | a bond | NH | O | a bond | Q3a | OH |
| 3378 | CH | O | Q1n | a bond | Me | a bond | NH | O | a bond | Q3d | OH |
| 3379 | CH | O | Q1n | a bond | Me | a bond | NH | O | a bond | Q3e | OH |
| 3380 | CH | O | Q1n | a bond | Me | a bond | NH | O | a bond | Q3f | OH |
| 3381 | CH | O | Q1n | a bond | Me | a bond | NH | O | NH | Q3a | OH |
| 3382 | CH | O | Q1n | a bond | Me | a bond | NH | O | NH | Q3d | OH |
| 3383 | CH | O | Q1n | a bond | Me | a bond | NH | O | NH | Q3e | OH |
| 3384 | CH | O | Q1n | a bond | Me | a bond | NH | O | NH | Q3f | OH |
| 3385 | CH | O | Q1n | a bond | Me | a bond | NH | S | a bond | Q3a | OH |
| 3386 | CH | O | Q1n | a bond | Me | a bond | NH | S | a bond | Q3d | OH |
| 3387 | CH | O | Q1n | a bond | Me | a bond | NH | S | a bond | Q3e | OH |
| 3388 | CH | O | Q1n | a bond | Me | a bond | NH | S | a bond | Q3f | OH |
| 3389 | CH | O | Q1n | a bond | Me | a bond | NH | S | NH | Q3a | OH |
| 3390 | CH | O | Q1n | a bond | Me | a bond | NH | S | NH | Q3d | OH |
| 3391 | CH | O | Q1n | a bond | Me | a bond | NH | S | NH | Q3e | OH |
| 3392 | CH | O | Q1n | a bond | Me | a bond | NH | S | NH | Q3f | OH |
| 3393 | CMe | NMe | Q1k | a bond | Me | a bond | NH | O | a bond | Q3a | OH |
| 3394 | CMe | NMe | Q1k | a bond | Me | a bond | NH | O | a bond | Q3d | OH |
| 3395 | CMe | NMe | Q1k | a bond | Me | a bond | NH | O | a bond | Q3e | OH |
| 3396 | CMe | NMe | Q1k | a bond | Me | a bond | NH | O | a bond | Q3f | OH |
| 3397 | CMe | NMe | Q1k | a bond | Me | a bond | NH | O | NH | Q3a | OH |
| 3398 | CMe | NMe | Q1k | a bond | Me | a bond | NH | O | NH | Q3d | OH |
| 3399 | CMe | NMe | Q1k | a bond | Me | a bond | NH | O | NH | Q3e | OH |
| 3400 | CMe | NMe | Q1k | a bond | Me | a bond | NH | O | NH | Q3f | OH |
| 3401 | CMe | NMe | Q1k | a bond | Me | a bond | NH | S | a bond | Q3a | OH |
| 3402 | CMe | NMe | Q1k | a bond | Me | a bond | NH | S | a bond | Q3d | OH |
| 3403 | CMe | NMe | Q1k | a bond | Me | a bond | NH | S | a bond | Q3e | OH |
| 3404 | CMe | NMe | Q1k | a bond | Me | a bond | NH | S | a bond | Q3f | OH |
| 3405 | CMe | NMe | Q1k | a bond | Me | a bond | NH | S | NH | Q3a | OH |
| 3406 | CMe | NMe | Q1k | a bond | Me | a bond | NH | S | NH | Q3d | OH |
| 3407 | CMe | NMe | Q1k | a bond | Me | a bond | NH | S | NH | Q3e | OH |
| 3408 | CMe | NMe | Q1k | a bond | Me | a bond | NH | S | NH | Q3f | OH |
| 3409 | CMe | NMe | Q1l | a bond | Me | a bond | NH | O | a bond | Q3a | OH |
| 3410 | CMe | NMe | Q1l | a bond | Me | a bond | NH | O | a bond | Q3d | OH |
| 3411 | CMe | NMe | Q1l | a bond | Me | a bond | NH | O | a bond | Q3e | OH |
| 3412 | CMe | NMe | Q1l | a bond | Me | a bond | NH | O | a bond | Q3f | OH |
| 3413 | CMe | NMe | Q1l | a bond | Me | a bond | NH | O | NH | Q3a | OH |
| 3414 | CMe | NMe | Q1l | a bond | Me | a bond | NH | O | NH | Q3d | OH |
| 3415 | CMe | NMe | Q1l | a bond | Me | a bond | NH | O | NH | Q3e | OH |
| 3416 | CMe | NMe | Q1l | a bond | Me | a bond | NH | O | NH | Q3f | OH |
| 3417 | CMe | NMe | Q1l | a bond | Me | a bond | NH | S | a bond | Q3a | OH |
| 3418 | CMe | NMe | Q1l | a bond | Me | a bond | NH | S | a bond | Q3d | OH |
| 3419 | CMe | NMe | Q1l | a bond | Me | a bond | NH | S | a bond | Q3e | OH |
| 3420 | CMe | NMe | Q1l | a bond | Me | a bond | NH | S | a bond | Q3f | OH |
| 3421 | CMe | NMe | Q1l | a bond | Me | a bond | NH | S | NH | Q3a | OH |
| 3422 | CMe | NMe | Q1l | a bond | Me | a bond | NH | S | NH | Q3d | OH |
| 3423 | CMe | NMe | Q1l | a bond | Me | a bond | NH | S | NH | Q3e | OH |
| 3424 | CMe | NMe | Q1l | a bond | Me | a bond | NH | S | NH | Q3f | OH |
| 3425 | CMe | NMe | Q1m | a bond | Me | a bond | NH | O | a bond | Q3a | OH |
| 3426 | CMe | NMe | Q1m | a bond | Me | a bond | NH | O | a bond | Q3d | OH |
| 3427 | CMe | NMe | Q1m | a bond | Me | a bond | NH | O | a bond | Q3e | OH |
| 3428 | CMe | NMe | Q1m | a bond | Me | a bond | NH | O | a bond | Q3f | OH |
| 3429 | CMe | NMe | Q1m | a bond | Me | a bond | NH | O | NH | Q3a | OH |
| 3430 | CMe | NMe | Q1m | a bond | Me | a bond | NH | O | NH | Q3d | OH |
| 3431 | CMe | NMe | Q1m | a bond | Me | a bond | NH | O | NH | Q3e | OH |
| 3432 | CMe | NMe | Q1m | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3433 | CMe | NMe | Q1m | a bond | Me | a bond | NH | S | a bond | Q3a | OH |
| 3434 | CMe | NMe | Q1m | a bond | Me | a bond | NH | S | a bond | Q3d | OH |
| 3435 | CMe | NMe | Q1m | a bond | Me | a bond | NH | S | a bond | Q3e | OH |
| 3436 | CMe | NMe | Q1m | a bond | Me | a bond | NH | S | a bond | Q3f | OH |
| 3437 | CMe | NMe | Q1m | a bond | Me | a bond | NH | S | NH | Q3a | OH |
| 3438 | CMe | NMe | Q1m | a bond | Me | a bond | NH | S | NH | Q3d | OH |
| 3439 | CMe | NMe | Q1m | a bond | Me | a bond | NH | S | NH | Q3e | OH |
| 3440 | CMe | NMe | Q1m | a bond | Me | a bond | NH | S | NH | Q3f | OH |
| 3441 | CMe | NMe | Q1n | a bond | Me | a bond | NH | O | a bond | Q3a | OH |
| 3442 | CMe | NMe | Q1n | a bond | Me | a bond | NH | O | a bond | Q3d | OH |
| 3443 | CMe | NMe | Q1n | a bond | Me | a bond | NH | O | a bond | Q3e | OH |
| 3444 | CMe | NMe | Q1n | a bond | Me | a bond | NH | O | a bond | Q3f | OH |
| 3445 | CMe | NMe | Q1n | a bond | Me | a bond | NH | O | NH | Q3a | OH |
| 3446 | CMe | NMe | Q1n | a bond | Me | a bond | NH | O | NH | Q3d | OH |
| 3447 | CMe | NMe | Q1n | a bond | Me | a bond | NH | O | NH | Q3e | OH |
| 3448 | CMe | NMe | Q1n | a bond | Me | a bond | NH | O | NH | Q3f | OH |
| 3449 | CMe | NMe | Q1n | a bond | Me | a bond | NH | S | a bond | Q3a | OH |
| 3450 | CMe | NMe | Q1n | a bond | Me | a bond | NH | S | a bond | Q3d | OH |
| 3451 | CMe | NMe | Q1n | a bond | Me | a bond | NH | S | a bond | Q3e | OH |
| 3452 | CMe | NMe | Q1n | a bond | Me | a bond | NH | S | a bond | Q3f | OH |
| 3453 | CMe | NMe | Q1n | a bond | Me | a bond | NH | S | NH | Q3a | OH |
| 3454 | CMe | NMe | Q1n | a bond | Me | a bond | NH | S | NH | Q3d | OH |
| 3455 | CMe | NMe | Q1n | a bond | Me | a bond | NH | S | NH | Q3e | OH |
| 3456 | CMe | NMe | Q1n | a bond | Me | a bond | NH | S | NH | Q3f | OH |
| 3457 | CMe | NEt | Q1k | a bond | Me | a bond | NH | O | a bond | Q3a | OH |
| 3458 | CMe | NEt | Q1k | a bond | Me | a bond | NH | O | a bond | Q3d | OH |
| 3459 | CMe | NEt | Q1k | a bond | Me | a bond | NH | O | a bond | Q3e | OH |
| 3460 | CMe | NEt | Q1k | a bond | Me | a bond | NH | O | a bond | Q3f | OH |
| 3461 | CMe | NEt | Q1k | a bond | Me | a bond | NH | O | NH | Q3a | OH |
| 3462 | CMe | NEt | Q1k | a bond | Me | a bond | NH | O | NH | Q3d | OH |
| 3463 | CMe | NEt | Q1k | a bond | Me | a bond | NH | O | NH | Q3e | OH |
| 3464 | CMe | NEt | Q1k | a bond | Me | a bond | NH | O | NH | Q3f | OH |
| 3465 | CMe | NEt | Q1k | a bond | Me | a bond | NH | S | a bond | Q3a | OH |
| 3466 | CMe | NEt | Q1k | a bond | Me | a bond | NH | S | a bond | Q3d | OH |
| 3467 | CMe | NEt | Q1k | a bond | Me | a bond | NH | S | a bond | Q3e | OH |
| 3468 | CMe | NEt | Q1k | a bond | Me | a bond | NH | S | a bond | Q3f | OH |
| 3469 | CMe | NEt | Q1k | a bond | Me | a bond | NH | S | NH | Q3a | OH |
| 3470 | CMe | NEt | Q1k | a bond | Me | a bond | NH | S | NH | Q3d | OH |
| 3471 | CMe | NEt | Q1k | a bond | Me | a bond | NH | S | NH | Q3e | OH |
| 3472 | CMe | NEt | Q1k | a bond | Me | a bond | NH | S | NH | Q3f | OH |
| 3473 | CMe | NEt | Q1l | a bond | Me | a bond | NH | O | a bond | Q3a | OH |
| 3474 | CMe | NEt | Q1l | a bond | Me | a bond | NH | O | a bond | Q3d | OH |
| 3475 | CMe | NEt | Q1l | a bond | Me | a bond | NH | O | a bond | Q3e | OH |
| 3476 | CMe | NEt | Q1l | a bond | Me | a bond | NH | O | a bond | Q3f | OH |
| 3477 | CMe | NEt | Q1l | a bond | Me | a bond | NH | O | NH | Q3a | OH |
| 3478 | CMe | NEt | Q1l | a bond | Me | a bond | NH | O | NH | Q3d | OH |
| 3479 | CMe | NEt | Q1l | a bond | Me | a bond | NH | O | NH | Q3e | OH |
| 3480 | CMe | NEt | Q1l | a bond | Me | a bond | NH | O | NH | Q3f | OH |
| 3481 | CMe | NEt | Q1l | a bond | Me | a bond | NH | S | a bond | Q3a | OH |
| 3482 | CMe | NEt | Q1l | a bond | Me | a bond | NH | S | a bond | Q3d | OH |
| 3483 | CMe | NEt | Q1l | a bond | Me | a bond | NH | S | a bond | Q3e | OH |
| 3484 | CMe | NEt | Q1l | a bond | Me | a bond | NH | S | a bond | Q3f | OH |
| 3485 | CMe | NEt | Q1l | a bond | Me | a bond | NH | S | NH | Q3a | OH |
| 3486 | CMe | NEt | Q1l | a bond | Me | a bond | NH | S | NH | Q3d | OH |
| 3487 | CMe | NEt | Q1l | a bond | Me | a bond | NH | S | NH | Q3e | OH |
| 3488 | CMe | NEt | Q1l | a bond | Me | a bond | NH | S | NH | Q3f | OH |
| 3489 | CMe | NEt | Q1m | a bond | Me | a bond | NH | O | a bond | Q3a | OH |
| 3490 | CMe | NEt | Q1m | a bond | Me | a bond | NH | O | a bond | Q3d | OH |
| 3491 | CMe | NEt | Q1m | a bond | Me | a bond | NH | O | a bond | Q3e | OH |
| 3492 | CMe | NEt | Q1m | a bond | Me | a bond | NH | O | a bond | Q3f | OH |
| 3493 | CMe | NEt | Q1m | a bond | Me | a bond | NH | O | NH | Q3a | OH |
| 3494 | CMe | NEt | Q1m | a bond | Me | a bond | NH | O | NH | Q3d | OH |
| 3495 | CMe | NEt | Q1m | a bond | Me | a bond | NH | O | NH | Q3e | OH |
| 3496 | CMe | NEt | Q1m | a bond | Me | a bond | NH | O | NH | Q3f | OH |
| 3497 | CMe | NEt | Q1m | a bond | Me | a bond | NH | S | a bond | Q3a | OH |
| 3498 | CMe | NEt | Q1m | a bond | Me | a bond | NH | S | a bond | Q3d | OH |
| 3499 | CMe | NEt | Q1m | a bond | Me | a bond | NH | S | a bond | Q3e | OH |
| 3500 | CMe | NEt | Q1m | a bond | Me | a bond | NH | S | a bond | Q3f | OH |
| 3501 | CMe | NEt | Q1m | a bond | Me | a bond | NH | S | NH | Q3a | OH |
| 3502 | CMe | NEt | Q1m | a bond | Me | a bond | NH | S | NH | Q3d | OH |
| 3503 | CMe | NEt | Q1m | a bond | Me | a bond | NH | S | NH | Q3e | OH |
| 3504 | CMe | NEt | Q1m | a bond | Me | a bond | NH | S | NH | Q3f | OH |
| 3505 | CMe | NEt | Q1n | a bond | Me | a bond | NH | O | a bond | Q3a | OH |
| 3506 | CMe | NEt | Q1n | a bond | Me | a bond | NH | O | a bond | Q3d | OH |
| 3507 | CMe | NEt | Q1n | a bond | Me | a bond | NH | O | a bond | Q3e | OH |
| 3508 | CMe | NEt | Q1n | a bond | Me | a bond | NH | O | a bond | Q3f | OH |
| 3509 | CMe | NEt | Q1n | a bond | Me | a bond | NH | O | NH | Q3a | OH |
| 3510 | CMe | NEt | Q1n | a bond | Me | a bond | NH | O | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3511 | CMe | NEt | Q1n | a bond | Me | a bond | NH | O | NH | Q3e | OH |
| 3512 | CMe | NEt | Q1n | a bond | Me | a bond | NH | O | NH | Q3f | OH |
| 3513 | CMe | NEt | Q1n | a bond | Me | a bond | NH | S | a bond | Q3a | OH |
| 3514 | CMe | NEt | Q1n | a bond | Me | a bond | NH | S | a bond | Q3d | OH |
| 3515 | CMe | NEt | Q1n | a bond | Me | a bond | NH | S | a bond | Q3e | OH |
| 3516 | CMe | NEt | Q1n | a bond | Me | a bond | NH | S | a bond | Q3f | OH |
| 3517 | CMe | NEt | Q1n | a bond | Me | a bond | NH | S | NH | Q3a | OH |
| 3518 | CMe | NEt | Q1n | a bond | Me | a bond | NH | S | NH | Q3d | OH |
| 3519 | CMe | NEt | Q1n | a bond | Me | a bond | NH | S | NH | Q3e | OH |
| 3520 | CMe | NEt | Q1n | a bond | Me | a bond | NH | S | NH | Q3f | OH |
| 3521 | CMe | S | Q1k | a bond | Me | a bond | NH | O | a bond | Q3a | OH |
| 3522 | CMe | S | Q1k | a bond | Me | a bond | NH | O | a bond | Q3d | OH |
| 3523 | CMe | S | Q1k | a bond | Me | a bond | NH | O | a bond | Q3e | OH |
| 3524 | CMe | S | Q1k | a bond | Me | a bond | NH | O | a bond | Q3f | OH |
| 3525 | CMe | S | Q1k | a bond | Me | a bond | NH | O | NH | Q3a | OH |
| 3526 | CMe | S | Q1k | a bond | Me | a bond | NH | O | NH | Q3d | OH |
| 3527 | CMe | S | Q1k | a bond | Me | a bond | NH | O | NH | Q3e | OH |
| 3528 | CMe | S | Q1k | a bond | Me | a bond | NH | O | NH | Q3f | OH |
| 3529 | CMe | S | Q1k | a bond | Me | a bond | NH | S | a bond | Q3a | OH |
| 3530 | CMe | S | Q1k | a bond | Me | a bond | NH | S | a bond | Q3d | OH |
| 3531 | CMe | S | Q1k | a bond | Me | a bond | NH | S | a bond | Q3e | OH |
| 3532 | CMe | S | Q1k | a bond | Me | a bond | NH | S | a bond | Q3f | OH |
| 3533 | CMe | S | Q1k | a bond | Me | a bond | NH | S | NH | Q3a | OH |
| 3534 | CMe | S | Q1k | a bond | Me | a bond | NH | S | NH | Q3d | OH |
| 3535 | CMe | S | Q1k | a bond | Me | a bond | NH | S | NH | Q3e | OH |
| 3536 | CMe | S | Q1k | a bond | Me | a bond | NH | S | NH | Q3f | OH |
| 3537 | CMe | S | Q1l | a bond | Me | a bond | NH | O | a bond | Q3a | OH |
| 3538 | CMe | S | Q1l | a bond | Me | a bond | NH | O | a bond | Q3d | OH |
| 3539 | CMe | S | Q1l | a bond | Me | a bond | NH | O | a bond | Q3e | OH |
| 3540 | CMe | S | Q1l | a bond | Me | a bond | NH | O | a bond | Q3f | OH |
| 3541 | CMe | S | Q1l | a bond | Me | a bond | NH | O | NH | Q3a | OH |
| 3542 | CMe | S | Q1l | a bond | Me | a bond | NH | O | NH | Q3d | OH |
| 3543 | CMe | S | Q1l | a bond | Me | a bond | NH | O | NH | Q3e | OH |
| 3544 | CMe | S | Q1l | a bond | Me | a bond | NH | O | NH | Q3f | OH |
| 3545 | CMe | S | Q1l | a bond | Me | a bond | NH | S | a bond | Q3a | OH |
| 3546 | CMe | S | Q1l | a bond | Me | a bond | NH | S | a bond | Q3d | OH |
| 3547 | CMe | S | Q1l | a bond | Me | a bond | NH | S | a bond | Q3e | OH |
| 3548 | CMe | S | Q1l | a bond | Me | a bond | NH | S | a bond | Q3f | OH |
| 3549 | CMe | S | Q1l | a bond | Me | a bond | NH | S | NH | Q3a | OH |
| 3550 | CMe | S | Q1l | a bond | Me | a bond | NH | S | NH | Q3d | OH |
| 3551 | CMe | S | Q1l | a bond | Me | a bond | NH | S | NH | Q3e | OH |
| 3552 | CMe | S | Q1l | a bond | Me | a bond | NH | S | NH | Q3f | OH |
| 3553 | CMe | S | Q1m | a bond | Me | a bond | NH | O | a bond | Q3a | OH |
| 3554 | CMe | S | Q1m | a bond | Me | a bond | NH | O | a bond | Q3d | OH |
| 3555 | CMe | S | Q1m | a bond | Me | a bond | NH | O | a bond | Q3e | OH |
| 3556 | CMe | S | Q1m | a bond | Me | a bond | NH | O | a bond | Q3f | OH |
| 3557 | CMe | S | Q1m | a bond | Me | a bond | NH | O | NH | Q3a | OH |
| 3558 | CMe | S | Q1m | a bond | Me | a bond | NH | O | NH | Q3d | OH |
| 3559 | CMe | S | Q1m | a bond | Me | a bond | NH | O | NH | Q3e | OH |
| 3560 | CMe | S | Q1m | a bond | Me | a bond | NH | O | NH | Q3f | OH |
| 3561 | CMe | S | Q1m | a bond | Me | a bond | NH | S | a bond | Q3a | OH |
| 3562 | CMe | S | Q1m | a bond | Me | a bond | NH | S | a bond | Q3d | OH |
| 3563 | CMe | S | Q1m | a bond | Me | a bond | NH | S | a bond | Q3e | OH |
| 3564 | CMe | S | Q1m | a bond | Me | a bond | NH | S | a bond | Q3f | OH |
| 3565 | CMe | S | Q1m | a bond | Me | a bond | NH | S | NH | Q3a | OH |
| 3566 | CMe | S | Q1m | a bond | Me | a bond | NH | S | NH | Q3d | OH |
| 3567 | CMe | S | Q1m | a bond | Me | a bond | NH | S | NH | Q3e | OH |
| 3568 | CMe | S | Q1m | a bond | Me | a bond | NH | S | NH | Q3f | OH |
| 3569 | CMe | S | Q1n | a bond | Me | a bond | NH | O | a bond | Q3a | OH |
| 3570 | CMe | S | Q1n | a bond | Me | a bond | NH | O | a bond | Q3d | OH |
| 3571 | CMe | S | Q1n | a bond | Me | a bond | NH | O | a bond | Q3e | OH |
| 3572 | CMe | S | Q1n | a bond | Me | a bond | NH | O | a bond | Q3f | OH |
| 3573 | CMe | S | Q1n | a bond | Me | a bond | NH | O | NH | Q3a | OH |
| 3574 | CMe | S | Q1n | a bond | Me | a bond | NH | O | NH | Q3d | OH |
| 3575 | CMe | S | Q1n | a bond | Me | a bond | NH | O | NH | Q3e | OH |
| 3576 | CMe | S | Q1n | a bond | Me | a bond | NH | O | NH | Q3f | OH |
| 3577 | CMe | S | Q1n | a bond | Me | a bond | NH | S | a bond | Q3a | OH |
| 3578 | CMe | S | Q1n | a bond | Me | a bond | NH | S | a bond | Q3d | OH |
| 3579 | CMe | S | Q1n | a bond | Me | a bond | NH | S | a bond | Q3e | OH |
| 3580 | CMe | S | Q1n | a bond | Me | a bond | NH | S | a bond | Q3f | OH |
| 3581 | CMe | S | Q1n | a bond | Me | a bond | NH | S | NH | Q3a | OH |
| 3582 | CMe | S | Q1n | a bond | Me | a bond | NH | S | NH | Q3d | OH |
| 3583 | CMe | S | Q1n | a bond | Me | a bond | NH | S | NH | Q3e | OH |
| 3584 | CMe | S | Q1n | a bond | Me | a bond | NH | S | NH | Q3f | OH |
| 3585 | CMe | O | Q1k | a bond | Me | a bond | NH | O | a bond | Q3a | OH |
| 3586 | CMe | O | Q1k | a bond | Me | a bond | NH | O | a bond | Q3d | OH |
| 3587 | CMe | O | Q1k | a bond | Me | a bond | NH | O | a bond | Q3e | OH |
| 3588 | CMe | O | Q1k | a bond | Me | a bond | NH | O | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3589 | CMe | O | Q1k | a bond | Me | a bond | NH | O | NH | Q3a | OH |
| 3590 | CMe | O | Q1k | a bond | Me | a bond | NH | O | NH | Q3d | OH |
| 3591 | CMe | O | Q1k | a bond | Me | a bond | NH | O | NH | Q3e | OH |
| 3592 | CMe | O | Q1k | a bond | Me | a bond | NH | O | NH | Q3f | OH |
| 3593 | CMe | O | Q1k | a bond | Me | a bond | NH | S | a bond | Q3a | OH |
| 3594 | CMe | O | Q1k | a bond | Me | a bond | NH | S | a bond | Q3d | OH |
| 3595 | CMe | O | Q1k | a bond | Me | a bond | NH | S | a bond | Q3e | OH |
| 3596 | CMe | O | Q1k | a bond | Me | a bond | NH | S | a bond | Q3f | OH |
| 3597 | CMe | O | Q1k | a bond | Me | a bond | NH | S | NH | Q3a | OH |
| 3598 | CMe | O | Q1k | a bond | Me | a bond | NH | S | NH | Q3d | OH |
| 3599 | CMe | O | Q1k | a bond | Me | a bond | NH | S | NH | Q3e | OH |
| 3600 | CMe | O | Q1k | a bond | Me | a bond | NH | S | NH | Q3f | OH |
| 3601 | CMe | O | Q1l | a bond | Me | a bond | NH | O | a bond | Q3a | OH |
| 3602 | CMe | O | Q1l | a bond | Me | a bond | NH | O | a bond | Q3d | OH |
| 3603 | CMe | O | Q1l | a bond | Me | a bond | NH | O | a bond | Q3e | OH |
| 3604 | CMe | O | Q1l | a bond | Me | a bond | NH | O | a bond | Q3f | OH |
| 3605 | CMe | O | Q1l | a bond | Me | a bond | NH | O | NH | Q3a | OH |
| 3606 | CMe | O | Q1l | a bond | Me | a bond | NH | O | NH | Q3d | OH |
| 3607 | CMe | O | Q1l | a bond | Me | a bond | NH | O | NH | Q3e | OH |
| 3608 | CMe | O | Q1l | a bond | Me | a bond | NH | O | NH | Q3f | OH |
| 3609 | CMe | O | Q1l | a bond | Me | a bond | NH | S | a bond | Q3a | OH |
| 3610 | CMe | O | Q1l | a bond | Me | a bond | NH | S | a bond | Q3d | OH |
| 3611 | CMe | O | Q1l | a bond | Me | a bond | NH | S | a bond | Q3e | OH |
| 3612 | CMe | O | Q1l | a bond | Me | a bond | NH | S | a bond | Q3f | OH |
| 3613 | CMe | O | Q1l | a bond | Me | a bond | NH | S | NH | Q3a | OH |
| 3614 | CMe | O | Q1l | a bond | Me | a bond | NH | S | NH | Q3d | OH |
| 3615 | CMe | O | Q1l | a bond | Me | a bond | NH | S | NH | Q3e | OH |
| 3616 | CMe | O | Q1l | a bond | Me | a bond | NH | S | NH | Q3f | OH |
| 3617 | CMe | O | Q1m | a bond | Me | a bond | NH | O | a bond | Q3a | OH |
| 3618 | CMe | O | Q1m | a bond | Me | a bond | NH | O | a bond | Q3d | OH |
| 3619 | CMe | O | Q1m | a bond | Me | a bond | NH | O | a bond | Q3e | OH |
| 3620 | CMe | O | Q1m | a bond | Me | a bond | NH | O | a bond | Q3f | OH |
| 3621 | CMe | O | Q1m | a bond | Me | a bond | NH | O | NH | Q3a | OH |
| 3622 | CMe | O | Q1m | a bond | Me | a bond | NH | O | NH | Q3d | OH |
| 3623 | CMe | O | Q1m | a bond | Me | a bond | NH | O | NH | Q3e | OH |
| 3624 | CMe | O | Q1m | a bond | Me | a bond | NH | O | NH | Q3f | OH |
| 3625 | CMe | O | Q1m | a bond | Me | a bond | NH | S | a bond | Q3a | OH |
| 3626 | CMe | O | Q1m | a bond | Me | a bond | NH | S | a bond | Q3d | OH |
| 3627 | CMe | O | Q1m | a bond | Me | a bond | NH | S | a bond | Q3e | OH |
| 3628 | CMe | O | Q1m | a bond | Me | a bond | NH | S | a bond | Q3f | OH |
| 3629 | CMe | O | Q1m | a bond | Me | a bond | NH | S | NH | Q3a | OH |
| 3630 | CMe | O | Q1m | a bond | Me | a bond | NH | S | NH | Q3d | OH |
| 3631 | CMe | O | Q1m | a bond | Me | a bond | NH | S | NH | Q3e | OH |
| 3632 | CMe | O | Q1m | a bond | Me | a bond | NH | S | NH | Q3f | OH |
| 3633 | CMe | O | Q1n | a bond | Me | a bond | NH | O | a bond | Q3a | OH |
| 3634 | CMe | O | Q1n | a bond | Me | a bond | NH | O | a bond | Q3d | OH |
| 3635 | CMe | O | Q1n | a bond | Me | a bond | NH | O | a bond | Q3e | OH |
| 3636 | CMe | O | Q1n | a bond | Me | a bond | NH | O | a bond | Q3f | OH |
| 3637 | CMe | O | Q1n | a bond | Me | a bond | NH | O | NH | Q3a | OH |
| 3638 | CMe | O | Q1n | a bond | Me | a bond | NH | O | NH | Q3d | OH |
| 3639 | CMe | O | Q1n | a bond | Me | a bond | NH | O | NH | Q3e | OH |
| 3640 | CMe | O | Q1n | a bond | Me | a bond | NH | O | NH | Q3f | OH |
| 3641 | CMe | O | Q1n | a bond | Me | a bond | NH | S | a bond | Q3a | OH |
| 3642 | CMe | O | Q1n | a bond | Me | a bond | NH | S | a bond | Q3d | OH |
| 3643 | CMe | O | Q1n | a bond | Me | a bond | NH | S | a bond | Q3e | OH |
| 3644 | CMe | O | Q1n | a bond | Me | a bond | NH | S | a bond | Q3f | OH |
| 3645 | CMe | O | Q1n | a bond | Me | a bond | NH | S | NH | Q3a | OH |
| 3646 | CMe | O | Q1n | a bond | Me | a bond | NH | S | NH | Q3d | OH |
| 3647 | CMe | O | Q1n | a bond | Me | a bond | NH | S | NH | Q3e | OH |
| 3648 | CMe | O | Q1n | a bond | Me | a bond | NH | S | NH | Q3f | OH |
| 3649 | N | NMe | Q1k' | a bond | Me | a bond | NH | O | a bond | Q3a | OH |
| 3650 | N | NMe | Q1k' | a bond | Me | a bond | NH | O | a bond | Q3d | OH |
| 3651 | N | NMe | Q1k' | a bond | Me | a bond | NH | O | a bond | Q3e | OH |
| 3652 | N | NMe | Q1k' | a bond | Me | a bond | NH | O | a bond | Q3f | OH |
| 3653 | N | NMe | Q1k' | a bond | Me | a bond | NH | O | NH | Q3a | OH |
| 3654 | N | NMe | Q1k' | a bond | Me | a bond | NH | O | NH | Q3d | OH |
| 3655 | N | NMe | Q1k' | a bond | Me | a bond | NH | O | NH | Q3e | OH |
| 3656 | N | NMe | Q1k' | a bond | Me | a bond | NH | O | NH | Q3f | OH |
| 3657 | N | NMe | Q1k' | a bond | Me | a bond | NH | S | a bond | Q3a | OH |
| 3658 | N | NMe | Q1k' | a bond | Me | a bond | NH | S | a bond | Q3d | OH |
| 3659 | N | NMe | Q1k' | a bond | Me | a bond | NH | S | a bond | Q3e | OH |
| 3660 | N | NMe | Q1k' | a bond | Me | a bond | NH | S | a bond | Q3f | OH |
| 3661 | N | NMe | Q1k' | a bond | Me | a bond | NH | S | NH | Q3a | OH |
| 3662 | N | NMe | Q1k' | a bond | Me | a bond | NH | S | NH | Q3d | OH |
| 3663 | N | NMe | Q1k' | a bond | Me | a bond | NH | S | NH | Q3e | OH |
| 3664 | N | NMe | Q1k' | a bond | Me | a bond | NH | S | NH | Q3f | OH |
| 3665 | N | NMe | Q1l' | a bond | Me | a bond | NH | O | a bond | Q3a | OH |
| 3666 | N | NMe | Q1l' | a bond | Me | a bond | NH | O | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3667 | N | NMe | Q1l' | a bond | Me | a bond | NH | O | a bond | Q3e | OH |
| 3668 | N | NMe | Q1l' | a bond | Me | a bond | NH | O | a bond | Q3f | OH |
| 3669 | N | NMe | Q1l' | a bond | Me | a bond | NH | O | NH | Q3a | OH |
| 3670 | N | NMe | Q1l' | a bond | Me | a bond | NH | O | NH | Q3d | OH |
| 3671 | N | NMe | Q1l' | a bond | Me | a bond | NH | O | NH | Q3e | OH |
| 3672 | N | NMe | Q1l' | a bond | Me | a bond | NH | O | NH | Q3f | OH |
| 3673 | N | NMe | Q1l' | a bond | Me | a bond | NH | S | a bond | Q3a | OH |
| 3674 | N | NMe | Q1l' | a bond | Me | a bond | NH | S | a bond | Q3d | OH |
| 3675 | N | NMe | Q1l' | a bond | Me | a bond | NH | S | a bond | Q3e | OH |
| 3676 | N | NMe | Q1l' | a bond | Me | a bond | NH | S | a bond | Q3f | OH |
| 3677 | N | NMe | Q1l' | a bond | Me | a bond | NH | S | NH | Q3a | OH |
| 3678 | N | NMe | Q1l' | a bond | Me | a bond | NH | S | NH | Q3d | OH |
| 3679 | N | NMe | Q1l' | a bond | Me | a bond | NH | S | NH | Q3e | OH |
| 3680 | N | NMe | Q1l' | a bond | Me | a bond | NH | S | NH | Q3f | OH |
| 3681 | N | NMe | Q1m' | a bond | Me | a bond | NH | O | a bond | Q3a | OH |
| 3682 | N | NMe | Q1m' | a bond | Me | a bond | NH | O | a bond | Q3d | OH |
| 3683 | N | NMe | Q1m' | a bond | Me | a bond | NH | O | a bond | Q3e | OH |
| 3684 | N | NMe | Q1m' | a bond | Me | a bond | NH | O | a bond | Q3f | OH |
| 3685 | N | NMe | Q1m' | a bond | Me | a bond | NH | O | NH | Q3a | OH |
| 3686 | N | NMe | Q1m' | a bond | Me | a bond | NH | O | NH | Q3d | OH |
| 3687 | N | NMe | Q1m' | a bond | Me | a bond | NH | O | NH | Q3e | OH |
| 3688 | N | NMe | Q1m' | a bond | Me | a bond | NH | O | NH | Q3f | OH |
| 3689 | N | NMe | Q1m' | a bond | Me | a bond | NH | S | a bond | Q3a | OH |
| 3690 | N | NMe | Q1m' | a bond | Me | a bond | NH | S | a bond | Q3d | OH |
| 3691 | N | NMe | Q1m' | a bond | Me | a bond | NH | S | a bond | Q3e | OH |
| 3692 | N | NMe | Q1m' | a bond | Me | a bond | NH | S | a bond | Q3f | OH |
| 3693 | N | NMe | Q1m' | a bond | Me | a bond | NH | S | NH | Q3a | OH |
| 3694 | N | NMe | Q1m' | a bond | Me | a bond | NH | S | NH | Q3d | OH |
| 3695 | N | NMe | Q1m' | a bond | Me | a bond | NH | S | NH | Q3e | OH |
| 3696 | N | NMe | Q1m' | a bond | Me | a bond | NH | S | NH | Q3f | OH |
| 3697 | N | NMe | Q1n' | a bond | Me | a bond | NH | O | a bond | Q3a | OH |
| 3698 | N | NMe | Q1n' | a bond | Me | a bond | NH | O | a bond | Q3d | OH |
| 3699 | N | NMe | Q1n' | a bond | Me | a bond | NH | O | a bond | Q3e | OH |
| 3700 | N | NMe | Q1n' | a bond | Me | a bond | NH | O | a bond | Q3f | OH |
| 3701 | N | NMe | Q1n' | a bond | Me | a bond | NH | O | NH | Q3a | OH |
| 3702 | N | NMe | Q1n' | a bond | Me | a bond | NH | O | NH | Q3d | OH |
| 3703 | N | NMe | Q1n' | a bond | Me | a bond | NH | O | NH | Q3e | OH |
| 3704 | N | NMe | Q1n' | a bond | Me | a bond | NH | O | NH | Q3f | OH |
| 3705 | N | NMe | Q1n' | a bond | Me | a bond | NH | S | a bond | Q3a | OH |
| 3706 | N | NMe | Q1n' | a bond | Me | a bond | NH | S | a bond | Q3d | OH |
| 3707 | N | NMe | Q1n' | a bond | Me | a bond | NH | S | a bond | Q3e | OH |
| 3708 | N | NMe | Q1n' | a bond | Me | a bond | NH | S | a bond | Q3f | OH |
| 3709 | N | NMe | Q1n' | a bond | Me | a bond | NH | S | NH | Q3a | OH |
| 3710 | N | NMe | Q1n' | a bond | Me | a bond | NH | S | NH | Q3d | OH |
| 3711 | N | NMe | Q1n' | a bond | Me | a bond | NH | S | NH | Q3e | OH |
| 3712 | N | NMe | Q1n' | a bond | Me | a bond | NH | S | NH | Q3f | OH |
| 3713 | N | NEt | Q1k' | a bond | Me | a bond | NH | O | a bond | Q3a | OH |
| 3714 | N | NEt | Q1k' | a bond | Me | a bond | NH | O | a bond | Q3d | OH |
| 3715 | N | NEt | Q1k' | a bond | Me | a bond | NH | O | a bond | Q3e | OH |
| 3716 | N | NEt | Q1k' | a bond | Me | a bond | NH | O | a bond | Q3f | OH |
| 3717 | N | NEt | Q1k' | a bond | Me | a bond | NH | O | NH | Q3a | OH |
| 3718 | N | NEt | Q1k' | a bond | Me | a bond | NH | O | NH | Q3d | OH |
| 3719 | N | NEt | Q1k' | a bond | Me | a bond | NH | O | NH | Q3e | OH |
| 3720 | N | NEt | Q1k' | a bond | Me | a bond | NH | O | NH | Q3f | OH |
| 3721 | N | NEt | Q1k' | a bond | Me | a bond | NH | S | a bond | Q3a | OH |
| 3722 | N | NEt | Q1k' | a bond | Me | a bond | NH | S | a bond | Q3d | OH |
| 3723 | N | NEt | Q1k' | a bond | Me | a bond | NH | S | a bond | Q3e | OH |
| 3724 | N | NEt | Q1k' | a bond | Me | a bond | NH | S | a bond | Q3f | OH |
| 3725 | N | NEt | Q1k' | a bond | Me | a bond | NH | S | NH | Q3a | OH |
| 3726 | N | NEt | Q1k' | a bond | Me | a bond | NH | S | NH | Q3d | OH |
| 3727 | N | NEt | Q1k' | a bond | Me | a bond | NH | S | NH | Q3e | OH |
| 3728 | N | NEt | Q1k' | a bond | Me | a bond | NH | S | NH | Q3f | OH |
| 3729 | N | NEt | Q1l' | a bond | Me | a bond | NH | O | a bond | Q3a | OH |
| 3730 | N | NEt | Q1l' | a bond | Me | a bond | NH | O | a bond | Q3d | OH |
| 3731 | N | NEt | Q1l' | a bond | Me | a bond | NH | O | a bond | Q3e | OH |
| 3732 | N | NEt | Q1l' | a bond | Me | a bond | NH | O | a bond | Q3f | OH |
| 3733 | N | NEt | Q1l' | a bond | Me | a bond | NH | O | NH | Q3a | OH |
| 3734 | N | NEt | Q1l' | a bond | Me | a bond | NH | O | NH | Q3d | OH |
| 3735 | N | NEt | Q1l' | a bond | Me | a bond | NH | O | NH | Q3e | OH |
| 3736 | N | NEt | Q1l' | a bond | Me | a bond | NH | O | NH | Q3f | OH |
| 3737 | N | NEt | Q1l' | a bond | Me | a bond | NH | S | a bond | Q3a | OH |
| 3738 | N | NEt | Q1l' | a bond | Me | a bond | NH | S | a bond | Q3d | OH |
| 3739 | N | NEt | Q1l' | a bond | Me | a bond | NH | S | a bond | Q3e | OH |
| 3740 | N | NEt | Q1l' | a bond | Me | a bond | NH | S | a bond | Q3f | OH |
| 3741 | N | NEt | Q1l' | a bond | Me | a bond | NH | S | NH | Q3a | OH |
| 3742 | N | NEt | Q1l' | a bond | Me | a bond | NH | S | NH | Q3d | OH |
| 3743 | N | NEt | Q1l' | a bond | Me | a bond | NH | S | NH | Q3e | OH |
| 3744 | N | NEt | Q1l' | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3745 | N | NEt | Q1m' | a bond | Me | a bond | NH | O | a bond | Q3a | OH |
| 3746 | N | NEt | Q1m' | a bond | Me | a bond | NH | O | a bond | Q3d | OH |
| 3747 | N | NEt | Q1m' | a bond | Me | a bond | NH | O | a bond | Q3e | OH |
| 3748 | N | NEt | Q1m' | a bond | Me | a bond | NH | O | a bond | Q3f | OH |
| 3749 | N | NEt | Q1m' | a bond | Me | a bond | NH | O | NH | Q3a | OH |
| 3750 | N | NEt | Q1m' | a bond | Me | a bond | NH | O | NH | Q3d | OH |
| 3751 | N | NEt | Q1m' | a bond | Me | a bond | NH | O | NH | Q3e | OH |
| 3752 | N | NEt | Q1m' | a bond | Me | a bond | NH | O | NH | Q3f | OH |
| 3753 | N | NEt | Q1m' | a bond | Me | a bond | NH | S | a bond | Q3a | OH |
| 3754 | N | NEt | Q1m' | a bond | Me | a bond | NH | S | a bond | Q3d | OH |
| 3755 | N | NEt | Q1m' | a bond | Me | a bond | NH | S | a bond | Q3e | OH |
| 3756 | N | NEt | Q1m' | a bond | Me | a bond | NH | S | a bond | Q3f | OH |
| 3757 | N | NEt | Q1m' | a bond | Me | a bond | NH | S | NH | Q3a | OH |
| 3758 | N | NEt | Q1m' | a bond | Me | a bond | NH | S | NH | Q3d | OH |
| 3759 | N | NEt | Q1m' | a bond | Me | a bond | NH | S | NH | Q3e | OH |
| 3760 | N | NEt | Q1m' | a bond | Me | a bond | NH | S | NH | Q3f | OH |
| 3761 | N | NEt | Q1n' | a bond | Me | a bond | NH | O | a bond | Q3a | OH |
| 3762 | N | NEt | Q1n' | a bond | Me | a bond | NH | O | a bond | Q3d | OH |
| 3763 | N | NEt | Q1n' | a bond | Me | a bond | NH | O | a bond | Q3e | OH |
| 3764 | N | NEt | Q1n' | a bond | Me | a bond | NH | O | a bond | Q3f | OH |
| 3765 | N | NEt | Q1n' | a bond | Me | a bond | NH | O | NH | Q3a | OH |
| 3766 | N | NEt | Q1n' | a bond | Me | a bond | NH | O | NH | Q3d | OH |
| 3767 | N | NEt | Q1n' | a bond | Me | a bond | NH | O | NH | Q3e | OH |
| 3768 | N | NEt | Q1n' | a bond | Me | a bond | NH | O | NH | Q3f | OH |
| 3769 | N | NEt | Q1n' | a bond | Me | a bond | NH | S | a bond | Q3a | OH |
| 3770 | N | NEt | Q1n' | a bond | Me | a bond | NH | S | a bond | Q3d | OH |
| 3771 | N | NEt | Q1n' | a bond | Me | a bond | NH | S | a bond | Q3e | OH |
| 3772 | N | NEt | Q1n' | a bond | Me | a bond | NH | S | a bond | Q3f | OH |
| 3773 | N | NEt | Q1n' | a bond | Me | a bond | NH | S | NH | Q3a | OH |
| 3774 | N | NEt | Q1n' | a bond | Me | a bond | NH | S | NH | Q3d | OH |
| 3775 | N | NEt | Q1n' | a bond | Me | a bond | NH | S | NH | Q3e | OH |
| 3776 | N | NEt | Q1n' | a bond | Me | a bond | NH | S | NH | Q3f | OH |
| 3777 | N | S | Q1k' | a bond | Me | a bond | NH | O | a bond | Q3a | OH |
| 3778 | N | S | Q1k' | a bond | Me | a bond | NH | O | a bond | Q3d | OH |
| 3779 | N | S | Q1k' | a bond | Me | a bond | NH | O | a bond | Q3e | OH |
| 3780 | N | S | Q1k' | a bond | Me | a bond | NH | O | a bond | Q3f | OH |
| 3781 | N | S | Q1k' | a bond | Me | a bond | NH | O | NH | Q3a | OH |
| 3782 | N | S | Q1k' | a bond | Me | a bond | NH | O | NH | Q3d | OH |
| 3783 | N | S | Q1k' | a bond | Me | a bond | NH | O | NH | Q3e | OH |
| 3784 | N | S | Q1k' | a bond | Me | a bond | NH | O | NH | Q3f | OH |
| 3785 | N | S | Q1k' | a bond | Me | a bond | NH | S | a bond | Q3a | OH |
| 3786 | N | S | Q1k' | a bond | Me | a bond | NH | S | a bond | Q3d | OH |
| 3787 | N | S | Q1k' | a bond | Me | a bond | NH | S | a bond | Q3e | OH |
| 3788 | N | S | Q1k' | a bond | Me | a bond | NH | S | a bond | Q3f | OH |
| 3789 | N | S | Q1k' | a bond | Me | a bond | NH | S | NH | Q3a | OH |
| 3790 | N | S | Q1k' | a bond | Me | a bond | NH | S | NH | Q3d | OH |
| 3791 | N | S | Q1k' | a bond | Me | a bond | NH | S | NH | Q3e | OH |
| 3792 | N | S | Q1k' | a bond | Me | a bond | NH | S | NH | Q3f | OH |
| 3793 | N | S | Q1l' | a bond | Me | a bond | NH | O | a bond | Q3a | OH |
| 3794 | N | S | Q1l' | a bond | Me | a bond | NH | O | a bond | Q3d | OH |
| 3795 | N | S | Q1l' | a bond | Me | a bond | NH | O | a bond | Q3e | OH |
| 3796 | N | S | Q1l' | a bond | Me | a bond | NH | O | a bond | Q3f | OH |
| 3797 | N | S | Q1l' | a bond | Me | a bond | NH | O | NH | Q3a | OH |
| 3798 | N | S | Q1l' | a bond | Me | a bond | NH | O | NH | Q3d | OH |
| 3799 | N | S | Q1l' | a bond | Me | a bond | NH | O | NH | Q3e | OH |
| 3800 | N | S | Q1l' | a bond | Me | a bond | NH | O | NH | Q3f | OH |
| 3801 | N | S | Q1l' | a bond | Me | a bond | NH | S | a bond | Q3a | OH |
| 3802 | N | S | Q1l' | a bond | Me | a bond | NH | S | a bond | Q3d | OH |
| 3803 | N | S | Q1l' | a bond | Me | a bond | NH | S | a bond | Q3e | OH |
| 3804 | N | S | Q1l' | a bond | Me | a bond | NH | S | a bond | Q3f | OH |
| 3805 | N | S | Q1l' | a bond | Me | a bond | NH | S | NH | Q3a | OH |
| 3806 | N | S | Q1l' | a bond | Me | a bond | NH | S | NH | Q3d | OH |
| 3807 | N | S | Q1l' | a bond | Me | a bond | NH | S | NH | Q3e | OH |
| 3808 | N | S | Q1l' | a bond | Me | a bond | NH | S | NH | Q3f | OH |
| 3809 | N | S | Q1m' | a bond | Me | a bond | NH | O | a bond | Q3a | OH |
| 3810 | N | S | Q1m' | a bond | Me | a bond | NH | O | a bond | Q3d | OH |
| 3811 | N | S | Q1m' | a bond | Me | a bond | NH | O | a bond | Q3e | OH |
| 3812 | N | S | Q1m' | a bond | Me | a bond | NH | O | a bond | Q3f | OH |
| 3813 | N | S | Q1m' | a bond | Me | a bond | NH | O | NH | Q3a | OH |
| 3814 | N | S | Q1m' | a bond | Me | a bond | NH | O | NH | Q3d | OH |
| 3815 | N | S | Q1m' | a bond | Me | a bond | NH | O | NH | Q3e | OH |
| 3816 | N | S | Q1m' | a bond | Me | a bond | NH | O | NH | Q3f | OH |
| 3817 | N | S | Q1m' | a bond | Me | a bond | NH | S | a bond | Q3a | OH |
| 3818 | N | S | Q1m' | a bond | Me | a bond | NH | S | a bond | Q3d | OH |
| 3819 | N | S | Q1m' | a bond | Me | a bond | NH | S | a bond | Q3e | OH |
| 3820 | N | S | Q1m' | a bond | Me | a bond | NH | S | a bond | Q3f | OH |
| 3821 | N | S | Q1m' | a bond | Me | a bond | NH | S | NH | Q3a | OH |
| 3822 | N | S | Q1m' | a bond | Me | a bond | NH | S | NH | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3823 | N | S | Q1m' | a bond | Me | a bond | NH | S | NH | Q3e | OH |
| 3824 | N | S | Q1m' | a bond | Me | a bond | NH | S | NH | Q3f | OH |
| 3825 | N | S | Q1n' | a bond | Me | a bond | NH | O | a bond | Q3a | OH |
| 3826 | N | S | Q1n' | a bond | Me | a bond | NH | O | a bond | Q3d | OH |
| 3827 | N | S | Q1n' | a bond | Me | a bond | NH | O | a bond | Q3e | OH |
| 3828 | N | S | Q1n' | a bond | Me | a bond | NH | O | a bond | Q3f | OH |
| 3829 | N | S | Q1n' | a bond | Me | a bond | NH | O | NH | Q3a | OH |
| 3830 | N | S | Q1n' | a bond | Me | a bond | NH | O | NH | Q3d | OH |
| 3831 | N | S | Q1n' | a bond | Me | a bond | NH | O | NH | Q3e | OH |
| 3832 | N | S | Q1n' | a bond | Me | a bond | NH | O | NH | Q3f | OH |
| 3833 | N | S | Q1n' | a bond | Me | a bond | NH | S | a bond | Q3a | OH |
| 3834 | N | S | Q1n' | a bond | Me | a bond | NH | S | a bond | Q3d | OH |
| 3835 | N | S | Q1n' | a bond | Me | a bond | NH | S | a bond | Q3e | OH |
| 3836 | N | S | Q1n' | a bond | Me | a bond | NH | S | a bond | Q3f | OH |
| 3837 | N | S | Q1n' | a bond | Me | a bond | NH | S | NH | Q3a | OH |
| 3838 | N | S | Q1n' | a bond | Me | a bond | NH | S | NH | Q3d | OH |
| 3839 | N | S | Q1n' | a bond | Me | a bond | NH | S | NH | Q3e | OH |
| 3840 | N | S | Q1n' | a bond | Me | a bond | NH | S | NH | Q3f | OH |
| 3841 | N | O | Q1k' | a bond | Me | a bond | NH | O | a bond | Q3a | OH |
| 3842 | N | O | Q1k' | a bond | Me | a bond | NH | O | a bond | Q3d | OH |
| 3843 | N | O | Q1k' | a bond | Me | a bond | NH | O | a bond | Q3e | OH |
| 3844 | N | O | Q1k' | a bond | Me | a bond | NH | O | a bond | Q3f | OH |
| 3845 | N | O | Q1k' | a bond | Me | a bond | NH | O | NH | Q3a | OH |
| 3846 | N | O | Q1k' | a bond | Me | a bond | NH | O | NH | Q3d | OH |
| 3847 | N | O | Q1k' | a bond | Me | a bond | NH | O | NH | Q3e | OH |
| 3848 | N | O | Q1k' | a bond | Me | a bond | NH | O | NH | Q3f | OH |
| 3849 | N | O | Q1k' | a bond | Me | a bond | NH | S | a bond | Q3a | OH |
| 3850 | N | O | Q1k' | a bond | Me | a bond | NH | S | a bond | Q3d | OH |
| 3851 | N | O | Q1k' | a bond | Me | a bond | NH | S | a bond | Q3e | OH |
| 3852 | N | O | Q1k' | a bond | Me | a bond | NH | S | a bond | Q3f | OH |
| 3853 | N | O | Q1k' | a bond | Me | a bond | NH | S | NH | Q3a | OH |
| 3854 | N | O | Q1k' | a bond | Me | a bond | NH | S | NH | Q3d | OH |
| 3855 | N | O | Q1k' | a bond | Me | a bond | NH | S | NH | Q3e | OH |
| 3856 | N | O | Q1k' | a bond | Me | a bond | NH | S | NH | Q3f | OH |
| 3857 | N | O | Q1l' | a bond | Me | a bond | NH | O | a bond | Q3a | OH |
| 3858 | N | O | Q1l' | a bond | Me | a bond | NH | O | a bond | Q3d | OH |
| 3859 | N | O | Q1l' | a bond | Me | a bond | NH | O | a bond | Q3e | OH |
| 3860 | N | O | Q1l' | a bond | Me | a bond | NH | O | a bond | Q3f | OH |
| 3861 | N | O | Q1l' | a bond | Me | a bond | NH | O | NH | Q3a | OH |
| 3862 | N | O | Q1l' | a bond | Me | a bond | NH | O | NH | Q3d | OH |
| 3863 | N | O | Q1l' | a bond | Me | a bond | NH | O | NH | Q3e | OH |
| 3864 | N | O | Q1l' | a bond | Me | a bond | NH | O | NH | Q3f | OH |
| 3865 | N | O | Q1l' | a bond | Me | a bond | NH | S | a bond | Q3a | OH |
| 3866 | N | O | Q1l' | a bond | Me | a bond | NH | S | a bond | Q3d | OH |
| 3867 | N | O | Q1l' | a bond | Me | a bond | NH | S | a bond | Q3e | OH |
| 3868 | N | O | Q1l' | a bond | Me | a bond | NH | S | a bond | Q3f | OH |
| 3869 | N | O | Q1l' | a bond | Me | a bond | NH | S | NH | Q3a | OH |
| 3870 | N | O | Q1l' | a bond | Me | a bond | NH | S | NH | Q3d | OH |
| 3871 | N | O | Q1l' | a bond | Me | a bond | NH | S | NH | Q3e | OH |
| 3872 | N | O | Q1l' | a bond | Me | a bond | NH | S | NH | Q3f | OH |
| 3873 | N | O | Q1m' | a bond | Me | a bond | NH | O | a bond | Q3a | OH |
| 3874 | N | O | Q1m' | a bond | Me | a bond | NH | O | a bond | Q3d | OH |
| 3875 | N | O | Q1m' | a bond | Me | a bond | NH | O | a bond | Q3e | OH |
| 3876 | N | O | Q1m' | a bond | Me | a bond | NH | O | a bond | Q3f | OH |
| 3877 | N | O | Q1m' | a bond | Me | a bond | NH | O | NH | Q3a | OH |
| 3878 | N | O | Q1m' | a bond | Me | a bond | NH | O | NH | Q3d | OH |
| 3879 | N | O | Q1m' | a bond | Me | a bond | NH | O | NH | Q3e | OH |
| 3880 | N | O | Q1m' | a bond | Me | a bond | NH | O | NH | Q3f | OH |
| 3881 | N | O | Q1m' | a bond | Me | a bond | NH | S | a bond | Q3a | OH |
| 3882 | N | O | Q1m' | a bond | Me | a bond | NH | S | a bond | Q3d | OH |
| 3883 | N | O | Q1m' | a bond | Me | a bond | NH | S | a bond | Q3e | OH |
| 3884 | N | O | Q1m' | a bond | Me | a bond | NH | S | a bond | Q3f | OH |
| 3885 | N | O | Q1m' | a bond | Me | a bond | NH | S | NH | Q3a | OH |
| 3886 | N | O | Q1m' | a bond | Me | a bond | NH | S | NH | Q3d | OH |
| 3887 | N | O | Q1m' | a bond | Me | a bond | NH | S | NH | Q3e | OH |
| 3888 | N | O | Q1m' | a bond | Me | a bond | NH | S | NH | Q3f | OH |
| 3889 | N | O | Q1n' | a bond | Me | a bond | NH | O | a bond | Q3a | OH |
| 3890 | N | O | Q1n' | a bond | Me | a bond | NH | O | a bond | Q3d | OH |
| 3891 | N | O | Q1n' | a bond | Me | a bond | NH | O | a bond | Q3e | OH |
| 3892 | N | O | Q1n' | a bond | Me | a bond | NH | O | a bond | Q3f | OH |
| 3893 | N | O | Q1n' | a bond | Me | a bond | NH | O | NH | Q3a | OH |
| 3894 | N | O | Q1n' | a bond | Me | a bond | NH | O | NH | Q3d | OH |
| 3895 | N | O | Q1n' | a bond | Me | a bond | NH | O | NH | Q3e | OH |
| 3896 | N | O | Q1n' | a bond | Me | a bond | NH | O | NH | Q3f | OH |
| 3897 | N | O | Q1n' | a bond | Me | a bond | NH | S | a bond | Q3a | OH |
| 3898 | N | O | Q1n' | a bond | Me | a bond | NH | S | a bond | Q3d | OH |
| 3899 | N | O | Q1n' | a bond | Me | a bond | NH | S | a bond | Q3e | OH |
| 3900 | N | O | Q1n' | a bond | Me | a bond | NH | S | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 3901 | N | O | Q1n' | a bond | Me | a bond | NH | S | NH | Q3a | OH |
| 3902 | N | O | Q1n' | a bond | Me | a bond | NH | S | NH | Q3d | OH |
| 3903 | N | O | Q1n' | a bond | Me | a bond | NH | S | NH | Q3e | OH |
| 3904 | N | O | Q1n' | a bond | Me | a bond | NH | S | NH | Q3f | OH |
| 3905 | CH | NMe | Q1k' | a bond | Me | a bond | NH | O | a bond | Q3a | OH |
| 3906 | CH | NMe | Q1k' | a bond | Me | a bond | NH | O | a bond | Q3d | OH |
| 3907 | CH | NMe | Q1k' | a bond | Me | a bond | NH | O | a bond | Q3e | OH |
| 3908 | CH | NMe | Q1k' | a bond | Me | a bond | NH | O | a bond | Q3f | OH |
| 3909 | CH | NMe | Q1k' | a bond | Me | a bond | NH | O | NH | Q3a | OH |
| 3910 | CH | NMe | Q1k' | a bond | Me | a bond | NH | O | NH | Q3d | OH |
| 3911 | CH | NMe | Q1k' | a bond | Me | a bond | NH | O | NH | Q3e | OH |
| 3912 | CH | NMe | Q1k' | a bond | Me | a bond | NH | O | NH | Q3f | OH |
| 3913 | CH | NMe | Q1k' | a bond | Me | a bond | NH | S | a bond | Q3a | OH |
| 3914 | CH | NMe | Q1k' | a bond | Me | a bond | NH | S | a bond | Q3d | OH |
| 3915 | CH | NMe | Q1k' | a bond | Me | a bond | NH | S | a bond | Q3e | OH |
| 3916 | CH | NMe | Q1k' | a bond | Me | a bond | NH | S | a bond | Q3f | OH |
| 3917 | CH | NMe | Q1k' | a bond | Me | a bond | NH | S | NH | Q3a | OH |
| 3918 | CH | NMe | Q1k' | a bond | Me | a bond | NH | S | NH | Q3d | OH |
| 3919 | CH | NMe | Q1k' | a bond | Me | a bond | NH | S | NH | Q3e | OH |
| 3920 | CH | NMe | Q1k' | a bond | Me | a bond | NH | S | NH | Q3f | OH |
| 3921 | CH | NMe | Q1l' | a bond | Me | a bond | NH | O | a bond | Q3a | OH |
| 3922 | CH | NMe | Q1l' | a bond | Me | a bond | NH | O | a bond | Q3d | OH |
| 3923 | CH | NMe | Q1l' | a bond | Me | a bond | NH | O | a bond | Q3e | OH |
| 3924 | CH | NMe | Q1l' | a bond | Me | a bond | NH | O | a bond | Q3f | OH |
| 3925 | CH | NMe | Q1l' | a bond | Me | a bond | NH | O | NH | Q3a | OH |
| 3926 | CH | NMe | Q1l' | a bond | Me | a bond | NH | O | NH | Q3d | OH |
| 3927 | CH | NMe | Q1l' | a bond | Me | a bond | NH | O | NH | Q3e | OH |
| 3928 | CH | NMe | Q1l' | a bond | Me | a bond | NH | O | NH | Q3f | OH |
| 3929 | CH | NMe | Q1l' | a bond | Me | a bond | NH | S | a bond | Q3a | OH |
| 3930 | CH | NMe | Q1l' | a bond | Me | a bond | NH | S | a bond | Q3d | OH |
| 3931 | CH | NMe | Q1l' | a bond | Me | a bond | NH | S | a bond | Q3e | OH |
| 3932 | CH | NMe | Q1l' | a bond | Me | a bond | NH | S | a bond | Q3f | OH |
| 3933 | CH | NMe | Q1l' | a bond | Me | a bond | NH | S | NH | Q3a | OH |
| 3934 | CH | NMe | Q1l' | a bond | Me | a bond | NH | S | NH | Q3d | OH |
| 3935 | CH | NMe | Q1l' | a bond | Me | a bond | NH | S | NH | Q3e | OH |
| 3936 | CH | NMe | Q1l' | a bond | Me | a bond | NH | S | NH | Q3f | OH |
| 3937 | CH | NMe | Q1m' | a bond | Me | a bond | NH | O | a bond | Q3a | OH |
| 3938 | CH | NMe | Q1m' | a bond | Me | a bond | NH | O | a bond | Q3d | OH |
| 3939 | CH | NMe | Q1m' | a bond | Me | a bond | NH | O | a bond | Q3e | OH |
| 3940 | CH | NMe | Q1m' | a bond | Me | a bond | NH | O | a bond | Q3f | OH |
| 3941 | CH | NMe | Q1m' | a bond | Me | a bond | NH | O | NH | Q3a | OH |
| 3942 | CH | NMe | Q1m' | a bond | Me | a bond | NH | O | NH | Q3d | OH |
| 3943 | CH | NMe | Q1m' | a bond | Me | a bond | NH | O | NH | Q3e | OH |
| 3944 | CH | NMe | Q1m' | a bond | Me | a bond | NH | O | NH | Q3f | OH |
| 3945 | CH | NMe | Q1m' | a bond | Me | a bond | NH | S | a bond | Q3a | OH |
| 3946 | CH | NMe | Q1m' | a bond | Me | a bond | NH | S | a bond | Q3d | OH |
| 3947 | CH | NMe | Q1m' | a bond | Me | a bond | NH | S | a bond | Q3e | OH |
| 3948 | CH | NMe | Q1m' | a bond | Me | a bond | NH | S | a bond | Q3f | OH |
| 3949 | CH | NMe | Q1m' | a bond | Me | a bond | NH | S | NH | Q3a | OH |
| 3950 | CH | NMe | Q1m' | a bond | Me | a bond | NH | S | NH | Q3d | OH |
| 3951 | CH | NMe | Q1m' | a bond | Me | a bond | NH | S | NH | Q3e | OH |
| 3952 | CH | NMe | Q1m' | a bond | Me | a bond | NH | S | NH | Q3f | OH |
| 3953 | CH | NMe | Q1n' | a bond | Me | a bond | NH | O | a bond | Q3a | OH |
| 3954 | CH | NMe | Q1n' | a bond | Me | a bond | NH | O | a bond | Q3d | OH |
| 3955 | CH | NMe | Q1n' | a bond | Me | a bond | NH | O | a bond | Q3e | OH |
| 3956 | CH | NMe | Q1n' | a bond | Me | a bond | NH | O | a bond | Q3f | OH |
| 3957 | CH | NMe | Q1n' | a bond | Me | a bond | NH | O | NH | Q3a | OH |
| 3958 | CH | NMe | Q1n' | a bond | Me | a bond | NH | O | NH | Q3d | OH |
| 3959 | CH | NMe | Q1n' | a bond | Me | a bond | NH | O | NH | Q3e | OH |
| 3960 | CH | NMe | Q1n' | a bond | Me | a bond | NH | O | NH | Q3f | OH |
| 3961 | CH | NMe | Q1n' | a bond | Me | a bond | NH | S | a bond | Q3a | OH |
| 3962 | CH | NMe | Q1n' | a bond | Me | a bond | NH | S | a bond | Q3d | OH |
| 3963 | CH | NMe | Q1n' | a bond | Me | a bond | NH | S | a bond | Q3e | OH |
| 3964 | CH | NMe | Q1n' | a bond | Me | a bond | NH | S | a bond | Q3f | OH |
| 3965 | CH | NMe | Q1n' | a bond | Me | a bond | NH | S | NH | Q3a | OH |
| 3966 | CH | NMe | Q1n' | a bond | Me | a bond | NH | S | NH | Q3d | OH |
| 3967 | CH | NMe | Q1n' | a bond | Me | a bond | NH | S | NH | Q3e | OH |
| 3968 | CH | NMe | Q1n' | a bond | Me | a bond | NH | S | NH | Q3f | OH |
| 3969 | CH | NEt | Q1k' | a bond | Me | a bond | NH | O | a bond | Q3a | OH |
| 3970 | CH | NEt | Q1k' | a bond | Me | a bond | NH | O | a bond | Q3d | OH |
| 3971 | CH | NEt | Q1k' | a bond | Me | a bond | NH | O | a bond | Q3e | OH |
| 3972 | CH | NEt | Q1k' | a bond | Me | a bond | NH | O | a bond | Q3f | OH |
| 3973 | CH | NEt | Q1k' | a bond | Me | a bond | NH | O | NH | Q3a | OH |
| 3974 | CH | NEt | Q1k' | a bond | Me | a bond | NH | O | NH | Q3d | OH |
| 3975 | CH | NEt | Q1k' | a bond | Me | a bond | NH | O | NH | Q3e | OH |
| 3976 | CH | NEt | Q1k' | a bond | Me | a bond | NH | O | NH | Q3f | OH |
| 3977 | CH | NEt | Q1k' | a bond | Me | a bond | NH | S | a bond | Q3a | OH |
| 3978 | CH | NEt | Q1k' | a bond | Me | a bond | NH | S | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 3979 | CH | NEt | Q1k' | a bond | Me | a bond | NH | S | a bond | Q3e | OH |
| 3980 | CH | NEt | Q1k' | a bond | Me | a bond | NH | S | a bond | Q3f | OH |
| 3981 | CH | NEt | Q1k' | a bond | Me | a bond | NH | S | NH | Q3a | OH |
| 3982 | CH | NEt | Q1k' | a bond | Me | a bond | NH | S | NH | Q3d | OH |
| 3983 | CH | NEt | Q1k' | a bond | Me | a bond | NH | S | NH | Q3e | OH |
| 3984 | CH | NEt | Q1k' | a bond | Me | a bond | NH | S | NH | Q3f | OH |
| 3985 | CH | NEt | Q1l' | a bond | Me | a bond | NH | O | a bond | Q3a | OH |
| 3986 | CH | NEt | Q1l' | a bond | Me | a bond | NH | O | a bond | Q3d | OH |
| 3987 | CH | NEt | Q1l' | a bond | Me | a bond | NH | O | a bond | Q3e | OH |
| 3988 | CH | NEt | Q1l' | a bond | Me | a bond | NH | O | a bond | Q3f | OH |
| 3989 | CH | NEt | Q1l' | a bond | Me | a bond | NH | O | NH | Q3a | OH |
| 3990 | CH | NEt | Q1l' | a bond | Me | a bond | NH | O | NH | Q3d | OH |
| 3991 | CH | NEt | Q1l' | a bond | Me | a bond | NH | O | NH | Q3e | OH |
| 3992 | CH | NEt | Q1l' | a bond | Me | a bond | NH | O | NH | Q3f | OH |
| 3993 | CH | NEt | Q1l' | a bond | Me | a bond | NH | S | a bond | Q3a | OH |
| 3994 | CH | NEt | Q1l' | a bond | Me | a bond | NH | S | a bond | Q3d | OH |
| 3995 | CH | NEt | Q1l' | a bond | Me | a bond | NH | S | a bond | Q3e | OH |
| 3996 | CH | NEt | Q1l' | a bond | Me | a bond | NH | S | a bond | Q3f | OH |
| 3997 | CH | NEt | Q1l' | a bond | Me | a bond | NH | S | NH | Q3a | OH |
| 3998 | CH | NEt | Q1l' | a bond | Me | a bond | NH | S | NH | Q3d | OH |
| 3999 | CH | NEt | Q1l' | a bond | Me | a bond | NH | S | NH | Q3e | OH |
| 4000 | CH | NEt | Q1l' | a bond | Me | a bond | NH | S | NH | Q3f | OH |
| 4001 | CH | NEt | Q1m' | a bond | Me | a bond | NH | O | a bond | Q3a | OH |
| 4002 | CH | NEt | Q1m' | a bond | Me | a bond | NH | O | a bond | Q3d | OH |
| 4003 | CH | NEt | Q1m' | a bond | Me | a bond | NH | O | a bond | Q3e | OH |
| 4004 | CH | NEt | Q1m' | a bond | Me | a bond | NH | O | a bond | Q3f | OH |
| 4005 | CH | NEt | Q1m' | a bond | Me | a bond | NH | O | NH | Q3a | OH |
| 4006 | CH | NEt | Q1m' | a bond | Me | a bond | NH | O | NH | Q3d | OH |
| 4007 | CH | NEt | Q1m' | a bond | Me | a bond | NH | O | NH | Q3e | OH |
| 4008 | CH | NEt | Q1m' | a bond | Me | a bond | NH | O | NH | Q3f | OH |
| 4009 | CH | NEt | Q1m' | a bond | Me | a bond | NH | S | a bond | Q3a | OH |
| 4010 | CH | NEt | Q1m' | a bond | Me | a bond | NH | S | a bond | Q3d | OH |
| 4011 | CH | NEt | Q1m' | a bond | Me | a bond | NH | S | a bond | Q3e | OH |
| 4012 | CH | NEt | Q1m' | a bond | Me | a bond | NH | S | a bond | Q3f | OH |
| 4013 | CH | NEt | Q1m' | a bond | Me | a bond | NH | S | NH | Q3a | OH |
| 4014 | CH | NEt | Q1m' | a bond | Me | a bond | NH | S | NH | Q3d | OH |
| 4015 | CH | NEt | Q1m' | a bond | Me | a bond | NH | S | NH | Q3e | OH |
| 4016 | CH | NEt | Q1m' | a bond | Me | a bond | NH | S | NH | Q3f | OH |
| 4017 | CH | NEt | Q1n' | a bond | Me | a bond | NH | O | a bond | Q3a | OH |
| 4018 | CH | NEt | Q1n' | a bond | Me | a bond | NH | O | a bond | Q3d | OH |
| 4019 | CH | NEt | Q1n' | a bond | Me | a bond | NH | O | a bond | Q3e | OH |
| 4020 | CH | NEt | Q1n' | a bond | Me | a bond | NH | O | a bond | Q3f | OH |
| 4021 | CH | NEt | Q1n' | a bond | Me | a bond | NH | O | NH | Q3a | OH |
| 4022 | CH | NEt | Q1n' | a bond | Me | a bond | NH | O | NH | Q3d | OH |
| 4023 | CH | NEt | Q1n' | a bond | Me | a bond | NH | O | NH | Q3e | OH |
| 4024 | CH | NEt | Q1n' | a bond | Me | a bond | NH | O | NH | Q3f | OH |
| 4025 | CH | NEt | Q1n' | a bond | Me | a bond | NH | S | a bond | Q3a | OH |
| 4026 | CH | NEt | Q1n' | a bond | Me | a bond | NH | S | a bond | Q3d | OH |
| 4027 | CH | NEt | Q1n' | a bond | Me | a bond | NH | S | a bond | Q3e | OH |
| 4028 | CH | NEt | Q1n' | a bond | Me | a bond | NH | S | a bond | Q3f | OH |
| 4029 | CH | NEt | Q1n' | a bond | Me | a bond | NH | S | NH | Q3a | OH |
| 4030 | CH | NEt | Q1n' | a bond | Me | a bond | NH | S | NH | Q3d | OH |
| 4031 | CH | NEt | Q1n' | a bond | Me | a bond | NH | S | NH | Q3e | OH |
| 4032 | CH | NEt | Q1n' | a bond | Me | a bond | NH | S | NH | Q3f | OH |
| 4033 | CH | S | Q1k' | a bond | Me | a bond | NH | O | a bond | Q3a | OH |
| 4034 | CH | S | Q1k' | a bond | Me | a bond | NH | O | a bond | Q3d | OH |
| 4035 | CH | S | Q1k' | a bond | Me | a bond | NH | O | a bond | Q3e | OH |
| 4036 | CH | S | Q1k' | a bond | Me | a bond | NH | O | a bond | Q3f | OH |
| 4037 | CH | S | Q1k' | a bond | Me | a bond | NH | O | NH | Q3a | OH |
| 4038 | CH | S | Q1k' | a bond | Me | a bond | NH | O | NH | Q3d | OH |
| 4039 | CH | S | Q1k' | a bond | Me | a bond | NH | O | NH | Q3e | OH |
| 4040 | CH | S | Q1k' | a bond | Me | a bond | NH | O | NH | Q3f | OH |
| 4041 | CH | S | Q1k' | a bond | Me | a bond | NH | S | a bond | Q3a | OH |
| 4042 | CH | S | Q1k' | a bond | Me | a bond | NH | S | a bond | Q3d | OH |
| 4043 | CH | S | Q1k' | a bond | Me | a bond | NH | S | a bond | Q3e | OH |
| 4044 | CH | S | Q1k' | a bond | Me | a bond | NH | S | a bond | Q3f | OH |
| 4045 | CH | S | Q1k' | a bond | Me | a bond | NH | S | NH | Q3a | OH |
| 4046 | CH | S | Q1k' | a bond | Me | a bond | NH | S | NH | Q3d | OH |
| 4047 | CH | S | Q1k' | a bond | Me | a bond | NH | S | NH | Q3e | OH |
| 4048 | CH | S | Q1k' | a bond | Me | a bond | NH | S | NH | Q3f | OH |
| 4049 | CH | S | Q1l' | a bond | Me | a bond | NH | O | a bond | Q3a | OH |
| 4050 | CH | S | Q1l' | a bond | Me | a bond | NH | O | a bond | Q3d | OH |
| 4051 | CH | S | Q1l' | a bond | Me | a bond | NH | O | a bond | Q3e | OH |
| 4052 | CH | S | Q1l' | a bond | Me | a bond | NH | O | a bond | Q3f | OH |
| 4053 | CH | S | Q1l' | a bond | Me | a bond | NH | O | NH | Q3a | OH |
| 4054 | CH | S | Q1l' | a bond | Me | a bond | NH | O | NH | Q3d | OH |
| 4055 | CH | S | Q1l' | a bond | Me | a bond | NH | O | NH | Q3e | OH |
| 4056 | CH | S | Q1l' | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4057 | CH | S | Q1l' | a bond | Me | a bond | NH | S | a bond | Q3a | OH |
| 4058 | CH | S | Q1l' | a bond | Me | a bond | NH | S | a bond | Q3d | OH |
| 4059 | CH | S | Q1l' | a bond | Me | a bond | NH | S | a bond | Q3e | OH |
| 4060 | CH | S | Q1l' | a bond | Me | a bond | NH | S | a bond | Q3f | OH |
| 4061 | CH | S | Q1l' | a bond | Me | a bond | NH | S | NH | Q3a | OH |
| 4062 | CH | S | Q1l' | a bond | Me | a bond | NH | S | NH | Q3d | OH |
| 4063 | CH | S | Q1l' | a bond | Me | a bond | NH | S | NH | Q3e | OH |
| 4064 | CH | S | Q1l' | a bond | Me | a bond | NH | S | NH | Q3f | OH |
| 4065 | CH | S | Q1m' | a bond | Me | a bond | NH | O | a bond | Q3a | OH |
| 4066 | CH | S | Q1m' | a bond | Me | a bond | NH | O | a bond | Q3d | OH |
| 4067 | CH | S | Q1m' | a bond | Me | a bond | NH | O | a bond | Q3e | OH |
| 4068 | CH | S | Q1m' | a bond | Me | a bond | NH | O | a bond | Q3f | OH |
| 4069 | CH | S | Q1m' | a bond | Me | a bond | NH | O | NH | Q3a | OH |
| 4070 | CH | S | Q1m' | a bond | Me | a bond | NH | O | NH | Q3d | OH |
| 4071 | CH | S | Q1m' | a bond | Me | a bond | NH | O | NH | Q3e | OH |
| 4072 | CH | S | Q1m' | a bond | Me | a bond | NH | O | NH | Q3f | OH |
| 4073 | CH | S | Q1m' | a bond | Me | a bond | NH | S | a bond | Q3a | OH |
| 4074 | CH | S | Q1m' | a bond | Me | a bond | NH | S | a bond | Q3d | OH |
| 4075 | CH | S | Q1m' | a bond | Me | a bond | NH | S | a bond | Q3e | OH |
| 4076 | CH | S | Q1m' | a bond | Me | a bond | NH | S | a bond | Q3f | OH |
| 4077 | CH | S | Q1m' | a bond | Me | a bond | NH | S | NH | Q3a | OH |
| 4078 | CH | S | Q1m' | a bond | Me | a bond | NH | S | NH | Q3d | OH |
| 4079 | CH | S | Q1m' | a bond | Me | a bond | NH | S | NH | Q3e | OH |
| 4080 | CH | S | Q1m' | a bond | Me | a bond | NH | S | NH | Q3f | OH |
| 4081 | CH | S | Q1n' | a bond | Me | a bond | NH | O | a bond | Q3a | OH |
| 4082 | CH | S | Q1n' | a bond | Me | a bond | NH | O | a bond | Q3d | OH |
| 4083 | CH | S | Q1n' | a bond | Me | a bond | NH | O | a bond | Q3e | OH |
| 4084 | CH | S | Q1n' | a bond | Me | a bond | NH | O | a bond | Q3f | OH |
| 4085 | CH | S | Q1n' | a bond | Me | a bond | NH | O | NH | Q3a | OH |
| 4086 | CH | S | Q1n' | a bond | Me | a bond | NH | O | NH | Q3d | OH |
| 4087 | CH | S | Q1n' | a bond | Me | a bond | NH | O | NH | Q3e | OH |
| 4088 | CH | S | Q1n' | a bond | Me | a bond | NH | O | NH | Q3f | OH |
| 4089 | CH | S | Q1n' | a bond | Me | a bond | NH | S | a bond | Q3a | OH |
| 4090 | CH | S | Q1n' | a bond | Me | a bond | NH | S | a bond | Q3d | OH |
| 4091 | CH | S | Q1n' | a bond | Me | a bond | NH | S | a bond | Q3e | OH |
| 4092 | CH | S | Q1n' | a bond | Me | a bond | NH | S | a bond | Q3f | OH |
| 4093 | CH | S | Q1n' | a bond | Me | a bond | NH | S | NH | Q3a | OH |
| 4094 | CH | S | Q1n' | a bond | Me | a bond | NH | S | NH | Q3d | OH |
| 4095 | CH | S | Q1n' | a bond | Me | a bond | NH | S | NH | Q3e | OH |
| 4096 | CH | S | Q1n' | a bond | Me | a bond | NH | S | NH | Q3f | OH |
| 4097 | CH | O | Q1k' | a bond | Me | a bond | NH | O | a bond | Q3a | OH |
| 4098 | CH | O | Q1k' | a bond | Me | a bond | NH | O | a bond | Q3d | OH |
| 4099 | CH | O | Q1k' | a bond | Me | a bond | NH | O | a bond | Q3e | OH |
| 4100 | CH | O | Q1k' | a bond | Me | a bond | NH | O | a bond | Q3f | OH |
| 4101 | CH | O | Q1k' | a bond | Me | a bond | NH | O | NH | Q3a | OH |
| 4102 | CH | O | Q1k' | a bond | Me | a bond | NH | O | NH | Q3d | OH |
| 4103 | CH | O | Q1k' | a bond | Me | a bond | NH | O | NH | Q3e | OH |
| 4104 | CH | O | Q1k' | a bond | Me | a bond | NH | O | NH | Q3f | OH |
| 4105 | CH | O | Q1k' | a bond | Me | a bond | NH | S | a bond | Q3a | OH |
| 4106 | CH | O | Q1k' | a bond | Me | a bond | NH | S | a bond | Q3d | OH |
| 4107 | CH | O | Q1k' | a bond | Me | a bond | NH | S | a bond | Q3e | OH |
| 4108 | CH | O | Q1k' | a bond | Me | a bond | NH | S | a bond | Q3f | OH |
| 4109 | CH | O | Q1k' | a bond | Me | a bond | NH | S | NH | Q3a | OH |
| 4110 | CH | O | Q1k' | a bond | Me | a bond | NH | S | NH | Q3d | OH |
| 4111 | CH | O | Q1k' | a bond | Me | a bond | NH | S | NH | Q3e | OH |
| 4112 | CH | O | Q1k' | a bond | Me | a bond | NH | S | NH | Q3f | OH |
| 4113 | CH | O | Q1l' | a bond | Me | a bond | NH | O | a bond | Q3a | OH |
| 4114 | CH | O | Q1l' | a bond | Me | a bond | NH | O | a bond | Q3d | OH |
| 4115 | CH | O | Q1l' | a bond | Me | a bond | NH | O | a bond | Q3e | OH |
| 4116 | CH | O | Q1l' | a bond | Me | a bond | NH | O | a bond | Q3f | OH |
| 4117 | CH | O | Q1l' | a bond | Me | a bond | NH | O | NH | Q3a | OH |
| 4118 | CH | O | Q1l' | a bond | Me | a bond | NH | O | NH | Q3d | OH |
| 4119 | CH | O | Q1l' | a bond | Me | a bond | NH | O | NH | Q3e | OH |
| 4120 | CH | O | Q1l' | a bond | Me | a bond | NH | O | NH | Q3f | OH |
| 4121 | CH | O | Q1l' | a bond | Me | a bond | NH | S | a bond | Q3a | OH |
| 4122 | CH | O | Q1l' | a bond | Me | a bond | NH | S | a bond | Q3d | OH |
| 4123 | CH | O | Q1l' | a bond | Me | a bond | NH | S | a bond | Q3e | OH |
| 4124 | CH | O | Q1l' | a bond | Me | a bond | NH | S | a bond | Q3f | OH |
| 4125 | CH | O | Q1l' | a bond | Me | a bond | NH | S | NH | Q3a | OH |
| 4126 | CH | O | Q1l' | a bond | Me | a bond | NH | S | NH | Q3d | OH |
| 4127 | CH | O | Q1l' | a bond | Me | a bond | NH | S | NH | Q3e | OH |
| 4128 | CH | O | Q1l' | a bond | Me | a bond | NH | S | NH | Q3f | OH |
| 4129 | CH | O | Q1m' | a bond | Me | a bond | NH | O | a bond | Q3a | OH |
| 4130 | CH | O | Q1m' | a bond | Me | a bond | NH | O | a bond | Q3d | OH |
| 4131 | CH | O | Q1m' | a bond | Me | a bond | NH | O | a bond | Q3e | OH |
| 4132 | CH | O | Q1m' | a bond | Me | a bond | NH | O | a bond | Q3f | OH |
| 4133 | CH | O | Q1m' | a bond | Me | a bond | NH | O | NH | Q3a | OH |
| 4134 | CH | O | Q1m' | a bond | Me | a bond | NH | O | NH | Q3d | OH |

TABLE 1-continued

| No | A | B | R$^1$ | L$^1$ | R$^2$ | L$^2$ | L$^3$ | Y | L$^4$ | R$^3$ | X |
|---|---|---|---|---|---|---|---|---|---|---|---|
| 4135 | CH | O | Q1m' | a bond | Me | a bond | NH | O | NH | Q3e | OH |
| 4136 | CH | O | Q1m' | a bond | Me | a bond | NH | O | NH | Q3f | OH |
| 4137 | CH | O | Q1m' | a bond | Me | a bond | NH | S | a bond | Q3a | OH |
| 4138 | CH | O | Q1m' | a bond | Me | a bond | NH | S | a bond | Q3d | OH |
| 4139 | CH | O | Q1m' | a bond | Me | a bond | NH | S | a bond | Q3e | OH |
| 4140 | CH | O | Q1m' | a bond | Me | a bond | NH | S | a bond | Q3f | OH |
| 4141 | CH | O | Q1m' | a bond | Me | a bond | NH | S | NH | Q3a | OH |
| 4142 | CH | O | Q1m' | a bond | Me | a bond | NH | S | NH | Q3d | OH |
| 4143 | CH | O | Q1m' | a bond | Me | a bond | NH | S | NH | Q3e | OH |
| 4144 | CH | O | Q1m' | a bond | Me | a bond | NH | S | NH | Q3f | OH |
| 4145 | CH | O | Q1n' | a bond | Me | a bond | NH | O | a bond | Q3a | OH |
| 4146 | CH | O | Q1n' | a bond | Me | a bond | NH | O | a bond | Q3d | OH |
| 4147 | CH | O | Q1n' | a bond | Me | a bond | NH | O | a bond | Q3e | OH |
| 4148 | CH | O | Q1n' | a bond | Me | a bond | NH | O | a bond | Q3f | OH |
| 4149 | CH | O | Q1n' | a bond | Me | a bond | NH | O | NH | Q3a | OH |
| 4150 | CH | O | Q1n' | a bond | Me | a bond | NH | O | NH | Q3d | OH |
| 4151 | CH | O | Q1n' | a bond | Me | a bond | NH | O | NH | Q3e | OH |
| 4152 | CH | O | Q1n' | a bond | Me | a bond | NH | O | NH | Q3f | OH |
| 4153 | CH | O | Q1n' | a bond | Me | a bond | NH | S | a bond | Q3a | OH |
| 4154 | CH | O | Q1n' | a bond | Me | a bond | NH | S | a bond | Q3d | OH |
| 4155 | CH | O | Q1n' | a bond | Me | a bond | NH | S | a bond | Q3e | OH |
| 4156 | CH | O | Q1n' | a bond | Me | a bond | NH | S | a bond | Q3f | OH |
| 4157 | CH | O | Q1n' | a bond | Me | a bond | NH | S | NH | Q3a | OH |
| 4158 | CH | O | Q1n' | a bond | Me | a bond | NH | S | NH | Q3d | OH |
| 4159 | CH | O | Q1n' | a bond | Me | a bond | NH | S | NH | Q3e | OH |
| 4160 | CH | O | Q1n' | a bond | Me | a bond | NH | S | NH | Q3f | OH |
| 4161 | CMe | NMe | Q1k' | a bond | Me | a bond | NH | O | a bond | Q3a | OH |
| 4162 | CMe | NMe | Q1k' | a bond | Me | a bond | NH | O | a bond | Q3d | OH |
| 4163 | CMe | NMe | Q1k' | a bond | Me | a bond | NH | O | a bond | Q3e | OH |
| 4164 | CMe | NMe | Q1k' | a bond | Me | a bond | NH | O | a bond | Q3f | OH |
| 4165 | CMe | NMe | Q1k' | a bond | Me | a bond | NH | O | NH | Q3a | OH |
| 4166 | CMe | NMe | Q1k' | a bond | Me | a bond | NH | O | NH | Q3d | OH |
| 4167 | CMe | NMe | Q1k' | a bond | Me | a bond | NH | O | NH | Q3e | OH |
| 4168 | CMe | NMe | Q1k' | a bond | Me | a bond | NH | O | NH | Q3f | OH |
| 4169 | CMe | NMe | Q1k' | a bond | Me | a bond | NH | S | a bond | Q3a | OH |
| 4170 | CMe | NMe | Q1k' | a bond | Me | a bond | NH | S | a bond | Q3d | OH |
| 4171 | CMe | NMe | Q1k' | a bond | Me | a bond | NH | S | a bond | Q3e | OH |
| 4172 | CMe | NMe | Q1k' | a bond | Me | a bond | NH | S | a bond | Q3f | OH |
| 4173 | CMe | NMe | Q1k' | a bond | Me | a bond | NH | S | NH | Q3a | OH |
| 4174 | CMe | NMe | Q1k' | a bond | Me | a bond | NH | S | NH | Q3d | OH |
| 4175 | CMe | NMe | Q1k' | a bond | Me | a bond | NH | S | NH | Q3e | OH |
| 4176 | CMe | NMe | Q1k' | a bond | Me | a bond | NH | S | NH | Q3f | OH |
| 4177 | CMe | NMe | Q1l' | a bond | Me | a bond | NH | O | a bond | Q3a | OH |
| 4178 | CMe | NMe | Q1l' | a bond | Me | a bond | NH | O | a bond | Q3d | OH |
| 4179 | CMe | NMe | Q1l' | a bond | Me | a bond | NH | O | a bond | Q3e | OH |
| 4180 | CMe | NMe | Q1l' | a bond | Me | a bond | NH | O | a bond | Q3f | OH |
| 4181 | CMe | NMe | Q1l' | a bond | Me | a bond | NH | O | NH | Q3a | OH |
| 4182 | CMe | NMe | Q1l' | a bond | Me | a bond | NH | O | NH | Q3d | OH |
| 4183 | CMe | NMe | Q1l' | a bond | Me | a bond | NH | O | NH | Q3e | OH |
| 4184 | CMe | NMe | Q1l' | a bond | Me | a bond | NH | O | NH | Q3f | OH |
| 4185 | CMe | NMe | Q1l' | a bond | Me | a bond | NH | S | a bond | Q3a | OH |
| 4186 | CMe | NMe | Q1l' | a bond | Me | a bond | NH | S | a bond | Q3d | OH |
| 4187 | CMe | NMe | Q1l' | a bond | Me | a bond | NH | S | a bond | Q3e | OH |
| 4188 | CMe | NMe | Q1l' | a bond | Me | a bond | NH | S | a bond | Q3f | OH |
| 4189 | CMe | NMe | Q1l' | a bond | Me | a bond | NH | S | NH | Q3a | OH |
| 4190 | CMe | NMe | Q1l' | a bond | Me | a bond | NH | S | NH | Q3d | OH |
| 4191 | CMe | NMe | Q1l' | a bond | Me | a bond | NH | S | NH | Q3e | OH |
| 4192 | CMe | NMe | Q1l' | a bond | Me | a bond | NH | S | NH | Q3f | OH |
| 4193 | CMe | NMe | Q1m' | a bond | Me | a bond | NH | O | a bond | Q3a | OH |
| 4194 | CMe | NMe | Q1m' | a bond | Me | a bond | NH | O | a bond | Q3d | OH |
| 4195 | CMe | NMe | Q1m' | a bond | Me | a bond | NH | O | a bond | Q3e | OH |
| 4196 | CMe | NMe | Q1m' | a bond | Me | a bond | NH | O | a bond | Q3f | OH |
| 4197 | CMe | NMe | Q1m' | a bond | Me | a bond | NH | O | NH | Q3a | OH |
| 4198 | CMe | NMe | Q1m' | a bond | Me | a bond | NH | O | NH | Q3d | OH |
| 4199 | CMe | NMe | Q1m' | a bond | Me | a bond | NH | O | NH | Q3e | OH |
| 4200 | CMe | NMe | Q1m' | a bond | Me | a bond | NH | O | NH | Q3f | OH |
| 4201 | CMe | NMe | Q1m' | a bond | Me | a bond | NH | S | a bond | Q3a | OH |
| 4202 | CMe | NMe | Q1m' | a bond | Me | a bond | NH | S | a bond | Q3d | OH |
| 4203 | CMe | NMe | Q1m' | a bond | Me | a bond | NH | S | a bond | Q3e | OH |
| 4204 | CMe | NMe | Q1m' | a bond | Me | a bond | NH | S | a bond | Q3f | OH |
| 4205 | CMe | NMe | Q1m' | a bond | Me | a bond | NH | S | NH | Q3a | OH |
| 4206 | CMe | NMe | Q1m' | a bond | Me | a bond | NH | S | NH | Q3d | OH |
| 4207 | CMe | NMe | Q1m' | a bond | Me | a bond | NH | S | NH | Q3e | OH |
| 4208 | CMe | NMe | Q1m' | a bond | Me | a bond | NH | S | NH | Q3f | OH |
| 4209 | CMe | NMe | Q1n' | a bond | Me | a bond | NH | O | a bond | Q3a | OH |
| 4210 | CMe | NMe | Q1n' | a bond | Me | a bond | NH | O | a bond | Q3d | OH |
| 4211 | CMe | NMe | Q1n' | a bond | Me | a bond | NH | O | a bond | Q3e | OH |
| 4212 | CMe | NMe | Q1n' | a bond | Me | a bond | NH | O | a bond | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4213 | CMe | NMe | Q1n' | a bond | Me | a bond | NH | O | NH | Q3a | OH |
| 4214 | CMe | NMe | Q1n' | a bond | Me | a bond | NH | O | NH | Q3d | OH |
| 4215 | CMe | NMe | Q1n' | a bond | Me | a bond | NH | O | NH | Q3e | OH |
| 4216 | CMe | NMe | Q1n' | a bond | Me | a bond | NH | O | NH | Q3f | OH |
| 4217 | CMe | NMe | Q1n' | a bond | Me | a bond | NH | S | a bond | Q3a | OH |
| 4218 | CMe | NMe | Q1n' | a bond | Me | a bond | NH | S | a bond | Q3d | OH |
| 4219 | CMe | NMe | Q1n' | a bond | Me | a bond | NH | S | a bond | Q3e | OH |
| 4220 | CMe | NMe | Q1n' | a bond | Me | a bond | NH | S | a bond | Q3f | OH |
| 4221 | CMe | NMe | Q1n' | a bond | Me | a bond | NH | S | NH | Q3a | OH |
| 4222 | CMe | NMe | Q1n' | a bond | Me | a bond | NH | S | NH | Q3d | OH |
| 4223 | CMe | NMe | Q1n' | a bond | Me | a bond | NH | S | NH | Q3e | OH |
| 4224 | CMe | NMe | Q1n' | a bond | Me | a bond | NH | S | NH | Q3f | OH |
| 4225 | CMe | NEt | Q1k' | a bond | Me | a bond | NH | O | a bond | Q3a | OH |
| 4226 | CMe | NEt | Q1k' | a bond | Me | a bond | NH | O | a bond | Q3d | OH |
| 4227 | CMe | NEt | Q1k' | a bond | Me | a bond | NH | O | a bond | Q3e | OH |
| 4228 | CMe | NEt | Q1k' | a bond | Me | a bond | NH | O | a bond | Q3f | OH |
| 4229 | CMe | NEt | Q1k' | a bond | Me | a bond | NH | O | NH | Q3a | OH |
| 4230 | CMe | NEt | Q1k' | a bond | Me | a bond | NH | O | NH | Q3d | OH |
| 4231 | CMe | NEt | Q1k' | a bond | Me | a bond | NH | O | NH | Q3e | OH |
| 4232 | CMe | NEt | Q1k' | a bond | Me | a bond | NH | O | NH | Q3f | OH |
| 4233 | CMe | NEt | Q1k' | a bond | Me | a bond | NH | S | a bond | Q3a | OH |
| 4234 | CMe | NEt | Q1k' | a bond | Me | a bond | NH | S | a bond | Q3d | OH |
| 4235 | CMe | NEt | Q1k' | a bond | Me | a bond | NH | S | a bond | Q3e | OH |
| 4236 | CMe | NEt | Q1k' | a bond | Me | a bond | NH | S | a bond | Q3f | OH |
| 4237 | CMe | NEt | Q1k' | a bond | Me | a bond | NH | S | NH | Q3a | OH |
| 4238 | CMe | NEt | Q1k' | a bond | Me | a bond | NH | S | NH | Q3d | OH |
| 4239 | CMe | NEt | Q1k' | a bond | Me | a bond | NH | S | NH | Q3e | OH |
| 4240 | CMe | NEt | Q1k' | a bond | Me | a bond | NH | S | NH | Q3f | OH |
| 4241 | CMe | NEt | Q1l' | a bond | Me | a bond | NH | O | a bond | Q3a | OH |
| 4242 | CMe | NEt | Q1l' | a bond | Me | a bond | NH | O | a bond | Q3d | OH |
| 4243 | CMe | NEt | Q1l' | a bond | Me | a bond | NH | O | a bond | Q3e | OH |
| 4244 | CMe | NEt | Q1l' | a bond | Me | a bond | NH | O | a bond | Q3f | OH |
| 4245 | CMe | NEt | Q1l' | a bond | Me | a bond | NH | O | NH | Q3a | OH |
| 4246 | CMe | NEt | Q1l' | a bond | Me | a bond | NH | O | NH | Q3d | OH |
| 4247 | CMe | NEt | Q1l' | a bond | Me | a bond | NH | O | NH | Q3e | OH |
| 4248 | CMe | NEt | Q1l' | a bond | Me | a bond | NH | O | NH | Q3f | OH |
| 4249 | CMe | NEt | Q1l' | a bond | Me | a bond | NH | S | a bond | Q3a | OH |
| 4250 | CMe | NEt | Q1l' | a bond | Me | a bond | NH | S | a bond | Q3d | OH |
| 4251 | CMe | NEt | Q1l' | a bond | Me | a bond | NH | S | a bond | Q3e | OH |
| 4252 | CMe | NEt | Q1l' | a bond | Me | a bond | NH | S | a bond | Q3f | OH |
| 4253 | CMe | NEt | Q1l' | a bond | Me | a bond | NH | S | NH | Q3a | OH |
| 4254 | CMe | NEt | Q1l' | a bond | Me | a bond | NH | S | NH | Q3d | OH |
| 4255 | CMe | NEt | Q1l' | a bond | Me | a bond | NH | S | NH | Q3e | OH |
| 4256 | CMe | NEt | Q1l' | a bond | Me | a bond | NH | S | NH | Q3f | OH |
| 4257 | CMe | NEt | Q1m' | a bond | Me | a bond | NH | O | a bond | Q3a | OH |
| 4258 | CMe | NEt | Q1m' | a bond | Me | a bond | NH | O | a bond | Q3d | OH |
| 4259 | CMe | NEt | Q1m' | a bond | Me | a bond | NH | O | a bond | Q3e | OH |
| 4260 | CMe | NEt | Q1m' | a bond | Me | a bond | NH | O | a bond | Q3f | OH |
| 4261 | CMe | NEt | Q1m' | a bond | Me | a bond | NH | O | NH | Q3a | OH |
| 4262 | CMe | NEt | Q1m' | a bond | Me | a bond | NH | O | NH | Q3d | OH |
| 4263 | CMe | NEt | Q1m' | a bond | Me | a bond | NH | O | NH | Q3e | OH |
| 4264 | CMe | NEt | Q1m' | a bond | Me | a bond | NH | O | NH | Q3f | OH |
| 4265 | CMe | NEt | Q1m' | a bond | Me | a bond | NH | S | a bond | Q3a | OH |
| 4266 | CMe | NEt | Q1m' | a bond | Me | a bond | NH | S | a bond | Q3d | OH |
| 4267 | CMe | NEt | Q1m' | a bond | Me | a bond | NH | S | a bond | Q3e | OH |
| 4268 | CMe | NEt | Q1m' | a bond | Me | a bond | NH | S | a bond | Q3f | OH |
| 4269 | CMe | NEt | Q1m' | a bond | Me | a bond | NH | S | NH | Q3a | OH |
| 4270 | CMe | NEt | Q1m' | a bond | Me | a bond | NH | S | NH | Q3d | OH |
| 4271 | CMe | NEt | Q1m' | a bond | Me | a bond | NH | S | NH | Q3e | OH |
| 4272 | CMe | NEt | Q1m' | a bond | Me | a bond | NH | S | NH | Q3f | OH |
| 4273 | CMe | NEt | Q1n' | a bond | Me | a bond | NH | O | a bond | Q3a | OH |
| 4274 | CMe | NEt | Q1n' | a bond | Me | a bond | NH | O | a bond | Q3d | OH |
| 4275 | CMe | NEt | Q1n' | a bond | Me | a bond | NH | O | a bond | Q3e | OH |
| 4276 | CMe | Net | Q1n' | a bond | Me | a bond | NH | O | a bond | Q3f | OH |
| 4277 | CMe | NEt | Q1n' | a bond | Me | a bond | NH | O | NH | Q3a | OH |
| 4278 | CMe | NEt | Q1n' | a bond | Me | a bond | NH | O | NH | Q3d | OH |
| 4279 | CMe | NEt | Q1n' | a bond | Me | a bond | NH | O | NH | Q3e | OH |
| 4280 | CMe | NEt | Q1n' | a bond | Me | a bond | NH | O | NH | Q3f | OH |
| 4281 | CMe | NEt | Q1n' | a bond | Me | a bond | NH | S | a bond | Q3a | OH |
| 4282 | CMe | NEt | Q1n' | a bond | Me | a bond | NH | S | a bond | Q3d | OH |
| 4283 | CMe | NEt | Q1n' | a bond | Me | a bond | NH | S | a bond | Q3e | OH |
| 4284 | CMe | NEt | Q1n' | a bond | Me | a bond | NH | S | a bond | Q3f | OH |
| 4285 | CMe | NEt | Q1n' | a bond | Me | a bond | NH | S | NH | Q3a | OH |
| 4286 | CMe | NEt | Q1n' | a bond | Me | a bond | NH | S | NH | Q3d | OH |
| 4287 | CMe | NEt | Q1n' | a bond | Me | a bond | NH | S | NH | Q3e | OH |
| 4288 | CMe | NEt | Q1n' | a bond | Me | a bond | NH | S | NH | Q3f | OH |
| 4289 | CMe | S | Q1k' | a bond | Me | a bond | NH | O | a bond | Q3a | OH |
| 4290 | CMe | S | Q1k' | a bond | Me | a bond | NH | O | a bond | Q3d | OH |

TABLE 1-continued

| No | A | B | R¹ | L¹ | R² | L² | L³ | Y | L⁴ | R³ | X |
|---|---|---|---|---|---|---|---|---|---|---|---|
| 4291 | CMe | S | Q1k' | a bond | Me | a bond | NH | O | a bond | Q3e | OH |
| 4292 | CMe | S | Q1k' | a bond | Me | a bond | NH | O | a bond | Q3f | OH |
| 4293 | CMe | S | Q1k' | a bond | Me | a bond | NH | O | NH | Q3a | OH |
| 4294 | CMe | S | Q1k' | a bond | Me | a bond | NH | O | NH | Q3d | OH |
| 4295 | CMe | S | Q1k' | a bond | Me | a bond | NH | O | NH | Q3e | OH |
| 4296 | CMe | S | Q1k' | a bond | Me | a bond | NH | O | NH | Q3f | OH |
| 4297 | CMe | S | Q1k' | a bond | Me | a bond | NH | S | a bond | Q3a | OH |
| 4298 | CMe | S | Q1k' | a bond | Me | a bond | NH | S | a bond | Q3d | OH |
| 4299 | CMe | S | Q1k' | a bond | Me | a bond | NH | S | a bond | Q3e | OH |
| 4300 | CMe | S | Q1k' | a bond | Me | a bond | NH | S | a bond | Q3f | OH |
| 4301 | CMe | S | Q1k' | a bond | Me | a bond | NH | S | NH | Q3a | OH |
| 4302 | CMe | S | Q1k' | a bond | Me | a bond | NH | S | NH | Q3d | OH |
| 4303 | CMe | S | Q1k' | a bond | Me | a bond | NH | S | NH | Q3e | OH |
| 4304 | CMe | S | Q1k' | a bond | Me | a bond | NH | S | NH | Q3f | OH |
| 4305 | CMe | S | Q1l' | a bond | Me | a bond | NH | O | a bond | Q3a | OH |
| 4306 | CMe | S | Q1l' | a bond | Me | a bond | NH | O | a bond | Q3d | OH |
| 4307 | CMe | S | Q1l' | a bond | Me | a bond | NH | O | a bond | Q3e | OH |
| 4308 | CMe | S | Q1l' | a bond | Me | a bond | NH | O | a bond | Q3f | OH |
| 4309 | CMe | S | Q1l' | a bond | Me | a bond | NH | O | NH | Q3a | OH |
| 4310 | CMe | S | Q1l' | a bond | Me | a bond | NH | O | NH | Q3d | OH |
| 4311 | CMe | S | Q1l' | a bond | Me | a bond | NH | O | NH | Q3e | OH |
| 4312 | CMe | S | Q1l' | a bond | Me | a bond | NH | O | NH | Q3f | OH |
| 4313 | CMe | S | Q1l' | a bond | Me | a bond | NH | S | a bond | Q3a | OH |
| 4314 | CMe | S | Q1l' | a bond | Me | a bond | NH | S | a bond | Q3d | OH |
| 4315 | CMe | S | Q1l' | a bond | Me | a bond | NH | S | a bond | Q3e | OH |
| 4316 | CMe | S | Q1l' | a bond | Me | a bond | NH | S | a bond | Q3f | OH |
| 4317 | CMe | S | Q1l' | a bond | Me | a bond | NH | S | NH | Q3a | OH |
| 4318 | CMe | S | Q1l' | a bond | Me | a bond | NH | S | NH | Q3d | OH |
| 4319 | CMe | S | Q1l' | a bond | Me | a bond | NH | S | NH | Q3e | OH |
| 4320 | CMe | S | Q1l' | a bond | Me | a bond | NH | S | NH | Q3f | OH |
| 4321 | CMe | S | Q1m' | a bond | Me | a bond | NH | O | a bond | Q3a | OH |
| 4322 | CMe | S | Q1m' | a bond | Me | a bond | NH | O | a bond | Q3d | OH |
| 4323 | CMe | S | Q1m' | a bond | Me | a bond | NH | O | a bond | Q3e | OH |
| 4324 | CMe | S | Q1m' | a bond | Me | a bond | NH | O | a bond | Q3f | OH |
| 4325 | CMe | S | Q1m' | a bond | Me | a bond | NH | O | NH | Q3a | OH |
| 4326 | CMe | S | Q1m' | a bond | Me | a bond | NH | O | NH | Q3d | OH |
| 4327 | CMe | S | Q1m' | a bond | Me | a bond | NH | O | NH | Q3e | OH |
| 4328 | CMe | S | Q1m' | a bond | Me | a bond | NH | O | NH | Q3f | OH |
| 4329 | CMe | S | Q1m' | a bond | Me | a bond | NH | S | a bond | Q3a | OH |
| 4330 | CMe | S | Q1m' | a bond | Me | a bond | NH | S | a bond | Q3d | OH |
| 4331 | CMe | S | Q1m' | a bond | Me | a bond | NH | S | a bond | Q3e | OH |
| 4332 | CMe | S | Q1m' | a bond | Me | a bond | NH | S | a bond | Q3f | OH |
| 4333 | CMe | S | Q1m' | a bond | Me | a bond | NH | S | NH | Q3a | OH |
| 4334 | CMe | S | Q1m' | a bond | Me | a bond | NH | S | NH | Q3d | OH |
| 4335 | CMe | S | Q1m' | a bond | Me | a bond | NH | S | NH | Q3e | OH |
| 4336 | CMe | S | Q1m' | a bond | Me | a bond | NH | S | NH | Q3f | OH |
| 4337 | CMe | S | Q1n' | a bond | Me | a bond | NH | O | a bond | Q3a | OH |
| 4338 | CMe | S | Q1n' | a bond | Me | a bond | NH | O | a bond | Q3d | OH |
| 4339 | CMe | S | Q1n' | a bond | Me | a bond | NH | O | a bond | Q3e | OH |
| 4340 | CMe | S | Q1n' | a bond | Me | a bond | NH | O | a bond | Q3f | OH |
| 4341 | CMe | S | Q1n' | a bond | Me | a bond | NH | O | NH | Q3a | OH |
| 4342 | CMe | S | Q1n' | a bond | Me | a bond | NH | O | NH | Q3d | OH |
| 4343 | CMe | S | Q1n' | a bond | Me | a bond | NH | O | NH | Q3e | OH |
| 4344 | CMe | S | Q1n' | a bond | Me | a bond | NH | O | NH | Q3f | OH |
| 4345 | CMe | S | Q1n' | a bond | Me | a bond | NH | S | a bond | Q3a | OH |
| 4346 | CMe | S | Q1n' | a bond | Me | a bond | NH | S | a bond | Q3d | OH |
| 4347 | CMe | S | Q1n' | a bond | Me | a bond | NH | S | a bond | Q3e | OH |
| 4348 | CMe | S | Q1n' | a bond | Me | a bond | NH | S | a bond | Q3f | OH |
| 4349 | CMe | S | Q1n' | a bond | Me | a bond | NH | S | NH | Q3a | OH |
| 4350 | CMe | S | Q1n' | a bond | Me | a bond | NH | S | NH | Q3d | OH |
| 4351 | CMe | S | Q1n' | a bond | Me | a bond | NH | S | NH | Q3e | OH |
| 4352 | CMe | S | Q1n' | a bond | Me | a bond | NH | S | NH | Q3f | OH |
| 4353 | CMe | O | Q1k' | a bond | Me | a bond | NH | O | a bond | Q3a | OH |
| 4354 | CMe | O | Q1k' | a bond | Me | a bond | NH | O | a bond | Q3d | OH |
| 4355 | CMe | O | Q1k' | a bond | Me | a bond | NH | O | a bond | Q3e | OH |
| 4356 | CMe | O | Q1k' | a bond | Me | a bond | NH | O | a bond | Q3f | OH |
| 4357 | CMe | O | Q1k' | a bond | Me | a bond | NH | O | NH | Q3a | OH |
| 4358 | CMe | O | Q1k' | a bond | Me | a bond | NH | O | NH | Q3d | OH |
| 4359 | CMe | O | Q1k' | a bond | Me | a bond | NH | O | NH | Q3e | OH |
| 4360 | CMe | O | Q1k' | a bond | Me | a bond | NH | O | NH | Q3f | OH |
| 4361 | CMe | O | Q1k' | a bond | Me | a bond | NH | S | a bond | Q3a | OH |
| 4362 | CMe | O | Q1k' | a bond | Me | a bond | NH | S | a bond | Q3d | OH |
| 4363 | CMe | O | Q1k' | a bond | Me | a bond | NH | S | a bond | Q3e | OH |
| 4364 | CMe | O | Q1k' | a bond | Me | a bond | NH | S | a bond | Q3f | OH |
| 4365 | CMe | O | Q1k' | a bond | Me | a bond | NH | S | NH | Q3a | OH |
| 4366 | CMe | O | Q1k' | a bond | Me | a bond | NH | S | NH | Q3d | OH |
| 4367 | CMe | O | Q1k' | a bond | Me | a bond | NH | S | NH | Q3e | OH |
| 4368 | CMe | O | Q1k' | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4369 | CMe | O | Q1l' | a bond | Me | a bond | NH | O | a bond | Q3a | OH |
| 4370 | CMe | O | Q1l' | a bond | Me | a bond | NH | O | a bond | Q3d | OH |
| 4371 | CMe | O | Q1l' | a bond | Me | a bond | NH | O | a bond | Q3e | OH |
| 4372 | CMe | O | Q1l' | a bond | Me | a bond | NH | O | a bond | Q3f | OH |
| 4373 | CMe | O | Q1l' | a bond | Me | a bond | NH | O | NH | Q3a | OH |
| 4374 | CMe | O | Q1l' | a bond | Me | a bond | NH | O | NH | Q3d | OH |
| 4375 | CMe | O | Q1l' | a bond | Me | a bond | NH | O | NH | Q3e | OH |
| 4376 | CMe | O | Q1l' | a bond | Me | a bond | NH | O | NH | Q3f | OH |
| 4377 | CMe | O | Q1l' | a bond | Me | a bond | NH | S | a bond | Q3a | OH |
| 4378 | CMe | O | Q1l' | a bond | Me | a bond | NH | S | a bond | Q3d | OH |
| 4379 | CMe | O | Q1l' | a bond | Me | a bond | NH | S | a bond | Q3e | OH |
| 4380 | CMe | O | Q1l' | a bond | Me | a bond | NH | S | a bond | Q3f | OH |
| 4381 | CMe | O | Q1l' | a bond | Me | a bond | NH | S | NH | Q3a | OH |
| 4382 | CMe | O | Q1l' | a bond | Me | a bond | NH | S | NH | Q3d | OH |
| 4383 | CMe | O | Q1l' | a bond | Me | a bond | NH | S | NH | Q3e | OH |
| 4384 | CMe | O | Q1l' | a bond | Me | a bond | NH | S | NH | Q3f | OH |
| 4385 | CMe | O | Q1m' | a bond | Me | a bond | NH | O | a bond | Q3a | OH |
| 4386 | CMe | O | Q1m' | a bond | Me | a bond | NH | O | a bond | Q3d | OH |
| 4387 | CMe | O | Q1m' | a bond | Me | a bond | NH | O | a bond | Q3e | OH |
| 4388 | CMe | O | Q1m' | a bond | Me | a bond | NH | O | a bond | Q3f | OH |
| 4389 | CMe | O | Q1m' | a bond | Me | a bond | NH | O | NH | Q3a | OH |
| 4390 | CMe | O | Q1m' | a bond | Me | a bond | NH | O | NH | Q3d | OH |
| 4391 | CMe | O | Q1m' | a bond | Me | a bond | NH | O | NH | Q3e | OH |
| 4392 | CMe | O | Q1m' | a bond | Me | a bond | NH | O | NH | Q3f | OH |
| 4393 | CMe | O | Q1m' | a bond | Me | a bond | NH | S | a bond | Q3a | OH |
| 4394 | CMe | O | Q1m' | a bond | Me | a bond | NH | S | a bond | Q3d | OH |
| 4395 | CMe | O | Q1m' | a bond | Me | a bond | NH | S | a bond | Q3e | OH |
| 4396 | CMe | O | Q1m' | a bond | Me | a bond | NH | S | a bond | Q3f | OH |
| 4397 | CMe | O | Q1m' | a bond | Me | a bond | NH | S | NH | Q3a | OH |
| 4398 | CMe | O | Q1m' | a bond | Me | a bond | NH | S | NH | Q3d | OH |
| 4399 | CMe | O | Q1m' | a bond | Me | a bond | NH | S | NH | Q3e | OH |
| 4400 | CMe | O | Q1m' | a bond | Me | a bond | NH | S | NH | Q3f | OH |
| 4401 | CMe | O | Q1n' | a bond | Me | a bond | NH | O | a bond | Q3a | OH |
| 4402 | CMe | O | Q1n' | a bond | Me | a bond | NH | O | a bond | Q3d | OH |
| 4403 | CMe | O | Q1n' | a bond | Me | a bond | NH | O | a bond | Q3e | OH |
| 4404 | CMe | O | Q1n' | a bond | Me | a bond | NH | O | a bond | Q3f | OH |
| 4405 | CMe | O | Q1n' | a bond | Me | a bond | NH | O | NH | Q3a | OH |
| 4406 | CMe | O | Q1n' | a bond | Me | a bond | NH | O | NH | Q3d | OH |
| 4407 | CMe | O | Q1n' | a bond | Me | a bond | NH | O | NH | Q3e | OH |
| 4408 | CMe | O | Q1n' | a bond | Me | a bond | NH | O | NH | Q3f | OH |
| 4409 | CMe | O | Q1n' | a bond | Me | a bond | NH | S | a bond | Q3a | OH |
| 4410 | CMe | O | Q1n' | a bond | Me | a bond | NH | S | a bond | Q3d | OH |
| 4411 | CMe | O | Q1n' | a bond | Me | a bond | NH | S | a bond | Q3e | OH |
| 4412 | CMe | O | Q1n' | a bond | Me | a bond | NH | S | a bond | Q3f | OH |
| 4413 | CMe | O | Q1n' | a bond | Me | a bond | NH | S | NH | Q3a | OH |
| 4414 | CMe | O | Q1n' | a bond | Me | a bond | NH | S | NH | Q3d | OH |
| 4415 | CMe | O | Q1n' | a bond | Me | a bond | NH | S | NH | Q3e | OH |
| 4416 | CMe | O | Q1n' | a bond | Me | a bond | NH | S | NH | Q3f | OH |
| 4417 | N | NMe | Q1a | a bond | Me | a bond | NH | O | a bond | Q3d | OH |
| 4418 | N | NMe | Q1a | a bond | Me | a bond | NH | O | a bond | Q3e | OH |
| 4419 | N | NMe | Q1a | a bond | Me | a bond | NH | O | a bond | Q3f | OH |
| 4420 | N | NMe | Q1a | a bond | Me | a bond | NH | O | NH | Q3d | OH |
| 4421 | N | NMe | Q1a | a bond | Me | a bond | NH | O | NH | Q3e | OH |
| 4422 | N | NMe | Q1a | a bond | Me | a bond | NH | O | NH | Q3f | OH |
| 4423 | N | NMe | Q1a | a bond | Me | a bond | NH | S | a bond | Q3d | OH |
| 4424 | N | NMe | Q1a | a bond | Me | a bond | NH | S | a bond | Q3e | OH |
| 4425 | N | NMe | Q1a | a bond | Me | a bond | NH | S | a bond | Q3f | OH |
| 4426 | N | NMe | Q1a | a bond | Me | a bond | NH | S | NH | Q3d | OH |
| 4427 | N | NMe | Q1a | a bond | Me | a bond | NH | S | NH | Q3e | OH |
| 4428 | N | NMe | Q1a | a bond | Me | a bond | NH | S | NH | Q3f | OH |
| 4429 | N | NMe | Q1b | a bond | Me | a bond | NH | O | a bond | Q3d | OH |
| 4430 | N | NMe | Q1b | a bond | Me | a bond | NH | O | a bond | Q3e | OH |
| 4431 | N | NMe | Q1b | a bond | Me | a bond | NH | O | a bond | Q3f | OH |
| 4432 | N | NMe | Q1b | a bond | Me | a bond | NH | O | NH | Q3d | OH |
| 4433 | N | NMe | Q1b | a bond | Me | a bond | NH | O | NH | Q3e | OH |
| 4434 | N | NMe | Q1b | a bond | Me | a bond | NH | O | NH | Q3f | OH |
| 4435 | N | NMe | Q1b | a bond | Me | a bond | NH | S | a bond | Q3d | OH |
| 4436 | N | NMe | Q1b | a bond | Me | a bond | NH | S | a bond | Q3e | OH |
| 4437 | N | NMe | Q1b | a bond | Me | a bond | NH | S | a bond | Q3f | OH |
| 4438 | N | NMe | Q1b | a bond | Me | a bond | NH | S | NH | Q3d | OH |
| 4439 | N | NMe | Q1b | a bond | Me | a bond | NH | S | NH | Q3e | OH |
| 4440 | N | NMe | Q1b | a bond | Me | a bond | NH | S | NH | Q3f | OH |
| 4441 | N | NMe | Q1c | a bond | Me | a bond | NH | O | a bond | Q3d | OH |
| 4442 | N | NMe | Q1c | a bond | Me | a bond | NH | O | a bond | Q3e | OH |
| 4443 | N | NMe | Q1c | a bond | Me | a bond | NH | O | a bond | Q3f | OH |
| 4444 | N | NMe | Q1c | a bond | Me | a bond | NH | O | NH | Q3d | OH |
| 4445 | N | NMe | Q1c | a bond | Me | a bond | NH | O | NH | Q3e | OH |
| 4446 | N | NMe | Q1c | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4447 | N | NMe | Q1c | a bond | Me | a bond | NH | S | a bond | Q3d | OH |
| 4448 | N | NMe | Q1c | a bond | Me | a bond | NH | S | a bond | Q3e | OH |
| 4449 | N | NMe | Q1c | a bond | Me | a bond | NH | S | a bond | Q3f | OH |
| 4450 | N | NMe | Q1c | a bond | Me | a bond | NH | S | NH | Q3d | OH |
| 4451 | N | NMe | Q1c | a bond | Me | a bond | NH | S | NH | Q3e | OH |
| 4452 | N | NMe | Q1c | a bond | Me | a bond | NH | S | NH | Q3f | OH |
| 4453 | N | NEt | Q1a | a bond | Me | a bond | NH | O | a bond | Q3d | OH |
| 4454 | N | NEt | Q1a | a bond | Me | a bond | NH | O | a bond | Q3e | OH |
| 4455 | N | NEt | Q1a | a bond | Me | a bond | NH | O | a bond | Q3f | OH |
| 4456 | N | NEt | Q1a | a bond | Me | a bond | NH | O | NH | Q3d | OH |
| 4457 | N | NEt | Q1a | a bond | Me | a bond | NH | O | NH | Q3e | OH |
| 4458 | N | NEt | Q1a | a bond | Me | a bond | NH | O | NH | Q3f | OH |
| 4459 | N | NEt | Q1a | a bond | Me | a bond | NH | S | a bond | Q3d | OH |
| 4460 | N | NEt | Q1a | a bond | Me | a bond | NH | S | a bond | Q3e | OH |
| 4461 | N | NEt | Q1a | a bond | Me | a bond | NH | S | a bond | Q3f | OH |
| 4462 | N | NEt | Q1a | a bond | Me | a bond | NH | S | NH | Q3d | OH |
| 4463 | N | NEt | Q1a | a bond | Me | a bond | NH | S | NH | Q3e | OH |
| 4464 | N | NEt | Q1a | a bond | Me | a bond | NH | S | NH | Q3f | OH |
| 4465 | N | NEt | Q1b | a bond | Me | a bond | NH | O | a bond | Q3d | OH |
| 4466 | N | NEt | Q1b | a bond | Me | a bond | NH | O | a bond | Q3e | OH |
| 4467 | N | NEt | Q1b | a bond | Me | a bond | NH | O | a bond | Q3f | OH |
| 4468 | N | NEt | Q1b | a bond | Me | a bond | NH | O | NH | Q3d | OH |
| 4469 | N | NEt | Q1b | a bond | Me | a bond | NH | O | NH | Q3e | OH |
| 4470 | N | NEt | Q1b | a bond | Me | a bond | NH | O | NH | Q3f | OH |
| 4471 | N | NEt | Q1b | a bond | Me | a bond | NH | S | a bond | Q3d | OH |
| 4472 | N | NEt | Q1b | a bond | Me | a bond | NH | S | a bond | Q3e | OH |
| 4473 | N | NEt | Q1b | a bond | Me | a bond | NH | S | a bond | Q3f | OH |
| 4474 | N | NEt | Q1b | a bond | Me | a bond | NH | S | NH | Q3d | OH |
| 4475 | N | NEt | Q1b | a bond | Me | a bond | NH | S | NH | Q3e | OH |
| 4476 | N | NEt | Q1b | a bond | Me | a bond | NH | S | NH | Q3f | OH |
| 4477 | N | NEt | Q1c | a bond | Me | a bond | NH | O | a bond | Q3d | OH |
| 4478 | N | NEt | Q1c | a bond | Me | a bond | NH | O | a bond | Q3e | OH |
| 4479 | N | NEt | Q1c | a bond | Me | a bond | NH | O | a bond | Q3f | OH |
| 4480 | N | NEt | Q1c | a bond | Me | a bond | NH | O | NH | Q3d | OH |
| 4481 | N | NEt | Q1c | a bond | Me | a bond | NH | O | NH | Q3e | OH |
| 4482 | N | NEt | Q1c | a bond | Me | a bond | NH | O | NH | Q3f | OH |
| 4483 | N | NEt | Q1c | a bond | Me | a bond | NH | S | a bond | Q3d | OH |
| 4484 | N | NEt | Q1c | a bond | Me | a bond | NH | S | a bond | Q3e | OH |
| 4485 | N | NEt | Q1c | a bond | Me | a bond | NH | S | a bond | Q3f | OH |
| 4486 | N | NEt | Q1c | a bond | Me | a bond | NH | S | NH | Q3d | OH |
| 4487 | N | NEt | Q1c | a bond | Me | a bond | NH | S | NH | Q3e | OH |
| 4488 | N | NEt | Q1c | a bond | Me | a bond | NH | S | NH | Q3f | OH |
| 4489 | N | S | Q1a | a bond | Me | a bond | NH | O | a bond | Q3d | OH |
| 4490 | N | S | Q1a | a bond | Me | a bond | NH | O | a bond | Q3e | OH |
| 4491 | N | S | Q1a | a bond | Me | a bond | NH | O | a bond | Q3f | OH |
| 4492 | N | S | Q1a | a bond | Me | a bond | NH | O | NH | Q3d | OH |
| 4493 | N | S | Q1a | a bond | Me | a bond | NH | O | NH | Q3e | OH |
| 4494 | N | S | Q1a | a bond | Me | a bond | NH | O | NH | Q3f | OH |
| 4495 | N | S | Q1a | a bond | Me | a bond | NH | S | a bond | Q3d | OH |
| 4496 | N | S | Q1a | a bond | Me | a bond | NH | S | a bond | Q3e | OH |
| 4497 | N | S | Q1a | a bond | Me | a bond | NH | S | a bond | Q3f | OH |
| 4498 | N | S | Q1a | a bond | Me | a bond | NH | S | NH | Q3d | OH |
| 4499 | N | S | Q1a | a bond | Me | a bond | NH | S | NH | Q3e | OH |
| 4500 | N | S | Q1a | a bond | Me | a bond | NH | S | NH | Q3f | OH |
| 4501 | N | S | Q1b | a bond | Me | a bond | NH | O | a bond | Q3d | OH |
| 4502 | N | S | Q1b | a bond | Me | a bond | NH | O | a bond | Q3e | OH |
| 4503 | N | S | Q1b | a bond | Me | a bond | NH | O | a bond | Q3f | OH |
| 4504 | N | S | Q1b | a bond | Me | a bond | NH | O | NH | Q3d | OH |
| 4505 | N | S | Q1b | a bond | Me | a bond | NH | O | NH | Q3e | OH |
| 4506 | N | S | Q1b | a bond | Me | a bond | NH | O | NH | Q3f | OH |
| 4507 | N | S | Q1b | a bond | Me | a bond | NH | S | a bond | Q3d | OH |
| 4508 | N | S | Q1b | a bond | Me | a bond | NH | S | a bond | Q3e | OH |
| 4509 | N | S | Q1b | a bond | Me | a bond | NH | S | a bond | Q3f | OH |
| 4510 | N | S | Q1b | a bond | Me | a bond | NH | S | NH | Q3d | OH |
| 4511 | N | S | Q1b | a bond | Me | a bond | NH | S | NH | Q3e | OH |
| 4512 | N | S | Q1b | a bond | Me | a bond | NH | S | NH | Q3f | OH |
| 4513 | N | S | Q1c | a bond | Me | a bond | NH | O | a bond | Q3d | OH |
| 4514 | N | S | Q1c | a bond | Me | a bond | NH | O | a bond | Q3e | OH |
| 4515 | N | S | Q1c | a bond | Me | a bond | NH | O | a bond | Q3f | OH |
| 4516 | N | S | Q1c | a bond | Me | a bond | NH | O | NH | Q3d | OH |
| 4517 | N | S | Q1c | a bond | Me | a bond | NH | O | NH | Q3e | OH |
| 4518 | N | S | Q1c | a bond | Me | a bond | NH | O | NH | Q3f | OH |
| 4519 | N | S | Q1c | a bond | Me | a bond | NH | S | a bond | Q3d | OH |
| 4520 | N | S | Q1c | a bond | Me | a bond | NH | S | a bond | Q3e | OH |
| 4521 | N | S | Q1c | a bond | Me | a bond | NH | S | a bond | Q3f | OH |
| 4522 | N | S | Q1c | a bond | Me | a bond | NH | S | NH | Q3d | OH |
| 4523 | N | S | Q1c | a bond | Me | a bond | NH | S | NH | Q3e | OH |
| 4524 | N | S | Q1c | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4525 | N | O | Q1a | a bond | Me | a bond | NH | O | a bond | Q3d | OH |
| 4526 | N | O | Q1a | a bond | Me | a bond | NH | O | a bond | Q3e | OH |
| 4527 | N | O | Q1a | a bond | Me | a bond | NH | O | a bond | Q3f | OH |
| 4528 | N | O | Q1a | a bond | Me | a bond | NH | O | NH | Q3d | OH |
| 4529 | N | O | Q1a | a bond | Me | a bond | NH | O | NH | Q3e | OH |
| 4530 | N | O | Q1a | a bond | Me | a bond | NH | O | NH | Q3f | OH |
| 4531 | N | O | Q1a | a bond | Me | a bond | NH | S | a bond | Q3d | OH |
| 4532 | N | O | Q1a | a bond | Me | a bond | NH | S | a bond | Q3e | OH |
| 4533 | N | O | Q1a | a bond | Me | a bond | NH | S | a bond | Q3f | OH |
| 4534 | N | O | Q1a | a bond | Me | a bond | NH | S | NH | Q3d | OH |
| 4535 | N | O | Q1a | a bond | Me | a bond | NH | S | NH | Q3e | OH |
| 4536 | N | O | Q1a | a bond | Me | a bond | NH | S | NH | Q3f | OH |
| 4537 | N | O | Q1b | a bond | Me | a bond | NH | O | a bond | Q3d | OH |
| 4538 | N | O | Q1b | a bond | Me | a bond | NH | O | a bond | Q3e | OH |
| 4539 | N | O | Q1b | a bond | Me | a bond | NH | O | a bond | Q3f | OH |
| 4540 | N | O | Q1b | a bond | Me | a bond | NH | O | NH | Q3d | OH |
| 4541 | N | O | Q1b | a bond | Me | a bond | NH | O | NH | Q3e | OH |
| 4542 | N | O | Q1b | a bond | Me | a bond | NH | O | NH | Q3f | OH |
| 4543 | N | O | Q1b | a bond | Me | a bond | NH | S | a bond | Q3d | OH |
| 4544 | N | O | Q1b | a bond | Me | a bond | NH | S | a bond | Q3e | OH |
| 4545 | N | O | Q1b | a bond | Me | a bond | NH | S | a bond | Q3f | OH |
| 4546 | N | O | Q1b | a bond | Me | a bond | NH | S | NH | Q3d | OH |
| 4547 | N | O | Q1b | a bond | Me | a bond | NH | S | NH | Q3e | OH |
| 4548 | N | O | Q1b | a bond | Me | a bond | NH | S | NH | Q3f | OH |
| 4549 | N | O | Q1c | a bond | Me | a bond | NH | O | a bond | Q3d | OH |
| 4550 | N | O | Q1c | a bond | Me | a bond | NH | O | a bond | Q3e | OH |
| 4551 | N | O | Q1c | a bond | Me | a bond | NH | O | a bond | Q3f | OH |
| 4552 | N | O | Q1c | a bond | Me | a bond | NH | O | NH | Q3d | OH |
| 4553 | N | O | Q1c | a bond | Me | a bond | NH | O | NH | Q3e | OH |
| 4554 | N | O | Q1c | a bond | Me | a bond | NH | O | NH | Q3f | OH |
| 4555 | N | O | Q1c | a bond | Me | a bond | NH | S | a bond | Q3d | OH |
| 4556 | N | O | Q1c | a bond | Me | a bond | NH | S | a bond | Q3e | OH |
| 4557 | N | O | Q1c | a bond | Me | a bond | NH | S | a bond | Q3f | OH |
| 4558 | N | O | Q1c | a bond | Me | a bond | NH | S | NH | Q3d | OH |
| 4559 | N | O | Q1c | a bond | Me | a bond | NH | S | NH | Q3e | OH |
| 4560 | N | O | Q1c | a bond | Me | a bond | NH | S | NH | Q3f | OH |
| 4561 | CH | NMe | Q1a | a bond | Me | a bond | NH | O | a bond | Q3d | OH |
| 4562 | CH | NMe | Q1a | a bond | Me | a bond | NH | O | a bond | Q3e | OH |
| 4563 | CH | NMe | Q1a | a bond | Me | a bond | NH | O | a bond | Q3f | OH |
| 4564 | CH | NMe | Q1a | a bond | Me | a bond | NH | O | NH | Q3d | OH |
| 4565 | CH | NMe | Q1a | a bond | Me | a bond | NH | O | NH | Q3e | OH |
| 4566 | CH | NMe | Q1a | a bond | Me | a bond | NH | O | NH | Q3f | OH |
| 4567 | CH | NMe | Q1a | a bond | Me | a bond | NH | S | a bond | Q3d | OH |
| 4568 | CH | NMe | Q1a | a bond | Me | a bond | NH | S | a bond | Q3e | OH |
| 4569 | CH | NMe | Q1a | a bond | Me | a bond | NH | S | a bond | Q3f | OH |
| 4570 | CH | NMe | Q1a | a bond | Me | a bond | NH | S | NH | Q3d | OH |
| 4571 | CH | NMe | Q1a | a bond | Me | a bond | NH | S | NH | Q3e | OH |
| 4572 | CH | NMe | Q1a | a bond | Me | a bond | NH | S | NH | Q3f | OH |
| 4573 | CH | NMe | Q1b | a bond | Me | a bond | NH | O | a bond | Q3d | OH |
| 4574 | CH | NMe | Q1b | a bond | Me | a bond | NH | O | a bond | Q3e | OH |
| 4575 | CH | NMe | Q1b | a bond | Me | a bond | NH | O | a bond | Q3f | OH |
| 4576 | CH | NMe | Q1b | a bond | Me | a bond | NH | O | NH | Q3d | OH |
| 4577 | CH | NMe | Q1b | a bond | Me | a bond | NH | O | NH | Q3e | OH |
| 4578 | CH | NMe | Q1b | a bond | Me | a bond | NH | O | NH | Q3f | OH |
| 4579 | CH | NMe | Q1b | a bond | Me | a bond | NH | S | a bond | Q3d | OH |
| 4580 | CH | NMe | Q1b | a bond | Me | a bond | NH | S | a bond | Q3e | OH |
| 4581 | CH | NMe | Q1b | a bond | Me | a bond | NH | S | a bond | Q3f | OH |
| 4582 | CH | NMe | Q1b | a bond | Me | a bond | NH | S | NH | Q3d | OH |
| 4583 | CH | NMe | Q1b | a bond | Me | a bond | NH | S | NH | Q3e | OH |
| 4584 | CH | NMe | Q1b | a bond | Me | a bond | NH | S | NH | Q3f | OH |
| 4585 | CH | NMe | Q1c | a bond | Me | a bond | NH | O | a bond | Q3d | OH |
| 4586 | CH | NMe | Q1c | a bond | Me | a bond | NH | O | a bond | Q3e | OH |
| 4587 | CH | NMe | Q1c | a bond | Me | a bond | NH | O | a bond | Q3f | OH |
| 4588 | CH | NMe | Q1c | a bond | Me | a bond | NH | O | NH | Q3d | OH |
| 4589 | CH | NMe | Q1c | a bond | Me | a bond | NH | O | NH | Q3e | OH |
| 4590 | CH | NMe | Q1c | a bond | Me | a bond | NH | O | NH | Q3f | OH |
| 4591 | CH | NMe | Q1c | a bond | Me | a bond | NH | S | a bond | Q3d | OH |
| 4592 | CH | NMe | Q1c | a bond | Me | a bond | NH | S | a bond | Q3e | OH |
| 4593 | CH | NMe | Q1c | a bond | Me | a bond | NH | S | a bond | Q3f | OH |
| 4594 | CH | NMe | Q1c | a bond | Me | a bond | NH | S | NH | Q3d | OH |
| 4595 | CH | NMe | Q1c | a bond | Me | a bond | NH | S | NH | Q3e | OH |
| 4596 | CH | NMe | Q1c | a bond | Me | a bond | NH | S | NH | Q3f | OH |
| 4597 | CH | NEt | Q1a | a bond | Me | a bond | NH | O | a bond | Q3d | OH |
| 4598 | CH | NEt | Q1a | a bond | Me | a bond | NH | O | a bond | Q3e | OH |
| 4599 | CH | NEt | Q1a | a bond | Me | a bond | NH | O | a bond | Q3f | OH |
| 4600 | CH | NEt | Q1a | a bond | Me | a bond | NH | O | NH | Q3d | OH |
| 4601 | CH | NEt | Q1a | a bond | Me | a bond | NH | O | NH | Q3e | OH |
| 4602 | CH | NEt | Q1a | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4603 | CH | NEt | Q1a | a bond | Me | a bond | NH | S | a bond | Q3d | OH |
| 4604 | CH | NEt | Q1a | a bond | Me | a bond | NH | S | a bond | Q3e | OH |
| 4605 | CH | NEt | Q1a | a bond | Me | a bond | NH | S | a bond | Q3f | OH |
| 4606 | CH | NEt | Q1a | a bond | Me | a bond | NH | S | NH | Q3d | OH |
| 4607 | CH | NEt | Q1a | a bond | Me | a bond | NH | S | NH | Q3e | OH |
| 4608 | CH | NEt | Q1a | a bond | Me | a bond | NH | S | NH | Q3f | OH |
| 4609 | CH | NEt | Q1b | a bond | Me | a bond | NH | O | a bond | Q3d | OH |
| 4610 | CH | NEt | Q1b | a bond | Me | a bond | NH | O | a bond | Q3e | OH |
| 4611 | CH | NEt | Q1b | a bond | Me | a bond | NH | O | a bond | Q3f | OH |
| 4612 | CH | NEt | Q1b | a bond | Me | a bond | NH | O | NH | Q3d | OH |
| 4613 | CH | NEt | Q1b | a bond | Me | a bond | NH | O | NH | Q3e | OH |
| 4614 | CH | NEt | Q1b | a bond | Me | a bond | NH | O | NH | Q3f | OH |
| 4615 | CH | NEt | Q1b | a bond | Me | a bond | NH | S | a bond | Q3d | OH |
| 4616 | CH | NEt | Q1b | a bond | Me | a bond | NH | S | a bond | Q3e | OH |
| 4617 | CH | NEt | Q1b | a bond | Me | a bond | NH | S | a bond | Q3f | OH |
| 4618 | CH | NEt | Q1b | a bond | Me | a bond | NH | S | NH | Q3d | OH |
| 4619 | CH | NEt | Q1b | a bond | Me | a bond | NH | S | NH | Q3e | OH |
| 4620 | CH | NEt | Q1b | a bond | Me | a bond | NH | S | NH | Q3f | OH |
| 4621 | CH | NEt | Q1c | a bond | Me | a bond | NH | O | a bond | Q3d | OH |
| 4622 | CH | NEt | Q1c | a bond | Me | a bond | NH | O | a bond | Q3e | OH |
| 4623 | CH | NEt | Q1c | a bond | Me | a bond | NH | O | a bond | Q3f | OH |
| 4624 | CH | NEt | Q1c | a bond | Me | a bond | NH | O | NH | Q3d | OH |
| 4625 | CH | NEt | Q1c | a bond | Me | a bond | NH | O | NH | Q3e | OH |
| 4626 | CH | NEt | Q1c | a bond | Me | a bond | NH | O | NH | Q3f | OH |
| 4627 | CH | NEt | Q1c | a bond | Me | a bond | NH | S | a bond | Q3d | OH |
| 4628 | CH | NEt | Q1c | a bond | Me | a bond | NH | S | a bond | Q3e | OH |
| 4629 | CH | NEt | Q1c | a bond | Me | a bond | NH | S | a bond | Q3f | OH |
| 4630 | CH | NEt | Q1c | a bond | Me | a bond | NH | S | NH | Q3d | OH |
| 4631 | CH | NEt | Q1c | a bond | Me | a bond | NH | S | NH | Q3e | OH |
| 4632 | CH | NEt | Q1c | a bond | Me | a bond | NH | S | NH | Q3f | OH |
| 4633 | CH | S | Q1a | a bond | Me | a bond | NH | O | a bond | Q3d | OH |
| 4634 | CH | S | Q1a | a bond | Me | a bond | NH | O | a bond | Q3e | OH |
| 4635 | CH | S | Q1a | a bond | Me | a bond | NH | O | a bond | Q3f | OH |
| 4636 | CH | S | Q1a | a bond | Me | a bond | NH | O | NH | Q3d | OH |
| 4637 | CH | S | Q1a | a bond | Me | a bond | NH | O | NH | Q3e | OH |
| 4638 | CH | S | Q1a | a bond | Me | a bond | NH | O | NH | Q3f | OH |
| 4639 | CH | S | Q1a | a bond | Me | a bond | NH | S | a bond | Q3d | OH |
| 4640 | CH | S | Q1a | a bond | Me | a bond | NH | S | a bond | Q3e | OH |
| 4641 | CH | S | Q1a | a bond | Me | a bond | NH | S | a bond | Q3f | OH |
| 4642 | CH | S | Q1a | a bond | Me | a bond | NH | S | NH | Q3d | OH |
| 4643 | CH | S | Q1a | a bond | Me | a bond | NH | S | NH | Q3e | OH |
| 4644 | CH | S | Q1a | a bond | Me | a bond | NH | S | NH | Q3f | OH |
| 4645 | CH | S | Q1b | a bond | Me | a bond | NH | O | a bond | Q3d | OH |
| 4646 | CH | S | Q1b | a bond | Me | a bond | NH | O | a bond | Q3e | OH |
| 4647 | CH | S | Q1b | a bond | Me | a bond | NH | O | a bond | Q3f | OH |
| 4648 | CH | S | Q1b | a bond | Me | a bond | NH | O | NH | Q3d | OH |
| 4649 | CH | S | Q1b | a bond | Me | a bond | NH | O | NH | Q3e | OH |
| 4650 | CH | S | Q1b | a bond | Me | a bond | NH | O | NH | Q3f | OH |
| 4651 | CH | S | Q1b | a bond | Me | a bond | NH | S | a bond | Q3d | OH |
| 4652 | CH | S | Q1b | a bond | Me | a bond | NH | S | a bond | Q3e | OH |
| 4653 | CH | S | Q1b | a bond | Me | a bond | NH | S | a bond | Q3f | OH |
| 4654 | CH | S | Q1b | a bond | Me | a bond | NH | S | NH | Q3d | OH |
| 4655 | CH | S | Q1b | a bond | Me | a bond | NH | S | NH | Q3e | OH |
| 4656 | CH | S | Q1b | a bond | Me | a bond | NH | S | NH | Q3f | OH |
| 4657 | CH | S | Q1c | a bond | Me | a bond | NH | O | a bond | Q3d | OH |
| 4658 | CH | S | Q1c | a bond | Me | a bond | NH | O | a bond | Q3e | OH |
| 4659 | CH | S | Q1c | a bond | Me | a bond | NH | O | a bond | Q3f | OH |
| 4660 | CH | S | Q1c | a bond | Me | a bond | NH | O | NH | Q3d | OH |
| 4661 | CH | S | Q1c | a bond | Me | a bond | NH | O | NH | Q3e | OH |
| 4662 | CH | S | Q1c | a bond | Me | a bond | NH | O | NH | Q3f | OH |
| 4663 | CH | S | Q1c | a bond | Me | a bond | NH | S | a bond | Q3d | OH |
| 4664 | CH | S | Q1c | a bond | Me | a bond | NH | S | a bond | Q3e | OH |
| 4665 | CH | S | Q1c | a bond | Me | a bond | NH | S | a bond | Q3f | OH |
| 4666 | CH | S | Q1c | a bond | Me | a bond | NH | S | NH | Q3d | OH |
| 4667 | CH | S | Q1c | a bond | Me | a bond | NH | S | NH | Q3e | OH |
| 4668 | CH | S | Q1c | a bond | Me | a bond | NH | S | NH | Q3f | OH |
| 4669 | CH | O | Q1a | a bond | Me | a bond | NH | O | a bond | Q3d | OH |
| 4670 | CH | O | Q1a | a bond | Me | a bond | NH | O | a bond | Q3e | OH |
| 4671 | CH | O | Q1a | a bond | Me | a bond | NH | O | a bond | Q3f | OH |
| 4672 | CH | O | Q1a | a bond | Me | a bond | NH | O | NH | Q3d | OH |
| 4673 | CH | O | Q1a | a bond | Me | a bond | NH | O | NH | Q3e | OH |
| 4674 | CH | O | Q1a | a bond | Me | a bond | NH | O | NH | Q3f | OH |
| 4675 | CH | O | Q1a | a bond | Me | a bond | NH | S | a bond | Q3d | OH |
| 4676 | CH | O | Q1a | a bond | Me | a bond | NH | S | a bond | Q3e | OH |
| 4677 | CH | O | Q1a | a bond | Me | a bond | NH | S | a bond | Q3f | OH |
| 4678 | CH | O | Q1a | a bond | Me | a bond | NH | S | NH | Q3d | OH |
| 4679 | CH | O | Q1a | a bond | Me | a bond | NH | S | NH | Q3e | OH |
| 4680 | CH | O | Q1a | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4681 | CH | O | Q1b | a bond | Me | a bond | NH | O | a bond | Q3d | OH |
| 4682 | CH | O | Q1b | a bond | Me | a bond | NH | O | a bond | Q3e | OH |
| 4683 | CH | O | Q1b | a bond | Me | a bond | NH | O | a bond | Q3f | OH |
| 4684 | CH | O | Q1b | a bond | Me | a bond | NH | O | NH | Q3d | OH |
| 4685 | CH | O | Q1b | a bond | Me | a bond | NH | O | NH | Q3e | OH |
| 4686 | CH | O | Q1b | a bond | Me | a bond | NH | O | NH | Q3f | OH |
| 4687 | CH | O | Q1b | a bond | Me | a bond | NH | S | a bond | Q3d | OH |
| 4688 | CH | O | Q1b | a bond | Me | a bond | NH | S | a bond | Q3e | OH |
| 4689 | CH | O | Q1b | a bond | Me | a bond | NH | S | a bond | Q3f | OH |
| 4690 | CH | O | Q1b | a bond | Me | a bond | NH | S | NH | Q3d | OH |
| 4691 | CH | O | Q1b | a bond | Me | a bond | NH | S | NH | Q3e | OH |
| 4692 | CH | O | Q1b | a bond | Me | a bond | NH | S | NH | Q3f | OH |
| 4693 | CH | O | Q1c | a bond | Me | a bond | NH | O | a bond | Q3d | OH |
| 4694 | CH | O | Q1c | a bond | Me | a bond | NH | O | a bond | Q3e | OH |
| 4695 | CH | O | Q1c | a bond | Me | a bond | NH | O | a bond | Q3f | OH |
| 4696 | CH | O | Q1c | a bond | Me | a bond | NH | O | NH | Q3d | OH |
| 4697 | CH | O | Q1c | a bond | Me | a bond | NH | O | NH | Q3e | OH |
| 4698 | CH | O | Q1c | a bond | Me | a bond | NH | O | NH | Q3f | OH |
| 4699 | CH | O | Q1c | a bond | Me | a bond | NH | S | a bond | Q3d | OH |
| 4700 | CH | O | Q1c | a bond | Me | a bond | NH | S | a bond | Q3e | OH |
| 4701 | CH | O | Q1c | a bond | Me | a bond | NH | S | a bond | Q3f | OH |
| 4702 | CH | O | Q1c | a bond | Me | a bond | NH | S | NH | Q3d | OH |
| 4703 | CH | O | Q1c | a bond | Me | a bond | NH | S | NH | Q3e | OH |
| 4704 | CH | O | Q1c | a bond | Me | a bond | NH | S | NH | Q3f | OH |
| 4705 | CMe | NMe | Q1a | a bond | Me | a bond | NH | O | a bond | Q3d | OH |
| 4706 | CMe | NMe | Q1a | a bond | Me | a bond | NH | O | a bond | Q3e | OH |
| 4707 | CMe | NMe | Q1a | a bond | Me | a bond | NH | O | a bond | Q3f | OH |
| 4708 | CMe | NMe | Q1a | a bond | Me | a bond | NH | O | NH | Q3d | OH |
| 4709 | CMe | NMe | Q1a | a bond | Me | a bond | NH | O | NH | Q3e | OH |
| 4710 | CMe | NMe | Q1a | a bond | Me | a bond | NH | O | NH | Q3f | OH |
| 4711 | CMe | NMe | Q1a | a bond | Me | a bond | NH | S | a bond | Q3d | OH |
| 4712 | CMe | NMe | Q1a | a bond | Me | a bond | NH | S | a bond | Q3e | OH |
| 4713 | CMe | NMe | Q1a | a bond | Me | a bond | NH | S | a bond | Q3f | OH |
| 4714 | CMe | NMe | Q1a | a bond | Me | a bond | NH | S | NH | Q3d | OH |
| 4715 | CMe | NMe | Q1a | a bond | Me | a bond | NH | S | NH | Q3e | OH |
| 4716 | CMe | NMe | Q1a | a bond | Me | a bond | NH | S | NH | Q3f | OH |
| 4717 | CMe | NMe | Q1b | a bond | Me | a bond | NH | O | a bond | Q3d | OH |
| 4718 | CMe | NMe | Q1b | a bond | Me | a bond | NH | O | a bond | Q3e | OH |
| 4719 | CMe | NMe | Q1b | a bond | Me | a bond | NH | O | a bond | Q3f | OH |
| 4720 | CMe | NMe | Q1b | a bond | Me | a bond | NH | O | NH | Q3d | OH |
| 4721 | CMe | NMe | Q1b | a bond | Me | a bond | NH | O | NH | Q3e | OH |
| 4722 | CMe | NMe | Q1b | a bond | Me | a bond | NH | O | NH | Q3f | OH |
| 4723 | CMe | NMe | Q1b | a bond | Me | a bond | NH | S | a bond | Q3d | OH |
| 4724 | CMe | NMe | Q1b | a bond | Me | a bond | NH | S | a bond | Q3e | OH |
| 4725 | CMe | NMe | Q1b | a bond | Me | a bond | NH | S | a bond | Q3f | OH |
| 4726 | CMe | NMe | Q1b | a bond | Me | a bond | NH | S | NH | Q3d | OH |
| 4727 | CMe | NMe | Q1b | a bond | Me | a bond | NH | S | NH | Q3e | OH |
| 4728 | CMe | NMe | Q1b | a bond | Me | a bond | NH | S | NH | Q3f | OH |
| 4729 | CMe | NMe | Q1c | a bond | Me | a bond | NH | O | a bond | Q3d | OH |
| 4730 | CMe | NMe | Q1c | a bond | Me | a bond | NH | O | a bond | Q3e | OH |
| 4731 | CMe | NMe | Q1c | a bond | Me | a bond | NH | O | a bond | Q3f | OH |
| 4732 | CMe | NMe | Q1c | a bond | Me | a bond | NH | O | NH | Q3d | OH |
| 4733 | CMe | NMe | Q1c | a bond | Me | a bond | NH | O | NH | Q3e | OH |
| 4734 | CMe | NMe | Q1c | a bond | Me | a bond | NH | O | NH | Q3f | OH |
| 4735 | CMe | NMe | Q1c | a bond | Me | a bond | NH | S | a bond | Q3d | OH |
| 4736 | CMe | NMe | Q1c | a bond | Me | a bond | NH | S | a bond | Q3e | OH |
| 4737 | CMe | NMe | Q1c | a bond | Me | a bond | NH | S | a bond | Q3f | OH |
| 4738 | CMe | NMe | Q1c | a bond | Me | a bond | NH | S | NH | Q3d | OH |
| 4739 | CMe | NMe | Q1c | a bond | Me | a bond | NH | S | NH | Q3e | OH |
| 4740 | CMe | NMe | Q1c | a bond | Me | a bond | NH | S | NH | Q3f | OH |
| 4741 | CMe | NEt | Q1a | a bond | Me | a bond | NH | O | a bond | Q3d | OH |
| 4742 | CMe | NEt | Q1a | a bond | Me | a bond | NH | O | a bond | Q3e | OH |
| 4743 | CMe | NEt | Q1a | a bond | Me | a bond | NH | O | a bond | Q3f | OH |
| 4744 | CMe | NEt | Q1a | a bond | Me | a bond | NH | O | NH | Q3d | OH |
| 4745 | CMe | NEt | Q1a | a bond | Me | a bond | NH | O | NH | Q3e | OH |
| 4746 | CMe | NEt | Q1a | a bond | Me | a bond | NH | O | NH | Q3f | OH |
| 4747 | CMe | NEt | Q1a | a bond | Me | a bond | NH | S | a bond | Q3d | OH |
| 4748 | CMe | NEt | Q1a | a bond | Me | a bond | NH | S | a bond | Q3e | OH |
| 4749 | CMe | NEt | Q1a | a bond | Me | a bond | NH | S | a bond | Q3f | OH |
| 4750 | CMe | NEt | Q1a | a bond | Me | a bond | NH | S | NH | Q3d | OH |
| 4751 | CMe | NEt | Q1a | a bond | Me | a bond | NH | S | NH | Q3e | OH |
| 4752 | CMe | NEt | Q1a | a bond | Me | a bond | NH | S | NH | Q3f | OH |
| 4753 | CMe | NEt | Q1b | a bond | Me | a bond | NH | O | a bond | Q3d | OH |
| 4754 | CMe | NEt | Q1b | a bond | Me | a bond | NH | O | a bond | Q3e | OH |
| 4755 | CMe | NEt | Q1b | a bond | Me | a bond | NH | O | a bond | Q3f | OH |
| 4756 | CMe | NEt | Q1b | a bond | Me | a bond | NH | O | NH | Q3d | OH |
| 4757 | CMe | NEt | Q1b | a bond | Me | a bond | NH | O | NH | Q3e | OH |
| 4758 | CMe | NEt | Q1b | a bond | Me | a bond | NH | O | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4759 | CMe | NEt | Q1b | a bond | Me | a bond | NH | S | a bond | Q3d | OH |
| 4760 | CMe | NEt | Q1b | a bond | Me | a bond | NH | S | a bond | Q3e | OH |
| 4761 | CMe | NEt | Q1b | a bond | Me | a bond | NH | S | a bond | Q3f | OH |
| 4762 | CMe | NEt | Q1b | a bond | Me | a bond | NH | S | NH | Q3d | OH |
| 4763 | CMe | NEt | Q1b | a bond | Me | a bond | NH | S | NH | Q3e | OH |
| 4764 | CMe | NEt | Q1b | a bond | Me | a bond | NH | S | NH | Q3f | OH |
| 4765 | CMe | NEt | Q1c | a bond | Me | a bond | NH | O | a bond | Q3d | OH |
| 4766 | CMe | NEt | Q1c | a bond | Me | a bond | NH | O | a bond | Q3e | OH |
| 4767 | CMe | NEt | Q1c | a bond | Me | a bond | NH | O | a bond | Q3f | OH |
| 4768 | CMe | NEt | Q1c | a bond | Me | a bond | NH | O | NH | Q3d | OH |
| 4769 | CMe | NEt | Q1c | a bond | Me | a bond | NH | O | NH | Q3e | OH |
| 4770 | CMe | NEt | Q1c | a bond | Me | a bond | NH | O | NH | Q3f | OH |
| 4771 | CMe | NEt | Q1c | a bond | Me | a bond | NH | S | a bond | Q3d | OH |
| 4772 | CMe | NEt | Q1c | a bond | Me | a bond | NH | S | a bond | Q3e | OH |
| 4773 | CMe | NEt | Q1c | a bond | Me | a bond | NH | S | a bond | Q3f | OH |
| 4774 | CMe | NEt | Q1c | a bond | Me | a bond | NH | S | NH | Q3d | OH |
| 4775 | CMe | NEt | Q1c | a bond | Me | a bond | NH | S | NH | Q3e | OH |
| 4776 | CMe | NEt | Q1c | a bond | Me | a bond | NH | S | NH | Q3f | OH |
| 4777 | CMe | S | Q1a | a bond | Me | a bond | NH | O | a bond | Q3d | OH |
| 4778 | CMe | S | Q1a | a bond | Me | a bond | NH | O | a bond | Q3e | OH |
| 4779 | CMe | S | Q1a | a bond | Me | a bond | NH | O | a bond | Q3f | OH |
| 4780 | CMe | S | Q1a | a bond | Me | a bond | NH | O | NH | Q3d | OH |
| 4781 | CMe | S | Q1a | a bond | Me | a bond | NH | O | NH | Q3e | OH |
| 4782 | CMe | S | Q1a | a bond | Me | a bond | NH | O | NH | Q3f | OH |
| 4783 | CMe | S | Q1a | a bond | Me | a bond | NH | S | a bond | Q3d | OH |
| 4784 | CMe | S | Q1a | a bond | Me | a bond | NH | S | a bond | Q3e | OH |
| 4785 | CMe | S | Q1a | a bond | Me | a bond | NH | S | a bond | Q3f | OH |
| 4786 | CMe | S | Q1a | a bond | Me | a bond | NH | S | NH | Q3d | OH |
| 4787 | CMe | S | Q1a | a bond | Me | a bond | NH | S | NH | Q3e | OH |
| 4788 | CMe | S | Q1a | a bond | Me | a bond | NH | S | NH | Q3f | OH |
| 4789 | CMe | S | Q1b | a bond | Me | a bond | NH | O | a bond | Q3d | OH |
| 4790 | CMe | S | Q1b | a bond | Me | a bond | NH | O | a bond | Q3e | OH |
| 4791 | CMe | S | Q1b | a bond | Me | a bond | NH | O | a bond | Q3f | OH |
| 4792 | CMe | S | Q1b | a bond | Me | a bond | NH | O | NH | Q3d | OH |
| 4793 | CMe | S | Q1b | a bond | Me | a bond | NH | O | NH | Q3e | OH |
| 4794 | CMe | S | Q1b | a bond | Me | a bond | NH | O | NH | Q3f | OH |
| 4795 | CMe | S | Q1b | a bond | Me | a bond | NH | S | a bond | Q3d | OH |
| 4796 | CMe | S | Q1b | a bond | Me | a bond | NH | S | a bond | Q3e | OH |
| 4797 | CMe | S | Q1b | a bond | Me | a bond | NH | S | a bond | Q3f | OH |
| 4798 | CMe | S | Q1b | a bond | Me | a bond | NH | S | NH | Q3d | OH |
| 4799 | CMe | S | Q1b | a bond | Me | a bond | NH | S | NH | Q3e | OH |
| 4800 | CMe | S | Q1b | a bond | Me | a bond | NH | S | NH | Q3f | OH |
| 4801 | CMe | S | Q1c | a bond | Me | a bond | NH | O | a bond | Q3d | OH |
| 4802 | CMe | S | Q1c | a bond | Me | a bond | NH | O | a bond | Q3e | OH |
| 4803 | CMe | S | Q1c | a bond | Me | a bond | NH | O | a bond | Q3f | OH |
| 4804 | CMe | S | Q1c | a bond | Me | a bond | NH | O | NH | Q3d | OH |
| 4805 | CMe | S | Q1c | a bond | Me | a bond | NH | O | NH | Q3e | OH |
| 4806 | CMe | S | Q1c | a bond | Me | a bond | NH | O | NH | Q3f | OH |
| 4807 | CMe | S | Q1c | a bond | Me | a bond | NH | S | a bond | Q3d | OH |
| 4808 | CMe | S | Q1c | a bond | Me | a bond | NH | S | a bond | Q3e | OH |
| 4809 | CMe | S | Q1c | a bond | Me | a bond | NH | S | a bond | Q3f | OH |
| 4810 | CMe | S | Q1c | a bond | Me | a bond | NH | S | NH | Q3d | OH |
| 4811 | CMe | S | Q1c | a bond | Me | a bond | NH | S | NH | Q3e | OH |
| 4812 | CMe | S | Q1c | a bond | Me | a bond | NH | S | NH | Q3f | OH |
| 4813 | CMe | O | Q1a | a bond | Me | a bond | NH | O | a bond | Q3d | OH |
| 4814 | CMe | O | Q1a | a bond | Me | a bond | NH | O | a bond | Q3e | OH |
| 4815 | CMe | O | Q1a | a bond | Me | a bond | NH | O | a bond | Q3f | OH |
| 4816 | CMe | O | Q1a | a bond | Me | a bond | NH | O | NH | Q3d | OH |
| 4817 | CMe | O | Q1a | a bond | Me | a bond | NH | O | NH | Q3e | OH |
| 4818 | CMe | O | Q1a | a bond | Me | a bond | NH | O | NH | Q3f | OH |
| 4819 | CMe | O | Q1a | a bond | Me | a bond | NH | S | a bond | Q3d | OH |
| 4820 | CMe | O | Q1a | a bond | Me | a bond | NH | S | a bond | Q3e | OH |
| 4821 | CMe | O | Q1a | a bond | Me | a bond | NH | S | a bond | Q3f | OH |
| 4822 | CMe | O | Q1a | a bond | Me | a bond | NH | S | NH | Q3d | OH |
| 4823 | CMe | O | Q1a | a bond | Me | a bond | NH | S | NH | Q3e | OH |
| 4824 | CMe | O | Q1a | a bond | Me | a bond | NH | S | NH | Q3f | OH |
| 4825 | CMe | O | Q1b | a bond | Me | a bond | NH | O | a bond | Q3d | OH |
| 4826 | CMe | O | Q1b | a bond | Me | a bond | NH | O | a bond | Q3e | OH |
| 4827 | CMe | O | Q1b | a bond | Me | a bond | NH | O | a bond | Q3f | OH |
| 4828 | CMe | O | Q1b | a bond | Me | a bond | NH | O | NH | Q3d | OH |
| 4829 | CMe | O | Q1b | a bond | Me | a bond | NH | O | NH | Q3e | OH |
| 4830 | CMe | O | Q1b | a bond | Me | a bond | NH | O | NH | Q3f | OH |
| 4831 | CMe | O | Q1b | a bond | Me | a bond | NH | S | a bond | Q3d | OH |
| 4832 | CMe | O | Q1b | a bond | Me | a bond | NH | S | a bond | Q3e | OH |
| 4833 | CMe | O | Q1b | a bond | Me | a bond | NH | S | a bond | Q3f | OH |
| 4834 | CMe | O | Q1b | a bond | Me | a bond | NH | S | NH | Q3d | OH |
| 4835 | CMe | O | Q1b | a bond | Me | a bond | NH | S | NH | Q3e | OH |
| 4836 | CMe | O | Q1b | a bond | Me | a bond | NH | S | NH | Q3f | OH |

TABLE 1-continued

| No | A | B | R¹ | L¹ | R² | L² | L³ | Y | L⁴ | R³ | X |
|---|---|---|---|---|---|---|---|---|---|---|---|
| 4837 | CMe | O | Q1c | a bond | Me | a bond | NH | O | a bond | Q3d | OH |
| 4838 | CMe | O | Q1c | a bond | Me | a bond | NH | O | a bond | Q3e | OH |
| 4839 | CMe | O | Q1c | a bond | Me | a bond | NH | O | a bond | Q3f | OH |
| 4840 | CMe | O | Q1c | a bond | Me | a bond | NH | O | NH | Q3d | OH |
| 4841 | CMe | O | Q1c | a bond | Me | a bond | NH | O | NH | Q3e | OH |
| 4842 | CMe | O | Q1c | a bond | Me | a bond | NH | O | NH | Q3f | OH |
| 4843 | CMe | O | Q1c | a bond | Me | a bond | NH | S | a bond | Q3d | OH |
| 4844 | CMe | O | Q1c | a bond | Me | a bond | NH | S | a bond | Q3e | OH |
| 4845 | CMe | O | Q1c | a bond | Me | a bond | NH | S | a bond | Q3f | OH |
| 4846 | CMe | O | Q1c | a bond | Me | a bond | NH | S | NH | Q3d | OH |
| 4847 | CMe | O | Q1c | a bond | Me | a bond | NH | S | NH | Q3e | OH |
| 4848 | CMe | O | Q1c | a bond | Me | a bond | NH | S | NH | Q3f | OH |
| 4849 | N | NMe | Q1a | a bond | Me | a bond | NH | S | NH | Q3g | OH |
| 4850 | N | NMe | Q1a | a bond | Me | a bond | NH | S | NH | Q3h | OH |
| 4851 | N | NMe | Q1b | a bond | Me | a bond | NH | S | NH | Q3g | OH |
| 4852 | N | NMe | Q1b | a bond | Me | a bond | NH | S | NH | Q3h | OH |
| 4853 | N | NMe | Q1c | a bond | Me | a bond | NH | S | NH | Q3g | OH |
| 4854 | N | NMe | Q1c | a bond | Me | a bond | NH | S | NH | Q3h | OH |
| 4855 | N | NEt | Q1a | a bond | Me | a bond | NH | S | NH | Q3g | OH |
| 4856 | N | NEt | Q1a | a bond | Me | a bond | NH | S | NH | Q3h | OH |
| 4857 | N | NEt | Q1b | a bond | Me | a bond | NH | S | NH | Q3g | OH |
| 4858 | N | NEt | Q1b | a bond | Me | a bond | NH | S | NH | Q3h | OH |
| 4859 | N | NEt | Q1c | a bond | Me | a bond | NH | S | NH | Q3g | OH |
| 4860 | N | NEt | Q1c | a bond | Me | a bond | NH | S | NH | Q3h | OH |
| 4861 | N | S | Q1a | a bond | Me | a bond | NH | S | NH | Q3g | OH |
| 4862 | N | S | Q1a | a bond | Me | a bond | NH | S | NH | Q3h | OH |
| 4863 | N | S | Q1b | a bond | Me | a bond | NH | S | NH | Q3g | OH |
| 4864 | N | S | Q1b | a bond | Me | a bond | NH | S | NH | Q3h | OH |
| 4865 | N | S | Q1c | a bond | Me | a bond | NH | S | NH | Q3g | OH |
| 4866 | N | S | Q1c | a bond | Me | a bond | NH | S | NH | Q3h | OH |
| 4867 | N | O | Q1a | a bond | Me | a bond | NH | S | NH | Q3g | OH |
| 4868 | N | O | Q1a | a bond | Me | a bond | NH | S | NH | Q3h | OH |
| 4869 | N | O | Q1b | a bond | Me | a bond | NH | S | NH | Q3g | OH |
| 4870 | N | O | Q1b | a bond | Me | a bond | NH | S | NH | Q3h | OH |
| 4871 | N | O | Q1c | a bond | Me | a bond | NH | S | NH | Q3g | OH |
| 4872 | N | O | Q1c | a bond | Me | a bond | NH | S | NH | Q3h | OH |
| 4873 | CH | NMe | Q1a | a bond | Me | a bond | NH | S | NH | Q3g | OH |
| 4874 | CH | NMe | Q1a | a bond | Me | a bond | NH | S | NH | Q3h | OH |
| 4875 | CH | NMe | Q1b | a bond | Me | a bond | NH | S | NH | Q3g | OH |
| 4876 | CH | NMe | Q1b | a bond | Me | a bond | NH | S | NH | Q3h | OH |
| 4877 | CH | NMe | Q1c | a bond | Me | a bond | NH | S | NH | Q3g | OH |
| 4878 | CH | NMe | Q1c | a bond | Me | a bond | NH | S | NH | Q3h | OH |
| 4879 | CH | NEt | Q1a | a bond | Me | a bond | NH | S | NH | Q3g | OH |
| 4880 | CH | NEt | Q1a | a bond | Me | a bond | NH | S | NH | Q3h | OH |
| 4881 | CH | NEt | Q1b | a bond | Me | a bond | NH | S | NH | Q3g | OH |
| 4882 | CH | NEt | Q1b | a bond | Me | a bond | NH | S | NH | Q3h | OH |
| 4883 | CH | NEt | Q1c | a bond | Me | a bond | NH | S | NH | Q3g | OH |
| 4884 | CH | NEt | Q1c | a bond | Me | a bond | NH | S | NH | Q3h | OH |
| 4885 | CH | S | Q1a | a bond | Me | a bond | NH | S | NH | Q3g | OH |
| 4886 | CH | S | Q1a | a bond | Me | a bond | NH | S | NH | Q3h | OH |
| 4887 | CH | S | Q1b | a bond | Me | a bond | NH | S | NH | Q3g | OH |
| 4888 | CH | S | Q1b | a bond | Me | a bond | NH | S | NH | Q3h | OH |
| 4889 | CH | S | Q1c | a bond | Me | a bond | NH | Y | NH | Q3g | OH |
| 4890 | CH | S | Q1c | a bond | Me | a bond | NH | S | NH | Q3h | OH |
| 4891 | CH | O | Q1a | a bond | Me | a bond | NH | S | NH | Q3g | OH |
| 4892 | CH | O | Q1a | a bond | Me | a bond | NH | S | NH | Q3h | OH |
| 4893 | CH | O | Q1b | a bond | Me | a bond | NH | S | NH | Q3g | OH |
| 4894 | CH | O | Q1b | a bond | Me | a bond | NH | S | NH | Q3h | OH |
| 4895 | CH | O | Q1c | a bond | Me | a bond | NH | S | NH | Q3g | OH |
| 4896 | CH | O | Q1c | a bond | Me | a bond | NH | S | NH | Q3h | OH |
| 4897 | CMe | NMe | Q1a | a bond | Me | a bond | NH | S | NH | Q3g | OH |
| 4898 | CMe | NMe | Q1a | a bond | Me | a bond | NH | S | NH | Q3h | OH |
| 4899 | CMe | NMe | Q1b | a bond | Me | a bond | NH | S | NH | Q3g | OH |
| 4900 | CMe | NMe | Q1b | a bond | Me | a bond | NH | S | NH | Q3h | OH |
| 4901 | CMe | NMe | Q1c | a bond | Me | a bond | NH | S | NH | Q3g | OH |
| 4902 | CMe | NMe | Q1c | a bond | Me | a bond | NH | S | NH | Q3h | OH |
| 4903 | CMe | NEt | Q1a | a bond | Me | a bond | NH | S | NH | Q3g | OH |
| 4904 | CMe | NEt | Q1a | a bond | Me | a bond | NH | S | NH | Q3h | OH |
| 4905 | CMe | NEt | Q1b | a bond | Me | a bond | NH | S | NH | Q3g | OH |
| 4906 | CMe | NEt | Q1b | a bond | Me | a bond | NH | S | NH | Q3h | OH |
| 4907 | CMe | NEt | Q1c | a bond | Me | a bond | NH | S | NH | Q3g | OH |
| 4908 | CMe | NEt | Q1c | a bond | Me | a bond | NH | S | NH | Q3h | OH |
| 4909 | CMe | S | Q1a | a bond | Me | a bond | NH | S | NH | Q3g | OH |
| 4910 | CMe | S | Q1a | a bond | Me | a bond | NH | S | NH | Q3h | OH |
| 4911 | CMe | S | Q1b | a bond | Me | a bond | NH | S | NH | Q3g | OH |
| 4912 | CMe | S | Q1b | a bond | Me | a bond | NH | S | NH | Q3h | OH |
| 4913 | CMe | S | Q1c | a bond | Me | a bond | NH | S | NH | Q3g | OH |
| 4914 | CMe | S | Q1c | a bond | Me | a bond | NH | S | NH | Q3h | OH |

TABLE 1-continued

| No | A | B | $R^1$ | $L^1$ | $R^2$ | $L^2$ | $L^3$ | Y | $L^4$ | $R^3$ | X |
|---|---|---|---|---|---|---|---|---|---|---|---|
| 4915 | CMe | O | Q1a | a bond | Me | a bond | NH | S | NH | Q3g | OH |
| 4916 | CMe | O | Q1a | a bond | Me | a bond | NH | S | NH | Q3h | OH |
| 4917 | CMe | O | Q1b | a bond | Me | a bond | NH | S | NH | Q3g | OH |
| 4918 | CMe | O | Q1b | a bond | Me | a bond | NH | S | NH | Q3h | OH |
| 4919 | CMe | O | Q1c | a bond | Me | a bond | NH | S | NH | Q3g | OH |
| 4920 | CMe | O | Q1c | a bond | Me | a bond | NH | S | NH | Q3h | OH |
| 4921 | N | NMe | Q1a | a bond | Me | a bond | NH | O | a bond | Q3g | OH |
| 4922 | N | NMe | Q1a | a bond | Me | a bond | NH | O | a bond | Q3h | OH |
| 4923 | N | NMe | Q1b | a bond | Me | a bond | NH | O | a bond | Q3g | OH |
| 4924 | N | NMe | Q1b | a bond | Me | a bond | NH | O | a bond | Q3h | OH |
| 4925 | N | NMe | Q1c | a bond | Me | a bond | NH | O | a bond | Q3g | OH |
| 4926 | N | NMe | Q1c | a bond | Me | a bond | NH | O | a bond | Q3h | OH |
| 4927 | N | NEt | Q1a | a bond | Me | a bond | NH | O | a bond | Q3g | OH |
| 4928 | N | NEt | Q1a | a bond | Me | a bond | NH | O | a bond | Q3h | OH |
| 4929 | N | NEt | Q1b | a bond | Me | a bond | NH | O | a bond | Q3g | OH |
| 4930 | N | NEt | Q1b | a bond | Me | a bond | NH | O | a bond | Q3h | OH |
| 4931 | N | NEt | Q1c | a bond | Me | a bond | NH | O | a bond | Q3g | OH |
| 4932 | N | NEt | Q1c | a bond | Me | a bond | NH | O | a bond | Q3h | OH |
| 4933 | N | S | Q1a | a bond | Me | a bond | NH | O | a bond | Q3g | OH |
| 4934 | N | S | Q1a | a bond | Me | a bond | NH | O | a bond | Q3h | OH |
| 4935 | N | S | Q1b | a bond | Me | a bond | NH | O | a bond | Q3g | OH |
| 4936 | N | S | Q1b | a bond | Me | a bond | NH | O | a bond | Q3h | OH |
| 4937 | N | S | Q1c | a bond | Me | a bond | NH | O | a bond | Q3g | OH |
| 4938 | N | S | Q1c | a bond | Me | a bond | NH | O | a bond | Q3h | OH |
| 4939 | N | O | Q1a | a bond | Me | a bond | NH | O | a bond | Q3g | OH |
| 4940 | N | O | Q1a | a bond | Me | a bond | NH | O | a bond | Q3h | OH |
| 4941 | N | O | Q1b | a bond | Me | a bond | NH | O | a bond | Q3g | OH |
| 4942 | N | O | Q1b | a bond | Me | a bond | NH | O | a bond | Q3h | OH |
| 4943 | N | O | Q1c | a bond | Me | a bond | NH | O | a bond | Q3g | OH |
| 4944 | N | O | Q1c | a bond | Me | a bond | NH | O | a bond | Q3h | OH |
| 4945 | CH | NMe | Q1a | a bond | Me | a bond | NH | O | a bond | Q3g | OH |
| 4946 | CH | NMe | Q1a | a bond | Me | a bond | NH | O | a bond | Q3h | OH |
| 4947 | CH | NMe | Q1b | a bond | Me | a bond | NH | O | a bond | Q3g | OH |
| 4948 | CH | NMe | Q1b | a bond | Me | a bond | NH | O | a bond | Q3h | OH |
| 4949 | CH | NMe | Q1c | a bond | Me | a bond | NH | O | a bond | Q3g | OH |
| 4950 | CH | NMe | Q1c | a bond | Me | a bond | NH | O | a bond | Q3h | OH |
| 4951 | CH | NEt | Q1a | a bond | Me | a bond | NH | O | a bond | Q3g | OH |
| 4952 | CH | NEt | Q1a | a bond | Me | a bond | NH | O | a bond | Q3h | OH |
| 4953 | CH | NEt | Q1b | a bond | Me | a bond | NH | O | a bond | Q3g | OH |
| 4954 | CH | NEt | Q1b | a bond | Me | a bond | NH | O | a bond | Q3h | OH |
| 4955 | CH | NEt | Q1c | a bond | Me | a bond | NH | O | a bond | Q3g | OH |
| 4956 | CH | NEt | Q1c | a bond | Me | a bond | NH | O | a bond | Q3h | OH |
| 4957 | CH | S | Q1a | a bond | Me | a bond | NH | O | a bond | Q3g | OH |
| 4958 | CH | S | Q1a | a bond | Me | a bond | NH | O | a bond | Q3h | OH |
| 4959 | CH | S | Q1b | a bond | Me | a bond | NH | O | a bond | Q3g | OH |
| 4960 | CH | S | Q1b | a bond | Me | a bond | NH | O | a bond | Q3h | OH |
| 4961 | CH | S | Q1c | a bond | Me | a bond | NH | O | a bond | Q3g | OH |
| 4962 | CH | S | Q1c | a bond | Me | a bond | NH | O | a bond | Q3h | OH |
| 4963 | CH | O | Q1a | a bond | Me | a bond | NH | O | a bond | Q3g | OH |
| 4964 | CH | O | Q1a | a bond | Me | a bond | NH | O | a bond | Q3h | OH |
| 4965 | CH | O | Q1b | a bond | Me | a bond | NH | O | a bond | Q3g | OH |
| 4966 | CH | O | Q1b | a bond | Me | a bond | NH | O | a bond | Q3h | OH |
| 4967 | CH | O | Q1c | a bond | Me | a bond | NH | O | a bond | Q3g | OH |
| 4968 | CH | O | Q1c | a bond | Me | a bond | NH | O | a bond | Q3h | OH |
| 4969 | CMe | NMe | Q1a | a bond | Me | a bond | NH | O | a bond | Q3g | OH |
| 4970 | CMe | NMe | Q1a | a bond | Me | a bond | NH | O | a bond | Q3h | OH |
| 4971 | CMe | NMe | Q1b | a bond | Me | a bond | NH | O | a bond | Q3g | OH |
| 4972 | CMe | NMe | Q1b | a bond | Me | a bond | NH | O | a bond | Q3h | OH |
| 4973 | CMe | NMe | Q1c | a bond | Me | a bond | NH | O | a bond | Q3g | OH |
| 4974 | CMe | NMe | Q1c | a bond | Me | a bond | NH | O | a bond | Q3h | OH |
| 4975 | CMe | NEt | Q1a | a bond | Me | a bond | NH | O | a bond | Q3g | OH |
| 4976 | CMe | NEt | Q1a | a bond | Me | a bond | NH | O | a bond | Q3h | OH |
| 4977 | CMe | NEt | Q1b | a bond | Me | a bond | NH | O | a bond | Q3g | OH |
| 4978 | CMe | NEt | Q1b | a bond | Me | a bond | NH | O | a bond | Q3h | OH |
| 4979 | CMe | NEt | Q1c | a bond | Me | a bond | NH | O | a bond | Q3g | OH |
| 4980 | CMe | NEt | Q1c | a bond | Me | a bond | NH | O | a bond | Q3h | OH |
| 4981 | CMe | S | Q1a | a bond | Me | a bond | NH | O | a bond | Q3g | OH |
| 4982 | CMe | S | Q1a | a bond | Me | a bond | NH | O | a bond | Q3h | OH |
| 4983 | CMe | S | Q1b | a bond | Me | a bond | NH | O | a bond | Q3g | OH |
| 4984 | CMe | S | Q1b | a bond | Me | a bond | NH | O | a bond | Q3h | OH |
| 4985 | CMe | S | Q1c | a bond | Me | a bond | NH | O | a bond | Q3g | OH |
| 4986 | CMe | S | Q1c | a bond | Me | a bond | NH | O | a bond | Q3h | OH |
| 4987 | CMe | O | Q1a | a bond | Me | a bond | NH | O | a bond | Q3g | OH |
| 4988 | CMe | O | Q1a | a bond | Me | a bond | NH | O | a bond | Q3h | OH |
| 4989 | CMe | O | Q1b | a bond | Me | a bond | NH | O | a bond | Q3g | OH |
| 4990 | CMe | O | Q1b | a bond | Me | a bond | NH | O | a bond | Q3h | OH |
| 4991 | CMe | O | Q1c | a bond | Me | a bond | NH | O | a bond | Q3g | OH |
| 4992 | CMe | O | Q1c | a bond | Me | a bond | NH | O | a bond | Q3h | OH |

TABLE 1-continued

| No | A | B | R¹ | L¹ | R² | L² | L³ | Y | L⁴ | R³ | X |
|---|---|---|---|---|---|---|---|---|---|---|---|
| 4992 | CMe | O | Q1c | a bond | Me | a bond | NH | O | a bond | Q3h | OH |
| 4993 | CH | NH | Q1a | a bond | Me | a bond | NH | S | NH | Q3a | OH |
| 4994 | CH | NH | Q1a | a bond | Me | a bond | NH | S | NH | Q3b | OH |
| 4995 | CH | NH | Q1a | a bond | Me | a bond | NH | S | NH | Q3c | OH |
| 4996 | CH | NH | Q1a | a bond | Me | a bond | NH | S | a bond | Q3a | OH |
| 4997 | CH | NH | Q1a | a bond | Me | a bond | NH | S | a bond | Q3b | OH |
| 4998 | CH | NH | Q1a | a bond | Me | a bond | NH | S | a bond | Q3c | OH |
| 4999 | CH | NH | Q1a | a bond | Me | a bond | NH | O | NH | Q3a | OH |
| 5000 | CH | NH | Q1a | a bond | Me | a bond | NH | O | NH | Q3b | OH |
| 5001 | CH | NH | Q1a | a bond | Me | a bond | NH | O | NH | Q3c | OH |
| 5002 | CH | NH | Q1a | a bond | Me | a bond | NH | O | a bond | Q3a | OH |
| 5003 | CH | NH | Q1a | a bond | Me | a bond | NH | O | a bond | Q3b | OH |
| 5004 | CH | NH | Q1a | a bond | Me | a bond | NH | O | a bond | Q3c | OH |
| 5005 | CH | NH | Q1a | a bond | H | a bond | NH | S | NH | Q3a | OH |
| 5006 | CH | NH | Q1a | a bond | H | a bond | NH | S | NH | Q3b | OH |
| 5007 | CH | NH | Q1a | a bond | H | a bond | NH | S | NH | Q3c | OH |
| 5008 | CH | NH | Q1a | a bond | H | a bond | NH | S | a bond | Q3a | OH |
| 5009 | CH | NH | Q1a | a bond | H | a bond | NH | S | a bond | Q3b | OH |
| 5010 | CH | NH | Q1a | a bond | H | a bond | NH | S | a bond | Q3c | OH |
| 5011 | CH | NH | Q1a | a bond | H | a bond | NH | O | NH | Q3a | OH |
| 5012 | CH | NH | Q1a | a bond | H | a bond | NH | O | NH | Q3b | OH |
| 5013 | CH | NH | Q1a | a bond | H | a bond | NH | O | NH | Q3c | OH |
| 5014 | CH | NH | Q1a | a bond | H | a bond | NH | O | a bond | Q3a | OH |
| 5015 | CH | NH | Q1a | a bond | H | a bond | NH | O | a bond | Q3b | OH |
| 5016 | CH | NH | Q1a | a bond | H | a bond | NH | O | a bond | Q3c | OH |
| 5017 | CH | NH | Q1b | a bond | Me | a bond | NH | S | NH | Q3a | OH |
| 5018 | CH | NH | Q1b | a bond | Me | a bond | NH | S | NH | Q3b | OH |
| 5019 | CH | NH | Q1b | a bond | Me | a bond | NH | S | NH | Q3c | OH |
| 5020 | CH | NH | Q1b | a bond | Me | a bond | NH | S | a bond | Q3a | OH |
| 5021 | CH | NH | Q1b | a bond | Me | a bond | NH | S | a bond | Q3b | OH |
| 5022 | CH | NH | Q1b | a bond | Me | a bond | NH | S | a bond | Q3c | OH |
| 5023 | CH | NH | Q1b | a bond | Me | a bond | NH | O | NH | Q3a | OH |
| 5024 | CH | NH | Q1b | a bond | Me | a bond | NH | O | NH | Q3b | OH |
| 5025 | CH | NH | Q1b | a bond | Me | a bond | NH | O | NH | Q3c | OH |
| 5026 | CH | NH | Q1b | a bond | Me | a bond | NH | O | a bond | Q3a | OH |
| 5027 | CH | NH | Q1b | a bond | Me | a bond | NH | O | a bond | Q3b | OH |
| 5028 | CH | NH | Q1b | a bond | Me | a bond | NH | O | a bond | Q3c | OH |
| 5029 | CH | NH | Q1b | a bond | H | a bond | NH | S | NH | Q3a | OH |
| 5030 | CH | NH | Q1b | a bond | H | a bond | NH | S | NH | Q3b | OH |
| 5031 | CH | NH | Q1b | a bond | H | a bond | NH | S | NH | Q3c | OH |
| 5032 | CH | NH | Q1b | a bond | H | a bond | NH | S | a bond | Q3a | OH |
| 5033 | CH | NH | Q1b | a bond | H | a bond | NH | S | a bond | Q3b | OH |
| 5034 | CH | NH | Q1b | a bond | H | a bond | NH | S | a bond | Q3c | OH |
| 5035 | CH | NH | Q1b | a bond | H | a bond | NH | O | NH | Q3a | OH |
| 5036 | CH | NH | Q1b | a bond | H | a bond | NH | O | NH | Q3b | OH |
| 5037 | CH | NH | Q1b | a bond | H | a bond | NH | O | NH | Q3c | OH |
| 5038 | CH | NH | Q1b | a bond | H | a bond | NH | O | a bond | Q3a | OH |
| 5039 | CH | NH | Q1b | a bond | H | a bond | NH | O | a bond | Q3b | OH |
| 5040 | CH | NH | Q1b | a bond | H | a bond | NH | O | a bond | Q3c | OH |
| 5041 | CH | NH | Q1c | a bond | Me | a bond | NH | S | NH | Q3a | OH |
| 5042 | CH | NH | Q1c | a bond | Me | a bond | NH | S | NH | Q3b | OH |
| 5043 | CH | NH | Q1c | a bond | Me | a bond | NH | S | NH | Q3c | OH |
| 5044 | CH | NH | Q1c | a bond | Me | a bond | NH | S | a bond | Q3a | OH |
| 5045 | CH | NH | Q1c | a bond | Me | a bond | NH | S | a bond | Q3b | OH |
| 5046 | CH | NH | Q1c | a bond | Me | a bond | NH | S | a bond | Q3c | OH |
| 5047 | CH | NH | Q1c | a bond | Me | a bond | NH | O | NH | Q3a | OH |
| 5048 | CH | NH | Q1c | a bond | Me | a bond | NH | O | NH | Q3b | OH |
| 5049 | CH | NH | Q1c | a bond | Me | a bond | NH | O | NH | Q3c | OH |
| 5050 | CH | NH | Q1c | a bond | Me | a bond | NH | O | a bond | Q3a | OH |
| 5051 | CH | NH | Q1c | a bond | Me | a bond | NH | O | a bond | Q3b | OH |
| 5052 | CH | NH | Q1c | a bond | Me | a bond | NH | O | a bond | Q3c | OH |
| 5053 | CH | NH | Q1c | a bond | H | a bond | NH | S | NH | Q3a | OH |
| 5054 | CH | NH | Q1c | a bond | H | a bond | NH | S | NH | Q3b | OH |
| 5055 | CH | NH | Q1c | a bond | H | a bond | NH | S | NH | Q3c | OH |
| 5056 | CH | NH | Q1c | a bond | H | a bond | NH | S | a bond | Q3a | OH |
| 5057 | CH | NH | Q1c | a bond | H | a bond | NH | S | a bond | Q3b | OH |
| 5058 | CH | NH | Q1c | a bond | H | a bond | NH | S | a bond | Q3c | OH |
| 5059 | CH | NH | Q1c | a bond | H | a bond | NH | O | NH | Q3a | OH |
| 5060 | CH | NH | Q1c | a bond | H | a bond | NH | O | NH | Q3b | OH |
| 5061 | CH | NH | Q1c | a bond | H | a bond | NH | O | NH | Q3c | OH |
| 5062 | CH | NH | Q1c | a bond | H | a bond | NH | O | a bond | Q3a | OH |
| 5063 | CH | NH | Q1c | a bond | H | a bond | NH | O | a bond | Q3b | OH |
| 5064 | CH | NH | Q1c | a bond | H | a bond | NH | O | a bond | Q3c | OH |
| 5065 | CH | NH | Q1d | a bond | Me | a bond | NH | S | NH | Q3a | OH |
| 5066 | CH | NH | Q1d | a bond | Me | a bond | NH | S | NH | Q3b | OH |
| 5067 | CH | NH | Q1d | a bond | Me | a bond | NH | S | NH | Q3c | OH |
| 5068 | CH | NH | Q1d | a bond | Me | a bond | NH | S | a bond | Q3a | OH |
| 5069 | CH | NH | Q1d | a bond | Me | a bond | NH | S | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5070 | CH | NH | Q1d | a bond | Me | a bond | NH | S | a bond | Q3c | OH |
| 5071 | CH | NH | Q1d | a bond | Me | a bond | NH | O | NH | Q3a | OH |
| 5072 | CH | NH | Q1d | a bond | Me | a bond | NH | O | NH | Q3b | OH |
| 5073 | CH | NH | Q1d | a bond | Me | a bond | NH | O | NH | Q3c | OH |
| 5074 | CH | NH | Q1d | a bond | Me | a bond | NH | O | a bond | Q3a | OH |
| 5075 | CH | NH | Q1d | a bond | Me | a bond | NH | O | a bond | Q3b | OH |
| 5076 | CH | NH | Q1d | a bond | Me | a bond | NH | O | a bond | Q3c | OH |
| 5077 | CH | NH | Q1d | a bond | H | a bond | NH | S | NH | Q3a | OH |
| 5078 | CH | NH | Q1d | a bond | H | a bond | NH | S | NH | Q3b | OH |
| 5079 | CH | NH | Q1d | a bond | H | a bond | NH | S | NH | Q3c | OH |
| 5080 | CH | NH | Q1d | a bond | H | a bond | NH | S | a bond | Q3a | OH |
| 5081 | CH | NH | Q1d | a bond | H | a bond | NH | S | a bond | Q3b | OH |
| 5082 | CH | NH | Q1d | a bond | H | a bond | NH | S | a bond | Q3c | OH |
| 5083 | CH | NH | Q1d | a bond | H | a bond | NH | O | NH | Q3a | OH |
| 5084 | CH | NH | Q1d | a bond | H | a bond | NH | O | NH | Q3b | OH |
| 5085 | CH | NH | Q1d | a bond | H | a bond | NH | O | NH | Q3c | OH |
| 5086 | CH | NH | Q1d | a bond | H | a bond | NH | O | a bond | Q3a | OH |
| 5087 | CH | NH | Q1d | a bond | H | a bond | NH | O | a bond | Q3b | OH |
| 5088 | CH | NH | Q1d | a bond | H | a bond | NH | O | a bond | Q3c | OH |
| 5089 | CH | NH | Q1e | a bond | Me | a bond | NH | S | NH | Q3a | OH |
| 5090 | CH | NH | Q1e | a bond | Me | a bond | NH | S | NH | Q3b | OH |
| 5091 | CH | NH | Q1e | a bond | Me | a bond | NH | S | NH | Q3c | OH |
| 5092 | CH | NH | Q1e | a bond | Me | a bond | NH | S | a bond | Q3a | OH |
| 5093 | CH | NH | Q1e | a bond | Me | a bond | NH | S | a bond | Q3b | OH |
| 5094 | CH | NH | Q1e | a bond | Me | a bond | NH | S | a bond | Q3c | OH |
| 5095 | CH | NH | Q1e | a bond | Me | a bond | NH | O | NH | Q3a | OH |
| 5096 | CH | NH | Q1e | a bond | Me | a bond | NH | O | NH | Q3b | OH |
| 5097 | CH | NH | Q1e | a bond | Me | a bond | NH | O | NH | Q3c | OH |
| 5098 | CH | NH | Q1e | a bond | Me | a bond | NH | O | a bond | Q3a | OH |
| 5099 | CH | NH | Q1e | a bond | Me | a bond | NH | O | a bond | Q3b | OH |
| 5100 | CH | NH | Q1e | a bond | Me | a bond | NH | O | a bond | Q3c | OH |
| 5101 | CH | NH | Q1e | a bond | H | a bond | NH | S | NH | Q3a | OH |
| 5102 | CH | NH | Q1e | a bond | H | a bond | NH | S | NH | Q3b | OH |
| 5103 | CH | NH | Q1e | a bond | H | a bond | NH | S | NH | Q3c | OH |
| 5104 | CH | NH | Q1e | a bond | H | a bond | NH | S | a bond | Q3a | OH |
| 5105 | CH | NH | Q1e | a bond | H | a bond | NH | S | a bond | Q3b | OH |
| 5106 | CH | NH | Q1e | a bond | H | a bond | NH | S | a bond | Q3c | OH |
| 5107 | CH | NH | Q1e | a bond | H | a bond | NH | O | NH | Q3a | OH |
| 5108 | CH | NH | Q1e | a bond | H | a bond | NH | O | NH | Q3b | OH |
| 5109 | CH | NH | Q1e | a bond | H | a bond | NH | O | NH | Q3c | OH |
| 5110 | CH | NH | Q1e | a bond | H | a bond | NH | O | a bond | Q3a | OH |
| 5111 | CH | NH | Q1e | a bond | H | a bond | NH | O | a bond | Q3b | OH |
| 5112 | CH | NH | Q1e | a bond | H | a bond | NH | O | a bond | Q3c | OH |
| 5113 | CH | NH | Q1f | a bond | Me | a bond | NH | S | NH | Q3a | OH |
| 5114 | CH | NH | Q1f | a bond | Me | a bond | NH | S | NH | Q3b | OH |
| 5115 | CH | NH | Q1f | a bond | Me | a bond | NH | S | NH | Q3c | OH |
| 5116 | CH | NH | Q1f | a bond | Me | a bond | NH | S | a bond | Q3a | OH |
| 5117 | CH | NH | Q1f | a bond | Me | a bond | NH | S | a bond | Q3b | OH |
| 5118 | CH | NH | Q1f | a bond | Me | a bond | NH | S | a bond | Q3c | OH |
| 5119 | CH | NH | Q1f | a bond | Me | a bond | NH | O | NH | Q3a | OH |
| 5120 | CH | NH | Q1f | a bond | Me | a bond | NH | O | NH | Q3b | OH |
| 5121 | CH | NH | Q1f | a bond | Me | a bond | NH | O | NH | Q3c | OH |
| 5122 | CH | NH | Q1f | a bond | Me | a bond | NH | O | a bond | Q3a | OH |
| 5123 | CH | NH | Q1f | a bond | Me | a bond | NH | O | a bond | Q3b | OH |
| 5124 | CH | NH | Q1f | a bond | Me | a bond | NH | O | a bond | Q3c | OH |
| 5125 | CH | NH | Q1f | a bond | H | a bond | NH | S | NH | Q3a | OH |
| 5126 | CH | NH | Q1f | a bond | H | a bond | NH | S | NH | Q3b | OH |
| 5127 | CH | NH | Q1f | a bond | H | a bond | NH | S | NH | Q3c | OH |
| 5128 | CH | NH | Q1f | a bond | H | a bond | NH | S | a bond | Q3a | OH |
| 5129 | CH | NH | Q1f | a bond | H | a bond | NH | S | a bond | Q3b | OH |
| 5130 | CH | NH | Q1f | a bond | H | a bond | NH | S | a bond | Q3c | OH |
| 5131 | CH | NH | Q1f | a bond | H | a bond | NH | O | NH | Q3a | OH |
| 5132 | CH | NH | Q1f | a bond | H | a bond | NH | O | NH | Q3b | OH |
| 5133 | CH | NH | Q1f | a bond | H | a bond | NH | O | NH | Q3c | OH |
| 5134 | CH | NH | Q1f | a bond | H | a bond | NH | O | a bond | Q3a | OH |
| 5135 | CH | NH | Q1f | a bond | H | a bond | NH | O | a bond | Q3b | OH |
| 5136 | CH | NH | Q1f | a bond | H | a bond | NH | O | a bond | Q3c | OH |
| 5137 | CH | NH | Q1g | a bond | Me | a bond | NH | S | NH | Q3a | OH |
| 5138 | CH | NH | Q1g | a bond | Me | a bond | NH | S | NH | Q3b | OH |
| 5139 | CH | NH | Q1g | a bond | Me | a bond | NH | S | NH | Q3c | OH |
| 5140 | CH | NH | Q1g | a bond | Me | a bond | NH | S | a bond | Q3a | OH |
| 5141 | CH | NH | Q1g | a bond | Me | a bond | NH | S | a bond | Q3b | OH |
| 5142 | CH | NH | Q1g | a bond | Me | a bond | NH | S | a bond | Q3c | OH |
| 5143 | CH | NH | Q1g | a bond | Me | a bond | NH | O | NH | Q3a | OH |
| 5144 | CH | NH | Q1g | a bond | Me | a bond | NH | O | NH | Q3b | OH |
| 5145 | CH | NH | Q1g | a bond | Me | a bond | NH | O | NH | Q3c | OH |
| 5146 | CH | NH | Q1g | a bond | Me | a bond | NH | O | a bond | Q3a | OH |
| 5147 | CH | NH | Q1g | a bond | Me | a bond | NH | O | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5148 | CH | NH | Q1g | a bond | Me | a bond | NH | O | a bond | Q3c | OH |
| 5149 | CH | NH | Q1g | a bond | H | a bond | NH | S | NH | Q3a | OH |
| 5150 | CH | NH | Q1g | a bond | H | a bond | NH | S | NH | Q3b | OH |
| 5151 | CH | NH | Q1g | a bond | H | a bond | NH | S | NH | Q3c | OH |
| 5152 | CH | NH | Q1g | a bond | H | a bond | NH | S | a bond | Q3a | OH |
| 5153 | CH | NH | Q1g | a bond | H | a bond | NH | S | a bond | Q3b | OH |
| 5154 | CH | NH | Q1g | a bond | H | a bond | NH | S | a bond | Q3c | OH |
| 5155 | CH | NH | Q1g | a bond | H | a bond | NH | O | NH | Q3a | OH |
| 5156 | CH | NH | Q1g | a bond | H | a bond | NH | O | NH | Q3b | OH |
| 5157 | CH | NH | Q1g | a bond | H | a bond | NH | O | NH | Q3c | OH |
| 5158 | CH | NH | Q1g | a bond | H | a bond | NH | O | a bond | Q3a | OH |
| 5159 | CH | NH | Q1g | a bond | H | a bond | NH | O | a bond | Q3b | OH |
| 5160 | CH | NH | Q1g | a bond | H | a bond | NH | O | a bond | Q3c | OH |
| 5161 | CH | NH | Q1h | a bond | Me | a bond | NH | S | NH | Q3a | OH |
| 5162 | CH | NH | Q1h | a bond | Me | a bond | NH | S | NH | Q3b | OH |
| 5163 | CH | NH | Q1h | a bond | Me | a bond | NH | S | NH | Q3c | OH |
| 5164 | CH | NH | Q1h | a bond | Me | a bond | NH | S | a bond | Q3a | OH |
| 5165 | CH | NH | Q1h | a bond | Me | a bond | NH | S | a bond | Q3b | OH |
| 5166 | CH | NH | Q1h | a bond | Me | a bond | NH | S | a bond | Q3c | OH |
| 5167 | CH | NH | Q1h | a bond | Me | a bond | NH | O | NH | Q3a | OH |
| 5168 | CH | NH | Q1h | a bond | Me | a bond | NH | O | NH | Q3b | OH |
| 5169 | CH | NH | Q1h | a bond | Me | a bond | NH | O | NH | Q3c | OH |
| 5170 | CH | NH | Q1h | a bond | Me | a bond | NH | O | a bond | Q3a | OH |
| 5171 | CH | NH | Q1h | a bond | Me | a bond | NH | O | a bond | Q3b | OH |
| 5172 | CH | NH | Q1h | a bond | Me | a bond | NH | O | a bond | Q3c | OH |
| 5173 | CH | NH | Q1h | a bond | H | a bond | NH | S | NH | Q3a | OH |
| 5174 | CH | NH | Q1h | a bond | H | a bond | NH | S | NH | Q3b | OH |
| 5175 | CH | NH | Q1h | a bond | H | a bond | NH | S | NH | Q3c | OH |
| 5176 | CH | NH | Q1h | a bond | H | a bond | NH | S | a bond | Q3a | OH |
| 5177 | CH | NH | Q1h | a bond | H | a bond | NH | S | a bond | Q3b | OH |
| 5178 | CH | NH | Q1h | a bond | H | a bond | NH | S | a bond | Q3c | OH |
| 5179 | CH | NH | Q1h | a bond | H | a bond | NH | O | NH | Q3a | OH |
| 5180 | CH | NH | Q1h | a bond | H | a bond | NH | O | NH | Q3b | OH |
| 5181 | CH | NH | Q1h | a bond | H | a bond | NH | O | NH | Q3c | OH |
| 5182 | CH | NH | Q1h | a bond | H | a bond | NH | O | a bond | Q3a | OH |
| 5183 | CH | NH | Q1h | a bond | H | a bond | NH | O | a bond | Q3b | OH |
| 5184 | CH | NH | Q1h | a bond | H | a bond | NH | O | a bond | Q3c | OH |
| 5185 | CH | NH | Q1i | a bond | Me | a bond | NH | S | NH | Q3a | OH |
| 5186 | CH | NH | Q1i | a bond | Me | a bond | NH | S | NH | Q3b | OH |
| 5187 | CH | NH | Q1i | a bond | Me | a bond | NH | S | NH | Q3c | OH |
| 5188 | CH | NH | Q1i | a bond | Me | a bond | NH | S | a bond | Q3a | OH |
| 5189 | CH | NH | Q1i | a bond | Me | a bond | NH | S | a bond | Q3b | OH |
| 5190 | CH | NH | Q1i | a bond | Me | a bond | NH | S | a bond | Q3c | OH |
| 5191 | CH | NH | Q1i | a bond | Me | a bond | NH | O | NH | Q3a | OH |
| 5192 | CH | NH | Q1i | a bond | Me | a bond | NH | O | NH | Q3b | OH |
| 5193 | CH | NH | Q1i | a bond | Me | a bond | NH | O | NH | Q3c | OH |
| 5194 | CH | NH | Q1i | a bond | Me | a bond | NH | O | a bond | Q3a | OH |
| 5195 | CH | NH | Q1i | a bond | Me | a bond | NH | O | a bond | Q3b | OH |
| 5196 | CH | NH | Q1i | a bond | Me | a bond | NH | O | a bond | Q3c | OH |
| 5197 | CH | NH | Q1i | a bond | H | a bond | NH | S | NH | Q3a | OH |
| 5198 | CH | NH | Q1i | a bond | H | a bond | NH | S | NH | Q3b | OH |
| 5199 | CH | NH | Q1i | a bond | H | a bond | NH | S | NH | Q3c | OH |
| 5200 | CH | NH | Q1i | a bond | H | a bond | NH | S | a bond | Q3a | OH |
| 5201 | CH | NH | Q1i | a bond | H | a bond | NH | S | a bond | Q3b | OH |
| 5202 | CH | NH | Q1i | a bond | H | a bond | NH | S | a bond | Q3c | OH |
| 5203 | CH | NH | Q1i | a bond | H | a bond | NH | O | NH | Q3a | OH |
| 5204 | CH | NH | Q1i | a bond | H | a bond | NH | O | NH | Q3b | OH |
| 5205 | CH | NH | Q1i | a bond | H | a bond | NH | O | NH | Q3c | OH |
| 5206 | CH | NH | Q1i | a bond | H | a bond | NH | O | a bond | Q3a | OH |
| 5207 | CH | NH | Q1i | a bond | H | a bond | NH | O | a bond | Q3b | OH |
| 5208 | CH | NH | Q1i | a bond | H | a bond | NH | O | a bond | Q3c | OH |
| 5209 | CH | NH | Q1j | a bond | Me | a bond | NH | S | NH | Q3a | OH |
| 5210 | CH | NH | Q1j | a bond | Me | a bond | NH | S | NH | Q3b | OH |
| 5211 | CH | NH | Q1j | a bond | Me | a bond | NH | S | NH | Q3c | OH |
| 5212 | CH | NH | Q1j | a bond | Me | a bond | NH | S | a bond | Q3a | OH |
| 5213 | CH | NH | Q1j | a bond | Me | a bond | NH | S | a bond | Q3b | OH |
| 5214 | CH | NH | Q1j | a bond | Me | a bond | NH | S | a bond | Q3c | OH |
| 5215 | CH | NH | Q1j | a bond | Me | a bond | NH | O | NH | Q3a | OH |
| 5216 | CH | NH | Q1j | a bond | Me | a bond | NH | O | NH | Q3b | OH |
| 5217 | CH | NH | Q1j | a bond | Me | a bond | NH | O | NH | Q3c | OH |
| 5218 | CH | NH | Q1j | a bond | Me | a bond | NH | O | a bond | Q3a | OH |
| 5219 | CH | NH | Q1j | a bond | Me | a bond | NH | O | a bond | Q3b | OH |
| 5220 | CH | NH | Q1j | a bond | Me | a bond | NH | O | a bond | Q3c | OH |
| 5221 | CH | NH | Q1j | a bond | H | a bond | NH | S | NH | Q3a | OH |
| 5222 | CH | NH | Q1j | a bond | H | a bond | NH | S | NH | Q3b | OH |
| 5223 | CH | NH | Q1j | a bond | H | a bond | NH | S | NH | Q3c | OH |
| 5224 | CH | NH | Q1j | a bond | H | a bond | NH | S | a bond | Q3a | OH |
| 5225 | CH | NH | Q1j | a bond | H | a bond | NH | S | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5226 | CH | NH | Q1j | a bond | H | a bond | NH | S | a bond | Q3c | OH |
| 5227 | CH | NH | Q1j | a bond | H | a bond | NH | O | NH | Q3a | OH |
| 5228 | CH | NH | Q1j | a bond | H | a bond | NH | O | NH | Q3b | OH |
| 5229 | CH | NH | Q1j | a bond | H | a bond | NH | O | NH | Q3c | OH |
| 5230 | CH | NH | Q1j | a bond | H | a bond | NH | O | a bond | Q3a | OH |
| 5231 | CH | NH | Q1j | a bond | H | a bond | NH | O | a bond | Q3b | OH |
| 5232 | CH | NH | Q1j | a bond | H | a bond | NH | O | a bond | Q3c | OH |
| 5233 | CMe | NH | Q1a | a bond | Me | a bond | NH | S | NH | Q3a | OH |
| 5234 | CMe | NH | Q1a | a bond | Me | a bond | NH | S | NH | Q3b | OH |
| 5235 | CMe | NH | Q1a | a bond | Me | a bond | NH | S | NH | Q3c | OH |
| 5236 | CMe | NH | Q1a | a bond | Me | a bond | NH | S | a bond | Q3a | OH |
| 5237 | CMe | NH | Q1a | a bond | Me | a bond | NH | S | a bond | Q3b | OH |
| 5238 | CMe | NH | Q1a | a bond | Me | a bond | NH | S | a bond | Q3c | OH |
| 5239 | CMe | NH | Q1a | a bond | Me | a bond | NH | O | NH | Q3a | OH |
| 5240 | CMe | NH | Q1a | a bond | Me | a bond | NH | O | NH | Q3b | OH |
| 5241 | CMe | NH | Q1a | a bond | Me | a bond | NH | O | NH | Q3c | OH |
| 5242 | CMe | NH | Q1a | a bond | Me | a bond | NH | O | a bond | Q3a | OH |
| 5243 | CMe | NH | Q1a | a bond | Me | a bond | NH | O | a bond | Q3b | OH |
| 5244 | CMe | NH | Q1a | a bond | Me | a bond | NH | O | a bond | Q3c | OH |
| 5245 | CMe | NH | Q1a | a bond | H | a bond | NH | S | NH | Q3a | OH |
| 5246 | CMe | NH | Q1a | a bond | H | a bond | NH | S | NH | Q3b | OH |
| 5247 | CMe | NH | Q1a | a bond | H | a bond | NH | S | NH | Q3c | OH |
| 5248 | CMe | NH | Q1a | a bond | H | a bond | NH | S | a bond | Q3a | OH |
| 5249 | CMe | NH | Q1a | a bond | H | a bond | NH | S | a bond | Q3b | OH |
| 5250 | CMe | NH | Q1a | a bond | H | a bond | NH | S | a bond | Q3c | OH |
| 5251 | CMe | NH | Q1a | a bond | H | a bond | NH | O | NH | Q3a | OH |
| 5252 | CMe | NH | Q1a | a bond | H | a bond | NH | O | NH | Q3b | OH |
| 5253 | CMe | NH | Q1a | a bond | H | a bond | NH | O | NH | Q3c | OH |
| 5254 | CMe | NH | Q1a | a bond | H | a bond | NH | O | a bond | Q3a | OH |
| 5255 | CMe | NH | Q1a | a bond | H | a bond | NH | O | a bond | Q3b | OH |
| 5256 | CMe | NH | Q1a | a bond | H | a bond | NH | O | a bond | Q3c | OH |
| 5257 | CMe | NH | Q1b | a bond | Me | a bond | NH | S | NH | Q3a | OH |
| 5258 | CMe | NH | Q1b | a bond | Me | a bond | NH | S | NH | Q3b | OH |
| 5259 | CMe | NH | Q1b | a bond | Me | a bond | NH | S | NH | Q3c | OH |
| 5260 | CMe | NH | Q1b | a bond | Me | a bond | NH | S | a bond | Q3a | OH |
| 5261 | CMe | NH | Q1b | a bond | Me | a bond | NH | S | a bond | Q3b | OH |
| 5262 | CMe | NH | Q1b | a bond | Me | a bond | NH | S | a bond | Q3c | OH |
| 5263 | CMe | NH | Q1b | a bond | Me | a bond | NH | O | NH | Q3a | OH |
| 5264 | CMe | NH | Q1b | a bond | Me | a bond | NH | O | NH | Q3b | OH |
| 5265 | CMe | NH | Q1b | a bond | Me | a bond | NH | O | NH | Q3c | OH |
| 5266 | CMe | NH | Q1b | a bond | Me | a bond | NH | O | a bond | Q3a | OH |
| 5267 | CMe | NH | Q1b | a bond | Me | a bond | NH | O | a bond | Q3b | OH |
| 5268 | CMe | NH | Q1b | a bond | Me | a bond | NH | O | a bond | Q3c | OH |
| 5269 | CMe | NH | Q1b | a bond | H | a bond | NH | S | NH | Q3a | OH |
| 5270 | CMe | NH | Q1b | a bond | H | a bond | NH | S | NH | Q3b | OH |
| 5271 | CMe | NH | Q1b | a bond | H | a bond | NH | S | NH | Q3c | OH |
| 5272 | CMe | NH | Q1b | a bond | H | a bond | NH | S | a bond | Q3a | OH |
| 5273 | CMe | NH | Q1b | a bond | H | a bond | NH | S | a bond | Q3b | OH |
| 5274 | CMe | NH | Q1b | a bond | H | a bond | NH | S | a bond | Q3c | OH |
| 5275 | CMe | NH | Q1b | a bond | H | a bond | NH | O | NH | Q3a | OH |
| 5276 | CMe | NH | Q1b | a bond | H | a bond | NH | O | NH | Q3b | OH |
| 5277 | CMe | NH | Q1b | a bond | H | a bond | NH | O | NH | Q3c | OH |
| 5278 | CMe | NH | Q1b | a bond | H | a bond | NH | O | a bond | Q3a | OH |
| 5279 | CMe | NH | Q1b | a bond | H | a bond | NH | O | a bond | Q3b | OH |
| 5280 | CMe | NH | Q1b | a bond | H | a bond | NH | O | a bond | Q3c | OH |
| 5281 | CMe | NH | Q1c | a bond | Me | a bond | NH | S | NH | Q3a | OH |
| 5282 | CMe | NH | Q1c | a bond | Me | a bond | NH | S | NH | Q3b | OH |
| 5283 | CMe | NH | Q1c | a bond | Me | a bond | NH | S | NH | Q3c | OH |
| 5284 | CMe | NH | Q1c | a bond | Me | a bond | NH | S | a bond | Q3a | OH |
| 5285 | CMe | NH | Q1c | a bond | Me | a bond | NH | S | a bond | Q3b | OH |
| 5286 | CMe | NH | Q1c | a bond | Me | a bond | NH | S | a bond | Q3c | OH |
| 5287 | CMe | NH | Q1c | a bond | Me | a bond | NH | O | NH | Q3a | OH |
| 5288 | CMe | NH | Q1c | a bond | Me | a bond | NH | O | NH | Q3b | OH |
| 5289 | CMe | NH | Q1c | a bond | Me | a bond | NH | O | NH | Q3c | OH |
| 5290 | CMe | NH | Q1c | a bond | Me | a bond | NH | O | a bond | Q3a | OH |
| 5291 | CMe | NH | Q1c | a bond | Me | a bond | NH | O | a bond | Q3b | OH |
| 5292 | CMe | NH | Q1c | a bond | Me | a bond | NH | O | a bond | Q3c | OH |
| 5293 | CMe | NH | Q1c | a bond | H | a bond | NH | S | NH | Q3a | OH |
| 5294 | CMe | NH | Q1c | a bond | H | a bond | NH | S | NH | Q3b | OH |
| 5295 | CMe | NH | Q1c | a bond | H | a bond | NH | S | NH | Q3c | OH |
| 5296 | CMe | NH | Q1c | a bond | H | a bond | NH | S | a bond | Q3a | OH |
| 5297 | CMe | NH | Q1c | a bond | H | a bond | NH | S | a bond | Q3b | OH |
| 5298 | CMe | NH | Q1c | a bond | H | a bond | NH | S | a bond | Q3c | OH |
| 5299 | CMe | NH | Q1c | a bond | H | a bond | NH | O | NH | Q3a | OH |
| 5300 | CMe | NH | Q1c | a bond | H | a bond | NH | O | NH | Q3b | OH |
| 5301 | CMe | NH | Q1c | a bond | H | a bond | NH | O | NH | Q3c | OH |
| 5302 | CMe | NH | Q1c | a bond | H | a bond | NH | O | a bond | Q3a | OH |
| 5303 | CMe | NH | Q1c | a bond | H | a bond | NH | O | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5304 | CMe | NH | Q1c | a bond | H | a bond | NH | O | a bond | Q3c | OH |
| 5305 | CMe | NH | Q1d | a bond | Me | a bond | NH | S | NH | Q3a | OH |
| 5306 | CMe | NH | Q1d | a bond | Me | a bond | NH | S | NH | Q3b | OH |
| 5307 | CMe | NH | Q1d | a bond | Me | a bond | NH | S | NH | Q3c | OH |
| 5308 | CMe | NH | Q1d | a bond | Me | a bond | NH | S | a bond | Q3a | OH |
| 5309 | CMe | NH | Q1d | a bond | Me | a bond | NH | S | a bond | Q3b | OH |
| 5310 | CMe | NH | Q1d | a bond | Me | a bond | NH | S | a bond | Q3c | OH |
| 5311 | CMe | NH | Q1d | a bond | Me | a bond | NH | O | NH | Q3a | OH |
| 5312 | CMe | NH | Q1d | a bond | Me | a bond | NH | O | NH | Q3b | OH |
| 5313 | CMe | NH | Q1d | a bond | Me | a bond | NH | O | NH | Q3c | OH |
| 5314 | CMe | NH | Q1d | a bond | Me | a bond | NH | O | a bond | Q3a | OH |
| 5315 | CMe | NH | Q1d | a bond | Me | a bond | NH | O | a bond | Q3b | OH |
| 5316 | CMe | NH | Q1d | a bond | Me | a bond | NH | O | a bond | Q3c | OH |
| 5317 | CMe | NH | Q1d | a bond | H | a bond | NH | S | NH | Q3a | OH |
| 5318 | CMe | NH | Q1d | a bond | H | a bond | NH | S | NH | Q3b | OH |
| 5319 | CMe | NH | Q1d | a bond | H | a bond | NH | S | NH | Q3c | OH |
| 5320 | CMe | NH | Q1d | a bond | H | a bond | NH | S | a bond | Q3a | OH |
| 5321 | CMe | NH | Q1d | a bond | H | a bond | NH | S | a bond | Q3b | OH |
| 5322 | CMe | NH | Q1d | a bond | H | a bond | NH | S | a bond | Q3c | OH |
| 5323 | CMe | NH | Q1d | a bond | H | a bond | NH | O | NH | Q3a | OH |
| 5324 | CMe | NH | Q1d | a bond | H | a bond | NH | O | NH | Q3b | OH |
| 5325 | CMe | NH | Q1d | a bond | H | a bond | NH | O | NH | Q3c | OH |
| 5326 | CMe | NH | Q1d | a bond | H | a bond | NH | O | a bond | Q3a | OH |
| 5327 | CMe | NH | Q1d | a bond | H | a bond | NH | O | a bond | Q3b | OH |
| 5328 | CMe | NH | Q1d | a bond | H | a bond | NH | O | a bond | Q3c | OH |
| 5329 | CMe | NH | Q1e | a bond | Me | a bond | NH | S | NH | Q3a | OH |
| 5330 | CMe | NH | Q1e | a bond | Me | a bond | NH | S | NH | Q3b | OH |
| 5331 | CMe | NH | Q1e | a bond | Me | a bond | NH | S | NH | Q3c | OH |
| 5332 | CMe | NH | Q1e | a bond | Me | a bond | NH | S | a bond | Q3a | OH |
| 5333 | CMe | NH | Q1e | a bond | Me | a bond | NH | S | a bond | Q3b | OH |
| 5334 | CMe | NH | Q1e | a bond | Me | a bond | NH | S | a bond | Q3c | OH |
| 5335 | CMe | NH | Q1e | a bond | Me | a bond | NH | O | NH | Q3a | OH |
| 5336 | CMe | NH | Q1e | a bond | Me | a bond | NH | O | NH | Q3b | OH |
| 5337 | CMe | NH | Q1e | a bond | Me | a bond | NH | O | NH | Q3c | OH |
| 5338 | CMe | NH | Q1e | a bond | Me | a bond | NH | O | a bond | Q3a | OH |
| 5339 | CMe | NH | Q1e | a bond | Me | a bond | NH | O | a bond | Q3b | OH |
| 5340 | CMe | NH | Q1e | a bond | Me | a bond | NH | O | a bond | Q3c | OH |
| 5341 | CMe | NH | Q1e | a bond | H | a bond | NH | S | NH | Q3a | OH |
| 5342 | CMe | NH | Q1e | a bond | H | a bond | NH | S | NH | Q3b | OH |
| 5343 | CMe | NH | Q1e | a bond | H | a bond | NH | S | NH | Q3c | OH |
| 5344 | CMe | NH | Q1e | a bond | H | a bond | NH | S | a bond | Q3a | OH |
| 5345 | CMe | NH | Q1e | a bond | H | a bond | NH | S | a bond | Q3b | OH |
| 5346 | CMe | NH | Q1e | a bond | H | a bond | NH | S | a bond | Q3c | OH |
| 5347 | CMe | NH | Q1e | a bond | H | a bond | NH | O | NH | Q3a | OH |
| 5348 | CMe | NH | Q1e | a bond | H | a bond | NH | O | NH | Q3b | OH |
| 5349 | CMe | NH | Q1e | a bond | H | a bond | NH | O | NH | Q3c | OH |
| 5350 | CMe | NH | Q1e | a bond | H | a bond | NH | O | a bond | Q3a | OH |
| 5351 | CMe | NH | Q1e | a bond | H | a bond | NH | O | a bond | Q3b | OH |
| 5352 | CMe | NH | Q1e | a bond | H | a bond | NH | O | a bond | Q3c | OH |
| 5353 | CMe | NH | Q1f | a bond | Me | a bond | NH | S | NH | Q3a | OH |
| 5354 | CMe | NH | Q1f | a bond | Me | a bond | NH | S | NH | Q3b | OH |
| 5355 | CMe | NH | Q1f | a bond | Me | a bond | NH | S | NH | Q3c | OH |
| 5356 | CMe | NH | Q1f | a bond | Me | a bond | NH | S | a bond | Q3a | OH |
| 5357 | CMe | NH | Q1f | a bond | Me | a bond | NH | S | a bond | Q3b | OH |
| 5358 | CMe | NH | Q1f | a bond | Me | a bond | NH | S | a bond | Q3c | OH |
| 5359 | CMe | NH | Q1f | a bond | Me | a bond | NH | O | NH | Q3a | OH |
| 5360 | CMe | NH | Q1f | a bond | Me | a bond | NH | O | NH | Q3b | OH |
| 5361 | CMe | NH | Q1f | a bond | Me | a bond | NH | O | NH | Q3c | OH |
| 5362 | CMe | NH | Q1f | a bond | Me | a bond | NH | O | a bond | Q3a | OH |
| 5363 | CMe | NH | Q1f | a bond | Me | a bond | NH | O | a bond | Q3b | OH |
| 5364 | CMe | NH | Q1f | a bond | Me | a bond | NH | O | a bond | Q3c | OH |
| 5365 | CMe | NH | Q1f | a bond | H | a bond | NH | S | NH | Q3a | OH |
| 5366 | CMe | NH | Q1f | a bond | H | a bond | NH | S | NH | Q3b | OH |
| 5367 | CMe | NH | Q1f | a bond | H | a bond | NH | S | NH | Q3c | OH |
| 5368 | CMe | NH | Q1f | a bond | H | a bond | NH | S | a bond | Q3a | OH |
| 5369 | CMe | NH | Q1f | a bond | H | a bond | NH | S | a bond | Q3b | OH |
| 5370 | CMe | NH | Q1f | a bond | H | a bond | NH | S | a bond | Q3c | OH |
| 5371 | CMe | NH | Q1f | a bond | H | a bond | NH | O | NH | Q3a | OH |
| 5372 | CMe | NH | Q1f | a bond | H | a bond | NH | O | NH | Q3b | OH |
| 5373 | CMe | NH | Q1f | a bond | H | a bond | NH | O | NH | Q3c | OH |
| 5374 | CMe | NH | Q1f | a bond | H | a bond | NH | O | a bond | Q3a | OH |
| 5375 | CMe | NH | Q1f | a bond | H | a bond | NH | O | a bond | Q3b | OH |
| 5376 | CMe | NH | Q1f | a bond | H | a bond | NH | O | a bond | Q3c | OH |
| 5377 | CMe | NH | Q1g | a bond | Me | a bond | NH | S | NH | Q3a | OH |
| 5378 | CMe | NH | Q1g | a bond | Me | a bond | NH | S | NH | Q3b | OH |
| 5379 | CMe | NH | Q1g | a bond | Me | a bond | NH | S | NH | Q3c | OH |
| 5380 | CMe | NH | Q1g | a bond | Me | a bond | NH | S | a bond | Q3a | OH |
| 5381 | CMe | NH | Q1g | a bond | Me | a bond | NH | S | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5382 | CMe | NH | Q1g | a bond | Me | a bond | NH | S | a bond | Q3c | OH |
| 5383 | CMe | NH | Q1g | a bond | Me | a bond | NH | O | NH | Q3a | OH |
| 5384 | CMe | NH | Q1g | a bond | Me | a bond | NH | O | NH | Q3b | OH |
| 5385 | CMe | NH | Q1g | a bond | Me | a bond | NH | O | NH | Q3c | OH |
| 5386 | CMe | NH | Q1g | a bond | Me | a bond | NH | O | a bond | Q3a | OH |
| 5387 | CMe | NH | Q1g | a bond | Me | a bond | NH | O | a bond | Q3b | OH |
| 5388 | CMe | NH | Q1g | a bond | Me | a bond | NH | O | a bond | Q3c | OH |
| 5389 | CMe | NH | Q1g | a bond | H | a bond | NH | S | NH | Q3a | OH |
| 5390 | CMe | NH | Q1g | a bond | H | a bond | NH | S | NH | Q3b | OH |
| 5391 | CMe | NH | Q1g | a bond | H | a bond | NH | S | NH | Q3c | OH |
| 5392 | CMe | NH | Q1g | a bond | H | a bond | NH | S | a bond | Q3a | OH |
| 5393 | CMe | NH | Q1g | a bond | H | a bond | NH | S | a bond | Q3b | OH |
| 5394 | CMe | NH | Q1g | a bond | H | a bond | NH | S | a bond | Q3c | OH |
| 5395 | CMe | NH | Q1g | a bond | H | a bond | NH | O | NH | Q3a | OH |
| 5396 | CMe | NH | Q1g | a bond | H | a bond | NH | O | NH | Q3b | OH |
| 5397 | CMe | NH | Q1g | a bond | H | a bond | NH | O | NH | Q3c | OH |
| 5398 | CMe | NH | Q1g | a bond | H | a bond | NH | O | a bond | Q3a | OH |
| 5399 | CMe | NH | Q1g | a bond | H | a bond | NH | O | a bond | Q3b | OH |
| 5400 | CMe | NH | Q1g | a bond | H | a bond | NH | O | a bond | Q3c | OH |
| 5401 | CMe | NH | Q1h | a bond | Me | a bond | NH | S | NH | Q3a | OH |
| 5402 | CMe | NH | Q1h | a bond | Me | a bond | NH | S | NH | Q3b | OH |
| 5403 | CMe | NH | Q1h | a bond | Me | a bond | NH | S | NH | Q3c | OH |
| 5404 | CMe | NH | Q1h | a bond | Me | a bond | NH | S | a bond | Q3a | OH |
| 5405 | CMe | NH | Q1h | a bond | Me | a bond | NH | S | a bond | Q3b | OH |
| 5406 | CMe | NH | Q1h | a bond | Me | a bond | NH | S | a bond | Q3c | OH |
| 5407 | CMe | NH | Q1h | a bond | Me | a bond | NH | O | NH | Q3a | OH |
| 5408 | CMe | NH | Q1h | a bond | Me | a bond | NH | O | NH | Q3b | OH |
| 5409 | CMe | NH | Q1h | a bond | Me | a bond | NH | O | NH | Q3c | OH |
| 5410 | CMe | NH | Q1h | a bond | Me | a bond | NH | O | a bond | Q3a | OH |
| 5411 | CMe | NH | Q1h | a bond | Me | a bond | NH | O | a bond | Q3b | OH |
| 5412 | CMe | NH | Q1h | a bond | Me | a bond | NH | O | a bond | Q3c | OH |
| 5413 | CMe | NH | Q1h | a bond | H | a bond | NH | S | NH | Q3a | OH |
| 5414 | CMe | NH | Q1h | a bond | H | a bond | NH | S | NH | Q3b | OH |
| 5415 | CMe | NH | Q1h | a bond | H | a bond | NH | S | NH | Q3c | OH |
| 5416 | CMe | NH | Q1h | a bond | H | a bond | NH | S | a bond | Q3a | OH |
| 5417 | CMe | NH | Q1h | a bond | H | a bond | NH | S | a bond | Q3b | OH |
| 5418 | CMe | NH | Q1h | a bond | H | a bond | NH | S | a bond | Q3c | OH |
| 5419 | CMe | NH | Q1h | a bond | H | a bond | NH | O | NH | Q3a | OH |
| 5420 | CMe | NH | Q1h | a bond | H | a bond | NH | O | NH | Q3b | OH |
| 5421 | CMe | NH | Q1h | a bond | H | a bond | NH | O | NH | Q3c | OH |
| 5422 | CMe | NH | Q1h | a bond | H | a bond | NH | O | a bond | Q3a | OH |
| 5423 | CMe | NH | Q1h | a bond | H | a bond | NH | O | a bond | Q3b | OH |
| 5424 | CMe | NH | Q1h | a bond | H | a bond | NH | O | a bond | Q3c | OH |
| 5425 | CMe | NH | Q1i | a bond | Me | a bond | NH | S | NH | Q3a | OH |
| 5426 | CMe | NH | Q1i | a bond | Me | a bond | NH | S | NH | Q3b | OH |
| 5427 | CMe | NH | Q1i | a bond | Me | a bond | NH | S | NH | Q3c | OH |
| 5428 | CMe | NH | Q1i | a bond | Me | a bond | NH | S | a bond | Q3a | OH |
| 5429 | CMe | NH | Q1i | a bond | Me | a bond | NH | S | a bond | Q3b | OH |
| 5430 | CMe | NH | Q1i | a bond | Me | a bond | NH | S | a bond | Q3c | OH |
| 5431 | CMe | NH | Q1i | a bond | Me | a bond | NH | O | NH | Q3a | OH |
| 5432 | CMe | NH | Q1i | a bond | Me | a bond | NH | O | NH | Q3b | OH |
| 5433 | CMe | NH | Q1i | a bond | Me | a bond | NH | O | NH | Q3c | OH |
| 5434 | CMe | NH | Q1i | a bond | Me | a bond | NH | O | a bond | Q3a | OH |
| 5435 | CMe | NH | Q1i | a bond | Me | a bond | NH | O | a bond | Q3b | OH |
| 5436 | CMe | NH | Q1i | a bond | Me | a bond | NH | O | a bond | Q3c | OH |
| 5437 | CMe | NH | Q1i | a bond | H | a bond | NH | S | NH | Q3a | OH |
| 5438 | CMe | NH | Q1i | a bond | H | a bond | NH | S | NH | Q3b | OH |
| 5439 | CMe | NH | Q1i | a bond | H | a bond | NH | S | NH | Q3c | OH |
| 5440 | CMe | NH | Q1i | a bond | H | a bond | NH | S | a bond | Q3a | OH |
| 5441 | CMe | NH | Q1i | a bond | H | a bond | NH | S | a bond | Q3b | OH |
| 5442 | CMe | NH | Q1i | a bond | H | a bond | NH | S | a bond | Q3c | OH |
| 5443 | CMe | NH | Q1i | a bond | H | a bond | NH | O | NH | Q3a | OH |
| 5444 | CMe | NH | Q1i | a bond | H | a bond | NH | O | NH | Q3b | OH |
| 5445 | CMe | NH | Q1i | a bond | H | a bond | NH | O | NH | Q3c | OH |
| 5446 | CMe | NH | Q1i | a bond | H | a bond | NH | O | a bond | Q3a | OH |
| 5447 | CMe | NH | Q1i | a bond | H | a bond | NH | O | a bond | Q3b | OH |
| 5448 | CMe | NH | Q1i | a bond | H | a bond | NH | O | a bond | Q3c | OH |
| 5449 | CMe | NH | Q1j | a bond | Me | a bond | NH | S | NH | Q3a | OH |
| 5450 | CMe | NH | Q1j | a bond | Me | a bond | NH | S | NH | Q3b | OH |
| 5451 | CMe | NH | Q1j | a bond | Me | a bond | NH | S | NH | Q3c | OH |
| 5452 | CMe | NH | Q1j | a bond | Me | a bond | NH | S | a bond | Q3a | OH |
| 5453 | CMe | NH | Q1j | a bond | Me | a bond | NH | S | a bond | Q3b | OH |
| 5454 | CMe | NH | Q1j | a bond | Me | a bond | NH | S | a bond | Q3c | OH |
| 5455 | CMe | NH | Q1j | a bond | Me | a bond | NH | O | NH | Q3a | OH |
| 5456 | CMe | NH | Q1j | a bond | Me | a bond | NH | O | NH | Q3b | OH |
| 5457 | CMe | NH | Q1j | a bond | Me | a bond | NH | O | NH | Q3c | OH |
| 5458 | CMe | NH | Q1j | a bond | Me | a bond | NH | O | a bond | Q3a | OH |
| 5459 | CMe | NH | Q1j | a bond | Me | a bond | NH | O | a bond | Q3b | OH |

TABLE 1-continued

| No | A | B | R¹ | L¹ | R² | L² | L³ | Y | L⁴ | R³ | X |
|---|---|---|---|---|---|---|---|---|---|---|---|
| 5460 | CMe | NH | Q1j | a bond | Me | a bond | NH | O | a bond | Q3c | OH |
| 5461 | CMe | NH | Q1j | a bond | H | a bond | NH | S | NH | Q3a | OH |
| 5462 | CMe | NH | Q1j | a bond | H | a bond | NH | S | NH | Q3b | OH |
| 5463 | CMe | NH | Q1j | a bond | H | a bond | NH | S | NH | Q3c | OH |
| 5464 | CMe | NH | Q1j | a bond | H | a bond | NH | S | a bond | Q3a | OH |
| 5465 | CMe | NH | Q1j | a bond | H | a bond | NH | S | a bond | Q3b | OH |
| 5466 | CMe | NH | Q1j | a bond | H | a bond | NH | S | a bond | Q3c | OH |
| 5467 | CMe | NH | Q1j | a bond | H | a bond | NH | O | NH | Q3a | OH |
| 5468 | CMe | NH | Q1j | a bond | H | a bond | NH | O | NH | Q3b | OH |
| 5469 | CMe | NH | Q1j | a bond | H | a bond | NH | O | NH | Q3c | OH |
| 5470 | CMe | NH | Q1j | a bond | H | a bond | NH | O | a bond | Q3a | OH |
| 5471 | CMe | NH | Q1j | a bond | H | a bond | NH | O | a bond | Q3b | OH |
| 5472 | CMe | NH | Q1j | a bond | H | a bond | NH | O | a bond | Q3c | OH |

69) The compounds wherein A, B, R¹, L¹, R², L², L³, Y, L⁴, R³ and X are any of the following combinations in Table 2, tautomers, prodrugs or pharmaceutically acceptable salts of the compounds or solvates thereof. The symbols in Table 2 denote the flowing substituents.

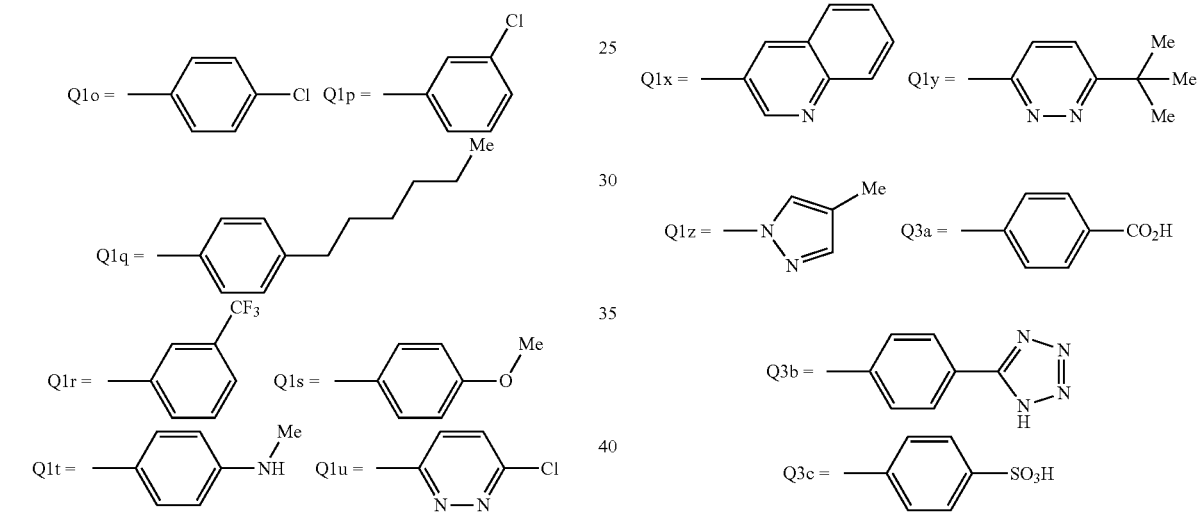

TABLE 2

| No | A | B | R¹ | L¹ | R² | L² | L³ | Y | L⁴ | R³ | X |
|---|---|---|---|---|---|---|---|---|---|---|---|
| 1 | N | NMe | Q1o | a bond | Me | a bond | NH | S | NH | Q3a | OH |
| 2 | N | NMe | Q1o | a bond | Me | a bond | NH | S | NH | Q3b | OH |
| 3 | N | NMe | Q1o | a bond | Me | a bond | NH | S | NH | Q3c | OH |
| 4 | N | NMe | Q1o | a bond | Me | a bond | NH | S | a bond | Q3a | OH |
| 5 | N | NMe | Q1o | a bond | Me | a bond | NH | S | a bond | Q3b | OH |
| 6 | N | NMe | Q1o | a bond | Me | a bond | NH | S | a bond | Q3c | OH |
| 7 | N | NMe | Q1o | a bond | Me | a bond | NH | O | NH | Q3a | OH |
| 8 | N | NMe | Q1o | a bond | Me | a bond | NH | O | NH | Q3b | OH |
| 9 | N | NMe | Q1o | a bond | Me | a bond | NH | O | NH | Q3c | OH |
| 10 | N | NMe | Q1o | a bond | Me | a bond | NH | O | a bond | Q3a | OH |
| 11 | N | NMe | Q1o | a bond | Me | a bond | NH | O | a bond | Q3b | OH |
| 12 | N | NMe | Q1o | a bond | Me | a bond | NH | O | a bond | Q3c | OH |
| 13 | N | NMe | Q1o | a bond | H | a bond | NH | S | NH | Q3a | OH |
| 14 | N | NMe | Q1o | a bond | H | a bond | NH | S | NH | Q3b | OH |
| 15 | N | NMe | Q1o | a bond | H | a bond | NH | S | NH | Q3c | OH |
| 16 | N | NMe | Q1o | a bond | H | a bond | NH | S | a bond | Q3a | OH |
| 17 | N | NMe | Q1o | a bond | H | a bond | NH | S | a bond | Q3b | OH |
| 18 | N | NMe | Q1o | a bond | H | a bond | NH | S | a bond | Q3c | OH |
| 19 | N | NMe | Q1o | a bond | H | a bond | NH | O | NH | Q3a | OH |
| 20 | N | NMe | Q1o | a bond | H | a bond | NH | O | NH | Q3b | OH |
| 21 | N | NMe | Q1o | a bond | H | a bond | NH | O | NH | Q3c | OH |
| 22 | N | NMe | Q1o | a bond | H | a bond | NH | O | a bond | Q3a | OH |
| 23 | N | NMe | Q1o | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 24 | N | NMe | Q1o | a bond | H | a bond | NH | O | a bond | Q3c | OH |
| 25 | N | NMe | Q1p | a bond | Me | a bond | NH | S | NH | Q3a | OH |
| 26 | N | NMe | Q1p | a bond | Me | a bond | NH | S | NH | Q3b | OH |
| 27 | N | NMe | Q1p | a bond | Me | a bond | NH | S | NH | Q3c | OH |
| 28 | N | NMe | Q1p | a bond | Me | a bond | NH | S | a bond | Q3a | OH |
| 29 | N | NMe | Q1p | a bond | Me | a bond | NH | S | a bond | Q3b | OH |
| 30 | N | NMe | Q1p | a bond | Me | a bond | NH | S | a bond | Q3c | OH |
| 31 | N | NMe | Q1p | a bond | Me | a bond | NH | O | NH | Q3a | OH |
| 32 | N | NMe | Q1p | a bond | Me | a bond | NH | O | NH | Q3b | OH |
| 33 | N | NMe | Q1p | a bond | Me | a bond | NH | O | NH | Q3c | OH |
| 34 | N | NMe | Q1p | a bond | Me | a bond | NH | O | a bond | Q3a | OH |
| 35 | N | NMe | Q1p | a bond | Me | a bond | NH | O | a bond | Q3b | OH |
| 36 | N | NMe | Q1p | a bond | Me | a bond | NH | O | a bond | Q3c | OH |
| 37 | N | NMe | Q1p | a bond | H | a bond | NH | S | NH | Q3a | OH |
| 38 | N | NMe | Q1p | a bond | H | a bond | NH | S | NH | Q3b | OH |
| 39 | N | NMe | Q1p | a bond | H | a bond | NH | S | NH | Q3c | OH |
| 40 | N | NMe | Q1p | a bond | H | a bond | NH | S | a bond | Q3a | OH |
| 41 | N | NMe | Q1p | a bond | H | a bond | NH | S | a bond | Q3b | OH |
| 42 | N | NMe | Q1p | a bond | H | a bond | NH | S | a bond | Q3c | OH |
| 43 | N | NMe | Q1p | a bond | H | a bond | NH | O | NH | Q3a | OH |
| 44 | N | NMe | Q1p | a bond | H | a bond | NH | O | NH | Q3b | OH |
| 45 | N | NMe | Q1p | a bond | H | a bond | NH | O | NH | Q3c | OH |
| 46 | N | NMe | Q1p | a bond | H | a bond | NH | O | a bond | Q3a | OH |
| 47 | N | NMe | Q1p | a bond | H | a bond | NH | O | a bond | Q3b | OH |
| 48 | N | NMe | Q1p | a bond | H | a bond | NH | O | a bond | Q3c | OH |
| 49 | N | NMe | Q1q | a bond | Me | a bond | NH | S | NH | Q3a | OH |
| 50 | N | NMe | Q1q | a bond | Me | a bond | NH | S | NH | Q3b | OH |
| 51 | N | NMe | Q1q | a bond | Me | a bond | NH | S | NH | Q3c | OH |
| 52 | N | NMe | Q1q | a bond | Me | a bond | NH | S | a bond | Q3a | OH |
| 53 | N | NMe | Q1q | a bond | Me | a bond | NH | S | a bond | Q3b | OH |
| 54 | N | NMe | Q1q | a bond | Me | a bond | NH | S | a bond | Q3c | OH |
| 55 | N | NMe | Q1q | a bond | Me | a bond | NH | O | NH | Q3a | OH |
| 56 | N | NMe | Q1q | a bond | Me | a bond | NH | O | NH | Q3b | OH |
| 57 | N | NMe | Q1q | a bond | Me | a bond | NH | O | NH | Q3c | OH |
| 58 | N | NMe | Q1q | a bond | Me | a bond | NH | O | a bond | Q3a | OH |
| 59 | N | NMe | Q1q | a bond | Me | a bond | NH | O | a bond | Q3b | OH |
| 60 | N | NMe | Q1q | a bond | Me | a bond | NH | O | a bond | Q3c | OH |
| 61 | N | NMe | Q1q | a bond | H | a bond | NH | S | NH | Q3a | OH |
| 62 | N | NMe | Q1q | a bond | H | a bond | NH | S | NH | Q3b | OH |
| 63 | N | NMe | Q1q | a bond | H | a bond | NH | S | NH | Q3c | OH |
| 64 | N | NMe | Q1q | a bond | H | a bond | NH | S | a bond | Q3a | OH |
| 65 | N | NMe | Q1q | a bond | H | a bond | NH | S | a bond | Q3b | OH |
| 66 | N | NMe | Q1q | a bond | H | a bond | NH | S | a bond | Q3c | OH |
| 67 | N | NMe | Q1q | a bond | H | a bond | NH | O | NH | Q3a | OH |
| 68 | N | NMe | Q1q | a bond | H | a bond | NH | O | NH | Q3b | OH |
| 69 | N | NMe | Q1q | a bond | H | a bond | NH | O | NH | Q3c | OH |
| 70 | N | NMe | Q1q | a bond | H | a bond | NH | O | a bond | Q3a | OH |
| 71 | N | NMe | Q1q | a bond | H | a bond | NH | O | a bond | Q3b | OH |
| 72 | N | NMe | Q1q | a bond | H | a bond | NH | O | a bond | Q3c | OH |
| 73 | N | NMe | Q1r | a bond | Me | a bond | NH | S | NH | Q3a | OH |
| 74 | N | NMe | Q1r | a bond | Me | a bond | NH | S | NH | Q3b | OH |
| 75 | N | NMe | Q1r | a bond | Me | a bond | NH | S | NH | Q3c | OH |
| 76 | N | NMe | Q1r | a bond | Me | a bond | NH | S | a bond | Q3a | OH |
| 77 | N | NMe | Q1r | a bond | Me | a bond | NH | S | a bond | Q3b | OH |
| 78 | N | NMe | Q1r | a bond | Me | a bond | NH | S | a bond | Q3c | OH |
| 79 | N | NMe | Q1r | a bond | Me | a bond | NH | O | NH | Q3a | OH |
| 80 | N | NMe | Q1r | a bond | Me | a bond | NH | O | NH | Q3b | OH |
| 81 | N | NMe | Q1r | a bond | Me | a bond | NH | O | NH | Q3c | OH |
| 82 | N | NMe | Q1r | a bond | Me | a bond | NH | O | a bond | Q3a | OH |
| 83 | N | NMe | Q1r | a bond | Me | a bond | NH | O | a bond | Q3b | OH |
| 84 | N | NMe | Q1r | a bond | Me | a bond | NH | O | a bond | Q3c | OH |
| 85 | N | NMe | Q1r | a bond | H | a bond | NH | S | NH | Q3a | OH |
| 86 | N | NMe | Q1r | a bond | H | a bond | NH | S | NH | Q3b | OH |
| 87 | N | NMe | Q1r | a bond | H | a bond | NH | S | NH | Q3c | OH |
| 88 | N | NMe | Q1r | a bond | H | a bond | NH | S | a bond | Q3a | OH |
| 89 | N | NMe | Q1r | a bond | H | a bond | NH | S | a bond | Q3b | OH |
| 90 | N | NMe | Q1r | a bond | H | a bond | NH | S | a bond | Q3c | OH |
| 91 | N | NMe | Q1r | a bond | H | a bond | NH | O | NH | Q3a | OH |
| 92 | N | NMe | Q1r | a bond | H | a bond | NH | O | NH | Q3b | OH |
| 93 | N | NMe | Q1r | a bond | H | a bond | NH | O | NH | Q3c | OH |
| 94 | N | NMe | Q1r | a bond | H | a bond | NH | O | a bond | Q3a | OH |
| 95 | N | NMe | Q1r | a bond | H | a bond | NH | O | a bond | Q3b | OH |
| 96 | N | NMe | Q1r | a bond | H | a bond | NH | O | a bond | Q3c | OH |
| 97 | N | NMe | Q1s | a bond | Me | a bond | NH | S | NH | Q3a | OH |
| 98 | N | NMe | Q1s | a bond | Me | a bond | NH | S | NH | Q3b | OH |
| 99 | N | NMe | Q1s | a bond | Me | a bond | NH | S | NH | Q3c | OH |
| 100 | N | NMe | Q1s | a bond | Me | a bond | NH | S | a bond | Q3a | OH |
| 101 | N | NMe | Q1s | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 102 | N | NMe | Q1s | a bond | Me | a bond | NH | S | a bond | Q3c | OH |
| 103 | N | NMe | Q1s | a bond | Me | a bond | NH | O | NH | Q3a | OH |
| 104 | N | NMe | Q1s | a bond | Me | a bond | NH | O | NH | Q3b | OH |
| 105 | N | NMe | Q1s | a bond | Me | a bond | NH | O | NH | Q3c | OH |
| 106 | N | NMe | Q1s | a bond | Me | a bond | NH | O | a bond | Q3a | OH |
| 107 | N | NMe | Q1s | a bond | Me | a bond | NH | O | a bond | Q3b | OH |
| 108 | N | NMe | Q1s | a bond | Me | a bond | NH | O | a bond | Q3c | OH |
| 109 | N | NMe | Q1s | a bond | H | a bond | NH | S | NH | Q3a | OH |
| 110 | N | NMe | Q1s | a bond | H | a bond | NH | S | NH | Q3b | OH |
| 111 | N | NMe | Q1s | a bond | H | a bond | NH | S | NH | Q3c | OH |
| 112 | N | NMe | Q1s | a bond | H | a bond | NH | S | a bond | Q3a | OH |
| 113 | N | NMe | Q1s | a bond | H | a bond | NH | S | a bond | Q3b | OH |
| 114 | N | NMe | Q1s | a bond | H | a bond | NH | S | a bond | Q3c | OH |
| 115 | N | NMe | Q1s | a bond | H | a bond | NH | O | NH | Q3a | OH |
| 116 | N | NMe | Q1s | a bond | H | a bond | NH | O | NH | Q3b | OH |
| 117 | N | NMe | Q1s | a bond | H | a bond | NH | O | NH | Q3c | OH |
| 118 | N | NMe | Q1s | a bond | H | a bond | NH | O | a bond | Q3a | OH |
| 119 | N | NMe | Q1s | a bond | H | a bond | NH | O | a bond | Q3b | OH |
| 120 | N | NMe | Q1s | a bond | H | a bond | NH | O | a bond | Q3c | OH |
| 121 | N | NMe | Q1t | a bond | Me | a bond | NH | S | NH | Q3a | OH |
| 122 | N | NMe | Q1t | a bond | Me | a bond | NH | S | NH | Q3b | OH |
| 123 | N | NMe | Q1t | a bond | Me | a bond | NH | S | NH | Q3c | OH |
| 124 | N | NMe | Q1t | a bond | Me | a bond | NH | S | a bond | Q3a | OH |
| 125 | N | NMe | Q1t | a bond | Me | a bond | NH | S | a bond | Q3b | OH |
| 126 | N | NMe | Q1t | a bond | Me | a bond | NH | S | a bond | Q3c | OH |
| 127 | N | NMe | Q1t | a bond | Me | a bond | NH | O | NH | Q3a | OH |
| 128 | N | NMe | Q1t | a bond | Me | a bond | NH | O | NH | Q3b | OH |
| 129 | N | NMe | Q1t | a bond | Me | a bond | NH | O | NH | Q3c | OH |
| 130 | N | NMe | Q1t | a bond | Me | a bond | NH | O | a bond | Q3a | OH |
| 131 | N | NMe | Q1t | a bond | Me | a bond | NH | O | a bond | Q3b | OH |
| 132 | N | NMe | Q1t | a bond | Me | a bond | NH | O | a bond | Q3c | OH |
| 133 | N | NMe | Q1t | a bond | H | a bond | NH | S | NH | Q3a | OH |
| 134 | N | NMe | Q1t | a bond | H | a bond | NH | S | NH | Q3b | OH |
| 135 | N | NMe | Q1t | a bond | H | a bond | NH | S | NH | Q3c | OH |
| 136 | N | NMe | Q1t | a bond | H | a bond | NH | S | a bond | Q3a | OH |
| 137 | N | NMe | Q1t | a bond | H | a bond | NH | S | a bond | Q3b | OH |
| 138 | N | NMe | Q1t | a bond | H | a bond | NH | S | a bond | Q3c | OH |
| 139 | N | NMe | Q1t | a bond | H | a bond | NH | O | NH | Q3a | OH |
| 140 | N | NMe | Q1t | a bond | H | a bond | NH | O | NH | Q3b | OH |
| 141 | N | NMe | Q1t | a bond | H | a bond | NH | O | NH | Q3c | OH |
| 142 | N | NMe | Q1t | a bond | H | a bond | NH | O | a bond | Q3a | OH |
| 143 | N | NMe | Q1t | a bond | H | a bond | NH | O | a bond | Q3b | OH |
| 144 | N | NMe | Q1t | a bond | H | a bond | NH | O | a bond | Q3c | OH |
| 145 | N | NMe | Q1u | a bond | Me | a bond | NH | S | NH | Q3a | OH |
| 146 | N | NMe | Q1u | a bond | Me | a bond | NH | S | NH | Q3b | OH |
| 147 | N | NMe | Q1u | a bond | Me | a bond | NH | S | NH | Q3c | OH |
| 148 | N | NMe | Q1u | a bond | Me | a bond | NH | S | a bond | Q3a | OH |
| 149 | N | NMe | Q1u | a bond | Me | a bond | NH | S | a bond | Q3b | OH |
| 150 | N | NMe | Q1u | a bond | Me | a bond | NH | S | a bond | Q3c | OH |
| 151 | N | NMe | Q1u | a bond | Me | a bond | NH | O | NH | Q3a | OH |
| 152 | N | NMe | Q1u | a bond | Me | a bond | NH | O | NH | Q3b | OH |
| 153 | N | NMe | Q1u | a bond | Me | a bond | NH | O | NH | Q3c | OH |
| 154 | N | NMe | Q1u | a bond | Me | a bond | NH | O | a bond | Q3a | OH |
| 155 | N | NMe | Q1u | a bond | Me | a bond | NH | O | a bond | Q3b | OH |
| 156 | N | NMe | Q1u | a bond | Me | a bond | NH | O | a bond | Q3c | OH |
| 157 | N | NMe | Q1u | a bond | H | a bond | NH | S | NH | Q3a | OH |
| 158 | N | NMe | Q1u | a bond | H | a bond | NH | S | NH | Q3b | OH |
| 159 | N | NMe | Q1u | a bond | H | a bond | NH | S | NH | Q3c | OH |
| 160 | N | NMe | Q1u | a bond | H | a bond | NH | S | a bond | Q3a | OH |
| 161 | N | NMe | Q1u | a bond | H | a bond | NH | S | a bond | Q3b | OH |
| 162 | N | NMe | Q1u | a bond | H | a bond | NH | S | a bond | Q3c | OH |
| 163 | N | NMe | Q1u | a bond | H | a bond | NH | O | NH | Q3a | OH |
| 164 | N | NMe | Q1u | a bond | H | a bond | NH | O | NH | Q3b | OH |
| 165 | N | NMe | Q1u | a bond | H | a bond | NH | O | NH | Q3c | OH |
| 166 | N | NMe | Q1u | a bond | H | a bond | NH | O | a bond | Q3a | OH |
| 167 | N | NMe | Q1u | a bond | H | a bond | NH | O | a bond | Q3b | OH |
| 168 | N | NMe | Q1u | a bond | H | a bond | NH | O | a bond | Q3c | OH |
| 169 | N | NMe | Q1v | a bond | Me | a bond | NH | S | NH | Q3a | OH |
| 170 | N | NMe | Q1v | a bond | Me | a bond | NH | S | NH | Q3b | OH |
| 171 | N | NMe | Q1v | a bond | Me | a bond | NH | S | NH | Q3c | OH |
| 172 | N | NMe | Q1v | a bond | Me | a bond | NH | S | a bond | Q3a | OH |
| 173 | N | NMe | Q1v | a bond | Me | a bond | NH | S | a bond | Q3b | OH |
| 174 | N | NMe | Q1v | a bond | Me | a bond | NH | S | a bond | Q3c | OH |
| 175 | N | NMe | Q1v | a bond | Me | a bond | NH | O | NH | Q3a | OH |
| 176 | N | NMe | Q1v | a bond | Me | a bond | NH | O | NH | Q3b | OH |
| 177 | N | NMe | Q1v | a bond | Me | a bond | NH | O | NH | Q3c | OH |
| 178 | N | NMe | Q1v | a bond | Me | a bond | NH | O | a bond | Q3a | OH |
| 179 | N | NMe | Q1v | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 180 | N | NMe | Q1v | a bond | Me | a bond | NH | O | a bond | Q3c | OH |
| 181 | N | NMe | Q1v | a bond | H | a bond | NH | S | NH | Q3a | OH |
| 182 | N | NMe | Q1v | a bond | H | a bond | NH | S | NH | Q3b | OH |
| 183 | N | NMe | Q1v | a bond | H | a bond | NH | S | NH | Q3c | OH |
| 184 | N | NMe | Q1v | a bond | H | a bond | NH | S | a bond | Q3a | OH |
| 185 | N | NMe | Q1v | a bond | H | a bond | NH | S | a bond | Q3b | OH |
| 186 | N | NMe | Q1v | a bond | H | a bond | NH | S | a bond | Q3c | OH |
| 187 | N | NMe | Q1v | a bond | H | a bond | NH | O | NH | Q3a | OH |
| 188 | N | NMe | Q1v | a bond | H | a bond | NH | O | NH | Q3b | OH |
| 189 | N | NMe | Q1v | a bond | H | a bond | NH | O | NH | Q3c | OH |
| 190 | N | NMe | Q1v | a bond | H | a bond | NH | O | a bond | Q3a | OH |
| 191 | N | NMe | Q1v | a bond | H | a bond | NH | O | a bond | Q3b | OH |
| 192 | N | NMe | Q1v | a bond | H | a bond | NH | O | a bond | Q3c | OH |
| 193 | N | NMe | Q1w | a bond | Me | a bond | NH | S | NH | Q3a | OH |
| 194 | N | NMe | Q1w | a bond | Me | a bond | NH | S | NH | Q3b | OH |
| 195 | N | NMe | Q1w | a bond | Me | a bond | NH | S | NH | Q3c | OH |
| 196 | N | NMe | Q1w | a bond | Me | a bond | NH | S | a bond | Q3a | OH |
| 197 | N | NMe | Q1w | a bond | Me | a bond | NH | S | a bond | Q3b | OH |
| 198 | N | NMe | Q1w | a bond | Me | a bond | NH | S | a bond | Q3c | OH |
| 199 | N | NMe | Q1w | a bond | Me | a bond | NH | O | NH | Q3a | OH |
| 200 | N | NMe | Q1w | a bond | Me | a bond | NH | O | NH | Q3b | OH |
| 201 | N | NMe | Q1w | a bond | Me | a bond | NH | O | NH | Q3c | OH |
| 202 | N | NMe | Q1w | a bond | Me | a bond | NH | O | a bond | Q3a | OH |
| 203 | N | NMe | Q1w | a bond | Me | a bond | NH | O | a bond | Q3b | OH |
| 204 | N | NMe | Q1w | a bond | Me | a bond | NH | O | a bond | Q3c | OH |
| 205 | N | NMe | Q1w | a bond | H | a bond | NH | S | NH | Q3a | OH |
| 206 | N | NMe | Q1w | a bond | H | a bond | NH | S | NH | Q3b | OH |
| 207 | N | NMe | Q1w | a bond | H | a bond | NH | S | NH | Q3c | OH |
| 208 | N | NMe | Q1w | a bond | H | a bond | NH | S | a bond | Q3a | OH |
| 209 | N | NMe | Q1w | a bond | H | a bond | NH | S | a bond | Q3b | OH |
| 210 | N | NMe | Q1w | a bond | H | a bond | NH | S | a bond | Q3c | OH |
| 211 | N | NMe | Q1w | a bond | H | a bond | NH | O | NH | Q3a | OH |
| 212 | N | NMe | Q1w | a bond | H | a bond | NH | O | NH | Q3b | OH |
| 213 | N | NMe | Q1w | a bond | H | a bond | NH | O | NH | Q3c | OH |
| 214 | N | NMe | Q1w | a bond | H | a bond | NH | O | a bond | Q3a | OH |
| 215 | N | NMe | Q1w | a bond | H | a bond | NH | O | a bond | Q3b | OH |
| 216 | N | NMe | Q1w | a bond | H | a bond | NH | O | a bond | Q3c | OH |
| 217 | N | NMe | Q1x | a bond | Me | a bond | NH | S | NH | Q3a | OH |
| 218 | N | NMe | Q1x | a bond | Me | a bond | NH | S | NH | Q3b | OH |
| 219 | N | NMe | Q1x | a bond | Me | a bond | NH | S | NH | Q3c | OH |
| 220 | N | NMe | Q1x | a bond | Me | a bond | NH | S | a bond | Q3a | OH |
| 221 | N | NMe | Q1x | a bond | Me | a bond | NH | S | a bond | Q3b | OH |
| 222 | N | NMe | Q1x | a bond | Me | a bond | NH | S | a bond | Q3c | OH |
| 223 | N | NMe | Q1x | a bond | Me | a bond | NH | O | NH | Q3a | OH |
| 224 | N | NMe | Q1x | a bond | Me | a bond | NH | O | NH | Q3b | OH |
| 225 | N | NMe | Q1x | a bond | Me | a bond | NH | O | NH | Q3c | OH |
| 226 | N | NMe | Q1x | a bond | Me | a bond | NH | O | a bond | Q3a | OH |
| 227 | N | NMe | Q1x | a bond | Me | a bond | NH | O | a bond | Q3b | OH |
| 228 | N | NMe | Q1x | a bond | Me | a bond | NH | O | a bond | Q3c | OH |
| 229 | N | NMe | Q1x | a bond | H | a bond | NH | S | NH | Q3a | OH |
| 230 | N | NMe | Q1x | a bond | H | a bond | NH | S | NH | Q3b | OH |
| 231 | N | NMe | Q1x | a bond | H | a bond | NH | S | NH | Q3c | OH |
| 232 | N | NMe | Q1x | a bond | H | a bond | NH | S | a bond | Q3a | OH |
| 233 | N | NMe | Q1x | a bond | H | a bond | NH | S | a bond | Q3b | OH |
| 234 | N | NMe | Q1x | a bond | H | a bond | NH | S | a bond | Q3c | OH |
| 235 | N | NMe | Q1x | a bond | H | a bond | NH | O | NH | Q3a | OH |
| 236 | N | NMe | Q1x | a bond | H | a bond | NH | O | NH | Q3b | OH |
| 237 | N | NMe | Q1x | a bond | H | a bond | NH | O | NH | Q3c | OH |
| 238 | N | NMe | Q1x | a bond | H | a bond | NH | O | a bond | Q3a | OH |
| 239 | N | NMe | Q1x | a bond | H | a bond | NH | O | a bond | Q3b | OH |
| 240 | N | NMe | Q1x | a bond | H | a bond | NH | O | a bond | Q3c | OH |
| 241 | N | NEt | Q1o | a bond | Me | a bond | NH | S | NH | Q3a | OH |
| 242 | N | NEt | Q1o | a bond | Me | a bond | NH | S | NH | Q3b | OH |
| 243 | N | NEt | Q1o | a bond | Me | a bond | NH | S | NH | Q3c | OH |
| 244 | N | NEt | Q1o | a bond | Me | a bond | NH | S | a bond | Q3a | OH |
| 245 | N | NEt | Q1o | a bond | Me | a bond | NH | S | a bond | Q3b | OH |
| 246 | N | NEt | Q1o | a bond | Me | a bond | NH | S | a bond | Q3c | OH |
| 247 | N | NEt | Q1o | a bond | Me | a bond | NH | O | NH | Q3a | OH |
| 248 | N | NEt | Q1o | a bond | Me | a bond | NH | O | NH | Q3b | OH |
| 249 | N | NEt | Q1o | a bond | Me | a bond | NH | O | NH | Q3c | OH |
| 250 | N | NEt | Q1o | a bond | Me | a bond | NH | O | a bond | Q3a | OH |
| 251 | N | NEt | Q1o | a bond | Me | a bond | NH | O | a bond | Q3b | OH |
| 252 | N | NEt | Q1o | a bond | Me | a bond | NH | O | a bond | Q3c | OH |
| 253 | N | NEt | Q1o | a bond | H | a bond | NH | S | NH | Q3a | OH |
| 254 | N | NEt | Q1o | a bond | H | a bond | NH | S | NH | Q3b | OH |
| 255 | N | NEt | Q1o | a bond | H | a bond | NH | S | NH | Q3c | OH |
| 256 | N | NEt | Q1o | a bond | H | a bond | NH | S | a bond | Q3a | OH |
| 257 | N | NEt | Q1o | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 258 | N | NEt | Q1o | a bond | H | a bond | NH | S | a bond | Q3c | OH |
| 259 | N | NEt | Q1o | a bond | H | a bond | NH | O | NH | Q3a | OH |
| 260 | N | NEt | Q1o | a bond | H | a bond | NH | O | NH | Q3b | OH |
| 261 | N | NEt | Q1o | a bond | H | a bond | NH | O | NH | Q3c | OH |
| 262 | N | NEt | Q1o | a bond | H | a bond | NH | O | a bond | Q3a | OH |
| 263 | N | NEt | Q1o | a bond | H | a bond | NH | O | a bond | Q3b | OH |
| 264 | N | NEt | Q1o | a bond | H | a bond | NH | O | a bond | Q3c | OH |
| 265 | N | NEt | Q1p | a bond | Me | a bond | NH | S | NH | Q3a | OH |
| 266 | N | NEt | Q1p | a bond | Me | a bond | NH | S | NH | Q3b | OH |
| 267 | N | NEt | Q1p | a bond | Me | a bond | NH | S | NH | Q3c | OH |
| 268 | N | NEt | Q1p | a bond | Me | a bond | NH | S | a bond | Q3a | OH |
| 269 | N | NEt | Q1p | a bond | Me | a bond | NH | S | a bond | Q3b | OH |
| 270 | N | NEt | Q1p | a bond | Me | a bond | NH | S | a bond | Q3c | OH |
| 271 | N | NEt | Q1p | a bond | Me | a bond | NH | O | NH | Q3a | OH |
| 272 | N | NEt | Q1p | a bond | Me | a bond | NH | O | NH | Q3b | OH |
| 273 | N | NEt | Q1p | a bond | Me | a bond | NH | O | NH | Q3c | OH |
| 274 | N | NEt | Q1p | a bond | Me | a bond | NH | O | a bond | Q3a | OH |
| 275 | N | NEt | Q1p | a bond | Me | a bond | NH | O | a bond | Q3b | OH |
| 276 | N | NEt | Q1p | a bond | Me | a bond | NH | O | a bond | Q3c | OH |
| 277 | N | NEt | Q1p | a bond | H | a bond | NH | S | NH | Q3a | OH |
| 278 | N | NEt | Q1p | a bond | H | a bond | NH | S | NH | Q3b | OH |
| 279 | N | NEt | Q1p | a bond | H | a bond | NH | S | NH | Q3c | OH |
| 280 | N | NEt | Q1p | a bond | H | a bond | NH | S | a bond | Q3a | OH |
| 281 | N | NEt | Q1p | a bond | H | a bond | NH | S | a bond | Q3b | OH |
| 282 | N | NEt | Q1p | a bond | H | a bond | NH | S | a bond | Q3c | OH |
| 283 | N | NEt | Q1p | a bond | H | a bond | NH | O | NH | Q3a | OH |
| 284 | N | NEt | Q1p | a bond | H | a bond | NH | O | NH | Q3b | OH |
| 285 | N | NEt | Q1p | a bond | H | a bond | NH | O | NH | Q3c | OH |
| 286 | N | NEt | Q1p | a bond | H | a bond | NH | O | a bond | Q3a | OH |
| 287 | N | NEt | Q1p | a bond | H | a bond | NH | O | a bond | Q3b | OH |
| 288 | N | NEt | Q1p | a bond | H | a bond | NH | O | a bond | Q3c | OH |
| 289 | N | NEt | Q1q | a bond | Me | a bond | NH | S | NH | Q3a | OH |
| 290 | N | NEt | Q1q | a bond | Me | a bond | NH | S | NH | Q3b | OH |
| 291 | N | NEt | Q1q | a bond | Me | a bond | NH | S | NH | Q3c | OH |
| 292 | N | NEt | Q1q | a bond | Me | a bond | NH | S | a bond | Q3a | OH |
| 293 | N | NEt | Q1q | a bond | Me | a bond | NH | S | a bond | Q3b | OH |
| 294 | N | NEt | Q1q | a bond | Me | a bond | NH | S | a bond | Q3c | OH |
| 295 | N | NEt | Q1q | a bond | Me | a bond | NH | O | NH | Q3a | OH |
| 296 | N | NEt | Q1q | a bond | Me | a bond | NH | O | NH | Q3b | OH |
| 297 | N | NEt | Q1q | a bond | Me | a bond | NH | O | NH | Q3c | OH |
| 298 | N | NEt | Q1q | a bond | Me | a bond | NH | O | a bond | Q3a | OH |
| 299 | N | NEt | Q1q | a bond | Me | a bond | NH | O | a bond | Q3b | OH |
| 300 | N | NEt | Q1q | a bond | Me | a bond | NH | O | a bond | Q3c | OH |
| 301 | N | NEt | Q1q | a bond | H | a bond | NH | S | NH | Q3a | OH |
| 302 | N | NEt | Q1q | a bond | H | a bond | NH | S | NH | Q3b | OH |
| 303 | N | NEt | Q1q | a bond | H | a bond | NH | S | NH | Q3c | OH |
| 304 | N | NEt | Q1q | a bond | H | a bond | NH | S | a bond | Q3a | OH |
| 305 | N | NEt | Q1q | a bond | H | a bond | NH | S | a bond | Q3b | OH |
| 306 | N | NEt | Q1q | a bond | H | a bond | NH | S | a bond | Q3c | OH |
| 307 | N | NEt | Q1q | a bond | H | a bond | NH | O | NH | Q3a | OH |
| 308 | N | NEt | Q1q | a bond | H | a bond | NH | O | NH | Q3b | OH |
| 309 | N | NEt | Q1q | a bond | H | a bond | NH | O | NH | Q3c | OH |
| 310 | N | NEt | Q1q | a bond | H | a bond | NH | O | a bond | Q3a | OH |
| 311 | N | NEt | Q1q | a bond | H | a bond | NH | O | a bond | Q3b | OH |
| 312 | N | NEt | Q1q | a bond | H | a bond | NH | O | a bond | Q3c | OH |
| 313 | N | NEt | Q1r | a bond | Me | a bond | NH | S | NH | Q3a | OH |
| 314 | N | NEt | Q1r | a bond | Me | a bond | NH | S | NH | Q3b | OH |
| 315 | N | NEt | Q1r | a bond | Me | a bond | NH | S | NH | Q3c | OH |
| 316 | N | NEt | Q1r | a bond | Me | a bond | NH | S | a bond | Q3a | OH |
| 317 | N | NEt | Q1r | a bond | Me | a bond | NH | S | a bond | Q3b | OH |
| 318 | N | NEt | Q1r | a bond | Me | a bond | NH | S | a bond | Q3c | OH |
| 319 | N | NEt | Q1r | a bond | Me | a bond | NH | O | NH | Q3a | OH |
| 320 | N | NEt | Q1r | a bond | Me | a bond | NH | O | NH | Q3b | OH |
| 321 | N | NEt | Q1r | a bond | Me | a bond | NH | O | NH | Q3c | OH |
| 322 | N | NEt | Q1r | a bond | Me | a bond | NH | O | a bond | Q3a | OH |
| 323 | N | NEt | Q1r | a bond | Me | a bond | NH | O | a bond | Q3b | OH |
| 324 | N | NEt | Q1r | a bond | Me | a bond | NH | O | a bond | Q3c | OH |
| 325 | N | NEt | Q1r | a bond | H | a bond | NH | S | NH | Q3a | OH |
| 326 | N | NEt | Q1r | a bond | H | a bond | NH | S | NH | Q3b | OH |
| 327 | N | NEt | Q1r | a bond | H | a bond | NH | S | NH | Q3c | OH |
| 328 | N | NEt | Q1r | a bond | H | a bond | NH | S | a bond | Q3a | OH |
| 329 | N | NEt | Q1r | a bond | H | a bond | NH | S | a bond | Q3b | OH |
| 330 | N | NEt | Q1r | a bond | H | a bond | NH | S | a bond | Q3c | OH |
| 331 | N | NEt | Q1r | a bond | H | a bond | NH | O | NH | Q3a | OH |
| 332 | N | NEt | Q1r | a bond | H | a bond | NH | O | NH | Q3b | OH |
| 333 | N | NEt | Q1r | a bond | H | a bond | NH | O | NH | Q3c | OH |
| 334 | N | NEt | Q1r | a bond | H | a bond | NH | O | a bond | Q3a | OH |
| 335 | N | NEt | Q1r | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 336 | N | NEt | Q1r | a bond | H | a bond | NH | O | a bond | Q3c | OH |
| 337 | N | NEt | Q1s | a bond | Me | a bond | NH | S | NH | Q3a | OH |
| 338 | N | NEt | Q1s | a bond | Me | a bond | NH | S | NH | Q3b | OH |
| 339 | N | NEt | Q1s | a bond | Me | a bond | NH | S | NH | Q3c | OH |
| 340 | N | NEt | Q1s | a bond | Me | a bond | NH | S | a bond | Q3a | OH |
| 341 | N | NEt | Q1s | a bond | Me | a bond | NH | S | a bond | Q3b | OH |
| 342 | N | NEt | Q1s | a bond | Me | a bond | NH | S | a bond | Q3c | OH |
| 343 | N | NEt | Q1s | a bond | Me | a bond | NH | O | NH | Q3a | OH |
| 344 | N | NEt | Q1s | a bond | Me | a bond | NH | O | NH | Q3b | OH |
| 345 | N | NEt | Q1s | a bond | Me | a bond | NH | O | NH | Q3c | OH |
| 346 | N | NEt | Q1s | a bond | Me | a bond | NH | O | a bond | Q3a | OH |
| 347 | N | NEt | Q1s | a bond | Me | a bond | NH | O | a bond | Q3b | OH |
| 348 | N | NEt | Q1s | a bond | Me | a bond | NH | O | a bond | Q3c | OH |
| 349 | N | NEt | Q1s | a bond | H | a bond | NH | S | NH | Q3a | OH |
| 350 | N | NEt | Q1s | a bond | H | a bond | NH | S | NH | Q3b | OH |
| 351 | N | NEt | Q1s | a bond | H | a bond | NH | S | NH | Q3c | OH |
| 352 | N | NEt | Q1s | a bond | H | a bond | NH | S | a bond | Q3a | OH |
| 353 | N | NEt | Q1s | a bond | H | a bond | NH | S | a bond | Q3b | OH |
| 354 | N | NEt | Q1s | a bond | H | a bond | NH | S | a bond | Q3c | OH |
| 355 | N | NEt | Q1s | a bond | H | a bond | NH | O | NH | Q3a | OH |
| 356 | N | NEt | Q1s | a bond | H | a bond | NH | O | NH | Q3b | OH |
| 357 | N | NEt | Q1s | a bond | H | a bond | NH | O | NH | Q3c | OH |
| 358 | N | NEt | Q1s | a bond | H | a bond | NH | O | a bond | Q3a | OH |
| 359 | N | NEt | Q1s | a bond | H | a bond | NH | O | a bond | Q3b | OH |
| 360 | N | NEt | Q1s | a bond | H | a bond | NH | O | a bond | Q3c | OH |
| 361 | N | NEt | Q1t | a bond | Me | a bond | NH | S | NH | Q3a | OH |
| 362 | N | NEt | Q1t | a bond | Me | a bond | NH | S | NH | Q3b | OH |
| 363 | N | NEt | Q1t | a bond | Me | a bond | NH | S | NH | Q3c | OH |
| 364 | N | NEt | Q1t | a bond | Me | a bond | NH | S | a bond | Q3a | OH |
| 365 | N | NEt | Q1t | a bond | Me | a bond | NH | S | a bond | Q3b | OH |
| 366 | N | NEt | Q1t | a bond | Me | a bond | NH | S | a bond | Q3c | OH |
| 367 | N | NEt | Q1t | a bond | Me | a bond | NH | O | NH | Q3a | OH |
| 368 | N | NEt | Q1t | a bond | Me | a bond | NH | O | NH | Q3b | OH |
| 369 | N | NEt | Q1t | a bond | Me | a bond | NH | O | NH | Q3c | OH |
| 370 | N | NEt | Q1t | a bond | Me | a bond | NH | O | a bond | Q3a | OH |
| 371 | N | NEt | Q1t | a bond | Me | a bond | NH | O | a bond | Q3b | OH |
| 372 | N | NEt | Q1t | a bond | Me | a bond | NH | O | a bond | Q3c | OH |
| 373 | N | NEt | Q1t | a bond | H | a bond | NH | S | NH | Q3a | OH |
| 374 | N | NEt | Q1t | a bond | H | a bond | NH | S | NH | Q3b | OH |
| 375 | N | NEt | Q1t | a bond | H | a bond | NH | S | NH | Q3c | OH |
| 376 | N | NEt | Q1t | a bond | H | a bond | NH | S | a bond | Q3a | OH |
| 377 | N | NEt | Q1t | a bond | H | a bond | NH | S | a bond | Q3b | OH |
| 378 | N | NEt | Q1t | a bond | H | a bond | NH | S | a bond | Q3c | OH |
| 379 | N | NEt | Q1t | a bond | H | a bond | NH | O | NH | Q3a | OH |
| 380 | N | NEt | Q1t | a bond | H | a bond | NH | O | NH | Q3b | OH |
| 381 | N | NEt | Q1t | a bond | H | a bond | NH | O | NH | Q3c | OH |
| 382 | N | NEt | Q1t | a bond | H | a bond | NH | O | a bond | Q3a | OH |
| 383 | N | NEt | Q1t | a bond | H | a bond | NH | O | a bond | Q3b | OH |
| 384 | N | NEt | Q1t | a bond | H | a bond | NH | O | a bond | Q3c | OH |
| 385 | N | NEt | Q1u | a bond | Me | a bond | NH | S | NH | Q3a | OH |
| 386 | N | NEt | Q1u | a bond | Me | a bond | NH | S | NH | Q3b | OH |
| 387 | N | NEt | Q1u | a bond | Me | a bond | NH | S | NH | Q3c | OH |
| 388 | N | NEt | Q1u | a bond | Me | a bond | NH | S | a bond | Q3a | OH |
| 389 | N | NEt | Q1u | a bond | Me | a bond | NH | S | a bond | Q3b | OH |
| 390 | N | NEt | Q1u | a bond | Me | a bond | NH | S | a bond | Q3c | OH |
| 391 | N | NEt | Q1u | a bond | Me | a bond | NH | O | NH | Q3a | OH |
| 392 | N | NEt | Q1u | a bond | Me | a bond | NH | O | NH | Q3b | OH |
| 393 | N | NEt | Q1u | a bond | Me | a bond | NH | O | NH | Q3c | OH |
| 394 | N | NEt | Q1u | a bond | Me | a bond | NH | O | a bond | Q3a | OH |
| 395 | N | NEt | Q1u | a bond | Me | a bond | NH | O | a bond | Q3b | OH |
| 396 | N | NEt | Q1u | a bond | Me | a bond | NH | O | a bond | Q3c | OH |
| 397 | N | NEt | Q1u | a bond | H | a bond | NH | S | NH | Q3a | OH |
| 398 | N | NEt | Q1u | a bond | H | a bond | NH | S | NH | Q3b | OH |
| 399 | N | NEt | Q1u | a bond | H | a bond | NH | S | NH | Q3c | OH |
| 400 | N | NEt | Q1u | a bond | H | a bond | NH | S | a bond | Q3a | OH |
| 401 | N | NEt | Q1u | a bond | H | a bond | NH | S | a bond | Q3b | OH |
| 402 | N | NEt | Q1u | a bond | H | a bond | NH | S | a bond | Q3c | OH |
| 403 | N | NEt | Q1u | a bond | H | a bond | NH | O | NH | Q3a | OH |
| 404 | N | NEt | Q1u | a bond | H | a bond | NH | O | NH | Q3b | OH |
| 405 | N | NEt | Q1u | a bond | H | a bond | NH | O | NH | Q3c | OH |
| 406 | N | NEt | Q1u | a bond | H | a bond | NH | O | a bond | Q3a | OH |
| 407 | N | NEt | Q1u | a bond | H | a bond | NH | O | a bond | Q3b | OH |
| 408 | N | NEt | Q1u | a bond | H | a bond | NH | O | a bond | Q3c | OH |
| 409 | N | NEt | Q1v | a bond | Me | a bond | NH | S | NH | Q3a | OH |
| 410 | N | NEt | Q1v | a bond | Me | a bond | NH | S | NH | Q3b | OH |
| 411 | N | NEt | Q1v | a bond | Me | a bond | NH | S | NH | Q3c | OH |
| 412 | N | NEt | Q1v | a bond | Me | a bond | NH | S | a bond | Q3a | OH |
| 413 | N | NEt | Q1v | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 414 | N | NEt | Q1v | a bond | Me | a bond | NH | S | a bond | Q3c | OH |
| 415 | N | NEt | Q1v | a bond | Me | a bond | NH | O | NH | Q3a | OH |
| 416 | N | NEt | Q1v | a bond | Me | a bond | NH | O | NH | Q3b | OH |
| 417 | N | NEt | Q1v | a bond | Me | a bond | NH | O | NH | Q3c | OH |
| 418 | N | NEt | Q1v | a bond | Me | a bond | NH | O | a bond | Q3a | OH |
| 419 | N | NEt | Q1v | a bond | Me | a bond | NH | O | a bond | Q3b | OH |
| 420 | N | NEt | Q1v | a bond | Me | a bond | NH | O | a bond | Q3c | OH |
| 421 | N | NEt | Q1v | a bond | H | a bond | NH | S | NH | Q3a | OH |
| 422 | N | NEt | Q1v | a bond | H | a bond | NH | S | NH | Q3b | OH |
| 423 | N | NEt | Q1v | a bond | H | a bond | NH | S | NH | Q3c | OH |
| 424 | N | NEt | Q1v | a bond | H | a bond | NH | S | a bond | Q3a | OH |
| 425 | N | NEt | Q1v | a bond | H | a bond | NH | S | a bond | Q3b | OH |
| 426 | N | NEt | Q1v | a bond | H | a bond | NH | S | a bond | Q3c | OH |
| 427 | N | NEt | Q1v | a bond | H | a bond | NH | O | NH | Q3a | OH |
| 428 | N | NEt | Q1v | a bond | H | a bond | NH | O | NH | Q3b | OH |
| 429 | N | NEt | Q1v | a bond | H | a bond | NH | O | NH | Q3c | OH |
| 430 | N | NEt | Q1v | a bond | H | a bond | NH | O | a bond | Q3a | OH |
| 431 | N | NEt | Q1v | a bond | H | a bond | NH | O | a bond | Q3b | OH |
| 432 | N | NEt | Q1v | a bond | H | a bond | NH | O | a bond | Q3c | OH |
| 433 | N | NEt | Q1w | a bond | Me | a bond | NH | S | NH | Q3a | OH |
| 434 | N | NEt | Q1w | a bond | Me | a bond | NH | S | NH | Q3b | OH |
| 435 | N | NEt | Q1w | a bond | Me | a bond | NH | S | NH | Q3c | OH |
| 436 | N | NEt | Q1w | a bond | Me | a bond | NH | S | a bond | Q3a | OH |
| 437 | N | NEt | Q1w | a bond | Me | a bond | NH | S | a bond | Q3b | OH |
| 438 | N | NEt | Q1w | a bond | Me | a bond | NH | S | a bond | Q3c | OH |
| 439 | N | NEt | Q1w | a bond | Me | a bond | NH | O | NH | Q3a | OH |
| 440 | N | NEt | Q1w | a bond | Me | a bond | NH | O | NH | Q3b | OH |
| 441 | N | NEt | Q1w | a bond | Me | a bond | NH | O | NH | Q3c | OH |
| 442 | N | NEt | Q1w | a bond | Me | a bond | NH | O | a bond | Q3a | OH |
| 443 | N | NEt | Q1w | a bond | Me | a bond | NH | O | a bond | Q3b | OH |
| 444 | N | NEt | Q1w | a bond | Me | a bond | NH | O | a bond | Q3c | OH |
| 445 | N | NEt | Q1w | a bond | H | a bond | NH | S | NH | Q3a | OH |
| 446 | N | NEt | Q1w | a bond | H | a bond | NH | S | NH | Q3b | OH |
| 447 | N | NEt | Q1w | a bond | H | a bond | NH | S | NH | Q3c | OH |
| 448 | N | NEt | Q1w | a bond | H | a bond | NH | S | a bond | Q3a | OH |
| 449 | N | NEt | Q1w | a bond | H | a bond | NH | S | a bond | Q3b | OH |
| 450 | N | NEt | Q1w | a bond | H | a bond | NH | S | a bond | Q3c | OH |
| 451 | N | NEt | Q1w | a bond | H | a bond | NH | O | NH | Q3a | OH |
| 452 | N | NEt | Q1w | a bond | H | a bond | NH | O | NH | Q3b | OH |
| 453 | N | NEt | Q1w | a bond | H | a bond | NH | O | NH | Q3c | OH |
| 454 | N | NEt | Q1w | a bond | H | a bond | NH | O | a bond | Q3a | OH |
| 455 | N | NEt | Q1w | a bond | H | a bond | NH | O | a bond | Q3b | OH |
| 456 | N | NEt | Q1w | a bond | H | a bond | NH | O | a bond | Q3c | OH |
| 457 | N | NEt | Q1x | a bond | Me | a bond | NH | S | NH | Q3a | OH |
| 458 | N | NEt | Q1x | a bond | Me | a bond | NH | S | NH | Q3b | OH |
| 459 | N | NEt | Q1x | a bond | Me | a bond | NH | S | NH | Q3c | OH |
| 460 | N | NEt | Q1x | a bond | Me | a bond | NH | S | a bond | Q3a | OH |
| 461 | N | NEt | Q1x | a bond | Me | a bond | NH | S | a bond | Q3b | OH |
| 462 | N | NEt | Q1x | a bond | Me | a bond | NH | S | a bond | Q3c | OH |
| 463 | N | NEt | Q1x | a bond | Me | a bond | NH | O | NH | Q3a | OH |
| 464 | N | NEt | Q1x | a bond | Me | a bond | NH | O | NH | Q3b | OH |
| 465 | N | NEt | Q1x | a bond | Me | a bond | NH | O | NH | Q3c | OH |
| 466 | N | NEt | Q1x | a bond | Me | a bond | NH | O | a bond | Q3a | OH |
| 467 | N | NEt | Q1x | a bond | Me | a bond | NH | O | a bond | Q3b | OH |
| 468 | N | NEt | Q1x | a bond | Me | a bond | NH | O | a bond | Q3c | OH |
| 469 | N | NEt | Q1x | a bond | H | a bond | NH | S | NH | Q3a | OH |
| 470 | N | NEt | Q1x | a bond | H | a bond | NH | S | NH | Q3b | OH |
| 471 | N | NEt | Q1x | a bond | H | a bond | NH | S | NH | Q3c | OH |
| 472 | N | NEt | Q1x | a bond | H | a bond | NH | S | a bond | Q3a | OH |
| 473 | N | NEt | Q1x | a bond | H | a bond | NH | S | a bond | Q3b | OH |
| 474 | N | NEt | Q1x | a bond | H | a bond | NH | S | a bond | Q3c | OH |
| 475 | N | NEt | Q1x | a bond | H | a bond | NH | O | NH | Q3a | OH |
| 476 | N | NEt | Q1x | a bond | H | a bond | NH | O | NH | Q3b | OH |
| 477 | N | NEt | Q1x | a bond | H | a bond | NH | O | NH | Q3c | OH |
| 478 | N | NEt | Q1x | a bond | H | a bond | NH | O | a bond | Q3a | OH |
| 479 | N | NEt | Q1x | a bond | H | a bond | NH | O | a bond | Q3b | OH |
| 480 | N | NEt | Q1x | a bond | H | a bond | NH | O | a bond | Q3c | OH |
| 481 | N | S | Q1o | a bond | Me | a bond | NH | S | NH | Q3a | OH |
| 482 | N | S | Q1o | a bond | Me | a bond | NH | S | NH | Q3b | OH |
| 483 | N | S | Q1o | a bond | Me | a bond | NH | S | NH | Q3c | OH |
| 484 | N | S | Q1o | a bond | Me | a bond | NH | S | a bond | Q3a | OH |
| 485 | N | S | Q1o | a bond | Me | a bond | NH | S | a bond | Q3b | OH |
| 486 | N | S | Q1o | a bond | Me | a bond | NH | S | a bond | Q3c | OH |
| 487 | N | S | Q1o | a bond | Me | a bond | NH | O | NH | Q3a | OH |
| 488 | N | S | Q1o | a bond | Me | a bond | NH | O | NH | Q3b | OH |
| 489 | N | S | Q1o | a bond | Me | a bond | NH | O | NH | Q3c | OH |
| 490 | N | S | Q1o | a bond | Me | a bond | NH | O | a bond | Q3a | OH |
| 491 | N | S | Q1o | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 492 | N | S | Q1o | a bond | Me | a bond | NH | O | a bond | Q3c | OH |
| 493 | N | S | Q1o | a bond | H | a bond | NH | S | NH | Q3a | OH |
| 494 | N | S | Q1o | a bond | H | a bond | NH | S | NH | Q3b | OH |
| 495 | N | S | Q1o | a bond | H | a bond | NH | S | NH | Q3c | OH |
| 496 | N | S | Q1o | a bond | H | a bond | NH | S | a bond | Q3a | OH |
| 497 | N | S | Q1o | a bond | H | a bond | NH | S | a bond | Q3b | OH |
| 498 | N | S | Q1o | a bond | H | a bond | NH | S | a bond | Q3c | OH |
| 499 | N | S | Q1o | a bond | H | a bond | NH | O | NH | Q3a | OH |
| 500 | N | S | Q1o | a bond | H | a bond | NH | O | NH | Q3b | OH |
| 501 | N | S | Q1o | a bond | H | a bond | NH | O | NH | Q3c | OH |
| 502 | N | S | Q1o | a bond | H | a bond | NH | O | a bond | Q3a | OH |
| 503 | N | S | Q1o | a bond | H | a bond | NH | O | a bond | Q3b | OH |
| 504 | N | S | Q1o | a bond | H | a bond | NH | O | a bond | Q3c | OH |
| 505 | N | S | Q1p | a bond | Me | a bond | NH | S | NH | Q3a | OH |
| 506 | N | S | Q1p | a bond | Me | a bond | NH | S | NH | Q3b | OH |
| 507 | N | S | Q1p | a bond | Me | a bond | NH | S | NH | Q3c | OH |
| 508 | N | S | Q1p | a bond | Me | a bond | NH | S | a bond | Q3a | OH |
| 509 | N | S | Q1p | a bond | Me | a bond | NH | S | a bond | Q3b | OH |
| 510 | N | S | Q1p | a bond | Me | a bond | NH | S | a bond | Q3c | OH |
| 511 | N | S | Q1p | a bond | Me | a bond | NH | O | NH | Q3a | OH |
| 512 | N | S | Q1p | a bond | Me | a bond | NH | O | NH | Q3b | OH |
| 513 | N | S | Q1p | a bond | Me | a bond | NH | O | NH | Q3c | OH |
| 514 | N | S | Q1p | a bond | Me | a bond | NH | O | a bond | Q3a | OH |
| 515 | N | S | Q1p | a bond | Me | a bond | NH | O | a bond | Q3b | OH |
| 516 | N | S | Q1p | a bond | Me | a bond | NH | O | a bond | Q3c | OH |
| 517 | N | S | Q1p | a bond | H | a bond | NH | S | NH | Q3a | OH |
| 518 | N | S | Q1p | a bond | H | a bond | NH | S | NH | Q3b | OH |
| 519 | N | S | Q1p | a bond | H | a bond | NH | S | NH | Q3c | OH |
| 520 | N | S | Q1p | a bond | H | a bond | NH | S | a bond | Q3a | OH |
| 521 | N | S | Q1p | a bond | H | a bond | NH | S | a bond | Q3b | OH |
| 522 | N | S | Q1p | a bond | H | a bond | NH | S | a bond | Q3c | OH |
| 523 | N | S | Q1p | a bond | H | a bond | NH | O | NH | Q3a | OH |
| 524 | N | S | Q1p | a bond | H | a bond | NH | O | NH | Q3b | OH |
| 525 | N | S | Q1p | a bond | H | a bond | NH | O | NH | Q3c | OH |
| 526 | N | S | Q1p | a bond | H | a bond | NH | O | a bond | Q3a | OH |
| 527 | N | S | Q1p | a bond | H | a bond | NH | O | a bond | Q3b | OH |
| 528 | N | S | Q1p | a bond | H | a bond | NH | O | a bond | Q3c | OH |
| 529 | N | S | Q1q | a bond | Me | a bond | NH | S | NH | Q3a | OH |
| 530 | N | S | Q1q | a bond | Me | a bond | NH | S | NH | Q3b | OH |
| 531 | N | S | Q1q | a bond | Me | a bond | NH | S | NH | Q3c | OH |
| 532 | N | S | Q1q | a bond | Me | a bond | NH | S | a bond | Q3a | OH |
| 533 | N | S | Q1q | a bond | Me | a bond | NH | S | a bond | Q3b | OH |
| 534 | N | S | Q1q | a bond | Me | a bond | NH | S | a bond | Q3c | OH |
| 535 | N | S | Q1q | a bond | Me | a bond | NH | O | NH | Q3a | OH |
| 536 | N | S | Q1q | a bond | Me | a bond | NH | O | NH | Q3b | OH |
| 537 | N | S | Q1q | a bond | Me | a bond | NH | O | NH | Q3c | OH |
| 538 | N | S | Q1q | a bond | Me | a bond | NH | O | a bond | Q3a | OH |
| 539 | N | S | Q1q | a bond | Me | a bond | NH | O | a bond | Q3b | OH |
| 540 | N | S | Q1q | a bond | Me | a bond | NH | O | a bond | Q3c | OH |
| 541 | N | S | Q1q | a bond | H | a bond | NH | S | NH | Q3a | OH |
| 542 | N | S | Q1q | a bond | H | a bond | NH | S | NH | Q3b | OH |
| 543 | N | S | Q1q | a bond | H | a bond | NH | S | NH | Q3c | OH |
| 544 | N | S | Q1q | a bond | H | a bond | NH | S | a bond | Q3a | OH |
| 545 | N | S | Q1q | a bond | H | a bond | NH | S | a bond | Q3b | OH |
| 546 | N | S | Q1q | a bond | H | a bond | NH | S | a bond | Q3c | OH |
| 547 | N | S | Q1q | a bond | H | a bond | NH | O | NH | Q3a | OH |
| 548 | N | S | Q1q | a bond | H | a bond | NH | O | NH | Q3b | OH |
| 549 | N | S | Q1q | a bond | H | a bond | NH | O | NH | Q3c | OH |
| 550 | N | S | Q1q | a bond | H | a bond | NH | O | a bond | Q3a | OH |
| 551 | N | S | Q1q | a bond | H | a bond | NH | O | a bond | Q3b | OH |
| 552 | N | S | Q1q | a bond | H | a bond | NH | O | a bond | Q3c | OH |
| 553 | N | S | Q1r | a bond | Me | a bond | NH | S | NH | Q3a | OH |
| 554 | N | S | Q1r | a bond | Me | a bond | NH | S | NH | Q3b | OH |
| 555 | N | S | Q1r | a bond | Me | a bond | NH | S | NH | Q3c | OH |
| 556 | N | S | Q1r | a bond | Me | a bond | NH | S | a bond | Q3a | OH |
| 557 | N | S | Q1r | a bond | Me | a bond | NH | S | a bond | Q3b | OH |
| 558 | N | S | Q1r | a bond | Me | a bond | NH | S | a bond | Q3c | OH |
| 559 | N | S | Q1r | a bond | Me | a bond | NH | O | NH | Q3a | OH |
| 560 | N | S | Q1r | a bond | Me | a bond | NH | O | NH | Q3b | OH |
| 561 | N | S | Q1r | a bond | Me | a bond | NH | O | NH | Q3c | OH |
| 562 | N | S | Q1r | a bond | Me | a bond | NH | O | a bond | Q3a | OH |
| 563 | N | S | Q1r | a bond | Me | a bond | NH | O | a bond | Q3b | OH |
| 564 | N | S | Q1r | a bond | Me | a bond | NH | O | a bond | Q3c | OH |
| 565 | N | S | Q1r | a bond | H | a bond | NH | S | NH | Q3a | OH |
| 566 | N | S | Q1r | a bond | H | a bond | NH | S | NH | Q3b | OH |
| 567 | N | S | Q1r | a bond | H | a bond | NH | S | NH | Q3c | OH |
| 568 | N | S | Q1r | a bond | H | a bond | NH | S | a bond | Q3a | OH |
| 569 | N | S | Q1r | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 570 | N | S | Q1r | a bond | H | a bond | NH | S | a bond | Q3c | OH |
| 571 | N | S | Q1r | a bond | H | a bond | NH | O | NH | Q3a | OH |
| 572 | N | S | Q1r | a bond | H | a bond | NH | O | NH | Q3b | OH |
| 573 | N | S | Q1r | a bond | H | a bond | NH | O | NH | Q3c | OH |
| 574 | N | S | Q1r | a bond | H | a bond | NH | O | a bond | Q3a | OH |
| 575 | N | S | Q1r | a bond | H | a bond | NH | O | a bond | Q3b | OH |
| 576 | N | S | Q1r | a bond | H | a bond | NH | O | a bond | Q3c | OH |
| 577 | N | S | Q1s | a bond | Me | a bond | NH | S | NH | Q3a | OH |
| 578 | N | S | Q1s | a bond | Me | a bond | NH | S | NH | Q3b | OH |
| 579 | N | S | Q1s | a bond | Me | a bond | NH | S | NH | Q3c | OH |
| 580 | N | S | Q1s | a bond | Me | a bond | NH | S | a bond | Q3a | OH |
| 581 | N | S | Q1s | a bond | Me | a bond | NH | S | a bond | Q3b | OH |
| 582 | N | S | Q1s | a bond | Me | a bond | NH | S | a bond | Q3c | OH |
| 583 | N | S | Q1s | a bond | Me | a bond | NH | O | NH | Q3a | OH |
| 584 | N | S | Q1s | a bond | Me | a bond | NH | O | NH | Q3b | OH |
| 585 | N | S | Q1s | a bond | Me | a bond | NH | O | NH | Q3c | OH |
| 586 | N | S | Q1s | a bond | Me | a bond | NH | O | a bond | Q3a | OH |
| 587 | N | S | Q1s | a bond | Me | a bond | NH | O | a bond | Q3b | OH |
| 588 | N | S | Q1s | a bond | Me | a bond | NH | O | a bond | Q3c | OH |
| 589 | N | S | Q1s | a bond | H | a bond | NH | S | NH | Q3a | OH |
| 590 | N | S | Q1s | a bond | H | a bond | NH | S | NH | Q3b | OH |
| 591 | N | S | Q1s | a bond | H | a bond | NH | S | NH | Q3c | OH |
| 592 | N | S | Q1s | a bond | H | a bond | NH | S | a bond | Q3a | OH |
| 593 | N | S | Q1s | a bond | H | a bond | NH | S | a bond | Q3b | OH |
| 594 | N | S | Q1s | a bond | H | a bond | NH | S | a bond | Q3c | OH |
| 595 | N | S | Q1s | a bond | H | a bond | NH | O | NH | Q3a | OH |
| 596 | N | S | Q1s | a bond | H | a bond | NH | O | NH | Q3b | OH |
| 597 | N | S | Q1s | a bond | H | a bond | NH | O | NH | Q3c | OH |
| 598 | N | S | Q1s | a bond | H | a bond | NH | O | a bond | Q3a | OH |
| 599 | N | S | Q1s | a bond | H | a bond | NH | O | a bond | Q3b | OH |
| 600 | N | S | Q1s | a bond | H | a bond | NH | O | a bond | Q3c | OH |
| 601 | N | S | Q1t | a bond | Me | a bond | NH | S | NH | Q3a | OH |
| 602 | N | S | Q1t | a bond | Me | a bond | NH | S | NH | Q3b | OH |
| 603 | N | S | Q1t | a bond | Me | a bond | NH | S | NH | Q3c | OH |
| 604 | N | S | Q1t | a bond | Me | a bond | NH | S | a bond | Q3a | OH |
| 605 | N | S | Q1t | a bond | Me | a bond | NH | S | a bond | Q3b | OH |
| 606 | N | S | Q1t | a bond | Me | a bond | NH | S | a bond | Q3c | OH |
| 607 | N | S | Q1t | a bond | Me | a bond | NH | O | NH | Q3a | OH |
| 608 | N | S | Q1t | a bond | Me | a bond | NH | O | NH | Q3b | OH |
| 609 | N | S | Q1t | a bond | Me | a bond | NH | O | NH | Q3c | OH |
| 610 | N | S | Q1t | a bond | Me | a bond | NH | O | a bond | Q3a | OH |
| 611 | N | S | Q1t | a bond | Me | a bond | NH | O | a bond | Q3b | OH |
| 612 | N | S | Q1t | a bond | Me | a bond | NH | O | a bond | Q3c | OH |
| 613 | N | S | Q1t | a bond | H | a bond | NH | S | NH | Q3a | OH |
| 614 | N | S | Q1t | a bond | H | a bond | NH | S | NH | Q3b | OH |
| 615 | N | S | Q1t | a bond | H | a bond | NH | S | NH | Q3c | OH |
| 616 | N | S | Q1t | a bond | H | a bond | NH | S | a bond | Q3a | OH |
| 617 | N | S | Q1t | a bond | H | a bond | NH | S | a bond | Q3b | OH |
| 618 | N | S | Q1t | a bond | H | a bond | NH | S | a bond | Q3c | OH |
| 619 | N | S | Q1t | a bond | H | a bond | NH | O | NH | Q3a | OH |
| 620 | N | S | Q1t | a bond | H | a bond | NH | O | NH | Q3b | OH |
| 621 | N | S | Q1t | a bond | H | a bond | NH | O | NH | Q3c | OH |
| 622 | N | S | Q1t | a bond | H | a bond | NH | O | a bond | Q3a | OH |
| 623 | N | S | Q1t | a bond | H | a bond | NH | O | a bond | Q3b | OH |
| 624 | N | S | Q1t | a bond | H | a bond | NH | O | a bond | Q3c | OH |
| 625 | N | S | Q1u | a bond | Me | a bond | NH | S | NH | Q3a | OH |
| 626 | N | S | Q1u | a bond | Me | a bond | NH | S | NH | Q3b | OH |
| 627 | N | S | Q1u | a bond | Me | a bond | NH | S | NH | Q3c | OH |
| 628 | N | S | Q1u | a bond | Me | a bond | NH | S | a bond | Q3a | OH |
| 629 | N | S | Q1u | a bond | Me | a bond | NH | S | a bond | Q3b | OH |
| 630 | N | S | Q1u | a bond | Me | a bond | NH | S | a bond | Q3c | OH |
| 631 | N | S | Q1u | a bond | Me | a bond | NH | O | NH | Q3a | OH |
| 632 | N | S | Q1u | a bond | Me | a bond | NH | O | NH | Q3b | OH |
| 633 | N | S | Q1u | a bond | Me | a bond | NH | O | NH | Q3c | OH |
| 634 | N | S | Q1u | a bond | Me | a bond | NH | O | a bond | Q3a | OH |
| 635 | N | S | Q1u | a bond | Me | a bond | NH | O | a bond | Q3b | OH |
| 636 | N | S | Q1u | a bond | Me | a bond | NH | O | a bond | Q3c | OH |
| 637 | N | S | Q1u | a bond | H | a bond | NH | S | NH | Q3a | OH |
| 638 | N | S | Q1u | a bond | H | a bond | NH | S | NH | Q3b | OH |
| 639 | N | S | Q1u | a bond | H | a bond | NH | S | NH | Q3c | OH |
| 640 | N | S | Q1u | a bond | H | a bond | NH | S | a bond | Q3a | OH |
| 641 | N | S | Q1u | a bond | H | a bond | NH | S | a bond | Q3b | OH |
| 642 | N | S | Q1u | a bond | H | a bond | NH | S | a bond | Q3c | OH |
| 643 | N | S | Q1u | a bond | H | a bond | NH | O | NH | Q3a | OH |
| 644 | N | S | Q1u | a bond | H | a bond | NH | O | NH | Q3b | OH |
| 645 | N | S | Q1u | a bond | H | a bond | NH | O | NH | Q3c | OH |
| 646 | N | S | Q1u | a bond | H | a bond | NH | O | a bond | Q3a | OH |
| 647 | N | S | Q1u | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 648 | N | S | Q1u | a bond | H | a bond | NH | O | a bond | Q3c | OH |
| 649 | N | S | Q1v | a bond | Me | a bond | NH | S | NH | Q3a | OH |
| 650 | N | S | Q1v | a bond | Me | a bond | NH | S | NH | Q3b | OH |
| 651 | N | S | Q1v | a bond | Me | a bond | NH | S | NH | Q3c | OH |
| 652 | N | S | Q1v | a bond | Me | a bond | NH | S | a bond | Q3a | OH |
| 653 | N | S | Q1v | a bond | Me | a bond | NH | S | a bond | Q3b | OH |
| 654 | N | S | Q1v | a bond | Me | a bond | NH | S | a bond | Q3c | OH |
| 655 | N | S | Q1v | a bond | Me | a bond | NH | O | NH | Q3a | OH |
| 656 | N | S | Q1v | a bond | Me | a bond | NH | O | NH | Q3b | OH |
| 657 | N | S | Q1v | a bond | Me | a bond | NH | O | NH | Q3c | OH |
| 658 | N | S | Q1v | a bond | Me | a bond | NH | O | a bond | Q3a | OH |
| 659 | N | S | Q1v | a bond | Me | a bond | NH | O | a bond | Q3b | OH |
| 660 | N | S | Q1v | a bond | Me | a bond | NH | O | a bond | Q3c | OH |
| 661 | N | S | Q1v | a bond | H | a bond | NH | S | NH | Q3a | OH |
| 662 | N | S | Q1v | a bond | H | a bond | NH | S | NH | Q3b | OH |
| 663 | N | S | Q1v | a bond | H | a bond | NH | S | NH | Q3c | OH |
| 664 | N | S | Q1v | a bond | H | a bond | NH | S | a bond | Q3a | OH |
| 665 | N | S | Q1v | a bond | H | a bond | NH | S | a bond | Q3b | OH |
| 666 | N | S | Q1v | a bond | H | a bond | NH | S | a bond | Q3c | OH |
| 667 | N | S | Q1v | a bond | H | a bond | NH | O | NH | Q3a | OH |
| 668 | N | S | Q1v | a bond | H | a bond | NH | O | NH | Q3b | OH |
| 669 | N | S | Q1v | a bond | H | a bond | NH | O | NH | Q3c | OH |
| 670 | N | S | Q1v | a bond | H | a bond | NH | O | a bond | Q3a | OH |
| 671 | N | S | Q1v | a bond | H | a bond | NH | O | a bond | Q3b | OH |
| 672 | N | S | Q1v | a bond | H | a bond | NH | O | a bond | Q3c | OH |
| 673 | N | S | Q1w | a bond | Me | a bond | NH | S | NH | Q3a | OH |
| 674 | N | S | Q1w | a bond | Me | a bond | NH | S | NH | Q3b | OH |
| 675 | N | S | Q1w | a bond | Me | a bond | NH | S | NH | Q3c | OH |
| 676 | N | S | Q1w | a bond | Me | a bond | NH | S | a bond | Q3a | OH |
| 677 | N | S | Q1w | a bond | Me | a bond | NH | S | a bond | Q3b | OH |
| 678 | N | S | Q1w | a bond | Me | a bond | NH | S | a bond | Q3c | OH |
| 679 | N | S | Q1w | a bond | Me | a bond | NH | O | NH | Q3a | OH |
| 680 | N | S | Q1w | a bond | Me | a bond | NH | O | NH | Q3b | OH |
| 681 | N | S | Q1w | a bond | Me | a bond | NH | O | NH | Q3c | OH |
| 682 | N | S | Q1w | a bond | Me | a bond | NH | O | a bond | Q3a | OH |
| 683 | N | S | Q1w | a bond | Me | a bond | NH | O | a bond | Q3b | OH |
| 684 | N | S | Q1w | a bond | Me | a bond | NH | O | a bond | Q3c | OH |
| 685 | N | S | Q1w | a bond | H | a bond | NH | S | NH | Q3a | OH |
| 686 | N | S | Q1w | a bond | H | a bond | NH | S | NH | Q3b | OH |
| 687 | N | S | Q1w | a bond | H | a bond | NH | S | NH | Q3c | OH |
| 688 | N | S | Q1w | a bond | H | a bond | NH | S | a bond | Q3a | OH |
| 689 | N | S | Q1w | a bond | H | a bond | NH | S | a bond | Q3b | OH |
| 690 | N | S | Q1w | a bond | H | a bond | NH | S | a bond | Q3c | OH |
| 691 | N | S | Q1w | a bond | H | a bond | NH | O | NH | Q3a | OH |
| 692 | N | S | Q1w | a bond | H | a bond | NH | O | NH | Q3b | OH |
| 693 | N | S | Q1w | a bond | H | a bond | NH | O | NH | Q3c | OH |
| 694 | N | S | Q1w | a bond | H | a bond | NH | O | a bond | Q3a | OH |
| 695 | N | S | Q1w | a bond | H | a bond | NH | O | a bond | Q3b | OH |
| 696 | N | S | Q1w | a bond | H | a bond | NH | O | a bond | Q3c | OH |
| 697 | N | S | Q1x | a bond | Me | a bond | NH | S | NH | Q3a | OH |
| 698 | N | S | Q1x | a bond | Me | a bond | NH | S | NH | Q3b | OH |
| 699 | N | S | Q1x | a bond | Me | a bond | NH | S | NH | Q3c | OH |
| 700 | N | S | Q1x | a bond | Me | a bond | NH | S | a bond | Q3a | OH |
| 701 | N | S | Q1x | a bond | Me | a bond | NH | S | a bond | Q3b | OH |
| 702 | N | S | Q1x | a bond | Me | a bond | NH | S | a bond | Q3c | OH |
| 703 | N | S | Q1x | a bond | Me | a bond | NH | O | NH | Q3a | OH |
| 704 | N | S | Q1x | a bond | Me | a bond | NH | O | NH | Q3b | OH |
| 705 | N | S | Q1x | a bond | Me | a bond | NH | O | NH | Q3c | OH |
| 706 | N | S | Q1x | a bond | Me | a bond | NH | O | a bond | Q3a | OH |
| 707 | N | S | Q1x | a bond | Me | a bond | NH | O | a bond | Q3b | OH |
| 708 | N | S | Q1x | a bond | Me | a bond | NH | O | a bond | Q3c | OH |
| 709 | N | S | Q1x | a bond | H | a bond | NH | S | NH | Q3a | OH |
| 710 | N | S | Q1x | a bond | H | a bond | NH | S | NH | Q3b | OH |
| 711 | N | S | Q1x | a bond | H | a bond | NH | S | NH | Q3c | OH |
| 712 | N | S | Q1x | a bond | H | a bond | NH | S | a bond | Q3a | OH |
| 713 | N | S | Q1x | a bond | H | a bond | NH | S | a bond | Q3b | OH |
| 714 | N | S | Q1x | a bond | H | a bond | NH | S | a bond | Q3c | OH |
| 715 | N | S | Q1x | a bond | H | a bond | NH | O | NH | Q3a | OH |
| 716 | N | S | Q1x | a bond | H | a bond | NH | O | NH | Q3b | OH |
| 717 | N | S | Q1x | a bond | H | a bond | NH | O | NH | Q3c | OH |
| 718 | N | S | Q1x | a bond | H | a bond | NH | O | a bond | Q3a | OH |
| 719 | N | S | Q1x | a bond | H | a bond | NH | O | a bond | Q3b | OH |
| 720 | N | S | Q1x | a bond | H | a bond | NH | O | a bond | Q3c | OH |
| 721 | N | O | Q1o | a bond | Me | a bond | NH | S | NH | Q3a | OH |
| 722 | N | O | Q1o | a bond | Me | a bond | NH | S | NH | Q3b | OH |
| 723 | N | O | Q1o | a bond | Me | a bond | NH | S | NH | Q3c | OH |
| 724 | N | O | Q1o | a bond | Me | a bond | NH | S | a bond | Q3a | OH |
| 725 | N | O | Q1o | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 726 | N | O | Q1o | a bond | Me | a bond | NH | S | a bond | Q3c | OH |
| 727 | N | O | Q1o | a bond | Me | a bond | NH | O | NH | Q3a | OH |
| 728 | N | O | Q1o | a bond | Me | a bond | NH | O | NH | Q3b | OH |
| 729 | N | O | Q1o | a bond | Me | a bond | NH | O | NH | Q3c | OH |
| 730 | N | O | Q1o | a bond | Me | a bond | NH | O | a bond | Q3a | OH |
| 731 | N | O | Q1o | a bond | Me | a bond | NH | O | a bond | Q3b | OH |
| 732 | N | O | Q1o | a bond | Me | a bond | NH | O | a bond | Q3c | OH |
| 733 | N | O | Q1o | a bond | H | a bond | NH | S | NH | Q3a | OH |
| 734 | N | O | Q1o | a bond | H | a bond | NH | S | NH | Q3b | OH |
| 735 | N | O | Q1o | a bond | H | a bond | NH | S | NH | Q3c | OH |
| 736 | N | O | Q1o | a bond | H | a bond | NH | S | a bond | Q3a | OH |
| 737 | N | O | Q1o | a bond | H | a bond | NH | S | a bond | Q3b | OH |
| 738 | N | O | Q1o | a bond | H | a bond | NH | S | a bond | Q3c | OH |
| 739 | N | O | Q1o | a bond | H | a bond | NH | O | NH | Q3a | OH |
| 740 | N | O | Q1o | a bond | H | a bond | NH | O | NH | Q3b | OH |
| 741 | N | O | Q1o | a bond | H | a bond | NH | O | NH | Q3c | OH |
| 742 | N | O | Q1o | a bond | H | a bond | NH | O | a bond | Q3a | OH |
| 743 | N | O | Q1o | a bond | H | a bond | NH | O | a bond | Q3b | OH |
| 744 | N | O | Q1o | a bond | H | a bond | NH | O | a bond | Q3c | OH |
| 745 | N | O | Q1p | a bond | Me | a bond | NH | S | NH | Q3a | OH |
| 746 | N | O | Q1p | a bond | Me | a bond | NH | S | NH | Q3b | OH |
| 747 | N | O | Q1p | a bond | Me | a bond | NH | S | NH | Q3c | OH |
| 748 | N | O | Q1p | a bond | Me | a bond | NH | S | a bond | Q3a | OH |
| 749 | N | O | Q1p | a bond | Me | a bond | NH | S | a bond | Q3b | OH |
| 750 | N | O | Q1p | a bond | Me | a bond | NH | S | a bond | Q3c | OH |
| 751 | N | O | Q1p | a bond | Me | a bond | NH | O | NH | Q3a | OH |
| 752 | N | O | Q1p | a bond | Me | a bond | NH | O | NH | Q3b | OH |
| 753 | N | O | Q1p | a bond | Me | a bond | NH | O | NH | Q3c | OH |
| 754 | N | O | Q1p | a bond | Me | a bond | NH | O | a bond | Q3a | OH |
| 755 | N | O | Q1p | a bond | Me | a bond | NH | O | a bond | Q3b | OH |
| 756 | N | O | Q1p | a bond | Me | a bond | NH | O | a bond | Q3c | OH |
| 757 | N | O | Q1p | a bond | H | a bond | NH | S | NH | Q3a | OH |
| 758 | N | O | Q1p | a bond | H | a bond | NH | S | NH | Q3b | OH |
| 759 | N | O | Q1p | a bond | H | a bond | NH | S | NH | Q3c | OH |
| 760 | N | O | Q1p | a bond | H | a bond | NH | S | a bond | Q3a | OH |
| 761 | N | O | Q1p | a bond | H | a bond | NH | S | a bond | Q3b | OH |
| 762 | N | O | Q1p | a bond | H | a bond | NH | S | a bond | Q3c | OH |
| 763 | N | O | Q1p | a bond | H | a bond | NH | O | NH | Q3a | OH |
| 764 | N | O | Q1p | a bond | H | a bond | NH | O | NH | Q3b | OH |
| 765 | N | O | Q1p | a bond | H | a bond | NH | O | NH | Q3c | OH |
| 766 | N | O | Q1p | a bond | H | a bond | NH | O | a bond | Q3a | OH |
| 767 | N | O | Q1p | a bond | H | a bond | NH | O | a bond | Q3b | OH |
| 768 | N | O | Q1p | a bond | H | a bond | NH | O | a bond | Q3c | OH |
| 769 | N | O | Q1q | a bond | Me | a bond | NH | S | NH | Q3a | OH |
| 770 | N | O | Q1q | a bond | Me | a bond | NH | S | NH | Q3b | OH |
| 771 | N | O | Q1q | a bond | Me | a bond | NH | S | NH | Q3c | OH |
| 772 | N | O | Q1q | a bond | Me | a bond | NH | S | a bond | Q3a | OH |
| 773 | N | O | Q1q | a bond | Me | a bond | NH | S | a bond | Q3b | OH |
| 774 | N | O | Q1q | a bond | Me | a bond | NH | S | a bond | Q3c | OH |
| 775 | N | O | Q1q | a bond | Me | a bond | NH | O | NH | Q3a | OH |
| 776 | N | O | Q1q | a bond | Me | a bond | NH | O | NH | Q3b | OH |
| 777 | N | O | Q1q | a bond | Me | a bond | NH | O | NH | Q3c | OH |
| 778 | N | O | Q1q | a bond | Me | a bond | NH | O | a bond | Q3a | OH |
| 779 | N | O | Q1q | a bond | Me | a bond | NH | O | a bond | Q3b | OH |
| 780 | N | O | Q1q | a bond | Me | a bond | NH | O | a bond | Q3c | OH |
| 781 | N | O | Q1q | a bond | H | a bond | NH | S | NH | Q3a | OH |
| 782 | N | O | Q1q | a bond | H | a bond | NH | S | NH | Q3b | OH |
| 783 | N | O | Q1q | a bond | H | a bond | NH | S | NH | Q3c | OH |
| 784 | N | O | Q1q | a bond | H | a bond | NH | S | a bond | Q3a | OH |
| 785 | N | O | Q1q | a bond | H | a bond | NH | S | a bond | Q3b | OH |
| 786 | N | O | Q1q | a bond | H | a bond | NH | S | a bond | Q3c | OH |
| 787 | N | O | Q1q | a bond | H | a bond | NH | O | NH | Q3a | OH |
| 788 | N | O | Q1q | a bond | H | a bond | NH | O | NH | Q3b | OH |
| 789 | N | O | Q1q | a bond | H | a bond | NH | O | NH | Q3c | OH |
| 790 | N | O | Q1q | a bond | H | a bond | NH | O | a bond | Q3a | OH |
| 791 | N | O | Q1q | a bond | H | a bond | NH | O | a bond | Q3b | OH |
| 792 | N | O | Q1q | a bond | H | a bond | NH | O | a bond | Q3c | OH |
| 793 | N | O | Q1r | a bond | Me | a bond | NH | S | NH | Q3a | OH |
| 794 | N | O | Q1r | a bond | Me | a bond | NH | S | NH | Q3b | OH |
| 795 | N | O | Q1r | a bond | Me | a bond | NH | S | NH | Q3c | OH |
| 796 | N | O | Q1r | a bond | Me | a bond | NH | S | a bond | Q3a | OH |
| 797 | N | O | Q1r | a bond | Me | a bond | NH | S | a bond | Q3b | OH |
| 798 | N | O | Q1r | a bond | Me | a bond | NH | S | a bond | Q3c | OH |
| 799 | N | O | Q1r | a bond | Me | a bond | NH | O | NH | Q3a | OH |
| 800 | N | O | Q1r | a bond | Me | a bond | NH | O | NH | Q3b | OH |
| 801 | N | O | Q1r | a bond | Me | a bond | NH | O | NH | Q3c | OH |
| 802 | N | O | Q1r | a bond | Me | a bond | NH | O | a bond | Q3a | OH |
| 803 | N | O | Q1r | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 804 | N | O | Q1r | a bond | Me | a bond | NH | O | a bond | Q3c | OH |
| 805 | N | O | Q1r | a bond | H | a bond | NH | S | NH | Q3a | OH |
| 806 | N | O | Q1r | a bond | H | a bond | NH | S | NH | Q3b | OH |
| 807 | N | O | Q1r | a bond | H | a bond | NH | S | NH | Q3c | OH |
| 808 | N | O | Q1r | a bond | H | a bond | NH | S | a bond | Q3a | OH |
| 809 | N | O | Q1r | a bond | H | a bond | NH | S | a bond | Q3b | OH |
| 810 | N | O | Q1r | a bond | H | a bond | NH | S | a bond | Q3c | OH |
| 811 | N | O | Q1r | a bond | H | a bond | NH | O | NH | Q3a | OH |
| 812 | N | O | Q1r | a bond | H | a bond | NH | O | NH | Q3b | OH |
| 813 | N | O | Q1r | a bond | H | a bond | NH | O | NH | Q3c | OH |
| 814 | N | O | Q1r | a bond | H | a bond | NH | O | a bond | Q3a | OH |
| 815 | N | O | Q1r | a bond | H | a bond | NH | O | a bond | Q3b | OH |
| 816 | N | O | Q1r | a bond | H | a bond | NH | O | a bond | Q3c | OH |
| 817 | N | O | Q1s | a bond | Me | a bond | NH | S | NH | Q3a | OH |
| 818 | N | O | Q1s | a bond | Me | a bond | NH | S | NH | Q3b | OH |
| 819 | N | O | Q1s | a bond | Me | a bond | NH | S | NH | Q3c | OH |
| 820 | N | O | Q1s | a bond | Me | a bond | NH | S | a bond | Q3a | OH |
| 821 | N | O | Q1s | a bond | Me | a bond | NH | S | a bond | Q3b | OH |
| 822 | N | O | Q1s | a bond | Me | a bond | NH | S | a bond | Q3c | OH |
| 823 | N | O | Q1s | a bond | Me | a bond | NH | O | NH | Q3a | OH |
| 824 | N | O | Q1s | a bond | Me | a bond | NH | O | NH | Q3b | OH |
| 825 | N | O | Q1s | a bond | Me | a bond | NH | O | NH | Q3c | OH |
| 826 | N | O | Q1s | a bond | Me | a bond | NH | O | a bond | Q3a | OH |
| 827 | N | O | Q1s | a bond | Me | a bond | NH | O | a bond | Q3b | OH |
| 828 | N | O | Q1s | a bond | Me | a bond | NH | O | a bond | Q3c | OH |
| 829 | N | O | Q1s | a bond | H | a bond | NH | S | NH | Q3a | OH |
| 830 | N | O | Q1s | a bond | H | a bond | NH | S | NH | Q3b | OH |
| 831 | N | O | Q1s | a bond | H | a bond | NH | S | NH | Q3c | OH |
| 832 | N | O | Q1s | a bond | H | a bond | NH | S | a bond | Q3a | OH |
| 833 | N | O | Q1s | a bond | H | a bond | NH | S | a bond | Q3b | OH |
| 834 | N | O | Q1s | a bond | H | a bond | NH | S | a bond | Q3c | OH |
| 835 | N | O | Q1s | a bond | H | a bond | NH | O | NH | Q3a | OH |
| 836 | N | O | Q1s | a bond | H | a bond | NH | O | NH | Q3b | OH |
| 837 | N | O | Q1s | a bond | H | a bond | NH | O | NH | Q3c | OH |
| 838 | N | O | Q1s | a bond | H | a bond | NH | O | a bond | Q3a | OH |
| 839 | N | O | Q1s | a bond | H | a bond | NH | O | a bond | Q3b | OH |
| 840 | N | O | Q1s | a bond | H | a bond | NH | O | a bond | Q3c | OH |
| 841 | N | O | Q1t | a bond | Me | a bond | NH | S | NH | Q3a | OH |
| 842 | N | O | Q1t | a bond | Me | a bond | NH | S | NH | Q3b | OH |
| 843 | N | O | Q1t | a bond | Me | a bond | NH | S | NH | Q3c | OH |
| 844 | N | O | Q1t | a bond | Me | a bond | NH | S | a bond | Q3a | OH |
| 845 | N | O | Q1t | a bond | Me | a bond | NH | S | a bond | Q3b | OH |
| 846 | N | O | Q1t | a bond | Me | a bond | NH | S | a bond | Q3c | OH |
| 847 | N | O | Q1t | a bond | Me | a bond | NH | O | NH | Q3a | OH |
| 848 | N | O | Q1t | a bond | Me | a bond | NH | O | NH | Q3b | OH |
| 849 | N | O | Q1t | a bond | Me | a bond | NH | O | NH | Q3c | OH |
| 850 | N | O | Q1t | a bond | Me | a bond | NH | O | a bond | Q3a | OH |
| 851 | N | O | Q1t | a bond | Me | a bond | NH | O | a bond | Q3b | OH |
| 852 | N | O | Q1t | a bond | Me | a bond | NH | O | a bond | Q3c | OH |
| 853 | N | O | Q1t | a bond | H | a bond | NH | S | NH | Q3a | OH |
| 854 | N | O | Q1t | a bond | H | a bond | NH | S | NH | Q3b | OH |
| 855 | N | O | Q1t | a bond | H | a bond | NH | S | NH | Q3c | OH |
| 856 | N | O | Q1t | a bond | H | a bond | NH | S | a bond | Q3a | OH |
| 857 | N | O | Q1t | a bond | H | a bond | NH | S | a bond | Q3b | OH |
| 858 | N | O | Q1t | a bond | H | a bond | NH | S | a bond | Q3c | OH |
| 859 | N | O | Q1t | a bond | H | a bond | NH | O | NH | Q3a | OH |
| 860 | N | O | Q1t | a bond | H | a bond | NH | O | NH | Q3b | OH |
| 861 | N | O | Q1t | a bond | H | a bond | NH | O | NH | Q3c | OH |
| 862 | N | O | Q1t | a bond | H | a bond | NH | O | a bond | Q3a | OH |
| 863 | N | O | Q1t | a bond | H | a bond | NH | O | a bond | Q3b | OH |
| 864 | N | O | Q1t | a bond | H | a bond | NH | O | a bond | Q3c | OH |
| 865 | N | O | Q1u | a bond | Me | a bond | NH | S | NH | Q3a | OH |
| 866 | N | O | Q1u | a bond | Me | a bond | NH | S | NH | Q3b | OH |
| 867 | N | O | Q1u | a bond | Me | a bond | NH | S | NH | Q3c | OH |
| 868 | N | O | Q1u | a bond | Me | a bond | NH | S | a bond | Q3a | OH |
| 869 | N | O | Q1u | a bond | Me | a bond | NH | S | a bond | Q3b | OH |
| 870 | N | O | Q1u | a bond | Me | a bond | NH | S | a bond | Q3c | OH |
| 871 | N | O | Q1u | a bond | Me | a bond | NH | O | NH | Q3a | OH |
| 872 | N | O | Q1u | a bond | Me | a bond | NH | O | NH | Q3b | OH |
| 873 | N | O | Q1u | a bond | Me | a bond | NH | O | NH | Q3c | OH |
| 874 | N | O | Q1u | a bond | Me | a bond | NH | O | a bond | Q3a | OH |
| 875 | N | O | Q1u | a bond | Me | a bond | NH | O | a bond | Q3b | OH |
| 876 | N | O | Q1u | a bond | Me | a bond | NH | O | a bond | Q3c | OH |
| 877 | N | O | Q1u | a bond | H | a bond | NH | S | NH | Q3a | OH |
| 878 | N | O | Q1u | a bond | H | a bond | NH | S | NH | Q3b | OH |
| 879 | N | O | Q1u | a bond | H | a bond | NH | S | NH | Q3c | OH |
| 880 | N | O | Q1u | a bond | H | a bond | NH | S | a bond | Q3a | OH |
| 881 | N | O | Q1u | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 882 | N | O | Q1u | a bond | H | a bond | NH | S | a bond | Q3c | OH |
| 883 | N | O | Q1u | a bond | H | a bond | NH | O | NH | Q3a | OH |
| 884 | N | O | Q1u | a bond | H | a bond | NH | O | NH | Q3b | OH |
| 885 | N | O | Q1u | a bond | H | a bond | NH | O | NH | Q3c | OH |
| 886 | N | O | Q1u | a bond | H | a bond | NH | O | a bond | Q3a | OH |
| 887 | N | O | Q1u | a bond | H | a bond | NH | O | a bond | Q3b | OH |
| 888 | N | O | Q1u | a bond | H | a bond | NH | O | a bond | Q3c | OH |
| 889 | N | O | Q1v | a bond | Me | a bond | NH | S | NH | Q3a | OH |
| 890 | N | O | Q1v | a bond | Me | a bond | NH | S | NH | Q3b | OH |
| 891 | N | O | Q1v | a bond | Me | a bond | NH | S | NH | Q3c | OH |
| 892 | N | O | Q1v | a bond | Me | a bond | NH | S | a bond | Q3a | OH |
| 893 | N | O | Q1v | a bond | Me | a bond | NH | S | a bond | Q3b | OH |
| 894 | N | O | Q1v | a bond | Me | a bond | NH | S | a bond | Q3c | OH |
| 895 | N | O | Q1v | a bond | Me | a bond | NH | O | NH | Q3a | OH |
| 896 | N | O | Q1v | a bond | Me | a bond | NH | O | NH | Q3b | OH |
| 897 | N | O | Q1v | a bond | Me | a bond | NH | O | NH | Q3c | OH |
| 898 | N | O | Q1v | a bond | Me | a bond | NH | O | a bond | Q3a | OH |
| 899 | N | O | Q1v | a bond | Me | a bond | NH | O | a bond | Q3b | OH |
| 900 | N | O | Q1v | a bond | Me | a bond | NH | O | a bond | Q3c | OH |
| 901 | N | O | Q1v | a bond | H | a bond | NH | S | NH | Q3a | OH |
| 902 | N | O | Q1v | a bond | H | a bond | NH | S | NH | Q3b | OH |
| 903 | N | O | Q1v | a bond | H | a bond | NH | S | NH | Q3c | OH |
| 904 | N | O | Q1v | a bond | H | a bond | NH | S | a bond | Q3a | OH |
| 905 | N | O | Q1v | a bond | H | a bond | NH | S | a bond | Q3b | OH |
| 906 | N | O | Q1v | a bond | H | a bond | NH | S | a bond | Q3c | OH |
| 907 | N | O | Q1v | a bond | H | a bond | NH | O | NH | Q3a | OH |
| 908 | N | O | Q1v | a bond | H | a bond | NH | O | NH | Q3b | OH |
| 909 | N | O | Q1v | a bond | H | a bond | NH | O | NH | Q3c | OH |
| 910 | N | O | Q1v | a bond | H | a bond | NH | O | a bond | Q3a | OH |
| 911 | N | O | Q1v | a bond | H | a bond | NH | O | a bond | Q3b | OH |
| 912 | N | O | Q1v | a bond | H | a bond | NH | O | a bond | Q3c | OH |
| 913 | N | O | Q1w | a bond | Me | a bond | NH | S | NH | Q3a | OH |
| 914 | N | O | Q1w | a bond | Me | a bond | NH | S | NH | Q3b | OH |
| 915 | N | O | Q1w | a bond | Me | a bond | NH | S | NH | Q3c | OH |
| 916 | N | O | Q1w | a bond | Me | a bond | NH | S | a bond | Q3a | OH |
| 917 | N | O | Q1w | a bond | Me | a bond | NH | S | a bond | Q3b | OH |
| 918 | N | O | Q1w | a bond | Me | a bond | NH | S | a bond | Q3c | OH |
| 919 | N | O | Q1w | a bond | Me | a bond | NH | O | NH | Q3a | OH |
| 920 | N | O | Q1w | a bond | Me | a bond | NH | O | NH | Q3b | OH |
| 921 | N | O | Q1w | a bond | Me | a bond | NH | O | NH | Q3c | OH |
| 922 | N | O | Q1w | a bond | Me | a bond | NH | O | a bond | Q3a | OH |
| 923 | N | O | Q1w | a bond | Me | a bond | NH | O | a bond | Q3b | OH |
| 924 | N | O | Q1w | a bond | Me | a bond | NH | O | a bond | Q3c | OH |
| 925 | N | O | Q1w | a bond | H | a bond | NH | S | NH | Q3a | OH |
| 926 | N | O | Q1w | a bond | H | a bond | NH | S | NH | Q3b | OH |
| 927 | N | O | Q1w | a bond | H | a bond | NH | S | NH | Q3c | OH |
| 928 | N | O | Q1w | a bond | H | a bond | NH | S | a bond | Q3a | OH |
| 929 | N | O | Q1w | a bond | H | a bond | NH | S | a bond | Q3b | OH |
| 930 | N | O | Q1w | a bond | H | a bond | NH | S | a bond | Q3c | OH |
| 931 | N | O | Q1w | a bond | H | a bond | NH | O | NH | Q3a | OH |
| 932 | N | O | Q1w | a bond | H | a bond | NH | O | NH | Q3b | OH |
| 933 | N | O | Q1w | a bond | H | a bond | NH | O | NH | Q3c | OH |
| 934 | N | O | Q1w | a bond | H | a bond | NH | O | a bond | Q3a | OH |
| 935 | N | O | Q1w | a bond | H | a bond | NH | O | a bond | Q3b | OH |
| 936 | N | O | Q1w | a bond | H | a bond | NH | O | a bond | Q3c | OH |
| 937 | N | O | Q1x | a bond | Me | a bond | NH | S | NH | Q3a | OH |
| 938 | N | O | Q1x | a bond | Me | a bond | NH | S | NH | Q3b | OH |
| 939 | N | O | Q1x | a bond | Me | a bond | NH | S | NH | Q3c | OH |
| 940 | N | O | Q1x | a bond | Me | a bond | NH | S | a bond | Q3a | OH |
| 941 | N | O | Q1x | a bond | Me | a bond | NH | S | a bond | Q3b | OH |
| 942 | N | O | Q1x | a bond | Me | a bond | NH | S | a bond | Q3c | OH |
| 943 | N | O | Q1x | a bond | Me | a bond | NH | O | NH | Q3a | OH |
| 944 | N | O | Q1x | a bond | Me | a bond | NH | O | NH | Q3b | OH |
| 945 | N | O | Q1x | a bond | Me | a bond | NH | O | NH | Q3c | OH |
| 946 | N | O | Q1x | a bond | Me | a bond | NH | O | a bond | Q3a | OH |
| 947 | N | O | Q1x | a bond | Me | a bond | NH | O | a bond | Q3b | OH |
| 948 | N | O | Q1x | a bond | Me | a bond | NH | O | a bond | Q3c | OH |
| 949 | N | O | Q1x | a bond | H | a bond | NH | S | NH | Q3a | OH |
| 950 | N | O | Q1x | a bond | H | a bond | NH | S | NH | Q3b | OH |
| 951 | N | O | Q1x | a bond | H | a bond | NH | S | NH | Q3c | OH |
| 952 | N | O | Q1x | a bond | H | a bond | NH | S | a bond | Q3a | OH |
| 953 | N | O | Q1x | a bond | H | a bond | NH | S | a bond | Q3b | OH |
| 954 | N | O | Q1x | a bond | H | a bond | NH | S | a bond | Q3c | OH |
| 955 | N | O | Q1x | a bond | H | a bond | NH | O | NH | Q3a | OH |
| 956 | N | O | Q1x | a bond | H | a bond | NH | O | NH | Q3b | OH |
| 957 | N | O | Q1x | a bond | H | a bond | NH | O | NH | Q3c | OH |
| 958 | N | O | Q1x | a bond | H | a bond | NH | O | a bond | Q3a | OH |
| 959 | N | O | Q1x | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 960 | N | O | Q1x | a bond | H | a bond | NH | O | a bond | Q3c | OH |
| 961 | CH | NMe | Q1o | a bond | Me | a bond | NH | S | NH | Q3a | OH |
| 962 | CH | NMe | Q1o | a bond | Me | a bond | NH | S | NH | Q3b | OH |
| 963 | CH | NMe | Q1o | a bond | Me | a bond | NH | S | NH | Q3c | OH |
| 964 | CH | NMe | Q1o | a bond | Me | a bond | NH | S | a bond | Q3a | OH |
| 965 | CH | NMe | Q1o | a bond | Me | a bond | NH | S | a bond | Q3b | OH |
| 966 | CH | NMe | Q1o | a bond | Me | a bond | NH | S | a bond | Q3c | OH |
| 967 | CH | NMe | Q1o | a bond | Me | a bond | NH | O | NH | Q3a | OH |
| 968 | CH | NMe | Q1o | a bond | Me | a bond | NH | O | NH | Q3b | OH |
| 969 | CH | NMe | Q1o | a bond | Me | a bond | NH | O | NH | Q3c | OH |
| 970 | CH | NMe | Q1o | a bond | Me | a bond | NH | O | a bond | Q3a | OH |
| 971 | CH | NMe | Q1o | a bond | Me | a bond | NH | O | a bond | Q3b | OH |
| 972 | CH | NMe | Q1o | a bond | Me | a bond | NH | O | a bond | Q3c | OH |
| 973 | CH | NMe | Q1o | a bond | H | a bond | NH | S | NH | Q3a | OH |
| 974 | CH | NMe | Q1o | a bond | H | a bond | NH | S | NH | Q3b | OH |
| 975 | CH | NMe | Q1o | a bond | H | a bond | NH | S | NH | Q3c | OH |
| 976 | CH | NMe | Q1o | a bond | H | a bond | NH | S | a bond | Q3a | OH |
| 977 | CH | NMe | Q1o | a bond | H | a bond | NH | S | a bond | Q3b | OH |
| 978 | CH | NMe | Q1o | a bond | H | a bond | NH | S | a bond | Q3c | OH |
| 979 | CH | NMe | Q1o | a bond | H | a bond | NH | O | NH | Q3a | OH |
| 980 | CH | NMe | Q1o | a bond | H | a bond | NH | O | NH | Q3b | OH |
| 981 | CH | NMe | Q1o | a bond | H | a bond | NH | O | NH | Q3c | OH |
| 982 | CH | NMe | Q1o | a bond | H | a bond | NH | O | a bond | Q3a | OH |
| 983 | CH | NMe | Q1o | a bond | H | a bond | NH | O | a bond | Q3b | OH |
| 984 | CH | NMe | Q1o | a bond | H | a bond | NH | O | a bond | Q3c | OH |
| 985 | CH | NMe | Q1p | a bond | Me | a bond | NH | S | NH | Q3a | OH |
| 986 | CH | NMe | Q1p | a bond | Me | a bond | NH | S | NH | Q3b | OH |
| 987 | CH | NMe | Q1p | a bond | Me | a bond | NH | S | NH | Q3c | OH |
| 988 | CH | NMe | Q1p | a bond | Me | a bond | NH | S | a bond | Q3a | OH |
| 989 | CH | NMe | Q1p | a bond | Me | a bond | NH | S | a bond | Q3b | OH |
| 990 | CH | NMe | Q1p | a bond | Me | a bond | NH | S | a bond | Q3c | OH |
| 991 | CH | NMe | Q1p | a bond | Me | a bond | NH | O | NH | Q3a | OH |
| 992 | CH | NMe | Q1p | a bond | Me | a bond | NH | O | NH | Q3b | OH |
| 993 | CH | NMe | Q1p | a bond | Me | a bond | NH | O | NH | Q3c | OH |
| 994 | CH | NMe | Q1p | a bond | Me | a bond | NH | O | a bond | Q3a | OH |
| 995 | CH | NMe | Q1p | a bond | Me | a bond | NH | O | a bond | Q3b | OH |
| 996 | CH | NMe | Q1p | a bond | Me | a bond | NH | O | a bond | Q3c | OH |
| 997 | CH | NMe | Q1p | a bond | H | a bond | NH | S | NH | Q3a | OH |
| 998 | CH | NMe | Q1p | a bond | H | a bond | NH | S | NH | Q3b | OH |
| 999 | CH | NMe | Q1p | a bond | H | a bond | NH | S | NH | Q3c | OH |
| 1000 | CH | NMe | Q1p | a bond | H | a bond | NH | S | a bond | Q3a | OH |
| 1001 | CH | NMe | Q1p | a bond | H | a bond | NH | S | a bond | Q3b | OH |
| 1002 | CH | NMe | Q1p | a bond | H | a bond | NH | S | a bond | Q3c | OH |
| 1003 | CH | NMe | Q1p | a bond | H | a bond | NH | O | NH | Q3a | OH |
| 1004 | CH | NMe | Q1p | a bond | H | a bond | NH | O | NH | Q3b | OH |
| 1005 | CH | NMe | Q1p | a bond | H | a bond | NH | O | NH | Q3c | OH |
| 1006 | CH | NMe | Q1p | a bond | H | a bond | NH | O | a bond | Q3a | OH |
| 1007 | CH | NMe | Q1p | a bond | H | a bond | NH | O | a bond | Q3b | OH |
| 1008 | CH | NMe | Q1p | a bond | H | a bond | NH | O | a bond | Q3c | OH |
| 1009 | CH | NMe | Q1q | a bond | Me | a bond | NH | S | NH | Q3a | OH |
| 1010 | CH | NMe | Q1q | a bond | Me | a bond | NH | S | NH | Q3b | OH |
| 1011 | CH | NMe | Q1q | a bond | Me | a bond | NH | S | NH | Q3c | OH |
| 1012 | CH | NMe | Q1q | a bond | Me | a bond | NH | S | a bond | Q3a | OH |
| 1013 | CH | NMe | Q1q | a bond | Me | a bond | NH | S | a bond | Q3b | OH |
| 1014 | CH | NMe | Q1q | a bond | Me | a bond | NH | S | a bond | Q3c | OH |
| 1015 | CH | NMe | Q1q | a bond | Me | a bond | NH | O | NH | Q3a | OH |
| 1016 | CH | NMe | Q1q | a bond | Me | a bond | NH | O | NH | Q3b | OH |
| 1017 | CH | NMe | Q1q | a bond | Me | a bond | NH | O | NH | Q3c | OH |
| 1018 | CH | NMe | Q1q | a bond | Me | a bond | NH | O | a bond | Q3a | OH |
| 1019 | CH | NMe | Q1q | a bond | Me | a bond | NH | O | a bond | Q3b | OH |
| 1020 | CH | NMe | Q1q | a bond | Me | a bond | NH | O | a bond | Q3c | OH |
| 1021 | CH | NMe | Q1q | a bond | H | a bond | NH | S | NH | Q3a | OH |
| 1022 | CH | NMe | Q1q | a bond | H | a bond | NH | S | NH | Q3b | OH |
| 1023 | CH | NMe | Q1q | a bond | H | a bond | NH | S | NH | Q3c | OH |
| 1024 | CH | NMe | Q1q | a bond | H | a bond | NH | S | a bond | Q3a | OH |
| 1025 | CH | NMe | Q1q | a bond | H | a bond | NH | S | a bond | Q3b | OH |
| 1026 | CH | NMe | Q1q | a bond | H | a bond | NH | S | a bond | Q3c | OH |
| 1027 | CH | NMe | Q1q | a bond | H | a bond | NH | O | NH | Q3a | OH |
| 1028 | CH | NMe | Q1q | a bond | H | a bond | NH | O | NH | Q3b | OH |
| 1029 | CH | NMe | Q1q | a bond | H | a bond | NH | O | NH | Q3c | OH |
| 1030 | CH | NMe | Q1q | a bond | H | a bond | NH | O | a bond | Q3a | OH |
| 1031 | CH | NMe | Q1q | a bond | H | a bond | NH | O | a bond | Q3b | OH |
| 1032 | CH | NMe | Q1q | a bond | H | a bond | NH | O | a bond | Q3c | OH |
| 1033 | CH | NMe | Q1r | a bond | Me | a bond | NH | S | NH | Q3a | OH |
| 1034 | CH | NMe | Q1r | a bond | Me | a bond | NH | S | NH | Q3b | OH |
| 1035 | CH | NMe | Q1r | a bond | Me | a bond | NH | S | NH | Q3c | OH |
| 1036 | CH | NMe | Q1r | a bond | Me | a bond | NH | S | a bond | Q3a | OH |
| 1037 | CH | NMe | Q1r | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1038 | CH | NMe | Q1r | a bond | Me | a bond | NH | S | a bond | Q3c | OH |
| 1039 | CH | NMe | Q1r | a bond | Me | a bond | NH | O | NH | Q3a | OH |
| 1040 | CH | NMe | Q1r | a bond | Me | a bond | NH | O | NH | Q3b | OH |
| 1041 | CH | NMe | Q1r | a bond | Me | a bond | NH | O | NH | Q3c | OH |
| 1042 | CH | NMe | Q1r | a bond | Me | a bond | NH | O | a bond | Q3a | OH |
| 1043 | CH | NMe | Q1r | a bond | Me | a bond | NH | O | a bond | Q3b | OH |
| 1044 | CH | NMe | Q1r | a bond | Me | a bond | NH | O | a bond | Q3c | OH |
| 1045 | CH | NMe | Q1r | a bond | H | a bond | NH | S | NH | Q3a | OH |
| 1046 | CH | NMe | Q1r | a bond | H | a bond | NH | S | NH | Q3b | OH |
| 1047 | CH | NMe | Q1r | a bond | H | a bond | NH | S | NH | Q3c | OH |
| 1048 | CH | NMe | Q1r | a bond | H | a bond | NH | S | a bond | Q3a | OH |
| 1049 | CH | NMe | Q1r | a bond | H | a bond | NH | S | a bond | Q3b | OH |
| 1050 | CH | NMe | Q1r | a bond | H | a bond | NH | S | a bond | Q3c | OH |
| 1051 | CH | NMe | Q1r | a bond | H | a bond | NH | O | NH | Q3a | OH |
| 1052 | CH | NMe | Q1r | a bond | H | a bond | NH | O | NH | Q3b | OH |
| 1053 | CH | NMe | Q1r | a bond | H | a bond | NH | O | NH | Q3c | OH |
| 1054 | CH | NMe | Q1r | a bond | H | a bond | NH | O | a bond | Q3a | OH |
| 1055 | CH | NMe | Q1r | a bond | H | a bond | NH | O | a bond | Q3b | OH |
| 1056 | CH | NMe | Q1r | a bond | H | a bond | NH | O | a bond | Q3c | OH |
| 1057 | CH | NMe | Q1s | a bond | Me | a bond | NH | S | NH | Q3a | OH |
| 1058 | CH | NMe | Q1s | a bond | Me | a bond | NH | S | NH | Q3b | OH |
| 1059 | CH | NMe | Q1s | a bond | Me | a bond | NH | S | NH | Q3c | OH |
| 1060 | CH | NMe | Q1s | a bond | Me | a bond | NH | S | a bond | Q3a | OH |
| 1061 | CH | NMe | Q1s | a bond | Me | a bond | NH | S | a bond | Q3b | OH |
| 1062 | CH | NMe | Q1s | a bond | Me | a bond | NH | S | a bond | Q3c | OH |
| 1063 | CH | NMe | Q1s | a bond | Me | a bond | NH | O | NH | Q3a | OH |
| 1064 | CH | NMe | Q1s | a bond | Me | a bond | NH | O | NH | Q3b | OH |
| 1065 | CH | NMe | Q1s | a bond | Me | a bond | NH | O | NH | Q3c | OH |
| 1066 | CH | NMe | Q1s | a bond | Me | a bond | NH | O | a bond | Q3a | OH |
| 1067 | CH | NMe | Q1s | a bond | Me | a bond | NH | O | a bond | Q3b | OH |
| 1068 | CH | NMe | Q1s | a bond | Me | a bond | NH | O | a bond | Q3c | OH |
| 1069 | CH | NMe | Q1s | a bond | H | a bond | NH | S | NH | Q3a | OH |
| 1070 | CH | NMe | Q1s | a bond | H | a bond | NH | S | NH | Q3b | OH |
| 1071 | CH | NMe | Q1s | a bond | H | a bond | NH | S | NH | Q3c | OH |
| 1072 | CH | NMe | Q1s | a bond | H | a bond | NH | S | a bond | Q3a | OH |
| 1073 | CH | NMe | Q1s | a bond | H | a bond | NH | S | a bond | Q3b | OH |
| 1074 | CH | NMe | Q1s | a bond | H | a bond | NH | S | a bond | Q3c | OH |
| 1075 | CH | NMe | Q1s | a bond | H | a bond | NH | O | NH | Q3a | OH |
| 1076 | CH | NMe | Q1s | a bond | H | a bond | NH | O | NH | Q3b | OH |
| 1077 | CH | NMe | Q1s | a bond | H | a bond | NH | O | NH | Q3c | OH |
| 1078 | CH | NMe | Q1s | a bond | H | a bond | NH | O | a bond | Q3a | OH |
| 1079 | CH | NMe | Q1s | a bond | H | a bond | NH | O | a bond | Q3b | OH |
| 1080 | CH | NMe | Q1s | a bond | H | a bond | NH | O | a bond | Q3c | OH |
| 1081 | CH | NMe | Q1t | a bond | Me | a bond | NH | S | NH | Q3a | OH |
| 1082 | CH | NMe | Q1t | a bond | Me | a bond | NH | S | NH | Q3b | OH |
| 1083 | CH | NMe | Q1t | a bond | Me | a bond | NH | S | NH | Q3c | OH |
| 1084 | CH | NMe | Q1t | a bond | Me | a bond | NH | S | a bond | Q3a | OH |
| 1085 | CH | NMe | Q1t | a bond | Me | a bond | NH | S | a bond | Q3b | OH |
| 1086 | CH | NMe | Q1t | a bond | Me | a bond | NH | S | a bond | Q3c | OH |
| 1087 | CH | NMe | Q1t | a bond | Me | a bond | NH | O | NH | Q3a | OH |
| 1088 | CH | NMe | Q1t | a bond | Me | a bond | NH | O | NH | Q3b | OH |
| 1089 | CH | NMe | Q1t | a bond | Me | a bond | NH | O | NH | Q3c | OH |
| 1090 | CH | NMe | Q1t | a bond | Me | a bond | NH | O | a bond | Q3a | OH |
| 1091 | CH | NMe | Q1t | a bond | Me | a bond | NH | O | a bond | Q3b | OH |
| 1092 | CH | NMe | Q1t | a bond | Me | a bond | NH | O | a bond | Q3c | OH |
| 1093 | CH | NMe | Q1t | a bond | H | a bond | NH | S | NH | Q3a | OH |
| 1094 | CH | NMe | Q1t | a bond | H | a bond | NH | S | NH | Q3b | OH |
| 1095 | CH | NMe | Q1t | a bond | H | a bond | NH | S | NH | Q3c | OH |
| 1096 | CH | NMe | Q1t | a bond | H | a bond | NH | S | a bond | Q3a | OH |
| 1097 | CH | NMe | Q1t | a bond | H | a bond | NH | S | a bond | Q3b | OH |
| 1098 | CH | NMe | Q1t | a bond | H | a bond | NH | S | a bond | Q3c | OH |
| 1099 | CH | NMe | Q1t | a bond | H | a bond | NH | O | NH | Q3a | OH |
| 1100 | CH | NMe | Q1t | a bond | H | a bond | NH | O | NH | Q3b | OH |
| 1101 | CH | NMe | Q1t | a bond | H | a bond | NH | O | NH | Q3c | OH |
| 1102 | CH | NMe | Q1t | a bond | H | a bond | NH | O | a bond | Q3a | OH |
| 1103 | CH | NMe | Q1t | a bond | H | a bond | NH | O | a bond | Q3b | OH |
| 1104 | CH | NMe | Q1t | a bond | H | a bond | NH | O | a bond | Q3c | OH |
| 1105 | CH | NMe | Q1u | a bond | Me | a bond | NH | S | NH | Q3a | OH |
| 1106 | CH | NMe | Q1u | a bond | Me | a bond | NH | S | NH | Q3b | OH |
| 1107 | CH | NMe | Q1u | a bond | Me | a bond | NH | S | NH | Q3c | OH |
| 1108 | CH | NMe | Q1u | a bond | Me | a bond | NH | S | a bond | Q3a | OH |
| 1109 | CH | NMe | Q1u | a bond | Me | a bond | NH | S | a bond | Q3b | OH |
| 1110 | CH | NMe | Q1u | a bond | Me | a bond | NH | S | a bond | Q3c | OH |
| 1111 | CH | NMe | Q1u | a bond | Me | a bond | NH | O | NH | Q3a | OH |
| 1112 | CH | NMe | Q1u | a bond | Me | a bond | NH | O | NH | Q3b | OH |
| 1113 | CH | NMe | Q1u | a bond | Me | a bond | NH | O | NH | Q3c | OH |
| 1114 | CH | NMe | Q1u | a bond | Me | a bond | NH | O | a bond | Q3a | OH |
| 1115 | CH | NMe | Q1u | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1116 | CH | NMe | Q1u | a bond | Me | a bond | NH | O | a bond | Q3c | OH |
| 1117 | CH | NMe | Q1u | a bond | H | a bond | NH | S | NH | Q3a | OH |
| 1118 | CH | NMe | Q1u | a bond | H | a bond | NH | S | NH | Q3b | OH |
| 1119 | CH | NMe | Q1u | a bond | H | a bond | NH | S | NH | Q3c | OH |
| 1120 | CH | NMe | Q1u | a bond | H | a bond | NH | S | a bond | Q3a | OH |
| 1121 | CH | NMe | Q1u | a bond | H | a bond | NH | S | a bond | Q3b | OH |
| 1122 | CH | NMe | Q1u | a bond | H | a bond | NH | S | a bond | Q3c | OH |
| 1123 | CH | NMe | Q1u | a bond | H | a bond | NH | O | NH | Q3a | OH |
| 1124 | CH | NMe | Q1u | a bond | H | a bond | NH | O | NH | Q3b | OH |
| 1125 | CH | NMe | Q1u | a bond | H | a bond | NH | O | NH | Q3c | OH |
| 1126 | CH | NMe | Q1u | a bond | H | a bond | NH | O | a bond | Q3a | OH |
| 1127 | CH | NMe | Q1u | a bond | H | a bond | NH | O | a bond | Q3b | OH |
| 1128 | CH | NMe | Q1u | a bond | H | a bond | NH | O | a bond | Q3c | OH |
| 1129 | CH | NMe | Q1v | a bond | Me | a bond | NH | S | NH | Q3a | OH |
| 1130 | CH | NMe | Q1v | a bond | Me | a bond | NH | S | NH | Q3b | OH |
| 1131 | CH | NMe | Q1v | a bond | Me | a bond | NH | S | NH | Q3c | OH |
| 1132 | CH | NMe | Q1v | a bond | Me | a bond | NH | S | a bond | Q3a | OH |
| 1133 | CH | NMe | Q1v | a bond | Me | a bond | NH | S | a bond | Q3b | OH |
| 1134 | CH | NMe | Q1v | a bond | Me | a bond | NH | S | a bond | Q3c | OH |
| 1135 | CH | NMe | Q1v | a bond | Me | a bond | NH | O | NH | Q3a | OH |
| 1136 | CH | NMe | Q1v | a bond | Me | a bond | NH | O | NH | Q3b | OH |
| 1137 | CH | NMe | Q1v | a bond | Me | a bond | NH | O | NH | Q3c | OH |
| 1138 | CH | NMe | Q1v | a bond | Me | a bond | NH | O | a bond | Q3a | OH |
| 1139 | CH | NMe | Q1v | a bond | Me | a bond | NH | O | a bond | Q3b | OH |
| 1140 | CH | NMe | Q1v | a bond | Me | a bond | NH | O | a bond | Q3c | OH |
| 1141 | CH | NMe | Q1v | a bond | H | a bond | NH | S | NH | Q3a | OH |
| 1142 | CH | NMe | Q1v | a bond | H | a bond | NH | S | NH | Q3b | OH |
| 1143 | CH | NMe | Q1v | a bond | H | a bond | NH | S | NH | Q3c | OH |
| 1144 | CH | NMe | Q1v | a bond | H | a bond | NH | S | a bond | Q3a | OH |
| 1145 | CH | NMe | Q1v | a bond | H | a bond | NH | S | a bond | Q3b | OH |
| 1146 | CH | NMe | Q1v | a bond | H | a bond | NH | S | a bond | Q3c | OH |
| 1147 | CH | NMe | Q1v | a bond | H | a bond | NH | O | NH | Q3a | OH |
| 1148 | CH | NMe | Q1v | a bond | H | a bond | NH | O | NH | Q3b | OH |
| 1149 | CH | NMe | Q1v | a bond | H | a bond | NH | O | NH | Q3c | OH |
| 1150 | CH | NMe | Q1v | a bond | H | a bond | NH | O | a bond | Q3a | OH |
| 1151 | CH | NMe | Q1v | a bond | H | a bond | NH | O | a bond | Q3b | OH |
| 1152 | CH | NMe | Q1v | a bond | H | a bond | NH | O | a bond | Q3c | OH |
| 1153 | CH | NMe | Q1w | a bond | Me | a bond | NH | S | NH | Q3a | OH |
| 1154 | CH | NMe | Q1w | a bond | Me | a bond | NH | S | NH | Q3b | OH |
| 1155 | CH | NMe | Q1w | a bond | Me | a bond | NH | S | NH | Q3c | OH |
| 1156 | CH | NMe | Q1w | a bond | Me | a bond | NH | S | a bond | Q3a | OH |
| 1157 | CH | NMe | Q1w | a bond | Me | a bond | NH | S | a bond | Q3b | OH |
| 1158 | CH | NMe | Q1w | a bond | Me | a bond | NH | S | a bond | Q3c | OH |
| 1159 | CH | NMe | Q1w | a bond | Me | a bond | NH | O | NH | Q3a | OH |
| 1160 | CH | NMe | Q1w | a bond | Me | a bond | NH | O | NH | Q3b | OH |
| 1161 | CH | NMe | Q1w | a bond | Me | a bond | NH | O | NH | Q3c | OH |
| 1162 | CH | NMe | Q1w | a bond | Me | a bond | NH | O | a bond | Q3a | OH |
| 1163 | CH | NMe | Q1w | a bond | Me | a bond | NH | O | a bond | Q3b | OH |
| 1164 | CH | NMe | Q1w | a bond | Me | a bond | NH | O | a bond | Q3c | OH |
| 1165 | CH | NMe | Q1w | a bond | H | a bond | NH | S | NH | Q3a | OH |
| 1166 | CH | NMe | Q1w | a bond | H | a bond | NH | S | NH | Q3b | OH |
| 1167 | CH | NMe | Q1w | a bond | H | a bond | NH | S | NH | Q3c | OH |
| 1168 | CH | NMe | Q1w | a bond | H | a bond | NH | S | a bond | Q3a | OH |
| 1169 | CH | NMe | Q1w | a bond | H | a bond | NH | S | a bond | Q3b | OH |
| 1170 | CH | NMe | Q1w | a bond | H | a bond | NH | S | a bond | Q3c | OH |
| 1171 | CH | NMe | Q1w | a bond | H | a bond | NH | O | NH | Q3a | OH |
| 1172 | CH | NMe | Q1w | a bond | H | a bond | NH | O | NH | Q3b | OH |
| 1173 | CH | NMe | Q1w | a bond | H | a bond | NH | O | NH | Q3c | OH |
| 1174 | CH | NMe | Q1w | a bond | H | a bond | NH | O | a bond | Q3a | OH |
| 1175 | CH | NMe | Q1w | a bond | H | a bond | NH | O | a bond | Q3b | OH |
| 1176 | CH | NMe | Q1w | a bond | H | a bond | NH | O | a bond | Q3c | OH |
| 1177 | CH | NMe | Q1x | a bond | Me | a bond | NH | S | NH | Q3a | OH |
| 1178 | CH | NMe | Q1x | a bond | Me | a bond | NH | S | NH | Q3b | OH |
| 1179 | CH | NMe | Q1x | a bond | Me | a bond | NH | S | NH | Q3c | OH |
| 1180 | CH | NMe | Q1x | a bond | Me | a bond | NH | S | a bond | Q3a | OH |
| 1181 | CH | NMe | Q1x | a bond | Me | a bond | NH | S | a bond | Q3b | OH |
| 1182 | CH | NMe | Q1x | a bond | Me | a bond | NH | S | a bond | Q3c | OH |
| 1183 | CH | NMe | Q1x | a bond | Me | a bond | NH | O | NH | Q3a | OH |
| 1184 | CH | NMe | Q1x | a bond | Me | a bond | NH | O | NH | Q3b | OH |
| 1185 | CH | NMe | Q1x | a bond | Me | a bond | NH | O | NH | Q3c | OH |
| 1186 | CH | NMe | Q1x | a bond | Me | a bond | NH | O | a bond | Q3a | OH |
| 1187 | CH | NMe | Q1x | a bond | Me | a bond | NH | O | a bond | Q3b | OH |
| 1188 | CH | NMe | Q1x | a bond | Me | a bond | NH | O | a bond | Q3c | OH |
| 1189 | CH | NMe | Q1x | a bond | H | a bond | NH | S | NH | Q3a | OH |
| 1190 | CH | NMe | Q1x | a bond | H | a bond | NH | S | NH | Q3b | OH |
| 1191 | CH | NMe | Q1x | a bond | H | a bond | NH | S | NH | Q3c | OH |
| 1192 | CH | NMe | Q1x | a bond | H | a bond | NH | S | a bond | Q3a | OH |
| 1193 | CH | NMe | Q1x | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1194 | CH | NMe | Q1x | a bond | H | a bond | NH | S | a bond | Q3c | OH |
| 1195 | CH | NMe | Q1x | a bond | H | a bond | NH | O | NH | Q3a | OH |
| 1196 | CH | NMe | Q1x | a bond | H | a bond | NH | O | NH | Q3b | OH |
| 1197 | CH | NMe | Q1x | a bond | H | a bond | NH | O | NH | Q3c | OH |
| 1198 | CH | NMe | Q1x | a bond | H | a bond | NH | O | a bond | Q3a | OH |
| 1199 | CH | NMe | Q1x | a bond | H | a bond | NH | O | a bond | Q3b | OH |
| 1200 | CH | NMe | Q1x | a bond | H | a bond | NH | O | a bond | Q3c | OH |
| 1201 | CH | NEt | Q1o | a bond | Me | a bond | NH | S | NH | Q3a | OH |
| 1202 | CH | NEt | Q1o | a bond | Me | a bond | NH | S | NH | Q3b | OH |
| 1203 | CH | NEt | Q1o | a bond | Me | a bond | NH | S | NH | Q3c | OH |
| 1204 | CH | NEt | Q1o | a bond | Me | a bond | NH | S | a bond | Q3a | OH |
| 1205 | CH | NEt | Q1o | a bond | Me | a bond | NH | S | a bond | Q3b | OH |
| 1206 | CH | NEt | Q1o | a bond | Me | a bond | NH | S | a bond | Q3c | OH |
| 1207 | CH | NEt | Q1o | a bond | Me | a bond | NH | O | NH | Q3a | OH |
| 1208 | CH | NEt | Q1o | a bond | Me | a bond | NH | O | NH | Q3b | OH |
| 1209 | CH | NEt | Q1o | a bond | Me | a bond | NH | O | NH | Q3c | OH |
| 1210 | CH | NEt | Q1o | a bond | Me | a bond | NH | O | a bond | Q3a | OH |
| 1211 | CH | NEt | Q1o | a bond | Me | a bond | NH | O | a bond | Q3b | OH |
| 1212 | CH | NEt | Q1o | a bond | Me | a bond | NH | O | a bond | Q3c | OH |
| 1213 | CH | NEt | Q1o | a bond | H | a bond | NH | S | NH | Q3a | OH |
| 1214 | CH | NEt | Q1o | a bond | H | a bond | NH | S | NH | Q3b | OH |
| 1215 | CH | NEt | Q1o | a bond | H | a bond | NH | S | NH | Q3c | OH |
| 1216 | CH | NEt | Q1o | a bond | H | a bond | NH | S | a bond | Q3a | OH |
| 1217 | CH | NEt | Q1o | a bond | H | a bond | NH | S | a bond | Q3b | OH |
| 1218 | CH | NEt | Q1o | a bond | H | a bond | NH | S | a bond | Q3c | OH |
| 1219 | CH | NEt | Q1o | a bond | H | a bond | NH | O | NH | Q3a | OH |
| 1220 | CH | NEt | Q1o | a bond | H | a bond | NH | O | NH | Q3b | OH |
| 1221 | CH | NEt | Q1o | a bond | H | a bond | NH | O | NH | Q3c | OH |
| 1222 | CH | NEt | Q1o | a bond | H | a bond | NH | O | a bond | Q3a | OH |
| 1223 | CH | NEt | Q1o | a bond | H | a bond | NH | O | a bond | Q3b | OH |
| 1224 | CH | NEt | Q1o | a bond | H | a bond | NH | O | a bond | Q3c | OH |
| 1225 | CH | NEt | Q1p | a bond | Me | a bond | NH | S | NH | Q3a | OH |
| 1226 | CH | NEt | Q1p | a bond | Me | a bond | NH | S | NH | Q3b | OH |
| 1227 | CH | NEt | Q1p | a bond | Me | a bond | NH | S | NH | Q3c | OH |
| 1228 | CH | NEt | Q1p | a bond | Me | a bond | NH | S | a bond | Q3a | OH |
| 1229 | CH | NEt | Q1p | a bond | Me | a bond | NH | S | a bond | Q3b | OH |
| 1230 | CH | NEt | Q1p | a bond | Me | a bond | NH | S | a bond | Q3c | OH |
| 1231 | CH | NEt | Q1p | a bond | Me | a bond | NH | O | NH | Q3a | OH |
| 1232 | CH | NEt | Q1p | a bond | Me | a bond | NH | O | NH | Q3b | OH |
| 1233 | CH | NEt | Q1p | a bond | Me | a bond | NH | O | NH | Q3c | OH |
| 1234 | CH | NEt | Q1p | a bond | Me | a bond | NH | O | a bond | Q3a | OH |
| 1235 | CH | NEt | Q1p | a bond | Me | a bond | NH | O | a bond | Q3b | OH |
| 1236 | CH | NEt | Q1p | a bond | Me | a bond | NH | O | a bond | Q3c | OH |
| 1237 | CH | NEt | Q1p | a bond | H | a bond | NH | S | NH | Q3a | OH |
| 1238 | CH | NEt | Q1p | a bond | H | a bond | NH | S | NH | Q3b | OH |
| 1239 | CH | NEt | Q1p | a bond | H | a bond | NH | S | NH | Q3c | OH |
| 1240 | CH | NEt | Q1p | a bond | H | a bond | NH | S | a bond | Q3a | OH |
| 1241 | CH | NEt | Q1p | a bond | H | a bond | NH | S | a bond | Q3b | OH |
| 1242 | CH | NEt | Q1p | a bond | H | a bond | NH | S | a bond | Q3c | OH |
| 1243 | CH | NEt | Q1p | a bond | H | a bond | NH | O | NH | Q3a | OH |
| 1244 | CH | NEt | Q1p | a bond | H | a bond | NH | O | NH | Q3b | OH |
| 1245 | CH | NEt | Q1p | a bond | H | a bond | NH | O | NH | Q3c | OH |
| 1246 | CH | NEt | Q1p | a bond | H | a bond | NH | O | a bond | Q3a | OH |
| 1247 | CH | NEt | Q1p | a bond | H | a bond | NH | O | a bond | Q3b | OH |
| 1248 | CH | NEt | Q1p | a bond | H | a bond | NH | O | a bond | Q3c | OH |
| 1249 | CH | NEt | Q1q | a bond | Me | a bond | NH | S | NH | Q3a | OH |
| 1250 | CH | NEt | Q1q | a bond | Me | a bond | NH | S | NH | Q3b | OH |
| 1251 | CH | NEt | Q1q | a bond | Me | a bond | NH | S | NH | Q3c | OH |
| 1252 | CH | NEt | Q1q | a bond | Me | a bond | NH | S | a bond | Q3a | OH |
| 1253 | CH | NEt | Q1q | a bond | Me | a bond | NH | S | a bond | Q3b | OH |
| 1254 | CH | NEt | Q1q | a bond | Me | a bond | NH | S | a bond | Q3c | OH |
| 1255 | CH | NEt | Q1q | a bond | Me | a bond | NH | O | NH | Q3a | OH |
| 1256 | CH | NEt | Q1q | a bond | Me | a bond | NH | O | NH | Q3b | OH |
| 1257 | CH | NEt | Q1q | a bond | Me | a bond | NH | O | NH | Q3c | OH |
| 1258 | CH | NEt | Q1q | a bond | Me | a bond | NH | O | a bond | Q3a | OH |
| 1259 | CH | NEt | Q1q | a bond | Me | a bond | NH | O | a bond | Q3b | OH |
| 1260 | CH | NEt | Q1q | a bond | Me | a bond | NH | O | a bond | Q3c | OH |
| 1261 | CH | NEt | Q1q | a bond | H | a bond | NH | S | NH | Q3a | OH |
| 1262 | CH | NEt | Q1q | a bond | H | a bond | NH | S | NH | Q3b | OH |
| 1263 | CH | NEt | Q1q | a bond | H | a bond | NH | S | NH | Q3c | OH |
| 1264 | CH | NEt | Q1q | a bond | H | a bond | NH | S | a bond | Q3a | OH |
| 1265 | CH | NEt | Q1q | a bond | H | a bond | NH | S | a bond | Q3b | OH |
| 1266 | CH | NEt | Q1q | a bond | H | a bond | NH | S | a bond | Q3c | OH |
| 1267 | CH | NEt | Q1q | a bond | H | a bond | NH | O | NH | Q3a | OH |
| 1268 | CH | NEt | Q1q | a bond | H | a bond | NH | O | NH | Q3b | OH |
| 1269 | CH | NEt | Q1q | a bond | H | a bond | NH | O | NH | Q3c | OH |
| 1270 | CH | NEt | Q1q | a bond | H | a bond | NH | O | a bond | Q3a | OH |
| 1271 | CH | NEt | Q1q | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1272 | CH | NEt | Q1q | a bond | H | a bond | NH | O | a bond | Q3c | OH |
| 1273 | CH | NEt | Q1r | a bond | Me | a bond | NH | S | NH | Q3a | OH |
| 1274 | CH | NEt | Q1r | a bond | Me | a bond | NH | S | NH | Q3b | OH |
| 1275 | CH | NEt | Q1r | a bond | Me | a bond | NH | S | NH | Q3c | OH |
| 1276 | CH | NEt | Q1r | a bond | Me | a bond | NH | S | a bond | Q3a | OH |
| 1277 | CH | NEt | Q1r | a bond | Me | a bond | NH | S | a bond | Q3b | OH |
| 1278 | CH | NEt | Q1r | a bond | Me | a bond | NH | S | a bond | Q3c | OH |
| 1279 | CH | NEt | Q1r | a bond | Me | a bond | NH | O | NH | Q3a | OH |
| 1280 | CH | NEt | Q1r | a bond | Me | a bond | NH | O | NH | Q3b | OH |
| 1281 | CH | NEt | Q1r | a bond | Me | a bond | NH | O | NH | Q3c | OH |
| 1282 | CH | NEt | Q1r | a bond | Me | a bond | NH | O | a bond | Q3a | OH |
| 1283 | CH | NEt | Q1r | a bond | Me | a bond | NH | O | a bond | Q3b | OH |
| 1284 | CH | NEt | Q1r | a bond | Me | a bond | NH | O | a bond | Q3c | OH |
| 1285 | CH | NEt | Q1r | a bond | H | a bond | NH | S | NH | Q3a | OH |
| 1286 | CH | NEt | Q1r | a bond | H | a bond | NH | S | NH | Q3b | OH |
| 1287 | CH | NEt | Q1r | a bond | H | a bond | NH | S | NH | Q3c | OH |
| 1288 | CH | NEt | Q1r | a bond | H | a bond | NH | S | a bond | Q3a | OH |
| 1289 | CH | NEt | Q1r | a bond | H | a bond | NH | S | a bond | Q3b | OH |
| 1290 | CH | NEt | Q1r | a bond | H | a bond | NH | S | a bond | Q3c | OH |
| 1291 | CH | NEt | Q1r | a bond | H | a bond | NH | O | NH | Q3a | OH |
| 1292 | CH | NEt | Q1r | a bond | H | a bond | NH | O | NH | Q3b | OH |
| 1293 | CH | NEt | Q1r | a bond | H | a bond | NH | O | NH | Q3c | OH |
| 1294 | CH | NEt | Q1r | a bond | H | a bond | NH | O | a bond | Q3a | OH |
| 1295 | CH | NEt | Q1r | a bond | H | a bond | NH | O | a bond | Q3b | OH |
| 1296 | CH | NEt | Q1r | a bond | H | a bond | NH | O | a bond | Q3c | OH |
| 1297 | CH | NEt | Q1s | a bond | Me | a bond | NH | S | NH | Q3a | OH |
| 1298 | CH | NEt | Q1s | a bond | Me | a bond | NH | S | NH | Q3b | OH |
| 1299 | CH | NEt | Q1s | a bond | Me | a bond | NH | S | NH | Q3c | OH |
| 1300 | CH | NEt | Q1s | a bond | Me | a bond | NH | S | a bond | Q3a | OH |
| 1301 | CH | NEt | Q1s | a bond | Me | a bond | NH | S | a bond | Q3b | OH |
| 1302 | CH | NEt | Q1s | a bond | Me | a bond | NH | S | a bond | Q3c | OH |
| 1303 | CH | NEt | Q1s | a bond | Me | a bond | NH | O | NH | Q3a | OH |
| 1304 | CH | NEt | Q1s | a bond | Me | a bond | NH | O | NH | Q3b | OH |
| 1305 | CH | NEt | Q1s | a bond | Me | a bond | NH | O | NH | Q3c | OH |
| 1306 | CH | NEt | Q1s | a bond | Me | a bond | NH | O | a bond | Q3a | OH |
| 1307 | CH | NEt | Q1s | a bond | Me | a bond | NH | O | a bond | Q3b | OH |
| 1308 | CH | NEt | Q1s | a bond | Me | a bond | NH | O | a bond | Q3c | OH |
| 1309 | CH | NEt | Q1s | a bond | H | a bond | NH | S | NH | Q3a | OH |
| 1310 | CH | NEt | Q1s | a bond | H | a bond | NH | S | NH | Q3b | OH |
| 1311 | CH | NEt | Q1s | a bond | H | a bond | NH | S | NH | Q3c | OH |
| 1312 | CH | NEt | Q1s | a bond | H | a bond | NH | S | a bond | Q3a | OH |
| 1313 | CH | NEt | Q1s | a bond | H | a bond | NH | S | a bond | Q3b | OH |
| 1314 | CH | NEt | Q1s | a bond | H | a bond | NH | S | a bond | Q3c | OH |
| 1315 | CH | NEt | Q1s | a bond | H | a bond | NH | O | NH | Q3a | OH |
| 1316 | CH | NEt | Q1s | a bond | H | a bond | NH | O | NH | Q3b | OH |
| 1317 | CH | NEt | Q1s | a bond | H | a bond | NH | O | NH | Q3c | OH |
| 1318 | CH | NEt | Q1s | a bond | H | a bond | NH | O | a bond | Q3a | OH |
| 1319 | CH | NEt | Q1s | a bond | H | a bond | NH | O | a bond | Q3b | OH |
| 1320 | CH | NEt | Q1s | a bond | H | a bond | NH | O | a bond | Q3c | OH |
| 1321 | CH | NEt | Q1t | a bond | Me | a bond | NH | S | NH | Q3a | OH |
| 1322 | CH | NEt | Q1t | a bond | Me | a bond | NH | S | NH | Q3b | OH |
| 1323 | CH | NEt | Q1t | a bond | Me | a bond | NH | S | NH | Q3c | OH |
| 1324 | CH | NEt | Q1t | a bond | Me | a bond | NH | S | a bond | Q3a | OH |
| 1325 | CH | NEt | Q1t | a bond | Me | a bond | NH | S | a bond | Q3b | OH |
| 1326 | CH | NEt | Q1t | a bond | Me | a bond | NH | S | a bond | Q3c | OH |
| 1327 | CH | NEt | Q1t | a bond | Me | a bond | NH | O | NH | Q3a | OH |
| 1328 | CH | NEt | Q1t | a bond | Me | a bond | NH | O | NH | Q3b | OH |
| 1329 | CH | NEt | Q1t | a bond | Me | a bond | NH | O | NH | Q3c | OH |
| 1330 | CH | NEt | Q1t | a bond | Me | a bond | NH | O | a bond | Q3a | OH |
| 1331 | CH | NEt | Q1t | a bond | Me | a bond | NH | O | a bond | Q3b | OH |
| 1332 | CH | NEt | Q1t | a bond | Me | a bond | NH | O | a bond | Q3c | OH |
| 1333 | CH | NEt | Q1t | a bond | H | a bond | NH | S | NH | Q3a | OH |
| 1334 | CH | NEt | Q1t | a bond | H | a bond | NH | S | NH | Q3b | OH |
| 1335 | CH | NEt | Q1t | a bond | H | a bond | NH | S | NH | Q3c | OH |
| 1336 | CH | NEt | Q1t | a bond | H | a bond | NH | S | a bond | Q3a | OH |
| 1337 | CH | NEt | Q1t | a bond | H | a bond | NH | S | a bond | Q3b | OH |
| 1338 | CH | NEt | Q1t | a bond | H | a bond | NH | S | a bond | Q3c | OH |
| 1339 | CH | NEt | Q1t | a bond | H | a bond | NH | O | NH | Q3a | OH |
| 1340 | CH | NEt | Q1t | a bond | H | a bond | NH | O | NH | Q3b | OH |
| 1341 | CH | NEt | Q1t | a bond | H | a bond | NH | O | NH | Q3c | OH |
| 1342 | CH | NEt | Q1t | a bond | H | a bond | NH | O | a bond | Q3a | OH |
| 1343 | CH | NEt | Q1t | a bond | H | a bond | NH | O | a bond | Q3b | OH |
| 1344 | CH | NEt | Q1t | a bond | H | a bond | NH | O | a bond | Q3c | OH |
| 1345 | CH | NEt | Q1u | a bond | Me | a bond | NH | S | NH | Q3a | OH |
| 1346 | CH | NEt | Q1u | a bond | Me | a bond | NH | S | NH | Q3b | OH |
| 1347 | CH | NEt | Q1u | a bond | Me | a bond | NH | S | NH | Q3c | OH |
| 1348 | CH | NEt | Q1u | a bond | Me | a bond | NH | S | a bond | Q3a | OH |
| 1349 | CH | NEt | Q1u | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1350 | CH | NEt | Q1u | a bond | Me | a bond | NH | S | a bond | Q3c | OH |
| 1351 | CH | NEt | Q1u | a bond | Me | a bond | NH | O | NH | Q3a | OH |
| 1352 | CH | NEt | Q1u | a bond | Me | a bond | NH | O | NH | Q3b | OH |
| 1353 | CH | NEt | Q1u | a bond | Me | a bond | NH | O | NH | Q3c | OH |
| 1354 | CH | NEt | Q1u | a bond | Me | a bond | NH | O | a bond | Q3a | OH |
| 1355 | CH | NEt | Q1u | a bond | Me | a bond | NH | O | a bond | Q3b | OH |
| 1356 | CH | NEt | Q1u | a bond | Me | a bond | NH | O | a bond | Q3c | OH |
| 1357 | CH | NEt | Q1u | a bond | H | a bond | NH | S | NH | Q3a | OH |
| 1358 | CH | NEt | Q1u | a bond | H | a bond | NH | S | NH | Q3b | OH |
| 1359 | CH | NEt | Q1u | a bond | H | a bond | NH | S | NH | Q3c | OH |
| 1360 | CH | NEt | Q1u | a bond | H | a bond | NH | S | a bond | Q3a | OH |
| 1361 | CH | NEt | Q1u | a bond | H | a bond | NH | S | a bond | Q3b | OH |
| 1362 | CH | NEt | Q1u | a bond | H | a bond | NH | S | a bond | Q3c | OH |
| 1363 | CH | NEt | Q1u | a bond | H | a bond | NH | O | NH | Q3a | OH |
| 1364 | CH | NEt | Q1u | a bond | H | a bond | NH | O | NH | Q3b | OH |
| 1365 | CH | NEt | Q1u | a bond | H | a bond | NH | O | NH | Q3c | OH |
| 1366 | CH | NEt | Q1u | a bond | H | a bond | NH | O | a bond | Q3a | OH |
| 1367 | CH | NEt | Q1u | a bond | H | a bond | NH | O | a bond | Q3b | OH |
| 1368 | CH | NEt | Q1u | a bond | H | a bond | NH | O | a bond | Q3c | OH |
| 1369 | CH | NEt | Q1v | a bond | Me | a bond | NH | S | NH | Q3a | OH |
| 1370 | CH | NEt | Q1v | a bond | Me | a bond | NH | S | NH | Q3b | OH |
| 1371 | CH | NEt | Q1v | a bond | Me | a bond | NH | S | NH | Q3c | OH |
| 1372 | CH | NEt | Q1v | a bond | Me | a bond | NH | S | a bond | Q3a | OH |
| 1373 | CH | NEt | Q1v | a bond | Me | a bond | NH | S | a bond | Q3b | OH |
| 1374 | CH | NEt | Q1v | a bond | Me | a bond | NH | S | a bond | Q3c | OH |
| 1375 | CH | NEt | Q1v | a bond | Me | a bond | NH | O | NH | Q3a | OH |
| 1376 | CH | NEt | Q1v | a bond | Me | a bond | NH | O | NH | Q3b | OH |
| 1377 | CH | NEt | Q1v | a bond | Me | a bond | NH | O | NH | Q3c | OH |
| 1378 | CH | NEt | Q1v | a bond | Me | a bond | NH | O | a bond | Q3a | OH |
| 1379 | CH | NEt | Q1v | a bond | Me | a bond | NH | O | a bond | Q3b | OH |
| 1380 | CH | NEt | Q1v | a bond | Me | a bond | NH | O | a bond | Q3c | OH |
| 1381 | CH | NEt | Q1v | a bond | H | a bond | NH | S | NH | Q3a | OH |
| 1382 | CH | NEt | Q1v | a bond | H | a bond | NH | S | NH | Q3b | OH |
| 1383 | CH | NEt | Q1v | a bond | H | a bond | NH | S | NH | Q3c | OH |
| 1384 | CH | NEt | Q1v | a bond | H | a bond | NH | S | a bond | Q3a | OH |
| 1385 | CH | NEt | Q1v | a bond | H | a bond | NH | S | a bond | Q3b | OH |
| 1386 | CH | NEt | Q1v | a bond | H | a bond | NH | S | a bond | Q3c | OH |
| 1387 | CH | NEt | Q1v | a bond | H | a bond | NH | O | NH | Q3a | OH |
| 1388 | CH | NEt | Q1v | a bond | H | a bond | NH | O | NH | Q3b | OH |
| 1389 | CH | NEt | Q1v | a bond | H | a bond | NH | O | NH | Q3c | OH |
| 1390 | CH | NEt | Q1v | a bond | H | a bond | NH | O | a bond | Q3a | OH |
| 1391 | CH | NEt | Q1v | a bond | H | a bond | NH | O | a bond | Q3b | OH |
| 1392 | CH | NEt | Q1v | a bond | H | a bond | NH | O | a bond | Q3c | OH |
| 1393 | CH | NEt | Q1w | a bond | Me | a bond | NH | S | NH | Q3a | OH |
| 1394 | CH | NEt | Q1w | a bond | Me | a bond | NH | S | NH | Q3b | OH |
| 1395 | CH | NEt | Q1w | a bond | Me | a bond | NH | S | NH | Q3c | OH |
| 1396 | CH | NEt | Q1w | a bond | Me | a bond | NH | S | a bond | Q3a | OH |
| 1397 | CH | NEt | Q1w | a bond | Me | a bond | NH | S | a bond | Q3b | OH |
| 1398 | CH | NEt | Q1w | a bond | Me | a bond | NH | S | a bond | Q3c | OH |
| 1399 | CH | NEt | Q1w | a bond | Me | a bond | NH | O | NH | Q3a | OH |
| 1400 | CH | NEt | Q1w | a bond | Me | a bond | NH | O | NH | Q3b | OH |
| 1401 | CH | NEt | Q1w | a bond | Me | a bond | NH | O | NH | Q3c | OH |
| 1402 | CH | NEt | Q1w | a bond | Me | a bond | NH | O | a bond | Q3a | OH |
| 1403 | CH | NEt | Q1w | a bond | Me | a bond | NH | O | a bond | Q3b | OH |
| 1404 | CH | NEt | Q1w | a bond | Me | a bond | NH | O | a bond | Q3c | OH |
| 1405 | CH | NEt | Q1w | a bond | H | a bond | NH | S | NH | Q3a | OH |
| 1406 | CH | NEt | Q1w | a bond | H | a bond | NH | S | NH | Q3b | OH |
| 1407 | CH | NEt | Q1w | a bond | H | a bond | NH | S | NH | Q3c | OH |
| 1408 | CH | NEt | Q1w | a bond | H | a bond | NH | S | a bond | Q3a | OH |
| 1409 | CH | NEt | Q1w | a bond | H | a bond | NH | S | a bond | Q3b | OH |
| 1410 | CH | NEt | Q1w | a bond | H | a bond | NH | S | a bond | Q3c | OH |
| 1411 | CH | NEt | Q1w | a bond | H | a bond | NH | O | NH | Q3a | OH |
| 1412 | CH | NEt | Q1w | a bond | H | a bond | NH | O | NH | Q3b | OH |
| 1413 | CH | NEt | Q1w | a bond | H | a bond | NH | O | NH | Q3c | OH |
| 1414 | CH | NEt | Q1w | a bond | H | a bond | NH | O | a bond | Q3a | OH |
| 1415 | CH | NEt | Q1w | a bond | H | a bond | NH | O | a bond | Q3b | OH |
| 1416 | CH | NEt | Q1w | a bond | H | a bond | NH | O | a bond | Q3c | OH |
| 1417 | CH | NEt | Q1x | a bond | Me | a bond | NH | S | NH | Q3a | OH |
| 1418 | CH | NEt | Q1x | a bond | Me | a bond | NH | S | NH | Q3b | OH |
| 1419 | CH | NEt | Q1x | a bond | Me | a bond | NH | S | NH | Q3c | OH |
| 1420 | CH | NEt | Q1x | a bond | Me | a bond | NH | S | a bond | Q3a | OH |
| 1421 | CH | NEt | Q1x | a bond | Me | a bond | NH | S | a bond | Q3b | OH |
| 1422 | CH | NEt | Q1x | a bond | Me | a bond | NH | S | a bond | Q3c | OH |
| 1423 | CH | NEt | Q1x | a bond | Me | a bond | NH | O | NH | Q3a | OH |
| 1424 | CH | NEt | Q1x | a bond | Me | a bond | NH | O | NH | Q3b | OH |
| 1425 | CH | NEt | Q1x | a bond | Me | a bond | NH | O | NH | Q3c | OH |
| 1426 | CH | NEt | Q1x | a bond | Me | a bond | NH | O | a bond | Q3a | OH |
| 1427 | CH | NEt | Q1x | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1428 | CH | NEt | Q1x | a bond | Me | a bond | NH | O | a bond | Q3c | OH |
| 1429 | CH | NEt | Q1x | a bond | H | a bond | NH | S | NH | Q3a | OH |
| 1430 | CH | NEt | Q1x | a bond | H | a bond | NH | S | NH | Q3b | OH |
| 1431 | CH | NEt | Q1x | a bond | H | a bond | NH | S | NH | Q3c | OH |
| 1432 | CH | NEt | Q1x | a bond | H | a bond | NH | S | a bond | Q3a | OH |
| 1433 | CH | NEt | Q1x | a bond | H | a bond | NH | S | a bond | Q3b | OH |
| 1434 | CH | NEt | Q1x | a bond | H | a bond | NH | S | a bond | Q3c | OH |
| 1435 | CH | NEt | Q1x | a bond | H | a bond | NH | O | NH | Q3a | OH |
| 1436 | CH | NEt | Q1x | a bond | H | a bond | NH | O | NH | Q3b | OH |
| 1437 | CH | NEt | Q1x | a bond | H | a bond | NH | O | NH | Q3c | OH |
| 1438 | CH | NEt | Q1x | a bond | H | a bond | NH | O | a bond | Q3a | OH |
| 1439 | CH | NEt | Q1x | a bond | H | a bond | NH | O | a bond | Q3b | OH |
| 1440 | CH | NEt | Q1x | a bond | H | a bond | NH | O | a bond | Q3c | OH |
| 1441 | CH | S | Q1o | a bond | Me | a bond | NH | S | NH | Q3a | OH |
| 1442 | CH | S | Q1o | a bond | Me | a bond | NH | S | NH | Q3b | OH |
| 1443 | CH | S | Q1o | a bond | Me | a bond | NH | S | NH | Q3c | OH |
| 1444 | CH | S | Q1o | a bond | Me | a bond | NH | S | a bond | Q3a | OH |
| 1445 | CH | S | Q1o | a bond | Me | a bond | NH | S | a bond | Q3b | OH |
| 1446 | CH | S | Q1o | a bond | Me | a bond | NH | S | a bond | Q3c | OH |
| 1447 | CH | S | Q1o | a bond | Me | a bond | NH | O | NH | Q3a | OH |
| 1448 | CH | S | Q1o | a bond | Me | a bond | NH | O | NH | Q3b | OH |
| 1449 | CH | S | Q1o | a bond | Me | a bond | NH | O | NH | Q3c | OH |
| 1450 | CH | S | Q1o | a bond | Me | a bond | NH | O | a bond | Q3a | OH |
| 1451 | CH | S | Q1o | a bond | Me | a bond | NH | O | a bond | Q3b | OH |
| 1452 | CH | S | Q1o | a bond | Me | a bond | NH | O | a bond | Q3c | OH |
| 1453 | CH | S | Q1o | a bond | H | a bond | NH | S | NH | Q3a | OH |
| 1454 | CH | S | Q1o | a bond | H | a bond | NH | S | NH | Q3b | OH |
| 1455 | CH | S | Q1o | a bond | H | a bond | NH | S | NH | Q3c | OH |
| 1456 | CH | S | Q1o | a bond | H | a bond | NH | S | a bond | Q3a | OH |
| 1457 | CH | S | Q1o | a bond | H | a bond | NH | S | a bond | Q3b | OH |
| 1458 | CH | S | Q1o | a bond | H | a bond | NH | S | a bond | Q3c | OH |
| 1459 | CH | S | Q1o | a bond | H | a bond | NH | O | NH | Q3a | OH |
| 1460 | CH | S | Q1o | a bond | H | a bond | NH | O | NH | Q3b | OH |
| 1461 | CH | S | Q1o | a bond | H | a bond | NH | O | NH | Q3c | OH |
| 1462 | CH | S | Q1o | a bond | H | a bond | NH | O | a bond | Q3a | OH |
| 1463 | CH | S | Q1o | a bond | H | a bond | NH | O | a bond | Q3b | OH |
| 1464 | CH | S | Q1o | a bond | H | a bond | NH | O | a bond | Q3c | OH |
| 1465 | CH | S | Q1p | a bond | Me | a bond | NH | S | NH | Q3a | OH |
| 1466 | CH | S | Q1p | a bond | Me | a bond | NH | S | NH | Q3b | OH |
| 1467 | CH | S | Q1p | a bond | Me | a bond | NH | S | NH | Q3c | OH |
| 1468 | CH | S | Q1p | a bond | Me | a bond | NH | S | a bond | Q3a | OH |
| 1469 | CH | S | Q1p | a bond | Me | a bond | NH | S | a bond | Q3b | OH |
| 1470 | CH | S | Q1p | a bond | Me | a bond | NH | S | a bond | Q3c | OH |
| 1471 | CH | S | Q1p | a bond | Me | a bond | NH | O | NH | Q3a | OH |
| 1472 | CH | S | Q1p | a bond | Me | a bond | NH | O | NH | Q3b | OH |
| 1473 | CH | S | Q1p | a bond | Me | a bond | NH | O | NH | Q3c | OH |
| 1474 | CH | S | Q1p | a bond | Me | a bond | NH | O | a bond | Q3a | OH |
| 1475 | CH | S | Q1p | a bond | Me | a bond | NH | O | a bond | Q3b | OH |
| 1476 | CH | S | Q1p | a bond | Me | a bond | NH | O | a bond | Q3c | OH |
| 1477 | CH | S | Q1p | a bond | H | a bond | NH | S | NH | Q3a | OH |
| 1478 | CH | S | Q1p | a bond | H | a bond | NH | S | NH | Q3b | OH |
| 1479 | CH | S | Q1p | a bond | H | a bond | NH | S | NH | Q3c | OH |
| 1480 | CH | S | Q1p | a bond | H | a bond | NH | S | a bond | Q3a | OH |
| 1481 | CH | S | Q1p | a bond | H | a bond | NH | S | a bond | Q3b | OH |
| 1482 | CH | S | Q1p | a bond | H | a bond | NH | S | a bond | Q3c | OH |
| 1483 | CH | S | Q1p | a bond | H | a bond | NH | O | NH | Q3a | OH |
| 1484 | CH | S | Q1p | a bond | H | a bond | NH | O | NH | Q3b | OH |
| 1485 | CH | S | Q1p | a bond | H | a bond | NH | O | NH | Q3c | OH |
| 1486 | CH | S | Q1p | a bond | H | a bond | NH | O | a bond | Q3a | OH |
| 1487 | CH | S | Q1p | a bond | H | a bond | NH | O | a bond | Q3b | OH |
| 1488 | CH | S | Q1p | a bond | H | a bond | NH | O | a bond | Q3c | OH |
| 1489 | CH | S | Q1q | a bond | Me | a bond | NH | S | NH | Q3a | OH |
| 1490 | CH | S | Q1q | a bond | Me | a bond | NH | S | NH | Q3b | OH |
| 1491 | CH | S | Q1q | a bond | Me | a bond | NH | S | NH | Q3c | OH |
| 1492 | CH | S | Q1q | a bond | Me | a bond | NH | S | a bond | Q3a | OH |
| 1493 | CH | S | Q1q | a bond | Me | a bond | NH | S | a bond | Q3b | OH |
| 1494 | CH | S | Q1q | a bond | Me | a bond | NH | S | a bond | Q3c | OH |
| 1495 | CH | S | Q1q | a bond | Me | a bond | NH | O | NH | Q3a | OH |
| 1496 | CH | S | Q1q | a bond | Me | a bond | NH | O | NH | Q3b | OH |
| 1497 | CH | S | Q1q | a bond | Me | a bond | NH | O | NH | Q3c | OH |
| 1498 | CH | S | Q1q | a bond | Me | a bond | NH | O | a bond | Q3a | OH |
| 1499 | CH | S | Q1q | a bond | Me | a bond | NH | O | a bond | Q3b | OH |
| 1500 | CH | S | Q1q | a bond | Me | a bond | NH | O | a bond | Q3c | OH |
| 1501 | CH | S | Q1q | a bond | H | a bond | NH | S | NH | Q3a | OH |
| 1502 | CH | S | Q1q | a bond | H | a bond | NH | S | NH | Q3b | OH |
| 1503 | CH | S | Q1q | a bond | H | a bond | NH | S | NH | Q3c | OH |
| 1504 | CH | S | Q1q | a bond | H | a bond | NH | S | a bond | Q3a | OH |
| 1505 | CH | S | Q1q | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1506 | CH | S | Q1q | a bond | H | a bond | NH | S | a bond | Q3c | OH |
| 1507 | CH | S | Q1q | a bond | H | a bond | NH | O | NH | Q3a | OH |
| 1508 | CH | S | Q1q | a bond | H | a bond | NH | O | NH | Q3b | OH |
| 1509 | CH | S | Q1q | a bond | H | a bond | NH | O | NH | Q3c | OH |
| 1510 | CH | S | Q1q | a bond | H | a bond | NH | O | a bond | Q3a | OH |
| 1511 | CH | S | Q1q | a bond | H | a bond | NH | O | a bond | Q3b | OH |
| 1512 | CH | S | Q1q | a bond | H | a bond | NH | O | a bond | Q3c | OH |
| 1513 | CH | S | Q1r | a bond | Me | a bond | NH | S | NH | Q3a | OH |
| 1514 | CH | S | Q1r | a bond | Me | a bond | NH | S | NH | Q3b | OH |
| 1515 | CH | S | Q1r | a bond | Me | a bond | NH | S | NH | Q3c | OH |
| 1516 | CH | S | Q1r | a bond | Me | a bond | NH | S | a bond | Q3a | OH |
| 1517 | CH | S | Q1r | a bond | Me | a bond | NH | S | a bond | Q3b | OH |
| 1518 | CH | S | Q1r | a bond | Me | a bond | NH | S | a bond | Q3c | OH |
| 1519 | CH | S | Q1r | a bond | Me | a bond | NH | O | NH | Q3a | OH |
| 1520 | CH | S | Q1r | a bond | Me | a bond | NH | O | NH | Q3b | OH |
| 1521 | CH | S | Q1r | a bond | Me | a bond | NH | O | NH | Q3c | OH |
| 1522 | CH | S | Q1r | a bond | Me | a bond | NH | O | a bond | Q3a | OH |
| 1523 | CH | S | Q1r | a bond | Me | a bond | NH | O | a bond | Q3b | OH |
| 1524 | CH | S | Q1r | a bond | Me | a bond | NH | O | a bond | Q3c | OH |
| 1525 | CH | S | Q1r | a bond | H | a bond | NH | S | NH | Q3a | OH |
| 1526 | CH | S | Q1r | a bond | H | a bond | NH | S | NH | Q3b | OH |
| 1527 | CH | S | Q1r | a bond | H | a bond | NH | S | NH | Q3c | OH |
| 1528 | CH | S | Q1r | a bond | H | a bond | NH | S | a bond | Q3a | OH |
| 1529 | CH | S | Q1r | a bond | H | a bond | NH | S | a bond | Q3b | OH |
| 1530 | CH | S | Q1r | a bond | H | a bond | NH | S | a bond | Q3c | OH |
| 1531 | CH | S | Q1r | a bond | H | a bond | NH | O | NH | Q3a | OH |
| 1532 | CH | S | Q1r | a bond | H | a bond | NH | O | NH | Q3b | OH |
| 1533 | CH | S | Q1r | a bond | H | a bond | NH | O | NH | Q3c | OH |
| 1534 | CH | S | Q1r | a bond | H | a bond | NH | O | a bond | Q3a | OH |
| 1535 | CH | S | Q1r | a bond | H | a bond | NH | O | a bond | Q3b | OH |
| 1536 | CH | S | Q1r | a bond | H | a bond | NH | O | a bond | Q3c | OH |
| 1537 | CH | S | Q1s | a bond | Me | a bond | NH | S | NH | Q3a | OH |
| 1538 | CH | S | Q1s | a bond | Me | a bond | NH | S | NH | Q3b | OH |
| 1539 | CH | S | Q1s | a bond | Me | a bond | NH | S | NH | Q3c | OH |
| 1540 | CH | S | Q1s | a bond | Me | a bond | NH | S | a bond | Q3a | OH |
| 1541 | CH | S | Q1s | a bond | Me | a bond | NH | S | a bond | Q3b | OH |
| 1542 | CH | S | Q1s | a bond | Me | a bond | NH | S | a bond | Q3c | OH |
| 1543 | CH | S | Q1s | a bond | Me | a bond | NH | O | NH | Q3a | OH |
| 1544 | CH | S | Q1s | a bond | Me | a bond | NH | O | NH | Q3b | OH |
| 1545 | CH | S | Q1s | a bond | Me | a bond | NH | O | NH | Q3c | OH |
| 1546 | CH | S | Q1s | a bond | Me | a bond | NH | O | a bond | Q3a | OH |
| 1547 | CH | S | Q1s | a bond | Me | a bond | NH | O | a bond | Q3b | OH |
| 1548 | CH | S | Q1s | a bond | Me | a bond | NH | O | a bond | Q3c | OH |
| 1549 | CH | S | Q1s | a bond | H | a bond | NH | S | NH | Q3a | OH |
| 1550 | CH | S | Q1s | a bond | H | a bond | NH | S | NH | Q3b | OH |
| 1551 | CH | S | Q1s | a bond | H | a bond | NH | S | NH | Q3c | OH |
| 1552 | CH | S | Q1s | a bond | H | a bond | NH | S | a bond | Q3a | OH |
| 1553 | CH | S | Q1s | a bond | H | a bond | NH | S | a bond | Q3b | OH |
| 1554 | CH | S | Q1s | a bond | H | a bond | NH | S | a bond | Q3c | OH |
| 1555 | CH | S | Q1s | a bond | H | a bond | NH | O | NH | Q3a | OH |
| 1556 | CH | S | Q1s | a bond | H | a bond | NH | O | NH | Q3b | OH |
| 1557 | CH | S | Q1s | a bond | H | a bond | NH | O | NH | Q3c | OH |
| 1558 | CH | S | Q1s | a bond | H | a bond | NH | O | a bond | Q3a | OH |
| 1559 | CH | S | Q1s | a bond | H | a bond | NH | O | a bond | Q3b | OH |
| 1560 | CH | S | Q1s | a bond | H | a bond | NH | O | a bond | Q3c | OH |
| 1561 | CH | S | Q1t | a bond | Me | a bond | NH | S | NH | Q3a | OH |
| 1562 | CH | S | Q1t | a bond | Me | a bond | NH | S | NH | Q3b | OH |
| 1563 | CH | S | Q1t | a bond | Me | a bond | NH | S | NH | Q3c | OH |
| 1564 | CH | S | Q1t | a bond | Me | a bond | NH | S | a bond | Q3a | OH |
| 1565 | CH | S | Q1t | a bond | Me | a bond | NH | S | a bond | Q3b | OH |
| 1566 | CH | S | Q1t | a bond | Me | a bond | NH | S | a bond | Q3c | OH |
| 1567 | CH | S | Q1t | a bond | Me | a bond | NH | O | NH | Q3a | OH |
| 1568 | CH | S | Q1t | a bond | Me | a bond | NH | O | NH | Q3b | OH |
| 1569 | CH | S | Q1t | a bond | Me | a bond | NH | O | NH | Q3c | OH |
| 1570 | CH | S | Q1t | a bond | Me | a bond | NH | O | a bond | Q3a | OH |
| 1571 | CH | S | Q1t | a bond | Me | a bond | NH | O | a bond | Q3b | OH |
| 1572 | CH | S | Q1t | a bond | Me | a bond | NH | O | a bond | Q3c | OH |
| 1573 | CH | S | Q1t | a bond | H | a bond | NH | S | NH | Q3a | OH |
| 1574 | CH | S | Q1t | a bond | H | a bond | NH | S | NH | Q3b | OH |
| 1575 | CH | S | Q1t | a bond | H | a bond | NH | S | NH | Q3c | OH |
| 1576 | CH | S | Q1t | a bond | H | a bond | NH | S | a bond | Q3a | OH |
| 1577 | CH | S | Q1t | a bond | H | a bond | NH | S | a bond | Q3b | OH |
| 1578 | CH | S | Q1t | a bond | H | a bond | NH | S | a bond | Q3c | OH |
| 1579 | CH | S | Q1t | a bond | H | a bond | NH | O | NH | Q3a | OH |
| 1580 | CH | S | Q1t | a bond | H | a bond | NH | O | NH | Q3b | OH |
| 1581 | CH | S | Q1t | a bond | H | a bond | NH | O | NH | Q3c | OH |
| 1582 | CH | S | Q1t | a bond | H | a bond | NH | O | a bond | Q3a | OH |
| 1583 | CH | S | Q1t | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1584 | CH | S | Q1t | a bond | H | a bond | NH | O | a bond | Q3c | OH |
| 1585 | CH | S | Q1u | a bond | Me | a bond | NH | S | NH | Q3a | OH |
| 1586 | CH | S | Q1u | a bond | Me | a bond | NH | S | NH | Q3b | OH |
| 1587 | CH | S | Q1u | a bond | Me | a bond | NH | S | NH | Q3c | OH |
| 1588 | CH | S | Q1u | a bond | Me | a bond | NH | S | a bond | Q3a | OH |
| 1589 | CH | S | Q1u | a bond | Me | a bond | NH | S | a bond | Q3b | OH |
| 1590 | CH | S | Q1u | a bond | Me | a bond | NH | S | a bond | Q3c | OH |
| 1591 | CH | S | Q1u | a bond | Me | a bond | NH | O | NH | Q3a | OH |
| 1592 | CH | S | Q1u | a bond | Me | a bond | NH | O | NH | Q3b | OH |
| 1593 | CH | S | Q1u | a bond | Me | a bond | NH | O | NH | Q3c | OH |
| 1594 | CH | S | Q1u | a bond | Me | a bond | NH | O | a bond | Q3a | OH |
| 1595 | CH | S | Q1u | a bond | Me | a bond | NH | O | a bond | Q3b | OH |
| 1596 | CH | S | Q1u | a bond | Me | a bond | NH | O | a bond | Q3c | OH |
| 1597 | CH | S | Q1u | a bond | H | a bond | NH | S | NH | Q3a | OH |
| 1598 | CH | S | Q1u | a bond | H | a bond | NH | S | NH | Q3b | OH |
| 1599 | CH | S | Q1u | a bond | H | a bond | NH | S | NH | Q3c | OH |
| 1600 | CH | S | Q1u | a bond | H | a bond | NH | S | a bond | Q3a | OH |
| 1601 | CH | S | Q1u | a bond | H | a bond | NH | S | a bond | Q3b | OH |
| 1602 | CH | S | Q1u | a bond | H | a bond | NH | S | a bond | Q3c | OH |
| 1603 | CH | S | Q1u | a bond | H | a bond | NH | O | NH | Q3a | OH |
| 1604 | CH | S | Q1u | a bond | H | a bond | NH | O | NH | Q3b | OH |
| 1605 | CH | S | Q1u | a bond | H | a bond | NH | O | NH | Q3c | OH |
| 1606 | CH | S | Q1u | a bond | H | a bond | NH | O | a bond | Q3a | OH |
| 1607 | CH | S | Q1u | a bond | H | a bond | NH | O | a bond | Q3b | OH |
| 1608 | CH | S | Q1u | a bond | H | a bond | NH | O | a bond | Q3c | OH |
| 1609 | CH | S | Q1v | a bond | Me | a bond | NH | S | NH | Q3a | OH |
| 1610 | CH | S | Q1v | a bond | Me | a bond | NH | S | NH | Q3b | OH |
| 1611 | CH | S | Q1v | a bond | Me | a bond | NH | S | NH | Q3c | OH |
| 1612 | CH | S | Q1v | a bond | Me | a bond | NH | S | a bond | Q3a | OH |
| 1613 | CH | S | Q1v | a bond | Me | a bond | NH | S | a bond | Q3b | OH |
| 1614 | CH | S | Q1v | a bond | Me | a bond | NH | S | a bond | Q3c | OH |
| 1615 | CH | S | Q1v | a bond | Me | a bond | NH | O | NH | Q3a | OH |
| 1616 | CH | S | Q1v | a bond | Me | a bond | NH | O | NH | Q3b | OH |
| 1617 | CH | S | Q1v | a bond | Me | a bond | NH | O | NH | Q3c | OH |
| 1618 | CH | S | Q1v | a bond | Me | a bond | NH | O | a bond | Q3a | OH |
| 1619 | CH | S | Q1v | a bond | Me | a bond | NH | O | a bond | Q3b | OH |
| 1620 | CH | S | Q1v | a bond | Me | a bond | NH | O | a bond | Q3c | OH |
| 1621 | CH | S | Q1v | a bond | H | a bond | NH | S | NH | Q3a | OH |
| 1622 | CH | S | Q1v | a bond | H | a bond | NH | S | NH | Q3b | OH |
| 1623 | CH | S | Q1v | a bond | H | a bond | NH | S | NH | Q3c | OH |
| 1624 | CH | S | Q1v | a bond | H | a bond | NH | S | a bond | Q3a | OH |
| 1625 | CH | S | Q1v | a bond | H | a bond | NH | S | a bond | Q3b | OH |
| 1626 | CH | S | Q1v | a bond | H | a bond | NH | S | a bond | Q3c | OH |
| 1627 | CH | S | Q1v | a bond | H | a bond | NH | O | NH | Q3a | OH |
| 1628 | CH | S | Q1v | a bond | H | a bond | NH | O | NH | Q3b | OH |
| 1629 | CH | S | Q1v | a bond | H | a bond | NH | O | NH | Q3c | OH |
| 1630 | CH | S | Q1v | a bond | H | a bond | NH | O | a bond | Q3a | OH |
| 1631 | CH | S | Q1v | a bond | H | a bond | NH | O | a bond | Q3b | OH |
| 1632 | CH | S | Q1v | a bond | H | a bond | NH | O | a bond | Q3c | OH |
| 1633 | CH | S | Q1w | a bond | Me | a bond | NH | S | NH | Q3a | OH |
| 1634 | CH | S | Q1w | a bond | Me | a bond | NH | S | NH | Q3b | OH |
| 1635 | CH | S | Q1w | a bond | Me | a bond | NH | S | NH | Q3c | OH |
| 1636 | CH | S | Q1w | a bond | Me | a bond | NH | S | a bond | Q3a | OH |
| 1637 | CH | S | Q1w | a bond | Me | a bond | NH | S | a bond | Q3b | OH |
| 1638 | CH | S | Q1w | a bond | Me | a bond | NH | S | a bond | Q3c | OH |
| 1639 | CH | S | Q1w | a bond | Me | a bond | NH | O | NH | Q3a | OH |
| 1640 | CH | S | Q1w | a bond | Me | a bond | NH | O | NH | Q3b | OH |
| 1641 | CH | S | Q1w | a bond | Me | a bond | NH | O | NH | Q3c | OH |
| 1642 | CH | S | Q1w | a bond | Me | a bond | NH | O | a bond | Q3a | OH |
| 1643 | CH | S | Q1w | a bond | Me | a bond | NH | O | a bond | Q3b | OH |
| 1644 | CH | S | Q1w | a bond | Me | a bond | NH | O | a bond | Q3c | OH |
| 1645 | CH | S | Q1w | a bond | H | a bond | NH | S | NH | Q3a | OH |
| 1646 | CH | S | Q1w | a bond | H | a bond | NH | S | NH | Q3b | OH |
| 1647 | CH | S | Q1w | a bond | H | a bond | NH | S | NH | Q3c | OH |
| 1648 | CH | S | Q1w | a bond | H | a bond | NH | S | a bond | Q3a | OH |
| 1649 | CH | S | Q1w | a bond | H | a bond | NH | S | a bond | Q3b | OH |
| 1650 | CH | S | Q1w | a bond | H | a bond | NH | S | a bond | Q3c | OH |
| 1651 | CH | S | Q1w | a bond | H | a bond | NH | O | NH | Q3a | OH |
| 1652 | CH | S | Q1w | a bond | H | a bond | NH | O | NH | Q3b | OH |
| 1653 | CH | S | Q1w | a bond | H | a bond | NH | O | NH | Q3c | OH |
| 1654 | CH | S | Q1w | a bond | H | a bond | NH | O | a bond | Q3a | OH |
| 1655 | CH | S | Q1w | a bond | H | a bond | NH | O | a bond | Q3b | OH |
| 1656 | CH | S | Q1w | a bond | H | a bond | NH | O | a bond | Q3c | OH |
| 1657 | CH | S | Q1x | a bond | Me | a bond | NH | S | NH | Q3a | OH |
| 1658 | CH | S | Q1x | a bond | Me | a bond | NH | S | NH | Q3b | OH |
| 1659 | CH | S | Q1x | a bond | Me | a bond | NH | S | NH | Q3c | OH |
| 1660 | CH | S | Q1x | a bond | Me | a bond | NH | S | a bond | Q3a | OH |
| 1661 | CH | S | Q1x | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1662 | CH | S | Q1x | a bond | Me | a bond | NH | S | a bond | Q3c | OH |
| 1663 | CH | S | Q1x | a bond | Me | a bond | NH | O | NH | Q3a | OH |
| 1664 | CH | S | Q1x | a bond | Me | a bond | NH | O | NH | Q3b | OH |
| 1665 | CH | S | Q1x | a bond | Me | a bond | NH | O | NH | Q3c | OH |
| 1666 | CH | S | Q1x | a bond | Me | a bond | NH | O | a bond | Q3a | OH |
| 1667 | CH | S | Q1x | a bond | Me | a bond | NH | O | a bond | Q3b | OH |
| 1668 | CH | S | Q1x | a bond | Me | a bond | NH | O | a bond | Q3c | OH |
| 1669 | CH | S | Q1x | a bond | H | a bond | NH | S | NH | Q3a | OH |
| 1670 | CH | S | Q1x | a bond | H | a bond | NH | S | NH | Q3b | OH |
| 1671 | CH | S | Q1x | a bond | H | a bond | NH | S | NH | Q3c | OH |
| 1672 | CH | S | Q1x | a bond | H | a bond | NH | S | a bond | Q3a | OH |
| 1673 | CH | S | Q1x | a bond | H | a bond | NH | S | a bond | Q3b | OH |
| 1674 | CH | S | Q1x | a bond | H | a bond | NH | S | a bond | Q3c | OH |
| 1675 | CH | S | Q1x | a bond | H | a bond | NH | O | NH | Q3a | OH |
| 1676 | CH | S | Q1x | a bond | H | a bond | NH | O | NH | Q3b | OH |
| 1677 | CH | S | Q1x | a bond | H | a bond | NH | O | NH | Q3c | OH |
| 1678 | CH | S | Q1x | a bond | H | a bond | NH | O | a bond | Q3a | OH |
| 1679 | CH | S | Q1x | a bond | H | a bond | NH | O | a bond | Q3b | OH |
| 1680 | CH | S | Q1x | a bond | H | a bond | NH | O | a bond | Q3c | OH |
| 1681 | CH | O | Q1o | a bond | Me | a bond | NH | S | NH | Q3a | OH |
| 1682 | CH | O | Q1o | a bond | Me | a bond | NH | S | NH | Q3b | OH |
| 1683 | CH | O | Q1o | a bond | Me | a bond | NH | S | NH | Q3c | OH |
| 1684 | CH | O | Q1o | a bond | Me | a bond | NH | S | a bond | Q3a | OH |
| 1685 | CH | O | Q1o | a bond | Me | a bond | NH | S | a bond | Q3b | OH |
| 1686 | CH | O | Q1o | a bond | Me | a bond | NH | S | a bond | Q3c | OH |
| 1687 | CH | O | Q1o | a bond | Me | a bond | NH | O | NH | Q3a | OH |
| 1688 | CH | O | Q1o | a bond | Me | a bond | NH | O | NH | Q3b | OH |
| 1689 | CH | O | Q1o | a bond | Me | a bond | NH | O | NH | Q3c | OH |
| 1690 | CH | O | Q1o | a bond | Me | a bond | NH | O | a bond | Q3a | OH |
| 1691 | CH | O | Q1o | a bond | Me | a bond | NH | O | a bond | Q3b | OH |
| 1692 | CH | O | Q1o | a bond | Me | a bond | NH | O | a bond | Q3c | OH |
| 1693 | CH | O | Q1o | a bond | H | a bond | NH | S | NH | Q3a | OH |
| 1694 | CH | O | Q1o | a bond | H | a bond | NH | S | NH | Q3b | OH |
| 1695 | CH | O | Q1o | a bond | H | a bond | NH | S | NH | Q3c | OH |
| 1696 | CH | O | Q1o | a bond | H | a bond | NH | S | a bond | Q3a | OH |
| 1697 | CH | O | Q1o | a bond | H | a bond | NH | S | a bond | Q3b | OH |
| 1698 | CH | O | Q1o | a bond | H | a bond | NH | S | a bond | Q3c | OH |
| 1699 | CH | O | Q1o | a bond | H | a bond | NH | O | NH | Q3a | OH |
| 1700 | CH | O | Q1o | a bond | H | a bond | NH | O | NH | Q3b | OH |
| 1701 | CH | O | Q1o | a bond | H | a bond | NH | O | NH | Q3c | OH |
| 1702 | CH | O | Q1o | a bond | H | a bond | NH | O | a bond | Q3a | OH |
| 1703 | CH | O | Q1o | a bond | H | a bond | NH | O | a bond | Q3b | OH |
| 1704 | CH | O | Q1o | a bond | H | a bond | NH | O | a bond | Q3c | OH |
| 1705 | CH | O | Q1p | a bond | Me | a bond | NH | S | NH | Q3a | OH |
| 1706 | CH | O | Q1p | a bond | Me | a bond | NH | S | NH | Q3b | OH |
| 1707 | CH | O | Q1p | a bond | Me | a bond | NH | S | NH | Q3c | OH |
| 1708 | CH | O | Q1p | a bond | Me | a bond | NH | S | a bond | Q3a | OH |
| 1709 | CH | O | Q1p | a bond | Me | a bond | NH | S | a bond | Q3b | OH |
| 1710 | CH | O | Q1p | a bond | Me | a bond | NH | S | a bond | Q3c | OH |
| 1711 | CH | O | Q1p | a bond | Me | a bond | NH | O | NH | Q3a | OH |
| 1712 | CH | O | Q1p | a bond | Me | a bond | NH | O | NH | Q3b | OH |
| 1713 | CH | O | Q1p | a bond | Me | a bond | NH | O | NH | Q3c | OH |
| 1714 | CH | O | Q1p | a bond | Me | a bond | NH | O | a bond | Q3a | OH |
| 1715 | CH | O | Q1p | a bond | Me | a bond | NH | O | a bond | Q3b | OH |
| 1716 | CH | O | Q1p | a bond | Me | a bond | NH | O | a bond | Q3c | OH |
| 1717 | CH | O | Q1p | a bond | H | a bond | NH | S | NH | Q3a | OH |
| 1718 | CH | O | Q1p | a bond | H | a bond | NH | S | NH | Q3b | OH |
| 1719 | CH | O | Q1p | a bond | H | a bond | NH | S | NH | Q3c | OH |
| 1720 | CH | O | Q1p | a bond | H | a bond | NH | S | a bond | Q3a | OH |
| 1721 | CH | O | Q1p | a bond | H | a bond | NH | S | a bond | Q3b | OH |
| 1722 | CH | O | Q1p | a bond | H | a bond | NH | S | a bond | Q3c | OH |
| 1723 | CH | O | Q1p | a bond | H | a bond | NH | O | NH | Q3a | OH |
| 1724 | CH | O | Q1p | a bond | H | a bond | NH | O | NH | Q3b | OH |
| 1725 | CH | O | Q1p | a bond | H | a bond | NH | O | NH | Q3c | OH |
| 1726 | CH | O | Q1p | a bond | H | a bond | NH | O | a bond | Q3a | OH |
| 1727 | CH | O | Q1p | a bond | H | a bond | NH | O | a bond | Q3b | OH |
| 1728 | CH | O | Q1p | a bond | H | a bond | NH | O | a bond | Q3c | OH |
| 1729 | CH | O | Q1q | a bond | Me | a bond | NH | S | NH | Q3a | OH |
| 1730 | CH | O | Q1q | a bond | Me | a bond | NH | S | NH | Q3b | OH |
| 1731 | CH | O | Q1q | a bond | Me | a bond | NH | S | NH | Q3c | OH |
| 1732 | CH | O | Q1q | a bond | Me | a bond | NH | S | a bond | Q3a | OH |
| 1733 | CH | O | Q1q | a bond | Me | a bond | NH | S | a bond | Q3b | OH |
| 1734 | CH | O | Q1q | a bond | Me | a bond | NH | S | a bond | Q3c | OH |
| 1735 | CH | O | Q1q | a bond | Me | a bond | NH | O | NH | Q3a | OH |
| 1736 | CH | O | Q1q | a bond | Me | a bond | NH | O | NH | Q3b | OH |
| 1737 | CH | O | Q1q | a bond | Me | a bond | NH | O | NH | Q3c | OH |
| 1738 | CH | O | Q1q | a bond | Me | a bond | NH | O | a bond | Q3a | OH |
| 1739 | CH | O | Q1q | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1740 | CH | O | Q1q | a bond | Me | a bond | NH | O | a bond | Q3c | OH |
| 1741 | CH | O | Q1q | a bond | H | a bond | NH | S | NH | Q3a | OH |
| 1742 | CH | O | Q1q | a bond | H | a bond | NH | S | NH | Q3b | OH |
| 1743 | CH | O | Q1q | a bond | H | a bond | NH | S | NH | Q3c | OH |
| 1744 | CH | O | Q1q | a bond | H | a bond | NH | S | a bond | Q3a | OH |
| 1745 | CH | O | Q1q | a bond | H | a bond | NH | S | a bond | Q3b | OH |
| 1746 | CH | O | Q1q | a bond | H | a bond | NH | S | a bond | Q3c | OH |
| 1747 | CH | O | Q1q | a bond | H | a bond | NH | O | NH | Q3a | OH |
| 1748 | CH | O | Q1q | a bond | H | a bond | NH | O | NH | Q3b | OH |
| 1749 | CH | O | Q1q | a bond | H | a bond | NH | O | NH | Q3c | OH |
| 1750 | CH | O | Q1q | a bond | H | a bond | NH | O | a bond | Q3a | OH |
| 1751 | CH | O | Q1q | a bond | H | a bond | NH | O | a bond | Q3b | OH |
| 1752 | CH | O | Q1q | a bond | H | a bond | NH | O | a bond | Q3c | OH |
| 1753 | CH | O | Q1r | a bond | Me | a bond | NH | S | NH | Q3a | OH |
| 1754 | CH | O | Q1r | a bond | Me | a bond | NH | S | NH | Q3b | OH |
| 1755 | CH | O | Q1r | a bond | Me | a bond | NH | S | NH | Q3c | OH |
| 1756 | CH | O | Q1r | a bond | Me | a bond | NH | S | a bond | Q3a | OH |
| 1757 | CH | O | Q1r | a bond | Me | a bond | NH | S | a bond | Q3b | OH |
| 1758 | CH | O | Q1r | a bond | Me | a bond | NH | S | a bond | Q3c | OH |
| 1759 | CH | O | Q1r | a bond | Me | a bond | NH | O | NH | Q3a | OH |
| 1760 | CH | O | Q1r | a bond | Me | a bond | NH | O | NH | Q3b | OH |
| 1761 | CH | O | Q1r | a bond | Me | a bond | NH | O | NH | Q3c | OH |
| 1762 | CH | O | Q1r | a bond | Me | a bond | NH | O | a bond | Q3a | OH |
| 1763 | CH | O | Q1r | a bond | Me | a bond | NH | O | a bond | Q3b | OH |
| 1764 | CH | O | Q1r | a bond | Me | a bond | NH | O | a bond | Q3c | OH |
| 1765 | CH | O | Q1r | a bond | H | a bond | NH | S | NH | Q3a | OH |
| 1766 | CH | O | Q1r | a bond | H | a bond | NH | S | NH | Q3b | OH |
| 1767 | CH | O | Q1r | a bond | H | a bond | NH | S | NH | Q3c | OH |
| 1768 | CH | O | Q1r | a bond | H | a bond | NH | S | a bond | Q3a | OH |
| 1769 | CH | O | Q1r | a bond | H | a bond | NH | S | a bond | Q3b | OH |
| 1770 | CH | O | Q1r | a bond | H | a bond | NH | S | a bond | Q3c | OH |
| 1771 | CH | O | Q1r | a bond | H | a bond | NH | O | NH | Q3a | OH |
| 1772 | CH | O | Q1r | a bond | H | a bond | NH | O | NH | Q3b | OH |
| 1773 | CH | O | Q1r | a bond | H | a bond | NH | O | NH | Q3c | OH |
| 1774 | CH | O | Q1r | a bond | H | a bond | NH | O | a bond | Q3a | OH |
| 1775 | CH | O | Q1r | a bond | H | a bond | NH | O | a bond | Q3b | OH |
| 1776 | CH | O | Q1r | a bond | H | a bond | NH | O | a bond | Q3c | OH |
| 1777 | CH | O | Q1s | a bond | Me | a bond | NH | S | NH | Q3a | OH |
| 1778 | CH | O | Q1s | a bond | Me | a bond | NH | S | NH | Q3b | OH |
| 1779 | CH | O | Q1s | a bond | Me | a bond | NH | S | NH | Q3c | OH |
| 1780 | CH | O | Q1s | a bond | Me | a bond | NH | S | a bond | Q3a | OH |
| 1781 | CH | O | Q1s | a bond | Me | a bond | NH | S | a bond | Q3b | OH |
| 1782 | CH | O | Q1s | a bond | Me | a bond | NH | S | a bond | Q3c | OH |
| 1783 | CH | O | Q1s | a bond | Me | a bond | NH | O | NH | Q3a | OH |
| 1784 | CH | O | Q1s | a bond | Me | a bond | NH | O | NH | Q3b | OH |
| 1785 | CH | O | Q1s | a bond | Me | a bond | NH | O | NH | Q3c | OH |
| 1786 | CH | O | Q1s | a bond | Me | a bond | NH | O | a bond | Q3a | OH |
| 1787 | CH | O | Q1s | a bond | Me | a bond | NH | O | a bond | Q3b | OH |
| 1788 | CH | O | Q1s | a bond | Me | a bond | NH | O | a bond | Q3c | OH |
| 1789 | CH | O | Q1s | a bond | H | a bond | NH | S | NH | Q3a | OH |
| 1790 | CH | O | Q1s | a bond | H | a bond | NH | S | NH | Q3b | OH |
| 1791 | CH | O | Q1s | a bond | H | a bond | NH | S | NH | Q3c | OH |
| 1792 | CH | O | Q1s | a bond | H | a bond | NH | S | a bond | Q3a | OH |
| 1793 | CH | O | Q1s | a bond | H | a bond | NH | S | a bond | Q3b | OH |
| 1794 | CH | O | Q1s | a bond | H | a bond | NH | S | a bond | Q3c | OH |
| 1795 | CH | O | Q1s | a bond | H | a bond | NH | O | NH | Q3a | OH |
| 1796 | CH | O | Q1s | a bond | H | a bond | NH | O | NH | Q3b | OH |
| 1797 | CH | O | Q1s | a bond | H | a bond | NH | O | NH | Q3c | OH |
| 1798 | CH | O | Q1s | a bond | H | a bond | NH | O | a bond | Q3a | OH |
| 1799 | CH | O | Q1s | a bond | H | a bond | NH | O | a bond | Q3b | OH |
| 1800 | CH | O | Q1s | a bond | H | a bond | NH | O | a bond | Q3c | OH |
| 1801 | CH | O | Q1t | a bond | Me | a bond | NH | S | NH | Q3a | OH |
| 1802 | CH | O | Q1t | a bond | Me | a bond | NH | S | NH | Q3b | OH |
| 1803 | CH | O | Q1t | a bond | Me | a bond | NH | S | NH | Q3c | OH |
| 1804 | CH | O | Q1t | a bond | Me | a bond | NH | S | a bond | Q3a | OH |
| 1805 | CH | O | Q1t | a bond | Me | a bond | NH | S | a bond | Q3b | OH |
| 1806 | CH | O | Q1t | a bond | Me | a bond | NH | S | a bond | Q3c | OH |
| 1807 | CH | O | Q1t | a bond | Me | a bond | NH | O | NH | Q3a | OH |
| 1808 | CH | O | Q1t | a bond | Me | a bond | NH | O | NH | Q3b | OH |
| 1809 | CH | O | Q1t | a bond | Me | a bond | NH | O | NH | Q3c | OH |
| 1810 | CH | O | Q1t | a bond | Me | a bond | NH | O | a bond | Q3a | OH |
| 1811 | CH | O | Q1t | a bond | Me | a bond | NH | O | a bond | Q3b | OH |
| 1812 | CH | O | Q1t | a bond | Me | a bond | NH | O | a bond | Q3c | OH |
| 1813 | CH | O | Q1t | a bond | H | a bond | NH | S | NH | Q3a | OH |
| 1814 | CH | O | Q1t | a bond | H | a bond | NH | S | NH | Q3b | OH |
| 1815 | CH | O | Q1t | a bond | H | a bond | NH | S | NH | Q3c | OH |
| 1816 | CH | O | Q1t | a bond | H | a bond | NH | S | a bond | Q3a | OH |
| 1817 | CH | O | Q1t | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1818 | CH | O | Q1t | a bond | H | a bond | NH | S | a bond | Q3c | OH |
| 1819 | CH | O | Q1t | a bond | H | a bond | NH | O | NH | Q3a | OH |
| 1820 | CH | O | Q1t | a bond | H | a bond | NH | O | NH | Q3b | OH |
| 1821 | CH | O | Q1t | a bond | H | a bond | NH | O | NH | Q3c | OH |
| 1822 | CH | O | Q1t | a bond | H | a bond | NH | O | a bond | Q3a | OH |
| 1823 | CH | O | Q1t | a bond | H | a bond | NH | O | a bond | Q3b | OH |
| 1824 | CH | O | Q1t | a bond | H | a bond | NH | O | a bond | Q3c | OH |
| 1825 | CH | O | Q1u | a bond | Me | a bond | NH | S | NH | Q3a | OH |
| 1826 | CH | O | Q1u | a bond | Me | a bond | NH | S | NH | Q3b | OH |
| 1827 | CH | O | Q1u | a bond | Me | a bond | NH | S | NH | Q3c | OH |
| 1828 | CH | O | Q1u | a bond | Me | a bond | NH | S | a bond | Q3a | OH |
| 1829 | CH | O | Q1u | a bond | Me | a bond | NH | S | a bond | Q3b | OH |
| 1830 | CH | O | Q1u | a bond | Me | a bond | NH | S | a bond | Q3c | OH |
| 1831 | CH | O | Q1u | a bond | Me | a bond | NH | O | NH | Q3a | OH |
| 1832 | CH | O | Q1u | a bond | Me | a bond | NH | O | NH | Q3b | OH |
| 1833 | CH | O | Q1u | a bond | Me | a bond | NH | O | NH | Q3c | OH |
| 1834 | CH | O | Q1u | a bond | Me | a bond | NH | O | a bond | Q3a | OH |
| 1835 | CH | O | Q1u | a bond | Me | a bond | NH | O | a bond | Q3b | OH |
| 1836 | CH | O | Q1u | a bond | Me | a bond | NH | O | a bond | Q3c | OH |
| 1837 | CH | O | Q1u | a bond | H | a bond | NH | S | NH | Q3a | OH |
| 1838 | CH | O | Q1u | a bond | H | a bond | NH | S | NH | Q3b | OH |
| 1839 | CH | O | Q1u | a bond | H | a bond | NH | S | NH | Q3c | OH |
| 1840 | CH | O | Q1u | a bond | H | a bond | NH | S | a bond | Q3a | OH |
| 1841 | CH | O | Q1u | a bond | H | a bond | NH | S | a bond | Q3b | OH |
| 1842 | CH | O | Q1u | a bond | H | a bond | NH | S | a bond | Q3c | OH |
| 1843 | CH | O | Q1u | a bond | H | a bond | NH | O | NH | Q3a | OH |
| 1844 | CH | O | Q1u | a bond | H | a bond | NH | O | NH | Q3b | OH |
| 1845 | CH | O | Q1u | a bond | H | a bond | NH | O | NH | Q3c | OH |
| 1846 | CH | O | Q1u | a bond | H | a bond | NH | O | a bond | Q3a | OH |
| 1847 | CH | O | Q1u | a bond | H | a bond | NH | O | a bond | Q3b | OH |
| 1848 | CH | O | Q1u | a bond | H | a bond | NH | O | a bond | Q3c | OH |
| 1849 | CH | O | Q1v | a bond | Me | a bond | NH | S | NH | Q3a | OH |
| 1850 | CH | O | Q1v | a bond | Me | a bond | NH | S | NH | Q3b | OH |
| 1851 | CH | O | Q1v | a bond | Me | a bond | NH | S | NH | Q3c | OH |
| 1852 | CH | O | Q1v | a bond | Me | a bond | NH | S | a bond | Q3a | OH |
| 1853 | CH | O | Q1v | a bond | Me | a bond | NH | S | a bond | Q3b | OH |
| 1854 | CH | O | Q1v | a bond | Me | a bond | NH | S | a bond | Q3c | OH |
| 1855 | CH | O | Q1v | a bond | Me | a bond | NH | O | NH | Q3a | OH |
| 1856 | CH | O | Q1v | a bond | Me | a bond | NH | O | NH | Q3b | OH |
| 1857 | CH | O | Q1v | a bond | Me | a bond | NH | O | NH | Q3c | OH |
| 1858 | CH | O | Q1v | a bond | Me | a bond | NH | O | a bond | Q3a | OH |
| 1859 | CH | O | Q1v | a bond | Me | a bond | NH | O | a bond | Q3b | OH |
| 1860 | CH | O | Q1v | a bond | Me | a bond | NH | O | a bond | Q3c | OH |
| 1861 | CH | O | Q1v | a bond | H | a bond | NH | S | NH | Q3a | OH |
| 1862 | CH | O | Q1v | a bond | H | a bond | NH | S | NH | Q3b | OH |
| 1863 | CH | O | Q1v | a bond | H | a bond | NH | S | NH | Q3c | OH |
| 1864 | CH | O | Q1v | a bond | H | a bond | NH | S | a bond | Q3a | OH |
| 1865 | CH | O | Q1v | a bond | H | a bond | NH | S | a bond | Q3b | OH |
| 1866 | CH | O | Q1v | a bond | H | a bond | NH | S | a bond | Q3c | OH |
| 1867 | CH | O | Q1v | a bond | H | a bond | NH | O | NH | Q3a | OH |
| 1868 | CH | O | Q1v | a bond | H | a bond | NH | O | NH | Q3b | OH |
| 1869 | CH | O | Q1v | a bond | H | a bond | NH | O | NH | Q3c | OH |
| 1870 | CH | O | Q1v | a bond | H | a bond | NH | O | a bond | Q3a | OH |
| 1871 | CH | O | Q1v | a bond | H | a bond | NH | O | a bond | Q3b | OH |
| 1872 | CH | O | Q1v | a bond | H | a bond | NH | O | a bond | Q3c | OH |
| 1873 | CH | O | Q1w | a bond | Me | a bond | NH | S | NH | Q3a | OH |
| 1874 | CH | O | Q1w | a bond | Me | a bond | NH | S | NH | Q3b | OH |
| 1875 | CH | O | Q1w | a bond | Me | a bond | NH | S | NH | Q3c | OH |
| 1876 | CH | O | Q1w | a bond | Me | a bond | NH | S | a bond | Q3a | OH |
| 1877 | CH | O | Q1w | a bond | Me | a bond | NH | S | a bond | Q3b | OH |
| 1878 | CH | O | Q1w | a bond | Me | a bond | NH | S | a bond | Q3c | OH |
| 1879 | CH | O | Q1w | a bond | Me | a bond | NH | O | NH | Q3a | OH |
| 1880 | CH | O | Q1w | a bond | Me | a bond | NH | O | NH | Q3b | OH |
| 1881 | CH | O | Q1w | a bond | Me | a bond | NH | O | NH | Q3c | OH |
| 1882 | CH | O | Q1w | a bond | Me | a bond | NH | O | a bond | Q3a | OH |
| 1883 | CH | O | Q1w | a bond | Me | a bond | NH | O | a bond | Q3b | OH |
| 1884 | CH | O | Q1w | a bond | Me | a bond | NH | O | a bond | Q3c | OH |
| 1885 | CH | O | Q1w | a bond | H | a bond | NH | S | NH | Q3a | OH |
| 1886 | CH | O | Q1w | a bond | H | a bond | NH | S | NH | Q3b | OH |
| 1887 | CH | O | Q1w | a bond | H | a bond | NH | S | NH | Q3c | OH |
| 1888 | CH | O | Q1w | a bond | H | a bond | NH | S | a bond | Q3a | OH |
| 1889 | CH | O | Q1w | a bond | H | a bond | NH | S | a bond | Q3b | OH |
| 1890 | CH | O | Q1w | a bond | H | a bond | NH | S | a bond | Q3c | OH |
| 1891 | CH | O | Q1w | a bond | H | a bond | NH | O | NH | Q3a | OH |
| 1892 | CH | O | Q1w | a bond | H | a bond | NH | O | NH | Q3b | OH |
| 1893 | CH | O | Q1w | a bond | H | a bond | NH | O | NH | Q3c | OH |
| 1894 | CH | O | Q1w | a bond | H | a bond | NH | O | a bond | Q3a | OH |
| 1895 | CH | O | Q1w | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1896 | CH | O | Q1w | a bond | H | a bond | NH | O | a bond | Q3c | OH |
| 1897 | CH | O | Q1x | a bond | Me | a bond | NH | S | NH | Q3a | OH |
| 1898 | CH | O | Q1x | a bond | Me | a bond | NH | S | NH | Q3b | OH |
| 1899 | CH | O | Q1x | a bond | Me | a bond | NH | S | NH | Q3c | OH |
| 1900 | CH | O | Q1x | a bond | Me | a bond | NH | S | a bond | Q3a | OH |
| 1901 | CH | O | Q1x | a bond | Me | a bond | NH | S | a bond | Q3b | OH |
| 1902 | CH | O | Q1x | a bond | Me | a bond | NH | S | a bond | Q3c | OH |
| 1903 | CH | O | Q1x | a bond | Me | a bond | NH | O | NH | Q3a | OH |
| 1904 | CH | O | Q1x | a bond | Me | a bond | NH | O | NH | Q3b | OH |
| 1905 | CH | O | Q1x | a bond | Me | a bond | NH | O | NH | Q3c | OH |
| 1906 | CH | O | Q1x | a bond | Me | a bond | NH | O | a bond | Q3a | OH |
| 1907 | CH | O | Q1x | a bond | Me | a bond | NH | O | a bond | Q3b | OH |
| 1908 | CH | O | Q1x | a bond | Me | a bond | NH | O | a bond | Q3c | OH |
| 1909 | CH | O | Q1x | a bond | H | a bond | NH | S | NH | Q3a | OH |
| 1910 | CH | O | Q1x | a bond | H | a bond | NH | S | NH | Q3b | OH |
| 1911 | CH | O | Q1x | a bond | H | a bond | NH | S | NH | Q3c | OH |
| 1912 | CH | O | Q1x | a bond | H | a bond | NH | S | a bond | Q3a | OH |
| 1913 | CH | O | Q1x | a bond | H | a bond | NH | S | a bond | Q3b | OH |
| 1914 | CH | O | Q1x | a bond | H | a bond | NH | S | a bond | Q3c | OH |
| 1915 | CH | O | Q1x | a bond | H | a bond | NH | O | NH | Q3a | OH |
| 1916 | CH | O | Q1x | a bond | H | a bond | NH | O | NH | Q3b | OH |
| 1917 | CH | O | Q1x | a bond | H | a bond | NH | O | NH | Q3c | OH |
| 1918 | CH | O | Q1x | a bond | H | a bond | NH | O | a bond | Q3a | OH |
| 1919 | CH | O | Q1x | a bond | H | a bond | NH | O | a bond | Q3b | OH |
| 1920 | CH | O | Q1x | a bond | H | a bond | NH | O | a bond | Q3c | OH |
| 1921 | CMe | NMe | Q1o | a bond | Me | a bond | NH | S | NH | Q3a | OH |
| 1922 | CMe | NMe | Q1o | a bond | Me | a bond | NH | S | NH | Q3b | OH |
| 1923 | CMe | NMe | Q1o | a bond | Me | a bond | NH | S | NH | Q3c | OH |
| 1924 | CMe | NMe | Q1o | a bond | Me | a bond | NH | S | a bond | Q3a | OH |
| 1925 | CMe | NMe | Q1o | a bond | Me | a bond | NH | S | a bond | Q3b | OH |
| 1926 | CMe | NMe | Q1o | a bond | Me | a bond | NH | S | a bond | Q3c | OH |
| 1927 | CMe | NMe | Q1o | a bond | Me | a bond | NH | O | NH | Q3a | OH |
| 1928 | CMe | NMe | Q1o | a bond | Me | a bond | NH | O | NH | Q3b | OH |
| 1929 | CMe | NMe | Q1o | a bond | Me | a bond | NH | O | NH | Q3c | OH |
| 1930 | CMe | NMe | Q1o | a bond | Me | a bond | NH | O | a bond | Q3a | OH |
| 1931 | CMe | NMe | Q1o | a bond | Me | a bond | NH | O | a bond | Q3b | OH |
| 1932 | CMe | NMe | Q1o | a bond | Me | a bond | NH | O | a bond | Q3c | OH |
| 1933 | CMe | NMe | Q1o | a bond | H | a bond | NH | S | NH | Q3a | OH |
| 1934 | CMe | NMe | Q1o | a bond | H | a bond | NH | S | NH | Q3b | OH |
| 1935 | CMe | NMe | Q1o | a bond | H | a bond | NH | S | NH | Q3c | OH |
| 1936 | CMe | NMe | Q1o | a bond | H | a bond | NH | S | a bond | Q3a | OH |
| 1937 | CMe | NMe | Q1o | a bond | H | a bond | NH | S | a bond | Q3b | OH |
| 1938 | CMe | NMe | Q1o | a bond | H | a bond | NH | S | a bond | Q3c | OH |
| 1939 | CMe | NMe | Q1o | a bond | H | a bond | NH | O | NH | Q3a | OH |
| 1940 | CMe | NMe | Q1o | a bond | H | a bond | NH | O | NH | Q3b | OH |
| 1941 | CMe | NMe | Q1o | a bond | H | a bond | NH | O | NH | Q3c | OH |
| 1942 | CMe | NMe | Q1o | a bond | H | a bond | NH | O | a bond | Q3a | OH |
| 1943 | CMe | NMe | Q1o | a bond | H | a bond | NH | O | a bond | Q3b | OH |
| 1944 | CMe | NMe | Q1o | a bond | H | a bond | NH | O | a bond | Q3c | OH |
| 1945 | CMe | NMe | Q1p | a bond | Me | a bond | NH | S | NH | Q3a | OH |
| 1946 | CMe | NMe | Q1p | a bond | Me | a bond | NH | S | NH | Q3b | OH |
| 1947 | CMe | NMe | Q1p | a bond | Me | a bond | NH | S | NH | Q3c | OH |
| 1948 | CMe | NMe | Q1p | a bond | Me | a bond | NH | S | a bond | Q3a | OH |
| 1949 | CMe | NMe | Q1p | a bond | Me | a bond | NH | S | a bond | Q3b | OH |
| 1950 | CMe | NMe | Q1p | a bond | Me | a bond | NH | S | a bond | Q3c | OH |
| 1951 | CMe | NMe | Q1p | a bond | Me | a bond | NH | O | NH | Q3a | OH |
| 1952 | CMe | NMe | Q1p | a bond | Me | a bond | NH | O | NH | Q3b | OH |
| 1953 | CMe | NMe | Q1p | a bond | Me | a bond | NH | O | NH | Q3c | OH |
| 1954 | CMe | NMe | Q1p | a bond | Me | a bond | NH | O | a bond | Q3a | OH |
| 1955 | CMe | NMe | Q1p | a bond | Me | a bond | NH | O | a bond | Q3b | OH |
| 1956 | CMe | NMe | Q1p | a bond | Me | a bond | NH | O | a bond | Q3c | OH |
| 1957 | CMe | NMe | Q1p | a bond | H | a bond | NH | S | NH | Q3a | OH |
| 1958 | CMe | NMe | Q1p | a bond | H | a bond | NH | S | NH | Q3b | OH |
| 1959 | CMe | NMe | Q1p | a bond | H | a bond | NH | S | NH | Q3c | OH |
| 1960 | CMe | NMe | Q1p | a bond | H | a bond | NH | S | a bond | Q3a | OH |
| 1961 | CMe | NMe | Q1p | a bond | H | a bond | NH | S | a bond | Q3b | OH |
| 1962 | CMe | NMe | Q1p | a bond | H | a bond | NH | S | a bond | Q3c | OH |
| 1963 | CMe | NMe | Q1p | a bond | H | a bond | NH | O | NH | Q3a | OH |
| 1964 | CMe | NMe | Q1p | a bond | H | a bond | NH | O | NH | Q3b | OH |
| 1965 | CMe | NMe | Q1p | a bond | H | a bond | NH | O | NH | Q3c | OH |
| 1966 | CMe | NMe | Q1p | a bond | H | a bond | NH | O | a bond | Q3a | OH |
| 1967 | CMe | NMe | Q1p | a bond | H | a bond | NH | O | a bond | Q3b | OH |
| 1968 | CMe | NMe | Q1p | a bond | H | a bond | NH | O | a bond | Q3c | OH |
| 1969 | CMe | NMe | Q1q | a bond | Me | a bond | NH | S | NH | Q3a | OH |
| 1970 | CMe | NMe | Q1q | a bond | Me | a bond | NH | S | NH | Q3b | OH |
| 1971 | CMe | NMe | Q1q | a bond | Me | a bond | NH | S | NH | Q3c | OH |
| 1972 | CMe | NMe | Q1q | a bond | Me | a bond | NH | S | a bond | Q3a | OH |
| 1973 | CMe | NMe | Q1q | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 1974 | CMe | NMe | Q1q | a bond | Me | a bond | NH | S | a bond | Q3c | OH |
| 1975 | CMe | NMe | Q1q | a bond | Me | a bond | NH | O | NH | Q3a | OH |
| 1976 | CMe | NMe | Q1q | a bond | Me | a bond | NH | O | NH | Q3b | OH |
| 1977 | CMe | NMe | Q1q | a bond | Me | a bond | NH | O | NH | Q3c | OH |
| 1978 | CMe | NMe | Q1q | a bond | Me | a bond | NH | O | a bond | Q3a | OH |
| 1979 | CMe | NMe | Q1q | a bond | Me | a bond | NH | O | a bond | Q3b | OH |
| 1980 | CMe | NMe | Q1q | a bond | Me | a bond | NH | O | a bond | Q3c | OH |
| 1981 | CMe | NMe | Q1q | a bond | H | a bond | NH | S | NH | Q3a | OH |
| 1982 | CMe | NMe | Q1q | a bond | H | a bond | NH | S | NH | Q3b | OH |
| 1983 | CMe | NMe | Q1q | a bond | H | a bond | NH | S | NH | Q3c | OH |
| 1984 | CMe | NMe | Q1q | a bond | H | a bond | NH | S | a bond | Q3a | OH |
| 1985 | CMe | NMe | Q1q | a bond | H | a bond | NH | S | a bond | Q3b | OH |
| 1986 | CMe | NMe | Q1q | a bond | H | a bond | NH | S | a bond | Q3c | OH |
| 1987 | CMe | NMe | Q1q | a bond | H | a bond | NH | O | NH | Q3a | OH |
| 1988 | CMe | NMe | Q1q | a bond | H | a bond | NH | O | NH | Q3b | OH |
| 1989 | CMe | NMe | Q1q | a bond | H | a bond | NH | O | NH | Q3c | OH |
| 1990 | CMe | NMe | Q1q | a bond | H | a bond | NH | O | a bond | Q3a | OH |
| 1991 | CMe | NMe | Q1q | a bond | H | a bond | NH | O | a bond | Q3b | OH |
| 1992 | CMe | NMe | Q1q | a bond | H | a bond | NH | O | a bond | Q3c | OH |
| 1993 | CMe | NMe | Q1r | a bond | Me | a bond | NH | S | NH | Q3a | OH |
| 1994 | CMe | NMe | Q1r | a bond | Me | a bond | NH | S | NH | Q3b | OH |
| 1995 | CMe | NMe | Q1r | a bond | Me | a bond | NH | S | NH | Q3c | OH |
| 1996 | CMe | NMe | Q1r | a bond | Me | a bond | NH | S | a bond | Q3a | OH |
| 1997 | CMe | NMe | Q1r | a bond | Me | a bond | NH | S | a bond | Q3b | OH |
| 1998 | CMe | NMe | Q1r | a bond | Me | a bond | NH | S | a bond | Q3c | OH |
| 1999 | CMe | NMe | Q1r | a bond | Me | a bond | NH | O | NH | Q3a | OH |
| 2000 | CMe | NMe | Q1r | a bond | Me | a bond | NH | O | NH | Q3b | OH |
| 2001 | CMe | NMe | Q1r | a bond | Me | a bond | NH | O | NH | Q3c | OH |
| 2002 | CMe | NMe | Q1r | a bond | Me | a bond | NH | O | a bond | Q3a | OH |
| 2003 | CMe | NMe | Q1r | a bond | Me | a bond | NH | O | a bond | Q3b | OH |
| 2004 | CMe | NMe | Q1r | a bond | Me | a bond | NH | O | a bond | Q3c | OH |
| 2005 | CMe | NMe | Q1r | a bond | H | a bond | NH | S | NH | Q3a | OH |
| 2006 | CMe | NMe | Q1r | a bond | H | a bond | NH | S | NH | Q3b | OH |
| 2007 | CMe | NMe | Q1r | a bond | H | a bond | NH | S | NH | Q3c | OH |
| 2008 | CMe | NMe | Q1r | a bond | H | a bond | NH | S | a bond | Q3a | OH |
| 2009 | CMe | NMe | Q1r | a bond | H | a bond | NH | S | a bond | Q3b | OH |
| 2010 | CMe | NMe | Q1r | a bond | H | a bond | NH | S | a bond | Q3c | OH |
| 2011 | CMe | NMe | Q1r | a bond | H | a bond | NH | O | NH | Q3a | OH |
| 2012 | CMe | NMe | Q1r | a bond | H | a bond | NH | O | NH | Q3b | OH |
| 2013 | CMe | NMe | Q1r | a bond | H | a bond | NH | O | NH | Q3c | OH |
| 2014 | CMe | NMe | Q1r | a bond | H | a bond | NH | O | a bond | Q3a | OH |
| 2015 | CMe | NMe | Q1r | a bond | H | a bond | NH | O | a bond | Q3b | OH |
| 2016 | CMe | NMe | Q1r | a bond | H | a bond | NH | O | a bond | Q3c | OH |
| 2017 | CMe | NMe | Q1s | a bond | Me | a bond | NH | S | NH | Q3a | OH |
| 2018 | CMe | NMe | Q1s | a bond | Me | a bond | NH | S | NH | Q3b | OH |
| 2019 | CMe | NMe | Q1s | a bond | Me | a bond | NH | S | NH | Q3c | OH |
| 2020 | CMe | NMe | Q1s | a bond | Me | a bond | NH | S | a bond | Q3a | OH |
| 2021 | CMe | NMe | Q1s | a bond | Me | a bond | NH | S | a bond | Q3b | OH |
| 2022 | CMe | NMe | Q1s | a bond | Me | a bond | NH | S | a bond | Q3c | OH |
| 2023 | CMe | NMe | Q1s | a bond | Me | a bond | NH | O | NH | Q3a | OH |
| 2024 | CMe | NMe | Q1s | a bond | Me | a bond | NH | O | NH | Q3b | OH |
| 2025 | CMe | NMe | Q1s | a bond | Me | a bond | NH | O | NH | Q3c | OH |
| 2026 | CMe | NMe | Q1s | a bond | Me | a bond | NH | O | a bond | Q3a | OH |
| 2027 | CMe | NMe | Q1s | a bond | Me | a bond | NH | O | a bond | Q3b | OH |
| 2028 | CMe | NMe | Q1s | a bond | Me | a bond | NH | O | a bond | Q3c | OH |
| 2029 | CMe | NMe | Q1s | a bond | H | a bond | NH | S | NH | Q3a | OH |
| 2030 | CMe | NMe | Q1s | a bond | H | a bond | NH | S | NH | Q3b | OH |
| 2031 | CMe | NMe | Q1s | a bond | H | a bond | NH | S | NH | Q3c | OH |
| 2032 | CMe | NMe | Q1s | a bond | H | a bond | NH | S | a bond | Q3a | OH |
| 2033 | CMe | NMe | Q1s | a bond | H | a bond | NH | S | a bond | Q3b | OH |
| 2034 | CMe | NMe | Q1s | a bond | H | a bond | NH | S | a bond | Q3c | OH |
| 2035 | CMe | NMe | Q1s | a bond | H | a bond | NH | O | NH | Q3a | OH |
| 2036 | CMe | NMe | Q1s | a bond | H | a bond | NH | O | NH | Q3b | OH |
| 2037 | CMe | NMe | Q1s | a bond | H | a bond | NH | O | NH | Q3c | OH |
| 2038 | CMe | NMe | Q1s | a bond | H | a bond | NH | O | a bond | Q3a | OH |
| 2039 | CMe | NMe | Q1s | a bond | H | a bond | NH | O | a bond | Q3b | OH |
| 2040 | CMe | NMe | Q1s | a bond | H | a bond | NH | O | a bond | Q3c | OH |
| 2041 | CMe | NMe | Q1t | a bond | Me | a bond | NH | S | NH | Q3a | OH |
| 2042 | CMe | NMe | Q1t | a bond | Me | a bond | NH | S | NH | Q3b | OH |
| 2043 | CMe | NMe | Q1t | a bond | Me | a bond | NH | S | NH | Q3c | OH |
| 2044 | CMe | NMe | Q1t | a bond | Me | a bond | NH | S | a bond | Q3a | OH |
| 2045 | CMe | NMe | Q1t | a bond | Me | a bond | NH | S | a bond | Q3b | OH |
| 2046 | CMe | NMe | Q1t | a bond | Me | a bond | NH | S | a bond | Q3c | OH |
| 2047 | CMe | NMe | Q1t | a bond | Me | a bond | NH | O | NH | Q3a | OH |
| 2048 | CMe | NMe | Q1t | a bond | Me | a bond | NH | O | NH | Q3b | OH |
| 2049 | CMe | NMe | Q1t | a bond | Me | a bond | NH | O | NH | Q3c | OH |
| 2050 | CMe | NMe | Q1t | a bond | Me | a bond | NH | O | a bond | Q3a | OH |
| 2051 | CMe | NMe | Q1t | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2052 | CMe | NMe | Q1t | a bond | Me | a bond | NH | O | a bond | Q3c | OH |
| 2053 | CMe | NMe | Q1t | a bond | H | a bond | NH | S | NH | Q3a | OH |
| 2054 | CMe | NMe | Q1t | a bond | H | a bond | NH | S | NH | Q3b | OH |
| 2055 | CMe | NMe | Q1t | a bond | H | a bond | NH | S | NH | Q3c | OH |
| 2056 | CMe | NMe | Q1t | a bond | H | a bond | NH | S | a bond | Q3a | OH |
| 2057 | CMe | NMe | Q1t | a bond | H | a bond | NH | S | a bond | Q3b | OH |
| 2058 | CMe | NMe | Q1t | a bond | H | a bond | NH | S | a bond | Q3c | OH |
| 2059 | CMe | NMe | Q1t | a bond | H | a bond | NH | O | NH | Q3a | OH |
| 2060 | CMe | NMe | Q1t | a bond | H | a bond | NH | O | NH | Q3b | OH |
| 2061 | CMe | NMe | Q1t | a bond | H | a bond | NH | O | NH | Q3c | OH |
| 2062 | CMe | NMe | Q1t | a bond | H | a bond | NH | O | a bond | Q3a | OH |
| 2063 | CMe | NMe | Q1t | a bond | H | a bond | NH | O | a bond | Q3b | OH |
| 2064 | CMe | NMe | Q1t | a bond | H | a bond | NH | O | a bond | Q3c | OH |
| 2065 | CMe | NMe | Q1u | a bond | Me | a bond | NH | S | NH | Q3a | OH |
| 2066 | CMe | NMe | Q1u | a bond | Me | a bond | NH | S | NH | Q3b | OH |
| 2067 | CMe | NMe | Q1u | a bond | Me | a bond | NH | S | NH | Q3c | OH |
| 2068 | CMe | NMe | Q1u | a bond | Me | a bond | NH | S | a bond | Q3a | OH |
| 2069 | CMe | NMe | Q1u | a bond | Me | a bond | NH | S | a bond | Q3b | OH |
| 2070 | CMe | NMe | Q1u | a bond | Me | a bond | NH | S | a bond | Q3c | OH |
| 2071 | CMe | NMe | Q1u | a bond | Me | a bond | NH | O | NH | Q3a | OH |
| 2072 | CMe | NMe | Q1u | a bond | Me | a bond | NH | O | NH | Q3b | OH |
| 2073 | CMe | NMe | Q1u | a bond | Me | a bond | NH | O | NH | Q3c | OH |
| 2074 | CMe | NMe | Q1u | a bond | Me | a bond | NH | O | a bond | Q3a | OH |
| 2075 | CMe | NMe | Q1u | a bond | Me | a bond | NH | O | a bond | Q3b | OH |
| 2076 | CMe | NMe | Q1u | a bond | Me | a bond | NH | O | a bond | Q3c | OH |
| 2077 | CMe | NMe | Q1u | a bond | H | a bond | NH | S | NH | Q3a | OH |
| 2078 | CMe | NMe | Q1u | a bond | H | a bond | NH | S | NH | Q3b | OH |
| 2079 | CMe | NMe | Q1u | a bond | H | a bond | NH | S | NH | Q3c | OH |
| 2080 | CMe | NMe | Q1u | a bond | H | a bond | NH | S | a bond | Q3a | OH |
| 2081 | CMe | NMe | Q1u | a bond | H | a bond | NH | S | a bond | Q3b | OH |
| 2082 | CMe | NMe | Q1u | a bond | H | a bond | NH | S | a bond | Q3c | OH |
| 2083 | CMe | NMe | Q1u | a bond | H | a bond | NH | O | NH | Q3a | OH |
| 2084 | CMe | NMe | Q1u | a bond | H | a bond | NH | O | NH | Q3b | OH |
| 2085 | CMe | NMe | Q1u | a bond | H | a bond | NH | O | NH | Q3c | OH |
| 2086 | CMe | NMe | Q1u | a bond | H | a bond | NH | O | a bond | Q3a | OH |
| 2087 | CMe | NMe | Q1u | a bond | H | a bond | NH | O | a bond | Q3b | OH |
| 2088 | CMe | NMe | Q1u | a bond | H | a bond | NH | O | a bond | Q3c | OH |
| 2089 | CMe | NMe | Q1v | a bond | Me | a bond | NH | S | NH | Q3a | OH |
| 2090 | CMe | NMe | Q1v | a bond | Me | a bond | NH | S | NH | Q3b | OH |
| 2091 | CMe | NMe | Q1v | a bond | Me | a bond | NH | S | NH | Q3c | OH |
| 2092 | CMe | NMe | Q1v | a bond | Me | a bond | NH | S | a bond | Q3a | OH |
| 2093 | CMe | NMe | Q1v | a bond | Me | a bond | NH | S | a bond | Q3b | OH |
| 2094 | CMe | NMe | Q1v | a bond | Me | a bond | NH | S | a bond | Q3c | OH |
| 2095 | CMe | NMe | Q1v | a bond | Me | a bond | NH | O | NH | Q3a | OH |
| 2096 | CMe | NMe | Q1v | a bond | Me | a bond | NH | O | NH | Q3b | OH |
| 2097 | CMe | NMe | Q1v | a bond | Me | a bond | NH | O | NH | Q3c | OH |
| 2098 | CMe | NMe | Q1v | a bond | Me | a bond | NH | O | a bond | Q3a | OH |
| 2099 | CMe | NMe | Q1v | a bond | Me | a bond | NH | O | a bond | Q3b | OH |
| 2100 | CMe | NMe | Q1v | a bond | Me | a bond | NH | O | a bond | Q3c | OH |
| 2101 | CMe | NMe | Q1v | a bond | H | a bond | NH | S | NH | Q3a | OH |
| 2102 | CMe | NMe | Q1v | a bond | H | a bond | NH | S | NH | Q3b | OH |
| 2103 | CMe | NMe | Q1v | a bond | H | a bond | NH | S | NH | Q3c | OH |
| 2104 | CMe | NMe | Q1v | a bond | H | a bond | NH | S | a bond | Q3a | OH |
| 2105 | CMe | NMe | Q1v | a bond | H | a bond | NH | S | a bond | Q3b | OH |
| 2106 | CMe | NMe | Q1v | a bond | H | a bond | NH | S | a bond | Q3c | OH |
| 2107 | CMe | NMe | Q1v | a bond | H | a bond | NH | O | NH | Q3a | OH |
| 2108 | CMe | NMe | Q1v | a bond | H | a bond | NH | O | NH | Q3b | OH |
| 2109 | CMe | NMe | Q1v | a bond | H | a bond | NH | O | NH | Q3c | OH |
| 2110 | CMe | NMe | Q1v | a bond | H | a bond | NH | O | a bond | Q3a | OH |
| 2111 | CMe | NMe | Q1v | a bond | H | a bond | NH | O | a bond | Q3b | OH |
| 2112 | CMe | NMe | Q1v | a bond | H | a bond | NH | O | a bond | Q3c | OH |
| 2113 | CMe | NMe | Q1w | a bond | Me | a bond | NH | S | NH | Q3a | OH |
| 2114 | CMe | NMe | Q1w | a bond | Me | a bond | NH | S | NH | Q3b | OH |
| 2115 | CMe | NMe | Q1w | a bond | Me | a bond | NH | S | NH | Q3c | OH |
| 2116 | CMe | NMe | Q1w | a bond | Me | a bond | NH | S | a bond | Q3a | OH |
| 2117 | CMe | NMe | Q1w | a bond | Me | a bond | NH | S | a bond | Q3b | OH |
| 2118 | CMe | NMe | Q1w | a bond | Me | a bond | NH | S | a bond | Q3c | OH |
| 2119 | CMe | NMe | Q1w | a bond | Me | a bond | NH | O | NH | Q3a | OH |
| 2120 | CMe | NMe | Q1w | a bond | Me | a bond | NH | O | NH | Q3b | OH |
| 2121 | CMe | NMe | Q1w | a bond | Me | a bond | NH | O | NH | Q3c | OH |
| 2122 | CMe | NMe | Q1w | a bond | Me | a bond | NH | O | a bond | Q3a | OH |
| 2123 | CMe | NMe | Q1w | a bond | Me | a bond | NH | O | a bond | Q3b | OH |
| 2124 | CMe | NMe | Q1w | a bond | Me | a bond | NH | O | a bond | Q3c | OH |
| 2125 | CMe | NMe | Q1w | a bond | H | a bond | NH | S | NH | Q3a | OH |
| 2126 | CMe | NMe | Q1w | a bond | H | a bond | NH | S | NH | Q3b | OH |
| 2127 | CMe | NMe | Q1w | a bond | H | a bond | NH | S | NH | Q3c | OH |
| 2128 | CMe | NMe | Q1w | a bond | H | a bond | NH | S | a bond | Q3a | OH |
| 2129 | CMe | NMe | Q1w | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2130 | CMe | NMe | Q1w | a bond | H | a bond | NH | S | a bond | Q3c | OH |
| 2131 | CMe | NMe | Q1w | a bond | H | a bond | NH | O | NH | Q3a | OH |
| 2132 | CMe | NMe | Q1w | a bond | H | a bond | NH | O | NH | Q3b | OH |
| 2133 | CMe | NMe | Q1w | a bond | H | a bond | NH | O | NH | Q3c | OH |
| 2134 | CMe | NMe | Q1w | a bond | H | a bond | NH | O | a bond | Q3a | OH |
| 2135 | CMe | NMe | Q1w | a bond | H | a bond | NH | O | a bond | Q3b | OH |
| 2136 | CMe | NMe | Q1w | a bond | H | a bond | NH | O | a bond | Q3c | OH |
| 2137 | CMe | NMe | Q1x | a bond | Me | a bond | NH | S | NH | Q3a | OH |
| 2138 | CMe | NMe | Q1x | a bond | Me | a bond | NH | S | NH | Q3b | OH |
| 2139 | CMe | NMe | Q1x | a bond | Me | a bond | NH | S | NH | Q3c | OH |
| 2140 | CMe | NMe | Q1x | a bond | Me | a bond | NH | S | a bond | Q3a | OH |
| 2141 | CMe | NMe | Q1x | a bond | Me | a bond | NH | S | a bond | Q3b | OH |
| 2142 | CMe | NMe | Q1x | a bond | Me | a bond | NH | S | a bond | Q3c | OH |
| 2143 | CMe | NMe | Q1x | a bond | Me | a bond | NH | O | NH | Q3a | OH |
| 2144 | CMe | NMe | Q1x | a bond | Me | a bond | NH | O | NH | Q3b | OH |
| 2145 | CMe | NMe | Q1x | a bond | Me | a bond | NH | O | NH | Q3c | OH |
| 2146 | CMe | NMe | Q1x | a bond | Me | a bond | NH | O | a bond | Q3a | OH |
| 2147 | CMe | NMe | Q1x | a bond | Me | a bond | NH | O | a bond | Q3b | OH |
| 2148 | CMe | NMe | Q1x | a bond | Me | a bond | NH | O | a bond | Q3c | OH |
| 2149 | CMe | NMe | Q1x | a bond | H | a bond | NH | S | NH | Q3a | OH |
| 2150 | CMe | NMe | Q1x | a bond | H | a bond | NH | S | NH | Q3b | OH |
| 2151 | CMe | NMe | Q1x | a bond | H | a bond | NH | S | NH | Q3c | OH |
| 2152 | CMe | NMe | Q1x | a bond | H | a bond | NH | S | a bond | Q3a | OH |
| 2153 | CMe | NMe | Q1x | a bond | H | a bond | NH | S | a bond | Q3b | OH |
| 2154 | CMe | NMe | Q1x | a bond | H | a bond | NH | S | a bond | Q3c | OH |
| 2155 | CMe | NMe | Q1x | a bond | H | a bond | NH | O | NH | Q3a | OH |
| 2156 | CMe | NMe | Q1x | a bond | H | a bond | NH | O | NH | Q3b | OH |
| 2157 | CMe | NMe | Q1x | a bond | H | a bond | NH | O | NH | Q3c | OH |
| 2158 | CMe | NMe | Q1x | a bond | H | a bond | NH | O | a bond | Q3a | OH |
| 2159 | CMe | NMe | Q1x | a bond | H | a bond | NH | O | a bond | Q3b | OH |
| 2160 | CMe | NMe | Q1x | a bond | H | a bond | NH | O | a bond | Q3c | OH |
| 2161 | CMe | NEt | Q1o | a bond | Me | a bond | NH | S | NH | Q3a | OH |
| 2162 | CMe | NEt | Q1o | a bond | Me | a bond | NH | S | NH | Q3b | OH |
| 2163 | CMe | NEt | Q1o | a bond | Me | a bond | NH | S | NH | Q3c | OH |
| 2164 | CMe | NEt | Q1o | a bond | Me | a bond | NH | S | a bond | Q3a | OH |
| 2165 | CMe | NEt | Q1o | a bond | Me | a bond | NH | S | a bond | Q3b | OH |
| 2166 | CMe | NEt | Q1o | a bond | Me | a bond | NH | S | a bond | Q3c | OH |
| 2167 | CMe | NEt | Q1o | a bond | Me | a bond | NH | O | NH | Q3a | OH |
| 2168 | CMe | NEt | Q1o | a bond | Me | a bond | NH | O | NH | Q3b | OH |
| 2169 | CMe | NEt | Q1o | a bond | Me | a bond | NH | O | NH | Q3c | OH |
| 2170 | CMe | NEt | Q1o | a bond | Me | a bond | NH | O | a bond | Q3a | OH |
| 2171 | CMe | NEt | Q1o | a bond | Me | a bond | NH | O | a bond | Q3b | OH |
| 2172 | CMe | NEt | Q1o | a bond | Me | a bond | NH | O | a bond | Q3c | OH |
| 2173 | CMe | NEt | Q1o | a bond | H | a bond | NH | S | NH | Q3a | OH |
| 2174 | CMe | NEt | Q1o | a bond | H | a bond | NH | S | NH | Q3b | OH |
| 2175 | CMe | NEt | Q1o | a bond | H | a bond | NH | S | NH | Q3c | OH |
| 2176 | CMe | NEt | Q1o | a bond | H | a bond | NH | S | a bond | Q3a | OH |
| 2177 | CMe | NEt | Q1o | a bond | H | a bond | NH | S | a bond | Q3b | OH |
| 2178 | CMe | NEt | Q1o | a bond | H | a bond | NH | S | a bond | Q3c | OH |
| 2179 | CMe | NEt | Q1o | a bond | H | a bond | NH | O | NH | Q3a | OH |
| 2180 | CMe | NEt | Q1o | a bond | H | a bond | NH | O | NH | Q3b | OH |
| 2181 | CMe | NEt | Q1o | a bond | H | a bond | NH | O | NH | Q3c | OH |
| 2182 | CMe | NEt | Q1o | a bond | H | a bond | NH | O | a bond | Q3a | OH |
| 2183 | CMe | NEt | Q1o | a bond | H | a bond | NH | O | a bond | Q3b | OH |
| 2184 | CMe | NEt | Q1o | a bond | H | a bond | NH | O | a bond | Q3c | OH |
| 2185 | CMe | NEt | Q1p | a bond | Me | a bond | NH | S | NH | Q3a | OH |
| 2186 | CMe | NEt | Q1p | a bond | Me | a bond | NH | S | NH | Q3b | OH |
| 2187 | CMe | NEt | Q1p | a bond | Me | a bond | NH | S | NH | Q3c | OH |
| 2188 | CMe | NEt | Q1p | a bond | Me | a bond | NH | S | a bond | Q3a | OH |
| 2189 | CMe | NEt | Q1p | a bond | Me | a bond | NH | S | a bond | Q3b | OH |
| 2190 | CMe | NEt | Q1p | a bond | Me | a bond | NH | S | a bond | Q3c | OH |
| 2191 | CMe | NEt | Q1p | a bond | Me | a bond | NH | O | NH | Q3a | OH |
| 2192 | CMe | NEt | Q1p | a bond | Me | a bond | NH | O | NH | Q3b | OH |
| 2193 | CMe | NEt | Q1p | a bond | Me | a bond | NH | O | NH | Q3c | OH |
| 2194 | CMe | NEt | Q1p | a bond | Me | a bond | NH | O | a bond | Q3a | OH |
| 2195 | CMe | NEt | Q1p | a bond | Me | a bond | NH | O | a bond | Q3b | OH |
| 2196 | CMe | NEt | Q1p | a bond | Me | a bond | NH | O | a bond | Q3c | OH |
| 2197 | CMe | NEt | Q1p | a bond | H | a bond | NH | S | NH | Q3a | OH |
| 2198 | CMe | NEt | Q1p | a bond | H | a bond | NH | S | NH | Q3b | OH |
| 2199 | CMe | NEt | Q1p | a bond | H | a bond | NH | S | NH | Q3c | OH |
| 2200 | CMe | NEt | Q1p | a bond | H | a bond | NH | S | a bond | Q3a | OH |
| 2201 | CMe | NEt | Q1p | a bond | H | a bond | NH | S | a bond | Q3b | OH |
| 2202 | CMe | NEt | Q1p | a bond | H | a bond | NH | S | a bond | Q3c | OH |
| 2203 | CMe | NEt | Q1p | a bond | H | a bond | NH | O | NH | Q3a | OH |
| 2204 | CMe | NEt | Q1p | a bond | H | a bond | NH | O | NH | Q3b | OH |
| 2205 | CMe | NEt | Q1p | a bond | H | a bond | NH | O | NH | Q3c | OH |
| 2206 | CMe | NEt | Q1p | a bond | H | a bond | NH | O | a bond | Q3a | OH |
| 2207 | CMe | NEt | Q1p | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2208 | CMe | NEt | Q1p | a bond | H | a bond | NH | O | a bond | Q3c | OH |
| 2209 | CMe | NEt | Q1q | a bond | Me | a bond | NH | S | NH | Q3a | OH |
| 2210 | CMe | NEt | Q1q | a bond | Me | a bond | NH | S | NH | Q3b | OH |
| 2211 | CMe | NEt | Q1q | a bond | Me | a bond | NH | S | NH | Q3c | OH |
| 2212 | CMe | NEt | Q1q | a bond | Me | a bond | NH | S | a bond | Q3a | OH |
| 2213 | CMe | NEt | Q1q | a bond | Me | a bond | NH | S | a bond | Q3b | OH |
| 2214 | CMe | NEt | Q1q | a bond | Me | a bond | NH | S | a bond | Q3c | OH |
| 2215 | CMe | NEt | Q1q | a bond | Me | a bond | NH | O | NH | Q3a | OH |
| 2216 | CMe | NEt | Q1q | a bond | Me | a bond | NH | O | NH | Q3b | OH |
| 2217 | CMe | NEt | Q1q | a bond | Me | a bond | NH | O | NH | Q3c | OH |
| 2218 | CMe | NEt | Q1q | a bond | Me | a bond | NH | O | a bond | Q3a | OH |
| 2219 | CMe | NEt | Q1q | a bond | Me | a bond | NH | O | a bond | Q3b | OH |
| 2220 | CMe | NEt | Q1q | a bond | Me | a bond | NH | O | a bond | Q3c | OH |
| 2221 | CMe | NEt | Q1q | a bond | H | a bond | NH | S | NH | Q3a | OH |
| 2222 | CMe | NEt | Q1q | a bond | H | a bond | NH | S | NH | Q3b | OH |
| 2223 | CMe | NEt | Q1q | a bond | H | a bond | NH | S | NH | Q3c | OH |
| 2224 | CMe | NEt | Q1q | a bond | H | a bond | NH | S | a bond | Q3a | OH |
| 2225 | CMe | NEt | Q1q | a bond | H | a bond | NH | S | a bond | Q3b | OH |
| 2226 | CMe | NEt | Q1q | a bond | H | a bond | NH | S | a bond | Q3c | OH |
| 2227 | CMe | NEt | Q1q | a bond | H | a bond | NH | O | NH | Q3a | OH |
| 2228 | CMe | NEt | Q1q | a bond | H | a bond | NH | O | NH | Q3b | OH |
| 2229 | CMe | NEt | Q1q | a bond | H | a bond | NH | O | NH | Q3c | OH |
| 2230 | CMe | NEt | Q1q | a bond | H | a bond | NH | O | a bond | Q3a | OH |
| 2231 | CMe | NEt | Q1q | a bond | H | a bond | NH | O | a bond | Q3b | OH |
| 2232 | CMe | NEt | Q1q | a bond | H | a bond | NH | O | a bond | Q3c | OH |
| 2233 | CMe | NEt | Q1r | a bond | Me | a bond | NH | S | NH | Q3a | OH |
| 2234 | CMe | NEt | Q1r | a bond | Me | a bond | NH | S | NH | Q3b | OH |
| 2235 | CMe | NEt | Q1r | a bond | Me | a bond | NH | S | NH | Q3c | OH |
| 2236 | CMe | NEt | Q1r | a bond | Me | a bond | NH | S | a bond | Q3a | OH |
| 2237 | CMe | NEt | Q1r | a bond | Me | a bond | NH | S | a bond | Q3b | OH |
| 2238 | CMe | NEt | Q1r | a bond | Me | a bond | NH | S | a bond | Q3c | OH |
| 2239 | CMe | NEt | Q1r | a bond | Me | a bond | NH | O | NH | Q3a | OH |
| 2240 | CMe | NEt | Q1r | a bond | Me | a bond | NH | O | NH | Q3b | OH |
| 2241 | CMe | NEt | Q1r | a bond | Me | a bond | NH | O | NH | Q3c | OH |
| 2242 | CMe | NEt | Q1r | a bond | Me | a bond | NH | O | a bond | Q3a | OH |
| 2243 | CMe | NEt | Q1r | a bond | Me | a bond | NH | O | a bond | Q3b | OH |
| 2244 | CMe | NEt | Q1r | a bond | Me | a bond | NH | O | a bond | Q3c | OH |
| 2245 | CMe | NEt | Q1r | a bond | H | a bond | NH | S | NH | Q3a | OH |
| 2246 | CMe | NEt | Q1r | a bond | H | a bond | NH | S | NH | Q3b | OH |
| 2247 | CMe | NEt | Q1r | a bond | H | a bond | NH | S | NH | Q3c | OH |
| 2248 | CMe | NEt | Q1r | a bond | H | a bond | NH | S | a bond | Q3a | OH |
| 2249 | CMe | NEt | Q1r | a bond | H | a bond | NH | S | a bond | Q3b | OH |
| 2250 | CMe | NEt | Q1r | a bond | H | a bond | NH | S | a bond | Q3c | OH |
| 2251 | CMe | NEt | Q1r | a bond | H | a bond | NH | O | NH | Q3a | OH |
| 2252 | CMe | NEt | Q1r | a bond | H | a bond | NH | O | NH | Q3b | OH |
| 2253 | CMe | NEt | Q1r | a bond | H | a bond | NH | O | NH | Q3c | OH |
| 2254 | CMe | NEt | Q1r | a bond | H | a bond | NH | O | a bond | Q3a | OH |
| 2255 | CMe | NEt | Q1r | a bond | H | a bond | NH | O | a bond | Q3b | OH |
| 2256 | CMe | NEt | Q1r | a bond | H | a bond | NH | O | a bond | Q3c | OH |
| 2257 | CMe | NEt | Q1s | a bond | Me | a bond | NH | S | NH | Q3a | OH |
| 2258 | CMe | NEt | Q1s | a bond | Me | a bond | NH | S | NH | Q3b | OH |
| 2259 | CMe | NEt | Q1s | a bond | Me | a bond | NH | S | NH | Q3c | OH |
| 2260 | CMe | NEt | Q1s | a bond | Me | a bond | NH | S | a bond | Q3a | OH |
| 2261 | CMe | NEt | Q1s | a bond | Me | a bond | NH | S | a bond | Q3b | OH |
| 2262 | CMe | NEt | Q1s | a bond | Me | a bond | NH | S | a bond | Q3c | OH |
| 2263 | CMe | NEt | Q1s | a bond | Me | a bond | NH | O | NH | Q3a | OH |
| 2264 | CMe | NEt | Q1s | a bond | Me | a bond | NH | O | NH | Q3b | OH |
| 2265 | CMe | NEt | Q1s | a bond | Me | a bond | NH | O | NH | Q3c | OH |
| 2266 | CMe | NEt | Q1s | a bond | Me | a bond | NH | O | a bond | Q3a | OH |
| 2267 | CMe | NEt | Q1s | a bond | Me | a bond | NH | O | a bond | Q3b | OH |
| 2268 | CMe | NEt | Q1s | a bond | Me | a bond | NH | O | a bond | Q3c | OH |
| 2269 | CMe | NEt | Q1s | a bond | H | a bond | NH | S | NH | Q3a | OH |
| 2270 | CMe | NEt | Q1s | a bond | H | a bond | NH | S | NH | Q3b | OH |
| 2271 | CMe | NEt | Q1s | a bond | H | a bond | NH | S | NH | Q3c | OH |
| 2272 | CMe | NEt | Q1s | a bond | H | a bond | NH | S | a bond | Q3a | OH |
| 2273 | CMe | NEt | Q1s | a bond | H | a bond | NH | S | a bond | Q3b | OH |
| 2274 | CMe | NEt | Q1s | a bond | H | a bond | NH | S | a bond | Q3c | OH |
| 2275 | CMe | NEt | Q1s | a bond | H | a bond | NH | O | NH | Q3a | OH |
| 2276 | CMe | NEt | Q1s | a bond | H | a bond | NH | O | NH | Q3b | OH |
| 2277 | CMe | NEt | Q1s | a bond | H | a bond | NH | O | NH | Q3c | OH |
| 2278 | CMe | NEt | Q1s | a bond | H | a bond | NH | O | a bond | Q3a | OH |
| 2279 | CMe | NEt | Q1s | a bond | H | a bond | NH | O | a bond | Q3b | OH |
| 2280 | CMe | NEt | Q1s | a bond | H | a bond | NH | O | a bond | Q3c | OH |
| 2281 | CMe | NEt | Q1t | a bond | Me | a bond | NH | S | NH | Q3a | OH |
| 2282 | CMe | NEt | Q1t | a bond | Me | a bond | NH | S | NH | Q3b | OH |
| 2283 | CMe | NEt | Q1t | a bond | Me | a bond | NH | S | NH | Q3c | OH |
| 2284 | CMe | NEt | Q1t | a bond | Me | a bond | NH | S | a bond | Q3a | OH |
| 2285 | CMe | NEt | Q1t | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2286 | CMe | NEt | Q1t | a bond | Me | a bond | NH | S | a bond | Q3c | OH |
| 2287 | CMe | NEt | Q1t | a bond | Me | a bond | NH | O | NH | Q3a | OH |
| 2288 | CMe | NEt | Q1t | a bond | Me | a bond | NH | O | NH | Q3b | OH |
| 2289 | CMe | NEt | Q1t | a bond | Me | a bond | NH | O | NH | Q3c | OH |
| 2290 | CMe | NEt | Q1t | a bond | Me | a bond | NH | O | a bond | Q3a | OH |
| 2291 | CMe | NEt | Q1t | a bond | Me | a bond | NH | O | a bond | Q3b | OH |
| 2292 | CMe | NEt | Q1t | a bond | Me | a bond | NH | O | a bond | Q3c | OH |
| 2293 | CMe | NEt | Q1t | a bond | H | a bond | NH | S | NH | Q3a | OH |
| 2294 | CMe | NEt | Q1t | a bond | H | a bond | NH | S | NH | Q3b | OH |
| 2295 | CMe | NEt | Q1t | a bond | H | a bond | NH | S | NH | Q3c | OH |
| 2296 | CMe | NEt | Q1t | a bond | H | a bond | NH | S | a bond | Q3a | OH |
| 2297 | CMe | NEt | Q1t | a bond | H | a bond | NH | S | a bond | Q3b | OH |
| 2298 | CMe | NEt | Q1t | a bond | H | a bond | NH | S | a bond | Q3c | OH |
| 2299 | CMe | NEt | Q1t | a bond | H | a bond | NH | O | NH | Q3a | OH |
| 2300 | CMe | NEt | Q1t | a bond | H | a bond | NH | O | NH | Q3b | OH |
| 2301 | CMe | NEt | Q1t | a bond | H | a bond | NH | O | NH | Q3c | OH |
| 2302 | CMe | NEt | Q1t | a bond | H | a bond | NH | O | a bond | Q3a | OH |
| 2303 | CMe | NEt | Q1t | a bond | H | a bond | NH | O | a bond | Q3b | OH |
| 2304 | CMe | NEt | Q1t | a bond | H | a bond | NH | O | a bond | Q3c | OH |
| 2305 | CMe | NEt | Q1u | a bond | Me | a bond | NH | S | NH | Q3a | OH |
| 2306 | CMe | NEt | Q1u | a bond | Me | a bond | NH | S | NH | Q3b | OH |
| 2307 | CMe | NEt | Q1u | a bond | Me | a bond | NH | S | NH | Q3c | OH |
| 2308 | CMe | NEt | Q1u | a bond | Me | a bond | NH | S | a bond | Q3a | OH |
| 2309 | CMe | NEt | Q1u | a bond | Me | a bond | NH | S | a bond | Q3b | OH |
| 2310 | CMe | NEt | Q1u | a bond | Me | a bond | NH | S | a bond | Q3c | OH |
| 2311 | CMe | NEt | Q1u | a bond | Me | a bond | NH | O | NH | Q3a | OH |
| 2312 | CMe | NEt | Q1u | a bond | Me | a bond | NH | O | NH | Q3b | OH |
| 2313 | CMe | NEt | Q1u | a bond | Me | a bond | NH | O | NH | Q3c | OH |
| 2314 | CMe | NEt | Q1u | a bond | Me | a bond | NH | O | a bond | Q3a | OH |
| 2315 | CMe | NEt | Q1u | a bond | Me | a bond | NH | O | a bond | Q3b | OH |
| 2316 | CMe | NEt | Q1u | a bond | Me | a bond | NH | O | a bond | Q3c | OH |
| 2317 | CMe | NEt | Q1u | a bond | H | a bond | NH | S | NH | Q3a | OH |
| 2318 | CMe | NEt | Q1u | a bond | H | a bond | NH | S | NH | Q3b | OH |
| 2319 | CMe | NEt | Q1u | a bond | H | a bond | NH | S | NH | Q3c | OH |
| 2320 | CMe | NEt | Q1u | a bond | H | a bond | NH | S | a bond | Q3a | OH |
| 2321 | CMe | NEt | Q1u | a bond | H | a bond | NH | S | a bond | Q3b | OH |
| 2322 | CMe | NEt | Q1u | a bond | H | a bond | NH | S | a bond | Q3c | OH |
| 2323 | CMe | NEt | Q1u | a bond | H | a bond | NH | O | NH | Q3a | OH |
| 2324 | CMe | NEt | Q1u | a bond | H | a bond | NH | O | NH | Q3b | OH |
| 2325 | CMe | NEt | Q1u | a bond | H | a bond | NH | O | NH | Q3c | OH |
| 2326 | CMe | NEt | Q1u | a bond | H | a bond | NH | O | a bond | Q3a | OH |
| 2327 | CMe | NEt | Q1u | a bond | H | a bond | NH | O | a bond | Q3b | OH |
| 2328 | CMe | NEt | Q1u | a bond | H | a bond | NH | O | a bond | Q3c | OH |
| 2329 | CMe | NEt | Q1v | a bond | Me | a bond | NH | S | NH | Q3a | OH |
| 2330 | CMe | NEt | Q1v | a bond | Me | a bond | NH | S | NH | Q3b | OH |
| 2331 | CMe | NEt | Q1v | a bond | Me | a bond | NH | S | NH | Q3c | OH |
| 2332 | CMe | NEt | Q1v | a bond | Me | a bond | NH | S | a bond | Q3a | OH |
| 2333 | CMe | NEt | Q1v | a bond | Me | a bond | NH | S | a bond | Q3b | OH |
| 2334 | CMe | NEt | Q1v | a bond | Me | a bond | NH | S | a bond | Q3c | OH |
| 2335 | CMe | NEt | Q1v | a bond | Me | a bond | NH | O | NH | Q3a | OH |
| 2336 | CMe | NEt | Q1v | a bond | Me | a bond | NH | O | NH | Q3b | OH |
| 2337 | CMe | NEt | Q1v | a bond | Me | a bond | NH | O | NH | Q3c | OH |
| 2338 | CMe | NEt | Q1v | a bond | Me | a bond | NH | O | a bond | Q3a | OH |
| 2339 | CMe | NEt | Q1v | a bond | Me | a bond | NH | O | a bond | Q3b | OH |
| 2340 | CMe | NEt | Q1v | a bond | Me | a bond | NH | O | a bond | Q3c | OH |
| 2341 | CMe | NEt | Q1v | a bond | H | a bond | NH | S | NH | Q3a | OH |
| 2342 | CMe | NEt | Q1v | a bond | H | a bond | NH | S | NH | Q3b | OH |
| 2343 | CMe | NEt | Q1v | a bond | H | a bond | NH | S | NH | Q3c | OH |
| 2344 | CMe | NEt | Q1v | a bond | H | a bond | NH | S | a bond | Q3a | OH |
| 2345 | CMe | NEt | Q1v | a bond | H | a bond | NH | S | a bond | Q3b | OH |
| 2346 | CMe | NEt | Q1v | a bond | H | a bond | NH | S | a bond | Q3c | OH |
| 2347 | CMe | NEt | Q1v | a bond | H | a bond | NH | O | NH | Q3a | OH |
| 2348 | CMe | NEt | Q1v | a bond | H | a bond | NH | O | NH | Q3b | OH |
| 2349 | CMe | NEt | Q1v | a bond | H | a bond | NH | O | NH | Q3c | OH |
| 2350 | CMe | NEt | Q1v | a bond | H | a bond | NH | O | a bond | Q3a | OH |
| 2351 | CMe | NEt | Q1v | a bond | H | a bond | NH | O | a bond | Q3b | OH |
| 2352 | CMe | NEt | Q1v | a bond | H | a bond | NH | O | a bond | Q3c | OH |
| 2353 | CMe | NEt | Q1w | a bond | Me | a bond | NH | S | NH | Q3a | OH |
| 2354 | CMe | NEt | Q1w | a bond | Me | a bond | NH | S | NH | Q3b | OH |
| 2355 | CMe | NEt | Q1w | a bond | Me | a bond | NH | S | NH | Q3c | OH |
| 2356 | CMe | NEt | Q1w | a bond | Me | a bond | NH | S | a bond | Q3a | OH |
| 2357 | CMe | NEt | Q1w | a bond | Me | a bond | NH | S | a bond | Q3b | OH |
| 2358 | CMe | NEt | Q1w | a bond | Me | a bond | NH | S | a bond | Q3c | OH |
| 2359 | CMe | NEt | Q1w | a bond | Me | a bond | NH | O | NH | Q3a | OH |
| 2360 | CMe | NEt | Q1w | a bond | Me | a bond | NH | O | NH | Q3b | OH |
| 2361 | CMe | NEt | Q1w | a bond | Me | a bond | NH | O | NH | Q3c | OH |
| 2362 | CMe | NEt | Q1w | a bond | Me | a bond | NH | O | a bond | Q3a | OH |
| 2363 | CMe | NEt | Q1w | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2364 | CMe | NEt | Q1w | a bond | Me | a bond | NH | O | a bond | Q3c | OH |
| 2365 | CMe | NEt | Q1w | a bond | H | a bond | NH | S | NH | Q3a | OH |
| 2366 | CMe | NEt | Q1w | a bond | H | a bond | NH | S | NH | Q3b | OH |
| 2367 | CMe | NEt | Q1w | a bond | H | a bond | NH | S | NH | Q3c | OH |
| 2368 | CMe | NEt | Q1w | a bond | H | a bond | NH | S | a bond | Q3a | OH |
| 2369 | CMe | NEt | Q1w | a bond | H | a bond | NH | S | a bond | Q3b | OH |
| 2370 | CMe | NEt | Q1w | a bond | H | a bond | NH | S | a bond | Q3c | OH |
| 2371 | CMe | NEt | Q1w | a bond | H | a bond | NH | O | NH | Q3a | OH |
| 2372 | CMe | NEt | Q1w | a bond | H | a bond | NH | O | NH | Q3b | OH |
| 2373 | CMe | NEt | Q1w | a bond | H | a bond | NH | O | NH | Q3c | OH |
| 2374 | CMe | NEt | Q1w | a bond | H | a bond | NH | O | a bond | Q3a | OH |
| 2375 | CMe | NEt | Q1w | a bond | H | a bond | NH | O | a bond | Q3b | OH |
| 2376 | CMe | NEt | Q1w | a bond | H | a bond | NH | O | a bond | Q3c | OH |
| 2377 | CMe | NEt | Q1x | a bond | Me | a bond | NH | S | NH | Q3a | OH |
| 2378 | CMe | NEt | Q1x | a bond | Me | a bond | NH | S | NH | Q3b | OH |
| 2379 | CMe | NEt | Q1x | a bond | Me | a bond | NH | S | NH | Q3c | OH |
| 2380 | CMe | NEt | Q1x | a bond | Me | a bond | NH | S | a bond | Q3a | OH |
| 2381 | CMe | NEt | Q1x | a bond | Me | a bond | NH | S | a bond | Q3b | OH |
| 2382 | CMe | NEt | Q1x | a bond | Me | a bond | NH | S | a bond | Q3c | OH |
| 2383 | CMe | NEt | Q1x | a bond | Me | a bond | NH | O | NH | Q3a | OH |
| 2384 | CMe | NEt | Q1x | a bond | Me | a bond | NH | O | NH | Q3b | OH |
| 2385 | CMe | NEt | Q1x | a bond | Me | a bond | NH | O | NH | Q3c | OH |
| 2386 | CMe | NEt | Q1x | a bond | Me | a bond | NH | O | a bond | Q3a | OH |
| 2387 | CMe | NEt | Q1x | a bond | Me | a bond | NH | O | a bond | Q3b | OH |
| 2388 | CMe | NEt | Q1x | a bond | Me | a bond | NH | O | a bond | Q3c | OH |
| 2389 | CMe | NEt | Q1x | a bond | H | a bond | NH | S | NH | Q3a | OH |
| 2390 | CMe | NEt | Q1x | a bond | H | a bond | NH | S | NH | Q3b | OH |
| 2391 | CMe | NEt | Q1x | a bond | H | a bond | NH | S | NH | Q3c | OH |
| 2392 | CMe | NEt | Q1x | a bond | H | a bond | NH | S | a bond | Q3a | OH |
| 2393 | CMe | NEt | Q1x | a bond | H | a bond | NH | S | a bond | Q3b | OH |
| 2394 | CMe | NEt | Q1x | a bond | H | a bond | NH | S | a bond | Q3c | OH |
| 2395 | CMe | NEt | Q1x | a bond | H | a bond | NH | O | NH | Q3a | OH |
| 2396 | CMe | NEt | Q1x | a bond | H | a bond | NH | O | NH | Q3b | OH |
| 2397 | CMe | NEt | Q1x | a bond | H | a bond | NH | O | NH | Q3c | OH |
| 2398 | CMe | NEt | Q1x | a bond | H | a bond | NH | O | a bond | Q3a | OH |
| 2399 | CMe | NEt | Q1x | a bond | H | a bond | NH | O | a bond | Q3b | OH |
| 2400 | CMe | NEt | Q1x | a bond | H | a bond | NH | O | a bond | Q3c | OH |
| 2401 | CMe | S | Q1o | a bond | Me | a bond | NH | S | NH | Q3a | OH |
| 2402 | CMe | S | Q1o | a bond | Me | a bond | NH | S | NH | Q3b | OH |
| 2403 | CMe | S | Q1o | a bond | Me | a bond | NH | S | NH | Q3c | OH |
| 2404 | CMe | S | Q1o | a bond | Me | a bond | NH | S | a bond | Q3a | OH |
| 2405 | CMe | S | Q1o | a bond | Me | a bond | NH | S | a bond | Q3b | OH |
| 2406 | CMe | S | Q1o | a bond | Me | a bond | NH | S | a bond | Q3c | OH |
| 2407 | CMe | S | Q1o | a bond | Me | a bond | NH | O | NH | Q3a | OH |
| 2408 | CMe | S | Q1o | a bond | Me | a bond | NH | O | NH | Q3b | OH |
| 2409 | CMe | S | Q1o | a bond | Me | a bond | NH | O | NH | Q3c | OH |
| 2410 | CMe | S | Q1o | a bond | Me | a bond | NH | O | a bond | Q3a | OH |
| 2411 | CMe | S | Q1o | a bond | Me | a bond | NH | O | a bond | Q3b | OH |
| 2412 | CMe | S | Q1o | a bond | Me | a bond | NH | O | a bond | Q3c | OH |
| 2413 | CMe | S | Q1o | a bond | H | a bond | NH | S | NH | Q3a | OH |
| 2414 | CMe | S | Q1o | a bond | H | a bond | NH | S | NH | Q3b | OH |
| 2415 | CMe | S | Q1o | a bond | H | a bond | NH | S | NH | Q3c | OH |
| 2416 | CMe | S | Q1o | a bond | H | a bond | NH | S | a bond | Q3a | OH |
| 2417 | CMe | S | Q1o | a bond | H | a bond | NH | S | a bond | Q3b | OH |
| 2418 | CMe | S | Q1o | a bond | H | a bond | NH | S | a bond | Q3c | OH |
| 2419 | CMe | S | Q1o | a bond | H | a bond | NH | O | NH | Q3a | OH |
| 2420 | CMe | S | Q1o | a bond | H | a bond | NH | O | NH | Q3b | OH |
| 2421 | CMe | S | Q1o | a bond | H | a bond | NH | O | NH | Q3c | OH |
| 2422 | CMe | S | Q1o | a bond | H | a bond | NH | O | a bond | Q3a | OH |
| 2423 | CMe | S | Q1o | a bond | H | a bond | NH | O | a bond | Q3b | OH |
| 2424 | CMe | S | Q1o | a bond | H | a bond | NH | O | a bond | Q3c | OH |
| 2425 | CMe | S | Q1p | a bond | Me | a bond | NH | S | NH | Q3a | OH |
| 2426 | CMe | S | Q1p | a bond | Me | a bond | NH | S | NH | Q3b | OH |
| 2427 | CMe | S | Q1p | a bond | Me | a bond | NH | S | NH | Q3c | OH |
| 2428 | CMe | S | Q1p | a bond | Me | a bond | NH | S | a bond | Q3a | OH |
| 2429 | CMe | S | Q1p | a bond | Me | a bond | NH | S | a bond | Q3b | OH |
| 2430 | CMe | S | Q1p | a bond | Me | a bond | NH | S | a bond | Q3c | OH |
| 2431 | CMe | S | Q1p | a bond | Me | a bond | NH | O | NH | Q3a | OH |
| 2432 | CMe | S | Q1p | a bond | Me | a bond | NH | O | NH | Q3b | OH |
| 2433 | CMe | S | Q1p | a bond | Me | a bond | NH | O | NH | Q3c | OH |
| 2434 | CMe | S | Q1p | a bond | Me | a bond | NH | O | a bond | Q3a | OH |
| 2435 | CMe | S | Q1p | a bond | Me | a bond | NH | O | a bond | Q3b | OH |
| 2436 | CMe | S | Q1p | a bond | Me | a bond | NH | O | a bond | Q3c | OH |
| 2437 | CMe | S | Q1p | a bond | H | a bond | NH | S | NH | Q3a | OH |
| 2438 | CMe | S | Q1p | a bond | H | a bond | NH | S | NH | Q3b | OH |
| 2439 | CMe | S | Q1p | a bond | H | a bond | NH | S | NH | Q3c | OH |
| 2440 | CMe | S | Q1p | a bond | H | a bond | NH | S | a bond | Q3a | OH |
| 2441 | CMe | S | Q1p | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2442 | CMe | S | Q1p | a bond | H | a bond | NH | S | a bond | Q3c | OH |
| 2443 | CMe | S | Q1p | a bond | H | a bond | NH | O | NH | Q3a | OH |
| 2444 | CMe | S | Q1p | a bond | H | a bond | NH | O | NH | Q3b | OH |
| 2445 | CMe | S | Q1p | a bond | H | a bond | NH | O | NH | Q3c | OH |
| 2446 | CMe | S | Q1p | a bond | H | a bond | NH | O | a bond | Q3a | OH |
| 2447 | CMe | S | Q1p | a bond | H | a bond | NH | O | a bond | Q3b | OH |
| 2448 | CMe | S | Q1p | a bond | H | a bond | NH | O | a bond | Q3c | OH |
| 2449 | CMe | S | Q1q | a bond | Me | a bond | NH | S | NH | Q3a | OH |
| 2450 | CMe | S | Q1q | a bond | Me | a bond | NH | S | NH | Q3b | OH |
| 2451 | CMe | S | Q1q | a bond | Me | a bond | NH | S | NH | Q3c | OH |
| 2452 | CMe | S | Q1q | a bond | Me | a bond | NH | S | a bond | Q3a | OH |
| 2453 | CMe | S | Q1q | a bond | Me | a bond | NH | S | a bond | Q3b | OH |
| 2454 | CMe | S | Q1q | a bond | Me | a bond | NH | S | a bond | Q3c | OH |
| 2455 | CMe | S | Q1q | a bond | Me | a bond | NH | O | NH | Q3a | OH |
| 2456 | CMe | S | Q1q | a bond | Me | a bond | NH | O | NH | Q3b | OH |
| 2457 | CMe | S | Q1q | a bond | Me | a bond | NH | O | NH | Q3c | OH |
| 2458 | CMe | S | Q1q | a bond | Me | a bond | NH | O | a bond | Q3a | OH |
| 2459 | CMe | S | Q1q | a bond | Me | a bond | NH | O | a bond | Q3b | OH |
| 2460 | CMe | S | Q1q | a bond | Me | a bond | NH | O | a bond | Q3c | OH |
| 2461 | CMe | S | Q1q | a bond | H | a bond | NH | S | NH | Q3a | OH |
| 2462 | CMe | S | Q1q | a bond | H | a bond | NH | S | NH | Q3b | OH |
| 2463 | CMe | S | Q1q | a bond | H | a bond | NH | S | NH | Q3c | OH |
| 2464 | CMe | S | Q1q | a bond | H | a bond | NH | S | a bond | Q3a | OH |
| 2465 | CMe | S | Q1q | a bond | H | a bond | NH | S | a bond | Q3b | OH |
| 2466 | CMe | S | Q1q | a bond | H | a bond | NH | S | a bond | Q3c | OH |
| 2467 | CMe | S | Q1q | a bond | H | a bond | NH | O | NH | Q3a | OH |
| 2468 | CMe | S | Q1q | a bond | H | a bond | NH | O | NH | Q3b | OH |
| 2469 | CMe | S | Q1q | a bond | H | a bond | NH | O | NH | Q3c | OH |
| 2470 | CMe | S | Q1q | a bond | H | a bond | NH | O | a bond | Q3a | OH |
| 2471 | CMe | S | Q1q | a bond | H | a bond | NH | O | a bond | Q3b | OH |
| 2472 | CMe | S | Q1q | a bond | H | a bond | NH | O | a bond | Q3c | OH |
| 2473 | CMe | S | Q1r | a bond | Me | a bond | NH | S | NH | Q3a | OH |
| 2474 | CMe | S | Q1r | a bond | Me | a bond | NH | S | NH | Q3b | OH |
| 2475 | CMe | S | Q1r | a bond | Me | a bond | NH | S | NH | Q3c | OH |
| 2476 | CMe | S | Q1r | a bond | Me | a bond | NH | S | a bond | Q3a | OH |
| 2477 | CMe | S | Q1r | a bond | Me | a bond | NH | S | a bond | Q3b | OH |
| 2478 | CMe | S | Q1r | a bond | Me | a bond | NH | S | a bond | Q3c | OH |
| 2479 | CMe | S | Q1r | a bond | Me | a bond | NH | O | NH | Q3a | OH |
| 2480 | CMe | S | Q1r | a bond | Me | a bond | NH | O | NH | Q3b | OH |
| 2481 | CMe | S | Q1r | a bond | Me | a bond | NH | O | NH | Q3c | OH |
| 2482 | CMe | S | Q1r | a bond | Me | a bond | NH | O | a bond | Q3a | OH |
| 2483 | CMe | S | Q1r | a bond | Me | a bond | NH | O | a bond | Q3b | OH |
| 2484 | CMe | S | Q1r | a bond | Me | a bond | NH | O | a bond | Q3c | OH |
| 2485 | CMe | S | Q1r | a bond | H | a bond | NH | S | NH | Q3a | OH |
| 2486 | CMe | S | Q1r | a bond | H | a bond | NH | S | NH | Q3b | OH |
| 2487 | CMe | S | Q1r | a bond | H | a bond | NH | S | NH | Q3c | OH |
| 2488 | CMe | S | Q1r | a bond | H | a bond | NH | S | a bond | Q3a | OH |
| 2489 | CMe | S | Q1r | a bond | H | a bond | NH | S | a bond | Q3b | OH |
| 2490 | CMe | S | Q1r | a bond | H | a bond | NH | S | a bond | Q3c | OH |
| 2491 | CMe | S | Q1r | a bond | H | a bond | NH | O | NH | Q3a | OH |
| 2492 | CMe | S | Q1r | a bond | H | a bond | NH | O | NH | Q3b | OH |
| 2493 | CMe | S | Q1r | a bond | H | a bond | NH | O | NH | Q3c | OH |
| 2494 | CMe | S | Q1r | a bond | H | a bond | NH | O | a bond | Q3a | OH |
| 2495 | CMe | S | Q1r | a bond | H | a bond | NH | O | a bond | Q3b | OH |
| 2496 | CMe | S | Q1r | a bond | H | a bond | NH | O | a bond | Q3c | OH |
| 2497 | CMe | S | Q1s | a bond | Me | a bond | NH | S | NH | Q3a | OH |
| 2498 | CMe | S | Q1s | a bond | Me | a bond | NH | S | NH | Q3b | OH |
| 2499 | CMe | S | Q1s | a bond | Me | a bond | NH | S | NH | Q3c | OH |
| 2500 | CMe | S | Q1s | a bond | Me | a bond | NH | S | a bond | Q3a | OH |
| 2501 | CMe | S | Q1s | a bond | Me | a bond | NH | S | a bond | Q3b | OH |
| 2502 | CMe | S | Q1s | a bond | Me | a bond | NH | S | a bond | Q3c | OH |
| 2503 | CMe | S | Q1s | a bond | Me | a bond | NH | O | NH | Q3a | OH |
| 2504 | CMe | S | Q1s | a bond | Me | a bond | NH | O | NH | Q3b | OH |
| 2505 | CMe | S | Q1s | a bond | Me | a bond | NH | O | NH | Q3c | OH |
| 2506 | CMe | S | Q1s | a bond | Me | a bond | NH | O | a bond | Q3a | OH |
| 2507 | CMe | S | Q1s | a bond | Me | a bond | NH | O | a bond | Q3b | OH |
| 2508 | CMe | S | Q1s | a bond | Me | a bond | NH | O | a bond | Q3c | OH |
| 2509 | CMe | S | Q1s | a bond | H | a bond | NH | S | NH | Q3a | OH |
| 2510 | CMe | S | Q1s | a bond | H | a bond | NH | S | NH | Q3b | OH |
| 2511 | CMe | S | Q1s | a bond | H | a bond | NH | S | NH | Q3c | OH |
| 2512 | CMe | S | Q1s | a bond | H | a bond | NH | S | a bond | Q3a | OH |
| 2513 | CMe | S | Q1s | a bond | H | a bond | NH | S | a bond | Q3b | OH |
| 2514 | CMe | S | Q1s | a bond | H | a bond | NH | S | a bond | Q3c | OH |
| 2515 | CMe | S | Q1s | a bond | H | a bond | NH | O | NH | Q3a | OH |
| 2516 | CMe | S | Q1s | a bond | H | a bond | NH | O | NH | Q3b | OH |
| 2517 | CMe | S | Q1s | a bond | H | a bond | NH | O | NH | Q3c | OH |
| 2518 | CMe | S | Q1s | a bond | H | a bond | NH | O | a bond | Q3a | OH |
| 2519 | CMe | S | Q1s | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2520 | CMe | S | Q1s | a bond | H | a bond | NH | O | a bond | Q3c | OH |
| 2521 | CMe | S | Q1t | a bond | Me | a bond | NH | S | NH | Q3a | OH |
| 2522 | CMe | S | Q1t | a bond | Me | a bond | NH | S | NH | Q3b | OH |
| 2523 | CMe | S | Q1t | a bond | Me | a bond | NH | S | NH | Q3c | OH |
| 2524 | CMe | S | Q1t | a bond | Me | a bond | NH | S | a bond | Q3a | OH |
| 2525 | CMe | S | Q1t | a bond | Me | a bond | NH | S | a bond | Q3b | OH |
| 2526 | CMe | S | Q1t | a bond | Me | a bond | NH | S | a bond | Q3c | OH |
| 2527 | CMe | S | Q1t | a bond | Me | a bond | NH | O | NH | Q3a | OH |
| 2528 | CMe | S | Q1t | a bond | Me | a bond | NH | O | NH | Q3b | OH |
| 2529 | CMe | S | Q1t | a bond | Me | a bond | NH | O | NH | Q3c | OH |
| 2530 | CMe | S | Q1t | a bond | Me | a bond | NH | O | a bond | Q3a | OH |
| 2531 | CMe | S | Q1t | a bond | Me | a bond | NH | O | a bond | Q3b | OH |
| 2532 | CMe | S | Q1t | a bond | Me | a bond | NH | O | a bond | Q3c | OH |
| 2533 | CMe | S | Q1t | a bond | H | a bond | NH | S | NH | Q3a | OH |
| 2534 | CMe | S | Q1t | a bond | H | a bond | NH | S | NH | Q3b | OH |
| 2535 | CMe | S | Q1t | a bond | H | a bond | NH | S | NH | Q3c | OH |
| 2536 | CMe | S | Q1t | a bond | H | a bond | NH | S | a bond | Q3a | OH |
| 2537 | CMe | S | Q1t | a bond | H | a bond | NH | S | a bond | Q3b | OH |
| 2538 | CMe | S | Q1t | a bond | H | a bond | NH | S | a bond | Q3c | OH |
| 2539 | CMe | S | Q1t | a bond | H | a bond | NH | O | NH | Q3a | OH |
| 2540 | CMe | S | Q1t | a bond | H | a bond | NH | O | NH | Q3b | OH |
| 2541 | CMe | S | Q1t | a bond | H | a bond | NH | O | NH | Q3c | OH |
| 2542 | CMe | S | Q1t | a bond | H | a bond | NH | O | a bond | Q3a | OH |
| 2543 | CMe | S | Q1t | a bond | H | a bond | NH | O | a bond | Q3b | OH |
| 2544 | CMe | S | Q1t | a bond | H | a bond | NH | O | a bond | Q3c | OH |
| 2545 | CMe | S | Q1u | a bond | Me | a bond | NH | S | NH | Q3a | OH |
| 2546 | CMe | S | Q1u | a bond | Me | a bond | NH | S | NH | Q3b | OH |
| 2547 | CMe | S | Q1u | a bond | Me | a bond | NH | S | NH | Q3c | OH |
| 2548 | CMe | S | Q1u | a bond | Me | a bond | NH | S | a bond | Q3a | OH |
| 2549 | CMe | S | Q1u | a bond | Me | a bond | NH | S | a bond | Q3b | OH |
| 2550 | CMe | S | Q1u | a bond | Me | a bond | NH | S | a bond | Q3c | OH |
| 2551 | CMe | S | Q1u | a bond | Me | a bond | NH | O | NH | Q3a | OH |
| 2552 | CMe | S | Q1u | a bond | Me | a bond | NH | O | NH | Q3b | OH |
| 2553 | CMe | S | Q1u | a bond | Me | a bond | NH | O | NH | Q3c | OH |
| 2554 | CMe | S | Q1u | a bond | Me | a bond | NH | O | a bond | Q3a | OH |
| 2555 | CMe | S | Q1u | a bond | Me | a bond | NH | O | a bond | Q3b | OH |
| 2556 | CMe | S | Q1u | a bond | Me | a bond | NH | O | a bond | Q3c | OH |
| 2557 | CMe | S | Q1u | a bond | H | a bond | NH | S | NH | Q3a | OH |
| 2558 | CMe | S | Q1u | a bond | H | a bond | NH | S | NH | Q3b | OH |
| 2559 | CMe | S | Q1u | a bond | H | a bond | NH | S | NH | Q3c | OH |
| 2560 | CMe | S | Q1u | a bond | H | a bond | NH | S | a bond | Q3a | OH |
| 2561 | CMe | S | Q1u | a bond | H | a bond | NH | S | a bond | Q3b | OH |
| 2562 | CMe | S | Q1u | a bond | H | a bond | NH | S | a bond | Q3c | OH |
| 2563 | CMe | S | Q1u | a bond | H | a bond | NH | O | NH | Q3a | OH |
| 2564 | CMe | S | Q1u | a bond | H | a bond | NH | O | NH | Q3b | OH |
| 2565 | CMe | S | Q1u | a bond | H | a bond | NH | O | NH | Q3c | OH |
| 2566 | CMe | S | Q1u | a bond | H | a bond | NH | O | a bond | Q3a | OH |
| 2567 | CMe | S | Q1u | a bond | H | a bond | NH | O | a bond | Q3b | OH |
| 2568 | CMe | S | Q1u | a bond | H | a bond | NH | O | a bond | Q3c | OH |
| 2569 | CMe | S | Q1v | a bond | Me | a bond | NH | S | NH | Q3a | OH |
| 2570 | CMe | S | Q1v | a bond | Me | a bond | NH | S | NH | Q3b | OH |
| 2571 | CMe | S | Q1v | a bond | Me | a bond | NH | S | NH | Q3c | OH |
| 2572 | CMe | S | Q1v | a bond | Me | a bond | NH | S | a bond | Q3a | OH |
| 2573 | CMe | S | Q1v | a bond | Me | a bond | NH | S | a bond | Q3b | OH |
| 2574 | CMe | S | Q1v | a bond | Me | a bond | NH | S | a bond | Q3c | OH |
| 2575 | CMe | S | Q1v | a bond | Me | a bond | NH | O | NH | Q3a | OH |
| 2576 | CMe | S | Q1v | a bond | Me | a bond | NH | O | NH | Q3b | OH |
| 2577 | CMe | S | Q1v | a bond | Me | a bond | NH | O | NH | Q3c | OH |
| 2578 | CMe | S | Q1v | a bond | Me | a bond | NH | O | a bond | Q3a | OH |
| 2579 | CMe | S | Q1v | a bond | Me | a bond | NH | O | a bond | Q3b | OH |
| 2580 | CMe | S | Q1v | a bond | Me | a bond | NH | O | a bond | Q3c | OH |
| 2581 | CMe | S | Q1v | a bond | H | a bond | NH | S | NH | Q3a | OH |
| 2582 | CMe | S | Q1v | a bond | H | a bond | NH | S | NH | Q3b | OH |
| 2583 | CMe | S | Q1v | a bond | H | a bond | NH | S | NH | Q3c | OH |
| 2584 | CMe | S | Q1v | a bond | H | a bond | NH | S | a bond | Q3a | OH |
| 2585 | CMe | S | Q1v | a bond | H | a bond | NH | S | a bond | Q3b | OH |
| 2586 | CMe | S | Q1v | a bond | H | a bond | NH | S | a bond | Q3c | OH |
| 2587 | CMe | S | Q1v | a bond | H | a bond | NH | O | NH | Q3a | OH |
| 2588 | CMe | S | Q1v | a bond | H | a bond | NH | O | NH | Q3b | OH |
| 2589 | CMe | S | Q1v | a bond | H | a bond | NH | O | NH | Q3c | OH |
| 2590 | CMe | S | Q1v | a bond | H | a bond | NH | O | a bond | Q3a | OH |
| 2591 | CMe | S | Q1v | a bond | H | a bond | NH | O | a bond | Q3b | OH |
| 2592 | CMe | S | Q1v | a bond | H | a bond | NH | O | a bond | Q3c | OH |
| 2593 | CMe | S | Q1w | a bond | Me | a bond | NH | S | NH | Q3a | OH |
| 2594 | CMe | S | Q1w | a bond | Me | a bond | NH | S | NH | Q3b | OH |
| 2595 | CMe | S | Q1w | a bond | Me | a bond | NH | S | NH | Q3c | OH |
| 2596 | CMe | S | Q1w | a bond | Me | a bond | NH | S | a bond | Q3a | OH |
| 2597 | CMe | S | Q1w | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2598 | CMe | S | Q1w | a bond | Me | a bond | NH | S | a bond | Q3c | OH |
| 2599 | CMe | S | Q1w | a bond | Me | a bond | NH | O | NH | Q3a | OH |
| 2600 | CMe | S | Q1w | a bond | Me | a bond | NH | O | NH | Q3b | OH |
| 2601 | CMe | S | Q1w | a bond | Me | a bond | NH | O | NH | Q3c | OH |
| 2602 | CMe | S | Q1w | a bond | Me | a bond | NH | O | a bond | Q3a | OH |
| 2603 | CMe | S | Q1w | a bond | Me | a bond | NH | O | a bond | Q3b | OH |
| 2604 | CMe | S | Q1w | a bond | Me | a bond | NH | O | a bond | Q3c | OH |
| 2605 | CMe | S | Q1w | a bond | H | a bond | NH | S | NH | Q3a | OH |
| 2606 | CMe | S | Q1w | a bond | H | a bond | NH | S | NH | Q3b | OH |
| 2607 | CMe | S | Q1w | a bond | H | a bond | NH | S | NH | Q3c | OH |
| 2608 | CMe | S | Q1w | a bond | H | a bond | NH | S | a bond | Q3a | OH |
| 2609 | CMe | S | Q1w | a bond | H | a bond | NH | S | a bond | Q3b | OH |
| 2610 | CMe | S | Q1w | a bond | H | a bond | NH | S | a bond | Q3c | OH |
| 2611 | CMe | S | Q1w | a bond | H | a bond | NH | O | NH | Q3a | OH |
| 2612 | CMe | S | Q1w | a bond | H | a bond | NH | O | NH | Q3b | OH |
| 2613 | CMe | S | Q1w | a bond | H | a bond | NH | O | NH | Q3c | OH |
| 2614 | CMe | S | Q1w | a bond | H | a bond | NH | O | a bond | Q3a | OH |
| 2615 | CMe | S | Q1w | a bond | H | a bond | NH | O | a bond | Q3b | OH |
| 2616 | CMe | S | Q1w | a bond | H | a bond | NH | O | a bond | Q3c | OH |
| 2617 | CMe | S | Q1x | a bond | Me | a bond | NH | S | NH | Q3a | OH |
| 2618 | CMe | S | Q1x | a bond | Me | a bond | NH | S | NH | Q3b | OH |
| 2619 | CMe | S | Q1x | a bond | Me | a bond | NH | S | NH | Q3c | OH |
| 2620 | CMe | S | Q1x | a bond | Me | a bond | NH | S | a bond | Q3a | OH |
| 2621 | CMe | S | Q1x | a bond | Me | a bond | NH | S | a bond | Q3b | OH |
| 2622 | CMe | S | Q1x | a bond | Me | a bond | NH | S | a bond | Q3c | OH |
| 2623 | CMe | S | Q1x | a bond | Me | a bond | NH | O | NH | Q3a | OH |
| 2624 | CMe | S | Q1x | a bond | Me | a bond | NH | O | NH | Q3b | OH |
| 2625 | CMe | S | Q1x | a bond | Me | a bond | NH | O | NH | Q3c | OH |
| 2626 | CMe | S | Q1x | a bond | Me | a bond | NH | O | a bond | Q3a | OH |
| 2627 | CMe | S | Q1x | a bond | Me | a bond | NH | O | a bond | Q3b | OH |
| 2628 | CMe | S | Q1x | a bond | Me | a bond | NH | O | a bond | Q3c | OH |
| 2629 | CMe | S | Q1x | a bond | H | a bond | NH | S | NH | Q3a | OH |
| 2630 | CMe | S | Q1x | a bond | H | a bond | NH | S | NH | Q3b | OH |
| 2631 | CMe | S | Q1x | a bond | H | a bond | NH | S | NH | Q3c | OH |
| 2632 | CMe | S | Q1x | a bond | H | a bond | NH | S | a bond | Q3a | OH |
| 2633 | CMe | S | Q1x | a bond | H | a bond | NH | S | a bond | Q3b | OH |
| 2634 | CMe | S | Q1x | a bond | H | a bond | NH | S | a bond | Q3c | OH |
| 2635 | CMe | S | Q1x | a bond | H | a bond | NH | O | NH | Q3a | OH |
| 2636 | CMe | S | Q1x | a bond | H | a bond | NH | O | NH | Q3b | OH |
| 2637 | CMe | S | Q1x | a bond | H | a bond | NH | O | NH | Q3c | OH |
| 2638 | CMe | S | Q1x | a bond | H | a bond | NH | O | a bond | Q3a | OH |
| 2639 | CMe | S | Q1x | a bond | H | a bond | NH | O | a bond | Q3b | OH |
| 2640 | CMe | S | Q1x | a bond | H | a bond | NH | O | a bond | Q3c | OH |
| 2641 | CMe | O | Q1o | a bond | Me | a bond | NH | S | NH | Q3a | OH |
| 2642 | CMe | O | Q1o | a bond | Me | a bond | NH | S | NH | Q3b | OH |
| 2643 | CMe | O | Q1o | a bond | Me | a bond | NH | S | NH | Q3c | OH |
| 2644 | CMe | O | Q1o | a bond | Me | a bond | NH | S | a bond | Q3a | OH |
| 2645 | CMe | O | Q1o | a bond | Me | a bond | NH | S | a bond | Q3b | OH |
| 2646 | CMe | O | Q1o | a bond | Me | a bond | NH | S | a bond | Q3c | OH |
| 2647 | CMe | O | Q1o | a bond | Me | a bond | NH | O | NH | Q3a | OH |
| 2648 | CMe | O | Q1o | a bond | Me | a bond | NH | O | NH | Q3b | OH |
| 2649 | CMe | O | Q1o | a bond | Me | a bond | NH | O | NH | Q3c | OH |
| 2650 | CMe | O | Q1o | a bond | Me | a bond | NH | O | a bond | Q3a | OH |
| 2651 | CMe | O | Q1o | a bond | Me | a bond | NH | O | a bond | Q3b | OH |
| 2652 | CMe | O | Q1o | a bond | Me | a bond | NH | O | a bond | Q3c | OH |
| 2653 | CMe | O | Q1o | a bond | H | a bond | NH | S | NH | Q3a | OH |
| 2654 | CMe | O | Q1o | a bond | H | a bond | NH | S | NH | Q3b | OH |
| 2655 | CMe | O | Q1o | a bond | H | a bond | NH | S | NH | Q3c | OH |
| 2656 | CMe | O | Q1o | a bond | H | a bond | NH | S | a bond | Q3a | OH |
| 2657 | CMe | O | Q1o | a bond | H | a bond | NH | S | a bond | Q3b | OH |
| 2658 | CMe | O | Q1o | a bond | H | a bond | NH | S | a bond | Q3c | OH |
| 2659 | CMe | O | Q1o | a bond | H | a bond | NH | O | NH | Q3a | OH |
| 2660 | CMe | O | Q1o | a bond | H | a bond | NH | O | NH | Q3b | OH |
| 2661 | CMe | O | Q1o | a bond | H | a bond | NH | O | NH | Q3c | OH |
| 2662 | CMe | O | Q1o | a bond | H | a bond | NH | O | a bond | Q3a | OH |
| 2663 | CMe | O | Q1o | a bond | H | a bond | NH | O | a bond | Q3b | OH |
| 2664 | CMe | O | Q1o | a bond | H | a bond | NH | O | a bond | Q3c | OH |
| 2665 | CMe | O | Q1p | a bond | Me | a bond | NH | S | NH | Q3a | OH |
| 2666 | CMe | O | Q1p | a bond | Me | a bond | NH | S | NH | Q3b | OH |
| 2667 | CMe | O | Q1p | a bond | Me | a bond | NH | S | NH | Q3c | OH |
| 2668 | CMe | O | Q1p | a bond | Me | a bond | NH | S | a bond | Q3a | OH |
| 2669 | CMe | O | Q1p | a bond | Me | a bond | NH | S | a bond | Q3b | OH |
| 2670 | CMe | O | Q1p | a bond | Me | a bond | NH | S | a bond | Q3c | OH |
| 2671 | CMe | O | Q1p | a bond | Me | a bond | NH | O | NH | Q3a | OH |
| 2672 | CMe | O | Q1p | a bond | Me | a bond | NH | O | NH | Q3b | OH |
| 2673 | CMe | O | Q1p | a bond | Me | a bond | NH | O | NH | Q3c | OH |
| 2674 | CMe | O | Q1p | a bond | Me | a bond | NH | O | a bond | Q3a | OH |
| 2675 | CMe | O | Q1p | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2676 | CMe | O | Q1p | a bond | Me | a bond | NH | O | a bond | Q3c | OH |
| 2677 | CMe | O | Q1p | a bond | H | a bond | NH | S | NH | Q3a | OH |
| 2678 | CMe | O | Q1p | a bond | H | a bond | NH | S | NH | Q3b | OH |
| 2679 | CMe | O | Q1p | a bond | H | a bond | NH | S | NH | Q3c | OH |
| 2680 | CMe | O | Q1p | a bond | H | a bond | NH | S | a bond | Q3a | OH |
| 2681 | CMe | O | Q1p | a bond | H | a bond | NH | S | a bond | Q3b | OH |
| 2682 | CMe | O | Q1p | a bond | H | a bond | NH | S | a bond | Q3c | OH |
| 2683 | CMe | O | Q1p | a bond | H | a bond | NH | O | NH | Q3a | OH |
| 2684 | CMe | O | Q1p | a bond | H | a bond | NH | O | NH | Q3b | OH |
| 2685 | CMe | O | Q1p | a bond | H | a bond | NH | O | NH | Q3c | OH |
| 2686 | CMe | O | Q1p | a bond | H | a bond | NH | O | a bond | Q3a | OH |
| 2687 | CMe | O | Q1p | a bond | H | a bond | NH | O | a bond | Q3b | OH |
| 2688 | CMe | O | Q1p | a bond | H | a bond | NH | O | a bond | Q3c | OH |
| 2689 | CMe | O | Q1q | a bond | Me | a bond | NH | S | NH | Q3a | OH |
| 2690 | CMe | O | Q1q | a bond | Me | a bond | NH | S | NH | Q3b | OH |
| 2691 | CMe | O | Q1q | a bond | Me | a bond | NH | S | NH | Q3c | OH |
| 2692 | CMe | O | Q1q | a bond | Me | a bond | NH | S | a bond | Q3a | OH |
| 2693 | CMe | O | Q1q | a bond | Me | a bond | NH | S | a bond | Q3b | OH |
| 2694 | CMe | O | Q1q | a bond | Me | a bond | NH | S | a bond | Q3c | OH |
| 2695 | CMe | O | Q1q | a bond | Me | a bond | NH | O | NH | Q3a | OH |
| 2696 | CMe | O | Q1q | a bond | Me | a bond | NH | O | NH | Q3b | OH |
| 2697 | CMe | O | Q1q | a bond | Me | a bond | NH | O | NH | Q3c | OH |
| 2698 | CMe | O | Q1q | a bond | Me | a bond | NH | O | a bond | Q3a | OH |
| 2699 | CMe | O | Q1q | a bond | Me | a bond | NH | O | a bond | Q3b | OH |
| 2700 | CMe | O | Q1q | a bond | Me | a bond | NH | O | a bond | Q3c | OH |
| 2701 | CMe | O | Q1q | a bond | H | a bond | NH | S | NH | Q3a | OH |
| 2702 | CMe | O | Q1q | a bond | H | a bond | NH | S | NH | Q3b | OH |
| 2703 | CMe | O | Q1q | a bond | H | a bond | NH | S | NH | Q3c | OH |
| 2704 | CMe | O | Q1q | a bond | H | a bond | NH | S | a bond | Q3a | OH |
| 2705 | CMe | O | Q1q | a bond | H | a bond | NH | S | a bond | Q3b | OH |
| 2706 | CMe | O | Q1q | a bond | H | a bond | NH | S | a bond | Q3c | OH |
| 2707 | CMe | O | Q1q | a bond | H | a bond | NH | O | NH | Q3a | OH |
| 2708 | CMe | O | Q1q | a bond | H | a bond | NH | O | NH | Q3b | OH |
| 2709 | CMe | O | Q1q | a bond | H | a bond | NH | O | NH | Q3c | OH |
| 2710 | CMe | O | Q1q | a bond | H | a bond | NH | O | a bond | Q3a | OH |
| 2711 | CMe | O | Q1q | a bond | H | a bond | NH | O | a bond | Q3b | OH |
| 2712 | CMe | O | Q1q | a bond | H | a bond | NH | O | a bond | Q3c | OH |
| 2713 | CMe | O | Q1r | a bond | Me | a bond | NH | S | NH | Q3a | OH |
| 2714 | CMe | O | Q1r | a bond | Me | a bond | NH | S | NH | Q3b | OH |
| 2715 | CMe | O | Q1r | a bond | Me | a bond | NH | S | NH | Q3c | OH |
| 2716 | CMe | O | Q1r | a bond | Me | a bond | NH | S | a bond | Q3a | OH |
| 2717 | CMe | O | Q1r | a bond | Me | a bond | NH | S | a bond | Q3b | OH |
| 2718 | CMe | O | Q1r | a bond | Me | a bond | NH | S | a bond | Q3c | OH |
| 2719 | CMe | O | Q1r | a bond | Me | a bond | NH | O | NH | Q3a | OH |
| 2720 | CMe | O | Q1r | a bond | Me | a bond | NH | O | NH | Q3b | OH |
| 2721 | CMe | O | Q1r | a bond | Me | a bond | NH | O | NH | Q3c | OH |
| 2722 | CMe | O | Q1r | a bond | Me | a bond | NH | O | a bond | Q3a | OH |
| 2723 | CMe | O | Q1r | a bond | Me | a bond | NH | O | a bond | Q3b | OH |
| 2724 | CMe | O | Q1r | a bond | Me | a bond | NH | O | a bond | Q3c | OH |
| 2725 | CMe | O | Q1r | a bond | H | a bond | NH | S | NH | Q3a | OH |
| 2726 | CMe | O | Q1r | a bond | H | a bond | NH | S | NH | Q3b | OH |
| 2727 | CMe | O | Q1r | a bond | H | a bond | NH | S | NH | Q3c | OH |
| 2728 | CMe | O | Q1r | a bond | H | a bond | NH | S | a bond | Q3a | OH |
| 2729 | CMe | O | Q1r | a bond | H | a bond | NH | S | a bond | Q3b | OH |
| 2730 | CMe | O | Q1r | a bond | H | a bond | NH | S | a bond | Q3c | OH |
| 2731 | CMe | O | Q1r | a bond | H | a bond | NH | O | NH | Q3a | OH |
| 2732 | CMe | O | Q1r | a bond | H | a bond | NH | O | NH | Q3b | OH |
| 2733 | CMe | O | Q1r | a bond | H | a bond | NH | O | NH | Q3c | OH |
| 2734 | CMe | O | Q1r | a bond | H | a bond | NH | O | a bond | Q3a | OH |
| 2735 | CMe | O | Q1r | a bond | H | a bond | NH | O | a bond | Q3b | OH |
| 2736 | CMe | O | Q1r | a bond | H | a bond | NH | O | a bond | Q3c | OH |
| 2737 | CMe | O | Q1s | a bond | Me | a bond | NH | S | NH | Q3a | OH |
| 2738 | CMe | O | Q1s | a bond | Me | a bond | NH | S | NH | Q3b | OH |
| 2739 | CMe | O | Q1s | a bond | Me | a bond | NH | S | NH | Q3c | OH |
| 2740 | CMe | O | Q1s | a bond | Me | a bond | NH | S | a bond | Q3a | OH |
| 2741 | CMe | O | Q1s | a bond | Me | a bond | NH | S | a bond | Q3b | OH |
| 2742 | CMe | O | Q1s | a bond | Me | a bond | NH | S | a bond | Q3c | OH |
| 2743 | CMe | O | Q1s | a bond | Me | a bond | NH | O | NH | Q3a | OH |
| 2744 | CMe | O | Q1s | a bond | Me | a bond | NH | O | NH | Q3b | OH |
| 2745 | CMe | O | Q1s | a bond | Me | a bond | NH | O | NH | Q3c | OH |
| 2746 | CMe | O | Q1s | a bond | Me | a bond | NH | O | a bond | Q3a | OH |
| 2747 | CMe | O | Q1s | a bond | Me | a bond | NH | O | a bond | Q3b | OH |
| 2748 | CMe | O | Q1s | a bond | Me | a bond | NH | O | a bond | Q3c | OH |
| 2749 | CMe | O | Q1s | a bond | H | a bond | NH | S | NH | Q3a | OH |
| 2750 | CMe | O | Q1s | a bond | H | a bond | NH | S | NH | Q3b | OH |
| 2751 | CMe | O | Q1s | a bond | H | a bond | NH | S | NH | Q3c | OH |
| 2752 | CMe | O | Q1s | a bond | H | a bond | NH | S | a bond | Q3a | OH |
| 2753 | CMe | O | Q1s | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2754 | CMe | O | Q1s | a bond | H | a bond | NH | S | a bond | Q3c | OH |
| 2755 | CMe | O | Q1s | a bond | H | a bond | NH | O | NH | Q3a | OH |
| 2756 | CMe | O | Q1s | a bond | H | a bond | NH | O | NH | Q3b | OH |
| 2757 | CMe | O | Q1s | a bond | H | a bond | NH | O | NH | Q3c | OH |
| 2758 | CMe | O | Q1s | a bond | H | a bond | NH | O | a bond | Q3a | OH |
| 2759 | CMe | O | Q1s | a bond | H | a bond | NH | O | a bond | Q3b | OH |
| 2760 | CMe | O | Q1s | a bond | H | a bond | NH | O | a bond | Q3c | OH |
| 2761 | CMe | O | Q1t | a bond | Me | a bond | NH | S | NH | Q3a | OH |
| 2762 | CMe | O | Q1t | a bond | Me | a bond | NH | S | NH | Q3b | OH |
| 2763 | CMe | O | Q1t | a bond | Me | a bond | NH | S | NH | Q3c | OH |
| 2764 | CMe | O | Q1t | a bond | Me | a bond | NH | S | a bond | Q3a | OH |
| 2765 | CMe | O | Q1t | a bond | Me | a bond | NH | S | a bond | Q3b | OH |
| 2766 | CMe | O | Q1t | a bond | Me | a bond | NH | S | a bond | Q3c | OH |
| 2767 | CMe | O | Q1t | a bond | Me | a bond | NH | O | NH | Q3a | OH |
| 2768 | CMe | O | Q1t | a bond | Me | a bond | NH | O | NH | Q3b | OH |
| 2769 | CMe | O | Q1t | a bond | Me | a bond | NH | O | NH | Q3c | OH |
| 2770 | CMe | O | Q1t | a bond | Me | a bond | NH | O | a bond | Q3a | OH |
| 2771 | CMe | O | Q1t | a bond | Me | a bond | NH | O | a bond | Q3b | OH |
| 2772 | CMe | O | Q1t | a bond | Me | a bond | NH | O | a bond | Q3c | OH |
| 2773 | CMe | O | Q1t | a bond | H | a bond | NH | S | NH | Q3a | OH |
| 2774 | CMe | O | Q1t | a bond | H | a bond | NH | S | NH | Q3b | OH |
| 2775 | CMe | O | Q1t | a bond | H | a bond | NH | S | NH | Q3c | OH |
| 2776 | CMe | O | Q1t | a bond | H | a bond | NH | S | a bond | Q3a | OH |
| 2777 | CMe | O | Q1t | a bond | H | a bond | NH | S | a bond | Q3b | OH |
| 2778 | CMe | O | Q1t | a bond | H | a bond | NH | S | a bond | Q3c | OH |
| 2779 | CMe | O | Q1t | a bond | H | a bond | NH | O | NH | Q3a | OH |
| 2780 | CMe | O | Q1t | a bond | H | a bond | NH | O | NH | Q3b | OH |
| 2781 | CMe | O | Q1t | a bond | H | a bond | NH | O | NH | Q3c | OH |
| 2782 | CMe | O | Q1t | a bond | H | a bond | NH | O | a bond | Q3a | OH |
| 2783 | CMe | O | Q1t | a bond | H | a bond | NH | O | a bond | Q3b | OH |
| 2784 | CMe | O | Q1t | a bond | H | a bond | NH | O | a bond | Q3c | OH |
| 2785 | CMe | O | Q1u | a bond | Me | a bond | NH | S | NH | Q3a | OH |
| 2786 | CMe | O | Q1u | a bond | Me | a bond | NH | S | NH | Q3b | OH |
| 2787 | CMe | O | Q1u | a bond | Me | a bond | NH | S | NH | Q3c | OH |
| 2788 | CMe | O | Q1u | a bond | Me | a bond | NH | S | a bond | Q3a | OH |
| 2789 | CMe | O | Q1u | a bond | Me | a bond | NH | S | a bond | Q3b | OH |
| 2790 | CMe | O | Q1u | a bond | Me | a bond | NH | S | a bond | Q3c | OH |
| 2791 | CMe | O | Q1u | a bond | Me | a bond | NH | O | NH | Q3a | OH |
| 2792 | CMe | O | Q1u | a bond | Me | a bond | NH | O | NH | Q3b | OH |
| 2793 | CMe | O | Q1u | a bond | Me | a bond | NH | O | NH | Q3c | OH |
| 2794 | CMe | O | Q1u | a bond | Me | a bond | NH | O | a bond | Q3a | OH |
| 2795 | CMe | O | Q1u | a bond | Me | a bond | NH | O | a bond | Q3b | OH |
| 2796 | CMe | O | Q1u | a bond | Me | a bond | NH | O | a bond | Q3c | OH |
| 2797 | CMe | O | Q1u | a bond | H | a bond | NH | S | NH | Q3a | OH |
| 2798 | CMe | O | Q1u | a bond | H | a bond | NH | S | NH | Q3b | OH |
| 2799 | CMe | O | Q1u | a bond | H | a bond | NH | S | NH | Q3c | OH |
| 2800 | CMe | O | Q1u | a bond | H | a bond | NH | S | a bond | Q3a | OH |
| 2801 | CMe | O | Q1u | a bond | H | a bond | NH | S | a bond | Q3b | OH |
| 2802 | CMe | O | Q1u | a bond | H | a bond | NH | S | a bond | Q3c | OH |
| 2803 | CMe | O | Q1u | a bond | H | a bond | NH | O | NH | Q3a | OH |
| 2804 | CMe | O | Q1u | a bond | H | a bond | NH | O | NH | Q3b | OH |
| 2805 | CMe | O | Q1u | a bond | H | a bond | NH | O | NH | Q3c | OH |
| 2806 | CMe | O | Q1u | a bond | H | a bond | NH | O | a bond | Q3a | OH |
| 2807 | CMe | O | Q1u | a bond | H | a bond | NH | O | a bond | Q3b | OH |
| 2808 | CMe | O | Q1u | a bond | H | a bond | NH | O | a bond | Q3c | OH |
| 2809 | CMe | O | Q1v | a bond | Me | a bond | NH | S | NH | Q3a | OH |
| 2810 | CMe | O | Q1v | a bond | Me | a bond | NH | S | NH | Q3b | OH |
| 2811 | CMe | O | Q1v | a bond | Me | a bond | NH | S | NH | Q3c | OH |
| 2812 | CMe | O | Q1v | a bond | Me | a bond | NH | S | a bond | Q3a | OH |
| 2813 | CMe | O | Q1v | a bond | Me | a bond | NH | S | a bond | Q3b | OH |
| 2814 | CMe | O | Q1v | a bond | Me | a bond | NH | S | a bond | Q3c | OH |
| 2815 | CMe | O | Q1v | a bond | Me | a bond | NH | O | NH | Q3a | OH |
| 2816 | CMe | O | Q1v | a bond | Me | a bond | NH | O | NH | Q3b | OH |
| 2817 | CMe | O | Q1v | a bond | Me | a bond | NH | O | NH | Q3c | OH |
| 2818 | CMe | O | Q1v | a bond | Me | a bond | NH | O | a bond | Q3a | OH |
| 2819 | CMe | O | Q1v | a bond | Me | a bond | NH | O | a bond | Q3b | OH |
| 2820 | CMe | O | Q1v | a bond | Me | a bond | NH | O | a bond | Q3c | OH |
| 2821 | CMe | O | Q1v | a bond | H | a bond | NH | S | NH | Q3a | OH |
| 2822 | CMe | O | Q1v | a bond | H | a bond | NH | S | NH | Q3b | OH |
| 2823 | CMe | O | Q1v | a bond | H | a bond | NH | S | NH | Q3c | OH |
| 2824 | CMe | O | Q1v | a bond | H | a bond | NH | S | a bond | Q3a | OH |
| 2825 | CMe | O | Q1v | a bond | H | a bond | NH | S | a bond | Q3b | OH |
| 2826 | CMe | O | Q1v | a bond | H | a bond | NH | S | a bond | Q3c | OH |
| 2827 | CMe | O | Q1v | a bond | H | a bond | NH | O | NH | Q3a | OH |
| 2828 | CMe | O | Q1v | a bond | H | a bond | NH | O | NH | Q3b | OH |
| 2829 | CMe | O | Q1v | a bond | H | a bond | NH | O | NH | Q3c | OH |
| 2830 | CMe | O | Q1v | a bond | H | a bond | NH | O | a bond | Q3a | OH |
| 2831 | CMe | O | Q1v | a bond | H | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2832 | CMe | O | Q1v | a bond | H | a bond | NH | O | a bond | Q3c | OH |
| 2833 | CMe | O | Q1w | a bond | Me | a bond | NH | S | NH | Q3a | OH |
| 2834 | CMe | O | Q1w | a bond | Me | a bond | NH | S | NH | Q3b | OH |
| 2835 | CMe | O | Q1w | a bond | Me | a bond | NH | S | NH | Q3c | OH |
| 2836 | CMe | O | Q1w | a bond | Me | a bond | NH | S | a bond | Q3a | OH |
| 2837 | CMe | O | Q1w | a bond | Me | a bond | NH | S | a bond | Q3b | OH |
| 2838 | CMe | O | Q1w | a bond | Me | a bond | NH | S | a bond | Q3c | OH |
| 2839 | CMe | O | Q1w | a bond | Me | a bond | NH | O | NH | Q3a | OH |
| 2840 | CMe | O | Q1w | a bond | Me | a bond | NH | O | NH | Q3b | OH |
| 2841 | CMe | O | Q1w | a bond | Me | a bond | NH | O | NH | Q3c | OH |
| 2842 | CMe | O | Q1w | a bond | Me | a bond | NH | O | a bond | Q3a | OH |
| 2843 | CMe | O | Q1w | a bond | Me | a bond | NH | O | a bond | Q3b | OH |
| 2844 | CMe | O | Q1w | a bond | Me | a bond | NH | O | a bond | Q3c | OH |
| 2845 | CMe | O | Q1w | a bond | H | a bond | NH | S | NH | Q3a | OH |
| 2846 | CMe | O | Q1w | a bond | H | a bond | NH | S | NH | Q3b | OH |
| 2847 | CMe | O | Q1w | a bond | H | a bond | NH | S | NH | Q3c | OH |
| 2848 | CMe | O | Q1w | a bond | H | a bond | NH | S | a bond | Q3a | OH |
| 2849 | CMe | O | Q1w | a bond | H | a bond | NH | S | a bond | Q3b | OH |
| 2850 | CMe | O | Q1w | a bond | H | a bond | NH | S | a bond | Q3c | OH |
| 2851 | CMe | O | Q1w | a bond | H | a bond | NH | O | NH | Q3a | OH |
| 2852 | CMe | O | Q1w | a bond | H | a bond | NH | O | NH | Q3b | OH |
| 2853 | CMe | O | Q1w | a bond | H | a bond | NH | O | NH | Q3c | OH |
| 2854 | CMe | O | Q1w | a bond | H | a bond | NH | O | a bond | Q3a | OH |
| 2855 | CMe | O | Q1w | a bond | H | a bond | NH | O | a bond | Q3b | OH |
| 2856 | CMe | O | Q1w | a bond | H | a bond | NH | O | a bond | Q3c | OH |
| 2857 | CMe | O | Q1x | a bond | Me | a bond | NH | S | NH | Q3a | OH |
| 2858 | CMe | O | Q1x | a bond | Me | a bond | NH | S | NH | Q3b | OH |
| 2859 | CMe | O | Q1x | a bond | Me | a bond | NH | S | NH | Q3c | OH |
| 2860 | CMe | O | Q1x | a bond | Me | a bond | NH | S | a bond | Q3a | OH |
| 2861 | CMe | O | Q1x | a bond | Me | a bond | NH | S | a bond | Q3b | OH |
| 2862 | CMe | O | Q1x | a bond | Me | a bond | NH | S | a bond | Q3c | OH |
| 2863 | CMe | O | Q1x | a bond | Me | a bond | NH | O | NH | Q3a | OH |
| 2864 | CMe | O | Q1x | a bond | Me | a bond | NH | O | NH | Q3b | OH |
| 2865 | CMe | O | Q1x | a bond | Me | a bond | NH | O | NH | Q3c | OH |
| 2866 | CMe | O | Q1x | a bond | Me | a bond | NH | O | a bond | Q3a | OH |
| 2867 | CMe | O | Q1x | a bond | Me | a bond | NH | O | a bond | Q3b | OH |
| 2868 | CMe | O | Q1x | a bond | Me | a bond | NH | O | a bond | Q3c | OH |
| 2869 | CMe | O | Q1x | a bond | H | a bond | NH | S | NH | Q3a | OH |
| 2870 | CMe | O | Q1x | a bond | H | a bond | NH | S | NH | Q3b | OH |
| 2871 | CMe | O | Q1x | a bond | H | a bond | NH | S | NH | Q3c | OH |
| 2872 | CMe | O | Q1x | a bond | H | a bond | NH | S | a bond | Q3a | OH |
| 2873 | CMe | O | Q1x | a bond | H | a bond | NH | S | a bond | Q3b | OH |
| 2874 | CMe | O | Q1x | a bond | H | a bond | NH | S | a bond | Q3c | OH |
| 2875 | CMe | O | Q1x | a bond | H | a bond | NH | O | NH | Q3a | OH |
| 2876 | CMe | O | Q1x | a bond | H | a bond | NH | O | NH | Q3b | OH |
| 2877 | CMe | O | Q1x | a bond | H | a bond | NH | O | NH | Q3c | OH |
| 2878 | CMe | O | Q1x | a bond | H | a bond | NH | O | a bond | Q3a | OH |
| 2879 | CMe | O | Q1x | a bond | H | a bond | NH | O | a bond | Q3b | OH |
| 2880 | CMe | O | Q1x | a bond | H | a bond | NH | O | a bond | Q3c | OH |
| 2881 | CH | NH | Q1o | a bond | Me | a bond | NH | S | NH | Q3a | OH |
| 2882 | CH | NH | Q1o | a bond | Me | a bond | NH | S | NH | Q3b | OH |
| 2883 | CH | NH | Q1o | a bond | Me | a bond | NH | S | NH | Q3c | OH |
| 2884 | CH | NH | Q1o | a bond | Me | a bond | NH | S | a bond | Q3a | OH |
| 2885 | CH | NH | Q1o | a bond | Me | a bond | NH | S | a bond | Q3b | OH |
| 2886 | CH | NH | Q1o | a bond | Me | a bond | NH | S | a bond | Q3c | OH |
| 2887 | CH | NH | Q1o | a bond | Me | a bond | NH | O | NH | Q3a | OH |
| 2888 | CH | NH | Q1o | a bond | Me | a bond | NH | O | NH | Q3b | OH |
| 2889 | CH | NH | Q1o | a bond | Me | a bond | NH | O | NH | Q3c | OH |
| 2890 | CH | NH | Q1o | a bond | Me | a bond | NH | O | a bond | Q3a | OH |
| 2891 | CH | NH | Q1o | a bond | Me | a bond | NH | O | a bond | Q3b | OH |
| 2892 | CH | NH | Q1o | a bond | Me | a bond | NH | O | a bond | Q3c | OH |
| 2893 | CH | NH | Q1o | a bond | H | a bond | NH | S | NH | Q3a | OH |
| 2894 | CH | NH | Q1o | a bond | H | a bond | NH | S | NH | Q3b | OH |
| 2895 | CH | NH | Q1o | a bond | H | a bond | NH | S | NH | Q3c | OH |
| 2896 | CH | NH | Q1o | a bond | H | a bond | NH | S | a bond | Q3a | OH |
| 2897 | CH | NH | Q1o | a bond | H | a bond | NH | S | a bond | Q3b | OH |
| 2898 | CH | NH | Q1o | a bond | H | a bond | NH | S | a bond | Q3c | OH |
| 2899 | CH | NH | Q1o | a bond | H | a bond | NH | O | NH | Q3a | OH |
| 2900 | CH | NH | Q1o | a bond | H | a bond | NH | O | NH | Q3b | OH |
| 2901 | CH | NH | Q1o | a bond | H | a bond | NH | O | NH | Q3c | OH |
| 2902 | CH | NH | Q1o | a bond | H | a bond | NH | O | a bond | Q3a | OH |
| 2903 | CH | NH | Q1o | a bond | H | a bond | NH | O | a bond | Q3b | OH |
| 2904 | CH | NH | Q1o | a bond | H | a bond | NH | O | a bond | Q3c | OH |
| 2905 | CH | NH | Q1p | a bond | Me | a bond | NH | S | NH | Q3a | OH |
| 2906 | CH | NH | Q1p | a bond | Me | a bond | NH | S | NH | Q3b | OH |
| 2907 | CH | NH | Q1p | a bond | Me | a bond | NH | S | NH | Q3c | OH |
| 2908 | CH | NH | Q1p | a bond | Me | a bond | NH | S | a bond | Q3a | OH |
| 2909 | CH | NH | Q1p | a bond | Me | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2910 | CH | NH | Q1p | a bond | Me | a bond | NH | S | a bond | Q3c | OH |
| 2911 | CH | NH | Q1p | a bond | Me | a bond | NH | O | NH | Q3a | OH |
| 2912 | CH | NH | Q1p | a bond | Me | a bond | NH | O | NH | Q3b | OH |
| 2913 | CH | NH | Q1p | a bond | Me | a bond | NH | O | NH | Q3c | OH |
| 2914 | CH | NH | Q1p | a bond | Me | a bond | NH | O | a bond | Q3a | OH |
| 2915 | CH | NH | Q1p | a bond | Me | a bond | NH | O | a bond | Q3b | OH |
| 2916 | CH | NH | Q1p | a bond | Me | a bond | NH | O | a bond | Q3c | OH |
| 2917 | CH | NH | Q1p | a bond | H | a bond | NH | S | NH | Q3a | OH |
| 2918 | CH | NH | Q1p | a bond | H | a bond | NH | S | NH | Q3b | OH |
| 2919 | CH | NH | Q1p | a bond | H | a bond | NH | S | NH | Q3c | OH |
| 2920 | CH | NH | Q1p | a bond | H | a bond | NH | S | a bond | Q3a | OH |
| 2921 | CH | NH | Q1p | a bond | H | a bond | NH | S | a bond | Q3b | OH |
| 2922 | CH | NH | Q1p | a bond | H | a bond | NH | S | a bond | Q3c | OH |
| 2923 | CH | NH | Q1p | a bond | H | a bond | NH | O | NH | Q3a | OH |
| 2924 | CH | NH | Q1p | a bond | H | a bond | NH | O | NH | Q3b | OH |
| 2925 | CH | NH | Q1p | a bond | H | a bond | NH | O | NH | Q3c | OH |
| 2926 | CH | NH | Q1p | a bond | H | a bond | NH | O | a bond | Q3a | OH |
| 2927 | CH | NH | Q1p | a bond | H | a bond | NH | O | a bond | Q3b | OH |
| 2928 | CH | NH | Q1p | a bond | H | a bond | NH | O | a bond | Q3c | OH |
| 2929 | CH | NH | Q1q | a bond | Me | a bond | NH | S | NH | Q3a | OH |
| 2930 | CH | NH | Q1q | a bond | Me | a bond | NH | S | NH | Q3b | OH |
| 2931 | CH | NH | Q1q | a bond | Me | a bond | NH | S | NH | Q3c | OH |
| 2932 | CH | NH | Q1q | a bond | Me | a bond | NH | S | a bond | Q3a | OH |
| 2933 | CH | NH | Q1q | a bond | Me | a bond | NH | S | a bond | Q3b | OH |
| 2934 | CH | NH | Q1q | a bond | Me | a bond | NH | S | a bond | Q3c | OH |
| 2935 | CH | NH | Q1q | a bond | Me | a bond | NH | O | NH | Q3a | OH |
| 2936 | CH | NH | Q1q | a bond | Me | a bond | NH | O | NH | Q3b | OH |
| 2937 | CH | NH | Q1q | a bond | Me | a bond | NH | O | NH | Q3c | OH |
| 2938 | CH | NH | Q1q | a bond | Me | a bond | NH | O | a bond | Q3a | OH |
| 2939 | CH | NH | Q1q | a bond | Me | a bond | NH | O | a bond | Q3b | OH |
| 2940 | CH | NH | Q1q | a bond | Me | a bond | NH | O | a bond | Q3c | OH |
| 2941 | CH | NH | Q1q | a bond | H | a bond | NH | S | NH | Q3a | OH |
| 2942 | CH | NH | Q1q | a bond | H | a bond | NH | S | NH | Q3b | OH |
| 2943 | CH | NH | Q1q | a bond | H | a bond | NH | S | NH | Q3c | OH |
| 2944 | CH | NH | Q1q | a bond | H | a bond | NH | S | a bond | Q3a | OH |
| 2945 | CH | NH | Q1q | a bond | H | a bond | NH | S | a bond | Q3b | OH |
| 2946 | CH | NH | Q1q | a bond | H | a bond | NH | S | a bond | Q3c | OH |
| 2947 | CH | NH | Q1q | a bond | H | a bond | NH | O | NH | Q3a | OH |
| 2948 | CH | NH | Q1q | a bond | H | a bond | NH | O | NH | Q3b | OH |
| 2949 | CH | NH | Q1q | a bond | H | a bond | NH | O | NH | Q3c | OH |
| 2950 | CH | NH | Q1q | a bond | H | a bond | NH | O | a bond | Q3a | OH |
| 2951 | CH | NH | Q1q | a bond | H | a bond | NH | O | a bond | Q3b | OH |
| 2952 | CH | NH | Q1q | a bond | H | a bond | NH | O | a bond | Q3c | OH |
| 2953 | CH | NH | Q1r | a bond | Me | a bond | NH | S | NH | Q3a | OH |
| 2954 | CH | NH | Q1r | a bond | Me | a bond | NH | S | NH | Q3b | OH |
| 2955 | CH | NH | Q1r | a bond | Me | a bond | NH | S | NH | Q3c | OH |
| 2956 | CH | NH | Q1r | a bond | Me | a bond | NH | S | a bond | Q3a | OH |
| 2957 | CH | NH | Q1r | a bond | Me | a bond | NH | S | a bond | Q3b | OH |
| 2958 | CH | NH | Q1r | a bond | Me | a bond | NH | S | a bond | Q3c | OH |
| 2959 | CH | NH | Q1r | a bond | Me | a bond | NH | O | NH | Q3a | OH |
| 2960 | CH | NH | Q1r | a bond | Me | a bond | NH | O | NH | Q3b | OH |
| 2961 | CH | NH | Q1r | a bond | Me | a bond | NH | O | NH | Q3c | OH |
| 2962 | CH | NH | Q1r | a bond | Me | a bond | NH | O | a bond | Q3a | OH |
| 2963 | CH | NH | Q1r | a bond | Me | a bond | NH | O | a bond | Q3b | OH |
| 2964 | CH | NH | Q1r | a bond | Me | a bond | NH | O | a bond | Q3c | OH |
| 2965 | CH | NH | Q1r | a bond | H | a bond | NH | S | NH | Q3a | OH |
| 2966 | CH | NH | Q1r | a bond | H | a bond | NH | S | NH | Q3b | OH |
| 2967 | CH | NH | Q1r | a bond | H | a bond | NH | S | NH | Q3c | OH |
| 2968 | CH | NH | Q1r | a bond | H | a bond | NH | S | a bond | Q3a | OH |
| 2969 | CH | NH | Q1r | a bond | H | a bond | NH | S | a bond | Q3b | OH |
| 2970 | CH | NH | Q1r | a bond | H | a bond | NH | S | a bond | Q3c | OH |
| 2971 | CH | NH | Q1r | a bond | H | a bond | NH | O | NH | Q3a | OH |
| 2972 | CH | NH | Q1r | a bond | H | a bond | NH | O | NH | Q3b | OH |
| 2973 | CH | NH | Q1r | a bond | H | a bond | NH | O | NH | Q3c | OH |
| 2974 | CH | NH | Q1r | a bond | H | a bond | NH | O | a bond | Q3a | OH |
| 2975 | CH | NH | Q1r | a bond | H | a bond | NH | O | a bond | Q3b | OH |
| 2976 | CH | NH | Q1r | a bond | H | a bond | NH | O | a bond | Q3c | OH |
| 2977 | CH | NH | Q1s | a bond | Me | a bond | NH | S | NH | Q3a | OH |
| 2978 | CH | NH | Q1s | a bond | Me | a bond | NH | S | NH | Q3b | OH |
| 2979 | CH | NH | Q1s | a bond | Me | a bond | NH | S | NH | Q3c | OH |
| 2980 | CH | NH | Q1s | a bond | Me | a bond | NH | S | a bond | Q3a | OH |
| 2981 | CH | NH | Q1s | a bond | Me | a bond | NH | S | a bond | Q3b | OH |
| 2982 | CH | NH | Q1s | a bond | Me | a bond | NH | S | a bond | Q3c | OH |
| 2983 | CH | NH | Q1s | a bond | Me | a bond | NH | O | NH | Q3a | OH |
| 2984 | CH | NH | Q1s | a bond | Me | a bond | NH | O | NH | Q3b | OH |
| 2985 | CH | NH | Q1s | a bond | Me | a bond | NH | O | NH | Q3c | OH |
| 2986 | CH | NH | Q1s | a bond | Me | a bond | NH | O | a bond | Q3a | OH |
| 2987 | CH | NH | Q1s | a bond | Me | a bond | NH | O | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 2988 | CH | NH | Q1s | a bond | Me | a bond | NH | O | a bond | Q3c | OH |
| 2989 | CH | NH | Q1s | a bond | H | a bond | NH | S | NH | Q3a | OH |
| 2990 | CH | NH | Q1s | a bond | H | a bond | NH | S | NH | Q3b | OH |
| 2991 | CH | NH | Q1s | a bond | H | a bond | NH | S | NH | Q3c | OH |
| 2992 | CH | NH | Q1s | a bond | H | a bond | NH | S | a bond | Q3a | OH |
| 2993 | CH | NH | Q1s | a bond | H | a bond | NH | S | a bond | Q3b | OH |
| 2994 | CH | NH | Q1s | a bond | H | a bond | NH | S | a bond | Q3c | OH |
| 2995 | CH | NH | Q1s | a bond | H | a bond | NH | O | NH | Q3a | OH |
| 2996 | CH | NH | Q1s | a bond | H | a bond | NH | O | NH | Q3b | OH |
| 2997 | CH | NH | Q1s | a bond | H | a bond | NH | O | NH | Q3c | OH |
| 2998 | CH | NH | Q1s | a bond | H | a bond | NH | O | a bond | Q3a | OH |
| 2999 | CH | NH | Q1s | a bond | H | a bond | NH | O | a bond | Q3b | OH |
| 3000 | CH | NH | Q1s | a bond | H | a bond | NH | O | a bond | Q3c | OH |
| 3001 | CH | NH | Q1t | a bond | Me | a bond | NH | S | NH | Q3a | OH |
| 3002 | CH | NH | Q1t | a bond | Me | a bond | NH | S | NH | Q3b | OH |
| 3003 | CH | NH | Q1t | a bond | Me | a bond | NH | S | NH | Q3c | OH |
| 3004 | CH | NH | Q1t | a bond | Me | a bond | NH | S | a bond | Q3a | OH |
| 3005 | CH | NH | Q1t | a bond | Me | a bond | NH | S | a bond | Q3b | OH |
| 3006 | CH | NH | Q1t | a bond | Me | a bond | NH | S | a bond | Q3c | OH |
| 3007 | CH | NH | Q1t | a bond | Me | a bond | NH | O | NH | Q3a | OH |
| 3008 | CH | NH | Q1t | a bond | Me | a bond | NH | O | NH | Q3b | OH |
| 3009 | CH | NH | Q1t | a bond | Me | a bond | NH | O | NH | Q3c | OH |
| 3010 | CH | NH | Q1t | a bond | Me | a bond | NH | O | a bond | Q3a | OH |
| 3011 | CH | NH | Q1t | a bond | Me | a bond | NH | O | a bond | Q3b | OH |
| 3012 | CH | NH | Q1t | a bond | Me | a bond | NH | O | a bond | Q3c | OH |
| 3013 | CH | NH | Q1t | a bond | H | a bond | NH | S | NH | Q3a | OH |
| 3014 | CH | NH | Q1t | a bond | H | a bond | NH | S | NH | Q3b | OH |
| 3015 | CH | NH | Q1t | a bond | H | a bond | NH | S | NH | Q3c | OH |
| 3016 | CH | NH | Q1t | a bond | H | a bond | NH | S | a bond | Q3a | OH |
| 3017 | CH | NH | Q1t | a bond | H | a bond | NH | S | a bond | Q3b | OH |
| 3018 | CH | NH | Q1t | a bond | H | a bond | NH | S | a bond | Q3c | OH |
| 3019 | CH | NH | Q1t | a bond | H | a bond | NH | O | NH | Q3a | OH |
| 3020 | CH | NH | Q1t | a bond | H | a bond | NH | O | NH | Q3b | OH |
| 3021 | CH | NH | Q1t | a bond | H | a bond | NH | O | NH | Q3c | OH |
| 3022 | CH | NH | Q1t | a bond | H | a bond | NH | O | a bond | Q3a | OH |
| 3023 | CH | NH | Q1t | a bond | H | a bond | NH | O | a bond | Q3b | OH |
| 3024 | CH | NH | Q1t | a bond | H | a bond | NH | O | a bond | Q3c | OH |
| 3025 | CH | NH | Q1u | a bond | Me | a bond | NH | S | NH | Q3a | OH |
| 3026 | CH | NH | Q1u | a bond | Me | a bond | NH | S | NH | Q3b | OH |
| 3027 | CH | NH | Q1u | a bond | Me | a bond | NH | S | NH | Q3c | OH |
| 3028 | CH | NH | Q1u | a bond | Me | a bond | NH | S | a bond | Q3a | OH |
| 3029 | CH | NH | Q1u | a bond | Me | a bond | NH | S | a bond | Q3b | OH |
| 3030 | CH | NH | Q1u | a bond | Me | a bond | NH | S | a bond | Q3c | OH |
| 3031 | CH | NH | Q1u | a bond | Me | a bond | NH | O | NH | Q3a | OH |
| 3032 | CH | NH | Q1u | a bond | Me | a bond | NH | O | NH | Q3b | OH |
| 3033 | CH | NH | Q1u | a bond | Me | a bond | NH | O | NH | Q3c | OH |
| 3034 | CH | NH | Q1u | a bond | Me | a bond | NH | O | a bond | Q3a | OH |
| 3035 | CH | NH | Q1u | a bond | Me | a bond | NH | O | a bond | Q3b | OH |
| 3036 | CH | NH | Q1u | a bond | Me | a bond | NH | O | a bond | Q3c | OH |
| 3037 | CH | NH | Q1u | a bond | H | a bond | NH | S | NH | Q3a | OH |
| 3038 | CH | NH | Q1u | a bond | H | a bond | NH | S | NH | Q3b | OH |
| 3039 | CH | NH | Q1u | a bond | H | a bond | NH | S | NH | Q3c | OH |
| 3040 | CH | NH | Q1u | a bond | H | a bond | NH | S | a bond | Q3a | OH |
| 3041 | CH | NH | Q1u | a bond | H | a bond | NH | S | a bond | Q3b | OH |
| 3042 | CH | NH | Q1u | a bond | H | a bond | NH | S | a bond | Q3c | OH |
| 3043 | CH | NH | Q1u | a bond | H | a bond | NH | O | NH | Q3a | OH |
| 3044 | CH | NH | Q1u | a bond | H | a bond | NH | O | NH | Q3b | OH |
| 3045 | CH | NH | Q1u | a bond | H | a bond | NH | O | NH | Q3c | OH |
| 3046 | CH | NH | Q1u | a bond | H | a bond | NH | O | a bond | Q3a | OH |
| 3047 | CH | NH | Q1u | a bond | H | a bond | NH | O | a bond | Q3b | OH |
| 3048 | CH | NH | Q1u | a bond | H | a bond | NH | O | a bond | Q3c | OH |
| 3049 | CH | NH | Q1v | a bond | Me | a bond | NH | S | NH | Q3a | OH |
| 3050 | CH | NH | Q1v | a bond | Me | a bond | NH | S | NH | Q3b | OH |
| 3051 | CH | NH | Q1v | a bond | Me | a bond | NH | S | NH | Q3c | OH |
| 3052 | CH | NH | Q1v | a bond | Me | a bond | NH | S | a bond | Q3a | OH |
| 3053 | CH | NH | Q1v | a bond | Me | a bond | NH | S | a bond | Q3b | OH |
| 3054 | CH | NH | Q1v | a bond | Me | a bond | NH | S | a bond | Q3c | OH |
| 3055 | CH | NH | Q1v | a bond | Me | a bond | NH | O | NH | Q3a | OH |
| 3056 | CH | NH | Q1v | a bond | Me | a bond | NH | O | NH | Q3b | OH |
| 3057 | CH | NH | Q1v | a bond | Me | a bond | NH | O | NH | Q3c | OH |
| 3058 | CH | NH | Q1v | a bond | Me | a bond | NH | O | a bond | Q3a | OH |
| 3059 | CH | NH | Q1v | a bond | Me | a bond | NH | O | a bond | Q3b | OH |
| 3060 | CH | NH | Q1v | a bond | Me | a bond | NH | O | a bond | Q3c | OH |
| 3061 | CH | NH | Q1v | a bond | H | a bond | NH | S | NH | Q3a | OH |
| 3062 | CH | NH | Q1v | a bOnd | H | a bond | NH | S | NH | Q3b | OH |
| 3063 | CH | NH | Q1v | a bond | H | a bond | NH | S | NH | Q3c | OH |
| 3064 | CH | NH | Q1v | a bond | H | a bond | NH | S | a bond | Q3a | OH |
| 3065 | CH | NH | Q1v | a bond | H | a bond | NH | S | a bond | Q3b | OH |

TABLE 2-continued

| No | A | B | R¹ | L¹ | R² | L² | L³ | Y | L⁴ | R³ | X |
|---|---|---|---|---|---|---|---|---|---|---|---|
| 3066 | CH | NH | Q1v | a bond | H | a bond | NH | S | a bond | Q3c | OH |
| 3067 | CH | NH | Q1v | a bond | H | a bond | NH | O | NH | Q3a | OH |
| 3068 | CH | NH | Q1v | a bond | H | a bond | NH | O | NH | Q3b | OH |
| 3069 | CH | NH | Q1v | a bond | H | a bond | NH | O | NH | Q3c | OH |
| 3070 | CH | NH | Q1v | a bond | H | a bond | NH | O | a bond | Q3a | OH |
| 3071 | CH | NH | Q1v | a bond | H | a bond | NH | O | a bond | Q3b | OH |
| 3072 | CH | NH | Q1v | a bond | H | a bond | NH | O | a bond | Q3c | OH |
| 3073 | CH | NH | Q1w | a bond | Me | a bond | NH | S | NH | Q3a | OH |
| 3074 | CH | NH | Q1w | a bond | Me | a bond | NH | S | NH | Q3b | OH |
| 3075 | CH | NH | Q1w | a bond | Me | a bond | NH | S | NH | Q3c | OH |
| 3076 | N | NMe | Q1y | a bond | Me | a bond | NH | O | a bond | Q3a | OH |
| 3077 | N | NMe | Q1z | a bond | Me | a bond | NH | O | a bond | Q3a | OH |
| 3078 | CH | NH | Q1w | a bond | Me | a bond | NH | S | a bond | Q3a | OH |
| 3079 | CH | NH | Q1w | a bond | Me | a bond | NH | S | a bond | Q3b | OH |
| 3080 | CH | NH | Q1w | a bond | Me | a bond | NH | S | a bond | Q3c | OH |
| 3081 | CH | NH | Q1w | a bond | Me | a bond | NH | O | NH | Q3a | OH |
| 3082 | CH | NH | Q1w | a bond | Me | a bond | NH | O | NH | Q3b | OH |
| 3083 | CH | NH | Q1w | a bond | Me | a bond | NH | O | NH | Q3c | OH |
| 3084 | CH | NH | Q1w | a bond | Me | a bond | NH | O | a bond | Q3a | OH |
| 3085 | CH | NH | Q1w | a bond | Me | a bond | NH | O | a bond | Q3b | OH |
| 3086 | CH | NH | Q1w | a bond | Me | a bond | NH | O | a bond | Q3c | OH |
| 3087 | CH | NH | Q1w | a bond | H | a bond | NH | S | NH | Q3a | OH |
| 3088 | CH | NH | Q1w | a bond | H | a bond | NH | S | NH | Q3b | OH |
| 3089 | CH | NH | Q1w | a bond | H | a bond | NH | S | NH | Q3c | OH |
| 3090 | CH | NH | Q1w | a bond | H | a bond | NH | S | a bond | Q3a | OH |
| 3091 | CH | NH | Q1w | a bond | H | a bond | NH | S | a bond | Q3b | OH |
| 3092 | CH | NH | Q1w | a bond | H | a bond | NH | S | a bond | Q3c | OH |
| 3093 | CH | NH | Q1w | a bond | H | a bond | NH | O | NH | Q3a | OH |
| 3094 | CH | NH | Q1w | a bond | H | a bond | NH | O | NH | Q3b | OH |
| 3095 | CH | NH | Q1w | a bond | H | a bond | NH | O | NH | Q3c | OH |
| 3096 | CH | NH | Q1w | a bond | H | a bond | NH | O | a bond | Q3a | OH |
| 3097 | CH | NH | Q1w | a bond | H | a bond | NH | O | a bond | Q3b | OH |
| 3098 | CH | NH | Q1w | a bond | H | a bond | NH | O | a bond | Q3c | OH |
| 3099 | CH | NH | Q1x | a bond | Me | a bond | NH | S | NH | Q3a | OH |
| 3100 | CH | NH | Q1x | a bond | Me | a bond | NH | S | NH | Q3b | OH |
| 3101 | CH | NH | Q1x | a bond | Me | a bond | NH | S | NH | Q3c | OH |
| 3102 | CH | NH | Q1x | a bond | Me | a bond | NH | S | a bond | Q3a | OH |
| 3103 | CH | NH | Q1x | a bond | Me | a bond | NH | S | a bond | Q3b | OH |
| 3104 | CH | NH | Q1x | a bond | Me | a bond | NH | S | a bond | Q3c | OH |
| 3105 | CH | NH | Q1x | a bond | Me | a bond | NH | O | NH | Q3a | OH |
| 3106 | CH | NH | Q1x | a bond | Me | a bond | NH | O | NH | Q3b | OH |
| 3107 | CH | NH | Q1x | a bond | Me | a bond | NH | O | NH | Q3c | OH |
| 3108 | CH | NH | Q1x | a bond | Me | a bond | NH | O | a bond | Q3a | OH |
| 3109 | CH | NH | Q1x | a bond | Me | a bond | NH | O | a bond | Q3b | OH |
| 3110 | CH | NH | Q1x | a bond | Me | a bond | NH | O | a bond | Q3c | OH |
| 3111 | CH | NH | Q1x | a bond | H | a bond | NH | S | NH | Q3a | OH |
| 3112 | CH | NH | Q1x | a bond | H | a bond | NH | S | NH | Q3b | OH |
| 3113 | CH | NH | Q1x | a bond | H | a bond | NH | S | NH | Q3c | OH |
| 3114 | CH | NH | Q1x | a bond | H | a bond | NH | S | a bond | Q3a | OH |
| 3115 | CH | NH | Q1x | a bond | H | a bond | NH | S | a bond | Q3b | OH |
| 3116 | CH | NH | Q1x | a bond | H | a bond | NH | S | a bond | Q3c | OH |
| 3117 | CH | NH | Q1x | a bond | H | a bond | NH | O | NH | Q3a | OH |
| 3118 | CH | NH | Q1x | a bond | H | a bond | NH | O | NH | Q3b | OH |
| 3119 | CH | NH | Q1x | a bond | H | a bond | NH | O | NH | Q3c | OH |
| 3120 | CH | NH | Q1x | a bond | H | a bond | NH | O | a bond | Q3a | OH |
| 3121 | CH | NH | Q1x | a bond | H | a bond | NH | O | a bond | Q3b | OH |
| 3122 | CH | NH | Q1x | a bond | H | a bond | NH | O | a bond | Q3c | OH |
| 3123 | CMe | NH | Q1o | a bond | Me | a bond | NH | S | NH | Q3a | OH |
| 3124 | CMe | NH | Q1o | a bond | Me | a bond | NH | S | NH | Q3b | OH |
| 3125 | CMe | NH | Q1o | a bond | Me | a bond | NH | S | NH | Q3c | OH |
| 3126 | CMe | NH | Q1o | a bond | Me | a bond | NH | S | a bond | Q3a | OH |
| 3127 | CMe | NH | Q1o | a bond | Me | a bond | NH | S | a bond | Q3b | OH |
| 3128 | CMe | NH | Q1o | a bond | Me | a bond | NH | S | a bond | Q3c | OH |
| 3129 | CMe | NH | Q1o | a bond | Me | a bond | NH | O | NH | Q3a | OH |
| 3130 | CMe | NH | Q1o | a bond | Me | a bond | NH | O | NH | Q3b | OH |
| 3131 | CMe | NH | Q1o | a bond | Me | a bond | NH | O | NH | Q3c | OH |
| 3132 | CMe | NH | Q1o | a bond | Me | a bond | NH | O | a bond | Q3a | OH |
| 3133 | CMe | NH | Q1o | a bond | Me | a bond | NH | O | a bond | Q3b | OH |
| 3134 | CMe | NH | Q1o | a bond | Me | a bond | NH | O | a bond | Q3c | OH |
| 3135 | CMe | NH | Q1o | a bond | H | a bond | NH | S | NH | Q3a | OH |
| 3136 | CMe | NH | Q1o | a bond | H | a bond | NH | S | NH | Q3b | OH |
| 3137 | CMe | NH | Q1o | a bond | H | a bond | NH | S | NH | Q3c | OH |
| 3138 | CMe | NH | Q1o | a bond | H | a bond | NH | S | a bond | Q3a | OH |
| 3139 | CMe | NH | Q1o | a bond | H | a bond | NH | S | a bond | Q3b | OH |
| 3140 | CMe | NH | Q1o | a bond | H | a bond | NH | S | a bond | Q3c | OH |
| 3141 | CMe | NH | Q1o | a bond | H | a bond | NH | O | NH | Q3a | OH |
| 3142 | CMe | NH | Q1o | a bond | H | a bond | NH | O | NH | Q3b | OH |
| 3143 | CMe | NH | Q1o | a bond | H | a bond | NH | O | NH | Q3c | OH |

TABLE 2-continued

| No | A | B | R¹ | L¹ | R² | L² | L³ | Y | L⁴ | R³ | X |
|---|---|---|---|---|---|---|---|---|---|---|---|
| 3144 | CMe | NH | Q1o | a bond | H | a bond | NH | O | a bond | Q3a | OH |
| 3145 | CMe | NH | Q1o | a bond | H | a bond | NH | O | a bond | Q3b | OH |
| 3146 | CMe | NH | Q1o | a bond | H | a bond | NH | O | a bond | Q3c | OH |
| 3147 | CMe | NH | Q1p | a bond | Me | a bond | NH | S | NH | Q3a | OH |
| 3148 | CMe | NH | Q1p | a bond | Me | a bond | NH | S | NH | Q3b | OH |
| 3149 | CMe | NH | Q1p | a bond | Me | a bond | NH | S | NH | Q3c | OH |
| 3150 | CMe | NH | Q1p | a bond | Me | a bond | NH | S | a bond | Q3a | OH |
| 3151 | CMe | NH | Q1p | a bond | Me | a bond | NH | S | a bond | Q3b | OH |
| 3152 | CMe | NH | Q1p | a bond | Me | a bond | NH | S | a bond | Q3c | OH |
| 3153 | CMe | NH | Q1p | a bond | Me | a bond | NH | O | NH | Q3a | OH |
| 3154 | CMe | NH | Q1p | a bond | Me | a bond | NH | O | NH | Q3b | OH |
| 3155 | CMe | NH | Q1p | a bond | Me | a bond | NH | O | NH | Q3c | OH |
| 3156 | CMe | NH | Q1p | a bond | Me | a bond | NH | O | a bond | Q3a | OH |
| 3157 | CMe | NH | Q1p | a bond | Me | a bond | NH | O | a bond | Q3b | OH |
| 3158 | CMe | NH | Q1p | a bond | Me | a bond | NH | O | a bond | Q3c | OH |
| 3159 | CMe | NH | Q1p | a bond | H | a bond | NH | S | NH | Q3a | OH |
| 3160 | CMe | NH | Q1p | a bond | H | a bond | NH | S | NH | Q3b | OH |
| 3161 | CMe | NH | Q1p | a bond | H | a bond | NH | S | NH | Q3c | OH |
| 3162 | CMe | NH | Q1p | a bond | H | a bond | NH | S | a bond | Q3a | OH |
| 3163 | CMe | NH | Q1p | a bond | H | a bond | NH | S | a bond | Q3b | OH |
| 3164 | CMe | NH | Q1p | a bond | H | a bond | NH | S | a bond | Q3c | OH |
| 3165 | CMe | NH | Q1p | a bond | H | a bond | NH | O | NH | Q3a | OH |
| 3166 | CMe | NH | Q1p | a bond | H | a bond | NH | O | NH | Q3b | OH |
| 3167 | CMe | NH | Q1p | a bond | H | a bond | NH | O | NH | Q3c | OH |
| 3168 | CMe | NH | Q1p | a bond | H | a bond | NH | O | a bond | Q3a | OH |
| 3169 | CMe | NH | Q1p | a bond | H | a bond | NH | O | a bond | Q3b | OH |
| 3170 | CMe | NH | Q1p | a bond | H | a bond | NH | O | a bond | Q3c | OH |
| 3171 | CMe | NH | Q1q | a bond | Me | a bond | NH | S | NH | Q3a | OH |
| 3172 | CMe | NH | Q1q | a bond | Me | a bond | NH | S | NH | Q3b | OH |
| 3173 | CMe | NH | Q1q | a bond | Me | a bond | NH | S | NH | Q3c | OH |
| 3174 | CMe | NH | Q1q | a bond | Me | a bond | NH | S | a bond | Q3a | OH |
| 3175 | CMe | NH | Q1q | a bond | Me | a bond | NH | S | a bond | Q3b | OH |
| 3176 | CMe | NH | Q1q | a bond | Me | a bond | NH | S | a bond | Q3c | OH |
| 3177 | CMe | NH | Q1q | a bond | Me | a bond | NH | O | NH | Q3a | OH |
| 3178 | CMe | NH | Q1q | a bond | Me | a bond | NH | O | NH | Q3b | OH |
| 3179 | CMe | NH | Q1q | a bond | Me | a bond | NH | O | NH | Q3c | OH |
| 3180 | CMe | NH | Q1q | a bond | Me | a bond | NH | O | a bond | Q3a | OH |
| 3181 | CMe | NH | Q1q | a bond | Me | a bond | NH | O | a bond | Q3b | OH |
| 3182 | CMe | NH | Q1q | a bond | Me | a bond | NH | O | a bond | Q3c | OH |
| 3183 | CMe | NH | Q1q | a bond | H | a bond | NH | S | NH | Q3a | OH |
| 3184 | CMe | NH | Q1q | a bond | H | a bond | NH | S | NH | Q3b | OH |
| 3185 | CMe | NH | Q1q | a bond | H | a bond | NH | S | NH | Q3c | OH |
| 3186 | CMe | NH | Q1q | a bond | H | a bond | NH | S | a bond | Q3a | OH |
| 3187 | CMe | NH | Q1q | a bond | H | a bond | NH | S | a bond | Q3b | OH |
| 3188 | CMe | NH | Q1q | a bond | H | a bond | NH | S | a bond | Q3c | OH |
| 3189 | CMe | NH | Q1q | a bond | H | a bond | NH | O | NH | Q3a | OH |
| 3190 | CMe | NH | Q1q | a bond | H | a bond | NH | O | NH | Q3b | OH |
| 3191 | CMe | NH | Q1q | a bond | H | a bond | NH | O | NH | Q3c | OH |
| 3192 | CMe | NH | Q1q | a bond | H | a bond | NH | O | a bond | Q3a | OH |
| 3193 | CMe | NH | Q1q | a bond | H | a bond | NH | O | a bond | Q3b | OH |
| 3194 | CMe | NH | Q1q | a bond | H | a bond | NH | O | a bond | Q3c | OH |
| 3195 | CMe | NH | Q1r | a bond | Me | a bond | NH | S | NH | Q3a | OH |
| 3196 | CMe | NH | Q1r | a bond | Me | a bond | NH | S | NH | Q3b | OH |
| 3197 | CMe | NH | Q1r | a bond | Me | a bond | NH | S | NH | Q3c | OH |
| 3198 | CMe | NH | Q1r | a bond | Me | a bond | NH | S | a bond | Q3a | OH |
| 3199 | CMe | NH | Q1r | a bond | Me | a bond | NH | S | a bond | Q3b | OH |
| 3200 | CMe | NH | Q1r | a bond | Me | a bond | NH | S | a bond | Q3c | OH |
| 3201 | CMe | NH | Q1r | a bond | Me | a bond | NH | O | NH | Q3a | OH |
| 3202 | CMe | NH | Q1r | a bond | Me | a bond | NH | O | NH | Q3b | OH |
| 3203 | CMe | NH | Q1r | a bond | Me | a bond | NH | O | NH | Q3c | OH |
| 3204 | CMe | NH | Q1r | a bond | Me | a bond | NH | O | a bond | Q3a | OH |
| 3205 | CMe | NH | Q1r | a bond | Me | a bond | NH | O | a bond | Q3b | OH |
| 3206 | CMe | NH | Q1r | a bond | Me | a bond | NH | O | a bond | Q3c | OH |
| 3207 | CMe | NH | Q1r | a bond | H | a bond | NH | S | NH | Q3a | OH |
| 3208 | CMe | NH | Q1r | a bond | H | a bond | NH | S | NH | Q3b | OH |
| 3209 | CMe | NH | Q1r | a bond | H | a bond | NH | S | NH | Q3c | OH |
| 3210 | CMe | NH | Q1r | a bond | H | a bond | NH | S | a bond | Q3a | OH |
| 3211 | CMe | NH | Q1r | a bond | H | a bond | NH | S | a bond | Q3b | OH |
| 3212 | CMe | NH | Q1r | a bond | H | a bond | NH | S | a bond | Q3c | OH |
| 3213 | CMe | NH | Q1r | a bond | H | a bond | NH | O | NH | Q3a | OH |
| 3214 | CMe | NH | Q1r | a bond | H | a bond | NH | O | NH | Q3b | OH |
| 3215 | CMe | NH | Q1r | a bond | H | a bond | NH | O | NH | Q3c | OH |
| 3216 | CMe | NH | Q1r | a bond | H | a bond | NH | O | a bond | Q3a | OH |
| 3217 | CMe | NH | Q1r | a bond | H | a bond | NH | O | a bond | Q3b | OH |
| 3218 | CMe | NH | Q1r | a bond | H | a bond | NH | O | a bond | Q3c | OH |
| 3219 | CMe | NH | Q1s | a bond | Me | a bond | NH | S | NH | Q3a | OH |
| 3220 | CMe | NH | Q1s | a bond | Me | a bond | NH | S | NH | Q3b | OH |
| 3221 | CMe | NH | Q1s | a bond | Me | a bond | NH | S | NH | Q3c | OH |

TABLE 2-continued

| No | A | B | R¹ | L¹ | R² | L² | L³ | Y | L⁴ | R³ | X |
|---|---|---|---|---|---|---|---|---|---|---|---|
| 3222 | CMe | NH | Q1s | a bond | Me | a bond | NH | S | a bond | Q3a | OH |
| 3223 | CMe | NH | Q1s | a bond | Me | a bond | NH | S | a bond | Q3b | OH |
| 3224 | CMe | NH | Q1s | a bond | Me | a bond | NH | S | a bond | Q3c | OH |
| 3225 | CMe | NH | Q1s | a bond | Me | a bond | NH | O | NH | Q3a | OH |
| 3226 | CMe | NH | Q1s | a bond | Me | a bond | NH | O | NH | Q3b | OH |
| 3227 | CMe | NH | Q1s | a bond | Me | a bond | NH | O | NH | Q3c | OH |
| 3228 | CMe | NH | Q1s | a bond | Me | a bond | NH | O | a bond | Q3a | OH |
| 3229 | CMe | NH | Q1s | a bond | Me | a bond | NH | O | a bond | Q3b | OH |
| 3230 | CMe | NH | Q1s | a bond | Me | a bond | NH | O | a bond | Q3c | OH |
| 3231 | CMe | NH | Q1s | a bond | H | a bond | NH | S | NH | Q3a | OH |
| 3232 | CMe | NH | Q1s | a bond | H | a bond | NH | S | NH | Q3b | OH |
| 3233 | CMe | NH | Q1s | a bond | H | a bond | NH | S | NH | Q3c | OH |
| 3234 | CMe | NH | Q1s | a bond | H | a bond | NH | S | a bond | Q3a | OH |
| 3235 | CMe | NH | Q1s | a bond | H | a bond | NH | S | a bond | Q3b | OH |
| 3236 | CMe | NH | Q1s | a bond | H | a bond | NH | S | a bond | Q3c | OH |
| 3237 | CMe | NH | Q1s | a bond | H | a bond | NH | O | NH | Q3a | OH |
| 3238 | CMe | NH | Q1s | a bond | H | a bond | NH | O | NH | Q3b | OH |
| 3239 | CMe | NH | Q1s | a bond | H | a bond | NH | O | NH | Q3c | OH |
| 3240 | CMe | NH | Q1s | a bond | H | a bond | NH | O | a bond | Q3a | OH |
| 3241 | CMe | NH | Q1s | a bond | H | a bond | NH | O | a bond | Q3b | OH |
| 3242 | CMe | NH | Q1s | a bond | H | a bond | NH | O | a bond | Q3c | OH |
| 3243 | CMe | NH | Q1t | a bond | Me | a bond | NH | S | NH | Q3a | OH |
| 3244 | CMe | NH | Q1t | a bond | Me | a bond | NH | S | NH | Q3b | OH |
| 3245 | CMe | NH | Q1t | a bond | Me | a bond | NH | S | NH | Q3c | OH |
| 3246 | CMe | NH | Q1t | a bond | Me | a bond | NH | S | a bond | Q3a | OH |
| 3247 | CMe | NH | Q1t | a bond | Me | a bond | NH | S | a bond | Q3b | OH |
| 3248 | CMe | NH | Q1t | a bond | Me | a bond | NH | S | a bond | Q3c | OH |
| 3249 | CMe | NH | Q1t | a bond | Me | a bond | NH | O | NH | Q3a | OH |
| 3250 | CMe | NH | Q1t | a bond | Me | a bond | NH | O | NH | Q3b | OH |
| 3251 | CMe | NH | Q1t | a bond | Me | a bond | NH | O | NH | Q3c | OH |
| 3252 | CMe | NH | Q1t | a bond | Me | a bond | NH | O | a bond | Q3a | OH |
| 3253 | CMe | NH | Q1t | a bond | Me | a bond | NH | O | a bond | Q3b | OH |
| 3254 | CMe | NH | Q1t | a bond | Me | a bond | NH | O | a bond | Q3c | OH |
| 3255 | CMe | NH | Q1t | a bond | H | a bond | NH | S | NH | Q3a | OH |
| 3256 | CMe | NH | Q1t | a bond | H | a bond | NH | S | NH | Q3b | OH |
| 3257 | CMe | NH | Q1t | a bond | H | a bond | NH | S | NH | Q3c | OH |
| 3258 | CMe | NH | Q1t | a bond | H | a bond | NH | S | a bond | Q3a | OH |
| 3259 | CMe | NH | Q1t | a bond | H | a bond | NH | S | a bond | Q3b | OH |
| 3260 | CMe | NH | Q1t | a bond | H | a bond | NH | S | a bond | Q3c | OH |
| 3261 | CMe | NH | Q1t | a bond | H | a bond | NH | O | NH | Q3a | OH |
| 3262 | CMe | NH | Q1t | a bond | H | a bond | NH | O | NH | Q3b | OH |
| 3263 | CMe | NH | Q1t | a bond | H | a bond | NH | O | NH | Q3c | OH |
| 3264 | CMe | NH | Q1t | a bond | H | a bond | NH | O | a bond | Q3a | OH |
| 3265 | CMe | NH | Q1t | a bond | H | a bond | NH | O | a bond | Q3b | OH |
| 3266 | CMe | NH | Q1t | a bond | H | a bond | NH | O | a bond | Q3c | OH |
| 3267 | CMe | NH | Q1u | a bond | Me | a bond | NH | S | NH | Q3a | OH |
| 3268 | CMe | NH | Q1u | a bond | Me | a bond | NH | S | NH | Q3b | OH |
| 3269 | CMe | NH | Q1u | a bond | Me | a bond | NH | S | NH | Q3c | OH |
| 3270 | CMe | NH | Q1u | a bond | Me | a bond | NH | S | a bond | Q3a | OH |
| 3271 | CMe | NH | Q1u | a bond | Me | a bond | NH | S | a bond | Q3b | OH |
| 3272 | CMe | NH | Q1u | a bond | Me | a bond | NH | S | a bond | Q3c | OH |
| 3273 | CMe | NH | Q1u | a bond | Me | a bond | NH | O | NH | Q3a | OH |
| 3274 | CMe | NH | Q1u | a bond | Me | a bond | NH | O | NH | Q3b | OH |
| 3275 | CMe | NH | Q1u | a bond | Me | a bond | NH | O | NH | Q3c | OH |
| 3276 | CMe | NH | Q1u | a bond | Me | a bond | NH | O | a bond | Q3a | OH |
| 3277 | CMe | NH | Q1u | a bond | Me | a bond | NH | O | a bond | Q3b | OH |
| 3278 | CMe | NH | Q1u | a bond | Me | a bond | NH | O | a bond | Q3c | OH |
| 3279 | CMe | NH | Q1u | a bond | H | a bond | NH | S | NH | Q3a | OH |
| 3280 | CMe | NH | Q1u | a bond | H | a bond | NH | S | NH | Q3b | OH |
| 3281 | CMe | NH | Q1u | a bond | H | a bond | NH | S | NH | Q3c | OH |
| 3282 | CMe | NH | Q1u | a bond | H | a bond | NH | S | a bond | Q3a | OH |
| 3283 | CMe | NH | Q1u | a bond | H | a bond | NH | S | a bond | Q3b | OH |
| 3284 | CMe | NH | Q1u | a bond | H | a bond | NH | S | a bond | Q3c | OH |
| 3285 | CMe | NH | Q1u | a bond | H | a bond | NH | O | NH | Q3a | OH |
| 3286 | CMe | NH | Q1u | a bond | H | a bond | NH | O | NH | Q3b | OH |
| 3287 | CMe | NH | Q1u | a bond | H | a bond | NH | O | NH | Q3c | OH |
| 3288 | CMe | NH | Q1u | a bond | H | a bond | NH | O | a bond | Q3a | OH |
| 3289 | CMe | NH | Q1u | a bond | H | a bond | NH | O | a bond | Q3b | OH |
| 3290 | CMe | NH | Q1u | a bond | H | a bond | NH | O | a bond | Q3c | OH |
| 3291 | CMe | NH | Q1v | a bond | Me | a bond | NH | S | NH | Q3a | OH |
| 3292 | CMe | NH | Q1v | a bond | Me | a bond | NH | S | NH | Q3b | OH |
| 3293 | CMe | NH | Q1v | a bond | Me | a bond | NH | S | NH | Q3c | OH |
| 3294 | CMe | NH | Q1v | a bond | Me | a bond | NH | S | a bond | Q3a | OH |
| 3295 | CMe | NH | Q1v | a bond | Me | a bond | NH | S | a bond | Q3b | OH |
| 3296 | CMe | NH | Q1v | a bond | Me | a bond | NH | S | a bond | Q3c | OH |
| 3297 | CMe | NH | Q1v | a bond | Me | a bond | NH | O | NH | Q3a | OH |
| 3298 | CMe | NH | Q1v | a bond | Me | a bond | NH | O | NH | Q3b | OH |
| 3299 | CMe | NH | Q1v | a bond | Me | a bond | NH | O | NH | Q3c | OH |

TABLE 2-continued

| No | A | B | R¹ | L¹ | R² | L² | L³ | Y | L⁴ | R³ | X |
|---|---|---|---|---|---|---|---|---|---|---|---|
| 3300 | CMe | NH | Q1v | a bond | Me | a bond | NH | O | a bond | Q3a | OH |
| 3301 | CMe | NH | Q1v | a bond | Me | a bond | NH | O | a bond | Q3b | OH |
| 3302 | CMe | NH | Q1v | a bond | Me | a bond | NH | O | a bond | Q3c | OH |
| 3303 | CMe | NH | Q1v | a bond | H | a bond | NH | S | NH | Q3a | OH |
| 3304 | CMe | NH | Q1v | a bond | H | a bond | NH | S | NH | Q3b | OH |
| 3305 | CMe | NH | Q1v | a bond | H | a bond | NH | S | NH | Q3c | OH |
| 3306 | CMe | NH | Q1v | a bond | H | a bond | NH | S | a bond | Q3a | OH |
| 3307 | CMe | NH | Q1v | a bond | H | a bond | NH | S | a bond | Q3b | OH |
| 3308 | CMe | NH | Q1v | a bond | H | a bond | NH | S | a bond | Q3c | OH |
| 3309 | CMe | NH | Q1v | a bond | H | a bond | NH | O | NH | Q3a | OH |
| 3310 | CMe | NH | Q1v | a bond | H | a bond | NH | O | NH | Q3b | OH |
| 3311 | CMe | NH | Q1v | a bond | H | a bond | NH | O | NH | Q3c | OH |
| 3312 | CMe | NH | Q1v | a bond | H | a bond | NH | O | a bond | Q3a | OH |
| 3313 | CMe | NH | Q1v | a bond | H | a bond | NH | O | a bond | Q3b | OH |
| 3314 | CMe | NH | Q1v | a bond | H | a bond | NH | O | a bond | Q3c | OH |
| 3315 | CMe | NH | Q1w | a bond | Me | a bond | NH | S | NH | Q3a | OH |
| 3316 | CMe | NH | Q1w | a bond | Me | a bond | NH | S | NH | Q3b | OH |
| 3317 | CMe | NH | Q1w | a bond | Me | a bond | NH | S | NH | Q3c | OH |
| 3318 | CMe | NH | Q1w | a bond | Me | a bond | NH | S | a bond | Q3a | OH |
| 3319 | CMe | NH | Q1w | a bond | Me | a bond | NH | S | a bond | Q3b | OH |
| 3320 | CMe | NH | Q1w | a bond | Me | a bond | NH | S | a bond | Q3c | OH |
| 3321 | CMe | NH | Q1w | a bond | Me | a bond | NH | O | NH | Q3a | OH |
| 3322 | CMe | NH | Q1w | a bond | Me | a bond | NH | O | NH | Q3b | OH |
| 3323 | CMe | NH | Q1w | a bond | Me | a bond | NH | O | NH | Q3c | OH |
| 3324 | CMe | NH | Q1w | a bond | Me | a bond | NH | O | a bond | Q3a | OH |
| 3325 | CMe | NH | Q1w | a bond | Me | a bond | NH | O | a bond | Q3b | OH |
| 3326 | CMe | NH | Q1w | a bond | Me | a bond | NH | O | a bond | Q3c | OH |
| 3327 | CMe | NH | Q1w | a bond | H | a bond | NH | S | NH | Q3a | OH |
| 3328 | CMe | NH | Q1w | a bond | H | a bond | NH | S | NH | Q3b | OH |
| 3329 | CMe | NH | Q1w | a bond | H | a bond | NH | S | NH | Q3c | OH |
| 3330 | CMe | NH | Q1w | a bond | H | a bond | NH | S | a bond | Q3a | OH |
| 3331 | CMe | NH | Q1w | a bond | H | a bond | NH | S | a bond | Q3b | OH |
| 3332 | CMe | NH | Q1w | a bond | H | a bond | NH | S | a bond | Q3c | OH |
| 3333 | CMe | NH | Q1w | a bond | H | a bond | NH | O | NH | Q3a | OH |
| 3334 | CMe | NH | Q1w | a bond | H | a bond | NH | O | NH | Q3b | OH |
| 3335 | CMe | NH | Q1w | a bond | H | a bond | NH | O | NH | Q3c | OH |
| 3336 | CMe | NH | Q1w | a bond | H | a bond | NH | O | a bond | Q3a | OH |
| 3337 | CMe | NH | Q1w | a bond | H | a bond | NH | O | a bond | Q3b | OH |
| 3338 | CMe | NH | Q1w | a bond | H | a bond | NH | O | a bond | Q3c | OH |
| 3339 | CMe | NH | Q1x | a bond | Me | a bond | NH | S | NH | Q3a | OH |
| 3340 | CMe | NH | Q1x | a bond | Me | a bond | NH | S | NH | Q3b | OH |
| 3341 | CMe | NH | Q1x | a bond | Me | a bond | NH | S | NH | Q3c | OH |
| 3342 | CMe | NH | Q1x | a bond | Me | a bond | NH | S | a bond | Q3a | OH |
| 3343 | CMe | NH | Q1x | a bond | Me | a bond | NH | S | a bond | Q3b | OH |
| 3344 | CMe | NH | Q1x | a bond | Me | a bond | NH | S | a bond | Q3c | OH |
| 3345 | CMe | NH | Q1x | a bond | Me | a bond | NH | O | NH | Q3a | OH |
| 3346 | CMe | NH | Q1x | a bond | Me | a bond | NH | O | NH | Q3b | OH |
| 3347 | CMe | NH | Q1x | a bond | Me | a bond | NH | O | NH | Q3c | OH |
| 3348 | CMe | NH | Q1x | a bond | Me | a bond | NH | O | a bond | Q3a | OH |
| 3349 | CMe | NH | Q1x | a bond | Me | a bond | NH | O | a bond | Q3b | OH |
| 3350 | CMe | NH | Q1x | a bond | Me | a bond | NH | O | a bond | Q3c | OH |
| 3351 | CMe | NH | Q1x | a bond | H | a bond | NH | S | NH | Q3a | OH |
| 3352 | CMe | NH | Q1x | a bond | H | a bond | NH | S | NH | Q3b | OH |
| 3353 | CMe | NH | Q1x | a bond | H | a bond | NH | S | NH | Q3c | OH |
| 3354 | CMe | NH | Q1x | a bond | H | a bond | NH | S | a bond | Q3a | OH |
| 3355 | CMe | NH | Q1x | a bond | H | a bond | NH | S | a bond | Q3b | OH |
| 3356 | CMe | NH | Q1x | a bond | H | a bond | NH | S | a bond | Q3c | OH |
| 3357 | CMe | NH | Q1x | a bond | H | a bond | NH | O | NH | Q3a | OH |
| 3358 | CMe | NH | Q1x | a bond | H | a bond | NH | O | NH | Q3b | OH |
| 3359 | CMe | NH | Q1x | a bond | H | a bond | NH | O | NH | Q3c | OH |
| 3360 | CMe | NH | Q1x | a bond | H | a bond | NH | O | a bond | Q3a | OH |
| 3361 | CMe | NH | Q1x | a bond | H | a bond | NH | O | a bond | Q3b | OH |
| 3362 | CMe | NH | Q1x | a bond | H | a bond | NH | O | a bond | Q3c | OH |

70) The compounds wherein A, B, $R^1$, $L^1$, $R^2$, $L^2$, $L^3$, Y, $L^4$, $R^3$ and X are any of the following combinations in Table 3, tautomers, prodrugs or pharmaceutically acceptable salts of the compounds or solvates thereof. The symbols in Table 3 denote the flowing substituents.

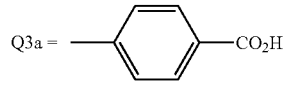

TABLE 3

| No | A | B | $R^1$ | $L^1$ | $R^2$ | $L^2$ | $L^3$ | Y | $L^4$ | $R^3$ | X |
|---|---|---|---|---|---|---|---|---|---|---|---|
| 1 | N | NMe | Q1a | NH | Me | a bond | NH | S | NH | Q3a | OH |
| 2 | N | NMe | Q1a | NH | Me | a bond | NH | S | a bond | Q3a | OH |
| 3 | N | NMe | Q1a | NH | Me | a bond | NH | O | NH | Q3a | OH |
| 4 | N | NMe | Q1a | NH | Me | a bond | NH | O | a bond | Q3a | OH |
| 5 | N | NMe | Q1a | NH | H | a bond | NH | S | NH | Q3a | OH |
| 6 | N | NMe | Q1a | NH | H | a bond | NH | S | a bond | Q3a | OH |
| 7 | N | NMe | Q1a | NH | H | a bond | NH | O | NH | Q3a | OH |
| 8 | N | NMe | Q1a | NH | H | a bond | NH | O | a bond | Q3a | OH |
| 9 | N | NMe | Q1b | NH | Me | a bond | NH | S | NH | Q3a | OH |
| 10 | N | NMe | Q1b | NH | Me | a bond | NH | S | a bond | Q3a | OH |
| 11 | N | NMe | Q1b | NH | Me | a bond | NH | O | NH | Q3a | OH |
| 12 | N | NMe | Q1b | NH | Me | a bond | NH | O | a bond | Q3a | OH |
| 13 | N | NMe | Q1b | NH | H | a bond | NH | S | NH | Q3a | OH |
| 14 | N | NMe | Q1b | NH | H | a bond | NH | S | a bond | Q3a | OH |
| 15 | N | NMe | Q1b | NH | H | a bond | NH | O | NH | Q3a | OH |
| 16 | N | NMe | Q1b | NH | H | a bond | NH | O | a bond | Q3a | OH |
| 17 | N | S | Q1a | NH | Me | a bond | NH | S | NH | Q3a | OH |
| 18 | N | S | Q1a | NH | Me | a bond | NH | S | a bond | Q3a | OH |
| 19 | N | S | Q1a | NH | Me | a bond | NH | O | NH | Q3a | OH |
| 20 | N | S | Q1a | NH | Me | a bond | NH | O | a bond | Q3a | OH |
| 21 | N | S | Q1a | NH | H | a bond | NH | S | NH | Q3a | OH |
| 22 | N | S | Q1a | NH | H | a bond | NH | S | a bond | Q3a | OH |
| 23 | N | S | Q1a | NH | H | a bond | NH | O | NH | Q3a | OH |
| 24 | N | S | Q1a | NH | H | a bond | NH | O | a bond | Q3a | OH |
| 25 | N | S | Q1b | NH | Me | a bond | NH | S | NH | Q3a | OH |
| 26 | N | S | Q1b | NH | Me | a bond | NH | S | a bond | Q3a | OH |
| 27 | N | S | Q1b | NH | Me | a bond | NH | O | NH | Q3a | OH |
| 28 | N | S | Q1b | NH | Me | a bond | NH | O | a bond | Q3a | OH |
| 29 | N | S | Q1b | NH | H | a bond | NH | S | NH | Q3a | OH |
| 30 | N | S | Q1b | NH | H | a bond | NH | S | a bond | Q3a | OH |
| 31 | N | S | Q1b | NH | H | a bond | NH | O | NH | Q3a | OH |
| 32 | N | S | Q1b | NH | H | a bond | NH | O | a bond | Q3a | OH |
| 33 | N | O | Q1a | NH | Me | a bond | NH | S | NH | Q3a | OH |
| 34 | N | O | Q1a | NH | Me | a bond | NH | S | a bond | Q3a | OH |
| 35 | N | O | Q1a | NH | Me | a bond | NH | O | NH | Q3a | OH |
| 36 | N | O | Q1a | NH | Me | a bond | NH | O | a bond | Q3a | OH |
| 37 | N | O | Q1a | NH | H | a bond | NH | S | NH | Q3a | OH |
| 38 | N | O | Q1a | NH | H | a bond | NH | S | a bond | Q3a | OH |
| 39 | N | O | Q1a | NH | H | a bond | NH | O | NH | Q3a | OH |
| 40 | N | O | Q1a | NH | H | a bond | NH | O | a bond | Q3a | OH |
| 41 | N | O | Q1b | NH | Me | a bond | NH | S | NH | Q3a | OH |
| 42 | N | O | Q1b | NH | Me | a bond | NH | S | a bond | Q3a | OH |
| 43 | N | O | Q1b | NH | Me | a bond | NH | O | NH | Q3a | OH |
| 44 | N | O | Q1b | NH | Me | a bond | NH | O | a bond | Q3a | OH |
| 45 | N | O | Q1b | NH | H | a bond | NH | S | NH | Q3a | OH |
| 46 | N | O | Q1b | NH | H | a bond | NH | S | a bond | Q3a | OH |
| 47 | N | O | Q1b | NH | H | a bond | NH | O | NH | Q3a | OH |
| 48 | N | O | Q1b | NH | H | a bond | NH | O | a bond | Q3a | OH |
| 49 | CH | NMe | Q1a | NH | Me | a bond | NH | S | NH | Q3a | OH |
| 50 | CH | NMe | Q1a | NH | Me | a bond | NH | S | a bond | Q3a | OH |
| 51 | CH | NMe | Q1a | NH | Me | a bond | NH | O | NH | Q3a | OH |
| 52 | CH | NMe | Q1a | NH | Me | a bond | NH | O | a bond | Q3a | OH |
| 53 | CH | NMe | Q1a | NH | H | a bond | NH | S | NH | Q3a | OH |
| 54 | CH | NMe | Q1a | NH | H | a bond | NH | S | a bond | Q3a | OH |
| 55 | CH | NMe | Q1a | NH | H | a bond | NH | O | NH | Q3a | OH |
| 56 | CH | NMe | Q1a | NH | H | a bond | NH | O | a bond | Q3a | OH |
| 57 | CH | NMe | Q1b | NH | Me | a bond | NH | S | NH | Q3a | OH |
| 58 | CH | NMe | Q1b | NH | Me | a bond | NH | S | a bond | Q3a | OH |
| 59 | CH | NMe | Q1b | NH | Me | a bond | NH | O | NH | Q3a | OH |
| 60 | CH | NMe | Q1b | NH | Me | a bond | NH | O | a bond | Q3a | OH |
| 61 | CH | NMe | Q1b | NH | H | a bond | NH | S | NH | Q3a | OH |
| 62 | CH | NMe | Q1b | NH | H | a bond | NH | S | a bond | Q3a | OH |
| 63 | CH | NMe | Q1b | NH | H | a bond | NH | O | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 64 | CH | NMe | Q1b | NH | H | a bond | NH | O | a bond | Q3a | OH |
| 65 | CH | S | Q1a | NH | Me | a bond | NH | S | NH | Q3a | OH |
| 66 | CH | S | Q1a | NH | Me | a bond | NH | S | a bond | Q3a | OH |
| 67 | CH | S | Q1a | NH | Me | a bond | NH | O | NH | Q3a | OH |
| 68 | CH | S | Q1a | NH | Me | a bond | NH | O | a bond | Q3a | OH |
| 69 | CH | S | Q1a | NH | H | a bond | NH | S | NH | Q3a | OH |
| 70 | CH | S | Q1a | NH | H | a bond | NH | S | a bond | Q3a | OH |
| 71 | CH | S | Q1a | NH | H | a bond | NH | O | NH | Q3a | OH |
| 72 | CH | S | Q1a | NH | H | a bond | NH | O | a bond | Q3a | OH |
| 73 | CH | S | Q1b | NH | Me | a bond | NH | S | NH | Q3a | OH |
| 74 | CH | S | Q1b | NH | Me | a bond | NH | S | a bond | Q3a | OH |
| 75 | CH | S | Q1b | NH | Me | a bond | NH | O | NH | Q3a | OH |
| 76 | CH | S | Q1b | NH | Me | a bond | NH | O | a bond | Q3a | OH |
| 77 | CH | S | Q1b | NH | H | a bond | NH | S | NH | Q3a | OH |
| 78 | CH | S | Q1b | NH | H | a bond | NH | S | a bond | Q3a | OH |
| 79 | CH | S | Q1b | NH | H | a bond | NH | O | NH | Q3a | OH |
| 80 | CH | S | Q1b | NH | H | a bond | NH | O | a bond | Q3a | OH |
| 81 | CH | O | Q1a | NH | Me | a bond | NH | S | NH | Q3a | OH |
| 82 | CH | O | Q1a | NH | Me | a bond | NH | S | a bond | Q3a | OH |
| 83 | CH | O | Q1a | NH | Me | a bond | NH | O | NH | Q3a | OH |
| 84 | CH | O | Q1a | NH | Me | a bond | NH | O | a bond | Q3a | OH |
| 85 | CH | O | Q1a | NH | H | a bond | NH | S | NH | Q3a | OH |
| 86 | CH | O | Q1a | NH | H | a bond | NH | S | a bond | Q3a | OH |
| 87 | CH | O | Q1a | NH | H | a bond | NH | O | NH | Q3a | OH |
| 88 | CH | O | Q1a | NH | H | a bond | NH | O | a bond | Q3a | OH |
| 89 | CH | O | Q1b | NH | Me | a bond | NH | S | NH | Q3a | OH |
| 90 | CH | O | Q1b | NH | Me | a bond | NH | S | a bond | Q3a | OH |
| 91 | CH | O | Q1b | NH | Me | a bond | NH | O | NH | Q3a | OH |
| 92 | CH | O | Q1b | NH | Me | a bond | NH | O | a bond | Q3a | OH |
| 93 | CH | O | Q1b | NH | H | a bond | NH | S | NH | Q3a | OH |
| 94 | CH | O | Q1b | NH | H | a bond | NH | S | a bond | Q3a | OH |
| 95 | CH | O | Q1b | NH | H | a bond | NH | O | NH | Q3a | OH |
| 96 | CH | O | Q1b | NH | H | a bond | NH | O | a bond | Q3a | OH |
| 97 | CMe | NMe | Q1a | NH | Me | a bond | NH | S | NH | Q3a | OH |
| 98 | CMe | NMe | Q1a | NH | Me | a bond | NH | S | a bond | Q3a | OH |
| 99 | CMe | NMe | Q1a | NH | Me | a bond | NH | O | NH | Q3a | OH |
| 100 | CMe | NMe | Q1a | NH | Me | a bond | NH | O | a bond | Q3a | OH |
| 101 | CMe | NMe | Q1a | NH | H | a bond | NH | S | NH | Q3a | OH |
| 102 | CMe | NMe | Q1a | NH | H | a bond | NH | S | a bond | Q3a | OH |
| 103 | CMe | NMe | Q1a | NH | H | a bond | NH | O | NH | Q3a | OH |
| 104 | CMe | NMe | Q1a | NH | H | a bond | NH | O | a bond | Q3a | OH |
| 105 | CMe | NMe | Q1b | NH | Me | a bond | NH | S | NH | Q3a | OH |
| 106 | CMe | NMe | Q1b | NH | Me | a bond | NH | S | a bond | Q3a | OH |
| 107 | CMe | NMe | Q1b | NH | Me | a bond | NH | O | NH | Q3a | OH |
| 108 | CMe | NMe | Q1b | NH | Me | a bond | NH | O | a bond | Q3a | OH |
| 109 | CMe | NMe | Q1b | NH | H | a bond | NH | S | NH | Q3a | OH |
| 110 | CMe | NMe | Q1b | NH | H | a bond | NH | S | a bond | Q3a | OH |
| 111 | CMe | NMe | Q1b | NH | H | a bond | NH | O | NH | Q3a | OH |
| 112 | CMe | NMe | Q1b | NH | H | a bond | NH | O | a bond | Q3a | OH |
| 113 | CMe | S | Q1a | NH | Me | a bond | NH | S | NH | Q3a | OH |
| 114 | CMe | S | Q1a | NH | Me | a bond | NH | S | a bond | Q3a | OH |
| 115 | CMe | S | Q1a | NH | Me | a bond | NH | O | NH | Q3a | OH |
| 116 | CMe | S | Q1a | NH | Me | a bond | NH | O | a bond | Q3a | OH |
| 117 | CMe | S | Q1a | NH | H | a bond | NH | S | NH | Q3a | OH |
| 118 | CMe | S | Q1a | NH | H | a bond | NH | S | a bond | Q3a | OH |
| 119 | CMe | S | Q1a | NH | H | a bond | NH | O | NH | Q3a | OH |
| 120 | CMe | S | Q1a | NH | H | a bond | NH | O | a bond | Q3a | OH |
| 121 | CMe | S | Q1b | NH | Me | a bond | NH | S | NH | Q3a | OH |
| 122 | CMe | S | Q1b | NH | Me | a bond | NH | S | a bond | Q3a | OH |
| 123 | CMe | S | Q1b | NH | Me | a bond | NH | O | NH | Q3a | OH |
| 124 | CMe | S | Q1b | NH | Me | a bond | NH | O | a bond | Q3a | OH |
| 125 | CMe | S | Q1b | NH | H | a bond | NH | S | NH | Q3a | OH |
| 126 | CMe | S | Q1b | NH | H | a bond | NH | S | a bond | Q3a | OH |
| 127 | CMe | S | Q1b | NH | H | a bond | NH | O | NH | Q3a | OH |
| 128 | CMe | S | Q1b | NH | H | a bond | NH | O | a bond | Q3a | OH |
| 129 | CMe | O | Q1a | NH | Me | a bond | NH | S | NH | Q3a | OH |
| 130 | CMe | O | Q1a | NH | Me | a bond | NH | S | a bond | Q3a | OH |
| 131 | CMe | O | Q1a | NH | Me | a bond | NH | O | NH | Q3a | OH |
| 132 | CMe | O | Q1a | NH | Me | a bond | NH | O | a bond | Q3a | OH |
| 133 | CMe | O | Q1a | NH | H | a bond | NH | S | NH | Q3a | OH |
| 134 | CMe | O | Q1a | NH | H | a bond | NH | S | a bond | Q3a | OH |
| 135 | CMe | O | Q1a | NH | H | a bond | NH | O | NH | Q3a | OH |
| 136 | CMe | O | Q1a | NH | H | a bond | NH | O | a bond | Q3a | OH |
| 137 | CMe | O | Q1b | NH | Me | a bond | NH | S | NH | Q3a | OH |
| 138 | CMe | O | Q1b | NH | Me | a bond | NH | S | a bond | Q3a | OH |
| 139 | CMe | O | Q1b | NH | Me | a bond | NH | O | NH | Q3a | OH |
| 140 | CMe | O | Q1b | NH | Me | a bond | NH | O | a bond | Q3a | OH |
| 141 | CMe | O | Q1b | NH | H | a bond | NH | S | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 142 | CMe | O | Q1b | NH | H | a bond | NH | S | a bond | Q3a | OH |
| 143 | CMe | O | Q1b | NH | H | a bond | NH | O | NH | Q3a | OH |
| 144 | CMe | O | Q1b | NH | H | a bond | NH | O | a bond | Q3a | OH |
| 145 | N | NMe | Q1a | O | Me | a bond | NH | S | NH | Q3a | OH |
| 146 | N | NMe | Q1a | O | Me | a bond | NH | S | a bond | Q3a | OH |
| 147 | N | NMe | Q1a | O | Me | a bond | NH | O | NH | Q3a | OH |
| 148 | N | NMe | Q1a | O | Me | a bond | NH | O | a bond | Q3a | OH |
| 149 | N | NMe | Q1a | O | H | a bond | NH | S | NH | Q3a | OH |
| 150 | N | NMe | Q1a | O | H | a bond | NH | S | a bond | Q3a | OH |
| 151 | N | NMe | Q1a | O | H | a bond | NH | O | NH | Q3a | OH |
| 152 | N | NMe | Q1a | O | H | a bond | NH | O | a bond | Q3a | OH |
| 153 | N | NMe | Q1b | O | Me | a bond | NH | S | NH | Q3a | OH |
| 154 | N | NMe | Q1b | O | Me | a bond | NH | S | a bond | Q3a | OH |
| 155 | N | NMe | Q1b | O | Me | a bond | NH | O | NH | Q3a | OH |
| 156 | N | NMe | Q1b | O | Me | a bond | NH | O | a bond | Q3a | OH |
| 157 | N | NMe | Q1b | O | H | a bond | NH | S | NH | Q3a | OH |
| 158 | N | NMe | Q1b | O | H | a bond | NH | S | a bond | Q3a | OH |
| 159 | N | NMe | Q1b | O | H | a bond | NH | O | NH | Q3a | OH |
| 160 | N | NMe | Q1b | O | H | a bond | NH | O | a bond | Q3a | OH |
| 161 | N | S | Q1a | O | Me | a bond | NH | S | NH | Q3a | OH |
| 162 | N | S | Q1a | O | Me | a bond | NH | S | a bond | Q3a | OH |
| 163 | N | S | Q1a | O | Me | a bond | NH | O | NH | Q3a | OH |
| 164 | N | S | Q1a | O | Me | a bond | NH | O | a bond | Q3a | OH |
| 165 | N | S | Q1a | O | H | a bond | NH | S | NH | Q3a | OH |
| 166 | N | S | Q1a | O | H | a bond | NH | S | a bond | Q3a | OH |
| 167 | N | S | Q1a | O | H | a bond | NH | O | NH | Q3a | OH |
| 168 | N | S | Q1a | O | H | a bond | NH | O | a bond | Q3a | OH |
| 169 | N | S | Q1b | O | Me | a bond | NH | S | NH | Q3a | OH |
| 170 | N | S | Q1b | O | Me | a bond | NH | S | a bond | Q3a | OH |
| 171 | N | S | Q1b | O | Me | a bond | NH | O | NH | Q3a | OH |
| 172 | N | S | Q1b | O | Me | a bond | NH | O | a bond | Q3a | OH |
| 173 | N | S | Q1b | O | H | a bond | NH | S | NH | Q3a | OH |
| 174 | N | S | Q1b | O | H | a bond | NH | S | a bond | Q3a | OH |
| 175 | N | S | Q1b | O | H | a bond | NH | O | NH | Q3a | OH |
| 176 | N | S | Q1b | O | H | a bond | NH | O | a bond | Q3a | OH |
| 177 | N | O | Q1a | O | Me | a bond | NH | S | NH | Q3a | OH |
| 178 | N | O | Q1a | O | Me | a bond | NH | S | a bond | Q3a | OH |
| 179 | N | O | Q1a | O | Me | a bond | NH | O | NH | Q3a | OH |
| 180 | N | O | Q1a | O | Me | a bond | NH | O | a bond | Q3a | OH |
| 181 | N | O | Q1a | O | H | a bond | NH | S | NH | Q3a | OH |
| 182 | N | O | Q1a | O | H | a bond | NH | S | a bond | Q3a | OH |
| 183 | N | O | Q1a | O | H | a bond | NH | O | NH | Q3a | OH |
| 184 | N | O | Q1a | O | H | a bond | NH | O | a bond | Q3a | OH |
| 185 | N | O | Q1b | O | Me | a bond | NH | S | NH | Q3a | OH |
| 186 | N | O | Q1b | O | Me | a bond | NH | S | a bond | Q3a | OH |
| 187 | N | O | Q1b | O | Me | a bond | NH | O | NH | Q3a | OH |
| 188 | N | O | Q1b | O | Me | a bond | NH | O | a bond | Q3a | OH |
| 189 | N | O | Q1b | O | H | a bond | NH | S | NH | Q3a | OH |
| 190 | N | O | Q1b | O | H | a bond | NH | S | a bond | Q3a | OH |
| 191 | N | O | Q1b | O | H | a bond | NH | O | NH | Q3a | OH |
| 192 | N | O | Q1b | O | H | a bond | NH | O | a bond | Q3a | OH |
| 193 | CH | NMe | Q1a | O | Me | a bond | NH | S | NH | Q3a | OH |
| 194 | CH | NMe | Q1a | O | Me | a bond | NH | S | a bond | Q3a | OH |
| 195 | CH | NMe | Q1a | O | Me | a bond | NH | O | NH | Q3a | OH |
| 196 | CH | NMe | Q1a | O | Me | a bond | NH | O | a bond | Q3a | OH |
| 197 | CH | NMe | Q1a | O | H | a bond | NH | S | NH | Q3a | OH |
| 198 | CH | NMe | Q1a | O | H | a bond | NH | S | a bond | Q3a | OH |
| 199 | CH | NMe | Q1a | O | H | a bond | NH | O | NH | Q3a | OH |
| 200 | CH | NMe | Q1a | O | H | a bond | NH | O | a bond | Q3a | OH |
| 201 | CH | NMe | Q1b | O | Me | a bond | NH | S | NH | Q3a | OH |
| 202 | CH | NMe | Q1b | O | Me | a bond | NH | S | a bond | Q3a | OH |
| 203 | CH | NMe | Q1b | O | Me | a bond | NH | O | NH | Q3a | OH |
| 204 | CH | NMe | Q1b | O | Me | a bond | NH | O | a bond | Q3a | OH |
| 205 | CH | NMe | Q1b | O | H | a bond | NH | S | NH | Q3a | OH |
| 206 | CH | NMe | Q1b | O | H | a bond | NH | S | a bond | Q3a | OH |
| 207 | CH | NMe | Q1b | O | H | a bond | NH | O | NH | Q3a | OH |
| 208 | CH | NMe | Q1b | O | H | a bond | NH | O | a bond | Q3a | OH |
| 209 | CH | S | Q1a | O | Me | a bond | NH | S | NH | Q3a | OH |
| 210 | CH | S | Q1a | O | Me | a bond | NH | S | a bond | Q3a | OH |
| 211 | CH | S | Q1a | O | Me | a bond | NH | O | NH | Q3a | OH |
| 212 | CH | S | Q1a | O | Me | a bond | NH | O | a bond | Q3a | OH |
| 213 | CH | S | Q1a | O | H | a bond | NH | S | NH | Q3a | OH |
| 214 | CH | S | Q1a | O | H | a bond | NH | S | a bond | Q3a | OH |
| 215 | CH | S | Q1a | O | H | a bond | NH | O | NH | Q3a | OH |
| 216 | CH | S | Q1a | O | H | a bond | NH | O | a bond | Q3a | OH |
| 217 | CH | S | Q1b | O | Me | a bond | NH | S | NH | Q3a | OH |
| 218 | CH | S | Q1b | O | Me | a bond | NH | S | a bond | Q3a | OH |
| 219 | CH | S | Q1b | O | Me | a bond | NH | O | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 220 | CH | S | Q1b | O | Me | a bond | NH | O | a bond | Q3a | OH |
| 221 | CH | S | Q1b | O | H | a bond | NH | S | NH | Q3a | OH |
| 222 | CH | S | Q1b | O | H | a bond | NH | S | a bond | Q3a | OH |
| 223 | CH | S | Q1b | O | H | a bond | NH | O | NH | Q3a | OH |
| 224 | CH | S | Q1b | O | H | a bond | NH | O | a bond | Q3a | OH |
| 225 | CH | O | Q1a | O | Me | a bond | NH | S | NH | Q3a | OH |
| 226 | CH | O | Q1a | O | Me | a bond | NH | S | a bond | Q3a | OH |
| 227 | CH | O | Q1a | O | Me | a bond | NH | O | NH | Q3a | OH |
| 228 | CH | O | Q1a | O | Me | a bond | NH | O | a bond | Q3a | OH |
| 229 | CH | O | Q1a | O | H | a bond | NH | S | NH | Q3a | OH |
| 230 | CH | O | Q1a | O | H | a bond | NH | S | a bond | Q3a | OH |
| 231 | CH | O | Q1a | O | H | a bond | NH | O | NH | Q3a | OH |
| 232 | CH | O | Q1a | O | H | a bond | NH | O | a bond | Q3a | OH |
| 233 | CH | O | Q1b | O | Me | a bond | NH | S | NH | Q3a | OH |
| 234 | CH | O | Q1b | O | Me | a bond | NH | S | a bond | Q3a | OH |
| 235 | CH | O | Q1b | O | Me | a bond | NH | O | NH | Q3a | OH |
| 236 | CH | O | Q1b | O | Me | a bond | NH | O | a bond | Q3a | OH |
| 237 | CH | O | Q1b | O | H | a bond | NH | S | NH | Q3a | OH |
| 238 | CH | O | Q1b | O | H | a bond | NH | S | a bond | Q3a | OH |
| 239 | CH | O | Q1b | O | H | a bond | NH | O | NH | Q3a | OH |
| 240 | CH | O | Q1b | O | H | a bond | NH | O | a bond | Q3a | OH |
| 241 | CMe | NMe | Q1a | O | Me | a bond | NH | S | NH | Q3a | OH |
| 242 | CMe | NMe | Q1a | O | Me | a bond | NH | S | a bond | Q3a | OH |
| 243 | CMe | NMe | Q1a | O | Me | a bond | NH | O | NH | Q3a | OH |
| 244 | CMe | NMe | Q1a | O | Me | a bond | NH | O | a bond | Q3a | OH |
| 245 | CMe | NMe | Q1a | O | H | a bond | NH | S | NH | Q3a | OH |
| 246 | CMe | NMe | Q1a | O | H | a bond | NH | S | a bond | Q3a | OH |
| 247 | CMe | NMe | Q1a | O | H | a bond | NH | O | NH | Q3a | OH |
| 248 | CMe | NMe | Q1a | O | H | a bond | NH | O | a bond | Q3a | OH |
| 249 | CMe | NMe | Q1b | O | Me | a bond | NH | S | NH | Q3a | OH |
| 250 | CMe | NMe | Q1b | O | Me | a bond | NH | S | a bond | Q3a | OH |
| 251 | CMe | NMe | Q1b | O | Me | a bond | NH | O | NH | Q3a | OH |
| 252 | CMe | NMe | Q1b | O | Me | a bond | NH | O | a bond | Q3a | OH |
| 253 | CMe | NMe | Q1b | O | H | a bond | NH | S | NH | Q3a | OH |
| 254 | CMe | NMe | Q1b | O | H | a bond | NH | S | a bond | Q3a | OH |
| 255 | CMe | NMe | Q1b | O | H | a bond | NH | O | NH | Q3a | OH |
| 256 | CMe | NMe | Q1b | O | H | a bond | NH | O | a bond | Q3a | OH |
| 257 | CMe | S | Q1a | O | Me | a bond | NH | S | NH | Q3a | OH |
| 258 | CMe | S | Q1a | O | Me | a bond | NH | S | a bond | Q3a | OH |
| 259 | CMe | S | Q1a | O | Me | a bond | NH | O | NH | Q3a | OH |
| 260 | CMe | S | Q1a | O | Me | a bond | NH | O | a bond | Q3a | OH |
| 261 | CMe | S | Q1a | O | H | a bond | NH | S | NH | Q3a | OH |
| 262 | CMe | S | Q1a | O | H | a bond | NH | S | a bond | Q3a | OH |
| 263 | CMe | S | Q1a | O | H | a bond | NH | O | NH | Q3a | OH |
| 264 | CMe | S | Q1a | O | H | a bond | NH | O | a bond | Q3a | OH |
| 265 | CMe | S | Q1b | O | Me | a bond | NH | S | NH | Q3a | OH |
| 266 | CMe | S | Q1b | O | Me | a bond | NH | S | a bond | Q3a | OH |
| 267 | CMe | S | Q1b | O | Me | a bond | NH | O | NH | Q3a | OH |
| 268 | CMe | S | Q1b | O | Me | a bond | NH | O | a bond | Q3a | OH |
| 269 | CMe | S | Q1b | O | H | a bond | NH | S | NH | Q3a | OH |
| 270 | CMe | S | Q1b | O | H | a bond | NH | S | a bond | Q3a | OH |
| 271 | CMe | S | Q1b | O | H | a bond | NH | O | NH | Q3a | OH |
| 272 | CMe | S | Q1b | O | H | a bond | NH | O | a bond | Q3a | OH |
| 273 | CMe | O | Q1a | O | Me | a bond | NH | S | NH | Q3a | OH |
| 274 | CMe | O | Q1a | O | Me | a bond | NH | S | a bond | Q3a | OH |
| 275 | CMe | O | Q1a | O | Me | a bond | NH | O | NH | Q3a | OH |
| 276 | CMe | O | Q1a | O | Me | a bond | NH | O | a bond | Q3a | OH |
| 277 | CMe | O | Q1a | O | H | a bond | NH | S | NH | Q3a | OH |
| 278 | CMe | O | Q1a | O | H | a bond | NH | S | a bond | Q3a | OH |
| 279 | CMe | O | Q1a | O | H | a bond | NH | O | NH | Q3a | OH |
| 280 | CMe | O | Q1a | O | H | a bond | NH | O | a bond | Q3a | OH |
| 281 | CMe | O | Q1b | O | Me | a bond | NH | S | NH | Q3a | OH |
| 282 | CMe | O | Q1b | O | Me | a bond | NH | S | a bond | Q3a | OH |
| 283 | CMe | O | Q1b | O | Me | a bond | NH | O | NH | Q3a | OH |
| 284 | CMe | O | Q1b | O | Me | a bond | NH | O | a bond | Q3a | OH |
| 285 | CMe | O | Q1b | O | H | a bond | NH | S | NH | Q3a | OH |
| 286 | CMe | O | Q1b | O | H | a bond | NH | S | a bond | Q3a | OH |
| 287 | CMe | O | Q1b | O | H | a bond | NH | O | NH | Q3a | OH |
| 288 | CMe | O | Q1b | O | H | a bond | NH | O | a bond | Q3a | OH |
| 289 | N | NMe | Q1a | CH2 | Me | a bond | NH | S | NH | Q3a | OH |
| 290 | N | NMe | Q1a | CH2 | Me | a bond | NH | S | a bond | Q3a | OH |
| 291 | N | NMe | Q1a | CH2 | Me | a bond | NH | O | NH | Q3a | OH |
| 292 | N | NMe | Q1a | CH2 | Me | a bond | NH | O | a bond | Q3a | OH |
| 293 | N | NMe | Q1a | CH2 | H | a bond | NH | S | NH | Q3a | OH |
| 294 | N | NMe | Q1a | CH2 | H | a bond | NH | S | a bond | Q3a | OH |
| 295 | N | NMe | Q1a | CH2 | H | a bond | NH | O | NH | Q3a | OH |
| 296 | N | NMe | Q1a | CH2 | H | a bond | NH | O | a bond | Q3a | OH |
| 297 | N | NMe | Q1b | CH2 | Me | a bond | NH | S | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 298 | N | NMe | Q1b | CH2 | Me | a bond | NH | S | a bond | Q3a | OH |
| 299 | N | NMe | Q1b | CH2 | Me | a bond | NH | O | NH | Q3a | OH |
| 300 | N | NMe | Q1b | CH2 | Me | a bond | NH | O | a bond | Q3a | OH |
| 301 | N | NMe | Q1b | CH2 | H | a bond | NH | S | NH | Q3a | OH |
| 302 | N | NMe | Q1b | CH2 | H | a bond | NH | S | a bond | Q3a | OH |
| 303 | N | NMe | Q1b | CH2 | H | a bond | NH | O | NH | Q3a | OH |
| 304 | N | NMe | Q1b | CH2 | H | a bond | NH | O | a bond | Q3a | OH |
| 305 | N | S | Q1a | CH2 | Me | a bond | NH | S | NH | Q3a | OH |
| 306 | N | S | Q1a | CH2 | Me | a bond | NH | S | a bond | Q3a | OH |
| 307 | N | S | Q1a | CH2 | Me | a bond | NH | O | NH | Q3a | OH |
| 308 | N | S | Q1a | CH2 | Me | a bond | NH | O | a bond | Q3a | OH |
| 309 | N | S | Q1a | CH2 | H | a bond | NH | S | NH | Q3a | OH |
| 310 | N | S | Q1a | CH2 | H | a bond | NH | S | a bond | Q3a | OH |
| 311 | N | S | Q1a | CH2 | H | a bond | NH | O | NH | Q3a | OH |
| 312 | N | S | Q1a | CH2 | H | a bond | NH | O | a bond | Q3a | OH |
| 313 | N | S | Q1b | CH2 | Me | a bond | NH | S | NH | Q3a | OH |
| 314 | N | S | Q1b | CH2 | Me | a bond | NH | S | a bond | Q3a | OH |
| 315 | N | S | Q1b | CH2 | Me | a bond | NH | O | NH | Q3a | OH |
| 316 | N | S | Q1b | CH2 | Me | a bond | NH | O | a bond | Q3a | OH |
| 317 | N | S | Q1b | CH2 | H | a bond | NH | S | NH | Q3a | OH |
| 318 | N | S | Q1b | CH2 | H | a bond | NH | S | a bond | Q3a | OH |
| 319 | N | S | Q1b | CH2 | H | a bond | NH | O | NH | Q3a | OH |
| 320 | N | S | Q1b | CH2 | H | a bond | NH | O | a bond | Q3a | OH |
| 321 | N | O | Q1a | CH2 | Me | a bond | NH | S | NH | Q3a | OH |
| 322 | N | O | Q1a | CH2 | Me | a bond | NH | S | a bond | Q3a | OH |
| 323 | N | O | Q1a | CH2 | Me | a bond | NH | O | NH | Q3a | OH |
| 324 | N | O | Q1a | CH2 | Me | a bond | NH | O | a bond | Q3a | OH |
| 325 | N | O | Q1a | CH2 | H | a bond | NH | S | NH | Q3a | OH |
| 326 | N | O | Q1a | CH2 | H | a bond | NH | S | a bond | Q3a | OH |
| 327 | N | O | Q1a | CH2 | H | a bond | NH | O | NH | Q3a | OH |
| 328 | N | O | Q1a | CH2 | H | a bond | NH | O | a bond | Q3a | OH |
| 329 | N | O | Q1b | CH2 | Me | a bond | NH | S | NH | Q3a | OH |
| 330 | N | O | Q1b | CH2 | Me | a bond | NH | S | a bond | Q3a | OH |
| 331 | N | O | Q1b | CH2 | Me | a bond | NH | O | NH | Q3a | OH |
| 332 | N | O | Q1b | CH2 | Me | a bond | NH | O | a bond | Q3a | OH |
| 333 | N | O | Q1b | CH2 | H | a bond | NH | S | NH | Q3a | OH |
| 334 | N | O | Q1b | CH2 | H | a bond | NH | S | a bond | Q3a | OH |
| 335 | N | O | Q1b | CH2 | H | a bond | NH | O | NH | Q3a | OH |
| 336 | N | O | Q1b | CH2 | H | a bond | NH | O | a bond | Q3a | OH |
| 337 | CH | NMe | Q1a | CH2 | Me | a bond | NH | S | NH | Q3a | OH |
| 338 | CH | NMe | Q1a | CH2 | Me | a bond | NH | S | a bond | Q3a | OH |
| 339 | CH | NMe | Q1a | CH2 | Me | a bond | NH | O | NH | Q3 | OH |
| 340 | CH | NMe | Q1a | CH2 | Me | a bond | NH | O | a bond | Q3a | OH |
| 341 | CH | NMe | Q1a | CH2 | H | a bond | NH | S | NH | Q3a | OH |
| 342 | CH | NMe | Q1a | CH2 | H | a bond | NH | S | a bond | Q3a | OH |
| 343 | CH | NMe | Q1a | CH2 | H | a bond | NH | O | NH | Q3a | OH |
| 344 | CH | NMe | Q1a | CH2 | H | a bond | NH | O | a bond | 3a | OH |
| 345 | CH | NMe | Q1b | CH2 | Me | a bond | NH | S | NH | Q3a | OH |
| 346 | CH | NMe | Q1b | CH2 | Me | a bond | NH | S | a bond | Q3a | OH |
| 347 | CH | NMe | Q1b | CH2 | Me | a bond | NH | O | NH | Q3a | OH |
| 348 | CH | NMe | Q1b | CH2 | Me | a bond | NH | O | a bond | Q3a | OH |
| 349 | CH | NMe | Q1b | CH2 | H | a bond | NH | S | NH | Q3a | OH |
| 350 | CH | NMe | Q1b | CH2 | H | a bond | NH | S | a bond | Q3a | OH |
| 351 | CH | NMe | Q1b | CH2 | H | a bond | NH | O | NH | Q3a | OH |
| 352 | CH | NMe | Q1b | CH2 | H | a bond | NH | O | a bond | Q3a | OH |
| 353 | CH | S | Q1a | CH2 | Me | a bond | NH | S | NH | Q3a | OH |
| 354 | CH | S | Q1a | CH2 | Me | a bond | NH | S | a bond | Q3a | OH |
| 355 | CH | S | Q1a | CH2 | Me | a bond | NH | O | NH | Q3a | OH |
| 356 | CH | S | Q1a | CH2 | Me | a bond | NH | O | a bond | Q3a | OH |
| 357 | CH | S | Q1a | CH2 | H | a bond | NH | S | NH | Q3a | OH |
| 358 | CH | S | Q1a | CH2 | H | a bond | NH | S | a bond | Q3a | OH |
| 359 | CH | S | Q1a | CH2 | H | a bond | NH | O | NH | Q3a | OH |
| 360 | CH | S | Q1a | CH2 | H | a bond | NH | O | a bond | Q3a | OH |
| 361 | CH | S | Q1b | CH2 | Me | a bond | NH | S | NH | Q3a | OH |
| 362 | CH | S | Q1b | CH2 | Me | a bond | NH | S | a bond | Q3a | OH |
| 363 | CH | S | Q1b | CH2 | Me | a bond | NH | O | NH | Q3a | OH |
| 364 | CH | S | Q1b | CH2 | Me | a bond | NH | O | a bond | Q3a | OH |
| 365 | CH | S | Q1b | CH2 | H | a bond | NH | S | NH | Q3a | OH |
| 366 | CH | S | Q1b | CH2 | H | a bond | NH | S | a bond | Q3a | OH |
| 367 | CH | S | Q1b | CH2 | H | a bond | NH | O | NH | Q3a | OH |
| 368 | CH | S | Q1b | CH2 | H | a bond | NH | O | a bond | Q3a | OH |
| 369 | CH | O | Q1a | CH2 | Me | a bond | NH | S | NH | Q3a | OH |
| 370 | CH | O | Q1a | CH2 | Me | a bond | NH | S | a bond | Q3a | OH |
| 371 | CH | O | Q1a | CH2 | Me | a bond | NH | O | NH | Q3a | OH |
| 372 | CH | O | Q1a | CH2 | Me | a bond | NH | O | a bond | Q3a | OH |
| 373 | CH | O | Q1a | CH2 | H | a bond | NH | S | NH | Q3a | OH |
| 374 | CH | O | Q1a | CH2 | H | a bond | NH | S | a bond | Q3a | OH |
| 375 | CH | O | Q1a | CH2 | H | a bond | NH | O | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 376 | CH | O | Q1a | CH2 | H | a bond | NH | O | a bond | Q3a | OH |
| 377 | CH | O | Q1b | CH2 | Me | a bond | NH | S | NH | Q3a | OH |
| 378 | CH | O | Q1b | CH2 | Me | a bond | NH | S | a bond | Q3a | OH |
| 379 | CH | O | Q1b | CH2 | Me | a bond | NH | O | NH | Q3a | OH |
| 380 | CH | O | Q1b | CH2 | Me | a bond | NH | O | a bond | Q3a | OH |
| 381 | CH | O | Q1b | CH2 | H | a bond | NH | S | NH | Q3a | OH |
| 382 | CH | O | Q1b | CH2 | H | a bond | NH | S | a bond | Q3a | OH |
| 383 | CH | O | Q1b | CH2 | H | a bond | NH | O | NH | Q3a | OH |
| 384 | CH | O | Q1b | CH2 | H | a bond | NH | O | a bond | Q3a | OH |
| 385 | CMe | NMe | Q1a | CH2 | Me | a bond | NH | S | NH | Q3a | OH |
| 386 | CMe | NMe | Q1a | CH2 | Me | a bond | NH | S | a bond | Q3a | OH |
| 387 | CMe | NMe | Q1a | CH2 | Me | a bond | NH | O | NH | Q3a | OH |
| 388 | CMe | NMe | Q1a | CH2 | Me | a bond | NH | O | a bond | Q3a | OH |
| 389 | CMe | NMe | Q1a | CH2 | H | a bond | NH | S | NH | Q3a | OH |
| 390 | CMe | NMe | Q1a | CH2 | H | a bond | NH | S | a bond | Q3a | OH |
| 391 | CMe | NMe | Q1a | CH2 | H | a bond | NH | O | NH | Q3a | OH |
| 392 | CMe | NMe | Q1a | CH2 | H | a bond | NH | O | a bond | Q3a | OH |
| 393 | CMe | NMe | Q1b | CH2 | Me | a bond | NH | S | NH | Q3a | OH |
| 394 | CMe | NMe | Q1b | CH2 | Me | a bond | NH | S | a bond | Q3a | OH |
| 395 | CMe | NMe | Q1b | CH2 | Me | a bond | NH | O | NH | Q3a | OH |
| 396 | CMe | NMe | Q1b | CH2 | Me | a bond | NH | O | a bond | Q3a | OH |
| 397 | CMe | NMe | Q1b | CH2 | H | a bond | NH | S | NH | Q3a | OH |
| 398 | CMe | NMe | Q1b | CH2 | H | a bond | NH | S | a bond | Q3a | OH |
| 399 | CMe | NMe | Q1b | CH2 | H | a bond | NH | O | NH | Q3a | OH |
| 400 | CMe | NMe | Q1b | CH2 | H | a bond | NH | O | a bond | Q3a | OH |
| 401 | CMe | S | Q1a | CH2 | Me | a bond | NH | S | NH | Q3a | OH |
| 402 | CMe | S | Q1a | CH2 | Me | a bond | NH | S | a bond | Q3a | OH |
| 403 | CMe | S | Q1a | CH2 | Me | a bond | NH | O | NH | Q3a | OH |
| 404 | CMe | S | Q1a | CH2 | Me | a bond | NH | O | a bond | Q3a | OH |
| 405 | CMe | S | Q1a | CH2 | H | a bond | NH | S | NH | Q3a | OH |
| 406 | CMe | S | Q1a | CH2 | H | a bond | NH | S | a bond | Q3a | OH |
| 407 | CMe | S | Q1a | CH2 | H | a bond | NH | O | NH | Q3a | OH |
| 408 | CMe | S | Q1a | CH2 | H | a bond | NH | O | a bond | Q3a | OH |
| 409 | CMe | S | Q1b | CH2 | Me | a bond | NH | S | NH | Q3a | OH |
| 410 | CMe | S | Q1b | CH2 | Me | a bond | NH | S | a bond | Q3a | OH |
| 411 | CMe | S | Q1b | CH2 | Me | a bond | NH | O | NH | Q3a | OH |
| 412 | CMe | S | Q1b | CH2 | Me | a bond | NH | O | a bond | Q3a | OH |
| 413 | CMe | S | Q1b | CH2 | H | a bond | NH | S | NH | Q3a | OH |
| 414 | CMe | S | Q1b | CH2 | H | a bond | NH | S | a bond | Q3a | OH |
| 415 | CMe | S | Q1b | CH2 | H | a bond | NH | O | NH | Q3a | OH |
| 416 | CMe | S | Q1b | CH2 | H | a bond | NH | O | a bond | Q3a | OH |
| 417 | CMe | O | Q1a | CH2 | Me | a bond | NH | S | NH | Q3a | OH |
| 418 | CMe | O | Q1a | CH2 | Me | a bond | NH | S | a bond | Q3a | OH |
| 419 | CMe | O | Q1a | CH2 | Me | a bond | NH | O | NH | Q3a | OH |
| 420 | CMe | O | Q1a | CH2 | Me | a bond | NH | O | a bond | Q3a | OH |
| 421 | CMe | O | Q1a | CH2 | H | a bond | NH | S | NH | Q3a | OH |
| 422 | CMe | O | Q1a | CH2 | H | a bond | NH | S | a bond | Q3a | OH |
| 423 | CMe | O | Q1a | CH2 | H | a bond | NH | O | NH | Q3a | OH |
| 424 | CMe | O | Q1a | CH2 | H | a bond | NH | O | a bond | Q3a | OH |
| 425 | CMe | O | Q1b | CH2 | Me | a bond | NH | S | NH | Q3a | OH |
| 426 | CMe | O | Q1b | CH2 | Me | a bond | NH | S | a bond | Q3a | OH |
| 427 | CMe | O | Q1b | CH2 | Me | a bond | NH | O | NH | Q3a | OH |
| 428 | CMe | O | Q1b | CH2 | Me | a bond | NH | O | a bond | Q3a | OH |
| 429 | CMe | O | Q1b | CH2 | H | a bond | NH | S | NH | Q3a | OH |
| 430 | CMe | O | Q1b | CH2 | H | a bond | NH | S | a bond | Q3a | OH |
| 431 | CMe | O | Q1b | CH2 | H | a bond | NH | O | NH | Q3a | OH |
| 432 | CMe | O | Q1b | CH2 | H | a bond | NH | O | a bond | Q3a | OH |
| 433 | N | NMe | Q1a | a bond | Me | a bond | NH | S | CH2 | Q3a | OH |
| 434 | N | NMe | Q1a | a bond | Me | a bond | NH | O | CH2 | Q3a | OH |
| 435 | N | NMe | Q1a | a bond | H | a bond | NH | S | CH2 | Q3a | OH |
| 436 | N | NMe | Q1a | a bond | H | a bond | NH | O | CH2 | Q3a | OH |
| 437 | N | NMe | Q1b | a bond | Me | a bond | NH | S | CH2 | Q3a | OH |
| 438 | N | NMe | Q1b | a bond | Me | a bond | NH | O | CH2 | Q3a | OH |
| 439 | N | NMe | Q1b | a bond | H | a bond | NH | S | CH2 | Q3a | OH |
| 440 | N | NMe | Q1b | a bond | H | a bond | NH | O | CH2 | Q3a | OH |
| 441 | N | S | Q1a | a bond | Me | a bond | NH | S | CH2 | Q3a | OH |
| 442 | N | S | Q1a | a bond | Me | a bond | NH | O | CH2 | Q3a | OH |
| 443 | N | S | Q1a | a bond | H | a bond | NH | S | CH2 | Q3a | OH |
| 444 | N | S | Q1a | a bond | H | a bond | NH | O | CH2 | Q3a | OH |
| 445 | N | S | Q1b | a bond | Me | a bond | NH | S | CH2 | Q3a | OH |
| 446 | N | S | Q1b | a bond | Me | a bond | NH | O | CH2 | Q3a | OH |
| 447 | N | S | Q1b | a bond | H | a bond | NH | S | CH2 | Q3a | OH |
| 448 | N | S | Q1b | a bond | H | a bond | NH | O | CH2 | Q3a | OH |
| 449 | N | O | Q1a | a bond | Me | a bond | NH | S | CH2 | Q3a | OH |
| 450 | N | O | Q1a | a bond | Me | a bond | NH | O | CH2 | Q3a | OH |
| 451 | N | O | Q1a | a bond | H | a bond | NH | S | CH2 | Q3a | OH |
| 452 | N | O | Q1a | a bond | H | a bond | NH | O | CH2 | Q3a | OH |
| 453 | N | O | Q1b | a bond | Me | a bond | NH | S | CH2 | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 454 | N | O | Q1b | a bond | Me | a bond | NH | O | CH2 | Q3a | OH |
| 455 | N | O | Q1b | a bond | H | a bond | NH | S | CH2 | Q3a | OH |
| 456 | N | O | Q1b | a bond | H | a bond | NH | O | CH2 | Q3a | OH |
| 457 | CH | NMe | Q1a | a bond | Me | a bond | NH | S | CH2 | Q3a | OH |
| 458 | CH | NMe | Q1a | a bond | Me | a bond | NH | O | CH2 | Q3a | OH |
| 459 | CH | NMe | Q1a | a bond | H | a bond | NH | S | CH2 | Q3a | OH |
| 460 | CH | NMe | Q1a | a bond | H | a bond | NH | O | CH2 | Q3a | OH |
| 461 | CH | NMe | Q1b | a bond | Me | a bond | NH | S | CH2 | Q3a | OH |
| 462 | CH | NMe | Q1b | a bond | Me | a bond | NH | O | CH2 | Q3a | OH |
| 463 | CH | NMe | Q1b | a bond | H | a bond | NH | S | CH2 | Q3a | OH |
| 464 | CH | NMe | Q1b | a bond | H | a bond | NH | O | CH2 | Q3a | OH |
| 465 | CH | S | Q1a | a bond | Me | a bond | NH | S | CH2 | Q3a | OH |
| 466 | CH | S | Q1a | a bond | Me | a bond | NH | O | CH2 | Q3a | OH |
| 467 | CH | S | Q1a | a bond | H | a bond | NH | S | CH2 | Q3a | OH |
| 468 | CH | S | Q1a | a bond | H | a bond | NH | O | CH2 | Q3a | OH |
| 469 | CH | S | Q1b | a bond | Me | a bond | NH | S | CH2 | Q3a | OH |
| 470 | CH | S | Q1b | a bond | Me | a bond | NH | O | CH2 | Q3a | OH |
| 471 | CH | S | Q1b | a bond | H | a bond | NH | S | CH2 | Q3a | OH |
| 472 | CH | S | Q1b | a bond | H | a bond | NH | O | CH2 | Q3a | OH |
| 473 | CH | O | Q1a | a bond | Me | a bond | NH | S | CH2 | Q3a | OH |
| 474 | CH | O | Q1a | a bond | Me | a bond | NH | O | CH2 | Q3a | OH |
| 475 | CH | O | Q1a | a bond | H | a bond | NH | S | CH2 | Q3a | OH |
| 476 | CH | O | Q1a | a bond | H | a bond | NH | O | CH2 | Q3a | OH |
| 477 | CH | O | Q1b | a bond | Me | a bond | NH | S | CH2 | Q3a | OH |
| 478 | CH | O | Q1b | a bond | Me | a bond | NH | O | CH2 | Q3a | OH |
| 479 | CH | O | Q1b | a bond | H | a bond | NH | S | CH2 | Q3a | OH |
| 480 | CH | O | Q1b | a bond | H | a bond | NH | O | CH2 | Q3a | OH |
| 481 | CMe | NMe | Q1a | a bond | Me | a bond | NH | S | CH2 | Q3a | OH |
| 482 | CMe | NMe | Q1a | a bond | Me | a bond | NH | O | CH2 | Q3a | OH |
| 483 | CMe | NMe | Q1a | a bond | H | a bond | NH | S | CH2 | Q3a | OH |
| 484 | CMe | NMe | Q1a | a bond | H | a bond | NH | O | CH2 | Q3a | OH |
| 485 | CMe | NMe | Q1b | a bond | Me | a bond | NH | S | CH2 | Q3a | OH |
| 486 | CMe | NMe | Q1b | a bond | Me | a bond | NH | O | CH2 | Q3a | OH |
| 487 | CMe | NMe | Q1b | a bond | H | a bond | NH | S | CH2 | Q3a | OH |
| 488 | CMe | NMe | Q1b | a bond | H | a bond | NH | O | CH2 | Q3a | OH |
| 489 | CMe | S | Q1a | a bond | Me | a bond | NH | S | CH2 | Q3a | OH |
| 490 | CMe | S | Q1a | a bond | Me | a bond | NH | O | CH2 | Q3a | OH |
| 491 | CMe | S | Q1a | a bond | H | a bond | NH | S | CH2 | Q3a | OH |
| 492 | CMe | S | Q1a | a bond | H | a bond | NH | O | CH2 | Q3a | OH |
| 493 | CMe | S | Q1b | a bond | Me | a bond | NH | S | CH2 | Q3a | OH |
| 494 | CMe | S | Q1b | a bond | Me | a bond | NH | O | CH2 | Q3a | OH |
| 495 | CMe | S | Q1b | a bond | H | a bond | NH | S | CH2 | Q3a | OH |
| 496 | CMe | S | Q1b | a bond | H | a bond | NH | O | CH2 | Q3a | OH |
| 497 | CMe | O | Q1a | a bond | Me | a bond | NH | S | CH2 | Q3a | OH |
| 498 | CMe | O | Q1a | a bond | Me | a bond | NH | O | CH2 | Q3a | OH |
| 499 | CMe | O | Q1a | a bond | H | a bond | NH | S | CH2 | Q3a | OH |
| 500 | CMe | O | Q1a | a bond | H | a bond | NH | O | CH2 | Q3a | OH |
| 501 | CMe | O | Q1b | a bond | Me | a bond | NH | S | CH2 | Q3a | OH |
| 502 | CMe | O | Q1b | a bond | Me | a bond | NH | O | CH2 | Q3a | OH |
| 503 | CMe | O | Q1b | a bond | H | a bond | NH | S | CH2 | Q3a | OH |
| 504 | CMe | O | Q1b | a bond | H | a bond | NH | O | CH2 | Q3a | OH |
| 505 | N | NMe | Q1a | a bond | Me | a bond | CH2 | S | a bond | Q3a | OH |
| 506 | N | NMe | Q1a | a bond | Me | a bond | CH2 | S | NH | Q3a | OH |
| 507 | N | NMe | Q1a | a bond | Me | a bond | CH2 | O | a bond | Q3a | OH |
| 508 | N | NMe | Q1a | a bond | Me | a bond | CH2 | O | NH | Q3a | OH |
| 509 | N | NMe | Q1a | a bond | H | a bond | CH2 | S | a bond | Q3a | OH |
| 510 | N | NMe | Q1a | a bond | H | a bond | CH2 | S | NH | Q3a | OH |
| 511 | N | NMe | Q1a | a bond | H | a bond | CH2 | O | a bond | Q3a | OH |
| 512 | N | NMe | Q1a | a bond | H | a bond | CH2 | O | NH | Q3a | OH |
| 513 | N | NMe | Q1b | a bond | Me | a bond | CH2 | S | a bond | Q3a | OH |
| 514 | N | NMe | Q1b | a bond | Me | a bond | CH2 | S | NH | Q3a | OH |
| 515 | N | NMe | Q1b | a bond | Me | a bond | CH2 | O | a bond | Q3a | OH |
| 516 | N | NMe | Q1b | a bond | Me | a bond | CH2 | O | NH | Q3a | OH |
| 517 | N | NMe | Q1b | a bond | H | a bond | CH2 | S | a bond | Q3a | OH |
| 518 | N | NMe | Q1b | a bond | H | a bond | CH2 | S | NH | Q3a | OH |
| 519 | N | NMe | Q1b | a bond | H | a bond | CH2 | O | a bond | Q3a | OH |
| 520 | N | NMe | Q1b | a bond | H | a bond | CH2 | O | NH | Q3a | OH |
| 521 | N | S | Q1a | a bond | Me | a bond | CH2 | S | a bond | Q3a | OH |
| 522 | N | S | Q1a | a bond | Me | a bond | CH2 | S | NH | Q3a | OH |
| 523 | N | S | Q1a | a bond | Me | a bond | CH2 | O | a bond | Q3a | OH |
| 524 | N | S | Q1a | a bond | Me | a bond | CH2 | O | NH | Q3a | OH |
| 525 | N | S | Q1a | a bond | H | a bond | CH2 | S | a bond | Q3a | OH |
| 526 | N | S | Q1a | a bond | H | a bond | CH2 | S | NH | Q3a | OH |
| 527 | N | S | Q1a | a bond | H | a bond | CH2 | O | a bond | Q3a | OH |
| 528 | N | S | Q1a | a bond | H | a bond | CH2 | O | NH | Q3a | OH |
| 529 | N | S | Q1b | a bond | Me | a bond | CH2 | S | a bond | Q3a | OH |
| 530 | N | S | Q1b | a bond | Me | a bond | CH2 | S | NH | Q3a | OH |
| 531 | N | S | Q1b | a bond | Me | a bond | CH2 | O | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 532 | N | S | Q1b | a bond | Me | a bond | CH2 | O | NH | Q3a | OH |
| 533 | N | S | Q1b | a bond | H | a bond | CH2 | S | a bond | Q3a | OH |
| 534 | N | S | Q1b | a bond | H | a bond | CH2 | S | NH | Q3a | OH |
| 535 | N | S | Q1b | a bond | H | a bond | CH2 | O | a bond | Q3a | OH |
| 536 | N | S | Q1b | a bond | H | a bond | CH2 | O | NH | Q3a | OH |
| 537 | N | O | Q1a | a bond | Me | a bond | CH2 | S | a bond | Q3a | OH |
| 538 | N | O | Q1a | a bond | Me | a bond | CH2 | S | NH | Q3a | OH |
| 539 | N | O | Q1a | a bond | Me | a bond | CH2 | O | a bond | Q3a | OH |
| 540 | N | O | Q1a | a bond | Me | a bond | CH2 | O | NH | Q3a | OH |
| 541 | N | O | Q1a | a bond | H | a bond | CH2 | S | a bond | Q3a | OH |
| 542 | N | O | Q1a | a bond | H | a bond | CH2 | S | NH | Q3a | OH |
| 543 | N | O | Q1a | a bond | H | a bond | CH2 | O | a bond | Q3a | OH |
| 544 | N | O | Q1a | a bond | H | a bond | CH2 | O | NH | Q3a | OH |
| 545 | N | O | Q1b | a bond | Me | a bond | CH2 | S | a bond | Q3a | OH |
| 546 | N | O | Q1b | a bond | Me | a bond | CH2 | S | NH | Q3a | OH |
| 547 | N | O | Q1b | a bond | Me | a bond | CH2 | O | a bond | Q3a | OH |
| 548 | N | O | Q1b | a bond | Me | a bond | CH2 | O | NH | Q3a | OH |
| 549 | N | O | Q1b | a bond | H | a bond | CH2 | S | a bond | Q3a | OH |
| 550 | N | O | Q1b | a bond | H | a bond | CH2 | S | NH | Q3a | OH |
| 551 | N | O | Q1b | a bond | H | a bond | CH2 | O | a bond | Q3a | OH |
| 552 | N | O | Q1b | a bond | H | a bond | CH2 | O | NH | Q3a | OH |
| 553 | CH | NMe | Q1a | a bond | Me | a bond | CH2 | S | a bond | Q3a | OH |
| 554 | CH | NMe | Q1a | a bond | Me | a bond | CH2 | S | NH | Q3a | OH |
| 555 | CH | NMe | Q1a | a bond | Me | a bond | CH2 | O | a bond | Q3a | OH |
| 556 | CH | NMe | Q1a | a bond | Me | a bond | CH2 | O | NH | Q3a | OH |
| 557 | CH | NMe | Q1a | a bond | H | a bond | CH2 | S | a bond | Q3a | OH |
| 558 | CH | NMe | Q1a | a bond | H | a bond | CH2 | S | NH | Q3a | OH |
| 559 | CH | NMe | Q1a | a bond | H | a bond | CH2 | O | a bond | Q3a | OH |
| 560 | CH | NMe | Q1a | a bond | H | a bond | CH2 | O | NH | Q3a | OH |
| 561 | CH | NMe | Q1b | a bond | Me | a bond | CH2 | S | a bond | Q3a | OH |
| 562 | CH | NMe | Q1b | a bond | Me | a bond | CH2 | S | NH | Q3a | OH |
| 563 | CH | NMe | Q1b | a bond | Me | a bond | CH2 | O | a bond | Q3a | OH |
| 564 | CH | NMe | Q1b | a bond | Me | a bond | CH2 | O | NH | Q3a | OH |
| 565 | CH | NMe | Q1b | a bond | H | a bond | CH2 | S | a bond | Q3a | OH |
| 566 | CH | NMe | Q1b | a bond | H | a bond | CH2 | S | NH | Q3a | OH |
| 567 | CH | NMe | Q1b | a bond | H | a bond | CH2 | O | a bond | Q3a | OH |
| 568 | CH | NMe | Q1b | a bond | H | a bond | CH2 | O | NH | Q3a | OH |
| 569 | CH | S | Q1a | a bond | Me | a bond | CH2 | S | a bond | Q3a | OH |
| 570 | CH | S | Q1a | a bond | Me | a bond | CH2 | S | NH | Q3a | OH |
| 571 | CH | S | Q1a | a bond | Me | a bond | CH2 | O | a bond | Q3a | OH |
| 572 | CH | S | Q1a | a bond | Me | a bond | CH2 | O | NH | Q3a | OH |
| 573 | CH | S | Q1a | a bond | H | a bond | CH2 | S | a bond | Q3a | OH |
| 574 | CH | S | Q1a | a bond | H | a bond | CH2 | S | NH | Q3a | OH |
| 575 | CH | S | Q1a | a bond | H | a bond | CH2 | O | a bond | Q3a | OH |
| 576 | CH | S | Q1a | a bond | H | a bond | CH2 | O | NH | Q3a | OH |
| 577 | CH | S | Q1b | a bond | Me | a bond | CH2 | S | a bond | Q3a | OH |
| 578 | CH | S | Q1b | a bond | Me | a bond | CH2 | S | NH | Q3a | OH |
| 579 | CH | S | Q1b | a bond | Me | a bond | CH2 | O | a bond | Q3a | OH |
| 580 | CH | S | Q1b | a bond | Me | a bond | CH2 | O | NH | Q3a | OH |
| 581 | CH | S | Q1b | a bond | H | a bond | CH2 | S | a bond | Q3a | OH |
| 582 | CH | S | Q1b | a bond | H | a bond | CH2 | S | NH | Q3a | OH |
| 583 | CH | S | Q1b | a bond | H | a bond | CH2 | O | a bond | Q3a | OH |
| 584 | CH | S | Q1b | a bond | H | a bond | CH2 | O | NH | Q3a | OH |
| 585 | CH | O | Q1a | a bond | Me | a bond | CH2 | S | a bond | Q3a | OH |
| 586 | CH | O | Q1a | a bond | Me | a bond | CH2 | S | NH | Q3a | OH |
| 587 | CH | O | Q1a | a bond | Me | a bond | CH2 | O | a bond | Q3a | OH |
| 588 | CH | O | Q1a | a bond | Me | a bond | CH2 | O | NH | Q3a | OH |
| 589 | CH | O | Q1a | a bond | H | a bond | CH2 | S | a bond | Q3a | OH |
| 590 | CH | O | Q1a | a bond | H | a bond | CH2 | S | NH | Q3a | OH |
| 591 | CH | O | Q1a | a bond | H | a bond | CH2 | O | a bond | Q3a | OH |
| 592 | CH | O | Q1a | a bond | H | a bond | CH2 | O | NH | Q3a | OH |
| 593 | CH | O | Q1b | a bond | Me | a bond | CH2 | S | a bond | Q3a | OH |
| 594 | CH | O | Q1b | a bond | Me | a bond | CH2 | S | NH | Q3a | OH |
| 595 | CH | O | Q1b | a bond | Me | a bond | CH2 | O | a bond | Q3a | OH |
| 596 | CH | O | Q1b | a bond | Me | a bond | CH2 | O | NH | Q3a | OH |
| 597 | CH | O | Q1b | a bond | H | a bond | CH2 | S | a bond | Q3a | OH |
| 598 | CH | O | Q1b | a bond | H | a bond | CH2 | S | NH | Q3a | OH |
| 599 | CH | O | Q1b | a bond | H | a bond | CH2 | O | a bond | Q3a | OH |
| 600 | CH | O | Q1b | a bond | H | a bond | CH2 | O | NH | Q3a | OH |
| 601 | CMe | NMe | Q1a | a bond | Me | a bond | CH2 | S | a bond | Q3a | OH |
| 602 | CMe | NMe | Q1a | a bond | Me | a bond | CH2 | S | NH | Q3a | OH |
| 603 | CMe | NMe | Q1a | a bond | Me | a bond | CH2 | O | a bond | Q3a | OH |
| 604 | CMe | NMe | Q1a | a bond | Me | a bond | CH2 | O | NH | Q3a | OH |
| 605 | CMe | NMe | Q1a | a bond | H | a bond | CH2 | S | a bond | Q3a | OH |
| 606 | CMe | NMe | Q1a | a bond | H | a bond | CH2 | S | NH | Q3a | OH |
| 607 | CMe | NMe | Q1a | a bond | H | a bond | CH2 | O | a bond | Q3a | OH |
| 608 | CMe | NMe | Q1a | a bond | H | a bond | CH2 | O | NH | Q3a | OH |
| 609 | CMe | NMe | Q1b | a bond | Me | a bond | CH2 | S | a bond | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 610 | CMe | NMe | Q1b | a bond | Me | a bond | CH2 | S | NH | Q3a | OH |
| 611 | CMe | NMe | Q1b | a bond | Me | a bond | CH2 | O | a bond | Q3a | OH |
| 612 | CMe | NMe | Q1b | a bond | Me | a bond | CH2 | O | NH | Q3a | OH |
| 613 | CMe | NMe | Q1b | a bond | H | a bond | CH2 | S | a bond | Q3a | OH |
| 614 | CMe | NMe | Q1b | a bond | H | a bond | CH2 | S | NH | Q3a | OH |
| 615 | CMe | NMe | Q1b | a bond | H | a bond | CH2 | O | a bond | Q3a | OH |
| 616 | CMe | NMe | Q1b | a bond | H | a bond | CH2 | O | NH | Q3a | OH |
| 617 | CMe | S | Q1a | a bond | Me | a bond | CH2 | S | a bond | Q3a | OH |
| 618 | CMe | S | Q1a | a bond | Me | a bond | CH2 | S | NH | Q3a | OH |
| 619 | CMe | S | Q1a | a bond | Me | a bond | CH2 | O | a bond | Q3a | OH |
| 620 | CMe | S | Q1a | a bond | Me | a bond | CH2 | O | NH | Q3a | OH |
| 621 | CMe | S | Q1a | a bond | H | a bond | CH2 | S | a bond | Q3a | OH |
| 622 | CMe | S | Q1a | a bond | H | a bond | CH2 | S | NH | Q3a | OH |
| 623 | CMe | S | Q1a | a bond | H | a bond | CH2 | O | a bond | Q3a | OH |
| 624 | CMe | S | Q1a | a bond | H | a bond | CH2 | O | NH | Q3a | OH |
| 625 | CMe | S | Q1b | a bond | Me | a bond | CH2 | S | a bond | Q3a | OH |
| 626 | CMe | S | Q1b | a bond | Me | a bond | CH2 | S | NH | Q3a | OH |
| 627 | CMe | S | Q1b | a bond | Me | a bond | CH2 | O | a bond | Q3a | OH |
| 628 | CMe | S | Q1b | a bond | Me | a bond | CH2 | O | NH | Q3a | OH |
| 629 | CMe | S | Q1b | a bond | H | a bond | CH2 | S | a bond | Q3a | OH |
| 630 | CMe | S | Q1b | a bond | H | a bond | CH2 | S | NH | Q3a | OH |
| 631 | CMe | S | Q1b | a bond | H | a bond | CH2 | O | a bond | Q3a | OH |
| 632 | CMe | S | Q1b | a bond | H | a bond | CH2 | O | NH | Q3a | OH |
| 633 | CMe | O | Q1a | a bond | Me | a bond | CH2 | S | a bond | Q3a | OH |
| 634 | CMe | O | Q1a | a bond | Me | a bond | CH2 | S | NH | Q3a | OH |
| 635 | CMe | O | Q1a | a bond | Me | a bond | CH2 | O | a bond | Q3a | OH |
| 636 | CMe | O | Q1a | a bond | Me | a bond | CH2 | O | NH | Q3a | OH |
| 637 | CMe | O | Q1a | a bond | H | a bond | CH2 | S | a bond | Q3a | OH |
| 638 | CMe | O | Q1a | a bond | H | a bond | CH2 | S | NH | Q3a | OH |
| 639 | CMe | O | Q1a | a bond | H | a bond | CH2 | O | a bond | Q3a | OH |
| 640 | CMe | O | Q1a | a bond | H | a bond | CH2 | O | NH | Q3a | OH |
| 641 | CMe | O | Q1b | a bond | Me | a bond | CH2 | S | a bond | Q3a | OH |
| 642 | CMe | O | Q1b | a bond | Me | a bond | CH2 | S | NH | Q3a | OH |
| 643 | CMe | O | Q1b | a bond | Me | a bond | CH2 | O | a bond | Q3a | OH |
| 644 | CMe | O | Q1b | a bond | Me | a bond | CH2 | O | NH | Q3a | OH |
| 645 | CMe | O | Q1b | a bond | H | a bond | CH2 | S | a bond | Q3a | OH |
| 646 | CMe | O | Q1b | a bond | H | a bond | CH2 | S | NH | Q3a | OH |
| 647 | CMe | O | Q1b | a bond | H | a bond | CH2 | O | a bond | Q3a | OH |
| 648 | CMe | O | Q1b | a bond | H | a bond | CH2 | O | NH | Q3a | OH |
| 649 | CMe | NH | Q1a | NH | Me | a bond | NH | S | NH | Q3a | OH |
| 650 | CMe | NH | Q1a | NH | Me | a bond | NH | S | a bond | Q3a | OH |
| 651 | CMe | NH | Q1a | NH | Me | a bond | NH | O | NH | Q3a | OH |
| 652 | CMe | NH | Q1a | NH | Me | a bond | NH | O | a bond | Q3a | OH |
| 653 | CMe | NH | Q1a | NH | H | a bond | NH | S | NH | Q3a | OH |
| 654 | CMe | NH | Q1a | NH | H | a bond | NH | S | a bond | Q3a | OH |
| 655 | CMe | NH | Q1a | NH | H | a bond | NH | O | NH | Q3a | OH |
| 656 | CMe | NH | Q1a | NH | H | a bond | NH | O | a bond | Q3a | OH |
| 657 | CMe | NH | Q1b | NH | Me | a bond | NH | S | NH | Q3a | OH |
| 658 | CMe | NH | Q1b | NH | Me | a bond | NH | S | a bond | Q3a | OH |
| 659 | CMe | NH | Q1b | NH | Me | a bond | NH | O | NH | Q3a | OH |
| 660 | CMe | NH | Q1b | NH | Me | a bond | NH | O | a bond | Q3a | OH |
| 661 | CMe | NH | Q1b | NH | H | a bond | NH | S | NH | Q3a | OH |
| 662 | CMe | NH | Q1b | NH | H | a bond | NH | S | a bond | Q3a | OH |
| 663 | CMe | NH | Q1b | NH | H | a bond | NH | O | NH | Q3a | OH |
| 664 | CMe | NH | Q1b | NH | H | a bond | NH | O | a bond | Q3a | OH |
| 665 | CMe | NH | Q1a | O | Me | a bond | NH | S | NH | Q3a | OH |
| 666 | CMe | NH | Q1a | O | Me | a bond | NH | S | a bond | Q3a | OH |
| 667 | CMe | NH | Q1a | O | Me | a bond | NH | O | NH | Q3a | OH |
| 668 | CMe | NH | Q1a | O | Me | a bond | NH | O | a bond | Q3a | OH |
| 669 | CMe | NH | Q1a | O | H | a bond | NH | S | NH | Q3a | OH |
| 670 | CMe | NH | Q1a | O | H | a bond | NH | S | a bond | Q3a | OH |
| 671 | CMe | NH | Q1a | O | H | a bond | NH | O | NH | Q3a | OH |
| 672 | CMe | NH | Q1a | O | H | a bond | NH | O | a bond | Q3a | OH |
| 673 | CMe | NH | Q1b | O | Me | a bond | NH | S | NH | Q3a | OH |
| 674 | CMe | NH | Q1b | O | Me | a bond | NH | S | a bond | Q3a | OH |
| 675 | CMe | NH | Q1b | O | Me | a bond | NH | O | NH | Q3a | OH |
| 676 | CMe | NH | Q1b | O | Me | a bond | NH | O | a bond | Q3a | OH |
| 677 | CMe | NH | Q1b | O | H | a bond | NH | S | NH | Q3a | OH |
| 678 | CMe | NH | Q1b | O | H | a bond | NH | S | a bond | Q3a | OH |
| 679 | CMe | NH | Q1b | O | H | a bond | NH | O | NH | Q3a | OH |
| 680 | CMe | NH | Q1b | O | H | a bond | NH | O | a bond | Q3a | OH |
| 681 | CMe | NH | Q1a | CH2 | Me | a bond | NH | S | NH | Q3a | OH |
| 682 | CMe | NH | Q1a | CH2 | Me | a bond | NH | S | a bond | Q3a | OH |
| 683 | CMe | NH | Q1a | CH2 | Me | a bond | NH | O | NH | Q3a | OH |
| 684 | CMe | NH | Q1a | CH2 | Me | a bond | NH | O | a bond | Q3a | OH |
| 685 | CMe | NH | Q1a | CH2 | H | a bond | NH | S | NH | Q3a | OH |
| 686 | CMe | NH | Q1a | CH2 | H | a bond | NH | S | a bond | Q3a | OH |
| 687 | CMe | NH | Q1a | CH2 | H | a bond | NH | O | NH | Q3a | OH |

TABLE 3-continued

| No | A | B | R¹ | L¹ | R² | L² | L³ | Y | L⁴ | R³ | X |
|---|---|---|---|---|---|---|---|---|---|---|---|
| 688 | CMe | NH | Q1a | CH2 | H | a bond | NH | O | a bond | Q3a | OH |
| 689 | CMe | NH | Q1b | CH2 | Me | a bond | NH | S | NH | Q3a | OH |
| 690 | CMe | NH | Q1b | CH2 | Me | a bond | NH | S | a bond | Q3a | OH |
| 691 | CMe | NH | Q1b | CH2 | Me | a bond | NH | O | NH | Q3a | OH |
| 692 | CMe | NH | Q1b | CH2 | Me | a bond | NH | O | a bond | Q3a | OH |
| 693 | CMe | NH | Q1b | CH2 | H | a bond | NH | S | NH | Q3a | OH |
| 694 | CMe | NH | Q1b | CH2 | H | a bond | NH | S | a bond | Q3a | OH |
| 695 | CMe | NH | Q1b | CH2 | H | a bond | NH | O | NH | Q3a | OH |
| 696 | CMe | NH | Q1b | CH2 | H | a bond | NH | O | a bond | Q3a | OH |
| 697 | CMe | NH | Q1a | a bond | Me | a bond | NH | S | CH2 | Q3a | OH |
| 698 | CMe | NH | Q1a | a bond | Me | a bond | NH | O | CH2 | Q3a | OH |
| 699 | CMe | NH | Q1a | a bond | H | a bond | NH | S | CH2 | Q3a | OH |
| 700 | CMe | NH | Q1a | a bond | H | a bond | NH | O | CH2 | Q3a | OH |
| 701 | CMe | NH | Q1b | a bond | Me | a bond | NH | S | CH2 | Q3a | OH |
| 702 | CMe | NH | Q1b | a bond | Me | a bond | NH | O | CH2 | Q3a | OH |
| 703 | CMe | NH | Q1b | a bond | H | a bond | NH | S | CH2 | Q3a | OH |
| 704 | CMe | NH | Q1b | a bond | H | a bond | NH | O | CH2 | Q3a | OH |
| 705 | CMe | NH | Q1a | a bond | Me | a bond | CH2 | S | a bond | Q3a | OH |
| 706 | CMe | NH | Q1a | a bond | Me | a bond | CH2 | S | NH | Q3a | OH |
| 707 | CMe | NH | Q1a | a bond | Me | a bond | CH2 | O | a bond | Q3a | OH |
| 708 | CMe | NH | Q1a | a bond | Me | a bond | CH2 | O | NH | Q3a | OH |
| 709 | CMe | NH | Q1a | a bond | H | a bond | CH2 | S | a bond | Q3a | OH |
| 710 | CMe | NH | Q1a | a bond | H | a bond | CH2 | S | NH | Q3a | OH |
| 711 | CMe | NH | Q1a | a bond | H | a bond | CH2 | O | a bond | Q3a | OH |
| 712 | CMe | NH | Q1a | a bond | H | a bond | CH2 | O | NH | Q3a | OH |
| 713 | CMe | NH | Q1b | a bond | Me | a bond | CH2 | S | a bond | Q3a | OH |
| 714 | CMe | NH | Q1b | a bond | Me | a bond | CH2 | S | NH | Q3a | OH |
| 715 | CMe | NH | Q1b | a bond | Me | a bond | CH2 | O | a bond | Q3a | OH |
| 716 | CMe | NH | Q1b | a bond | Me | a bond | CH2 | O | NH | Q3a | OH |
| 717 | CMe | NH | Q1b | a bond | H | a bond | CH2 | S | a bond | Q3a | OH |
| 718 | CMe | NH | Q1b | a bond | H | a bond | CH2 | S | NH | Q3a | OH |
| 719 | CMe | NH | Q1b | a bond | H | a bond | CH2 | O | a bond | Q3a | OH |
| 720 | CMe | NH | Q1b | a bond | H | a bond | CH2 | O | NH | Q3a | OH |

71) The compounds wherein A, B, R¹, L¹, R², L², L³, Y, L⁴, R³ and X are any of the following combinations in Table 4, tautomers, prodrugs or pharmaceutically acceptable salts of the compounds or solvates thereof. The symbols in Table 4 denote the flowing substituents.

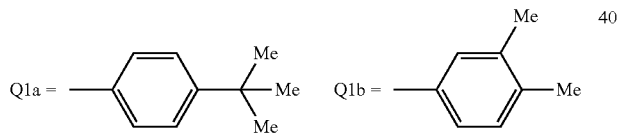

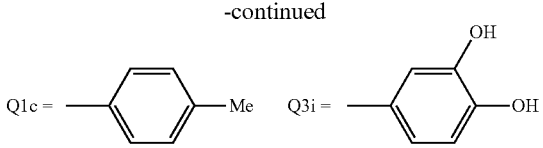

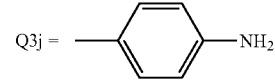

TABLE 4

| No | A | B | R¹ | L¹ | R² | L² | L³ | Y | L⁴ | R³ | X |
|---|---|---|---|---|---|---|---|---|---|---|---|
| 1 | N | NMe | Q1a | a bond | Me | a bond | NH | S | NH | Q3i | OH |
| 2 | N | NMe | Q1a | a bond | Me | a bond | NH | S | NH | Q3j | OH |
| 3 | N | NMe | Q1b | a bond | Me | a bond | NH | S | NH | Q3i | OH |
| 4 | N | NMe | Q1b | a bond | Me | a bond | NH | S | NH | Q3j | OH |
| 5 | N | NMe | Q1c | a bond | Me | a bond | NH | S | NH | Q3i | OH |
| 6 | N | NMe | Q1c | a bond | Me | a bond | NH | S | NH | Q3j | OH |
| 7 | N | NEt | Q1a | a bond | Me | a bond | NH | S | NH | Q3i | OH |
| 8 | N | NEt | Q1a | a bond | Me | a bond | NH | S | NH | Q3j | OH |
| 9 | N | NEt | Q1b | a bond | Me | a bond | NH | S | NH | Q3i | OH |
| 10 | N | NEt | Q1b | a bond | Me | a bond | NH | S | NH | Q3j | OH |
| 11 | N | NEt | Q1c | a bond | Me | a bond | NH | S | NH | Q3i | OH |
| 12 | N | NEt | Q1c | a bond | Me | a bond | NH | S | NH | Q3j | OH |
| 13 | N | S | Q1a | a bond | Me | a bond | NH | S | NH | Q3i | OH |
| 14 | N | S | Q1a | a bond | Me | a bond | NH | S | NH | Q3j | OH |
| 15 | N | S | Q1b | a bond | Me | a bond | NH | S | NH | Q3i | OH |
| 16 | N | S | Q1b | a bond | Me | a bond | NH | S | NH | Q3j | OH |
| 17 | N | S | Q1c | a bond | Me | a bond | NH | S | NH | Q3i | OH |
| 18 | N | S | Q1c | a bond | Me | a bond | NH | S | NH | Q3j | OH |
| 19 | N | O | Q1a | a bond | Me | a bond | NH | S | NH | Q3i | OH |
| 20 | N | O | Q1a | a bond | Me | a bond | NH | S | NH | Q3j | OH |
| 21 | N | O | Q1b | a bond | Me | a bond | NH | S | NH | Q3i | OH |

TABLE 4-continued

| No | A | B | R¹ | L¹ | R² | L² | L³ | Y | L⁴ | R³ | X |
|---|---|---|---|---|---|---|---|---|---|---|---|
| 22 | N | O | Q1b | a bond | Me | a bond | NH | S | NH | Q3j | OH |
| 23 | N | O | Q1c | a bond | Me | a bond | NH | S | NH | Q3i | OH |
| 24 | N | O | Q1c | a bond | Me | a bond | NH | S | NH | Q3j | OH |
| 25 | CH | NMe | Q1a | a bond | Me | a bond | NH | S | NH | Q3i | OH |
| 26 | CH | NMe | Q1a | a bond | Me | a bond | NH | S | NH | Q3j | OH |
| 27 | CH | NMe | Q1b | a bond | Me | a bond | NH | S | NH | Q3i | OH |
| 28 | CH | NMe | Q1b | a bond | Me | a bond | NH | S | NH | Q3j | OH |
| 29 | CH | NMe | Q1c | a bond | Me | a bond | NH | S | NH | Q3i | OH |
| 30 | CH | NMe | Q1c | a bond | Me | a bond | NH | S | NH | Q3j | OH |
| 31 | CH | NEt | Q1a | a bond | Me | a bond | NH | S | NH | Q3i | OH |
| 32 | CH | NEt | Q1a | a bond | Me | a bond | NH | S | NH | Q3j | OH |
| 33 | CH | NEt | Q1b | a bond | Me | a bond | NH | S | NH | Q3i | OH |
| 34 | CH | NEt | Q1b | a bond | Me | a bond | NH | S | NH | Q3j | OH |
| 35 | CH | NEt | Q1c | a bond | Me | a bond | NH | S | NH | Q3i | OH |
| 36 | CH | NEt | Q1c | a bond | Me | a bond | NH | S | NH | Q3j | OH |
| 37 | CH | S | Q1a | a bond | Me | a bond | NH | S | NH | Q3i | OH |
| 38 | CH | S | Q1a | a bond | Me | a bond | NH | S | NH | Q3j | OH |
| 39 | CH | S | Q1b | a bond | Me | a bond | NH | S | NH | Q3i | OH |
| 40 | CH | S | Q1b | a bond | Me | a bond | NH | S | NH | Q3j | OH |
| 41 | CH | S | Q1c | a bond | Me | a bond | NH | S | NH | Q3i | OH |
| 42 | CH | S | Q1c | a bond | Me | a bond | NH | S | NH | Q3j | OH |
| 43 | CH | O | Q1a | a bond | Me | a bond | NH | S | NH | Q3i | OH |
| 44 | CH | O | Q1a | a bond | Me | a bond | NH | S | NH | Q3j | OH |
| 45 | CH | O | Q1b | a bond | Me | a bond | NH | S | NH | Q3i | OH |
| 46 | CH | O | Q1b | a bond | Me | a bond | NH | S | NH | Q3j | OH |
| 47 | CH | O | Q1c | a bond | Me | a bond | NH | S | NH | Q3i | OH |
| 48 | CH | O | Q1c | a bond | Me | a bond | NH | S | NH | Q3j | OH |
| 49 | CMe | NMe | Q1a | a bond | Me | a bond | NH | S | NH | Q3i | OH |
| 50 | CMe | NMe | Q1a | a bond | Me | a bond | NH | S | NH | Q3j | OH |
| 51 | CMe | NMe | Q1b | a bond | Me | a bond | NH | S | NH | Q3i | OH |
| 52 | CMe | NMe | Q1b | a bond | Me | a bond | NH | S | NH | Q3j | OH |
| 53 | CMe | NMe | Q1c | a bond | Me | a bond | NH | S | NH | Q3i | OH |
| 54 | CMe | NMe | Q1c | a bond | Me | a bond | NH | S | NH | Q3j | OH |
| 55 | CMe | NEt | Q1a | a bond | Me | a bond | NH | S | NH | Q3i | OH |
| 56 | CMe | NEt | Q1a | a bond | Me | a bond | NH | S | NH | Q3j | OH |
| 57 | CMe | NEt | Q1b | a bond | Me | a bond | NH | S | NH | Q3i | OH |
| 58 | CMe | NEt | Q1b | a bond | Me | a bond | NH | S | NH | Q3j | OH |
| 59 | CMe | NEt | Q1c | a bond | Me | a bond | NH | S | NH | Q3i | OH |
| 60 | CMe | NEt | Q1c | a bond | Me | a bond | NH | S | NH | Q3j | OH |
| 61 | CMe | S | Q1a | a bond | Me | a bond | NH | S | NH | Q3i | OH |
| 62 | CMe | S | Q1a | a bond | Me | a bond | NH | S | NH | Q3j | OH |
| 63 | CMe | S | Q1b | a bond | Me | a bond | NH | S | NH | Q3i | OH |
| 64 | CMe | S | Q1b | a bond | Me | a bond | NH | S | NH | Q3j | OH |
| 65 | CMe | S | Q1c | a bond | Me | a bond | NH | S | NH | Q3i | OH |
| 66 | CMe | S | Q1c | a bond | Me | a bond | NH | S | NH | Q3j | OH |
| 67 | CMe | O | Q1a | a bond | Me | a bond | NH | S | NH | Q3i | OH |
| 68 | CMe | O | Q1a | a bond | Me | a bond | NH | S | NH | Q3j | OH |
| 69 | CMe | O | Q1b | a bond | Me | a bond | NH | S | NH | Q3i | OH |
| 70 | CMe | O | Q1b | a bond | Me | a bond | NH | S | NH | Q3j | OH |
| 71 | CMe | O | Q1c | a bond | Me | a bond | NH | S | NH | Q3i | OH |
| 72 | CMe | O | Q1c | a bond | Me | a bond | NH | S | NH | Q3j | OH |
| 73 | N | NMe | Q1a | a bond | Me | a bond | NH | O | a bond | Q3i | OH |
| 74 | N | NMe | Q1a | a bond | Me | a bond | NH | O | a bond | Q3j | OH |
| 75 | N | NMe | Q1b | a bond | Me | a bond | NH | O | a bond | Q3i | OH |
| 76 | N | NMe | Q1b | a bond | Me | a bond | NH | O | a bond | Q3j | OH |
| 77 | N | NMe | Q1c | a bond | Me | a bond | NH | O | a bond | Q3i | OH |
| 78 | N | NMe | Q1c | a bond | Me | a bond | NH | O | a bond | Q3j | OH |
| 79 | N | NEt | Q1a | a bond | Me | a bond | NH | O | a bond | Q3i | OH |
| 80 | N | NEt | Q1a | a bond | Me | a bond | NH | O | a bond | Q3j | OH |
| 81 | N | NEt | Q1b | a bond | Me | a bond | NH | O | a bond | Q3i | OH |
| 82 | N | NEt | Q1b | a bond | Me | a bond | NH | O | a bond | Q3j | OH |
| 83 | N | NEt | Q1c | a bond | Me | a bond | NH | O | a bond | Q3i | OH |
| 84 | N | NEt | Q1c | a bond | Me | a bond | NH | O | a bond | Q3j | OH |
| 85 | N | S | Q1a | a bond | Me | a bond | NH | O | a bond | Q3i | OH |
| 86 | N | S | Q1a | a bond | Me | a bond | NH | O | a bond | Q3j | OH |
| 87 | N | S | Q1b | a bond | Me | a bond | NH | O | a bond | Q3i | OH |
| 88 | N | S | Q1b | a bond | Me | a bond | NH | O | a bond | Q3j | OH |
| 89 | N | S | Q1c | a bond | Me | a bond | NH | O | a bond | Q3i | OH |
| 90 | N | S | Q1c | a bond | Me | a bond | NH | O | a bond | Q3j | OH |
| 91 | N | O | Q1a | a bond | Me | a bond | NH | O | a bond | Q3i | OH |
| 92 | N | O | Q1a | a bond | Me | a bond | NH | O | a bond | Q3j | OH |
| 93 | N | O | Q1b | a bond | Me | a bond | NH | O | a bond | Q3i | OH |
| 94 | N | O | Q1b | a bond | Me | a bond | NH | O | a bond | Q3j | OH |
| 95 | N | O | Q1c | a bond | Me | a bond | NH | O | a bond | Q3i | OH |
| 96 | N | O | Q1c | a bond | Me | a bond | NH | O | a bond | Q3j | OH |
| 97 | CH | NMe | Q1a | a bond | Me | a bond | NH | O | a bond | Q3i | OH |
| 98 | CH | NMe | Q1a | a bond | Me | a bond | NH | O | a bond | Q3j | OH |
| 99 | CH | NMe | Q1b | a bond | Me | a bond | NH | O | a bond | Q3i | OH |

TABLE 4-continued

| No | A | B | $R^1$ | $L^1$ | $R^2$ | $L^2$ | $L^3$ | Y | $L^4$ | $R^3$ | X |
|---|---|---|---|---|---|---|---|---|---|---|---|
| 100 | CH | NMe | Q1b | a bond | Me | a bond | NH | O | a bond | Q3j | OH |
| 101 | CH | NMe | Q1c | a bond | Me | a bond | NH | O | a bond | Q3i | OH |
| 102 | CH | NMe | Q1c | a bond | Me | a bond | NH | O | a bond | Q3j | OH |
| 103 | CH | NEt | Q1a | a bond | Me | a bond | NH | O | a bond | Q3i | OH |
| 104 | CH | NEt | Q1a | a bond | Me | a bond | NH | O | a bond | Q3j | OH |
| 105 | CH | NEt | Q1b | a bond | Me | a bond | NH | O | a bond | Q3i | OH |
| 106 | CH | NEt | Q1b | a bond | Me | a bond | NH | O | a bond | Q3j | OH |
| 107 | CH | NEt | Q1c | a bond | Me | a bond | NH | O | a bond | Q3i | OH |
| 108 | CH | NEt | Q1c | a bond | Me | a bond | NH | O | a bond | Q3j | OH |
| 109 | CH | S | Q1a | a bond | Me | a bond | NH | O | a bond | Q3i | OH |
| 110 | CH | S | Q1a | a bond | Me | a bond | NH | O | a bond | Q3j | OH |
| 111 | CH | S | Q1b | a bond | Me | a bond | NH | O | a bond | Q3i | OH |
| 112 | CH | S | Q1b | a bond | Me | a bond | NH | O | a bond | Q3j | OH |
| 113 | CH | S | Q1c | a bond | Me | a bond | NH | O | a bond | Q3i | OH |
| 114 | CH | S | Q1c | a bond | Me | a bond | NH | O | a bond | Q3j | OH |
| 115 | CH | O | Q1a | a bond | Me | a bond | NH | O | a bond | Q3i | OH |
| 116 | CH | O | Q1a | a bond | Me | a bond | NH | O | a bond | Q3j | OH |
| 117 | CH | O | Q1b | a bond | Me | a bond | NH | O | a bond | Q3i | OH |
| 118 | CH | O | Q1b | a bond | Me | a bond | NH | O | a bond | Q3j | OH |
| 119 | CH | O | Q1c | a bond | Me | a bond | NH | O | a bond | Q3i | OH |
| 120 | CH | O | Q1c | a bond | Me | a bond | NH | O | a bond | Q3j | OH |
| 121 | CMe | NMe | Q1a | a bond | Me | a bond | NH | O | a bond | Q3i | OH |
| 122 | CMe | NMe | Q1a | a bond | Me | a bond | NH | O | a bond | Q3j | OH |
| 123 | CMe | NMe | Q1b | a bond | Me | a bond | NH | O | a bond | Q3i | OH |
| 124 | CMe | NMe | Q1b | a bond | Me | a bond | NH | O | a bond | Q3j | OH |
| 125 | CMe | NMe | Q1c | a bond | Me | a bond | NH | O | a bond | Q3i | OH |
| 126 | CMe | NMe | Q1c | a bond | Me | a bond | NH | O | a bond | Q3j | OH |
| 127 | CMe | NEt | Q1a | a bond | Me | a bond | NH | O | a bond | Q3i | OH |
| 128 | CMe | NEt | Q1a | a bond | Me | a bond | NH | O | a bond | Q3j | OH |
| 129 | CMe | NEt | Q1b | a bond | Me | a bond | NH | O | a bond | Q3i | OH |
| 130 | CMe | NEt | Q1b | a bond | Me | a bond | NH | O | a bond | Q3j | OH |
| 131 | CMe | NEt | Q1c | a bond | Me | a bond | NH | O | a bond | Q3i | OH |
| 132 | CMe | NEt | Q1c | a bond | Me | a bond | NH | O | a bond | Q3j | OH |
| 133 | CMe | S | Q1a | a bond | Me | a bond | NH | O | a bond | Q3i | OH |
| 134 | CMe | S | Q1a | a bond | Me | a bond | NH | O | a bond | Q3j | OH |
| 135 | CMe | S | Q1b | a bond | Me | a bond | NH | O | a bond | Q3i | OH |
| 136 | CMe | S | Q1b | a bond | Me | a bond | NH | O | a bond | Q3j | OH |
| 137 | CMe | S | Q1c | a bond | Me | a bond | NH | O | a bond | Q3i | OH |
| 138 | CMe | S | Q1c | a bond | Me | a bond | NH | O | a bond | Q3j | OH |
| 139 | CMe | O | Q1a | a bond | Me | a bond | NH | O | a bond | Q3i | OH |
| 140 | CMe | O | Q1a | a bond | Me | a bond | NH | O | a bond | Q3j | OH |
| 141 | CMe | O | Q1b | a bond | Me | a bond | NH | O | a bond | Q3i | OH |
| 142 | CMe | O | Q1b | a bond | Me | a bond | NH | O | a bond | Q3j | OH |
| 143 | CMe | O | Q1c | a bond | Me | a bond | NH | O | a bond | Q3i | OH |
| 144 | CMe | O | Q1c | a bond | Me | a bond | NH | O | a bond | Q3j | OH |
| 145 | CMe | NH | Q1a | a bond | Me | a bond | NH | S | NH | Q3i | OH |
| 146 | CMe | NH | Q1a | a bond | Me | a bond | NH | S | NH | Q3j | OH |
| 147 | CMe | NH | Q1b | a bond | Me | a bond | NH | S | NH | Q3i | OH |
| 148 | CMe | NH | Q1b | a bond | Me | a bond | NH | S | NH | Q3j | OH |
| 149 | CMe | NH | Q1c | a bond | Me | a bond | NH | S | NH | Q3i | OH |
| 150 | CMe | NH | Q1c | a bond | Me | a bond | NH | S | NH | Q3j | OH |
| 151 | CH | NH | Q1a | a bond | Me | a bond | NH | O | a bond | Q3i | OH |
| 152 | CH | NH | Q1a | a bond | Me | a bond | NH | O | a bond | Q3j | OH |
| 153 | CH | NH | Q1b | a bond | Me | a bond | NH | O | a bond | Q3i | OH |
| 154 | CH | NH | Q1b | a bond | Me | a bond | NH | O | a bond | Q3j | OH |
| 155 | CH | NH | Q1c | a bond | Me | a bond | NH | O | a bond | Q3i | OH |
| 156 | CH | NH | Q1c | a bond | Me | a bond | NH | O | a bond | Q3j | OH |

72) The compounds wherein A, B, $R^1$, $L^1$, $R^2$, $L^2$, $L^3$, Y, $L^4$, $R^3$ and X are any of the following combinations in Table 5, tautomers, prodrugs or pharmaceutically acceptable salts of the compounds or solvates thereof. The symbols in Table 5 denote the flowing substituents.

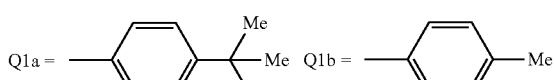

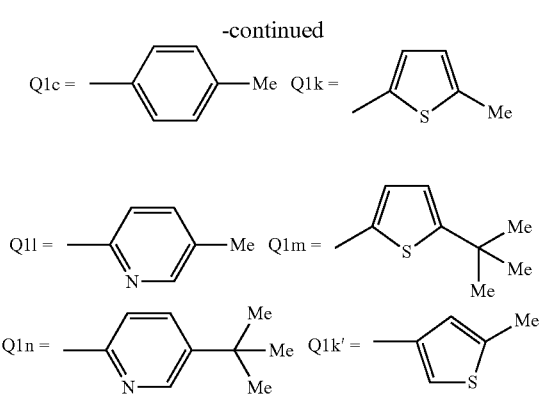

-continued

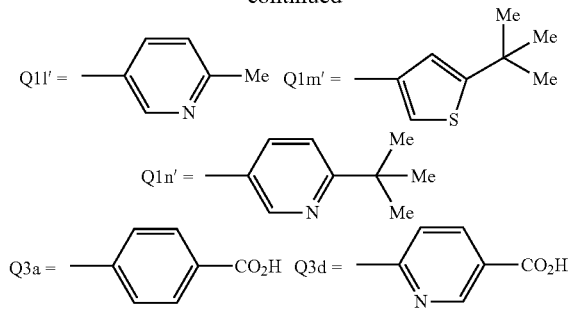

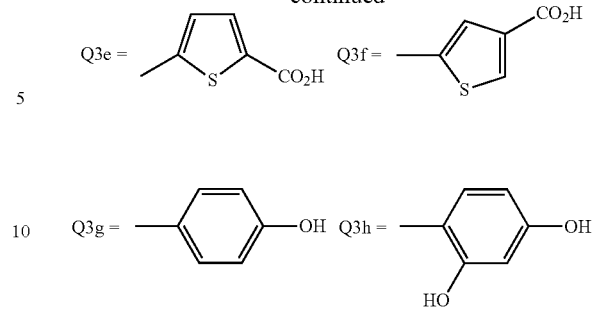

TABLE 5

| No | A | B | R¹ | L¹ | R² | L² | L³ | Y | L⁴ | R³ | X |
|---|---|---|---|---|---|---|---|---|---|---|---|
| 1 | CMe | NH | Q1k | a bond | Me | a bond | NH | O | a bond | Q3a | OH |
| 2 | CMe | NH | Q1k | a bond | Me | a bond | NH | O | a bond | Q3d | OH |
| 3 | CMe | NH | Q1k | a bond | Me | a bond | NH | O | a bond | Q3e | OH |
| 4 | CMe | NH | Q1k | a bond | Me | a bond | NH | O | a bond | Q3f | OH |
| 5 | CMe | NH | Q1k | a bond | Me | a bond | NH | O | NH | Q3a | OH |
| 6 | CMe | NH | Q1k | a bond | Me | a bond | NH | O | NH | Q3d | OH |
| 7 | CMe | NH | Q1k | a bond | Me | a bond | NH | O | NH | Q3e | OH |
| 8 | CMe | NH | Q1k | a bond | Me | a bond | NH | O | NH | Q3f | OH |
| 9 | CMe | NH | Q1k | a bond | Me | a bond | NH | S | a bond | Q3a | OH |
| 10 | CMe | NH | Q1k | a bond | Me | a bond | NH | S | a bond | Q3d | OH |
| 11 | CMe | NH | Q1k | a bond | Me | a bond | NH | S | a bond | Q3e | OH |
| 12 | CMe | NH | Q1k | a bond | Me | a bond | NH | S | a bond | Q3f | OH |
| 13 | CMe | NH | Q1k | a bond | Me | a bond | NH | S | NH | Q3a | OH |
| 14 | CMe | NH | Q1k | a bond | Me | a bond | NH | S | NH | Q3d | OH |
| 15 | CMe | NH | Q1k | a bond | Me | a bond | NH | S | NH | Q3e | OH |
| 16 | CMe | NH | Q1k | a bond | Me | a bond | NH | S | NH | Q3f | OH |
| 17 | CMe | NH | Q1l | a bond | Me | a bond | NH | O | a bond | Q3a | OH |
| 18 | CMe | NH | Q1l | a bond | Me | a bond | NH | O | a bond | Q3d | OH |
| 19 | CMe | NH | Q1l | a bond | Me | a bond | NH | O | a bond | Q3e | OH |
| 20 | CMe | NH | Q1l | a bond | Me | a bond | NH | O | a bond | Q3f | OH |
| 21 | CMe | NH | Q1l | a bond | Me | a bond | NH | O | NH | Q3a | OH |
| 22 | CMe | NH | Q1l | a bond | Me | a bond | NH | O | NH | Q3d | OH |
| 23 | CMe | NH | Q1l | a bond | Me | a bond | NH | O | NH | Q3e | OH |
| 24 | CMe | NH | Q1l | a bond | Me | a bond | NH | O | NH | Q3f | OH |
| 25 | CMe | NH | Q1l | a bond | Me | a bond | NH | S | a bond | Q3a | OH |
| 26 | CMe | NH | Q1l | a bond | Me | a bond | NH | S | a bond | Q3d | OH |
| 27 | CMe | NH | Q1l | a bond | Me | a bond | NH | S | a bond | Q3e | OH |
| 28 | CMe | NH | Q1l | a bond | Me | a bond | NH | S | a bond | Q3f | OH |
| 29 | CMe | NH | Q1l | a bond | Me | a bond | NH | S | NH | Q3a | OH |
| 30 | CMe | NH | Q1l | a bond | Me | a bond | NH | S | NH | Q3d | OH |
| 31 | CMe | NH | Q1l | a bond | Me | a bond | NH | S | NH | Q3e | OH |
| 32 | CMe | NH | Q1l | a bond | Me | a bond | NH | S | NH | Q3f | OH |
| 33 | CMe | NH | Q1m | a bond | Me | a bond | NH | O | a bond | Q3a | OH |
| 34 | CMe | NH | Q1m | a bond | Me | a bond | NH | O | a bond | Q3d | OH |
| 35 | CMe | NH | Q1m | a bond | Me | a bond | NH | O | a bond | Q3e | OH |
| 36 | CMe | NH | Q1m | a bond | Me | a bond | NH | O | a bond | Q3f | OH |
| 37 | CMe | NH | Q1m | a bond | Me | a bond | NH | O | NH | Q3a | OH |
| 38 | CMe | NH | Q1m | a bond | Me | a bond | NH | O | NH | Q3d | OH |
| 39 | CMe | NH | Q1m | a bond | Me | a bond | NH | O | NH | Q3e | OH |
| 40 | CMe | NH | Q1m | a bond | Me | a bond | NH | O | NH | Q3f | OH |
| 41 | CMe | NH | Q1m | a bond | Me | a bond | NH | S | a bond | Q3a | OH |
| 42 | CMe | NH | Q1m | a bond | Me | a bond | NH | S | a bond | Q3d | OH |
| 43 | CMe | NH | Q1m | a bond | Me | a bond | NH | S | a bond | Q3e | OH |
| 44 | CMe | NH | Q1m | a bond | Me | a bond | NH | S | a bond | Q3f | OH |
| 45 | CMe | NH | Q1m | a bond | Me | a bond | NH | S | NH | Q3a | OH |
| 46 | CMe | NH | Q1m | a bond | Me | a bond | NH | S | NH | Q3d | OH |
| 47 | CMe | NH | Q1m | a bond | Me | a bond | NH | S | NH | Q3e | OH |
| 48 | CMe | NH | Q1m | a bond | Me | a bond | NH | S | NH | Q3f | OH |
| 49 | CMe | NH | Q1n | a bond | Me | a bond | NH | O | a bond | Q3a | OH |
| 50 | CMe | NH | Q1n | a bond | Me | a bond | NH | O | a bond | Q3d | OH |
| 51 | CMe | NH | Q1n | a bond | Me | a bond | NH | O | a bond | Q3e | OH |
| 52 | CMe | NH | Q1n | a bond | Me | a bond | NH | O | a bond | Q3f | OH |
| 53 | CMe | NH | Q1n | a bond | Me | a bond | NH | O | NH | Q3a | OH |
| 54 | CMe | NH | Q1n | a bond | Me | a bond | NH | O | NH | Q3d | OH |
| 55 | CMe | NH | Q1n | a bond | Me | a bond | NH | O | NH | Q3e | OH |
| 56 | CMe | NH | Q1n | a bond | Me | a bond | NH | O | NH | Q3f | OH |
| 57 | CMe | NH | Q1n | a bond | Me | a bond | NH | S | a bond | Q3a | OH |
| 58 | CMe | NH | Q1n | a bond | Me | a bond | NH | S | a bond | Q3d | OH |
| 59 | CMe | NH | Q1n | a bond | Me | a bond | NH | S | a bond | Q3e | OH |
| 60 | CMe | NH | Q1n | a bond | Me | a bond | NH | S | a bond | Q3f | OH |

TABLE 5-continued

| No | A | B | R¹ | L¹ | R² | L² | L³ | Y | L⁴ | R³ | X |
|----|---|---|----|----|----|----|----|---|----|----|---|
| 61 | CMe | NH | Q1n | a bond | Me | a bond | NH | S | NH | Q3a | OH |
| 62 | CMe | NH | Q1n | a bond | Me | a bond | NH | S | NH | Q3d | OH |
| 63 | CMe | NH | Q1n | a bond | Me | a bond | NH | S | NH | Q3e | OH |
| 64 | CMe | NH | Q1n | a bond | Me | a bond | NH | S | NH | Q3f | OH |
| 65 | CMe | NH | Q1k' | a bond | Me | a bond | NH | O | a bond | Q3a | OH |
| 66 | CMe | NH | Q1k' | a bond | Me | a bond | NH | O | a bond | Q3d | OH |
| 67 | CMe | NH | Q1k' | a bond | Me | a bond | NH | O | a bond | Q3e | OH |
| 68 | CMe | NH | Q1k' | a bond | Me | a bond | NH | O | a bond | Q3f | OH |
| 69 | CMe | NH | Q1k' | a bond | Me | a bond | NH | O | NH | Q3a | OH |
| 70 | CMe | NH | Q1k' | a bond | Me | a bond | NH | O | NH | Q3d | OH |
| 71 | CMe | NH | Q1k' | a bond | Me | a bond | NH | O | NH | Q3e | OH |
| 72 | CMe | NH | Q1k' | a bond | Me | a bond | NH | O | NH | Q3f | OH |
| 73 | CMe | NH | Q1k' | a bond | Me | a bond | NH | S | a bond | Q3a | OH |
| 74 | CMe | NH | Q1k' | a bond | Me | a bond | NH | S | a bond | Q3d | OH |
| 75 | CMe | NH | Q1k' | a bond | Me | a bond | NH | S | a bond | Q3e | OH |
| 76 | CMe | NH | Q1k' | a bond | Me | a bond | NH | S | a bond | Q3f | OH |
| 77 | CMe | NH | Q1k' | a bond | Me | a bond | NH | S | NH | Q3a | OH |
| 78 | CMe | NH | Q1k' | a bond | Me | a bond | NH | S | NH | Q3d | OH |
| 79 | CMe | NH | Q1k' | a bond | Me | a bond | NH | S | NH | Q3e | OH |
| 80 | CMe | NH | Q1k' | a bond | Me | a bond | NH | S | NH | Q3f | OH |
| 81 | CMe | NH | Q1l' | a bond | Me | a bond | NH | O | a bond | Q3a | OH |
| 82 | CMe | NH | Q1l' | a bond | Me | a bond | NH | O | a bond | Q3d | OH |
| 83 | CMe | NH | Q1l' | a bond | Me | a bond | NH | O | a bond | Q3e | OH |
| 84 | CMe | NH | Q1l' | a bond | Me | a bond | NH | O | a bond | Q3f | OH |
| 85 | CMe | NH | Q1l' | a bond | Me | a bond | NH | O | NH | Q3a | OH |
| 86 | CMe | NH | Q1l' | a bond | Me | a bond | NH | O | NH | Q3d | OH |
| 87 | CMe | NH | Q1l' | a bond | Me | a bond | NH | O | NH | Q3e | OH |
| 88 | CMe | NH | Q1l' | a bond | Me | a bond | NH | O | NH | Q3f | OH |
| 89 | CMe | NH | Q1l' | a bond | Me | a bond | NH | S | a bond | Q3a | OH |
| 90 | CMe | NH | Q1l' | a bond | Me | a bond | NH | S | a bond | Q3d | OH |
| 91 | CMe | NH | Q1l' | a bond | Me | a bond | NH | S | a bond | Q3e | OH |
| 92 | CMe | NH | Q1l' | a bond | Me | a bond | NH | S | a bond | Q3f | OH |
| 93 | CMe | NH | Q1l' | a bond | Me | a bond | NH | S | NH | Q3a | OH |
| 94 | CMe | NH | Q1l' | a bond | Me | a bond | NH | S | NH | Q3d | OH |
| 95 | CMe | NH | Q1l' | a bond | Me | a bond | NH | S | NH | Q3e | OH |
| 96 | CMe | NH | Q1l' | a bond | Me | a bond | NH | S | NH | Q3f | OH |
| 97 | CMe | NH | Q1m' | a bond | Me | a bond | NH | O | a bond | Q3a | OH |
| 98 | CMe | NH | Q1m' | a bond | Me | a bond | NH | O | a bond | Q3d | OH |
| 99 | CMe | NH | Q1m' | a bond | Me | a bond | NH | O | a bond | Q3e | OH |
| 100 | CMe | NH | Q1m' | a bond | Me | a bond | NH | O | a bond | Q3f | OH |
| 101 | CMe | NH | Q1m' | a bond | Me | a bond | NH | O | NH | Q3a | OH |
| 102 | CMe | NH | Q1m' | a bond | Me | a bond | NH | O | NH | Q3d | OH |
| 103 | CMe | NH | Q1m' | a bond | Me | a bond | NH | O | NH | Q3e | OH |
| 104 | CMe | NH | Q1m' | a bond | Me | a bond | NH | O | NH | Q3f | OH |
| 105 | CMe | NH | Q1m' | a bond | Me | a bond | NH | S | a bond | Q3a | OH |
| 106 | CMe | NH | Q1m' | a bond | Me | a bond | NH | S | a bond | Q3d | OH |
| 107 | CMe | NH | Q1m' | a bond | Me | a bond | NH | S | a bond | Q3e | OH |
| 108 | CMe | NH | Q1m' | a bond | Me | a bond | NH | S | a bond | Q3f | OH |
| 109 | CMe | NH | Q1m' | a bond | Me | a bond | NH | S | NH | Q3a | OH |
| 110 | CMe | NH | Q1m' | a bond | Me | a bond | NH | S | NH | Q3d | OH |
| 111 | CMe | NH | Q1m' | a bond | Me | a bond | NH | S | NH | Q3e | OH |
| 112 | CMe | NH | Q1m' | a bond | Me | a bond | NH | S | NH | Q3f | OH |
| 113 | CMe | NH | Q1n' | a bond | Me | a bond | NH | O | a bond | Q3a | OH |
| 114 | CMe | NH | Q1n' | a bond | Me | a bond | NH | O | a bond | Q3d | OH |
| 115 | CMe | NH | Q1n' | a bond | Me | a bond | NH | O | a bond | Q3e | OH |
| 116 | CMe | NH | Q1n' | a bond | Me | a bond | NH | O | a bond | Q3f | OH |
| 117 | CMe | NH | Q1n' | a bond | Me | a bond | NH | O | NH | Q3a | OH |
| 118 | CMe | NH | Q1n' | a bond | Me | a bond | NH | O | NH | Q3d | OH |
| 119 | CMe | NH | Q1n' | a bond | Me | a bond | NH | O | NH | Q3e | OH |
| 120 | CMe | NH | Q1n' | a bond | Me | a bond | NH | O | NH | Q3f | OH |
| 121 | CMe | NH | Q1n' | a bond | Me | a bond | NH | S | a bond | Q3a | OH |
| 122 | CMe | NH | Q1n' | a bond | Me | a bond | NH | S | a bond | Q3d | OH |
| 123 | CMe | NH | Q1n' | a bond | Me | a bond | NH | S | a bond | Q3e | OH |
| 124 | CMe | NH | Q1n' | a bond | Me | a bond | NH | S | a bond | Q3f | OH |
| 125 | CMe | NH | Q1n' | a bond | Me | a bond | NH | S | NH | Q3a | OH |
| 126 | CMe | NH | Q1n' | a bond | Me | a bond | NH | S | NH | Q3d | OH |
| 127 | CMe | NH | Q1n' | a bond | Me | a bond | NH | S | NH | Q3e | OH |
| 128 | CMe | NH | Q1n' | a bond | Me | a bond | NH | S | NH | Q3f | OH |
| 129 | CMe | NH | Q1a | a bond | Me | a bond | NH | O | a bond | Q3d | OH |
| 130 | CMe | NH | Q1a | a bond | Me | a bond | NH | O | a bond | Q3e | OH |
| 131 | CMe | NH | Q1a | a bond | Me | a bond | NH | O | a bond | Q3f | OH |
| 132 | CMe | NH | Q1a | a bond | Me | a bond | NH | O | NH | Q3d | OH |
| 133 | CMe | NH | Q1a | a bond | Me | a bond | NH | O | NH | Q3e | OH |
| 134 | CMe | NH | Q1a | a bond | Me | a bond | NH | O | NH | Q3f | OH |
| 135 | CMe | NH | Q1a | a bond | Me | a bond | NH | S | a bond | Q3d | OH |
| 136 | CMe | NH | Q1a | a bond | Me | a bond | NH | S | a bond | Q3e | OH |
| 137 | CMe | NH | Q1a | a bond | Me | a bond | NH | S | a bond | Q3f | OH |
| 138 | CMe | NH | Q1a | a bond | Me | a bond | NH | S | NH | Q3d | OH |

TABLE 5-continued

| No | A | B | R¹ | L¹ | R² | L² | L³ | Y | L⁴ | R³ | X |
|---|---|---|---|---|---|---|---|---|---|---|---|
| 139 | CMe | NH | Q1a | a bond | Me | a bond | NH | S | NH | Q3e | OH |
| 140 | CMe | NH | Q1a | a bond | Me | a bond | NH | S | NH | Q3f | OH |
| 141 | CMe | NH | Q1b | a bond | Me | a bond | NH | O | a bond | Q3d | OH |
| 142 | CMe | NH | Q1b | a bond | Me | a bond | NH | O | a bond | Q3e | OH |
| 143 | CMe | NH | Q1b | a bond | Me | a bond | NH | O | a bond | Q3f | OH |
| 144 | CMe | NH | Q1b | a bond | Me | a bond | NH | O | NH | Q3d | OH |
| 145 | CMe | NH | Q1b | a bond | Me | a bond | NH | O | NH | Q3e | OH |
| 146 | CMe | NH | Q1b | a bond | Me | a bond | NH | O | NH | Q3f | OH |
| 147 | CMe | NH | Q1b | a bond | Me | a bond | NH | S | a bond | Q3d | OH |
| 148 | CMe | NH | Q1b | a bond | Me | a bond | NH | S | a bond | Q3e | OH |
| 149 | CMe | NH | Q1b | a bond | Me | a bond | NH | S | a bond | Q3f | OH |
| 150 | CMe | NH | Q1b | a bond | Me | a bond | NH | S | NH | Q3d | OH |
| 151 | CMe | NH | Q1b | a bond | Me | a bond | NH | S | NH | Q3e | OH |
| 152 | CMe | NH | Q1b | a bond | Me | a bond | NH | S | NH | Q3f | OH |
| 153 | CMe | NH | Q1c | a bond | Me | a bond | NH | O | a bond | Q3d | OH |
| 154 | CMe | NH | Q1c | a bond | Me | a bond | NH | O | a bond | Q3e | OH |
| 155 | CMe | NH | Q1c | a bond | Me | a bond | NH | O | a bond | Q3f | OH |
| 156 | CMe | NH | Q1c | a bond | Me | a bond | NH | O | NH | Q3d | OH |
| 157 | CMe | NH | Q1c | a bond | Me | a bond | NH | O | NH | Q3e | OH |
| 158 | CMe | NH | Q1c | a bond | Me | a bond | NH | O | NH | Q3f | OH |
| 159 | CMe | NH | Q1c | a bond | Me | a bond | NH | S | a bond | Q3d | OH |
| 160 | CMe | NH | Q1c | a bond | Me | a bond | NH | S | a bond | Q3e | OH |
| 161 | CMe | NH | Q1c | a bond | Me | a bond | NH | S | a bond | Q3f | OH |
| 162 | CMe | NH | Q1c | a bond | Me | a bond | NH | S | NH | Q3d | OH |
| 163 | CMe | NH | Q1c | a bond | Me | a bond | NH | S | NH | Q3e | OH |
| 164 | CMe | NH | Q1a | a bond | Me | a bond | NH | S | NH | Q3g | OH |
| 165 | CMe | NH | Q1a | a bond | Me | a bond | NH | S | NH | Q3h | OH |
| 166 | CMe | NH | Q1b | a bond | Me | a bond | NH | S | NH | Q3g | OH |
| 167 | CMe | NH | Q1b | a bond | Me | a bond | NH | S | NH | Q3h | OH |
| 168 | CMe | NH | Q1c | a bond | Me | a bond | NH | S | NH | Q3g | OH |
| 169 | CMe | NH | Q1c | a bond | Me | a bond | NH | S | NH | Q3h | OH |
| 170 | CMe | NH | Q1a | a bond | Me | a bond | NH | O | a bond | Q3g | OH |
| 171 | CMe | NH | Q1a | a bond | Me | a bond | NH | O | a bond | Q3h | OH |
| 172 | CMe | NH | Q1b | a bond | Me | a bond | NH | O | a bond | Q3g | OH |
| 173 | CMe | NH | Q1b | a bond | Me | a bond | NH | O | a bond | Q3h | OH |
| 174 | CMe | NH | Q1c | a bond | Me | a bond | NH | S | a bond | Q3g | OH |
| 175 | CMe | NH | Q1c | a bond | Me | a bond | NH | S | a bond | Q3h | OH |
| 176 | CMe | NH | Q1c | a bond | Me | a bond | NH | S | NH | Q3f | OH |

73) The compounds wherein A, B, R¹, L¹, R², L², L³, Y, L⁴, R³ and X are any of the following combinations in Table 6, tautomers, prodrugs or pharmaceutically acceptable salts of the compounds or solvates thereof. The symbols in Table 6 denote the following substituents.

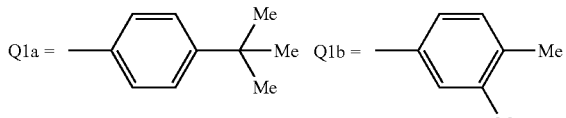

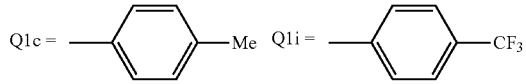

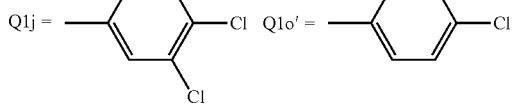

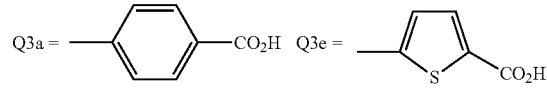

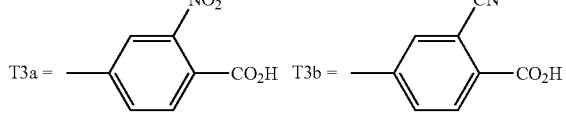

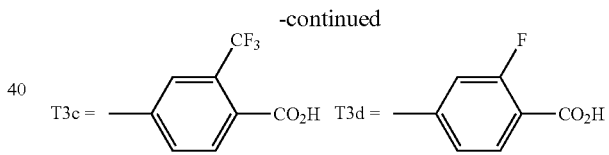

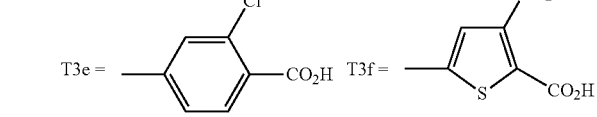

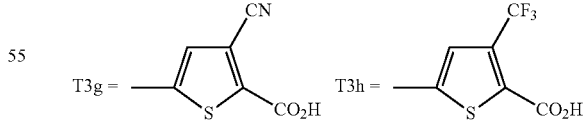

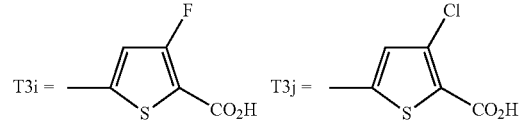

TABLE 6

| No | A | B | R¹ | L¹ | R² | L² | L³ | Y | L⁴ | R³ | X |
|---|---|---|---|---|---|---|---|---|---|---|---|
| 1 | N | NMe | Q1a | a bond | Me | a bond | NH | S | NH | T3a | OH |
| 2 | N | NMe | Q1a | a bond | Me | a bond | NH | S | NH | T3b | OH |
| 3 | N | NMe | Q1a | a bond | Me | a bond | NH | S | NH | T3c | OH |
| 4 | N | NMe | Q1a | a bond | Me | a bond | NH | S | NH | T3d | OH |
| 5 | N | NMe | Q1a | a bond | Me | a bond | NH | S | NH | T3e | OH |
| 6 | N | NMe | Q1a | a bond | Me | a bond | NH | S | NH | T3f | OH |
| 7 | N | NMe | Q1a | a bond | Me | a bond | NH | S | NH | T3g | OH |
| 8 | N | NMe | Q1a | a bond | Me | a bond | NH | S | NH | T3h | OH |
| 9 | N | NMe | Q1a | a bond | Me | a bond | NH | S | NH | T3i | OH |
| 10 | N | NMe | Q1a | a bond | Me | a bond | NH | S | NH | T3j | OH |
| 11 | N | NMe | Q1a | a bond | Me | a bond | NH | S | a bond | T3a | OH |
| 12 | N | NMe | Q1a | a bond | Me | a bond | NH | S | a bond | T3b | OH |
| 13 | N | NMe | Q1a | a bond | Me | a bond | NH | S | a bond | T3c | OH |
| 14 | N | NMe | Q1a | a bond | Me | a bond | NH | S | a bond | T3d | OH |
| 15 | N | NMe | Q1a | a bond | Me | a bond | NH | S | a bond | T3e | OH |
| 16 | N | NMe | Q1a | a bond | Me | a bond | NH | S | a bond | T3f | OH |
| 17 | N | NMe | Q1a | a bond | Me | a bond | NH | S | a bond | T3g | OH |
| 18 | N | NMe | Q1a | a bond | Me | a bond | NH | S | a bond | T3h | OH |
| 19 | N | NMe | Q1a | a bond | Me | a bond | NH | S | a bond | T3i | OH |
| 20 | N | NMe | Q1a | a bond | Me | a bond | NH | S | a bond | T3j | OH |
| 21 | N | NMe | Q1a | a bond | Me | a bond | NH | O | NH | T3a | OH |
| 22 | N | NMe | Q1a | a bond | Me | a bond | NH | O | NH | T3b | OH |
| 23 | N | NMe | Q1a | a bond | Me | a bond | NH | O | NH | T3c | OH |
| 24 | N | NMe | Q1a | a bond | Me | a bond | NH | O | NH | T3d | OH |
| 25 | N | NMe | Q1a | a bond | Me | a bond | NH | O | NH | T3e | OH |
| 26 | N | NMe | Q1a | a bond | Me | a bond | NH | O | NH | T3f | OH |
| 27 | N | NMe | Q1a | a bond | Me | a bond | NH | O | NH | T3g | OH |
| 28 | N | NMe | Q1a | a bond | Me | a bond | NH | O | NH | T3h | OH |
| 29 | N | NMe | Q1a | a bond | Me | a bond | NH | O | NH | T3i | OH |
| 30 | N | NMe | Q1a | a bond | Me | a bond | NH | O | NH | T3j | OH |
| 31 | N | NMe | Q1a | a bond | Me | a bond | NH | O | a bond | T3a | OH |
| 32 | N | NMe | Q1a | a bond | Me | a bond | NH | O | a bond | T3b | OH |
| 33 | N | NMe | Q1a | a bond | Me | a bond | NH | O | a bond | T3c | OH |
| 34 | N | NMe | Q1a | a bond | Me | a bond | NH | O | a bond | T3d | OH |
| 35 | N | NMe | Q1a | a bond | Me | a bond | NH | O | a bond | T3e | OH |
| 36 | N | NMe | Q1a | a bond | Me | a bond | NH | O | a bond | T3f | OH |
| 37 | N | NMe | Q1a | a bond | Me | a bond | NH | O | a bond | T3g | OH |
| 38 | N | NMe | Q1a | a bond | Me | a bond | NH | O | a bond | T3h | OH |
| 39 | N | NMe | Q1a | a bond | Me | a bond | NH | O | a bond | T3i | OH |
| 40 | N | NMe | Q1a | a bond | Me | a bond | NH | O | a bond | T3j | OH |
| 41 | N | NMe | Q1a | a bond | H | a bond | NH | S | NH | T3a | OH |
| 42 | N | NMe | Q1a | a bond | H | a bond | NH | S | NH | T3b | OH |
| 43 | N | NMe | Q1a | a bond | H | a bond | NH | S | NH | T3c | OH |
| 44 | N | NMe | Q1a | a bond | H | a bond | NH | S | NH | T3d | OH |
| 45 | N | NMe | Q1a | a bond | H | a bond | NH | S | NH | T3e | OH |
| 46 | N | NMe | Q1a | a bond | H | a bond | NH | S | NH | T3f | OH |
| 47 | N | NMe | Q1a | a bond | H | a bond | NH | S | NH | T3g | OH |
| 48 | N | NMe | Q1a | a bond | H | a bond | NH | S | NH | T3h | OH |
| 49 | N | NMe | Q1a | a bond | H | a bond | NH | S | NH | T3i | OH |
| 50 | N | NMe | Q1a | a bond | H | a bond | NH | S | NH | T3j | OH |
| 51 | N | NMe | Q1a | a bond | H | a bond | NH | S | a bond | T3a | OH |
| 52 | N | NMe | Q1a | a bond | H | a bond | NH | S | a bond | T3b | OH |
| 53 | N | NMe | Q1a | a bond | H | a bond | NH | S | a bond | T3c | OH |
| 54 | N | NMe | Q1a | a bond | H | a bond | NH | S | a bond | T3d | OH |
| 55 | N | NMe | Q1a | a bond | H | a bond | NH | S | a bond | T3e | OH |
| 56 | N | NMe | Q1a | a bond | H | a bond | NH | S | a bond | T3f | OH |
| 57 | N | NMe | Q1a | a bond | H | a bond | NH | S | a bond | T3g | OH |
| 58 | N | NMe | Q1a | a bond | H | a bond | NH | S | a bond | T3h | OH |
| 59 | N | NMe | Q1a | a bond | H | a bond | NH | S | a bond | T3i | OH |
| 60 | N | NMe | Q1a | a bond | H | a bond | NH | S | a bond | T3j | OH |
| 61 | N | NMe | Q1a | a bond | H | a bond | NH | O | NH | T3a | OH |
| 62 | N | NMe | Q1a | a bond | H | a bond | NH | O | NH | T3b | OH |
| 63 | N | NMe | Q1a | a bond | H | a bond | NH | O | NH | T3c | OH |
| 64 | N | NMe | Q1a | a bond | H | a bond | NH | O | NH | T3d | OH |
| 65 | N | NMe | Q1a | a bond | H | a bond | NH | O | NH | T3e | OH |
| 66 | N | NMe | Q1a | a bond | H | a bond | NH | O | NH | T3f | OH |
| 67 | N | NMe | Q1a | a bond | H | a bond | NH | O | NH | T3g | OH |
| 68 | N | NMe | Q1a | a bond | H | a bond | NH | O | NH | T3h | OH |
| 69 | N | NMe | Q1a | a bond | H | a bond | NH | O | NH | T3i | OH |
| 70 | N | NMe | Q1a | a bond | H | a bond | NH | O | NH | T3j | OH |
| 71 | N | NMe | Q1a | a bond | H | a bond | NH | O | a bond | T3a | OH |
| 72 | N | NMe | Q1a | a bond | H | a bond | NH | O | a bond | T3b | OH |
| 73 | N | NMe | Q1a | a bond | H | a bond | NH | O | a bond | T3c | OH |
| 74 | N | NMe | Q1a | a bond | H | a bond | NH | O | a bond | T3d | OH |
| 75 | N | NMe | Q1a | a bond | H | a bond | NH | O | a bond | T3e | OH |
| 76 | N | NMe | Q1a | a bond | H | a bond | NH | O | a bond | T3f | OH |
| 77 | N | NMe | Q1a | a bond | H | a bond | NH | O | a bond | T3g | OH |
| 78 | N | NMe | Q1a | a bond | H | a bond | NH | O | a bond | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 79 | N | NMe | Q1a | a bond | H | a bond | NH | O | a bond | T3i | OH |
| 80 | N | NMe | Q1a | a bond | H | a bond | NH | O | a bond | T3j | OH |
| 81 | N | NMe | Q1b | a bond | Me | a bond | NH | S | NH | T3a | OH |
| 82 | N | NMe | Q1b | a bond | Me | a bond | NH | S | NH | T3b | OH |
| 83 | N | NMe | Q1b | a bond | Me | a bond | NH | S | NH | T3c | OH |
| 84 | N | NMe | Q1b | a bond | Me | a bond | NH | S | NH | T3d | OH |
| 85 | N | NMe | Q1b | a bond | Me | a bond | NH | S | NH | T3e | OH |
| 86 | N | NMe | Q1b | a bond | Me | a bond | NH | S | NH | T3f | OH |
| 87 | N | NMe | Q1b | a bond | Me | a bond | NH | S | NH | T3g | OH |
| 88 | N | NMe | Q1b | a bond | Me | a bond | NH | S | NH | T3h | OH |
| 89 | N | NMe | Q1b | a bond | Me | a bond | NH | S | NH | T3i | OH |
| 90 | N | NMe | Q1b | a bond | Me | a bond | NH | S | NH | T3j | OH |
| 91 | N | NMe | Q1b | a bond | Me | a bond | NH | S | a bond | T3a | OH |
| 92 | N | NMe | Q1b | a bond | Me | a bond | NH | S | a bond | T3b | OH |
| 93 | N | NMe | Q1b | a bond | Me | a bond | NH | S | a bond | T3c | OH |
| 94 | N | NMe | Q1b | a bond | Me | a bond | NH | S | a bond | T3d | OH |
| 95 | N | NMe | Q1b | a bond | Me | a bond | NH | S | a bond | T3e | OH |
| 96 | N | NMe | Q1b | a bond | Me | a bond | NH | S | a bond | T3f | OH |
| 97 | N | NMe | Q1b | a bond | Me | a bond | NH | S | a bond | T3g | OH |
| 98 | N | NMe | Q1b | a bond | Me | a bond | NH | S | a bond | T3h | OH |
| 99 | N | NMe | Q1b | a bond | Me | a bond | NH | S | a bond | T3i | OH |
| 100 | N | NMe | Q1b | a bond | Me | a bond | NH | S | a bond | T3j | OH |
| 101 | N | NMe | Q1b | a bond | Me | a bond | NH | O | NH | T3a | OH |
| 102 | N | NMe | Q1b | a bond | Me | a bond | NH | O | NH | T3b | OH |
| 103 | N | NMe | Q1b | a bond | Me | a bond | NH | O | NH | T3c | OH |
| 104 | N | NMe | Q1b | a bond | Me | a bond | NH | O | NH | T3d | OH |
| 105 | N | NMe | Q1b | a bond | Me | a bond | NH | O | NH | T3e | OH |
| 106 | N | NMe | Q1b | a bond | Me | a bond | NH | O | NH | T3f | OH |
| 107 | N | NMe | Q1b | a bond | Me | a bond | NH | O | NH | T3g | OH |
| 108 | N | NMe | Q1b | a bond | Me | a bond | NH | O | NH | T3h | OH |
| 109 | N | NMe | Q1b | a bond | Me | a bond | NH | O | NH | T3i | OH |
| 110 | N | NMe | Q1b | a bond | Me | a bond | NH | O | NH | T3j | OH |
| 111 | N | NMe | Q1b | a bond | Me | a bond | NH | O | a bond | T3a | OH |
| 112 | N | NMe | Q1b | a bond | Me | a bond | NH | O | a bond | T3b | OH |
| 113 | N | NMe | Q1b | a bond | Me | a bond | NH | O | a bond | T3c | OH |
| 114 | N | NMe | Q1b | a bond | Me | a bond | NH | O | a bond | T3d | OH |
| 115 | N | NMe | Q1b | a bond | Me | a bond | NH | O | a bond | T3e | OH |
| 116 | N | NMe | Q1b | a bond | Me | a bond | NH | O | a bond | T3f | OH |
| 117 | N | NMe | Q1b | a bond | Me | a bond | NH | O | a bond | T3g | OH |
| 118 | N | NMe | Q1b | a bond | Me | a bond | NH | O | a bond | T3h | OH |
| 119 | N | NMe | Q1b | a bond | Me | a bond | NH | O | a bond | T3i | OH |
| 120 | N | NMe | Q1b | a bond | Me | a bond | NH | O | a bond | T3j | OH |
| 121 | N | NMe | Q1b | a bond | H | a bond | NH | S | NH | T3a | OH |
| 122 | N | NMe | Q1b | a bond | H | a bond | NH | S | NH | T3b | OH |
| 123 | N | NMe | Q1b | a bond | H | a bond | NH | S | NH | T3c | OH |
| 124 | N | NMe | Q1b | a bond | H | a bond | NH | S | NH | T3d | OH |
| 125 | N | NMe | Q1b | a bond | H | a bond | NH | S | NH | T3e | OH |
| 126 | N | NMe | Q1b | a bond | H | a bond | NH | S | NH | T3f | OH |
| 127 | N | NMe | Q1b | a bond | H | a bond | NH | S | NH | T3g | OH |
| 128 | N | NMe | Q1b | a bond | H | a bond | NH | S | NH | T3h | OH |
| 129 | N | NMe | Q1b | a bond | H | a bond | NH | S | NH | T3i | OH |
| 130 | N | NMe | Q1b | a bond | H | a bond | NH | S | NH | T3j | OH |
| 131 | N | NMe | Q1b | a bond | H | a bond | NH | S | a bond | T3a | OH |
| 132 | N | NMe | Q1b | a bond | H | a bond | NH | S | a bond | T3b | OH |
| 133 | N | NMe | Q1b | a bond | H | a bond | NH | S | a bond | T3c | OH |
| 134 | N | NMe | Q1b | a bond | H | a bond | NH | S | a bond | T3d | OH |
| 135 | N | NMe | Q1b | a bond | H | a bond | NH | S | a bond | T3e | OH |
| 136 | N | NMe | Q1b | a bond | H | a bond | NH | S | a bond | T3f | OH |
| 137 | N | NMe | Q1b | a bond | H | a bond | NH | S | a bond | T3g | OH |
| 138 | N | NMe | Q1b | a bond | H | a bond | NH | S | a bond | T3h | OH |
| 139 | N | NMe | Q1b | a bond | H | a bond | NH | S | a bond | T3i | OH |
| 140 | N | NMe | Q1b | a bond | H | a bond | NH | S | a bond | T3j | OH |
| 141 | N | NMe | Q1b | a bond | H | a bond | NH | O | NH | T3a | OH |
| 142 | N | NMe | Q1b | a bond | H | a bond | NH | O | NH | T3b | OH |
| 143 | N | NMe | Q1b | a bond | H | a bond | NH | O | NH | T3c | OH |
| 144 | N | NMe | Q1b | a bond | H | a bond | NH | O | NH | T3d | OH |
| 145 | N | NMe | Q1b | a bond | H | a bond | NH | O | NH | T3e | OH |
| 146 | N | NMe | Q1b | a bond | H | a bond | NH | O | NH | T3f | OH |
| 147 | N | NMe | Q1b | a bond | H | a bond | NH | O | NH | T3g | OH |
| 148 | N | NMe | Q1b | a bond | H | a bond | NH | O | NH | T3h | OH |
| 149 | N | NMe | Q1b | a bond | H | a bond | NH | O | NH | T3i | OH |
| 150 | N | NMe | Q1b | a bond | H | a bond | NH | O | NH | T3j | OH |
| 151 | N | NMe | Q1b | a bond | H | a bond | NH | O | a bond | T3a | OH |
| 152 | N | NMe | Q1b | a bond | H | a bond | NH | O | a bond | T3b | OH |
| 153 | N | NMe | Q1b | a bond | H | a bond | NH | O | a bond | T3c | OH |
| 154 | N | NMe | Q1b | a bond | H | a bond | NH | O | a bond | T3d | OH |
| 155 | N | NMe | Q1b | a bond | H | a bond | NH | O | a bond | T3e | OH |
| 156 | N | NMe | Q1b | a bond | H | a bond | NH | O | a bond | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 157 | N | NMe | Q1b | a bond | H | a bond | NH | O | a bond | T3g | OH |
| 158 | N | NMe | Q1b | a bond | H | a bond | NH | O | a bond | T3h | OH |
| 159 | N | NMe | Q1b | a bond | H | a bond | NH | O | a bond | T3i | OH |
| 160 | N | NMe | Q1b | a bond | H | a bond | NH | O | a bond | T3j | OH |
| 161 | N | NMe | Q1c | a bond | Me | a bond | NH | S | NH | T3a | OH |
| 162 | N | NMe | Q1c | a bond | Me | a bond | NH | S | NH | T3b | OH |
| 163 | N | NMe | Q1c | a bond | Me | a bond | NH | S | NH | T3c | OH |
| 164 | N | NMe | Q1c | a bond | Me | a bond | NH | S | NH | T3d | OH |
| 165 | N | NMe | Q1c | a bond | Me | a bond | NH | S | NH | T3e | OH |
| 166 | N | NMe | Q1c | a bond | Me | a bond | NH | S | NH | T3f | OH |
| 167 | N | NMe | Q1c | a bond | Me | a bond | NH | S | NH | T3g | OH |
| 168 | N | NMe | Q1c | a bond | Me | a bond | NH | S | NH | T3h | OH |
| 169 | N | NMe | Q1c | a bond | Me | a bond | NH | S | NH | T3i | OH |
| 170 | N | NMe | Q1c | a bond | Me | a bond | NH | S | NH | T3j | OH |
| 171 | N | NMe | Q1c | a bond | Me | a bond | NH | S | a bond | T3a | OH |
| 172 | N | NMe | Q1c | a bond | Me | a bond | NH | S | a bond | T3b | OH |
| 173 | N | NMe | Q1c | a bond | Me | a bond | NH | S | a bond | T3c | OH |
| 174 | N | NMe | Q1c | a bond | Me | a bond | NH | S | a bond | T3d | OH |
| 175 | N | NMe | Q1c | a bond | Me | a bond | NH | S | a bond | T3e | OH |
| 176 | N | NMe | Q1c | a bond | Me | a bond | NH | S | a bond | T3f | OH |
| 177 | N | NMe | Q1c | a bond | Me | a bond | NH | S | a bond | T3g | OH |
| 178 | N | NMe | Q1c | a bond | Me | a bond | NH | S | a bond | T3h | OH |
| 179 | N | NMe | Q1c | a bond | Me | a bond | NH | S | a bond | T3i | OH |
| 180 | N | NMe | Q1c | a bond | Me | a bond | NH | S | a bond | T3j | OH |
| 181 | N | NMe | Q1c | a bond | Me | a bond | NH | O | NH | T3a | OH |
| 182 | N | NMe | Q1c | a bond | Me | a bond | NH | O | NH | T3b | OH |
| 183 | N | NMe | Q1c | a bond | Me | a bond | NH | O | NH | T3c | OH |
| 184 | N | NMe | Q1c | a bond | Me | a bond | NH | O | NH | T3d | OH |
| 185 | N | NMe | Q1c | a bond | Me | a bond | NH | O | NH | T3e | OH |
| 186 | N | NMe | Q1c | a bond | Me | a bond | NH | O | NH | T3f | OH |
| 187 | N | NMe | Q1c | a bond | Me | a bond | NH | O | NH | T3g | OH |
| 188 | N | NMe | Q1c | a bond | Me | a bond | NH | O | NH | T3h | OH |
| 189 | N | NMe | Q1c | a bond | Me | a bond | NH | O | NH | T3i | OH |
| 190 | N | NMe | Q1c | a bond | Me | a bond | NH | O | NH | T3j | OH |
| 191 | N | NMe | Q1c | a bond | Me | a bond | NH | O | a bond | T3a | OH |
| 192 | N | NMe | Q1c | a bond | Me | a bond | NH | O | a bond | T3b | OH |
| 193 | N | NMe | Q1c | a bond | Me | a bond | NH | O | a bond | T3c | OH |
| 194 | N | NMe | Q1c | a bond | Me | a bond | NH | O | a bond | T3d | OH |
| 195 | N | NMe | Q1c | a bond | Me | a bond | NH | O | a bond | T3e | OH |
| 196 | N | NMe | Q1c | a bond | Me | a bond | NH | O | a bond | T3f | OH |
| 197 | N | NMe | Q1c | a bond | Me | a bond | NH | O | a bond | T3g | OH |
| 198 | N | NMe | Q1c | a bond | Me | a bond | NH | O | a bond | T3h | OH |
| 199 | N | NMe | Q1c | a bond | Me | a bond | NH | O | a bond | T3i | OH |
| 200 | N | NMe | Q1c | a bond | Me | a bond | NH | O | a bond | T3j | OH |
| 201 | N | NMe | Q1c | a bond | H | a bond | NH | S | NH | T3a | OH |
| 202 | N | NMe | Q1c | a bond | H | a bond | NH | S | NH | T3b | OH |
| 203 | N | NMe | Q1c | a bond | H | a bond | NH | S | NH | T3c | OH |
| 204 | N | NMe | Q1c | a bond | H | a bond | NH | S | NH | T3d | OH |
| 205 | N | NMe | Q1c | a bond | H | a bond | NH | S | NH | T3e | OH |
| 206 | N | NMe | Q1c | a bond | H | a bond | NH | S | NH | T3f | OH |
| 207 | N | NMe | Q1c | a bond | H | a bond | NH | S | NH | T3g | OH |
| 208 | N | NMe | Q1c | a bond | H | a bond | NH | S | NH | T3h | OH |
| 209 | N | NMe | Q1c | a bond | H | a bond | NH | S | NH | T3i | OH |
| 210 | N | NMe | Q1c | a bond | H | a bond | NH | S | NH | T3j | OH |
| 211 | N | NMe | Q1c | a bond | H | a bond | NH | S | a bond | T3a | OH |
| 212 | N | NMe | Q1c | a bond | H | a bond | NH | S | a bond | T3b | OH |
| 213 | N | NMe | Q1c | a bond | H | a bond | NH | S | a bond | T3c | OH |
| 214 | N | NMe | Q1c | a bond | H | a bond | NH | S | a bond | T3d | OH |
| 215 | N | NMe | Q1c | a bond | H | a bond | NH | S | a bond | T3e | OH |
| 216 | N | NMe | Q1c | a bond | H | a bond | NH | S | a bond | T3f | OH |
| 217 | N | NMe | Q1c | a bond | H | a bond | NH | S | a bond | T3g | OH |
| 218 | N | NMe | Q1c | a bond | H | a bond | NH | S | a bond | T3h | OH |
| 219 | N | NMe | Q1c | a bond | H | a bond | NH | S | a bond | T3i | OH |
| 220 | N | NMe | Q1c | a bond | H | a bond | NH | S | a bond | T3j | OH |
| 221 | N | NMe | Q1c | a bond | H | a bond | NH | O | NH | T3a | OH |
| 222 | N | NMe | Q1c | a bond | H | a bond | NH | O | NH | T3b | OH |
| 223 | N | NMe | Q1c | a bond | H | a bond | NH | O | NH | T3c | OH |
| 224 | N | NMe | Q1c | a bond | H | a bond | NH | O | NH | T3d | OH |
| 225 | N | NMe | Q1c | a bond | H | a bond | NH | O | NH | T3e | OH |
| 226 | N | NMe | Q1c | a bond | H | a bond | NH | O | NH | T3f | OH |
| 227 | N | NMe | Q1c | a bond | H | a bond | NH | O | NH | T3g | OH |
| 228 | N | NMe | Q1c | a bond | H | a bond | NH | O | NH | T3h | OH |
| 229 | N | NMe | Q1c | a bond | H | a bond | NH | O | NH | T3i | OH |
| 230 | N | NMe | Q1c | a bond | H | a bond | NH | O | NH | T3j | OH |
| 231 | N | NMe | Q1c | a bond | H | a bond | NH | O | a bond | T3a | OH |
| 232 | N | NMe | Q1c | a bond | H | a bond | NH | O | a bond | T3b | OH |
| 233 | N | NMe | Q1c | a bond | H | a bond | NH | O | a bond | T3c | OH |
| 234 | N | NMe | Q1c | a bond | H | a bond | NH | O | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 235 | N | NMe | Q1c | a bond | H | a bond | NH | O | a bond | T3e | OH |
| 236 | N | NMe | Q1c | a bond | H | a bond | NH | O | a bond | T3f | OH |
| 237 | N | NMe | Q1c | a bond | H | a bond | NH | O | a bond | T3g | OH |
| 238 | N | NMe | Q1c | a bond | H | a bond | NH | O | a bond | T3h | OH |
| 239 | N | NMe | Q1c | a bond | H | a bond | NH | O | a bond | T3i | OH |
| 240 | N | NMe | Q1c | a bond | H | a bond | NH | O | a bond | T3j | OH |
| 241 | N | NMe | Q1i | a bond | Me | a bond | NH | S | NH | T3a | OH |
| 242 | N | NMe | Q1i | a bond | Me | a bond | NH | S | NH | T3b | OH |
| 243 | N | NMe | Q1i | a bond | Me | a bond | NH | S | NH | T3c | OH |
| 244 | N | NMe | Q1i | a bond | Me | a bond | NH | S | NH | T3d | OH |
| 245 | N | NMe | Q1i | a bond | Me | a bond | NH | S | NH | T3e | OH |
| 246 | N | NMe | Q1i | a bond | Me | a bond | NH | S | NH | T3f | OH |
| 247 | N | NMe | Q1i | a bond | Me | a bond | NH | S | NH | T3g | OH |
| 248 | N | NMe | Q1i | a bond | Me | a bond | NH | S | NH | T3h | OH |
| 249 | N | NMe | Q1i | a bond | Me | a bond | NH | S | NH | T3i | OH |
| 250 | N | NMe | Q1i | a bond | Me | a bond | NH | S | NH | T3j | OH |
| 251 | N | NMe | Q1i | a bond | Me | a bond | NH | S | a bond | T3a | OH |
| 252 | N | NMe | Q1i | a bond | Me | a bond | NH | S | a bond | T3b | OH |
| 253 | N | NMe | Q1i | a bond | Me | a bond | NH | S | a bond | T3c | OH |
| 254 | N | NMe | Q1i | a bond | Me | a bond | NH | S | a bond | T3d | OH |
| 255 | N | NMe | Q1i | a bond | Me | a bond | NH | S | a bond | T3e | OH |
| 256 | N | NMe | Q1i | a bond | Me | a bond | NH | S | a bond | T3f | OH |
| 257 | N | NMe | Q1i | a bond | Me | a bond | NH | S | a bond | T3g | OH |
| 258 | N | NMe | Q1i | a bond | Me | a bond | NH | S | a bond | T3h | OH |
| 259 | N | NMe | Q1i | a bond | Me | a bond | NH | S | a bond | T3i | OH |
| 260 | N | NMe | Q1i | a bond | Me | a bond | NH | S | a bond | T3j | OH |
| 261 | N | NMe | Q1i | a bond | Me | a bond | NH | O | NH | T3a | OH |
| 262 | N | NMe | Q1i | a bond | Me | a bond | NH | O | NH | T3b | OH |
| 263 | N | NMe | Q1i | a bond | Me | a bond | NH | O | NH | T3c | OH |
| 264 | N | NMe | Q1i | a bond | Me | a bond | NH | O | NH | T3d | OH |
| 265 | N | NMe | Q1i | a bond | Me | a bond | NH | O | NH | T3e | OH |
| 266 | N | NMe | Q1i | a bond | Me | a bond | NH | O | NH | T3f | OH |
| 267 | N | NMe | Q1i | a bond | Me | a bond | NH | O | NH | T3g | OH |
| 268 | N | NMe | Q1i | a bond | Me | a bond | NH | O | NH | T3h | OH |
| 269 | N | NMe | Q1i | a bond | Me | a bond | NH | O | NH | T3i | OH |
| 270 | N | NMe | Q1i | a bond | Me | a bond | NH | O | NH | T3j | OH |
| 271 | N | NMe | Q1i | a bond | Me | a bond | NH | O | a bond | T3a | OH |
| 272 | N | NMe | Q1i | a bond | Me | a bond | NH | O | a bond | T3b | OH |
| 273 | N | NMe | Q1i | a bond | Me | a bond | NH | O | a bond | T3c | OH |
| 274 | N | NMe | Q1i | a bond | Me | a bond | NH | O | a bond | T3d | OH |
| 275 | N | NMe | Q1i | a bond | Me | a bond | NH | O | a bond | T3e | OH |
| 276 | N | NMe | Q1i | a bond | Me | a bond | NH | O | a bond | T3f | OH |
| 277 | N | NMe | Q1i | a bond | Me | a bond | NH | O | a bond | T3g | OH |
| 278 | N | NMe | Q1i | a bond | Me | a bond | NH | O | a bond | T3h | OH |
| 279 | N | NMe | Q1i | a bond | Me | a bond | NH | O | a bond | T3i | OH |
| 280 | N | NMe | Q1i | a bond | Me | a bond | NH | O | a bond | T3j | OH |
| 281 | N | NMe | Q1i | a bond | H | a bond | NH | S | NH | T3a | OH |
| 282 | N | NMe | Q1i | a bond | H | a bond | NH | S | NH | T3b | OH |
| 283 | N | NMe | Q1i | a bond | H | a bond | NH | S | NH | T3c | OH |
| 284 | N | NMe | Q1i | a bond | H | a bond | NH | S | NH | T3d | OH |
| 285 | N | NMe | Q1i | a bond | H | a bond | NH | S | NH | T3e | OH |
| 286 | N | NMe | Q1i | a bond | H | a bond | NH | S | NH | T3f | OH |
| 287 | N | NMe | Q1i | a bond | H | a bond | NH | S | NH | T3g | OH |
| 288 | N | NMe | Q1i | a bond | H | a bond | NH | S | NH | T3h | OH |
| 289 | N | NMe | Q1i | a bond | H | a bond | NH | S | NH | T3i | OH |
| 290 | N | NMe | Q1i | a bond | H | a bond | NH | S | NH | T3j | OH |
| 291 | N | NMe | Q1i | a bond | H | a bond | NH | S | a bond | T3a | OH |
| 292 | N | NMe | Q1i | a bond | H | a bond | NH | S | a bond | T3b | OH |
| 293 | N | NMe | Q1i | a bond | H | a bond | NH | S | a bond | T3c | OH |
| 294 | N | NMe | Q1i | a bond | H | a bond | NH | S | a bond | T3d | OH |
| 295 | N | NMe | Q1i | a bond | H | a bond | NH | S | a bond | T3e | OH |
| 296 | N | NMe | Q1i | a bond | H | a bond | NH | S | a bond | T3f | OH |
| 297 | N | NMe | Q1i | a bond | H | a bond | NH | S | a bond | T3g | OH |
| 298 | N | NMe | Q1i | a bond | H | a bond | NH | S | a bond | T3h | OH |
| 299 | N | NMe | Q1i | a bond | H | a bond | NH | S | a bond | T3i | OH |
| 300 | N | NMe | Q1i | a bond | H | a bond | NH | S | a bond | T3j | OH |
| 301 | N | NMe | Q1i | a bond | H | a bond | NH | O | NH | T3a | OH |
| 302 | N | NMe | Q1i | a bond | H | a bond | NH | O | NH | T3b | OH |
| 303 | N | NMe | Q1i | a bond | H | a bond | NH | O | NH | T3c | OH |
| 304 | N | NMe | Q1i | a bond | H | a bond | NH | O | NH | T3d | OH |
| 305 | N | NMe | Q1i | a bond | H | a bond | NH | O | NH | T3e | OH |
| 306 | N | NMe | Q1i | a bond | H | a bond | NH | O | NH | T3f | OH |
| 307 | N | NMe | Q1i | a bond | H | a bond | NH | O | NH | T3g | OH |
| 308 | N | NMe | Q1i | a bond | H | a bond | NH | O | NH | T3h | OH |
| 309 | N | NMe | Q1i | a bond | H | a bond | NH | O | NH | T3i | OH |
| 310 | N | NMe | Q1i | a bond | H | a bond | NH | O | NH | T3j | OH |
| 311 | N | NMe | Q1i | a bond | H | a bond | NH | O | a bond | T3a | OH |
| 312 | N | NMe | Q1i | a bond | H | a bond | NH | O | a bond | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 313 | N | NMe | Q1i | a bond | H | a bond | NH | O | a bond | T3c | OH |
| 314 | N | NMe | Q1i | a bond | H | a bond | NH | O | a bond | T3d | OH |
| 315 | N | NMe | Q1i | a bond | H | a bond | NH | O | a bond | T3e | OH |
| 316 | N | NMe | Q1i | a bond | H | a bond | NH | O | a bond | T3f | OH |
| 317 | N | NMe | Q1i | a bond | H | a bond | NH | O | a bond | T3g | OH |
| 318 | N | NMe | Q1i | a bond | H | a bond | NH | O | a bond | T3h | OH |
| 319 | N | NMe | Q1i | a bond | H | a bond | NH | O | a bond | T3i | OH |
| 320 | N | NMe | Q1i | a bond | H | a bond | NH | O | a bond | T3j | OH |
| 321 | N | NMe | Q1j | a bond | Me | a bond | NH | S | NH | T3a | OH |
| 322 | N | NMe | Q1j | a bond | Me | a bond | NH | S | NH | T3b | OH |
| 323 | N | NMe | Q1j | a bond | Me | a bond | NH | S | NH | T3c | OH |
| 324 | N | NMe | Q1j | a bond | Me | a bond | NH | S | NH | T3d | OH |
| 325 | N | NMe | Q1j | a bond | Me | a bond | NH | S | NH | T3e | OH |
| 326 | N | NMe | Q1j | a bond | Me | a bond | NH | S | NH | T3f | OH |
| 327 | N | NMe | Q1j | a bond | Me | a bond | NH | S | NH | T3g | OH |
| 328 | N | NMe | Q1j | a bond | Me | a bond | NH | S | NH | T3h | OH |
| 329 | N | NMe | Q1j | a bond | Me | a bond | NH | S | NH | T3i | OH |
| 330 | N | NMe | Q1j | a bond | Me | a bond | NH | S | NH | T3j | OH |
| 331 | N | NMe | Q1j | a bond | Me | a bond | NH | S | a bond | T3a | OH |
| 332 | N | NMe | Q1j | a bond | Me | a bond | NH | S | a bond | T3b | OH |
| 333 | N | NMe | Q1j | a bond | Me | a bond | NH | S | a bond | T3c | OH |
| 334 | N | NMe | Q1j | a bond | Me | a bond | NH | S | a bond | T3d | OH |
| 335 | N | NMe | Q1j | a bond | Me | a bond | NH | S | a bond | T3e | OH |
| 336 | N | NMe | Q1j | a bond | Me | a bond | NH | S | a bond | T3f | OH |
| 337 | N | NMe | Q1j | a bond | Me | a bond | NH | S | a bond | T3g | OH |
| 338 | N | NMe | Q1j | a bond | Me | a bond | NH | S | a bond | T3h | OH |
| 339 | N | NMe | Q1j | a bond | Me | a bond | NH | S | a bond | T3i | OH |
| 340 | N | NMe | Q1j | a bond | Me | a bond | NH | S | a bond | T3j | OH |
| 341 | N | NMe | Q1j | a bond | Me | a bond | NH | O | NH | T3a | OH |
| 342 | N | NMe | Q1j | a bond | Me | a bond | NH | O | NH | T3b | OH |
| 343 | N | NMe | Q1j | a bond | Me | a bond | NH | O | NH | T3c | OH |
| 344 | N | NMe | Q1j | a bond | Me | a bond | NH | O | NH | T3d | OH |
| 345 | N | NMe | Q1j | a bond | Me | a bond | NH | O | NH | T3e | OH |
| 346 | N | NMe | Q1j | a bond | Me | a bond | NH | O | NH | T3f | OH |
| 347 | N | NMe | Q1j | a bond | Me | a bond | NH | O | NH | T3g | OH |
| 348 | N | NMe | Q1j | a bond | Me | a bond | NH | O | NH | T3h | OH |
| 349 | N | NMe | Q1j | a bond | Me | a bond | NH | O | NH | T3i | OH |
| 350 | N | NMe | Q1j | a bond | Me | a bond | NH | O | NH | T3j | OH |
| 351 | N | NMe | Q1j | a bond | Me | a bond | NH | O | a bond | T3a | OH |
| 352 | N | NMe | Q1j | a bond | Me | a bond | NH | O | a bond | T3b | OH |
| 353 | N | NMe | Q1j | a bond | Me | a bond | NH | O | a bond | T3c | OH |
| 354 | N | NMe | Q1j | a bond | Me | a bond | NH | O | a bond | T3d | OH |
| 355 | N | NMe | Q1j | a bond | Me | a bond | NH | O | a bond | T3e | OH |
| 356 | N | NMe | Q1j | a bond | Me | a bond | NH | O | a bond | T3f | OH |
| 357 | N | NMe | Q1j | a bond | Me | a bond | NH | O | a bond | T3g | OH |
| 358 | N | NMe | Q1j | a bond | Me | a bond | NH | O | a bond | T3h | OH |
| 359 | N | NMe | Q1j | a bond | Me | a bond | NH | O | a bond | T3i | OH |
| 360 | N | NMe | Q1j | a bond | Me | a bond | NH | O | a bond | T3j | OH |
| 361 | N | NMe | Q1j | a bond | H | a bond | NH | S | NH | T3a | OH |
| 362 | N | NMe | Q1j | a bond | H | a bond | NH | S | NH | T3b | OH |
| 363 | N | NMe | Q1j | a bond | H | a bond | NH | S | NH | T3c | OH |
| 364 | N | NMe | Q1j | a bond | H | a bond | NH | S | NH | T3d | OH |
| 365 | N | NMe | Q1j | a bond | H | a bond | NH | S | NH | T3e | OH |
| 366 | N | NMe | Q1j | a bond | H | a bond | NH | S | NH | T3f | OH |
| 367 | N | NMe | Q1j | a bond | H | a bond | NH | S | NH | T3g | OH |
| 368 | N | NMe | Q1j | a bond | H | a bond | NH | S | NH | T3h | OH |
| 369 | N | NMe | Q1j | a bond | H | a bond | NH | S | NH | T3i | OH |
| 370 | N | NMe | Q1j | a bond | H | a bond | NH | S | NH | T3j | OH |
| 371 | N | NMe | Q1j | a bond | H | a bond | NH | S | a bond | T3a | OH |
| 372 | N | NMe | Q1j | a bond | H | a bond | NH | S | a bond | T3b | OH |
| 373 | N | NMe | Q1j | a bond | H | a bond | NH | S | a bond | T3c | OH |
| 374 | N | NMe | Q1j | a bond | H | a bond | NH | S | a bond | T3d | OH |
| 375 | N | NMe | Q1j | a bond | H | a bond | NH | S | a bond | T3e | OH |
| 376 | N | NMe | Q1j | a bond | H | a bond | NH | S | a bond | T3f | OH |
| 377 | N | NMe | Q1j | a bond | H | a bond | NH | S | a bond | T3g | OH |
| 378 | N | NMe | Q1j | a bond | H | a bond | NH | S | a bond | T3h | OH |
| 379 | N | NMe | Q1j | a bond | H | a bond | NH | S | a bond | T3i | OH |
| 380 | N | NMe | Q1j | a bond | H | a bond | NH | S | a bond | T3j | OH |
| 381 | N | NMe | Q1j | a bond | H | a bond | NH | O | NH | T3a | OH |
| 382 | N | NMe | Q1j | a bond | H | a bond | NH | O | NH | T3b | OH |
| 383 | N | NMe | Q1j | a bond | H | a bond | NH | O | NH | T3c | OH |
| 384 | N | NMe | Q1j | a bond | H | a bond | NH | O | NH | T3d | OH |
| 385 | N | NMe | Q1j | a bond | H | a bond | NH | O | NH | T3e | OH |
| 386 | N | NMe | Q1j | a bond | H | a bond | NH | O | NH | T3f | OH |
| 387 | N | NMe | Q1j | a bond | H | a bond | NH | O | NH | T3g | OH |
| 388 | N | NMe | Q1j | a bond | H | a bond | NH | O | NH | T3h | OH |
| 389 | N | NMe | Q1j | a bond | H | a bond | NH | O | NH | T3i | OH |
| 390 | N | NMe | Q1j | a bond | H | a bond | NH | O | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 391 | N | NMe | Q1j | a bond | H | a bond | NH | O | a bond | T3a | OH |
| 392 | N | NMe | Q1j | a bond | H | a bond | NH | O | a bond | T3b | OH |
| 393 | N | NMe | Q1j | a bond | H | a bond | NH | O | a bond | T3c | OH |
| 394 | N | NMe | Q1j | a bond | H | a bond | NH | O | a bond | T3d | OH |
| 395 | N | NMe | Q1j | a bond | H | a bond | NH | O | a bond | T3e | OH |
| 396 | N | NMe | Q1j | a bond | H | a bond | NH | O | a bond | T3f | OH |
| 397 | N | NMe | Q1j | a bond | H | a bond | NH | O | a bond | T3g | OH |
| 398 | N | NMe | Q1j | a bond | H | a bond | NH | O | a bond | T3h | OH |
| 399 | N | NMe | Q1j | a bond | H | a bond | NH | O | a bond | T3i | OH |
| 400 | N | NMe | Q1j | a bond | H | a bond | NH | O | a bond | T3j | OH |
| 401 | N | S | Q1a | a bond | Me | a bond | NH | S | NH | T3a | OH |
| 402 | N | S | Q1a | a bond | Me | a bond | NH | S | NH | T3b | OH |
| 403 | N | S | Q1a | a bond | Me | a bond | NH | S | NH | T3c | OH |
| 404 | N | S | Q1a | a bond | Me | a bond | NH | S | NH | T3d | OH |
| 405 | N | S | Q1a | a bond | Me | a bond | NH | S | NH | T3e | OH |
| 406 | N | S | Q1a | a bond | Me | a bond | NH | S | NH | T3f | OH |
| 407 | N | S | Q1a | a bond | Me | a bond | NH | S | NH | T3g | OH |
| 408 | N | S | Q1a | a bond | Me | a bond | NH | S | NH | T3h | OH |
| 409 | N | S | Q1a | a bond | Me | a bond | NH | S | NH | T3i | OH |
| 410 | N | S | Q1a | a bond | Me | a bond | NH | S | NH | T3j | OH |
| 411 | N | S | Q1a | a bond | Me | a bond | NH | S | a bond | T3a | OH |
| 412 | N | S | Q1a | a bond | Me | a bond | NH | S | a bond | T3b | OH |
| 413 | N | S | Q1a | a bond | Me | a bond | NH | S | a bond | T3c | OH |
| 414 | N | S | Q1a | a bond | Me | a bond | NH | S | a bond | T3d | OH |
| 415 | N | S | Q1a | a bond | Me | a bond | NH | S | a bond | T3e | OH |
| 416 | N | S | Q1a | a bond | Me | a bond | NH | S | a bond | T3f | OH |
| 417 | N | S | Q1a | a bond | Me | a bond | NH | S | a bond | T3g | OH |
| 418 | N | S | Q1a | a bond | Me | a bond | NH | S | a bond | T3h | OH |
| 419 | N | S | Q1a | a bond | Me | a bond | NH | S | a bond | T3i | OH |
| 420 | N | S | Q1a | a bond | Me | a bond | NH | S | a bond | T3j | OH |
| 421 | N | S | Q1a | a bond | Me | a bond | NH | O | NH | T3a | OH |
| 422 | N | S | Q1a | a bond | Me | a bond | NH | O | NH | T3b | OH |
| 423 | N | S | Q1a | a bond | Me | a bond | NH | O | NH | T3c | OH |
| 424 | N | S | Q1a | a bond | Me | a bond | NH | O | NH | T3d | OH |
| 425 | N | S | Q1a | a bond | Me | a bond | NH | O | NH | T3e | OH |
| 426 | N | S | Q1a | a bond | Me | a bond | NH | O | NH | T3f | OH |
| 427 | N | S | Q1a | a bond | Me | a bond | NH | O | NH | T3g | OH |
| 428 | N | S | Q1a | a bond | Me | a bond | NH | O | NH | T3h | OH |
| 429 | N | S | Q1a | a bond | Me | a bond | NH | O | NH | T3i | OH |
| 430 | N | S | Q1a | a bond | Me | a bond | NH | O | NH | T3j | OH |
| 431 | N | S | Q1a | a bond | Me | a bond | NH | O | a bond | T3a | OH |
| 432 | N | S | Q1a | a bond | Me | a bond | NH | O | a bond | T3b | OH |
| 433 | N | S | Q1a | a bond | Me | a bond | NH | O | a bond | T3c | OH |
| 434 | N | S | Q1a | a bond | Me | a bond | NH | O | a bond | T3d | OH |
| 435 | N | S | Q1a | a bond | Me | a bond | NH | O | a bond | T3e | OH |
| 436 | N | S | Q1a | a bond | Me | a bond | NH | O | a bond | T3f | OH |
| 437 | N | S | Q1a | a bond | Me | a bond | NH | O | a bond | T3g | OH |
| 438 | N | S | Q1a | a bond | Me | a bond | NH | O | a bond | T3h | OH |
| 439 | N | S | Q1a | a bond | Me | a bond | NH | O | a bond | T3i | OH |
| 440 | N | S | Q1a | a bond | Me | a bond | NH | O | a bond | T3j | OH |
| 441 | N | S | Q1a | a bond | H | a bond | NH | S | NH | T3a | OH |
| 442 | N | S | Q1a | a bond | H | a bond | NH | S | NH | T3b | OH |
| 443 | N | S | Q1a | a bond | H | a bond | NH | S | NH | T3c | OH |
| 444 | N | S | Q1a | a bond | H | a bond | NH | S | NH | T3d | OH |
| 445 | N | S | Q1a | a bond | H | a bond | NH | S | NH | T3e | OH |
| 446 | N | S | Q1a | a bond | H | a bond | NH | S | NH | T3f | OH |
| 447 | N | S | Q1a | a bond | H | a bond | NH | S | NH | T3g | OH |
| 448 | N | S | Q1a | a bond | H | a bond | NH | S | NH | T3h | OH |
| 449 | N | S | Q1a | a bond | H | a bond | NH | S | NH | T3i | OH |
| 450 | N | S | Q1a | a bond | H | a bond | NH | S | NH | T3j | OH |
| 451 | N | S | Q1a | a bond | H | a bond | NH | S | a bond | T3a | OH |
| 452 | N | S | Q1a | a bond | H | a bond | NH | S | a bond | T3b | OH |
| 453 | N | S | Q1a | a bond | H | a bond | NH | S | a bond | T3c | OH |
| 454 | N | S | Q1a | a bond | H | a bond | NH | S | a bond | T3d | OH |
| 455 | N | S | Q1a | a bond | H | a bond | NH | S | a bond | T3e | OH |
| 456 | N | S | Q1a | a bond | H | a bond | NH | S | a bond | T3f | OH |
| 457 | N | S | Q1a | a bond | H | a bond | NH | S | a bond | T3g | OH |
| 458 | N | S | Q1a | a bond | H | a bond | NH | S | a bond | T3h | OH |
| 459 | N | S | Q1a | a bond | H | a bond | NH | S | a bond | T3i | OH |
| 460 | N | S | Q1a | a bond | H | a bond | NH | S | a bond | T3j | OH |
| 461 | N | S | Q1a | a bond | H | a bond | NH | O | NH | T3a | OH |
| 462 | N | S | Q1a | a bond | H | a bond | NH | O | NH | T3b | OH |
| 463 | N | S | Q1a | a bond | H | a bond | NH | O | NH | T3c | OH |
| 464 | N | S | Q1a | a bond | H | a bond | NH | O | NH | T3d | OH |
| 465 | N | S | Q1a | a bond | H | a bond | NH | O | NH | T3e | OH |
| 466 | N | S | Q1a | a bond | H | a bond | NH | O | NH | T3f | OH |
| 467 | N | S | Q1a | a bond | H | a bond | NH | O | NH | T3g | OH |
| 468 | N | S | Q1a | a bond | H | a bond | NH | O | NH | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 469 | N | S | Q1a | a bond | H | a bond | NH | O | NH | T3i | OH |
| 470 | N | S | Q1a | a bond | H | a bond | NH | O | NH | T3j | OH |
| 471 | N | S | Q1a | a bond | H | a bond | NH | O | a bond | T3a | OH |
| 472 | N | S | Q1a | a bond | H | a bond | NH | O | a bond | T3b | OH |
| 473 | N | S | Q1a | a bond | H | a bond | NH | O | a bond | T3c | OH |
| 474 | N | S | Q1a | a bond | H | a bond | NH | O | a bond | T3d | OH |
| 475 | N | S | Q1a | a bond | H | a bond | NH | O | a bond | T3e | OH |
| 476 | N | S | Q1a | a bond | H | a bond | NH | O | a bond | T3f | OH |
| 477 | N | S | Q1a | a bond | H | a bond | NH | O | a bond | T3g | OH |
| 478 | N | S | Q1a | a bond | H | a bond | NH | O | a bond | T3h | OH |
| 479 | N | S | Q1a | a bond | H | a bond | NH | O | a bond | T3i | OH |
| 480 | N | S | Q1a | a bond | H | a bond | NH | O | a bond | T3j | OH |
| 481 | N | S | Q1b | a bond | Me | a bond | NH | S | NH | T3a | OH |
| 482 | N | S | Q1b | a bond | Me | a bond | NH | S | NH | T3b | OH |
| 483 | N | S | Q1b | a bond | Me | a bond | NH | S | NH | T3c | OH |
| 484 | N | S | Q1b | a bond | Me | a bond | NH | S | NH | T3d | OH |
| 485 | N | S | Q1b | a bond | Me | a bond | NH | S | NH | T3e | OH |
| 486 | N | S | Q1b | a bond | Me | a bond | NH | S | NH | T3f | OH |
| 487 | N | S | Q1b | a bond | Me | a bond | NH | S | NH | T3g | OH |
| 488 | N | S | Q1b | a bond | Me | a bond | NH | S | NH | T3h | OH |
| 489 | N | S | Q1b | a bond | Me | a bond | NH | S | NH | T3i | OH |
| 490 | N | S | Q1b | a bond | Me | a bond | NH | S | NH | T3j | OH |
| 491 | N | S | Q1b | a bond | Me | a bond | NH | S | a bond | T3a | OH |
| 492 | N | S | Q1b | a bond | Me | a bond | NH | S | a bond | T3b | OH |
| 493 | N | S | Q1b | a bond | Me | a bond | NH | S | a bond | T3c | OH |
| 494 | N | S | Q1b | a bond | Me | a bond | NH | S | a bond | T3d | OH |
| 495 | N | S | Q1b | a bond | Me | a bond | NH | S | a bond | T3e | OH |
| 496 | N | S | Q1b | a bond | Me | a bond | NH | S | a bond | T3f | OH |
| 497 | N | S | Q1b | a bond | Me | a bond | NH | S | a bond | T3g | OH |
| 498 | N | S | Q1b | a bond | Me | a bond | NH | S | a bond | T3h | OH |
| 499 | N | S | Q1b | a bond | Me | a bond | NH | S | a bond | T3i | OH |
| 500 | N | S | Q1b | a bond | Me | a bond | NH | S | a bond | T3j | OH |
| 501 | N | S | Q1b | a bond | Me | a bond | NH | O | NH | T3a | OH |
| 502 | N | S | Q1b | a bond | Me | a bond | NH | O | NH | T3b | OH |
| 503 | N | S | Q1b | a bond | Me | a bond | NH | O | NH | T3c | OH |
| 504 | N | S | Q1b | a bond | Me | a bond | NH | O | NH | T3d | OH |
| 505 | N | S | Q1b | a bond | Me | a bond | NH | O | NH | T3e | OH |
| 506 | N | S | Q1b | a bond | Me | a bond | NH | O | NH | T3f | OH |
| 507 | N | S | Q1b | a bond | Me | a bond | NH | O | NH | T3g | OH |
| 508 | N | S | Q1b | a bond | Me | a bond | NH | O | NH | T3h | OH |
| 509 | N | S | Q1b | a bond | Me | a bond | NH | O | NH | T3i | OH |
| 510 | N | S | Q1b | a bond | Me | a bond | NH | O | NH | T3j | OH |
| 511 | N | S | Q1b | a bond | Me | a bond | NH | O | a bond | T3a | OH |
| 512 | N | S | Q1b | a bond | Me | a bond | NH | O | a bond | T3b | OH |
| 513 | N | S | Q1b | a bond | Me | a bond | NH | O | a bond | T3c | OH |
| 514 | N | S | Q1b | a bond | Me | a bond | NH | O | a bond | T3d | OH |
| 515 | N | S | Q1b | a bond | Me | a bond | NH | O | a bond | T3e | OH |
| 516 | N | S | Q1b | a bond | Me | a bond | NH | O | a bond | T3f | OH |
| 517 | N | S | Q1b | a bond | Me | a bond | NH | O | a bond | T3g | OH |
| 518 | N | S | Q1b | a bond | Me | a bond | NH | O | a bond | T3h | OH |
| 519 | N | S | Q1b | a bond | Me | a bond | NH | O | a bond | T3i | OH |
| 520 | N | S | Q1b | a bond | Me | a bond | NH | O | a bond | T3j | OH |
| 521 | N | S | Q1b | a bond | H | a bond | NH | S | NH | T3a | OH |
| 522 | N | S | Q1b | a bond | H | a bond | NH | S | NH | T3b | OH |
| 523 | N | S | Q1b | a bond | H | a bond | NH | S | NH | T3c | OH |
| 524 | N | S | Q1b | a bond | H | a bond | NH | S | NH | T3d | OH |
| 525 | N | S | Q1b | a bond | H | a bond | NH | S | NH | T3e | OH |
| 526 | N | S | Q1b | a bond | H | a bond | NH | S | NH | T3f | OH |
| 527 | N | S | Q1b | a bond | H | a bond | NH | S | NH | T3g | OH |
| 528 | N | S | Q1b | a bond | H | a bond | NH | S | NH | T3h | OH |
| 529 | N | S | Q1b | a bond | H | a bond | NH | S | NH | T3i | OH |
| 530 | N | S | Q1b | a bond | H | a bond | NH | S | NH | T3j | OH |
| 531 | N | S | Q1b | a bond | H | a bond | NH | S | a bond | T3a | OH |
| 532 | N | S | Q1b | a bond | H | a bond | NH | S | a bond | T3b | OH |
| 533 | N | S | Q1b | a bond | H | a bond | NH | S | a bond | T3c | OH |
| 534 | N | S | Q1b | a bond | H | a bond | NH | S | a bond | T3d | OH |
| 535 | N | S | Q1b | a bond | H | a bond | NH | S | a bond | T3e | OH |
| 536 | N | S | Q1b | a bond | H | a bond | NH | S | a bond | T3f | OH |
| 537 | N | S | Q1b | a bond | H | a bond | NH | S | a bond | T3g | OH |
| 538 | N | S | Q1b | a bond | H | a bond | NH | S | a bond | T3h | OH |
| 539 | N | S | Q1b | a bond | H | a bond | NH | S | a bond | T3i | OH |
| 540 | N | S | Q1b | a bond | H | a bond | NH | S | a bond | T3j | OH |
| 541 | N | S | Q1b | a bond | H | a bond | NH | O | NH | T3a | OH |
| 542 | N | S | Q1b | a bond | H | a bond | NH | O | NH | T3b | OH |
| 543 | N | S | Q1b | a bond | H | a bond | NH | O | NH | T3c | OH |
| 544 | N | S | Q1b | a bond | H | a bond | NH | O | NH | T3d | OH |
| 545 | N | S | Q1b | a bond | H | a bond | NH | O | NH | T3e | OH |
| 546 | N | S | Q1b | a bond | H | a bond | NH | O | NH | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 547 | N | S | Q1b | a bond | H | a bond | NH | O | NH | T3g | OH |
| 548 | N | S | Q1b | a bond | H | a bond | NH | O | NH | T3h | OH |
| 549 | N | S | Q1b | a bond | H | a bond | NH | O | NH | T3i | OH |
| 550 | N | S | Q1b | a bond | H | a bond | NH | O | NH | T3j | OH |
| 551 | N | S | Q1b | a bond | H | a bond | NH | O | a bond | T3a | OH |
| 552 | N | S | Q1b | a bond | H | a bond | NH | O | a bond | T3b | OH |
| 553 | N | S | Q1b | a bond | H | a bond | NH | O | a bond | T3c | OH |
| 554 | N | S | Q1b | a bond | H | a bond | NH | O | a bond | T3d | OH |
| 555 | N | S | Q1b | a bond | H | a bond | NH | O | a bond | T3e | OH |
| 556 | N | S | Q1b | a bond | H | a bond | NH | O | a bond | T3f | OH |
| 557 | N | S | Q1b | a bond | H | a bond | NH | O | a bond | T3g | OH |
| 558 | N | S | Q1b | a bond | H | a bond | NH | O | a bond | T3h | OH |
| 559 | N | S | Q1b | a bond | H | a bond | NH | O | a bond | T3i | OH |
| 560 | N | S | Q1b | a bond | H | a bond | NH | O | a bond | T3j | OH |
| 561 | N | S | Q1c | a bond | Me | a bond | NH | S | NH | T3a | OH |
| 562 | N | S | Q1c | a bond | Me | a bond | NH | S | NH | T3b | OH |
| 563 | N | S | Q1c | a bond | Me | a bond | NH | S | NH | T3c | OH |
| 564 | N | S | Q1c | a bond | Me | a bond | NH | S | NH | T3d | OH |
| 565 | N | S | Q1c | a bond | Me | a bond | NH | S | NH | T3e | OH |
| 566 | N | S | Q1c | a bond | Me | a bond | NH | S | NH | T3f | OH |
| 567 | N | S | Q1c | a bond | Me | a bond | NH | S | NH | T3g | OH |
| 568 | N | S | Q1c | a bond | Me | a bond | NH | S | NH | T3h | OH |
| 569 | N | S | Q1c | a bond | Me | a bond | NH | S | NH | T3i | OH |
| 570 | N | S | Q1c | a bond | Me | a bond | NH | S | NH | T3j | OH |
| 571 | N | S | Q1c | a bond | Me | a bond | NH | S | a bond | T3a | OH |
| 572 | N | S | Q1c | a bond | Me | a bond | NH | S | a bond | T3b | OH |
| 573 | N | S | Q1c | a bond | Me | a bond | NH | S | a bond | T3c | OH |
| 574 | N | S | Q1c | a bond | Me | a bond | NH | S | a bond | T3d | OH |
| 575 | N | S | Q1c | a bond | Me | a bond | NH | S | a bond | T3e | OH |
| 576 | N | S | Q1c | a bond | Me | a bond | NH | S | a bond | T3f | OH |
| 577 | N | S | Q1c | a bond | Me | a bond | NH | S | a bond | T3g | OH |
| 578 | N | S | Q1c | a bond | Me | a bond | NH | S | a bond | T3h | OH |
| 579 | N | S | Q1c | a bond | Me | a bond | NH | S | a bond | T3i | OH |
| 580 | N | S | Q1c | a bond | Me | a bond | NH | S | a bond | T3j | OH |
| 581 | N | S | Q1c | a bond | Me | a bond | NH | O | NH | T3a | OH |
| 582 | N | S | Q1c | a bond | Me | a bond | NH | O | NH | T3b | OH |
| 583 | N | S | Q1c | a bond | Me | a bond | NH | O | NH | T3c | OH |
| 584 | N | S | Q1c | a bond | Me | a bond | NH | O | NH | T3d | OH |
| 585 | N | S | Q1c | a bond | Me | a bond | NH | O | NH | T3e | OH |
| 586 | N | S | Q1c | a bond | Me | a bond | NH | O | NH | T3f | OH |
| 587 | N | S | Q1c | a bond | Me | a bond | NH | O | NH | T3g | OH |
| 588 | N | S | Q1c | a bond | Me | a bond | NH | O | NH | T3h | OH |
| 589 | N | S | Q1c | a bond | Me | a bond | NH | O | NH | T3i | OH |
| 590 | N | S | Q1c | a bond | Me | a bond | NH | O | NH | T3j | OH |
| 591 | N | S | Q1c | a bond | Me | a bond | NH | O | a bond | T3a | OH |
| 592 | N | S | Q1c | a bond | Me | a bond | NH | O | a bond | T3b | OH |
| 593 | N | S | Q1c | a bond | Me | a bond | NH | O | a bond | T3c | OH |
| 594 | N | S | Q1c | a bond | Me | a bond | NH | O | a bond | T3d | OH |
| 595 | N | S | Q1c | a bond | Me | a bond | NH | O | a bond | T3e | OH |
| 596 | N | S | Q1c | a bond | Me | a bond | NH | O | a bond | T3f | OH |
| 597 | N | S | Q1c | a bond | Me | a bond | NH | O | a bond | T3g | OH |
| 598 | N | S | Q1c | a bond | Me | a bond | NH | O | a bond | T3h | OH |
| 599 | N | S | Q1c | a bond | Me | a bond | NH | O | a bond | T3i | OH |
| 600 | N | S | Q1c | a bond | Me | a bond | NH | O | a bond | T3j | OH |
| 601 | N | S | Q1c | a bond | H | a bond | NH | S | NH | T3a | OH |
| 602 | N | S | Q1c | a bond | H | a bond | NH | S | NH | T3b | OH |
| 603 | N | S | Q1c | a bond | H | a bond | NH | S | NH | T3c | OH |
| 604 | N | S | Q1c | a bond | H | a bond | NH | S | NH | T3d | OH |
| 605 | N | S | Q1c | a bond | H | a bond | NH | S | NH | T3e | OH |
| 606 | N | S | Q1c | a bond | H | a bond | NH | S | NH | T3f | OH |
| 607 | N | S | Q1c | a bond | H | a bond | NH | S | NH | T3g | OH |
| 608 | N | S | Q1c | a bond | H | a bond | NH | S | NH | T3h | OH |
| 609 | N | S | Q1c | a bond | H | a bond | NH | S | NH | T3i | OH |
| 610 | N | S | Q1c | a bond | H | a bond | NH | S | NH | T3j | OH |
| 611 | N | S | Q1c | a bond | H | a bond | NH | S | a bond | T3a | OH |
| 612 | N | S | Q1c | a bond | H | a bond | NH | S | a bond | T3b | OH |
| 613 | N | S | Q1c | a bond | H | a bond | NH | S | a bond | T3c | OH |
| 614 | N | S | Q1c | a bond | H | a bond | NH | S | a bond | T3d | OH |
| 615 | N | S | Q1c | a bond | H | a bond | NH | S | a bond | T3e | OH |
| 616 | N | S | Q1c | a bond | H | a bond | NH | S | a bond | T3f | OH |
| 617 | N | S | Q1c | a bond | H | a bond | NH | S | a bond | T3g | OH |
| 618 | N | S | Q1c | a bond | H | a bond | NH | S | a bond | T3h | OH |
| 619 | N | S | Q1c | a bond | H | a bond | NH | S | a bond | T3i | OH |
| 620 | N | S | Q1c | a bond | H | a bond | NH | S | a bond | T3j | OH |
| 621 | N | S | Q1c | a bond | H | a bond | NH | O | NH | T3a | OH |
| 622 | N | S | Q1c | a bond | H | a bond | NH | O | NH | T3b | OH |
| 623 | N | S | Q1c | a bond | H | a bond | NH | O | NH | T3c | OH |
| 624 | N | S | Q1c | a bond | H | a bond | NH | O | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 625 | N | S | Q1c | a bond | H | a bond | NH | O | NH | T3e | OH |
| 626 | N | S | Q1c | a bond | H | a bond | NH | O | NH | T3f | OH |
| 627 | N | S | Q1c | a bond | H | a bond | NH | O | NH | T3g | OH |
| 628 | N | S | Q1c | a bond | H | a bond | NH | O | NH | T3h | OH |
| 629 | N | S | Q1c | a bond | H | a bond | NH | O | NH | T3i | OH |
| 630 | N | S | Q1c | a bond | H | a bond | NH | O | NH | T3j | OH |
| 631 | N | S | Q1c | a bond | H | a bond | NH | O | a bond | T3a | OH |
| 632 | N | S | Q1c | a bond | H | a bond | NH | O | a bond | T3b | OH |
| 633 | N | S | Q1c | a bond | H | a bond | NH | O | a bond | T3c | OH |
| 634 | N | S | Q1c | a bond | H | a bond | NH | O | a bond | T3d | OH |
| 635 | N | S | Q1c | a bond | H | a bond | NH | O | a bond | T3e | OH |
| 636 | N | S | Q1c | a bond | H | a bond | NH | O | a bond | T3f | OH |
| 637 | N | S | Q1c | a bond | H | a bond | NH | O | a bond | T3g | OH |
| 638 | N | S | Q1c | a bond | H | a bond | NH | O | a bond | T3h | OH |
| 639 | N | S | Q1c | a bond | H | a bond | NH | O | a bond | T3i | OH |
| 640 | N | S | Q1c | a bond | H | a bond | NH | O | a bond | T3j | OH |
| 641 | N | S | Q1i | a bond | Me | a bond | NH | S | NH | T3a | OH |
| 642 | N | S | Q1i | a bond | Me | a bond | NH | S | NH | T3b | OH |
| 643 | N | S | Q1i | a bond | Me | a bond | NH | S | NH | T3c | OH |
| 644 | N | S | Q1i | a bond | Me | a bond | NH | S | NH | T3d | OH |
| 645 | N | S | Q1i | a bond | Me | a bond | NH | S | NH | T3e | OH |
| 646 | N | S | Q1i | a bond | Me | a bond | NH | S | NH | T3f | OH |
| 647 | N | S | Q1i | a bond | Me | a bond | NH | S | NH | T3g | OH |
| 648 | N | S | Q1i | a bond | Me | a bond | NH | S | NH | T3h | OH |
| 649 | N | S | Q1i | a bond | Me | a bond | NH | S | NH | T3i | OH |
| 650 | N | S | Q1i | a bond | Me | a bond | NH | S | NH | T3j | OH |
| 651 | N | S | Q1i | a bond | Me | a bond | NH | S | a bond | T3a | OH |
| 652 | N | S | Q1i | a bond | Me | a bond | NH | S | a bond | T3b | OH |
| 653 | N | S | Q1i | a bond | Me | a bond | NH | S | a bond | T3c | OH |
| 654 | N | S | Q1i | a bond | Me | a bond | NH | S | a bond | T3d | OH |
| 655 | N | S | Q1i | a bond | Me | a bond | NH | S | a bond | T3e | OH |
| 656 | N | S | Q1i | a bond | Me | a bond | NH | S | a bond | T3f | OH |
| 657 | N | S | Q1i | a bond | Me | a bond | NH | S | a bond | T3g | OH |
| 658 | N | S | Q1i | a bond | Me | a bond | NH | S | a bond | T3h | OH |
| 659 | N | S | Q1i | a bond | Me | a bond | NH | S | a bond | T3i | OH |
| 660 | N | S | Q1i | a bond | Me | a bond | NH | S | a bond | T3j | OH |
| 661 | N | S | Q1i | a bond | Me | a bond | NH | O | NH | T3a | OH |
| 662 | N | S | Q1i | a bond | Me | a bond | NH | O | NH | T3b | OH |
| 663 | N | S | Q1i | a bond | Me | a bond | NH | O | NH | T3c | OH |
| 664 | N | S | Q1i | a bond | Me | a bond | NH | O | NH | T3d | OH |
| 665 | N | S | Q1i | a bond | Me | a bond | NH | O | NH | T3e | OH |
| 666 | N | S | Q1i | a bond | Me | a bond | NH | O | NH | T3f | OH |
| 667 | N | S | Q1i | a bond | Me | a bond | NH | O | NH | T3g | OH |
| 668 | N | S | Q1i | a bond | Me | a bond | NH | O | NH | T3h | OH |
| 669 | N | S | Q1i | a bond | Me | a bond | NH | O | NH | T3i | OH |
| 670 | N | S | Q1i | a bond | Me | a bond | NH | O | NH | T3j | OH |
| 671 | N | S | Q1i | a bond | Me | a bond | NH | O | a bond | T3a | OH |
| 672 | N | S | Q1i | a bond | Me | a bond | NH | O | a bond | T3b | OH |
| 673 | N | S | Q1i | a bond | Me | a bond | NH | O | a bond | T3c | OH |
| 674 | N | S | Q1i | a bond | Me | a bond | NH | O | a bond | T3d | OH |
| 675 | N | S | Q1i | a bond | Me | a bond | NH | O | a bond | T3e | OH |
| 676 | N | S | Q1i | a bond | Me | a bond | NH | O | a bond | T3f | OH |
| 677 | N | S | Q1i | a bond | Me | a bond | NH | O | a bond | T3g | OH |
| 678 | N | S | Q1i | a bond | Me | a bond | NH | O | a bond | T3h | OH |
| 679 | N | S | Q1i | a bond | Me | a bond | NH | O | a bond | T3i | OH |
| 680 | N | S | Q1i | a bond | Me | a bond | NH | O | a bond | T3j | OH |
| 681 | N | S | Q1i | a bond | H | a bond | NH | S | NH | T3a | OH |
| 682 | N | S | Q1i | a bond | H | a bond | NH | S | NH | T3b | OH |
| 683 | N | S | Q1i | a bond | H | a bond | NH | S | NH | T3c | OH |
| 684 | N | S | Q1i | a bond | H | a bond | NH | S | NH | T3d | OH |
| 685 | N | S | Q1i | a bond | H | a bond | NH | S | NH | T3e | OH |
| 686 | N | S | Q1i | a bond | H | a bond | NH | S | NH | T3f | OH |
| 687 | N | S | Q1i | a bond | H | a bond | NH | S | NH | T3g | OH |
| 688 | N | S | Q1i | a bond | H | a bond | NH | S | NH | T3h | OH |
| 689 | N | S | Q1i | a bond | H | a bond | NH | S | NH | T3i | OH |
| 690 | N | S | Q1i | a bond | H | a bond | NH | S | NH | T3j | OH |
| 691 | N | S | Q1i | a bond | H | a bond | NH | S | a bond | T3a | OH |
| 692 | N | S | Q1i | a bond | H | a bond | NH | S | a bond | T3b | OH |
| 693 | N | S | Q1i | a bond | H | a bond | NH | S | a bond | T3c | OH |
| 694 | N | S | Q1i | a bond | H | a bond | NH | S | a bond | T3d | OH |
| 695 | N | S | Q1i | a bond | H | a bond | NH | S | a bond | T3e | OH |
| 696 | N | S | Q1i | a bond | H | a bond | NH | S | a bond | T3f | OH |
| 697 | N | S | Q1i | a bond | H | a bond | NH | S | a bond | T3g | OH |
| 698 | N | S | Q1i | a bond | H | a bond | NH | S | a bond | T3h | OH |
| 699 | N | S | Q1i | a bond | H | a bond | NH | S | a bond | T3i | OH |
| 700 | N | S | Q1i | a bond | H | a bond | NH | S | a bond | T3j | OH |
| 701 | N | S | Q1i | a bond | H | a bond | NH | O | NH | T3a | OH |
| 702 | N | S | Q1i | a bond | H | a bond | NH | O | NH | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 703 | N | S | Q1i | a bond | H | a bond | NH | O | NH | T3c | OH |
| 704 | N | S | Q1i | a bond | H | a bond | NH | O | NH | T3d | OH |
| 705 | N | S | Q1i | a bond | H | a bond | NH | O | NH | T3e | OH |
| 706 | N | S | Q1i | a bond | H | a bond | NH | O | NH | T3f | OH |
| 707 | N | S | Q1i | a bond | H | a bond | NH | O | NH | T3g | OH |
| 708 | N | S | Q1i | a bond | H | a bond | NH | O | NH | T3h | OH |
| 709 | N | S | Q1i | a bond | H | a bond | NH | O | NH | T3i | OH |
| 710 | N | S | Q1i | a bond | H | a bond | NH | O | NH | T3j | OH |
| 711 | N | S | Q1i | a bond | H | a bond | NH | O | a bond | T3a | OH |
| 712 | N | S | Q1i | a bond | H | a bond | NH | O | a bond | T3b | OH |
| 713 | N | S | Q1i | a bond | H | a bond | NH | O | a bond | T3c | OH |
| 714 | N | S | Q1i | a bond | H | a bond | NH | O | a bond | T3d | OH |
| 715 | N | S | Q1i | a bond | H | a bond | NH | O | a bond | T3e | OH |
| 716 | N | S | Q1i | a bond | H | a bond | NH | O | a bond | T3f | OH |
| 717 | N | S | Q1i | a bond | H | a bond | NH | O | a bond | T3g | OH |
| 718 | N | S | Q1i | a bond | H | a bond | NH | O | a bond | T3h | OH |
| 719 | N | S | Q1i | a bond | H | a bond | NH | O | a bond | T3i | OH |
| 720 | N | S | Q1i | a bond | H | a bond | NH | O | a bond | T3j | OH |
| 721 | N | S | Q1j | a bond | Me | a bond | NH | S | NH | T3a | OH |
| 722 | N | S | Q1j | a bond | Me | a bond | NH | S | NH | T3b | OH |
| 723 | N | S | Q1j | a bond | Me | a bond | NH | S | NH | T3c | OH |
| 724 | N | S | Q1j | a bond | Me | a bond | NH | S | NH | T3d | OH |
| 725 | N | S | Q1j | a bond | Me | a bond | NH | S | NH | T3e | OH |
| 726 | N | S | Q1j | a bond | Me | a bond | NH | S | NH | T3f | OH |
| 727 | N | S | Q1j | a bond | Me | a bond | NH | S | NH | T3g | OH |
| 728 | N | S | Q1j | a bond | Me | a bond | NH | S | NH | T3h | OH |
| 729 | N | S | Q1j | a bond | Me | a bond | NH | S | NH | T3i | OH |
| 730 | N | S | Q1j | a bond | Me | a bond | NH | S | NH | T3j | OH |
| 731 | N | S | Q1j | a bond | Me | a bond | NH | S | a bond | T3a | OH |
| 732 | N | S | Q1j | a bond | Me | a bond | NH | S | a bond | T3b | OH |
| 733 | N | S | Q1j | a bond | Me | a bond | NH | S | a bond | T3c | OH |
| 734 | N | S | Q1j | a bond | Me | a bond | NH | S | a bond | T3d | OH |
| 735 | N | S | Q1j | a bond | Me | a bond | NH | S | a bond | T3e | OH |
| 736 | N | S | Q1j | a bond | Me | a bond | NH | S | a bond | T3f | OH |
| 737 | N | S | Q1j | a bond | Me | a bond | NH | S | a bond | T3g | OH |
| 738 | N | S | Q1j | a bond | Me | a bond | NH | S | a bond | T3h | OH |
| 739 | N | S | Q1j | a bond | Me | a bond | NH | S | a bond | T3i | OH |
| 740 | N | S | Q1j | a bond | Me | a bond | NH | S | a bond | T3j | OH |
| 741 | N | S | Q1j | a bond | Me | a bond | NH | O | NH | T3a | OH |
| 742 | N | S | Q1j | a bond | Me | a bond | NH | O | NH | T3b | OH |
| 743 | N | S | Q1j | a bond | Me | a bond | NH | O | NH | T3c | OH |
| 744 | N | S | Q1j | a bond | Me | a bond | NH | O | NH | T3d | OH |
| 745 | N | S | Q1j | a bond | Me | a bond | NH | O | NH | T3e | OH |
| 746 | N | S | Q1j | a bond | Me | a bond | NH | O | NH | T3f | OH |
| 747 | N | S | Q1j | a bond | Me | a bond | NH | O | NH | T3g | OH |
| 748 | N | S | Q1j | a bond | Me | a bond | NH | O | NH | T3h | OH |
| 749 | N | S | Q1j | a bond | Me | a bond | NH | O | NH | T3i | OH |
| 750 | N | S | Q1j | a bond | Me | a bond | NH | O | NH | T3j | OH |
| 751 | N | S | Q1j | a bond | Me | a bond | NH | O | a bond | T3a | OH |
| 752 | N | S | Q1j | a bond | Me | a bond | NH | O | a bond | T3b | OH |
| 753 | N | S | Q1j | a bond | Me | a bond | NH | O | a bond | T3c | OH |
| 754 | N | S | Q1j | a bond | Me | a bond | NH | O | a bond | T3d | OH |
| 755 | N | S | Q1j | a bond | Me | a bond | NH | O | a bond | T3e | OH |
| 756 | N | S | Q1j | a bond | Me | a bond | NH | O | a bond | T3f | OH |
| 757 | N | S | Q1j | a bond | Me | a bond | NH | O | a bond | T3g | OH |
| 758 | N | S | Q1j | a bond | Me | a bond | NH | O | a bond | T3h | OH |
| 759 | N | S | Q1j | a bond | Me | a bond | NH | O | a bond | T3i | OH |
| 760 | N | S | Q1j | a bond | Me | a bond | NH | O | a bond | T3j | OH |
| 761 | N | S | Q1j | a bond | H | a bond | NH | S | NH | T3a | OH |
| 762 | N | S | Q1j | a bond | H | a bond | NH | S | NH | T3b | OH |
| 763 | N | S | Q1j | a bond | H | a bond | NH | S | NH | T3c | OH |
| 764 | N | S | Q1j | a bond | H | a bond | NH | S | NH | T3d | OH |
| 765 | N | S | Q1j | a bond | H | a bond | NH | S | NH | T3e | OH |
| 766 | N | S | Q1j | a bond | H | a bond | NH | S | NH | T3f | OH |
| 767 | N | S | Q1j | a bond | H | a bond | NH | S | NH | T3g | OH |
| 768 | N | S | Q1j | a bond | H | a bond | NH | S | NH | T3h | OH |
| 769 | N | S | Q1j | a bond | H | a bond | NH | S | NH | T3i | OH |
| 770 | N | S | Q1j | a bond | H | a bond | NH | S | NH | T3j | OH |
| 771 | N | S | Q1j | a bond | H | a bond | NH | S | a bond | T3a | OH |
| 772 | N | S | Q1j | a bond | H | a bond | NH | S | a bond | T3b | OH |
| 773 | N | S | Q1j | a bond | H | a bond | NH | S | a bond | T3c | OH |
| 774 | N | S | Q1j | a bond | H | a bond | NH | S | a bond | T3d | OH |
| 775 | N | S | Q1j | a bond | H | a bond | NH | S | a bond | T3e | OH |
| 776 | N | S | Q1j | a bond | H | a bond | NH | S | a bond | T3f | OH |
| 777 | N | S | Q1j | a bond | H | a bond | NH | S | a bond | T3g | OH |
| 778 | N | S | Q1j | a bond | H | a bond | NH | S | a bond | T3h | OH |
| 779 | N | S | Q1j | a bond | H | a bond | NH | S | a bond | T3i | OH |
| 780 | N | S | Q1j | a bond | H | a bond | NH | S | a bond | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 781 | N | S | Q1j | a bond | H | a bond | NH | O | NH | T3a | OH |
| 782 | N | S | Q1j | a bond | H | a bond | NH | O | NH | T3b | OH |
| 783 | N | S | Q1j | a bond | H | a bond | NH | O | NH | T3c | OH |
| 784 | N | S | Q1j | a bond | H | a bond | NH | O | NH | T3d | OH |
| 785 | N | S | Q1j | a bond | H | a bond | NH | O | NH | T3e | OH |
| 786 | N | S | Q1j | a bond | H | a bond | NH | O | NH | T3f | OH |
| 787 | N | S | Q1j | a bond | H | a bond | NH | O | NH | T3g | OH |
| 788 | N | S | Q1j | a bond | H | a bond | NH | O | NH | T3h | OH |
| 789 | N | S | Q1j | a bond | H | a bond | NH | O | NH | T3i | OH |
| 790 | N | S | Q1j | a bond | H | a bond | NH | O | NH | T3j | OH |
| 791 | N | S | Q1j | a bond | H | a bond | NH | O | a bond | T3a | OH |
| 792 | N | S | Q1j | a bond | H | a bond | NH | O | a bond | T3b | OH |
| 793 | N | S | Q1j | a bond | H | a bond | NH | O | a bond | T3c | OH |
| 794 | N | S | Q1j | a bond | H | a bond | NH | O | a bond | T3d | OH |
| 795 | N | S | Q1j | a bond | H | a bond | NH | O | a bond | T3e | OH |
| 796 | N | S | Q1j | a bond | H | a bond | NH | O | a bond | T3f | OH |
| 797 | N | S | Q1j | a bond | H | a bond | NH | O | a bond | T3g | OH |
| 798 | N | S | Q1j | a bond | H | a bond | NH | O | a bond | T3h | OH |
| 799 | N | S | Q1j | a bond | H | a bond | NH | O | a bond | T3i | OH |
| 800 | N | S | Q1j | a bond | H | a bond | NH | O | a bond | T3j | OH |
| 801 | N | O | Q1a | a bond | Me | a bond | NH | S | NH | T3a | OH |
| 802 | N | O | Q1a | a bond | Me | a bond | NH | S | NH | T3b | OH |
| 803 | N | O | Q1a | a bond | Me | a bond | NH | S | NH | T3c | OH |
| 804 | N | O | Q1a | a bond | Me | a bond | NH | S | NH | T3d | OH |
| 805 | N | O | Q1a | a bond | Me | a bond | NH | S | NH | T3e | OH |
| 806 | N | O | Q1a | a bond | Me | a bond | NH | S | NH | T3f | OH |
| 807 | N | O | Q1a | a bond | Me | a bond | NH | S | NH | T3g | OH |
| 808 | N | O | Q1a | a bond | Me | a bond | NH | S | NH | T3h | OH |
| 809 | N | O | Q1a | a bond | Me | a bond | NH | S | NH | T3i | OH |
| 810 | N | O | Q1a | a bond | Me | a bond | NH | S | NH | T3j | OH |
| 811 | N | O | Q1a | a bond | Me | a bond | NH | S | a bond | T3a | OH |
| 812 | N | O | Q1a | a bond | Me | a bond | NH | S | a bond | T3b | OH |
| 813 | N | O | Q1a | a bond | Me | a bond | NH | S | a bond | T3c | OH |
| 814 | N | O | Q1a | a bond | Me | a bond | NH | S | a bond | T3d | OH |
| 815 | N | O | Q1a | a bond | Me | a bond | NH | S | a bond | T3e | OH |
| 816 | N | O | Q1a | a bond | Me | a bond | NH | S | a bond | T3f | OH |
| 817 | N | O | Q1a | a bond | Me | a bond | NH | S | a bond | T3g | OH |
| 818 | N | O | Q1a | a bond | Me | a bond | NH | S | a bond | T3h | OH |
| 819 | N | O | Q1a | a bond | Me | a bond | NH | S | a bond | T3i | OH |
| 820 | N | O | Q1a | a bond | Me | a bond | NH | S | a bond | T3j | OH |
| 821 | N | O | Q1a | a bond | Me | a bond | NH | O | NH | T3a | OH |
| 822 | N | O | Q1a | a bond | Me | a bond | NH | O | NH | T3b | OH |
| 823 | N | O | Q1a | a bond | Me | a bond | NH | O | NH | T3c | OH |
| 824 | N | O | Q1a | a bond | Me | a bond | NH | O | NH | T3d | OH |
| 825 | N | O | Q1a | a bond | Me | a bond | NH | O | NH | T3e | OH |
| 826 | N | O | Q1a | a bond | Me | a bond | NH | O | NH | T3f | OH |
| 827 | N | O | Q1a | a bond | Me | a bond | NH | O | NH | T3g | OH |
| 828 | N | O | Q1a | a bond | Me | a bond | NH | O | NH | T3h | OH |
| 829 | N | O | Q1a | a bond | Me | a bond | NH | O | NH | T3i | OH |
| 830 | N | O | Q1a | a bond | Me | a bond | NH | O | NH | T3j | OH |
| 831 | N | O | Q1a | a bond | Me | a bond | NH | O | a bond | T3a | OH |
| 832 | N | O | Q1a | a bond | Me | a bond | NH | O | a bond | T3b | OH |
| 833 | N | O | Q1a | a bond | Me | a bond | NH | O | a bond | T3c | OH |
| 834 | N | O | Q1a | a bond | Me | a bond | NH | O | a bond | T3d | OH |
| 835 | N | O | Q1a | a bond | Me | a bond | NH | O | a bond | T3e | OH |
| 836 | N | O | Q1a | a bond | Me | a bond | NH | O | a bond | T3f | OH |
| 837 | N | O | Q1a | a bond | Me | a bond | NH | O | a bond | T3g | OH |
| 838 | N | O | Q1a | a bond | Me | a bond | NH | O | a bond | T3h | OH |
| 839 | N | O | Q1a | a bond | Me | a bond | NH | O | a bond | T3i | OH |
| 840 | N | O | Q1a | a bond | Me | a bond | NH | O | a bond | T3j | OH |
| 841 | N | O | Q1a | a bond | H | a bond | NH | S | NH | T3a | OH |
| 842 | N | O | Q1a | a bond | H | a bond | NH | S | NH | T3b | OH |
| 843 | N | O | Q1a | a bond | H | a bond | NH | S | NH | T3c | OH |
| 844 | N | O | Q1a | a bond | H | a bond | NH | S | NH | T3d | OH |
| 845 | N | O | Q1a | a bond | H | a bond | NH | S | NH | T3e | OH |
| 846 | N | O | Q1a | a bond | H | a bond | NH | S | NH | T3f | OH |
| 847 | N | O | Q1a | a bond | H | a bond | NH | S | NH | T3g | OH |
| 848 | N | O | Q1a | a bond | H | a bond | NH | S | NH | T3h | OH |
| 849 | N | O | Q1a | a bond | H | a bond | NH | S | NH | T3i | OH |
| 850 | N | O | Q1a | a bond | H | a bond | NH | S | NH | T3j | OH |
| 851 | N | O | Q1a | a bond | H | a bond | NH | S | a bond | T3a | OH |
| 852 | N | O | Q1a | a bond | H | a bond | NH | S | a bond | T3b | OH |
| 853 | N | O | Q1a | a bond | H | a bond | NH | S | a bond | T3c | OH |
| 854 | N | O | Q1a | a bond | H | a bond | NH | S | a bond | T3d | OH |
| 855 | N | O | Q1a | a bond | H | a bond | NH | S | a bond | T3e | OH |
| 856 | N | O | Q1a | a bond | H | a bond | NH | S | a bond | T3f | OH |
| 857 | N | O | Q1a | a bond | H | a bond | NH | S | a bond | T3g | OH |
| 858 | N | O | Q1a | a bond | H | a bond | NH | S | a bond | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 859 | N | O | Q1a | a bond | H | a bond | NH | S | a bond | T3i | OH |
| 860 | N | O | Q1a | a bond | H | a bond | NH | S | a bond | T3j | OH |
| 861 | N | O | Q1a | a bond | H | a bond | NH | O | NH | T3a | OH |
| 862 | N | O | Q1a | a bond | H | a bond | NH | O | NH | T3b | OH |
| 863 | N | O | Q1a | a bond | H | a bond | NH | O | NH | T3c | OH |
| 864 | N | O | Q1a | a bond | H | a bond | NH | O | NH | T3d | OH |
| 865 | N | O | Q1a | a bond | H | a bond | NH | O | NH | T3e | OH |
| 866 | N | O | Q1a | a bond | H | a bond | NH | O | NH | T3f | OH |
| 867 | N | O | Q1a | a bond | H | a bond | NH | O | NH | T3g | OH |
| 868 | N | O | Q1a | a bond | H | a bond | NH | O | NH | T3h | OH |
| 869 | N | O | Q1a | a bond | H | a bond | NH | O | NH | T3i | OH |
| 870 | N | O | Q1a | a bond | H | a bond | NH | O | NH | T3j | OH |
| 871 | N | O | Q1a | a bond | H | a bond | NH | O | a bond | T3a | OH |
| 872 | N | O | Q1a | a bond | H | a bond | NH | O | a bond | T3b | OH |
| 873 | N | O | Q1a | a bond | H | a bond | NH | O | a bond | T3c | OH |
| 874 | N | O | Q1a | a bond | H | a bond | NH | O | a bond | T3d | OH |
| 875 | N | O | Q1a | a bond | H | a bond | NH | O | a bond | T3e | OH |
| 876 | N | O | Q1a | a bond | H | a bond | NH | O | a bond | T3f | OH |
| 877 | N | O | Q1a | a bond | H | a bond | NH | O | a bond | T3g | OH |
| 878 | N | O | Q1a | a bond | H | a bond | NH | O | a bond | T3h | OH |
| 879 | N | O | Q1a | a bond | H | a bond | NH | O | a bond | T3i | OH |
| 880 | N | O | Q1a | a bond | H | a bond | NH | O | a bond | T3j | OH |
| 881 | N | O | Q1b | a bond | Me | a bond | NH | S | NH | T3a | OH |
| 882 | N | O | Q1b | a bond | Me | a bond | NH | S | NH | T3b | OH |
| 883 | N | O | Q1b | a bond | Me | a bond | NH | S | NH | T3c | OH |
| 884 | N | O | Q1b | a bond | Me | a bond | NH | S | NH | T3d | OH |
| 885 | N | O | Q1b | a bond | Me | a bond | NH | S | NH | T3e | OH |
| 886 | N | O | Q1b | a bond | Me | a bond | NH | S | NH | T3f | OH |
| 887 | N | O | Q1b | a bond | Me | a bond | NH | S | NH | T3g | OH |
| 888 | N | O | Q1b | a bond | Me | a bond | NH | S | NH | T3h | OH |
| 889 | N | O | Q1b | a bond | Me | a bond | NH | S | NH | T3i | OH |
| 890 | N | O | Q1b | a bond | Me | a bond | NH | S | NH | T3j | OH |
| 891 | N | O | Q1b | a bond | Me | a bond | NH | S | a bond | T3a | OH |
| 892 | N | O | Q1b | a bond | Me | a bond | NH | S | a bond | T3b | OH |
| 893 | N | O | Q1b | a bond | Me | a bond | NH | S | a bond | T3c | OH |
| 894 | N | O | Q1b | a bond | Me | a bond | NH | S | a bond | T3d | OH |
| 895 | N | O | Q1b | a bond | Me | a bond | NH | S | a bond | T3e | OH |
| 896 | N | O | Q1b | a bond | Me | a bond | NH | S | a bond | T3f | OH |
| 897 | N | O | Q1b | a bond | Me | a bond | NH | S | a bond | T3g | OH |
| 898 | N | O | Q1b | a bond | Me | a bond | NH | S | a bond | T3h | OH |
| 899 | N | O | Q1b | a bond | Me | a bond | NH | S | a bond | T3i | OH |
| 900 | N | O | Q1b | a bond | Me | a bond | NH | S | a bond | T3j | OH |
| 901 | N | O | Q1b | a bond | Me | a bond | NH | O | NH | T3a | OH |
| 902 | N | O | Q1b | a bond | Me | a bond | NH | O | NH | T3b | OH |
| 903 | N | O | Q1b | a bond | Me | a bond | NH | O | NH | T3c | OH |
| 904 | N | O | Q1b | a bond | Me | a bond | NH | O | NH | T3d | OH |
| 905 | N | O | Q1b | a bond | Me | a bond | NH | O | NH | T3e | OH |
| 906 | N | O | Q1b | a bond | Me | a bond | NH | O | NH | T3f | OH |
| 907 | N | O | Q1b | a bond | Me | a bond | NH | O | NH | T3g | OH |
| 908 | N | O | Q1b | a bond | Me | a bond | NH | O | NH | T3h | OH |
| 909 | N | O | Q1b | a bond | Me | a bond | NH | O | NH | T3i | OH |
| 910 | N | O | Q1b | a bond | Me | a bond | NH | O | NH | T3j | OH |
| 911 | N | O | Q1b | a bond | Me | a bond | NH | O | a bond | T3a | OH |
| 912 | N | O | Q1b | a bond | Me | a bond | NH | O | a bond | T3b | OH |
| 913 | N | O | Q1b | a bond | Me | a bond | NH | O | a bond | T3c | OH |
| 914 | N | O | Q1b | a bond | Me | a bond | NH | O | a bond | T3d | OH |
| 915 | N | O | Q1b | a bond | Me | a bond | NH | O | a bond | T3e | OH |
| 916 | N | O | Q1b | a bond | Me | a bond | NH | O | a bond | T3f | OH |
| 917 | N | O | Q1b | a bond | Me | a bond | NH | O | a bond | T3g | OH |
| 918 | N | O | Q1b | a bond | Me | a bond | NH | O | a bond | T3h | OH |
| 919 | N | O | Q1b | a bond | Me | a bond | NH | O | a bond | T3i | OH |
| 920 | N | O | Q1b | a bond | Me | a bond | NH | O | a bond | T3j | OH |
| 921 | N | O | Q1b | a bond | H | a bond | NH | S | NH | T3a | OH |
| 922 | N | O | Q1b | a bond | H | a bond | NH | S | NH | T3b | OH |
| 923 | N | O | Q1b | a bond | H | a bond | NH | S | NH | T3c | OH |
| 924 | N | O | Q1b | a bond | H | a bond | NH | S | NH | T3d | OH |
| 925 | N | O | Q1b | a bond | H | a bond | NH | S | NH | T3e | OH |
| 926 | N | O | Q1b | a bond | H | a bond | NH | S | NH | T3f | OH |
| 927 | N | O | Q1b | a bond | H | a bond | NH | S | NH | T3g | OH |
| 928 | N | O | Q1b | a bond | H | a bond | NH | S | NH | T3h | OH |
| 929 | N | O | Q1b | a bond | H | a bond | NH | S | NH | T3i | OH |
| 930 | N | O | Q1b | a bond | H | a bond | NH | S | NH | T3j | OH |
| 931 | N | O | Q1b | a bond | H | a bond | NH | S | a bond | T3a | OH |
| 932 | N | O | Q1b | a bond | H | a bond | NH | S | a bond | T3b | OH |
| 933 | N | O | Q1b | a bond | H | a bond | NH | S | a bond | T3c | OH |
| 934 | N | O | Q1b | a bond | H | a bond | NH | S | a bond | T3d | OH |
| 935 | N | O | Q1b | a bond | H | a bond | NH | S | a bond | T3e | OH |
| 936 | N | O | Q1b | a bond | H | a bond | NH | S | a bond | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 937 | N | O | Q1b | a bond | H | a bond | NH | S | a bond | T3g | OH |
| 938 | N | O | Q1b | a bond | H | a bond | NH | S | a bond | T3h | OH |
| 939 | N | O | Q1b | a bond | H | a bond | NH | S | a bond | T3i | OH |
| 940 | N | O | Q1b | a bond | H | a bond | NH | S | a bond | T3j | OH |
| 941 | N | O | Q1b | a bond | H | a bond | NH | O | NH | T3a | OH |
| 942 | N | O | Q1b | a bond | H | a bond | NH | O | NH | T3b | OH |
| 943 | N | O | Q1b | a bond | H | a bond | NH | O | NH | T3c | OH |
| 944 | N | O | Q1b | a bond | H | a bond | NH | O | NH | T3d | OH |
| 945 | N | O | Q1b | a bond | H | a bond | NH | O | NH | T3e | OH |
| 946 | N | O | Q1b | a bond | H | a bond | NH | O | NH | T3f | OH |
| 947 | N | O | Q1b | a bond | H | a bond | NH | O | NH | T3g | OH |
| 948 | N | O | Q1b | a bond | H | a bond | NH | O | NH | T3h | OH |
| 949 | N | O | Q1b | a bond | H | a bond | NH | O | NH | T3i | OH |
| 950 | N | O | Q1b | a bond | H | a bond | NH | O | NH | T3j | OH |
| 951 | N | O | Q1b | a bond | H | a bond | NH | O | a bond | T3a | OH |
| 952 | N | O | Q1b | a bond | H | a bond | NH | O | a bond | T3b | OH |
| 953 | N | O | Q1b | a bond | H | a bond | NH | O | a bond | T3c | OH |
| 954 | N | O | Q1b | a bond | H | a bond | NH | O | a bond | T3d | OH |
| 955 | N | O | Q1b | a bond | H | a bond | NH | O | a bond | T3e | OH |
| 956 | N | O | Q1b | a bond | H | a bond | NH | O | a bond | T3f | OH |
| 957 | N | O | Q1b | a bond | H | a bond | NH | O | a bond | T3g | OH |
| 958 | N | O | Q1b | a bond | H | a bond | NH | O | a bond | T3h | OH |
| 959 | N | O | Q1b | a bond | H | a bond | NH | O | a bond | T3i | OH |
| 960 | N | O | Q1b | a bond | H | a bond | NH | O | a bond | T3j | OH |
| 961 | N | O | Q1c | a bond | Me | a bond | NH | S | NH | T3a | OH |
| 962 | N | O | Q1c | a bond | Me | a bond | NH | S | NH | T3b | OH |
| 963 | N | O | Q1c | a bond | Me | a bond | NH | S | NH | T3c | OH |
| 964 | N | O | Q1c | a bond | Me | a bond | NH | S | NH | T3d | OH |
| 965 | N | O | Q1c | a bond | Me | a bond | NH | S | NH | T3e | OH |
| 966 | N | O | Q1c | a bond | Me | a bond | NH | S | NH | T3f | OH |
| 967 | N | O | Q1c | a bond | Me | a bond | NH | S | NH | T3g | OH |
| 968 | N | O | Q1c | a bond | Me | a bond | NH | S | NH | T3h | OH |
| 969 | N | O | Q1c | a bond | Me | a bond | NH | S | NH | T3i | OH |
| 970 | N | O | Q1c | a bond | Me | a bond | NH | S | NH | T3j | OH |
| 971 | N | O | Q1c | a bond | Me | a bond | NH | S | a bond | T3a | OH |
| 972 | N | O | Q1c | a bond | Me | a bond | NH | S | a bond | T3b | OH |
| 973 | N | O | Q1c | a bond | Me | a bond | NH | S | a bond | T3c | OH |
| 974 | N | O | Q1c | a bond | Me | a bond | NH | S | a bond | T3d | OH |
| 975 | N | O | Q1c | a bond | Me | a bond | NH | S | a bond | T3e | OH |
| 976 | N | O | Q1c | a bond | Me | a bond | NH | S | a bond | T3f | OH |
| 977 | N | O | Q1c | a bond | Me | a bond | NH | S | a bond | T3g | OH |
| 978 | N | O | Q1c | a bond | Me | a bond | NH | S | a bond | T3h | OH |
| 979 | N | O | Q1c | a bond | Me | a bond | NH | S | a bond | T3i | OH |
| 980 | N | O | Q1c | a bond | Me | a bond | NH | S | a bond | T3j | OH |
| 981 | N | O | Q1c | a bond | Me | a bond | NH | O | NH | T3a | OH |
| 982 | N | O | Q1c | a bond | Me | a bond | NH | O | NH | T3b | OH |
| 983 | N | O | Q1c | a bond | Me | a bond | NH | O | NH | T3c | OH |
| 984 | N | O | Q1c | a bond | Me | a bond | NH | O | NH | T3d | OH |
| 985 | N | O | Q1c | a bond | Me | a bond | NH | O | NH | T3e | OH |
| 986 | N | O | Q1c | a bond | Me | a bond | NH | O | NH | T3f | OH |
| 987 | N | O | Q1c | a bond | Me | a bond | NH | O | NH | T3g | OH |
| 988 | N | O | Q1c | a bond | Me | a bond | NH | O | NH | T3h | OH |
| 989 | N | O | Q1c | a bond | Me | a bond | NH | O | NH | T3i | OH |
| 990 | N | O | Q1c | a bond | Me | a bond | NH | O | NH | T3j | OH |
| 991 | N | O | Q1c | a bond | Me | a bond | NH | O | a bond | T3a | OH |
| 992 | N | O | Q1c | a bond | Me | a bond | NH | O | a bond | T3b | OH |
| 993 | N | O | Q1c | a bond | Me | a bond | NH | O | a bond | T3c | OH |
| 994 | N | O | Q1c | a bond | Me | a bond | NH | O | a bond | T3d | OH |
| 995 | N | O | Q1c | a bond | Me | a bond | NH | O | a bond | T3e | OH |
| 996 | N | O | Q1c | a bond | Me | a bond | NH | O | a bond | T3f | OH |
| 997 | N | O | Q1c | a bond | Me | a bond | NH | O | a bond | T3g | OH |
| 998 | N | O | Q1c | a bond | Me | a bond | NH | O | a bond | T3h | OH |
| 999 | N | O | Q1c | a bond | Me | a bond | NH | O | a bond | T3i | OH |
| 1000 | N | O | Q1c | a bond | Me | a bond | NH | O | a bond | T3j | OH |
| 1001 | N | O | Q1c | a bond | H | a bond | NH | S | NH | T3a | OH |
| 1002 | N | O | Q1c | a bond | H | a bond | NH | S | NH | T3b | OH |
| 1003 | N | O | Q1c | a bond | H | a bond | NH | S | NH | T3c | OH |
| 1004 | N | O | Q1c | a bond | H | a bond | NH | S | NH | T3d | OH |
| 1005 | N | O | Q1c | a bond | H | a bond | NH | S | NH | T3e | OH |
| 1006 | N | O | Q1c | a bond | H | a bond | NH | S | NH | T3f | OH |
| 1007 | N | O | Q1c | a bond | H | a bond | NH | S | NH | T3g | OH |
| 1008 | N | O | Q1c | a bond | H | a bond | NH | S | NH | T3h | OH |
| 1009 | N | O | Q1c | a bond | H | a bond | NH | S | NH | T3i | OH |
| 1010 | N | O | Q1c | a bond | H | a bond | NH | S | NH | T3j | OH |
| 1011 | N | O | Q1c | a bond | H | a bond | NH | S | a bond | T3a | OH |
| 1012 | N | O | Q1c | a bond | H | a bond | NH | S | a bond | T3b | OH |
| 1013 | N | O | Q1c | a bond | H | a bond | NH | S | a bond | T3c | OH |
| 1014 | N | O | Q1c | a bond | H | a bond | NH | S | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 1015 | N | O | Q1c | a bond | H | a bond | NH | S | a bond | T3e | OH |
| 1016 | N | O | Q1c | a bond | H | a bond | NH | S | a bond | T3f | OH |
| 1017 | N | O | Q1c | a bond | H | a bond | NH | S | a bond | T3g | OH |
| 1018 | N | O | Q1c | a bond | H | a bond | NH | S | a bond | T3h | OH |
| 1019 | N | O | Q1c | a bond | H | a bond | NH | S | a bond | T3i | OH |
| 1020 | N | O | Q1c | a bond | H | a bond | NH | S | a bond | T3j | OH |
| 1021 | N | O | Q1c | a bond | H | a bond | NH | O | NH | T3a | OH |
| 1022 | N | O | Q1c | a bond | H | a bond | NH | O | NH | T3b | OH |
| 1023 | N | O | Q1c | a bond | H | a bond | NH | O | NH | T3c | OH |
| 1024 | N | O | Q1c | a bond | H | a bond | NH | O | NH | T3d | OH |
| 1025 | N | O | Q1c | a bond | H | a bond | NH | O | NH | T3e | OH |
| 1026 | N | O | Q1c | a bond | H | a bond | NH | O | NH | T3f | OH |
| 1027 | N | O | Q1c | a bond | H | a bond | NH | O | NH | T3g | OH |
| 1028 | N | O | Q1c | a bond | H | a bond | NH | O | NH | T3h | OH |
| 1029 | N | O | Q1c | a bond | H | a bond | NH | O | NH | T3i | OH |
| 1030 | N | O | Q1c | a bond | H | a bond | NH | O | NH | T3j | OH |
| 1031 | N | O | Q1c | a bond | H | a bond | NH | O | a bond | T3a | OH |
| 1032 | N | O | Q1c | a bond | H | a bond | NH | O | a bond | T3b | OH |
| 1033 | N | O | Q1c | a bond | H | a bond | NH | O | a bond | T3c | OH |
| 1034 | N | O | Q1c | a bond | H | a bond | NH | O | a bond | T3d | OH |
| 1035 | N | O | Q1c | a bond | H | a bond | NH | O | a bond | T3e | OH |
| 1036 | N | O | Q1c | a bond | H | a bond | NH | O | a bond | T3f | OH |
| 1037 | N | O | Q1c | a bond | H | a bond | NH | O | a bond | T3g | OH |
| 1038 | N | O | Q1c | a bond | H | a bond | NH | O | a bond | T3h | OH |
| 1039 | N | O | Q1c | a bond | H | a bond | NH | O | a bond | T3i | OH |
| 1040 | N | O | Q1c | a bond | H | a bond | NH | O | a bond | T3j | OH |
| 1041 | N | O | Q1i | a bond | Me | a bond | NH | S | NH | T3a | OH |
| 1042 | N | O | Q1i | a bond | Me | a bond | NH | S | NH | T3b | OH |
| 1043 | N | O | Q1i | a bond | Me | a bond | NH | S | NH | T3c | OH |
| 1044 | N | O | Q1i | a bond | Me | a bond | NH | S | NH | T3d | OH |
| 1045 | N | O | Q1i | a bond | Me | a bond | NH | S | NH | T3e | OH |
| 1046 | N | O | Q1i | a bond | Me | a bond | NH | S | NH | T3f | OH |
| 1047 | N | O | Q1i | a bond | Me | a bond | NH | S | NH | T3g | OH |
| 1048 | N | O | Q1i | a bond | Me | a bond | NH | S | NH | T3h | OH |
| 1049 | N | O | Q1i | a bond | Me | a bond | NH | S | NH | T3i | OH |
| 1050 | N | O | Q1i | a bond | Me | a bond | NH | S | NH | T3j | OH |
| 1051 | N | O | Q1i | a bond | Me | a bond | NH | S | a bond | T3a | OH |
| 1052 | N | O | Q1i | a bond | Me | a bond | NH | S | a bond | T3b | OH |
| 1053 | N | O | Q1i | a bond | Me | a bond | NH | S | a bond | T3c | OH |
| 1054 | N | O | Q1i | a bond | Me | a bond | NH | S | a bond | T3d | OH |
| 1055 | N | O | Q1i | a bond | Me | a bond | NH | S | a bond | T3e | OH |
| 1056 | N | O | Q1i | a bond | Me | a bond | NH | S | a bond | T3f | OH |
| 1057 | N | O | Q1i | a bond | Me | a bond | NH | S | a bond | T3g | OH |
| 1058 | N | O | Q1i | a bond | Me | a bond | NH | S | a bond | T3h | OH |
| 1059 | N | O | Q1i | a bond | Me | a bond | NH | S | a bond | T3i | OH |
| 1060 | N | O | Q1i | a bond | Me | a bond | NH | S | a bond | T3j | OH |
| 1061 | N | O | Q1i | a bond | Me | a bond | NH | O | NH | T3a | OH |
| 1062 | N | O | Q1i | a bond | Me | a bond | NH | O | NH | T3b | OH |
| 1063 | N | O | Q1i | a bond | Me | a bond | NH | O | NH | T3c | OH |
| 1064 | N | O | Q1i | a bond | Me | a bond | NH | O | NH | T3d | OH |
| 1065 | N | O | Q1i | a bond | Me | a bond | NH | O | NH | T3e | OH |
| 1066 | N | O | Q1i | a bond | Me | a bond | NH | O | NH | T3f | OH |
| 1067 | N | O | Q1i | a bond | Me | a bond | NH | O | NH | T3g | OH |
| 1068 | N | O | Q1i | a bond | Me | a bond | NH | O | NH | T3h | OH |
| 1069 | N | O | Q1i | a bond | Me | a bond | NH | O | NH | T3i | OH |
| 1070 | N | O | Q1i | a bond | Me | a bond | NH | O | NH | T3j | OH |
| 1071 | N | O | Q1i | a bond | Me | a bond | NH | O | a bond | T3a | OH |
| 1072 | N | O | Q1i | a bond | Me | a bond | NH | O | a bond | T3b | OH |
| 1073 | N | O | Q1i | a bond | Me | a bond | NH | O | a bond | T3c | OH |
| 1074 | N | O | Q1i | a bond | Me | a bond | NH | O | a bond | T3d | OH |
| 1075 | N | O | Q1i | a bond | Me | a bond | NH | O | a bond | T3e | OH |
| 1076 | N | O | Q1i | a bond | Me | a bond | NH | O | a bond | T3f | OH |
| 1077 | N | O | Q1i | a bond | Me | a bond | NH | O | a bond | T3g | OH |
| 1078 | N | O | Q1i | a bond | Me | a bond | NH | O | a bond | T3h | OH |
| 1079 | N | O | Q1i | a bond | Me | a bond | NH | O | a bond | T3i | OH |
| 1080 | N | O | Q1i | a bond | Me | a bond | NH | O | a bond | T3j | OH |
| 1081 | N | O | Q1i | a bond | H | a bond | NH | S | NH | T3a | OH |
| 1082 | N | O | Q1i | a bond | H | a bond | NH | S | NH | T3b | OH |
| 1083 | N | O | Q1i | a bond | H | a bond | NH | S | NH | T3c | OH |
| 1084 | N | O | Q1i | a bond | H | a bond | NH | S | NH | T3d | OH |
| 1085 | N | O | Q1i | a bond | H | a bond | NH | S | NH | T3e | OH |
| 1086 | N | O | Q1i | a bond | H | a bond | NH | S | NH | T3f | OH |
| 1087 | N | O | Q1i | a bond | H | a bond | NH | S | NH | T3g | OH |
| 1088 | N | O | Q1i | a bond | H | a bond | NH | S | NH | T3h | OH |
| 1089 | N | O | Q1i | a bond | H | a bond | NH | S | NH | T3i | OH |
| 1090 | N | O | Q1i | a bond | H | a bond | NH | S | NH | T3j | OH |
| 1091 | N | O | Q1i | a bond | H | a bond | NH | S | a bond | T3a | OH |
| 1092 | N | O | Q1i | a bond | H | a bond | NH | S | a bond | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 1093 | N | O | Q1i | a bond | H | a bond | NH | S | a bond | T3c | OH |
| 1094 | N | O | Q1i | a bond | H | a bond | NH | S | a bond | T3d | OH |
| 1095 | N | O | Q1i | a bond | H | a bond | NH | S | a bond | T3e | OH |
| 1096 | N | O | Q1i | a bond | H | a bond | NH | S | a bond | T3f | OH |
| 1097 | N | O | Q1i | a bond | H | a bond | NH | S | a bond | T3g | OH |
| 1098 | N | O | Q1i | a bond | H | a bond | NH | S | a bond | T3h | OH |
| 1099 | N | O | Q1i | a bond | H | a bond | NH | S | a bond | T3i | OH |
| 1100 | N | O | Q1i | a bond | H | a bond | NH | S | a bond | T3j | OH |
| 1101 | N | O | Q1i | a bond | H | a bond | NH | O | NH | T3a | OH |
| 1102 | N | O | Q1i | a bond | H | a bond | NH | O | NH | T3b | OH |
| 1103 | N | O | Q1i | a bond | H | a bond | NH | O | NH | T3c | OH |
| 1104 | N | O | Q1i | a bond | H | a bond | NH | O | NH | T3d | OH |
| 1105 | N | O | Q1i | a bond | H | a bond | NH | O | NH | T3e | OH |
| 1106 | N | O | Q1i | a bond | H | a bond | NH | O | NH | T3f | OH |
| 1107 | N | O | Q1i | a bond | H | a bond | NH | O | NH | T3g | OH |
| 1108 | N | O | Q1i | a bond | H | a bond | NH | O | NH | T3h | OH |
| 1109 | N | O | Q1i | a bond | H | a bond | NH | O | NH | T3i | OH |
| 1110 | N | O | Q1i | a bond | H | a bond | NH | O | NH | T3j | OH |
| 1111 | N | O | Q1i | a bond | H | a bond | NH | O | a bond | T3a | OH |
| 1112 | N | O | Q1i | a bond | H | a bond | NH | O | a bond | T3b | OH |
| 1113 | N | O | Q1i | a bond | H | a bond | NH | O | a bond | T3c | OH |
| 1114 | N | O | Q1i | a bond | H | a bond | NH | O | a bond | T3d | OH |
| 1115 | N | O | Q1i | a bond | H | a bond | NH | O | a bond | T3e | OH |
| 1116 | N | O | Q1i | a bond | H | a bond | NH | O | a bond | T3f | OH |
| 1117 | N | O | Q1i | a bond | H | a bond | NH | O | a bond | T3g | OH |
| 1118 | N | O | Q1i | a bond | H | a bond | NH | O | a bond | T3h | OH |
| 1119 | N | O | Q1i | a bond | H | a bond | NH | O | a bond | T3i | OH |
| 1120 | N | O | Q1i | a bond | H | a bond | NH | O | a bond | T3j | OH |
| 1121 | N | O | Q1j | a bond | Me | a bond | NH | S | NH | T3a | OH |
| 1122 | N | O | Q1j | a bond | Me | a bond | NH | S | NH | T3b | OH |
| 1123 | N | O | Q1j | a bond | Me | a bond | NH | S | NH | T3c | OH |
| 1124 | N | O | Q1j | a bond | Me | a bond | NH | S | NH | T3d | OH |
| 1125 | N | O | Q1j | a bond | Me | a bond | NH | S | NH | T3e | OH |
| 1126 | N | O | Q1j | a bond | Me | a bond | NH | S | NH | T3f | OH |
| 1127 | N | O | Q1j | a bond | Me | a bond | NH | S | NH | T3g | OH |
| 1128 | N | O | Q1j | a bond | Me | a bond | NH | S | NH | T3h | OH |
| 1129 | N | O | Q1j | a bond | Me | a bond | NH | S | NH | T3i | OH |
| 1130 | N | O | Q1j | a bond | Me | a bond | NH | S | NH | T3j | OH |
| 1131 | N | O | Q1j | a bond | Me | a bond | NH | S | a bond | T3a | OH |
| 1132 | N | O | Q1j | a bond | Me | a bond | NH | S | a bond | T3b | OH |
| 1133 | N | O | Q1j | a bond | Me | a bond | NH | S | a bond | T3c | OH |
| 1134 | N | O | Q1j | a bond | Me | a bond | NH | S | a bond | T3d | OH |
| 1135 | N | O | Q1j | a bond | Me | a bond | NH | S | a bond | T3e | OH |
| 1136 | N | O | Q1j | a bond | Me | a bond | NH | S | a bond | T3f | OH |
| 1137 | N | O | Q1j | a bond | Me | a bond | NH | S | a bond | T3g | OH |
| 1138 | N | O | Q1j | a bond | Me | a bond | NH | S | a bond | T3h | OH |
| 1139 | N | O | Q1j | a bond | Me | a bond | NH | S | a bond | T3i | OH |
| 1140 | N | O | Q1j | a bond | Me | a bond | NH | S | a bond | T3j | OH |
| 1141 | N | O | Q1j | a bond | Me | a bond | NH | O | NH | T3a | OH |
| 1142 | N | O | Q1j | a bond | Me | a bond | NH | O | NH | T3b | OH |
| 1143 | N | O | Q1j | a bond | Me | a bond | NH | O | NH | T3c | OH |
| 1144 | N | O | Q1j | a bond | Me | a bond | NH | O | NH | T3d | OH |
| 1145 | N | O | Q1j | a bond | Me | a bond | NH | O | NH | T3e | OH |
| 1146 | N | O | Q1j | a bond | Me | a bond | NH | O | NH | T3f | OH |
| 1147 | N | O | Q1j | a bond | Me | a bond | NH | O | NH | T3g | OH |
| 1148 | N | O | Q1j | a bond | Me | a bond | NH | O | NH | T3h | OH |
| 1149 | N | O | Q1j | a bond | Me | a bond | NH | O | NH | T3i | OH |
| 1150 | N | O | Q1j | a bond | Me | a bond | NH | O | NH | T3j | OH |
| 1151 | N | O | Q1j | a bond | Me | a bond | NH | O | a bond | T3a | OH |
| 1152 | N | O | Q1j | a bond | Me | a bond | NH | O | a bond | T3b | OH |
| 1153 | N | O | Q1j | a bond | Me | a bond | NH | O | a bond | T3c | OH |
| 1154 | N | O | Q1j | a bond | Me | a bond | NH | O | a bond | T3d | OH |
| 1155 | N | O | Q1j | a bond | Me | a bond | NH | O | a bond | T3e | OH |
| 1156 | N | O | Q1j | a bond | Me | a bond | NH | O | a bond | T3f | OH |
| 1157 | N | O | Q1j | a bond | Me | a bond | NH | O | a bond | T3g | OH |
| 1158 | N | O | Q1j | a bond | Me | a bond | NH | O | a bond | T3h | OH |
| 1159 | N | O | Q1j | a bond | Me | a bond | NH | O | a bond | T3i | OH |
| 1160 | N | O | Q1j | a bond | Me | a bond | NH | O | a bond | T3j | OH |
| 1161 | N | O | Q1j | a bond | H | a bond | NH | S | NH | T3a | OH |
| 1162 | N | O | Q1j | a bond | H | a bond | NH | S | NH | T3b | OH |
| 1163 | N | O | Q1j | a bond | H | a bond | NH | S | NH | T3c | OH |
| 1164 | N | O | Q1j | a bond | H | a bond | NH | S | NH | T3d | OH |
| 1165 | N | O | Q1j | a bond | H | a bond | NH | S | NH | T3e | OH |
| 1166 | N | O | Q1j | a bond | H | a bond | NH | S | NH | T3f | OH |
| 1167 | N | O | Q1j | a bond | H | a bond | NH | S | NH | T3g | OH |
| 1168 | N | O | Q1j | a bond | H | a bond | NH | S | NH | T3h | OH |
| 1169 | N | O | Q1j | a bond | H | a bond | NH | S | NH | T3i | OH |
| 1170 | N | O | Q1j | a bond | H | a bond | NH | S | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 1171 | N | O | Q1j | a bond | H | a bond | NH | S | a bond | T3a | OH |
| 1172 | N | O | Q1j | a bond | H | a bond | NH | S | a bond | T3b | OH |
| 1173 | N | O | Q1j | a bond | H | a bond | NH | S | a bond | T3c | OH |
| 1174 | N | O | Q1j | a bond | H | a bond | NH | S | a bond | T3d | OH |
| 1175 | N | O | Q1j | a bond | H | a bond | NH | S | a bond | T3e | OH |
| 1176 | N | O | Q1j | a bond | H | a bond | NH | S | a bond | T3f | OH |
| 1177 | N | O | Q1j | a bond | H | a bond | NH | S | a bond | T3g | OH |
| 1178 | N | O | Q1j | a bond | H | a bond | NH | S | a bond | T3h | OH |
| 1179 | N | O | Q1j | a bond | H | a bond | NH | S | a bond | T3i | OH |
| 1180 | N | O | Q1j | a bond | H | a bond | NH | S | a bond | T3j | OH |
| 1181 | N | O | Q1j | a bond | H | a bond | NH | O | NH | T3a | OH |
| 1182 | N | O | Q1j | a bond | H | a bond | NH | O | NH | T3b | OH |
| 1183 | N | O | Q1j | a bond | H | a bond | NH | O | NH | T3c | OH |
| 1184 | N | O | Q1j | a bond | H | a bond | NH | O | NH | T3d | OH |
| 1185 | N | O | Q1j | a bond | H | a bond | NH | O | NH | T3e | OH |
| 1186 | N | O | Q1j | a bond | H | a bond | NH | O | NH | T3f | OH |
| 1187 | N | O | Q1j | a bond | H | a bond | NH | O | NH | T3g | OH |
| 1188 | N | O | Q1j | a bond | H | a bond | NH | O | NH | T3h | OH |
| 1189 | N | O | Q1j | a bond | H | a bond | NH | O | NH | T3i | OH |
| 1190 | N | O | Q1j | a bond | H | a bond | NH | O | NH | T3j | OH |
| 1191 | N | O | Q1j | a bond | H | a bond | NH | O | a bond | T3a | OH |
| 1192 | N | O | Q1j | a bond | H | a bond | NH | O | a bond | T3b | OH |
| 1193 | N | O | Q1j | a bond | H | a bond | NH | O | a bond | T3c | OH |
| 1194 | N | O | Q1j | a bond | H | a bond | NH | O | a bond | T3d | OH |
| 1195 | N | O | Q1j | a bond | H | a bond | NH | O | a bond | T3e | OH |
| 1196 | N | O | Q1j | a bond | H | a bond | NH | O | a bond | T3f | OH |
| 1197 | N | O | Q1j | a bond | H | a bond | NH | O | a bond | T3g | OH |
| 1198 | N | O | Q1j | a bond | H | a bond | NH | O | a bond | T3h | OH |
| 1199 | N | O | Q1j | a bond | H | a bond | NH | O | a bond | T3i | OH |
| 1200 | N | O | Q1j | a bond | H | a bond | NH | O | a bond | T3j | OH |
| 1201 | CH | NMe | Q1a | a bond | Me | a bond | NH | S | NH | T3a | OH |
| 1202 | CH | NMe | Q1a | a bond | Me | a bond | NH | S | NH | T3b | OH |
| 1203 | CH | NMe | Q1a | a bond | Me | a bond | NH | S | NH | T3c | OH |
| 1204 | CH | NMe | Q1a | a bond | Me | a bond | NH | S | NH | T3d | OH |
| 1205 | CH | NMe | Q1a | a bond | Me | a bond | NH | S | NH | T3e | OH |
| 1206 | CH | NMe | Q1a | a bond | Me | a bond | NH | S | NH | T3f | OH |
| 1207 | CH | NMe | Q1a | a bond | Me | a bond | NH | S | NH | T3g | OH |
| 1208 | CH | NMe | Q1a | a bond | Me | a bond | NH | S | NH | T3h | OH |
| 1209 | CH | NMe | Q1a | a bond | Me | a bond | NH | S | NH | T3i | OH |
| 1210 | CH | NMe | Q1a | a bond | Me | a bond | NH | S | NH | T3j | OH |
| 1211 | CH | NMe | Q1a | a bond | Me | a bond | NH | S | a bond | T3a | OH |
| 1212 | CH | NMe | Q1a | a bond | Me | a bond | NH | S | a bond | T3b | OH |
| 1213 | CH | NMe | Q1a | a bond | Me | a bond | NH | S | a bond | T3c | OH |
| 1214 | CH | NMe | Q1a | a bond | Me | a bond | NH | S | a bond | T3d | OH |
| 1215 | CH | NMe | Q1a | a bond | Me | a bond | NH | S | a bond | T3e | OH |
| 1216 | CH | NMe | Q1a | a bond | Me | a bond | NH | S | a bond | T3f | OH |
| 1217 | CH | NMe | Q1a | a bond | Me | a bond | NH | S | a bond | T3g | OH |
| 1218 | CH | NMe | Q1a | a bond | Me | a bond | NH | S | a bond | T3h | OH |
| 1219 | CH | NMe | Q1a | a bond | Me | a bond | NH | S | a bond | T3i | OH |
| 1220 | CH | NMe | Q1a | a bond | Me | a bond | NH | S | a bond | T3j | OH |
| 1221 | CH | NMe | Q1a | a bond | Me | a bond | NH | O | NH | T3a | OH |
| 1222 | CH | NMe | Q1a | a bond | Me | a bond | NH | O | NH | T3b | OH |
| 1223 | CH | NMe | Q1a | a bond | Me | a bond | NH | O | NH | T3c | OH |
| 1224 | CH | NMe | Q1a | a bond | Me | a bond | NH | O | NH | T3d | OH |
| 1225 | CH | NMe | Q1a | a bond | Me | a bond | NH | O | NH | T3e | OH |
| 1226 | CH | NMe | Q1a | a bond | Me | a bond | NH | O | NH | T3f | OH |
| 1227 | CH | NMe | Q1a | a bond | Me | a bond | NH | O | NH | T3g | OH |
| 1228 | CH | NMe | Q1a | a bond | Me | a bond | NH | O | NH | T3h | OH |
| 1229 | CH | NMe | Q1a | a bond | Me | a bond | NH | O | NH | T3i | OH |
| 1230 | CH | NMe | Q1a | a bond | Me | a bond | NH | O | NH | T3j | OH |
| 1231 | CH | NMe | Q1a | a bond | Me | a bond | NH | O | a bond | T3a | OH |
| 1232 | CH | NMe | Q1a | a bond | Me | a bond | NH | O | a bond | T3b | OH |
| 1233 | CH | NMe | Q1a | a bond | Me | a bond | NH | O | a bond | T3c | OH |
| 1234 | CH | NMe | Q1a | a bond | Me | a bond | NH | O | a bond | T3d | OH |
| 1235 | CH | NMe | Q1a | a bond | Me | a bond | NH | O | a bond | T3e | OH |
| 1236 | CH | NMe | Q1a | a bond | Me | a bond | NH | O | a bond | T3f | OH |
| 1237 | CH | NMe | Q1a | a bond | Me | a bond | NH | O | a bond | T3g | OH |
| 1238 | CH | NMe | Q1a | a bond | Me | a bond | NH | O | a bond | T3h | OH |
| 1239 | CH | NMe | Q1a | a bond | Me | a bond | NH | O | a bond | T3i | OH |
| 1240 | CH | NMe | Q1a | a bond | Me | a bond | NH | O | a bond | T3j | OH |
| 1241 | CH | NMe | Q1a | a bond | H | a bond | NH | S | NH | T3a | OH |
| 1242 | CH | NMe | Q1a | a bond | H | a bond | NH | S | NH | T3b | OH |
| 1243 | CH | NMe | Q1a | a bond | H | a bond | NH | S | NH | T3c | OH |
| 1244 | CH | NMe | Q1a | a bond | H | a bond | NH | S | NH | T3d | OH |
| 1245 | CH | NMe | Q1a | a bond | H | a bond | NH | S | NH | T3e | OH |
| 1246 | CH | NMe | Q1a | a bond | H | a bond | NH | S | NH | T3f | OH |
| 1247 | CH | NMe | Q1a | a bond | H | a bond | NH | S | NH | T3g | OH |
| 1248 | CH | NMe | Q1a | a bond | H | a bond | NH | S | NH | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 1249 | CH | NMe | Q1a | a bond | H | a bond | NH | S | NH | T3i | OH |
| 1250 | CH | NMe | Q1a | a bond | H | a bond | NH | S | NH | T3j | OH |
| 1251 | CH | NMe | Q1a | a bond | H | a bond | NH | S | a bond | T3a | OH |
| 1252 | CH | NMe | Q1a | a bond | H | a bond | NH | S | a bond | T3b | OH |
| 1253 | CH | NMe | Q1a | a bond | H | a bond | NH | S | a bond | T3c | OH |
| 1254 | CH | NMe | Q1a | a bond | H | a bond | NH | S | a bond | T3d | OH |
| 1255 | CH | NMe | Q1a | a bond | H | a bond | NH | S | a bond | T3e | OH |
| 1256 | CH | NMe | Q1a | a bond | H | a bond | NH | S | a bond | T3f | OH |
| 1257 | CH | NMe | Q1a | a bond | H | a bond | NH | S | a bond | T3g | OH |
| 1258 | CH | NMe | Q1a | a bond | H | a bond | NH | S | a bond | T3h | OH |
| 1259 | CH | NMe | Q1a | a bond | H | a bond | NH | S | a bond | T3i | OH |
| 1260 | CH | NMe | Q1a | a bond | H | a bond | NH | S | a bond | T3j | OH |
| 1261 | CH | NMe | Q1a | a bond | H | a bond | NH | O | NH | T3a | OH |
| 1262 | CH | NMe | Q1a | a bond | H | a bond | NH | O | NH | T3b | OH |
| 1263 | CH | NMe | Q1a | a bond | H | a bond | NH | O | NH | T3c | OH |
| 1264 | CH | NMe | Q1a | a bond | H | a bond | NH | O | NH | T3d | OH |
| 1265 | CH | NMe | Q1a | a bond | H | a bond | NH | O | NH | T3e | OH |
| 1266 | CH | NMe | Q1a | a bond | H | a bond | NH | O | NH | T3f | OH |
| 1267 | CH | NMe | Q1a | a bond | H | a bond | NH | O | NH | T3g | OH |
| 1268 | CH | NMe | Q1a | a bond | H | a bond | NH | O | NH | T3h | OH |
| 1269 | CH | NMe | Q1a | a bond | H | a bond | NH | O | NH | T3i | OH |
| 1270 | CH | NMe | Q1a | a bond | H | a bond | NH | O | NH | T3j | OH |
| 1271 | CH | NMe | Q1a | a bond | H | a bond | NH | O | a bond | T3a | OH |
| 1272 | CH | NMe | Q1a | a bond | H | a bond | NH | O | a bond | T3b | OH |
| 1273 | CH | NMe | Q1a | a bond | H | a bond | NH | O | a bond | T3c | OH |
| 1274 | CH | NMe | Q1a | a bond | H | a bond | NH | O | a bond | T3d | OH |
| 1275 | CH | NMe | Q1a | a bond | H | a bond | NH | O | a bond | T3e | OH |
| 1276 | CH | NMe | Q1a | a bond | H | a bond | NH | O | a bond | T3f | OH |
| 1277 | CH | NMe | Q1a | a bond | H | a bond | NH | O | a bond | T3g | OH |
| 1278 | CH | NMe | Q1a | a bond | H | a bond | NH | O | a bond | T3h | OH |
| 1279 | CH | NMe | Q1a | a bond | H | a bond | NH | O | a bond | T3i | OH |
| 1280 | CH | NMe | Q1a | a bond | H | a bond | NH | O | a bond | T3j | OH |
| 1281 | CH | NMe | Q1b | a bond | Me | a bond | NH | S | NH | T3a | OH |
| 1282 | CH | NMe | Q1b | a bond | Me | a bond | NH | S | NH | T3b | OH |
| 1283 | CH | NMe | Q1b | a bond | Me | a bond | NH | S | NH | T3c | OH |
| 1284 | CH | NMe | Q1b | a bond | Me | a bond | NH | S | NH | T3d | OH |
| 1285 | CH | NMe | Q1b | a bond | Me | a bond | NH | S | NH | T3e | OH |
| 1286 | CH | NMe | Q1b | a bond | Me | a bond | NH | S | NH | T3f | OH |
| 1287 | CH | NMe | Q1b | a bond | Me | a bond | NH | S | NH | T3g | OH |
| 1288 | CH | NMe | Q1b | a bond | Me | a bond | NH | S | NH | T3h | OH |
| 1289 | CH | NMe | Q1b | a bond | Me | a bond | NH | S | NH | T3i | OH |
| 1290 | CH | NMe | Q1b | a bond | Me | a bond | NH | S | NH | T3j | OH |
| 1291 | CH | NMe | Q1b | a bond | Me | a bond | NH | S | a bond | T3a | OH |
| 1292 | CH | NMe | Q1b | a bond | Me | a bond | NH | S | a bond | T3b | OH |
| 1293 | CH | NMe | Q1b | a bond | Me | a bond | NH | S | a bond | T3c | OH |
| 1294 | CH | NMe | Q1b | a bond | Me | a bond | NH | S | a bond | T3d | OH |
| 1295 | CH | NMe | Q1b | a bond | Me | a bond | NH | S | a bond | T3e | OH |
| 1296 | CH | NMe | Q1b | a bond | Me | a bond | NH | S | a bond | T3f | OH |
| 1297 | CH | NMe | Q1b | a bond | Me | a bond | NH | S | a bond | T3g | OH |
| 1298 | CH | NMe | Q1b | a bond | Me | a bond | NH | S | a bond | T3h | OH |
| 1299 | CH | NMe | Q1b | a bond | Me | a bond | NH | S | a bond | T3i | OH |
| 1300 | CH | NMe | Q1b | a bond | Me | a bond | NH | S | a bond | T3j | OH |
| 1301 | CH | NMe | Q1b | a bond | Me | a bond | NH | O | NH | T3a | OH |
| 1302 | CH | NMe | Q1b | a bond | Me | a bond | NH | O | NH | T3b | OH |
| 1303 | CH | NMe | Q1b | a bond | Me | a bond | NH | O | NH | T3c | OH |
| 1304 | CH | NMe | Q1b | a bond | Me | a bond | NH | O | NH | T3d | OH |
| 1305 | CH | NMe | Q1b | a bond | Me | a bond | NH | O | NH | T3e | OH |
| 1306 | CH | NMe | Q1b | a bond | Me | a bond | NH | O | NH | T3f | OH |
| 1307 | CH | NMe | Q1b | a bond | Me | a bond | NH | O | NH | T3g | OH |
| 1308 | CH | NMe | Q1b | a bond | Me | a bond | NH | O | NH | T3h | OH |
| 1309 | CH | NMe | Q1b | a bond | Me | a bond | NH | O | NH | T3i | OH |
| 1310 | CH | NMe | Q1b | a bond | Me | a bond | NH | O | NH | T3j | OH |
| 1311 | CH | NMe | Q1b | a bond | Me | a bond | NH | O | a bond | T3a | OH |
| 1312 | CH | NMe | Q1b | a bond | Me | a bond | NH | O | a bond | T3b | OH |
| 1313 | CH | NMe | Q1b | a bond | Me | a bond | NH | O | a bond | T3c | OH |
| 1314 | CH | NMe | Q1b | a bond | Me | a bond | NH | O | a bond | T3d | OH |
| 1315 | CH | NMe | Q1b | a bond | Me | a bond | NH | O | a bond | T3e | OH |
| 1316 | CH | NMe | Q1b | a bond | Me | a bond | NH | O | a bond | T3f | OH |
| 1317 | CH | NMe | Q1b | a bond | Me | a bond | NH | O | a bond | T3g | OH |
| 1318 | CH | NMe | Q1b | a bond | Me | a bond | NH | O | a bond | T3h | OH |
| 1319 | CH | NMe | Q1b | a bond | Me | a bond | NH | O | a bond | T3i | OH |
| 1320 | CH | NMe | Q1b | a bond | Me | a bond | NH | O | a bond | T3j | OH |
| 1321 | CH | NMe | Q1b | a bond | H | a bond | NH | S | NH | T3a | OH |
| 1322 | CH | NMe | Q1b | a bond | H | a bond | NH | S | NH | T3b | OH |
| 1323 | CH | NMe | Q1b | a bond | H | a bond | NH | S | NH | T3c | OH |
| 1324 | CH | NMe | Q1b | a bond | H | a bond | NH | S | NH | T3d | OH |
| 1325 | CH | NMe | Q1b | a bond | H | a bond | NH | S | NH | T3e | OH |
| 1326 | CH | NMe | Q1b | a bond | H | a bond | NH | S | NH | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 1327 | CH | NMe | Q1b | a bond | H | a bond | NH | S | NH | T3g | OH |
| 1328 | CH | NMe | Q1b | a bond | H | a bond | NH | S | NH | T3h | OH |
| 1329 | CH | NMe | Q1b | a bond | H | a bond | NH | S | NH | T3i | OH |
| 1330 | CH | NMe | Q1b | a bond | H | a bond | NH | S | NH | T3j | OH |
| 1331 | CH | NMe | Q1b | a bond | H | a bond | NH | S | a bond | T3a | OH |
| 1332 | CH | NMe | Q1b | a bond | H | a bond | NH | S | a bond | T3b | OH |
| 1333 | CH | NMe | Q1b | a bond | H | a bond | NH | S | a bond | T3c | OH |
| 1334 | CH | NMe | Q1b | a bond | H | a bond | NH | S | a bond | T3d | OH |
| 1335 | CH | NMe | Q1b | a bond | H | a bond | NH | S | a bond | T3e | OH |
| 1336 | CH | NMe | Q1b | a bond | H | a bond | NH | S | a bond | T3f | OH |
| 1337 | CH | NMe | Q1b | a bond | H | a bond | NH | S | a bond | T3g | OH |
| 1338 | CH | NMe | Q1b | a bond | H | a bond | NH | S | a bond | T3h | OH |
| 1339 | CH | NMe | Q1b | a bond | H | a bond | NH | S | a bond | T3i | OH |
| 1340 | CH | NMe | Q1b | a bond | H | a bond | NH | S | a bond | T3j | OH |
| 1341 | CH | NMe | Q1b | a bond | H | a bond | NH | O | NH | T3a | OH |
| 1342 | CH | NMe | Q1b | a bond | H | a bond | NH | O | NH | T3b | OH |
| 1343 | CH | NMe | Q1b | a bond | H | a bond | NH | O | NH | T3c | OH |
| 1344 | CH | NMe | Q1b | a bond | H | a bond | NH | O | NH | T3d | OH |
| 1345 | CH | NMe | Q1b | a bond | H | a bond | NH | O | NH | T3e | OH |
| 1346 | CH | NMe | Q1b | a bond | H | a bond | NH | O | NH | T3f | OH |
| 1347 | CH | NMe | Q1b | a bond | H | a bond | NH | O | NH | T3g | OH |
| 1348 | CH | NMe | Q1b | a bond | H | a bond | NH | O | NH | T3h | OH |
| 1349 | CH | NMe | Q1b | a bond | H | a bond | NH | O | NH | T3i | OH |
| 1350 | CH | NMe | Q1b | a bond | H | a bond | NH | O | NH | T3j | OH |
| 1351 | CH | NMe | Q1b | a bond | H | a bond | NH | O | a bond | T3a | OH |
| 1352 | CH | NMe | Q1b | a bond | H | a bond | NH | O | a bond | T3b | OH |
| 1353 | CH | NMe | Q1b | a bond | H | a bond | NH | O | a bond | T3c | OH |
| 1354 | CH | NMe | Q1b | a bond | H | a bond | NH | O | a bond | T3d | OH |
| 1355 | CH | NMe | Q1b | a bond | H | a bond | NH | O | a bond | T3e | OH |
| 1356 | CH | NMe | Q1b | a bond | H | a bond | NH | O | a bond | T3f | OH |
| 1357 | CH | NMe | Q1b | a bond | H | a bond | NH | O | a bond | T3g | OH |
| 1358 | CH | NMe | Q1b | a bond | H | a bond | NH | O | a bond | T3h | OH |
| 1359 | CH | NMe | Q1b | a bond | H | a bond | NH | O | a bond | T3i | OH |
| 1360 | CH | NMe | Q1b | a bond | H | a bond | NH | O | a bond | T3j | OH |
| 1361 | CH | NMe | Q1c | a bond | Me | a bond | NH | S | NH | T3a | OH |
| 1362 | CH | NMe | Q1c | a bond | Me | a bond | NH | S | NH | T3b | OH |
| 1363 | CH | NMe | Q1c | a bond | Me | a bond | NH | S | NH | T3c | OH |
| 1364 | CH | NMe | Q1c | a bond | Me | a bond | NH | S | NH | T3d | OH |
| 1365 | CH | NMe | Q1c | a bond | Me | a bond | NH | S | NH | T3e | OH |
| 1366 | CH | NMe | Q1c | a bond | Me | a bond | NH | S | NH | T3f | OH |
| 1367 | CH | NMe | Q1c | a bond | Me | a bond | NH | S | NH | T3g | OH |
| 1368 | CH | NMe | Q1c | a bond | Me | a bond | NH | S | NH | T3h | OH |
| 1369 | CH | NMe | Q1c | a bond | Me | a bond | NH | S | NH | T3i | OH |
| 1370 | CH | NMe | Q1c | a bond | Me | a bond | NH | S | NH | T3j | OH |
| 1371 | CH | NMe | Q1c | a bond | Me | a bond | NH | S | a bond | T3a | OH |
| 1372 | CH | NMe | Q1c | a bond | Me | a bond | NH | S | a bond | T3b | OH |
| 1373 | CH | NMe | Q1c | a bond | Me | a bond | NH | S | a bond | T3c | OH |
| 1374 | CH | NMe | Q1c | a bond | Me | a bond | NH | S | a bond | T3d | OH |
| 1375 | CH | NMe | Q1c | a bond | Me | a bond | NH | S | a bond | T3e | OH |
| 1376 | CH | NMe | Q1c | a bond | Me | a bond | NH | S | a bond | T3f | OH |
| 1377 | CH | NMe | Q1c | a bond | Me | a bond | NH | S | a bond | T3g | OH |
| 1378 | CH | NMe | Q1c | a bond | Me | a bond | NH | S | a bond | T3h | OH |
| 1379 | CH | NMe | Q1c | a bond | Me | a bond | NH | S | a bond | T3i | OH |
| 1380 | CH | NMe | Q1c | a bond | Me | a bond | NH | S | a bond | T3j | OH |
| 1381 | CH | NMe | Q1c | a bond | Me | a bond | NH | O | NH | T3a | OH |
| 1382 | CH | NMe | Q1c | a bond | Me | a bond | NH | O | NH | T3b | OH |
| 1383 | CH | NMe | Q1c | a bond | Me | a bond | NH | O | NH | T3c | OH |
| 1384 | CH | NMe | Q1c | a bond | Me | a bond | NH | O | NH | T3d | OH |
| 1385 | CH | NMe | Q1c | a bond | Me | a bond | NH | O | NH | T3e | OH |
| 1386 | CH | NMe | Q1c | a bond | Me | a bond | NH | O | NH | T3f | OH |
| 1387 | CH | NMe | Q1c | a bond | Me | a bond | NH | O | NH | T3g | OH |
| 1388 | CH | NMe | Q1c | a bond | Me | a bond | NH | O | NH | T3h | OH |
| 1389 | CH | NMe | Q1c | a bond | Me | a bond | NH | O | NH | T3i | OH |
| 1390 | CH | NMe | Q1c | a bond | Me | a bond | NH | O | NH | T3j | OH |
| 1391 | CH | NMe | Q1c | a bond | Me | a bond | NH | O | a bond | T3a | OH |
| 1392 | CH | NMe | Q1c | a bond | Me | a bond | NH | O | a bond | T3b | OH |
| 1393 | CH | NMe | Q1c | a bond | Me | a bond | NH | O | a bond | T3c | OH |
| 1394 | CH | NMe | Q1c | a bond | Me | a bond | NH | O | a bond | T3d | OH |
| 1395 | CH | NMe | Q1c | a bond | Me | a bond | NH | O | a bond | T3e | OH |
| 1396 | CH | NMe | Q1c | a bond | Me | a bond | NH | O | a bond | T3f | OH |
| 1397 | CH | NMe | Q1c | a bond | Me | a bond | NH | O | a bond | T3g | OH |
| 1398 | CH | NMe | Q1c | a bond | Me | a bond | NH | O | a bond | T3h | OH |
| 1399 | CH | NMe | Q1c | a bond | Me | a bond | NH | O | a bond | T3i | OH |
| 1400 | CH | NMe | Q1c | a bond | Me | a bond | NH | O | a bond | T3j | OH |
| 1401 | CH | NMe | Q1c | a bond | H | a bond | NH | S | NH | T3a | OH |
| 1402 | CH | NMe | Q1c | a bond | H | a bond | NH | S | NH | T3b | OH |
| 1403 | CH | NMe | Q1c | a bond | H | a bond | NH | S | NH | T3c | OH |
| 1404 | CH | NMe | Q1c | a bond | H | a bond | NH | S | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 1405 | CH | NMe | Q1c | a bond | H | a bond | NH | S | NH | T3e | OH |
| 1406 | CH | NMe | Q1c | a bond | H | a bond | NH | S | NH | T3f | OH |
| 1407 | CH | NMe | Q1c | a bond | H | a bond | NH | S | NH | T3g | OH |
| 1408 | CH | NMe | Q1c | a bond | H | a bond | NH | S | NH | T3h | OH |
| 1409 | CH | NMe | Q1c | a bond | H | a bond | NH | S | NH | T3i | OH |
| 1410 | CH | NMe | Q1c | a bond | H | a bond | NH | S | NH | T3j | OH |
| 1411 | CH | NMe | Q1c | a bond | H | a bond | NH | S | a bond | T3a | OH |
| 1412 | CH | NMe | Q1c | a bond | H | a bond | NH | S | a bond | T3b | OH |
| 1413 | CH | NMe | Q1c | a bond | H | a bond | NH | S | a bond | T3c | OH |
| 1414 | CH | NMe | Q1c | a bond | H | a bond | NH | S | a bond | T3d | OH |
| 1415 | CH | NMe | Q1c | a bond | H | a bond | NH | S | a bond | T3e | OH |
| 1416 | CH | NMe | Q1c | a bond | H | a bond | NH | S | a bond | T3f | OH |
| 1417 | CH | NMe | Q1c | a bond | H | a bond | NH | S | a bond | T3g | OH |
| 1418 | CH | NMe | Q1c | a bond | H | a bond | NH | S | a bond | T3h | OH |
| 1419 | CH | NMe | Q1c | a bond | H | a bond | NH | S | a bond | T3i | OH |
| 1420 | CH | NMe | Q1c | a bond | H | a bond | NH | S | a bond | T3j | OH |
| 1421 | CH | NMe | Q1c | a bond | H | a bond | NH | O | NH | T3a | OH |
| 1422 | CH | NMe | Q1c | a bond | H | a bond | NH | O | NH | T3b | OH |
| 1423 | CH | NMe | Q1c | a bond | H | a bond | NH | O | NH | T3c | OH |
| 1424 | CH | NMe | Q1c | a bond | H | a bond | NH | O | NH | T3d | OH |
| 1425 | CH | NMe | Q1c | a bond | H | a bond | NH | O | NH | T3e | OH |
| 1426 | CH | NMe | Q1c | a bond | H | a bond | NH | O | NH | T3f | OH |
| 1427 | CH | NMe | Q1c | a bond | H | a bond | NH | O | NH | T3g | OH |
| 1428 | CH | NMe | Q1c | a bond | H | a bond | NH | O | NH | T3h | OH |
| 1429 | CH | NMe | Q1c | a bond | H | a bond | NH | O | NH | T3i | OH |
| 1430 | CH | NMe | Q1c | a bond | H | a bond | NH | O | NH | T3j | OH |
| 1431 | CH | NMe | Q1c | a bond | H | a bond | NH | O | a bond | T3a | OH |
| 1432 | CH | NMe | Q1c | a bond | H | a bond | NH | O | a bond | T3b | OH |
| 1433 | CH | NMe | Q1c | a bond | H | a bond | NH | O | a bond | T3c | OH |
| 1434 | CH | NMe | Q1c | a bond | H | a bond | NH | O | a bond | T3d | OH |
| 1435 | CH | NMe | Q1c | a bond | H | a bond | NH | O | a bond | T3e | OH |
| 1436 | CH | NMe | Q1c | a bond | H | a bond | NH | O | a bond | T3f | OH |
| 1437 | CH | NMe | Q1c | a bond | H | a bond | NH | O | a bond | T3g | OH |
| 1438 | CH | NMe | Q1c | a bond | H | a bond | NH | O | a bond | T3h | OH |
| 1439 | CH | NMe | Q1c | a bond | H | a bond | NH | O | a bond | T3i | OH |
| 1440 | CH | NMe | Q1c | a bond | H | a bond | NH | O | a bond | T3j | OH |
| 1441 | CH | NMe | Q1i | a bond | Me | a bond | NH | S | NH | T3a | OH |
| 1442 | CH | NMe | Q1i | a bond | Me | a bond | NH | S | NH | T3b | OH |
| 1443 | CH | NMe | Q1i | a bond | Me | a bond | NH | S | NH | T3c | OH |
| 1444 | CH | NMe | Q1i | a bond | Me | a bond | NH | S | NH | T3d | OH |
| 1445 | CH | NMe | Q1i | a bond | Me | a bond | NH | S | NH | T3e | OH |
| 1446 | CH | NMe | Q1i | a bond | Me | a bond | NH | S | NH | T3f | OH |
| 1447 | CH | NMe | Q1i | a bond | Me | a bond | NH | S | NH | T3g | OH |
| 1448 | CH | NMe | Q1i | a bond | Me | a bond | NH | S | NH | T3h | OH |
| 1449 | CH | NMe | Q1i | a bond | Me | a bond | NH | S | NH | T3i | OH |
| 1450 | CH | NMe | Q1i | a bond | Me | a bond | NH | S | NH | T3j | OH |
| 1451 | CH | NMe | Q1i | a bond | Me | a bond | NH | S | a bond | T3a | OH |
| 1452 | CH | NMe | Q1i | a bond | Me | a bond | NH | S | a bond | T3b | OH |
| 1453 | CH | NMe | Q1i | a bond | Me | a bond | NH | S | a bond | T3c | OH |
| 1454 | CH | NMe | Q1i | a bond | Me | a bond | NH | S | a bond | T3d | OH |
| 1455 | CH | NMe | Q1i | a bond | Me | a bond | NH | S | a bond | T3e | OH |
| 1456 | CH | NMe | Q1i | a bond | Me | a bond | NH | S | a bond | T3f | OH |
| 1457 | CH | NMe | Q1i | a bond | Me | a bond | NH | S | a bond | T3g | OH |
| 1458 | CH | NMe | Q1i | a bond | Me | a bond | NH | S | a bond | T3h | OH |
| 1459 | CH | NMe | Q1i | a bond | Me | a bond | NH | S | a bond | T3i | OH |
| 1460 | CH | NMe | Q1i | a bond | Me | a bond | NH | S | a bond | T3j | OH |
| 1461 | CH | NMe | Q1i | a bond | Me | a bond | NH | O | NH | T3a | OH |
| 1462 | CH | NMe | Q1i | a bond | Me | a bond | NH | O | NH | T3b | OH |
| 1463 | CH | NMe | Q1i | a bond | Me | a bond | NH | O | NH | T3c | OH |
| 1464 | CH | NMe | Q1i | a bond | Me | a bond | NH | O | NH | T3d | OH |
| 1465 | CH | NMe | Q1i | a bond | Me | a bond | NH | O | NH | T3e | OH |
| 1466 | CH | NMe | Q1i | a bond | Me | a bond | NH | O | NH | T3f | OH |
| 1467 | CH | NMe | Q1i | a bond | Me | a bond | NH | O | NH | T3g | OH |
| 1468 | CH | NMe | Q1i | a bond | Me | a bond | NH | O | NH | T3h | OH |
| 1469 | CH | NMe | Q1i | a bond | Me | a bond | NH | O | NH | T3i | OH |
| 1470 | CH | NMe | Q1i | a bond | Me | a bond | NH | O | NH | T3j | OH |
| 1471 | CH | NMe | Q1i | a bond | Me | a bond | NH | O | a bond | T3a | OH |
| 1472 | CH | NMe | Q1i | a bond | Me | a bond | NH | O | a bond | T3b | OH |
| 1473 | CH | NMe | Q1i | a bond | Me | a bond | NH | O | a bond | T3c | OH |
| 1474 | CH | NMe | Q1i | a bond | Me | a bond | NH | O | a bond | T3d | OH |
| 1475 | CH | NMe | Q1i | a bond | Me | a bond | NH | O | a bond | T3e | OH |
| 1476 | CH | NMe | Q1i | a bond | Me | a bond | NH | O | a bond | T3f | OH |
| 1477 | CH | NMe | Q1i | a bond | Me | a bond | NH | O | a bond | T3g | OH |
| 1478 | CH | NMe | Q1i | a bond | Me | a bond | NH | O | a bond | T3h | OH |
| 1479 | CH | NMe | Q1i | a bond | Me | a bond | NH | O | a bond | T3i | OH |
| 1480 | CH | NMe | Q1i | a bond | Me | a bond | NH | O | a bond | T3j | OH |
| 1481 | CH | NMe | Q1i | a bond | H | a bond | NH | S | NH | T3a | OH |
| 1482 | CH | NMe | Q1i | a bond | H | a bond | NH | S | NH | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 1483 | CH | NMe | Q1i | a bond | H | a bond | NH | S | NH | T3c | OH |
| 1484 | CH | NMe | Q1i | a bond | H | a bond | NH | S | NH | T3d | OH |
| 1485 | CH | NMe | Q1i | a bond | H | a bond | NH | S | NH | T3e | OH |
| 1486 | CH | NMe | Q1i | a bond | H | a bond | NH | S | NH | T3f | OH |
| 1487 | CH | NMe | Q1i | a bond | H | a bond | NH | S | NH | T3g | OH |
| 1488 | CH | NMe | Q1i | a bond | H | a bond | NH | S | NH | T3h | OH |
| 1489 | CH | NMe | Q1i | a bond | H | a bond | NH | S | NH | T3i | OH |
| 1490 | CH | NMe | Q1i | a bond | H | a bond | NH | S | NH | T3j | OH |
| 1491 | CH | NMe | Q1i | a bond | H | a bond | NH | S | a bond | T3a | OH |
| 1492 | CH | NMe | Q1i | a bond | H | a bond | NH | S | a bond | T3b | OH |
| 1493 | CH | NMe | Q1i | a bond | H | a bond | NH | S | a bond | T3c | OH |
| 1494 | CH | NMe | Q1i | a bond | H | a bond | NH | S | a bond | T3d | OH |
| 1495 | CH | NMe | Q1i | a bond | H | a bond | NH | S | a bond | T3e | OH |
| 1496 | CH | NMe | Q1i | a bond | H | a bond | NH | S | a bond | T3f | OH |
| 1497 | CH | NMe | Q1i | a bond | H | a bond | NH | S | a bond | T3g | OH |
| 1498 | CH | NMe | Q1i | a bond | H | a bond | NH | S | a bond | T3h | OH |
| 1499 | CH | NMe | Q1i | a bond | H | a bond | NH | S | a bond | T3i | OH |
| 1500 | CH | NMe | Q1i | a bond | H | a bond | NH | S | a bond | T3j | OH |
| 1501 | CH | NMe | Q1i | a bond | H | a bond | NH | O | NH | T3a | OH |
| 1502 | CH | NMe | Q1i | a bond | H | a bond | NH | O | NH | T3b | OH |
| 1503 | CH | NMe | Q1i | a bond | H | a bond | NH | O | NH | T3c | OH |
| 1504 | CH | NMe | Q1i | a bond | H | a bond | NH | O | NH | T3d | OH |
| 1505 | CH | NMe | Q1i | a bond | H | a bond | NH | O | NH | T3e | OH |
| 1506 | CH | NMe | Q1i | a bond | H | a bond | NH | O | NH | T3f | OH |
| 1507 | CH | NMe | Q1i | a bond | H | a bond | NH | O | NH | T3g | OH |
| 1508 | CH | NMe | Q1i | a bond | H | a bond | NH | O | NH | T3h | OH |
| 1509 | CH | NMe | Q1i | a bond | H | a bond | NH | O | NH | T3i | OH |
| 1510 | CH | NMe | Q1i | a bond | H | a bond | NH | O | NH | T3j | OH |
| 1511 | CH | NMe | Q1i | a bond | H | a bond | NH | O | a bond | T3a | OH |
| 1512 | CH | NMe | Q1i | a bond | H | a bond | NH | O | a bond | T3b | OH |
| 1513 | CH | NMe | Q1i | a bond | H | a bond | NH | O | a bond | T3c | OH |
| 1514 | CH | NMe | Q1i | a bond | H | a bond | NH | O | a bond | T3d | OH |
| 1515 | CH | NMe | Q1i | a bond | H | a bond | NH | O | a bond | T3e | OH |
| 1516 | CH | NMe | Q1i | a bond | H | a bond | NH | O | a bond | T3f | OH |
| 1517 | CH | NMe | Q1i | a bond | H | a bond | NH | O | a bond | T3g | OH |
| 1518 | CH | NMe | Q1i | a bond | H | a bond | NH | O | a bond | T3h | OH |
| 1519 | CH | NMe | Q1i | a bond | H | a bond | NH | O | a bond | T3i | OH |
| 1520 | CH | NMe | Q1i | a bond | H | a bond | NH | O | a bond | T3j | OH |
| 1521 | CH | NMe | Q1j | a bond | Me | a bond | NH | S | NH | T3a | OH |
| 1522 | CH | NMe | Q1j | a bond | Me | a bond | NH | S | NH | T3b | OH |
| 1523 | CH | NMe | Q1j | a bond | Me | a bond | NH | S | NH | T3c | OH |
| 1524 | CH | NMe | Q1j | a bond | Me | a bond | NH | S | NH | T3d | OH |
| 1525 | CH | NMe | Q1j | a bond | Me | a bond | NH | S | NH | T3e | OH |
| 1526 | CH | NMe | Q1j | a bond | Me | a bond | NH | S | NH | T3f | OH |
| 1527 | CH | NMe | Q1j | a bond | Me | a bond | NH | S | NH | T3g | OH |
| 1528 | CH | NMe | Q1j | a bond | Me | a bond | NH | S | NH | T3h | OH |
| 1529 | CH | NMe | Q1j | a bond | Me | a bond | NH | S | NH | T3i | OH |
| 1530 | CH | NMe | Q1j | a bond | Me | a bond | NH | S | NH | T3j | OH |
| 1531 | CH | NMe | Q1j | a bond | Me | a bond | NH | S | a bond | T3a | OH |
| 1532 | CH | NMe | Q1j | a bond | Me | a bond | NH | S | a bond | T3b | OH |
| 1533 | CH | NMe | Q1j | a bond | Me | a bond | NH | S | a bond | T3c | OH |
| 1534 | CH | NMe | Q1j | a bond | Me | a bond | NH | S | a bond | T3d | OH |
| 1535 | CH | NMe | Q1j | a bond | Me | a bond | NH | S | a bond | T3e | OH |
| 1536 | CH | NMe | Q1j | a bond | Me | a bond | NH | S | a bond | T3f | OH |
| 1537 | CH | NMe | Q1j | a bond | Me | a bond | NH | S | a bond | T3g | OH |
| 1538 | CH | NMe | Q1j | a bond | Me | a bond | NH | S | a bond | T3h | OH |
| 1539 | CH | NMe | Q1j | a bond | Me | a bond | NH | S | a bond | T3i | OH |
| 1540 | CH | NMe | Q1j | a bond | Me | a bond | NH | S | a bond | T3j | OH |
| 1541 | CH | NMe | Q1j | a bond | Me | a bond | NH | O | NH | T3a | OH |
| 1542 | CH | NMe | Q1j | a bond | Me | a bond | NH | O | NH | T3b | OH |
| 1543 | CH | NMe | Q1j | a bond | Me | a bond | NH | O | NH | T3c | OH |
| 1544 | CH | NMe | Q1j | a bond | Me | a bond | NH | O | NH | T3d | OH |
| 1545 | CH | NMe | Q1j | a bond | Me | a bond | NH | O | NH | T3e | OH |
| 1546 | CH | NMe | Q1j | a bond | Me | a bond | NH | O | NH | T3f | OH |
| 1547 | CH | NMe | Q1j | a bond | Me | a bond | NH | O | NH | T3g | OH |
| 1548 | CH | NMe | Q1j | a bond | Me | a bond | NH | O | NH | T3h | OH |
| 1549 | CH | NMe | Q1j | a bond | Me | a bond | NH | O | NH | T3i | OH |
| 1550 | CH | NMe | Q1j | a bond | Me | a bond | NH | O | NH | T3j | OH |
| 1551 | CH | NMe | Q1j | a bond | Me | a bond | NH | O | a bond | T3a | OH |
| 1552 | CH | NMe | Q1j | a bond | Me | a bond | NH | O | a bond | T3b | OH |
| 1553 | CH | NMe | Q1j | a bond | Me | a bond | NH | O | a bond | T3c | OH |
| 1554 | CH | NMe | Q1j | a bond | Me | a bond | NH | O | a bond | T3d | OH |
| 1555 | CH | NMe | Q1j | a bond | Me | a bond | NH | O | a bond | T3e | OH |
| 1556 | CH | NMe | Q1j | a bond | Me | a bond | NH | O | a bond | T3f | OH |
| 1557 | CH | NMe | Q1j | a bond | Me | a bond | NH | O | a bond | T3g | OH |
| 1558 | CH | NMe | Q1j | a bond | Me | a bond | NH | O | a bond | T3h | OH |
| 1559 | CH | NMe | Q1j | a bond | Me | a bond | NH | O | a bond | T3i | OH |
| 1560 | CH | NMe | Q1j | a bond | Me | a bond | NH | O | a bond | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 1561 | CH | NMe | Q1j | a bond | H | a bond | NH | S | NH | T3a | OH |
| 1562 | CH | NMe | Q1j | a bond | H | a bond | NH | S | NH | T3b | OH |
| 1563 | CH | NMe | Q1j | a bond | H | a bond | NH | S | NH | T3c | OH |
| 1564 | CH | NMe | Q1j | a bond | H | a bond | NH | S | NH | T3d | OH |
| 1565 | CH | NMe | Q1j | a bond | H | a bond | NH | S | NH | T3e | OH |
| 1566 | CH | NMe | Q1j | a bond | H | a bond | NH | S | NH | T3f | OH |
| 1567 | CH | NMe | Q1j | a bond | H | a bond | NH | S | NH | T3g | OH |
| 1568 | CH | NMe | Q1j | a bond | H | a bond | NH | S | NH | T3h | OH |
| 1569 | CH | NMe | Q1j | a bond | H | a bond | NH | S | NH | T3i | OH |
| 1570 | CH | NMe | Q1j | a bond | H | a bond | NH | S | NH | T3j | OH |
| 1571 | CH | NMe | Q1j | a bond | H | a bond | NH | S | a bond | T3a | OH |
| 1572 | CH | NMe | Q1j | a bond | H | a bond | NH | S | a bond | T3b | OH |
| 1573 | CH | NMe | Q1j | a bond | H | a bond | NH | S | a bond | T3c | OH |
| 1574 | CH | NMe | Q1j | a bond | H | a bond | NH | S | a bond | T3d | OH |
| 1575 | CH | NMe | Q1j | a bond | H | a bond | NH | S | a bond | T3e | OH |
| 1576 | CH | NMe | Q1j | a bond | H | a bond | NH | S | a bond | T3f | OH |
| 1577 | CH | NMe | Q1j | a bond | H | a bond | NH | S | a bond | T3g | OH |
| 1578 | CH | NMe | Q1j | a bond | H | a bond | NH | S | a bond | T3h | OH |
| 1579 | CH | NMe | Q1j | a bond | H | a bond | NH | S | a bond | T3i | OH |
| 1580 | CH | NMe | Q1j | a bond | H | a bond | NH | S | a bond | T3j | OH |
| 1581 | CH | NMe | Q1j | a bond | H | a bond | NH | O | NH | T3a | OH |
| 1582 | CH | NMe | Q1j | a bond | H | a bond | NH | O | NH | T3b | OH |
| 1583 | CH | NMe | Q1j | a bond | H | a bond | NH | O | NH | T3c | OH |
| 1584 | CH | NMe | Q1j | a bond | H | a bond | NH | O | NH | T3d | OH |
| 1585 | CH | NMe | Q1j | a bond | H | a bond | NH | O | NH | T3e | OH |
| 1586 | CH | NMe | Q1j | a bond | H | a bond | NH | O | NH | T3f | OH |
| 1587 | CH | NMe | Q1j | a bond | H | a bond | NH | O | NH | T3g | OH |
| 1588 | CH | NMe | Q1j | a bond | H | a bond | NH | O | NH | T3h | OH |
| 1589 | CH | NMe | Q1j | a bond | H | a bond | NH | O | NH | T3i | OH |
| 1590 | CH | NMe | Q1j | a bond | H | a bond | NH | O | NH | T3j | OH |
| 1591 | CH | NMe | Q1j | a bond | H | a bond | NH | O | a bond | T3a | OH |
| 1592 | CH | NMe | Q1j | a bond | H | a bond | NH | O | a bond | T3b | OH |
| 1593 | CH | NMe | Q1j | a bond | H | a bond | NH | O | a bond | T3c | OH |
| 1594 | CH | NMe | Q1j | a bond | H | a bond | NH | O | a bond | T3d | OH |
| 1595 | CH | NMe | Q1j | a bond | H | a bond | NH | O | a bond | T3e | OH |
| 1596 | CH | NMe | Q1j | a bond | H | a bond | NH | O | a bond | T3f | OH |
| 1597 | CH | NMe | Q1j | a bond | H | a bond | NH | O | a bond | T3g | OH |
| 1598 | CH | NMe | Q1j | a bond | H | a bond | NH | O | a bond | T3h | OH |
| 1599 | CH | NMe | Q1j | a bond | H | a bond | NH | O | a bond | T3i | OH |
| 1600 | CH | NMe | Q1j | a bond | H | a bond | NH | O | a bond | T3j | OH |
| 1601 | CH | S | Q1a | a bond | Me | a bond | NH | S | NH | T3a | OH |
| 1602 | CH | S | Q1a | a bond | Me | a bond | NH | S | NH | T3b | OH |
| 1603 | CH | S | Q1a | a bond | Me | a bond | NH | S | NH | T3c | OH |
| 1604 | CH | S | Q1a | a bond | Me | a bond | NH | S | NH | T3d | OH |
| 1605 | CH | S | Q1a | a bond | Me | a bond | NH | S | NH | T3e | OH |
| 1606 | CH | S | Q1a | a bond | Me | a bond | NH | S | NH | T3f | OH |
| 1607 | CH | S | Q1a | a bond | Me | a bond | NH | S | NH | T3g | OH |
| 1608 | CH | S | Q1a | a bond | Me | a bond | NH | S | NH | T3h | OH |
| 1609 | CH | S | Q1a | a bond | Me | a bond | NH | S | NH | T3i | OH |
| 1610 | CH | S | Q1a | a bond | Me | a bond | NH | S | NH | T3j | OH |
| 1611 | CH | S | Q1a | a bond | Me | a bond | NH | S | a bond | T3a | OH |
| 1612 | CH | S | Q1a | a bond | Me | a bond | NH | S | a bond | T3b | OH |
| 1613 | CH | S | Q1a | a bond | Me | a bond | NH | S | a bond | T3c | OH |
| 1614 | CH | S | Q1a | a bond | Me | a bond | NH | S | a bond | T3d | OH |
| 1615 | CH | S | Q1a | a bond | Me | a bond | NH | S | a bond | T3e | OH |
| 1616 | CH | S | Q1a | a bond | Me | a bond | NH | S | a bond | T3f | OH |
| 1617 | CH | S | Q1a | a bond | Me | a bond | NH | S | a bond | T3g | OH |
| 1618 | CH | S | Q1a | a bond | Me | a bond | NH | S | a bond | T3h | OH |
| 1619 | CH | S | Q1a | a bond | Me | a bond | NH | S | a bond | T3i | OH |
| 1620 | CH | S | Q1a | a bond | Me | a bond | NH | S | a bond | T3j | OH |
| 1621 | CH | S | Q1a | a bond | Me | a bond | NH | O | NH | T3a | OH |
| 1622 | CH | S | Q1a | a bond | Me | a bond | NH | O | NH | T3b | OH |
| 1623 | CH | S | Q1a | a bond | Me | a bond | NH | O | NH | T3c | OH |
| 1624 | CH | S | Q1a | a bond | Me | a bond | NH | O | NH | T3d | OH |
| 1625 | CH | S | Q1a | a bond | Me | a bond | NH | O | NH | T3e | OH |
| 1626 | CH | S | Q1a | a bond | Me | a bond | NH | O | NH | T3f | OH |
| 1627 | CH | S | Q1a | a bond | Me | a bond | NH | O | NH | T3g | OH |
| 1628 | CH | S | Q1a | a bond | Me | a bond | NH | O | NH | T3h | OH |
| 1629 | CH | S | Q1a | a bond | Me | a bond | NH | O | NH | T3i | OH |
| 1630 | CH | S | Q1a | a bond | Me | a bond | NH | O | NH | T3j | OH |
| 1631 | CH | S | Q1a | a bond | Me | a bond | NH | O | a bond | T3a | OH |
| 1632 | CH | S | Q1a | a bond | Me | a bond | NH | O | a bond | T3b | OH |
| 1633 | CH | S | Q1a | a bond | Me | a bond | NH | O | a bond | T3c | OH |
| 1634 | CH | S | Q1a | a bond | Me | a bond | NH | O | a bond | T3d | OH |
| 1635 | CH | S | Q1a | a bond | Me | a bond | NH | O | a bond | T3e | OH |
| 1636 | CH | S | Q1a | a bond | Me | a bond | NH | O | a bond | T3f | OH |
| 1637 | CH | S | Q1a | a bond | Me | a bond | NH | O | a bond | T3g | OH |
| 1638 | CH | S | Q1a | a bond | Me | a bond | NH | O | a bond | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 1639 | CH | S | Q1a | a bond | Me | a bond | NH | O | a bond | T3i | OH |
| 1640 | CH | S | Q1a | a bond | Me | a bond | NH | O | a bond | T3j | OH |
| 1641 | CH | S | Q1a | a bond | H | a bond | NH | S | NH | T3a | OH |
| 1642 | CH | S | Q1a | a bond | H | a bond | NH | S | NH | T3b | OH |
| 1643 | CH | S | Q1a | a bond | H | a bond | NH | S | NH | T3c | OH |
| 1644 | CH | S | Q1a | a bond | H | a bond | NH | S | NH | T3d | OH |
| 1645 | CH | S | Q1a | a bond | H | a bond | NH | S | NH | T3e | OH |
| 1646 | CH | S | Q1a | a bond | H | a bond | NH | S | NH | T3f | OH |
| 1647 | CH | S | Q1a | a bond | H | a bond | NH | S | NH | T3g | OH |
| 1648 | CH | S | Q1a | a bond | H | a bond | NH | S | NH | T3h | OH |
| 1649 | CH | S | Q1a | a bond | H | a bond | NH | S | NH | T3i | OH |
| 1650 | CH | S | Q1a | a bond | H | a bond | NH | S | NH | T3j | OH |
| 1651 | CH | S | Q1a | a bond | H | a bond | NH | S | a bond | T3a | OH |
| 1652 | CH | S | Q1a | a bond | H | a bond | NH | S | a bond | T3b | OH |
| 1653 | CH | S | Q1a | a bond | H | a bond | NH | S | a bond | T3c | OH |
| 1654 | CH | S | Q1a | a bond | H | a bond | NH | S | a bond | T3d | OH |
| 1655 | CH | S | Q1a | a bond | H | a bond | NH | S | a bond | T3e | OH |
| 1656 | CH | S | Q1a | a bond | H | a bond | NH | S | a bond | T3f | OH |
| 1657 | CH | S | Q1a | a bond | H | a bond | NH | S | a bond | T3g | OH |
| 1658 | CH | S | Q1a | a bond | H | a bond | NH | S | a bond | T3h | OH |
| 1659 | CH | S | Q1a | a bond | H | a bond | NH | S | a bond | T3i | OH |
| 1660 | CH | S | Q1a | a bond | H | a bond | NH | S | a bond | T3j | OH |
| 1661 | CH | S | Q1a | a bond | H | a bond | NH | O | NH | T3a | OH |
| 1662 | CH | S | Q1a | a bond | H | a bond | NH | O | NH | T3b | OH |
| 1663 | CH | S | Q1a | a bond | H | a bond | NH | O | NH | T3c | OH |
| 1664 | CH | S | Q1a | a bond | H | a bond | NH | O | NH | T3d | OH |
| 1665 | CH | S | Q1a | a bond | H | a bond | NH | O | NH | T3e | OH |
| 1666 | CH | S | Q1a | a bond | H | a bond | NH | O | NH | T3f | OH |
| 1667 | CH | S | Q1a | a bond | H | a bond | NH | O | NH | T3g | OH |
| 1668 | CH | S | Q1a | a bond | H | a bond | NH | O | NH | T3h | OH |
| 1669 | CH | S | Q1a | a bond | H | a bond | NH | O | NH | T3i | OH |
| 1670 | CH | S | Q1a | a bond | H | a bond | NH | O | NH | T3j | OH |
| 1671 | CH | S | Q1a | a bond | H | a bond | NH | O | a bond | T3a | OH |
| 1672 | CH | S | Q1a | a bond | H | a bond | NH | O | a bond | T3b | OH |
| 1673 | CH | S | Q1a | a bond | H | a bond | NH | O | a bond | T3c | OH |
| 1674 | CH | S | Q1a | a bond | H | a bond | NH | O | a bond | T3d | OH |
| 1675 | CH | S | Q1a | a bond | H | a bond | NH | O | a bond | T3e | OH |
| 1676 | CH | S | Q1a | a bond | H | a bond | NH | O | a bond | T3f | OH |
| 1677 | CH | S | Q1a | a bond | H | a bond | NH | O | a bond | T3g | OH |
| 1678 | CH | S | Q1a | a bond | H | a bond | NH | O | a bond | T3h | OH |
| 1679 | CH | S | Q1a | a bond | H | a bond | NH | O | a bond | T3i | OH |
| 1680 | CH | S | Q1a | a bond | H | a bond | NH | O | a bond | T3j | OH |
| 1681 | CH | S | Q1b | a bond | Me | a bond | NH | S | NH | T3a | OH |
| 1682 | CH | S | Q1b | a bond | Me | a bond | NH | S | NH | T3b | OH |
| 1683 | CH | S | Q1b | a bond | Me | a bond | NH | S | NH | T3c | OH |
| 1684 | CH | S | Q1b | a bond | Me | a bond | NH | S | NH | T3d | OH |
| 1685 | CH | S | Q1b | a bond | Me | a bond | NH | S | NH | T3e | OH |
| 1686 | CH | S | Q1b | a bond | Me | a bond | NH | S | NH | T3f | OH |
| 1687 | CH | S | Q1b | a bond | Me | a bond | NH | S | NH | T3g | OH |
| 1688 | CH | S | Q1b | a bond | Me | a bond | NH | S | NH | T3h | OH |
| 1689 | CH | S | Q1b | a bond | Me | a bond | NH | S | NH | T3i | OH |
| 1690 | CH | S | Q1b | a bond | Me | a bond | NH | S | NH | T3j | OH |
| 1691 | CH | S | Q1b | a bond | Me | a bond | NH | S | a bond | T3a | OH |
| 1692 | CH | S | Q1b | a bond | Me | a bond | NH | S | a bond | T3b | OH |
| 1693 | CH | S | Q1b | a bond | Me | a bond | NH | S | a bond | T3c | OH |
| 1694 | CH | S | Q1b | a bond | Me | a bond | NH | S | a bond | T3d | OH |
| 1695 | CH | S | Q1b | a bond | Me | a bond | NH | S | a bond | T3e | OH |
| 1696 | CH | S | Q1b | a bond | Me | a bond | NH | S | a bond | T3f | OH |
| 1697 | CH | S | Q1b | a bond | Me | a bond | NH | S | a bond | T3g | OH |
| 1698 | CH | S | Q1b | a bond | Me | a bond | NH | S | a bond | T3h | OH |
| 1699 | CH | S | Q1b | a bond | Me | a bond | NH | S | a bond | T3i | OH |
| 1700 | CH | S | Q1b | a bond | Me | a bond | NH | S | a bond | T3j | OH |
| 1701 | CH | S | Q1b | a bond | Me | a bond | NH | O | NH | T3a | OH |
| 1702 | CH | S | Q1b | a bond | Me | a bond | NH | O | NH | T3b | OH |
| 1703 | CH | S | Q1b | a bond | Me | a bond | NH | O | NH | T3c | OH |
| 1704 | CH | S | Q1b | a bond | Me | a bond | NH | O | NH | T3d | OH |
| 1705 | CH | S | Q1b | a bond | Me | a bond | NH | O | NH | T3e | OH |
| 1706 | CH | S | Q1b | a bond | Me | a bond | NH | O | NH | T3f | OH |
| 1707 | CH | S | Q1b | a bond | Me | a bond | NH | O | NH | T3g | OH |
| 1708 | CH | S | Q1b | a bond | Me | a bond | NH | O | NH | T3h | OH |
| 1709 | CH | S | Q1b | a bond | Me | a bond | NH | O | NH | T3i | OH |
| 1710 | CH | S | Q1b | a bond | Me | a bond | NH | O | NH | T3j | OH |
| 1711 | CH | S | Q1b | a bond | Me | a bond | NH | O | a bond | T3a | OH |
| 1712 | CH | S | Q1b | a bond | Me | a bond | NH | O | a bond | T3b | OH |
| 1713 | CH | S | Q1b | a bond | Me | a bond | NH | O | a bond | T3c | OH |
| 1714 | CH | S | Q1b | a bond | Me | a bond | NH | O | a bond | T3d | OH |
| 1715 | CH | S | Q1b | a bond | Me | a bond | NH | O | a bond | T3e | OH |
| 1716 | CH | S | Q1b | a bond | Me | a bond | NH | O | a bond | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 1717 | CH | S | Q1b | a bond | Me | a bond | NH | O | a bond | T3g | OH |
| 1718 | CH | S | Q1b | a bond | Me | a bond | NH | O | a bond | T3h | OH |
| 1719 | CH | S | Q1b | a bond | Me | a bond | NH | O | a bond | T3i | OH |
| 1720 | CH | S | Q1b | a bond | Me | a bond | NH | O | a bond | T3j | OH |
| 1721 | CH | S | Q1b | a bond | H | a bond | NH | S | NH | T3a | OH |
| 1722 | CH | S | Q1b | a bond | H | a bond | NH | S | NH | T3b | OH |
| 1723 | CH | S | Q1b | a bond | H | a bond | NH | S | NH | T3c | OH |
| 1724 | CH | S | Q1b | a bond | H | a bond | NH | S | NH | T3d | OH |
| 1725 | CH | S | Q1b | a bond | H | a bond | NH | S | NH | T3e | OH |
| 1726 | CH | S | Q1b | a bond | H | a bond | NH | S | NH | T3f | OH |
| 1727 | CH | S | Q1b | a bond | H | a bond | NH | S | NH | T3g | OH |
| 1728 | CH | S | Q1b | a bond | H | a bond | NH | S | NH | T3h | OH |
| 1729 | CH | S | Q1b | a bond | H | a bond | NH | S | NH | T3i | OH |
| 1730 | CH | S | Q1b | a bond | H | a bond | NH | S | NH | T3j | OH |
| 1731 | CH | S | Q1b | a bond | H | a bond | NH | S | a bond | T3a | OH |
| 1732 | CH | S | Q1b | a bond | H | a bond | NH | S | a bond | T3b | OH |
| 1733 | CH | S | Q1b | a bond | H | a bond | NH | S | a bond | T3c | OH |
| 1734 | CH | S | Q1b | a bond | H | a bond | NH | S | a bond | T3d | OH |
| 1735 | CH | S | Q1b | a bond | H | a bond | NH | S | a bond | T3e | OH |
| 1736 | CH | S | Q1b | a bond | H | a bond | NH | S | a bond | T3f | OH |
| 1737 | CH | S | Q1b | a bond | H | a bond | NH | S | a bond | T3g | OH |
| 1738 | CH | S | Q1b | a bond | H | a bond | NH | S | a bond | T3h | OH |
| 1739 | CH | S | Q1b | a bond | H | a bond | NH | S | a bond | T3i | OH |
| 1740 | CH | S | Q1b | a bond | H | a bond | NH | S | a bond | T3j | OH |
| 1741 | CH | S | Q1b | a bond | H | a bond | NH | O | NH | T3a | OH |
| 1742 | CH | S | Q1b | a bond | H | a bond | NH | O | NH | T3b | OH |
| 1743 | CH | S | Q1b | a bond | H | a bond | NH | O | NH | T3c | OH |
| 1744 | CH | S | Q1b | a bond | H | a bond | NH | O | NH | T3d | OH |
| 1745 | CH | S | Q1b | a bond | H | a bond | NH | O | NH | T3e | OH |
| 1746 | CH | S | Q1b | a bond | H | a bond | NH | O | NH | T3f | OH |
| 1747 | CH | S | Q1b | a bond | H | a bond | NH | O | NH | T3g | OH |
| 1748 | CH | S | Q1b | a bond | H | a bond | NH | O | NH | T3h | OH |
| 1749 | CH | S | Q1b | a bond | H | a bond | NH | O | NH | T3i | OH |
| 1750 | CH | S | Q1b | a bond | H | a bond | NH | O | NH | T3j | OH |
| 1751 | CH | S | Q1b | a bond | H | a bond | NH | O | a bond | T3a | OH |
| 1752 | CH | S | Q1b | a bond | H | a bond | NH | O | a bond | T3b | OH |
| 1753 | CH | S | Q1b | a bond | H | a bond | NH | O | a bond | T3c | OH |
| 1754 | CH | S | Q1b | a bond | H | a bond | NH | O | a bond | T3d | OH |
| 1755 | CH | S | Q1b | a bond | H | a bond | NH | O | a bond | T3e | OH |
| 1756 | CH | S | Q1b | a bond | H | a bond | NH | O | a bond | T3f | OH |
| 1757 | CH | S | Q1b | a bond | H | a bond | NH | O | a bond | T3g | OH |
| 1758 | CH | S | Q1b | a bond | H | a bond | NH | O | a bond | T3h | OH |
| 1759 | CH | S | Q1b | a bond | H | a bond | NH | O | a bond | T3i | OH |
| 1760 | CH | S | Q1b | a bond | H | a bond | NH | O | a bond | T3j | OH |
| 1761 | CH | S | Q1c | a bond | Me | a bond | NH | S | NH | T3a | OH |
| 1762 | CH | S | Q1c | a bond | Me | a bond | NH | S | NH | T3b | OH |
| 1763 | CH | S | Q1c | a bond | Me | a bond | NH | S | NH | T3c | OH |
| 1764 | CH | S | Q1c | a bond | Me | a bond | NH | S | NH | T3d | OH |
| 1765 | CH | S | Q1c | a bond | Me | a bond | NH | S | NH | T3e | OH |
| 1766 | CH | S | Q1c | a bond | Me | a bond | NH | S | NH | T3f | OH |
| 1767 | CH | S | Q1c | a bond | Me | a bond | NH | S | NH | T3g | OH |
| 1768 | CH | S | Q1c | a bond | Me | a bond | NH | S | NH | T3h | OH |
| 1769 | CH | S | Q1c | a bond | Me | a bond | NH | S | NH | T3i | OH |
| 1770 | CH | S | Q1c | a bond | Me | a bond | NH | S | NH | T3j | OH |
| 1771 | CH | S | Q1c | a bond | Me | a bond | NH | S | a bond | T3a | OH |
| 1772 | CH | S | Q1c | a bond | Me | a bond | NH | S | a bond | T3b | OH |
| 1773 | CH | S | Q1c | a bond | Me | a bond | NH | S | a bond | T3c | OH |
| 1774 | CH | S | Q1c | a bond | Me | a bond | NH | S | a bond | T3d | OH |
| 1775 | CH | S | Q1c | a bond | Me | a bond | NH | S | a bond | T3e | OH |
| 1776 | CH | S | Q1c | a bond | Me | a bond | NH | S | a bond | T3f | OH |
| 1777 | CH | S | Q1c | a bond | Me | a bond | NH | S | a bond | T3g | OH |
| 1778 | CH | S | Q1c | a bond | Me | a bond | NH | S | a bond | T3h | OH |
| 1779 | CH | S | Q1c | a bond | Me | a bond | NH | S | a bond | T3i | OH |
| 1780 | CH | S | Q1c | a bond | Me | a bond | NH | S | a bond | T3j | OH |
| 1781 | CH | S | Q1c | a bond | Me | a bond | NH | O | NH | T3a | OH |
| 1782 | CH | S | Q1c | a bond | Me | a bond | NH | O | NH | T3b | OH |
| 1783 | CH | S | Q1c | a bond | Me | a bond | NH | O | NH | T3c | OH |
| 1784 | CH | S | Q1c | a bond | Me | a bond | NH | O | NH | T3d | OH |
| 1785 | CH | S | Q1c | a bond | Me | a bond | NH | O | NH | T3e | OH |
| 1786 | CH | S | Q1c | a bond | Me | a bond | NH | O | NH | T3f | OH |
| 1787 | CH | S | Q1c | a bond | Me | a bond | NH | O | NH | T3g | OH |
| 1788 | CH | S | Q1c | a bond | Me | a bond | NH | O | NH | T3h | OH |
| 1789 | CH | S | Q1c | a bond | Me | a bond | NH | O | NH | T3i | OH |
| 1790 | CH | S | Q1c | a bond | Me | a bond | NH | O | NH | T3j | OH |
| 1791 | CH | S | Q1c | a bond | Me | a bond | NH | O | a bond | T3a | OH |
| 1792 | CH | S | Q1c | a bond | Me | a bond | NH | O | a bond | T3b | OH |
| 1793 | CH | S | Q1c | a bond | Me | a bond | NH | O | a bond | T3c | OH |
| 1794 | CH | S | Q1c | a bond | Me | a bond | NH | O | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 1795 | CH | S | Q1c | a bond | Me | a bond | NH | O | a bond | T3e | OH |
| 1796 | CH | S | Q1c | a bond | Me | a bond | NH | O | a bond | T3f | OH |
| 1797 | CH | S | Q1c | a bond | Me | a bond | NH | O | a bond | T3g | OH |
| 1798 | CH | S | Q1c | a bond | Me | a bond | NH | O | a bond | T3h | OH |
| 1799 | CH | S | Q1c | a bond | Me | a bond | NH | O | a bond | T3i | OH |
| 1800 | CH | S | Q1c | a bond | Me | a bond | NH | O | a bond | T3j | OH |
| 1801 | CH | S | Q1c | a bond | H | a bond | NH | S | NH | T3a | OH |
| 1802 | CH | S | Q1c | a bond | H | a bond | NH | S | NH | T3b | OH |
| 1803 | CH | S | Q1c | a bond | H | a bond | NH | S | NH | T3c | OH |
| 1804 | CH | S | Q1c | a bond | H | a bond | NH | S | NH | T3d | OH |
| 1805 | CH | S | Q1c | a bond | H | a bond | NH | S | NH | T3e | OH |
| 1806 | CH | S | Q1c | a bond | H | a bond | NH | S | NH | T3f | OH |
| 1807 | CH | S | Q1c | a bond | H | a bond | NH | S | NH | T3g | OH |
| 1808 | CH | S | Q1c | a bond | H | a bond | NH | S | NH | T3h | OH |
| 1809 | CH | S | Q1c | a bond | H | a bond | NH | S | NH | T3i | OH |
| 1810 | CH | S | Q1c | a bond | H | a bond | NH | S | NH | T3j | OH |
| 1811 | CH | S | Q1c | a bond | H | a bond | NH | S | a bond | T3a | OH |
| 1812 | CH | S | Q1c | a bond | H | a bond | NH | S | a bond | T3b | OH |
| 1813 | CH | S | Q1c | a bond | H | a bond | NH | S | a bond | T3c | OH |
| 1814 | CH | S | Q1c | a bond | H | a bond | NH | S | a bond | T3d | OH |
| 1815 | CH | S | Q1c | a bond | H | a bond | NH | S | a bond | T3e | OH |
| 1816 | CH | S | Q1c | a bond | H | a bond | NH | S | a bond | T3f | OH |
| 1817 | CH | S | Q1c | a bond | H | a bond | NH | S | a bond | T3g | OH |
| 1818 | CH | S | Q1c | a bond | H | a bond | NH | S | a bond | T3h | OH |
| 1819 | CH | S | Q1c | a bond | H | a bond | NH | S | a bond | T3i | OH |
| 1820 | CH | S | Q1c | a bond | H | a bond | NH | S | a bond | T3j | OH |
| 1821 | CH | S | Q1c | a bond | H | a bond | NH | O | NH | T3a | OH |
| 1822 | CH | S | Q1c | a bond | H | a bond | NH | O | NH | T3b | OH |
| 1823 | CH | S | Q1c | a bond | H | a bond | NH | O | NH | T3c | OH |
| 1824 | CH | S | Q1c | a bond | H | a bond | NH | O | NH | T3d | OH |
| 1825 | CH | S | Q1c | a bond | H | a bond | NH | O | NH | T3e | OH |
| 1826 | CH | S | Q1c | a bond | H | a bond | NH | O | NH | T3f | OH |
| 1827 | CH | S | Q1c | a bond | H | a bond | NH | O | NH | T3g | OH |
| 1828 | CH | S | Q1c | a bond | H | a bond | NH | O | NH | T3h | OH |
| 1829 | CH | S | Q1c | a bond | H | a bond | NH | O | NH | T3i | OH |
| 1830 | CH | S | Q1c | a bond | H | a bond | NH | O | NH | T3j | OH |
| 1831 | CH | S | Q1c | a bond | H | a bond | NH | O | a bond | T3a | OH |
| 1832 | CH | S | Q1c | a bond | H | a bond | NH | O | a bond | T3b | OH |
| 1833 | CH | S | Q1c | a bond | H | a bond | NH | O | a bond | T3c | OH |
| 1834 | CH | S | Q1c | a bond | H | a bond | NH | O | a bond | T3d | OH |
| 1835 | CH | S | Q1c | a bond | H | a bond | NH | O | a bond | T3e | OH |
| 1836 | CH | S | Q1c | a bond | H | a bond | NH | O | a bond | T3f | OH |
| 1837 | CH | S | Q1c | a bond | H | a bond | NH | O | a bond | T3g | OH |
| 1838 | CH | S | Q1c | a bond | H | a bond | NH | O | a bond | T3h | OH |
| 1839 | CH | S | Q1c | a bond | H | a bond | NH | O | a bond | T3i | OH |
| 1840 | CH | S | Q1c | a bond | H | a bond | NH | O | a bond | T3j | OH |
| 1841 | CH | S | Q1i | a bond | Me | a bond | NH | S | NH | T3a | OH |
| 1842 | CH | S | Q1i | a bond | Me | a bond | NH | S | NH | T3b | OH |
| 1843 | CH | S | Q1i | a bond | Me | a bond | NH | S | NH | T3c | OH |
| 1844 | CH | S | Q1i | a bond | Me | a bond | NH | S | NH | T3d | OH |
| 1845 | CH | S | Q1i | a bond | Me | a bond | NH | S | NH | T3e | OH |
| 1846 | CH | S | Q1i | a bond | Me | a bond | NH | S | NH | T3f | OH |
| 1847 | CH | S | Q1i | a bond | Me | a bond | NH | S | NH | T3g | OH |
| 1848 | CH | S | Q1i | a bond | Me | a bond | NH | S | NH | T3h | OH |
| 1849 | CH | S | Q1i | a bond | Me | a bond | NH | S | NH | T3i | OH |
| 1850 | CH | S | Q1i | a bond | Me | a bond | NH | S | NH | T3j | OH |
| 1851 | CH | S | Q1i | a bond | Me | a bond | NH | S | a bond | T3a | OH |
| 1852 | CH | S | Q1i | a bond | Me | a bond | NH | S | a bond | T3b | OH |
| 1853 | CH | S | Q1i | a bond | Me | a bond | NH | S | a bond | T3c | OH |
| 1854 | CH | S | Q1i | a bond | Me | a bond | NH | S | a bond | T3d | OH |
| 1855 | CH | S | Q1i | a bond | Me | a bond | NH | S | a bond | T3e | OH |
| 1856 | CH | S | Q1i | a bond | Me | a bond | NH | S | a bond | T3f | OH |
| 1857 | CH | S | Q1i | a bond | Me | a bond | NH | S | a bond | T3g | OH |
| 1858 | CH | S | Q1i | a bond | Me | a bond | NH | S | a bond | T3h | OH |
| 1859 | CH | S | Q1i | a bond | Me | a bond | NH | S | a bond | T3i | OH |
| 1860 | CH | S | Q1i | a bond | Me | a bond | NH | S | a bond | T3j | OH |
| 1861 | CH | S | Q1i | a bond | Me | a bond | NH | O | NH | T3a | OH |
| 1862 | CH | S | Q1i | a bond | Me | a bond | NH | O | NH | T3b | OH |
| 1863 | CH | S | Q1i | a bond | Me | a bond | NH | O | NH | T3c | OH |
| 1864 | CH | S | Q1i | a bond | Me | a bond | NH | O | NH | T3d | OH |
| 1865 | CH | S | Q1i | a bond | Me | a bond | NH | O | NH | T3e | OH |
| 1866 | CH | S | Q1i | a bond | Me | a bond | NH | O | NH | T3f | OH |
| 1867 | CH | S | Q1i | a bond | Me | a bond | NH | O | NH | T3g | OH |
| 1868 | CH | S | Q1i | a bond | Me | a bond | NH | O | NH | T3h | OH |
| 1869 | CH | S | Q1i | a bond | Me | a bond | NH | O | NH | T3i | OH |
| 1870 | CH | S | Q1i | a bond | Me | a bond | NH | O | NH | T3j | OH |
| 1871 | CH | S | Q1i | a bond | Me | a bond | NH | O | a bond | T3a | OH |
| 1872 | CH | S | Q1i | a bond | Me | a bond | NH | O | a bond | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 1873 | CH | S | Q1i | a bond | Me | a bond | NH | O | a bond | T3c | OH |
| 1874 | CH | S | Q1i | a bond | Me | a bond | NH | O | a bond | T3d | OH |
| 1875 | CH | S | Q1i | a bond | Me | a bond | NH | O | a bond | T3e | OH |
| 1876 | CH | S | Q1i | a bond | Me | a bond | NH | O | a bond | T3f | OH |
| 1877 | CH | S | Q1i | a bond | Me | a bond | NH | O | a bond | T3g | OH |
| 1878 | CH | S | Q1i | a bond | Me | a bond | NH | O | a bond | T3h | OH |
| 1879 | CH | S | Q1i | a bond | Me | a bond | NH | O | a bond | T3i | OH |
| 1880 | CH | S | Q1i | a bond | Me | a bond | NH | O | a bond | T3j | OH |
| 1881 | CH | S | Q1i | a bond | H | a bond | NH | S | NH | T3a | OH |
| 1882 | CH | S | Q1i | a bond | H | a bond | NH | S | NH | T3b | OH |
| 1883 | CH | S | Q1i | a bond | H | a bond | NH | S | NH | T3c | OH |
| 1884 | CH | S | Q1i | a bond | H | a bond | NH | S | NH | T3d | OH |
| 1885 | CH | S | Q1i | a bond | H | a bond | NH | S | NH | T3e | OH |
| 1886 | CH | S | Q1i | a bond | H | a bond | NH | S | NH | T3f | OH |
| 1887 | CH | S | Q1i | a bond | H | a bond | NH | S | NH | T3g | OH |
| 1888 | CH | S | Q1i | a bond | H | a bond | NH | S | NH | T3h | OH |
| 1889 | CH | S | Q1i | a bond | H | a bond | NH | S | NH | T3i | OH |
| 1890 | CH | S | Q1i | a bond | H | a bond | NH | S | NH | T3j | OH |
| 1891 | CH | S | Q1i | a bond | H | a bond | NH | S | a bond | T3a | OH |
| 1892 | CH | S | Q1i | a bond | H | a bond | NH | S | a bond | T3b | OH |
| 1893 | CH | S | Q1i | a bond | H | a bond | NH | S | a bond | T3c | OH |
| 1894 | CH | S | Q1i | a bond | H | a bond | NH | S | a bond | T3d | OH |
| 1895 | CH | S | Q1i | a bond | H | a bond | NH | S | a bond | T3e | OH |
| 1896 | CH | S | Q1i | a bond | H | a bond | NH | S | a bond | T3f | OH |
| 1897 | CH | S | Q1i | a bond | H | a bond | NH | S | a bond | T3g | OH |
| 1898 | CH | S | Q1i | a bond | H | a bond | NH | S | a bond | T3h | OH |
| 1899 | CH | S | Q1i | a bond | H | a bond | NH | S | a bond | T3i | OH |
| 1900 | CH | S | Q1i | a bond | H | a bond | NH | S | a bond | T3j | OH |
| 1901 | CH | S | Q1i | a bond | H | a bond | NH | O | NH | T3a | OH |
| 1902 | CH | S | Q1i | a bond | H | a bond | NH | O | NH | T3b | OH |
| 1903 | CH | S | Q1i | a bond | H | a bond | NH | O | NH | T3c | OH |
| 1904 | CH | S | Q1i | a bond | H | a bond | NH | O | NH | T3d | OH |
| 1905 | CH | S | Q1i | a bond | H | a bond | NH | O | NH | T3e | OH |
| 1906 | CH | S | Q1i | a bond | H | a bond | NH | O | NH | T3f | OH |
| 1907 | CH | S | Q1i | a bond | H | a bond | NH | O | NH | T3g | OH |
| 1908 | CH | S | Q1i | a bond | H | a bond | NH | O | NH | T3h | OH |
| 1909 | CH | S | Q1i | a bond | H | a bond | NH | O | NH | T3i | OH |
| 1910 | CH | S | Q1i | a bond | H | a bond | NH | O | NH | T3j | OH |
| 1911 | CH | S | Q1i | a bond | H | a bond | NH | O | a bond | T3a | OH |
| 1912 | CH | S | Q1i | a bond | H | a bond | NH | O | a bond | T3b | OH |
| 1913 | CH | S | Q1i | a bond | H | a bond | NH | O | a bond | T3c | OH |
| 1914 | CH | S | Q1i | a bond | H | a bond | NH | O | a bond | T3d | OH |
| 1915 | CH | S | Q1i | a bond | H | a bond | NH | O | a bond | T3e | OH |
| 1916 | CH | S | Q1i | a bond | H | a bond | NH | O | a bond | T3f | OH |
| 1917 | CH | S | Q1i | a bond | H | a bond | NH | O | a bond | T3g | OH |
| 1918 | CH | S | Q1i | a bond | H | a bond | NH | O | a bond | T3h | OH |
| 1919 | CH | S | Q1i | a bond | H | a bond | NH | O | a bond | T3i | OH |
| 1920 | CH | S | Q1i | a bond | H | a bond | NH | O | a bond | T3j | OH |
| 1921 | CH | S | Q1j | a bond | Me | a bond | NH | S | NH | T3a | OH |
| 1922 | CH | S | Q1j | a bond | Me | a bond | NH | S | NH | T3b | OH |
| 1923 | CH | S | Q1j | a bond | Me | a bond | NH | S | NH | T3c | OH |
| 1924 | CH | S | Q1j | a bond | Me | a bond | NH | S | NH | T3d | OH |
| 1925 | CH | S | Q1j | a bond | Me | a bond | NH | S | NH | T3e | OH |
| 1926 | CH | S | Q1j | a bond | Me | a bond | NH | S | NH | T3f | OH |
| 1927 | CH | S | Q1j | a bond | Me | a bond | NH | S | NH | T3g | OH |
| 1928 | CH | S | Q1j | a bond | Me | a bond | NH | S | NH | T3h | OH |
| 1929 | CH | S | Q1j | a bond | Me | a bond | NH | S | NH | T3i | OH |
| 1930 | CH | S | Q1j | a bond | Me | a bond | NH | S | NH | T3j | OH |
| 1931 | CH | S | Q1j | a bond | Me | a bond | NH | S | a bond | T3a | OH |
| 1932 | CH | S | Q1j | a bond | Me | a bond | NH | S | a bond | T3b | OH |
| 1933 | CH | S | Q1j | a bond | Me | a bond | NH | S | a bond | T3c | OH |
| 1934 | CH | S | Q1j | a bond | Me | a bond | NH | S | a bond | T3d | OH |
| 1935 | CH | S | Q1j | a bond | Me | a bond | NH | S | a bond | T3e | OH |
| 1936 | CH | S | Q1j | a bond | Me | a bond | NH | S | a bond | T3f | OH |
| 1937 | CH | S | Q1j | a bond | Me | a bond | NH | S | a bond | T3g | OH |
| 1938 | CH | S | Q1j | a bond | Me | a bond | NH | S | a bond | T3h | OH |
| 1939 | CH | S | Q1j | a bond | Me | a bond | NH | S | a bond | T3i | OH |
| 1940 | CH | S | Q1j | a bond | Me | a bond | NH | S | a bond | T3j | OH |
| 1941 | CH | S | Q1j | a bond | Me | a bond | NH | O | NH | T3a | OH |
| 1942 | CH | S | Q1j | a bond | Me | a bond | NH | O | NH | T3b | OH |
| 1943 | CH | S | Q1j | a bond | Me | a bond | NH | O | NH | T3c | OH |
| 1944 | CH | S | Q1j | a bond | Me | a bond | NH | O | NH | T3d | OH |
| 1945 | CH | S | Q1j | a bond | Me | a bond | NH | O | NH | T3e | OH |
| 1946 | CH | S | Q1j | a bond | Me | a bond | NH | O | NH | T3f | OH |
| 1947 | CH | S | Q1j | a bond | Me | a bond | NH | O | NH | T3g | OH |
| 1948 | CH | S | Q1j | a bond | Me | a bond | NH | O | NH | T3h | OH |
| 1949 | CH | S | Q1j | a bond | Me | a bond | NH | O | NH | T3i | OH |
| 1950 | CH | S | Q1j | a bond | Me | a bond | NH | O | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 1951 | CH | S | Q1j | a bond | Me | a bond | NH | O | a bond | T3a | OH |
| 1952 | CH | S | Q1j | a bond | Me | a bond | NH | O | a bond | T3b | OH |
| 1953 | CH | S | Q1j | a bond | Me | a bond | NH | O | a bond | T3c | OH |
| 1954 | CH | S | Q1j | a bond | Me | a bond | NH | O | a bond | T3d | OH |
| 1955 | CH | S | Q1j | a bond | Me | a bond | NH | O | a bond | T3e | OH |
| 1956 | CH | S | Q1j | a bond | Me | a bond | NH | O | a bond | T3f | OH |
| 1957 | CH | S | Q1j | a bond | Me | a bond | NH | O | a bond | T3g | OH |
| 1958 | CH | S | Q1j | a bond | Me | a bond | NH | O | a bond | T3h | OH |
| 1959 | CH | S | Q1j | a bond | Me | a bond | NH | O | a bond | T3i | OH |
| 1960 | CH | S | Q1j | a bond | Me | a bond | NH | O | a bond | T3j | OH |
| 1961 | CH | S | Q1j | a bond | H | a bond | NH | S | NH | T3a | OH |
| 1962 | CH | S | Q1j | a bond | H | a bond | NH | S | NH | T3b | OH |
| 1963 | CH | S | Q1j | a bond | H | a bond | NH | S | NH | T3c | OH |
| 1964 | CH | S | Q1j | a bond | H | a bond | NH | S | NH | T3d | OH |
| 1965 | CH | S | Q1j | a bond | H | a bond | NH | S | NH | T3e | OH |
| 1966 | CH | S | Q1j | a bond | H | a bond | NH | S | NH | T3f | OH |
| 1967 | CH | S | Q1j | a bond | H | a bond | NH | S | NH | T3g | OH |
| 1968 | CH | S | Q1j | a bond | H | a bond | NH | S | NH | T3h | OH |
| 1969 | CH | S | Q1j | a bond | H | a bond | NH | S | NH | T3i | OH |
| 1970 | CH | S | Q1j | a bond | H | a bond | NH | S | NH | T3j | OH |
| 1971 | CH | S | Q1j | a bond | H | a bond | NH | S | a bond | T3a | OH |
| 1972 | CH | S | Q1j | a bond | H | a bond | NH | S | a bond | T3b | OH |
| 1973 | CH | S | Q1j | a bond | H | a bond | NH | S | a bond | T3c | OH |
| 1974 | CH | S | Q1j | a bond | H | a bond | NH | S | a bond | T3d | OH |
| 1975 | CH | S | Q1j | a bond | H | a bond | NH | S | a bond | T3e | OH |
| 1976 | CH | S | Q1j | a bond | H | a bond | NH | S | a bond | T3f | OH |
| 1977 | CH | S | Q1j | a bond | H | a bond | NH | S | a bond | T3g | OH |
| 1978 | CH | S | Q1i | a bond | H | a bond | NH | S | a bond | T3h | OH |
| 1979 | CH | S | Q1j | a bond | H | a bond | NH | S | a bond | T3i | OH |
| 1980 | CH | S | Q1j | a bond | H | a bond | NH | S | a bond | T3j | OH |
| 1981 | CH | S | Q1j | a bond | H | a bond | NH | O | NH | T3a | OH |
| 1982 | CH | S | Q1j | a bond | H | a bond | NH | O | NH | T3b | OH |
| 1983 | CH | S | Q1j | a bond | H | a bond | NH | O | NH | T3c | OH |
| 1984 | CH | S | Q1j | a bond | H | a bond | NH | O | NH | T3d | OH |
| 1985 | CH | S | Q1j | a bond | H | a bond | NH | O | NH | T3e | OH |
| 1986 | CH | S | Q1j | a bond | H | a bond | NH | O | NH | T3f | OH |
| 1987 | CH | S | Q1j | a bond | H | a bond | NH | O | NH | T3g | OH |
| 1988 | CH | S | Q1j | a bond | H | a bond | NH | O | NH | T3h | OH |
| 1989 | CH | S | Q1j | a bond | H | a bond | NH | O | NH | T3i | OH |
| 1990 | CH | S | Q1j | a bond | H | a bond | NH | O | NH | T3j | OH |
| 1991 | CH | S | Q1j | a bond | H | a bond | NH | O | a bond | T3a | OH |
| 1992 | CH | S | Q1j | a bond | H | a bond | NH | O | a bond | T3b | OH |
| 1993 | CH | S | Q1j | a bond | H | a bond | NH | O | a bond | T3c | OH |
| 1994 | CH | S | Q1j | a bond | H | a bond | NH | O | a bond | T3d | OH |
| 1995 | CH | S | Q1j | a bond | H | a bond | NH | O | a bond | T3e | OH |
| 1996 | CH | S | Q1j | a bond | H | a bond | NH | O | a bond | T3f | OH |
| 1997 | CH | S | Q1j | a bond | H | a bond | NH | O | a bond | T3g | OH |
| 1998 | CH | S | Q1j | a bond | H | a bond | NH | O | a bond | T3h | OH |
| 1999 | CH | S | Q1j | a bond | H | a bond | NH | O | a bond | T3i | OH |
| 2000 | CH | S | Q1j | a bond | H | a bond | NH | O | a bond | T3j | OH |
| 2001 | CH | O | Q1a | a bond | Me | a bond | NH | S | NH | T3a | OH |
| 2002 | CH | O | Q1a | a bond | Me | a bond | NH | S | NH | T3b | OH |
| 2003 | CH | O | Q1a | a bond | Me | a bond | NH | S | NH | T3c | OH |
| 2004 | CH | O | Q1a | a bond | Me | a bond | NH | S | NH | T3d | OH |
| 2005 | CH | O | Q1a | a bond | Me | a bond | NH | S | NH | T3e | OH |
| 2006 | CH | O | Q1a | a bond | Me | a bond | NH | S | NH | T3f | OH |
| 2007 | CH | O | Q1a | a bond | Me | a bond | NH | S | NH | T3g | OH |
| 2008 | CH | O | Q1a | a bond | Me | a bond | NH | S | NH | T3h | OH |
| 2009 | CH | O | Q1a | a bond | Me | a bond | NH | S | NH | T3i | OH |
| 2010 | CH | O | Q1a | a bond | Me | a bond | NH | S | NH | T3j | OH |
| 2011 | CH | O | Q1a | a bond | Me | a bond | NH | S | a bond | T3a | OH |
| 2012 | CH | O | Q1a | a bond | Me | a bond | NH | S | a bond | T3b | OH |
| 2013 | CH | O | Q1a | a bond | Me | a bond | NH | S | a bond | T3c | OH |
| 2014 | CH | O | Q1a | a bond | Me | a bond | NH | S | a bond | T3d | OH |
| 2015 | CH | O | Q1a | a bond | Me | a bond | NH | S | a bond | T3e | OH |
| 2016 | CH | O | Q1a | a bond | Me | a bond | NH | S | a bond | T3f | OH |
| 2017 | CH | O | Q1a | a bond | Me | a bond | NH | S | a bond | T3g | OH |
| 2018 | CH | O | Q1a | a bond | Me | a bond | NH | S | a bond | T3h | OH |
| 2019 | CH | O | Q1a | a bond | Me | a bond | NH | S | a bond | T3i | OH |
| 2020 | CH | O | Q1a | a bond | Me | a bond | NH | S | a bond | T3j | OH |
| 2021 | CH | O | Q1a | a bond | Me | a bond | NH | O | NH | T3a | OH |
| 2022 | CH | O | Q1a | a bond | Me | a bond | NH | O | NH | T3b | OH |
| 2023 | CH | O | Q1a | a bond | Me | a bond | NH | O | NH | T3c | OH |
| 2024 | CH | O | Q1a | a bond | Me | a bond | NH | O | NH | T3d | OH |
| 2025 | CH | O | Q1a | a bond | Me | a bond | NH | O | NH | T3e | OH |
| 2026 | CH | O | Q1a | a bond | Me | a bond | NH | O | NH | T3f | OH |
| 2027 | CH | O | Q1a | a bond | Me | a bond | NH | O | NH | T3g | OH |
| 2028 | CH | O | Q1a | a bond | Me | a bond | NH | O | NH | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 2029 | CH | O | Q1a | a bond | Me | a bond | NH | O | NH | T3i | OH |
| 2030 | CH | O | Q1a | a bond | Me | a bond | NH | O | NH | T3j | OH |
| 2031 | CH | O | Q1a | a bond | Me | a bond | NH | O | a bond | T3a | OH |
| 2032 | CH | O | Q1a | a bond | Me | a bond | NH | O | a bond | T3b | OH |
| 2033 | CH | O | Q1a | a bond | Me | a bond | NH | O | a bond | T3c | OH |
| 2034 | CH | O | Q1a | a bond | Me | a bond | NH | O | a bond | T3d | OH |
| 2035 | CH | O | Q1a | a bond | Me | a bond | NH | O | a bond | T3e | OH |
| 2036 | CH | O | Q1a | a bond | Me | a bond | NH | O | a bond | T3f | OH |
| 2037 | CH | O | Q1a | a bond | Me | a bond | NH | O | a bond | T3g | OH |
| 2038 | CH | O | Q1a | a bond | Me | a bond | NH | O | a bond | T3h | OH |
| 2039 | CH | O | Q1a | a bond | Me | a bond | NH | O | a bond | T3i | OH |
| 2040 | CH | O | Q1a | a bond | Me | a bond | NH | O | a bond | T3j | OH |
| 2041 | CH | O | Q1a | a bond | H | a bond | NH | S | NH | T3a | OH |
| 2042 | CH | O | Q1a | a bond | H | a bond | NH | S | NH | T3b | OH |
| 2043 | CH | O | Q1a | a bond | H | a bond | NH | S | NH | T3c | OH |
| 2044 | CH | O | Q1a | a bond | H | a bond | NH | S | NH | T3d | OH |
| 2045 | CH | O | Q1a | a bond | H | a bond | NH | S | NH | T3e | OH |
| 2046 | CH | O | Q1a | a bond | H | a bond | NH | S | NH | T3f | OH |
| 2047 | CH | O | Q1a | a bond | H | a bond | NH | S | NH | T3g | OH |
| 2048 | CH | O | Q1a | a bond | H | a bond | NH | S | NH | T3h | OH |
| 2049 | CH | O | Q1a | a bond | H | a bond | NH | S | NH | T3i | OH |
| 2050 | CH | O | Q1a | a bond | H | a bond | NH | S | NH | T3j | OH |
| 2051 | CH | O | Q1a | a bond | H | a bond | NH | S | a bond | T3a | OH |
| 2052 | CH | O | Q1a | a bond | H | a bond | NH | S | a bond | T3b | OH |
| 2053 | CH | O | Q1a | a bond | H | a bond | NH | S | a bond | T3c | OH |
| 2054 | CH | O | Q1a | a bond | H | a bond | NH | S | a bond | T3d | OH |
| 2055 | CH | O | Q1a | a bond | H | a bond | NH | S | a bond | T3e | OH |
| 2056 | CH | O | Q1a | a bond | H | a bond | NH | S | a bond | T3f | OH |
| 2057 | CH | O | Q1a | a bond | H | a bond | NH | S | a bond | T3g | OH |
| 2058 | CH | O | Q1a | a bond | H | a bond | NH | S | a bond | T3h | OH |
| 2059 | CH | O | Q1a | a bond | H | a bond | NH | S | a bond | T3i | OH |
| 2060 | CH | O | Q1a | a bond | H | a bond | NH | S | a bond | T3j | OH |
| 2061 | CH | O | Q1a | a bond | H | a bond | NH | O | NH | T3a | OH |
| 2062 | CH | O | Q1a | a bond | H | a bond | NH | O | NH | T3b | OH |
| 2063 | CH | O | Q1a | a bond | H | a bond | NH | O | NH | T3c | OH |
| 2064 | CH | O | Q1a | a bond | H | a bond | NH | O | NH | T3d | OH |
| 2065 | CH | O | Q1a | a bond | H | a bond | NH | O | NH | T3e | OH |
| 2066 | CH | O | Q1a | a bond | H | a bond | NH | O | NH | T3f | OH |
| 2067 | CH | O | Q1a | a bond | H | a bond | NH | O | NH | T3g | OH |
| 2068 | CH | O | Q1a | a bond | H | a bond | NH | O | NH | T3h | OH |
| 2069 | CH | O | Q1a | a bond | H | a bond | NH | O | NH | T3i | OH |
| 2070 | CH | O | Q1a | a bond | H | a bond | NH | O | NH | T3j | OH |
| 2071 | CH | O | Q1a | a bond | H | a bond | NH | O | a bond | T3a | OH |
| 2072 | CH | O | Q1a | a bond | H | a bond | NH | O | a bond | T3b | OH |
| 2073 | CH | O | Q1a | a bond | H | a bond | NH | O | a bond | T3c | OH |
| 2074 | CH | O | Q1a | a bond | H | a bond | NH | O | a bond | T3d | OH |
| 2075 | CH | O | Q1a | a bond | H | a bond | NH | O | a bond | T3e | OH |
| 2076 | CH | O | Q1a | a bond | H | a bond | NH | O | a bond | T3f | OH |
| 2077 | CH | O | Q1a | a bond | H | a bond | NH | O | a bond | T3g | OH |
| 2078 | CH | O | Q1a | a bond | H | a bond | NH | O | a bond | T3h | OH |
| 2079 | CH | O | Q1a | a bond | H | a bond | NH | O | a bond | T3i | OH |
| 2080 | CH | O | Q1a | a bond | H | a bond | NH | O | a bond | T3j | OH |
| 2081 | CH | O | Q1b | a bond | Me | a bond | NH | S | NH | T3a | OH |
| 2082 | CH | O | Q1b | a bond | Me | a bond | NH | S | NH | T3b | OH |
| 2083 | CH | O | Q1b | a bond | Me | a bond | NH | S | NH | T3c | OH |
| 2084 | CH | O | Q1b | a bond | Me | a bond | NH | S | NH | T3d | OH |
| 2085 | CH | O | Q1b | a bond | Me | a bond | NH | S | NH | T3e | OH |
| 2086 | CH | O | Q1b | a bond | Me | a bond | NH | S | NH | T3f | OH |
| 2087 | CH | O | Q1b | a bond | Me | a bond | NH | S | NH | T3g | OH |
| 2088 | CH | O | Q1b | a bond | Me | a bond | NH | S | NH | T3h | OH |
| 2089 | CH | O | Q1b | a bond | Me | a bond | NH | S | NH | T3i | OH |
| 2090 | CH | O | Q1b | a bond | Me | a bond | NH | S | NH | T3j | OH |
| 2091 | CH | O | Q1b | a bond | Me | a bond | NH | S | a bond | T3a | OH |
| 2092 | CH | O | Q1b | a bond | Me | a bond | NH | S | a bond | T3b | OH |
| 2093 | CH | O | Q1b | a bond | Me | a bond | NH | S | a bond | T3c | OH |
| 2094 | CH | O | Q1b | a bond | Me | a bond | NH | S | a bond | T3d | OH |
| 2095 | CH | O | Q1b | a bond | Me | a bond | NH | S | a bond | T3e | OH |
| 2096 | CH | O | Q1b | a bond | Me | a bond | NH | S | a bond | T3f | OH |
| 2097 | CH | O | Q1b | a bond | Me | a bond | NH | S | a bond | T3g | OH |
| 2098 | CH | O | Q1b | a bond | Me | a bond | NH | S | a bond | T3h | OH |
| 2099 | CH | O | Q1b | a bond | Me | a bond | NH | S | a bond | T3i | OH |
| 2100 | CH | O | Q1b | a bond | Me | a bond | NH | S | a bond | T3j | OH |
| 2101 | CH | O | Q1b | a bond | Me | a bond | NH | O | NH | T3a | OH |
| 2102 | CH | O | Q1b | a bond | Me | a bond | NH | O | NH | T3b | OH |
| 2103 | CH | O | Q1b | a bond | Me | a bond | NH | O | NH | T3c | OH |
| 2104 | CH | O | Q1b | a bond | Me | a bond | NH | O | NH | T3d | OH |
| 2105 | CH | O | Q1b | a bond | Me | a bond | NH | O | NH | T3e | OH |
| 2106 | CH | O | Q1b | a bond | Me | a bond | NH | O | NH | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 2107 | CH | O | Q1b | a bond | Me | a bond | NH | O | NH | T3g | OH |
| 2108 | CH | O | Q1b | a bond | Me | a bond | NH | O | NH | T3h | OH |
| 2109 | CH | O | Q1b | a bond | Me | a bond | NH | O | NH | T3i | OH |
| 2110 | CH | O | Q1b | a bond | Me | a bond | NH | O | NH | T3j | OH |
| 2111 | CH | O | Q1b | a bond | Me | a bond | NH | O | a bond | T3a | OH |
| 2112 | CH | O | Q1b | a bond | Me | a bond | NH | O | a bond | T3b | OH |
| 2113 | CH | O | Q1b | a bond | Me | a bond | NH | O | a bond | T3c | OH |
| 2114 | CH | O | Q1b | a bond | Me | a bond | NH | O | a bond | T3d | OH |
| 2115 | CH | O | Q1b | a bond | Me | a bond | NH | O | a bond | T3e | OH |
| 2116 | CH | O | Q1b | a bond | Me | a bond | NH | O | a bond | T3f | OH |
| 2117 | CH | O | Q1b | a bond | Me | a bond | NH | O | a bond | T3g | OH |
| 2118 | CH | O | Q1b | a bond | Me | a bond | NH | O | a bond | T3h | OH |
| 2119 | CH | O | Q1b | a bond | Me | a bond | NH | O | a bond | T3i | OH |
| 2120 | CH | O | Q1b | a bond | Me | a bond | NH | O | a bond | T3j | OH |
| 2121 | CH | O | Q1b | a bond | H | a bond | NH | S | NH | T3a | OH |
| 2122 | CH | O | Q1b | a bond | H | a bond | NH | S | NH | T3b | OH |
| 2123 | CH | O | Q1b | a bond | H | a bond | NH | S | NH | T3c | OH |
| 2124 | CH | O | Q1b | a bond | H | a bond | NH | S | NH | T3d | OH |
| 2125 | CH | O | Q1b | a bond | H | a bond | NH | S | NH | T3e | OH |
| 2126 | CH | O | Q1b | a bond | H | a bond | NH | S | NH | T3f | OH |
| 2127 | CH | O | Q1b | a bond | H | a bond | NH | S | NH | T3g | OH |
| 2128 | CH | O | Q1b | a bond | H | a bond | NH | S | NH | T3h | OH |
| 2129 | CH | O | Q1b | a bond | H | a bond | NH | S | NH | T3i | OH |
| 2130 | CH | O | Q1b | a bond | H | a bond | NH | S | NH | T3j | OH |
| 2131 | CH | O | Q1b | a bond | H | a bond | NH | S | a bond | T3a | OH |
| 2132 | CH | O | Q1b | a bond | H | a bond | NH | S | a bond | T3b | OH |
| 2133 | CH | O | Q1b | a bond | H | a bond | NH | S | a bond | T3c | OH |
| 2134 | CH | O | Q1b | a bond | H | a bond | NH | S | a bond | T3d | OH |
| 2135 | CH | O | Q1b | a bond | H | a bond | NH | S | a bond | T3e | OH |
| 2136 | CH | O | Q1b | a bond | H | a bond | NH | S | a bond | T3f | OH |
| 2137 | CH | O | Q1b | a bond | H | a bond | NH | S | a bond | T3g | OH |
| 2138 | CH | O | Q1b | a bond | H | a bond | NH | S | a bond | T3h | OH |
| 2139 | CH | O | Q1b | a bond | H | a bond | NH | S | a bond | T3i | OH |
| 2140 | CH | O | Q1b | a bond | H | a bond | NH | S | a bond | T3j | OH |
| 2141 | CH | O | Q1b | a bond | H | a bond | NH | O | NH | T3a | OH |
| 2142 | CH | O | Q1b | a bond | H | a bond | NH | O | NH | T3b | OH |
| 2143 | CH | O | Q1b | a bond | H | a bond | NH | O | NH | T3c | OH |
| 2144 | CH | O | Q1b | a bond | H | a bond | NH | O | NH | T3d | OH |
| 2145 | CH | O | Q1b | a bond | H | a bond | NH | O | NH | T3e | OH |
| 2146 | CH | O | Q1b | a bond | H | a bond | NH | O | NH | T3f | OH |
| 2147 | CH | O | Q1b | a bond | H | a bond | NH | O | NH | T3g | OH |
| 2148 | CH | O | Q1b | a bond | H | a bond | NH | O | NH | T3h | OH |
| 2149 | CH | O | Q1b | a bond | H | a bond | NH | O | NH | T3i | OH |
| 2150 | CH | O | Q1b | a bond | H | a bond | NH | O | NH | T3j | OH |
| 2151 | CH | O | Q1b | a bond | H | a bond | NH | O | a bond | T3a | OH |
| 2152 | CH | O | Q1b | a bond | H | a bond | NH | O | a bond | T3b | OH |
| 2153 | CH | O | Q1b | a bond | H | a bond | NH | O | a bond | T3c | OH |
| 2154 | CH | O | Q1b | a bond | H | a bond | NH | O | a bond | T3d | OH |
| 2155 | CH | O | Q1b | a bond | H | a bond | NH | O | a bond | T3e | OH |
| 2156 | CH | O | Q1b | a bond | H | a bond | NH | O | a bond | T3f | OH |
| 2157 | CH | O | Q1b | a bond | H | a bond | NH | O | a bond | T3g | OH |
| 2158 | CH | O | Q1b | a bond | H | a bond | NH | O | a bond | T3h | OH |
| 2159 | CH | O | Q1b | a bond | H | a bond | NH | O | a bond | T3i | OH |
| 2160 | CH | O | Q1b | a bond | H | a bond | NH | O | a bond | T3j | OH |
| 2161 | CH | O | Q1c | a bond | Me | a bond | NH | S | NH | T3a | OH |
| 2162 | CH | O | Q1c | a bond | Me | a bond | NH | S | NH | T3b | OH |
| 2163 | CH | O | Q1c | a bond | Me | a bond | NH | S | NH | T3c | OH |
| 2164 | CH | O | Q1c | a bond | Me | a bond | NH | S | NH | T3d | OH |
| 2165 | CH | O | Q1c | a bond | Me | a bond | NH | S | NH | T3e | OH |
| 2166 | CH | O | Q1c | a bond | Me | a bond | NH | S | NH | T3f | OH |
| 2167 | CH | O | Q1c | a bond | Me | a bond | NH | S | NH | T3g | OH |
| 2168 | CH | O | Q1c | a bond | Me | a bond | NH | S | NH | T3h | OH |
| 2169 | CH | O | Q1c | a bond | Me | a bond | NH | S | NH | T3i | OH |
| 2170 | CH | O | Q1c | a bond | Me | a bond | NH | S | NH | T3j | OH |
| 2171 | CH | O | Q1c | a bond | Me | a bond | NH | S | a bond | T3a | OH |
| 2172 | CH | O | Q1c | a bond | Me | a bond | NH | S | a bond | T3b | OH |
| 2173 | CH | O | Q1c | a bond | Me | a bond | NH | S | a bond | T3c | OH |
| 2174 | CH | O | Q1c | a bond | Me | a bond | NH | S | a bond | T3d | OH |
| 2175 | CH | O | Q1c | a bond | Me | a bond | NH | S | a bond | T3e | OH |
| 2176 | CH | O | Q1c | a bond | Me | a bond | NH | S | a bond | T3f | OH |
| 2177 | CH | O | Q1c | a bond | Me | a bond | NH | S | a bond | T3g | OH |
| 2178 | CH | O | Q1c | a bond | Me | a bond | NH | S | a bond | T3h | OH |
| 2179 | CH | O | Q1c | a bond | Me | a bond | NH | S | a bond | T3i | OH |
| 2180 | CH | O | Q1c | a bond | Me | a bond | NH | S | a bond | T3j | OH |
| 2181 | CH | O | Q1c | a bond | Me | a bond | NH | O | NH | T3a | OH |
| 2182 | CH | O | Q1c | a bond | Me | a bond | NH | O | NH | T3b | OH |
| 2183 | CH | O | Q1c | a bond | Me | a bond | NH | O | NH | T3c | OH |
| 2184 | CH | O | Q1c | a bond | Me | a bond | NH | O | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 2185 | CH | O | Q1c | a bond | Me | a bond | NH | O | NH | T3e | OH |
| 2186 | CH | O | Q1c | a bond | Me | a bond | NH | O | NH | T3f | OH |
| 2187 | CH | O | Q1c | a bond | Me | a bond | NH | O | NH | T3g | OH |
| 2188 | CH | O | Q1c | a bond | Me | a bond | NH | O | NH | T3h | OH |
| 2189 | CH | O | Q1c | a bond | Me | a bond | NH | O | NH | T3i | OH |
| 2190 | CH | O | Q1c | a bond | Me | a bond | NH | O | NH | T3j | OH |
| 2191 | CH | O | Q1c | a bond | Me | a bond | NH | O | a bond | T3a | OH |
| 2192 | CH | O | Q1c | a bond | Me | a bond | NH | O | a bond | T3b | OH |
| 2193 | CH | O | Q1c | a bond | Me | a bond | NH | O | a bond | T3c | OH |
| 2194 | CH | O | Q1c | a bond | Me | a bond | NH | O | a bond | T3d | OH |
| 2195 | CH | O | Q1c | a bond | Me | a bond | NH | O | a bond | T3e | OH |
| 2196 | CH | O | Q1c | a bond | Me | a bond | NH | O | a bond | T3f | OH |
| 2197 | CH | O | Q1c | a bond | Me | a bond | NH | O | a bond | T3g | OH |
| 2198 | CH | O | Q1c | a bond | Me | a bond | NH | O | a bond | T3h | OH |
| 2199 | CH | O | Q1c | a bond | Me | a bond | NH | O | a bond | T3i | OH |
| 2200 | CH | O | Q1c | a bond | Me | a bond | NH | O | a bond | T3j | OH |
| 2201 | CH | O | Q1c | a bond | H | a bond | NH | S | NH | T3a | OH |
| 2202 | CH | O | Q1c | a bond | H | a bond | NH | S | NH | T3b | OH |
| 2203 | CH | O | Q1c | a bond | H | a bond | NH | S | NH | T3c | OH |
| 2204 | CH | O | Q1c | a bond | H | a bond | NH | S | NH | T3d | OH |
| 2205 | CH | O | Q1c | a bond | H | a bond | NH | S | NH | T3e | OH |
| 2206 | CH | O | Q1c | a bond | H | a bond | NH | S | NH | T3f | OH |
| 2207 | CH | O | Q1c | a bond | H | a bond | NH | S | NH | T3g | OH |
| 2208 | CH | O | Q1c | a bond | H | a bond | NH | S | NH | T3h | OH |
| 2209 | CH | O | Q1c | a bond | H | a bond | NH | S | NH | T3i | OH |
| 2210 | CH | O | Q1c | a bond | H | a bond | NH | S | NH | T3j | OH |
| 2211 | CH | O | Q1c | a bond | H | a bond | NH | S | a bond | T3a | OH |
| 2212 | CH | O | Q1c | a bond | H | a bond | NH | S | a bond | T3b | OH |
| 2213 | CH | O | Q1c | a bond | H | a bond | NH | S | a bond | T3c | OH |
| 2214 | CH | O | Q1c | a bond | H | a bond | NH | S | a bond | T3d | OH |
| 2215 | CH | O | Q1c | a bond | H | a bond | NH | S | a bond | T3e | OH |
| 2216 | CH | O | Q1c | a bond | H | a bond | NH | S | a bond | T3f | OH |
| 2217 | CH | O | Q1c | a bond | H | a bond | NH | S | a bond | T3g | OH |
| 2218 | CH | O | Q1c | a bond | H | a bond | NH | S | a bond | T3h | OH |
| 2219 | CH | O | Q1c | a bond | H | a bond | NH | S | a bond | T3i | OH |
| 2220 | CH | O | Q1c | a bond | H | a bond | NH | S | a bond | T3j | OH |
| 2221 | CH | O | Q1c | a bond | H | a bond | NH | O | NH | T3a | OH |
| 2222 | CH | O | Q1c | a bond | H | a bond | NH | O | NH | T3b | OH |
| 2223 | CH | O | Q1c | a bond | H | a bond | NH | O | NH | T3c | OH |
| 2224 | CH | O | Q1c | a bond | H | a bond | NH | O | NH | T3d | OH |
| 2225 | CH | O | Q1c | a bond | H | a bond | NH | O | NH | T3e | OH |
| 2226 | CH | O | Q1c | a bond | H | a bond | NH | O | NH | T3f | OH |
| 2227 | CH | O | Q1c | a bond | H | a bond | NH | O | NH | T3g | OH |
| 2228 | CH | O | Q1c | a bond | H | a bond | NH | O | NH | T3h | OH |
| 2229 | CH | O | Q1c | a bond | H | a bond | NH | O | NH | T3i | OH |
| 2230 | CH | O | Q1c | a bond | H | a bond | NH | O | NH | T3j | OH |
| 2231 | CH | O | Q1c | a bond | H | a bond | NH | O | a bond | T3a | OH |
| 2232 | CH | O | Q1c | a bond | H | a bond | NH | O | a bond | T3b | OH |
| 2233 | CH | O | Q1c | a bond | H | a bond | NH | O | a bond | T3c | OH |
| 2234 | CH | O | Q1c | a bond | H | a bond | NH | O | a bond | T3d | OH |
| 2235 | CH | O | Q1c | a bond | H | a bond | NH | O | a bond | T3e | OH |
| 2236 | CH | O | Q1c | a bond | H | a bond | NH | O | a bond | T3f | OH |
| 2237 | CH | O | Q1c | a bond | H | a bond | NH | O | a bond | T3g | OH |
| 2238 | CH | O | Q1c | a bond | H | a bond | NH | O | a bond | T3h | OH |
| 2239 | CH | O | Q1c | a bond | H | a bond | NH | O | a bond | T3i | OH |
| 2240 | CH | O | Q1c | a bond | H | a bond | NH | O | a bond | T3j | OH |
| 2241 | CH | O | Q1i | a bond | Me | a bond | NH | S | NH | T3a | OH |
| 2242 | CH | O | Q1i | a bond | Me | a bond | NH | S | NH | T3b | OH |
| 2243 | CH | O | Q1i | a bond | Me | a bond | NH | S | NH | T3c | OH |
| 2244 | CH | O | Q1i | a bond | Me | a bond | NH | S | NH | T3d | OH |
| 2245 | CH | O | Q1i | a bond | Me | a bond | NH | S | NH | T3e | OH |
| 2246 | CH | O | Q1i | a bond | Me | a bond | NH | S | NH | T3f | OH |
| 2247 | CH | O | Q1i | a bond | Me | a bond | NH | S | NH | T3g | OH |
| 2248 | CH | O | Q1i | a bond | Me | a bond | NH | S | NH | T3h | OH |
| 2249 | CH | O | Q1i | a bond | Me | a bond | NH | S | NH | T3i | OH |
| 2250 | CH | O | Q1i | a bond | Me | a bond | NH | S | NH | T3j | OH |
| 2251 | CH | O | Q1i | a bond | Me | a bond | NH | S | a bond | T3a | OH |
| 2252 | CH | O | Q1i | a bond | Me | a bond | NH | S | a bond | T3b | OH |
| 2253 | CH | O | Q1i | a bond | Me | a bond | NH | S | a bond | T3c | OH |
| 2254 | CH | O | Q1i | a bond | Me | a bond | NH | S | a bond | T3d | OH |
| 2255 | CH | O | Q1i | a bond | Me | a bond | NH | S | a bond | T3e | OH |
| 2256 | CH | O | Q1i | a bond | Me | a bond | NH | S | a bond | T3f | OH |
| 2257 | CH | O | Q1i | a bond | Me | a bond | NH | S | a bond | T3g | OH |
| 2258 | CH | O | Q1i | a bond | Me | a bond | NH | S | a bond | T3h | OH |
| 2259 | CH | O | Q1i | a bond | Me | a bond | NH | S | a bond | T3i | OH |
| 2260 | CH | O | Q1i | a bond | Me | a bond | NH | S | a bond | T3j | OH |
| 2261 | CH | O | Q1i | a bond | Me | a bond | NH | O | NH | T3a | OH |
| 2262 | CH | O | Q1i | a bond | Me | a bond | NH | O | NH | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 2263 | CH | O | Q1i | a bond | Me | a bond | NH | O | NH | T3c | OH |
| 2264 | CH | O | Q1i | a bond | Me | a bond | NH | O | NH | T3d | OH |
| 2265 | CH | O | Q1i | a bond | Me | a bond | NH | O | NH | T3e | OH |
| 2266 | CH | O | Q1i | a bond | Me | a bond | NH | O | NH | T3f | OH |
| 2267 | CH | O | Q1i | a bond | Me | a bond | NH | O | NH | T3g | OH |
| 2268 | CH | O | Q1i | a bond | Me | a bond | NH | O | NH | T3h | OH |
| 2269 | CH | O | Q1i | a bond | Me | a bond | NH | O | NH | T3i | OH |
| 2270 | CH | O | Q1i | a bond | Me | a bond | NH | O | NH | T3j | OH |
| 2271 | CH | O | Q1i | a bond | Me | a bond | NH | O | a bond | T3a | OH |
| 2272 | CH | O | Q1i | a bond | Me | a bond | NH | O | a bond | T3b | OH |
| 2273 | CH | O | Q1i | a bond | Me | a bond | NH | O | a bond | T3c | OH |
| 2274 | CH | O | Q1i | a bond | Me | a bond | NH | O | a bond | T3d | OH |
| 2275 | CH | O | Q1i | a bond | Me | a bond | NH | O | a bond | T3e | OH |
| 2276 | CH | O | Q1i | a bond | Me | a bond | NH | O | a bond | T3f | OH |
| 2277 | CH | O | Q1i | a bond | Me | a bond | NH | O | a bond | T3g | OH |
| 2278 | CH | O | Q1i | a bond | Me | a bond | NH | O | a bond | T3h | OH |
| 2279 | CH | O | Q1i | a bond | Me | a bond | NH | O | a bond | T3i | OH |
| 2280 | CH | O | Q1i | a bond | Me | a bond | NH | O | a bond | T3j | OH |
| 2281 | CH | O | Q1i | a bond | H | a bond | NH | S | NH | T3a | OH |
| 2282 | CH | O | Q1i | a bond | H | a bond | NH | S | NH | T3b | OH |
| 2283 | CH | O | Q1i | a bond | H | a bond | NH | S | NH | T3c | OH |
| 2284 | CH | O | Q1i | a bond | H | a bond | NH | S | NH | T3d | OH |
| 2285 | CH | O | Q1i | a bond | H | a bond | NH | S | NH | T3e | OH |
| 2286 | CH | O | Q1i | a bond | H | a bond | NH | S | NH | T3f | OH |
| 2287 | CH | O | Q1i | a bond | H | a bond | NH | S | NH | T3g | OH |
| 2288 | CH | O | Q1i | a bond | H | a bond | NH | S | NH | T3h | OH |
| 2289 | CH | O | Q1i | a bond | H | a bond | NH | S | NH | T3i | OH |
| 2290 | CH | O | Q1i | a bond | H | a bond | NH | S | NH | T3j | OH |
| 2291 | CH | O | Q1i | a bond | H | a bond | NH | S | a bond | T3a | OH |
| 2292 | CH | O | Q1i | a bond | H | a bond | NH | S | a bond | T3b | OH |
| 2293 | CH | O | Q1i | a bond | H | a bond | NH | S | a bond | T3c | OH |
| 2294 | CH | O | Q1i | a bond | H | a bond | NH | S | a bond | T3d | OH |
| 2295 | CH | O | Q1i | a bond | H | a bond | NH | S | a bond | T3e | OH |
| 2296 | CH | O | Q1i | a bond | H | a bond | NH | S | a bond | T3f | OH |
| 2297 | CH | O | Q1i | a bond | H | a bond | NH | S | a bond | T3g | OH |
| 2298 | CH | O | Q1i | a bond | H | a bond | NH | S | a bond | T3h | OH |
| 2299 | CH | O | Q1i | a bond | H | a bond | NH | S | a bond | T3i | OH |
| 2300 | CH | O | Q1i | a bond | H | a bond | NH | S | a bond | T3j | OH |
| 2301 | CH | O | Q1i | a bond | H | a bond | NH | O | NH | T3a | OH |
| 2302 | CH | O | Q1i | a bond | H | a bond | NH | O | NH | T3b | OH |
| 2303 | CH | O | Q1i | a bond | H | a bond | NH | O | NH | T3c | OH |
| 2304 | CH | O | Q1i | a bond | H | a bond | NH | O | NH | T3d | OH |
| 2305 | CH | O | Q1i | a bond | H | a bond | NH | O | NH | T3e | OH |
| 2306 | CH | O | Q1i | a bond | H | a bond | NH | O | NH | T3f | OH |
| 2307 | CH | O | Q1i | a bond | H | a bond | NH | O | NH | T3g | OH |
| 2308 | CH | O | Q1i | a bond | H | a bond | NH | O | NH | T3h | OH |
| 2309 | CH | O | Q1i | a bond | H | a bond | NH | O | NH | T3i | OH |
| 2310 | CH | O | Q1i | a bond | H | a bond | NH | O | NH | T3j | OH |
| 2311 | CH | O | Q1i | a bond | H | a bond | NH | O | a bond | T3a | OH |
| 2312 | CH | O | Q1i | a bond | H | a bond | NH | O | a bond | T3b | OH |
| 2313 | CH | O | Q1i | a bond | H | a bond | NH | O | a bond | T3c | OH |
| 2314 | CH | O | Q1i | a bond | H | a bond | NH | O | a bond | T3d | OH |
| 2315 | CH | O | Q1i | a bond | H | a bond | NH | O | a bond | T3e | OH |
| 2316 | CH | O | Q1i | a bond | H | a bond | NH | O | a bond | T3f | OH |
| 2317 | CH | O | Q1i | a bond | H | a bond | NH | O | a bond | T3g | OH |
| 2318 | CH | O | Q1i | a bond | H | a bond | NH | O | a bond | T3h | OH |
| 2319 | CH | O | Q1i | a bond | H | a bond | NH | O | a bond | T3i | OH |
| 2320 | CH | O | Q1i | a bond | H | a bond | NH | O | a bond | T3j | OH |
| 2321 | CH | O | Q1j | a bond | Me | a bond | NH | S | NH | T3a | OH |
| 2322 | CH | O | Q1j | a bond | Me | a bond | NH | S | NH | T3b | OH |
| 2323 | CH | O | Q1j | a bond | Me | a bond | NH | S | NH | T3c | OH |
| 2324 | CH | O | Q1j | a bond | Me | a bond | NH | S | NH | T3d | OH |
| 2325 | CH | O | Q1j | a bond | Me | a bond | NH | S | NH | T3e | OH |
| 2326 | CH | O | Q1j | a bond | Me | a bond | NH | S | NH | T3f | OH |
| 2327 | CH | O | Q1j | a bond | Me | a bond | NH | S | NH | T3g | OH |
| 2328 | CH | O | Q1j | a bond | Me | a bond | NH | S | NH | T3h | OH |
| 2329 | CH | O | Q1j | a bond | Me | a bond | NH | S | NH | T3i | OH |
| 2330 | CH | O | Q1j | a bond | Me | a bond | NH | S | NH | T3j | OH |
| 2331 | CH | O | Q1j | a bond | Me | a bond | NH | S | a bond | T3a | OH |
| 2332 | CH | O | Q1j | a bond | Me | a bond | NH | S | a bond | T3b | OH |
| 2333 | CH | O | Q1j | a bond | Me | a bond | NH | S | a bond | T3c | OH |
| 2334 | CH | O | Q1j | a bond | Me | a bond | NH | S | a bond | T3d | OH |
| 2335 | CH | O | Q1j | a bond | Me | a bond | NH | S | a bond | T3e | OH |
| 2336 | CH | O | Q1j | a bond | Me | a bond | NH | S | a bond | T3f | OH |
| 2337 | CH | O | Q1j | a bond | Me | a bond | NH | S | a bond | T3g | OH |
| 2338 | CH | O | Q1j | a bond | Me | a bond | NH | S | a bond | T3h | OH |
| 2339 | CH | O | Q1j | a bond | Me | a bond | NH | S | a bond | T3i | OH |
| 2340 | CH | O | Q1j | a bond | Me | a bond | NH | S | a bond | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 2341 | CH | O | Q1j | a bond | Me | a bond | NH | O | NH | T3a | OH |
| 2342 | CH | O | Q1j | a bond | Me | a bond | NH | O | NH | T3b | OH |
| 2343 | CH | O | Q1j | a bond | Me | a bond | NH | O | NH | T3c | OH |
| 2344 | CH | O | Q1j | a bond | Me | a bond | NH | O | NH | T3d | OH |
| 2345 | CH | O | Q1j | a bond | Me | a bond | NH | O | NH | T3e | OH |
| 2346 | CH | O | Q1j | a bond | Me | a bond | NH | O | NH | T3f | OH |
| 2347 | CH | O | Q1j | a bond | Me | a bond | NH | O | NH | T3g | OH |
| 2348 | CH | O | Q1j | a bond | Me | a bond | NH | O | NH | T3h | OH |
| 2349 | CH | O | Q1j | a bond | Me | a bond | NH | O | NH | T3i | OH |
| 2350 | CH | O | Q1j | a bond | Me | a bond | NH | O | NH | T3j | OH |
| 2351 | CH | O | Q1j | a bond | Me | a bond | NH | O | a bond | T3a | OH |
| 2352 | CH | O | Q1j | a bond | Me | a bond | NH | O | a bond | T3b | OH |
| 2353 | CH | O | Q1j | a bond | Me | a bond | NH | O | a bond | T3c | OH |
| 2354 | CH | O | Q1j | a bond | Me | a bond | NH | O | a bond | T3d | OH |
| 2355 | CH | O | Q1j | a bond | Me | a bond | NH | O | a bond | T3e | OH |
| 2356 | CH | O | Q1j | a bond | Me | a bond | NH | O | a bond | T3f | OH |
| 2357 | CH | O | Q1j | a bond | Me | a bond | NH | O | a bond | T3g | OH |
| 2358 | CH | O | Q1j | a bond | Me | a bond | NH | O | a bond | T3h | OH |
| 2359 | CH | O | Q1j | a bond | Me | a bond | NH | O | a bond | T3i | OH |
| 2360 | CH | O | Q1j | a bond | Me | a bond | NH | O | a bond | T3j | OH |
| 2361 | CH | O | Q1j | a bond | H | a bond | NH | S | NH | T3a | OH |
| 2362 | CH | O | Q1j | a bond | H | a bond | NH | S | NH | T3b | OH |
| 2363 | CH | O | Q1j | a bond | H | a bond | NH | S | NH | T3c | OH |
| 2364 | CH | O | Q1j | a bond | H | a bond | NH | S | NH | T3d | OH |
| 2365 | CH | O | Q1j | a bond | H | a bond | NH | S | NH | T3e | OH |
| 2366 | CH | O | Q1j | a bond | H | a bond | NH | S | NH | T3f | OH |
| 2367 | CH | O | Q1j | a bond | H | a bond | NH | S | NH | T3g | OH |
| 2368 | CH | O | Q1j | a bond | H | a bond | NH | S | NH | T3h | OH |
| 2369 | CH | O | Q1j | a bond | H | a bond | NH | S | NH | T3i | OH |
| 2370 | CH | O | Q1j | a bond | H | a bond | NH | S | NH | T3j | OH |
| 2371 | CH | O | Q1j | a bond | H | a bond | NH | S | a bond | T3a | OH |
| 2372 | CH | O | Q1j | a bond | H | a bond | NH | S | a bond | T3b | OH |
| 2373 | CH | O | Q1j | a bond | H | a bond | NH | S | a bond | T3c | OH |
| 2374 | CH | O | Q1j | a bond | H | a bond | NH | S | a bond | T3d | OH |
| 2375 | CH | O | Q1j | a bond | H | a bond | NH | S | a bond | T3e | OH |
| 2376 | CH | O | Q1j | a bond | H | a bond | NH | S | a bond | T3f | OH |
| 2377 | CH | O | Q1j | a bond | H | a bond | NH | S | a bond | T3g | OH |
| 2378 | CH | O | Q1j | a bond | H | a bond | NH | S | a bond | T3h | OH |
| 2379 | CH | O | Q1j | a bond | H | a bond | NH | S | a bond | T3i | OH |
| 2380 | CH | O | Q1j | a bond | H | a bond | NH | S | a bond | T3j | OH |
| 2381 | CH | O | Q1j | a bond | H | a bond | NH | O | NH | T3a | OH |
| 2382 | CH | O | Q1j | a bond | H | a bond | NH | O | NH | T3b | OH |
| 2383 | CH | O | Q1j | a bond | H | a bond | NH | O | NH | T3c | OH |
| 2384 | CH | O | Q1j | a bond | H | a bond | NH | O | NH | T3d | OH |
| 2385 | CH | O | Q1j | a bond | H | a bond | NH | O | NH | T3e | OH |
| 2386 | CH | O | Q1j | a bond | H | a bond | NH | O | NH | T3f | OH |
| 2387 | CH | O | Q1j | a bond | H | a bond | NH | O | NH | T3g | OH |
| 2388 | CH | O | Q1j | a bond | H | a bond | NH | O | NH | T3h | OH |
| 2389 | CH | O | Q1j | a bond | H | a bond | NH | O | NH | T3i | OH |
| 2390 | CH | O | Q1j | a bond | H | a bond | NH | O | NH | T3j | OH |
| 2391 | CH | O | Q1j | a bond | H | a bond | NH | O | a bond | T3a | OH |
| 2392 | CH | O | Q1j | a bond | H | a bond | NH | O | a bond | T3b | OH |
| 2393 | CH | O | Q1j | a bond | H | a bond | NH | O | a bond | T3c | OH |
| 2394 | CH | O | Q1j | a bond | H | a bond | NH | O | a bond | T3d | OH |
| 2395 | CH | O | Q1j | a bond | H | a bond | NH | O | a bond | T3e | OH |
| 2396 | CH | O | Q1j | a bond | H | a bond | NH | O | a bond | T3f | OH |
| 2397 | CH | O | Q1j | a bond | H | a bond | NH | O | a bond | T3g | OH |
| 2398 | CH | O | Q1j | a bond | H | a bond | NH | O | a bond | T3h | OH |
| 2399 | CH | O | Q1j | a bond | H | a bond | NH | O | a bond | T3i | OH |
| 2400 | CH | O | Q1j | a bond | H | a bond | NH | O | a bond | T3j | OH |
| 2401 | CMe | NMe | Q1a | a bond | Me | a bond | NH | S | NH | T3a | OH |
| 2402 | CMe | NMe | Q1a | a bond | Me | a bond | NH | S | NH | T3b | OH |
| 2403 | CMe | NMe | Q1a | a bond | Me | a bond | NH | S | NH | T3c | OH |
| 2404 | CMe | NMe | Q1a | a bond | Me | a bond | NH | S | NH | T3d | OH |
| 2405 | CMe | NMe | Q1a | a bond | Me | a bond | NH | S | NH | T3e | OH |
| 2406 | CMe | NMe | Q1a | a bond | Me | a bond | NH | S | NH | T3f | OH |
| 2407 | CMe | NMe | Q1a | a bond | Me | a bond | NH | S | NH | T3g | OH |
| 2408 | CMe | NMe | Q1a | a bond | Me | a bond | NH | S | NH | T3h | OH |
| 2409 | CMe | NMe | Q1a | a bond | Me | a bond | NH | S | NH | T3i | OH |
| 2410 | CMe | NMe | Q1a | a bond | Me | a bond | NH | S | NH | T3j | OH |
| 2411 | CMe | NMe | Q1a | a bond | Me | a bond | NH | S | a bond | T3a | OH |
| 2412 | CMe | NMe | Q1a | a bond | Me | a bond | NH | S | a bond | T3b | OH |
| 2413 | CMe | NMe | Q1a | a bond | Me | a bond | NH | S | a bond | T3c | OH |
| 2414 | CMe | NMe | Q1a | a bond | Me | a bond | NH | S | a bond | T3d | OH |
| 2415 | CMe | NMe | Q1a | a bond | Me | a bond | NH | S | a bond | T3e | OH |
| 2416 | CMe | NMe | Q1a | a bond | Me | a bond | NH | S | a bond | T3f | OH |
| 2417 | CMe | NMe | Q1a | a bond | Me | a bond | NH | S | a bond | T3g | OH |
| 2418 | CMe | NMe | Q1a | a bond | Me | a bond | NH | S | a bond | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 2419 | CMe | NMe | Q1a | a bond | Me | a bond | NH | S | a bond | T3i | OH |
| 2420 | CMe | NMe | Q1a | a bond | Me | a bond | NH | S | a bond | T3j | OH |
| 2421 | CMe | NMe | Q1a | a bond | Me | a bond | NH | O | NH | T3a | OH |
| 2422 | CMe | NMe | Q1a | a bond | Me | a bond | NH | O | NH | T3b | OH |
| 2423 | CMe | NMe | Q1a | a bond | Me | a bond | NH | O | NH | T3c | OH |
| 2424 | CMe | NMe | Q1a | a bond | Me | a bond | NH | O | NH | T3d | OH |
| 2425 | CMe | NMe | Q1a | a bond | Me | a bond | NH | O | NH | T3e | OH |
| 2426 | CMe | NMe | Q1a | a bond | Me | a bond | NH | O | NH | T3f | OH |
| 2427 | CMe | NMe | Q1a | a bond | Me | a bond | NH | O | NH | T3g | OH |
| 2428 | CMe | NMe | Q1a | a bond | Me | a bond | NH | O | NH | T3h | OH |
| 2429 | CMe | NMe | Q1a | a bond | Me | a bond | NH | O | NH | T3i | OH |
| 2430 | CMe | NMe | Q1a | a bond | Me | a bond | NH | O | NH | T3j | OH |
| 2431 | CMe | NMe | Q1a | a bond | Me | a bond | NH | O | a bond | T3a | OH |
| 2432 | CMe | NMe | Q1a | a bond | Me | a bond | NH | O | a bond | T3b | OH |
| 2433 | CMe | NMe | Q1a | a bond | Me | a bond | NH | O | a bond | T3c | OH |
| 2434 | CMe | NMe | Q1a | a bond | Me | a bond | NH | O | a bond | T3d | OH |
| 2435 | CMe | NMe | Q1a | a bond | Me | a bond | NH | O | a bond | T3e | OH |
| 2436 | CMe | NMe | Q1a | a bond | Me | a bond | NH | O | a bond | T3f | OH |
| 2437 | CMe | NMe | Q1a | a bond | Me | a bond | NH | O | a bond | T3g | OH |
| 2438 | CMe | NMe | Q1a | a bond | Me | a bond | NH | O | a bond | T3h | OH |
| 2439 | CMe | NMe | Q1a | a bond | Me | a bond | NH | O | a bond | T3i | OH |
| 2440 | CMe | NMe | Q1a | a bond | Me | a bond | NH | O | a bond | T3j | OH |
| 2441 | CMe | NMe | Q1a | a bond | H | a bond | NH | S | NH | T3a | OH |
| 2442 | CMe | NMe | Q1a | a bond | H | a bond | NH | S | NH | T3b | OH |
| 2443 | CMe | NMe | Q1a | a bond | H | a bond | NH | S | NH | T3c | OH |
| 2444 | CMe | NMe | Q1a | a bond | H | a bond | NH | S | NH | T3d | OH |
| 2445 | CMe | NMe | Q1a | a bond | H | a bond | NH | S | NH | T3e | OH |
| 2446 | CMe | NMe | Q1a | a bond | H | a bond | NH | S | NH | T3f | OH |
| 2447 | CMe | NMe | Q1a | a bond | H | a bond | NH | S | NH | T3g | OH |
| 2448 | CMe | NMe | Q1a | a bond | H | a bond | NH | S | NH | T3h | OH |
| 2449 | CMe | NMe | Q1a | a bond | H | a bond | NH | S | NH | T3i | OH |
| 2450 | CMe | NMe | Q1a | a bond | H | a bond | NH | S | NH | T3j | OH |
| 2451 | CMe | NMe | Q1a | a bond | H | a bond | NH | S | a bond | T3a | OH |
| 2452 | CMe | NMe | Q1a | a bond | H | a bond | NH | S | a bond | T3b | OH |
| 2453 | CMe | NMe | Q1a | a bond | H | a bond | NH | S | a bond | T3c | OH |
| 2454 | CMe | NMe | Q1a | a bond | H | a bond | NH | S | a bond | T3d | OH |
| 2455 | CMe | NMe | Q1a | a bond | H | a bond | NH | S | a bond | T3e | OH |
| 2456 | CMe | NMe | Q1a | a bond | H | a bond | NH | S | a bond | T3f | OH |
| 2457 | CMe | NMe | Q1a | a bond | H | a bond | NH | S | a bond | T3g | OH |
| 2458 | CMe | NMe | Q1a | a bond | H | a bond | NH | S | a bond | T3h | OH |
| 2459 | CMe | NMe | Q1a | a bond | H | a bond | NH | S | a bond | T3i | OH |
| 2460 | CMe | NMe | Q1a | a bond | H | a bond | NH | S | a bond | T3j | OH |
| 2461 | CMe | NMe | Q1a | a bond | H | a bond | NH | O | NH | T3a | OH |
| 2462 | CMe | NMe | Q1a | a bond | H | a bond | NH | O | NH | T3b | OH |
| 2463 | CMe | NMe | Q1a | a bond | H | a bond | NH | O | NH | T3c | OH |
| 2464 | CMe | NMe | Q1a | a bond | H | a bond | NH | O | NH | T3d | OH |
| 2465 | CMe | NMe | Q1a | a bond | H | a bond | NH | O | NH | T3e | OH |
| 2466 | CMe | NMe | Q1a | a bond | H | a bond | NH | O | NH | T3f | OH |
| 2467 | CMe | NMe | Q1a | a bond | H | a bond | NH | O | NH | T3g | OH |
| 2468 | CMe | NMe | Q1a | a bond | H | a bond | NH | O | NH | T3h | OH |
| 2469 | CMe | NMe | Q1a | a bond | H | a bond | NH | O | NH | T3i | OH |
| 2470 | CMe | NMe | Q1a | a bond | H | a bond | NH | O | NH | T3j | OH |
| 2471 | CMe | NMe | Q1a | a bond | H | a bond | NH | O | a bond | T3a | OH |
| 2472 | CMe | NMe | Q1a | a bond | H | a bond | NH | O | a bond | T3b | OH |
| 2473 | CMe | NMe | Q1a | a bond | H | a bond | NH | O | a bond | T3c | OH |
| 2474 | CMe | NMe | Q1a | a bond | H | a bond | NH | O | a bond | T3d | OH |
| 2475 | CMe | NMe | Q1a | a bond | H | a bond | NH | O | a bond | T3e | OH |
| 2476 | CMe | NMe | Q1a | a bond | H | a bond | NH | O | a bond | T3f | OH |
| 2477 | CMe | NMe | Q1a | a bond | H | a bond | NH | O | a bond | T3g | OH |
| 2478 | CMe | NMe | Q1a | a bond | H | a bond | NH | O | a bond | T3h | OH |
| 2479 | CMe | NMe | Q1a | a bond | H | a bond | NH | O | a bond | T3i | OH |
| 2480 | CMe | NMe | Q1a | a bond | H | a bond | NH | O | a bond | T3j | OH |
| 2481 | CMe | NMe | Q1b | a bond | Me | a bond | NH | S | NH | T3a | OH |
| 2482 | CMe | NMe | Q1b | a bond | Me | a bond | NH | S | NH | T3b | OH |
| 2483 | CMe | NMe | Q1b | a bond | Me | a bond | NH | S | NH | T3c | OH |
| 2484 | CMe | NMe | Q1b | a bond | Me | a bond | NH | S | NH | T3d | OH |
| 2485 | CMe | NMe | Q1b | a bond | Me | a bond | NH | S | NH | T3e | OH |
| 2486 | CMe | NMe | Q1b | a bond | Me | a bond | NH | S | NH | T3f | OH |
| 2487 | CMe | NMe | Q1b | a bond | Me | a bond | NH | S | NH | T3g | OH |
| 2488 | CMe | NMe | Q1b | a bond | Me | a bond | NH | S | NH | T3h | OH |
| 2489 | CMe | NMe | Q1b | a bond | Me | a bond | NH | S | NH | T3i | OH |
| 2490 | CMe | NMe | Q1b | a bond | Me | a bond | NH | S | NH | T3j | OH |
| 2491 | CMe | NMe | Q1b | a bond | Me | a bond | NH | S | a bond | T3a | OH |
| 2492 | CMe | NMe | Q1b | a bond | Me | a bond | NH | S | a bond | T3b | OH |
| 2493 | CMe | NMe | Q1b | a bond | Me | a bond | NH | S | a bond | T3c | OH |
| 2494 | CMe | NMe | Q1b | a bond | Me | a bond | NH | S | a bond | T3d | OH |
| 2495 | CMe | NMe | Q1b | a bond | Me | a bond | NH | S | a bond | T3e | OH |
| 2496 | CMe | NMe | Q1b | a bond | Me | a bond | NH | S | a bond | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 2497 | CMe | NMe | Q1b | a bond | Me | a bond | NH | S | a bond | T3g | OH |
| 2498 | CMe | NMe | Q1b | a bond | Me | a bond | NH | S | a bond | T3h | OH |
| 2499 | CMe | NMe | Q1b | a bond | Me | a bond | NH | S | a bond | T3i | OH |
| 2500 | CMe | NMe | Q1b | a bond | Me | a bond | NH | S | a bond | T3j | OH |
| 2501 | CMe | NMe | Q1b | a bond | Me | a bond | NH | O | NH | T3a | OH |
| 2502 | CMe | NMe | Q1b | a bond | Me | a bond | NH | O | NH | T3b | OH |
| 2503 | CMe | NMe | Q1b | a bond | Me | a bond | NH | O | NH | T3c | OH |
| 2504 | CMe | NMe | Q1b | a bond | Me | a bond | NH | O | NH | T3d | OH |
| 2505 | CMe | NMe | Q1b | a bond | Me | a bond | NH | O | NH | T3e | OH |
| 2506 | CMe | NMe | Q1b | a bond | Me | a bond | NH | O | NH | T3f | OH |
| 2507 | CMe | NMe | Q1b | a bond | Me | a bond | NH | O | NH | T3g | OH |
| 2508 | CMe | NMe | Q1b | a bond | Me | a bond | NH | O | NH | T3h | OH |
| 2509 | CMe | NMe | Q1b | a bond | Me | a bond | NH | O | NH | T3i | OH |
| 2510 | CMe | NMe | Q1b | a bond | Me | a bond | NH | O | NH | T3j | OH |
| 2511 | CMe | NMe | Q1b | a bond | Me | a bond | NH | O | a bond | T3a | OH |
| 2512 | CMe | NMe | Q1b | a bond | Me | a bond | NH | O | a bond | T3b | OH |
| 2513 | CMe | NMe | Q1b | a bond | Me | a bond | NH | O | a bond | T3c | OH |
| 2514 | CMe | NMe | Q1b | a bond | Me | a bond | NH | O | a bond | T3d | OH |
| 2515 | CMe | NMe | Q1b | a bond | Me | a bond | NH | O | a bond | T3e | OH |
| 2516 | CMe | NMe | Q1b | a bond | Me | a bond | NH | O | a bond | T3f | OH |
| 2517 | CMe | NMe | Q1b | a bond | Me | a bond | NH | O | a bond | T3g | OH |
| 2518 | CMe | NMe | Q1b | a bond | Me | a bond | NH | O | a bond | T3h | OH |
| 2519 | CMe | NMe | Q1b | a bond | Me | a bond | NH | O | a bond | T3i | OH |
| 2520 | CMe | NMe | Q1b | a bond | Me | a bond | NH | O | a bond | T3j | OH |
| 2521 | CMe | NMe | Q1b | a bond | H | a bond | NH | S | NH | T3a | OH |
| 2522 | CMe | NMe | Q1b | a bond | H | a bond | NH | S | NH | T3b | OH |
| 2523 | CMe | NMe | Q1b | a bond | H | a bond | NH | S | NH | T3c | OH |
| 2524 | CMe | NMe | Q1b | a bond | H | a bond | NH | S | NH | T3d | OH |
| 2525 | CMe | NMe | Q1b | a bond | H | a bond | NH | S | NH | T3e | OH |
| 2526 | CMe | NMe | Q1b | a bond | H | a bond | NH | S | NH | T3f | OH |
| 2527 | CMe | NMe | Q1b | a bond | H | a bond | NH | S | NH | T3g | OH |
| 2528 | CMe | NMe | Q1b | a bond | H | a bond | NH | S | NH | T3h | OH |
| 2529 | CMe | NMe | Q1b | a bond | H | a bond | NH | S | NH | T3i | OH |
| 2530 | CMe | NMe | Q1b | a bond | H | a bond | NH | S | NH | T3j | OH |
| 2531 | CMe | NMe | Q1b | a bond | H | a bond | NH | S | a bond | T3a | OH |
| 2532 | CMe | NMe | Q1b | a bond | H | a bond | NH | S | a bond | T3b | OH |
| 2533 | CMe | NMe | Q1b | a bond | H | a bond | NH | S | a bond | T3c | OH |
| 2534 | CMe | NMe | Q1b | a bond | H | a bond | NH | S | a bond | T3d | OH |
| 2535 | CMe | NMe | Q1b | a bond | H | a bond | NH | S | a bond | T3e | OH |
| 2536 | CMe | NMe | Q1b | a bond | H | a bond | NH | S | a bond | T3f | OH |
| 2537 | CMe | NMe | Q1b | a bond | H | a bond | NH | S | a bond | T3g | OH |
| 2538 | CMe | NMe | Q1b | a bond | H | a bond | NH | S | a bond | T3h | OH |
| 2539 | CMe | NMe | Q1b | a bond | H | a bond | NH | S | a bond | T3i | OH |
| 2540 | CMe | NMe | Q1b | a bond | H | a bond | NH | S | a bond | T3j | OH |
| 2541 | CMe | NMe | Q1b | a bond | H | a bond | NH | O | NH | T3a | OH |
| 2542 | CMe | NMe | Q1b | a bond | H | a bond | NH | O | NH | T3b | OH |
| 2543 | CMe | NMe | Q1b | a bond | H | a bond | NH | O | NH | T3c | OH |
| 2544 | CMe | NMe | Q1b | a bond | H | a bond | NH | O | NH | T3d | OH |
| 2545 | CMe | NMe | Q1b | a bond | H | a bond | NH | O | NH | T3e | OH |
| 2546 | CMe | NMe | Q1b | a bond | H | a bond | NH | O | NH | T3f | OH |
| 2547 | CMe | NMe | Q1b | a bond | H | a bond | NH | O | NH | T3g | OH |
| 2548 | CMe | NMe | Q1b | a bond | H | a bond | NH | O | NH | T3h | OH |
| 2549 | CMe | NMe | Q1b | a bond | H | a bond | NH | O | NH | T3i | OH |
| 2550 | CMe | NMe | Q1b | a bond | H | a bond | NH | O | NH | T3j | OH |
| 2551 | CMe | NMe | Q1b | a bond | H | a bond | NH | O | a bond | T3a | OH |
| 2552 | CMe | NMe | Q1b | a bond | H | a bond | NH | O | a bond | T3b | OH |
| 2553 | CMe | NMe | Q1b | a bond | H | a bond | NH | O | a bond | T3c | OH |
| 2554 | CMe | NMe | Q1b | a bond | H | a bond | NH | O | a bond | T3d | OH |
| 2555 | CMe | NMe | Q1b | a bond | H | a bond | NH | O | a bond | T3e | OH |
| 2556 | CMe | NMe | Q1b | a bond | H | a bond | NH | O | a bond | T3f | OH |
| 2557 | CMe | NMe | Q1b | a bond | H | a bond | NH | O | a bond | T3g | OH |
| 2558 | CMe | NMe | Q1b | a bond | H | a bond | NH | O | a bond | T3h | OH |
| 2559 | CMe | NMe | Q1b | a bond | H | a bond | NH | O | a bond | T3i | OH |
| 2560 | CMe | NMe | Q1b | a bond | H | a bond | NH | O | a bond | T3j | OH |
| 2561 | CMe | NMe | Q1c | a bond | Me | a bond | NH | S | NH | T3a | OH |
| 2562 | CMe | NMe | Q1c | a bond | Me | a bond | NH | S | NH | T3b | OH |
| 2563 | CMe | NMe | Q1c | a bond | Me | a bond | NH | S | NH | T3c | OH |
| 2564 | CMe | NMe | Q1c | a bond | Me | a bond | NH | S | NH | T3d | OH |
| 2565 | CMe | NMe | Q1c | a bond | Me | a bond | NH | S | NH | T3e | OH |
| 2566 | CMe | NMe | Q1c | a bond | Me | a bond | NH | S | NH | T3f | OH |
| 2567 | CMe | NMe | Q1c | a bond | Me | a bond | NH | S | NH | T3g | OH |
| 2568 | CMe | NMe | Q1c | a bond | Me | a bond | NH | S | NH | T3h | OH |
| 2569 | CMe | NMe | Q1c | a bond | Me | a bond | NH | S | NH | T3i | OH |
| 2570 | CMe | NMe | Q1c | a bond | Me | a bond | NH | S | NH | T3j | OH |
| 2571 | CMe | NMe | Q1c | a bond | Me | a bond | NH | S | a bond | T3a | OH |
| 2572 | CMe | NMe | Q1c | a bond | Me | a bond | NH | S | a bond | T3b | OH |
| 2573 | CMe | NMe | Q1c | a bond | Me | a bond | NH | S | a bond | T3c | OH |
| 2574 | CMe | NMe | Q1c | a bond | Me | a bond | NH | S | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 2575 | CMe | NMe | Q1c | a bond | Me | a bond | NH | S | a bond | T3e | OH |
| 2576 | CMe | NMe | Q1c | a bond | Me | a bond | NH | S | a bond | T3f | OH |
| 2577 | CMe | NMe | Q1c | a bond | Me | a bond | NH | S | a bond | T3g | OH |
| 2578 | CMe | NMe | Q1c | a bond | Me | a bond | NH | S | a bond | T3h | OH |
| 2579 | CMe | NMe | Q1c | a bond | Me | a bond | NH | S | a bond | T3i | OH |
| 2580 | CMe | NMe | Q1c | a bond | Me | a bond | NH | S | a bond | T3j | OH |
| 2581 | CMe | NMe | Q1c | a bond | Me | a bond | NH | O | NH | T3a | OH |
| 2582 | CMe | NMe | Q1c | a bond | Me | a bond | NH | O | NH | T3b | OH |
| 2583 | CMe | NMe | Q1c | a bond | Me | a bond | NH | O | NH | T3c | OH |
| 2584 | CMe | NMe | Q1c | a bond | Me | a bond | NH | O | NH | T3d | OH |
| 2585 | CMe | NMe | Q1c | a bond | Me | a bond | NH | O | NH | T3e | OH |
| 2586 | CMe | NMe | Q1c | a bond | Me | a bond | NH | O | NH | T3f | OH |
| 2587 | CMe | NMe | Q1c | a bond | Me | a bond | NH | O | NH | T3g | OH |
| 2588 | CMe | NMe | Q1c | a bond | Me | a bond | NH | O | NH | T3h | OH |
| 2589 | CMe | NMe | Q1c | a bond | Me | a bond | NH | O | NH | T3i | OH |
| 2590 | CMe | NMe | Q1c | a bond | Me | a bond | NH | O | NH | T3j | OH |
| 2591 | CMe | NMe | Q1c | a bond | Me | a bond | NH | O | a bond | T3a | OH |
| 2592 | CMe | NMe | Q1c | a bond | Me | a bond | NH | O | a bond | T3b | OH |
| 2593 | CMe | NMe | Q1c | a bond | Me | a bond | NH | O | a bond | T3c | OH |
| 2594 | CMe | NMe | Q1c | a bond | Me | a bond | NH | O | a bond | T3d | OH |
| 2595 | CMe | NMe | Q1c | a bond | Me | a bond | NH | O | a bond | T3e | OH |
| 2596 | CMe | NMe | Q1c | a bond | Me | a bond | NH | O | a bond | T3f | OH |
| 2597 | CMe | NMe | Q1c | a bond | Me | a bond | NH | O | a bond | T3g | OH |
| 2598 | CMe | NMe | Q1c | a bond | Me | a bond | NH | O | a bond | T3h | OH |
| 2599 | CMe | NMe | Q1c | a bond | Me | a bond | NH | O | a bond | T3i | OH |
| 2600 | CMe | NMe | Q1c | a bond | Me | a bond | NH | O | a bond | T3j | OH |
| 2601 | CMe | NMe | Q1c | a bond | H | a bond | NH | S | NH | T3a | OH |
| 2602 | CMe | NMe | Q1c | a bond | H | a bond | NH | S | NH | T3b | OH |
| 2603 | CMe | NMe | Q1c | a bond | H | a bond | NH | S | NH | T3c | OH |
| 2604 | CMe | NMe | Q1c | a bond | H | a bond | NH | S | NH | T3d | OH |
| 2605 | CMe | NMe | Q1c | a bond | H | a bond | NH | S | NH | T3e | OH |
| 2606 | CMe | NMe | Q1c | a bond | H | a bond | NH | S | NH | T3f | OH |
| 2607 | CMe | NMe | Q1c | a bond | H | a bond | NH | S | NH | T3g | OH |
| 2608 | CMe | NMe | Q1c | a bond | H | a bond | NH | S | NH | T3h | OH |
| 2609 | CMe | NMe | Q1c | a bond | H | a bond | NH | S | NH | T3i | OH |
| 2610 | CMe | NMe | Q1c | a bond | H | a bond | NH | S | NH | T3j | OH |
| 2611 | CMe | NMe | Q1c | a bond | H | a bond | NH | S | a bond | T3a | OH |
| 2612 | CMe | NMe | Q1c | a bond | H | a bond | NH | S | a bond | T3b | OH |
| 2613 | CMe | NMe | Q1c | a bond | H | a bond | NH | S | a bond | T3c | OH |
| 2614 | CMe | NMe | Q1c | a bond | H | a bond | NH | S | a bond | T3d | OH |
| 2615 | CMe | NMe | Q1c | a bond | H | a bond | NH | S | a bond | T3e | OH |
| 2616 | CMe | NMe | Q1c | a bond | H | a bond | NH | S | a bond | T3f | OH |
| 2617 | CMe | NMe | Q1c | a bond | H | a bond | NH | S | a bond | T3g | OH |
| 2618 | CMe | NMe | Q1c | a bond | H | a bond | NH | S | a bond | T3h | OH |
| 2619 | CMe | NMe | Q1c | a bond | H | a bond | NH | S | a bond | T3i | OH |
| 2620 | CMe | NMe | Q1c | a bond | H | a bond | NH | S | a bond | T3j | OH |
| 2621 | CMe | NMe | Q1c | a bond | H | a bond | NH | O | NH | T3a | OH |
| 2622 | CMe | NMe | Q1c | a bond | H | a bond | NH | O | NH | T3b | OH |
| 2623 | CMe | NMe | Q1c | a bond | H | a bond | NH | O | NH | T3c | OH |
| 2624 | CMe | NMe | Q1c | a bond | H | a bond | NH | O | NH | T3d | OH |
| 2625 | CMe | NMe | Q1c | a bond | H | a bond | NH | O | NH | T3e | OH |
| 2626 | CMe | NMe | Q1c | a bond | H | a bond | NH | O | NH | T3f | OH |
| 2627 | CMe | NMe | Q1c | a bond | H | a bond | NH | O | NH | T3g | OH |
| 2628 | CMe | NMe | Q1c | a bond | H | a bond | NH | O | NH | T3h | OH |
| 2629 | CMe | NMe | Q1c | a bond | H | a bond | NH | O | NH | T3i | OH |
| 2630 | CMe | NMe | Q1c | a bond | H | a bond | NH | O | NH | T3j | OH |
| 2631 | CMe | NMe | Q1c | a bond | H | a bond | NH | O | a bond | T3a | OH |
| 2632 | CMe | NMe | Q1c | a bond | H | a bond | NH | O | a bond | T3b | OH |
| 2633 | CMe | NMe | Q1c | a bond | H | a bond | NH | O | a bond | T3c | OH |
| 2634 | CMe | NMe | Q1c | a bond | H | a bond | NH | O | a bond | T3d | OH |
| 2635 | CMe | NMe | Q1c | a bond | H | a bond | NH | O | a bond | T3e | OH |
| 2636 | CMe | NMe | Q1c | a bond | H | a bond | NH | O | a bond | T3f | OH |
| 2637 | CMe | NMe | Q1c | a bond | H | a bond | NH | O | a bond | T3g | OH |
| 2638 | CMe | NMe | Q1c | a bond | H | a bond | NH | O | a bond | T3h | OH |
| 2639 | CMe | NMe | Q1c | a bond | H | a bond | NH | O | a bond | T3i | OH |
| 2640 | CMe | NMe | Q1c | a bond | H | a bond | NH | O | a bond | T3j | OH |
| 2641 | CMe | NMe | Q1i | a bond | Me | a bond | NH | S | NH | T3a | OH |
| 2642 | CMe | NMe | Q1i | a bond | Me | a bond | NH | S | NH | T3b | OH |
| 2643 | CMe | NMe | Q1i | a bond | Me | a bond | NH | S | NH | T3c | OH |
| 2644 | CMe | NMe | Q1i | a bond | Me | a bond | NH | S | NH | T3d | OH |
| 2645 | CMe | NMe | Q1i | a bond | Me | a bond | NH | S | NH | T3e | OH |
| 2646 | CMe | NMe | Q1i | a bond | Me | a bond | NH | S | NH | T3f | OH |
| 2647 | CMe | NMe | Q1i | a bond | Me | a bond | NH | S | NH | T3g | OH |
| 2648 | CMe | NMe | Q1i | a bond | Me | a bond | NH | S | NH | T3h | OH |
| 2649 | CMe | NMe | Q1i | a bond | Me | a bond | NH | S | NH | T3i | OH |
| 2650 | CMe | NMe | Q1i | a bond | Me | a bond | NH | S | NH | T3j | OH |
| 2651 | CMe | NMe | Q1i | a bond | Me | a bond | NH | S | a bond | T3a | OH |
| 2652 | CMe | NMe | Q1i | a bond | Me | a bond | NH | S | a bond | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 2653 | CMe | NMe | Q1i | a bond | Me | a bond | NH | S | a bond | T3c | OH |
| 2654 | CMe | NMe | Q1i | a bond | Me | a bond | NH | S | a bond | T3d | OH |
| 2655 | CMe | NMe | Q1i | a bond | Me | a bond | NH | S | a bond | T3e | OH |
| 2656 | CMe | NMe | Q1i | a bond | Me | a bond | NH | S | a bond | T3f | OH |
| 2657 | CMe | NMe | Q1i | a bond | Me | a bond | NH | S | a bond | T3g | OH |
| 2658 | CMe | NMe | Q1i | a bond | Me | a bond | NH | S | a bond | T3h | OH |
| 2659 | CMe | NMe | Q1i | a bond | Me | a bond | NH | S | a bond | T3i | OH |
| 2660 | CMe | NMe | Q1i | a bond | Me | a bond | NH | S | a bond | T3j | OH |
| 2661 | CMe | NMe | Q1i | a bond | Me | a bond | NH | O | NH | T3a | OH |
| 2662 | CMe | NMe | Q1i | a bond | Me | a bond | NH | O | NH | T3b | OH |
| 2663 | CMe | NMe | Q1i | a bond | Me | a bond | NH | O | NH | T3c | OH |
| 2664 | CMe | NMe | Q1i | a bond | Me | a bond | NH | O | NH | T3d | OH |
| 2665 | CMe | NMe | Q1i | a bond | Me | a bond | NH | O | NH | T3e | OH |
| 2666 | CMe | NMe | Q1i | a bond | Me | a bond | NH | O | NH | T3f | OH |
| 2667 | CMe | NMe | Q1i | a bond | Me | a bond | NH | O | NH | T3g | OH |
| 2668 | CMe | NMe | Q1i | a bond | Me | a bond | NH | O | NH | T3h | OH |
| 2669 | CMe | NMe | Q1i | a bond | Me | a bond | NH | O | NH | T3i | OH |
| 2670 | CMe | NMe | Q1i | a bond | Me | a bond | NH | O | NH | T3j | OH |
| 2671 | CMe | NMe | Q1i | a bond | Me | a bond | NH | O | a bond | T3a | OH |
| 2672 | CMe | NMe | Q1i | a bond | Me | a bond | NH | O | a bond | T3b | OH |
| 2673 | CMe | NMe | Q1i | a bond | Me | a bond | NH | O | a bond | T3c | OH |
| 2674 | CMe | NMe | Q1i | a bond | Me | a bond | NH | O | a bond | T3d | OH |
| 2675 | CMe | NMe | Q1i | a bond | Me | a bond | NH | O | a bond | T3e | OH |
| 2676 | CMe | NMe | Q1i | a bond | Me | a bond | NH | O | a bond | T3f | OH |
| 2677 | CMe | NMe | Q1i | a bond | Me | a bond | NH | O | a bond | T3g | OH |
| 2678 | CMe | NMe | Q1i | a bond | Me | a bond | NH | O | a bond | T3h | OH |
| 2679 | CMe | NMe | Q1i | a bond | Me | a bond | NH | O | a bond | T3i | OH |
| 2680 | CMe | NMe | Q1i | a bond | Me | a bond | NH | O | a bond | T3j | OH |
| 2681 | CMe | NMe | Q1i | a bond | H | a bond | NH | S | NH | T3a | OH |
| 2682 | CMe | NMe | Q1i | a bond | H | a bond | NH | S | NH | T3b | OH |
| 2683 | CMe | NMe | Q1i | a bond | H | a bond | NH | S | NH | T3c | OH |
| 2684 | CMe | NMe | Q1i | a bond | H | a bond | NH | S | NH | T3d | OH |
| 2685 | CMe | NMe | Q1i | a bond | H | a bond | NH | S | NH | T3e | OH |
| 2686 | CMe | NMe | Q1i | a bond | H | a bond | NH | S | NH | T3f | OH |
| 2687 | CMe | NMe | Q1i | a bond | H | a bond | NH | S | NH | T3g | OH |
| 2688 | CMe | NMe | Q1i | a bond | H | a bond | NH | S | NH | T3h | OH |
| 2689 | CMe | NMe | Q1i | a bond | H | a bond | NH | S | NH | T3i | OH |
| 2690 | CMe | NMe | Q1i | a bond | H | a bond | NH | S | NH | T3j | OH |
| 2691 | CMe | NMe | Q1i | a bond | H | a bond | NH | S | a bond | T3a | OH |
| 2692 | CMe | NMe | Q1i | a bond | H | a bond | NH | S | a bond | T3b | OH |
| 2693 | CMe | NMe | Q1i | a bond | H | a bond | NH | S | a bond | T3c | OH |
| 2694 | CMe | NMe | Q1i | a bond | H | a bond | NH | S | a bond | T3d | OH |
| 2695 | CMe | NMe | Q1i | a bond | H | a bond | NH | S | a bond | T3e | OH |
| 2696 | CMe | NMe | Q1i | a bond | H | a bond | NH | S | a bond | T3f | OH |
| 2697 | CMe | NMe | Q1i | a bond | H | a bond | NH | S | a bond | T3g | OH |
| 2698 | CMe | NMe | Q1i | a bond | H | a bond | NH | S | a bond | T3h | OH |
| 2699 | CMe | NMe | Q1i | a bond | H | a bond | NH | S | a bond | T3i | OH |
| 2700 | CMe | NMe | Q1i | a bond | H | a bond | NH | S | a bond | T3j | OH |
| 2701 | CMe | NMe | Q1i | a bond | H | a bond | NH | O | NH | T3a | OH |
| 2702 | CMe | NMe | Q1i | a bond | H | a bond | NH | O | NH | T3b | OH |
| 2703 | CMe | NMe | Q1i | a bond | H | a bond | NH | O | NH | T3c | OH |
| 2704 | CMe | NMe | Q1i | a bond | H | a bond | NH | O | NH | T3d | OH |
| 2705 | CMe | NMe | Q1i | a bond | H | a bond | NH | O | NH | T3e | OH |
| 2706 | CMe | NMe | Q1i | a bond | H | a bond | NH | O | NH | T3f | OH |
| 2707 | CMe | NMe | Q1i | a bond | H | a bond | NH | O | NH | T3g | OH |
| 2708 | CMe | NMe | Q1i | a bond | H | a bond | NH | O | NH | T3h | OH |
| 2709 | CMe | NMe | Q1i | a bond | H | a bond | NH | O | NH | T3i | OH |
| 2710 | CMe | NMe | Q1i | a bond | H | a bond | NH | O | NH | T3j | OH |
| 2711 | CMe | NMe | Q1i | a bond | H | a bond | NH | O | a bond | T3a | OH |
| 2712 | CMe | NMe | Q1i | a bond | H | a bond | NH | O | a bond | T3b | OH |
| 2713 | CMe | NMe | Q1i | a bond | H | a bond | NH | O | a bond | T3c | OH |
| 2714 | CMe | NMe | Q1i | a bond | H | a bond | NH | O | a bond | T3d | OH |
| 2715 | CMe | NMe | Q1i | a bond | H | a bond | NH | O | a bond | T3e | OH |
| 2716 | CMe | NMe | Q1i | a bond | H | a bond | NH | O | a bond | T3f | OH |
| 2717 | CMe | NMe | Q1i | a bond | H | a bond | NH | O | a bond | T3g | OH |
| 2718 | CMe | NMe | Q1i | a bond | H | a bond | NH | O | a bond | T3h | OH |
| 2719 | CMe | NMe | Q1i | a bond | H | a bond | NH | O | a bond | T3i | OH |
| 2720 | CMe | NMe | Q1i | a bond | H | a bond | NH | O | a bond | T3j | OH |
| 2721 | CMe | NMe | Q1j | a bond | Me | a bond | NH | S | NH | T3a | OH |
| 2722 | CMe | NMe | Q1j | a bond | Me | a bond | NH | S | NH | T3b | OH |
| 2723 | CMe | NMe | Q1j | a bond | Me | a bond | NH | S | NH | T3c | OH |
| 2724 | CMe | NMe | Q1j | a bond | Me | a bond | NH | S | NH | T3d | OH |
| 2725 | CMe | NMe | Q1j | a bond | Me | a bond | NH | S | NH | T3e | OH |
| 2726 | CMe | NMe | Q1j | a bond | Me | a bond | NH | S | NH | T3f | OH |
| 2727 | CMe | NMe | Q1j | a bond | Me | a bond | NH | S | NH | T3g | OH |
| 2728 | CMe | NMe | Q1j | a bond | Me | a bond | NH | S | NH | T3h | OH |
| 2729 | CMe | NMe | Q1j | a bond | Me | a bond | NH | S | NH | T3i | OH |
| 2730 | CMe | NMe | Q1j | a bond | Me | a bond | NH | S | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 2731 | CMe | NMe | Q1j | a bond | Me | a bond | NH | S | a bond | T3a | OH |
| 2732 | CMe | NMe | Q1j | a bond | Me | a bond | NH | S | a bond | T3b | OH |
| 2733 | CMe | NMe | Q1j | a bond | Me | a bond | NH | S | a bond | T3c | OH |
| 2734 | CMe | NMe | Q1j | a bond | Me | a bond | NH | S | a bond | T3d | OH |
| 2735 | CMe | NMe | Q1j | a bond | Me | a bond | NH | S | a bond | T3e | OH |
| 2736 | CMe | NMe | Q1j | a bond | Me | a bond | NH | S | a bond | T3f | OH |
| 2737 | CMe | NMe | Q1j | a bond | Me | a bond | NH | S | a bond | T3g | OH |
| 2738 | CMe | NMe | Q1j | a bond | Me | a bond | NH | S | a bond | T3h | OH |
| 2739 | CMe | NMe | Q1j | a bond | Me | a bond | NH | S | a bond | T3i | OH |
| 2740 | CMe | NMe | Q1j | a bond | Me | a bond | NH | S | a bond | T3j | OH |
| 2741 | CMe | NMe | Q1j | a bond | Me | a bond | NH | O | NH | T3a | OH |
| 2742 | CMe | NMe | Q1j | a bond | Me | a bond | NH | O | NH | T3b | OH |
| 2743 | CMe | NMe | Q1j | a bond | Me | a bond | NH | O | NH | T3c | OH |
| 2744 | CMe | NMe | Q1j | a bond | Me | a bond | NH | O | NH | T3d | OH |
| 2745 | CMe | NMe | Q1j | a bond | Me | a bond | NH | O | NH | T3e | OH |
| 2746 | CMe | NMe | Q1j | a bond | Me | a bond | NH | O | NH | T3f | OH |
| 2747 | CMe | NMe | Q1j | a bond | Me | a bond | NH | O | NH | T3g | OH |
| 2748 | CMe | NMe | Q1j | a bond | Me | a bond | NH | O | NH | T3h | OH |
| 2749 | CMe | NMe | Q1j | a bond | Me | a bond | NH | O | NH | T3i | OH |
| 2750 | CMe | NMe | Q1j | a bond | Me | a bond | NH | O | NH | T3j | OH |
| 2751 | CMe | NMe | Q1j | a bond | Me | a bond | NH | O | a bond | T3a | OH |
| 2752 | CMe | NMe | Q1j | a bond | Me | a bond | NH | O | a bond | T3b | OH |
| 2753 | CMe | NMe | Q1j | a bond | Me | a bond | NH | O | a bond | T3c | OH |
| 2754 | CMe | NMe | Q1j | a bond | Me | a bond | NH | O | a bond | T3d | OH |
| 2755 | CMe | NMe | Q1j | a bond | Me | a bond | NH | O | a bond | T3e | OH |
| 2756 | CMe | NMe | Q1j | a bond | Me | a bond | NH | O | a bond | T3f | OH |
| 2757 | CMe | NMe | Q1j | a bond | Me | a bond | NH | O | a bond | T3g | OH |
| 2758 | CMe | NMe | Q1j | a bond | Me | a bond | NH | O | a bond | T3h | OH |
| 2759 | CMe | NMe | Q1j | a bond | Me | a bond | NH | O | a bond | T3i | OH |
| 2760 | CMe | NMe | Q1j | a bond | Me | a bond | NH | O | a bond | T3j | OH |
| 2761 | CMe | NMe | Q1j | a bond | H | a bond | NH | S | NH | T3a | OH |
| 2762 | CMe | NMe | Q1j | a bond | H | a bond | NH | S | NH | T3b | OH |
| 2763 | CMe | NMe | Q1j | a bond | H | a bond | NH | S | NH | T3c | OH |
| 2764 | CMe | NMe | Q1j | a bond | H | a bond | NH | S | NH | T3d | OH |
| 2765 | CMe | NMe | Q1j | a bond | H | a bond | NH | S | NH | T3e | OH |
| 2766 | CMe | NMe | Q1j | a bond | H | a bond | NH | S | NH | T3f | OH |
| 2767 | CMe | NMe | Q1j | a bond | H | a bond | NH | S | NH | T3g | OH |
| 2768 | CMe | NMe | Q1j | a bond | H | a bond | NH | S | NH | T3h | OH |
| 2769 | CMe | NMe | Q1j | a bond | H | a bond | NH | S | NH | T3i | OH |
| 2770 | CMe | NMe | Q1j | a bond | H | a bond | NH | S | NH | T3j | OH |
| 2771 | CMe | NMe | Q1j | a bond | H | a bond | NH | S | a bond | T3a | OH |
| 2772 | CMe | NMe | Q1j | a bond | H | a bond | NH | S | a bond | T3b | OH |
| 2773 | CMe | NMe | Q1j | a bond | H | a bond | NH | S | a bond | T3c | OH |
| 2774 | CMe | NMe | Q1j | a bond | H | a bond | NH | S | a bond | T3d | OH |
| 2775 | CMe | NMe | Q1j | a bond | H | a bond | NH | S | a bond | T3e | OH |
| 2776 | CMe | NMe | Q1j | a bond | H | a bond | NH | S | a bond | T3f | OH |
| 2777 | CMe | NMe | Q1j | a bond | H | a bond | NH | S | a bond | T3g | OH |
| 2778 | CMe | NMe | Q1j | a bond | H | a bond | NH | S | a bond | T3h | OH |
| 2779 | CMe | NMe | Q1j | a bond | H | a bond | NH | S | a bond | T3i | OH |
| 2780 | CMe | NMe | Q1j | a bond | H | a bond | NH | S | a bond | T3j | OH |
| 2781 | CMe | NMe | Q1j | a bond | H | a bond | NH | O | NH | T3a | OH |
| 2782 | CMe | NMe | Q1j | a bond | H | a bond | NH | O | NH | T3b | OH |
| 2783 | CMe | NMe | Q1j | a bond | H | a bond | NH | O | NH | T3c | OH |
| 2784 | CMe | NMe | Q1j | a bond | H | a bond | NH | O | NH | T3d | OH |
| 2785 | CMe | NMe | Q1j | a bond | H | a bond | NH | O | NH | T3e | OH |
| 2786 | CMe | NMe | Q1j | a bond | H | a bond | NH | O | NH | T3f | OH |
| 2787 | CMe | NMe | Q1j | a bond | H | a bond | NH | O | NH | T3g | OH |
| 2788 | CMe | NMe | Q1j | a bond | H | a bond | NH | O | NH | T3h | OH |
| 2789 | CMe | NMe | Q1j | a bond | H | a bond | NH | O | NH | T3i | OH |
| 2790 | CMe | NMe | Q1j | a bond | H | a bond | NH | O | NH | T3j | OH |
| 2791 | CMe | NMe | Q1j | a bond | H | a bond | NH | O | a bond | T3a | OH |
| 2792 | CMe | NMe | Q1j | a bond | H | a bond | NH | O | a bond | T3b | OH |
| 2793 | CMe | NMe | Q1j | a bond | H | a bond | NH | O | a bond | T3c | OH |
| 2794 | CMe | NMe | Q1j | a bond | H | a bond | NH | O | a bond | T3d | OH |
| 2795 | CMe | NMe | Q1j | a bond | H | a bond | NH | O | a bond | T3e | OH |
| 2796 | CMe | NMe | Q1j | a bond | H | a bond | NH | O | a bond | T3f | OH |
| 2797 | CMe | NMe | Q1j | a bond | H | a bond | NH | O | a bond | T3g | OH |
| 2798 | CMe | NMe | Q1j | a bond | H | a bond | NH | O | a bond | T3h | OH |
| 2799 | CMe | NMe | Q1j | a bond | H | a bond | NH | O | a bond | T3i | OH |
| 2800 | CMe | NMe | Q1j | a bond | H | a bond | NH | O | a bond | T3j | OH |
| 2801 | CMe | S | Q1a | a bond | Me | a bond | NH | S | NH | T3a | OH |
| 2802 | CMe | S | Q1a | a bond | Me | a bond | NH | S | NH | T3b | OH |
| 2803 | CMe | S | Q1a | a bond | Me | a bond | NH | S | NH | T3c | OH |
| 2804 | CMe | S | Q1a | a bond | Me | a bond | NH | S | NH | T3d | OH |
| 2805 | CMe | S | Q1a | a bond | Me | a bond | NH | S | NH | T3e | OH |
| 2806 | CMe | S | Q1a | a bond | Me | a bond | NH | S | NH | T3f | OH |
| 2807 | CMe | S | Q1a | a bond | Me | a bond | NH | S | NH | T3g | OH |
| 2808 | CMe | S | Q1a | a bond | Me | a bond | NH | S | NH | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 2809 | CMe | S | Q1a | a bond | Me | a bond | NH | S | NH | T3i | OH |
| 2810 | CMe | S | Q1a | a bond | Me | a bond | NH | S | NH | T3j | OH |
| 2811 | CMe | S | Q1a | a bond | Me | a bond | NH | S | a bond | T3a | OH |
| 2812 | CMe | S | Q1a | a bond | Me | a bond | NH | S | a bond | T3b | OH |
| 2813 | CMe | S | Q1a | a bond | Me | a bond | NH | S | a bond | T3c | OH |
| 2814 | CMe | S | Q1a | a bond | Me | a bond | NH | S | a bond | T3d | OH |
| 2815 | CMe | S | Q1a | a bond | Me | a bond | NH | S | a bond | T3e | OH |
| 2816 | CMe | S | Q1a | a bond | Me | a bond | NH | S | a bond | T3f | OH |
| 2817 | CMe | S | Q1a | a bond | Me | a bond | NH | S | a bond | T3g | OH |
| 2818 | CMe | S | Q1a | a bond | Me | a bond | NH | S | a bond | T3h | OH |
| 2819 | CMe | S | Q1a | a bond | Me | a bond | NH | S | a bond | T3i | OH |
| 2820 | CMe | S | Q1a | a bond | Me | a bond | NH | S | a bond | T3j | OH |
| 2821 | CMe | S | Q1a | a bond | Me | a bond | NH | O | NH | T3a | OH |
| 2822 | CMe | S | Q1a | a bond | Me | a bond | NH | O | NH | T3b | OH |
| 2823 | CMe | S | Q1a | a bond | Me | a bond | NH | O | NH | T3c | OH |
| 2824 | CMe | S | Q1a | a bond | Me | a bond | NH | O | NH | T3d | OH |
| 2825 | CMe | S | Q1a | a bond | Me | a bond | NH | O | NH | T3e | OH |
| 2826 | CMe | S | Q1a | a bond | Me | a bond | NH | O | NH | T3f | OH |
| 2827 | CMe | S | Q1a | a bond | Me | a bond | NH | O | NH | T3g | OH |
| 2828 | CMe | S | Q1a | a bond | Me | a bond | NH | O | NH | T3h | OH |
| 2829 | CMe | S | Q1a | a bond | Me | a bond | NH | O | NH | T3i | OH |
| 2830 | CMe | S | Q1a | a bond | Me | a bond | NH | O | NH | T3j | OH |
| 2831 | CMe | S | Q1a | a bond | Me | a bond | NH | O | a bond | T3a | OH |
| 2832 | CMe | S | Q1a | a bond | Me | a bond | NH | O | a bond | T3b | OH |
| 2833 | CMe | S | Q1a | a bond | Me | a bond | NH | O | a bond | T3c | OH |
| 2834 | CMe | S | Q1a | a bond | Me | a bond | NH | O | a bond | T3d | OH |
| 2835 | CMe | S | Q1a | a bond | Me | a bond | NH | O | a bond | T3e | OH |
| 2836 | CMe | S | Q1a | a bond | Me | a bond | NH | O | a bond | T3f | OH |
| 2837 | CMe | S | Q1a | a bond | Me | a bond | NH | O | a bond | T3g | OH |
| 2838 | CMe | S | Q1a | a bond | Me | a bond | NH | O | a bond | T3h | OH |
| 2839 | CMe | S | Q1a | a bond | Me | a bond | NH | O | a bond | T3i | OH |
| 2840 | CMe | S | Q1a | a bond | Me | a bond | NH | O | a bond | T3j | OH |
| 2841 | CMe | S | Q1a | a bond | H | a bond | NH | S | NH | T3a | OH |
| 2842 | CMe | S | Q1a | a bond | H | a bond | NH | S | NH | T3b | OH |
| 2843 | CMe | S | Q1a | a bond | H | a bond | NH | S | NH | T3c | OH |
| 2844 | CMe | S | Q1a | a bond | H | a bond | NH | S | NH | T3d | OH |
| 2845 | CMe | S | Q1a | a bond | H | a bond | NH | S | NH | T3e | OH |
| 2846 | CMe | S | Q1a | a bond | H | a bond | NH | S | NH | T3f | OH |
| 2847 | CMe | S | Q1a | a bond | H | a bond | NH | S | NH | T3g | OH |
| 2848 | CMe | S | Q1a | a bond | H | a bond | NH | S | NH | T3h | OH |
| 2849 | CMe | S | Q1a | a bond | H | a bond | NH | S | NH | T3i | OH |
| 2850 | CMe | S | Q1a | a bond | H | a bond | NH | S | NH | T3j | OH |
| 2851 | CMe | S | Q1a | a bond | H | a bond | NH | S | a bond | T3a | OH |
| 2852 | CMe | S | Q1a | a bond | H | a bond | NH | S | a bond | T3b | OH |
| 2853 | CMe | S | Q1a | a bond | H | a bond | NH | S | a bond | T3c | OH |
| 2854 | CMe | S | Q1a | a bond | H | a bond | NH | S | a bond | T3d | OH |
| 2855 | CMe | S | Q1a | a bond | H | a bond | NH | S | a bond | T3e | OH |
| 2856 | CMe | S | Q1a | a bond | H | a bond | NH | S | a bond | T3f | OH |
| 2857 | CMe | S | Q1a | a bond | H | a bond | NH | S | a bond | T3g | OH |
| 2858 | CMe | S | Q1a | a bond | H | a bond | NH | S | a bond | T3h | OH |
| 2859 | CMe | S | Q1a | a bond | H | a bond | NH | S | a bond | T3i | OH |
| 2860 | CMe | S | Q1a | a bond | H | a bond | NH | S | a bond | T3j | OH |
| 2861 | CMe | S | Q1a | a bond | H | a bond | NH | O | NH | T3a | OH |
| 2862 | CMe | S | Q1a | a bond | H | a bond | NH | O | NH | T3b | OH |
| 2863 | CMe | S | Q1a | a bond | H | a bond | NH | O | NH | T3c | OH |
| 2864 | CMe | S | Q1a | a bond | H | a bond | NH | O | NH | T3d | OH |
| 2865 | CMe | S | Q1a | a bond | H | a bond | NH | O | NH | T3e | OH |
| 2866 | CMe | S | Q1a | a bond | H | a bond | NH | O | NH | T3f | OH |
| 2867 | CMe | S | Q1a | a bond | H | a bond | NH | O | NH | T3g | OH |
| 2868 | CMe | S | Q1a | a bond | H | a bond | NH | O | NH | T3h | OH |
| 2869 | CMe | S | Q1a | a bond | H | a bond | NH | O | NH | T3i | OH |
| 2870 | CMe | S | Q1a | a bond | H | a bond | NH | O | NH | T3j | OH |
| 2871 | CMe | S | Q1a | a bond | H | a bond | NH | O | a bond | T3a | OH |
| 2872 | CMe | S | Q1a | a bond | H | a bond | NH | O | a bond | T3b | OH |
| 2873 | CMe | S | Q1a | a bond | H | a bond | NH | O | a bond | T3c | OH |
| 2874 | CMe | S | Q1a | a bond | H | a bond | NH | O | a bond | T3d | OH |
| 2875 | CMe | S | Q1a | a bond | H | a bond | NH | O | a bond | T3e | OH |
| 2876 | CMe | S | Q1a | a bond | H | a bond | NH | O | a bond | T3f | OH |
| 2877 | CMe | S | Q1a | a bond | H | a bond | NH | O | a bond | T3g | OH |
| 2878 | CMe | S | Q1a | a bond | H | a bond | NH | O | a bond | T3h | OH |
| 2879 | CMe | S | Q1a | a bond | H | a bond | NH | O | a bond | T3i | OH |
| 2880 | CMe | S | Q1a | a bond | H | a bond | NH | O | a bond | T3j | OH |
| 2881 | CMe | S | Q1b | a bond | Me | a bond | NH | S | NH | T3a | OH |
| 2882 | CMe | S | Q1b | a bond | Me | a bond | NH | S | NH | T3b | OH |
| 2883 | CMe | S | Q1b | a bond | Me | a bond | NH | S | NH | T3c | OH |
| 2884 | CMe | S | Q1b | a bond | Me | a bond | NH | S | NH | T3d | OH |
| 2885 | CMe | S | Q1b | a bond | Me | a bond | NH | S | NH | T3e | OH |
| 2886 | CMe | S | Q1b | a bond | Me | a bond | NH | S | NH | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 2887 | CMe | S | Q1b | a bond | Me | a bond | NH | S | NH | T3g | OH |
| 2888 | CMe | S | Q1b | a bond | Me | a bond | NH | S | NH | T3h | OH |
| 2889 | CMe | S | Q1b | a bond | Me | a bond | NH | S | NH | T3i | OH |
| 2890 | CMe | S | Q1b | a bond | Me | a bond | NH | S | NH | T3j | OH |
| 2891 | CMe | S | Q1b | a bond | Me | a bond | NH | S | a bond | T3a | OH |
| 2892 | CMe | S | Q1b | a bond | Me | a bond | NH | S | a bond | T3b | OH |
| 2893 | CMe | S | Q1b | a bond | Me | a bond | NH | S | a bond | T3c | OH |
| 2894 | CMe | S | Q1b | a bond | Me | a bond | NH | S | a bond | T3d | OH |
| 2895 | CMe | S | Q1b | a bond | Me | a bond | NH | S | a bond | T3e | OH |
| 2896 | CMe | S | Q1b | a bond | Me | a bond | NH | S | a bond | T3f | OH |
| 2897 | CMe | S | Q1b | a bond | Me | a bond | NH | S | a bond | T3g | OH |
| 2898 | CMe | S | Q1b | a bond | Me | a bond | NH | S | a bond | T3h | OH |
| 2899 | CMe | S | Q1b | a bond | Me | a bond | NH | S | a bond | T3i | OH |
| 2900 | CMe | S | Q1b | a bond | Me | a bond | NH | S | a bond | T3j | OH |
| 2901 | CMe | S | Q1b | a bond | Me | a bond | NH | O | NH | T3a | OH |
| 2902 | CMe | S | Q1b | a bond | Me | a bond | NH | O | NH | T3b | OH |
| 2903 | CMe | S | Q1b | a bond | Me | a bond | NH | O | NH | T3c | OH |
| 2904 | CMe | S | Q1b | a bond | Me | a bond | NH | O | NH | T3d | OH |
| 2905 | CMe | S | Q1b | a bond | Me | a bond | NH | O | NH | T3e | OH |
| 2906 | CMe | S | Q1b | a bond | Me | a bond | NH | O | NH | T3f | OH |
| 2907 | CMe | S | Q1b | a bond | Me | a bond | NH | O | NH | T3g | OH |
| 2908 | CMe | S | Q1b | a bond | Me | a bond | NH | O | NH | T3h | OH |
| 2909 | CMe | S | Q1b | a bond | Me | a bond | NH | O | NH | T3i | OH |
| 2910 | CMe | S | Q1b | a bond | Me | a bond | NH | O | NH | T3j | OH |
| 2911 | CMe | S | Q1b | a bond | Me | a bond | NH | O | a bond | T3a | OH |
| 2912 | CMe | S | Q1b | a bond | Me | a bond | NH | O | a bond | T3b | OH |
| 2913 | CMe | S | Q1b | a bond | Me | a bond | NH | O | a bond | T3c | OH |
| 2914 | CMe | S | Q1b | a bond | Me | a bond | NH | O | a bond | T3d | OH |
| 2915 | CMe | S | Q1b | a bond | Me | a bond | NH | O | a bond | T3e | OH |
| 2916 | CMe | S | Q1b | a bond | Me | a bond | NH | O | a bond | T3f | OH |
| 2917 | CMe | S | Q1b | a bond | Me | a bond | NH | O | a bond | T3g | OH |
| 2918 | CMe | S | Q1b | a bond | Me | a bond | NH | O | a bond | T3h | OH |
| 2919 | CMe | S | Q1b | a bond | Me | a bond | NH | O | a bond | T3i | OH |
| 2920 | CMe | S | Q1b | a bond | Me | a bond | NH | O | a bond | T3j | OH |
| 2921 | CMe | S | Q1b | a bond | H | a bond | NH | S | NH | T3a | OH |
| 2922 | CMe | S | Q1b | a bond | H | a bond | NH | S | NH | T3b | OH |
| 2923 | CMe | S | Q1b | a bond | H | a bond | NH | S | NH | T3c | OH |
| 2924 | CMe | S | Q1b | a bond | H | a bond | NH | S | NH | T3d | OH |
| 2925 | CMe | S | Q1b | a bond | H | a bond | NH | S | NH | T3e | OH |
| 2926 | CMe | S | Q1b | a bond | H | a bond | NH | S | NH | T3f | OH |
| 2927 | CMe | S | Q1b | a bond | H | a bond | NH | S | NH | T3g | OH |
| 2928 | CMe | S | Q1b | a bond | H | a bond | NH | S | NH | T3h | OH |
| 2929 | CMe | S | Q1b | a bond | H | a bond | NH | S | NH | T3i | OH |
| 2930 | CMe | S | Q1b | a bond | H | a bond | NH | S | NH | T3j | OH |
| 2931 | CMe | S | Q1b | a bond | H | a bond | NH | S | a bond | T3a | OH |
| 2932 | CMe | S | Q1b | a bond | H | a bond | NH | S | a bond | T3b | OH |
| 2933 | CMe | S | Q1b | a bond | H | a bond | NH | S | a bond | T3c | OH |
| 2934 | CMe | S | Q1b | a bond | H | a bond | NH | S | a bond | T3d | OH |
| 2935 | CMe | S | Q1b | a bond | H | a bond | NH | S | a bond | T3e | OH |
| 2936 | CMe | S | Q1b | a bond | H | a bond | NH | S | a bond | T3f | OH |
| 2937 | CMe | S | Q1b | a bond | H | a bond | NH | S | a bond | T3g | OH |
| 2938 | CMe | S | Q1b | a bond | H | a bond | NH | S | a bond | T3h | OH |
| 2939 | CMe | S | Q1b | a bond | H | a bond | NH | S | a bond | T3i | OH |
| 2940 | CMe | S | Q1b | a bond | H | a bond | NH | S | a bond | T3j | OH |
| 2941 | CMe | S | Q1b | a bond | H | a bond | NH | O | NH | T3a | OH |
| 2942 | CMe | S | Q1b | a bond | H | a bond | NH | O | NH | T3b | OH |
| 2943 | CMe | S | Q1b | a bond | H | a bond | NH | O | NH | T3c | OH |
| 2944 | CMe | S | Q1b | a bond | H | a bond | NH | O | NH | T3d | OH |
| 2945 | CMe | S | Q1b | a bond | H | a bond | NH | O | NH | T3e | OH |
| 2946 | CMe | S | Q1b | a bond | H | a bond | NH | O | NH | T3f | OH |
| 2947 | CMe | S | Q1b | a bond | H | a bond | NH | O | NH | T3g | OH |
| 2948 | CMe | S | Q1b | a bond | H | a bond | NH | O | NH | T3h | OH |
| 2949 | CMe | S | Q1b | a bond | H | a bond | NH | O | NH | T3i | OH |
| 2950 | CMe | S | Q1b | a bond | H | a bond | NH | O | NH | T3j | OH |
| 2951 | CMe | S | Q1b | a bond | H | a bond | NH | O | a bond | T3a | OH |
| 2952 | CMe | S | Q1b | a bond | H | a bond | NH | O | a bond | T3b | OH |
| 2953 | CMe | S | Q1b | a bond | H | a bond | NH | O | a bond | T3c | OH |
| 2954 | CMe | S | Q1b | a bond | H | a bond | NH | O | a bond | T3d | OH |
| 2955 | CMe | S | Q1b | a bond | H | a bond | NH | O | a bond | T3e | OH |
| 2956 | CMe | S | Q1b | a bond | H | a bond | NH | O | a bond | T3f | OH |
| 2957 | CMe | S | Q1b | a bond | H | a bond | NH | O | a bond | T3g | OH |
| 2958 | CMe | S | Q1b | a bond | H | a bond | NH | O | a bond | T3h | OH |
| 2959 | CMe | S | Q1b | a bond | H | a bond | NH | O | a bond | T3i | OH |
| 2960 | CMe | S | Q1b | a bond | H | a bond | NH | O | a bond | T3j | OH |
| 2961 | CMe | S | Q1c | a bond | Me | a bond | NH | S | NH | T3a | OH |
| 2962 | CMe | S | Q1c | a bond | Me | a bond | NH | S | NH | T3b | OH |
| 2963 | CMe | S | Q1c | a bond | Me | a bond | NH | S | NH | T3c | OH |
| 2964 | CMe | S | Q1c | a bond | Me | a bond | NH | S | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 2965 | CMe | S | Q1c | a bond | Me | a bond | NH | S | NH | T3e | OH |
| 2966 | CMe | S | Q1c | a bond | Me | a bond | NH | S | NH | T3f | OH |
| 2967 | CMe | S | Q1c | a bond | Me | a bond | NH | S | NH | T3g | OH |
| 2968 | CMe | S | Q1c | a bond | Me | a bond | NH | S | NH | T3h | OH |
| 2969 | CMe | S | Q1c | a bond | Me | a bond | NH | S | NH | T3i | OH |
| 2970 | CMe | S | Q1c | a bond | Me | a bond | NH | S | NH | T3j | OH |
| 2971 | CMe | S | Q1c | a bond | Me | a bond | NH | S | a bond | T3a | OH |
| 2972 | CMe | S | Q1c | a bond | Me | a bond | NH | S | a bond | T3b | OH |
| 2973 | CMe | S | Q1c | a bond | Me | a bond | NH | S | a bond | T3c | OH |
| 2974 | CMe | S | Q1c | a bond | Me | a bond | NH | S | a bond | T3d | OH |
| 2975 | CMe | S | Q1c | a bond | Me | a bond | NH | S | a bond | T3e | OH |
| 2976 | CMe | S | Q1c | a bond | Me | a bond | NH | S | a bond | T3f | OH |
| 2977 | CMe | S | Q1c | a bond | Me | a bond | NH | S | a bond | T3g | OH |
| 2978 | CMe | S | Q1c | a bond | Me | a bond | NH | S | a bond | T3h | OH |
| 2979 | CMe | S | Q1c | a bond | Me | a bond | NH | S | a bond | T3i | OH |
| 2980 | CMe | S | Q1c | a bond | Me | a bond | NH | S | a bond | T3j | OH |
| 2981 | CMe | S | Q1c | a bond | Me | a bond | NH | O | NH | T3a | OH |
| 2982 | CMe | S | Q1c | a bond | Me | a bond | NH | O | NH | T3b | OH |
| 2983 | CMe | S | Q1c | a bond | Me | a bond | NH | O | NH | T3c | OH |
| 2984 | CMe | S | Q1c | a bond | Me | a bond | NH | O | NH | T3d | OH |
| 2985 | CMe | S | Q1c | a bond | Me | a bond | NH | O | NH | T3e | OH |
| 2986 | CMe | S | Q1c | a bond | Me | a bond | NH | O | NH | T3f | OH |
| 2987 | CMe | S | Q1c | a bond | Me | a bond | NH | O | NH | T3g | OH |
| 2988 | CMe | S | Q1c | a bond | Me | a bond | NH | O | NH | T3h | OH |
| 2989 | CMe | S | Q1c | a bond | Me | a bond | NH | O | NH | T3i | OH |
| 2990 | CMe | S | Q1c | a bond | Me | a bond | NH | O | NH | T3j | OH |
| 2991 | CMe | S | Q1c | a bond | Me | a bond | NH | O | a bond | T3a | OH |
| 2992 | CMe | S | Q1c | a bond | Me | a bond | NH | O | a bond | T3b | OH |
| 2993 | CMe | S | Q1c | a bond | Me | a bond | NH | O | a bond | T3c | OH |
| 2994 | CMe | S | Q1c | a bond | Me | a bond | NH | O | a bond | T3d | OH |
| 2995 | CMe | S | Q1c | a bond | Me | a bond | NH | O | a bond | T3e | OH |
| 2996 | CMe | S | Q1c | a bond | Me | a bond | NH | O | a bond | T3f | OH |
| 2997 | CMe | S | Q1c | a bond | Me | a bond | NH | O | a bond | T3g | OH |
| 2998 | CMe | S | Q1c | a bond | Me | a bond | NH | O | a bond | T3h | OH |
| 2999 | CMe | S | Q1c | a bond | Me | a bond | NH | O | a bond | T3i | OH |
| 3000 | CMe | S | Q1c | a bond | Me | a bond | NH | O | a bond | T3j | OH |
| 3001 | CMe | S | Q1c | a bond | H | a bond | NH | S | NH | T3a | OH |
| 3002 | CMe | S | Q1c | a bond | H | a bond | NH | S | NH | T3b | OH |
| 3003 | CMe | S | Q1c | a bond | H | a bond | NH | S | NH | T3c | OH |
| 3004 | CMe | S | Q1c | a bond | H | a bond | NH | S | NH | T3d | OH |
| 3005 | CMe | S | Q1c | a bond | H | a bond | NH | S | NH | T3e | OH |
| 3006 | CMe | S | Q1c | a bond | H | a bond | NH | S | NH | T3f | OH |
| 3007 | CMe | S | Q1c | a bond | H | a bond | NH | S | NH | T3g | OH |
| 3008 | CMe | S | Q1c | a bond | H | a bond | NH | S | NH | T3h | OH |
| 3009 | CMe | S | Q1c | a bond | H | a bond | NH | S | NH | T3i | OH |
| 3010 | CMe | S | Q1c | a bond | H | a bond | NH | S | NH | T3i | OH |
| 3011 | CMe | S | Q1c | a bond | H | a bond | NH | S | a bond | T3a | OH |
| 3012 | CMe | S | Q1c | a bond | H | a bond | NH | S | a bond | T3b | OH |
| 3013 | CMe | S | Q1c | a bond | H | a bond | NH | S | a bond | T3c | OH |
| 3014 | CMe | S | Q1c | a bond | H | a bond | NH | S | a bond | T3d | OH |
| 3015 | CMe | S | Q1c | a bond | H | a bond | NH | S | a bond | T3e | OH |
| 3016 | CMe | S | Q1c | a bond | H | a bond | NH | S | a bond | T3f | OH |
| 3017 | CMe | S | Q1c | a bond | H | a bond | NH | S | a bond | T3g | OH |
| 3018 | CMe | S | Q1c | a bond | H | a bond | NH | S | a bond | T3h | OH |
| 3019 | CMe | S | Q1c | a bond | H | a bond | NH | S | a bond | T3i | OH |
| 3020 | CMe | S | Q1c | a bond | H | a bond | NH | S | a bond | T3j | OH |
| 3021 | CMe | S | Q1c | a bond | H | a bond | NH | O | NH | T3a | OH |
| 3022 | CMe | S | Q1c | a bond | H | a bond | NH | O | NH | T3b | OH |
| 3023 | CMe | S | Q1c | a bond | H | a bond | NH | O | NH | T3c | OH |
| 3024 | CMe | S | Q1c | a bond | H | a bond | NH | O | NH | T3d | OH |
| 3025 | CMe | S | Q1c | a bond | H | a bond | NH | O | NH | T3e | OH |
| 3026 | CMe | S | Q1c | a bond | H | a bond | NH | O | NH | T3f | OH |
| 3027 | CMe | S | Q1c | a bond | H | a bond | NH | O | NH | T3g | OH |
| 3028 | CMe | S | Q1c | a bond | H | a bond | NH | O | NH | T3h | OH |
| 3029 | CMe | S | Q1c | a bond | H | a bond | NH | O | NH | T3i | OH |
| 3030 | CMe | S | Q1c | a bond | H | a bond | NH | O | NH | T3j | OH |
| 3031 | CMe | S | Q1c | a bond | H | a bond | NH | O | a bond | T3a | OH |
| 3032 | CMe | S | Q1c | a bond | H | a bond | NH | O | a bond | T3b | OH |
| 3033 | CMe | S | Q1c | a bond | H | a bond | NH | O | a bond | T3c | OH |
| 3034 | CMe | S | Q1c | a bond | H | a bond | NH | O | a bond | T3d | OH |
| 3035 | CMe | S | Q1c | a bond | H | a bond | NH | O | a bond | T3e | OH |
| 3036 | CMe | S | Q1c | a bond | H | a bond | NH | O | a bond | T3f | OH |
| 3037 | CMe | S | Q1c | a bond | H | a bond | NH | O | a bond | T3g | OH |
| 3038 | CMe | S | Q1c | a bond | H | a bond | NH | O | a bond | T3h | OH |
| 3039 | CMe | S | Q1c | a bond | H | a bond | NH | O | a bond | T3i | OH |
| 3040 | CMe | S | Q1c | a bond | H | a bond | NH | O | a bond | T3j | OH |
| 3041 | CMe | S | Q1i | a bond | Me | a bond | NH | S | NH | T3a | OH |
| 3042 | CMe | S | Q1i | a bond | Me | a bond | NH | S | NH | T3b | OH |

TABLE 6-continued

| No | A | B | R$^1$ | L$^1$ | R$^2$ | L$^2$ | L$^3$ | Y | L$^4$ | R$^3$ | X |
|---|---|---|---|---|---|---|---|---|---|---|---|
| 3043 | CMe | S | Q1i | a bond | Me | a bond | NH | S | NH | T3c | OH |
| 3044 | CMe | S | Q1i | a bond | Me | a bond | NH | S | NH | T3d | OH |
| 3045 | CMe | S | Q1i | a bond | Me | a bond | NH | S | NH | T3e | OH |
| 3046 | CMe | S | Q1i | a bond | Me | a bond | NH | S | NH | T3f | OH |
| 3047 | CMe | S | Q1i | a bond | Me | a bond | NH | S | NH | T3g | OH |
| 3048 | CMe | S | Q1i | a bond | Me | a bond | NH | S | NH | T3h | OH |
| 3049 | CMe | S | Q1i | a bond | Me | a bond | NH | S | NH | T3i | OH |
| 3050 | CMe | S | Q1i | a bond | Me | a bond | NH | S | NH | T3j | OH |
| 3051 | CMe | S | Q1i | a bond | Me | a bond | NH | S | a bond | T3a | OH |
| 3052 | CMe | S | Q1i | a bond | Me | a bond | NH | S | a bond | T3b | OH |
| 3053 | CMe | S | Q1i | a bond | Me | a bond | NH | S | a bond | T3c | OH |
| 3054 | CMe | S | Q1i | a bond | Me | a bond | NH | S | a bond | T3d | OH |
| 3055 | CMe | S | Q1i | a bond | Me | a bond | NH | S | a bond | T3e | OH |
| 3056 | CMe | S | Q1i | a bond | Me | a bond | NH | S | a bond | T3f | OH |
| 3057 | CMe | S | Q1i | a bond | Me | a bond | NH | S | a bond | T3g | OH |
| 3058 | CMe | S | Q1i | a bond | Me | a bond | NH | S | a bond | T3h | OH |
| 3059 | CMe | S | Q1i | a bond | Me | a bond | NH | S | a bond | T3i | OH |
| 3060 | CMe | S | Q1i | a bond | Me | a bond | NH | S | a bond | T3j | OH |
| 3061 | CMe | S | Q1i | a bond | Me | a bond | NH | O | NH | T3a | OH |
| 3062 | CMe | S | Q1i | a bond | Me | a bond | NH | O | NH | T3b | OH |
| 3063 | CMe | S | Q1i | a bond | Me | a bond | NH | O | NH | T3c | OH |
| 3064 | CMe | S | Q1i | a bond | Me | a bond | NH | O | NH | T3d | OH |
| 3065 | CMe | S | Q1i | a bond | Me | a bond | NH | O | NH | T3e | OH |
| 3066 | CMe | S | Q1i | a bond | Me | a bond | NH | O | NH | T3f | OH |
| 3067 | CMe | S | Q1i | a bond | Me | a bond | NH | O | NH | T3g | OH |
| 3068 | CMe | S | Q1i | a bond | Me | a bond | NH | O | NH | T3h | OH |
| 3069 | CMe | S | Q1i | a bond | Me | a bond | NH | O | NH | T3i | OH |
| 3070 | CMe | S | Q1i | a bond | Me | a bond | NH | O | NH | T3j | OH |
| 3071 | CMe | S | Q1i | a bond | Me | a bond | NH | O | a bond | T3a | OH |
| 3072 | CMe | S | Q1i | a bond | Me | a bond | NH | O | a bond | T3b | OH |
| 3073 | CMe | S | Q1i | a bond | Me | a bond | NH | O | a bond | T3c | OH |
| 3074 | CMe | S | Q1i | a bond | Me | a bond | NH | O | a bond | T3d | OH |
| 3075 | CMe | S | Q1i | a bond | Me | a bond | NH | O | a bond | T3e | OH |
| 3076 | CMe | S | Q1i | a bond | Me | a bond | NH | O | a bond | T3f | OH |
| 3077 | CMe | S | Q1i | a bond | Me | a bond | NH | O | a bond | T3g | OH |
| 3078 | CMe | S | Q1i | a bond | Me | a bond | NH | O | a bond | T3h | OH |
| 3079 | CMe | S | Q1i | a bond | Me | a bond | NH | O | a bond | T3i | OH |
| 3080 | CMe | S | Q1i | a bond | Me | a bond | NH | O | a bond | T3j | OH |
| 3081 | CMe | S | Q1i | a bond | H | a bond | NH | S | NH | T3a | OH |
| 3082 | CMe | S | Q1i | a bond | H | a bond | NH | S | NH | T3b | OH |
| 3083 | CMe | S | Q1i | a bond | H | a bond | NH | S | NH | T3c | OH |
| 3084 | CMe | S | Q1i | a bond | H | a bond | NH | S | NH | T3d | OH |
| 3085 | CMe | S | Q1i | a bond | H | a bond | NH | S | NH | T3e | OH |
| 3086 | CMe | S | Q1i | a bond | H | a bond | NH | S | NH | T3f | OH |
| 3087 | CMe | S | Q1i | a bond | H | a bond | NH | S | NH | T3g | OH |
| 3088 | CMe | S | Q1i | a bond | H | a bond | NH | S | NH | T3h | OH |
| 3089 | CMe | S | Q1i | a bond | H | a bond | NH | S | NH | T3i | OH |
| 3090 | CMe | S | Q1i | a bond | H | a bond | NH | S | NH | T3j | OH |
| 3091 | CMe | S | Q1i | a bond | H | a bond | NH | S | a bond | T3a | OH |
| 3092 | CMe | S | Q1i | a bond | H | a bond | NH | S | a bond | T3b | OH |
| 3093 | CMe | S | Q1i | a bond | H | a bond | NH | S | a bond | T3c | OH |
| 3094 | CMe | S | Q1i | a bond | H | a bond | NH | S | a bond | T3d | OH |
| 3095 | CMe | S | Q1i | a bond | H | a bond | NH | S | a bond | T3e | OH |
| 3096 | CMe | S | Q1i | a bond | H | a bond | NH | S | a bond | T3f | OH |
| 3097 | CMe | S | Q1i | a bond | H | a bond | NH | S | a bond | T3g | OH |
| 3098 | CMe | S | Q1i | a bond | H | a bond | NH | S | a bond | T3h | OH |
| 3099 | CMe | S | Q1i | a bond | H | a bond | NH | S | a bond | T3i | OH |
| 3100 | CMe | S | Q1i | a bond | H | a bond | NH | S | a bond | T3j | OH |
| 3101 | CMe | S | Q1i | a bond | H | a bond | NH | O | NH | T3a | OH |
| 3102 | CMe | S | Q1i | a bond | H | a bond | NH | O | NH | T3b | OH |
| 3103 | CMe | S | Q1i | a bond | H | a bond | NH | O | NH | T3c | OH |
| 3104 | CMe | S | Q1i | a bond | H | a bond | NH | O | NH | T3d | OH |
| 3105 | CMe | S | Q1i | a bond | H | a bond | NH | O | NH | T3e | OH |
| 3106 | CMe | S | Q1i | a bond | H | a bond | NH | O | NH | T3f | OH |
| 3107 | CMe | S | Q1i | a bond | H | a bond | NH | O | NH | T3g | OH |
| 3108 | CMe | S | Q1i | a bond | H | a bond | NH | O | NH | T3h | OH |
| 3109 | CMe | S | Q1i | a bond | H | a bond | NH | O | NH | T3i | OH |
| 3110 | CMe | S | Q1i | a bond | H | a bond | NH | O | NH | T3j | OH |
| 3111 | CMe | S | Q1i | a bond | H | a bond | NH | O | a bond | T3a | OH |
| 3112 | CMe | S | Q1i | a bond | H | a bond | NH | O | a bond | T3b | OH |
| 3113 | CMe | S | Q1i | a bond | H | a bond | NH | O | a bond | T3c | OH |
| 3114 | CMe | S | Q1i | a bond | H | a bond | NH | O | a bond | T3d | OH |
| 3115 | CMe | S | Q1i | a bond | H | a bond | NH | O | a bond | T3e | OH |
| 3116 | CMe | S | Q1i | a bond | H | a bond | NH | O | a bond | T3f | OH |
| 3117 | CMe | S | Q1i | a bond | H | a bond | NH | O | a bond | T3g | OH |
| 3118 | CMe | S | Q1i | a bond | H | a bond | NH | O | a bond | T3h | OH |
| 3119 | CMe | S | Q1i | a bond | H | a bond | NH | O | a bond | T3i | OH |
| 3120 | CMe | S | Q1i | a bond | H | a bond | NH | O | a bond | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 3121 | CMe | S | Q1j | a bond | Me | a bond | NH | S | NH | T3a | OH |
| 3122 | CMe | S | Q1j | a bond | Me | a bond | NH | S | NH | T3b | OH |
| 3123 | CMe | S | Q1j | a bond | Me | a bond | NH | S | NH | T3c | OH |
| 3124 | CMe | S | Q1j | a bond | Me | a bond | NH | S | NH | T3d | OH |
| 3125 | CMe | S | Q1j | a bond | Me | a bond | NH | S | NH | T3e | OH |
| 3126 | CMe | S | Q1j | a bond | Me | a bond | NH | S | NH | T3f | OH |
| 3127 | CMe | S | Q1j | a bond | Me | a bond | NH | S | NH | T3g | OH |
| 3128 | CMe | S | Q1j | a bond | Me | a bond | NH | S | NH | T3h | OH |
| 3129 | CMe | S | Q1j | a bond | Me | a bond | NH | S | NH | T3i | OH |
| 3130 | CMe | S | Q1j | a bond | Me | a bond | NH | S | NH | T3j | OH |
| 3131 | CMe | S | Q1j | a bond | Me | a bond | NH | S | a bond | T3a | OH |
| 3132 | CMe | S | Q1j | a bond | Me | a bond | NH | S | a bond | T3b | OH |
| 3133 | CMe | S | Q1j | a bond | Me | a bond | NH | S | a bond | T3c | OH |
| 3134 | CMe | S | Q1j | a bond | Me | a bond | NH | S | a bond | T3d | OH |
| 3135 | CMe | S | Q1j | a bond | Me | a bond | NH | S | a bond | T3e | OH |
| 3136 | CMe | S | Q1j | a bond | Me | a bond | NH | S | a bond | T3f | OH |
| 3137 | CMe | S | Q1j | a bond | Me | a bond | NH | S | a bond | T3g | OH |
| 3138 | CMe | S | Q1j | a bond | Me | a bond | NH | S | a bond | T3h | OH |
| 3139 | CMe | S | Q1j | a bond | Me | a bond | NH | S | a bond | T3i | OH |
| 3140 | CMe | S | Q1j | a bond | Me | a bond | NH | S | a bond | T3j | OH |
| 3141 | CMe | S | Q1j | a bond | Me | a bond | NH | O | NH | T3a | OH |
| 3142 | CMe | S | Q1j | a bond | Me | a bond | NH | O | NH | T3b | OH |
| 3143 | CMe | S | Q1j | a bond | Me | a bond | NH | O | NH | T3c | OH |
| 3144 | CMe | S | Q1j | a bond | Me | a bond | NH | O | NH | T3d | OH |
| 3145 | CMe | S | Q1j | a bond | Me | a bond | NH | O | NH | T3e | OH |
| 3146 | CMe | S | Q1j | a bond | Me | a bond | NH | O | NH | T3f | OH |
| 3147 | CMe | S | Q1j | a bond | Me | a bond | NH | O | NH | T3g | OH |
| 3148 | CMe | S | Q1j | a bond | Me | a bond | NH | O | NH | T3h | OH |
| 3149 | CMe | S | Q1j | a bond | Me | a bond | NH | O | NH | T3i | OH |
| 3150 | CMe | S | Q1j | a bond | Me | a bond | NH | O | NH | T3j | OH |
| 3151 | CMe | S | Q1j | a bond | Me | a bond | NH | O | a bond | T3a | OH |
| 3152 | CMe | S | Q1j | a bond | Me | a bond | NH | O | a bond | T3b | OH |
| 3153 | CMe | S | Q1j | a bond | Me | a bond | NH | O | a bond | T3c | OH |
| 3154 | CMe | S | Q1j | a bond | Me | a bond | NH | O | a bond | T3d | OH |
| 3155 | CMe | S | Q1j | a bond | Me | a bond | NH | O | a bond | T3e | OH |
| 3156 | CMe | S | Q1j | a bond | Me | a bond | NH | O | a bond | T3f | OH |
| 3157 | CMe | S | Q1j | a bond | Me | a bond | NH | O | a bond | T3g | OH |
| 3158 | CMe | S | Q1j | a bond | Me | a bond | NH | O | a bond | T3h | OH |
| 3159 | CMe | S | Q1j | a bond | Me | a bond | NH | O | a bond | T3i | OH |
| 3160 | CMe | S | Q1j | a bond | Me | a bond | NH | O | a bond | T3j | OH |
| 3161 | CMe | S | Q1j | a bond | H | a bond | NH | S | NH | T3a | OH |
| 3162 | CMe | S | Q1j | a bond | H | a bond | NH | S | NH | T3b | OH |
| 3163 | CMe | S | Q1j | a bond | H | a bond | NH | S | NH | T3c | OH |
| 3164 | CMe | S | Q1j | a bond | H | a bond | NH | S | NH | T3d | OH |
| 3165 | CMe | S | Q1j | a bond | H | a bond | NH | S | NH | T3e | OH |
| 3166 | CMe | S | Q1j | a bond | H | a bond | NH | S | NH | T3f | OH |
| 3167 | CMe | S | Q1j | a bond | H | a bond | NH | S | NH | T3g | OH |
| 3168 | CMe | S | Q1j | a bond | H | a bond | NH | S | NH | T3h | OH |
| 3169 | CMe | S | Q1j | a bond | H | a bond | NH | S | NH | T3i | OH |
| 3170 | CMe | S | Q1j | a bond | H | a bond | NH | S | NH | T3j | OH |
| 3171 | CMe | S | Q1j | a bond | H | a bond | NH | S | a bond | T3a | OH |
| 3172 | CMe | S | Q1j | a bond | H | a bond | NH | S | a bond | T3b | OH |
| 3173 | CMe | S | Q1j | a bond | H | a bond | NH | S | a bond | T3c | OH |
| 3174 | CMe | S | Q1j | a bond | H | a bond | NH | S | a bond | T3d | OH |
| 3175 | CMe | S | Q1j | a bond | H | a bond | NH | S | a bond | T3e | OH |
| 3176 | CMe | S | Q1j | a bond | H | a bond | NH | S | a bond | T3f | OH |
| 3177 | CMe | S | Q1j | a bond | H | a bond | NH | S | a bond | T3g | OH |
| 3178 | CMe | S | Q1j | a bond | H | a bond | NH | S | a bond | T3h | OH |
| 3179 | CMe | S | Q1j | a bond | H | a bond | NH | S | a bond | T3i | OH |
| 3180 | CMe | S | Q1j | a bond | H | a bond | NH | S | a bond | T3j | OH |
| 3181 | CMe | S | Q1j | a bond | H | a bond | NH | O | NH | T3a | OH |
| 3182 | CMe | S | Q1j | a bond | H | a bond | NH | O | NH | T3b | OH |
| 3183 | CMe | S | Q1j | a bond | H | a bond | NH | O | NH | T3c | OH |
| 3184 | CMe | S | Q1j | a bond | H | a bond | NH | O | NH | T3d | OH |
| 3185 | CMe | S | Q1j | a bond | H | a bond | NH | O | NH | T3e | OH |
| 3186 | CMe | S | Q1j | a bond | H | a bond | NH | O | NH | T3f | OH |
| 3187 | CMe | S | Q1j | a bond | H | a bond | NH | O | NH | T3g | OH |
| 3188 | CMe | S | Q1j | a bond | H | a bond | NH | O | NH | T3h | OH |
| 3189 | CMe | S | Q1j | a bond | H | a bond | NH | O | NH | T3i | OH |
| 3190 | CMe | S | Q1j | a bond | H | a bond | NH | O | NH | T3j | OH |
| 3191 | CMe | S | Q1j | a bond | H | a bond | NH | O | a bond | T3a | OH |
| 3192 | CMe | S | Q1j | a bond | H | a bond | NH | O | a bond | T3b | OH |
| 3193 | CMe | S | Q1j | a bond | H | a bond | NH | O | a bond | T3c | OH |
| 3194 | CMe | S | Q1j | a bond | H | a bond | NH | O | a bond | T3d | OH |
| 3195 | CMe | S | Q1j | a bond | H | a bond | NH | O | a bond | T3e | OH |
| 3196 | CMe | S | Q1j | a bond | H | a bond | NH | O | a bond | T3f | OH |
| 3197 | CMe | S | Q1j | a bond | H | a bond | NH | O | a bond | T3g | OH |
| 3198 | CMe | S | Q1j | a bond | H | a bond | NH | O | a bond | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 3199 | CMe | S | Q1j | a bond | H | a bond | NH | O | a bond | T3i | OH |
| 3200 | CMe | S | Q1j | a bond | H | a bond | NH | O | a bond | T3j | OH |
| 3201 | CMe | O | Q1a | a bond | Me | a bond | NH | S | NH | T3a | OH |
| 3202 | CMe | O | Q1a | a bond | Me | a bond | NH | S | NH | T3b | OH |
| 3203 | CMe | O | Q1a | a bond | Me | a bond | NH | S | NH | T3c | OH |
| 3204 | CMe | O | Q1a | a bond | Me | a bond | NH | S | NH | T3d | OH |
| 3205 | CMe | O | Q1a | a bond | Me | a bond | NH | S | NH | T3e | OH |
| 3206 | CMe | O | Q1a | a bond | Me | a bond | NH | S | NH | T3f | OH |
| 3207 | CMe | O | Q1a | a bond | Me | a bond | NH | S | NH | T3g | OH |
| 3208 | CMe | O | Q1a | a bond | Me | a bond | NH | S | NH | T3h | OH |
| 3209 | CMe | O | Q1a | a bond | Me | a bond | NH | S | NH | T3i | OH |
| 3210 | CMe | O | Q1a | a bond | Me | a bond | NH | S | NH | T3j | OH |
| 3211 | CMe | O | Q1a | a bond | Me | a bond | NH | S | a bond | T3a | OH |
| 3212 | CMe | O | Q1a | a bond | Me | a bond | NH | S | a bond | T3b | OH |
| 3213 | CMe | O | Q1a | a bond | Me | a bond | NH | S | a bond | T3c | OH |
| 3214 | CMe | O | Q1a | a bond | Me | a bond | NH | S | a bond | T3d | OH |
| 3215 | CMe | O | Q1a | a bond | Me | a bond | NH | S | a bond | T3e | OH |
| 3216 | CMe | O | Q1a | a bond | Me | a bond | NH | S | a bond | T3f | OH |
| 3217 | CMe | O | Q1a | a bond | Me | a bond | NH | S | a bond | T3g | OH |
| 3218 | CMe | O | Q1a | a bond | Me | a bond | NH | S | a bond | T3h | OH |
| 3219 | CMe | O | Q1a | a bond | Me | a bond | NH | S | a bond | T3i | OH |
| 3220 | CMe | O | Q1a | a bond | Me | a bond | NH | S | a bond | T3j | OH |
| 3221 | CMe | O | Q1a | a bond | Me | a bond | NH | O | NH | T3a | OH |
| 3222 | CMe | O | Q1a | a bond | Me | a bond | NH | O | NH | T3b | OH |
| 3223 | CMe | O | Q1a | a bond | Me | a bond | NH | O | NH | T3c | OH |
| 3224 | CMe | O | Q1a | a bond | Me | a bond | NH | O | NH | T3d | OH |
| 3225 | CMe | O | Q1a | a bond | Me | a bond | NH | O | NH | T3e | OH |
| 3226 | CMe | O | Q1a | a bond | Me | a bond | NH | O | NH | T3f | OH |
| 3227 | CMe | O | Q1a | a bond | Me | a bond | NH | O | NH | T3g | OH |
| 3228 | CMe | O | Q1a | a bond | Me | a bond | NH | O | NH | T3h | OH |
| 3229 | CMe | O | Q1a | a bond | Me | a bond | NH | O | NH | T3i | OH |
| 3230 | CMe | O | Q1a | a bond | Me | a bond | NH | O | NH | T3j | OH |
| 3231 | CMe | O | Q1a | a bond | Me | a bond | NH | O | a bond | T3a | OH |
| 3232 | CMe | O | Q1a | a bond | Me | a bond | NH | O | a bond | T3b | OH |
| 3233 | CMe | O | Q1a | a bond | Me | a bond | NH | O | a bond | T3c | OH |
| 3234 | CMe | O | Q1a | a bond | Me | a bond | NH | O | a bond | T3d | OH |
| 3235 | CMe | O | Q1a | a bond | Me | a bond | NH | O | a bond | T3e | OH |
| 3236 | CMe | O | Q1a | a bond | Me | a bond | NH | O | a bond | T3f | OH |
| 3237 | CMe | O | Q1a | a bond | Me | a bond | NH | O | a bond | T3g | OH |
| 3238 | CMe | O | Q1a | a bond | Me | a bond | NH | O | a bond | T3h | OH |
| 3239 | CMe | O | Q1a | a bond | Me | a bond | NH | O | a bond | T3i | OH |
| 3240 | CMe | O | Q1a | a bond | Me | a bond | NH | O | a bond | T3j | OH |
| 3241 | CMe | O | Q1a | a bond | H | a bond | NH | S | NH | T3a | OH |
| 3242 | CMe | O | Q1a | a bond | H | a bond | NH | S | NH | T3b | OH |
| 3243 | CMe | O | Q1a | a bond | H | a bond | NH | S | NH | T3c | OH |
| 3244 | CMe | O | Q1a | a bond | H | a bond | NH | S | NH | T3d | OH |
| 3245 | CMe | O | Q1a | a bond | H | a bond | NH | S | NH | T3e | OH |
| 3246 | CMe | O | Q1a | a bond | H | a bond | NH | S | NH | T3f | OH |
| 3247 | CMe | O | Q1a | a bond | H | a bond | NH | S | NH | T3g | OH |
| 3248 | CMe | O | Q1a | a bond | H | a bond | NH | S | NH | T3h | OH |
| 3249 | CMe | O | Q1a | a bond | H | a bond | NH | S | NH | T3i | OH |
| 3250 | CMe | O | Q1a | a bond | H | a bond | NH | S | NH | T3j | OH |
| 3251 | CMe | O | Q1a | a bond | H | a bond | NH | S | a bond | T3a | OH |
| 3252 | CMe | O | Q1a | a bond | H | a bond | NH | S | a bond | T3b | OH |
| 3253 | CMe | O | Q1a | a bond | H | a bond | NH | S | a bond | T3c | OH |
| 3254 | CMe | O | Q1a | a bond | H | a bond | NH | S | a bond | T3d | OH |
| 3255 | CMe | O | Q1a | a bond | H | a bond | NH | S | a bond | T3e | OH |
| 3256 | CMe | O | Q1a | a bond | H | a bond | NH | S | a bond | T3f | OH |
| 3257 | CMe | O | Q1a | a bond | H | a bond | NH | S | a bond | T3g | OH |
| 3258 | CMe | O | Q1a | a bond | H | a bond | NH | S | a bond | T3h | OH |
| 3259 | CMe | O | Q1a | a bond | H | a bond | NH | S | a bond | T3i | OH |
| 3260 | CMe | O | Q1a | a bond | H | a bond | NH | S | a bond | T3j | OH |
| 3261 | CMe | O | Q1a | a bond | H | a bond | NH | O | NH | T3a | OH |
| 3262 | CMe | O | Q1a | a bond | H | a bond | NH | O | NH | T3b | OH |
| 3263 | CMe | O | Q1a | a bond | H | a bond | NH | O | NH | T3c | OH |
| 3264 | CMe | O | Q1a | a bond | H | a bond | NH | O | NH | T3d | OH |
| 3265 | CMe | O | Q1a | a bond | H | a bond | NH | O | NH | T3e | OH |
| 3266 | CMe | O | Q1a | a bond | H | a bond | NH | O | NH | T3f | OH |
| 3267 | CMe | O | Q1a | a bond | H | a bond | NH | O | NH | T3g | OH |
| 3268 | CMe | O | Q1a | a bond | H | a bond | NH | O | NH | T3h | OH |
| 3269 | CMe | O | Q1a | a bond | H | a bond | NH | O | NH | T3i | OH |
| 3270 | CMe | O | Q1a | a bond | H | a bond | NH | O | NH | T3j | OH |
| 3271 | CMe | O | Q1a | a bond | H | a bond | NH | O | a bond | T3a | OH |
| 3272 | CMe | O | Q1a | a bond | H | a bond | NH | O | a bond | T3b | OH |
| 3273 | CMe | O | Q1a | a bond | H | a bond | NH | O | a bond | T3c | OH |
| 3274 | CMe | O | Q1a | a bond | H | a bond | NH | O | a bond | T3d | OH |
| 3275 | CMe | O | Q1a | a bond | H | a bond | NH | O | a bond | T3e | OH |
| 3276 | CMe | O | Q1a | a bond | H | a bond | NH | O | a bond | T3f | OH |

TABLE 6-continued

| No | A | B | R¹ | L¹ | R² | L² | L³ | Y | L⁴ | R³ | X |
|---|---|---|---|---|---|---|---|---|---|---|---|
| 3277 | CMe | O | Q1a | a bond | H | a bond | NH | O | a bond | T3g | OH |
| 3278 | CMe | O | Q1a | a bond | H | a bond | NH | O | a bond | T3h | OH |
| 3279 | CMe | O | Q1a | a bond | H | a bond | NH | O | a bond | T3i | OH |
| 3280 | CMe | O | Q1a | a bond | H | a bond | NH | O | a bond | T3j | OH |
| 3281 | CMe | O | Q1b | a bond | Me | a bond | NH | S | NH | T3a | OH |
| 3282 | CMe | O | Q1b | a bond | Me | a bond | NH | S | NH | T3b | OH |
| 3283 | CMe | O | Q1b | a bond | Me | a bond | NH | S | NH | T3c | OH |
| 3284 | CMe | O | Q1b | a bond | Me | a bond | NH | S | NH | T3d | OH |
| 3285 | CMe | O | Q1b | a bond | Me | a bond | NH | S | NH | T3e | OH |
| 3286 | CMe | O | Q1b | a bond | Me | a bond | NH | S | NH | T3f | OH |
| 3287 | CMe | O | Q1b | a bond | Me | a bond | NH | S | NH | T3g | OH |
| 3288 | CMe | O | Q1b | a bond | Me | a bond | NH | S | NH | T3h | OH |
| 3289 | CMe | O | Q1b | a bond | Me | a bond | NH | S | NH | T3i | OH |
| 3290 | CMe | O | Q1b | a bond | Me | a bond | NH | S | NH | T3j | OH |
| 3291 | CMe | O | Q1b | a bond | Me | a bond | NH | S | a bond | T3a | OH |
| 3292 | CMe | O | Q1b | a bond | Me | a bond | NH | S | a bond | T3b | OH |
| 3293 | CMe | O | Q1b | a bond | Me | a bond | NH | S | a bond | T3c | OH |
| 3294 | CMe | O | Q1b | a bond | Me | a bond | NH | S | a bond | T3d | OH |
| 3295 | CMe | O | Q1b | a bond | Me | a bond | NH | S | a bond | T3e | OH |
| 3296 | CMe | O | Q1b | a bond | Me | a bond | NH | S | a bond | T3f | OH |
| 3297 | CMe | O | Q1b | a bond | Me | a bond | NH | S | a bond | T3g | OH |
| 3298 | CMe | O | Q1b | a bond | Me | a bond | NH | S | a bond | T3h | OH |
| 3299 | CMe | O | Q1b | a bond | Me | a bond | NH | S | a bond | T3i | OH |
| 3300 | CMe | O | Q1b | a bond | Me | a bond | NH | S | a bond | T3j | OH |
| 3301 | CMe | O | Q1b | a bond | Me | a bond | NH | O | NH | T3a | OH |
| 3302 | CMe | O | Q1b | a bond | Me | a bond | NH | O | NH | T3b | OH |
| 3303 | CMe | O | Q1b | a bond | Me | a bond | NH | O | NH | T3c | OH |
| 3304 | CMe | O | Q1b | a bond | Me | a bond | NH | O | NH | T3d | OH |
| 3305 | CMe | O | Q1b | a bond | Me | a bond | NH | O | NH | T3e | OH |
| 3306 | CMe | O | Q1b | a bond | Me | a bond | NH | O | NH | T3f | OH |
| 3307 | CMe | O | Q1b | a bond | Me | a bond | NH | O | NH | T3g | OH |
| 3308 | CMe | O | Q1b | a bond | Me | a bond | NH | O | NH | T3h | OH |
| 3309 | CMe | O | Q1b | a bond | Me | a bond | NH | O | NH | T3i | OH |
| 3310 | CMe | O | Q1b | a bond | Me | a bond | NH | O | NH | T3j | OH |
| 3311 | CMe | O | Q1b | a bond | Me | a bond | NH | O | a bond | T3a | OH |
| 3312 | CMe | O | Q1b | a bond | Me | a bond | NH | O | a bond | T3b | OH |
| 3313 | CMe | O | Q1b | a bond | Me | a bond | NH | O | a bond | T3c | OH |
| 3314 | CMe | O | Q1b | a bond | Me | a bond | NH | O | a bond | T3d | OH |
| 3315 | CMe | O | Q1b | a bond | Me | a bond | NH | O | a bond | T3e | OH |
| 3316 | CMe | O | Q1b | a bond | Me | a bond | NH | O | a bond | T3f | OH |
| 3317 | CMe | O | Q1b | a bond | Me | a bond | NH | O | a bond | T3g | OH |
| 3318 | CMe | O | Q1b | a bond | Me | a bond | NH | O | a bond | T3h | OH |
| 3319 | CMe | O | Q1b | a bond | Me | a bond | NH | O | a bond | T3i | OH |
| 3320 | CMe | O | Q1b | a bond | Me | a bond | NH | O | a bond | T3j | OH |
| 3321 | CMe | O | Q1b | a bond | H | a bond | NH | S | NH | T3a | OH |
| 3322 | CMe | O | Q1b | a bond | H | a bond | NH | S | NH | T3b | OH |
| 3323 | CMe | O | Q1b | a bond | H | a bond | NH | S | NH | T3c | OH |
| 3324 | CMe | O | Q1b | a bond | H | a bond | NH | S | NH | T3d | OH |
| 3325 | CMe | O | Q1b | a bond | H | a bond | NH | S | NH | T3e | OH |
| 3326 | CMe | O | Q1b | a bond | H | a bond | NH | S | NH | T3f | OH |
| 3327 | CMe | O | Q1b | a bond | H | a bond | NH | S | NH | T3g | OH |
| 3328 | CMe | O | Q1b | a bond | H | a bond | NH | S | NH | T3h | OH |
| 3329 | CMe | O | Q1b | a bond | H | a bond | NH | S | NH | T3i | OH |
| 3330 | CMe | O | Q1b | a bond | H | a bond | NH | S | NH | T3j | OH |
| 3331 | CMe | O | Q1b | a bond | H | a bond | NH | S | a bond | T3a | OH |
| 3332 | CMe | O | Q1b | a bond | H | a bond | NH | S | a bond | T3b | OH |
| 3333 | CMe | O | Q1b | a bond | H | a bond | NH | S | a bond | T3c | OH |
| 3334 | CMe | O | Q1b | a bond | H | a bond | NH | S | a bond | T3d | OH |
| 3335 | CMe | O | Q1b | a bond | H | a bond | NH | S | a bond | T3e | OH |
| 3336 | CMe | O | Q1b | a bond | H | a bond | NH | S | a bond | T3f | OH |
| 3337 | CMe | O | Q1b | a bond | H | a bond | NH | S | a bond | T3g | OH |
| 3338 | CMe | O | Q1b | a bond | H | a bond | NH | S | a bond | T3h | OH |
| 3339 | CMe | O | Q1b | a bond | H | a bond | NH | S | a bond | T3i | OH |
| 3340 | CMe | O | Q1b | a bond | H | a bond | NH | S | a bond | T3j | OH |
| 3341 | CMe | O | Q1b | a bond | H | a bond | NH | O | NH | T3a | OH |
| 3342 | CMe | O | Q1b | a bond | H | a bond | NH | O | NH | T3b | OH |
| 3343 | CMe | O | Q1b | a bond | H | a bond | NH | O | NH | T3c | OH |
| 3344 | CMe | O | Q1b | a bond | H | a bond | NH | O | NH | T3d | OH |
| 3345 | CMe | O | Q1b | a bond | H | a bond | NH | O | NH | T3e | OH |
| 3346 | CMe | O | Q1b | a bond | H | a bond | NH | O | NH | T3f | OH |
| 3347 | CMe | O | Q1b | a bond | H | a bond | NH | O | NH | T3g | OH |
| 3348 | CMe | O | Q1b | a bond | H | a bond | NH | O | NH | T3h | OH |
| 3349 | CMe | O | Q1b | a bond | H | a bond | NH | O | NH | T3i | OH |
| 3350 | CMe | O | Q1b | a bond | H | a bond | NH | O | NH | T3j | OH |
| 3351 | CMe | O | Q1b | a bond | H | a bond | NH | O | a bond | T3a | OH |
| 3352 | CMe | O | Q1b | a bond | H | a bond | NH | O | a bond | T3b | OH |
| 3353 | CMe | O | Q1b | a bond | H | a bond | NH | O | a bond | T3c | OH |
| 3354 | CMe | O | Q1b | a bond | H | a bond | NH | O | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 3355 | CMe | O | Q1b | a bond | H | a bond | NH | O | a bond | T3e | OH |
| 3356 | CMe | O | Q1b | a bond | H | a bond | NH | O | a bond | T3f | OH |
| 3357 | CMe | O | Q1b | a bond | H | a bond | NH | O | a bond | T3g | OH |
| 3358 | CMe | O | Q1b | a bond | H | a bond | NH | O | a bond | T3h | OH |
| 3359 | CMe | O | Q1b | a bond | H | a bond | NH | O | a bond | T3i | OH |
| 3360 | CMe | O | Q1b | a bond | H | a bond | NH | O | a bond | T3j | OH |
| 3361 | CMe | O | Q1c | a bond | Me | a bond | NH | S | NH | T3a | OH |
| 3362 | CMe | O | Q1c | a bond | Me | a bond | NH | S | NH | T3b | OH |
| 3363 | CMe | O | Q1c | a bond | Me | a bond | NH | S | NH | T3c | OH |
| 3364 | CMe | O | Q1c | a bond | Me | a bond | NH | S | NH | T3d | OH |
| 3365 | CMe | O | Q1c | a bond | Me | a bond | NH | S | NH | T3e | OH |
| 3366 | CMe | O | Q1c | a bond | Me | a bond | NH | S | NH | T3f | OH |
| 3367 | CMe | O | Q1c | a bond | Me | a bond | NH | S | NH | T3g | OH |
| 3368 | CMe | O | Q1c | a bond | Me | a bond | NH | S | NH | T3h | OH |
| 3369 | CMe | O | Q1c | a bond | Me | a bond | NH | S | NH | T3i | OH |
| 3370 | CMe | O | Q1c | a bond | Me | a bond | NH | S | NH | T3j | OH |
| 3371 | CMe | O | Q1c | a bond | Me | a bond | NH | S | a bond | T3a | OH |
| 3372 | CMe | O | Q1c | a bond | Me | a bond | NH | S | a bond | T3b | OH |
| 3373 | CMe | O | Q1c | a bond | Me | a bond | NH | S | a bond | T3c | OH |
| 3374 | CMe | O | Q1c | a bond | Me | a bond | NH | S | a bond | T3d | OH |
| 3375 | CMe | O | Q1c | a bond | Me | a bond | NH | S | a bond | T3e | OH |
| 3376 | CMe | O | Q1c | a bond | Me | a bond | NH | S | a bond | T3f | OH |
| 3377 | CMe | O | Q1c | a bond | Me | a bond | NH | S | a bond | T3g | OH |
| 3378 | CMe | O | Q1c | a bond | Me | a bond | NH | S | a bond | T3h | OH |
| 3379 | CMe | O | Q1c | a bond | Me | a bond | NH | S | a bond | T3i | OH |
| 3380 | CMe | O | Q1c | a bond | Me | a bond | NH | S | a bond | T3j | OH |
| 3381 | CMe | O | Q1c | a bond | Me | a bond | NH | O | NH | T3a | OH |
| 3382 | CMe | O | Q1c | a bond | Me | a bond | NH | O | NH | T3b | OH |
| 3383 | CMe | O | Q1c | a bond | Me | a bond | NH | O | NH | T3c | OH |
| 3384 | CMe | O | Q1c | a bond | Me | a bond | NH | O | NH | T3d | OH |
| 3385 | CMe | O | Q1c | a bond | Me | a bond | NH | O | NH | T3e | OH |
| 3386 | CMe | O | Q1c | a bond | Me | a bond | NH | O | NH | T3f | OH |
| 3387 | CMe | O | Q1c | a bond | Me | a bond | NH | O | NH | T3g | OH |
| 3388 | CMe | O | Q1c | a bond | Me | a bond | NH | O | NH | T3h | OH |
| 3389 | CMe | O | Q1c | a bond | Me | a bond | NH | O | NH | T3i | OH |
| 3390 | CMe | O | Q1c | a bond | Me | a bond | NH | O | NH | T3j | OH |
| 3391 | CMe | O | Q1c | a bond | Me | a bond | NH | O | a bond | T3a | OH |
| 3392 | CMe | O | Q1c | a bond | Me | a bond | NH | O | a bond | T3b | OH |
| 3393 | CMe | O | Q1c | a bond | Me | a bond | NH | O | a bond | T3c | OH |
| 3394 | CMe | O | Q1c | a bond | Me | a bond | NH | O | a bond | T3d | OH |
| 3395 | CMe | O | Q1c | a bond | Me | a bond | NH | O | a bond | T3e | OH |
| 3396 | CMe | O | Q1c | a bond | Me | a bond | NH | O | a bond | T3f | OH |
| 3397 | CMe | O | Q1c | a bond | Me | a bond | NH | O | a bond | T3g | OH |
| 3398 | CMe | O | Q1c | a bond | Me | a bond | NH | O | a bond | T3h | OH |
| 3399 | CMe | O | Q1c | a bond | Me | a bond | NH | O | a bond | T3i | OH |
| 3400 | CMe | O | Q1c | a bond | Me | a bond | NH | O | a bond | T3j | OH |
| 3401 | CMe | O | Q1c | a bond | H | a bond | NH | S | NH | T3a | OH |
| 3402 | CMe | O | Q1c | a bond | H | a bond | NH | S | NH | T3b | OH |
| 3403 | CMe | O | Q1c | a bond | H | a bond | NH | S | NH | T3c | OH |
| 3404 | CMe | O | Q1c | a bond | H | a bond | NH | S | NH | T3d | OH |
| 3405 | CMe | O | Q1c | a bond | H | a bond | NH | S | NH | T3e | OH |
| 3406 | CMe | O | Q1c | a bond | H | a bond | NH | S | NH | T3f | OH |
| 3407 | CMe | O | Q1c | a bond | H | a bond | NH | S | NH | T3g | OH |
| 3408 | CMe | O | Q1c | a bond | H | a bond | NH | S | NH | T3h | OH |
| 3409 | CMe | O | Q1c | a bond | H | a bond | NH | S | NH | T3i | OH |
| 3410 | CMe | O | Q1c | a bond | H | a bond | NH | S | NH | T3j | OH |
| 3411 | CMe | O | Q1c | a bond | H | a bond | NH | S | a bond | T3a | OH |
| 3412 | CMe | O | Q1c | a bond | H | a bond | NH | S | a bond | T3b | OH |
| 3413 | CMe | O | Q1c | a bond | H | a bond | NH | S | a bond | T3c | OH |
| 3414 | CMe | O | Q1c | a bond | H | a bond | NH | S | a bond | T3d | OH |
| 3415 | CMe | O | Q1c | a bond | H | a bond | NH | S | a bond | T3e | OH |
| 3416 | CMe | O | Q1c | a bond | H | a bond | NH | S | a bond | T3f | OH |
| 3417 | CMe | O | Q1c | a bond | H | a bond | NH | S | a bond | T3g | OH |
| 3418 | CMe | O | Q1c | a bond | H | a bond | NH | S | a bond | T3h | OH |
| 3419 | CMe | O | Q1c | a bond | H | a bond | NH | S | a bond | T3i | OH |
| 3420 | CMe | O | Q1c | a bond | H | a bond | NH | S | a bond | T3j | OH |
| 3421 | CMe | O | Q1c | a bond | H | a bond | NH | O | NH | T3a | OH |
| 3422 | CMe | O | Q1c | a bond | H | a bond | NH | O | NH | T3b | OH |
| 3423 | CMe | O | Q1c | a bond | H | a bond | NH | O | NH | T3c | OH |
| 3424 | CMe | O | Q1c | a bond | H | a bond | NH | O | NH | T3d | OH |
| 3425 | CMe | O | Q1c | a bond | H | a bond | NH | O | NH | T3e | OH |
| 3426 | CMe | O | Q1c | a bond | H | a bond | NH | O | NH | T3f | OH |
| 3427 | CMe | O | Q1c | a bond | H | a bond | NH | O | NH | T3g | OH |
| 3428 | CMe | O | Q1c | a bond | H | a bond | NH | O | NH | T3h | OH |
| 3429 | CMe | O | Q1c | a bond | H | a bond | NH | O | NH | T3i | OH |
| 3430 | CMe | O | Q1c | a bond | H | a bond | NH | O | NH | T3j | OH |
| 3431 | CMe | O | Q1c | a bond | H | a bond | NH | O | a bond | T3a | OH |
| 3432 | CMe | O | Q1c | a bond | H | a bond | NH | O | a bond | T3b | OH |

TABLE 6-continued

| No | A | B | R¹ | L¹ | R² | L² | L³ | Y | L⁴ | R³ | X |
|---|---|---|---|---|---|---|---|---|---|---|---|
| 3433 | CMe | O | Q1c | a bond | H | a bond | NH | O | a bond | T3c | OH |
| 3434 | CMe | O | Q1c | a bond | H | a bond | NH | O | a bond | T3d | OH |
| 3435 | CMe | O | Q1c | a bond | H | a bond | NH | O | a bond | T3e | OH |
| 3436 | CMe | O | Q1c | a bond | H | a bond | NH | O | a bond | T3f | OH |
| 3437 | CMe | O | Q1c | a bond | H | a bond | NH | O | a bond | T3g | OH |
| 3438 | CMe | O | Q1c | a bond | H | a bond | NH | O | a bond | T3h | OH |
| 3439 | CMe | O | Q1c | a bond | H | a bond | NH | O | a bond | T3i | OH |
| 3440 | CMe | O | Q1c | a bond | H | a bond | NH | O | a bond | T3j | OH |
| 3441 | CMe | O | Q1i | a bond | Me | a bond | NH | S | NH | T3a | OH |
| 3442 | CMe | O | Q1i | a bond | Me | a bond | NH | S | NH | T3b | OH |
| 3443 | CMe | O | Q1i | a bond | Me | a bond | NH | S | NH | T3c | OH |
| 3444 | CMe | O | Q1i | a bond | Me | a bond | NH | S | NH | T3d | OH |
| 3445 | CMe | O | Q1i | a bond | Me | a bond | NH | S | NH | T3e | OH |
| 3446 | CMe | O | Q1i | a bond | Me | a bond | NH | S | NH | T3f | OH |
| 3447 | CMe | O | Q1i | a bond | Me | a bond | NH | S | NH | T3g | OH |
| 3448 | CMe | O | Q1i | a bond | Me | a bond | NH | S | NH | T3h | OH |
| 3449 | CMe | O | Q1i | a bond | Me | a bond | NH | S | NH | T3i | OH |
| 3450 | CMe | O | Q1i | a bond | Me | a bond | NH | S | NH | T3j | OH |
| 3451 | CMe | O | Q1i | a bond | Me | a bond | NH | S | a bond | T3a | OH |
| 3452 | CMe | O | Q1i | a bond | Me | a bond | NH | S | a bond | T3b | OH |
| 3453 | CMe | O | Q1i | a bond | Me | a bond | NH | S | a bond | T3c | OH |
| 3454 | CMe | O | Q1i | a bond | Me | a bond | NH | S | a bond | T3d | OH |
| 3455 | CMe | O | Q1i | a bond | Me | a bond | NH | S | a bond | T3e | OH |
| 3456 | CMe | O | Q1i | a bond | Me | a bond | NH | S | a bond | T3f | OH |
| 3457 | CMe | O | Q1i | a bond | Me | a bond | NH | S | a bond | T3g | OH |
| 3458 | CMe | O | Q1i | a bond | Me | a bond | NH | S | a bond | T3h | OH |
| 3459 | CMe | O | Q1i | a bond | Me | a bond | NH | S | a bond | T3i | OH |
| 3460 | CMe | O | Q1i | a bond | Me | a bond | NH | S | a bond | T3j | OH |
| 3461 | CMe | O | Q1i | a bond | Me | a bond | NH | O | NH | T3a | OH |
| 3462 | CMe | O | Q1i | a bond | Me | a bond | NH | O | NH | T3b | OH |
| 3463 | CMe | O | Q1i | a bond | Me | a bond | NH | O | NH | T3c | OH |
| 3464 | CMe | O | Q1i | a bond | Me | a bond | NH | O | NH | T3d | OH |
| 3465 | CMe | O | Q1i | a bond | Me | a bond | NH | O | NH | T3e | OH |
| 3466 | CMe | O | Q1i | a bond | Me | a bond | NH | O | NH | T3f | OH |
| 3467 | CMe | O | Q1i | a bond | Me | a bond | NH | O | NH | T3g | OH |
| 3468 | CMe | O | Q1i | a bond | Me | a bond | NH | O | NH | T3h | OH |
| 3469 | CMe | O | Q1i | a bond | Me | a bond | NH | O | NH | T3i | OH |
| 3470 | CMe | O | Q1i | a bond | Me | a bond | NH | O | NH | T3j | OH |
| 3471 | CMe | O | Q1i | a bond | Me | a bond | NH | O | a bond | T3a | OH |
| 3472 | CMe | O | Q1i | a bond | Me | a bond | NH | O | a bond | T3b | OH |
| 3473 | CMe | O | Q1i | a bond | Me | a bond | NH | O | a bond | T3c | OH |
| 3474 | CMe | O | Q1i | a bond | Me | a bond | NH | O | a bond | T3d | OH |
| 3475 | CMe | O | Q1i | a bond | Me | a bond | NH | O | a bond | T3e | OH |
| 3476 | CMe | O | Q1i | a bond | Me | a bond | NH | O | a bond | T3f | OH |
| 3477 | CMe | O | Q1i | a bond | Me | a bond | NH | O | a bond | T3g | OH |
| 3478 | CMe | O | Q1i | a bond | Me | a bond | NH | O | a bond | T3h | OH |
| 3479 | CMe | O | Q1i | a bond | Me | a bond | NH | O | a bond | T3i | OH |
| 3480 | CMe | O | Q1i | a bond | Me | a bond | NH | O | a bond | T3j | OH |
| 3481 | CMe | O | Q1i | a bond | H | a bond | NH | S | NH | T3a | OH |
| 3482 | CMe | O | Q1i | a bond | H | a bond | NH | S | NH | T3b | OH |
| 3483 | CMe | O | Q1i | a bond | H | a bond | NH | S | NH | T3c | OH |
| 3484 | CMe | O | Q1i | a bond | H | a bond | NH | S | NH | T3d | OH |
| 3485 | CMe | O | Q1i | a bond | H | a bond | NH | S | NH | T3e | OH |
| 3486 | CMe | O | Q1i | a bond | H | a bond | NH | S | NH | T3f | OH |
| 3487 | CMe | O | Q1i | a bond | H | a bond | NH | S | NH | T3g | OH |
| 3488 | CMe | O | Q1i | a bond | H | a bond | NH | S | NH | T3h | OH |
| 3489 | CMe | O | Q1i | a bond | H | a bond | NH | S | NH | T3i | OH |
| 3490 | CMe | O | Q1i | a bond | H | a bond | NH | S | NH | T3j | OH |
| 3491 | CMe | O | Q1i | a bond | H | a bond | NH | S | a bond | T3a | OH |
| 3492 | CMe | O | Q1i | a bond | H | a bond | NH | S | a bond | T3b | OH |
| 3493 | CMe | O | Q1i | a bond | H | a bond | NH | S | a bond | T3c | OH |
| 3494 | CMe | O | Q1i | a bond | H | a bond | NH | S | a bond | T3d | OH |
| 3495 | CMe | O | Q1i | a bond | H | a bond | NH | S | a bond | T3e | OH |
| 3496 | CMe | O | Q1i | a bond | H | a bond | NH | S | a bond | T3f | OH |
| 3497 | CMe | O | Q1i | a bond | H | a bond | NH | S | a bond | T3g | OH |
| 3498 | CMe | O | Q1i | a bond | H | a bond | NH | S | a bond | T3h | OH |
| 3499 | CMe | O | Q1i | a bond | H | a bond | NH | S | a bond | T3i | OH |
| 3500 | CMe | O | Q1i | a bond | H | a bond | NH | S | a bond | T3j | OH |
| 3501 | CMe | O | Q1i | a bond | H | a bond | NH | O | NH | T3a | OH |
| 3502 | CMe | O | Q1i | a bond | H | a bond | NH | O | NH | T3b | OH |
| 3503 | CMe | O | Q1i | a bond | H | a bond | NH | O | NH | T3c | OH |
| 3504 | CMe | O | Q1i | a bond | H | a bond | NH | O | NH | T3d | OH |
| 3505 | CMe | O | Q1i | a bond | H | a bond | NH | O | NH | T3e | OH |
| 3506 | CMe | O | Q1i | a bond | H | a bond | NH | O | NH | T3f | OH |
| 3507 | CMe | O | Q1i | a bond | H | a bond | NH | O | NH | T3g | OH |
| 3508 | CMe | O | Q1i | a bond | H | a bond | NH | O | NH | T3h | OH |
| 3509 | CMe | O | Q1i | a bond | H | a bond | NH | O | NH | T3i | OH |
| 3510 | CMe | O | Q1i | a bond | H | a bond | NH | O | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 3511 | CMe | O | Q1i | a bond | H | a bond | NH | O | a bond | T3a | OH |
| 3512 | CMe | O | Q1i | a bond | H | a bond | NH | O | a bond | T3b | OH |
| 3513 | CMe | O | Q1i | a bond | H | a bond | NH | O | a bond | T3c | OH |
| 3514 | CMe | O | Q1i | a bond | H | a bond | NH | O | a bond | T3d | OH |
| 3515 | CMe | O | Q1i | a bond | H | a bond | NH | O | a bond | T3e | OH |
| 3516 | CMe | O | Q1i | a bond | H | a bond | NH | O | a bond | T3f | OH |
| 3517 | CMe | O | Q1i | a bond | H | a bond | NH | O | a bond | T3g | OH |
| 3518 | CMe | O | Q1i | a bond | H | a bond | NH | O | a bond | T3h | OH |
| 3519 | CMe | O | Q1i | a bond | H | a bond | NH | O | a bond | T3i | OH |
| 3520 | CMe | O | Q1i | a bond | H | a bond | NH | O | a bond | T3j | OH |
| 3521 | CMe | O | Q1j | a bond | Me | a bond | NH | S | NH | T3a | OH |
| 3522 | CMe | O | Q1j | a bond | Me | a bond | NH | S | NH | T3b | OH |
| 3523 | CMe | O | Q1j | a bond | Me | a bond | NH | S | NH | T3c | OH |
| 3524 | CMe | O | Q1j | a bond | Me | a bond | NH | S | NH | T3d | OH |
| 3525 | CMe | O | Q1j | a bond | Me | a bond | NH | S | NH | T3e | OH |
| 3526 | CMe | O | Q1j | a bond | Me | a bond | NH | S | NH | T3f | OH |
| 3527 | CMe | O | Q1j | a bond | Me | a bond | NH | S | NH | T3g | OH |
| 3528 | CMe | O | Q1j | a bond | Me | a bond | NH | S | NH | T3h | OH |
| 3529 | CMe | O | Q1j | a bond | Me | a bond | NH | S | NH | T3i | OH |
| 3530 | CMe | O | Q1j | a bond | Me | a bond | NH | S | NH | T3j | OH |
| 3531 | CMe | O | Q1j | a bond | Me | a bond | NH | S | a bond | T3a | OH |
| 3532 | CMe | O | Q1j | a bond | Me | a bond | NH | S | a bond | T3b | OH |
| 3533 | CMe | O | Q1j | a bond | Me | a bond | NH | S | a bond | T3c | OH |
| 3534 | CMe | O | Q1j | a bond | Me | a bond | NH | S | a bond | T3d | OH |
| 3535 | CMe | O | Q1j | a bond | Me | a bond | NH | S | a bond | T3e | OH |
| 3536 | CMe | O | Q1j | a bond | Me | a bond | NH | S | a bond | T3f | OH |
| 3537 | CMe | O | Q1j | a bond | Me | a bond | NH | S | a bond | T3g | OH |
| 3538 | CMe | O | Q1j | a bond | Me | a bond | NH | S | a bond | T3h | OH |
| 3539 | CMe | O | Q1j | a bond | Me | a bond | NH | S | a bond | T3i | OH |
| 3540 | CMe | O | Q1j | a bond | Me | a bond | NH | S | a bond | T3j | OH |
| 3541 | CMe | O | Q1j | a bond | Me | a bond | NH | O | NH | T3a | OH |
| 3542 | CMe | O | Q1j | a bond | Me | a bond | NH | O | NH | T3b | OH |
| 3543 | CMe | O | Q1j | a bond | Me | a bond | NH | O | NH | T3c | OH |
| 3544 | CMe | O | Q1j | a bond | Me | a bond | NH | O | NH | T3d | OH |
| 3545 | CMe | O | Q1j | a bond | Me | a bond | NH | O | NH | T3e | OH |
| 3546 | CMe | O | Q1j | a bond | Me | a bond | NH | O | NH | T3f | OH |
| 3547 | CMe | O | Q1j | a bond | Me | a bond | NH | O | NH | T3g | OH |
| 3548 | CMe | O | Q1j | a bond | Me | a bond | NH | O | NH | T3h | OH |
| 3549 | CMe | O | Q1j | a bond | Me | a bond | NH | O | NH | T3i | OH |
| 3550 | CMe | O | Q1j | a bond | Me | a bond | NH | O | NH | T3j | OH |
| 3551 | CMe | O | Q1j | a bond | Me | a bond | NH | O | a bond | T3a | OH |
| 3552 | CMe | O | Q1j | a bond | Me | a bond | NH | O | a bond | T3b | OH |
| 3553 | CMe | O | Q1j | a bond | Me | a bond | NH | O | a bond | T3c | OH |
| 3554 | CMe | O | Q1j | a bond | Me | a bond | NH | O | a bond | T3d | OH |
| 3555 | CMe | O | Q1j | a bond | Me | a bond | NH | O | a bond | T3e | OH |
| 3556 | CMe | O | Q1j | a bond | Me | a bond | NH | O | a bond | T3f | OH |
| 3557 | CMe | O | Q1j | a bond | Me | a bond | NH | O | a bond | T3g | OH |
| 3558 | CMe | O | Q1j | a bond | Me | a bond | NH | O | a bond | T3h | OH |
| 3559 | CMe | O | Q1j | a bond | Me | a bond | NH | O | a bond | T3i | OH |
| 3560 | CMe | O | Q1j | a bond | Me | a bond | NH | O | a bond | T3j | OH |
| 3561 | CMe | O | Q1j | a bond | H | a bond | NH | S | NH | T3a | OH |
| 3562 | CMe | O | Q1j | a bond | H | a bond | NH | S | NH | T3b | OH |
| 3563 | CMe | O | Q1j | a bond | H | a bond | NH | S | NH | T3c | OH |
| 3564 | CMe | O | Q1j | a bond | H | a bond | NH | S | NH | T3d | OH |
| 3565 | CMe | O | Q1j | a bond | H | a bond | NH | S | NH | T3e | OH |
| 3566 | CMe | O | Q1j | a bond | H | a bond | NH | S | NH | T3f | OH |
| 3567 | CMe | O | Q1j | a bond | H | a bond | NH | S | NH | T3g | OH |
| 3568 | CMe | O | Q1j | a bond | H | a bond | NH | S | NH | T3h | OH |
| 3569 | CMe | O | Q1j | a bond | H | a bond | NH | S | NH | T3i | OH |
| 3570 | CMe | O | Q1j | a bond | H | a bond | NH | S | NH | T3j | OH |
| 3571 | CMe | O | Q1j | a bond | H | a bond | NH | S | a bond | T3a | OH |
| 3572 | CMe | O | Q1j | a bond | H | a bond | NH | S | a bond | T3b | OH |
| 3573 | CMe | O | Q1j | a bond | H | a bond | NH | S | a bond | T3c | OH |
| 3574 | CMe | O | Q1j | a bond | H | a bond | NH | S | a bond | T3d | OH |
| 3575 | CMe | O | Q1j | a bond | H | a bond | NH | S | a bond | T3e | OH |
| 3576 | CMe | O | Q1j | a bond | H | a bond | NH | S | a bond | T3f | OH |
| 3577 | CMe | O | Q1j | a bond | H | a bond | NH | S | a bond | T3g | OH |
| 3578 | CMe | O | Q1j | a bond | H | a bond | NH | S | a bond | T3h | OH |
| 3579 | CMe | O | Q1j | a bond | H | a bond | NH | S | a bond | T3i | OH |
| 3580 | CMe | O | Q1j | a bond | H | a bond | NH | S | a bond | T3j | OH |
| 3581 | CMe | O | Q1j | a bond | H | a bond | NH | O | NH | T3a | OH |
| 3582 | CMe | O | Q1j | a bond | H | a bond | NH | O | NH | T3b | OH |
| 3583 | CMe | O | Q1j | a bond | H | a bond | NH | O | NH | T3c | OH |
| 3584 | CMe | O | Q1j | a bond | H | a bond | NH | O | NH | T3d | OH |
| 3585 | CMe | O | Q1j | a bond | H | a bond | NH | O | NH | T3e | OH |
| 3586 | CMe | O | Q1j | a bond | H | a bond | NH | O | NH | T3f | OH |
| 3587 | CMe | O | Q1j | a bond | H | a bond | NH | O | NH | T3g | OH |
| 3588 | CMe | O | Q1j | a bond | H | a bond | NH | O | NH | T3h | OH |

TABLE 6-continued

| No | A | B | R¹ | L¹ | R² | L² | L³ | Y | L⁴ | R³ | X |
|---|---|---|---|---|---|---|---|---|---|---|---|
| 3589 | CMe | O | Q1j | a bond | H | a bond | NH | O | NH | T3i | OH |
| 3590 | CMe | O | Q1j | a bond | H | a bond | NH | O | NH | T3j | OH |
| 3591 | CMe | O | Q1j | a bond | H | a bond | NH | O | a bond | T3a | OH |
| 3592 | CMe | O | Q1j | a bond | H | a bond | NH | O | a bond | T3b | OH |
| 3593 | CMe | O | Q1j | a bond | H | a bond | NH | O | a bond | T3c | OH |
| 3594 | CMe | O | Q1j | a bond | H | a bond | NH | O | a bond | T3d | OH |
| 3595 | CMe | O | Q1j | a bond | H | a bond | NH | O | a bond | T3e | OH |
| 3596 | CMe | O | Q1j | a bond | H | a bond | NH | O | a bond | T3f | OH |
| 3597 | CMe | O | Q1j | a bond | H | a bond | NH | O | a bond | T3g | OH |
| 3598 | CMe | O | Q1j | a bond | H | a bond | NH | O | a bond | T3h | OH |
| 3599 | CMe | O | Q1j | a bond | H | a bond | NH | O | a bond | T3i | OH |
| 3600 | CMe | O | Q1j | a bond | H | a bond | NH | O | a bond | T3j | OH |
| 3601 | N | NMe | Q1i | a bond | Me | a bond | NH | S | NH | Q3e | OH |
| 3602 | N | NMe | Q1i | a bond | Me | a bond | NH | S | a bond | Q3e | OH |
| 3603 | N | NMe | Q1i | a bond | Me | a bond | NH | O | NH | Q3e | OH |
| 3604 | N | NMe | Q1i | a bond | Me | a bond | NH | O | a bond | Q3e | OH |
| 3605 | N | NMe | Q1i | a bond | H | a bond | NH | S | NH | Q3e | OH |
| 3606 | N | NMe | Q1i | a bond | H | a bond | NH | S | a bond | Q3e | OH |
| 3607 | N | NMe | Q1i | a bond | H | a bond | NH | O | NH | Q3e | OH |
| 3608 | N | NMe | Q1i | a bond | H | a bond | NH | O | a bond | Q3e | OH |
| 3609 | N | NMe | Q1j | a bond | Me | a bond | NH | S | NH | Q3e | OH |
| 3610 | N | NMe | Q1j | a bond | Me | a bond | NH | S | a bond | Q3e | OH |
| 3611 | N | NMe | Q1j | a bond | Me | a bond | NH | O | NH | Q3e | OH |
| 3612 | N | NMe | Q1j | a bond | Me | a bond | NH | O | a bond | Q3e | OH |
| 3613 | N | NMe | Q1j | a bond | H | a bond | NH | S | NH | Q3e | OH |
| 3614 | N | NMe | Q1j | a bond | H | a bond | NH | S | a bond | Q3e | OH |
| 3615 | N | NMe | Q1j | a bond | H | a bond | NH | O | NH | Q3e | OH |
| 3616 | N | NMe | Q1j | a bond | H | a bond | NH | O | a bond | Q3e | OH |
| 3617 | N | S | Q1i | a bond | Me | a bond | NH | S | NH | Q3e | OH |
| 3618 | N | S | Q1i | a bond | Me | a bond | NH | S | a bond | Q3e | OH |
| 3619 | N | S | Q1i | a bond | Me | a bond | NH | O | NH | Q3e | OH |
| 3620 | N | S | Q1i | a bond | Me | a bond | NH | O | a bond | Q3e | OH |
| 3621 | N | S | Q1i | a bond | H | a bond | NH | S | NH | Q3e | OH |
| 3622 | N | S | Q1i | a bond | H | a bond | NH | S | a bond | Q3e | OH |
| 3623 | N | S | Q1i | a bond | H | a bond | NH | O | NH | Q3e | OH |
| 3624 | N | S | Q1i | a bond | H | a bond | NH | O | a bond | Q3e | OH |
| 3625 | N | S | Q1j | a bond | Me | a bond | NH | S | NH | Q3e | OH |
| 3626 | N | S | Q1j | a bond | Me | a bond | NH | S | a bond | Q3e | OH |
| 3627 | N | S | Q1j | a bond | Me | a bond | NH | O | NH | Q3e | OH |
| 3628 | N | S | Q1j | a bond | Me | a bond | NH | O | a bond | Q3e | OH |
| 3629 | N | S | Q1j | a bond | H | a bond | NH | S | NH | Q3e | OH |
| 3630 | N | S | Q1j | a bond | H | a bond | NH | S | a bond | Q3e | OH |
| 3631 | N | S | Q1j | a bond | H | a bond | NH | O | NH | Q3e | OH |
| 3632 | N | S | Q1j | a bond | H | a bond | NH | O | a bond | Q3e | OH |
| 3633 | N | O | Q1i | a bond | Me | a bond | NH | S | NH | Q3e | OH |
| 3634 | N | O | Q1i | a bond | Me | a bond | NH | S | a bond | Q3e | OH |
| 3635 | N | O | Q1i | a bond | Me | a bond | NH | O | NH | Q3e | OH |
| 3636 | N | O | Q1i | a bond | Me | a bond | NH | O | a bond | Q3e | OH |
| 3637 | N | O | Q1i | a bond | H | a bond | NH | S | NH | Q3e | OH |
| 3638 | N | O | Q1i | a bond | H | a bond | NH | S | a bond | Q3e | OH |
| 3639 | N | O | Q1i | a bond | H | a bond | NH | O | NH | Q3e | OH |
| 3640 | N | O | Q1i | a bond | H | a bond | NH | O | a bond | Q3e | OH |
| 3641 | N | O | Q1j | a bond | Me | a bond | NH | S | NH | Q3e | OH |
| 3642 | N | O | Q1j | a bond | Me | a bond | NH | S | a bond | Q3e | OH |
| 3643 | N | O | Q1j | a bond | Me | a bond | NH | O | NH | Q3e | OH |
| 3644 | N | O | Q1j | a bond | Me | a bond | NH | O | a bond | Q3e | OH |
| 3645 | N | O | Q1j | a bond | H | a bond | NH | S | NH | Q3e | OH |
| 3646 | N | O | Q1j | a bond | H | a bond | NH | S | a bond | Q3e | OH |
| 3647 | N | O | Q1j | a bond | H | a bond | NH | O | NH | Q3e | OH |
| 3648 | N | O | Q1j | a bond | H | a bond | NH | O | a bond | Q3e | OH |
| 3649 | CH | NMe | Q1i | a bond | Me | a bond | NH | S | NH | Q3e | OH |
| 3650 | CH | NMe | Q1i | a bond | Me | a bond | NH | S | a bond | Q3e | OH |
| 3651 | CH | NMe | Q1i | a bond | Me | a bond | NH | O | NH | Q3e | OH |
| 3652 | CH | NMe | Q1i | a bond | Me | a bond | NH | O | a bond | Q3e | OH |
| 3653 | CH | NMe | Q1i | a bond | H | a bond | NH | S | NH | Q3e | OH |
| 3654 | CH | NMe | Q1i | a bond | H | a bond | NH | S | a bond | Q3e | OH |
| 3655 | CH | NMe | Q1i | a bond | H | a bond | NH | O | NH | Q3e | OH |
| 3656 | CH | NMe | Q1i | a bond | H | a bond | NH | O | a bond | Q3e | OH |
| 3657 | CH | NMe | Q1j | a bond | Me | a bond | NH | S | NH | Q3e | OH |
| 3658 | CH | NMe | Q1j | a bond | Me | a bond | NH | S | a bond | Q3e | OH |
| 3659 | CH | NMe | Q1j | a bond | Me | a bond | NH | O | NH | Q3e | OH |
| 3660 | CH | NMe | Q1j | a bond | Me | a bond | NH | O | a bond | Q3e | OH |
| 3661 | CH | NMe | Q1j | a bond | H | a bond | NH | S | NH | Q3e | OH |
| 3662 | CH | NMe | Q1j | a bond | H | a bond | NH | S | a bond | Q3e | OH |
| 3663 | CH | NMe | Q1j | a bond | H | a bond | NH | O | NH | Q3e | OH |
| 3664 | CH | NMe | Q1j | a bond | H | a bond | NH | O | a bond | Q3e | OH |
| 3665 | CH | S | Q1i | a bond | Me | a bond | NH | S | NH | Q3e | OH |
| 3666 | CH | S | Q1i | a bond | Me | a bond | NH | S | a bond | Q3e | OH |

TABLE 6-continued

| No | A | B | R¹ | L¹ | R² | L² | L³ | Y | L⁴ | R³ | X |
|---|---|---|---|---|---|---|---|---|---|---|---|
| 3667 | CH | S | Q1i | a bond | Me | a bond | NH | O | NH | Q3e | OH |
| 3668 | CH | S | Q1i | a bond | Me | a bond | NH | O | a bond | Q3e | OH |
| 3669 | CH | S | Q1i | a bond | H | a bond | NH | S | NH | Q3e | OH |
| 3670 | CH | S | Q1i | a bond | H | a bond | NH | S | a bond | Q3e | OH |
| 3671 | CH | S | Q1i | a bond | H | a bond | NH | O | NH | Q3e | OH |
| 3672 | CH | S | Q1i | a bond | H | a bond | NH | O | a bond | Q3e | OH |
| 3673 | CH | S | Q1j | a bond | Me | a bond | NH | S | NH | Q3e | OH |
| 3674 | CH | S | Q1j | a bond | Me | a bond | NH | S | a bond | Q3e | OH |
| 3675 | CH | S | Q1j | a bond | Me | a bond | NH | O | NH | Q3e | OH |
| 3676 | CH | S | Q1j | a bond | Me | a bond | NH | O | a bond | Q3e | OH |
| 3677 | CH | S | Q1j | a bond | H | a bond | NH | S | NH | Q3e | OH |
| 3678 | CH | S | Q1j | a bond | H | a bond | NH | S | a bond | Q3e | OH |
| 3679 | CH | S | Q1j | a bond | H | a bond | NH | O | NH | Q3e | OH |
| 3680 | CH | S | Q1j | a bond | H | a bond | NH | O | a bond | Q3e | OH |
| 3681 | CH | O | Q1i | a bond | Me | a bond | NH | S | NH | Q3e | OH |
| 3682 | CH | O | Q1i | a bond | Me | a bond | NH | S | a bond | Q3e | OH |
| 3683 | CH | O | Q1i | a bond | Me | a bond | NH | O | NH | Q3e | OH |
| 3684 | CH | O | Q1i | a bond | Me | a bond | NH | O | a bond | Q3e | OH |
| 3685 | CH | O | Q1i | a bond | H | a bond | NH | S | NH | Q3e | OH |
| 3686 | CH | O | Q1i | a bond | H | a bond | NH | S | a bond | Q3e | OH |
| 3687 | CH | O | Q1i | a bond | H | a bond | NH | O | NH | Q3e | OH |
| 3688 | CH | O | Q1i | a bond | H | a bond | NH | O | a bond | Q3e | OH |
| 3689 | CH | O | Q1j | a bond | Me | a bond | NH | S | NH | Q3e | OH |
| 3690 | CH | O | Q1j | a bond | Me | a bond | NH | S | a bond | Q3e | OH |
| 3691 | CH | O | Q1j | a bond | Me | a bond | NH | O | NH | Q3e | OH |
| 3692 | CH | O | Q1j | a bond | Me | a bond | NH | O | a bond | Q3e | OH |
| 3693 | CH | O | Q1j | a bond | H | a bond | NH | S | NH | Q3e | OH |
| 3694 | CH | O | Q1j | a bond | H | a bond | NH | S | a bond | Q3e | OH |
| 3695 | CH | O | Q1j | a bond | H | a bond | NH | O | NH | Q3e | OH |
| 3696 | CH | O | Q1j | a bond | H | a bond | NH | O | a bond | Q3e | OH |
| 3697 | CMe | NMe | Q1i | a bond | Me | a bond | NH | S | NH | Q3e | OH |
| 3698 | CMe | NMe | Q1i | a bond | Me | a bond | NH | S | a bond | Q3e | OH |
| 3699 | CMe | NMe | Q1i | a bond | Me | a bond | NH | O | NH | Q3e | OH |
| 3700 | CMe | NMe | Q1i | a bond | Me | a bond | NH | O | a bond | Q3e | OH |
| 3701 | CMe | NMe | Q1i | a bond | H | a bond | NH | S | NH | Q3e | OH |
| 3702 | CMe | NMe | Q1i | a bond | H | a bond | NH | S | a bond | Q3e | OH |
| 3703 | CMe | NMe | Q1i | a bond | H | a bond | NH | O | NH | Q3e | OH |
| 3704 | CMe | NMe | Q1i | a bond | H | a bond | NH | O | a bond | Q3e | OH |
| 3705 | CMe | NMe | Q1j | a bond | Me | a bond | NH | S | NH | Q3e | OH |
| 3706 | CMe | NMe | Q1j | a bond | Me | a bond | NH | S | a bond | Q3e | OH |
| 3707 | CMe | NMe | Q1j | a bond | Me | a bond | NH | O | NH | Q3e | OH |
| 3708 | CMe | NMe | Q1j | a bond | Me | a bond | NH | O | a bond | Q3e | OH |
| 3709 | CMe | NMe | Q1j | a bond | H | a bond | NH | S | NH | Q3e | OH |
| 3710 | CMe | NMe | Q1j | a bond | H | a bond | NH | S | a bond | Q3e | OH |
| 3711 | CMe | NMe | Q1j | a bond | H | a bond | NH | O | NH | Q3e | OH |
| 3712 | CMe | NMe | Q1j | a bond | H | a bond | NH | O | a bond | Q3e | OH |
| 3713 | CMe | S | Q1i | a bond | Me | a bond | NH | S | NH | Q3e | OH |
| 3714 | CMe | S | Q1i | a bond | Me | a bond | NH | S | a bond | Q3e | OH |
| 3715 | CMe | S | Q1i | a bond | Me | a bond | NH | O | NH | Q3e | OH |
| 3716 | CMe | S | Q1i | a bond | Me | a bond | NH | O | a bond | Q3e | OH |
| 3717 | CMe | S | Q1i | a bond | H | a bond | NH | S | NH | Q3e | OH |
| 3718 | CMe | S | Q1i | a bond | H | a bond | NH | S | a bond | Q3e | OH |
| 3719 | CMe | S | Q1i | a bond | H | a bond | NH | O | NH | Q3e | OH |
| 3720 | CMe | S | Q1i | a bond | H | a bond | NH | O | a bond | Q3e | OH |
| 3721 | CMe | S | Q1j | a bond | Me | a bond | NH | S | NH | Q3e | OH |
| 3722 | CMe | S | Q1j | a bond | Me | a bond | NH | S | a bond | Q3e | OH |
| 3723 | CMe | S | Q1j | a bond | Me | a bond | NH | O | NH | Q3e | OH |
| 3724 | CMe | S | Q1j | a bond | Me | a bond | NH | O | a bond | Q3e | OH |
| 3725 | CMe | S | Q1j | a bond | H | a bond | NH | S | NH | Q3e | OH |
| 3726 | CMe | S | Q1j | a bond | H | a bond | NH | S | a bond | Q3e | OH |
| 3727 | CMe | S | Q1j | a bond | H | a bond | NH | O | NH | Q3e | OH |
| 3728 | CMe | S | Q1j | a bond | H | a bond | NH | O | a bond | Q3e | OH |
| 3729 | CMe | O | Q1i | a bond | Me | a bond | NH | S | NH | Q3e | OH |
| 3730 | CMe | O | Q1i | a bond | Me | a bond | NH | S | a bond | Q3e | OH |
| 3731 | CMe | O | Q1i | a bond | Me | a bond | NH | O | NH | Q3e | OH |
| 3732 | CMe | O | Q1i | a bond | Me | a bond | NH | O | a bond | Q3e | OH |
| 3733 | CMe | O | Q1i | a bond | H | a bond | NH | S | NH | Q3e | OH |
| 3734 | CMe | O | Q1i | a bond | H | a bond | NH | S | a bond | Q3e | OH |
| 3735 | CMe | O | Q1i | a bond | H | a bond | NH | O | NH | Q3e | OH |
| 3736 | CMe | O | Q1i | a bond | H | a bond | NH | O | a bond | Q3e | OH |
| 3737 | CMe | O | Q1j | a bond | Me | a bond | NH | S | NH | Q3e | OH |
| 3738 | CMe | O | Q1j | a bond | Me | a bond | NH | S | a bond | Q3e | OH |
| 3739 | CMe | O | Q1j | a bond | Me | a bond | NH | O | NH | Q3e | OH |
| 3740 | CMe | O | Q1j | a bond | Me | a bond | NH | O | a bond | Q3e | OH |
| 3741 | CMe | O | Q1j | a bond | H | a bond | NH | S | NH | Q3e | OH |
| 3742 | CMe | O | Q1j | a bond | H | a bond | NH | S | a bond | Q3e | OH |
| 3743 | CMe | O | Q1j | a bond | H | a bond | NH | O | NH | Q3e | OH |
| 3744 | CMe | O | Q1j | a bond | H | a bond | NH | O | a bond | Q3e | OH |

TABLE 6-continued

| No | A | B | R¹ | L¹ | R² | L² | L³ | Y | L⁴ | R³ | X |
|---|---|---|---|---|---|---|---|---|---|---|---|
| 3745 | N | NMe | Q1o' | a bond | Me | a bond | NH | S | NH | Q3a | OH |
| 3746 | N | NMe | Q1o' | a bond | Me | a bond | NH | S | NH | Q3e | OH |
| 3747 | N | NMe | Q1o' | a bond | Me | a bond | NH | S | NH | T3a | OH |
| 3748 | N | NMe | Q1o' | a bond | Me | a bond | NH | S | NH | T3b | OH |
| 3749 | N | NMe | Q1o' | a bond | Me | a bond | NH | S | NH | T3c | OH |
| 3750 | N | NMe | Q1o' | a bond | Me | a bond | NH | S | NH | T3d | OH |
| 3751 | N | NMe | Q1o' | a bond | Me | a bond | NH | S | NH | T3e | OH |
| 3752 | N | NMe | Q1o' | a bond | Me | a bond | NH | S | NH | T3f | OH |
| 3753 | N | NMe | Q1o' | a bond | Me | a bond | NH | S | NH | T3g | OH |
| 3754 | N | NMe | Q1o' | a bond | Me | a bond | NH | S | NH | T3h | OH |
| 3755 | N | NMe | Q1o' | a bond | Me | a bond | NH | S | NH | T3i | OH |
| 3756 | N | NMe | Q1o' | a bond | Me | a bond | NH | S | NH | T3j | OH |
| 3757 | N | NMe | Q1o' | a bond | Me | a bond | NH | S | a bond | Q3a | OH |
| 3758 | N | NMe | Q1o' | a bond | Me | a bond | NH | S | a bond | Q3e | OH |
| 3759 | N | NMe | Q1o' | a bond | Me | a bond | NH | S | a bond | T3a | OH |
| 3760 | N | NMe | Q1o' | a bond | Me | a bond | NH | S | a bond | T3b | OH |
| 3761 | N | NMe | Q1o' | a bond | Me | a bond | NH | S | a bond | T3c | OH |
| 3762 | N | NMe | Q1o' | a bond | Me | a bond | NH | S | a bond | T3d | OH |
| 3763 | N | NMe | Q1o' | a bond | Me | a bond | NH | S | a bond | T3e | OH |
| 3764 | N | NMe | Q1o' | a bond | Me | a bond | NH | S | a bond | T3f | OH |
| 3765 | N | NMe | Q1o' | a bond | Me | a bond | NH | S | a bond | T3g | OH |
| 3766 | N | NMe | Q1o' | a bond | Me | a bond | NH | S | a bond | T3h | OH |
| 3767 | N | NMe | Q1o' | a bond | Me | a bond | NH | S | a bond | T3i | OH |
| 3768 | N | NMe | Q1o' | a bond | Me | a bond | NH | S | a bond | T3j | OH |
| 3769 | N | NMe | Q1o' | a bond | Me | a bond | NH | O | NH | Q3a | OH |
| 3770 | N | NMe | Q1o' | a bond | Me | a bond | NH | O | NH | Q3e | OH |
| 3771 | N | NMe | Q1o' | a bond | Me | a bond | NH | O | NH | T3a | OH |
| 3772 | N | NMe | Q1o' | a bond | Me | a bond | NH | O | NH | T3b | OH |
| 3773 | N | NMe | Q1o' | a bond | Me | a bond | NH | O | NH | T3c | OH |
| 3774 | N | NMe | Q1o' | a bond | Me | a bond | NH | O | NH | T3d | OH |
| 3775 | N | NMe | Q1o' | a bond | Me | a bond | NH | O | NH | T3e | OH |
| 3776 | N | NMe | Q1o' | a bond | Me | a bond | NH | O | NH | T3f | OH |
| 3777 | N | NMe | Q1o' | a bond | Me | a bond | NH | O | NH | T3g | OH |
| 3778 | N | NMe | Q1o' | a bond | Me | a bond | NH | O | NH | T3h | OH |
| 3779 | N | NMe | Q1o' | a bond | Me | a bond | NH | O | NH | T3i | OH |
| 3780 | N | NMe | Q1o' | a bond | Me | a bond | NH | O | NH | T3j | OH |
| 3781 | N | NMe | Q1o' | a bond | Me | a bond | NH | O | a bond | Q3a | OH |
| 3782 | N | NMe | Q1o' | a bond | Me | a bond | NH | O | a bond | Q3e | OH |
| 3783 | N | NMe | Q1o' | a bond | Me | a bond | NH | O | a bond | T3a | OH |
| 3784 | N | NMe | Q1o' | a bond | Me | a bond | NH | O | a bond | T3b | OH |
| 3785 | N | NMe | Q1o' | a bond | Me | a bond | NH | O | a bond | T3c | OH |
| 3786 | N | NMe | Q1o' | a bond | Me | a bond | NH | O | a bond | T3d | OH |
| 3787 | N | NMe | Q1o' | a bond | Me | a bond | NH | O | a bond | T3e | OH |
| 3788 | N | NMe | Q1o' | a bond | Me | a bond | NH | O | a bond | T3f | OH |
| 3789 | N | NMe | Q1o' | a bond | Me | a bond | NH | O | a bond | T3g | OH |
| 3790 | N | NMe | Q1o' | a bond | Me | a bond | NH | O | a bond | T3h | OH |
| 3791 | N | NMe | Q1o' | a bond | Me | a bond | NH | O | a bond | T3i | OH |
| 3792 | N | NMe | Q1o' | a bond | Me | a bond | NH | O | a bond | T3j | OH |
| 3793 | N | NMe | Q1o' | a bond | H | a bond | NH | S | NH | Q3a | OH |
| 3794 | N | NMe | Q1o' | a bond | H | a bond | NH | S | NH | Q3e | OH |
| 3795 | N | NMe | Q1o' | a bond | H | a bond | NH | S | NH | T3a | OH |
| 3796 | N | NMe | Q1o' | a bond | H | a bond | NH | S | NH | T3b | OH |
| 3797 | N | NMe | Q1o' | a bond | H | a bond | NH | S | NH | T3c | OH |
| 3798 | N | NMe | Q1o' | a bond | H | a bond | NH | S | NH | T3d | OH |
| 3799 | N | NMe | Q1o' | a bond | H | a bond | NH | S | NH | T3e | OH |
| 3800 | N | NMe | Q1o' | a bond | H | a bond | NH | S | NH | T3f | OH |
| 3801 | N | NMe | Q1o' | a bond | H | a bond | NH | S | NH | T3g | OH |
| 3802 | N | NMe | Q1o' | a bond | H | a bond | NH | S | NH | T3h | OH |
| 3803 | N | NMe | Q1o' | a bond | H | a bond | NH | S | NH | T3i | OH |
| 3804 | N | NMe | Q1o' | a bond | H | a bond | NH | S | NH | T3j | OH |
| 3805 | N | NMe | Q1o' | a bond | H | a bond | NH | S | a bond | Q3a | OH |
| 3806 | N | NMe | Q1o' | a bond | H | a bond | NH | S | a bond | Q3e | OH |
| 3807 | N | NMe | Q1o' | a bond | H | a bond | NH | S | a bond | T3a | OH |
| 3808 | N | NMe | Q1o' | a bond | H | a bond | NH | S | a bond | T3b | OH |
| 3809 | N | NMe | Q1o' | a bond | H | a bond | NH | S | a bond | T3c | OH |
| 3810 | N | NMe | Q1o' | a bond | H | a bond | NH | S | a bond | T3d | OH |
| 3811 | N | NMe | Q1o' | a bond | H | a bond | NH | S | a bond | T3e | OH |
| 3812 | N | NMe | Q1o' | a bond | H | a bond | NH | S | a bond | T3f | OH |
| 3813 | N | NMe | Q1o' | a bond | H | a bond | NH | S | a bond | T3g | OH |
| 3814 | N | NMe | Q1o' | a bond | H | a bond | NH | S | a bond | T3h | OH |
| 3815 | N | NMe | Q1o' | a bond | H | a bond | NH | S | a bond | T3i | OH |
| 3816 | N | NMe | Q1o' | a bond | H | a bond | NH | S | a bond | T3j | OH |
| 3817 | N | NMe | Q1o' | a bond | H | a bond | NH | O | NH | Q3a | OH |
| 3818 | N | NMe | Q1o' | a bond | H | a bond | NH | O | NH | Q3e | OH |
| 3819 | N | NMe | Q1o' | a bond | H | a bond | NH | O | NH | T3a | OH |
| 3820 | N | NMe | Q1o' | a bond | H | a bond | NH | O | NH | T3b | OH |
| 3821 | N | NMe | Q1o' | a bond | H | a bond | NH | O | NH | T3c | OH |
| 3822 | N | NMe | Q1o' | a bond | H | a bond | NH | O | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 3823 | N | NMe | Q1o' | a bond | H | a bond | NH | O | NH | T3e | OH |
| 3824 | N | NMe | Q1o' | a bond | H | a bond | NH | O | NH | T3f | OH |
| 3825 | N | NMe | Q1o' | a bond | H | a bond | NH | O | NH | T3g | OH |
| 3826 | N | NMe | Q1o' | a bond | H | a bond | NH | O | NH | T3h | OH |
| 3827 | N | NMe | Q1o' | a bond | H | a bond | NH | O | NH | T3i | OH |
| 3828 | N | NMe | Q1o' | a bond | H | a bond | NH | O | NH | T3j | OH |
| 3829 | N | NMe | Q1o' | a bond | H | a bond | NH | O | a bond | Q3a | OH |
| 3830 | N | NMe | Q1o' | a bond | H | a bond | NH | O | a bond | Q3e | OH |
| 3831 | N | NMe | Q1o' | a bond | H | a bond | NH | O | a bond | T3a | OH |
| 3832 | N | NMe | Q1o' | a bond | H | a bond | NH | O | a bond | T3b | OH |
| 3833 | N | NMe | Q1o' | a bond | H | a bond | NH | O | a bond | T3c | OH |
| 3834 | N | NMe | Q1o' | a bond | H | a bond | NH | O | a bond | T3d | OH |
| 3835 | N | NMe | Q1o' | a bond | H | a bond | NH | O | a bond | T3e | OH |
| 3836 | N | NMe | Q1o' | a bond | H | a bond | NH | O | a bond | T3f | OH |
| 3837 | N | NMe | Q1o' | a bond | H | a bond | NH | O | a bond | T3g | OH |
| 3838 | N | NMe | Q1o' | a bond | H | a bond | NH | O | a bond | T3h | OH |
| 3839 | N | NMe | Q1o' | a bond | H | a bond | NH | O | a bond | T3i | OH |
| 3840 | N | NMe | Q1o' | a bond | H | a bond | NH | O | a bond | T3j | OH |
| 3841 | N | S | Q1o' | a bond | Me | a bond | NH | S | NH | Q3a | OH |
| 3842 | N | S | Q1o' | a bond | Me | a bond | NH | S | NH | Q3e | OH |
| 3843 | N | S | Q1o' | a bond | Me | a bond | NH | S | NH | T3a | OH |
| 3844 | N | S | Q1o' | a bond | Me | a bond | NH | S | NH | T3b | OH |
| 3845 | N | S | Q1o' | a bond | Me | a bond | NH | S | NH | T3c | OH |
| 3846 | N | S | Q1o' | a bond | Me | a bond | NH | S | NH | T3d | OH |
| 3847 | N | S | Q1o' | a bond | Me | a bond | NH | S | NH | T3e | OH |
| 3848 | N | S | Q1o' | a bond | Me | a bond | NH | S | NH | T3f | OH |
| 3849 | N | S | Q1o' | a bond | Me | a bond | NH | S | NH | T3g | OH |
| 3850 | N | S | Q1o' | a bond | Me | a bond | NH | S | NH | T3h | OH |
| 3851 | N | S | Q1o' | a bond | Me | a bond | NH | S | NH | T3i | OH |
| 3852 | N | S | Q1o' | a bond | Me | a bond | NH | S | NH | T3j | OH |
| 3853 | N | S | Q1o' | a bond | Me | a bond | NH | S | a bond | Q3a | OH |
| 3854 | N | S | Q1o' | a bond | Me | a bond | NH | S | a bond | Q3e | OH |
| 3855 | N | S | Q1o' | a bond | Me | a bond | NH | S | a bond | T3a | OH |
| 3856 | N | S | Q1o' | a bond | Me | a bond | NH | S | a bond | T3b | OH |
| 3857 | N | S | Q1o' | a bond | Me | a bond | NH | S | a bond | T3c | OH |
| 3858 | N | S | Q1o' | a bond | Me | a bond | NH | S | a bond | T3d | OH |
| 3859 | N | S | Q1o' | a bond | Me | a bond | NH | S | a bond | T3e | OH |
| 3860 | N | S | Q1o' | a bond | Me | a bond | NH | S | a bond | T3f | OH |
| 3861 | N | S | Q1o' | a bond | Me | a bond | NH | S | a bond | T3g | OH |
| 3862 | N | S | Q1o' | a bond | Me | a bond | NH | S | a bond | T3h | OH |
| 3863 | N | S | Q1o' | a bond | Me | a bond | NH | S | a bond | T3i | OH |
| 3864 | N | S | Q1o' | a bond | Me | a bond | NH | S | a bond | T3j | OH |
| 3865 | N | S | Q1o' | a bond | Me | a bond | NH | O | NH | Q3a | OH |
| 3866 | N | S | Q1o' | a bond | Me | a bond | NH | O | NH | Q3e | OH |
| 3867 | N | S | Q1o' | a bond | Me | a bond | NH | O | NH | T3a | OH |
| 3868 | N | S | Q1o' | a bond | Me | a bond | NH | O | NH | T3b | OH |
| 3869 | N | S | Q1o' | a bond | Me | a bond | NH | O | NH | T3c | OH |
| 3870 | N | S | Q1o' | a bond | Me | a bond | NH | O | NH | T3d | OH |
| 3871 | N | S | Q1o' | a bond | Me | a bond | NH | O | NH | T3e | OH |
| 3872 | N | S | Q1o' | a bond | Me | a bond | NH | O | NH | T3f | OH |
| 3873 | N | S | Q1o' | a bond | Me | a bond | NH | O | NH | T3g | OH |
| 3874 | N | S | Q1o' | a bond | Me | a bond | NH | O | NH | T3h | OH |
| 3875 | N | S | Q1o' | a bond | Me | a bond | NH | O | NH | T3i | OH |
| 3876 | N | S | Q1o' | a bond | Me | a bond | NH | O | NH | T3j | OH |
| 3877 | N | S | Q1o' | a bond | Me | a bond | NH | O | a bond | Q3a | OH |
| 3878 | N | S | Q1o' | a bond | Me | a bond | NH | O | a bond | Q3e | OH |
| 3879 | N | S | Q1o' | a bond | Me | a bond | NH | O | a bond | T3a | OH |
| 3880 | N | S | Q1o' | a bond | Me | a bond | NH | O | a bond | T3b | OH |
| 3881 | N | S | Q1o' | a bond | Me | a bond | NH | O | a bond | T3c | OH |
| 3882 | N | S | Q1o' | a bond | Me | a bond | NH | O | a bond | T3d | OH |
| 3883 | N | S | Q1o' | a bond | Me | a bond | NH | O | a bond | T3e | OH |
| 3884 | N | S | Q1o' | a bond | Me | a bond | NH | O | a bond | T3f | OH |
| 3885 | N | S | Q1o' | a bond | Me | a bond | NH | O | a bond | T3g | OH |
| 3886 | N | S | Q1o' | a bond | Me | a bond | NH | O | a bond | T3h | OH |
| 3887 | N | S | Q1o' | a bond | Me | a bond | NH | O | a bond | T3i | OH |
| 3888 | N | S | Q1o' | a bond | Me | a bond | NH | O | a bond | T3j | OH |
| 3889 | N | S | Q1o' | a bond | H | a bond | NH | S | NH | Q3a | OH |
| 3890 | N | S | Q1o' | a bond | H | a bond | NH | S | NH | Q3e | OH |
| 3891 | N | S | Q1o' | a bond | H | a bond | NH | S | NH | T3a | OH |
| 3892 | N | S | Q1o' | a bond | H | a bond | NH | S | NH | T3b | OH |
| 3893 | N | S | Q1o' | a bond | H | a bond | NH | S | NH | T3c | OH |
| 3894 | N | S | Q1o' | a bond | H | a bond | NH | S | NH | T3d | OH |
| 3895 | N | S | Q1o' | a bond | H | a bond | NH | S | NH | T3e | OH |
| 3896 | N | S | Q1o' | a bond | H | a bond | NH | S | NH | T3f | OH |
| 3897 | N | S | Q1o' | a bond | H | a bond | NH | S | NH | T3g | OH |
| 3898 | N | S | Q1o' | a bond | H | a bond | NH | S | NH | T3h | OH |
| 3899 | N | S | Q1o' | a bond | H | a bond | NH | S | NH | T3i | OH |
| 3900 | N | S | Q1o' | a bond | H | a bond | NH | S | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 3901 | N | S | Q1o' | a bond | H | a bond | NH | S | a bond | Q3a | OH |
| 3902 | N | S | Q1o' | a bond | H | a bond | NH | S | a bond | Q3e | OH |
| 3903 | N | S | Q1o' | a bond | H | a bond | NH | S | a bond | T3a | OH |
| 3904 | N | S | Q1o' | a bond | H | a bond | NH | S | a bond | T3b | OH |
| 3905 | N | S | Q1o' | a bond | H | a bond | NH | S | a bond | T3c | OH |
| 3906 | N | S | Q1o' | a bond | H | a bond | NH | S | a bond | T3d | OH |
| 3907 | N | S | Q1o' | a bond | H | a bond | NH | S | a bond | T3e | OH |
| 3908 | N | S | Q1o' | a bond | H | a bond | NH | S | a bond | T3f | OH |
| 3909 | N | S | Q1o' | a bond | H | a bond | NH | S | a bond | T3g | OH |
| 3910 | N | S | Q1o' | a bond | H | a bond | NH | S | a bond | T3h | OH |
| 3911 | N | S | Q1o' | a bond | H | a bond | NH | S | a bond | T3i | OH |
| 3912 | N | S | Q1o' | a bond | H | a bond | NH | S | a bond | T3j | OH |
| 3913 | N | S | Q1o' | a bond | H | a bond | NH | O | NH | Q3a | OH |
| 3914 | N | S | Q1o' | a bond | H | a bond | NH | O | NH | Q3e | OH |
| 3915 | N | S | Q1o' | a bond | H | a bond | NH | O | NH | T3a | OH |
| 3916 | N | S | Q1o' | a bond | H | a bond | NH | O | NH | T3b | OH |
| 3917 | N | S | Q1o' | a bond | H | a bond | NH | O | NH | T3c | OH |
| 3918 | N | S | Q1o' | a bond | H | a bond | NH | O | NH | T3d | OH |
| 3919 | N | S | Q1o' | a bond | H | a bond | NH | O | NH | T3e | OH |
| 3920 | N | S | Q1o' | a bond | H | a bond | NH | O | NH | T3f | OH |
| 3921 | N | S | Q1o' | a bond | H | a bond | NH | O | NH | T3g | OH |
| 3922 | N | S | Q1o' | a bond | H | a bond | NH | O | NH | T3h | OH |
| 3923 | N | S | Q1o' | a bond | H | a bond | NH | O | NH | T3i | OH |
| 3924 | N | S | Q1o' | a bond | H | a bond | NH | O | NH | T3j | OH |
| 3925 | N | S | Q1o' | a bond | H | a bond | NH | O | a bond | Q3a | OH |
| 3926 | N | S | Q1o' | a bond | H | a bond | NH | O | a bond | Q3e | OH |
| 3927 | N | S | Q1o' | a bond | H | a bond | NH | O | a bond | T3a | OH |
| 3928 | N | S | Q1o' | a bond | H | a bond | NH | O | a bond | T3b | OH |
| 3929 | N | S | Q1o' | a bond | H | a bond | NH | O | a bond | T3c | OH |
| 3930 | N | S | Q1o' | a bond | H | a bond | NH | O | a bond | T3d | OH |
| 3931 | N | S | Q1o' | a bond | H | a bond | NH | O | a bond | T3e | OH |
| 3932 | N | S | Q1o' | a bond | H | a bond | NH | O | a bond | T3f | OH |
| 3933 | N | S | Q1o' | a bond | H | a bond | NH | O | a bond | T3g | OH |
| 3934 | N | S | Q1o' | a bond | H | a bond | NH | O | a bond | T3h | OH |
| 3935 | N | S | Q1o' | a bond | H | a bond | NH | O | a bond | T3i | OH |
| 3936 | N | S | Q1o' | a bond | H | a bond | NH | O | a bond | T3j | OH |
| 3937 | N | O | Q1o' | a bond | Me | a bond | NH | S | NH | Q3a | OH |
| 3938 | N | O | Q1o' | a bond | Me | a bond | NH | S | NH | Q3e | OH |
| 3939 | N | O | Q1o' | a bond | Me | a bond | NH | S | NH | T3a | OH |
| 3940 | N | O | Q1o' | a bond | Me | a bond | NH | S | NH | T3b | OH |
| 3941 | N | O | Q1o' | a bond | Me | a bond | NH | S | NH | T3c | OH |
| 3942 | N | O | Q1o' | a bond | Me | a bond | NH | S | NH | T3d | OH |
| 3943 | N | O | Q1o' | a bond | Me | a bond | NH | S | NH | T3e | OH |
| 3944 | N | O | Q1o' | a bond | Me | a bond | NH | S | NH | T3f | OH |
| 3945 | N | O | Q1o' | a bond | Me | a bond | NH | S | NH | T3g | OH |
| 3946 | N | O | Q1o' | a bond | Me | a bond | NH | S | NH | T3h | OH |
| 3947 | N | O | Q1o' | a bond | Me | a bond | NH | S | NH | T3i | OH |
| 3948 | N | O | Q1o' | a bond | Me | a bond | NH | S | NH | T3j | OH |
| 3949 | N | O | Q1o' | a bond | Me | a bond | NH | S | a bond | Q3a | OH |
| 3950 | N | O | Q1o' | a bond | Me | a bond | NH | S | a bond | Q3e | OH |
| 3951 | N | O | Q1o' | a bond | Me | a bond | NH | S | a bond | T3a | OH |
| 3952 | N | O | Q1o' | a bond | Me | a bond | NH | S | a bond | T3b | OH |
| 3953 | N | O | Q1o' | a bond | Me | a bond | NH | S | a bond | T3c | OH |
| 3954 | N | O | Q1o' | a bond | Me | a bond | NH | S | a bond | T3d | OH |
| 3955 | N | O | Q1o' | a bond | Me | a bond | NH | S | a bond | T3e | OH |
| 3956 | N | O | Q1o' | a bond | Me | a bond | NH | S | a bond | T3f | OH |
| 3957 | N | O | Q1o' | a bond | Me | a bond | NH | S | a bond | T3g | OH |
| 3958 | N | O | Q1o' | a bond | Me | a bond | NH | S | a bond | T3h | OH |
| 3959 | N | O | Q1o' | a bond | Me | a bond | NH | S | a bond | T3i | OH |
| 3960 | N | O | Q1o' | a bond | Me | a bond | NH | S | a bond | T3j | OH |
| 3961 | N | O | Q1o' | a bond | Me | a bond | NH | O | NH | Q3a | OH |
| 3962 | N | O | Q1o' | a bond | Me | a bond | NH | O | NH | Q3e | OH |
| 3963 | N | O | Q1o' | a bond | Me | a bond | NH | O | NH | T3a | OH |
| 3964 | N | O | Q1o' | a bond | Me | a bond | NH | O | NH | T3b | OH |
| 3965 | N | O | Q1o' | a bond | Me | a bond | NH | O | NH | T3c | OH |
| 3966 | N | O | Q1o' | a bond | Me | a bond | NH | O | NH | T3d | OH |
| 3967 | N | O | Q1o' | a bond | Me | a bond | NH | O | NH | T3e | OH |
| 3968 | N | O | Q1o' | a bond | Me | a bond | NH | O | NH | T3f | OH |
| 3969 | N | O | Q1o' | a bond | Me | a bond | NH | O | NH | T3g | OH |
| 3970 | N | O | Q1o' | a bond | Me | a bond | NH | O | NH | T3h | OH |
| 3971 | N | O | Q1o' | a bond | Me | a bond | NH | O | NH | T3i | OH |
| 3972 | N | O | Q1o' | a bond | Me | a bond | NH | O | NH | T3j | OH |
| 3973 | N | O | Q1o' | a bond | Me | a bond | NH | O | a bond | Q3a | OH |
| 3974 | N | O | Q1o' | a bond | Me | a bond | NH | O | a bond | Q3e | OH |
| 3975 | N | O | Q1o' | a bond | Me | a bond | NH | O | a bond | T3a | OH |
| 3976 | N | O | Q1o' | a bond | Me | a bond | NH | O | a bond | T3b | OH |
| 3977 | N | O | Q1o' | a bond | Me | a bond | NH | O | a bond | T3c | OH |
| 3978 | N | O | Q1o' | a bond | Me | a bond | NH | O | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 3979 | N | O | Q1o' | a bond | Me | a bond | NH | O | a bond | T3e | OH |
| 3980 | N | O | Q1o' | a bond | Me | a bond | NH | O | a bond | T3f | OH |
| 3981 | N | O | Q1o' | a bond | Me | a bond | NH | O | a bond | T3g | OH |
| 3982 | N | O | Q1o' | a bond | Me | a bond | NH | O | a bond | T3h | OH |
| 3983 | N | O | Q1o' | a bond | Me | a bond | NH | O | a bond | T3i | OH |
| 3984 | N | O | Q1o' | a bond | Me | a bond | NH | O | a bond | T3j | OH |
| 3985 | N | O | Q1o' | a bond | H | a bond | NH | S | NH | Q3a | OH |
| 3986 | N | O | Q1o' | a bond | H | a bond | NH | S | NH | Q3e | OH |
| 3987 | N | O | Q1o' | a bond | H | a bond | NH | S | NH | T3a | OH |
| 3988 | N | O | Q1o' | a bond | H | a bond | NH | S | NH | T3b | OH |
| 3989 | N | O | Q1o' | a bond | H | a bond | NH | S | NH | T3c | OH |
| 3990 | N | O | Q1o' | a bond | H | a bond | NH | S | NH | T3d | OH |
| 3991 | N | O | Q1o' | a bond | H | a bond | NH | S | NH | T3e | OH |
| 3992 | N | O | Q1o' | a bond | H | a bond | NH | S | NH | T3f | OH |
| 3993 | N | O | Q1o' | a bond | H | a bond | NH | S | NH | T3g | OH |
| 3994 | N | O | Q1o' | a bond | H | a bond | NH | S | NH | T3h | OH |
| 3995 | N | O | Q1o' | a bond | H | a bond | NH | S | NH | T3i | OH |
| 3996 | N | O | Q1o' | a bond | H | a bond | NH | S | NH | T3j | OH |
| 3997 | N | O | Q1o' | a bond | H | a bond | NH | S | a bond | Q3a | OH |
| 3998 | N | O | Q1o' | a bond | H | a bond | NH | S | a bond | Q3e | OH |
| 3999 | N | O | Q1o' | a bond | H | a bond | NH | S | a bond | T3a | OH |
| 4000 | N | O | Q1o' | a bond | H | a bond | NH | S | a bond | T3b | OH |
| 4001 | N | O | Q1o' | a bond | H | a bond | NH | S | a bond | T3c | OH |
| 4002 | N | O | Q1o' | a bond | H | a bond | NH | S | a bond | T3d | OH |
| 4003 | N | O | Q1o' | a bond | H | a bond | NH | S | a bond | T3e | OH |
| 4004 | N | O | Q1o' | a bond | H | a bond | NH | S | a bond | T3f | OH |
| 4005 | N | O | Q1o' | a bond | H | a bond | NH | S | a bond | T3g | OH |
| 4006 | N | O | Q1o' | a bond | H | a bond | NH | S | a bond | T3h | OH |
| 4007 | N | O | Q1o' | a bond | H | a bond | NH | S | a bond | T3i | OH |
| 4008 | N | O | Q1o' | a bond | H | a bond | NH | S | a bond | T3j | OH |
| 4009 | N | O | Q1o' | a bond | H | a bond | NH | O | NH | Q3a | OH |
| 4010 | N | O | Q1o' | a bond | H | a bond | NH | O | NH | Q3e | OH |
| 4011 | N | O | Q1o' | a bond | H | a bond | NH | O | NH | T3a | OH |
| 4012 | N | O | Q1o' | a bond | H | a bond | NH | O | NH | T3b | OH |
| 4013 | N | O | Q1o' | a bond | H | a bond | NH | O | NH | T3c | OH |
| 4014 | N | O | Q1o' | a bond | H | a bond | NH | O | NH | T3d | OH |
| 4015 | N | O | Q1o' | a bond | H | a bond | NH | O | NH | T3e | OH |
| 4016 | N | O | Q1o' | a bond | H | a bond | NH | O | NH | T3f | OH |
| 4017 | N | O | Q1o' | a bond | H | a bond | NH | O | NH | T3g | OH |
| 4018 | N | O | Q1o' | a bond | H | a bond | NH | O | NH | T3h | OH |
| 4019 | N | O | Q1o' | a bond | H | a bond | NH | O | NH | T3i | OH |
| 4020 | N | O | Q1o' | a bond | H | a bond | NH | O | NH | T3j | OH |
| 4021 | N | O | Q1o' | a bond | H | a bond | NH | O | a bond | Q3a | OH |
| 4022 | N | O | Q1o' | a bond | H | a bond | NH | O | a bond | Q3e | OH |
| 4023 | N | O | Q1o' | a bond | H | a bond | NH | O | a bond | T3a | OH |
| 4024 | N | O | Q1o' | a bond | H | a bond | NH | O | a bond | T3b | OH |
| 4025 | N | O | Q1o' | a bond | H | a bond | NH | O | a bond | T3c | OH |
| 4026 | N | O | Q1o' | a bond | H | a bond | NH | O | a bond | T3d | OH |
| 4027 | N | O | Q1o' | a bond | H | a bond | NH | O | a bond | T3e | OH |
| 4028 | N | O | Q1o' | a bond | H | a bond | NH | O | a bond | T3f | OH |
| 4029 | N | O | Q1o' | a bond | H | a bond | NH | O | a bond | T3g | OH |
| 4030 | N | O | Q1o' | a bond | H | a bond | NH | O | a bond | T3h | OH |
| 4031 | N | O | Q1o' | a bond | H | a bond | NH | O | a bond | T3i | OH |
| 4032 | N | O | Q1o' | a bond | H | a bond | NH | O | a bond | T3j | OH |
| 4033 | CH | NMe | Q1o' | a bond | Me | a bond | NH | S | NH | Q3a | OH |
| 4034 | CH | NMe | Q1o' | a bond | Me | a bond | NH | S | NH | Q3e | OH |
| 4035 | CH | NMe | Q1o' | a bond | Me | a bond | NH | S | NH | T3a | OH |
| 4036 | CH | NMe | Q1o' | a bond | Me | a bond | NH | S | NH | T3b | OH |
| 4037 | CH | NMe | Q1o' | a bond | Me | a bond | NH | S | NH | T3c | OH |
| 4038 | CH | NMe | Q1o' | a bond | Me | a bond | NH | S | NH | T3d | OH |
| 4039 | CH | NMe | Q1o' | a bond | Me | a bond | NH | S | NH | T3e | OH |
| 4040 | CH | NMe | Q1o' | a bond | Me | a bond | NH | S | NH | T3f | OH |
| 4041 | CH | NMe | Q1o' | a bond | Me | a bond | NH | S | NH | T3g | OH |
| 4042 | CH | NMe | Q1o' | a bond | Me | a bond | NH | S | NH | T3h | OH |
| 4043 | CH | NMe | Q1o' | a bond | Me | a bond | NH | S | NH | T3i | OH |
| 4044 | CH | NMe | Q1o' | a bond | Me | a bond | NH | S | NH | T3j | OH |
| 4045 | CH | NMe | Q1o' | a bond | Me | a bond | NH | S | a bond | Q3a | OH |
| 4046 | CH | NMe | Q1o' | a bond | Me | a bond | NH | S | a bond | Q3e | OH |
| 4047 | CH | NMe | Q1o' | a bond | Me | a bond | NH | S | a bond | T3a | OH |
| 4048 | CH | NMe | Q1o' | a bond | Me | a bond | NH | S | a bond | T3b | OH |
| 4049 | CH | NMe | Q1o' | a bond | Me | a bond | NH | S | a bond | T3c | OH |
| 4050 | CH | NMe | Q1o' | a bond | Me | a bond | NH | S | a bond | T3d | OH |
| 4051 | CH | NMe | Q1o' | a bond | Me | a bond | NH | S | a bond | T3e | OH |
| 4052 | CH | NMe | Q1o' | a bond | Me | a bond | NH | S | a bond | T3f | OH |
| 4053 | CH | NMe | Q1o' | a bond | Me | a bond | NH | S | a bond | T3g | OH |
| 4054 | CH | NMe | Q1o' | a bond | Me | a bond | NH | S | a bond | T3h | OH |
| 4055 | CH | NMe | Q1o' | a bond | Me | a bond | NH | S | a bond | T3i | OH |
| 4056 | CH | NMe | Q1o' | a bond | Me | a bond | NH | S | a bond | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 4057 | CH | NMe | Q1o' | a bond | Me | a bond | NH | O | NH | Q3a | OH |
| 4058 | CH | NMe | Q1o' | a bond | Me | a bond | NH | O | NH | Q3e | OH |
| 4059 | CH | NMe | Q1o' | a bond | Me | a bond | NH | O | NH | T3a | OH |
| 4060 | CH | NMe | Q1o' | a bond | Me | a bond | NH | O | NH | T3b | OH |
| 4061 | CH | NMe | Q1o' | a bond | Me | a bond | NH | O | NH | T3c | OH |
| 4062 | CH | NMe | Q1o' | a bond | Me | a bond | NH | O | NH | T3d | OH |
| 4063 | CH | NMe | Q1o' | a bond | Me | a bond | NH | O | NH | T3e | OH |
| 4064 | CH | NMe | Q1o' | a bond | Me | a bond | NH | O | NH | T3f | OH |
| 4065 | CH | NMe | Q1o' | a bond | Me | a bond | NH | O | NH | T3g | OH |
| 4066 | CH | NMe | Q1o' | a bond | Me | a bond | NH | O | NH | T3h | OH |
| 4067 | CH | NMe | Q1o' | a bond | Me | a bond | NH | O | NH | T3i | OH |
| 4068 | CH | NMe | Q1o' | a bond | Me | a bond | NH | O | NH | T3j | OH |
| 4069 | CH | NMe | Q1o' | a bond | Me | a bond | NH | O | a bond | Q3a | OH |
| 4070 | CH | NMe | Q1o' | a bond | Me | a bond | NH | O | a bond | Q3e | OH |
| 4071 | CH | NMe | Q1o' | a bond | Me | a bond | NH | O | a bond | T3a | OH |
| 4072 | CH | NMe | Q1o' | a bond | Me | a bond | NH | O | a bond | T3b | OH |
| 4073 | CH | NMe | Q1o' | a bond | Me | a bond | NH | O | a bond | T3c | OH |
| 4074 | CH | NMe | Q1o' | a bond | Me | a bond | NH | O | a bond | T3d | OH |
| 4075 | CH | NMe | Q1o' | a bond | Me | a bond | NH | O | a bond | T3e | OH |
| 4076 | CH | NMe | Q1o' | a bond | Me | a bond | NH | O | a bond | T3f | OH |
| 4077 | CH | NMe | Q1o' | a bond | Me | a bond | NH | O | a bond | T3g | OH |
| 4078 | CH | NMe | Q1o' | a bond | Me | a bond | NH | O | a bond | T3h | OH |
| 4079 | CH | NMe | Q1o' | a bond | Me | a bond | NH | O | a bond | T3i | OH |
| 4080 | CH | NMe | Q1o' | a bond | Me | a bond | NH | O | a bond | T3j | OH |
| 4081 | CH | NMe | Q1o' | a bond | H | a bond | NH | S | NH | Q3a | OH |
| 4082 | CH | NMe | Q1o' | a bond | H | a bond | NH | S | NH | Q3e | OH |
| 4083 | CH | NMe | Q1o' | a bond | H | a bond | NH | S | NH | T3a | OH |
| 4084 | CH | NMe | Q1o' | a bond | H | a bond | NH | S | NH | T3b | OH |
| 4085 | CH | NMe | Q1o' | a bond | H | a bond | NH | S | NH | T3c | OH |
| 4086 | CH | NMe | Q1o' | a bond | H | a bond | NH | S | NH | T3d | OH |
| 4087 | CH | NMe | Q1o' | a bond | H | a bond | NH | S | NH | T3e | OH |
| 4088 | CH | NMe | Q1o' | a bond | H | a bond | NH | S | NH | T3f | OH |
| 4089 | CH | NMe | Q1o' | a bond | H | a bond | NH | S | NH | T3g | OH |
| 4090 | CH | NMe | Q1o' | a bond | H | a bond | NH | S | NH | T3h | OH |
| 4091 | CH | NMe | Q1o' | a bond | H | a bond | NH | S | NH | T3i | OH |
| 4092 | CH | NMe | Q1o' | a bond | H | a bond | NH | S | NH | T3j | OH |
| 4093 | CH | NMe | Q1o' | a bond | H | a bond | NH | S | a bond | Q3a | OH |
| 4094 | CH | NMe | Q1o' | a bond | H | a bond | NH | S | a bond | Q3e | OH |
| 4095 | CH | NMe | Q1o' | a bond | H | a bond | NH | S | a bond | T3a | OH |
| 4096 | CH | NMe | Q1o' | a bond | H | a bond | NH | S | a bond | T3b | OH |
| 4097 | CH | NMe | Q1o' | a bond | H | a bond | NH | S | a bond | T3c | OH |
| 4098 | CH | NMe | Q1o' | a bond | H | a bond | NH | S | a bond | T3d | OH |
| 4099 | CH | NMe | Q1o' | a bond | H | a bond | NH | S | a bond | T3e | OH |
| 4100 | CH | NMe | Q1o' | a bond | H | a bond | NH | S | a bond | T3f | OH |
| 4101 | CH | NMe | Q1o' | a bond | H | a bond | NH | S | a bond | T3g | OH |
| 4102 | CH | NMe | Q1o' | a bond | H | a bond | NH | S | a bond | T3h | OH |
| 4103 | CH | NMe | Q1o' | a bond | H | a bond | NH | S | a bond | T3i | OH |
| 4104 | CH | NMe | Q1o' | a bond | H | a bond | NH | S | a bond | T3j | OH |
| 4105 | CH | NMe | Q1o' | a bond | H | a bond | NH | O | NH | Q3a | OH |
| 4106 | CH | NMe | Q1o' | a bond | H | a bond | NH | O | NH | Q3e | OH |
| 4107 | CH | NMe | Q1o' | a bond | H | a bond | NH | O | NH | T3a | OH |
| 4108 | CH | NMe | Q1o' | a bond | H | a bond | NH | O | NH | T3b | OH |
| 4109 | CH | NMe | Q1o' | a bond | H | a bond | NH | O | NH | T3c | OH |
| 4110 | CH | NMe | Q1o' | a bond | H | a bond | NH | O | NH | T3d | OH |
| 4111 | CH | NMe | Q1o' | a bond | H | a bond | NH | O | NH | T3e | OH |
| 4112 | CH | NMe | Q1o' | a bond | H | a bond | NH | O | NH | T3f | OH |
| 4113 | CH | NMe | Q1o' | a bond | H | a bond | NH | O | NH | T3g | OH |
| 4114 | CH | NMe | Q1o' | a bond | H | a bond | NH | O | NH | T3h | OH |
| 4115 | CH | NMe | Q1o' | a bond | H | a bond | NH | O | NH | T3i | OH |
| 4116 | CH | NMe | Q1o' | a bond | H | a bond | NH | O | NH | T3j | OH |
| 4117 | CH | NMe | Q1o' | a bond | H | a bond | NH | O | a bond | Q3a | OH |
| 4118 | CH | NMe | Q1o' | a bond | H | a bond | NH | O | a bond | Q3e | OH |
| 4119 | CH | NMe | Q1o' | a bond | H | a bond | NH | O | a bond | T3a | OH |
| 4120 | CH | NMe | Q1o' | a bond | H | a bond | NH | O | a bond | T3b | OH |
| 4121 | CH | NMe | Q1o' | a bond | H | a bond | NH | O | a bond | T3c | OH |
| 4122 | CH | NMe | Q1o' | a bond | H | a bond | NH | O | a bond | T3d | OH |
| 4123 | CH | NMe | Q1o' | a bond | H | a bond | NH | O | a bond | T3e | OH |
| 4124 | CH | NMe | Q1o' | a bond | H | a bond | NH | O | a bond | T3f | OH |
| 4125 | CH | NMe | Q1o' | a bond | H | a bond | NH | O | a bond | T3g | OH |
| 4126 | CH | NMe | Q1o' | a bond | H | a bond | NH | O | a bond | T3h | OH |
| 4127 | CH | NMe | Q1o' | a bond | H | a bond | NH | O | a bond | T3i | OH |
| 4128 | CH | NMe | Q1o' | a bond | H | a bond | NH | O | a bond | T3j | OH |
| 4129 | CH | S | Q1o' | a bond | Me | a bond | NH | S | NH | Q3a | OH |
| 4130 | CH | S | Q1o' | a bond | Me | a bond | NH | S | NH | Q3e | OH |
| 4131 | CH | S | Q1o' | a bond | Me | a bond | NH | S | NH | T3a | OH |
| 4132 | CH | S | Q1o' | a bond | Me | a bond | NH | S | NH | T3b | OH |
| 4133 | CH | S | Q1o' | a bond | Me | a bond | NH | S | NH | T3c | OH |
| 4134 | CH | S | Q1o' | a bond | Me | a bond | NH | S | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 4135 | CH | S | Q1o' | a bond | Me | a bond | NH | S | NH | T3e | OH |
| 4136 | CH | S | Q1o' | a bond | Me | a bond | NH | S | NH | T3f | OH |
| 4137 | CH | S | Q1o' | a bond | Me | a bond | NH | S | NH | T3g | OH |
| 4138 | CH | S | Q1o' | a bond | Me | a bond | NH | S | NH | T3h | OH |
| 4139 | CH | S | Q1o' | a bond | Me | a bond | NH | S | NH | T3i | OH |
| 4140 | CH | S | Q1o' | a bond | Me | a bond | NH | S | NH | T3j | OH |
| 4141 | CH | S | Q1o' | a bond | Me | a bond | NH | S | a bond | Q3a | OH |
| 4142 | CH | S | Q1o' | a bond | Me | a bond | NH | S | a bond | Q3e | OH |
| 4143 | CH | S | Q1o' | a bond | Me | a bond | NH | S | a bond | T3a | OH |
| 4144 | CH | S | Q1o' | a bond | Me | a bond | NH | S | a bond | T3b | OH |
| 4145 | CH | S | Q1o' | a bond | Me | a bond | NH | S | a bond | T3c | OH |
| 4146 | CH | S | Q1o' | a bond | Me | a bond | NH | S | a bond | T3d | OH |
| 4147 | CH | S | Q1o' | a bond | Me | a bond | NH | S | a bond | T3e | OH |
| 4148 | CH | S | Q1o' | a bond | Me | a bond | NH | S | a bond | T3f | OH |
| 4149 | CH | S | Q1o' | a bond | Me | a bond | NH | S | a bond | T3g | OH |
| 4150 | CH | S | Q1o' | a bond | Me | a bond | NH | S | a bond | T3h | OH |
| 4151 | CH | S | Q1o' | a bond | Me | a bond | NH | S | a bond | T3i | OH |
| 4152 | CH | S | Q1o' | a bond | Me | a bond | NH | S | a bond | T3j | OH |
| 4153 | CH | S | Q1o' | a bond | Me | a bond | NH | O | NH | Q3a | OH |
| 4154 | CH | S | Q1o' | a bond | Me | a bond | NH | O | NH | Q3e | OH |
| 4155 | CH | S | Q1o' | a bond | Me | a bond | NH | O | NH | T3a | OH |
| 4156 | CH | S | Q1o' | a bond | Me | a bond | NH | O | NH | T3b | OH |
| 4157 | CH | S | Q1o' | a bond | Me | a bond | NH | O | NH | T3c | OH |
| 4158 | CH | S | Q1o' | a bond | Me | a bond | NH | O | NH | T3d | OH |
| 4159 | CH | S | Q1o' | a bond | Me | a bond | NH | O | NH | T3e | OH |
| 4160 | CH | S | Q1o' | a bond | Me | a bond | NH | O | NH | T3f | OH |
| 4161 | CH | S | Q1o' | a bond | Me | a bond | NH | O | NH | T3g | OH |
| 4162 | CH | S | Q1o' | a bond | Me | a bond | NH | O | NH | T3h | OH |
| 4163 | CH | S | Q1o' | a bond | Me | a bond | NH | O | NH | T3i | OH |
| 4164 | CH | S | Q1o' | a bond | Me | a bond | NH | O | NH | T3j | OH |
| 4165 | CH | S | Q1o' | a bond | Me | a bond | NH | O | a bond | Q3a | OH |
| 4166 | CH | S | Q1o' | a bond | Me | a bond | NH | O | a bond | Q3e | OH |
| 4167 | CH | S | Q1o' | a bond | Me | a bond | NH | O | a bond | T3a | OH |
| 4168 | CH | S | Q1o' | a bond | Me | a bond | NH | O | a bond | T3b | OH |
| 4169 | CH | S | Q1o' | a bond | Me | a bond | NH | O | a bond | T3c | OH |
| 4170 | CH | S | Q1o' | a bond | Me | a bond | NH | O | a bond | T3d | OH |
| 4171 | CH | S | Q1o' | a bond | Me | a bond | NH | O | a bond | T3e | OH |
| 4172 | CH | S | Q1o' | a bond | Me | a bond | NH | O | a bond | T3f | OH |
| 4173 | CH | S | Q1o' | a bond | Me | a bond | NH | O | a bond | T3g | OH |
| 4174 | CH | S | Q1o' | a bond | Me | a bond | NH | O | a bond | T3h | OH |
| 4175 | CH | S | Q1o' | a bond | Me | a bond | NH | O | a bond | T3i | OH |
| 4176 | CH | S | Q1o' | a bond | Me | a bond | NH | O | a bond | T3j | OH |
| 4177 | CH | S | Q1o' | a bond | H | a bond | NH | S | NH | Q3a | OH |
| 4178 | CH | S | Q1o' | a bond | H | a bond | NH | S | NH | Q3e | OH |
| 4179 | CH | S | Q1o' | a bond | H | a bond | NH | S | NH | T3a | OH |
| 4180 | CH | S | Q1o' | a bond | H | a bond | NH | S | NH | T3b | OH |
| 4181 | CH | S | Q1o' | a bond | H | a bond | NH | S | NH | T3c | OH |
| 4182 | CH | S | Q1o' | a bond | H | a bond | NH | S | NH | T3d | OH |
| 4183 | CH | S | Q1o' | a bond | H | a bond | NH | S | NH | T3e | OH |
| 4184 | CH | S | Q1o' | a bond | H | a bond | NH | S | NH | T3f | OH |
| 4185 | CH | S | Q1o' | a bond | H | a bond | NH | S | NH | T3g | OH |
| 4186 | CH | S | Q1o' | a bond | H | a bond | NH | S | NH | T3h | OH |
| 4187 | CH | S | Q1o' | a bond | H | a bond | NH | S | NH | T3i | OH |
| 4188 | CH | S | Q1o' | a bond | H | a bond | NH | S | NH | T3j | OH |
| 4189 | CH | S | Q1o' | a bond | H | a bond | NH | S | a bond | Q3a | OH |
| 4190 | CH | S | Q1o' | a bond | H | a bond | NH | S | a bond | Q3e | OH |
| 4191 | CH | S | Q1o' | a bond | H | a bond | NH | S | a bond | T3a | OH |
| 4192 | CH | S | Q1o' | a bond | H | a bond | NH | S | a bond | T3b | OH |
| 4193 | CH | S | Q1o' | a bond | H | a bond | NH | S | a bond | T3c | OH |
| 4194 | CH | S | Q1o' | a bond | H | a bond | NH | S | a bond | T3d | OH |
| 4195 | CH | S | Q1o' | a bond | H | a bond | NH | S | a bond | T3e | OH |
| 4196 | CH | S | Q1o' | a bond | H | a bond | NH | S | a bond | T3f | OH |
| 4197 | CH | S | Q1o' | a bond | H | a bond | NH | S | a bond | T3g | OH |
| 4198 | CH | S | Q1o' | a bond | H | a bond | NH | S | a bond | T3h | OH |
| 4199 | CH | S | Q1o' | a bond | H | a bond | NH | S | a bond | T3i | OH |
| 4200 | CH | S | Q1o' | a bond | H | a bond | NH | S | a bond | T3j | OH |
| 4201 | CH | S | Q1o' | a bond | H | a bond | NH | O | NH | Q3a | OH |
| 4202 | CH | S | Q1o' | a bond | H | a bond | NH | O | NH | Q3e | OH |
| 4203 | CH | S | Q1o' | a bond | H | a bond | NH | O | NH | T3a | OH |
| 4204 | CH | S | Q1o' | a bond | H | a bond | NH | O | NH | T3b | OH |
| 4205 | CH | S | Q1o' | a bond | H | a bond | NH | O | NH | T3c | OH |
| 4206 | CH | S | Q1o' | a bond | H | a bond | NH | O | NH | T3d | OH |
| 4207 | CH | S | Q1o' | a bond | H | a bond | NH | O | NH | T3e | OH |
| 4208 | CH | S | Q1o' | a bond | H | a bond | NH | O | NH | T3f | OH |
| 4209 | CH | S | Q1o' | a bond | H | a bond | NH | O | NH | T3g | OH |
| 4210 | CH | S | Q1o' | a bond | H | a bond | NH | O | NH | T3h | OH |
| 4211 | CH | S | Q1o' | a bond | H | a bond | NH | O | NH | T3i | OH |
| 4212 | CH | S | Q1o' | a bond | H | a bond | NH | O | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 4213 | CH | S | Q1o' | a bond | H | a bond | NH | O | a bond | Q3a | OH |
| 4214 | CH | S | Q1o' | a bond | H | a bond | NH | O | a bond | Q3e | OH |
| 4215 | CH | S | Q1o' | a bond | H | a bond | NH | O | a bond | T3a | OH |
| 4216 | CH | S | Q1o' | a bond | H | a bond | NH | O | a bond | T3b | OH |
| 4217 | CH | S | Q1o' | a bond | H | a bond | NH | O | a bond | T3c | OH |
| 4218 | CH | S | Q1o' | a bond | H | a bond | NH | O | a bond | T3d | OH |
| 4219 | CH | S | Q1o' | a bond | H | a bond | NH | O | a bond | T3e | OH |
| 4220 | CH | S | Q1o' | a bond | H | a bond | NH | O | a bond | T3f | OH |
| 4221 | CH | S | Q1o' | a bond | H | a bond | NH | O | a bond | T3g | OH |
| 4222 | CH | S | Q1o' | a bond | H | a bond | NH | O | a bond | T3h | OH |
| 4223 | CH | S | Q1o' | a bond | H | a bond | NH | O | a bond | T3i | OH |
| 4224 | CH | S | Q1o' | a bond | H | a bond | NH | O | a bond | T3j | OH |
| 4225 | CH | O | Q1o' | a bond | Me | a bond | NH | S | NH | Q3a | OH |
| 4226 | CH | O | Q1o' | a bond | Me | a bond | NH | S | NH | Q3e | OH |
| 4227 | CH | O | Q1o' | a bond | Me | a bond | NH | S | NH | T3a | OH |
| 4228 | CH | O | Q1o' | a bond | Me | a bond | NH | S | NH | T3b | OH |
| 4229 | CH | O | Q1o' | a bond | Me | a bond | NH | S | NH | T3c | OH |
| 4230 | CH | O | Q1o' | a bond | Me | a bond | NH | S | NH | T3d | OH |
| 4231 | CH | O | Q1o' | a bond | Me | a bond | NH | S | NH | T3e | OH |
| 4232 | CH | O | Q1o' | a bond | Me | a bond | NH | S | NH | T3f | OH |
| 4233 | CH | O | Q1o' | a bond | Me | a bond | NH | S | NH | T3g | OH |
| 4234 | CH | O | Q1o' | a bond | Me | a bond | NH | S | NH | T3h | OH |
| 4235 | CH | O | Q1o' | a bond | Me | a bond | NH | S | NH | T3i | OH |
| 4236 | CH | O | Q1o' | a bond | Me | a bond | NH | S | NH | T3j | OH |
| 4237 | CH | O | Q1o' | a bond | Me | a bond | NH | S | a bond | Q3a | OH |
| 4238 | CH | O | Q1o' | a bond | Me | a bond | NH | S | a bond | Q3e | OH |
| 4239 | CH | O | Q1o' | a bond | Me | a bond | NH | S | a bond | T3a | OH |
| 4240 | CH | O | Q1o' | a bond | Me | a bond | NH | S | a bond | T3b | OH |
| 4241 | CH | O | Q1o' | a bond | Me | a bond | NH | S | a bond | T3c | OH |
| 4242 | CH | O | Q1o' | a bond | Me | a bond | NH | S | a bond | T3d | OH |
| 4243 | CH | O | Q1o' | a bond | Me | a bond | NH | S | a bond | T3e | OH |
| 4244 | CH | O | Q1o' | a bond | Me | a bond | NH | S | a bond | T3f | OH |
| 4245 | CH | O | Q1o' | a bond | Me | a bond | NH | S | a bond | T3g | OH |
| 4246 | CH | O | Q1o' | a bond | Me | a bond | NH | S | a bond | T3h | OH |
| 4247 | CH | O | Q1o' | a bond | Me | a bond | NH | S | a bond | T3i | OH |
| 4248 | CH | O | Q1o' | a bond | Me | a bond | NH | S | a bond | T3j | OH |
| 4249 | CH | O | Q1o' | a bond | Me | a bond | NH | O | NH | Q3a | OH |
| 4250 | CH | O | Q1o' | a bond | Me | a bond | NH | O | NH | Q3e | OH |
| 4251 | CH | O | Q1o' | a bond | Me | a bond | NH | O | NH | T3a | OH |
| 4252 | CH | O | Q1o' | a bond | Me | a bond | NH | O | NH | T3b | OH |
| 4253 | CH | O | Q1o' | a bond | Me | a bond | NH | O | NH | T3c | OH |
| 4254 | CH | O | Q1o' | a bond | Me | a bond | NH | O | NH | T3d | OH |
| 4255 | CH | O | Q1o' | a bond | Me | a bond | NH | O | NH | T3e | OH |
| 4256 | CH | O | Q1o' | a bond | Me | a bond | NH | O | NH | T3f | OH |
| 4257 | CH | O | Q1o' | a bond | Me | a bond | NH | O | NH | T3g | OH |
| 4258 | CH | O | Q1o' | a bond | Me | a bond | NH | O | NH | T3h | OH |
| 4259 | CH | O | Q1o' | a bond | Me | a bond | NH | O | NH | T3i | OH |
| 4260 | CH | O | Q1o' | a bond | Me | a bond | NH | O | NH | T3j | OH |
| 4261 | CH | O | Q1o' | a bond | Me | a bond | NH | O | a bond | Q3a | OH |
| 4262 | CH | O | Q1o' | a bond | Me | a bond | NH | O | a bond | Q3e | OH |
| 4263 | CH | O | Q1o' | a bond | Me | a bond | NH | O | a bond | T3a | OH |
| 4264 | CH | O | Q1o' | a bond | Me | a bond | NH | O | a bond | T3b | OH |
| 4265 | CH | O | Q1o' | a bond | Me | a bond | NH | O | a bond | T3c | OH |
| 4266 | CH | O | Q1o' | a bond | Me | a bond | NH | O | a bond | T3d | OH |
| 4267 | CH | O | Q1o' | a bond | Me | a bond | NH | O | a bond | T3e | OH |
| 4268 | CH | O | Q1o' | a bond | Me | a bond | NH | O | a bond | T3f | OH |
| 4269 | CH | O | Q1o' | a bond | Me | a bond | NH | O | a bond | T3g | OH |
| 4270 | CH | O | Q1o' | a bond | Me | a bond | NH | O | a bond | T3h | OH |
| 4271 | CH | O | Q1o' | a bond | Me | a bond | NH | O | a bond | T3i | OH |
| 4272 | CH | O | Q1o' | a bond | Me | a bond | NH | O | a bond | T3j | OH |
| 4273 | CH | O | Q1o' | a bond | H | a bond | NH | S | NH | Q3a | OH |
| 4274 | CH | O | Q1o' | a bond | H | a bond | NH | S | NH | Q3e | OH |
| 4275 | CH | O | Q1o' | a bond | H | a bond | NH | S | NH | T3a | OH |
| 4276 | CH | O | Q1o' | a bond | H | a bond | NH | S | NH | T3b | OH |
| 4277 | CH | O | Q1o' | a bond | H | a bond | NH | S | NH | T3c | OH |
| 4278 | CH | O | Q1o' | a bond | H | a bond | NH | S | NH | T3d | OH |
| 4279 | CH | O | Q1o' | a bond | H | a bond | NH | S | NH | T3e | OH |
| 4280 | CH | O | Q1o' | a bond | H | a bond | NH | S | NH | T3f | OH |
| 4281 | CH | O | Q1o' | a bond | H | a bond | NH | S | NH | T3g | OH |
| 4282 | CH | O | Q1o' | a bond | H | a bond | NH | S | NH | T3h | OH |
| 4283 | CH | O | Q1o' | a bond | H | a bond | NH | S | NH | T3i | OH |
| 4284 | CH | O | Q1o' | a bond | H | a bond | NH | S | NH | T3j | OH |
| 4285 | CH | O | Q1o' | a bond | H | a bond | NH | S | a bond | Q3a | OH |
| 4286 | CH | O | Q1o' | a bond | H | a bond | NH | S | a bond | Q3e | OH |
| 4287 | CH | O | Q1o' | a bond | H | a bond | NH | S | a bond | T3a | OH |
| 4288 | CH | O | Q1o' | a bond | H | a bond | NH | S | a bond | T3b | OH |
| 4289 | CH | O | Q1o' | a bond | H | a bond | NH | S | a bond | T3c | OH |
| 4290 | CH | O | Q1o' | a bond | H | a bond | NH | S | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 4291 | CH | O | Q1o' | a bond | H | a bond | NH | S | a bond | T3e | OH |
| 4292 | CH | O | Q1o' | a bond | H | a bond | NH | S | a bond | T3f | OH |
| 4293 | CH | O | Q1o' | a bond | H | a bond | NH | S | a bond | T3g | OH |
| 4294 | CH | O | Q1o' | a bond | H | a bond | NH | S | a bond | T3h | OH |
| 4295 | CH | O | Q1o' | a bond | H | a bond | NH | S | a bond | T3i | OH |
| 4296 | CH | O | Q1o' | a bond | H | a bond | NH | S | a bond | T3j | OH |
| 4297 | CH | O | Q1o' | a bond | H | a bond | NH | O | NH | Q3a | OH |
| 4298 | CH | O | Q1o' | a bond | H | a bond | NH | O | NH | Q3e | OH |
| 4299 | CH | O | Q1o' | a bond | H | a bond | NH | O | NH | T3a | OH |
| 4300 | CH | O | Q1o' | a bond | H | a bond | NH | O | NH | T3b | OH |
| 4301 | CH | O | Q1o' | a bond | H | a bond | NH | O | NH | T3c | OH |
| 4302 | CH | O | Q1o' | a bond | H | a bond | NH | O | NH | T3d | OH |
| 4303 | CH | O | Q1o' | a bond | H | a bond | NH | O | NH | T3e | OH |
| 4304 | CH | O | Q1o' | a bond | H | a bond | NH | O | NH | T3f | OH |
| 4305 | CH | O | Q1o' | a bond | H | a bond | NH | O | NH | T3g | OH |
| 4306 | CH | O | Q1o' | a bond | H | a bond | NH | O | NH | T3h | OH |
| 4307 | CH | O | Q1o' | a bond | H | a bond | NH | O | NH | T3i | OH |
| 4308 | CH | O | Q1o' | a bond | H | a bond | NH | O | NH | T3j | OH |
| 4309 | CH | O | Q1o' | a bond | H | a bond | NH | O | a bond | Q3a | OH |
| 4310 | CH | O | Q1o' | a bond | H | a bond | NH | O | a bond | Q3e | OH |
| 4311 | CH | O | Q1o' | a bond | H | a bond | NH | O | a bond | T3a | OH |
| 4312 | CH | O | Q1o' | a bond | H | a bond | NH | O | a bond | T3b | OH |
| 4313 | CH | O | Q1o' | a bond | H | a bond | NH | O | a bond | T3c | OH |
| 4314 | CH | O | Q1o' | a bond | H | a bond | NH | O | a bond | T3d | OH |
| 4315 | CH | O | Q1o' | a bond | H | a bond | NH | O | a bond | T3e | OH |
| 4316 | CH | O | Q1o' | a bond | H | a bond | NH | O | a bond | T3f | OH |
| 4317 | CH | O | Q1o' | a bond | H | a bond | NH | O | a bond | T3g | OH |
| 4318 | CH | O | Q1o' | a bond | H | a bond | NH | O | a bond | T3h | OH |
| 4319 | CH | O | Q1o' | a bond | H | a bond | NH | O | a bond | T3i | OH |
| 4320 | CH | O | Q1o' | a bond | H | a bond | NH | O | a bond | T3j | OH |
| 4321 | CMe | NMe | Q1o' | a bond | Me | a bond | NH | S | NH | Q3a | OH |
| 4322 | CMe | NMe | Q1o' | a bond | Me | a bond | NH | S | NH | Q3e | OH |
| 4323 | CMe | NMe | Q1o' | a bond | Me | a bond | NH | S | NH | T3a | OH |
| 4324 | CMe | NMe | Q1o' | a bond | Me | a bond | NH | S | NH | T3b | OH |
| 4325 | CMe | NMe | Q1o' | a bond | Me | a bond | NH | S | NH | T3c | OH |
| 4326 | CMe | NMe | Q1o' | a bond | Me | a bond | NH | S | NH | T3d | OH |
| 4327 | CMe | NMe | Q1o' | a bond | Me | a bond | NH | S | NH | T3e | OH |
| 4328 | CMe | NMe | Q1o' | a bond | Me | a bond | NH | S | NH | T3f | OH |
| 4329 | CMe | NMe | Q1o' | a bond | Me | a bond | NH | S | NH | T3g | OH |
| 4330 | CMe | NMe | Q1o' | a bond | Me | a bond | NH | S | NH | T3h | OH |
| 4331 | CMe | NMe | Q1o' | a bond | Me | a bond | NH | S | NH | T3i | OH |
| 4332 | CMe | NMe | Q1o' | a bond | Me | a bond | NH | S | NH | T3j | OH |
| 4333 | CMe | NMe | Q1o' | a bond | Me | a bond | NH | S | a bond | Q3a | OH |
| 4334 | CMe | NMe | Q1o' | a bond | Me | a bond | NH | S | a bond | Q3e | OH |
| 4335 | CMe | NMe | Q1o' | a bond | Me | a bond | NH | S | a bond | T3a | OH |
| 4336 | CMe | NMe | Q1o' | a bond | Me | a bond | NH | S | a bond | T3b | OH |
| 4337 | CMe | NMe | Q1o' | a bond | Me | a bond | NH | S | a bond | T3c | OH |
| 4338 | CMe | NMe | Q1o' | a bond | Me | a bond | NH | S | a bond | T3d | OH |
| 4339 | CMe | NMe | Q1o' | a bond | Me | a bond | NH | S | a bond | T3e | OH |
| 4340 | CMe | NMe | Q1o' | a bond | Me | a bond | NH | S | a bond | T3f | OH |
| 4341 | CMe | NMe | Q1o' | a bond | Me | a bond | NH | S | a bond | T3g | OH |
| 4342 | CMe | NMe | Q1o' | a bond | Me | a bond | NH | S | a bond | T3h | OH |
| 4343 | CMe | NMe | Q1o' | a bond | Me | a bond | NH | S | a bond | T3i | OH |
| 4344 | CMe | NMe | Q1o' | a bond | Me | a bond | NH | S | a bond | T3j | OH |
| 4345 | CMe | NMe | Q1o' | a bond | Me | a bond | NH | O | NH | Q3a | OH |
| 4346 | CMe | NMe | Q1o' | a bond | Me | a bond | NH | O | NH | Q3e | OH |
| 4347 | CMe | NMe | Q1o' | a bond | Me | a bond | NH | O | NH | T3a | OH |
| 4348 | CMe | NMe | Q1o' | a bond | Me | a bond | NH | O | NH | T3b | OH |
| 4349 | CMe | NMe | Q1o' | a bond | Me | a bond | NH | O | NH | T3c | OH |
| 4350 | CMe | NMe | Q1o' | a bond | Me | a bond | NH | O | NH | T3d | OH |
| 4351 | CMe | NMe | Q1o' | a bond | Me | a bond | NH | O | NH | T3e | OH |
| 4352 | CMe | NMe | Q1o' | a bond | Me | a bond | NH | O | NH | T3f | OH |
| 4353 | CMe | NMe | Q1o' | a bond | Me | a bond | NH | O | NH | T3g | OH |
| 4354 | CMe | NMe | Q1o' | a bond | Me | a bond | NH | O | NH | T3h | OH |
| 4355 | CMe | NMe | Q1o' | a bond | Me | a bond | NH | O | NH | T3i | OH |
| 4356 | CMe | NMe | Q1o' | a bond | Me | a bond | NH | O | NH | T3j | OH |
| 4357 | CMe | NMe | Q1o' | a bond | Me | a bond | NH | O | a bond | Q3a | OH |
| 4358 | CMe | NMe | Q1o' | a bond | Me | a bond | NH | O | a bond | Q3e | OH |
| 4359 | CMe | NMe | Q1o' | a bond | Me | a bond | NH | O | a bond | T3a | OH |
| 4360 | CMe | NMe | Q1o' | a bond | Me | a bond | NH | O | a bond | T3b | OH |
| 4361 | CMe | NMe | Q1o' | a bond | Me | a bond | NH | O | a bond | T3c | OH |
| 4362 | CMe | NMe | Q1o' | a bond | Me | a bond | NH | O | a bond | T3d | OH |
| 4363 | CMe | NMe | Q1o' | a bond | Me | a bond | NH | O | a bond | T3e | OH |
| 4364 | CMe | NMe | Q1o' | a bond | Me | a bond | NH | O | a bond | T3f | OH |
| 4365 | CMe | NMe | Q1o' | a bond | Me | a bond | NH | O | a bond | T3g | OH |
| 4366 | CMe | NMe | Q1o' | a bond | Me | a bond | NH | O | a bond | T3h | OH |
| 4367 | CMe | NMe | Q1o' | a bond | Me | a bond | NH | O | a bond | T3i | OH |
| 4368 | CMe | NMe | Q1o' | a bond | Me | a bond | NH | O | a bond | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 4369 | CMe | NMe | Q1o' | a bond | H | a bond | NH | S | NH | Q3a | OH |
| 4370 | CMe | NMe | Q1o' | a bond | H | a bond | NH | S | NH | Q3e | OH |
| 4371 | CMe | NMe | Q1o' | a bond | H | a bond | NH | S | NH | T3a | OH |
| 4372 | CMe | NMe | Q1o' | a bond | H | a bond | NH | S | NH | T3b | OH |
| 4373 | CMe | NMe | Q1o' | a bond | H | a bond | NH | S | NH | T3c | OH |
| 4374 | CMe | NMe | Q1o' | a bond | H | a bond | NH | S | NH | T3d | OH |
| 4375 | CMe | NMe | Q1o' | a bond | H | a bond | NH | S | NH | T3e | OH |
| 4376 | CMe | NMe | Q1o' | a bond | H | a bond | NH | S | NH | T3f | OH |
| 4377 | CMe | NMe | Q1o' | a bond | H | a bond | NH | S | NH | T3g | OH |
| 4378 | CMe | NMe | Q1o' | a bond | H | a bond | NH | S | NH | T3h | OH |
| 4379 | CMe | NMe | Q1o' | a bond | H | a bond | NH | S | NH | T3i | OH |
| 4380 | CMe | NMe | Q1o' | a bond | H | a bond | NH | S | NH | T3j | OH |
| 4381 | CMe | NMe | Q1o' | a bond | H | a bond | NH | S | a bond | Q3a | OH |
| 4382 | CMe | NMe | Q1o' | a bond | H | a bond | NH | S | a bond | Q3e | OH |
| 4383 | CMe | NMe | Q1o' | a bond | H | a bond | NH | S | a bond | T3a | OH |
| 4384 | CMe | NMe | Q1o' | a bond | H | a bond | NH | S | a bond | T3b | OH |
| 4385 | CMe | NMe | Q1o' | a bond | H | a bond | NH | S | a bond | T3c | OH |
| 4386 | CMe | NMe | Q1o' | a bond | H | a bond | NH | S | a bond | T3d | OH |
| 4387 | CMe | NMe | Q1o' | a bond | H | a bond | NH | S | a bond | T3e | OH |
| 4388 | CMe | NMe | Q1o' | a bond | H | a bond | NH | S | a bond | T3f | OH |
| 4389 | CMe | NMe | Q1o' | a bond | H | a bond | NH | S | a bond | T3g | OH |
| 4390 | CMe | NMe | Q1o' | a bond | H | a bond | NH | S | a bond | T3h | OH |
| 4391 | CMe | NMe | Q1o' | a bond | H | a bond | NH | S | a bond | T3i | OH |
| 4392 | CMe | NMe | Q1o' | a bond | H | a bond | NH | S | a bond | T3j | OH |
| 4393 | CMe | NMe | Q1o' | a bond | H | a bond | NH | O | NH | Q3a | OH |
| 4394 | CMe | NMe | Q1o' | a bond | H | a bond | NH | O | NH | Q3e | OH |
| 4395 | CMe | NMe | Q1o' | a bond | H | a bond | NH | O | NH | T3a | OH |
| 4396 | CMe | NMe | Q1o' | a bond | H | a bond | NH | O | NH | T3b | OH |
| 4397 | CMe | NMe | Q1o' | a bond | H | a bond | NH | O | NH | T3c | OH |
| 4398 | CMe | NMe | Q1o' | a bond | H | a bond | NH | O | NH | T3d | OH |
| 4399 | CMe | NMe | Q1o' | a bond | H | a bond | NH | O | NH | T3e | OH |
| 4400 | CMe | NMe | Q1o' | a bond | H | a bond | NH | O | NH | T3f | OH |
| 4401 | CMe | NMe | Q1o' | a bond | H | a bond | NH | O | NH | T3g | OH |
| 4402 | CMe | NMe | Q1o' | a bond | H | a bond | NH | O | NH | T3h | OH |
| 4403 | CMe | NMe | Q1o' | a bond | H | a bond | NH | O | NH | T3i | OH |
| 4404 | CMe | NMe | Q1o' | a bond | H | a bond | NH | O | NH | T3j | OH |
| 4405 | CMe | NMe | Q1o' | a bond | H | a bond | NH | O | a bond | Q3a | OH |
| 4406 | CMe | NMe | Q1o' | a bond | H | a bond | NH | O | a bond | Q3e | OH |
| 4407 | CMe | NMe | Q1o' | a bond | H | a bond | NH | O | a bond | T3a | OH |
| 4408 | CMe | NMe | Q1o' | a bond | H | a bond | NH | O | a bond | T3b | OH |
| 4409 | CMe | NMe | Q1o' | a bond | H | a bond | NH | O | a bond | T3c | OH |
| 4410 | CMe | NMe | Q1o' | a bond | H | a bond | NH | O | a bond | T3d | OH |
| 4411 | CMe | NMe | Q1o' | a bond | H | a bond | NH | O | a bond | T3e | OH |
| 4412 | CMe | NMe | Q1o' | a bond | H | a bond | NH | O | a bond | T3f | OH |
| 4413 | CMe | NMe | Q1o' | a bond | H | a bond | NH | O | a bond | T3g | OH |
| 4414 | CMe | NMe | Q1o' | a bond | H | a bond | NH | O | a bond | T3h | OH |
| 4415 | CMe | NMe | Q1o' | a bond | H | a bond | NH | O | a bond | T3i | OH |
| 4416 | CMe | NMe | Q1o' | a bond | H | a bond | NH | O | a bond | T3j | OH |
| 4417 | CMe | S | Q1o' | a bond | Me | a bond | NH | S | NH | Q3a | OH |
| 4418 | CMe | S | Q1o' | a bond | Me | a bond | NH | S | NH | Q3e | OH |
| 4419 | CMe | S | Q1o' | a bond | Me | a bond | NH | S | NH | T3a | OH |
| 4420 | CMe | S | Q1o' | a bond | Me | a bond | NH | S | NH | T3b | OH |
| 4421 | CMe | S | Q1o' | a bond | Me | a bond | NH | S | NH | T3c | OH |
| 4422 | CMe | S | Q1o' | a bond | Me | a bond | NH | S | NH | T3d | OH |
| 4423 | CMe | S | Q1o' | a bond | Me | a bond | NH | S | NH | T3e | OH |
| 4424 | CMe | S | Q1o' | a bond | Me | a bond | NH | S | NH | T3f | OH |
| 4425 | CMe | S | Q1o' | a bond | Me | a bond | NH | S | NH | T3g | OH |
| 4426 | CMe | S | Q1o' | a bond | Me | a bond | NH | S | NH | T3h | OH |
| 4427 | CMe | S | Q1o' | a bond | Me | a bond | NH | S | NH | T3i | OH |
| 4428 | CMe | S | Q1o' | a bond | Me | a bond | NH | S | NH | T3j | OH |
| 4429 | CMe | S | Q1o' | a bond | Me | a bond | NH | S | a bond | Q3a | OH |
| 4430 | CMe | S | Q1o' | a bond | Me | a bond | NH | S | a bond | Q3e | OH |
| 4431 | CMe | S | Q1o' | a bond | Me | a bond | NH | S | a bond | T3a | OH |
| 4432 | CMe | S | Q1o' | a bond | Me | a bond | NH | S | a bond | T3b | OH |
| 4433 | CMe | S | Q1o' | a bond | Me | a bond | NH | S | a bond | T3c | OH |
| 4434 | CMe | S | Q1o' | a bond | Me | a bond | NH | S | a bond | T3d | OH |
| 4435 | CMe | S | Q1o' | a bond | Me | a bond | NH | S | a bond | T3e | OH |
| 4436 | CMe | S | Q1o' | a bond | Me | a bond | NH | S | a bond | T3f | OH |
| 4437 | CMe | S | Q1o' | a bond | Me | a bond | NH | S | a bond | T3g | OH |
| 4438 | CMe | S | Q1o' | a bond | Me | a bond | NH | S | a bond | T3h | OH |
| 4439 | CMe | S | Q1o' | a bond | Me | a bond | NH | S | a bond | T3i | OH |
| 4440 | CMe | S | Q1o' | a bond | Me | a bond | NH | S | a bond | T3j | OH |
| 4441 | CMe | S | Q1o' | a bond | Me | a bond | NH | O | NH | Q3a | OH |
| 4442 | CMe | S | Q1o' | a bond | Me | a bond | NH | O | NH | Q3e | OH |
| 4443 | CMe | S | Q1o' | a bond | Me | a bond | NH | O | NH | T3a | OH |
| 4444 | CMe | S | Q1o' | a bond | Me | a bond | NH | O | NH | T3b | OH |
| 4445 | CMe | S | Q1o' | a bond | Me | a bond | NH | O | NH | T3c | OH |
| 4446 | CMe | S | Q1o' | a bond | Me | a bond | NH | O | NH | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 4447 | CMe | S | Q1o' | a bond | Me | a bond | NH | O | NH | T3e | OH |
| 4448 | CMe | S | Q1o' | a bond | Me | a bond | NH | O | NH | T3f | OH |
| 4449 | CMe | S | Q1o' | a bond | Me | a bond | NH | O | NH | T3g | OH |
| 4450 | CMe | S | Q1o' | a bond | Me | a bond | NH | O | NH | T3h | OH |
| 4451 | CMe | S | Q1o' | a bond | Me | a bond | NH | O | NH | T3i | OH |
| 4452 | CMe | S | Q1o' | a bond | Me | a bond | NH | O | NH | T3j | OH |
| 4453 | CMe | S | Q1o' | a bond | Me | a bond | NH | O | a bond | Q3a | OH |
| 4454 | CMe | S | Q1o' | a bond | Me | a bond | NH | O | a bond | Q3e | OH |
| 4455 | CMe | S | Q1o' | a bond | Me | a bond | NH | O | a bond | T3a | OH |
| 4456 | CMe | S | Q1o' | a bond | Me | a bond | NH | O | a bond | T3b | OH |
| 4457 | CMe | S | Q1o' | a bond | Me | a bond | NH | O | a bond | T3c | OH |
| 4458 | CMe | S | Q1o' | a bond | Me | a bond | NH | O | a bond | T3d | OH |
| 4459 | CMe | S | Q1o' | a bond | Me | a bond | NH | O | a bond | T3e | OH |
| 4460 | CMe | S | Q1o' | a bond | Me | a bond | NH | O | a bond | T3f | OH |
| 4461 | CMe | S | Q1o' | a bond | Me | a bond | NH | O | a bond | T3g | OH |
| 4462 | CMe | S | Q1o' | a bond | Me | a bond | NH | O | a bond | T3h | OH |
| 4463 | CMe | S | Q1o' | a bond | Me | a bond | NH | O | a bond | T3i | OH |
| 4464 | CMe | S | Q1o' | a bond | Me | a bond | NH | O | a bond | T3j | OH |
| 4465 | CMe | S | Q1o' | a bond | H | a bond | NH | S | NH | Q3a | OH |
| 4466 | CMe | S | Q1o' | a bond | H | a bond | NH | S | NH | Q3e | OH |
| 4467 | CMe | S | Q1o' | a bond | H | a bond | NH | S | NH | T3a | OH |
| 4468 | CMe | S | Q1o' | a bond | H | a bond | NH | S | NH | T3b | OH |
| 4469 | CMe | S | Q1o' | a bond | H | a bond | NH | S | NH | T3c | OH |
| 4470 | CMe | S | Q1o' | a bond | H | a bond | NH | S | NH | T3d | OH |
| 4471 | CMe | S | Q1o' | a bond | H | a bond | NH | S | NH | T3e | OH |
| 4472 | CMe | S | Q1o' | a bond | H | a bond | NH | S | NH | T3f | OH |
| 4473 | CMe | S | Q1o' | a bond | H | a bond | NH | S | NH | T3g | OH |
| 4474 | CMe | S | Q1o' | a bond | H | a bond | NH | S | NH | T3h | OH |
| 4475 | CMe | S | Q1o' | a bond | H | a bond | NH | S | NH | T3i | OH |
| 4476 | CMe | S | Q1o' | a bond | H | a bond | NH | S | NH | T3j | OH |
| 4477 | CMe | S | Q1o' | a bond | H | a bond | NH | S | a bond | Q3a | OH |
| 4478 | CMe | S | Q1o' | a bond | H | a bond | NH | S | a bond | Q3e | OH |
| 4479 | CMe | S | Q1o' | a bond | H | a bond | NH | S | a bond | T3a | OH |
| 4480 | CMe | S | Q1o' | a bond | H | a bond | NH | S | a bond | T3b | OH |
| 4481 | CMe | S | Q1o' | a bond | H | a bond | NH | S | a bond | T3c | OH |
| 4482 | CMe | S | Q1o' | a bond | H | a bond | NH | S | a bond | T3d | OH |
| 4483 | CMe | S | Q1o' | a bond | H | a bond | NH | S | a bond | T3e | OH |
| 4484 | CMe | S | Q1o' | a bond | H | a bond | NH | S | a bond | T3f | OH |
| 4485 | CMe | S | Q1o' | a bond | H | a bond | NH | S | a bond | T3g | OH |
| 4486 | CMe | S | Q1o' | a bond | H | a bond | NH | S | a bond | T3h | OH |
| 4487 | CMe | S | Q1o' | a bond | H | a bond | NH | S | a bond | T3i | OH |
| 4488 | CMe | S | Q1o' | a bond | H | a bond | NH | S | a bond | T3j | OH |
| 4489 | CMe | S | Q1o' | a bond | H | a bond | NH | O | NH | Q3a | OH |
| 4490 | CMe | S | Q1o' | a bond | H | a bond | NH | O | NH | Q3e | OH |
| 4491 | CMe | S | Q1o' | a bond | H | a bond | NH | O | NH | T3a | OH |
| 4492 | CMe | S | Q1o' | a bond | H | a bond | NH | O | NH | T3b | OH |
| 4493 | CMe | S | Q1o' | a bond | H | a bond | NH | O | NH | T3c | OH |
| 4494 | CMe | S | Q1o' | a bond | H | a bond | NH | O | NH | T3d | OH |
| 4495 | CMe | S | Q1o' | a bond | H | a bond | NH | O | NH | T3e | OH |
| 4496 | CMe | S | Q1o' | a bond | H | a bond | NH | O | NH | T3f | OH |
| 4497 | CMe | S | Q1o' | a bond | H | a bond | NH | O | NH | T3g | OH |
| 4498 | CMe | S | Q1o' | a bond | H | a bond | NH | O | NH | T3h | OH |
| 4499 | CMe | S | Q1o' | a bond | H | a bond | NH | O | NH | T3i | OH |
| 4500 | CMe | S | Q1o' | a bond | H | a bond | NH | O | NH | T3j | OH |
| 4501 | CMe | S | Q1o' | a bond | H | a bond | NH | O | a bond | Q3a | OH |
| 4502 | CMe | S | Q1o' | a bond | H | a bond | NH | O | a bond | Q3e | OH |
| 4503 | CMe | S | Q1o' | a bond | H | a bond | NH | O | a bond | T3a | OH |
| 4504 | CMe | S | Q1o' | a bond | H | a bond | NH | O | a bond | T3b | OH |
| 4505 | CMe | S | Q1o' | a bond | H | a bond | NH | O | a bond | T3c | OH |
| 4506 | CMe | S | Q1o' | a bond | H | a bond | NH | O | a bond | T3d | OH |
| 4507 | CMe | S | Q1o' | a bond | H | a bond | NH | O | a bond | T3e | OH |
| 4508 | CMe | S | Q1o' | a bond | H | a bond | NH | O | a bond | T3f | OH |
| 4509 | CMe | S | Q1o' | a bond | H | a bond | NH | O | a bond | T3g | OH |
| 4510 | CMe | S | Q1o' | a bond | H | a bond | NH | O | a bond | T3h | OH |
| 4511 | CMe | S | Q1o' | a bond | H | a bond | NH | O | a bond | T3i | OH |
| 4512 | CMe | S | Q1o' | a bond | H | a bond | NH | O | a bond | T3j | OH |
| 4513 | CMe | O | Q1o' | a bond | Me | a bond | NH | S | NH | Q3a | OH |
| 4514 | CMe | O | Q1o' | a bond | Me | a bond | NH | S | NH | Q3e | OH |
| 4515 | CMe | O | Q1o' | a bond | Me | a bond | NH | S | NH | T3a | OH |
| 4516 | CMe | O | Q1o' | a bond | Me | a bond | NH | S | NH | T3b | OH |
| 4517 | CMe | O | Q1o' | a bond | Me | a bond | NH | S | NH | T3c | OH |
| 4518 | CMe | O | Q1o' | a bond | Me | a bond | NH | S | NH | T3d | OH |
| 4519 | CMe | O | Q1o' | a bond | Me | a bond | NH | S | NH | T3e | OH |
| 4520 | CMe | O | Q1o' | a bond | Me | a bond | NH | S | NH | T3f | OH |
| 4521 | CMe | O | Q1o' | a bond | Me | a bond | NH | S | NH | T3g | OH |
| 4522 | CMe | O | Q1o' | a bond | Me | a bond | NH | S | NH | T3h | OH |
| 4523 | CMe | O | Q1o' | a bond | Me | a bond | NH | S | NH | T3i | OH |
| 4524 | CMe | O | Q1o' | a bond | Me | a bond | NH | S | NH | T3j | OH |

TABLE 6-continued

| No | A | B | R¹ | L¹ | R² | L² | L³ | Y | L⁴ | R³ | X |
|---|---|---|---|---|---|---|---|---|---|---|---|
| 4525 | CMe | O | Q1o' | a bond | Me | a bond | NH | S | a bond | Q3a | OH |
| 4526 | CMe | O | Q1o' | a bond | Me | a bond | NH | S | a bond | Q3e | OH |
| 4527 | CMe | O | Q1o' | a bond | Me | a bond | NH | S | a bond | T3a | OH |
| 4528 | CMe | O | Q1o' | a bond | Me | a bond | NH | S | a bond | T3b | OH |
| 4529 | CMe | O | Q1o' | a bond | Me | a bond | NH | S | a bond | T3c | OH |
| 4530 | CMe | O | Q1o' | a bond | Me | a bond | NH | S | a bond | T3d | OH |
| 4531 | CMe | O | Q1o' | a bond | Me | a bond | NH | S | a bond | T3e | OH |
| 4532 | CMe | O | Q1o' | a bond | Me | a bond | NH | S | a bond | T3f | OH |
| 4533 | CMe | O | Q1o' | a bond | Me | a bond | NH | S | a bond | T3g | OH |
| 4534 | CMe | O | Q1o' | a bond | Me | a bond | NH | S | a bond | T3h | OH |
| 4535 | CMe | O | Q1o' | a bond | Me | a bond | NH | S | a bond | T3i | OH |
| 4536 | CMe | O | Q1o' | a bond | Me | a bond | NH | S | a bond | T3j | OH |
| 4537 | CMe | O | Q1o' | a bond | Me | a bond | NH | O | NH | Q3a | OH |
| 4538 | CMe | O | Q1o' | a bond | Me | a bond | NH | O | NH | Q3e | OH |
| 4539 | CMe | O | Q1o' | a bond | Me | a bond | NH | O | NH | T3a | OH |
| 4540 | CMe | O | Q1o' | a bond | Me | a bond | NH | O | NH | T3b | OH |
| 4541 | CMe | O | Q1o' | a bond | Me | a bond | NH | O | NH | T3c | OH |
| 4542 | CMe | O | Q1o' | a bond | Me | a bond | NH | O | NH | T3d | OH |
| 4543 | CMe | O | Q1o' | a bond | Me | a bond | NH | O | NH | T3e | OH |
| 4544 | CMe | O | Q1o' | a bond | Me | a bond | NH | O | NH | T3f | OH |
| 4545 | CMe | O | Q1o' | a bond | Me | a bond | NH | O | NH | T3g | OH |
| 4546 | CMe | O | Q1o' | a bond | Me | a bond | NH | O | NH | T3h | OH |
| 4547 | CMe | O | Q1o' | a bond | Me | a bond | NH | O | NH | T3i | OH |
| 4548 | CMe | O | Q1o' | a bond | Me | a bond | NH | O | NH | T3j | OH |
| 4549 | CMe | O | Q1o' | a bond | Me | a bond | NH | O | a bond | Q3a | OH |
| 4550 | CMe | O | Q1o' | a bond | Me | a bond | NH | O | a bond | Q3e | OH |
| 4551 | CMe | O | Q1o' | a bond | Me | a bond | NH | O | a bond | T3a | OH |
| 4552 | CMe | O | Q1o' | a bond | Me | a bond | NH | O | a bond | T3b | OH |
| 4553 | CMe | O | Q1o' | a bond | Me | a bond | NH | O | a bond | T3c | OH |
| 4554 | CMe | O | Q1o' | a bond | Me | a bond | NH | O | a bond | T3d | OH |
| 4555 | CMe | O | Q1o' | a bond | Me | a bond | NH | O | a bond | T3e | OH |
| 4556 | CMe | O | Q1o' | a bond | Me | a bond | NH | O | a bond | T3f | OH |
| 4557 | CMe | O | Q1o' | a bond | Me | a bond | NH | O | a bond | T3g | OH |
| 4558 | CMe | O | Q1o' | a bond | Me | a bond | NH | O | a bond | T3h | OH |
| 4559 | CMe | O | Q1o' | a bond | Me | a bond | NH | O | a bond | T3i | OH |
| 4560 | CMe | O | Q1o' | a bond | Me | a bond | NH | O | a bond | T3j | OH |
| 4561 | CMe | O | Q1o' | a bond | H | a bond | NH | S | NH | Q3a | OH |
| 4562 | CMe | O | Q1o' | a bond | H | a bond | NH | S | NH | Q3e | OH |
| 4563 | CMe | O | Q1o' | a bond | H | a bond | NH | S | NH | T3a | OH |
| 4564 | CMe | O | Q1o' | a bond | H | a bond | NH | S | NH | T3b | OH |
| 4565 | CMe | O | Q1o' | a bond | H | a bond | NH | S | NH | T3c | OH |
| 4566 | CMe | O | Q1o' | a bond | H | a bond | NH | S | NH | T3d | OH |
| 4567 | CMe | O | Q1o' | a bond | H | a bond | NH | S | NH | T3e | OH |
| 4568 | CMe | O | Q1o' | a bond | H | a bond | NH | S | NH | T3f | OH |
| 4569 | CMe | O | Q1o' | a bond | H | a bond | NH | S | NH | T3g | OH |
| 4570 | CMe | O | Q1o' | a bond | H | a bond | NH | S | NH | T3h | OH |
| 4571 | CMe | O | Q1o' | a bond | H | a bond | NH | S | NH | T3i | OH |
| 4572 | CMe | O | Q1o' | a bond | H | a bond | NH | S | NH | T3j | OH |
| 4573 | CMe | O | Q1o' | a bond | H | a bond | NH | S | a bond | Q3a | OH |
| 4574 | CMe | O | Q1o' | a bond | H | a bond | NH | S | a bond | Q3e | OH |
| 4575 | CMe | O | Q1o' | a bond | H | a bond | NH | S | a bond | T3a | OH |
| 4576 | CMe | O | Q1o' | a bond | H | a bond | NH | S | a bond | T3b | OH |
| 4577 | CMe | O | Q1o' | a bond | H | a bond | NH | S | a bond | T3c | OH |
| 4578 | CMe | O | Q1o' | a bond | H | a bond | NH | S | a bond | T3d | OH |
| 4579 | CMe | O | Q1o' | a bond | H | a bond | NH | S | a bond | T3e | OH |
| 4580 | CMe | O | Q1o' | a bond | H | a bond | NH | S | a bond | T3f | OH |
| 4581 | CMe | O | Q1o' | a bond | H | a bond | NH | S | a bond | T3g | OH |
| 4582 | CMe | O | Q1o' | a bond | H | a bond | NH | S | a bond | T3h | OH |
| 4583 | CMe | O | Q1o' | a bond | H | a bond | NH | S | a bond | T3i | OH |
| 4584 | CMe | O | Q1o' | a bond | H | a bond | NH | S | a bond | T3j | OH |
| 4585 | CMe | O | Q1o' | a bond | H | a bond | NH | O | NH | Q3a | OH |
| 4586 | CMe | O | Q1o' | a bond | H | a bond | NH | O | NH | Q3e | OH |
| 4587 | CMe | O | Q1o' | a bond | H | a bond | NH | O | NH | T3a | OH |
| 4588 | CMe | O | Q1o' | a bond | H | a bond | NH | O | NH | T3b | OH |
| 4589 | CMe | O | Q1o' | a bond | H | a bond | NH | O | NH | T3c | OH |
| 4590 | CMe | O | Q1o' | a bond | H | a bond | NH | O | NH | T3d | OH |
| 4591 | CMe | O | Q1o' | a bond | H | a bond | NH | O | NH | T3e | OH |
| 4592 | CMe | O | Q1o' | a bond | H | a bond | NH | O | NH | T3f | OH |
| 4593 | CMe | O | Q1o' | a bond | H | a bond | NH | O | NH | T3g | OH |
| 4594 | CMe | O | Q1o' | a bond | H | a bond | NH | O | NH | T3h | OH |
| 4595 | CMe | O | Q1o' | a bond | H | a bond | NH | O | NH | T3i | OH |
| 4596 | CMe | O | Q1o' | a bond | H | a bond | NH | O | NH | T3j | OH |
| 4597 | CMe | O | Q1o' | a bond | H | a bond | NH | O | a bond | Q3a | OH |
| 4598 | CMe | O | Q1o' | a bond | H | a bond | NH | O | a bond | Q3e | OH |
| 4599 | CMe | O | Q1o' | a bond | H | a bond | NH | O | a bond | T3a | OH |
| 4600 | CMe | O | Q1o' | a bond | H | a bond | NH | O | a bond | T3b | OH |
| 4601 | CMe | O | Q1o' | a bond | H | a bond | NH | O | a bond | T3c | OH |
| 4602 | CMe | O | Q1o' | a bond | H | a bond | NH | O | a bond | T3d | OH |

TABLE 6-continued

| No | A | B | R¹ | L¹ | R² | L² | L³ | Y | L⁴ | R³ | X |
|---|---|---|---|---|---|---|---|---|---|---|---|
| 4603 | CMe | O | Q1o' | a bond | H | a bond | NH | O | a bond | T3e | OH |
| 4604 | CMe | O | Q1o' | a bond | H | a bond | NH | O | a bond | T3f | OH |
| 4605 | CMe | O | Q1o' | a bond | H | a bond | NH | O | a bond | T3g | OH |
| 4606 | CMe | O | Q1o' | a bond | H | a bond | NH | O | a bond | T3h | OH |
| 4607 | CMe | O | Q1o' | a bond | H | a bond | NH | O | a bond | T3i | OH |
| 4608 | CMe | O | Q1o' | a bond | H | a bond | NH | O | a bond | T3j | OH |

74) The compounds in Table 6 wherein A, B, R¹, L¹, R², L², L³, Y, L⁴, R³ and X are any of the following combinations in Table 6, tautomers, prodrugs or pharmaceutically acceptable salts of the compounds or solvates thereof (provided that in the case of 74), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

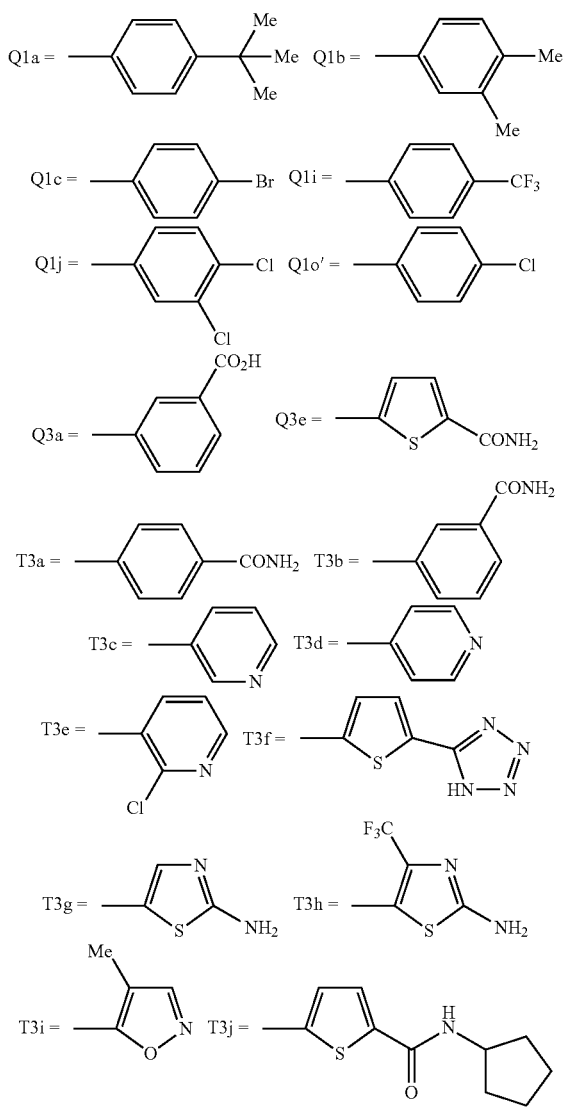

75) The compounds in Table 6 wherein A, B, R¹, L¹, R², L², L³, Y, L⁴, R³ and X are any of the following combinations in Table 6, tautomers, prodrugs or pharmaceutically acceptable salts of the compounds or solvates thereof (provided that in the case of 75), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

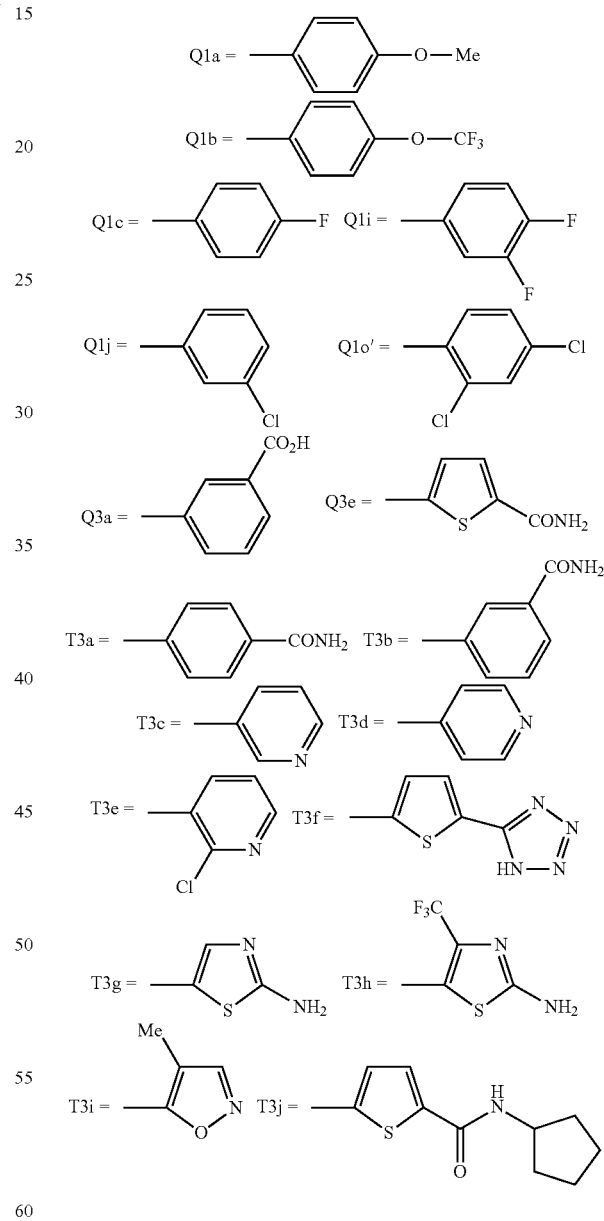

76) The compounds in Table 6 wherein A, B, R¹, L¹, R², L², L³, Y, L⁴, R³ and X are any of the following combinations in Table 6, tautomers, prodrugs or pharmaceutically acceptable salts of the compounds or solvates thereof (provided that in the case of 76), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

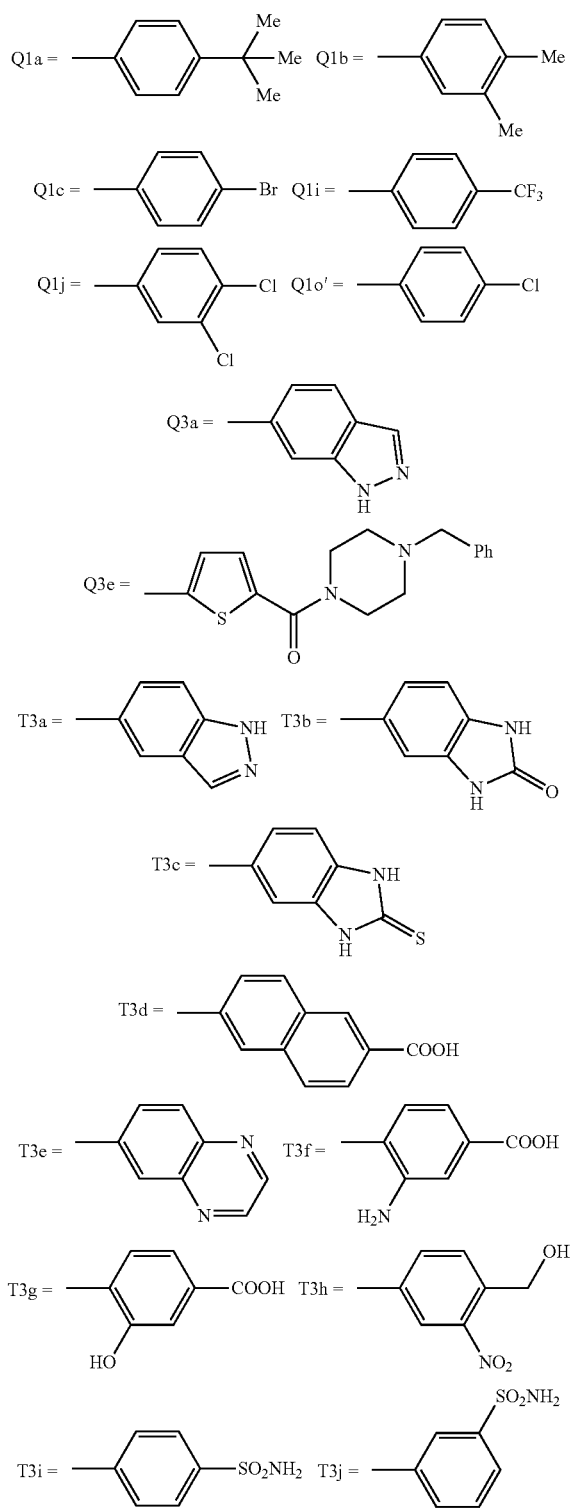

77) The compounds in Table 6 wherein A, B, $R^1$, $L^1$, $R^2$, $L^2$, $L^3$, Y, $L^4$, $R^3$ and X are any of the following combinations in Table 6, tautomers, prodrugs or pharmaceutically acceptable salts of the compounds or solvates thereof (provided that in the case of 77), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

78) The compounds in Table 6 wherein A, B, $L^1$, $R^2$, $L^2$, $L^3$, Y, $L^4$, $R^3$ and X are any of the following combinations in Table 6, tautomers, prodrugs or pharmaceutically acceptable salts of the compounds or solvates thereof (provided that in the case of 78), Q1a, Q1b, Q1c, Q1i, Q1j, Q1o', Q3a, T1a, T3b, T3c, T3d, T3e, Q3e, T3f, T3g, T3h, T3i and T3j in Table 6 denote the following substituents).

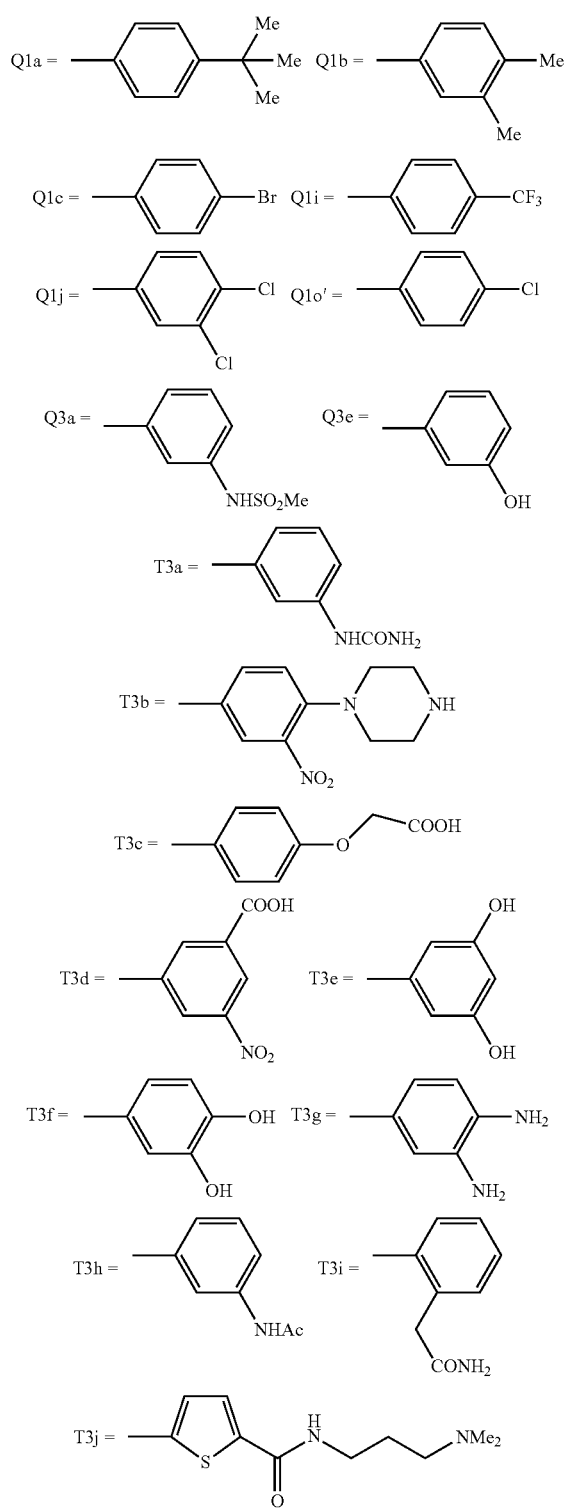

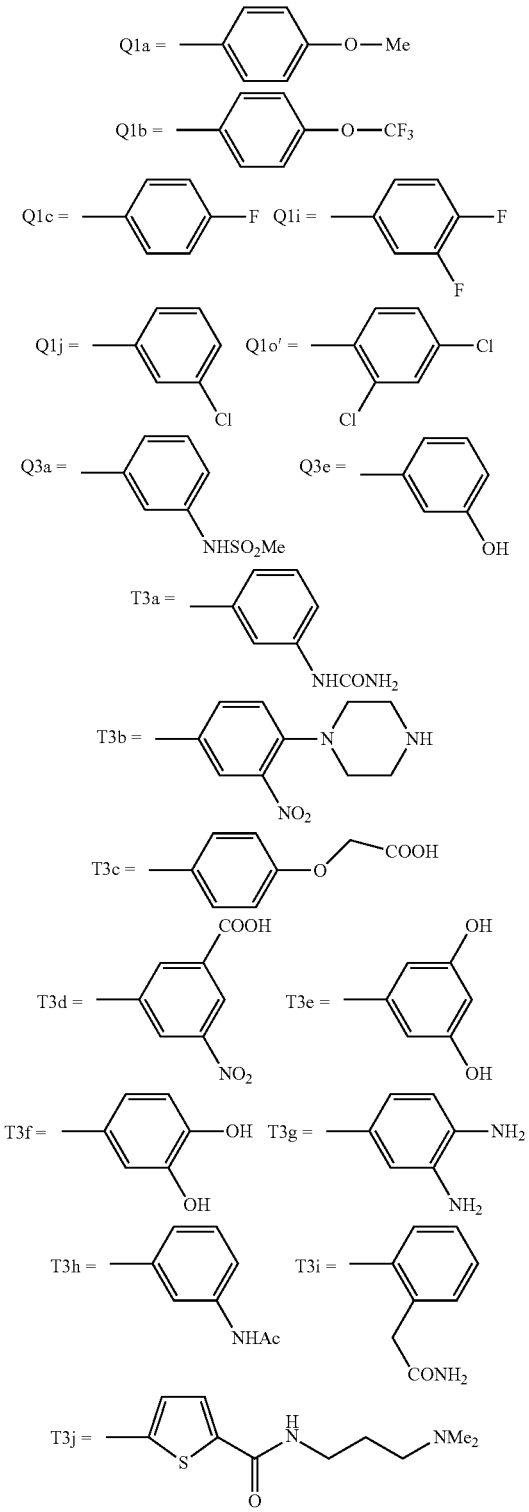

79) The compounds in Table 6 wherein A, B, R$^1$, L$^1$, R$^2$, L$^2$, L$^3$, Y, L$^4$, R$^3$ and X are any of the following combinations in Table 6, tautomers, prodrugs or pharmaceutically acceptable salts of the compounds or solvates thereof (provided that in the case of 79), Q1a, Q1b, Q1c, Q1i, Q1j, Q1o', Q3a, T1a, T3b, T3c, T3d, T3e, Q3e, T3f, T3g, T3h, T3i and T3j in Table 6 denote the following substituents).

80) The compounds in Table 6 wherein A, B, R$^1$, L$^1$, R$^2$, L$^2$, L$^3$, Y, L$^4$, R$^3$ and X are any of the following combinations in Table 6, tautomers, prodrugs or pharmaceutically acceptable salts of the compounds or solvates thereof (provided that in the case of 80), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

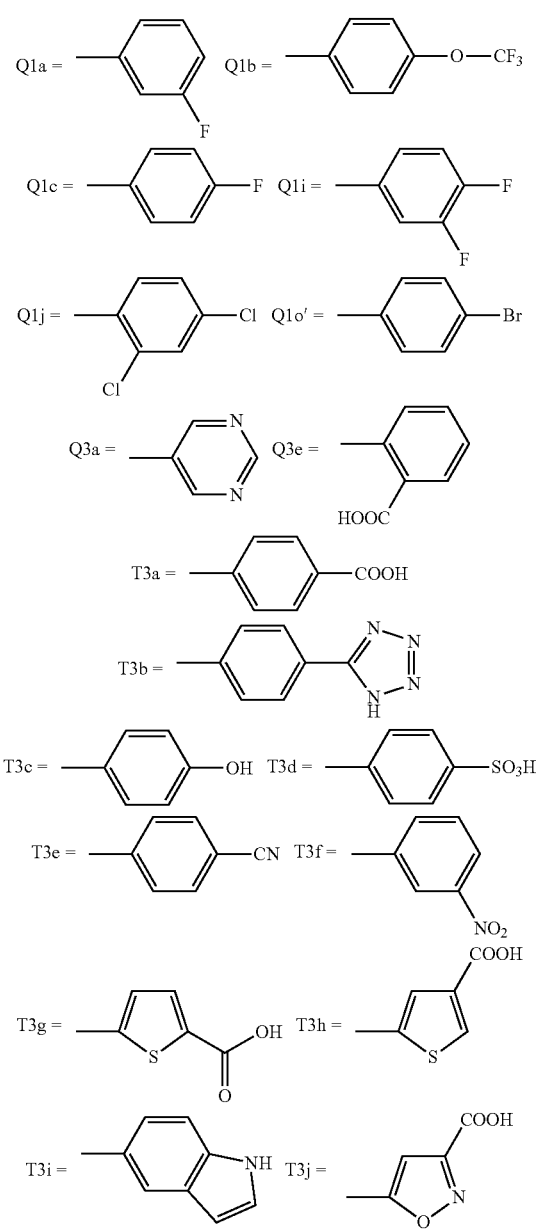

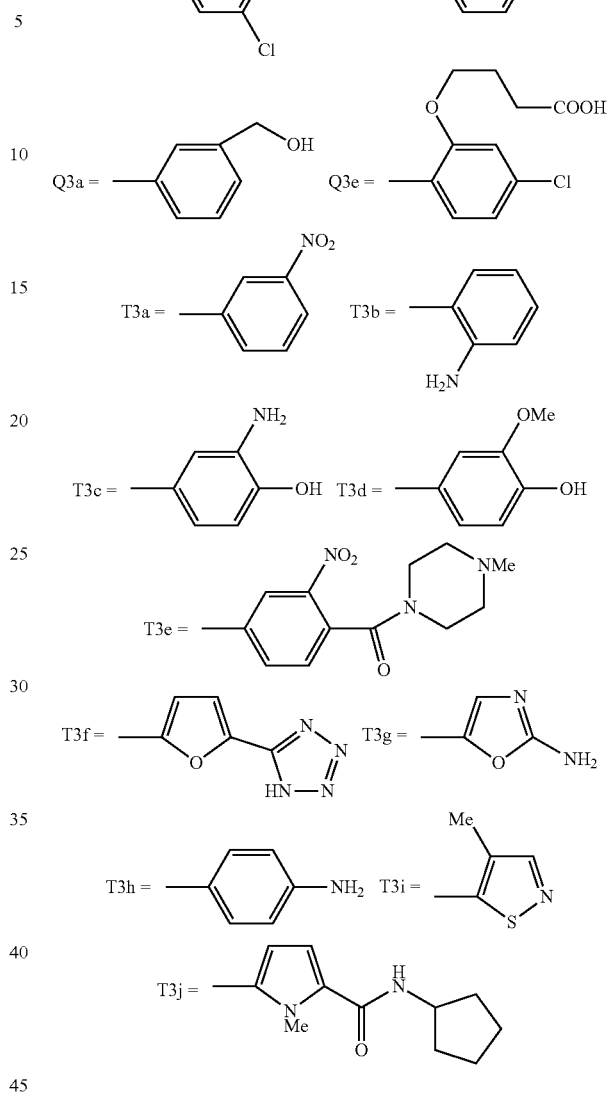

81) The compounds in Table 6 wherein A, B, $L^1$, $R^2$, $L^2$, $L^3$, Y, $L^4$, $R^3$ and X are any of the following combinations in Table 6, tautomers, prodrugs or pharmaceutically acceptable salts of the compounds or solvates thereof (provided that in the case of 81), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

82) The compounds in Table 6 wherein A, B, $R^1$, $L^1$, $R^2$, $L^2$, $L^3$, Y, $L^4$, $R^3$ and X are any of the following combinations in Table 6, tautomers, prodrugs or pharmaceutically acceptable salts of the compounds or solvates thereof (provided that in the case of 82), Q1a, Q1b, Q1c, Q1i, Q1j, Q1o', Q3a, T3a, T3b, T3c, T3d, T3e, Q3e, T3f, T3g, T3h, T3i and T3j in Table 6 denote the following substituents).

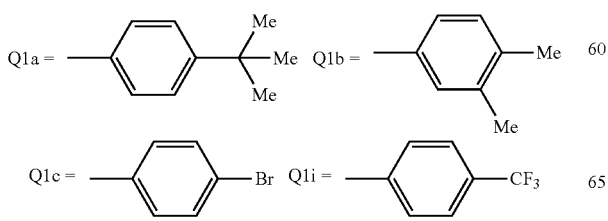

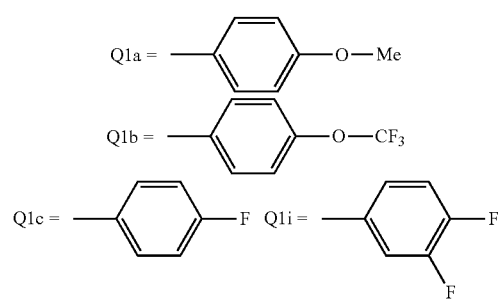

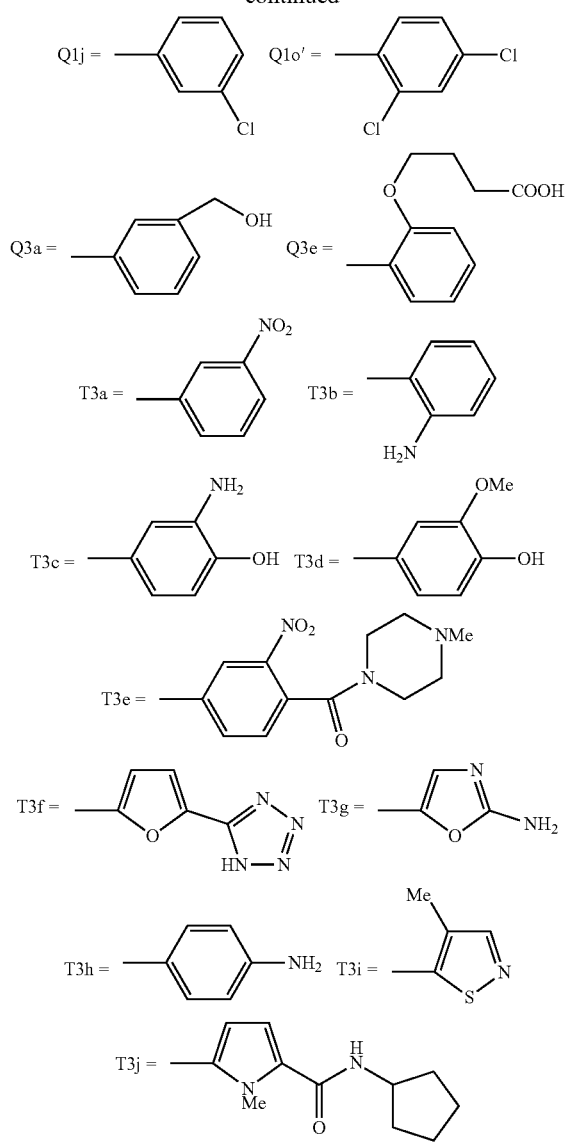

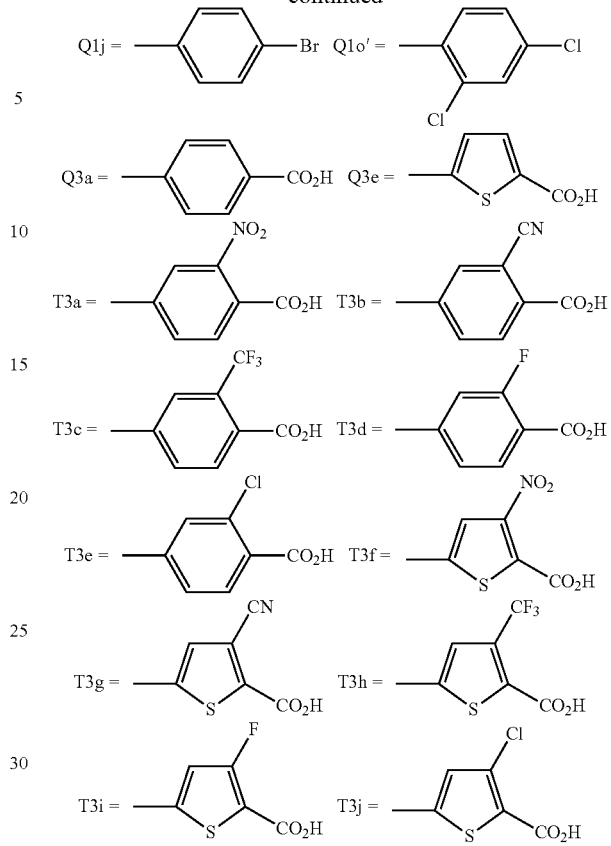

83) The compounds in Table 6 wherein A, B, R$^1$, L$^1$, R$^2$, L$^2$, L$^3$, Y, L$^4$, R$^3$ and X are any of the following combinations in Table 6, tautomers, prodrugs or pharmaceutically acceptable salts of the compounds or solvates thereof (provided that in the case of 83), Q1a, Q1b, Q1c, Q1i, Q1j, Q1o′, Q3a, T3a, T3b, T3c, T3d, T3e, Q3e, T3f, T3g, T3h, T3i and T3j in Table 6 denote the following substituents).

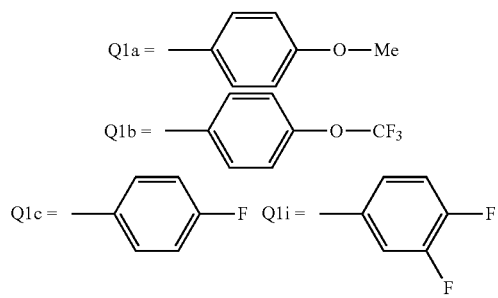

84) The compound represented by any of 68) to 83) wherein X is converted to SH, tautomers, prodrugs or pharmaceutically acceptable salts of the compounds or solvates thereof.

85) The compound represented by any of 68) to 83) wherein X is converted to NH$_2$, tautomers, prodrugs or pharmaceutically acceptable salts of the compounds or solvates thereof.

86) The compound represented by any of 68) to 83) wherein X is converted to OAc, tautomers, prodrugs or pharmaceutically acceptable salts of the compounds or solvates thereof.

87) The thrombopoietin receptor activators represented by any of 1) to 86).

88) Preventive, therapeutic and improving agents for diseases against which activation of the thrombopoietin receptor is effective which contain the thrombopoietin receptor activators represented by 87) or the formula (1), tautomers, prodrugs or pharmaceutically acceptable salts of the activators or solvates thereof, as an active ingredient.

89) Platelet increasing agents containing the thrombopoietin receptor activators represented by 87) or the formula (1), tautomers, prodrugs or pharmaceutically acceptable salts of the activators or solvates thereof, as an active ingredient.

90) Medicaments containing the compounds represented by any of 1) to 86) or the formula (1), tautomers, prodrugs or pharmaceutically acceptable salts of the compounds or solvates thereof, as an active ingredient.

In the present invention, the compounds of the present invention represented by the formula (1) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

For example, furan compounds, thiophene compounds and pyrrole compounds of the present invention may be present in the form of tetronic acid (4-hydroxy-2(5H)-furanone) analogues, thiotetronic acid (4-hydroxy-2(5H)-thiophenone) analogues and tetraminic acid (4-hydroxy-3-pyrrolin-2-one) analogues as shown below by the formulae (2), (3) and (4), mixtures thereof or mixtures of isomers thereof.

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrug (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —OCO(t-Bu), —$OCOC_{15}H_{31}$, —OCO(m-$CO_2$Na-Ph),

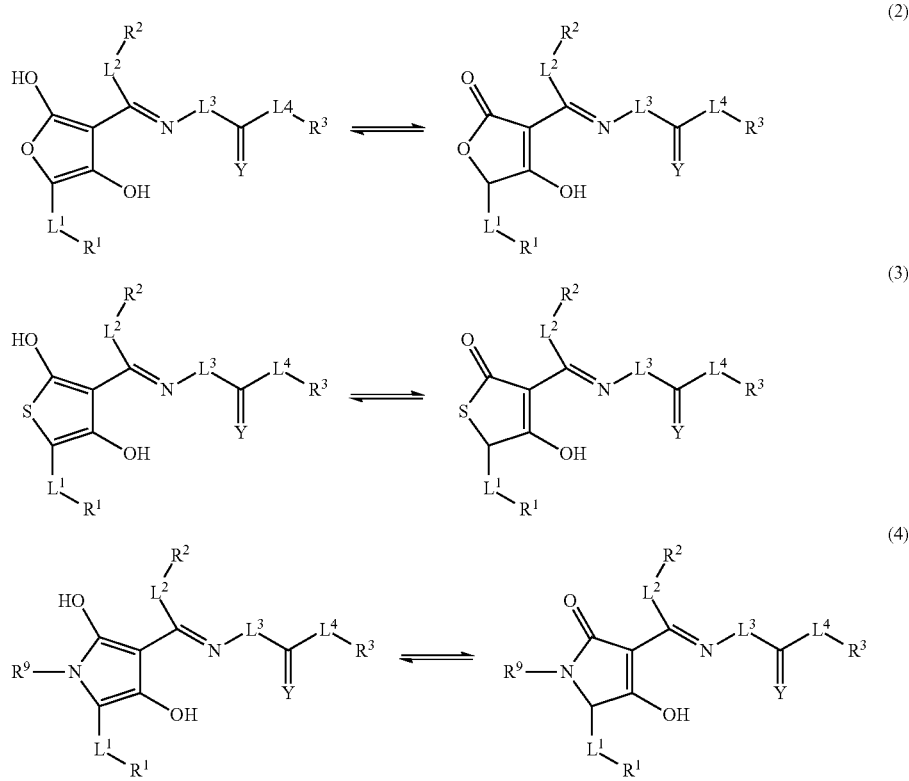

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid).

—$OCOCH_2CH_2CO_2Na$, —$OCOCH(NH_2)CH_3$, —$OCOCH_2N(CH_3)_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —$NHCO(CH_2)_{20}CH_3$, —$NHCOCH(NH_2)CH_3$ and the like. When the compound of the present invention has a carboxyl group, carboxylic acid esters with aliphatic alcohols or carboxylic-acid esters obtained by the reaction with an alcoholic free hydroxyl group of 1,2- or 1,3-digylcerides may, for example, be mentioned as prodrugs. Particularly preferred prodrugs are methyl esters and ethyl esters.

The preventive, therapeutic and improving agents for diseases against which activation of the thrombopoietin receptor is effective or platelet increasing agents which contain the thrombopoietin receptor activators of the present invention, tautomers, prodrugs or pharmaceutically acceptable salts of the activators or solvates thereof as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (1) are prepared by the process represented by the formula (5) illustrated below.

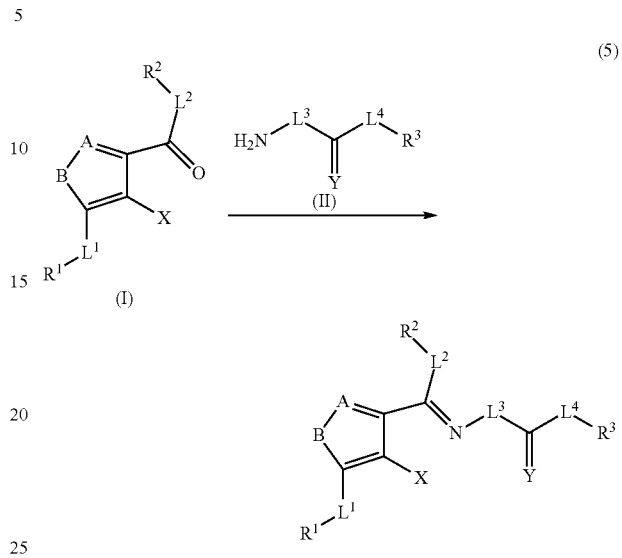

The reaction of the compound (I) with a —NH$_2$ compound (II) in a solvent, if necessary in the presence of a catalyst, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

For the syntheses of the intermediates (I), syntheses of the following heterocyclic compounds may be referred to.

1) Pyrazole (the formula (6))

J. Chem. Soc. Perkin. Transl, p. 81, (1985)

2) Isothiazole (the formula (7))

Liebigs. Annalen. der. Chemie., 10, 1534-1546 (1979)

3) Isoxazole (the formula (8))

Synthesis, 10, 664-665 (1975)

4) Thiophene (the formula (9))

JP-A-48-026755

5) Furan (the formula (10))

J. Org. Chem., 21, 1492-1509 (1956)

6) Pyrrole (the formula (11))

J. Heterocyclic Chem., 30, 1253 (1993) and Tetrahedron, 50(26), 7849-56 (1994)

7) Tetronic acid (4-hydroxy-2(5H)-furanone) analogue (the formula (12))

Synthesis, 7, 564-566 (1988) and Yakugaku Zasshi, 96(4), 536-543 (1976)

8) Tetraminic acid (4-hydroxy-3-pyrrolin-2-one) analogue (the formula (13))

Synthesis, 2, 190-192 (1987) and Agric. Biol. Chem., 43(8), 1641-1646 (1979)

(6)
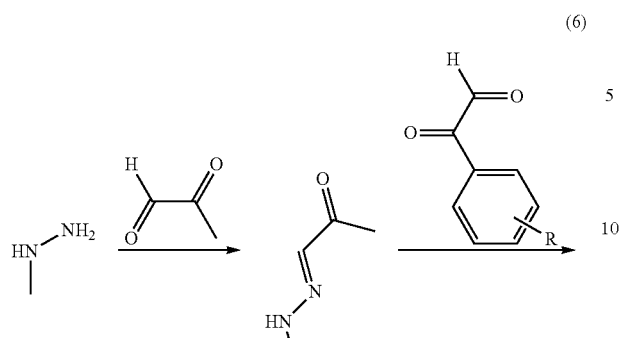
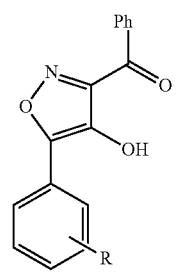
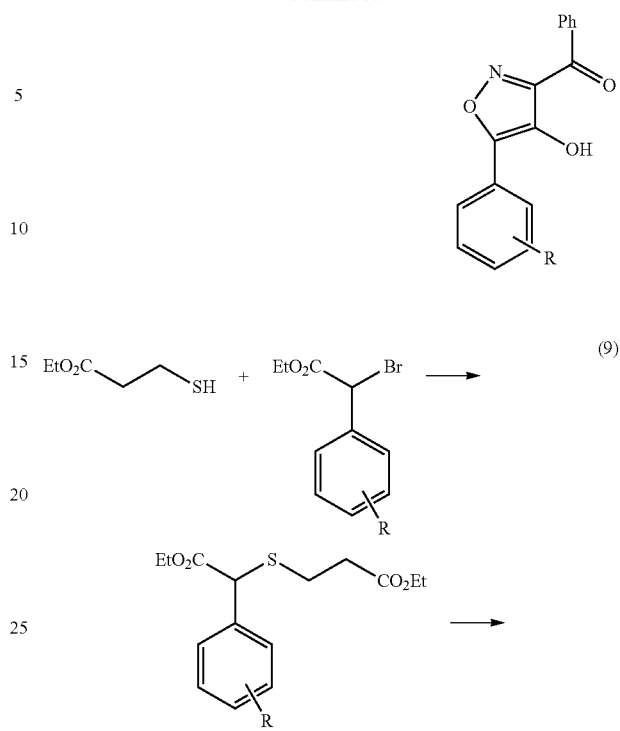
(9)
(7)
(10)
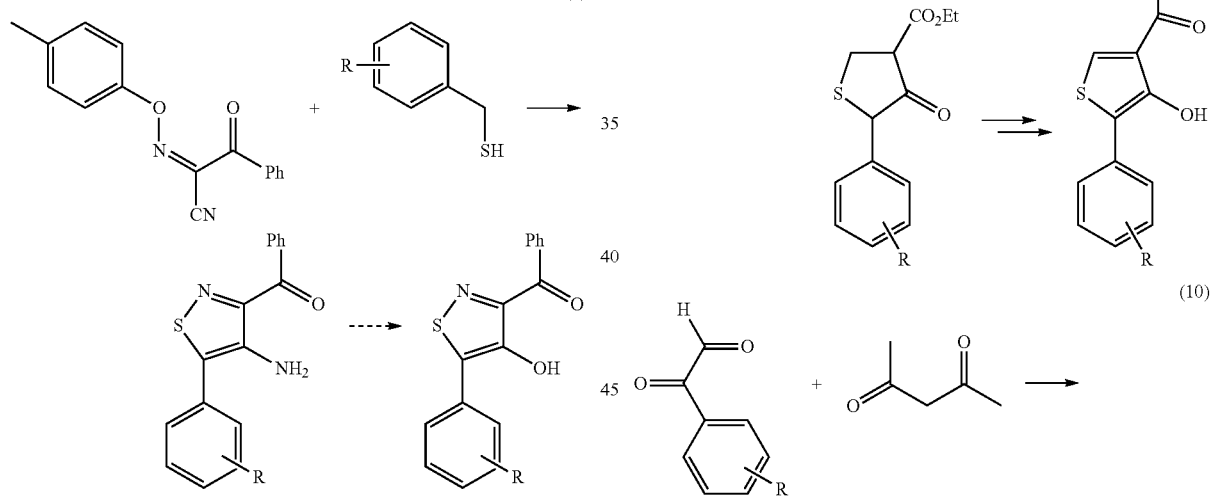
(8)
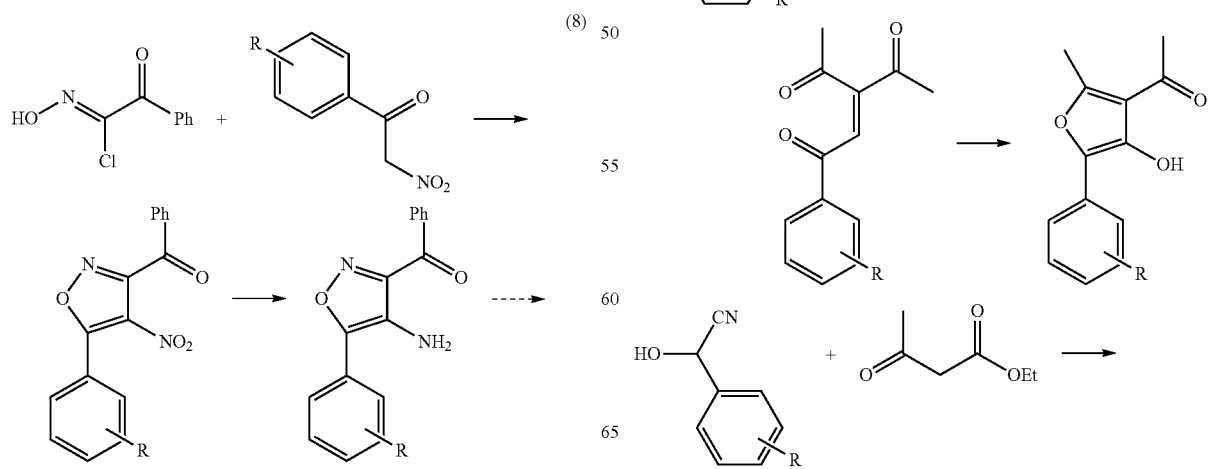

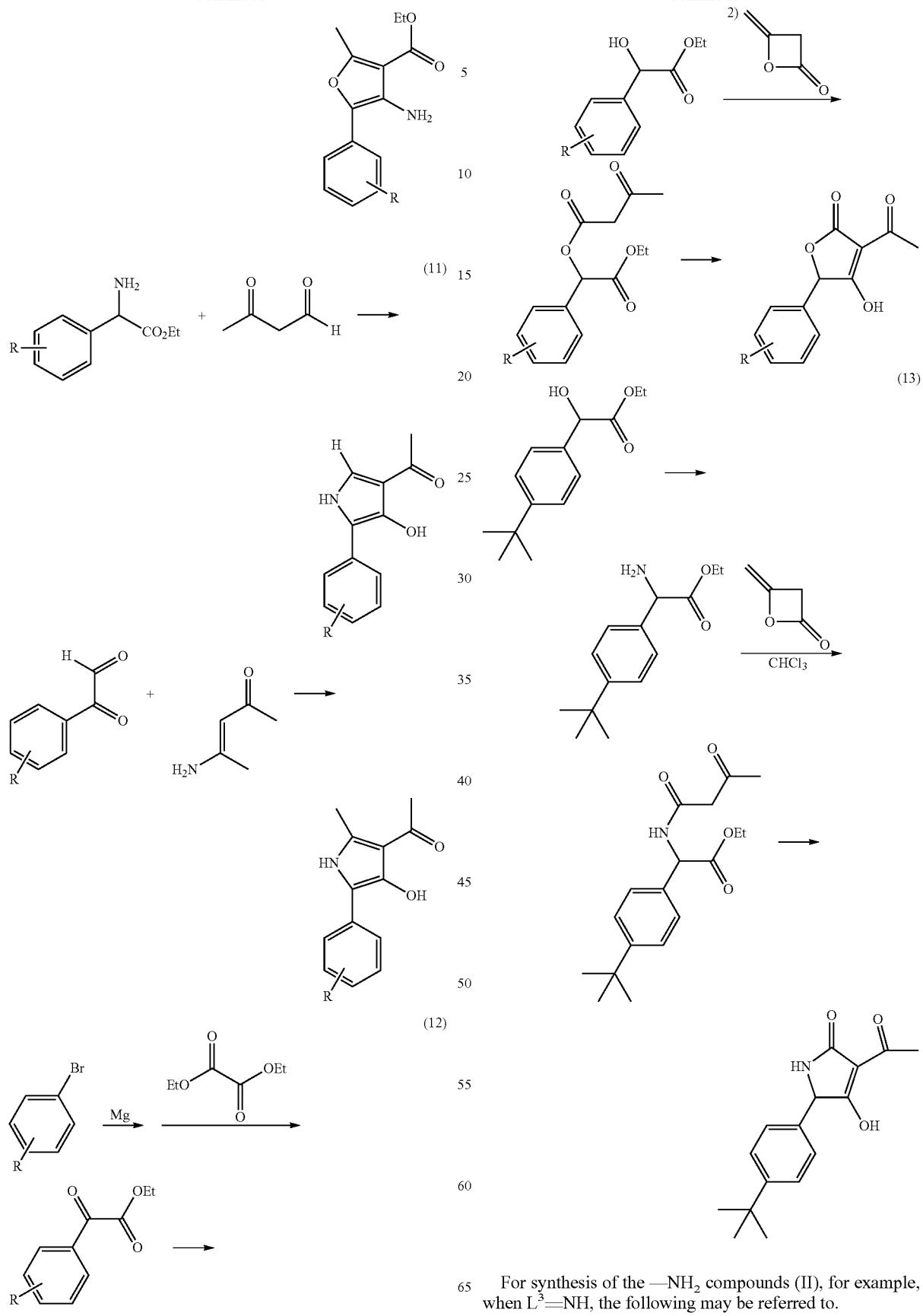
For synthesis of the —NH$_2$ compounds (II), for example, when L$^3$=NH, the following may be referred to.
1) L$^4$=a bond, Y=O Synthetic Commun., 28(7), 1223-1231 (1998), J. Chem. Soc., 1225 (1948) and J. Chem. Soc., 2831 (1952)
2) $L^4$=NH, Y=O
J. Am. Chem. Soc., 46, 2813 (1924) and J. Chem. Soc., 2654 (1952)
3) $L^4$=NH, Y=S
Can. J. Chem., 35, 834 (1957)
4) $L^4$=$CH_2$, Y=O
J. Org. Chem., 30, 2487 (1965)
5) $L^4$=O, Y=O
Bull. Soc. Chim. Belg., 68, 409, (1959)

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

The $^1$H-NMR analysis was carried out at 300 MHz.

In the REFERENCE SYNTHETIC EXAMPLE 59-75 and the SYNTHETIC EXAMPLE 124-240, LC/MS was measured on the following conditions.

LC/MS condition 1
column: Waters SunFire C18 (3.5 μm, 4.6×30 mm)
elute: MeCN/0.1% aq. HCOOH (10/90 to 30/70)
LC/MS condition 2
column: Waters SunFire C18 (3.5 μm, 4.6×30 mm)
elute: MeCN/0.1% aq. HCOOH (10/90 to 60/40)
LC/MS condition 3
column: Waters SunFire C18 (3.5 μm, 4.6×30 mm)
elute: MeCN/0.1% aq. HCOOH (10/90 to 85/15)
LC/MS condition 4
column: Waters Xterra MSC18 (5 μm, 4.6×50 mm)
elute: MeCN/0.1% aq. HCOOH (10/90 to 30/70)
LC/MS condition 5
column: Waters Xterra MSC18 (5 μm, 4.6×50 mm)
elute: MeCN/0.1% aq. HCOOH (10/90 to 60/40)
LC/MS condition 6
column: Waters Xterra MSC18 (5 μm, 4.6×50 mm)
elute: MeCN/0.1% aq. HCOOH (10/90 to 85/15)
LC/MS condition 7
column: Waters Xterra MSC18 (5 μm, 4.6×50 mm)
elute: MeCN/0.1% aq. HCOOH (20/80 to 100/0)
LC/MS condition 8
column: Waters Xterra MSC18 (3.5 μm, 2.1×20 mm).
elute: MeCN/0.2% aq. HCOOH (20/80 to 90/10)
LC/MS condition 9
column: Waters SunFire C18 (3.5 μm, 4.6×30 mm)
elute: MeCN/0.1% aq. HCOOH (20/80 to 100/0)

Reference Synthetic Example 1

Synthesis of 2-oxopropanal methylhydrazone

A mixed solution of methylhydrazine (8.34 mL, 158.22 mmol) in acetic acid (15 mL) and water (60 mL) was added to 10% methylglyoxal aqueous solution (92.5 mL, 151.21 mmol), and the mixture was stirred at room temperature for about 24 hours. The reaction solution was extracted with chloroform three times, and the extract was dried, filtered and concentrated. Purification of the resulting black solution by vacuum distillation gave the desired product as a yellow solid (5.357 g, yield 35%).

$^1$H-NMR (ppm in $CDCl_3$)
δ 6.86 (s, 1H), 6.59 (br.s, 1H), 2.98 (d, J=4.2 Hz, 3H), 2.30 (s, 3H)
LC-MS (ESI) 100 ($M^+$)

Reference Synthetic Example 2

Synthesis of 2-oxopropanal ethylhydrazone

Ethylhydrazine (8.46 mmol, 556 mg) was dissolved in methanol (4 mL), and the reactor was cooled to 0° C. Methylglyoxal (40% in $H_2O$, 9.3 mmol, 1.42 mL) was added, and the mixture was stirred for 15 minutes at the same temperature and then for 2.5 hours at room temperature. After addition of water, it was extracted with chloroform three times. The resulting organic layer was dried over anhydrous magnesium sulfate and filtered, and the solvent was evaporated with an evaporator. The residue was dried by means of a vacuum pump to give the desired product as an orange liquid (0.955 g (crude), yield 99%).

$^1$H-NMR (ppm in $CDCl_3$)
δ 9.29 (s, 1H), 6.32 (br.s, 1H), 3.58 (q, J=7.1 Hz, 1H), 3.57 (q, J=7.1 Hz, 1H), 1.79 (s, 3H), 1.29 (t, J=7.1 Hz, 3H)

Reference Synthetic Example 3

Synthesis of (3,4-dichlorophenyl)(oxo)acetaldehyde 3,4-dichloroacetophenone (5.39 mmol, 1.02 g) was dissolved in dimethyl sulfoxide (13 mL), and 48% hydrobromic acid (1.83 mL) was gradually added at room temperature. The mixture was stirred overnight at 60° C., and then the reactor was cooled to room temperature. The reaction solution was poured into water (50 mL) at 0° C. and stirred for about 1 hour. The precipitated solid was recovered by filtration, washed with water and dried by means of a vacuum pump to give the desired product as a pale yellow solid (0.780 g, yield 71%).

$^1$H-NMR (ppm in DMSO-$d_6$)
δ 8.26 (d, J=2.0 Hz, 1H), 8.01 (dd, J=2.0, 8.6 Hz, 1H), 7.82 (d, J=8.6 Hz, 1H), 7.01 (d, J=6.6 Hz, 2H, $H_2O$), 5.61 (br.s, 1H)
MS (EI) 173 ($M^+$-CHO)

Reference Synthetic Example 4

Synthesis of (4-t-butylphenyl)(oxo)acetaldehyde 4-t-Butylacetophenone (100 mmol, 18.74 mL) was dissolved in dimethyl sulfoxide (104 mL), then the reactor was cooled to 0° C., and 48% hydrobromic acid (34 mL) was gradually added. After 18 hours of stirring at 70° C., the reaction solution was poured into water (400 mL) and stirred for 24 hours. The precipitated yellow solid was recovered by filtration, washed with n-hexane several times and dried by means of a vacuum pump to give the desired product as a pale yellow solid (13.89 g, yield 73%).

$^1$H-NMR (ppm in DMSO-$d_6$)
δ 8.01 (ABq, J=8.4 Hz, 2H), 7.51 (ABq, J=8.4 Hz, 2H), 6.01 (s, 1H), 1.30 (s, 9H)
LC-MS (ESI) 190 ($M^+$)

Reference Synthetic Example 5

Synthesis of (3,4-dimethylphenyl)(oxo)acetaldehyde 3,4-dimethylacetophenone (13.52 mmol, 2.0 g) was dissolved in dimethyl sulfoxide (13 mL), and 48% hydrobromic acid (5.4 mL) was gradually added at room temperature. After 16 hours of stirring at 70° C., the reactor was cooled to room temperature. The reaction solution was poured into water and stirred for about 16 hours. The precipitated solid was recovered by filtration, washed with water and dried by means of a vacuum pump to give the desired product as a white solid (1.234 g, yield 57%).

$^1$H-NMR (ppm in DMSO-$d_6$)

δ 7.83-7.80 (multi, 2H), 7.33 (br.s, 2H, H$_2$O), 7.26 (d, J=7.5 Hz, 1H), 5.96 (br.s, 1H), 2.28 (s, 3H), 2.22 (s, 3H)

Reference Synthetic Example 6

Synthesis of (4-n-pentylphenyl)(oxo)acetaldehyde 4-n-Pentylacetophenone (10.66 mmol, 2.028 g) was dissolved in dimethyl sulfoxide (13 mL), and 48% hydrobromic acid (5.4 mL) was gradually added at room temperature. After 9.5 hours of stirring at 70° C., the reactor was cooled to room temperature. The reaction solution was poured into water and stirred for about 16 hours. The precipitated solid was recovered by filtration, washed with water and dried by means of a vacuum pump to give the desired product as a pale yellow solid (2.1784 g (crude), 100%).

$^1$H-NMR (ppm in DMSO-$d_6$)

δ 7.99 (ABq, J=8.3 Hz, 2H), 7.33 (ABq, J=8.3 Hz, 2H), 6.67 (br.s, 2H, H$_2$O), 5.67 (br.s, 1H), 2.69-2.61 (multi, 2H), 1.66-1.50 (multi, 2H), 1.36-1.20 (multi, 4H), 0.88-0.83 (multi, 3H).

Reference Synthetic Example 7

Synthesis of (4-trifluoromethylphenyl)(oxo)acetaldehyde

4-Trifluoromethylacetophenone (11.14 mmol, 2.096 g) was dissolved in dimethyl sulfoxide (13 mL), and 48% hydrobromic acid (5.4 mL) was gradually added at room temperature. After 9.5 hours of stirring at 70° C., the reactor was cooled to room temperature. The reaction solution was poured into water and stirred for about 16 hours. The precipitated solid was recovered by filtration, washed with water and dried by means of a vacuum pump to give the desired product as a yellow solid (1.3116 g, yield 59%).

$^1$H-NMR (ppm in DMSO-$d_6$)

δ 8.27 (ABq, J=8.3 Hz, 2H), 7.90 (ABq, J=8.3 Hz, 2H), 6.97 (br.s, 2H, H$_2$O), 5.68 (br.s, 1H)

Reference Synthetic Example 8

Synthesis of oxo[3-(trifluoromethyl)phenyl]acetaldehyde

3-Trifluoromethylacetophenone (11.80 mmol, 2.22 g) was dissolved in dimethyl sulfoxide (13 mL), and 48% hydrobromic acid (5.4 mL) was gradually added at room temperature. After overnight stirring at 70° C., the reactor was cooled to room temperature. After addition of water, the reaction solution was extracted with chloroform, and the extract was dried and filtered, and the solvent was evaporated to give the desired product as a yellow liquid (3.04 g (crude), yield 128%).

Reference Synthetic Example 9

Synthesis of (3-bromo-4-fluorophenyl)(oxo)acetaldehyde

From 3-bromo-4-fluoroacetophenone, the desired product was obtained in the same manner as in Reference Synthetic Example 8 as a yellow liquid (crude, yield 114%).

Reference Synthetic Example 10

Synthesis of (3,5-dimethylphenyl)(oxo)acetaldehyde

From 3,5-dimethylacetophenone, the desired product was obtained in the same manner as in Reference Synthetic Example 8 as a yellow solid (crude, yield 104%).

Reference Synthetic Example 11

Synthesis of (4-ethylphenyl)(oxo)acetaldehyde

4-Ethylacetophenone (26.72 mmol, 4 mL) was dissolved in dimethyl sulfoxide (27 mL), and 48% hydrobromic acid (11 mL) was gradually added at room temperature. After overnight stirring at 70° C., the reactor was cooled to room temperature. The reaction solution was poured into water (50 mL) and stirred for about 1 hour. The precipitated solid was recovered by filtration, washed with water and dried by means of a vacuum pump to give the desired product as a white solid (2.44 g, yield 56%).

Reference Synthetic Example 12

Synthesis of (4-isopropylphenyl)(oxo)acetaldehyde

From 4-isopropylacetophenone, the desired product was obtained in the same manner as in Reference Synthetic Example 8 as a yellow solid (crude, yield 103%).

Reference Synthetic Example 13

Synthesis of oxo(4-n-propylphenyl)acetaldehyde

From 4-n-propylacetophenone, the desired product was obtained in the same manner as in Reference Synthetic Example 11 as a yellow liquid (crude, yield 92%).

Reference Synthetic Example 14

Synthesis of (4-n-hexylphenyl)(oxo)acetaldehyde

From 4-n-hexylacetophenone, the desired product was obtained in the same manner as in Reference Synthetic Example 11 as a yellow solid (crude, yield 131%).

Reference Synthetic Example 15

Synthesis of (4-isobutylphenyl)(oxo)acetaldehyde

From 4-isobutylacetophenone, the desired product was obtained in the same manner as in Reference Synthetic Example 8 as a yellow liquid (crude, yield 108%).

Reference Synthetic Example 16

Synthesis of 2-(4-t-butylphenyl)-3-methoxymethyloxy-4-ethoxycarbonylthiophene

60% Sodium hydride (28 mg, 0.69 mmol) was added to a solution of 2-(4-t-butylphenyl)-3-hydroxy-4-ethoxycarbonylthiophene (0.20 g, 0.66 mmol) obtained in accordance with JP-A-48-26755 in dimethylformamide (1.0 mL) at room temperature, and the reaction solution was stirred at 60° C. for 15 minutes. After the reaction solution was cooled to room temperature, chloromethyl methyl ether (0.055 mL, 0.73 mmol) was added dropwise, and the reaction solution was stirred at room temperature for another 5 hours. After addition of saturated aqueous ammonium chloride, the reaction solution was extracted with ethyl acetate, and the organic layer was washed with saturated aqueous sodium chloride, dried over anhydrous sodium sulfate. The organic layer was concentrated and purified by silica gel column chromatography (chloroform) to give the desired product as a colorless oil (212 mg, yield 91%).

$^1$H-NMR (ppm in CDCl$_3$)

δ 1.34 (s, 9H), 1.38 (t, J=7.2 Hz, 3H), 3.23 (s, 3H), 4.34 (q, J=7.2 Hz, 2H), 5.00 (s, 2H), 7.41-7.44 (m, 2H), 7.60-7.63 (m, 2H), 7.97 (s, 1H).

LC/MS (ES$^+$) 371 (Na$^+$ adduct).

Reference Synthetic Example 17

Synthesis of 2-(3,4-dichlorophenyl)-3-methoxymethyloxy-4-ethoxycarbonylthiophene From 2-(3,4-dichlorophenyl)-3-hydroxy-4-ethoxycarbonylthiophene (7.7 g, 24 mmol), the desired product was obtained in the same manner as in Reference Synthetic Example 16 as a colorless oil (5.4 g, yield 62%).

$^1$H-NMR (ppm in CDCl$_3$)

δ 1.38 (t, J=7.2 Hz, 3H), 3.27 (s, 3H), 4.34 (q, J=7.2 Hz, 2H), 5.06 (s, 2H), 7.46-7.54 (m, 2H), 7.86 (d, J=1.9 Hz, 1H), 8.04 (s, 1H).

Reference Synthetic Example 18

Synthesis of 2-(4-trifluoromethylphenyl)-3-methoxymethyloxy-4-ethoxycarbonylthiophene From 2-(4-trifluoromethylphenyl)-3-hydroxy-4-ethoxycarbonylthiophene (1.6 g, 5.2 mmol), the desired product was obtained in the same manner as in Reference Synthetic Example 16 as a brown oil (1.8 g, yield 95%).

$^1$H-NMR (ppm in CDCl$_3$)

δ 1.39 (t, J=7.2 Hz, 3H), 3.21 (s, 3H), 4.35 (q, J=7.2 Hz, 2H), 5.05 (s, 2H), 7.67 (d, J=8.3 Hz, 2H), 7.83 (d, J=8.3 Hz, 2H), 8.07 (s, 1H).

Reference Synthetic Example 19

Synthesis of 2-(4-t-butylphenyl)-3-methoxymethyloxy-4-hydroxymethylthiophene

To lithium aluminium hydride (27 mg, 0.72 mmol) in THF (0.86 mL), 2-(4-t-butylphenyl)-3-methoxymethyloxy-4-ethoxycarbonylthiophene (0.21 g, 0.60 mmol) in THF (0.86 mL) was added dropwise under cooling with ice, and the reaction solution was stirred under cooling with ice for 1 hour. After addition of saturated aqueous ammonium chloride, the reaction solution was extracted with ethyl acetate, and the organic layer was washed with saturated aqueous sodium chloride, dried over anhydrous sodium sulfate, concentrated and purified by silica gel column chromatography (n-hexane/ethyl acetate=3/1) to give the desired product as a colorless oil (87 mg, yield 47%).

$^1$H-NMR (ppm in CDCl$_3$)

δ 1.25 (s, 9H), 3.05 (bs, 1H), 3.40 (s, 3H), 4.46 (d, J=5.8 Hz, 2H), 4.81 (s, 2H), 7.02 (s, 1H), 7.30-7.34 (m, 2H), 7.47-7.50 (m, 2H).

LC/MS (ES$^+$) 329 (Na$^+$ adduct).

Reference Synthetic Example 20

Synthesis of 2-(3,4-dichlorophenyl)-3-methoxymethyloxy-4-hydroxymethylthiophene

From 2-(3,4-dichlorophenyl)-3-methoxymethyloxy-4-ethoxycarbonylthiophene (5.0 g, 14 mmol), the desired product was obtained in the same manner as in Reference Synthetic Example 19 as a colorless oil (4.3 g, 98%).

$^1$H-NMR (ppm in CDCl$_3$)

δ 3.51 (s, 3H), 4.56 (d, J=5.8 Hz, 2H), 4.91 (s, 2H), 7.21 (s, 1H), 7.43-7.51 (m, 2H), 7.89 (s, 1H).

LC/MS (ES$^+$) 340, 342 (Na$^+$ adduct).

LC/MS (ES$^-$) 363, 364, 365 (HCO$_2^-$ adduct).

Reference Synthetic Example 21

Synthesis of 2-(4-trifluoromethylphenyl)-3-methoxymethyloxy-4-hydroxymethylthiophene From 2-(4-trifluoromethylphenyl)-3-methoxymethyloxy-4-ethoxycarbonylthiophene (1.8 g, 4.9 mmol), the desired product was obtained in the same manner as in Reference Synthetic Example 19 as a yellow oil (1.4 g, yield 92%).

$^1$H-NMR (ppm in CDCl$_3$)

δ 3.50 (s, 3H), 4.57 (s, 2H), 4.91 (s, 2H), 7.24 (s, 1H), 7.64 (d, J=8.4 Hz, 2H), 7.78 (d, J=8.4 Hz, 2H).

LC/MS (ES$^+$) 341 (Na$^+$ adduct).

Reference Synthetic Example 22

Synthesis of 2-(4-t-butylphenyl)-3-methoxymethyloxy-4-formylthiophene

Dimethyl sulfoxide (0.050 mL, 0.70 mmol) in dichloromethane (0.28 mL) was added to oxalyl chloride (0.049 mL, 0.56 mmol) in dichloromethane (2.8 mL) at −78° C., and after 10 minutes of stirring at −78° C., 2-(4-t-butylphenyl)-3-methoxymethyloxy-4-hydroxymethylthiophene (87 mg, 0.28 mmol) in dichloromethane (0.93 mL) was added dropwise. After the addition, the reaction solution was stirred at −78° C. for 20 minutes and at −40 to −50° C. for 1 hour. Triethylamine (0.28 mL, 2.0 mmol) was added dropwise, and the reaction solution was stirred for another 20 minutes under cooling with ice. After addition of saturated aqueous ammonium chloride, the reaction solution was extracted with chloroform, and the organic layer was washed with saturated aqueous sodium chloride, dried over anhydrous sodium sulfate and concentrated to give the desired product as a brown oil (58 mg, yield 68%).

$^1$H-NMR (ppm in CDCl$_3$)

δ 1.25 (s, 9H), 3.24 (s, 3H), 4.91 (s, 2H), 7.34-7.38 (m, 2H), 7.50-7.54 (m, 2H), 7.91 (s, 1H), 9.82 (s, 1H).

LC/MS (ES$^+$) 305.

Reference Synthetic Example 23

Synthesis of 2-(3,4-dichlorophenyl)-3-methoxymethyloxy-4-formylthiophene

From 2-(3,4-dichlorophenyl)-3-methoxymethyloxy-4-hydroxymethylthiophene (4.3 g, 14 mmol), the desired product was obtained in the same manner as in Reference Synthetic Example 22 as a colorless oil (5.2 g, yield 122%).
$^1$H-NMR (ppm in CDCl$_3$)
δ 3.50 (s, 3H), 5.04 (s, 2H), 7.48-7.54 (m, 2H), 7.84 (d, J=1.7 Hz, 1H), 8.04 (s, 1H), 9.88 (s, 1H).

Reference Synthetic Example 24

Synthesis of 2-(4-trifluoromethylphenyl)-3-methoxymethyloxy-4-formylthiophene 2-(4-trifluoromethylphenyl)-3-methoxymethyloxy-4-hydroxymethylthiophene (1.4 g, 4.3 mmol) in chloroform (22 ml) was stirred with manganese dioxide (3.7 g, 43 mmol) at room temperature for 20 hours and at 50° C. for 3 hours. The reaction solution was filtered, and the filtrate was concentrated and purified by silica gel column chromatography (n-hexane/ethyl acetate=3/1) to give the desired product as a colorless oil (0.79 g, yield 57%).
$^1$H-NMR (ppm in CDCl$_3$)
δ 3.29 (s, 3H), 5.03 (s, 2H), 7.68 (d, J=8.5 Hz, 2H), 7.82 (d, J=8.5 Hz, 2H), 8.08 (s, 1H), 9.91 (s, 1H).
LC/MS (ES$^+$) 339 (Na$^+$ adduct).

Reference Synthetic Example 25

Synthesis of 2-(4-t-butylphenyl)-3-hydroxy-4-formylthiophene

To 2-(4-t-butylphenyl)-3-methoxymethyloxy-4-formylthiophene (0.20 g, 0.66 mmol) in 1,4-dioxane (1.3 mL), 1 M hydrochloric acid (0.66 mL, 0.66 mmol) was added dropwise, and the reaction solution was stirred at 65° C. for 1 hour and at 80° C. for 1 hour. After addition of water, the reaction solution was extracted with ethyl acetate, and the organic layer was washed with saturated aqueous sodium chloride, dried over anhydrous sodium sulfate, concentrated and purified by silica gel column chromatography (chloroform) to give the desired product as a reddish brown oil (0.12 g, yield 68%).
$^1$H-NMR (ppm in CDCl$_3$)
δ 1.38 (s, 9H), 7.43 (d, J=8.4 Hz, 2H), 7.70 (d, J=8.4 Hz, 2H), 7.88 (s, 1H), 9.24 (s, 1H), 9.85 (s, 1H).

Reference Synthetic Example 2.6

Synthesis of 2-(3,4-dichlorophenyl)-3-hydroxy-4-formylthiophene

From 2-(3,4-dichlorophenyl)-3-methoxymethyloxy-4-formylthiophene (1.7 g, 5.4 mmol), the desired product was obtained in the same manner as in Reference Synthetic Example 25 as a brown oil (1.2 g, yield 83%).
$^1$H-NMR (ppm in DMSO-d$_6$)
δ 7.68 (s, 2H), 7.80 (s, 1H), 8.48 (s, 1H), 9.89 (s, 1H), 10.07 (s, 1H).
LC/MS (ES$^-$) 271, 273.

Reference Synthetic Example 27

Synthesis of 2-(4-t-butylphenyl)-3-methoxymethyloxy-4-(1-hydroxyethyl)thiophene 3.0 M Ethyl ether solution (2.0 mL, 6.0 mmol) of methylmagnesium bromide was added dropwise to 2-(4-t-butylphenyl)-3-methoxymethyloxy-4-formylthiophene (0.77 g, 2.5 mmol) in THF (2.5 mL) under cooling with ice, and the reaction solution was stirred for 1 hour under cooling with ice. After addition of saturated aqueous ammonium chloride, the reaction solution was extracted with ethyl acetate, and the organic layer was washed with saturated aqueous sodium chloride, dried over anhydrous sodium sulfate, concentrated and purified by silica gel column chromatography (n-hexane/ethyl acetate=9/1) to give the desired product as a pale yellow oil (0.64 g, yield 80%).
$^3$H-NMR (ppm in CDCl$_3$)
δ 1.34 (s, 9H), 1.58-1.60 (m, 3H), 3.24 (bs, 1H), 3.48 (s, 3H), 4.83-4.85 (m, 1H), 4.92-4.95 (m, 2H), 7.08 (s, 1H), 7.38-7.42 (m, 2H), 7.54-7.57 (m, 2H).
LC/MS (ES$^+$) 343 (Na$^+$ adduct).

Reference Synthetic Example 28

Synthesis of 2-(3,4-dichlorophenyl)-3-methoxymethyloxy-4-(1-hydroxyethyl) thiophene From 2-(3,4-dichlorophenyl)-3-methoxymethyloxy-4-formylthiophene (0.75 g, 2.4 mmol), the desired product was obtained in the same manner as in Reference Synthetic Example 27 as a pale yellow oil (0.76 g, yield 95%).
$^1$H-NMR (ppm in CDCl$_3$)
δ 1.57-1.62 (m, 3H), 3.05 (bs, 1H), 3.50 (s, 3H), 4.82-4.85 (m, 1H), 4.90-4.95 (m, 2H), 7.17 (d, J=2.5 Hz, 1H), 7.53-7.59 (m, 2H), 7.77 (s, 1H).

Reference Synthetic Example 29

Synthesis of 2-(4-trifluoromethylphenyl)-3-methoxymethyloxy-4-(1-hydroxyethyl)thiophene From 2-(4-trifluoromethylphenyl)-3-methoxymethyloxy-4-formylthiophene (0.79 g, 2.5 mmol), the desired product was obtained in the same manner as in Reference Synthetic Example 27 as a yellow oil (0.76 g, yield 92%).
$^1$H-NMR (ppm in CDCl$_3$)
δ 1.59 (d, J=6.3 Hz, 3H), 3.09 (bs, 1H), 3.48 (s, 3H), 4.83 (d, J=6.3 Hz, 1H), 4.92 (s, 2H), 7.20 (s, 1H), 7.64 (d, J=8.4 Hz, 2H), 7.76 (d, J=8.4 Hz, 2H).

Reference Synthetic Example 30

Synthesis of 2-(4-t-butylphenyl)-3-methoxymethyloxy-4-methylcarbonylthiophene 2-(4-t-Butylphenyl)-3-methoxymethyloxy-4-(1-hydroxyethyl)thiophene (0.64 g, 2.0 mmol) in dichloromethane (13 mL) was stirred with celite (2.0 g) and pyridinium chlorochromate (0.86 g, 4.0 mmol) at room temperature for 1 hour. The reaction solution was filtered through celite, and the filtrate was concentrated and purified by silica gel column chromatography (n-hexane/ethyl acetate=1/1) to give the desired product as a brown solid (0.53 g, yield 83%).
$^1$H-NMR (ppm in CDCl$_3$)
δ 1.34 (s, 9H), 2.57 (s, 3H), 3.23 (s, 3H), 4.93 (s, 2H), 7.41-7.44 (m, 2H), 7.57-7.61 (m, 2H), 7.88 (s, 1H).

Reference Synthetic Example 31

Synthesis of 2-(3,4-dichlorophenyl)-3-methoxymethyloxy-4-methylcarbonylthiophene From 2-(3,4-dichlorophenyl)-3-methoxymethyloxy-4-(1-hydroxyethyl)thiophene (0.76 g, 2.3 mmol), the desired product was obtained in the same manner as in Reference Synthetic Example 30 as a colorless solid (0.62 g, yield 81%).
$^1$H-NMR (ppm in CDCl$_3$)
δ 2.56 (s, 3H), 3.27 (s, 3H), 4.98 (s, 2H), 7.46-7.54 (m, 2H), 7.84 (d, J=1.9 Hz, 1H), 7.95 (s, 1H).

Reference Synthetic Example 32

Synthesis of 2-(4-trifluoromethylphenyl)-3-methoxymethyloxy-4-methylcarbonylthiophene From 2-(4-trifluoromethylphenyl)-3-methoxymethyloxy-4-(1-hydroxyethyl)thiophene (0.76 g, 2.3 mmol), the desired product was obtained in the same manner as in Reference Synthetic Example 30 as a yellow oil (0.64 g, yield 84%).
$^1$H-NMR (ppm in CDCl$_3$)
δ 2.57 (s, 3H), 3.20 (s, 3H), 4.96 (s, 2H), 7.67 (d, J=8.6 Hz, 2H), 7.82 (d, J=8.6 Hz, 2H), 7.98 (s, 1H).

Reference Synthetic Example 33

Synthesis of 2-(4-t-butylphenyl)-3-hydroxy-4-methylcarbonylthiophene

From 2-(4-t-butylphenyl)-3-methoxymethyloxy-4-methylcarbonylthiophene (0.53 g, 1.7 mmol), the desired product was obtained in the same manner as in Reference Synthetic Example 25 as a yellow solid (0.38 g, yield 80%).
$^1$H-NMR (ppm in CDCl$_3$)
δ 1.33 (s, 9H), 2.56 (s, 3H), 7.40-7.44 (m, 2H), 7.69-7.74 (m, 2H), 7.85 (s, 1H), 10.28 (s, 1H).
LC/MS (ES$^+$) 275.

Reference Synthetic Example 34

Synthesis of 2-(3,4-dichlorophenyl)-3-hydroxy-4-methylcarbonylthiophene

From 2-(3,4-dichlorophenyl)-3-methoxymethyloxy-4-methylcarbonylthiophene (0.62 g, 1.9 mmol), the desired product was obtained in the same manner as in Reference Synthetic Example 25 as a yellow solid (0.31 g, yield 57%).
$^1$H-NMR (ppm in DMSO-d$_6$)
δ 2.58 (s, 3H), 7.65-7.66 (m, 2H), 7.97 (d, J=1.0 Hz, 1H), 8.71 (s, 1H), 10.59 (s, 1H).

Reference Synthetic Example 35

Synthesis of 2-(4-trifluoromethylphenyl)-3-hydroxy-4-methylcarbonylthiophene

From 2-(4-trifluoromethylphenyl)-3-methoxymethyloxy-4-methylcarbonylthiophene (0.64 g, 1.9 mmol), the desired product was obtained in the same manner as in Reference Synthetic Example 25 as a yellow solid (0.47 g, yield 86%).
$^1$H-NMR (ppm in CDCl$_3$)
δ 2.59 (s, 3H), 7.63 (d, J=8.3 Hz, 2H), 7.91 (d, J=8.3 Hz, 2H), 7.96 (s, 1H), 10.57 (s, 1H).
LC/MS (ES$^+$) 287.

Reference Synthetic Example 36

Synthesis of oxo(phenyl)acetaldehyde methylhydrazone

A mixed solution of methylhydrazine (0.554 mL, 10.5 mmol)/acetic acid (1 mL)/water (7.6 mL) was added to phenylglyoxal (1.34 g, 10 mmol) in water (130 mL), and the mixture was stirred at room temperature for 20 hours. The reaction solution was extracted with chloroform, and the extract was dried, filtered, evaporated and dried by means of a vacuum pump to give oxo(phenyl)acetaldehyde methylhydrazone (1.44 g (crude), yield 89%) as a yellow solid.

Reference Synthetic Example 37

Synthesis of 4-hydrazinocarbonylmethyl benzoate

The known procedure disclosed in the literature (Synthetic Communications, 28(7), 1223-1231, (1998)) was followed using monomethyl terephthalate and tetramethylfluoroformamidinium hexafluorophosphate to give 1.36 g of the desired product as a colorless solid (yield 70%).
$^1$H-NMR (ppm in DMSO-d$_6$)
δ 3.86 (s, 3H), 4.56 (s, 2H), 7.93 (d, J=8.3 Hz, 2H), 8.02 (d, J=8.3 Hz, 2H), 9.96 (bs, 1H).

Reference Synthetic Example 38

Synthesis of 5-methoxycarbonyl-2-thiophenecarboxylic acid

Thiophene-2,5-dicarboxylic acid (1.72 g, 10 mmol) and sodium carbonate (3.18 g, 30 mmol) suspended in dimethylformamide (25 mL) were stirred with methyl iodide (623 µL) at room temperature overnight. The sodium salt of the desired product was extracted with water, and 12 M hydrochloric acid was added to the combined aqueous layer. The desired product was extracted with ethyl acetate, and the combined organic layer was washed with saturated aqueous ammonium chloride, dried over anhydrous magnesium sulfate and purified by silica gel column chromatography to give 0.49 g of the desired product as a colorless solid (yield 28%).
$^1$H-NMR (ppm in CDCl$_3$)
δ 3.93 (s, 3H), 7.77 (d, J=4.2 Hz, 1H), 7.83 (d, J=4.2 Hz, 1H).
LC/MS (ESI) 186 (M$^+$).

Reference Synthetic Example 39

Synthesis of methyl 5-hydrazinocarbonyl-2-thiophenecarboxylate

The known procedure disclosed in the literature (J. Heterocyclic Chem., 28, 17, (1991).) was followed using 5-methoxycarbonyl-2-thiophenecarboxylic acid synthesized in Reference Synthetic Example 38, thionyl chloride and hydrazine monohydrate to give 144 mg of the desired product as a white solid (yield 72%).
$^1$H-NMR (ppm in DMSO-d$_6$)
δ 3.84 (s, 3H), 4.57 (brs, 2H), 7.72 (d, J=4.2 Hz, 1H), 7.79 (d, J=4.2 Hz, 1H), 10.06 (brs, 1H).
LC/MS (ESI) 200 (M$^+$).

Reference Synthetic Example 40

Synthesis of methyl 2-nitro-4-hydrazinocarbonylbenzoate

From 4-methoxycarbonyl-3-nitrobenzoic acid, thionyl chloride and hydrazine monohydrate, 758 mg of the desired product was obtained in the same manner as in Reference Synthetic Example 39 as a white solid (yield 79%).
$^1$H-NMR (ppm in DMSO-$d_6$)
δ 3.88 (s, 3H), 4.67 (brs, 2H), 7.96 (d, J=7.8 Hz, 1H), 8.24 (dd, J=1.8, 7.8 Hz, 1H), 8.44 (d, J=1.8 Hz, 1H).
LC/MS (ESI) 239 (M$^+$).

Reference Synthetic Example 41

Synthesis of methyl 2-chloro-4-hydrazinocarbonylbenzoate

1) Synthesis of 3-chloro-4-methoxycarbonylbenzoic acid

To 3-amino-4-methoxycarbonylbenzoic acid (0.98 g, 5 mmol) suspended in 12 M hydrochloric acid (25 mL) and acetic acid (25 mL), an aqueous solution (10 mL) sodium nitrite (0.35 g, 5 mmol) was added at −10° C., and the resulting solution was stirred for 30 minutes. The solution was added to copper chloride (I) (0.99 g, 10 mmol) in 12 M hydrochloric acid (25 mL) at −10° C., and the resulting reaction mixture was stirred at room temperature for 1 hour. After addition of ethyl acetate, the reaction mixture was washed with water, dried over magnesium sulfate, filtered through celite and purified by silica gel column chromatography to give 0.44 g of the desired product as a colorless solid (yield 39%).
$^1$H-NMR (ppm in DMSO-$d_6$)
δ 3.98 (s, 3H), 7.89 (d, J=8.1 Hz, 1H), 8.02 (dd, J=1.5, 8.1 Hz, 1H), 8.17 (d, J=1.5 Hz, 1H).
LC/MS (ESI) 214 (M$^{+\ 35}$Cl), 216 (M$^{+\ 37}$Cl).

2) Synthesis of methyl 2-chloro-4-hydrazinocarbonylbenzoate

From 3-chloro-4-methoxycarbonylbenzoic acid, thionyl chloride and hydrazine monohydrate, 423 mg of the desired product was obtained in the same manner as in Reference Synthesis Example 39 as a while solid (yield 93%
$^1$H-NMR (ppm in DMSO-$d_6$)
δ 3.88 (s, 3H), 4.63 (brs, 2H), 7.87-7.96 (m, 3H), 10.05 (brs, 1H).
LC/MS (ESI) 228 (M$^{+\ 35}$Cl), 230 (M$^{+\ 37}$Cl).

Reference Synthetic Example 42

Synthesis of methyl 2-bromo-4-hydrazinocarbonylbenzoate

1) Synthesis of 3-bromo-4-methoxycarbonylbenzoic acid

To 3-amino-4-methoxycarbonylbenzoic acid (1.95 g, 10 mmol) suspended in 48% hydrobromic acid (50 mL) and acetic acid (50 mL), an aqueous solution (20 mL) of sodium nitrite (0.69 g, 10 mmol) was added at −10° C., and the resulting solution was stirred for 30 minutes. The solution was added to copper bromide (I) (1.44 g, 10 mmol) in 48% hydrobromic acid (50 mL) at −10° C., and the resulting reaction mixture was stirred at room temperature for 1 hour. After addition of ethyl acetate, the reaction mixture was washed with water, dried over magnesium sulfate, filtered through celite and purified by silica gel column chromatography to give 1.70 g of the desired product as a colorless solid (yield 59%).
$^1$H-NMR (ppm in DMSO-$d_6$)
δ 3.97 (s, 3H), 7.84 (d, J=8.1 Hz, 1H), 8.07 (dd, J=1.5, 8.1 Hz, 1H), 8.37 (d, J=1.5 Hz, 1H).
LC/MS (ESI) 258 (M$^{+\ 79}$Br), 260 (M$^{+\ 81}$Br).

2) Synthesis of methyl 2-bromo-4-hydrazinocarbonylbenzoate

From 3-bromo-4-methoxycarbonylbenzoic acid, thionyl chloride and hydrazine monohydrate, 489 mg of the desired product was obtained in the same manner as in Reference Synthesis Example 39 as a while solid (yield 90%).
$^1$H-NMR (ppm in DMSO-$d_6$)
δ 3.88 (s, 3H), 4.60 (brs, 2H), 7.83 (d, J=8.1 Hz, 1H), 7.90 (dd, J=1.5, 8.1 Hz, 1H), 8.13 (d, J=1.5 Hz, 1H), 10.04 (brs, 1H).
LC/MS (ESI) 272 (M$^{+\ 79}$Br), 274 (M$^{+\ 81}$Br)

Reference Synthetic Example 43

Synthesis of methyl 4-hydrazinocarbonyl-2-hydroxybenzoate

1) Synthesis of 3-hydroxy-4-methoxycarbonylbenzoic acid

To 3-amino-4-methoxycarbonylbenzoic acid (1.95 g, 10 mmol) suspended in 3 M hydrochloric acid (12.5 mL) and acetic acid (20 mL), an aqueous solution (20 mL) of sodium nitrite (0.69 g, 10 mmol) was added at −10° C., and the resulting solution was stirred for 30 minutes. The solution was added to 10% aqueous sulfuric acid (30 mL) at 0° C., and the resulting reaction mixture was heated with reflux for 1 hour. The desired product was extracted with ethyl acetate, and the extract was dried over magnesium sulfate and purified by silica gel column chromatography to give 1.04 g of the desired product as a white solid (yield 53%).
$^1$H-NMR (ppm in DMSO-$d_6$)
δ 3.86 (s, 3H), 7.43 (d, J=8.1 Hz, 1H), 7.49 (s, 1H), 7.75 (d, J=8.1 Hz, 1H), 10.55 (brs, 1H).
LC/MS (ESI) 196 (M$^+$).

2) Synthesis of methyl 4-hydrazinocarbonyl-2-hydroxybenzoate

From 3-hydroxy-4-methoxycarbonylbenzoic acid, thionyl chloride and hydrazine monohydrate, 241 mg of the desired product was obtained in the same manner as in Reference Synthesis Example 39 as a while solid (yield 57%).
$^1$H-NMR (ppm in DMSO-$d_6$)
δ 3.90 (s, 3H), 4.55 (brs, 2H), 7.34 (dd, J=1.5, 8.1 Hz, 1H), 7.38 (d, J=1.5 Hz, 1H), 7.82 (d, J=8.1 Hz, 1H), 9.91 (brs, 1H), 10.52 (brs, 1H).
LC/MS (ESI) 210 (M$^+$).

Reference Synthetic Example 44

Synthesis of 2-(3-trifluoromethylphenyl)-3-methoxymethyloxy-4-ethoxycarbonylthiophene From 2-(3-trifluoromethylphenyl)-3-hydroxy-4-ethoxycarbonylthiophene (1.2 g, 3.9 mmol), the desired product was obtained in the same manner as in Reference Synthesis. Example 16 as a brown oil (1.2 g; yield 88%).
$^1$H-NMR (ppm in CDCl$_3$)
δ 1.36-1.42 (m, 3H), 3.19 (s, 3H), 4.33-4.37 (m, 2H), 5.05 (s, 2H), 7.53-7.56 (m, 2H), 7.83-7.85 (m, 1H), 8.02-8.07 (m, 2H).
LC/MS (ES$^+$) 383 (Na$^+$ adduct).

Reference Synthetic Example 45

Synthesis of 2-(3-trifluoromethylphenyl)-3-methoxymethyloxy-4-hydroxymethylthiophene From 2-(3-trifluoromethylphenyl)-3-methoxymethyloxy-4-ethoxycarbonylthiophene (1.2 g, 3.4 mmol), the desired product was obtained in the same manner as in Reference Synthesis Example 19 as a pale yellow oil (1.0 g, yield 95%).
$^1$H-NMR (ppm in CDCl$_3$)
δ 3.50 (s, 3H), 4.57 (d, J=5.2 Hz, 2H), 4.91 (s, 2H), 7.23 (s, 1H), 7.48-7.56 (m, 2H), 7.80-7.82 (m, 1H), 7.96 (s, 1H).
LC/MS (ES$^+$) 341 (Na$^+$ adduct).

Reference Synthetic Example 46

Synthesis of 2-(3-trifluoromethylphenyl)-3-methoxymethyloxy-4-formylthiophene

From 2-(3-trifluoromethylphenyl)-3-methoxymethyloxy-4-hydroxymethylthiophene (1.0 g, 3.2 mmol), the desired product was obtained in the same manner as in Reference Synthesis Example 24 as a brown oil (0.97 g, yield 96%).
$^1$H-NMR (ppm in CDCl$_3$)
δ 3.29 (s, 3H), 5.03 (s, 2H), 7.53-7.62 (m, 2H), 7.83-8.06 (m, 3H), 9.91 (s, 1H).
LC/MS (ES$^+$) 339 (Na$^+$ adduct).

Reference Synthetic Example 47

Synthesis of 2-(3-trifluoromethylphenyl)-3-methoxymethyloxy-4-(1-hydroxyethyl)thiophene From 2-(3-trifluoromethylphenyl)-3-methoxymethyloxy-4-formylthiophene (0.97 g, 3.1 mmol), the desired product was obtained in the same manner as in Reference Synthesis Example 27 as a brown oil (0.97 g, yield 96%).
$^1$H-NMR (ppm in CDCl$_3$)
δ 1.59-1.62 (m, 3H), 3.47 (s, 3H), 4.82-4.94 (m, 3H), 7.19 (s, 1H), 7.48-7.56 (m, 2H), 7.79-7.81 (m, 1H), 7.94 (s, 1H).
LC/MS (ES$^+$) 355 (Na$^+$ adduct).

Reference Synthetic Example 48

Synthesis of 2-(3-trifluoromethylphenyl)-3-methoxymethyloxy-4-methylcarbonylthiophene From 2-(3-trifluoromethylphenyl)-3-methoxymethyloxy-4-(1-hydroxyethyl)thiophene (0.99 g, 2.3 mmol), the desired product was obtained in the same manner, as in Reference Synthesis Example 30 as a brown oil (0.76 g, yield 77%).
$^1$H-NMR (ppm in CDCl$_3$)
δ 2.57 (s, 3H), 3.19 (s, 3H), 4.97 (s, 2H), 7.54-7.58 (m, 2H), 7.83-8.01 (m, 3H).
LC/MS (ES$^+$) 353 (Na$^+$ adduct).

Reference Synthetic Example 49

Synthesis of 2-(3-trifluoromethylphenyl)-3-hydroxy-4-methylcarbonylthiophene

From 2-(3-trifluoromethylphenyl)-3-methoxymethyloxy-4-methylcarbonylthiophene (0.76 g, 2.3 mmol), the desired product was obtained in the same manner as in Reference Synthesis Example 25 as a pale brown solid (0.59 g, yield 90%).
$^1$H-NMR (ppm in CDCl$_3$)
δ 2.58 (s, 3H), 7.48-7.52 (m, 2H), 7.94-8.05 (m, 3H), 10.52 (s, 1H).
LC/MS (ES$^+$) 287.

Reference Synthetic Example 50

Synthesis of methyl 2-acetamino-4-hydrazinocarbonylbenzoate

1) Synthesis of 3-acetamino-4-methoxycarbonylbenzoic acid

Acetic anhydride (1.89 mL, 20 mmol) was added to a suspension of 3-amino-4-methoxycarbonylbenzoic acid (1.95 g, 10 mmol) in acetic acid (10 mL), and the mixture was heated with reflux for 6 hours. After cooling, the precipitated solid was filtered to obtain 2.12 g of the desired product as a colorless solid (yield 89%).
$^1$H-NMR (ppm in DMSO-d$_6$)
δ 2.13 (s, 3H), 3.87 (s, 3H), 7.71 (d, 1H, J=8.4 Hz), 7.96 (d, 1H, J=8.4 Hz), 8.68 (s, 1H), 10.51 (brs, 1H).
LC/MS (ESI) 237 (M$^+$).

2) Synthesis of methyl 2-acetamino-4-hydrazinocarbonylbenzoate

1-Hydroxybenzotriazole (HOBt) (270 mg, 2 mmol) and 1-(3-(dimethylamino)propyl)-3-ethylcarbodiimide hydrochloride (WSC) (498 mg, 2.6 mmol) were added to a solution of 3-acetamino-4-methoxycarbonylbenzoic acid (474 mg, 2 mmol) in dimethylformamide (10 mL), and the mixture was stirred at room temperature for 3 hours. Hydrazine monohydrate (485 μL, 10 mmol) was further added at 0° C., and the mixture was stirred overnight at room temperature. The precipitated solid was filtered, and then washed with water to obtain 400 mg of the desired product as a white solid (yield 80%).
$^1$H-NMR (ppm in DMSO-d$_6$)
δ 2.12 (s, 3H), 3.85 (s, 3H), 4.55 (brs, 2H), 7.55 (d, 1H, J=8.1 Hz), 7.90 (d, 1H, J=8.1 Hz), 8.49 (s, 1H), 9.92 (brs, 1H), 10.48 (brs, 1H).
LC/MS (ESI) 251 (M$^+$).

Reference Synthetic Example 51

Synthesis of methyl 2-fluoro-4-hydrazinocarbonylbenzoate

1) Synthesis of methyl 4-bromo-2-fluorobenzoate

Methyl iodide (1.49 mL, 24 mmol) was added to a suspension of 4-bromo-2-fluorobenzoic acid (4.38 g, 20 mmol) and sodium carbonate (6.36 g, 60 mmol) in dimethylformamide (50 mL), and the mixture was stirred overnight at room temperature. After completion of the reaction, ethyl acetate was added, and the mixture was washed with water and a saturated ammonium chloride aqueous solution. After drying over magnesium sulfate, concentration was carried out to obtain 4.50 g of the desired product as a colorless solid (yield 97%).
$^1$H-NMR (ppm in CDCl$_3$)
δ 3.93 (s, 3H), 7.33-7.38 (m, 2H), 7.80-7.85 (m, 1H).

2) Synthesis of methyl 4-benzyloxycarbonyl-2-fluorobenzoate

Palladium diacetate (4.5 mg, 0.02 mmol), 1,4-(bisdiphenylphosphino)butane (8.5 mg, 0.02 mmol), triethylamine (55.8 µL, 0.4 mmol) and benzyl alcohol (1 mL) were added to a solution of methyl 4-bromo-2-fluorobenzoate (46.6 mg, 0.2 mmol) in dimethylformamide (1 mL). In this solution, bubbling was carried out for a few minutes with carbon monoxide, and then this solution was heated at 120° C. for 12 hours under carbon monoxide atmosphere. After completion of the reaction, ethyl acetate was added, and the resultant product was washed with a saturated ammonium chloride aqueous solution, and purified with a silica gel column chromatography (hexane/ethyl acetate=19/1) to obtain 35.4 mg of the desired product as a yellow viscous liquid (yield 61%).

$^1$H-NMR (ppm in CDCl$_3$)

δ 3.95 (s, 3H), 5.38 (s, 2H), 7.35-7.46 (m, 5H), 7.79-8.02 (m, 3H).

3) Synthesis of 3-fluoro-4-methoxycarbonylbenzoic acid

Catalytic amount of 10 wt % palladium carbon was added to a solution of methyl 4-benzyloxycarbonyl-2-fluorobenzoate (35.4 mg, 0.123 mmol) in ethanol (2 mL), and the mixture was stirred overnight at room temperature under hydrogen atmosphere. After completion of the reaction, the mixture was filtered through celite and the filtrate was concentrated to obtain 26.0 mg of the desired product as a colorless solid (yield 100%).

$^1$H-NMR (ppm in CDCl$_3$)

δ 3.97 (s, 3H), 7.83-8.06 (m, 3H).

LC/MS (ESI) 198 (M$^+$).

4) Synthesis of methyl 2-fluoro-4-hydrazinocarbonylbenzoate

From 3-fluoro-4-methoxycarbonylbenzoic acid (198 mg, 1 mmol), 1-hydroxybenzotriazole (HOBt) (135 mg, 1 mmol), 1-(3-(dimethylamino)propyl)-3-ethylcarbodiimide hydrochloride (WSC) (249 mg, 1.3 mmol) and hydrazine monohydrate (73 µL, 1.5 mmol), 45.6 mg of the desired product was obtained in the same manner as in Reference Synthesis Example 50 as a white solid (yield 22%).

$^1$H-NMR (ppm in DMSO-d$_6$)

δ 3.87 (s, 3H), 4.60 (brs, 2H), 7.71-7.77 (m, 2H), 7.94-7.99 (m, 1H), 10.06 (brs, 1H).

LC/MS (ESI) 212 (M$^+$).

Reference Synthetic Example 52

Synthesis of 2-(4-t-butylphenyl)-3-methoxymethyloxy-4-(1-hydroxyisobutyl)thiophene To a solution of 2-(4-t-butylphenyl)-3-methoxymethyloxy-4-formylthiophene (3.0 g, 10 mmol) in THF (2.5 mL), 2.0 M ethyl ether solution (6.0 mL, 12 mmol) of isopropylmagnesium bromide was added dropwise under cooling with ice, followed by stirring for 2.5 hours under cooling with ice. A saturated ammonium chloride aqueous solution was added to the reaction solution, and then extraction was carried out with ethyl acetate, and the organic layer was washed with a saturated sodium chloride solution and then dried over anhydrous sodium sulfate. The obtained organic layer was concentrated, and then purification was carried out with a silica gel column chromatography (n-hexane/ethyl acetate=3/1) to obtain the desired product as a pale yellow oil (1.18 g, yield 34%).

$^1$H-NMR (ppm in CDCl$_3$)

δ 0.91 (d, J=6.6 Hz, 3H), 1.10 (d, J=6.6 Hz, 3H), 1.34 (s, 9H), 2.15-2.25 (m, 1H), 3.46 (s, 3H), 4.35 (d, J=8.0 Hz, 1H), 4.86 (s, 2H), 7.04 (s, 1H), 7.39 (d, J=8.8 Hz, 2H), 7.56 (d, J=8.8 Hz, 2H).

LC/MS (ES$^-$) 303.

Reference Synthetic Example 53

Synthesis of 2-(4-t-butylphenyl)-3-methoxymethyloxy-4-isopropylcarbonylthiophene Using 2-(4-t-butylphenyl)-3-methoxymethyloxy-4-(1-hydroxyisobutyl)thiophene (1.07 g, 3.07 mmol) as the starting material, the desired product was obtained in the same manner as in Reference Synthetic Example 30 as a brown oil (0.85 g, yield 80%).

$^1$H-NMR (ppm in CDCl$_3$)

δ 1.20 (s, 3H), 1.23 (s, 3H), 1.34 (s, 9H), 3.21 (s, 3H), 3.39-3.45 (m, 1H), 4.92 (s, 2H), 7.42 (d, J=8.7 Hz, 2H), 7.61 (d, J=8.7 Hz, 2H), 7.83 (s, 1H).

LC/MS (ES$^+$) 369 (Na$^+$ adduct).

Reference Synthetic Example 54

Synthesis of 2-(4-t-butylphenyl)-3-hydroxy-4-isopropylcarbonylthiophene

Using 2-(4-t-butylphenyl)-3-methoxymethyloxy-4-(isopropylcarbonyl)thiophene (0.85 g, 2.5 mmol) as the starting material, the desired product was obtained in the same manner as in Reference Synthetic Example 25 as a pale brown solid (0.42 g, yield 56%).

$^1$H-NMR (ppm in CDCl$_3$)

δ 1.26 (s, 3H), 1.28 (s, 3H), 1.34 (s, 9H), 3.36-3.41 (m, 1H), 7.42 (d, J=8.8 Hz, 2H), 7.72 (d, J=8.8 Hz, 2H), 7.89 (s, 1H), 10.50 (s, 1H).

LC/MS (ES$^+$) 303.

Reference Synthetic Example 55

Synthesis of 2-bromo-5-(4-t-butylphenyl)-4-hydroxy-3-methylcarbonylthiophene 2-(4-t-butylphenyl)-3-hydroxy-4-methylcarbonylthiophene (2.66 g, 9.7 mmol), N-bromosuccinimide (1.73 g, 9.7 mmol) and benzoyl peroxide (153 mg, 0.63 mmol) were heated with reflux for 2 hours in 65 ml of chloroform. Water was added, and the reaction solution was extracted three times with chloroform, and the organic layer was washed with a saturated aqueous sodium chloride solution, and then dried over anhydrous sodium sulfate. The obtained organic layer was concentrated, and then purified with a silica gel column chromatography (n-hexane/chloroform=3/2) to obtain the desired product as a yellow solid (2.93 g, yield 86%).

$^1$H-NMR (ppm in CDCl$_3$)

δ=1.33 (s, 9H), 2.79 (s, 3H), 7.39-7.43 (m, 2H), 7.62-7.66 (m, 2H), 10.91 (s, 1H).

LC/MS (ES$^-$) 351, 353.

Reference Synthetic Example 56

Synthesis of methyl 4-hydrazinocarbonothioylamino-2-nitrobenzoate

1) Synthesis of methyl 4-amino-2-nitrobenzoate

To a suspension of 4-amino-2-nitrobenzoic acid (200 mg, 1.10 mmol) synthesized in accordance with the synthesis method described in WO96/35666 and sodium carbonate (349 mg, 3.29 mmol) in dimethylformamide (5.5 mL), methyl iodide (0.21 ml) was added, and the mixture was stirred overnight at room temperature. Water was added to the reaction solution, and extraction was carried out with ethyl acetate, and the combined organic layer was washed with a saturated ammonium chloride aqueous solution and a saturated sodium chloride aqueous solution, followed by drying over anhydrous sodium sulfate. By concentrating the obtained organic layer, 216 mg of the desired product was obtained as a yellow solid (yield 100%).

$^1$H-NMR (ppm in CDCl$_3$)

δ 7.69 (d, J=8.5 Hz, 1H), 6.85 (d, J=2.4 Hz, 1H), 6.77 (dd, J=2.4, 8.5 Hz, 1H), 4.31 (bs, 2H), 3.84 (s, 3H).

LC/MS (ESI) 196.

2) Synthesis of 4-methoxycarbonyl-3-nitrophenyl isothiocyanate

A solution of the above synthesized methyl 4-amino-2-nitrobenzoate (50 mg, 0.25 mmol) and 1,1'-thiocarbonyldi-2 (1H)-pyridone (59 mg, 0.25 mmol) in dichloromethane (4.2 ml) was stirred at room temperature for 3 hours. After completion of the reaction, the solvent was evaporated, followed by purification with a silica gel column chromatography to obtain 42 mg of the desired product as a colorless oil (yield 69%).

$^1$H-NMR (ppm in CDCl$_3$)

δ 7.79 (d, J=8.3 Hz, 1H), 7.66 (d, J=2.1 Hz, 1H), 7.47 (dd, J=2.1, 8.3 Hz, 1H), 3.92 (s, 3H).

LC/MS (ES$^-$) 224 (M$^+$-CH$_2$).

3) Synthesis of methyl 4-hydrazinocarbonothioylamino-2-nitrobenzoate

A solution of the above synthesized 4-methoxycarbonyl-3-nitrophenyl isothiocyanate (149 mg, 0.62 mmol) in tetrahydrofuran (2.2 ml) was added dropwise to a solution of hydrazine monohydrate (94 mg, 1.87 mmol) in tetrahydrofuran (4.0 ml) at 0° C. over 20 minutes. After stirring at 0° C. for further 40 minutes, water was added, and the precipitated solid was filtered to obtain 142 mg of the desired product as a colorless solid (yield 85%).

$^1$H-NMR (ppm in DMSO)

δ 9.67 (bs, 1H), 8.71 (bs, 1H), 8.18-8.21 (m, 1H), 7.76-7.83 (m, 2H), 3.82 (s, 3H).

LC/MS (ESI) 270.

Reference Synthetic Example 57

Synthesis of methyl 5-hydrazinocarbonothioylamino-2-thiophenecarboxylate

1) Synthesis of methyl 5-nitro-2-thiophenecarboxylate

From 5-nitrothiophene-2-carboxylic acid (3 g, 17.3 mmol), the desired product was obtained in the same manner as in Reference Synthetic Example 56 as a pale pink solid (2.97 g, yield 92%).

$^1$H-NMR (ppm in CDCl$_3$)

δ 7.88 (d, J=4.3 Hz, 1H), 7.70 (d, J=4.3 Hz, 1H), 3.96 (s, 3H).

2) Synthesis of 5-methoxycarbonyl-2-thiophene isothiocyanate

To a solution of the above synthesized methyl 5-nitro-2-thiophenecarboxylate (2.67 g, 14.3 mmol) and iron (2.63 g, 47.1 mmol) in ethanol (50 ml) and water (9.9 ml), concentrated hydrochloric acid (0.12 ml, 1.43 mmol) was added at 90° C. And the mixture was stirred at 90° C. for 30 minutes. After completion of the reaction, 1 M sodium hydroxide aqueous solution (1.43 ml, 1.43 mmol) was added thereto. The insolubles were filtered off, and the filtrate was concentrated and extracted with ethyl acetate, then dried over anhydrous sodium sulfate. The obtained organic layer was concentrated and dried by means of a vacuum pump. From the resulting crude solid, the desired product was obtained in the same manner as in Reference Synthetic Example 56 as a pale yellow oil (904 mg, yield 32%).

$^1$H-NMR (ppm in CDCl$_3$)

δ 7.56 (d, J=4.0 Hz, 1H), 6.83 (d, J=4.0 Hz, 1H), 3.88 (s, 3H).

LC/MS (ES$^+$) 199.

3) Synthesis of methyl 5-hydrazinocarbonothioylamino-2-thiophenecarboxylate

From the above synthesized methyl 5-methoxycarbonyl-2-thiophene isothiocyanate (484 mg, 2.43 mmol), the desired product was obtained in the same manner as in Reference Synthetic Example 56 as a colorless solid (435 mg, yield 77%).

$^1$H-NMR (ppm in DMSO)

δ 9.63 (bs, 1H), 7.55-7.57 (m, 1H), 7.12 (bs, 1H), 6.95 (bs, 1H), 3.76 (s, 3H).

LC/MS (ESI) 231.

Reference Synthetic Example 58

Synthesis of methyl 4-hydrazinocarbonothioylamino-2-chlorobenzoate

1) Synthesis of methyl 4-amino-2-chlorobenzoate

From 4-amino-2-chlorobenzoic acid (500 mg, 2.91 mmol), the desired product was obtained in the same manner as in Reference Synthetic Example 56 as a pale brown solid (535 mg, yield 99%).

$^1$H-NMR (ppm in CDCl$_3$)

δ 7.78 (d, J=8.5 Hz, 1H), 6.70 (d, J=2.2 Hz, 1H), 6.53 (dd, J=2.2 Hz, 8.5 Hz, 1H), 4.07 (bs, 2H), 3.86 (s, 3H).

LC/MS (ES$^+$) 185.

2) Synthesis of 4-methoxycarbonyl-3-chlorophenyl isothiocyanate

From the above synthesized methyl 4-amino-2-chlorobenzoate (505 mg, 2.72 mmol), the desired product was obtained in the same manner as in Reference Synthetic Example 56 as a colorless solid (424 mg, yield 69%).

$^1$H-NMR (ppm in CDCl$_3$)

δ 7.87 (d, J=8.3 Hz, 1H), 7.31 (d, J=2.0 Hz, 1H), 7.15 (dd, J=2.0 Hz, 8.3 Hz, 1H), 3.93 (s, 3H).

LC/MS (ES$^+$) 227.

3) Synthesis of methyl 4-hydrazinocarbonothioylamino-2-chlorobenzoate

From the above synthesized 4-methoxycarbonyl-3-chlorophenyl isothiocyanate (420 mg, 1.85 mmol), the desired product was obtained in the same manner as in Reference Synthetic Example 56 as a colorless solid (364 mg, yield 76%).

¹H-NMR (ppm in DMSO)
δ 9.54 (bs, 1H), 8.24 (bs, 1H), 7.77-7.84 (m, 3H), 3.83 (s, 3H).
LC/MS (ESI) 259.

Reference Synthetic Example 59-66

Table 15 shows the number of the synthetic examples (S.E.) obtained in the similar manner as described in the reference synthetic example (R.S.E.) 33, yields, shapes, LC/MS conditions (L.C.), LC/MS observed peaks (O.P.) and retention times (R.T.).

TABLE 15

| R.S.E. | yields (%) | shapes | L.C. | O.P. ESI⁺ | ESI⁻ | R.T. (min) |
|---|---|---|---|---|---|---|
| 59 | 48 | pale brown solid | 2 | 297/299 | 295/297 | 4.54 |
| 60 | 73 | yellow solid | | | | |
| 61 | 83 | yellow solid | 9 | 303 | 301 | 3.34 |
| 62 | 93 | brown solid | 5 | 255 | 253 | 4.49 |
| 63 | 50 | yellow solid | 9 | 237 | 235 | 2.99 |
| 64 | 44 | green solid | 2 | 237 | 235 | 4.22 |
| 65 | 53 | yellow solid | 2 | 247 | 245 | 4.52 |
| 66 | 55 | pale green solid | 2 | 253/255 | 251/253 | 4.49 |

Reference Synthetic Example 67

Synthesis of 2-(3,4-dichlorophenyl)-4-(1-hydrorazonoethyl)thiophen-3-ol

To a suspension of 2-(3,4-dichlorophenyl)-3-hydroxy-4-methylcarbonylthiophene (300 mg, 1.05 mmol) in isopropanol (20 mL) was added hydrazine monohydrate (61 μL, 1.25 mmol). The reaction mixture was refluxed for 1.5 hours, stirred at room temperature for 0.5 hour and at 0° C. for 1 hour. The precipitated solid was collected by filtration and dried by means of a vacuum pump to give the desired product as a pale yellow solid (yield 100%). ¹H-NMR (DMSO-d₆) δ(ppm): 2.10 (s, 3H), 6.63 (br s, 2H), 7.58 (s, 2H), 7.61 (s, 1H), 7.98 (s, 1H)/12.88 (s, 1H).
LC/MS: condition 8, retention time 4.95 (min)
LC/MS (ESI⁺) m/z; 301, 303 [M+1]⁺
LC/MS (ESI⁻) m/z; 299, 301 [M−1]⁻

Reference Synthetic Example 68-75

Table 16 shows the number of the synthetic examples (S.E.) obtained in the similar manner as described in the reference synthetic example (R.S.E.) 67, yields, shapes, LC/MS conditions (L.C.), LC/MS observed peaks (O.P.) and retention times (R.T.).

TABLE 16

| R.S.E. | yields (%) | shapes | L.C. | O.P. ESI⁺ | ESI⁻ | R.T. (min) |
|---|---|---|---|---|---|---|
| 68 | 50 | pale yellow solid | 3 | 267/269 | 265/267 | 3.52 |
| 69 | 89 | pale yellow solid | 2 | 299 | 297 | 3.49 |
| 70 | 72 | pale yellow solid | | | | |
| 71 | 100 | pale yellow solid | | | | |
| 72 | 100 | yellow solid | 9 | 263 | 261 | 4.85 |
| 73 | 100 | pale yellow solid | 3 | 311/313 | 309/311 | 3.57 |
| 74 | 93 | yellow solid | 3 | 317 | 315 | 3.62 |
| 75 | 79 | pale yellow solid | 3 | 261 | 259 | 3.50 |

The structural formulae of the compounds obtained in the Reference Synthetic Example 59-75 are given below.

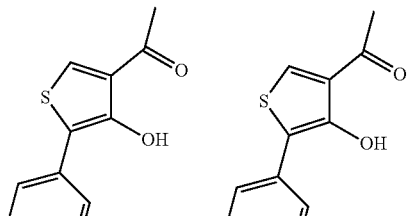

REFERENCE SYNTHETIC EX. 59    REFERENCE SYNTHETIC EX. 60

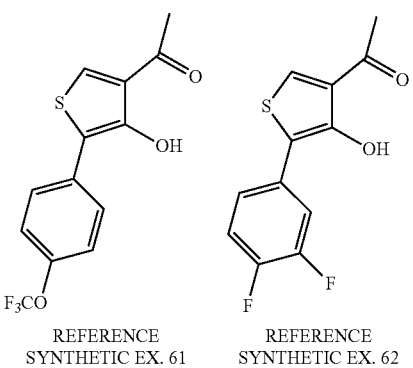

REFERENCE SYNTHETIC EX. 61    REFERENCE SYNTHETIC EX. 62

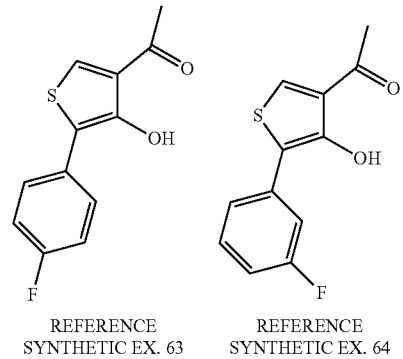

REFERENCE SYNTHETIC EX. 63    REFERENCE SYNTHETIC EX. 64

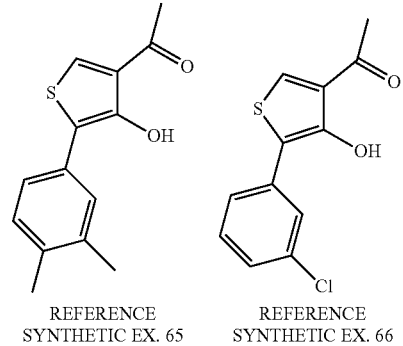

REFERENCE SYNTHETIC EX. 65    REFERENCE SYNTHETIC EX. 66

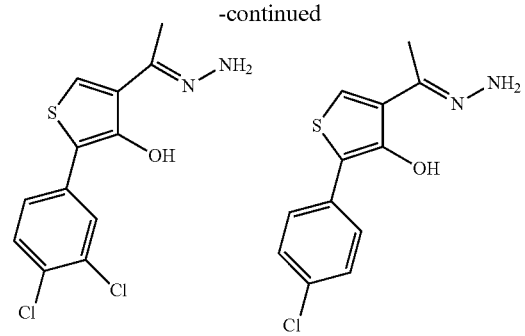

REFERENCE SYNTHETIC EX. 67

REFERENCE SYNTHETIC EX. 68

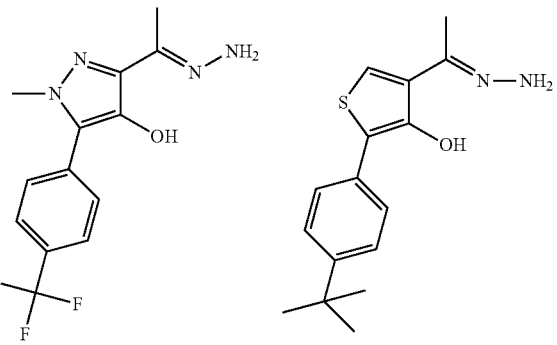

REFERENCE SYNTHETIC EX. 69

REFERENCE SYNTHETIC EX. 70

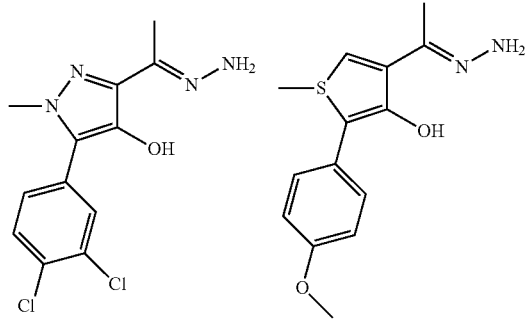

REFERENCE SYNTHETIC EX. 71

REFERENCE SYNTHETIC EX. 72

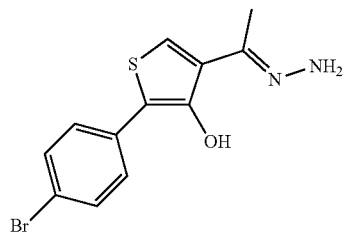

REFERENCE SYNTHETIC EX. 73

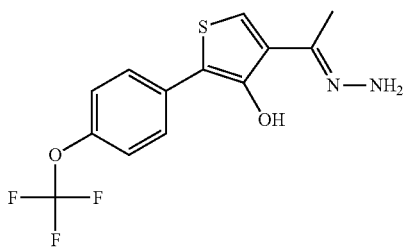

REFERENCE SYNTHETIC EX. 74

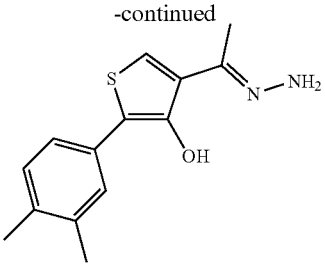

REFERENCE SYNTHETIC EX. 75

Synthetic Example 1

Synthesis of 4-[(2-{1-[5-(3,4-dichlorophenyl)-4-hydroxy-1-methyl-1H-pyrazol-3-yl]ethylidene}hydrazino)carbonyl]benzoic acid 1) Synthesis of 1-[5-(3,4-dichlorophenyl)-4-hydroxy-1-methyl-1H-pyrazol-3-yl]ethanone 2-Oxopropanal methylhydrazone (1.525 mmol, 152.7 mg) synthesized in Reference Synthetic Example 1 and (3,4-dichlorophenyl)(oxo)acetaldehyde (1.525 mmol, 310 mg) synthesized in Reference Synthetic Example 3 were dissolved in acetic acid (10 mL) and stirred at 110° C. for 1.5 hours. Then, the solvent was evaporated, and the residue was dried by means of a vacuum pump, resolved by silica gel thin layer chromatography (n-hexane/AcOEt=3/2) and purified by silica gel thin layer chromatography (n-hexane/AcOEt=2/1) to give the desired product as a yellow solid (57.8 mg, yield 13%).

$^1$H-NMR (ppm in CDCl$_3$)

δ 8.25 (s, 1H), 7.58 (br.s, 1H), 7.55 (br.s, 1H), 7.33 (br.dd, 1H), 3.92 (s, 3H), 2.58 (s, 3H).

$^{13}$C-NMR (ppm in CDCl$_3$)

δ 198.1, 143.8, 135.6, 133.2, 132.7, 130.9, 130.4, 127.8, 127.6, 125.8, 39.3, 25.6.

LC-MS (ESI) 284 (M$^+$).

2) Synthesis of 4-[(2-{1-[5-(3,4-dichlorophenyl)-4-hydroxy-1-methyl-1H-pyrazol-3-yl]ethylidene}hydrazino)carbonyl]methyl benzoate 1-[5-(3,4-Dichlorophenyl)-4-hydroxy-1-methyl-1H-pyrazol-3-yl]ethanone (0.1336 mmol, 38 mg), 4-hydrazinocarbonylmethyl benzoate (0.1336 mmol, 26 mg) and p-tosylic acid monohydrate (30 mol %, 6.9 mg) were dissolved in isopropyl alcohol (2.5 mL) and stirred at 100° C. for 3.5 hours. Then, the reactor was cooled to 0° C., and the precipitated solid was recovered by filtration and dried by means of a vacuum pump to give the desired product as a white solid (30.5 mg, yield 50%).

$^1$H-NMR (ppm in DMSO-d$_6$)

δ 11.46 (s, 1H), 9.95 (s, 1H), 8.10 (ABq, J=8.3 Hz, 2H), 8.04 (ABq, J=8.3 Hz, 2H), 7.86 (d, J=2.0 Hz, 1H), 7.80 (d, J=8.3 Hz, 1H), 7.61 (dd, J=2.0, 8.3 Hz, 1H), 3.90 (s, 3H), 3.90 (s, 3H), 2.45 (s, 3H).

LC-MS (ESI) 460 (M$^+$).

3) Synthesis of 4-[(2-{1-[5-(3,4-dichlorophenyl)-4-hydroxy-1-methyl-1H-pyrazol-3-yl]ethylidene}hydrazino)carbonyl]benzoic acid To 4-[(2-{1-[5-(3,4-dichlorophenyl)-4-hydroxy-1-methyl-1H-pyrazol-3-yl]ethylidene}hydrazino)carbonyl]methyl benzoate (0.0518 mmol, 23.9 mg), methanol (3 mL) was added, and 1 M aqueous sodium hydroxide (0.259 mmol, 0.259 mL) was added at room temperature. After 20 minutes of stirring at room temperature and 2 hours of stirring at 60° C., the reactor was cooled to room temperature, and 1 M hydrochloric acid (0.259 mmol, 0.259 mL) and water were added. The precipitated solid was recovered by filtration, washed with water and dried by means of a vacuum pump to give the desired product as a yellow solid (8.7 mg, yield 37%).

$^1$H-NMR (ppm in DMSO-$d_6$)

δ 11.43 (s, 1H), 9.96 (s, 1H), 8.13-7.98 (multi, 4H), 7.86-7.78 (multi, 2H), 7.62-7.51 (multi, 1H), 3.90-3.87 (multi, 3H), 2.46-2.45 (multi, 3H).

LC-MS (ESI) 446 (M$^+$).

Synthetic Example 2

Synthesis of 4-{[(2-{1-[5-(3,4-dichlorophenyl)-4-hydroxy-1-methyl-1H-pyrazol-3-yl] ethylidene}hydrazino)carbonothioyl]amino}benzoic acid 1-[5-(3,4-Dichlorophenyl)-4-hydroxy-1-methyl-1H-pyrazol-3-yl]ethanone (0.139 mmol, 39.7 mg) synthesized in Synthetic Example 1 and 4-hydrazinocarbonothioylaminobenzoic acid (0.139 mmol, 29.4 mg) were stirred with dimethylformamide (4 mL) and two drops of concentrated hydrochloric acid at room temperature for 22 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a yellow solid (39.5 mg, yield 59%).

$^1$H-NMR (ppm in DMSO-$d_6$)

δ10.36 (s, 1H), 10.33 (s, 1H), 9.15 (s, 1H), 7.93 (ABq, J=8.6 Hz, 2H), 7.85-7.83 (multi, 2H), 7.79 (ABq, J=8.6 Hz, 2H), 7.58 (d, J=8.4 Hz, 1H), 3.85 (s, 3H), 2.39 (s, 3H).

LC-MS (ESI) 477 (M$^+$).

Synthetic Example 3

Synthesis of 4-[(2-{1-[5-(4-tert-butylphenyl)-4-hydroxy-1-methyl-1H-pyrazol-3-yl] ethylidene}hydrazino)carbonyl]benzoic acid 1) Synthesis of 1-[5-(4-tert-butylphenyl)-4-hydroxy-1-methyl-1H-pyrazol-3-yl]ethanone 2-Oxopropanal methylhydrazone (46.375 mmol, 4.64 g) synthesized in Reference Synthetic Example 1 and (4-tert-butylphenyl)(oxo)acetaldehyde synthesized in Reference Synthetic Example 4 (46.375 mmol, 8.82 g) were dissolved in acetic acid (140 mL) and stirred at 100° C. for 2 hours. The reactor was cooled to room temperature, and after addition of water (100 mL) and saturated aqueous sodium chloride (50 mL), it was extracted with chloroform three times. The resulting organic layer was dried and filtered, and the solvent was evaporated. The residue was purified by silica gel column chromatography (n-hexane/ethyl acetate=4/1) to give the desired product as a yellow solid (5.79 g, yield 46%).

$^1$H-NMR (ppm in CDCl$_3$)

δ 8-16 (s, 1H, exchangeable with D$_2$O), 7.51 (ABq, J=8.4 Hz, 2H), 7.40 (ABq, J=8.4 Hz, 2H), 3.91 (s, 3H), 2.58 (s, 3H), 1.35 (s, 9H).

$^1$H-NMR (ppm in DMSO-$d_6$)

δ 8.50 (s, 1H), 7.53 (ABq, J=8.6 Hz, 2H), 7.44 (ABq, J=8.6 Hz, 2H), 3.83 (s, 3H), 2.46 (s, 3H), 1.32 (s, 9H).

$^{13}$C-NMR (ppm in CDCl$_3$)

δ 198.2, 151.6, 143.4, 135.6, 128.5, 128.3, 125.8, 124.7, 39.1, 34.7, 31.2, 25.6.

LC-MS (ESI) 272 (M$^+$).

2) Synthesis of 4-[(2-{1-[5-(4-tert-butylphenyl)-4*-hydroxy-1-methyl-1H-pyrazol-3-yl] ethylidene}hydrazino)carbonyl]methyl benzoate 1-[5-(4-tert-Butylphenyl)-4-hydroxy-1-methyl-1H-pyrazol-3-yl]ethanone (0.441 mmol, 120.0 mg), 4-hydrazinocarbonylmethyl benzoate (0.441 mmol, 85.6 mg) and p-tosylic acid monohydrate (30 mol %, 22.8 mg) were dissolved in isopropyl alcohol (10 mL) and stirred at 100° C. for about 3 hours and then at 50° C. overnight. The reactor was cooled to 0° C., and the reaction solution was filtered and dried by means of a vacuum pump to give the desired product as a white solid (145.1 mg, yield 73%).

$^1$H-NMR (ppm in CDCl$_3$)

δ 8.98 (s, 1H), 8.78 (br.s, 1H), 8.16-8.13 (multi, 2H), 7.92-7.80 (multi, 2H), 7.51-7.32 (multi, 4H), 3.95-3.88 (multi, 6H), 2.54 and 2.44 (sx2, 3H), 1.35 (s, 9H).

LC-MS (ESI) 448 (M$^+$).

3) Synthesis of 4-[(2-{1-[5-(4-tert-butylphenyl)-4-hydroxy-1-methyl-1H-pyrazol-3-yl] ethylidene}hydrazino)carbonyl]benzoic acid To 4-[(2-{1-[5-(4-tert-butylphenyl)-4-hydroxy-1-methyl-1H-pyrazol-3-yl]ethylidene}hydrazino)carbonyl]methyl benzoate (0.0816 mmol, 36.6 mg), methanol (2.5 mL) was added, and then 1 M aqueous sodium hydroxide (0.408 mmol. 0.408 mL) was added. After 22 hours of stirring at room temperature, 1 M hydrochloric acid (0.408 mmol, 0.408 mL) and water were added. The precipitated solid was recovered by filtration, washed with water, dried by means of a vacuum pump and purified by silica gel thin layer chromatography (chloroform/methanol=5/1) to give the desired product as a yellow solid (35.0 mg, yield 99%).

$^1$H-NMR (ppm in DMSO-$d_6$)

δ 8.13-7.98 (multi, 4H), 7.59-7.43 (multi, 4H), 3.88 and 3.84 (sx2, 3H), 2.46 and 2.45 (sx2, 3H), 1.34 and 1.32 (sx2, 9H).

LC-MS (ESI) 434 (M$^+$).

Synthetic Example 4

Synthesis of 3-[(2-{1-[5-(4-tert-butylphenyl)-4-hydroxy-1-methyl-1H-pyrazol-3-yl] ethylidene}hydrazino)-carbonyl]methyl benzoate 1-[5-(4-tert-Butylphenyl)-4-hydroxy-1-methyl-1H-pyrazol-3-yl]ethanone (0.192 mmol, 52.2 mg) synthesized in Synthetic Example 3,3-hydrazinocarbonylmethyl benzoate (0.192 mmol, 37.2 mg) and p-tosylic acid monohydrate (30 mol %, 9.9 mg) were dissolved in isopropyl alcohol (7 mL) and stirred at 100° C. for about 15 hours. Then, the reactor was cooled to room temperature, and the reaction solution was filtered and dried by means of a vacuum pump to give the desired product as a white solid (65.3 mg, yield 76%).

¹H-NMR (ppm in DMSO-d₆)
δ 11.42 (s, 1H), 9.70 (s, 1H), 8.47 (s, 1H), 8.19 (br.t, 2H), 7.71 (t, J=7.7 Hz, 1H), 7.55 (ABq, J=8.7 Hz, 2H), 7.51 (ABq, J=8.7 Hz, 2H), 3.92 (s, 3H), 3.85 (s, 3H), 2.46 (s, 3H), 1.34 (s, 9H).
LC-MS (ESI) 448 (M⁺).

Synthetic Example 5

Synthesis of 3-[(2-{1-[5-(4-tert-butylphenyl)-4-hydroxy-1-methyl-1H-pyrazol-3-yl]ethylidene}hydrazino)carbonyl]benzoic acid To 3-[(2-{1-[5-(4-tert-butylphenyl)-4-hydroxy-1-methyl-1H-pyrazol-3-yl]ethylidene}hydrazino)carbonyl]methyl benzoate (0.119 mmol, 53.4 mg), methanol (2.5 mL) was added, and then 1 M aqueous sodium hydroxide (0.595 mmol, 0.595 mL) was added. After 1 hour of stirring at room temperature and 1 hour of stirring at 60° C., the reactor was cooled to room temperature, and 1 M hydrochloric acid (0.595 mmol, 0.595 mL) and water were added. The precipitated solid was recovered by filtration, washed with water and dried by means of a vacuum pump. The resulting mixture was resolved by silica gel thin layer chromatography (CHCl₃/MeOH=10/1) to give the desired product as a pale yellow solid (34 mg, yield 66%).
¹H-NMR (ppm in DMSO-d₆)
δ 11.41 (s, 1H), 9.72 (s, 1H), 8.55 and 8.46 (sx2, 1H), 8.16-8.14 (multi, 2H), 7.71-7.63 (multi, 1H), 7.58-7.50 (multi, 4H), 3.94 and 3.85 (sx2, 3H), 2.46 (s, 3H), 1.34 (s, 9H).
LC-MS (ESI) 434 (M).

Synthetic Example 6

Synthesis of 4-{[(2-{1-[5-(4-tert-butylphenyl)-4-hydroxy-1-methyl-1H-pyrazol-3-yl]ethylidene}hydrazino)carbonothioyl]amino}benzoic acid 1-[5-(4-tert-Butylphenyl)-4-hydroxy-1-methyl-1H-pyrazol-3-yl]ethanone (0.163 mmol, 44.4 mg) synthesized in Synthetic Example 3 and 4-hydrazinocarbonothioylaminobenzoic acid (0.163 mmol, 34.4 mg) were stirred with dimethylformamide (3 mL) and two drops of concentrated hydrochloric acid at room temperature for 20 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a yellow solid (37 mg, yield 48%).
¹H-NMR (ppm in DMSO-d₆)
δ 10.88 (s, 1H), 10.34 (s, 1H), 8.86 (s, 1H), 7.95-7.84 (multi, 4H), 7.59-7.47 (multi, 4H), 3.83 and 3.81 (sx2, 3H), 2.46 and 2.39 (sx2, 3H), 1.34 and 1.33 (sx2, 9H).
LC-MS (ESI) 465 (M⁺).

Synthetic Example 7

Synthesis of 4-{[(2-{1-[5-(4-tert-butylphenyl)-1-ethyl-4-hydroxy-1H-pyrazol-3-yl]ethylidene}hydrazino)-carbonothioyl]amino}benzoic acid 1) Synthesis of 1-[5-(4-tert-butylphenyl)-1-ethyl-4-hydroxy-1H-pyrazol-3-yl]ethanone 2-Oxopropanal ethylhydrazone (4.736 mmol, 540.6 mg) synthesized in Reference Synthetic Example 2 and (4-tert-butylphenyl)(oxo)acetaldehyde (4.736 mmol, 901.0 mg) synthesized in Reference Synthetic Example 4 were dissolved in acetic acid (20 mL) and stirred at 100° C. for about 3.5 hours. Then, the solvent was evaporated, and the residue was dried by means of a vacuum pump and purified by silica gel thin layer chromatography (n-hexane/AcOEt=1/2, 3/1 and 4/1) to give the desired product as an orange liquid (212 mg, yield 160).
¹H-NMR (ppm in CDCl₃)
δ 8.12 (s, 1H), 7.50 (ABq, J=8.6 Hz, 2H), 7.36 (ABq, J=8.6 Hz, 2H), 4.19 (q, J=7.2 Hz, 2H), 2.59 (s, 3H), 1.42 (t, J=7.2 Hz, 3H), 1.36 (s, 9H).
LC-MS (ESI) 286 (M⁺).

2) Synthesis of 4-{[(2-{1-[5-(4-tert-butylphenyl)-1-ethyl-4-hydroxy-1H-pyrazol-3-yl]ethylidene}hydrazino)-carbonothioyl]amino}benzoic acid 1-[5-(4-tert-Butylphenyl)-1-ethyl-4-hydroxy-1H-pyrazol-3-yl]ethanone (0.1718 mmol, 49.2 mg) and 4-hydrazinocarbonothioylaminobenzoic acid (0.1718 mmol, 36.3 mg) were stirred with dimethylformamide (3 mL) and two drops of concentrated hydrochloric acid at room temperature for 21 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a yellow solid (59 mg, yield 72%).
¹H-NMR (ppm in DMSO-d₆)
δ 10.89 (s, 1H), 10.33 (s, 1H), 8.77 (s, 1H), 7.94-7.84 (multi, 4H), 7.60-7.41 (multi, 4H), 4.08 (q, J=7.2 Hz, 2H), 2.47 and 2.41 (sx2, 3H), 1.34 and 1.33 (sx2, 9H), 1.27 (t, J=7.2 Hz, 3H).
LC-MS (ESI) 479 (M⁺).

Synthetic Example 8

Synthesis of 4-{[(2-{1-[5-(4-tert-butylphenyl)-1-benzyl-4-hydroxy-1H-pyrazol-3-yl]ethylidene}hydrazino)-carbonothioyl]amino}benzoic acid 1) Synthesis of 1-[5-(4-tert-butylphenyl)-1-benzyl-4-hydroxy-1H-pyrazol-3-yl]ethanone 2-Oxopropanal benzylhydrazone (2.314 mmol, 408 mg) synthesized in the same manner as in Reference Synthetic Examples 1 and 2 and (4-tert-butylphenyl)(oxo)acetaldehyde (1.929 mmol, 366.9 mg) synthesized in Reference Synthetic Example 4 were dissolved in acetic acid (9 mL) and stirred at 100° C. for about 6 hours. Then, the solvent was evaporated, and the residue was dried by means of a vacuum pump and purified by silica gel column chromatography (n-hexane/AcOEt=3/1, and 4/1) to give the desired product as a yellow solid (74.1 mg, yield 11%).
³H-NMR (ppm in CDCl₃)
δ 8.15 (s, 1H), 7.43-7.40 (multi, 2H), 7.30-7.25 (multi, 5H), 7.06-7.03 (multi, 2H), 5.34 (s, 2H), 2.60 (s, 3H), 1.32 (s, 9H).
LC-MS (ESI) 348 (M⁺).

2) Synthesis of 4-{[(2-{1-[5-(4-tert-butylphenyl)-1-benzyl-4-hydroxy-1H-pyrazol-3-yl]ethylidene}hydrazino)carbonothioyl]amino}benzoic acid 1-[5-(4-tert-Butylphenyl)-1-benzyl-4-hydroxy-1H-pyrazol-3-yl]ethanone (0.218 mmol, 76 mg) and 4-hydrazinocarbonothioylaminobenzoic acid (0.218 mmol, 46 mg) were stirred with dimethylformamide (3.5 mL) and three drops of concentrated hydrochloric acid at room temperature for 22 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (83 mg, yield 70%).

$^1$H-NMR (ppm in DMSO-$d_6$)

δ 10.94 (br.s, 1H), 10.36-10.34 (br.s, 1H), 8.90 (s, 1H), 7.94-7.85 (multi, 4H), 7.56-7.47 (multi, 2H), 7.39-7.21 (multi, 5H), 7.09-6.95 (multi, 2H), 5.34 and 5.29 (sx2, 2H), 2.47 and 2.40 (sx2, 3H), 1.33 and 1.30 (sx2, 9H).

LC-MS (ESI) 541 (M$^+$).

Synthetic Example 9

Synthesis of 4-{[(2-{1-[(5-(3,4-dimethylphenyl)-1-methyl-4-hydroxy-1H-pyrazol-3-yl]ethylidene}hydrazino)carbonothioyl]amino}benzoic acid 1) Synthesis of 1-[5-(3,4-dimethylphenyl)-1-methyl-4-hydroxy-1H-pyrazol-3-yl]ethanone 2-Oxopropanal methylhydrazone (8.18 mmol, 819 mg) synthesized in Reference Synthetic Example 1 and (3,4-dimethylphenyl)(oxo)acetaldehyde (7.57 mmol, 1.227 g) synthesized in Reference Synthetic Example 5 were dissolved in acetic acid (30 mL) and stirred at 100° C. for about 5 hours. Then, the solvent was evaporated, and the residue was dried by means of a vacuum pump and subjected to silica gel column chromatography (n-hexane/AcOEt=2/1, and 4/1) to give the crude product. The crude product was stirred with CHCl$_3$/n-hexane for a while, and then recovered by filtration. The filtered solid was combined with a solid obtained by silica gel thin layer chromatography purification (n-hexane/AcOEt=4/1) of the filtrate to give the desired product as an orange solid (237.5 mg, yield 13%).

$^1$H-NMR (ppm in CDCl$_3$)

δ 8.13 (br.s, 1H), 7.23-7.15 (multi, 3H), 3.88 (s, 3H), 2.58 (s, 3H), 2.34-2.31 (multi, 6H).

LC-MS (ESI) 244 (M$^+$).

2) Synthesis of 4-{[(2-{1-[5-(3,4-dimethylphenyl)-1-methyl-4-hydroxy-1H-pyrazol-3-yl]ethylidene}hydrazino)carbonothioyl]amino}benzoic acid 1-[5-(3,4-Dimethylphenyl)-1-methyl-4-hydroxy-1H-pyrazol-3-yl]ethanone (0.2423 mmol, HPLC purity 84.3%, 70.2 mg) and 4-hydrazinocarbonothioylaminobenzoic acid (0.2423 mmol, 51.2 mg) were stirred with dimethylformamide (3 mL) and three drops of concentrated hydrochloric acid at room temperature for 8.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (72.3 mg, yield 68%).

$^1$H-NMR (ppm in DMSO-$d_6$)

δ 10.84 (br.s, 1H), 10.33 (s, 1H), 8.82 and 8.32 (sx2, 1H), 7.94-7.83 (multi, 4H), 7.32-7.23 (multi, 3H), 3.81 and 3.79 (sx2, 3H), 2.46 and 2.39 (sx2, 3H), 2.30-2.29 (multi, 6H).

LC-MS (ESI) 437 (M$^+$).

Synthetic Example 10

Synthesis of 4-{[(2-{1-[5-(4-n-pentylphenyl)-1-methyl-4-hydroxy-1H-pyrazol-3-yl]ethylidene}hydrazino)carbonothioyl]amino}benzoic acid 1) Synthesis of 1-[5-(4-n-pentylphenyl)-1-methyl-4-hydroxy-1H-pyrazol-3-yl]ethanone 2-Oxopropanal methylhydrazone (8.6 mmol, 861 mg) synthesized in Reference Synthetic Example 1 and (4-n-pentylphenyl)(oxo)acetaldehyde (8.6 mmol, 1.757 g) synthesized in Reference Synthetic Example 6 were dissolved in acetic acid (30 mL) and stirred at 100° C. for about 5 hours. Then, the solvent was evaporated, and the residue was dried by means of a vacuum pump and purified by silica gel column chromatography (n-hexane/AcOEt=2/1, and 4/1) to give the desired product as an orange solid (252.5 mg, yield 10.3%, crude).

$^1$H-NMR (ppm in CDCl$_3$)

δ 8.16 (br.s, 1H), 7.37 (ABq, J=8.3 Hz, 2H), 7.29 (ABq, J=8.3 Hz, 2H), 3.90 (s, 3H), 2.70-2.62 (multi, 2H), 2.58 (s, 3H), 1.70-1.60 (multi, 2H), 1.39-1.32 (multi, 4H), 0.93-0.87 (multi, 3H).

LC-MS (ESI) 286 (M$^+$).

2) Synthesis of 4-{[(2-{1-[5-(4-n-pentylphenyl)-methyl-4-hydroxy-1H-pyrazol-3-yl]ethylidene}hydrazino)carbonothioyl]amino}benzoic acid 1-[5-(4-n-Pentylphenyl)-1-methyl-4-hydroxy-1H-pyrazol-3-yl]ethanone (0.2381 mmol, HPLC purity 86.3%, 79.0 mg) and 4-hydrazinocarbonothioylaminobenzoic acid (0.2381 mmol, 50.3 mg) were stirred with dimethylformamide (3 mL) and three drops of concentrated hydrochloric acid at room temperature for 8.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (86.4 mg, yield 76%).

$^1$H-NMR (ppm in DMSO-$d_6$)

δ 10.90 (br.s, 1H), 10.34 (s, 1H), 8.85 (s, 1H), 7.94-7.84 (multi, 4H), 7.48-7.32 (multi, 4H), 3.82 and 3.80 (sx2, 3H), 2.65-2.60 (multi, 2H), 2.46 and 2.39 (sx2, 3H), 1.64-1.57 (multi, 2H), 1.34-1.30 (multi, 4H), 0.90-0.86 (multi, 3H).

LC-MS (ESI) 479 (M$^+$).

Synthetic Example 11

Synthesis of 4-{[(2-{1-[5-(4-trifluoromethylphenyl)-1-methyl-4-hydroxy-1H-pyrazol-3-yl]ethylidene}hydrazino)carbonothioyl]amino}benzoic acid 1) Synthesis of 1-[5-(4-trifluoromethylphenyl)-1-methyl-4-hydroxy-1H-pyrazol-3-yl]ethanone 2-Oxopropanal methylhydrazone (8.540 mmol, 855 mg) synthesized in Reference Synthetic Example 1 and (4-trifluoromethylphenyl)(oxo)acetaldehyde (6.432 mmol, 1.3 g) synthesized in Reference Synthetic Example 7 were dissolved in acetic acid (30 mL) and stirred at 100° C. for about 5 hours. Then, the solvent was evaporated, and the residue was dried by means of a vacuum pump and purified by silica gel column chromatography (n-hexane/AcOEt=2/1, and 4/1) to give the desired product as an orange solid (157.3 mg, yield 8.6%).

$^1$H-NMR (ppm in CDCl$_3$)

δ 8.28 (s, 1H), 7.75 (ABq, J=8.3 Hz, 2H), 7.62 (ABq, J=8.3 Hz, 2H), 3.95 (s, 3H), 2.59 (s, 3H).

LC-MS (ESI) 284 (M$^+$).

2) Synthesis of 4-{[(2-{1-[5-(4-trifluoromethylphenyl)-1-methyl-4-hydroxy-1H-pyrazol-3-yl]ethylidene}hydrazino)carbonothioyl]amino}benzoic acid 1-[5-(4-trifluoromethylphenyl)-1-methyl-4-hydroxy-1H-pyrazol-3-yl]ethanone (0.1694 mmol, HPLC purity 80%, 60.2 mg) and 4-hydrazinocarbonothioylaminobenzoic acid (0.1694 mmol, 35.8 mg) were stirred with dimethylformamide (3 mL) and three drops of concentrated hydrochloric acid at room temperature for 8.5 hours. After addition of water, the precipitated yellow solid was recovered by filtration, washed with water and dried by means of a vacuum pump. Chloroform/n-hexane was added to the resulting solid, and the precipitated solid was recovered by filtration and dried by means of a vacuum pump to give the desired product as a pale yellow solid (72.2 mg, yield 89%).

$^1$H-NMR (ppm in DMSO-d$_6$)

δ 10.93 (br.s, 1H), 10.36 and 10.35 (br.sx2, 1H), 9.14 (s, 1H), 7.95-7.80 (multi, 8H), 3.88 (s, 3H), 2.47 and 2.41 (sx2, 3H).

LC-MS (ESI) 477 (M$^+$).

Synthetic Example 12

Synthesis of 4-[(2-{(1-[5-(3,4-dimethylphenyl)-4-hydroxy-1-methyl-1H-pyrazol-3-yl]ethylidene}hydrazino)-carbonyl]benzoic acid 1) Synthesis of methyl 4-[(2-{1-[5-(3,4-dimethylphenyl)-4-hydroxy-1-methyl-1H-pyrazol-3-yl]ethylidene}hydrazino)carbonyl]benzoate 1-[5-(3,4-Dimethylphenyl)-4-hydroxy-1-methyl-1H-pyrazol-3-yl]ethanone (0.365 mmol, 105.8 mg), 4-hydrazinocarbonylmethyl benzoate (0.365 mmol, 70.9 mg) and p-tosylic acid monohydrate (30 mol %, 18.9 mg) were dissolved in isopropyl alcohol (12 mL) and stirred at 100° C. for about 19 hours. The reactor was cooled to room temperature, and the precipitated solid was recovered by filtration, dried by means of a vacuum pump and purified by silica gel thin layer chromatography (chloroform/methanol 10/1) to give the desired product as a white solid (21.7 mg, yield 14%).

$^1$H-NMR (ppm in DMSO-d$_6$)

δ 11.39 (br.s, 1H), 9.66 (br.s, 1H), 8.10 (ABq, J=8.3 Hz, 2H), 8.04 (ABq, J=8.3 Hz, 2H), 7.34 (br.s, 1H), 7.28 (br.s, 2H), 3.90 (s, 3H), 3.83 (s, 3H), 2.45 (s, 3H), 2.30 (s, 3H), 2.28 (s, 3H).

LC-MS (ESI) 420 (M$^+$).

2) Synthesis of 4-[(2-{1-[5-(3,4-dimethylphenyl)-4-hydroxy-1-methyl-1H-pyrazol-3-yl]ethylidene}hydrazino)carbonyl]benzoic acid To methyl 4-[(2-{1-[5-(3,4-dimethylphenyl)-4-hydroxy-1-methyl-1H-pyrazol-3-yl]ethylidene}hydrazino)carbonyl]benzoate (0.051 mmol, 21.6 mg), methanol (2.0 mL) was added, and 1 M aqueous sodium hydroxide (5 eq., 0.257 mL) was added at room temperature. After 30 minutes of stirring at room temperature and 1.5 hours of stirring at 60° C., the reactor was cooled to room temperature, and 1 M hydrochloric acid (5 eq., 0.257 mL) and water were added. The precipitated solid was recovered by filtration, washed with water and dried by means of a vacuum pump to give the desired product as a yellow solid (17.5 mg, yield 84%).

$^1$H-NMR (ppm in DMSO-d$_6$)

δ 11.35 (br.s, 1H), 9.69 (br.s, 1H), 8.07-7.96 (multi, 4H), 7.88-7.26 (multi, 3H), 3.82 (s, 3H), 2.45 (s, 3H), 2.30 (s, 3H), 2.28 (s, 3H).

LC-MS (ESI) 406 (M$^+$).

Synthetic Example 13

Synthesis of 4-[(2-{1-[4-hydroxy-1-methyl-5-(4-n-pentylphenyl)-1H-pyrazol-3-yl]ethylidene}hydrazino)carbonyl]benzoic acid 1) Synthesis of methyl 4-[(2-{1-[4-hydroxy-1-methyl-5-(4-n-pentylphenyl)-1H-pyrazol-3-yl]ethylidene}hydrazino)carbonyl]benzoate 1-[4-Hydroxy-1-methyl-5-(4-n-pentylphenyl)-1H-pyrazol-3-yl]ethanone (0.309 mmol, 102.4 mg), 4-hydrazinocarbonylmethyl benzoate (0.309 mmol, 59.9 mg) and p-tosylic acid monohydrate (30 mol %, 15.9 mg) were dissolved in isopropyl alcohol (12 mL) and stirred at 100° C. for about 20 hours. The reactor was cooled to room temperature, and the precipitated solid was recovered by filtration and dried by means of a vacuum pump to give the desired product as a white solid (87.9 mg, yield 62%).

$^1$H-NMR (ppm in DMSO-d$_6$)

δ 11.27 (br.s, 1H), 9.94 (br.s, 1H), 8.10-8.05 (multi, 4H), 7.48 (ABq, J=8.1 Hz, 2H), 7.34 (ABq, J=8.1 Hz, 2H), 3.90 (s, 3H), 3.84 (s, 3H), 2.63 (t, J=7.1 Hz, 2H), 2.44 (s, 3H), 1.62 (multi, 2H), 1.33-1.32 (multi, 4H), 0.88 (t, J=7.1 Hz, 3H).

LC-MS (ESI) 462 (M$^+$).

2) Synthesis of 4-[(2-{1-[4-hydroxy-1-methyl-5-(4-n-pentylphenyl)-1H-pyrazol-3-yl]ethylidene}hydrazino)carbonyl]benzoic acid To methyl 4-[(2-{1-[4-hydroxy-1-methyl-5-(4-n-pentylphenyl)-1H-pyrazol-3-yl]ethylidene}hydrazino)carbonyl]benzoate (0.121 mmol, 66.5 mg), methanol (3.5 mL) was added, and 1 M aqueous sodium hydroxide (5 eq., 0.605 mL) was added at room temperature. After 30 minutes of stirring at room temperature and 1.5 hours of stirring at 60° C., the reactor was cooled to room temperature, and 1 M hydrochloric acid (5 eq., 0.605 mL) and water were added. The precipitated solid was recovered by filtration, washed with water and dried by means of a vacuum pump to give the desired product as a yellow solid (40.4 mg, yield 74%).

$^1$H-NMR (ppm in DMSO-d$_6$)

δ 11.36 (br.s, 1H), 9.69 (br.s, 1H), 8.07 (ABq, J=8.3 Hz, 2H), 8.01 (ABq, J=8.3 Hz, 2H), 7.48 (ABq, J=8.0 Hz, 2H), 7.34 (ABq, J=8.0 Hz, 2H), 3.84 (s, 3H), 2.63 (t, J=7.7 Hz, 2H), 2.45 (s, 3H), 1.62 (multi, 2H), 1.33-1.32 (multi, 4H), 0.88 (t, J=6.8 Hz, 3H).

LC-MS (ESI) 448 (M$^+$).

Synthetic Example 14

Synthesis of 4-{[2-(1-{4-hydroxy-1-methyl-5-[4-(trifluoromethyl)phenyl]-1H-pyrazol-3-yl}ethylidene)hydrazino]carbonyl}benzoic acid 1) Synthesis of methyl 4-{[2-(1-{4-hydroxy-1-methyl-5-[4-(trifluoromethyl)phenyl]-1H-pyrazol-3-yl}ethylidene)hydrazino]carbonyl}benzoate 1-[4-Hydroxy-1-methyl-5-(4-trifluoromethylphenyl)-1H-pyrazol-3-yl]ethanone (0.231 mmol, 82.1 mg), 4-hydrazinocarbonylmethyl benzoate (0.231 mmol, 44.9 mg) and p-tosylic acid monohydrate (30 mol %, 11.9 mg) were dissolved in isopropyl alcohol (12 mL) and stirred at 100° C. for about 20 hours. The reactor was cooled to room temperature, and the precipitated solid was recovered by filtration and dried by means of a vacuum pump to give the desired product as a pale yellow solid (66.5 mg, yield 63%).

$^1$H-NMR (ppm in DMSO-$d_6$)

δ 11.46 (br.s, 1H), 9.97 (br.s, 1H), 8.11 (ABq, J=8.6 Hz, 2H), 8.04 (ABq, J=8.6 Hz, 2H), 7.89 (ABq, J=8.6 Hz, 2H), 7.84 (ABq, J=8.6 Hz, 2H), 3.92 (s, 3H), 3.90 (s, 3H), 2.47 (s, 3H).

LC-MS (ESI) 460 (M$^+$).

2) Synthesis of 4-{[2-(1-{4-hydroxy-1-methyl-5-[4-(trifluoromethyl)phenyl]-1H-pyrazol-3-yl}ethylidene)hydrazino]carbonyl}benzoic acid To methyl 4-{[2-(1-{4-hydroxy-1-methyl-5-[4-(trifluoromethyl)phenyl]-1H-pyrazol-3-yl}ethylidene)hydrazino]carbonyl}benzoate (0.116 mmol, 53.4 mg), methanol (2 mL) was added, and 1 M aqueous sodium hydroxide (5 eq., 0.580 mL) was added at room temperature. After 30 minutes of stirring at room temperature and 1 hour of stirring at 60° C., the reactor was cooled to room temperature, and 1 M hydrochloric acid (5 eq., 0.580 mL) and water were added. The precipitated solid was recovered by filtration, washed with water and dried by means of a vacuum pump to give the desired product as a yellow solid (37.7 mg, yield 73%).

$^1$H-NMR (ppm in DMSO-$d_6$)

δ 11.43 (br.s, 1H), 9.98 (br.s, 1H), 8.07 (ABq, J=8.4 Hz, 2H), 8.01 (ABq, J=8.4 Hz, 2H), 7.89 (ABq, J=8.3 Hz, 2H), 7.84 (ABq, J=8.3 Hz, 2H), 3.92 (s, 3H), 2.47 and 2.42 (sx2, 3H).

LC-MS (ESI) 446 (M$^+$).

Synthetic Example 15

Synthesis of 4-{[2-(1-{4-hydroxy-1-methyl-5-[3-(trifluoromethyl)phenyl]-1H-pyrazol-3-yl}ethylidene)hydrazino]carbonyl}benzoic acid 1) Synthesis of 1-[4-hydroxy-1-methyl-5-(3-trifluoromethylphenyl)-1H-pyrazol-3-yl]ethanone 2-Oxopropanal methylhydrazone (7.49 mmol, 750 mg) and (oxo)[3-trifluoromethylphenyl]acetaldehyde (7.0 mmol, 1.42 g) synthesized in Reference Synthetic Example 8 were dissolved in acetic acid (20 mL) and stirred at 100° C. for 4 hours. Then, the solvent was evaporated, and the residue was dried by means of a vacuum pump and purified by silica gel column chromatography (n-hexane/ethyl acetate=2/1) and then by silica gel thin layer chromatography (chloroform/methanol=30/1) to give the desired product as a reddish yellow liquid (221 mg, yield 11%).

$^1$H-NMR (ppm in CDCl$_3$)

δ 8.26 (s, 1H), 7.70-7.60 (multi, 4H), 3.93 (s, 3H), 2.59 (s, 3H).

LC-MS (ESI) 284 (M$^+$).

2) Synthesis of methyl 4-{[2-(1-{4-hydroxy-1-methyl-5-[3-(trifluoromethyl)phenyl]-1H-pyrazol-3-yl}ethylidene)hydrazino]carbonyl}benzoate 1-[4-Hydroxy-1-methyl-5-(3-trifluoromethylphenyl)-1H-pyrazol-3-yl]ethanone (0.502 mmol, 142.7 mg), 4-hydrazinocarbonylmethyl benzoate (0.502 mmol, 97.5 mg) and p-tosylic acid monohydrate (30 mol %, 26.0 mg) were dissolved in isopropyl alcohol (13 mL) and stirred at 100° C. for about 11 hours. The reactor was cooled to room temperature, and the precipitated solid was recovered by filtration, dried by means of a vacuum pump and purified by silica gel thin layer chromatography (chloroform/methanol=10/1) and then by silica gel thin layer chromatography (n-hexane/ethyl acetate=1/2) to give the desired product as a yellow solid (36.7 mg, yield 16%).

$^1$H-NMR (ppm in DMSO-$d_6$)

δ 11.46 (br.s, 1H), 9.94 (br.s, 1H), 8.10 (ABq, J=8.1 Hz, 2H), 8.05 (ABq, J=8.1 Hz, 2H), 7.95-7.90 (multi, 2H), 7.81-7.77 (multi, 2H), 3.91 (br.s, 6H), 2.47 (s, 3H).

LC-MS (ESI) 460 (M$^+$).

3) Synthesis of 4-{[2-(1-{4-hydroxy-1-methyl-5-[3-(trifluoromethyl)phenyl]-1H-pyrazol-3-yl}ethylidene)hydrazino]carbonyl}benzoic acid To methyl 4-{[2-(1-{4-hydroxy-1-methyl-5-[3-(trifluoromethyl)phenyl]-1H-pyrazol-3-yl}ethylidene)hydrazino]carbonyl}benzoate (0.072 mmol, 33.1 mg), methanol (2 mL) was added, and 1 M aqueous sodium hydroxide (5 eq., 0.360 mL) was added at room temperature. After 30 minutes of stirring at room temperature and 1.5 hours of stirring at 60° C., the reactor was cooled to 0° C., and 1 M hydrochloric acid (5 eq., 0.360 mL) and water were added. The precipitated solid was recovered by filtration, washed with water and dried by means of a vacuum pump to give the desired product as a yellow solid (17.6 mg, yield 55%).

$^1$H-NMR (ppm in DMSO-$d_6$)

δ 11.40 (br.s, 1H), 9.99 (br.s, 1H), 8.06-7.69 (multi, 8H), 3.91 and 3.89 (br.sx2, 3H), 2.47 and 2.39 (br.sx2, 3H).

LC-MS (ESI) 446 (M$^+$).

Synthetic Example 16

Synthesis of 4-[(2-{1-[5-(3,5-dimethylphenyl)-4-hydroxy-1-methyl-1H-pyrazol-3-yl]ethylidene}hydrazino)carbonyl]benzoic acid 1) Synthesis of 1-[5-(3,5-dimethylphenyl)-4-hydroxy-1-methyl-1H-pyrazol-3-yl]ethanone 2-Oxopropanal methylhydrazone (7.29 mmol, 730 mg) and (3,5-dimethylphenyl)(oxo)acetaldehyde (7.29 mmol, 1.18 g) synthesized in Reference Synthetic Example 10 were dissolved in acetic acid (25 mL) and stirred at 100° C. for 5 hours. Then, the solvent was evaporated, and the residue was dried by means of a vacuum pump and purified by silica gel column chromatography (n-hexane/ethyl acetate=3/1) and then by silica gel thin layer chromatography (n-hexane/ethyl acetate=3/1) to give the desired product as an orange liquid (93 mg, yield 5%).

$^1$H-NMR (ppm in CDCl$_3$)

δ 8.15 (s, 1H), 7.05 (br.s, 3H), 3.88 (s, 3H), 2.58 (s, 3H), 2.37 (s, 6H).

LC-MS (ESI) 244 (M$^+$).

2) Synthesis of methyl 4-[(2-{1-[5-(3,5-dimethylphenyl)-4-hydroxy-1-methyl-1H-pyrazol-3-yl]ethylidene}hydrazino)carbonyl]benzoate 1-[5-(3,5-Dimethylphenyl)-4-hydroxy-1-methyl-1H-pyrazol-3-yl]ethanone (0.120 mmol, 29.3 mg) and 4-hydrazinocarbonylmethyl benzoate (0.120 mmol, 23.3 mg) were dissolved in dimethylformamide (5 mL) and stirred at 110° C. for 23 hours. Then, the reactor was cooled to room temperature, and the solvent was evaporated with a centrifugal evaporator. The residue was dried and purified by silica gel thin layer chromatography (chloroform/methanol=10/1) to give the desired product as a yellow solid (23.4 mg, yield 46%).
LC-MS (ESI) 420 ($M^+$).

3) Synthesis of 4-[(2-{1-[5-(3,5-dimethylphenyl)-4-hydroxy-1-methyl-1H-pyrazol-3-yl]ethylidene}hydrazino)carbonyl]benzoic acid To methyl 4-[(2-{1-[(5-(3,5-dimethylphenyl)-4-hydroxy-1-methyl-1H-pyrazol-3-yl]ethylidene}hydrazino)carbonyl]benzoate (0.015 mmol, 6.5 mg), methanol (1 mL) was added, and 1 M aqueous sodium hydroxide (5 eq., 0.077 mL) was added at room temperature. After 20 minutes of stirring at room temperature and 1.5 hours of stirring at 60° C., the reactor was cooled to room temperature, and 1 M hydrochloric acid (5 eq., 0.077 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was recovered by filtration and dried to give the desired product as a yellow solid (1.7 mg, yield 27%).
LC-MS (MSI) 406 ($M^+$).

Synthetic Example 17

Synthesis of 4-[(2-{1-[4-hydroxy-5-(4-isopropylphenyl)-1-methyl-1H-pyrazol-3-yl]ethylidene}hydrazino)carbonyl]benzoic acid 1) Synthesis of 1-[5-(4-isopropylphenyl)-4-hydroxy-1-methyl-1H-pyrazol-3-yl]ethanone 2-Oxopropanal methylhydrazone (10.44 mmol, 1.05 g) and (4-isopropylphenyl)(oxo)acetaldehyde (10.44 mmol, 1.84 g) synthesized in Reference Synthetic Example 12 were dissolved in acetic acid (37 mL) and stirred at 100° C. for 4.5 hours. Then, the solvent was evaporated, and the residue was dried by means of a vacuum pump and purified by silica gel column chromatography (n-hexane/ethyl acetate=3/1) and then by silica gel thin layer chromatography (n-hexane/ethyl acetate=3/1) to give the desired product as an orange solid (113 mg, yield 4%).
$^1$H-NMR (ppm in $CDCl_3$)
δ 8.15 (s, 1H), 7.39 (ABq, J=8.3 Hz, 2H), 7.34 (ABq, J=8.3 Hz, 2H), 3.90 (s, 3H), 2.96 (sept, J=6.9 Hz, 1H), 2.58 (s, 3H), 1.28 (d, J=6.9 Hz, 6H).
LC-MS (ESI) 258 ($M^+$).

2) Synthesis of methyl 4-[(2-{(1-[4-hydroxy-5-(4-isopropylphenyl)-1-methyl-1H-pyrazol-3-yl]ethylidene}hydrazino)carbonyl]benzoate 1-[5-(4-Isopropylphenyl)-4-hydroxy-1-methyl-1H-pyrazol-3-yl]ethanone (0.170 mmol, 44.0 mg) and 4-hydrazinocarbonylmethyl benzoate (0.170 mmol, 33.1 mg) were dissolved in dimethylformamide (5.5 mL) and stirred at 110° C. for 23 hours. Then, the reactor was cooled to room temperature, and the solvent was evaporated with a centrifugal evaporator. The residue was dried, and chloroform was added. The precipitated solid was recovered by filtration to give the desired product as a yellow solid (39.1 mg, yield 53%).
LC-MS (ESI) 434 ($M^+$).

3) Synthesis of 4-[(2-{1-[4-hydroxy-5-(4-isopropylphenyl)-1-methyl-1H-pyrazol-3-yl]ethylidene}hydrazino)carbonyl]benzoic acid To methyl 4-[(2-{1-[4-hydroxy-5-(4-isopropylphenyl)-1-methyl-1H-pyrazol-3-yl]ethylidene}hydrazino)-carbonyl]benzoate (0.037 mmol, 16.0 mg), methanol (3 mL) was added, and 1 M aqueous sodium hydroxide (5 eq., 0.184 mL) was added at room temperature. After 15 minutes of stirring at room temperature and 1.5 hours of stirring at 60° C., the reactor was cooled to room temperature, and 1 M hydrochloric acid (5 eq., 0.184 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was dried to give the desired product as a yellow solid (6.8 mg, yield 44%).
$^1$H-NMR (ppm in $DMSO-d_6$)
δ 11.33 (br.s, 1H), 9.70 (br.s, 1H), 8.09-7.93 (multi, 4H), 7.51-7.38 (multi, 4H), 3.86 and 3.84 (sx2, 3H), 2.99-2.94 (multi, 1H), 2.45 and 2.43 (sx2, 3H), 1.26 (d, J=6.9 Hz, 6H).
LC-MS (ESI) 420 ($M^+$).

Synthetic Example 18

Synthesis of 4-[(2-{1-[4-hydroxy-5-(4-isobutylphenyl)-1-methyl-1H-pyrazol-3-yl]ethylidene}hydrazino)carbonyl]benzoic acid 1) Synthesis of 1-[4-hydroxy-5-(4-isobutylphenyl)-1-methyl-1H-pyrazol-3-yl]ethanone 2-Oxopropanal methylhydrazone (11.60 mmol, 1.16 g) and (4-isobutylphenyl)(oxo)acetaldehyde (11.60 mmol, 2.21 g) synthesized in Reference Synthetic Example 15 were dissolved in acetic acid (38 mL) and stirred at 100° C. for 4.5 hours. Then, the solvent was evaporated, and the residue was dried by means of a vacuum pump and purified by silica gel column chromatography (n-hexane/ethyl acetate=3/1), then by silica gel thin layer chromatography (chloroform) and by silica gel thin layer chromatography (n-hexane/ethyl acetate=3/1) to give the desired product as a brown solid (154 mg, yield 50).
$^1$H-NMR (ppm in $CDCl_3$)
δ 8.17 (s, 1H), 7.37 (ABq, J=8.3 Hz, 2H), 7.26 (ABq, J=8.3 Hz, 2H), 3.90 (s, 3H), 2.58 (s, 3H), 2.52 (d, J=6.9 Hz, 2H), 1.91 (sept, J=6.9 Hz, 1H), 0.94 (d, J=6.9 Hz, 6H).
LC-MS (ESI) 272 ($M^+$).

2) Synthesis of methyl 4-[(2-{1-[4-hydroxy-5-(4-isobutylphenyl)-1-methyl-1H-pyrazol-3-yl]ethylidene}hydrazino)carbonyl]benzoate 1-[4-Hydroxy-5-(4-isobutylphenyl)-1-methyl-1H-pyrazol-3-yl]ethanone (0.353 mmol, 96.0 mg) and 4-hydrazinocarbonylmethyl benzoate (0.353 mmol, 68.5 mg) were dissolved in dimethylformamide (7 mL) and stirred at 110° C.

for 23 hours. Then, the reactor was cooled to room temperature, and the solvent was evaporated with a centrifugal evaporator. The residue was dried, and chloroform was added. The precipitated solid was recovered by filtration to give the desired product as a yellow solid (93.2 mg, yield 59%).
LC-MS (ESI) 448 (M+).

3) Synthesis of (4-[(2-{1-[4-hydroxy-5-(4-isobutylphenyl)-1-methyl-1H-pyrazol-3-yl]ethylidene}hydrazino)carbonyl]benzoic acid To methyl 4-[(2-{1-[4-hydroxy-5-(4-isobutylphenyl)-1-methyl-1H-pyrazol-3-yl]ethylidene}hydrazino)carbonyl]benzoate (0.129 mmol, 57.7 mg), methanol (2.5 mL) was added, and 1 M aqueous sodium hydroxide (5 eq., 0.643 mL) was added at room temperature. After 15 minutes of stirring at room temperature and 1.5 hours of stirring at 60° C., the reactor was cooled to room temperature, and 1 M hydrochloric acid (Seq., 0.643 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was dried to give the desired product as a yellow solid (25.6 mg, yield 46%).
$^1$H-NMR (ppm in DMSO-$d_6$)
δ 11.34 (s, 1H), 9.72 (s, 1H), 8.10-7.95 (multi, 4H), 7.50-7.46 (multi, 2H), 7.34-7.30 (multi, 2H), 3.87 and 3.84 (sx2, 3H), 2.45 (s, 3H), 1.90 (sept, J=6.8 Hz, 1H), 0.91 (d, J=6.8 Hz, 6H).
LC-MS (ESI) 434 (M+).

Synthetic Example 19

Synthesis of 4-[(2-{1-[5-(3-bromo-4-fluorophenyl)-4-hydroxy-1-methyl-1H-pyrazol-3-s yl]ethylidene}hydrazino)carbonyl]benzoic acid 1) Synthesis of 1-[5-(3-bromo-4-fluorophenyl)-4-hydroxy-1-methyl-1H-pyrazol-3-yl]ethanone 2-Oxopropanal methylhydrazone (10.5.6 mmol, 1.06 g) and (3-bromo-4-fluorophenyl)(oxo)acetaldehyde (10.56 mmol, 2.44 g) synthesized in Reference Synthetic Example 9 were dissolved in acetic acid (37 mL) and stirred at 100° C. for 4.5 hours. Then, the solvent was evaporated, and the residue was dried by means of a vacuum pump and purified by silica gel column chromatography (n-hexane/ethyl acetate=3/1), then by silica gel thin layer chromatography (chloroform) and by silica gel thin layer chromatography (n-hexane/ethyl acetate=3/1) to give the desired product as a brown solid (160 mg, yield 5%).
$^1$H-NMR (ppm in CDCl$_3$)
δ 8.21 (s, 1H), 7.69-7.66 (multi, 1H), 7.41-7.37 (multi, 1H), 7.27-7.22 (multi, 1H), 3.89 (s, 3H), 2.58 (s, 3H).
LC-MS (ESI) 312, 314 (M+).

2) Synthesis of methyl 4-[(2-{1-[5-(3-bromo-4-fluorophenyl)-4-hydroxy-1-methyl-1H-pyrazol-3-yl]ethylidene}hydrazino) carbonyl]benzoate 1-[5-(3-Bromo-4-fluorophenyl)-4-hydroxy-1-methyl-1H-pyrazol-3-yl]ethanone (0.269 mmol, 84.1 mg) and 4-hydrazinocarbonylmethyl benzoate (0.269 mmol, 52.2 mg) were dissolved in dimethylformamide (7 mL) and stirred at 110° C. for 23 hours. Then, the reactor was cooled to room temperature, and the solvent was evaporated with a centrifugal evaporator. The residue was dried, and chloroform was added. The precipitated solid was recovered by filtration to give the desired product as a yellow solid (60.1 mg, yield 46%).
LC-MS (ESI) 488 (M+).

3) Synthesis of 4-[(2-{1-[5-(3-bromo-4-fluorophenyl)-4-hydroxy-1-methyl-1H-pyrazol-3-yl]ethylidene}hydrazino)carbonyl]benzoic acid To methyl 4-[(2-{1-[5-(3-bromo-4-fluorophenyl)-4-hydroxy-1-methyl-1H-pyrazol-3-yl]ethylidene}hydrazino)carbonyl]benzoate (0.051 mmol, 24.9 mg), methanol (2.5 mL) was added, and 1 M aqueous sodium hydroxide (5 eq., 0.255 mL) was added at room temperature. After 10 minutes of stirring at room temperature and 1.5 hours of stirring at 60° C., the reactor was cooled to room temperature, and 1 M hydrochloric acid (5 eq., 0.255 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was dried to give the desired product as a yellow solid (9.0 mg, yield 37%).
$^1$H-NMR (ppm in DMSO-$d_6$)
δ 11.40 (s, 1H), 9.87 (s, 1H), 8.12-7.91 (multi, 5H), 7.62-7.52 (multi, 2H), 3.86 (s, 3H), 2.45 and 2.43 (sx2, 3H).
LC-MS (ESI) 474 (M+).

Synthetic Example 20

Synthesis of 4-[(2-{1-[5-(4-ethylphenyl)-4-hydroxy-1-methyl-1H-pyrazol-3-yl]ethylidene}hydrazino)carbonyl]benzoic acid 1) Synthesis of 1-[5-(4-ethylphenyl)-4-hydroxy-1-methyl-1H-pyrazol-3-yl]ethanone 2-Oxopropanal methylhydrazone (13.7 mmol, 1.37 g) and (4-ethylphenyl)(oxo)acetaldehyde (13.5 mmol, 2.19 g) synthesized in Reference Synthetic Example 11 were dissolved in acetic acid (30 mL) and stirred at 100° C. for 6 hours. Then, the solvent was evaporated, and the residue was dried by means of a vacuum pump and purified by silica gel column chromatography (n-hexane/ethyl acetate=3/1), then by silica gel thin layer chromatography (chloroform) and by silica gel thin layer chromatography (n-hexane/ethyl acetate=7/2) to give the desired product as a brown solid (255 mg, yield 8%).
$^1$H-NMR (ppm in CDCl$_3$)
δ 8.15 (s, 1H), 7.38 (ABq, J=8.4 Hz, 2H), 7.32 (ABq, J=8.4 Hz, 2H), 3.90 (s, 3H), 2.70 (q, J=7.8 Hz, 2H), 2.58 (s, 3H), 1.28 (t, J=7.8 Hz, 3H).
LC-MS (ESI) 244 (M+).

2) Synthesis of methyl 4-[(2-{1-[5-(4-ethylphenyl)-4-hydroxy-1-methyl-1H-pyrazol-3-yl]ethylidene}hydrazino)carbonyl]benzoate 1-[5-(4-Ethylphenyl)-4-hydroxy-1-methyl-1H-pyrazol-3-yl]ethanone (0.459 mmol, 112.1 mg) and 4-hydrazinocarbonylmethyl benzoate (0.459 mmol, 89.1 mg) were dissolved in dimethylformamide (9 mL) and stirred at 110° C. for 23 hours. Then, the reactor was cooled to room temperature, and the solvent was evaporated with a centrifugal evaporator. The residue was dried, and chloroform was added. The precipitated solid was recovered by filtration to give the desired product as a yellow solid (130.5 mg, yield 68%).
LC-MS (ESI) 420 (M+).

3) Synthesis of 4-[(2-{1-[5-(4-ethylphenyl)-4-hydroxy-1-methyl-1H-pyrazol-3-yl]ethylidene}hydrazino)carbonyl]benzoic acid To methyl 4-[(2-{1-[5-(4-ethylphenyl)-4-hydroxy-1-methyl-1H-pyrazol-3-yl]ethylidene}hydrazino)carbonyl]benzoate (0.172 mmol, 72.4 mg), methanol (4 mL) was added, and 1 M aqueous sodium hydroxide (5 eq., 0.861 mL) was added at room temperature. After 10 minutes of stirring at room temperature and 2 hours of stirring at 60° C., the reactor was cooled to room temperature, and 1 M hydrochloric acid (5 eq., 0.861 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was dried to give the desired product as a yellow solid (29.1 mg, yield 42%).

$^1$H-NMR (ppm in DMSO-$d_6$)

δ 11.36 (s, 1H), 9.68 (s, 1H), 8.13-7.96 (multi, 4H), 7.50-7.35 (multi, 4H), 3.87 and 3.84 (sx2, 3H), 2.72-2.64 (multi, 2H), 2.45 (s, 3H), 1.26-1.21 (multi, 3H).

LC-MS (ESI) 406 (M$^+$).

Synthetic Example 21

Synthesis of 4-[(2-{1-[4-hydroxy-1-methyl-5-(4-n-propylphenyl)-1H-pyrazol-3-yl]ethylidene}hydrazino)carbonyl]benzoic acid

1) Synthesis of 1-[5-(4-n-propylphenyl)-4-hydroxy-1-methyl-1H-pyrazol-3-yl]ethanone 2-Oxopropanal methylhydrazone (19.36 mmol, 1.94 g) and oxo(4-n-propylphenyl)acetaldehyde (19.0 mmol, 3.35 g) synthesized in Reference Synthetic Example 13 were dissolved in acetic acid (42 mL) and stirred at 100° C. for 6 hours. Then, the solvent was evaporated, and the residue was dried by means of a vacuum pump and purified by silica gel column chromatography (n-hexane/ethyl acetate=3/1), then by silica gel thin layer chromatography (chloroform) and by silica gel thin layer chromatography (n-hexane/ethyl acetate=7/2) to give the desired product as a brown solid (304 mg, yield 6%).

$^1$H-NMR (ppm in CDCl$_3$)

δ 8.15 (s, 1H), 7.37 (ABq, J=8.3 Hz, 2H), 7.29 (ABq, J=8.3 Hz, 2H), 3.90 (s, 3H), 2.64 (t, J=7.5 Hz, 2H), 2.58 (s, 3H), 1.68 (q, J=7.2 Hz, 2H), 0.97 (t, J=7.2 Hz, 3H).

LC-MS (ESI) 258 (M$^+$).

2) Synthesis of methyl 4-[(2-{1-[4-hydroxy-1-methyl-5-(4-n-propylphenyl)-1H-pyrazol-3-yl]ethylidene}hydrazino)carbonyl]benzoate 1-[4-Hydroxy-1-methyl-5-(4-n-propylphenyl)-1H-pyrazol-3-yl]ethanone (0.445 mmol, 115.0 mg) and 4-hydrazinocarbonylmethyl benzoate (0.445 mmol, 86.5 mg) were dissolved in dimethylformamide (9 mL) and stirred at 110° C. for 23 hours. Then, the reactor was cooled to room temperature, and the solvent was evaporated with a centrifugal evaporator. The residue was dried, and chloroform was added. The precipitated solid was recovered by filtration to give the desired product as a yellow solid (143.3 mg, yield 74%).

LC-MS (ESI) 434 (M$^+$).

3) Synthesis of 4-[(2-{1-[4-hydroxy-1-methyl-5-(4-n-propylphenyl)-1H-pyrazol-3-yl]ethylidene}hydrazino)carbonyl]benzoic acid To methyl 4-[(2-{1-[4-hydroxy-1-methyl-5-(4-n-propylphenyl)-1H-pyrazol-3-yl]ethylidene}hydrazino)carbonyl]benzoate (0.166 mmol, 72.2 mg), methanol was added, and 1 M aqueous sodium hydroxide (5 eq., 0.831 mL) was added at room temperature. After 10 minutes of stirring at room temperature and 2 hours of stirring at 60° C., the reactor was cooled to room temperature, and 1 M hydrochloric acid (5 eq., 0.831 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was recovered by filtration and dried to give the desired product as a yellow solid (47.1 mg, yield 670).

$^1$H-NMR (ppm in DMSO-$d_6$)

δ 11.36 (s, 1H), 9.69 (s, 1H), 8.12-7.96 (multi, 4H), 7.50-7.45 (multi, 2H), 7.39-7.33 (multi, 2H), 3.87 and 3.84 (sx2, 3H), 2.66-2.59 (multi, 2H), 2.45 (s, 3H), 1.71-1.58 (multi, 2H), 0.96-0.91 (multi, 3H).

LC-MS (ESI) 420 (M$^+$).

Synthetic Example 22

Synthesis of 4-[(2-{1-[5-(4-n-hexylphenyl)-4-hydroxy-1-methyl-1H-pyrazol-3-yl]ethylidene}hydrazino)carbonyl]benzoic acid

1) Synthesis of 1-[5-(4-n-hexylphenyl)-4-hydroxy-1-methyl-1H-pyrazol-3-yl]ethanone 2-Oxopropanal methylhydrazone (16.1 mmol, 1.62 g) and (4-n-hexylphenyl)(oxo)acetaldehyde (16 mmol, 4.57 g) synthesized in Reference Synthetic Example 14 were dissolved in acetic acid (35 mL) and stirred at 100° C. for 6 hours. Then, the solvent was evaporated, and the residue was dried by means of a vacuum pump and purified by silica gel column chromatography (n-hexane/ethyl acetate=3/1), then by silica gel thin layer chromatography (chloroform) and by silica gel thin layer chromatography (n-hexane/ethyl acetate=7/2) to give the desired product as a brown solid (308 mg, yield 6%).

$^1$H-NMR (ppm in CDCl$_3$)

δ 8.16 (s, 1H), 7.37 (ABq, J=8.1 Hz, 2H), 7.29 (ABq, J=8.1 Hz, 2H), 3.90 (s, 3H), 2.65 (t, J=7.8 Hz, 2H), 2.58 (s, 3H), 1.64-1.62 (multi, 2H), 1.41-1.28 (multi, 6H), 0.92-0.87 (multi, 3H).

LC-MS (ESI) 300 (M$^+$).

2) Synthesis of methyl 4-[(2-{1-[5-(4-n-hexylphenyl)-4-hydroxy-1-methyl-1H-pyrazol-3-yl]ethylidene}hydrazino)carbonyl]benzoate 1-[5-(4-n-hexylphenyl)-4-hydroxy-1-methyl-1H-pyrazol-3-yl]ethanone (0.431 mmol, 129.6 mg) and 4-hydrazinocarbonylmethyl benzoate (0.431 mmol, 83.8 mg) were dissolved in dimethylformamide (8 mL) and stirred at 110° C. for 23 hours. Then, the reactor was cooled to room temperature, and the solvent was evaporated with a centrifugal evaporator. The residue was dried, and chloroform was added. The precipitated solid was recovered by filtration to give the desired product as a yellow solid (125.1 mg, yield 61%).

LC-MS (ESI) 476 (M$^+$).

3) Synthesis of 4-[(2-{1-[5-(4-n-hexylphenyl)-4-hydroxy-1-methyl-1H-pyrazol-3-yl]ethylidene}hydrazino)carbonyl]benzoic acid To methyl 4-[(2-{1-[5-(4-n-hexylphenyl)-4-hydroxy-1-methyl-1H-pyrazol-3-yl]ethylidene}hydrazino)carbonyl]benzoate (0.158 mmol, 75.2 mg), methanol was added, and 1 M aqueous sodium hydroxide (5 eq., 0.789 mL) was added at room temperature. After 10 minutes of stirring at room temperature and 2 hours of stirring at 60° C., the reactor was cooled to room temperature, and 1 M hydrochloric acid (5 eq., 0.789 mL) and water were added. The precipitated solid was recovered by filtration, washed with water and dried by means of a vacuum pump, and the residue was further purified by silica gel thin layer chromatography (chloroform/methanol=10/1). After addition of chloroform/n-hexane, the precipitated solid was dried to give the desired product as a yellow solid (29.4 mg, yield 40%).
$^1$H-NMR (ppm in DMSO-$d_6$)
δ 11.36 (s, 1H), 9.69 (s, 1H), 8.13-7.95 (multi, 4H), 7.49-7.45 (multi, 2H), 7.38-7.33 (multi, 2H), 3.87 and 3.84 (sx2, 3H), 2.67-2.61 (multi, 2H), 2.45 (s, 3H), 1.66-1.56 (multi, 2H), 1.36-1.24 (multi, 6H), 0.89-0.85 (multi, 3H).
LC-MS (ESI) 462 (M$^+$).

Synthetic Example 23

Synthesis of 4-({[2-(1-{4-hydroxy-1-methyl-5-[3-(trifluoromethyl)phenyl]-1H-pyrazol-3-yl}ethylidene)hydrazino]carbonothioyl}amino)benzoic acid 1-[4-Hydroxy-1-methyl-5-(3-trifluoromethylphenyl)-1H-pyrazol-3-yl]ethanone (0.229 mmol, 65.0 mg) and 4-hydrazinocarbonothioylaminobenzoic acid (0.229 mmol, 48.3 mg) were stirred with dimethylformamide (2.5 mL) and three drops of concentrated hydrochloric acid at room temperature for 24 hours. After addition of water, the precipitated yellow solid was recovered by filtration, washed with water and dried by means of a vacuum pump. Chloroform/n-hexane was added to the resulting solid, and the precipitated solid was recovered by filtration and dried by means of a vacuum pump to give the desired product as a yellow solid (74.7 mg, yield 68%).
$^1$H-NMR (ppm in DMSO-$d_6$)
δ 10-36 and 10.33 (br.sx2, 1H), 9.12 (s, 1H), 7.95-7.77 (multi, 8H), 3.86 (s, 3H), 2.41 (s, 3H).
LC-MS (ESI) 477 (M$^+$).

Synthetic Example 24

Synthesis of 4-{[(2-{1-[5-(3,5-dimethylphenyl)-4-hydroxy-1-methyl-1H-pyrazol-3-yl]ethylidene}hydrazino)carbonothioyl]amino}benzoic acid 1-[5-(3,5-Dimethylphenyl)-4-hydroxy-1-methyl-1H-pyrazol-3-yl]ethanone (0.122 mmol, 29.9 mg) and 4-hydrazinocarbonothioylaminobenzoic acid (0.122 mmol, 25.9 mg) were stirred with dimethylformamide (2 mL) and two drops of concentrated hydrochloric acid at room temperature for 24 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (34.7 mg, yield 65%).
$^1$H-NMR (ppm in DMSO-$d_6$)
δ 10.87 (br.s, 1H), 10.33 and 10.32 (br.sx2, 1H), 8.84 (s, 1H), 7.93 (ABq, J=8.1 Hz, 2H), 7.84 (ABq, J=8.1 Hz, 2H), 7.16-7.14 (multi, 2H), 7.06 (br.s, 1H), 3.81 and 3.79 (sx2, 3H), 2.46 and 2.39 (sx2, 3H), 2.35-2.31 (multi, 6H).
LC-MS (ESI) 437 (M$^+$).

Synthetic Example 25

Synthesis of 4-{[(2-{1-[4-hydroxy-5-(4-isopropylphenyl)-1-methyl-1H-pyrazol-3-yl]ethylidene}hydrazino)carbonothioyl]amino}benzoic acid 1-[4-Hydroxy-5-(4-isopropylphenyl)-1-methyl-1H-pyrazol-3-yl]ethanone (0.116 mmol, 29.9 mg) and 4-hydrazinocarbonothioylaminobenzoic acid (0.116 mmol, 24.5 mg) were stirred with dimethylformamide (2 mL) and two drops of concentrated hydrochloric acid at room temperature for 24 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (37.7 mg, yield 72%).
$^1$H-NMR (ppm in DMSO-$d_6$)
δ 10.90 (br.s, 1H), 10.35 and 10.33 (br.sx2, 1H), 8.85 (s, 1H), 7.93 (ABq, J=8.6 Hz, 2H), 7.85 (ABq, J=8.6 Hz, 2H), 7.47 (ABq, J=8.1 Hz, 2H), 7.39 (ABq, J=8.1 Hz, 2H), 3.83 and 3.81 (sx2, 3H), 2.95 (sept, J=6.9 Hz, 1H), 2.46 and 2.39 (sx2, 3H), 1.27-1.24 (multi, 6H).
LC-MS (ESI) 451 (M$^+$).

Synthetic Example 26

Synthesis of 4-{[(2-{1-[4-hydroxy-5-(4-isobutylphenyl)-1-methyl-1H-pyrazol-3-yl]ethylidene}hydrazino)carbonothioyl]amino}benzoic acid 1-[4-Hydroxy-5-(4-isobutylphenyl)-1-methyl-1H-pyrazol-3-yl]ethanone (0.179 mmol, 48.8 mg) and 4-hydrazinocarbonothioylaminobenzoic acid (0.179 mmol, 37.9 mg) were stirred with dimethylformamide (2.5 mL) and three drops of concentrated hydrochloric acid at room temperature for 24.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (62.6 mg, yield 75%).
$^1$H-NMR (ppm in DMSO-$d_6$)
δ 10.87 (br.s, 1H), 10.34 (br.s, 1H), 8.85 (s, 1H), 7.93 (ABq, J=8.6 Hz, 2H), 7.85 (ABq, J=8.6 Hz, 2H), 7.46 (ABq, J=8.3 Hz, 2H), 7.30 (ABq, J=8.3 Hz, 2H), 3.83 and 3.81 (sx2, 3H), 2.54-2.51 (multi, 2H), 2.46 and 2.39 (sx2, 3H), 1.89 (sept, J=6.8 Hz, 1H), 0.92-0.89 (multi, 6H).
LC-MS (ESI) 465 (M$^+$).

Synthetic Example 27

Synthesis of 4-{[(2-{1-[5-(3-bromo-4-fluorophenyl)-4-hydroxy-1-methyl-1H-pyrazol-3-yl]ethylidene}hydrazino)carbonothioyl]amino}benzoic acid 1-[5-(3-Bromo-4-fluorophenyl)-4-hydroxy-1-methyl-1H-pyrazol-3-yl]ethanone (0.139 mmol, 43.6 mg) and 4-hydrazinocarbonothioylaminobenzoic acid (0.139 mmol, 29.4 mg) were stirred with dimethylformamide (2.5 mL) and three drops of concentrated hydrochloric acid at room temperature for 24.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a yellow solid (51.8 mg, yield 74%).

$^1$H-NMR (ppm in DMSO-$d_6$)

δ 10.35 and 10.32 (br.sx2, 1H), 9.08 (s, 1H), 7.98-7.79 (multi, 5H), 7.65-7.51 (multi, 2H), 3.83 (s, 3H), 2.46 and 2.39 (sx2, 3H).

LC-MS (ESI) 505, 507 (M$^+$).

Synthetic Example 28

Synthesis of 4-{[(2-{1-[5-(4-ethylphenyl)-4-hydroxy-1-methyl-1H-pyrazol-3-yl]ethylidene}hydrazino)carbonothioyl]amino}benzoic acid 1-[5-(4-Ethylphenyl)-1-methyl-4-hydroxy-1H-pyrazol-3-yl]ethanone (0.159 mmol, 38.8 mg) and 4-hydrazinocarbonothioylaminobenzoic acid (0.159 mmol, 33.6 mg) were stirred with dimethylformamide (2.3 mL) and three drops of concentrated hydrochloric acid at room temperature for 23.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (50.6 mg, yield 730).

$^1$H-NMR (ppm in DMSO-$d_6$)

δ 10.87 (br.s, 1H), 10.33 (br.s, 1H), 8.85 (s, 1H), 7.93 (ABq, J=8.7 Hz, 2H), 7.85 (ABq, J=8.7 Hz, 2H), 7.46 (ABq, J=8.1 Hz, 2H), 7.36 (ABq, J=8.1 Hz, 2H), 3.82 and 3.80 (sx2, 3H), 2.67 (q, J=7.5 Hz, 2H), 2.46 and 2.39 (sx2, 3H), 1.26-1.20 (multi, 3H).

LC-MS (ESI) 437 (M$^+$).

Synthetic Example 29

Synthesis of 4-{[(2-{1-[4-hydroxy-1-methyl-5-(4-n-propylphenyl)-1H-pyrazol-3-yl]ethylidene}hydrazino)carbonothioyl]amino}benzoic acid 1-[4-Hydroxy-1-methyl-5-(4-n-propylphenyl)-1H-pyrazol-3-yl]ethanone (0.157 mmol, 40.5 mg) and 4-hydrazinocarbonothioylaminobenzoic acid (0.157 mmol, 33.1 mg) were stirred with dimethylformamide (2.3 mL) and three drops of concentrated hydrochloric acid at room temperature for 23.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (56.2 mg, yield 79%).

$^1$H-NMR (ppm in DMSO-$d_6$)

δ 10.32 (br.s, 1H), 8.85 (s, 1H), 7.93 (ABq, J=8.7 Hz, 2H), 7.85 (ABq, J=8.7 Hz, 2H), 7.46 (ABq, J=8.1 Hz, 2H), 7.34 (ABq, J=8.1 Hz, 2H), 3.82 and 3.80 (sx2, 3H), 2.62 (t, J=7.7 Hz, 2H), 2.46 and 2.39 (sx2, 3H), 1.70-1.57 (multi, 2H), 0.97-0.91 (multi, 3H).

LC-MS (ESI) 451 (M$^+$).

Synthetic Example 30

Synthesis of 4-{[(2-{1-[5-(4-n-hexylphenyl)-4-hydroxy-1-methyl-1H-pyrazol-3-yl]ethylidene}hydrazino)-carbonothioyl]amino}benzoic acid 1-[5-(4-n-Hexylphenyl)-1-methyl-4-hydroxy-1H-pyrazol-3-yl]ethanone (0.117 mmol, 35.1 mg) and 4-hydrazinocarbonothioylaminobenzoic acid (0.117 mmol, 24.7 mg) were stirred with dimethylformamide (2.3 mL) and three drops of concentrated hydrochloric acid at room temperature for 23.5 hours. After addition of water, the precipitated yellow solid was recovered by filtration, washed with water and dried by means of a vacuum pump. The resulting solid was stirred with chloroform/n-hexane for a while, then recovered by filtration and dried by means of a vacuum pump to give the desired product as a pale yellow solid (46.3 mg, yield 80%).

$^1$H-NMR (ppm in DMSO-$d_6$)

δ 10.87 (br.s, 1H), 10.33 (br.s, 1H), 8.84 (s, 1H), 7.93 (ABq, J=8.6 Hz, 2H), 7.84 (ABq, J=8.6 Hz, 2H), 7.45 (ABq, J=8.1 Hz, 2H), 7.33 (ABq, J=8.1 Hz, 2H), 3.82 and 3.80 (sx2, 3H), 2.63 (t, J=7.7 Hz, 2H), 2.46 and 2.39 (sx2, 3H), 1.61 (multi, 2H), 1.30 (multi, 6H), 0.86 (multi, 3H).

LC-MS (ESI) 493 (M$^+$).

Synthetic Example 31

Synthesis of 4-[(2-{1-[5-(4-t-butylphenyl)-1-ethyl-4-hydroxy-1H-pyrazol-3-yl]ethylidene}hydrazino)-carbonyl]benzoic acid 1) Synthesis of methyl 4-[(2-{1-[5-(4-t-butylphenyl)-1-ethyl-4-hydroxy-1H-pyrazol-3-yl]ethylidene}hydrazino)carbonyl]benzoate 1-[5-(4-t-Butylphenyl)-1-ethyl-4-hydroxy-1H-pyrazol-3-yl]ethanone (0.313 mmol, 89.5 mg), 4-hydrazinocarbonylmethyl benzoate (0.313 mmol, 60.7 mg) and p-tosylic acid monohydrate (30 mol %, 16.1 mg) were dissolved in isopropyl alcohol (16 mL) and stirred at 100° C. for 19 hours. The reactor was cooled to room temperature, and the solvent was evaporated. The resulting crude product was purified by silica gel column chromatography (chloroform/methanol=10/1) and then by silica gel column chromatography (n-hexane/ethyl acetate=1/2) to give the desired product as a yellow solid (16.8 mg, yield 12%).

$^1$H-NMR (ppm in DMSO-$d_6$)

δ 11.39 (br.s, 1H), 9.60 (br.s, 1H), 8.10 (ABq, J=8.3 Hz, 2H), 8.04 (ABq, J=8.3 Hz, 2H), 7.55 (ABq, J=8.1 Hz, 2H), 7.44 (ABq, J=8.1 Hz, 2H), 4.12 (q, J=7.2 Hz, 2H), 3.90 (s, 3H), 2.46 (s, 3H), 1.34 (s, 9H), 1.29 (t, J=7.2 Hz, 3H).

LC-MS (ESI) 462 (M$^+$).

2) Synthesis of 4-[(2-{1-[5-(4-t-butylphenyl)-1-ethyl-4-hydroxy-1H-pyrazol-3-yl]ethylidene}hydrazino)carbonyl]benzoic acid To methyl 4-[(2-{1-[5-(4-t-butylphenyl)-1-ethyl-4-hydroxy-1H-pyrazol-3-yl]ethylidene}hydrazino)carbonyl]benzoate (0.032 mmol, 15.0 mg), methanol (1.5 mL) was added, and 1 M aqueous sodium hydroxide (0.162 mmol, 0.162 mL) was added at room temperature. After 30 minutes of stirring at room temperature and 1.25 hours of stirring at 60° C., the reactor was cooled to 0° C., and 1 M hydrochloric acid (0.162 mmol, 0.162 mL) and water were added. The precipitated solid was recovered by filtration, washed with water, dried by means of a vacuum pump and purified by silica gel thin layer chromatography (chloroform/methanol=10/1) to give the desired product as a yellow solid (6.4 mg, yield 44%).

$^1$H-NMR (ppm in DMSO-$d_6$)

δ 11.33 (br.s, 1H), 9.64 (br.s, 1H), 8.06-7.94 (multi, 4H), 7.58-7.43 (multi, 4H), 4.12 (q, J=7.5 Hz, 2H), 2.46 and 2.44 (sx2, 3H), 1.34 (s, 9H), 1.27 (t, J=7.5 Hz, 3H).

LC-MS (ESI) 448 (M$^+$).

Synthetic Example 32

Synthesis of 4-[(2-{1-[1-benzyl-5-(4-t-butylphenyl)-4-hydroxy-1H-pyrazol-3-yl]ethylidene}hydrazino)carbonyl]benzoic acid 1) Synthesis of methyl 4-[(2-{1-[1-benzyl-5-(4-t-butylphenyl)-4-hydroxy-1H-pyrazol-3-yl]ethylidene}hydrazino)carbonyl]benzoate 1-[1-Benzyl-5-(4-t-butylphenyl)-4-hydroxy-1H-pyrazol-3-yl]ethanone (0.610 mmol, 212.6 mg), 4-hydrazinocarbonylmethyl benzoate (0.610 mmol, 118.5 mg) and p-tosylic acid monohydrate (30 mol %, 31.5 mg) were dissolved in isopropyl alcohol (20 mL) and stirred at 100° C. for 18 hours. The reactor was cooled to room temperature, and the solvent was evaporated. The resulting crude product was purified by silica gel column chromatography (chloroform/methanol=10/1) and then by silica gel column chromatography (n-hexane/ethyl acetate=1/2) to give the desired product as a yellow solid (56.6 mg, yield 18%).

$^1$H-NMR (ppm in DMSO-$d_6$)

δ 11.44 (br.s, 1H), 9.72 (br.s, 1H), 8.11 (ABq, J=8.1 Hz, 2H), 8.05 (ABq, J=8.1 Hz, 2H), 7.49 (ABq, J=8.3 Hz, 2H), 7.37 (ABq, J=8.3 Hz, 2H), 7.32-7.22 (multi, 3H), 6.99-6.97 (multi, 2H), 5.38 (s, 2H), 3.91 (s, 3H), 2.46 (s, 3H), 1.30 (s, 9H).

LC-MS (ESI) 524 (M$^+$).

2) Synthesis of 4-[(2-{1-[1-benzyl-5-(4-t-butylphenyl)-4-hydroxy-1H-pyrazol-3-yl]ethylidene}hydrazino)carbonyl]benzoic acid To methyl 4-[(2-{1-[1-benzyl-5-(4-t-butylphenyl)-4-hydroxy-1H-pyrazol-3-yl]ethylidene}hydrazino)carbonyl]benzoate (0.045 mmol, 23.5 mg), methanol was added, and 1 M aqueous sodium hydroxide (0.224 mmol, 0.224 mL) was added at room temperature. After 30 minutes of stirring at room temperature and 1.5 hours of stirring at 60° C., the reactor was cooled to 0° C., and 1 M hydrochloric acid (0.224 mmol, 0.224 mL) and water were added. The precipitated solid was recovered by filtration, washed with water, dried by means of a vacuum pump and purified by silica gel thin layer chromatography (chloroform/methanol=10/1) to give the desired product as a yellow solid (15.8 mg, yield 69%).

$^1$H-NMR (ppm in DMSO-$d_6$)

δ 11.41 (br.s, 1H), 9.74 (br.s, 1H), 8.06-6.97 (multi, 13H), 5.38 (s, 2H), 2.46 (s, 3H), 1.30 (s, 9H).

LC-MS (ESI) 510 (M$^+$).

Synthetic Example 33

Synthesis of methyl 5-[(2-{1-[5-(4-t-butylphenyl)-4-hydroxy-1-methyl-1H-pyrazol-3-yl]ethylidene}hydrazino)carbonyl]-2-thiophenecarboxylate 1-[5-(4-t-Butylphenyl)-4-hydroxy-1-methyl-1H-pyrazol-3-yl]ethanone (38.0 mg, 0.14 mmol) and methyl 5-hydrazinocarbonyl-2-thiophenecarboxylate (27.9 mg, 0.14 mmol) were dissolved in dimethylformamide (2.0 mL) and stirred at 110° C. for 12 hours. After cooling, the solvent was evaporated, and ethyl acetate was added to the resulting crude product. The precipitated solid was recovered by filtration to give 20.0 mg of the desired product as a pale yellow solid (yield 31%).

$^1$H-NMR (ppm in CDCl$_3$)

δ 7.78 (d, J=3.6 Hz, 1H), 7.42-7.52 (multi, 5H), 3.92 (s, 3H), 3.88 (s, 3H), 2.45 (s, 3H), 1.36 (s, 9H).

LC-MS (ESI) 454 (M$^+$).

Synthetic Example 34

Synthesis of 5-[(2-{1-[5-(4-t-butylphenyl)-4-hydroxy-1-methyl-1H-pyrazol-3-yl]ethylidene}hydrazino)carbonyl]-2-thiophenecarboxylic acid Methyl 5-[(2-{1-[5-(4-t-butylphenyl)-4-hydroxy-1-methyl-1H-pyrazol-3-yl]ethylidene}hydrazino)carbonyl]-2-thiophenecarboxylate (16.0 mg, 0.035 mmol) in methanol (1.5 mL) was stirred with 1 M aqueous sodium hydroxide (176 μL, 0.176 mmol) at room temperature for 17 hours. After the stirring, 1 M hydrochloric acid (176 μL, 0.176 mmol) was added, and the precipitated solid was recovered by filtration to give 6.2 mg of the desired product as yellow crystals (yield 40%).

$^1$H-NMR (ppm in DMSO-$d_6$)

δ 11.36 (br.s, 1H), 9.50 (br.s, 1H), 8.02 (d, J=4.5 Hz, 1H), 7.79 (d, J=4.5 Hz, 1H), 7.48-7.56 (multi, 4H), 3.84 (s, 3H), 2.45 (s, 3H), 1.33 (s, 9H).

LC-MS (ESI) 440 (M$^+$).

Synthetic Example 35

Synthesis of methyl 4-[(2-{1-[5-(4-t-butylphenyl)-4-hydroxy-3-thienyl]ethylidene}hydrazino)carbonyl]benzoate 2-(4-t-Butylphenyl)-3-hydroxy-4-methylcarbonylthiophene (100 mg, 0.36 mmol) synthesized in Reference Synthetic Example 33 and 4-hydrazinocarbonylmethyl benzoate (70 mg, 0.36 mmol) were stirred in dimethylformamide (3.6 mL) at 120° C. overnight. The reaction solution was partitioned between ethyl acetate-saturated aqueous ammonium chloride, and the organic layer was washed with saturated aqueous sodium chloride. The precipitated solid was recovered from the solution by filtration to give the desired product as a pale yellow solid (58 mg, yield 36%).

$^1$H-NMR (ppm in DMSO-$d_6$)

δ 1.30 (s, 9H), 3.91 (s, 3H), 7.43 (d, J=8.2 Hz, 2H), 7.71 (d, J=8.2 Hz, 2H), 7.99-8.13 (m, 5H), 11.48 (s, 1H), 12.23 (s, 1H).

$^1$H-NMR (ppm in MeOH-$d_4$)

δ 1.34 (s, 9H), 2.48 (s, 3H), 3.95 (s, 3H), 7.39-8.16 m, 9H).

LC/MS (ES$^+$) 451.

Synthetic Example 36

Synthesis of methyl 4-[(2-{1-[5-(3,4-dichlorophenyl)-4-hydroxy-3-thienyl]ethylidene}hydrazino)carbonyl]benzoate 2-(3,4-Dichlorophenyl)-3-hydroxy-4-methylcarbonylthiophene (100 mg, 0.35 mmol) synthesized in Reference Synthetic Example 34 and 4-hydrazinocarbonylmethyl benzoate (68 mg, 0.35 mmol) were stirred in dimethylformamide (3.6 mL) at 120° C. under heating overnight. The resulting reaction solution was concentrated, and ethyl acetate/n-hexane was added. The precipitated solid was recovered by filtration to give the desired product as a pale yellow solid (141 mg, yield 87%).
$^1$H-NMR (ppm in DMSO-$d_6$)
δ 3.91 (s, 3H), 7.64-7.73 (m, 2H), 8.05-8.13 (m, 6H), 11.55 (bs, 1H).
LC/MS (ES$^-$) 461, 462, 464.

Synthetic Example 37

Synthesis of methyl 4-[(2-{1-[5-(4-trifluoromethylphenyl)-4-hydroxy-3-thienyl]ethylidene}hydrazino)carbonyl]benzoate From 2-(4-trifluoromethylphenyl)-3-hydroxy-4-methylcarbonylthiophene (100 mg, 0.35 mmol) synthesized in Reference Synthetic Example 35, the desired product was obtained in the same manner as in Synthetic Example 36 as a pale yellow solid (132 mg, yield 82%).
$^1$H-NMR (ppm in MeOH-$d_4$)
δ 2.49 (s, 3H), 3.95 (s, 3H), 7.64-7.67 (m, 2H), 7.88 (s, 1H), 8.03-8.04 (m, 4H), 8.15-8.18 (m, 2H).
LC/MS (ES$^+$) 463.

Synthetic Example 38

Synthesis of methyl 2-nitro-4-[(2-{1-[5-(4-t-butylphenyl)-4-hydroxy-3-thienyl]ethylidene}-hydrazino)carbonyl]benzoate 2-(4-t-Butylphenyl)-3-hydroxy-4-methylcarbonylthiophene (80 mg, 0.29 mmol) and methyl 2-nitro-4-hyrazinocarbonylbenzoate (69 mg, 0.29 mmol) were stirred in dimethylformamide (2.9 mL) at 120° C. under heating overnight. The resulting reaction solution was concentrated, and ethyl acetate/n-hexane was added. The precipitated solid was recovered by filtration to give the desired product as a brown solid (92 mg, yield 64%).
$^1$H-NMR (ppm in DMSO-$d_6$)
δ 1.30 (s, 9H), 3.90 (s, 3H), 7.43 (d, J=8.4 Hz, 2H), 7.71 (d, J=8.4 Hz, 2H), 8.02-8.07 (m, 2H), 8.36 (d, J=7.4 Hz, 1H), 8.59 (s, 1H).
LC/MS (ES$^+$) 496.

Synthetic Example 39

Synthesis of methyl 5-[(2-{1-[5-(4-t-butylphenyl)-4-hydroxy-3-thienyl]ethylidene}hydrazino)carbonyl]-2-thiophenecarboxylate 2-(4-t-Butylphenyl)-3-hydroxy-4-methylcarbonylthiophene (80 mg, 0.29 mmol) and methyl 5-hydrazinocarbonyl-2-thiophenecarboxylate (58 mg, 0.29 mmol) were stirred in dimethylformamide (2.9 mL) at 120° C. under heating overnight. The resulting reaction solution was concentrated, and chloroform/n-hexane was added. The precipitated solid was recovered by filtration to give the desired product as a yellow solid (79 mg, yield 60%).
$^1$H-NMR (ppm in MeOH-$d_4$)
δ 1.34 (s, 9H), 2.48 (s, 3H), 3.91 (s, 3H), 7.38-7.81 (m, 7H).
LC/MS (ES$^4$) 457.

Synthetic Example 40

Synthesis of methyl 4-[(2-{[5-(4-t-butylphenyl)-4-hydroxy-3-thienyl]methylene}hydrazino)carbonyl]benzoate 2-(4-t-Butylphenyl)-3-hydroxy-4-formylthiophene (100 mg, 0.38 mmol) synthesized in Reference Synthetic Example 25 and 4-hydrazinocarbonylmethyl benzoate (74 mg, 0.38 mmol) were stirred in dimethylformamide (3.8 mL) at room temperature overnight. The reaction solution was partitioned between ethyl acetate-water, and the organic layer was washed with saturated aqueous sodium chloride. The resulting organic layer was concentrated and purified by silica gel column chromatography (chloroform) to give the desired product as a light brown solid (74 mg, yield 46%).
$^1$H-NMR (ppm in DMSO-$d_6$)
δ 1.30 (s, 9H), 3.91 (s, 3H), 7.44 (d, J=8.4 Hz, 2H), 7.69 (d, J=8.4 Hz, 2H), 7.93-7.95 (m, 2H), 8.06-8.15 (m, 4H), 8.57 (s, 1H), 10.87 (s, 1H), 12.40 (s, 1H).
LC/MS (ES$^+$) 437.

Synthetic Example 41

Synthesis of methyl 4-[(2-{[5-(3,4-dichlorophenyl)-4-hydroxy-3-thienyl]methylene}hydrazino)carbonyl]benzoate 2-(3,4-Dichlorophenyl)-3-hydroxy-4-formylthiophene (104 mg, 0.38 mmol) synthesized in Reference Synthetic Example 26 and 4-hydrazinocarbonylmethyl benzoate (74 mg, 0.38 mmol) were stirred in dimethylformamide (3.8 mL) at room temperature overnight. Water was added to the reaction solution, and the precipitated solid was recovered by filtration to give the desired product as a pale yellow solid (175 mg, yield 100%).
$^1$H-NMR (ppm in DMSO-$d_6$)
δ 3.91 (s, 3H), 7.65-7.72 (m, 2H), 7.96-8.14 (m, 7H), 8.62 (s, 1H), 11.37 (bs, 1H).
LC/MS (ES$^+$) 451, 452, 453.

Synthetic Example 42

Synthesis of 4-[(2-{1-[5-(4-t-butylphenyl)-4-hydroxy-3-thienyl]ethylidene}hydrazino)carbonyl]benzoic acid Methyl 4-[(2-{1-[5-(4-t-butylphenyl)-4-hydroxy-3-thienyl]ethylidene}hydrazino)carbonyl]benzoate (50 mg, 0.11 mmol) synthesized in Synthetic Example 35 was dissolved in methanol (1.1 mL) and stirred with 1 M aqueous sodium hydroxide (0.55 mL, 0.55 mmol) at 45° C. for 1.5 hours. After the stirring, 1 M hydrochloric acid (0.55 mL, 0.55 mmol) was added, and the precipitated pale yellow solid was recovered by filtration. The resulting solid was purified by silica gel chromatography (chloroform:methanol=9:1). The resulting solid was stirred with chloroform at room temperature and recovered by filtration to give the desired product as a pale yellow solid (11 mg, yield 23%).

¹H-NMR (ppm in MeOH-d₄)
δ 1.34 (s, 9H), 2.48 (s, 3H), 7.39-8.08 (m, 9H).
LC/MS (ES⁻) 437.

Synthetic Example 43

Synthesis of 4-[(2-{[5-(4-t-butylphenyl)-4-hydroxy-3-thienyl]methylene}hydrazino)carbonyl]benzoic acid From methyl 4-[(2-{[5-(4-t-butylphenyl)-4-hydroxy-3-thienyl]methylene}hydrazino)carbonyl]benzoate (62 mg, 0.14 mmol) synthesized in Synthetic Example 40, the desired product was obtained in the same manner as in Synthetic Example 42 as a pale yellow solid (34 mg, yield 57%).
¹H-NMR (ppm in DMSO-d₆)
δ 1.30 (s, 9H), 7.44 (d, J=8.4 Hz, 2H), 7.69 (d, J=8.4 Hz, 2H), 7.93 (s, 1H), 8.03-8.09 (m, 4H), 8.58 (s, 1H), 10.88 (s, 1H), 12.38 (bs, 1H).
LC/MS (ES⁺) 423.

Synthetic Example 44

Synthesis of 4-[(2-{[5-(3,4-dichlorophenyl)-4-hydroxy-3-thienyl]methylene}hydrazino)carbonyl]benzoic acid From methyl 4-[(2-{[5-(3,4-dichlorophenyl)-4-hydroxy-3-thienyl]methylene}hydrazino)carbonyl]benzoate (120 mg, 0.27 mmol) synthesized in Synthetic Example 41, the desired product was obtained in the same manner as in Synthetic Example 42 as a pale yellow solid (44 mg, yield 37%).
¹H-NMR (ppm in DMSO-d₆)
δ 7.66-7.72 (m, 2H), 8.03-8.21 (m, 6H), 8.58 (s, 1H), 11.37 (bs, 1H).

Synthetic Example 45

Synthesis of 4-[(2-{1-[5-(3,4-dichlorophenyl)-4-hydroxy-3-thienyl]ethylidene}hydrazino)carbonyl]benzoic acid From methyl 4-[(2-{1-[5-(3,4-dichlorophenyl)-4-hydroxy-3-thienyl]ethylidene}hydrazino)carbonyl]benzoate (100 mg, 0.22 mmol) synthesized in Synthetic Example 36, the desired product was obtained in the same manner as in Synthetic Example 42 as a pale yellow solid (9 mg, yield 9%).
¹H-NMR (ppm in DMSO-d₆)
δ 7.64-7.73 (m, 2H), 8.01-8.12 (m, 6H).
¹H-NMR (ppm in MeOH-d₄)
δ 2.47 (s, 3H), 7.47-8.16 (m, 8H).
LC/MS (ES⁺) 449, 450, 451.

Synthetic Example 46

Synthesis of 4-[(2-{(1-[5-(4-trifluoromethylphenyl)-4-hydroxy-3-thienyl]ethylidene}hydrazino)carbonyl]benzoic acid From methyl 4-[(2-{1-[5-(4-trifluoromethylphenyl)-4-hydroxy-3-thienyl]ethylidene}hydrazino)carbonyl]benzoate (100 mg, 0.22 mmol) synthesized in Synthetic Example 37, the desired product was obtained in the same manner as in Synthetic Example 42 as a colorless solid (34 mg, yield 34%).
¹H-NMR (ppm in DMSO-d₆)
δ 7.75-7.78 (m, 2H), 8.00-8.15 (m, 7H), 11.51 (bs, 1H).
LC/MS (ES⁻) 447.

Synthetic Example 47

Synthesis of 2-nitro-4-[(2-{1-[5-(4-t-butylphenyl)-4-hydroxy-3-thienyl]ethylidene}hydrazino)carbonyl]benzoic acid From methyl 2-nitro-4-[(2-{(1-[5-(4-t-butylphenyl)-4-hydroxy-3-thienyl]ethylidene}hydrazino)carbonyl]benzoate (60 mg, 0.12 mmol) synthesized in Synthetic Example 38, the desired product was obtained in the same manner as in Synthetic Example 42 as a yellow solid (10 mg, yield 17%).
¹H-NMR (ppm in DMSO-d₆)
δ 1.30 (s, 9H), 7.43 (d, J=8.4 Hz, 2H), 7.71 (d, J=8.4 Hz, 2H), 7.95-8.03 (m, 2H), 8.30 (d, J=8.0 Hz, 1H), 8.51 (s, 1H).
¹H-NMR (ppm in MeOH-d₄)
δ 1.34 (s, 9H), 2.49 (s, 3H), 7.39-8.46 (m, 8H).
LC/MS (ES⁺) 482.

Synthetic Example 48

Synthesis of 5-[(2-{1-[5-(4-t-butylphenyl)-4-hydroxy-3-thienyl]ethylidene}hydrazino) carbonyl]-2-thiophenecarboxylic acid From methyl 5-[(2-{1-[5-(4-t-butylphenyl)-4-hydroxy-3-thienyl]ethylidene}hydrazino)carbonyl]-2-thiophenecarboxylate (72 mg, 0.16 mmol) synthesized in Synthetic Example 39, the desired product was obtained in the same manner as in Synthetic Example 42 as a yellow solid (12 mg, yield 17%).
¹H-NMR (ppm in DMSO-d₆)
δ 1.30 (s, 9H), 7.43 (d, J=8.5 Hz, 2H), 7.70 (d, J=8.5 Hz, 2H), 7.81 (d, J=4.1 Hz, 1H), 8.00 (s, 1H), 8.04 (d, J=4.1 Hz, 1H).
LC/MS (ES⁻) 442.

Synthetic Example 49

Synthesis of 4-{[(2-{[5-(4-t-butylphenyl)-4-hydroxy-3-thienyl]methylene}hydrazino)carbonothioyl]amino}benzoic acid 2-(4-t-Butylphenyl)-3-hydroxy-4-formylthiophene (50 mg, 0.19 mmol) synthesized in Reference Synthetic Example 25 and 4-hydrazinocarbonothioylaminobenzoic acid (40 mg, 0.19 mmol) were stirred with dimethylformamide (1.9 mL) and concentrated hydrochloric acid (0.1 mL) at room temperature for 12 hours. The reaction solution was partitioned between ethyl acetate and water, and the organic layer was washed with saturated aqueous sodium chloride and dried over anhydrous sodium sulfate. The resulting organic layer was concentrated and purified by silica gel column chromatography (chloroform). Methanol/chloroform was added to the resulting crude product, and the precipitated yellow solid was recovered by filtration to give the desired product as a pale yellow solid (20 mg, yield 23%).
¹H-NMR (ppm in DMSO-d₆)
δ 1.30 (s, 9H), 7.43 (d, J=8.5 Hz, 2H), 7.67 (d, J=8.5 Hz, 2H), 7.79 (d, J=8.5 Hz, 2H), 7.93-7.99 (m, 3H), 8.24 (s, 1H), 10.32 (s, 1H), 11.93 (s, 1H).
LC/MS (ES⁺) 454.

Synthetic Example 50

Synthesis of 4-{[(2-{1-[5-(4-t-butylphenyl)-4-hydroxy-3-thienyl]ethylidene}hydrazino)carbonothioyl]amino}benzoic acid 2-(4-t-Butylphenyl)-3-hydroxy-4-methylcarbonylthiophene (31 mg, 0.11 mmol) synthesized in Reference Synthetic Example 33 and 4-hydrazinocarbonothioylaminobenzoic acid (23 mg, 0.11 mmol) were stirred with dimethylformamide (1.1 mL) and concentrated hydrochloric acid (0.05 mL) at room temperature for 30 hours. The reaction solution was partitioned between ethyl acetate and water, and the organic layer was washed with saturated aqueous sodium chloride and dried over anhydrous sodium sulfate. The resulting organic layer was concentrated and purified by silica gel column chromatography (chloroform) to give the desired product as a light brown solid (27 mg, yield 52%).

$^1$H-NMR (ppm in DMSO-$d_6$)

δ 1.30 (s, 9H), 2.39 (s, 3H), 7.43 (d, J=8.5 Hz, 2H), 7.69 (d, J=8.5 Hz, 2H), 7.86-7.95 (m, 5H), 10.40 (s, 1H), 11.08 (s, 1H).

LC/MS (ES$^+$) 468.

Synthetic Example 51

Synthesis of 4-{[(2-{[5-(3,4-dichlorophenyl)-4-hydroxy-3-thienyl]methylene}hydrazino)carbonothioyl]amino}benzoic acid 2-(3,4-Dichlorophenyl)-3-hydroxy-4-formylthiophene (52 mg, 0.19 mmol) synthesized in Reference Synthetic Example 26 and 4-hydrazinocarbonothioylaminobenzoic acid (40 mg, 0.19 mmol) were stirred with dimethylformamide (1.9 mL) and concentrated hydrochloric acid (0.1 mL) at room temperature for 14 hours. Water was added to the reaction solution, and the precipitated solid was recovered by filtration and dried. The crude product was stirred with chloroform at room temperature and recovered by filtration to give the desired product as a pale yellow solid (58 mg, yield 65%).

$^1$H-NMR (ppm in DMSO-$d_6$)

δ 7.67-8.10 (m, 8H), 8.25 (s, 1H), 10.34 (s, 1H), 11.95 (s, 1H).

LC/MS (ES$^+$) 465, 467, 469.

Synthetic Example 52

Synthesis of 4-{[(2-{1-[5-(3,4-dichlorophenyl)-4-hydroxy-3-thienyl]ethyliden}hydrazino)carbonothioyl]amino}benzoic acid From 2-(3,4-dichlorophenyl)-3-hydroxy-4-methylcarbonylthiophene (50 mg, 0.17 mmol) synthesized in Reference Synthetic Example 34, the desired product was obtained in the same manner as in Synthetic Example 51 as a pale yellow solid (23 mg, yield 28%).

LC/MS (ES$^+$) 480, 481, 482, 484.

Synthetic Example 53

Synthesis of 4-{[(2-{1-[5-(4-trifluoromethylphenyl)-4-hydroxy-3-thienyl]ethyliden}hydrazino)carbonothioyl]-amino}benzoic acid From 2-(4-trifluoromethylphenyl)-3-hydroxy-4-methylcarbonylthiophene (50 mg, 0.17 mmol) synthesized in Reference Synthetic Example 35, the desired product was obtained in the same manner as in Synthetic Example 51 as a pale yellow solid (48 mg, 59%).

$^1$H-NMR (ppm in DMSO-$d_6$)

δ 2.41 (s, 3H), 7.74-8.11 (m, 9H), 10.49 (s, 1H), 11.18 (s, 1H).

LC/MS (ES$^+$) 480.

Synthetic Example 54

Synthesis of 4-({2-[[5-(4-t-butylphenyl)-4-hydroxy-1-methyl-1H-pyrazol-3-yl](phenyl)methylene]hydrazino}carbonyl)benzoic acid 1) Synthesis of [5-(4-t-butylphenyl)-4-hydroxy-1-methyl-1H-pyrazol-3-yl](phenyl)methanone Oxo(phenyl)acetaldehyde methylhydrazone (5.46 mmol, 886 mg) synthesized in Reference Synthetic Example 36 and (4-t-butylphenyl)(oxo)acetaldehyde (5 mmol, 951 mg) were dissolved in acetic acid (26 mL) and stirred at 100° C. for about 2 hours. Then, the solvent was evaporated, and the residue was recrystallized from chloroform/n-hexane to give the desired product as a yellow solid (993 mg, yield 59%).

$^1$H-NMR (ppm in CDCl$_3$)

δ 9.04 (s, 1H), 8.51-8.48 (multi, 2H), 7.61-7.59 (multi, 1H), 7.55-7.44 (multi, 6H), 3.98 (s, 3H), 1.37 (s, 9H).

LC-MS (ESI) 334 (M$^+$).

2) Synthesis of methyl 4-({2-[[5-(4-t-butylphenyl)-4-hydroxy-1-methyl-1H-pyrazol-3-yl](phenyl)methylene]hydrazino}carbonyl)benzoate

[5-(4-t-Butylphenyl)-4-hydroxy-1-methyl-1H-pyrazol-3-yl](phenyl)methanone (0.299 mmol, 99.9 mg), 4-hydrazinocarbonylmethyl benzoate (0.299 mmol, 58.0 mg) and p-tosylic acid monohydrate (30 mol %, 15.4 mg) were dissolved in isopropyl alcohol (12 mL) and stirred at 100° C. for about 24 hours. Then, the reactor was cooled to room temperature, and the precipitated solid was recovered by filtration and dried by means of a vacuum pump to give the desired product as a pale yellow solid (119 mg, yield 78%).

$^1$H-NMR (ppm in DMSO-$d_6$)

δ 11.29 (s, 1H), 9.85 (s, 1H), 8.03 (ABq, J=8.3 Hz, 2H), 7.84 (ABq, J=8.3 Hz, 2H), 7.62-7.55 (multi, 9H), 3.90 and 3.87 (sx2, 3H), 3.77 and 3.73 (sx2, 3H), 1.34 and 1.32 (sx2, 9H).

LC-MS (ESI) 510 (M$^+$).

3) Synthesis of 4-({2-[[5-(4-t-butylphenyl)-4-hydroxy-1-methyl-1H-pyrazol-3-yl](phenyl)methylene]hydrazino}carbonyl)benzoic acid To methyl 4-({2-[[5-(4-t-butylphenyl)-4-hydroxy-1-methyl-1H-pyrazol-3-yl](phenyl)methylene]hydrazino}carbonyl)benzoate (0.196 mmol, 100 mg), methanol (4 mL) was added, and 1 M aqueous sodium hydroxide (0.981 mmol, 0.981 mL) was added at room temperature. After 15 minutes of stirring at room temperature and 1 hour of stirring at 60° C., the reactor was cooled to room temperature, and 1 M hydrochloric acid (0.981 mmol, 0.981 mL) and water were added. The precipitated solid was recovered by filtration, washed with water and dried by means of a vacuum pump to give the desired product as a yellow solid (93 mg, yield 95%).

¹H-NMR (ppm in DMSO-d₆)
δ 11.25 (s, 1H), 9.86 (s, 1H), 8.00 (ABq, J=8.3 Hz, 2H), 7.81 (ABq, J=8.3 Hz, 2H), 7.62-7.55 (multi, 9H), 3.77 and 3.73 (sx2, 3H), 1.3.4 and 1.32 (sx2, 9H).
LC-MS (ESI) 496 (M⁺).

Synthetic Example 55

Synthesis of 4-[(2-{1-[5-(4-t-butylphenyl)-4-hydroxy-1-methyl-1H-pyrazol-3-yl]ethylidene]hydrazino}carbonyl)-N-methylbenzenesulfonamide 1-[5-(4-t-Butylphenyl)-4-hydroxy-1-methyl-1H-pyrazol-3-yl]ethanone (0.228 mmol, 62 mg), 4-(hydrazinocarbonyl)-N-methylbenzenesulfonamide (0.228 mmol, 52 mg) and p-tosylic acid monohydrate (30 mol %, 11.8 mg) were dissolved in isopropyl alcohol (6 mL) and stirred at 100° C. for 19 hours. Then, the solvent was evaporated, and the residue was purified by silica gel thin layer chromatography (chloroform/methanol=10/1) to give the desired product as a yellow solid (30.3 mg, yield 28%).
¹H-NMR (ppm in DMSO-d₆)
δ 11.40 (s, 1H), 9.65 (s, 1H), 8.32 (s, 1H), 8.10 (ABq, J=8.4 Hz, 2H), 7.91 (ABq, J=8.4 Hz, 2H), 7.57-7.49 (multi, 4H), 3.89 and 3.85 (sx2, 3H), 2.46 (s, 3H), 2.45 (s, 3H), 1.34 (s, 9H).
LC-MS (ESI) 483 (M⁺).

Synthetic Example 56

Synthesis of 4-({2-[[5-(4-t-butylphenyl)-4-hydroxy-1-methyl-1H-pyrazol-3-yl](phenyl)methylene]hydrazino}carbonyl)-N-methylbenzenesulfonamide

[5-(4-t-Butylphenyl)-4-hydroxy-1-methyl-1H-pyrazol-3-yl](phenyl)methanone (0.254 mmol, 85 mg), 4-(hydrazinocarbonyl)-N-methylbenzenesulfonamide (0.254 mmol, 58 mg) and p-tosylic acid monohydrate (30 mol %, 13 mg) were dissolved in isopropyl alcohol (8.5 mL) and stirred at 100° C. for 19 hours. Then, the solvent was evaporated, and the residue was purified by silica gel thin layer chromatography (chloroform/methanol=10/1) to give the desired product as a yellow solid (30.3 mg, yield 22%).
¹H-NMR (ppm in DMSO-d₆)
δ 11.69 and 11.32 (sx2, 1H), 9.84 and 8.64 (sx2, 1H), 8.64 (s, 1H), 8.09-7.82 (multi, 4H), 7.69-7.44 (multi, 9H), 3.91-3.73 (multi, 3H), 2.47 and 2.38 (multi, 3H), 1.34-1.33 (sx2, 9H).
LC-MS (ESI) 545 (M⁺).

Synthetic Example 57

Synthesis of N'-{1-[5-(4-t-butylphenyl)-4-hydroxy-1-methyl-1H-pyrazol-3-yl]ethylidene}-4-(1H-tetrazol-5-yl)benzhydrazide 1-[5-(4-t-Butylphenyl)-4-hydroxy-1-methyl-1H-pyrazol-3-yl]ethanone (0.404 mmol, 110 mg) and 4-(1H-tetrazol-5-yl)benzhydrazide (0.404 mmol, 83 mg) synthesized in accordance with WO03/037328 were dissolved in dimethylformamide (5 mL) and stirred at 100° C. for 26 hours. The insolubles were filtered off and washed with methanol, and the filtrate was concentrated and separated by silica gel thin layer chromatography (chloroform/MeOH=4/1) to give the desired product as a yellow solid (25 mg, yield 13%).

¹H-NMR (ppm in DMSO-d₆)
δ 11.22 (s, 1H), 9.76 (s, 1H), 8.13 (ABq, J=8.3 Hz, 2H), 7.99 (ABq, J=8.3 Hz, 2H), 7.57-7.50 (multi, 4H), 3.91 and 3.85 (sx2, 3H), 2.46 and 2.42 (sx2, 3H), 1.34 (s, 9H).
LC-MS (ESI) 458 (M⁺).

Synthetic Example 58

Synthesis of 4-[(2-{1-[5-(4-tert-butylphenyl)-4-hydroxy-1-methyl-1H-pyrazol-3-yl]ethylidene}hydrazino)carbonyl]-2-nitrobenzoic acid 1) Synthesis of methyl 4-[(2-{1-[5-(4-tert-butylphenyl)-4-hydroxy-1-methyl-1H-pyrazol-3-yl]ethylidene}hydrazino)carbonyl]-2-nitrobenzoate 1-[5-(4-tert-Butylphenyl)-4-hydroxy-1-methyl-1H-pyrazol-3-yl]ethanone (1.149 mmol, 312.9 mg) synthesized in Synthetic Example 3, methyl 2-nitro-4-hydrazinocarbonylbenzoate (1.149 mmol, 274.8 mg) synthesized in Reference Synthetic Example 40 and p-tosylic acid monohydride (30 mol %, 59.4 mg) were dissolved in isopropyl alcohol (30 mL) and stirred under heating with reflux for 6 hours, and the reactor was cooled to 0° C. The reaction solution was filtered and dried by means of a vacuum pump to give the desired product as a yellow solid (470 mg, yield 83%).
¹H-NMR (ppm in DMSO-d₆)
δ 11.54 (s, 1H), 9.57 (s, 1H), 8.57 (s, 1H), 8.33 (d, J=8.0 Hz, 1H), 8.04 (d, J=8.0 Hz, 1H), 7.55 (ABq, J=8.4 Hz, 2H), 7.50 (ABq, J=8.4 Hz, 2H), 3.90 (s, 3H), 3.85 (s, 3H), 2.46 (s, 3H), 1.33 (s, 9H)
LC-MS (ESI) 493 (M⁺)

2) Synthesis of 4-[(2-{1-[5-(4-tert-butylphenyl)-4-hydroxy-1-methyl-1H-pyrazol-3-yl]ethylidene}hydrazino)carbonyl]-2-nitrobenzoic acid To methyl 4-[(2-{1-[5-(4-tert-butylphenyl)-4-hydroxy-1-methyl-1H-pyrazol-3-yl]ethylidene}hydrazino)carbonyl]-2-nitrobenzoate (0.945 mmol, 466.2 mg), methanol (33 mL) was added, and 1 M aqueous sodium hydroxide (4.7 mmol, 4.7 mL) was added. After about 26 hours of stirring at room temperature and 3 hours of stirring at 40° C., 1 M hydrochloric acid (4.7 mmol, 4.7 mL) and water were added. The precipitated solid was recovered by filtration, washed with water and dried by means of a vacuum pump. The resulting yellow solid (359.5 mg) was dissolved in THF (50 mL) and stirred at room temperature for 2 days. The insolubles were filtered off, and the filtrate was concentrated and dried by means of a vacuum pump. After addition of chloroform, the precipitated solid was recovered by filtration and dried by means of a vacuum pump to give the desired product as a pale yellow solid (260.7 mg, yield 58%).
¹H-NMR (ppm in DMSO-d₆)
δ 11.50 (s, 1H), 9.58 (s, 1H), 8.47 (s, 1H), 8.27 (d, J=8.1 Hz, 1H), 7.99 (d, J=8.1 Hz, 1H), 7.55 (ABq, J=8.4 Hz, 2H), 7.50 (ABq, J=8.4 Hz, 2H), 3.85 (s, 3H), 2.46 (s, 3H), 1.33 (s, 9H)
LC-MS (ESI) 479 (M⁺)

Synthetic Example 59

Synthesis of 4-[(2-{1-[5-(4-tert-butylphenyl)-4-hydroxy-1-methyl-1H-pyrazol-3-yl]ethylidene}hydrazino)carbonyl]-2-chlorobenzoic acid 1) Synthesis of methyl 4-[(2-{1-[5-(4-tert-butylphenyl)-4-hydroxy-1-methyl-1H-pyrazol-3-yl]ethylidene}hydrazino)carbonyl]-2-chlorobenzoate 1-[5-(4-tert-Butylphenyl)-4-hydroxy-1-methyl-1H-pyrazol-3-yl]ethanone (0.568 mmol, 154.8 mg) synthesized in Synthetic Example 3, methyl 2-chloro-4-hydrazinocarbonylbenzoate (0.568 mmol, 130.0 mg) synthesized in Reference Synthetic Example 41 and p-tosylic acid monohydride (30 mol %, 29.4 mg) were dissolved in isopropyl alcohol (15 mL) and stirred under heating with reflux for 8 hours, and the reactor was cooled to 0° C. The reaction solution was filtered and dried by means of a vacuum pump to give the desired product as a white solid (233.7 mg, yield 85%).

$^1$H-NMR (ppm in DMSO-$d_6$)

δ 11.42 (s, 1H), 9.61 (s, 1H), 8.10 (s, 1H), 7.95 (s, 2H), 7.55 (ABq, J=8.6 Hz, 2H), 7.50 (ABq, J=8.6 Hz, 2H), 3.91 (s, 3H), 3.85 (s, 3H), 2.45 (s, 3H), 1.33 (s, 9H)

LC-MS (ESI) 482 (M$^+$)

2) Synthesis of 4-[(2-{1-[5-(4-tert-butylphenyl)-4-hydroxy-1-methyl-1H-pyrazol-3-yl]ethylidene}hydrazino)carbonyl]-2-chlorobenzoic acid To methyl 4-[(2-{1-[5-(4-tert-butylphenyl)-4-hydroxy-1-methyl-1H-pyrazol-3-yl]ethylidene}hydrazino)carbonyl]-2-chlorobenzoate (0.465 mmol, 224.8 mg), methanol (20 mL) was added, and 1 M aqueous sodium hydroxide (2.3 mmol, 2.3 mL) was added. After 5 hours of stirring at 50° C., 14 hours of stirring at room temperature and 4 hours of stirring at 50° C., 1 M hydrochloric acid (2.3 mmol, 2.3 mL) and water were added. The precipitated solid was recovered by filtration, washed with water and dried by means of a vacuum pump to give the crude desired product as a yellow solid (193.3 mg). Further, 169 mg of the crude desired product was is dissolved in THF (35 mL) and stirred at room temperature for 2 days. The insolubles were filtered off, and the filtrate was concentrated and dried by means of a vacuum pump. After addition of chloroform, the precipitated solid was recovered by filtration and dried by means of a vacuum pump to give the desired product as a pale yellow solid (142.3 mg, yield 75%).

$^1$H-NMR (ppm in DMSO-$d_6$)

δ 11.40 (s, 1H), 9.63 (s, 1H), 8.06 (s, 1H), 7.93 (d, J=8.1 Hz, 1H), 7.89 (d, J=8.1 Hz, 1H), 7.55 (ABq, J=8.4 Hz, 2H), 7.50 (ABq, J=8.4 Hz, 2H), 3.85 (s, 3H), 2.45 (s, 3H), 1.33 (s, 9H)

LC-MS (ESI) 468 (M$^+$)

Synthetic Example 60

Synthesis of 2-bromo-4-[(2-{1-[5-(4-tert-butylphenyl)-4-hydroxy-1-methyl-1H-pyrazol-3-yl]ethylidene}hydrazino)carbonyl]benzoic acid 1) Synthesis of methyl 2-bromo-4-[(2-{1-[5-(4-tert-butylphenyl)-4-hydroxy-1-methyl-1H-pyrazol-3-yl]ethylidene}hydrazino)carbonyl]benzoate 1-[5-(4-tert-Butylphenyl)-4-hydroxy-1-methyl-1H-pyrazol-3-yl]ethanone (0.554 mmol, 150.9 mg) synthesized in Synthetic Example 3, methyl 2-bromo-4-hydrazinocarbonylbenzoate (0.554 mmol, 150.8 mg) synthesized in Reference Synthetic Example 42 and p-tosylic acid monohydride (30 mol %, 28.6 mg) were dissolved in isopropyl alcohol (15 mL) and stirred under heating with reflux for 8 hours, and the reactor was cooled to 0° C. The reaction solution was filtered and dried by means of a vacuum pump to give the desired product as a white solid (252.3 mg, yield 86%).

$^1$H-NMR (ppm in DMSO-$d_6$)

δ 11.42 (s, 1H), 9.61 (s, 1H), 8.25 (d, J=2.7 Hz, 1H), 8.00 (dd, J=2.7, 8.2 Hz, 1H), 7.89 (d, J=8.2 Hz, 1H), 7.55 (ABq, J=8.4 Hz, 2H), 7.50 (ABq, J=8.4 Hz, 2H), 3.90 (s, 3H), 3.85 (s, 3H), 2.45 (s, 3H), 1.33 (s, 9H)

LC-MS (ESI) 526 and 528 (M$^+$)

2) Synthesis of 2-bromo-4-[(2-{1-[5-(4-tert-butylphenyl)-4-hydroxy-1-methyl-1H-pyrazol-3-yl]ethylidene}hydrazino)carbonyl]benzoic acid To methyl 2-bromo-4-[(2-{1-[5-(4-tert-butylphenyl)-4-hydroxy-1-methyl-1H-pyrazol-3-yl]ethylidene}hydrazino)carbonyl]benzoate (0.455 mmol, 239.8 mg), methanol (20 mL) was added, and 1 M aqueous sodium hydroxide (2.3 mmol, 2.3 mL) was added. After 5 hours of stirring at 50° C., 14 hours of stirring at room temperature and 4 hours of stirring at 50° C., 1 M hydrochloric acid (2.3 mmol, 2.3 mL) and water were added. The precipitated solid was recovered by filtration, washed with water and dried by means of a vacuum pump to give the crude desired product as a yellow solid (203.8 mg). Further, 178 mg of the crude desired product was dissolved in THF (35 mL) and stirred at room temperature for 2 days. The insolubles were filtered off, and the filtrate was concentrated and dried by means of a vacuum pump. After addition of chloroform, the precipitated solid was recovered by filtration and dried by means of a vacuum pump to give the desired product as a pale yellow solid (150.9 mg, yield 74%).

$^1$H-NMR (ppm in DMSO-$d_6$)

δ 11.39 (s, 1H), 9.63 (s, 1H), 8.21 (s, 1H), 7.96 (d, J=8.0 Hz, 1H), 7.83 (d, J=8.0 Hz, 1H), 7.55 (ABq, J=8.7 Hz, 2H), 7.50 (ABq, J=8.7 Hz, 2H), 3.85 (s, 3H), 2.45 (s, 3H), 1.33 (s, 9H)

LC-MS (ESI) 512 and 514 (M$^+$)

Synthetic Example 61

Synthesis of 4-[(2-{1-[5-(4-tert-butylphenyl)-4-hydroxy-1-methyl-1H-pyrazol-3-yl]ethylidene}hydrazino)carbonyl]-2-hydroxybenzoic acid 1) Synthesis of methyl 4-[(2-{1-[5-(4-tert-butylphenyl)-4-hydroxy-1-methyl-1H-pyrazol-3-yl]ethylidene}hydrazino)carbonyl]-2-hydroxybenzoate 1-[5-(4-tert-Butylphenyl)-4-hydroxy-1-methyl-1H-pyrazol-3-yl]ethanone (0.578 mmol, 157.5 mg) synthesized in Synthetic Example 3, methyl 4-hydrazinocarbonyl-2-hydroxybenzoate (0.578 mmol, 121.6 mg) synthesized in Reference Synthetic Example 43 and p-tosylic acid monohydride (30 mol %, 30 mg) were dissolved in isopropyl alcohol (15 mL) and stirred under heating with reflux for 8 hours, and the reactor was cooled to 0° C. The reaction solution was filtered and dried by means of a vacuum pump to give the desired product as a white solid (216.6 mg, yield 81%).

$^1$H-NMR (ppm in DMSO-$d_6$)

δ 11.33 (s, 1H), 10.61 (s, 1H), 9.65 (s, 1H), 7.89 (d, J=8.1 Hz, 1H), 7.56-7.43 (multi, 6H), 3.92 (s, 3H), 3.85 (s, 3H), 2.45 and 2.44 (sx2, 3H), 1.33 (s, 9H)

LC-MS (ESI) 464 (M$^+$)

2) Synthesis of 4-[(2-{1-[5-(4-tert-butylphenyl)-4-hydroxy-1-methyl-1H-pyrazol-3-yl]ethylidene}hydrazino)carbonyl]-2-hydroxybenzoic acid To methyl 4-[(2-{1-[5-(4-tert-butylphenyl)-4-hydroxy-1-methyl-1H-pyrazol-3-yl]ethylidene}hydrazino)carbonyl]-2-hydroxybenzoate (0.438 mmol, 203.3 mg), methanol (20 mL) was added, and 1 M aqueous sodium hydroxide (2.2 mmol, 2.2 mL) was added. After 5 hours of stirring at 50° C., 14 hours of stirring at room temperature and 4 hours of stirring at 50° C., 1 M hydrochloric acid (2.2 mmol, 2.2 mL) and water were added. The precipitated solid was recovered by filtration, washed with water and dried by means of a vacuum pump to give the crude desired product as a yellow solid (175.0 mg). It was further dissolved in THF (35 mL) and stirred at room temperature for 2 days. The insolubles were filtered off, and the filtrate was concentrated and dried by means of a vacuum pump. After addition of chloroform, the precipitated solid was recovered by filtration and dried by means of a vacuum pump to give the desired product as a pale yellow solid (151.6 mg, yield 77%).

$^1$H-NMR (ppm in DMSO-$d_6$)

δ 11.30 (s, 1H), 10.61 (s, 1H), 9.66 (s, 1H), 7.90 (d, J=8.1 Hz, 1H), 7.56-7.38 (multi, 6H), 3.85 (s, 3H), 2.44 (s, 3H), 1.33 (s, 9H)

LC-MS (ESI) 450 (M$^+$)

Synthetic Example 62

Synthesis of methyl 4-[(2-{1-[5-(3-trifluoromethylphenyl)-4-hydroxy-3-thienyl]ethylidene}hydrazino)carbonyl]benzoate From 2-(3-trifluoromethylphenyl)-3-hydroxy-4-methylcarbonylthiophene (100 mg, 0.35 mmol) synthesized in Reference Synthetic Example 49, the desired product was obtained in the same manner as in Synthetic Example 36 as a light brown solid (143 mg, yield 91%).

$^1$H-NMR (ppm in DMSO-$d_6$)

δ 3.91 (s, 3H), 7.57-7.66 (m, 2H), 7.97-8.20 (m, 7H).

LC/MS (ES$^+$) 463.

Synthetic Example 63

Synthesis of 4-[(2-{1-[5-(3-trifluoromethylphenyl)-4-hydroxy-3-thienyl]ethylidene}hydrazino)carbonyl]benzoic acid From methyl 4-[(2-{1-[5-(3-trifluoromethylphenyl)-4-hydroxy-3-thienyl]ethylidene}hydrazino)carbonyl]benzoate (120 mg, 0.26 mmol) synthesized in Synthetic Example 62, the desired product was obtained in the same manner as in Synthetic Example 42 as a pale yellow solid (50 mg, yield 43%).

$^1$H-NMR (ppm in DMSO-$d_6$)

δ 7.58-7.68 (m, 2H), 7.97-8.60 (m, 7H).

LC/MS (ES$^-$) 447.

Synthetic Example 64

Synthesis of 4-{[(2-{1-[5-(3-trifluoromethylphenyl)-4-hydroxy-3-thienyl]ethylidene}hydrazino)-carbonothioyl]amino}benzoic acid From 2-(3-trifluoromethylphenyl)-3-hydroxy-4-methylcarbonylthiophene (50 mg, 0.17 mmol) synthesized in Reference Synthetic Example 49, the desired product was obtained in the same manner as in Synthetic Example 51 as a light brown solid (38 mg, 47%).

$^1$H-NMR (ppm in DMSO-$d_6$)

δ 2.41 (s, 3H), 7.57-8.44 (m, 9H).

LC/MS (ES$^+$) 480.

Synthetic Example 65

Synthesis of methyl 2-acetamino-4-[(2-{1-[5-(4-t-butylphenyl)-4-hydroxy-3-thienyl]ethylidene}hydrazino)carbonyl]benzoate To a suspension of 2-(4-t-butylphenyl)-3-hydroxy-4-methylcarbonylthiophene (54.8 mg, 0.2 mmol) and methyl 2-acetamino-4-hydrazinocarbonylbenzoate (50.2 mg, 0.2 mmol) in isopropyl alcohol (2 mL), tosylic acid monohydrate (11.4 mg, 0.06 mmol) was added, and the mixture was heated with reflux for 12 hours. The precipitated solid was filtered to obtain 84 mg of the desired product as a pale yellow solid (yield 83%).

$^1$H-NMR (ppm in DMSO-$d_6$)

δ 1.29 (s, 9H), 2.13 (s, 3H), 2.49 (s, 3H), 3.86 (s, 3H), 7.42 (d, 2H, J=8.4 Hz), 7.68-7.71 (m, 3H), 7.96-7.98 (m, 2H), 8.53 (s, 1H), 10.54 (brs, 1H), 11.48 (brs, 1H), 12.21 (brs, 1H).

LC/MS (ESI) 507 (M$^+$).

Synthetic Example 66

Synthesis of 2-acetamino-4-[(2-{1-[5-(4-t-butylphenyl)-4-hydroxy-3-thienyl]ethylidene}hydrazino)carbonyl]benzoic acid To a suspension of methyl 2-acetamino-4-[(2-{1-[5-(4-t-butylphenyl)-4-hydroxy-3-thienyl]ethylidene}-hydrazino)carbonyl]benzoate (50.8 mg, 0.1 mmol) in isopropyl alcohol (1.0 mL), 0.2 M sodium hydroxide aqueous solution (1.1 mL, 0.22 mmol) was added, and the mixture was stirred at room temperature for 6 hours. After completion of the stirring, 1 M hydrochloric acid (220 μL) was added, and the precipitated solid was filtered and then washed with methanol to obtain 17.5 mg of the desired product as a pale yellow solid (yield 35%).

$^1$H-NMR (ppm in DMSO-$d_6$)

δ 1.29 (s, 9H), 2.16 (s, 3H), 2.49 (s, 3H), 7.42 (d, 2H, J=8.4 Hz), 7.64 (d, 1H, J=8.1 Hz), 7.70 (d, 2H, J=8.4 Hz), 7.98 (s, 1H), 8.07 (d, 1H, J=8.1 Hz), 8.87 (s, 1H), 11.05 (brs, 1H), 11.47 (brs, 1H), 12.22 (brs, 1H).

LC/MS (ESI) 493 (M$^+$).

Synthetic Example 67

Synthesis of methyl 5-[(2-{1-[5-(3,4-dichlorophenyl)-4-hydroxy-3-thienyl]ethylidene}hydrazino)carbonyl]-2-thiophenecarboxylate From 2-(3,4-dichlorophenyl)-3-hydroxy-4-methylcarbonylthiophene (57.4 mg, 0.2 mmol), methyl 5-hydrazinocarbonyl-2-thiophenecarboxylate (40.0 mg, 0.2 mmol) and tosylic acid monohydrate (11.4 mg, 0.06 mmol), 81.2 mg of the desired product was obtained in the same manner as in Synthetic Example 65 as a pale yellow solid (yield 87%).

$^1$H-NMR (ppm in DMSO-$d_6$)

δ 3.88 (s, 3H), 7.64-7.71 (m, 2H), 7.91 (d, 1H, J=3.6 Hz), 8.05-8.13 (m, 3H), 11.57 (brs, 1H).

LC/MS (ESI) 468, 470 (M$^+$).

Synthetic Example 68

Synthesis of 5-[(2-{1-[(5-(3,4-dichlorophenyl)-4-hydroxy-3-thienyl]ethylidene}hydrazino)carbonyl]-2-thiophenecarboxylic acid From methyl 5-[(2-{1-[5-(3,4-dichlorophenyl)-4-hydroxy-3-thienyl]ethylidene}hydrazino)carbonyl]-2- thiophenecarboxylate (56.3 mg, 0.12 mmol) and 0.2 M sodium hydroxide aqueous solution (1.89 mL, 0.38 mmol), 7.5 mg of the desired product was obtained in the same manner as in Synthetic Example 66 as a pale yellow solid (yield 14%).
$^1$H-NMR (ppm in DMSO-$d_6$)
δ=7.64-7.72 (m, 2H), 7.91 (d, 1H, J=3.6 Hz), 8.06-8.14 (m, 3H), 11.54 (brs, 1H).
LC/MS (ESI) 454, 456 (M$^+$).

Synthetic Example 69

Synthesis of methyl 5-[(2-{1-[5-(4-trifluoromethylphenyl)-4-hydroxy-3-thienyl]ethylidene}hydrazino)carbonyl]-2-thiophenecarboxylate From 2-(4-trifluoromethylphenyl)-3-hydroxy-4-methylcarbonylthiophene (57.3 mg, 0.2 mmol), methyl 5-hydrazinocarbonyl-2-thiophenecarboxylate (40.0 mg, 0.2 mmol) and tosylic acid monohydrate (11.4 mg, 0.06 mmol), 68.0 mg of the desired product was obtained in the same manner as in Synthetic Example 65 as a pale yellow solid (yield 73%).
$^1$H-NMR (ppm in DMSO-$d_6$)
δ 3.86 (s, 3H), 7.75 (d, 2H, J=8.4 Hz), 7.90 (d, 1H, J=4.2 Hz), 7.98 (d, 2H, J=8.4 Hz), 8.08 (d, 1H, J=4.2 Hz), 8.15 (s, 1H), 11.56 (brs, 1H).
LC/MS (ESI) 468 (M$^+$).

Synthetic Example 70

Synthesis of 5-[(2-{1-[5-(4-trifluoromethylphenyl)-4-hydroxy-3-thienyl]ethylidene}hydrazino)carbonyl]-2-thiophenecarboxylic acid To a suspension of methyl 5-[(2-{1-[5-(4-trifluoromethylphenyl)-4-hydroxy-3-thienyl]ethylidene}hydrazino)carbonyl]-2-thiophenecarboxylate (56.2 mg, 0.12 mmol) in t-butanol (1.2 mL), 0.2 M sodium hydroxide aqueous solution (1.26 mL, 0.25 mmol) was added, and the mixture was stirred at room temperature for 4 hours. After completion of the stirring, 1 M hydrochloric acid (252 µL) was added, and the precipitated solid was filtered and washed with methanol to obtain 14.9 mg of the desired product as an orange solid (yield 27%).
$^1$H-NMR (ppm in DMSO-$d_6$)
δ 7.76 (d, 2H, J=8.4 Hz), 7.81 (d, 1H, J=3.9 Hz), 8.00 (d, 2H, J=8.4 Hz), 8.06 (d, 1H, J=3.9 Hz), 8.16 (s, 1H), 11.53 (brs, 1H).
LC/MS (ESI) 454 (Mt).

Synthetic Example 71

Synthesis of methyl 2-nitro-4-[(2-{1-[5-(4-trifluoromethylphenyl)-4-hydroxy-3-thienyl]ethylidene}hydrazino)carbonyl]benzoate From 2-(4-trifluoromethylphenyl)-3-hydroxy-4-methylcarbonylthiophene (57.3 mg, 0.2 mmol), methyl 4-hydrazinocarbonyl-2-nitrobenzoate (47.8 mg, 0.2 mmol) and tosylic acid monohydrate (11.4 mg, 0.06 mmol), 81.7 mg of the desired product was obtained in the same manner as in Synthetic Example 65 as a pale yellow solid (yield 81%).
$^1$H-NMR (ppm in DMSO-$d_6$)
δ=3.89 (s, 3H), 7.75 (d, 2H, J=8.4 Hz), 8.00 (d, 2H, J=8.4 Hz), 8.04 (d, 1H, J=7.8 Hz), 8.17 (s, 1H), 8.35 (d, 1H, J=7.8 Hz), 8.58 (s, 1H), 11.69 (brs, 1H).
LC/MS (ESI) 507 (M$^+$).

Synthetic Example 72

Synthesis of 2-nitro-4-[(2-{1-[5-(4-trifluoromethylphenyl)-4-hydroxy-3-thienyl]ethylidene}hydrazino)carbonyl]benzoic acid From methyl 2-nitro-4-[(2-{1-[5-(4-trifluoromethylphenyl)-4-hydroxy-3-thienyl]ethylidene}hydrazino)carbonyl]benzoate (60.9 mg (0.12 mmol) and 0.2 M sodium hydroxide aqueous solution (1.26 mL, 0.25 mmol), 38.2 mg of the desired product was obtained in the same manner as in Synthetic Example 70 as a pale yellow solid (yield 65%).
$^1$H-NMR (ppm in DMSO-$d_6$)
δ 7.76 (d, 2H, J=8.1 Hz), 8.00-8.05 (m, 3H), 8.18 (s, 1H), 8.31 (d, 1H, J=8.1 Hz), 8.52 (s, 1H), 11.68 (brs, 1H).
LC/MS (ESI) 493 (M$^+$).

Synthetic Example 73

Synthesis of methyl 2-fluoro-4-[(2-{1-[5-(4-t-butylphenyl)-4-hydroxy-3-thienyl]ethylidene}hydrazino)carbonyl]benzoate From 2-(4-t-butylphenyl)-3-hydroxy-4-methylcarbonylthiophene (59.0 mg, 0.215 mmol), methyl 2-fluoro-4-hydrazinocarbonylbenzoate (45.6 mg, 0.215 mmol) and tosylic acid monohydrate (12.3 mg, 0.0645 mmol), 94.9 mg of the desired product was obtained in the same manner as in Synthetic Example 65 as a pale yellow solid (yield 94%).
$^1$H-NMR (ppm in DMSO-$d_6$)
δ 1.29 (s, 9H), 3.91 (s, 3H), 7.43 (d, 2H, J=8.4 Hz), 7.71 (d, 2H, J=8.4 Hz), 7.85-7.94 (m, 2H), 8.01-8.08 (m, 2H), 11.50 (brs, 1H), 12.17 (brs, 1H).
LC/MS (ESI) 468 (M$^+$).

Synthetic Example 74

Synthesis of 2-fluoro-4-[(2-{1-[5-(4-t-butylphenyl)-4-hydroxy-3-thienyl]ethylidene}hydrazino)carbonyl]benzoic acid From methyl 2-fluoro-4-[(2-{1-[5-(4-t-butylphenyl)-4-hydroxy-3-thienyl]ethylidene}hydrazino)carbonyl]benzoate (56.2 mg, 0.12 mmol) and 0.2 M sodium hydroxide aqueous solution (1.26 mL, 0.25 mmol), 46.3 mg of the desired product was obtained in the same manner as in Synthetic Example 70 as a pale yellow solid (yield 85%).
$^1$H-NMR (ppm in DMSO-$d_6$)
δ 1.29 (s, 9H), 7.43 (d, 2H, J=8.4 Hz), 7.71 (d, 2H, J=8.4 Hz), 7.83-7.94 (m, 2H), 7.99-8.04 (m, 2H), 11.48 (brs, 1H), 12.18 (brs, 1H).
LC/MS (ESI) 452 (M$^+$).

Synthetic Example 75

Synthesis of methyl 4-[(2-{1-[5-(4-t-butylphenyl)-4-hydroxy-3-thienyl](isopropyl)methylene}hydrazino)carbonyl]benzoate A suspension of 2-(4-t-butylphenyl)-3-hydroxy-4-isopropylcarbonylthiophene (100 mg, 0.33 mmol), 4-hydrazinocarbonylmethylbenzoate (70 mg, 0.36 mmol) and p-tosylic acid monohydrate in isopropyl alcohol, was dehydrated with reflux for 2 days. After completion of the reaction, the reaction solution was cooled to room temperature and filtered to obtain the desired product as a yellow solid (92 mg, yield 58%).

$^1$H-NMR (ppm in DMSO-$d_6$)

δ 1.30 (s, 9H), 1.38 (s, 3H), 1.41 (s, 3H), 3.91 (s, 3H), 7.43 (d, J=8.3 Hz, 2H), 7.71 (d, J=8.3 Hz, 2H), 8.02-8.1.3 (m, 5H).

LC/MS (ES$^+$) 479.

Synthetic Example 76

Synthesis of 4-[(2-{1-[5-(4-t-butylphenyl)-4-hydroxy-3-thienyl](isopropyl)methylene}hydrazino)carbonyl]benzoic acid Using methyl 4-[(2-{1-[5-(4-t-butylphenyl)-4-hydroxy-3-thienyl](isopropyl)methylene}-hydrazino)carbonyl]benzoate (80 mg, 0.17 mmol) as the starting material, the desired product was obtained in the same manner as in Synthetic Example 70 as a pale yellow solid (19 mg, yield 24%).

$^1$H-NMR (ppm in DMSO-$d_6$)

δ 1.30 (s, 9H), 1.39-1.41 (m, 6H), 7.42-7.44 (m, 2H), 7.70-7.73 (m, 2H), 8.00-8.10 (m, 6H).

LC/MS (ES$^+$) 465.

Synthetic Example 77

Synthesis of methyl 2-nitro-4-[(2-{1-[5-(3,4-dichlorophenyl)-4-hydroxy-3-thienyl]ethylidene}hydrazino)carbonyl]benzoate Using 2-(3,4-dichlorophenyl)-3-hydroxy-4-methylcarbonylthiophene (100 mg, 0.35 mmol) and methyl 2-nitro-4-hydrazinocarbonylbenzoate (93 mg, 0.39 mmol) as the starting materials, the desired product was obtained in the same manner as in Synthetic Example 65 as a yellow solid (147 mg, yield 83%).

$^1$H-NMR (ppm in DMSO-$d_6$)

δ 3.91 (s, 3H), 7.55-7.75 (m, 2H), 8.05-8.20 (m, 3H), 8.30-8.40 (m, 1H), 8.50-8.65 (m, 1H).

LC/MS (ES$^-$) 507.

Synthetic Example 78

Synthesis of 2-nitro-4-[(2-{1-[5-(3,4-dichlorophenyl)-4-hydroxy-3-thienyl]ethylidene}hydrazino)carbonyl]benzoic acid Using methyl 2-nitro-4-[(2-{1-[5-(3,4-dichlorophenyl)-4-hydroxy-3-thienyl]ethylidene}hydrazino)carbonyl]benzoate (137 mg, 0.27 mmol) as the starting material, the desired product was obtained in the same manner as in Synthetic Example 66 as a yellow solid (68 mg, yield 51%).

LC/MS (ES$^+$) 494, 495.

Synthetic Example 79

Synthesis of methyl 2-bromo-4-[(2-{1-[5-(4-t-butylphenyl)-4-hydroxy-3-thienyl]ethylidene}hydrazino)carbonyl]benzoate Using 2-(4-t-butylphenyl)-3-hydroxy-4-methylcarbonylthiophene (55 mg, 0.20 mmol) and methyl 2-bromo-4-hydrazinocarbonylbenzoate (60 mg, 0.22 mmol) as the starting materials, the desired product was obtained in the same manner as in Synthetic Example 65 as a yellow solid (92 mg, yield 87%).

$^1$H-NMR (ppm in DMSO-$d_6$)

δ 1.30 (s, 9H), 3.91 (s, 3H), 7.43 (d, J=8.5 Hz, 2H), 7.71 (d, J=8.5 Hz, 2H), 7.91 (d, J=8.0 Hz, 1H), 8.01-8.03 (m, 2H), 8.27 (s, 1H).

LC/MS (ES$^-$) 528.

Synthetic Example 80

Synthesis of 2-bromo-4-[(2-{1-[5-(4-t-butylphenyl)-4-hydroxy-3-thienyl]ethylidene}hydrazino)carbonyl]benzoic acid Using methyl 2-bromo-4-[(2-{1-[5-(4-t-butylphenyl)-4-hydroxy-3-thienyl]ethylidene}hydrazino)carbonyl]benzoate (82 mg, 0.15 mmol) as the starting material, the desired product was obtained in the same manner as in Synthetic Example 66 as a yellow solid (67 mg, yield 870).

$^1$H-NMR (ppm in DMSO-$d_6$)

δ 1.31 (s, 9H), 7.43 (d, J=8.4 Hz, 2H), 7.71 (d, J=8.4 Hz, 2H), 7.87-7.89 (m, 1H), 7.97-8.01 (m, 2H), 8.24 (s, 1H).

LC/MS (ES$^+$) 517, 519.

Synthetic Example 81

Synthesis of methyl 2-chloro-4-[(2-{1-[5-(4-t-butylphenyl)-4-hydroxy-3-thienyl]ethylidene}hydrazino)carbonyl]benzoate Using 2-(4-t-butylphenyl)-3-hydroxy-4-methylcarbonylthiophene (55 mg, 0.20 mmol) and methyl 2-chloro-4-hydrazinocarbonylbenzoate (50 mg, 0.22 mmol) as the starting materials, the desired product was obtained in the same manner as in Synthetic Example 65 as a pale yellow solid (86 mg, yield 89%).

$^1$H-NMR (ppm in DMSO-$d_6$)

δ 1.30 (s, 9H), 3.91 (s, 3H), 7.43 (d, J=8.4 Hz, 2H), 7.71 (d, J=8.5 Hz, 2H), 7.97-8.01 (m, 3H), 8.12 (s, 1H).

LC/MS (ES$^-$) 483, 485.

Synthetic Example 82

Synthesis of 2-chloro-4-[(2-{1-[5-(4-t-butylphenyl)-4-hydroxy-3-thienyl]ethylidene}hydrazino)carbonyl]benzoic acid Using methyl 2-chloro-4-[(2-{1-[5-(4-t-butylphenyl)-4-hydroxy-3-thienyl]ethylidene}hydrazino)-carbonyl]benzoate (76 mg, 0.16 mmol) as the starting material, the desired product was obtained in the same manner as in Synthetic Example 66 as a pale yellow solid (60 mg, yield 80%).

LC/MS (ES$^+$) 471, 473.

Synthetic Example 83

Synthesis of methyl 4-[(2-{1-[2-bromo-5-(4-t-butylphenyl)-4-hydroxy-3-thienyl]ethylidene}hydrazino)carbonyl]benzoate To a suspension of 2-bromo-5-(4-t-butylphenyl)-4-hydroxy-3-methylcarbonylthiophene (1.00 g, 2.83 mmol) synthesized in Reference Synthetic Example 55 and 4-hydrazinocarbonylmethylbenzoate (550 mg, 2.83 mmol) in isopropyl alcohol (28.3 mL), tosylic acid monohydrate (146 mg, 0.85 mmol) was added, and the mixture was heated with reflux for about 1 hour. The reaction solution was concentrated, and then purified with a silica gel column chromatography (chloroform, and then chloroform/ethyl acetate=95/5) to obtain the desired product as a yellow solid (935 mg, yield 62%).

$^1$H-NMR (ppm in DMSO-$d_6$)

δ 1.29 (s, 9H), 2.61 (s, 3H), 3.91 (s, 3H), 7.44 (d, J=8.4 Hz, 2H), 7.65 (d, J=8.4 Hz, 2H), 8.06-8.14 (m, 4H), 11.69 (s, 1H), 12.29 (s, 1H).

LC/MS (ES$^+$) 529, 531.

Synthetic Example 84

Synthesis of methyl 4-[(2-{1-[5-(3,4-dichlorophenyl)-4-hydroxy-1-methyl-1H-pyrazol-3-yl]ethylidene}hydrazino)carbonyl]-2-nitrobenzoate From 1-[5-(3,4-dichlorophenyl)-4-hydroxy-1-methyl-1H-pyrazol-3-yl]ethanone (0.70 mmol, 200 mg) synthesized in Synthetic Example 1, methyl 2-nitro-4-hydrazinocarbonylbenzoate (0.70 mmol, 167.8 mg) of Reference Synthetic Example 40 and tosylic acid monohydrate (36.2 mg, 0.21 mmol), 311.1 mg of the desired product was obtained in the same manner as in Synthetic Example 58 as a yellow solid (yield 88%).

$^1$H-NMR (ppm in DMSO-$d_6$)

δ 11.61 (s, 1H), 9.85 (s, 1H), 8.58 (d, J=1.4 Hz, 1H), 8.34 (dd, J=1.4, 8.0 Hz, 1H), 8.04 (d, J=8.0 Hz, 1H), 7.86 (d, J=1.9 Hz, 2H), 7.80 (d, J=8.4 Hz, 1H), 7.61 (dd, J=1.9, 8.4 Hz, 1H), 3.90 (s, 6H), 2.46 (s, 3H).

LC-MS (ESI) 505 (M$^+$)

Synthetic Example 85

Synthesis of 4-[(2-{1-[5-(3,4-dichlorophenyl)-4-hydroxy-1-methyl-1H-pyrazol-3-yl]ethylidene}hydrazino)carbonyl]-2-nitrobenzoic acid From methyl 4-[(2-{1-[5-(3,4-dichlorophenyl)-4-hydroxy-1-methyl-1H-pyrazol-3-yl]ethylidene}hydrazino)carbonyl]-2-nitrobenzoate (0.40 mmol, 200 mg) and 1 M sodium hydroxide aqueous solution (1.98 mL, 1.98 mmol), 130.5 mg of the desired product was obtained in the same manner as in Synthetic Example 58 as a yellow solid (yield 67%).

$^1$H-NMR (ppm in DMSO-$d_6$)

δ 11.58 (s, 1H), 9.86 (s, 1H), 8.50 (s, 1H), 8.27-8.32 (m, 1H), 8.01 (d, J=8.0 Hz, 1H), 7.85-7.86 (m, 1H), 7.80 (d, J=8.5 Hz, 1H), 7.60-7.62 (m, 1H), 3.90 (s, 3H), 2.46 (s, 3H).

LC-MS (ESI) 491 (M$^+$)

Synthetic Example 86

Synthesis of methyl 4-{[2-(1-[4-hydroxy-1-methyl-5-[4-(trifluoromethyl)phenyl]-1H-pyrazol-3-yl]-ethylidene)hydrazino]carbonyl}-2-nitrobenzoate From 1-[4-hydroxy-1-methyl-5-(4-trifluoromethylphenyl)-1H-pyrazol-3-yl]ethanone (0.70 mmol, 200 mg) synthesized in Synthetic Example 11, methyl 2-nitro-4-hydrazinocarbonylbenzoate (0.70 mmol, 168.3 mg) of Reference Synthetic Example 40 and tosylic acid monohydrate (36.4 mg, 0.21 mmol), 214.7 mg of the desired product was obtained in the same manner as in Synthetic Example 58 as a yellow solid (yield 60%).

$^1$H-NMR (ppm in DMSO-$d_6$)

δ 11.62 (s, 1H), 9.88 (s, 1H), 8.58 (d, J=1.5 Hz, 1H), 8.35 (dd, J=1.5, 8.0 Hz, 1H), 8.05 (d, J=8.0 Hz, 1H), 7.90 (ABq, J=8.7 Hz, 2H), 7.84 (ABq, J=8.7 Hz, 2H), 3.93 (s, 3H), 3.90 (s, 3H), 2.48 (s, 3H).

LC-MS (ESI) 505 (M$^+$).

Synthetic Example 87

Synthesis of 4-{[2-(1-{4-hydroxy-1-methyl-5-[4-(trifluoromethyl)phenyl]-1H-pyrazol-3-yl}ethylidene)hydrazino]carbonyl}-2-nitrobenzoic acid From methyl 4-{[2-(1-{4-hydroxy-1-methyl-5-[4-(trifluoromethyl)phenyl]-1H-pyrazol-3-yl}ethylidene)hydrazino]carbonyl}-2-nitrobenzoate (0.30 mmol, 150 mg) and 1 M sodium hydroxide aqueous solution (1.48 mL, 1.48 mmol), 106.0 mg of the desired product was obtained in the same manner as in Synthetic Example 58 as a pale yellow solid (yield 73%).

$^1$H-NMR (ppm in DMSO-$d_6$)

δ 11.59 (s, 1H), 9.88 (s, 1H), 8.50 (s, 1H), 8.28-8.31 (m, 1H), 8.02 (d, J=8.0 Hz, 1H), 7.90 (ABq, J=8.7 Hz, 2H), 7.84 (ABq, J=8.7 Hz, 2H), 3.93 (s, 3H), 2.47 (s, 3H).

LC-MS (ESI) 491 (M$^+$).

Synthetic Example 88

Synthesis of methyl 5-[(2-{1-[5-(3,4-dichlorophenyl)-4-hydroxy-1-methyl-1H-pyrazol-3-yl]ethylidene}hydrazino)carbonyl]-2-thiophenecarboxylate From 1-[5-(3,4-dichlorophenyl)-4-hydroxy-1-methyl-1H-pyrazol-3-yl]ethanone (200 mg, 0.70 mmol) synthesized in Synthetic Example 1, methyl 5-hydrazinocarbonyl-2-thiophenecarboxylate (0.70 mmol, 140.4 mg) of Reference Synthetic Example 39 and tosylic acid monohydrate (36.2 mg, 0.21 mmol), 314.1 mg of the desired product was obtained in the same manner as in Synthetic Example 58 as a yellow solid (yield 96%).

$^1$H-NMR (ppm in DMSO-$d_6$)

δ 11.47 (s, 1H), 9.76 (s, 1H), 8.04-8.07 (m, 1H), 7.79-7.91 (m, 3H), 7.56-7.61 (s, 1H), 3.87 (s, 6H), 2.46 (s, 3H).

LC-MS (ESI) 466 (M$^+$).

Synthetic Example 89

Synthesis of 5-[(2-{1-[5-(3,4-dichlorophenyl)-4-hydroxy-1-methyl-1H-pyrazol-3-yl]ethylidene}hydrazino)carbonyl]-2-thiophenecarboxylic acid From methyl 5-[(2-{1-[5-(3,4-dichlorophenyl)-4-hydroxy-1-methyl-1H-pyrazol-3-yl]ethylidene}hydrazino)carbonyl]-2-thiophenecarboxylate (200 mg, 0.43 mmol) and 1 M sodium hydroxide aqueous solution (2.13 mL, 2.13 mmol), 153.3 mg of the desired product was obtained in the same manner as in Synthetic Example 58 as a yellow solid (yield 84%).

$^1$H-NMR (ppm in DMSO-$d_6$)

δ 11.43 (s, 1H), 9.78 (s, 1H), 8.03-8.32 (m, 1H), 7.79-7.85 (m, 3H), 7.58-7.61 (m, 1H), 3.89 (s, 3H), 2.46 (s, 3H).

LC-MS (ESI) 452 (M$^+$).

Synthetic Example 90

Synthesis of methyl 5-{[2-(1-{4-hydroxy-1-methyl-5-[4-(trifluoromethyl)phenyl]-1H-pyrazol-3-yl}ethylidene)hydrazino]carbonyl}-2-thiophenecarboxylate From 1-[4-hydroxy-1-methyl-5-(4-trifluoromethylphenyl)-1H-pyrazol-3-yl]ethanone (200 mg, 0.70 mmol) synthesized in Synthetic Example 11, methyl 5-hydrazinocarbonyl-2-thiophenecarboxylate (0.70 mmol, 140.9 mg) of Reference Synthetic Example 39 and tosylic acid monohydrate (36.4 mg, 0.21 mmol), 188.2 mg of the desired product was obtained in the same manner as in Synthetic Example 58 as a pale yellow solid (yield 57%).
$^1$H-NMR (ppm in DMSO-$d_6$)
δ 11.48 (s, 1H), 9.78 (s, 1H), 8.06-8.08 (m, 1H), 7.82-7.91 (m, 5H), 3.92 (s, 3H), 3.87 (s, 3H), 2.47 (s, 3H).
LC-MS (ESI) 466 ($M^+$).

Synthetic Example 91

Synthesis of 5-{[2-(1-{4-hydroxy-1-methyl-5-[4-(trifluoromethyl)phenyl]-1H-pyrazol-3-yl}ethylidene)hydrazino]carbonyl}-2-thiophenecarboxylic acid From methyl 5-{[2-(1-{4-hydroxy-1-methyl-5-[4-(trifluoromethyl)phenyl]-1H-pyrazol-3-yl}ethylidene)hydrazino]carbonyl}-2-thiophenecarboxylate (150 mg, 0.32 mmol) and 1 M sodium hydroxide aqueous solution (1.60 mL, 1.60 mmol), 89.0 mg of the desired product was obtained in the same manner as in Synthetic Example 58 as a pale yellow solid (yield 61%).
$^1$H-NMR (ppm in DMSO-$d_6$)
δ 11.44 (s, 1H), 9.80 (s, 1H), 8.03-8.04 (m, 1H), 7.80-7.91 (m, 5H), 3.92 (s, 3H), 2.47 (s, 3H).
LC-MS (ESI) 452 ($M^+$).

Synthetic Example 92

Synthesis of methyl 4-{[(2-{1-[5-(4-t-butylphenyl)-4-hydroxy-3-thienyl]ethylidene}hydrazino)-carbonothioyl]amino}-2-nitrobenzoate Dimethylformamide (1.3 mL) and conc. hydrochloric acid (1 drop) were added to 2-(4-t-butylphenyl)-3-hydroxy-4-methylcarbonylthiophene (71 mg, 0.26 mmol) synthesized in Reference Synthetic Example 33 and methyl 4-hydrazinocarbonothioylamino-2-nitrobenzoate (70 mg, 0.26 mmol) synthesized in Reference Synthetic Example 56, and the mixture was stirred at room temperature for 2 days. The precipitated solid was filtered to obtain 110 mg of the desired product as a pale yellow solid (yield 81%).
$^1$H-NMR (ppm in DMSO-$d_6$)
δ 11.29 (bs, 1H), 10.67 (bs, 1H), 8.57 (bs, 1H), 7.87-8.03 (m, 3H), 7.67 (d, J=8.4 Hz, 2H), 7.41 (d, J=8.4 Hz, 2H), 3.83 (s, 3H), 2.40 (s, 3H), 1.28 (s, 9H).
LC/MS (ESI) 526.

Synthetic Example 93

Synthesis of 4-{[(2-{1-[5-(4-t-butylphenyl)-4-hydroxy-3-thienyl]ethylidene}hydrazino)carbonothioyl]amino}-2-nitrobenzoic acid Methyl 4-{[(2-{1-[5-(4-t-butylphenyl)-4-hydroxy-3-thienyl]ethylidene}hydrazino)carbonothioyl]amino}-2-nitrobenzoate (95 mg, 0.18 mmol) synthesized in Synthetic Example 92 was dissolved in isopropyl alcohol (1.8 mL), and 0.2 M sodium hydroxide aqueous solution (2.0 mL, 0.40 mmol) was added thereto, followed by stirring overnight at room temperature. After completion of the stirring, 1 M hydrochloric acid (0.40 mL, 0.40 mmol) and water were added thereto, and the precipitated solid was filtered to obtain 57 mg of the desired product as a pale yellow solid (yield 61%).
$^1$H-NMR (ppm in DMSO-$d_6$)
δ 11.29 (bs, 1H), 10.64 (bs, 1H), 8.50 (bs, 1H), 7.87-8.00 (m, 3H), 7.69 (d, J=8.4 Hz, 2H), 7.43 (d, J=8.4 Hz, 2H), 2.41 (s, 3H), 1.29 (s, 9H).
LC/MS (ESI) 512.

Synthetic Example 94

Synthesis of methyl 4-{[(2-{1-[5-(3,4-dichlorophenyl)-4-hydroxy-3-thienyl]ethylidene}hydrazino)-carbonothioyl]amino}-2-nitrobenzoate From 2-(3,4-dichlorophenyl)-3-hydroxy-4-methylcarbonylthiophene (60 mg, 0.21 mmol) synthesized in Reference Synthetic Example 34, the desired product was obtained in the same manner as in Synthetic Example 92 as a yellow solid (88 mg, yield 78%).
$^1$H-NMR (ppm in DMSO)
δ 11.35 (bs, 1H), 10.70 (bs, 1H), 8.57 (bs, 1H), 8.14 (s, 1H), 8.01-8.04 (m, 2H), 7.89-7.91 (m, 1H), 7.65-7.74 (m, 2H), 3.84 (s, 3H), 2.42 (s, 3H).
LC/MS (ESI) 538.

Synthetic Example 95

Synthesis of 4-{[(2-{1-[5-(3,4-dichlorophenyl)-4-hydroxy-3-thienyl]ethylidene}hydrazino)carbonothioyl]amino}-2-nitrobenzoic acid From methyl 4-{[(2-{1-[5-(3,4-dichlorophenyl)-4-hydroxy-3-thienyl]ethylidene}hydrazino)-carbonothioyl]amino}-2-nitrobenzoate (70 mg, 0.13 mmol) synthesized in Synthetic Example 94, the desired product was obtained in the same manner as in Synthetic Example 93 as a pale yellow solid (43 mg, yield 63%).
$^1$H-NMR (ppm in DMSO)
δ 11.32 (bs, 1H), 10.66 (bs, 1H), 8.48 (bs, 1H), 8.13 (s, 1H), 7.87-8.02 (m, 3H), 7.64-7.74 (m, 2H), 2.41 (s, 3H).
LC/MS (ESI) 524.

Synthetic Example 96

Synthesis of methyl 4-{[(2-{1-[5-(4-trifluoromethylphenyl)-4-hydroxy-3-thienyl]ethylidene}hydrazino)carbonothioyl]amino}-2-nitrobenzoate From 2-(4-trifluoromethylphenyl)-3-hydroxy-4-methylcarbonylthiophene (60 mg, 0.21 mmol) synthesized in Reference Synthetic Example 35, the desired product was obtained in the same manner as in Synthetic Example 92 as a yellow solid (103 mg, yield 91%).
$^1$H-NMR (ppm in DMSO)
δ 11.36 (bs, 1H), 10.72 (bs, 1H), 8.58 (bs, 1H), 8.17 (s, 1H), 7.89-8.04 (m, 4H), 7.76 (d, J=8.3 Hz, 2H), 3.84 (s, 3H), 2.43 (s, 3H).
LC/MS (ESI) 538.

Synthetic Example 97

Synthesis of 4-{[(2-{(1-[5-(4-trifluoromethylphenyl)-4-hydroxy-3-thienyl]ethylidene}hydrazino)carbonothioyl]-amino}-2-nitrobenzoic acid From methyl 4-{[(2-{1-[5-(4-trifluoromethylphenyl)-4-hydroxy-3-thienyl]ethylidene}hydrazino)-carbonothioyl]

amino}-2-nitrobenzoate (90 mg, 0.17 mmol) synthesized in Synthetic Example 96, the desired product was obtained in the same manner as in Synthetic Example 93 as a pale yellow solid (69 mg, yield 79%).

$^1$H-NMR (ppm in DMSO)

δ 11.34 (bs, 1H), 10.65-10.67 (m, 1H), 8.49 (bs, 1H), 8.16 (s, 1H), 7.88-8.01 (m, 4H), 7.76 (d, J=8.5 Hz, 2H), 2.43 (s, 3H).

LC/MS (ESI) 524.

Synthetic Example 98

Synthesis of methyl 5-{[(2-{1-[5-(4-t-butylphenyl)-4-hydroxy-3-thienyl]ethylidene}hydrazino)-carbonothioyl]amino}-2-thiophenecarboxylate Dimethylformamide (1.3 ml) and conc. hydrochloric acid (1 drop) were added to 2-(4-t-butylphenyl)-3-hydroxy-4-methylcarbonylthiophene (70 mg, 0.26 mmol) synthesized in Reference Synthetic Example 33 and methyl 5-hydrazinocarbonothioylamino-2-thiophenecarboxylate (59 mg, 0.26 mmol) synthesized in Reference Synthetic Example 57, and the mixture was stirred overnight at room temperature. Water was added, and the precipitated solid was filtered. The obtained solid was extracted with chloroform, dried over anhydrous sodium sulfate. The organic layer was concentrated, and purified with a silica gel column chromatography (chloroform/methanol=95/5) to obtain the desired product as a pale yellow solid (112 mg, yield 90%).

$^1$H-NMR (ppm in DMSO)

δ 11.63 (bs, 1H), 11.18 (bs, 1H), 8.01 (bs, 1H), 7.72 (d, J=8.5 Hz, 2H), 7.67 (d, J=4.4 Hz, 1H), 7.46 (d, J=8.5 Hz, 2H), 6.92 (d, J=4.4 Hz, 1H), 3.82 (s, 3H), 2.41 (s, 3H), 1.32 (s, 9H).

LC/MS (ESI) 487.

Synthetic Example 99

Synthesis of 5-{[(2-{1-[5-(4-t-butylphenyl)-4-hydroxy-3-thienyl]ethylidene}hydrazino)carbonothioyl]amino}-2-thiophenecarboxylic acid Methyl 5-{[(2-{1-[5-(4-t-butylphenyl)-4-hydroxy-3-thienyl]ethylidene}hydrazino)carbonothioyl]amino}-2-thiophenecarboxylate (85 mg, 0.18 mmol) synthesized in Synthetic Example 98 was dissolved in isopropyl alcohol (1.8 ml), and 0.2 M sodium hydroxide aqueous solution (1.95 ml, 0.39 mmol) was added thereto, following by stirring overnight at room temperature. Then 0.2 M sodium hydroxide aqueous solution (0.96 ml, 0.19 mmol) was added thereto, following by stirring overnight at 45° C. After completion of the stirring, 1 M hydrochloric acid (0.58 ml, 0.58 mmol) was added. The precipitated solid was filtered to obtain 2.7 mg of the desired product as a pale yellow solid (yield 3%).

LC/MS (ESI) 473.

Synthetic Example 100

Synthesis of methyl 4-{[(2-{1-[5-(4-t-butylphenyl)-4-hydroxy-3-thienyl]ethylidene}hydrazino)-carbonothioyl]amino}-2-chlorobenzoate From 2-(4-t-butylphenyl)-3-hydroxy-4-methylcarbonylthiophene (60 mg, 0.22 mmol) synthesized in Reference Synthetic Example 33, the desired product was obtained in the same manner as in Synthetic Example 92 as a yellow solid (118 mg, yield 100%).

$^1$H-NMR (ppm in DMSO)

δ 11.21 (bs, 1H), 10.50 (bs, 1H), 8.21 (bs, 1H), 7.97 (d, J=8.5 Hz, 1H), 7.89 (d, J=8.5 Hz, 1H), 7.68-7.71 (m, 3H), 7.43 (d, J=8.3 Hz, 2H), 3.85 (s, 3H), 2.40 (s, 3H), 1.29 (s, 9H).

LC/MS (ESI) 515.

Synthetic Example 101

Synthesis of 4-{[(2-{1-[5-(4-t-butylphenyl)-4-hydroxy-3-thienyl]ethylidene}hydrazino)carbonothioyl]amino}-2-chlorobenzoic acid Methyl 4-{[(2-{1-[5-(4-t-butylphenyl)-4-hydroxy-3-thienyl]ethylidene}hydrazino)carbonothioyl]amino}-2-chlorobenzoate (100 mg, 0.19 mmol) synthesized in Synthetic Example 100 was dissolved in isopropyl alcohol (1.9 ml), and 0.2 M sodium hydroxide aqueous solution (2.1 ml, 0.42 mmol) was added thereto, following by stirring overnight at room temperature, then at 45° C. for 1 day. Then 0.2 M sodium hydroxide aqueous solution (1.1 ml, 0.22 mmol) was added thereto, following by stirring at 45° C. for 5.5 hours. After completion of the stirring, 1 M hydrochloric acid (0.64 ml, 0.64 mmol) was added. The precipitated solid was filtered, and purified with a silica gel plate (chloroform/methanol=9/1) to obtain the desired product as a yellow solid (24 mg, yield 25%).

$^1$H-NMR (ppm in DMSO)

δ 10.48 (bs, 1H), 8.18 (bs, 1H), 7.84-7.94 (m, 2H), 7.65-7.68 (m, 3H), 7.40-7.43 (m, 2H), 2.41 (s, 3H), 1.29 (s, 9H).

LC/MS (ESI) 501.

Synthetic Example 102

Synthesis of methyl 4-{[(2-{1-[5-(4-t-butylphenyl)-4-hydroxy-1-methyl-1H-pyrazol-3-yl]ethylidene}hydrazino)carbonothioyl]amino}-2-nitrobenzoate From 1-[5-(4-t-butylphenyl)-4-hydroxy-1-methyl-1H-pyrazol-3-yl]ethanone (63 mg, 0.23 mmol) synthesized in Synthetic Example 3, the desired product was obtained in the same manner as in Synthetic Example 92 as a yellow solid (121 mg, yield 100%).

$^1$H-NMR (ppm in DMSO)

δ 10.53 (bs, 1H), 8.60-8.61 (m, 1H), 7.87-8.06 (m, 2H), 7.47-7.60 (m, 4H), 3.84 (s, 3H), 3.82 (s, 3H), 2.41 (s, 3H), 1.33 (s, 9H).

LC/MS (ESI) 524.

Synthetic Example 103

Synthesis of 4-{[(2-{1-[5-(4-t-butylphenyl)-4-hydroxy-1-methyl-1H-pyrazol-3-yl]ethylidene}hydrazino)-carbonothioyl]amino}-2-nitrobenzoic acid Methyl 4-{[(2-{1-[5-(4-t-butylphenyl)-4-hydroxy-1-methyl-1H-pyrazol-3-yl]ethylidene}hydrazino)-carbonothioyl]amino}-2-nitrobenzoate (100 mg, 0.19 mmol) synthesized in Synthetic Example 102 was dissolved in methanol (6.7 ml), and 1 M sodium hydroxide aqueous solution (0.96 ml, 0.96 mmol) was added thereto, following by stirring overnight at room temperature. After, completion of the stirring, the reaction solution was washed with ethyl acetate, and to the aqueous layer, 1 M hydrochloric acid was added. The precipitated solid was filtered to obtain 27 mg of the desired product as a pale yellow solid (yield 28%).
$^1$H-NMR (ppm in DMSO)
δ 11.10 (bs, 1H), 10.50 (bs, 1H), 8.49 (bs, 1H), 7.86-7.97 (m, 2H), 7.47-7.59 (m, 4H), 3.82-3.83 (m, 3H), 2.41 (s, 3H), 1.33-1.34 (m, 9H).
LC/MS (ESI) 510.

Synthetic Example 104

Synthesis of methyl 4-{[(2-{1-[5-(3,4-dichlorophenyl)-4-hydroxy-1-methyl-1H-pyrazol-3-yl]ethylidene}-hydrazino)carbonothioyl]amino}-2-nitrobenzoate Dimethylformamide (1 ml) and conc. hydrochloric acid (1 drop) were added to 1-[5-(3,4-dichlorophenyl)-4-hydroxy-1-methyl-1H-pyrazol-3-yl]ethanone (60 mg, 0.21 mmol) synthesized in Synthetic Example 1 and methyl 4-hydrazinocarbonothioylamino-2-nitrobenzoate (57 mg, 0.21 mmol) synthesized in Reference Synthetic Example 56, and the mixture was stirred at room temperature for 21 hours. Water was added, and the precipitated solid was filtered, purified with a silica gel column chromatography (n-hexane/ethyl acetate=1/1 then chloroform/methanol=95/5). The obtained solid was extracted with ethyl acetate, washed with a saturated ammonium chloride aqueous solution, saturated sodium chloride aqueous solution. The organic layer was concentrated to obtain the desired product as a pale yellow solid (104 mg, yield 92%).
$^1$H-NMR (ppm in DMSO)
δ 8.57 (bs, 1H), 8.03-8.05 (m, 1H), 7.78-7.90 (m, 3H), 7.56-7.59 (m, 1H), 3.86 (s, 3H), 3.84 (s, 3H), 2.41 (s, 3H).
LC/MS (ESI) 536.

Synthetic Example 105

Synthesis of 4-{[(2-{1-[(5-(3,4-dichlorophenyl)-4-hydroxy-1-methyl-1H-pyrazol-3-yl]ethylidene}hydrazino)-carbonothioyl]amino}-2-nitrobenzoic acid Methyl 4-{[(2-{1-[5-(3,4-dichlorophenyl)-4-hydroxy-1-methyl-1H-pyrazol-3-yl]ethylidene}hydrazino)-carbonothioyl]amino}-2-nitrobenzoate (100 mg, 0.19 mmol) synthesized in Synthetic Example 104 was dissolved in methanol (3 ml), and 1 M sodium hydroxide aqueous solution (0.74 ml, 0.74 mmol) was added thereto, following by stirring overnight at room temperature. After completion of the stirring, 1 M hydrochloric acid (0.74 ml, 0.74 mmol) and water were added thereto. The precipitated solid was recovered by filtration, washed with water, isopropyl alcohol, and chloroform. The obtained solid was stirred in chloroform, and then filtered to obtain 37 mg of the desired product as a yellow solid (yield 48%).
$^1$H-NMR (ppm in DMSO)
δ 8.47 (bs, 1H), 7.77-7.93 (m, 4H), 7.56-7.59 (m, 1H), 3.86 (s, 3H), 2.42 (s, 3H).
LC/MS (ESI) 522.

Synthetic Example 106

Synthesis of 4-{[(2-{1-[5-(4-chlorophenyl)-4-hydroxy-1-methyl-1H-pyrazol-3-yl]ethylidene}hydrazino)-carbonothioyl]amino}-2-nitrobenzoic acid From 1-[5-(4-chlorophenyl)-4-hydroxy-1-methyl-1H-pyrazol-3-yl]ethanone, synthesized in the same manner as in Synthetic Example 1, the desired product was obtained in the same manner as in Synthetic Examples 102 and 103 as a yellow solid (22.6 mg).
$^1$H-NMR (ppm in DMSO)
δ 8.48 (bs, 1H), 7.50-8.00 (m, 6H), 3.88 (s, 3H), 2.42 (s, 3H).
LC/MS (ESI) 488

Synthetic Example 107

Synthesis of 4-[(2-{1-[5-(4-chlorophenyl)-4-hydroxy-1-methyl-1H-pyrazol-3-yl]ethylidene}hydrazino)carbonyl]-2-nitrobenzoic acid From 1-[5-(4-chlorophenyl)-4-hydroxy-1-methyl-1H-pyrazol-3-yl]ethanone synthesized in the same manner as in Synthetic Example 1, the desired product was obtained in the same manner as in Synthetic Example 58 as a pale yellow solid (19.1 mg).
$^1$H-NMR (ppm in DMSO)
δ 11.5 (1H, s), 9.73 (1H, s), 8.49 (1H, s), 8.28 (1H, d, J=8 Hz), 8.01 (1H, d, J=8 Hz), 7.65-7.55 (4H, m), 3.87 (3H, s), 2.46 (3H, s).
LC/MS (ESI) 457

Synthetic Example 108

Synthesis of 5-[(2-{1-[5-(4-chlorophenyl)-4-hydroxy-1-methyl-1H-pyrazol-3-yl]ethylidene}hydrazino)carbonyl]-2-thiophenecarboxylic acid From 1-[5-(4-chlorophenyl)-4-hydroxy-1-methyl-1H-pyrazol-3-yl]ethanone synthesized in the same manner as in Synthetic Example 1, the desired product was obtained in the same manner as in Synthetic Examples 33 and 34 as a yellow solid (20.2 mg).
$^1$H-NMR (ppm in DMSO)
δ11.4 (1H, s), 9.64 (1H, s), 8.02 (1H, d, J=3 Hz), 7.80 (1H, d, J=3 Hz), 7.5-7.7 (4H, m), 3.86 (3H, s), 2.45 (3H, s).
LC/MS (ESI) 418

Synthetic Example 109

Synthesis of 4-[(2-{1-[5-(4-chlorophenyl)-4-hydroxy-1-methyl-1H-pyrazol-3-yl]ethylidene}hydrazino)carbonyl]benzoic acid From 1-[5-(4-chlorophenyl)-4-hydroxy-1-methyl-1H-pyrazol-3-yl]ethanone synthesized in the same manner as in Synthetic Example 1, the desired product was obtained in the same manner as in Synthetic Example 3 as a yellow solid (47.4 mg).
$^1$H-NMR (ppm in DMSO)
δ 11.4 (1H, s), 9.83 (1H, s), 7.90-8.20 (4H, m), 7.50-7.70 (4H, m), 3.86 (3H, s), 2.45 (3H, s).
LC/MS (ESI) 412

Synthetic Example 110

Synthesis of 4-{[(2-{1-[5-(4-trifluoromethylphenyl)-4-hydroxy-1-methyl-1H-pyrazol-3-yl]ethylidene}hydrazino)-carbonothioyl]amino}-2-nitrobenzoic acid From methyl 4-{[(2-{1-[5-(4-trifluoromethylphenyl)-4-hydroxy-1-methyl-1H-pyrazol-3-yl]ethylidene}hydrazino)

carbonothioyl]amino}-2-nitrobenzoate (70 mg, 0.13 mmol), the desired product was obtained in the same manner as in Synthetic Examples 104 and 105 as a yellow solid (42 mg, yield 62%).

$^1$H-NMR (ppm in DMSO)

δ 8.48 (bs, 1H), 7.80-8.00 (m, 6H), 3.88 (s, 3H), 2.42 (s, 3H).

LC/MS (ESI) 522.

Synthetic Example 111

Synthesis of 4-{[(2-{1-[5-(4-t-butylphenyl)-4-hydroxy-1-methyl-1H-pyrazol-3-yl]ethylidene}hydrazino)-carbonothioyl]amino}-2-chlorobenzoic acid From methyl 4-{[(2-{1-[5-(4-t-butylphenyl)-4-hydroxy-1-methyl-1H-pyrazol-3-yl]ethylidene}hydrazino)carbonothioyl]amino}-2-chlorobenzoate (82 mg, 0.16 mmol), the desired product was obtained in the same manner as in Synthetic Examples 104 and 105 as a brown solid (40 mg, yield 50%).

$^1$H-NMR (ppm in DMSO)

δ 8.12-8.26 (m, 1H), 7.50-7.81 (m, 6H), 3.82 (s, 3H), 2.41 (s, 3H), 1.32 (s, 9H).

LC/MS (ESI) 499.

Synthetic Example 112

Synthesis of 4-{[(2-{1-[5-(3,4-dichlorophenyl)-4-hydroxy-1-methyl-1H-pyrazol-3-yl]ethylidene}hydrazino)-carbonothioyl]amino}-2-chlorobenzoic acid From methyl 4-{[(2-{1-[5-(3,4-dichlorophenyl)-4-hydroxy-1-methyl-1H-pyrazol-3-yl]ethylidene}hydrazino)carbonothioyl]amino}-2-chlorobenzoate (105 mg, 0.20 mmol), the desired product was obtained in the same manner as in Synthetic Examples 104 and 105 as a pale yellow solid (54 mg, yield 52%)

$^1$H-NMR (ppm in DMSO)

δ 8.09 (bs, 1H), 7.77-7.85 (m, 3H), 7.65-7.68 (m, 1H), 7.55-7.58 (m, 1H), 3.84 (s, 3H), 2.39 (s, 3H).

LC/MS (ESI) 511.

Synthetic Example 113

Synthesis of 4-{[(2-{1-[5-(4-trifluoromethylphenyl)-4-hydroxy-1-methyl-1H-pyrazol-3-yl]ethylidene}hydrazino)-carbonothioyl]amino}-2-chlorobenzoic acid From methyl 4-{[(2-{1-[5-(4-trifluoromethylphenyl)-4-hydroxy-1-methyl-1H-pyrazol-3-yl]ethylidene}hydrazino)carbonothioyl]amino}-2-chlorobenzoate (60 mg, 0.11 mmol), the desired product was obtained in the same manner as in Synthetic Examples 104 and 105 as a pale yellow solid (25 mg, yield 42%).

$^1$H-NMR (ppm in DMSO)

δ 8.11 (bs, 1H), 7.80-7.94 (m, 5H), 7.67-7.70 (m, 1H), 3.88 (s, 3H), 2.41 (s, 3H).

LC/MS (ESI) 511.

Synthetic Example 114

Synthesis of 5-{[(2-{1-[5-(4-t-butylphenyl)-4-hydroxy-1-methyl-1H-pyrazol-3-yl]ethylidene}hydrazino)-carbonothioyl]amino}-2-thiophenecarboxylic acid 1) Synthesis of 5-hydrazinocabonothioylamino-2-thiophenecarboxylic acid To methyl 5-hydrazinocabonothioylamino-2-thiophenecarboxylate (1.21 mmol, 280 mg) obtained in Reference Synthetic Example 57, methanol (2.4 ml) was added, and 0.2 M aqueous sodium hydroxide (3 eq, 18.2 ml) was added at room temperature. After stirring of 1.5 hours at 60° C., the reactor was cooled to room temperature, and 1 M hydrochloric acid (3 eq, 3.63 ml) was added. The precipitated solid was recovered by filtration, washed with water and chloroform and dried by means of a vacuum pump. The desired product was obtained as a pale yellow solid (230 mg, yield 87.6% (LC purity 90%)).

$^1$H-NMR (ppm in DMSO)

δ 9.56 (bs, 1H), 7.47 (d, J=4.1 Hz, 1H), 7.07 (bs, 1H), 6.91 (bs, 1H).

LC/MS (ESI) 217.

2) Synthesis of 5-{[(2-{1-[5-(4-t-butylphenyl)-4-hydroxy-1-methyl-1H-pyrazol-3-yl]ethylidene}hydrazino)-carbonothioyl]amino}-2-thiophenecarboxylic acid From 1-[5-(4-t-butylphenyl)-4-hydroxy-1-methyl-1H-pyrazol-3-yl]ethanone (40.0 mg, 0.15 mmol) and 5-hydrazinocabonothioylamino-2-thiophenecarboxylic acid (35.5 mg, 0.15 mmol), the desired product was obtained in the same manner as in Synthetic Example 2 as a yellow solid (57.3 mg, yield 83%).

$^1$H-NMR (ppm in DMSO)

δ 7.47-7.56 (m, 5H), 6.90 (bs, 1H), 3.82 (s, 3H), 2.39 (s, 3H), 1.34 (s, 9H).

LC/MS (ESI) 471.

Synthetic Example 115

Synthesis of 5-{[(2-{1-[5-(3,4-dichlorophenyl)-4-hydroxy-1-methyl-1H-pyrazol-3-yl]ethylidene}hydrazino)-carbonothioyl]amino}-2-thiophenecarboxylic acid From 1-[5-(3,4-dichlorophenyl)-4-hydroxy-1-methyl-1H-pyrazol-3-yl]ethanone (40.0 mg, 0.14 mmol) and 5-hydrazinocabonothioylamino-2-thiophenecarboxylic acid (33.9 mg, 0.14 mmol), the desired product was obtained in the same manner as in Synthetic Example 114 as a pale yellow solid (62.2 mg, yield 92%).

$^1$H-NMR (ppm in DMSO)

δ 7.84 (d, J=1.7 Hz, 1H), 7.80 (d, J=8.3 Hz, 1H), 7.54-7.60 (m, 2H), 6.90 (bs, 1H), 3.86 (s, 3H), 2.39 (s, 3H).

LC/MS (ESI) 483.

Synthetic Example 116

Synthesis of 5-{[(2-{1-[5-(4-trifluoromethylphenyl)-4-hydroxy-1-methyl-1H-pyrazol-3-yl]ethylidene}hydrazino)-carbonothioyl]amino}-2-thiophenecarboxylic acid From 1-[5-(4-trifluoromethylphenyl)-4-hydroxy-1-methyl-1H-pyrazol-3-yl]ethanone (40.0 mg, 0.14 mmol) and 5-hydrazinocabonothioylamino-2-thiophenecarboxylic acid (34.0 mg, 0.14 mmol), the desired product was obtained in the same manner as in Synthetic Example 114 as a pale yellow solid (55.8 mg, yield 82%).
$^1$H-NMR (ppm in DMSO)
δ 7.81-7.91 (m, 4H), 7.55 (d, J=4.1 Hz, 1H), 6.90 (bs, 1H), 3.89 (s, 3H), 2.40 (s, 3H).
LC/MS (ESI) 483.

Synthetic Example 117

Synthesis of 5-{[(2-{1-[5-(4-chlorophenyl)-4-hydroxy-1-methyl-1H-pyrazol-3-yl]ethylidene}hydrazino)-carbonothioyl]amino}-2-thiophenecarboxylic acid From 1-[5-(4-chlorophenyl)-4-hydroxy-1-methyl-1H-pyrazol-3-yl]ethanone (37.5 mg, 0.15 mmol) and 5-hydrazinocabonothioylamino-2-thiophenecarboxylic acid (33 mg, 0.14 mmol), the desired product was obtained in the same manner as in Synthetic Example 114 as a pale yellow solid (62.0 mg, yield 83%).
$^1$H-NMR (ppm in DMSO)
δ 7.45-7.56 (m, 5H), 6.94 (bs, 1H), 3.87 (s, 3H), 2.43 (s, 3H).
LC/MS (ESI) 449.

Synthetic Example 118

Synthesis of 4-{[(2-{1-[5-(3,4-dichlorophenyl)-4-hydroxy-3-thienyl]ethylidene}hydrazino)carbonothioyl]amino}-2-chlorobenzoic acid 1) Synthesis of 4-hydrazinocabonothioylamino-2-chlorobenzoic acid To methyl 4-hydrazinocabonothioylamino-2-chlorobenzoate (1.16 mmol, 300 mg) obtained in Reference Synthetic Example 58, methanol (2.3 ml) was added, and 0.2 M aqueous sodium hydroxide (2.1 eq, 12.1 ml) was added at room temperature. After stirring of 1.5 hours at 60° C., the reactor was cooled to room temperature, and 1 M hydrochloric acid (2.1 eq, 2.43 ml) was added. The precipitated solid was recovered by filtration, washed with water and dried by means of a vacuum pump. 4-Hydrazinocabonothioylamino-2-chlorobenzoic acid was obtained as a colorless solid (262.8 mg, yield 92.6%).
$^1$H-NMR (ppm in DMSO)
δ 9.48 (bs, 1H), 8.22 (bs, 1H), 7.75-7.77 (m, 3H).
LC/MS (ESI) 245.

2) Synthesis of 4-{[(2-{1-[5-(3,4-dichlorophenyl)-4-hydroxy-3-thienyl]ethylidene}hydrazino)-carbonothioyl]amino}-2-chlorobenzoic acid From 2-(3,4-dichlorophenyl)-3-hydroxy-4-methylcarbonylthiophene (50 mg, 0.17 mmol) and 4-hydrazinocabonothioylamino-2-chlorobenzoic acid (42.8 mg, 0.17 mmol), the desired product was obtained in the same manner as in Synthetic Example 50 as a pale yellow solid (61.1 mg, yield 68%).
$^1$H-NMR (ppm in DMSO)
δ 11.20 (bs, 1H), 10.46 (bs, 1H), 8.14 (bs, 1H), 8.11 (s, 1H), 8.02 (d, J=1.9 Hz, 1H), 7.87 (d, J=8.5 Hz, 1H), 7.64-7.74 (m, 3H), 2.40 (s, 3H).
LC/MS (ESI) 513.

Synthetic Example 119

Synthesis of 4-{[(2-{1-[5-(4-trifluoromethylphenyl)-4-hydroxy-3-thienyl]ethylidene}hydrazino)-carbonothioyl]amino}-2-chlorobenzoic acid From 2-(4-trifluoromethylphenyl)-3-hydroxy-4-methylcarbonylthiophene (50.0 mg, 0.17 mmol) and 4-hydrazinocabonothioylamino-2-chlorobenzoic acid (42.9 mg, 0.17 mmol), the desired product was obtained in the same manner as in Synthetic Example 118 as a pale yellow solid (58.3 mg, yield 65%).
$^1$H-NMR (ppm in DMSO)
δ 11.22 (bs, 1H), 10.47 (bs, 1H), 8.13-8.15 (m, 2H), 8.00 (d, J=8.3 Hz, 2H), 7.87 (d, J=8.5 Hz, 1H), 7.76 (d, J=8.3 Hz, 2H), 7.65-7.68 (m, 1H), 2.41 (s, 3H).
LC/MS (ESI) 513.

Synthetic Example 120

Synthesis of 4-{[(2-{1-[5-(4-chlorophenyl)-4-hydroxy-1-methyl-1H-pyrazol-3-yl]ethylidene}hydrazino)-carbonothioyl]amino}-2-chlorobenzoic acid From 1-[5-(4-dichlorophenyl)-4-hydroxy-1-methyl-1H-pyrazol-3-yl]ethanone (37.5 mg, 0.15 mmol) and 4-hydrazinocabonothioylamino-2-chlorobenzoic acid (36.9 mg, 0.15 mmol), the desired product was obtained in the same manner as in Synthetic Example 114 as a yellow solid (59.5 mg, yield 92%).
$^1$H-NMR (ppm in DMSO)
δ 7.40-8.40 (m, 7H), 3.78-3.84 (m, 3H), 2.40 (s, 3H).
LC/MS (ESI) 477.

Synthetic Example 121

Synthesis of 5-{[(2-{1-[5-(4-chlorophenyl)-4-hydroxy-3-thienyl]ethylidene}hydrazino)carbonothioyl]amino}-2-thiophenecarboxylic acid From 2-(4-chlorophenyl)-3-hydroxy-4-methylcarbonylthiophene (25.3 mg, 0.10 mmol) and 5-hydrazinocabonothioylamino-2-thiophenecarboxylic acid (21.8 mg, 0.10 mmol), the desired product was obtained in the same manner as in Synthetic Example 50 as a pale yellow solid (37.1 mg, yield 82%).
$^1$H-NMR (ppm in DMSO)
δ 11.54 (bs, 1H), 11.13 (bs, 1H), 8.04 (s, 1H), 7.80-7.82 (m, 2H), 7.87 (d, J=4.1 Hz, 1H), 7.46-7.50 (m, 2H), 6.86-6.87 (m, 1H), 2.39 (s, 3H).
LC/MS (ESI) 451.

Synthetic Example 122

Synthesis of 4-{[(2-{1-[5-(4-chlorophenyl)-4-hydroxy-3-thienyl]ethylidene}hydrazino)carbonothioyl]amino}-2-chlorobenzoic acid From 2-(4-chlorophenyl)-3-hydroxy-4-methylcarbonylthiophene (25.2 mg, 0.1 mmol) and 4-hydrazinocabonothioylamino-2-chlorobenzoic acid (24.5 mg, 0.1 mmol), the desired product was obtained in the same manner as in Synthetic Example 50 as a pale yellow solid (41.9 mg, yield 88%).

$^1$H-NMR (ppm in DMSO)

δ 11.21 (bs, 1H), 10.47 (bs, 1H), 8.15 (s, 1H), 8.05 (s, 1H), 7.87 (d, J=8.3 Hz, 1H), 7.77-7.81 (m, 2H), 7.66 (d, J=8.3 Hz, 1H), 7.46-7.48 (m, 2H), 2.40 (s, 3H).

LC/MS (ESI) 479.

Synthetic Example 123

Synthesis of 4-{[(2-{1-[5-(4-chlorophenyl)-4-hydroxy-3-thienyl]ethylidene}hydrazino)carbonothioyl]amino}-2-nitrobenzoic acid From 2-(4-chlorophenyl)-3-hydroxy-4-methylcarbonylthiophene (21 mg, 0.083 mmol), the desired product was obtained in the same manner as in Synthetic Examples 92 and 93 as a pale yellow solid (35.2 mg, yield 86%).

$^1$H-NMR (ppm in DMSO)

δ 11.32 (bs, 1H), 10.67 (bs, 1H), 8.49 (s, 1H), 8.07 (s, 1H), 7.95-7.98 (m, 1H), 7.89 (d, J=8.4 Hz, 1H), 7.80 (d, J=8.6 Hz, 2H), 7.47 (d, J=8.6 Hz, 2H), 2.41 (s, 3H)

LC/MS (ESI) 490.

Synthetic Example 124

Synthesis of 4-{[(2-{1-[5-(3,4-dichlorophenyl)-4-hydroxy-3-thienyl]ethylidene}hydrazine)carbonothioyl]-amino}-benzenesulfonic acid potassium salt A solution of 2-(3,4-dichlorophenyl)-4-(1-hydrorazonoethyl)thiophen-3-ol (20 mg, 0.066 mmol) and 4-sulfophenyl isothiocyanate sodium salt monohydrate (25 mg, 0.099 mmol) in dimethylformamide (0.2 mL) was stirred at room temperature for 1 hour. To the reaction mixture was added ethanol (2 mL), then the precipitated solid was collected by filtration and dried by means of a vacuum pump to give a pale red solid.

To a solution of the solid in methanol (0.8 mL) was added 0.1M potassium hydroxide methanol solution (0.4 mL), then the reaction mixture was stirred at 40° C. for 10 minutes, evaporated and dried by means of a vacuum pump to give the desired product as a pale red solid. (yield 59%).

LC/MS: condition 8, retention time 5.32 (min)

LC/MS (ESI$^-$) m/z; 514, 516 [M−1]$^-$

Synthetic Examples 125-146

Table 17 shows the number of the synthetic examples (S.E.) obtained in the similar manner as described in the synthetic example 124, yields, shapes, LC/MS conditions (L.C.), LC/MS observed peaks (O.P.) and retention times (R.T.).

TABLE 17

| S.E. | yields (%) | shapes | L.C. | O.P. ESI$^+$ | O.P. ESI$^-$ | R.T. (min) |
|---|---|---|---|---|---|---|
| 125 | 65 | pale yellow solid | 8 | 515/517 | 513/515 | 4.85 |
| 126 | 74 | pale yellow solid | 3 | 481/483 | 479/481 | 3.38 |
| 127 | 81 | white solid | 8 | 480/482 | 478/480 | 5.01 |
| 128 | 87 | white solid | 2 | 478 | 476 | 3.84 |
| 129 | 72 | white solid | | | | |
| 130 | 100 | pale yellow solid | 2 | 446/448 | 444/446 | 4.30 |

TABLE 17-continued

| S.E. | yields (%) | shapes | L.C. | O.P. ESI$^+$ | O.P. ESI$^-$ | R.T. (min) |
|---|---|---|---|---|---|---|
| 131 | 87 | white solid | 2 | 478/480 | 476/478 | 3.87 |
| 132 | 50 | pale yellow solid | 3 | 442 | 440 | 3.17 |
| 133 | 89 | white solid | 3 | 490/492 | 488/490 | 3.54 |
| 134 | 94 | white solid | 3 | 490/492 | 488/490 | 3.54 |
| 135 | 59 | white solid | 3 | 496 | 494 | 3.55 |
| 136 | 62 | white solid | 3 | 440 | 438 | 3.47 |
| 137 | 85 | pale yellow solid | 3 | 440 | 438 | 3.49 |
| 138 | 90 | yellow solid | 3 | 475 | 473 | 3.40 |
| 139 | 100 | white solid | 2 | 513 | 511 | 3.74 |
| 140 | 95 | white solid | 2 | 513/515 | 511/513 | 3.82 |
| 141 | 60 | pale yellow solid | 3 | 446/448 | 444/446 | 3.45 |
| 142 | 74 | pale yellow solid | 3 | 481/483 | 479/481 | 3.37 |
| 143 | 81 | pale yellow solid | 3 | 525/527 | 523/525 | 3.45 |
| 144 | 83 | white solid | 3 | 515 | 513 | 3.45 |
| 145 | 76 | pale yellow solid | 8 | 531 | 529 | 4.85 |
| 146 | 83 | pale yellow solid | 6 | 503 | 501 | 3.60 |
| 147 | | pale yellow solid | | | | |

Synthetic Example 148

Synthesis of 4-{[(2-{1-[5-(3,4-dichlorophenyl)-4-hydroxy-3-thienyl]ethylidene}hydrazine)carbonothioyl]-amino}-phenol To a solution of 4-aminophenol (11 mg, 0.099 mmol) in dimethylformamide (0.2 mL) was added N,N'-thiocarbonyl diimidazole (20 mg, 0.112 mmol), and the reaction mixture was stirred at room temperature for 0.5 hour. To the resultant mixture, 2-(3,4-dichlorophenyl)-4-(1-hydrorazonoethyl)thiophen-3-ol (20 mg, 0.066 mmol) was added portionwise. The reaction mixture was stirred at 35° C. for 1 hour and quenched with methanol (2 mL) and water (2 mL), and then the precipitated solid was collected by filtration and dried by means of a vacuum pump to give the desired product as a white solid (yield 50%).

LC/MS: condition 8, retention time 5.00 (min)

LC/MS (ESI$^+$) m/z; 452, 454 [M+1]$^{30}$

LC/MS (ESI$^-$) m/z; 450, 452 [M−1]$^-$

Synthetic Examples 149-166

Table 18 shows the number of the synthetic examples (S.E.) obtained in the similar manner as described in the synthetic example 148, yields, shapes, LC/MS conditions (L.C.), LC/MS observed peaks (O.P.) and retention times (R.T.).

TABLE 18

| S.E. | yields (%) | shapes | L.C. | O.P. ESI$^+$ | O.P. ESI$^-$ | R.T. (min) |
|---|---|---|---|---|---|---|
| 149 | 67 | white solid | 8 | 466/468 | 464/466 | 4.90 |
| 150 | 67 | white solid | 8 | 452/454 | 450/452 | 4.92 |
| 151 | 85 | pale yellow solid | 8 | 479/481 | 477/479 | 4.75 |
| 152 | 40 | pale yellow solid | 8 | 515/517 | 513/515 | 4.85 |
| 153 | 73 | white solid | 8 | 528/530 | 526/528 | 4.95 |
| 154 | 59 | white solid | 8 | 492/494 | 490/492 | 4.68 |
| 155 | 34 | pale yellow solid | 2 | 474/476 | 472/474 | 3.83 |
| 156 | 31 | white solid | 8 | 479/481 | 477/479 | 4.80 |
| 157 | 26 | white solid | 3 | 491 | 489 | 3.12 |
| 158 | 62 | yellow solid | 3 | 490 | 488 | 2.82 |
| 159 | 100 | yellow solid | 3 | 527 | 525 | 3.19 |
| 160 | 70 | pale green solid | 3 | 492 | 490 | 2.95 |
| 161 | 38 | pink solid | 3 | 491 | 489 | 3.13 |

TABLE 18-continued

| S.E. | yields (%) | shapes | L.C. | O.P. ESI+ | ESI− | R.T. (min) |
|---|---|---|---|---|---|---|
| 162 | 42 | yellow solid | 2 | 490/492 | 488/490 | 3.45 |
| 163 | 65 | pale yellow solid | 2 | 492/494 | 490/492 | 3.65 |
| 164 | 92 | yellow solid | 7 | 523/525 | 521/523 | 2.94 |
| 165 | 14 | pale yellow solid | | | | |
| 166 | 40 | pale yellow solid | 2 | 598/600 | 596/598 | 4.77 |

Synthetic Example 167

Synthesis of 4-(5-chloro-2-{[(2-{1-[4-hydroxy-1-methyl-5-(4-trifluoromethylphenyl)-1,4-pyrazol-3-yl]-ethylidene}-hydrazino)carbonothioyl]amino}-phenoxy)-butyric acid To a suspension of ethyl 4-(5-chloro-2-{[(2-{1-[4-hydroxy-1-methyl-5-(4-trifluoromethylphenyl)-1H-pyrazol-3-yl]ethylidene}hydrazino)carbonothioyl]amino}-phenoxy) butyrate (74 mg, 0.12 mmol) in ethanol (3.0 mL) was added 1 M aqueous sodium hydroxide (370 µL, 0.37 mmol). After the reaction mixture was stirred at room temperature for 19 hours, 1 M hydrochloric acid (370 µL, 0.37 mmol) was added then the precipitated solid was collected by filtration, washed with chloroform and dried by means of a vacuum pump to give the desired product as a yellow solid (yield 59%).
LC/MS: condition 3, retention time 3.60 (min)
LC/MS (ESI+) m/z; 570, 572 [M+1]+
LC/MS (ESI−) m/z; 568, 570 [M−1]−

Synthetic Example 168

Synthesis of 4-(5-chloro-2-{[(2-{1-[5-(3,4-dichlorophenyl)-4-hydroxy-1-methyl-1H-pyrazol-3-yl]-ethylidene}hydrazino)carbonothioyl]amino}phenoxy)-butyric acid This compound was obtained in the similar manner as described in the reference synthetic example 167.
Yield: 50%.
Shape: white solid.
LC/MS: condition 2, retention time 4.52 (min)
LC/MS (ESI+) m/z; 570, 572 [M+1]+
LC/MS (ESI−) m/z; 568, 570 [M−1]−

Synthetic Examples 169-183

Table 19 shows the number of the synthetic examples (S.E.) obtained in the similar manner as described in the synthetic example 31, yields, shapes, LC/MS conditions (L.C.), LC/MS observed peaks (O.P.) and retention times (R.T.).

TABLE 19

| S.E. | yields (%) | shapes | L.C. | O.P. ESI+ | ESI− | R.T. (min) |
|---|---|---|---|---|---|---|
| 169 | 37 | white solid | 8 | 499/501 | 497/499 | 5.32 |
| 170 | 79 | yellow solid | 5 | 437/439 | 435/437 | 5.07 |
| 171 | 87 | pale yellow solid | | | | |
| 172 | 91 | yellow solid | 5 | 406/408 | 404/406 | 4.57 |
| 173 | 33 | white solid | 8 | 437/439 | 435/437 | 4.78 |
| 174 | 62 | white solid | 8 | 406/408 | 404/406 | 4.79 |
| 175 | 50 | white solid | 8 | 420/422 | 418/420 | 4.97 |

TABLE 19-continued

| S.E. | yields (%) | shapes | L.C. | O.P. ESI+ | ESI− | R.T. (min) |
|---|---|---|---|---|---|---|
| 176 | 51 | white solid | 5 | 435/437 | 433/435 | 4.29 |
| 177 | 62 | white solid | 5 | 420/422 | 418/420 | 5.90 |
| 178 | 75 | white solid | 7 | 522/524 | 520/522 | 3.42 |
| 179 | 89 | white solid | 5 | 454/456 | 452/454 | 4.47 |
| 180 | 86 | pale yellow solid | 3 | 406 | 404 | 3.00 |
| 181 | 49 | yellow solid | 8 | 495/497 | 493/495 | 5.08 |
| 182 | 71 | white solid | 5 | 421/423 | 419/421 | 4.92 |
| 183 | 67 | pale yellow solid | | | | |
| 184 | 80 | white solid | 3 | 397 | 395 | 3.30 |

Synthetic Example 185

Synthesis of 4-{1-[4-acetoxy-5-(4-tert-butylphenyl)thiphen-3-yl]ethylidenehydrazinocarbonyl}-2-nitro benzoic acid 1) Synthesis of acetic acid 4-acetyl-2-(4-tert-butylphenyl)thiophen-3-yl ester To a solution of 2-(4-tert-butylphenyl)-3-hydroxy-4-methylcarbonylthiophene (137 mg, 0.5 mmol) in THF (2 mL) were added triethylamine (105 µL, 0.75 mmol) and acetyl chloride (53.3 µL, 0.75 mmol). The reaction mixture was stirred at room temperature for 0.5 h. After removing solvent, the residue was diluted with AcOEt, washed with a saturated aqueous $NH_4Cl$ solution, dried over $MgSO_4$ and concentrated to give product as a brown oil (146 mg, yield 92%).
LC/MS: condition 7, retention time 3.25 (min)
LC/MS (ESI+) m/z; 317 [M+1]+

2) Synthesis of 4-{1-[4-Acetoxy-5-(4-tert-butylphenyl)thiphen-3-yl]ethylidenehydrazinocarbonyl}-2-nitro benzoic acid To a solution of acetic acid 4-acetyl-2-(4-tert-butylphenyl)thiophen-3-yl ester (63.3 mg, 0.2 mmol) and 4-hydrazinocarbonyl-2-nitrobenzoic acid (54.0 mg, 0.24 mmol) in DMF (1 mL) was added 12 M aqueous HCl solution (16.7 µL, 0.2 mmol). The reaction mixture was stirred overnight, and then water was added. The precipitated solid was collected by filtration and washed with water and $CHCl_3$ to give product as a pale yellow solid (29.1 mg, yield 28%).
LC/MS: condition 7, retention time 3.20 (min)
LC/MS (ESI+) m/z; 524 [M+1]+
LC/MS (ESI−) m/z; 522 [M−1]−

Synthetic Example 186

Synthesis of 4-{1-[4-acetoxy-5-(3,4-dichlorophenyl)thiphen-3-yl]ethylidenehydrazinocarbonyl}-2-nitrobenzoic acid 1) Synthesis of acetic acid 4-acetyl-2-(3,4-dichlorophenyl)thiophen-3-yl ester The title compound was prepared from 2-(3,4-dichlorophenyl)-3-hydroxy-4-methylcarbonylthiophene (201 mg, 0.7 mmol) following the procedure described in the synthetic example 185.
colorless solid (223 mg, yield 97%).
LC/MS: condition 7, retention time 3.09 (min)
LC/MS (ESI+) m/z; 287, 289 [M-Ac]+
LC/MS (ESI−) m/z; 285, 287 [M-Ac]−

2) Synthesis of 4-{1-[4-Acetoxy-5-(3,4-dichlorophenyl)thiphen-3-yl]ethylidenehydrazinocarbonyl}-2-nitrobenzoic acid The title compound was prepared from acetic acid 4-acetyl-2-(3,4-dichlorophenyl)thiophen-3-yl ester (39.5 mg, 0.12 mmol) and 4-hydrazinocarbonyl-2-nitrobenzoic acid (40.5 mg, 0.18 mmol) following the procedure described in the synthetic example 185.
white solid (17.5 mg, yield 27%).
LC/MS: condition 7, retention time 3.07 (min)
LC/MS (ESI$^+$) m/z; 536, 538 [M+1]$^+$
LC/MS (ESI$^-$) m/z; 534, 536 [M−1]$^-$ Synthetic Example 187

Synthesis of (2-{1-[4-Acetoxy-5-(3,4-dichlorophenyl)thiphen-3-yl]ethylidene}hydrazinecarbothioamido)-2-chlorobenzoic acid The title compound was prepared from acetic acid 4-acetyl-2-(3,4-dichlorophenyl)thiophen-3-yl ester (39.5 mg, 0.12 mmol) and 2-chloro-4-(hydrazinecarbothioamido)benzoic acid (40.5 mg, 0.132 mmol) following the procedure described in the synthetic example 185.
pale yellow solid (15.1 mg, yield 23%)
LC/MS: condition 7, retention time 3.12 (min)
LC/MS (ESI$^+$) m/z; 556, 558 [M+1]$^+$
LC/MS (ESI$^-$) m/z; 554, 556 [M−1]$^-$ Synthetic Examples 188-224

Table 20 shows the number of the synthetic examples (S.E.) obtained in the similar manner as described in the synthetic example 50, yields, shapes, LC/MS conditions (L.C.), LC/MS observed peaks (O.P.) and retention times (R.T.).

TABLE 20

| S.E. | yields (%) | shapes | L.C. | O.P. ESI$^+$ | O.P. ESI$^-$ | R.T. (min) |
|---|---|---|---|---|---|---|
| 188 | 67 | pale yellow solid | 7 | 504/506 | 502/504 | 3.19 |
| 189 | 72 | pale yellow solid | 7 | 524/526 | 522/524 | 3.19 |
| 190 | 46 | white solid | 6 | 436/438 | 434/436 | 3.45 |
| 191 | 44 | white solid | 6 | 451/453 | 449/451 | 3.77 |
| 192 | 73 | pale yellow solid | 9 | 508/510 | 506/508 | 3.42 |
| 193 | 67 | yellow solid | 5 | 456 | 454 | 4.02 |
| 194 | 49 | brown solid | 5 | 476/478 | 474/476 | 4.17 |
| 195 | 47 | pale brown solid | 8 | 510 | 508 | 5.03 |
| 196 | 44 | brown solid | 2 | 530/532 | 528/530 | 4.49 |
| 197 | 31 | pale brown solid | 2 | 462 | 460 | 4.92 |
| 198 | 29 | pale yellow solid | 2 | 403/405 | 401/403 | 4.00 |
| 199 | 75 | white solid | 2 | 435 | 433 | 3.57 |
| 200 | 86 | white solid | 2 | 404/406 | 402/404 | 3.60 |
| 201 | 60 | pale yellow solid | 2 | 394 | 392 | 4.40 |
| 202 | 42 | white solid | | | | |
| 203 | 88 | white solid | 2 | 435/437 | 433/435 | 3.62 |
| 204 | 45 | pale brown solid | 9 | 444 | 442 | 3.82 |
| 205 | 65 | pale yellow solid | 9 | 464/466 | 462/464 | 2.92 |
| 206 | 53 | pale brown solid | 9 | 494/496 | 492/494 | 4.14 |
| 207 | 78 | pale yellow solid | 3 | 514/516 | 512/514 | 3.63 |
| 208 | 70 | white solid | 2 | 444 | 442 | 4.65 |
| 209 | 97 | yellow solid | 2 | 460/462 | 458/460 | 4.79 |
| 210 | 74 | brown solid | 2 | 480/482 | 478/480 | 4.42 |
| 211 | 40 | pale yellow solid | | | | |
| 212 | 80 | yellow solid | 3 | 454 | 452 | 4.25 |
| 213 | 100 | yellow solid | 3 | 474/476 | 472/474 | 3.60 |
| 214 | 99 | pale yellow solid | 3 | 366 | 364 | 3.34 |
| 215 | 33 | pale yellow solid | | | | |
| 216 | 40 | pale yellow solid | | | | |
| 217 | 67 | yellow solid | 8 | 430/432 | 428/430 | 4.78 |
| 218 | 60 | pale yellow solid | 8 | 473/475 | 471/473 | 4.92 |
| 219 | 66 | pale yellow solid | 8 | 479/481 | 477/479 | 5.10 |
| 220 | 84 | pale yellow solid | 8 | 489/491 | 487/489 | 4.78 |
| 221 | 46 | pale yellow solid | 8 | 495/497 | 493/495 | 4.82 |
| 222 | 50 | white solid | 8 | 465/467 | 463/465 | 5.07 |
| 223 | 47 | white solid | 8 | 481/483 | 479/481 | 4.93 |
| 224 | 57 | yellow solid | 2 | 494/496 | 492/494 | 4.52 |

Synthetic Example 225

Synthesis of quinoxaline-6-carboxylic acid {1-[5-(3,4-dichlorophenyl)-4-hydroxythiophen-3-yl]-ethylidene}-hydrazide A solution of 2-(3,4-dichlorophenyl)-3-hydroxy-4-methylcarbonylthiophene (25 mg, 0.087 mmol) and quinoxaline-6-carboxylic acid hydrazide (25 mg, 0.087 mmol) in dimethylsulfoxide (0.5 mL) was stirred at 100° C. for 12 hours and the reaction mixture was concentrated under the reduced pressure. To the residue was added chloroform and the precipitated solid was collected by filtration and dried by means of a vacuum pump to give the desired product as a pale yellow solid (yield 10%).
LC/MS: condition 8, retention time 3.77 (min)
LC/MS (ESI$^+$) m/z; 457, 459 [M+1]$^+$
LC/MS (ESI$^-$) m/z; 455, 457 [M−1]$^-$ Synthetic Examples 226-233

Table 21 shows the number of the synthetic examples (S.E.) obtained in the similar manner as described in the synthetic example 225, yields, shapes, LC/MS conditions (L.C.), LC/MS observed peaks (O.P.) and retention times (R.T.).

TABLE 21

| S.E. | yields (%) | shapes | L.C. | O.P. ESI$^+$ | O.P. ESI$^-$ | R.T. (min) |
|---|---|---|---|---|---|---|
| 226 | 45 | orange solid | 5 | 539/541 | 537/539 | 3.70 |
| 227 | 53 | orange solid | 5 | 525/527 | 523/525 | 3.63 |
| 228 | 84 | yellow solid | 2 | 462 | 460 | 3.74 |
| 229 | 49 | yellow solid | 6 | 480 | 478 | 3.54 |
| 230 | 80 | white solid | 9 | 464 | | 3.09 |
| 231 | 85 | yellow solid | 3 | 430/432 | 428/430 | 3.50 |
| 232 | 95 | red solid | 2 | 476/478 | 474/476 | 4.35 |
| 233 | 71 | pale yellow solid | 8 | 424 | 422 | 4.78 |

Synthetic Example 234

Synthesis of 1H-benzoimidazole-5-carboxylic acid {1-[5-(3,4-dichloro-phenyl)-4-hydroxy-thiophen-3-yl]-ethylidene}-hydrazide To a suspension of 1H-benzoimidazole-5-carboxylic acid (24 mg, 0.15 mmol) in toluene (0.5 mL) was added thionyl chloride (11 μL, 0.15 mmol). The reaction mixture was stirred at 100° C. for 1 hour and concentrated under the reduced pressure. To the residue was added a solution of 2-(3,4- dichlorophenyl)-4-(1-hydrorazonoethyl)thiophen-3-ol (30 mg, 0.10 mmol) in dimethylacetamide (0.6 mL) and the reaction mixture was stirred at room temperature for 2 hours. To the reaction mixture was added methanol and water then the precipitated solid was filtrated and dried by means of a vacuum pump to give the desired product as a gray solid (yield 38%).
LC/MS: condition 8, retention time 4.27 (min)
LC/MS (ESI$^+$) m/z; 445, 447 [M+1]$^+$
LC/MS (ESI$^-$) m/z; 443, 445 [M−1]$^-$ Synthetic Example 235

Synthesis of N'-{1-[5-(3,4-dichlorophenyl)-4-hydroxy-thiophen-3-yl]ethylidene}-4-methylisoxazole-5-carbohydrazide This compound was obtained in the similar manner as described in the reference synthetic example 234.
Yield: 46%.
Shape: yellow solid.
LC/MS: condition 8, retention time 5.02 (min)
LC/MS (ESI$^+$) m/z; 410, 412 [M+1]$^+$
LC/MS (ESI$^-$) m/z; 408, 410 [M−1]$^-$ Synthetic Example 236

Synthesis of 2-chloro-N'-{1-[5-(3,4-dichlorophenyl)-4-hydroxythiophen-3-yl]ethylidene}nicotinohydrazide This compound was obtained in the similar manner as described in the reference synthesis example 234.
Yield: 50%.
Shape: pale yellow solid.
LC/MS: condition 8, retention time 5.10 (min)
LC/MS (ESI$^1$) m/z; 440, 442 [M+1]$^+$
LC/MS (ESI$^-$) m/z; 438, 440 [M−1]$^-$ Synthetic Example 237

Synthesis of 4-hydroxymethyl-3-nitrobenzoic acid {1-[5-(4-tert-butylphenyl)-4-hydroxythiophen-3-yl]ethylidene}-hydrazide 1) Synthesis of 4-hydroxymethyl-3-nitrobenzoic acid 4-Bromomethyl-3-nitrobenzoic acid (3.00 g, 11.5 mmol) and sodium carbonate (6.12 g, 57.7 mmol) were dissolved in water (40 mL) and acetone (40 mL). The reaction mixture was refluxed for 4 hours and then concentrated under reduced pressure to remove acetone. The residue was washed with diethyl ether three times. The aqueous layer was acidified with 6M hydrochloric acid, and then extracted with ethyl acetate three times. The combined organic layer was washed with water and brine, dried with sodium sulfate, filtered, concentrated under the reduced pressure. The residue was dried by means of a vacuum pump to give the desired product as brown solid (2.17 g, yield 95%).
LC/MS: condition 5, retention time 1.59 (min)
LC/MS (ESI$^-$) m/z; 196 [M−1]$^-$ 2) Synthesis of 4-(tert-butyldimethylsilanyloxymethyl)-3-nitrobenzoic acid To a solution of 4-hydroxymethyl-3-nitrobenzoic acid (1.50 g, 7.62 mmol) and imidazole (1.55 g, 22.8 mmol) in dimethylformamide (20 mL) was added tert-butyldimethylsilyl chloride (2.23 g, 14.8 mmol), and then the reaction mixture was stirred at room temperature for 15 hours. To the reaction mixture, saturated ammonium chloride aqueous solution was added and acidified with 1 M hydrochloric acid. The aqueous layer was extracted with ethyl acetate three times. The combined organic layer was washed with saturated ammonium chloride aqueous solution, water and brine, dried with sodium sulfate, filtered, and concentrated under the reduced pressure. The residue was purified by silica gel column chromatography to give the desired product as a white solid (1.73 g, yield 73%).
LC/MS: condition 5, retention time 5.10 (min)
LC/MS (ESI$^-$) m/z; 310 [M−1]$^-$ 3) Synthesis of 4-(cert-butyldimethylsilanyloxymethyl)-3-nitrobenzoic acid hydrazide To a solution of 4-(tert-butyl-dimethylsilanyloxy-methyl)-3-nitrobenzoic acid (1.00 g, 3.22 mmol), N,N,N',N'-tetramethylfluoroformamidinium hexafluoro-phosphate (852 mg, 3.23 mmol) and triethylamine (0.90 mL, 6.44 mmol) in dimethylformamide (13 mL), hydrazine monohydrate (0.31 mL, 6.43 mmol) was added at 0° C., and then the reaction mixture was stirred at 0° C. for 8 hours. To the reaction mixture was added water (10 mL), then the precipitated solid was filtrated and dried by means of a vacuum pump to give the desired product as a pale gray solid (461 mg, yield 44%).
LC/MS: condition 5, retention time 4.14 (min)
LC/MS (ESI$^+$) m/z; 326 [M+1]$^+$
LC/MS (ESI$^-$) m/z; 324 [M−1]$^-$ 4) Synthesis of 4-hydroxymethyl-3-nitrobenzoic acid {1-[5-(4-tert-butylphenyl)-4-hydroxythiophen-3-yl]-ethylidene}hydrazide A solution of 2-(4-tert-butylphenyl)-3-hydroxy-4-methylcarbonylthiophene (27.8 mg, 0.10 mmol), 4-(tert-butyl-dimethylsilyloxymethyl)-3-nitrobenzoic acid hydrazide (34.9 mg, 0.11 mmol) and p-toluenesulfonic acid monohydrate (5.7 mg, 0.03 mmol) in isopropanol (1.0 mL) was stirred at 95° C. for 7 hours. The precipitated solid was collected by filtration and dried by means of a vacuum pump to give the desired product as yellow solid (34.8 mg, yield 73%).
LC/MS: condition 5, retention time 5.53 (min)
LC/MS (ESI$^+$) m/z; 468 [M+1]$^+$
LC/MS (ESI$^-$) m/z; 466 [M−1]$^-$ Synthetic Example 238

Synthesis of N'-[1-{(5-(3,4-dichlorophenyl)-4-hydroxy-thiophen-3-yl}ethylidene]-2-oxo-2,3-dihydro-1H-benzo-[d]imidazole-5-carbohydrazide To a suspension of 3,4-diamino-N'-[1-{5-(3,4-dichlorophenyl)-4-hydroxythiophen-3-yl}ethylidene]-benzohydrazide (30 mg, 0.064 mmol, see the synthetic example 176) in tetrahydrofuran (3.0 mL) was added sodium tert-butoxide (12 mg, 0.13 mmol) and N,N'-carbonyl diimidazole (15 mg, 0.095 mmol). The reaction mixture turned clear orange and was stirred at room temperature for 16 hours, and then N,N'-carbonyl diimidazole (15 mg, 0.095 mmol) was added. The reaction mixture was stirred further for 12 hours, acidified with 1M aqueous HCl solution (0.7 mL) and concentrated under the reduced pressure. To the residue was added water (4 mL), then the precipitated solid was collected by filtration and dried by means of a vacuum pump to give the desired product as a pale yellow solid (yield 97%).

¹H-NMR (DMSO-d₆) δ (ppm): 2.46 (s, 3H), 7.05 (d, J=8.0 Hz, 1H), 7.51 (s, 1H), 7.57-7.73 (m, 3H), 8.06 (s, 1H), 8.07 (s, 1H), 10.93 (s, 1H), 11.01 (s, 1H), 11.23 (s, 1H), 12.92 (br s, 1H).

Synthetic Example 239

Synthesis of N'-[1-{5-(4-tert-butylphenyl)-4-hydroxythiophen-3-yl}ethylidene]-4-(4-methylpiperazinecarbonyl)-3-nitrobenzohydrazide To a N-methyl-2-pyrrolidinone (1.0 mL) solution of 2-nitro-4-[(2-{1-[5-(4-t-butylphenyl)-4-hydroxy-3-thienyl]-ethylidene}hydrazino)carbonyl]benzoic acid (50 mg, 0.10 mmol, see the synthetic example 47) and triethylamine (16 μL, 0.11 mmol) was added isobutyl chloroformate (26 μL, 0.20 mmol) at 0° C. The reaction mixture was stirred for 2 hours at this temperature, and then N-methyl piperazine (45 μL, 0.40 mmol) was added. After stirring for 1 hour at room temperature, the reaction mixture was acidified with 1M aqueous HCl solution (1.0 mL) and concentrated under the reduced pressure. To the residue was added water, then the precipitate was collected by filtration, washed with water, isopropanol and methanol, then dried by means of a vacuum pump to give the desired product as a pale yellow solid (yield 10%).

LC/MS: condition 6, retention time 2.57 (min)
LC/MS (ESI⁺) m/z; 564 [M+1]⁺
LC/MS (ESI⁻) m/z; 562 [M−1]⁻

Synthetic Example 240

Synthesis of N'-[1-{5-(3,4-dichlorophenyl)-4-hydroxythiophen-3-yl}ethylidene]-2-thioxo-2,3-dihydro-1H-benzo[d]imidazole-5-carbohydrazide To a suspension of 3,4-diamino-N'-[1-{5-(3,4-dichlorophenyl)-4-hydroxythiophen-3-yl}ethylidene]benzohydrazide (30 mg, 0.064 mmol, see the synthetic example 176) in tetrahydrofuran (3.0 mL) was added sodium tert-butoxide (12 mg, 0.13 mmol) and N,N'-thiocarbonyldiimidazole (23 mg, 0.13 mmol). The reaction mixture turned clear orange and was stirred at room temperature for 16 hours, and then was acidified with 1M aqueous HCl solution (1.0 mL) and concentrated under the reduced pressure. The precipitated solid was collected by filtration, washed with chloroform, washed with methanol and dried by means of a vacuum pump to give the desired product as a pale brown solid (yield 52%).

¹H-NMR (DMSO-d₆) δ (ppm): 2.5 (s, 3H, overlapped by DMSO-d₆), 7.26 (d, J=8.3 Hz, 1H), 7.64 (d, J=8.5 Hz, 1H), 7.69 (dd, J=8.5&1.7 Hz, 1H), 7.71 (s, 1H), 7.77 (d, J=8.3 Hz, 1H), 8.06 (d, J=1.7 Hz, 1H), 8.09 (s, 1H), 11:37 (s, 1H), 14.85 (br s, 1H), 14.87 (br s, 1H).

The structural formulae of the compounds obtained in the Synthetic Examples are given below.

SYNTHETIC EX. 1

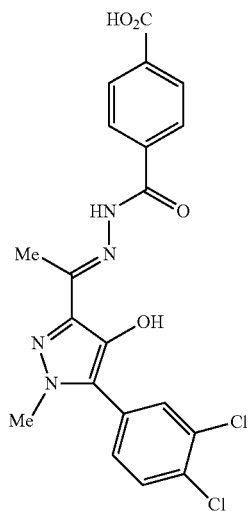

SYNTHETIC EX. 2

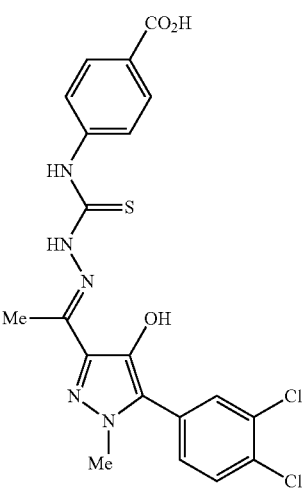

SYNTHETIC EX. 3

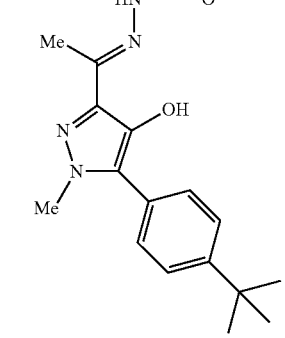

SYNTHETIC EX. 4
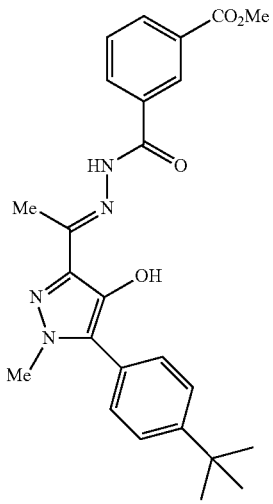
SYNTHETIC EX. 5
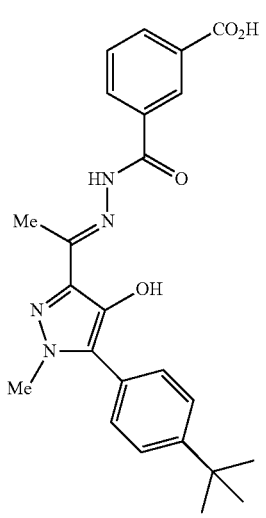
SYNTHETIC EX. 6
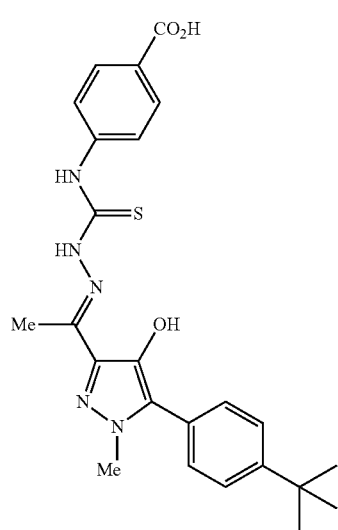
SYNTHETIC EX. 7
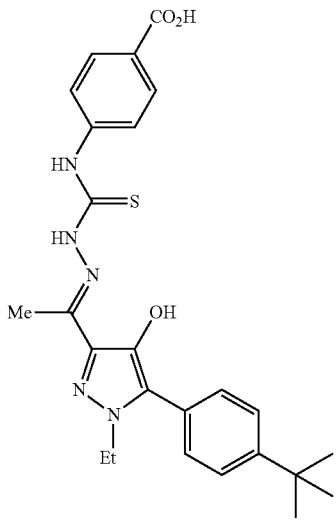
SYNTHETIC EX. 8
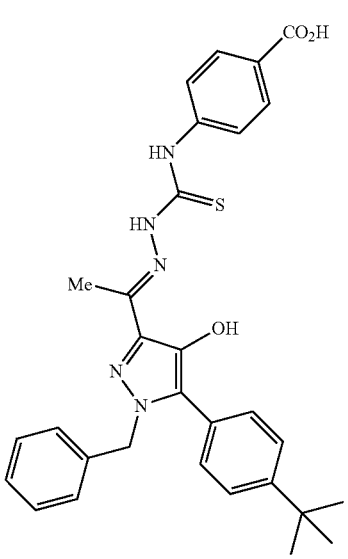
SYNTHETIC EX. 9
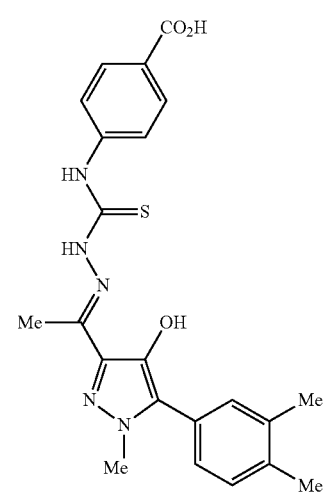

SYNTHETIC EX. 10
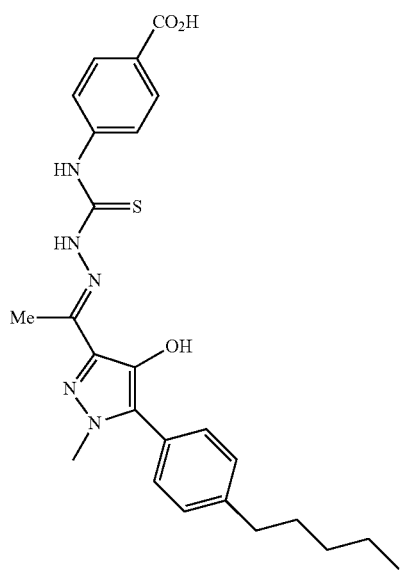
SYNTHETIC EX. 11
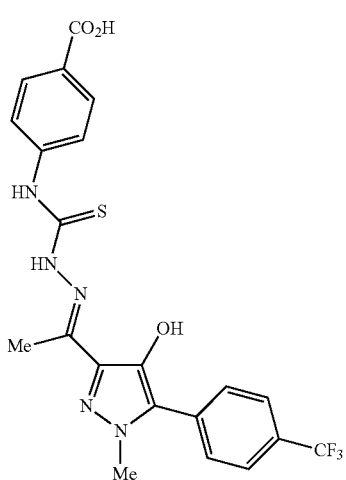
SYNTHETIC EX. 12
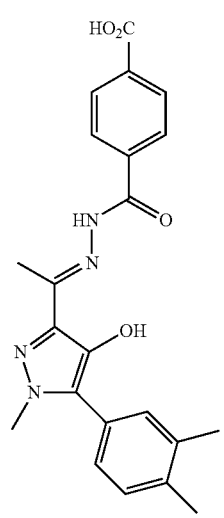
SYNTHETIC EX. 13
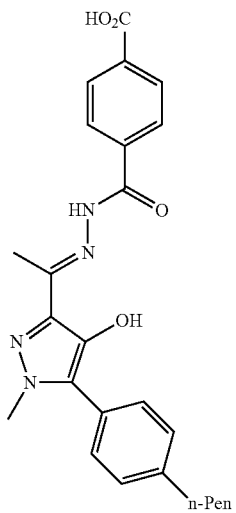
SYNTHETIC EX. 14
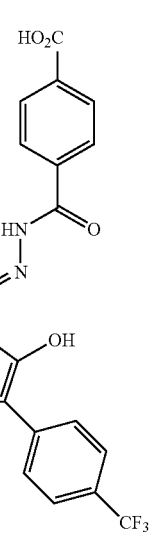
SYNTHETIC EX. 15
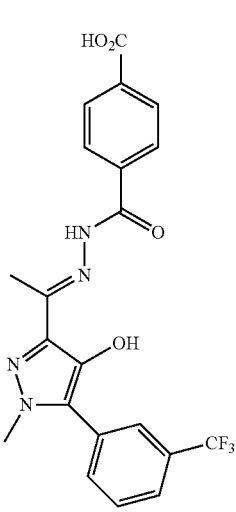

SYNTHETIC EX. 16
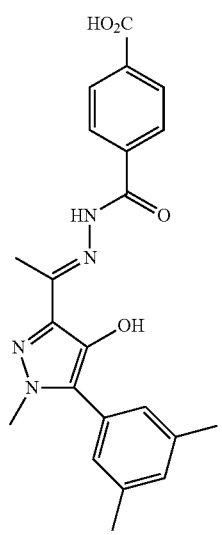
SYNTHETIC EX. 17
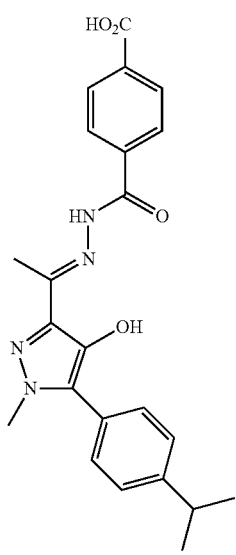
SYNTHETIC EX. 18
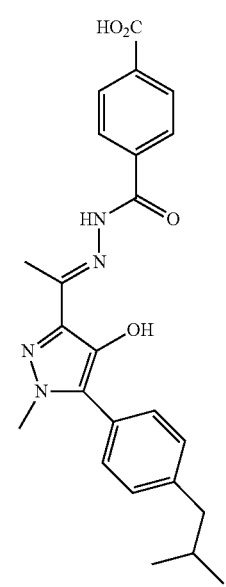
SYNTHETIC EX. 19
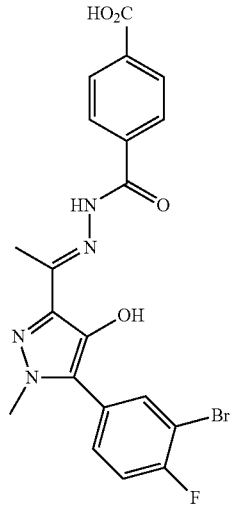
SYNTHETIC EX. 20
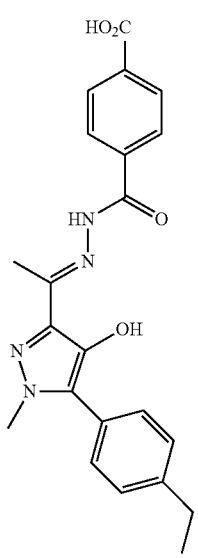
SYNTHETIC EX. 21
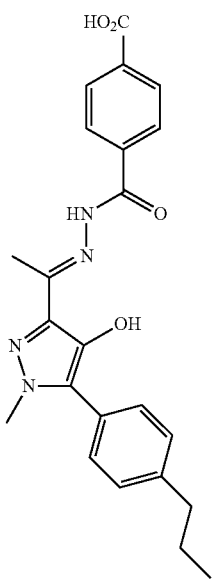

SYNTHETIC EX. 22
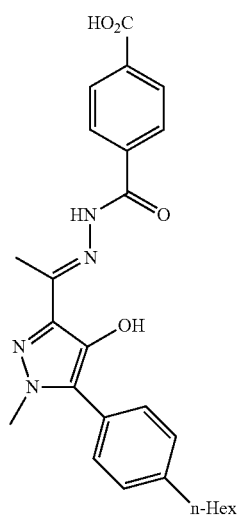
SYNTHETIC EX. 23
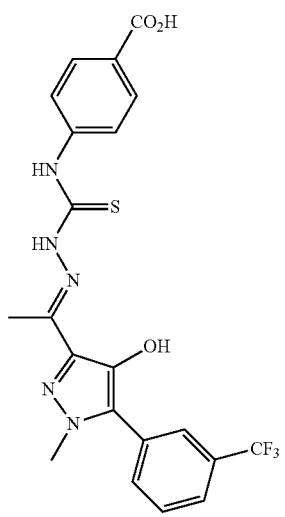
SYNTHETIC EX. 24
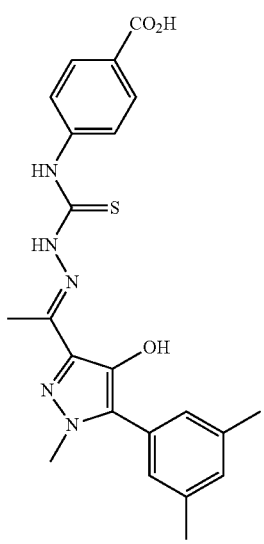
SYNTHETIC EX. 25
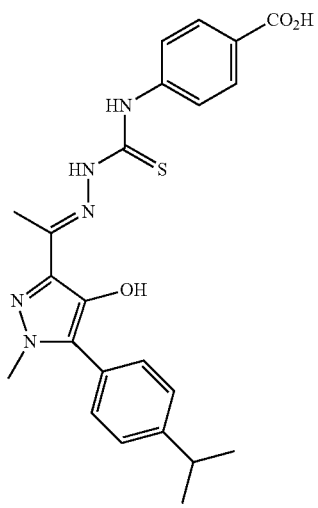
SYNTHETIC EX. 26
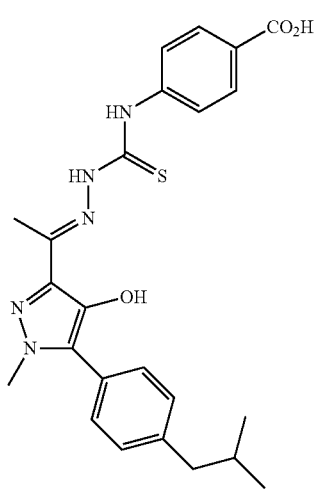
SYNTHETIC EX. 27
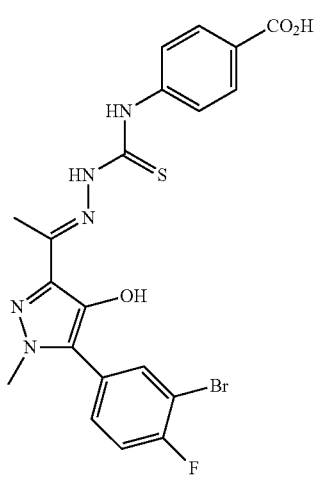

551
-continued
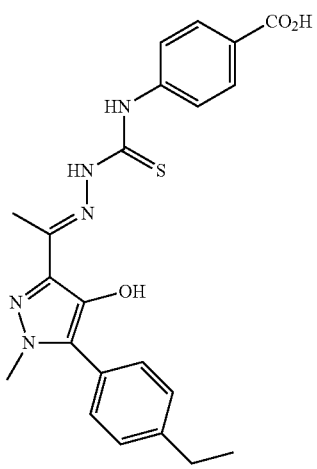
SYNTHETIC EX. 28
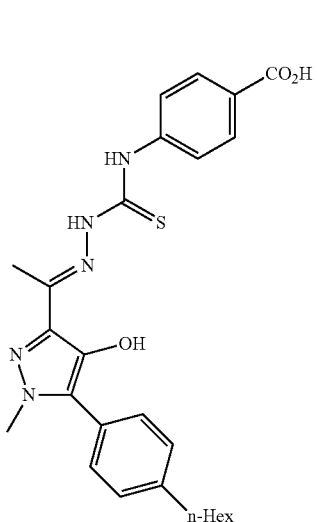
SYNTYHETIC EX. 29
SYNTHETIC EX. 30
552
-continued
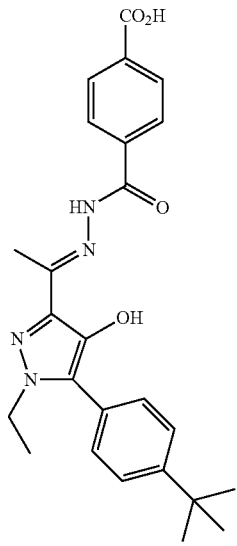
SYNTHETIC EX. 31
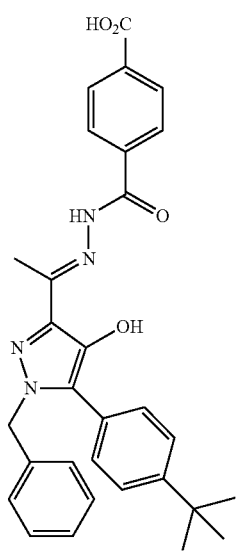
SYNTHETIC EX. 32
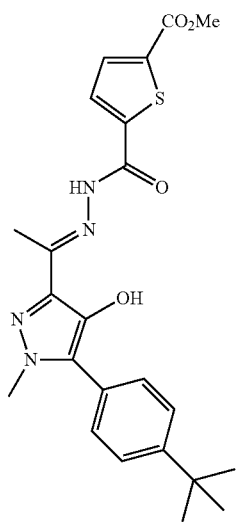
SYNTHETIC EX. 33

SYNTHETIC EX. 34
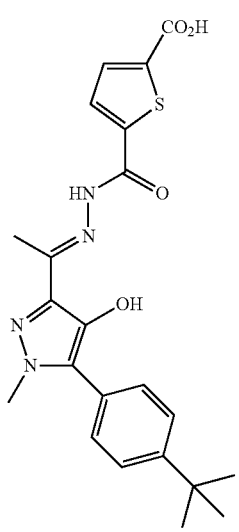
SYNTHETIC EX. 35
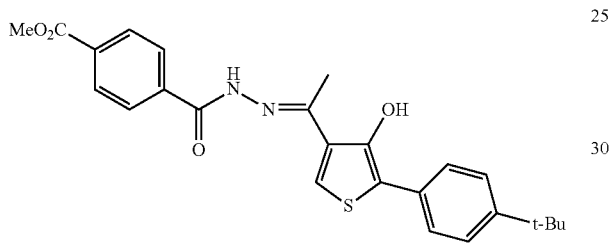
SYNTHETIC EX. 36
SYNTHETIC EX. 37
SYNTHETIC EX. 38
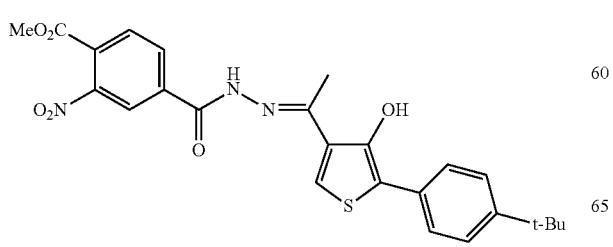
SYNTHETIC EX. 39
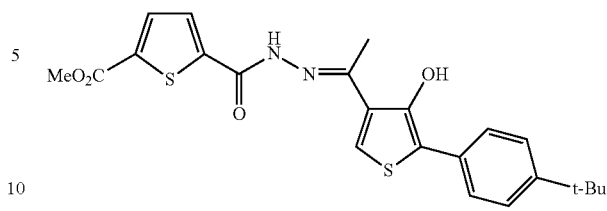
SYNTHETIC EX. 40
SYNTHETIC EX. 41
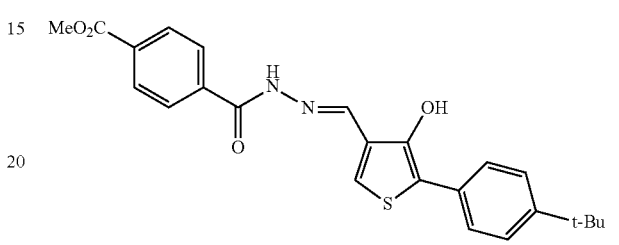
SYNTHETIC EX. 42
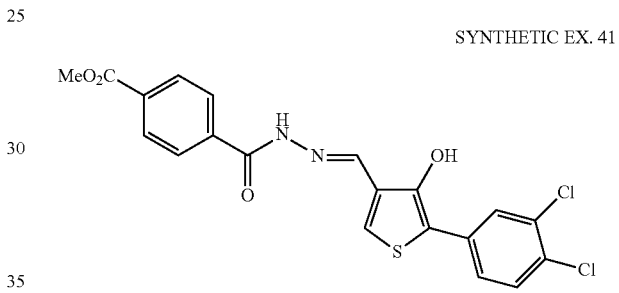
SYNTHETIC EX. 43
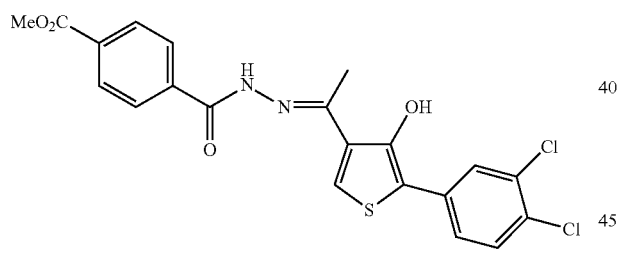
SYNTHETIC EX. 44
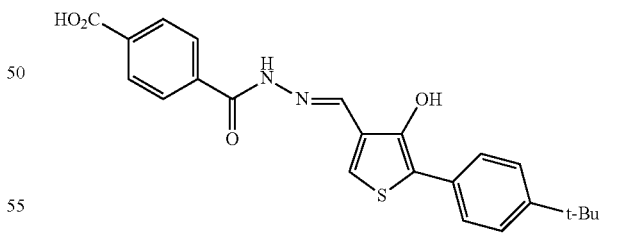
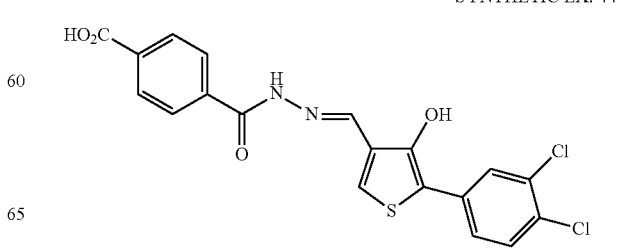
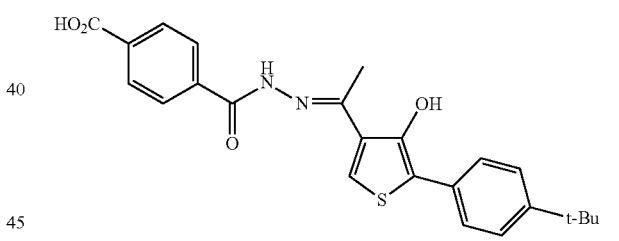

SYNTHETIC EX. 45
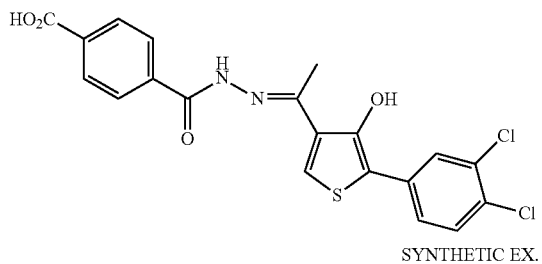
SYNTHETIC EX. 46
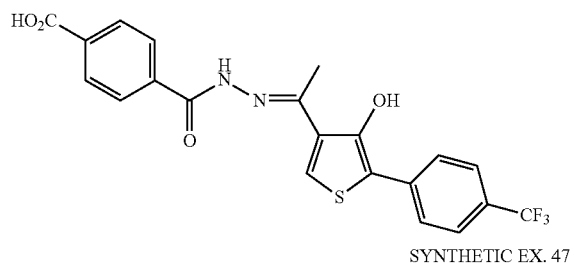
SYNTHETIC EX. 47
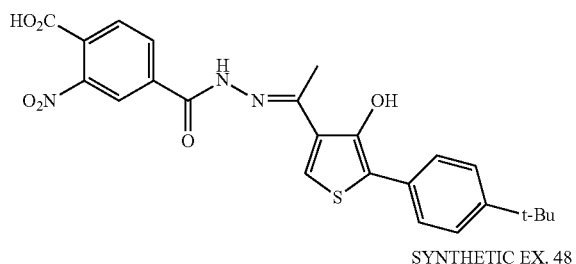
SYNTHETIC EX. 48
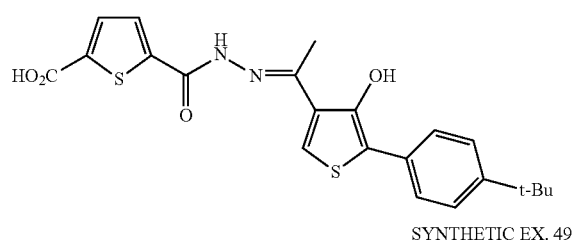
SYNTHETIC EX. 49
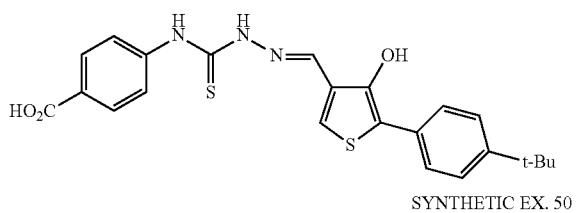
SYNTHETIC EX. 50
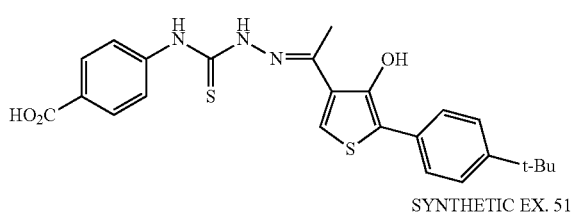
SYNTHETIC EX. 51
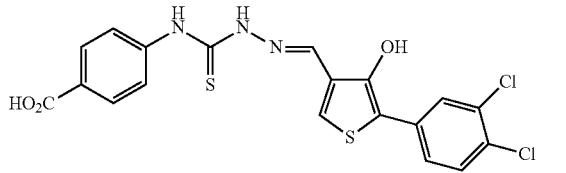
SYNTHETIC EX. 52
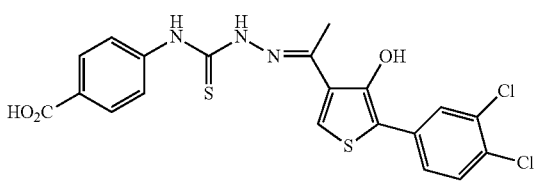
SYNTHETIC EX. 53
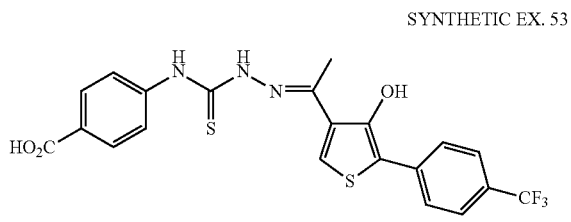
SYNTHETIC EX. 54
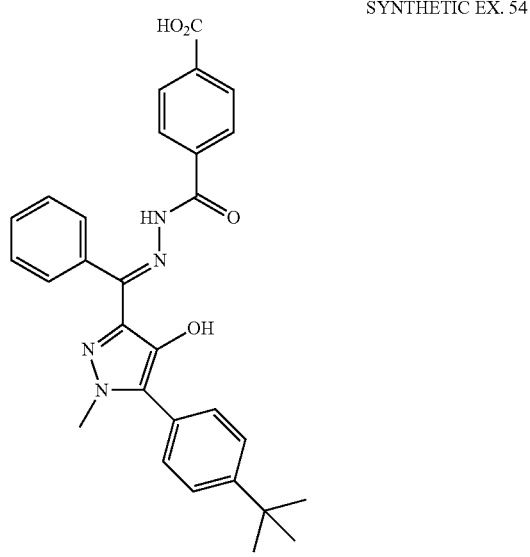
SYNTHETIC EX. 55
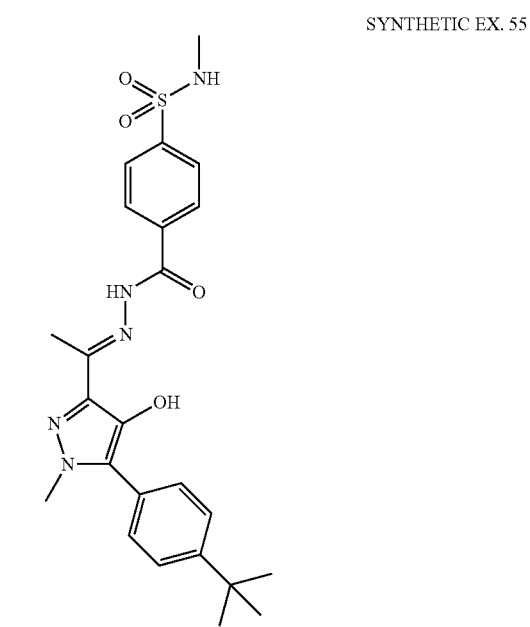

SYNTHETIC EX. 56
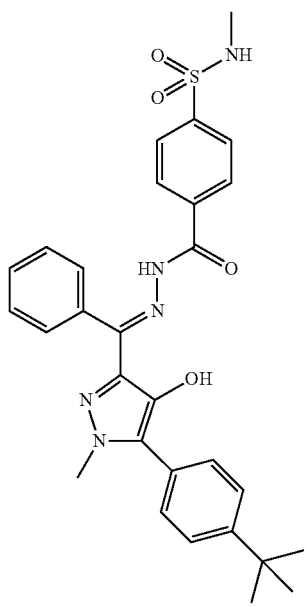
SYNTHETIC EX. 57
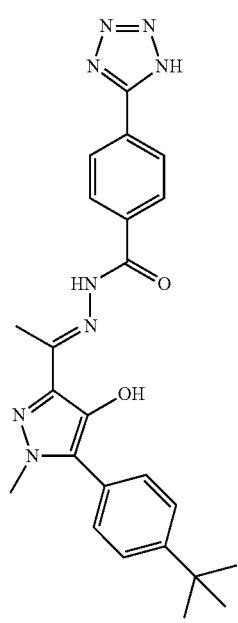
SYNTHETIC EX. 58
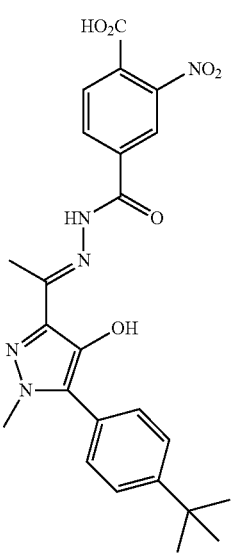
SYNTHETIC EX. 59
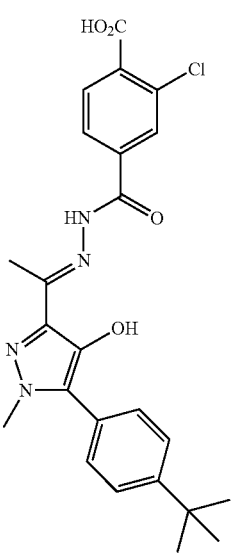
SYNTHETIC EX. 60
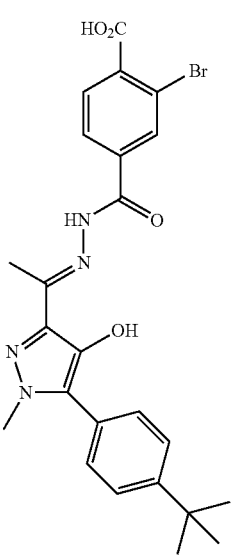

SYNTHETIC EX. 61
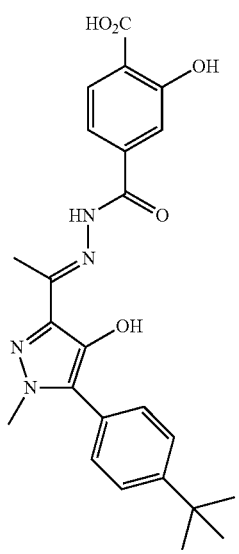
SYNTHETIC EX. 62
SYNTHETIC EX. 63
SYNTHETIC EX. 64
SYNTHETIC EX. 65
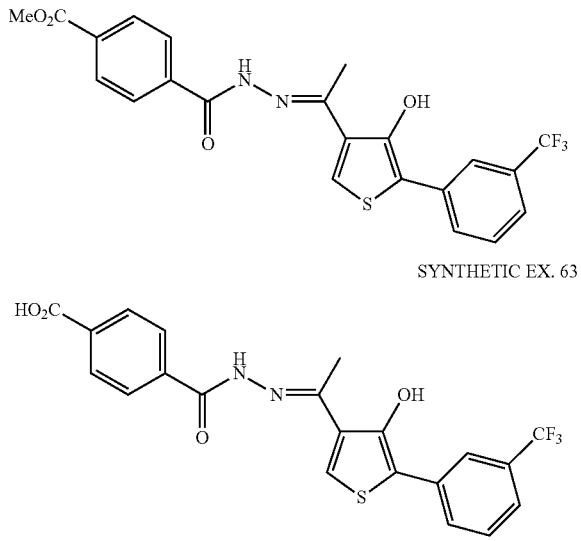
SYNTHETIC EX. 66
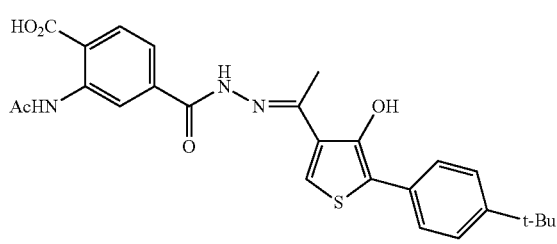
SYNTHETIC EX. 67
SYNTHETIC EX. 68
SYNTHETIC EX. 69
SYNTHETIC EX. 70
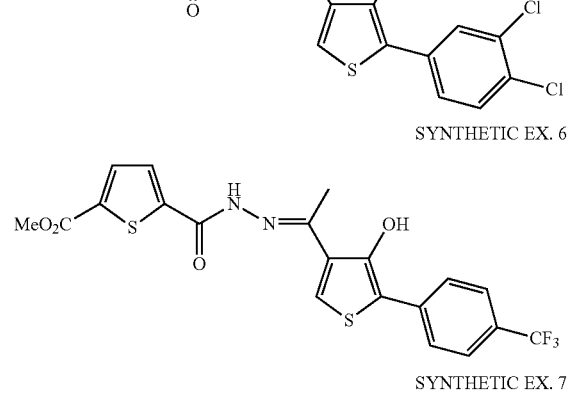
SYNTHETIC EX. 71
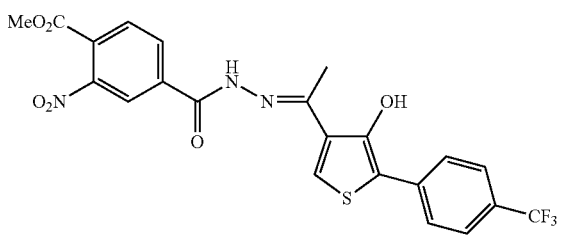
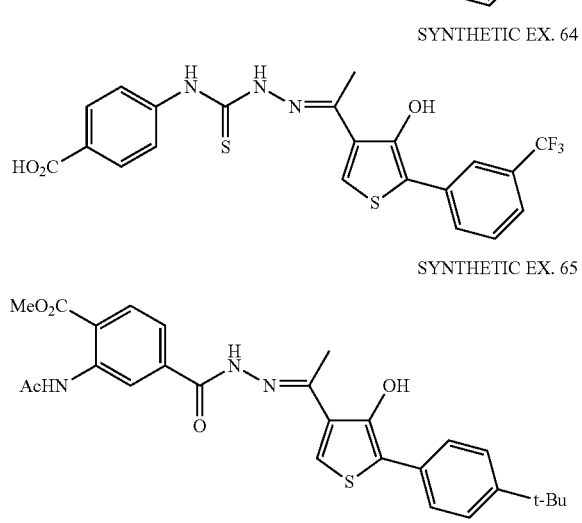

SYNTHETIC EX. 72
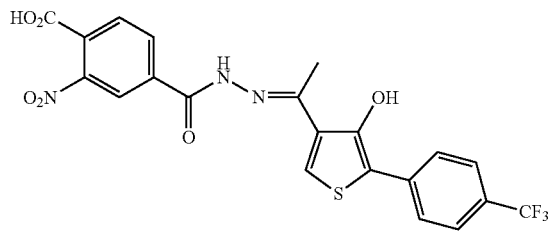
SYNTHETIC EX. 73
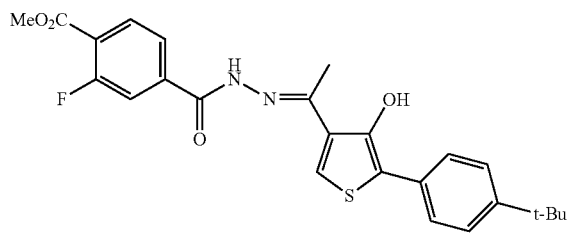
SYNTHETIC EX. 74
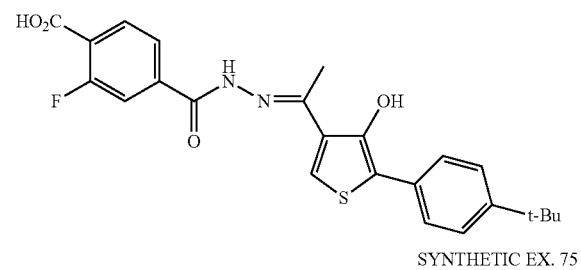
SYNTHETIC EX. 75
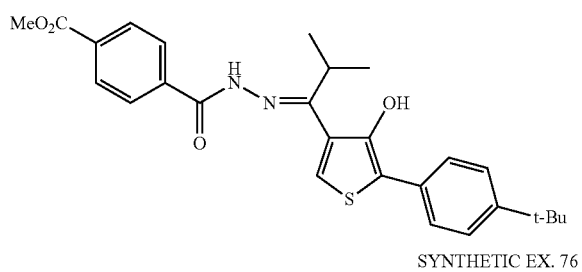
SYNTHETIC EX. 76
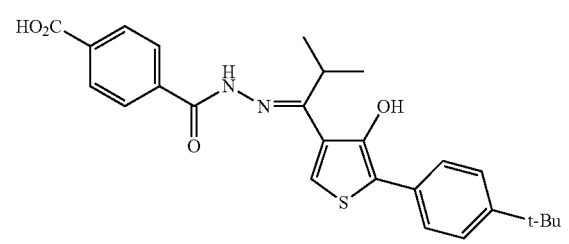
SYNTHETIC EX. 77
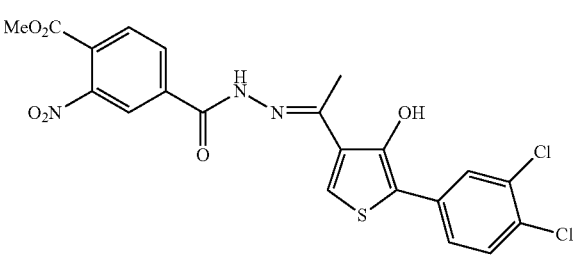
SYNTHETIC EX. 78
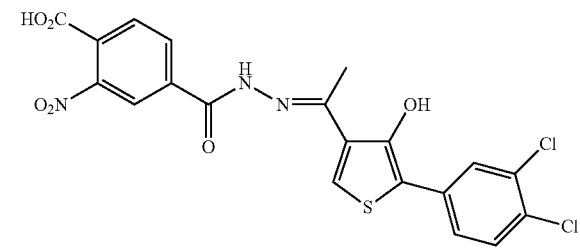
SYNTHETIC EX. 79
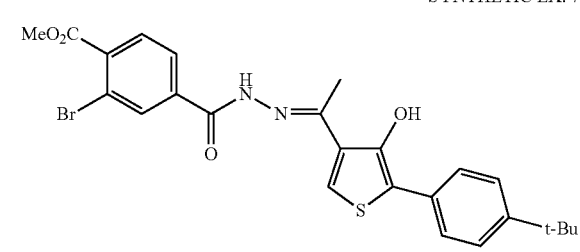
SYNTHETIC EX. 80
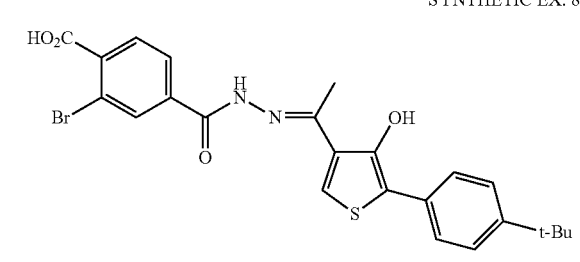
SYNTHETIC EX. 81
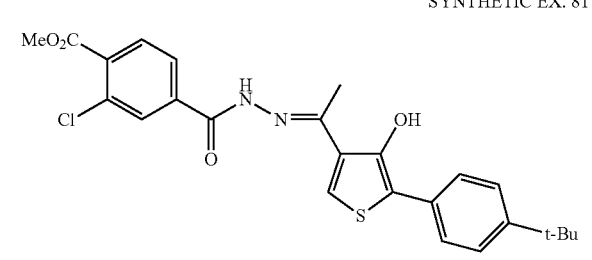
SYNTHETIC EX. 82
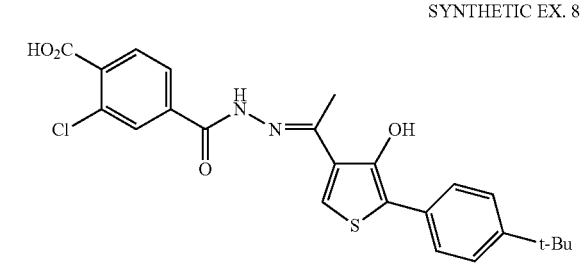
SYNTHETIC EX. 83
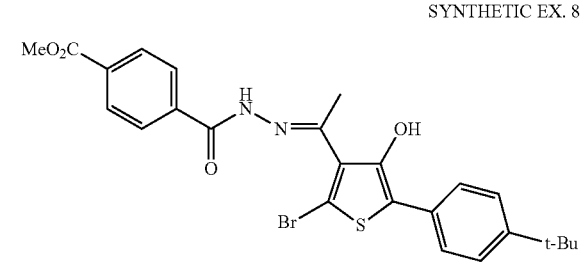

SYNTHETIC EX. 84
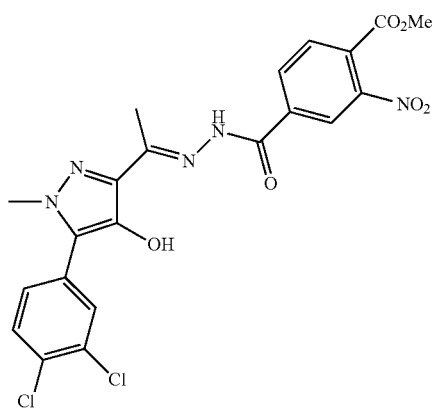
SYNTHETIC EX. 85
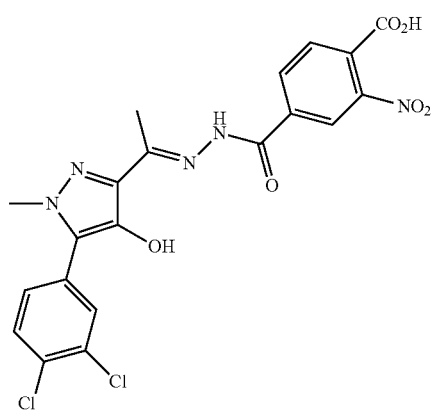
SYNTHETIC EX. 86
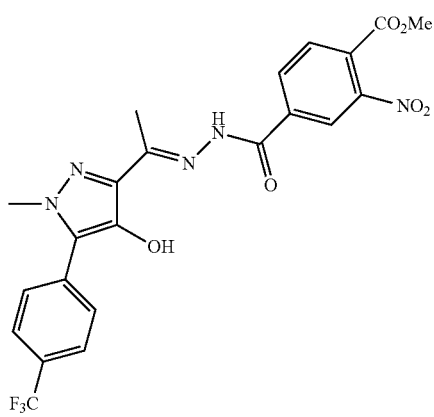
SYNTHETIC EX. 87
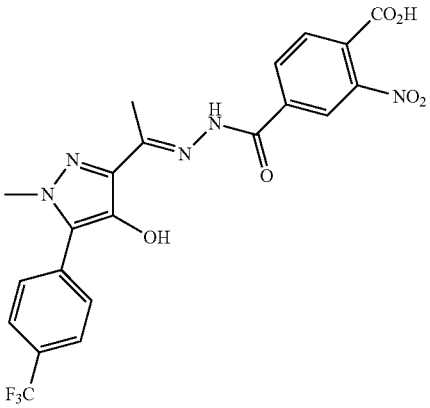
SYNTHETIC EX. 88
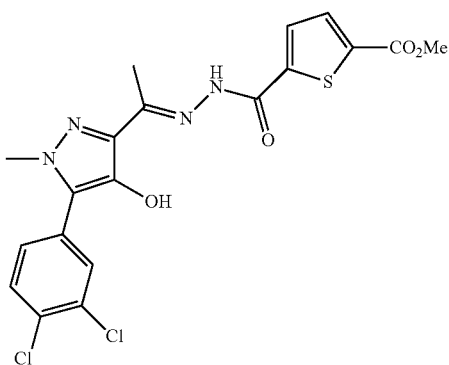
SYNTHETIC EX. 89
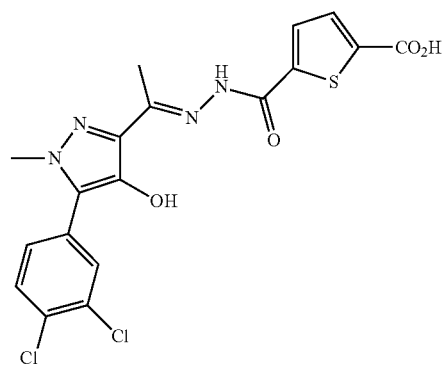
SYNTHETIC EX. 90
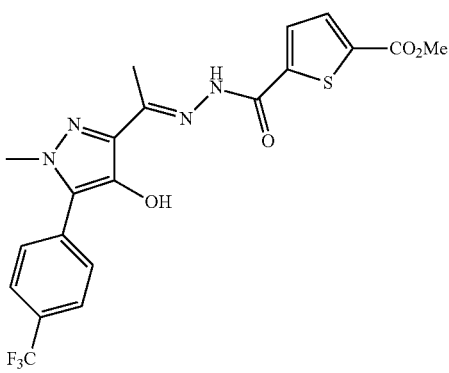

SYNTHETIC EX. 91
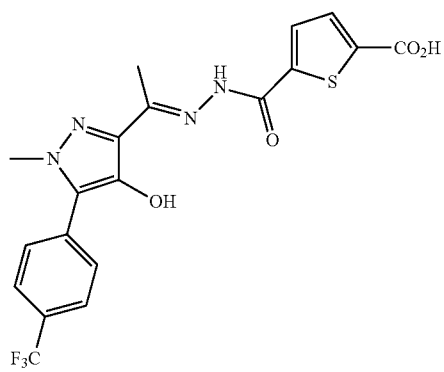
SYNTHETIC EX. 92
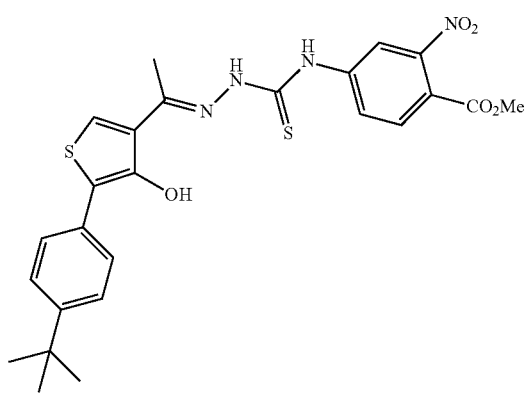
SYNTHETIC EX. 93
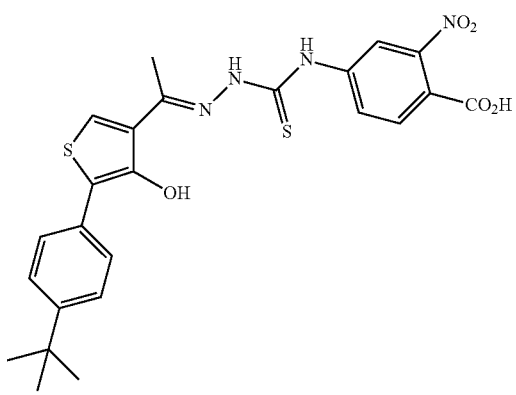
SYNTHETIC EX. 94
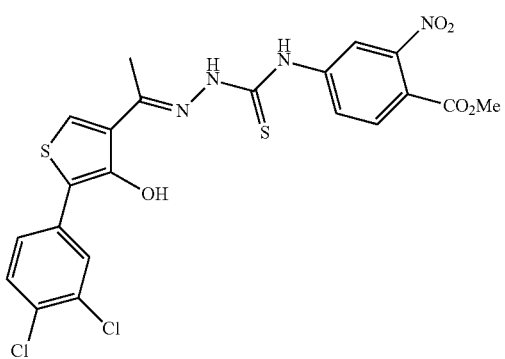
SYNTHETIC EX. 95
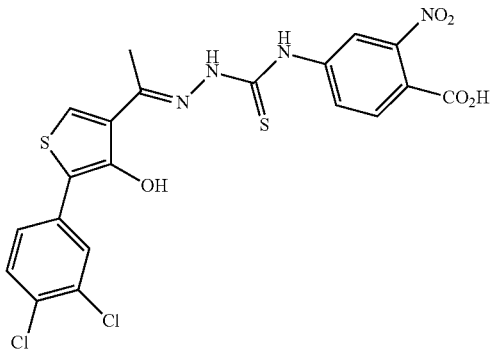
SYNTHETIC EX. 96
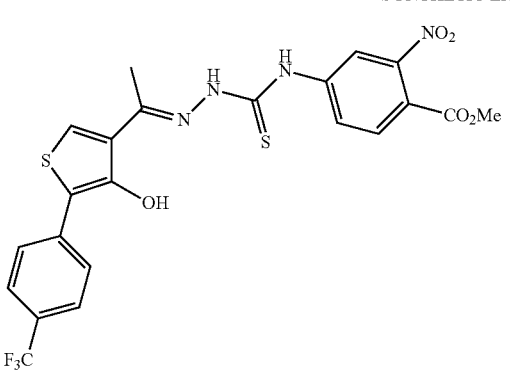
SYNTHETIC EX. 97
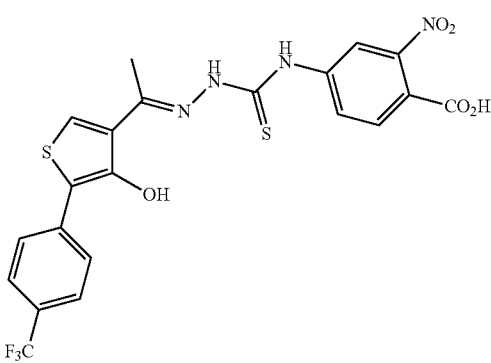
SYNTHETIC EX. 98
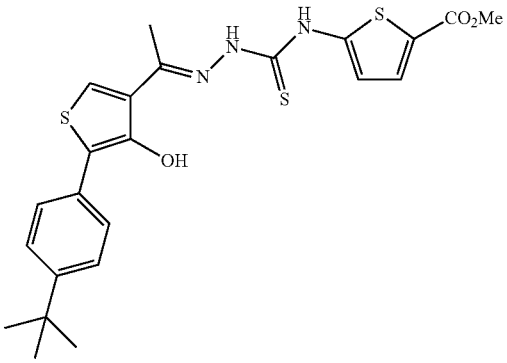

SYNTHETIC EX. 99
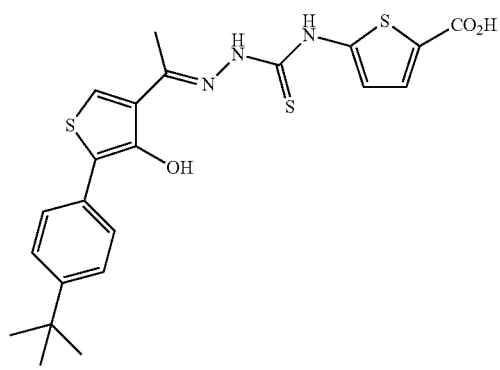
SYNTHETIC EX. 100
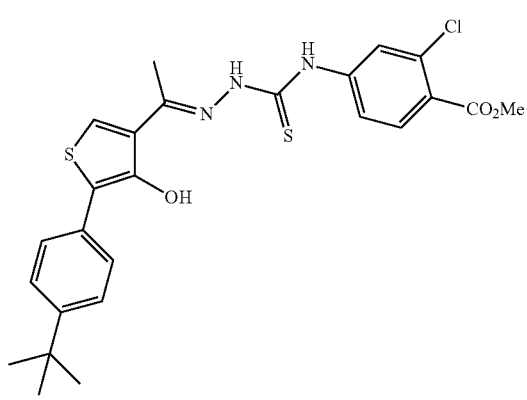
SYNTHETIC EX. 101
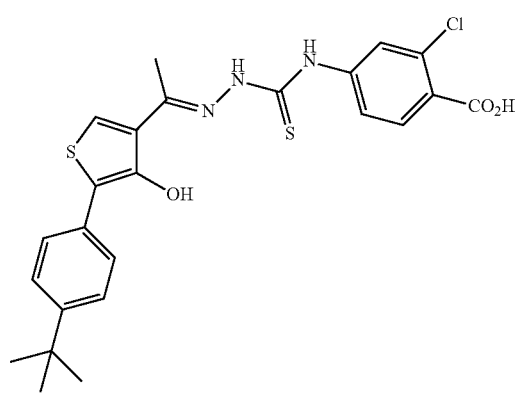
SYNTHETIC EX. 102
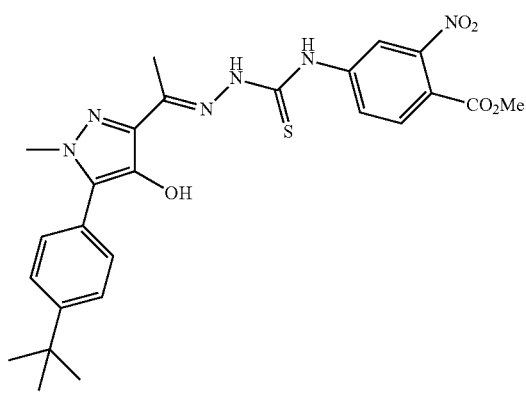
SYNTHETIC EX. 103
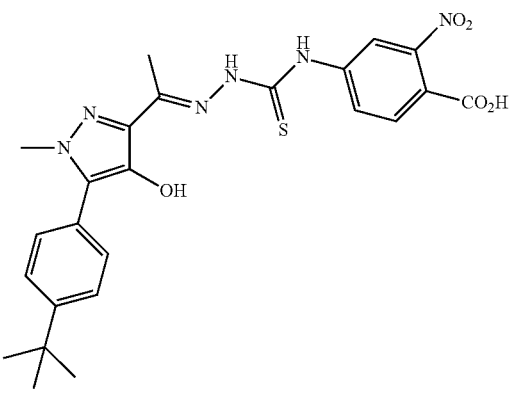
SYNTHETIC EX. 104
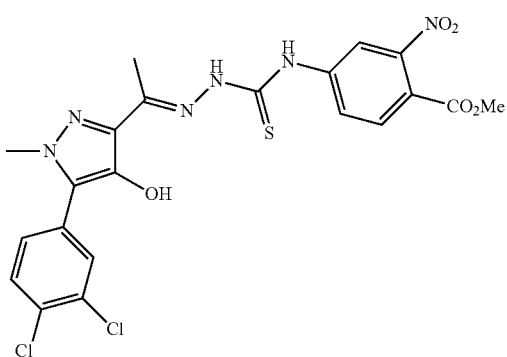
SYNTHETIC EX. 105
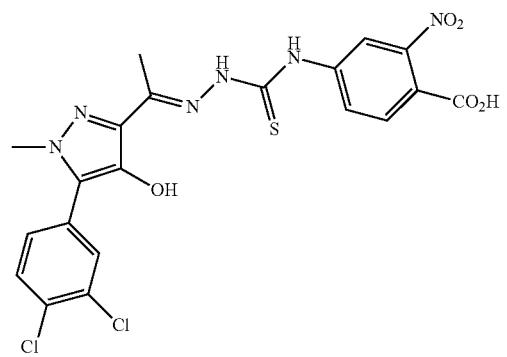
SYNTHETIC EX. 106
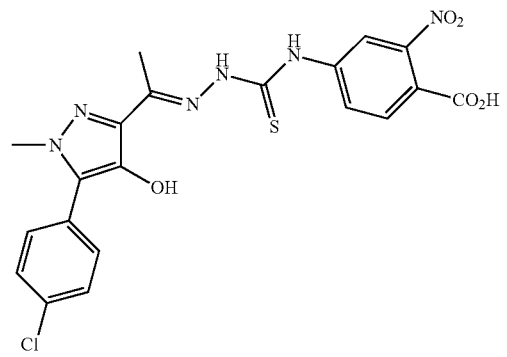

SYNTHETIC EX. 107
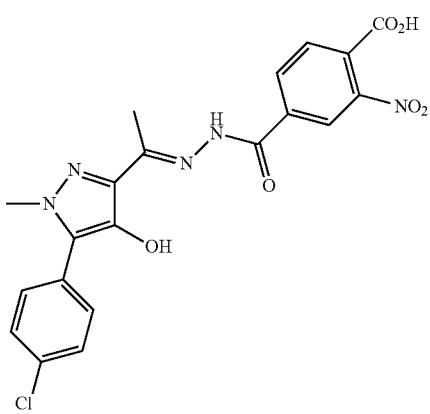
SYNTHETIC EX. 108
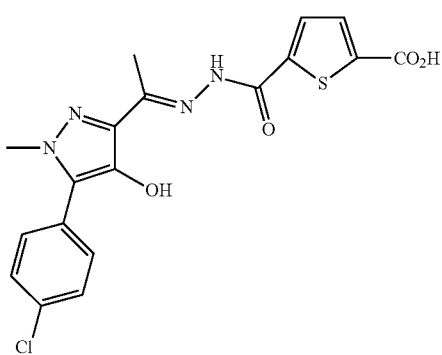
SYNTHETIC EX. 109
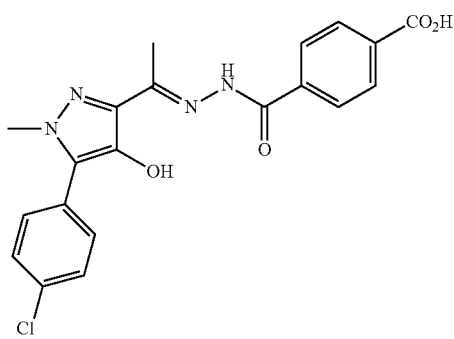
SYNTHETIC EX. 110
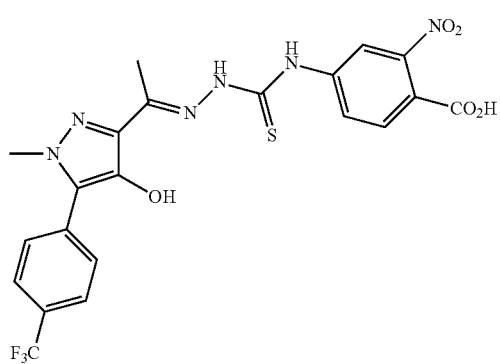
SYNTHETIC EX. 111
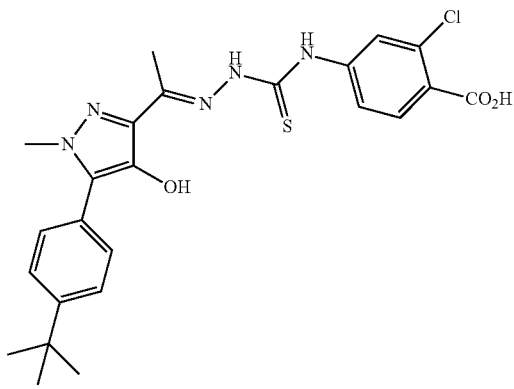
SYNTHETIC EX. 112
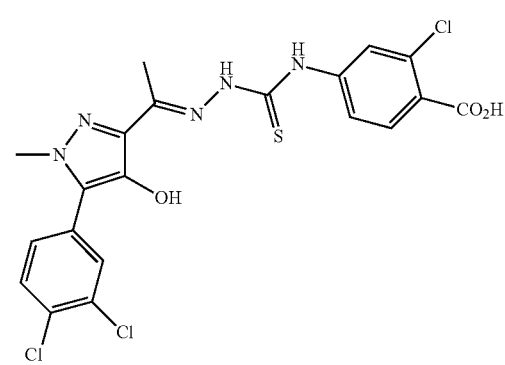
SYNTHETIC EX. 113
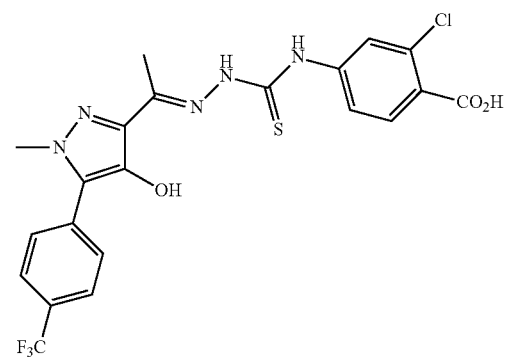
SYNTHETIC EX. 114
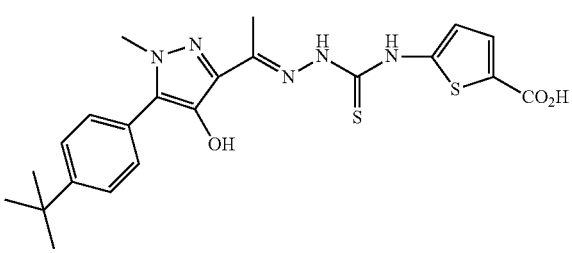

SYNTHETIC EX. 115
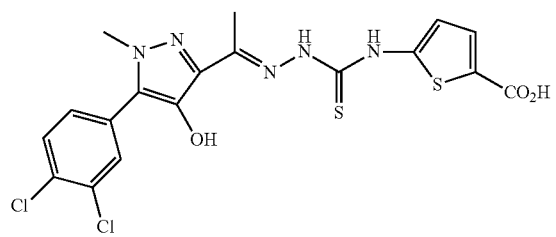
SYNTHETIC EX. 116
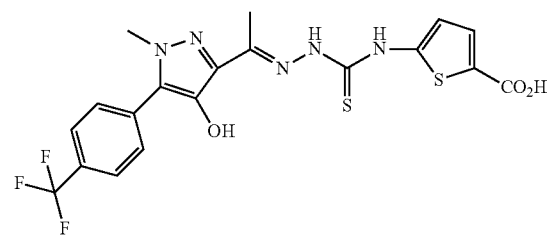
SYNTHETIC EX. 117
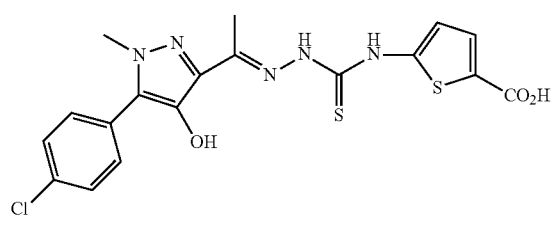
SYNTHETIC EX. 118
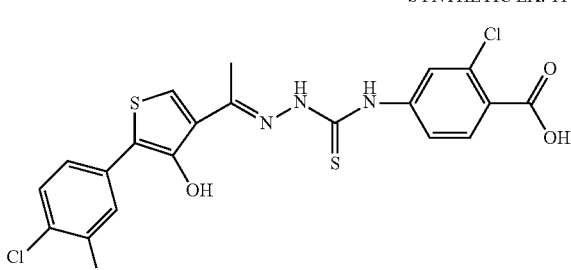
SYNTHETIC EX. 119
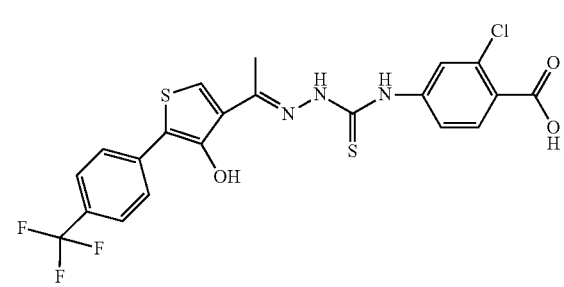
SYNTHETIC EX. 120
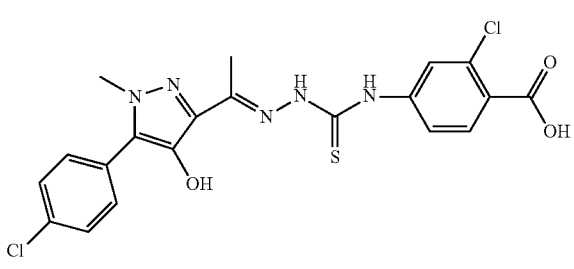
SYNTHETIC EX. 121
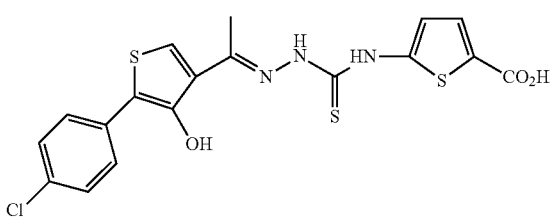
SYNTHETIC EX. 122
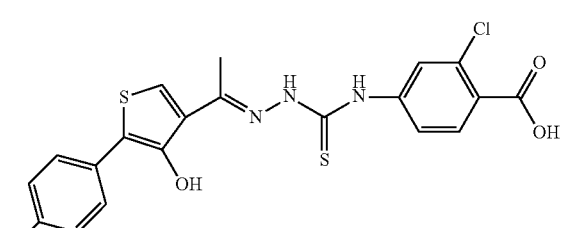
SYNTHETIC EX. 123
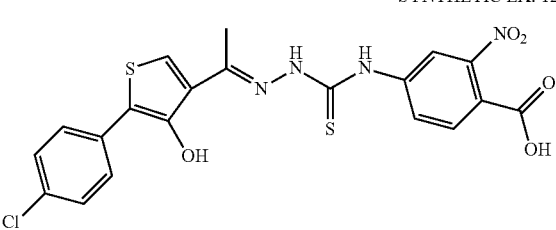
SYNTHETIC EX. 124
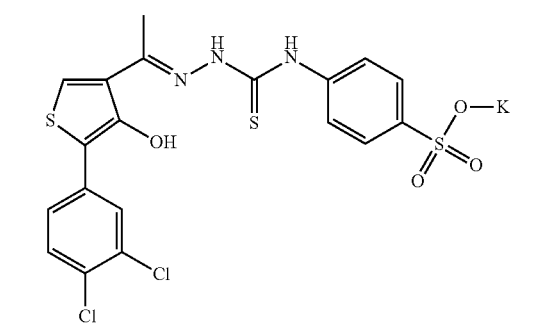
SYNTHETIC EX. 125
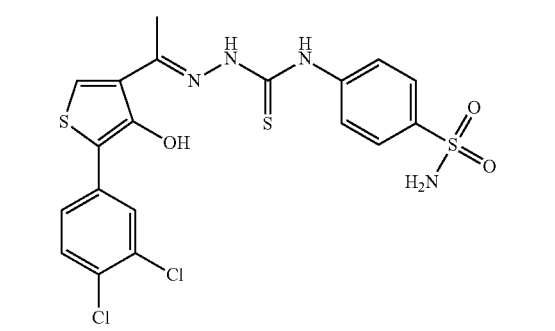

SYNTHETIC EX. 126
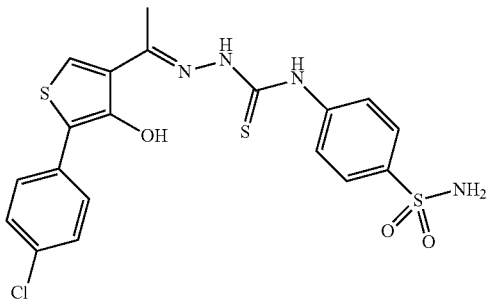
SYNTHETIC EX. 127
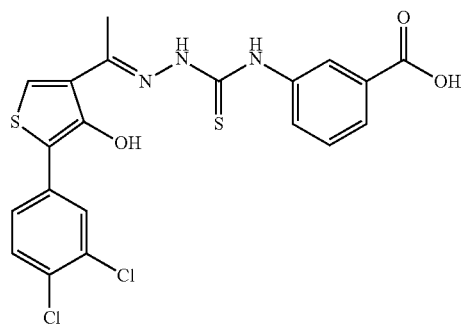
SYNTHETIC EX. 128
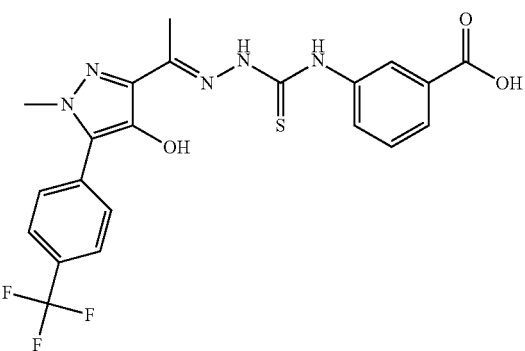
SYNTHETIC EX. 129
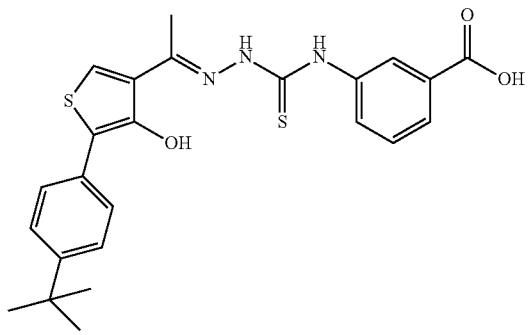
SYNTHETIC EX. 130
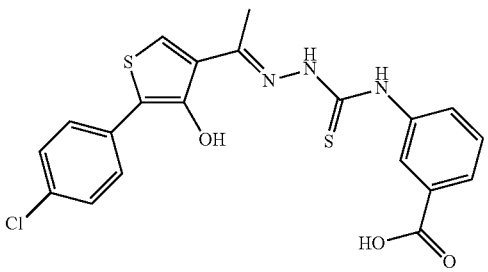
SYNTHETIC EX. 131
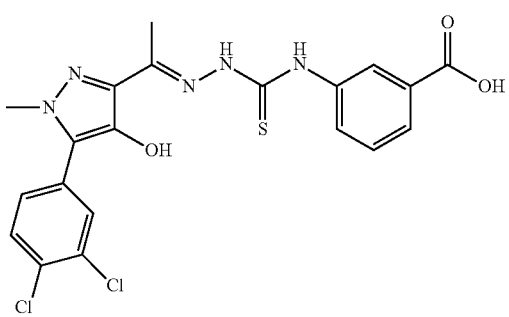
SYNTHETIC EX. 132
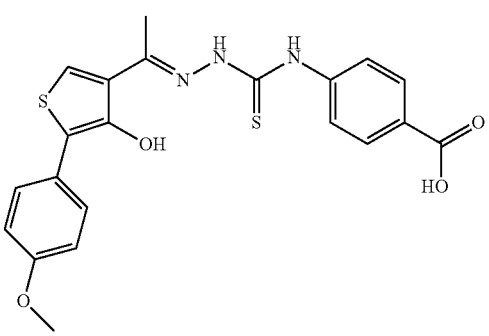
SYNTHETIC EX. 133
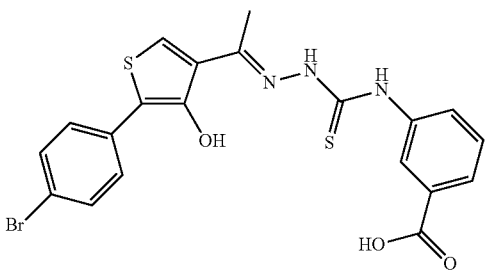
SYNTHETIC EX. 134
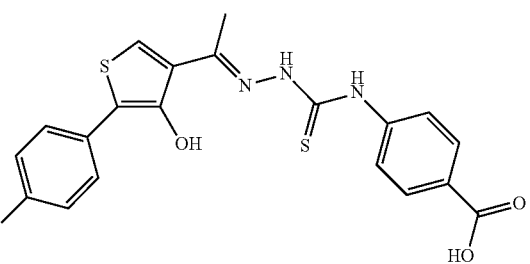

SYNTHETIC EX. 135
SYNTHETIC EX. 136
SYNTHETIC EX. 137
SYNTHETIC EX. 138
SYNTHETIC EX. 139
SYNTHETIC EX. 140
SYNTHETIC EX. 141
SYNTHETIC EX. 142
SYNTHETIC EX. 143
SYNTHETIC EX. 144

SYNTHETIC EX. 145
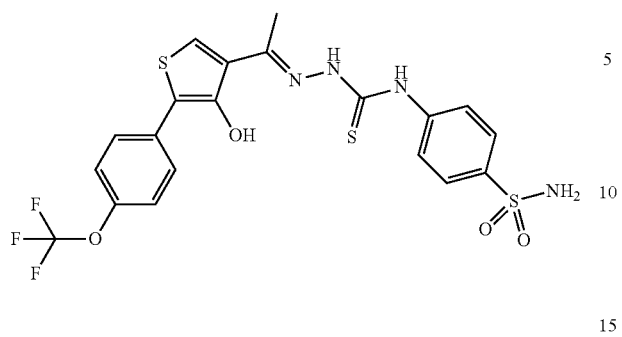
SYNTHETIC EX. 146
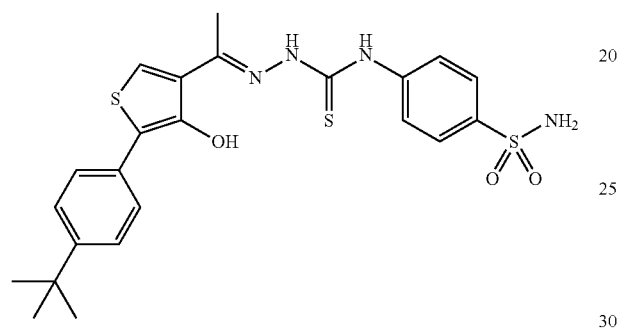
SYNTHETIC EX. 147
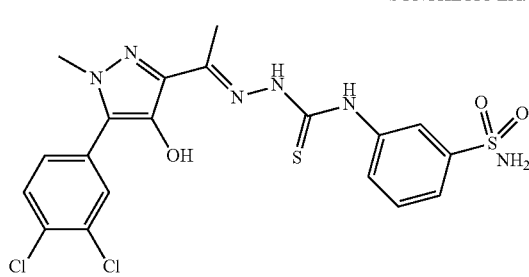
SYNTHETIC EX. 148
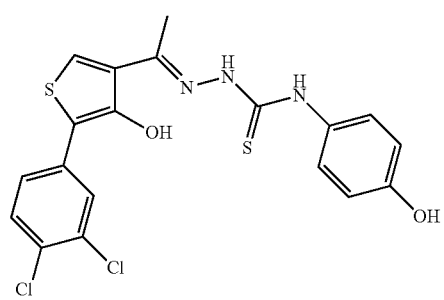
SYNTHETIC EX. 149
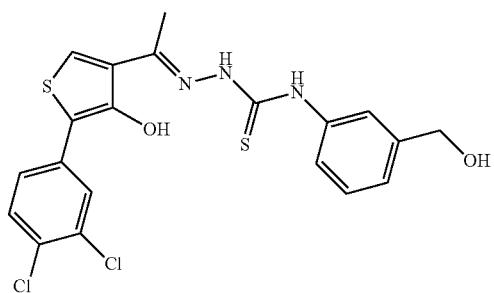
SYNTHETIC EX. 150
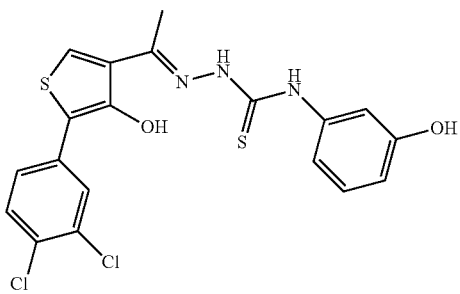
SYNTHETIC EX. 151
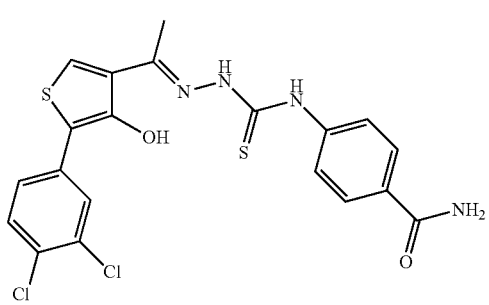
SYNTHETIC EX. 152
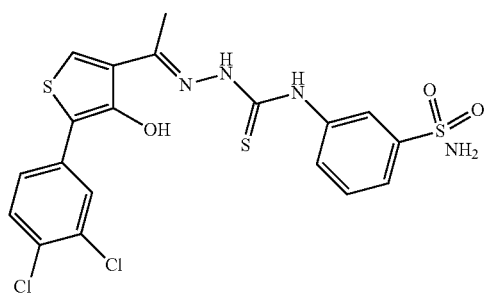
SYNTHETIC EX. 153
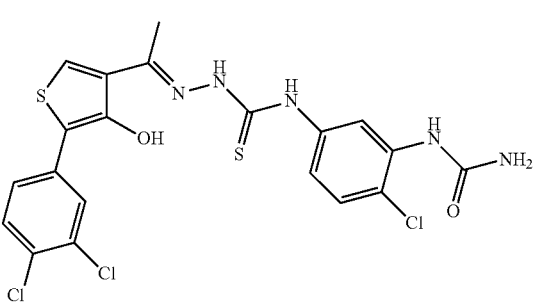
SYNTHETIC EX. 154
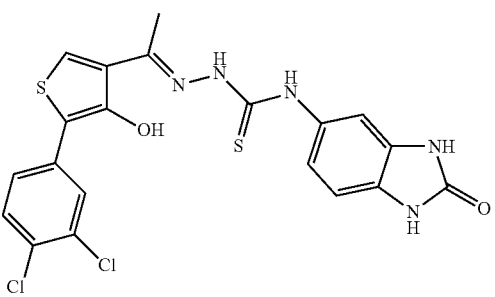

SYNTHETIC EX. 155
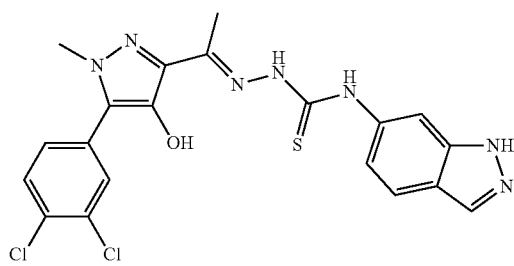
SYNTHETIC EX. 156
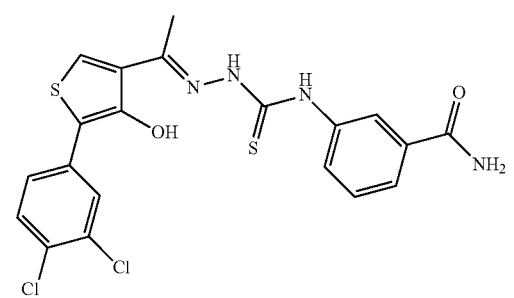
SYNTHETIC EX. 157
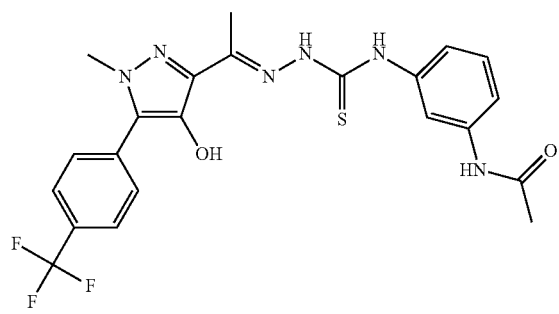
SYNTHETIC EX. 158
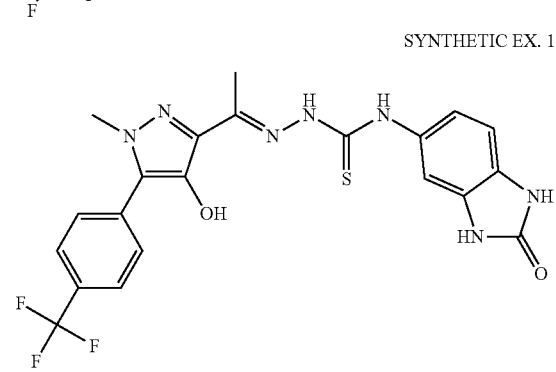
SYNTHETIC EX. 159
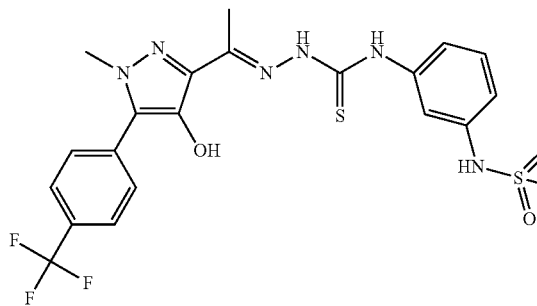
SYNTHETIC EX. 160
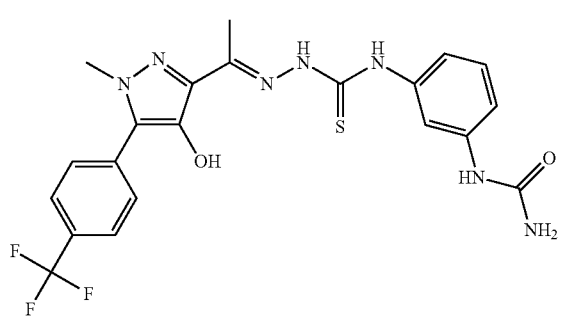
SYNTHETIC EX. 161
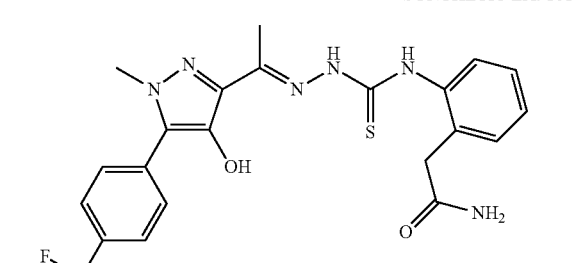
SYNTHETIC EX. 162
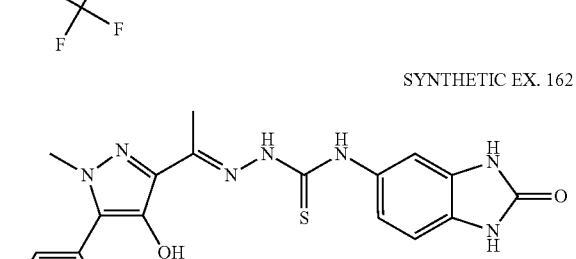
SYNTHETIC EX. 163
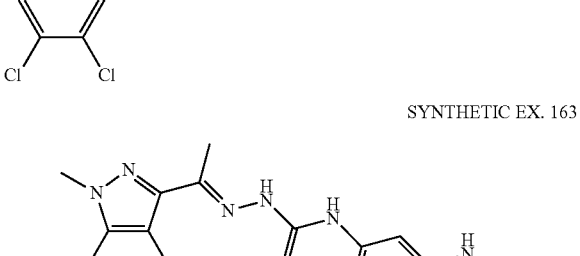
SYNTHETIC EX. 164
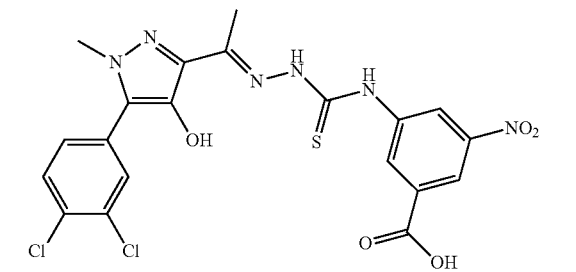

SYNTHETIC EX. 165
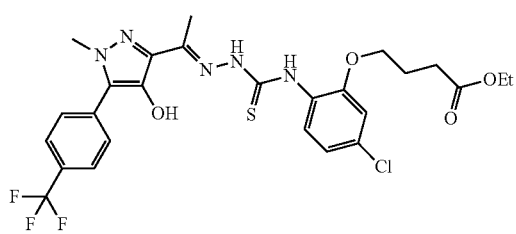
SYNTHETIC EX. 166
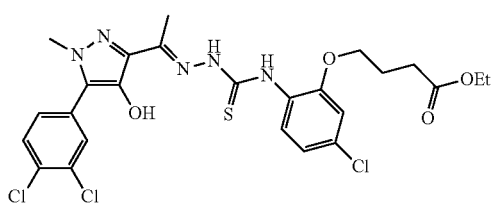
SYNTHETIC EX. 167
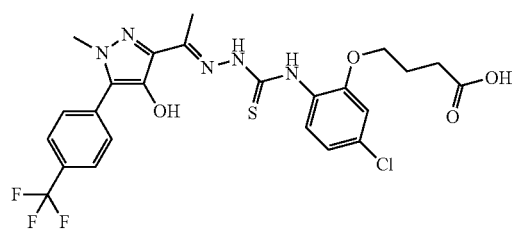
SYNTHETIC EX. 168
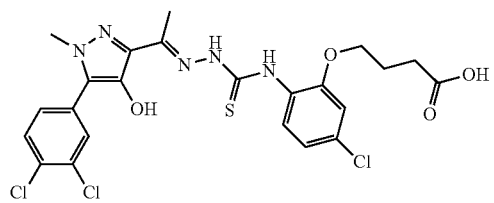
SYNTHETIC EX. 169
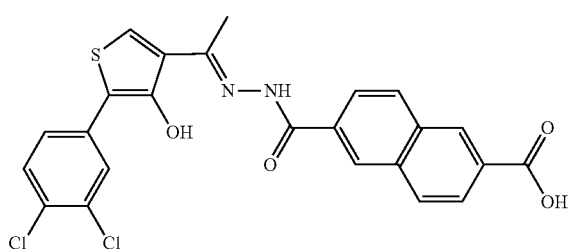
SYNTHETIC EX. 170
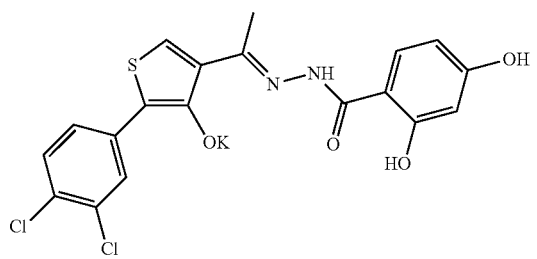
SYNTHETIC EX. 171
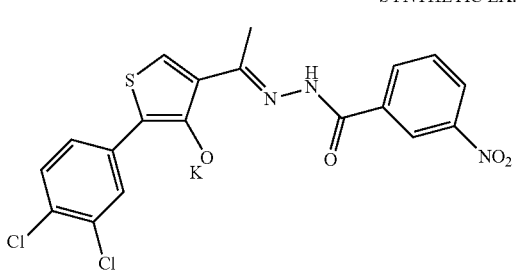
SYNTHETIC EX. 172
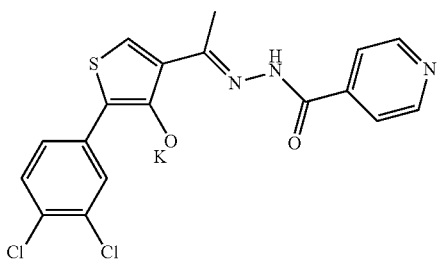
SYNTHETIC EX. 173
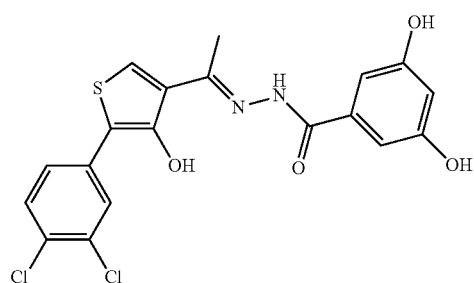
SYNTHETIC EX. 174
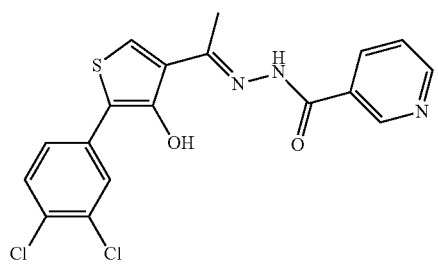
SYNTHETIC EX. 175
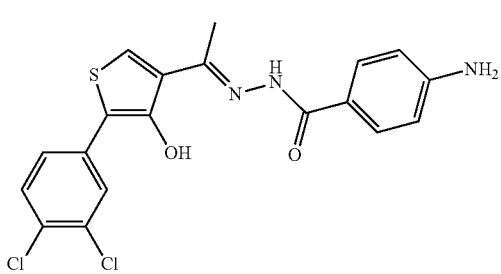

SYNTHETIC EX. 176
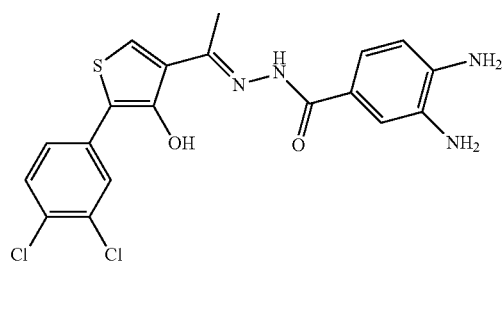
SYNTHETIC EX. 177
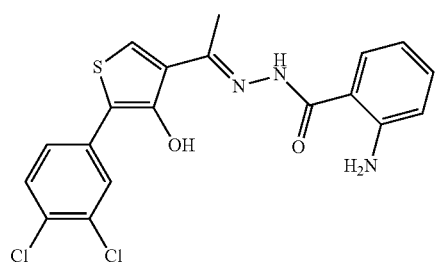
SYNTHETIC EX. 178
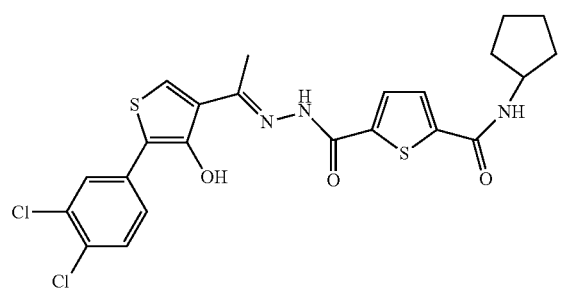
SYNTHETIC EX. 179
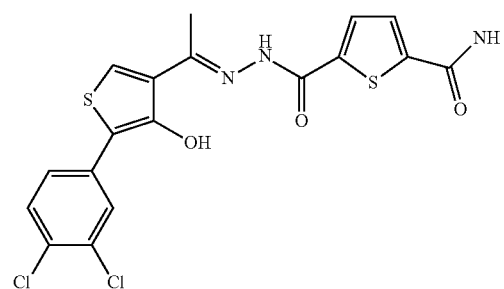
SYNTHETIC EX. 180
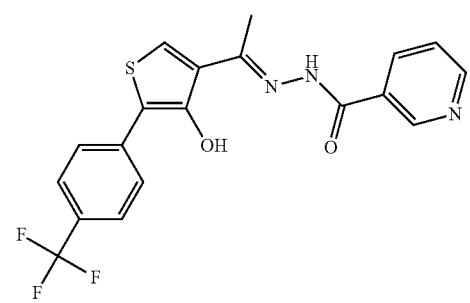
SYNTHETIC EX. 181
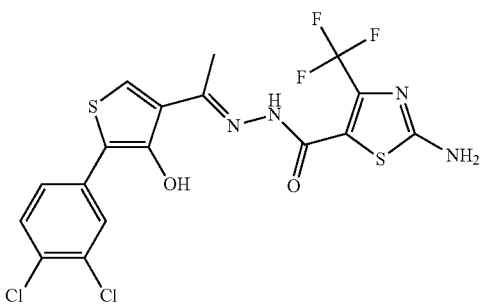
SYNTHETIC EX. 182
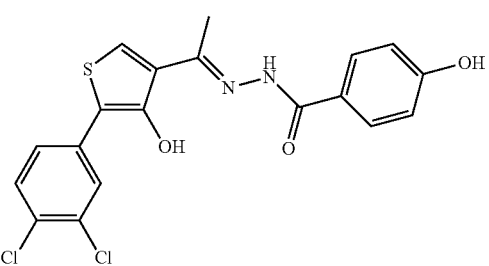
SYNTHETIC EX. 183
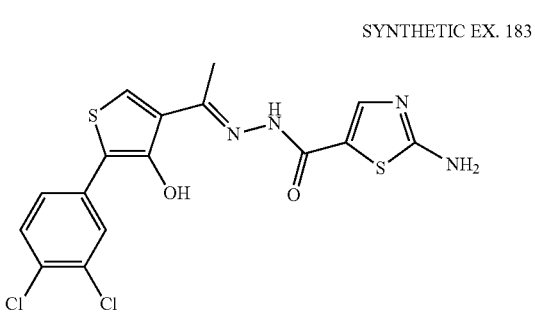
SYNTHETIC EX. 184
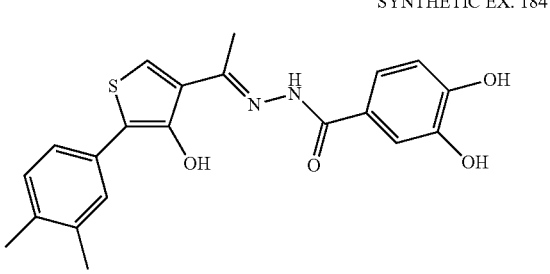
SYNTHETIC EX. 185
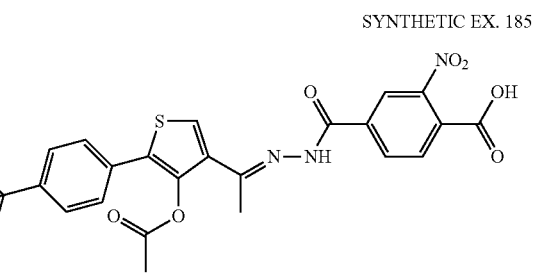

SYNTHETIC EX. 186
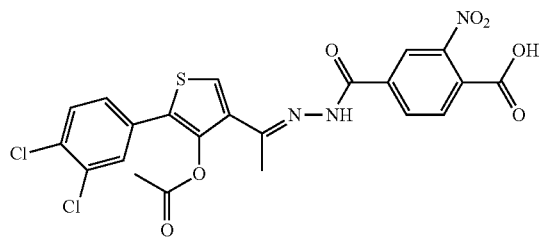
SYNTHETIC EX. 187
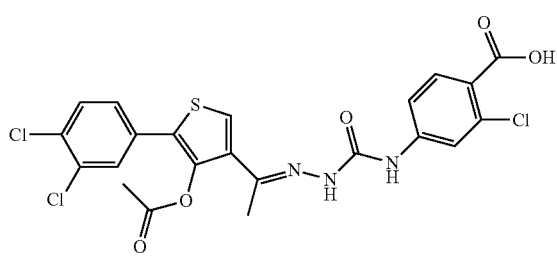
SYNTHETIC EX. 188
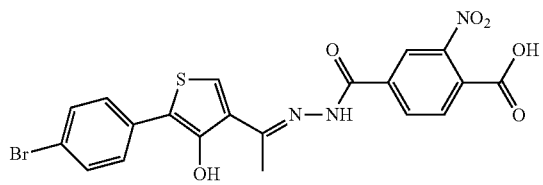
SYNTHETIC EX. 189
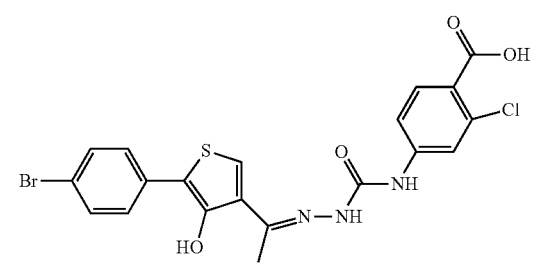
SYNTHETIC EX. 190
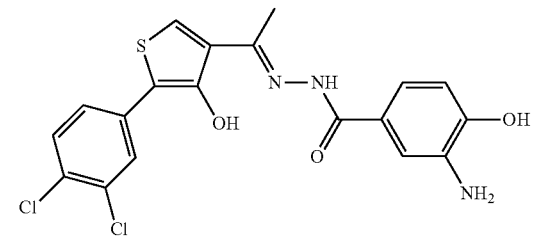
SYNTHETIC EX. 191
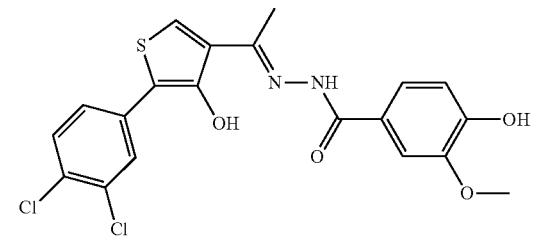
SYNTHETIC EX. 192
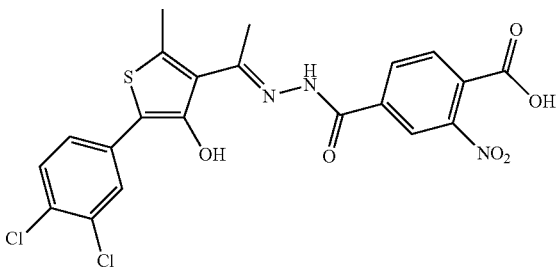
SYNTHETIC EX. 193
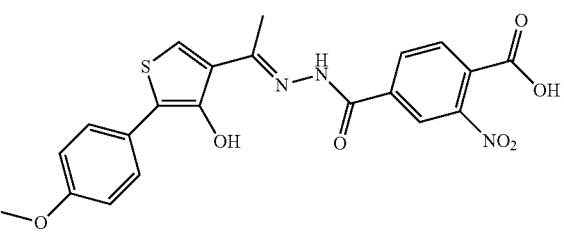
SYNTHETIC EX. 194
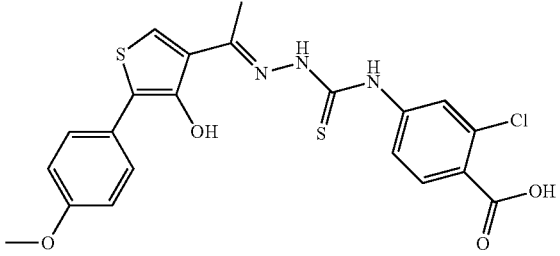
SYNTHETIC EX. 195
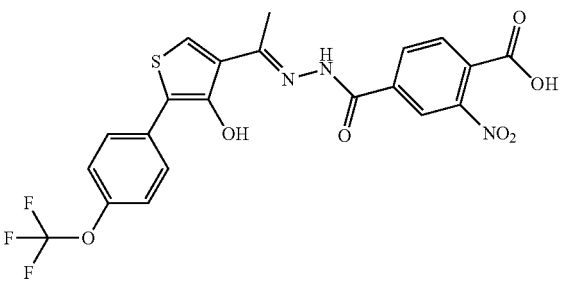
SYNTHETIC EX. 196
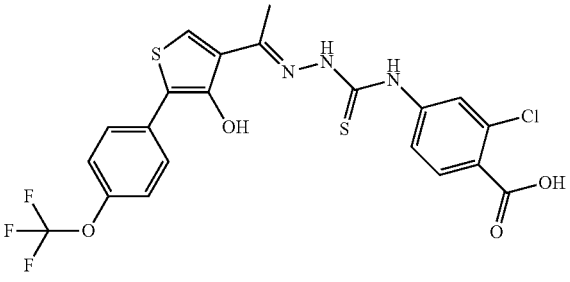

SYNTHETIC EX. 197
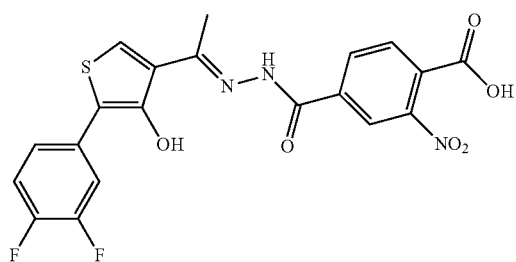
SYNTHETIC EX. 198
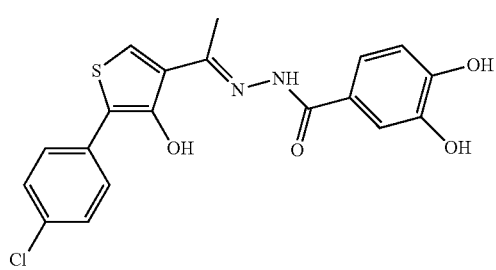
SYNTHETIC EX. 199
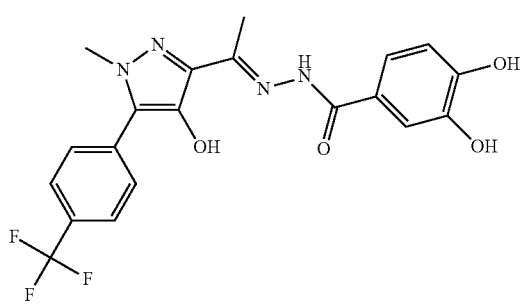
SYNTHETIC EX. 200
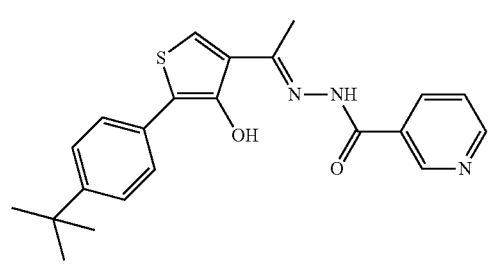
SYNTHETIC EX. 201
SYNTHETIC EX. 202
SYNTHETIC EX. 203
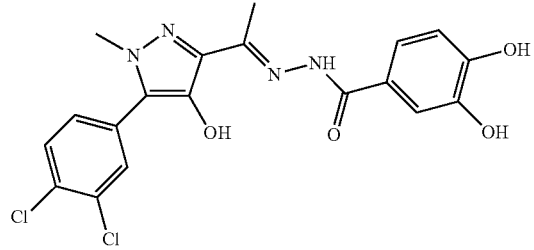
SYNTHETIC EX. 204
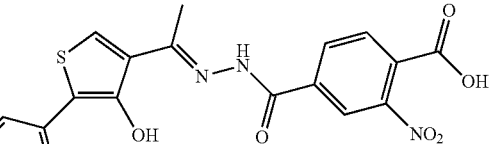
SYNTHETIC EX. 205
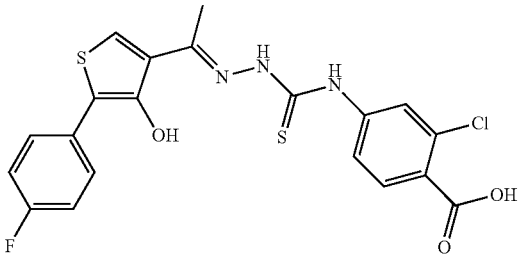
SYNTHETIC EX. 206
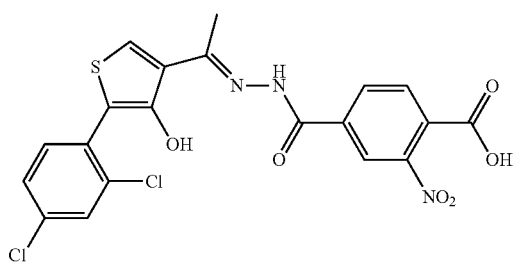

SYNTHETIC EX. 207
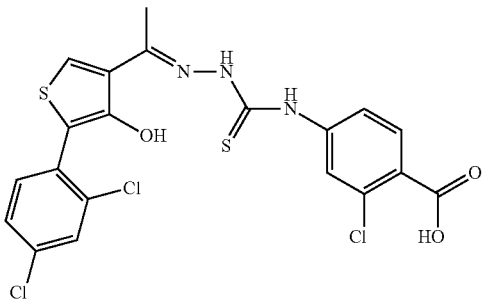
SYNTHETIC EX. 208
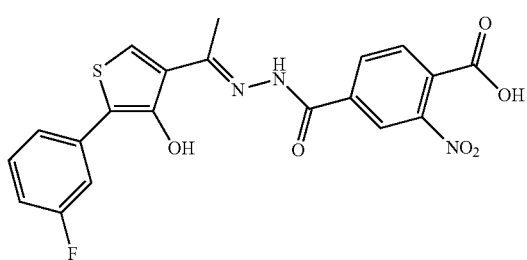
SYNTHETIC EX. 209
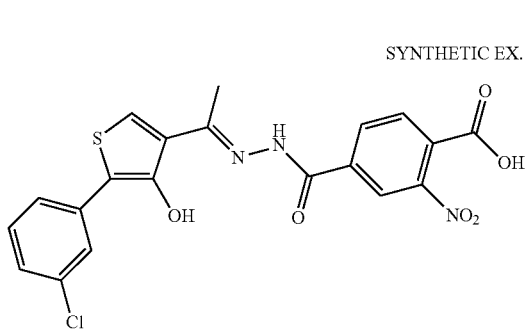
SYNTHETIC EX. 210
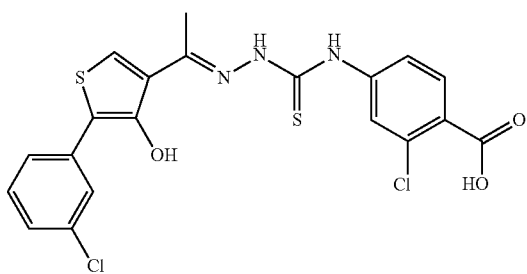
SYNTHETIC EX. 211
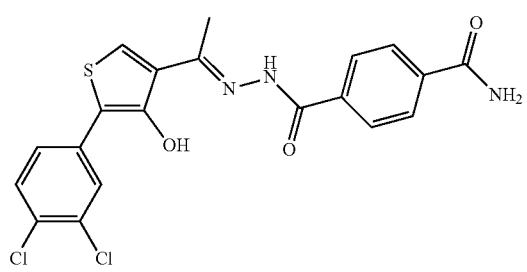
SYNTHETIC EX. 212
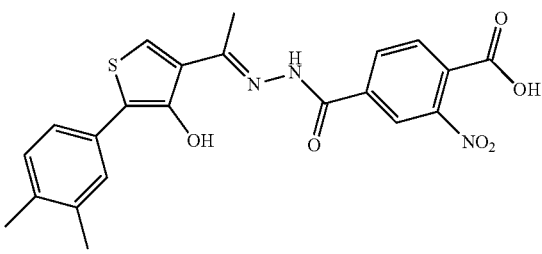
SYNTHETIC EX. 213
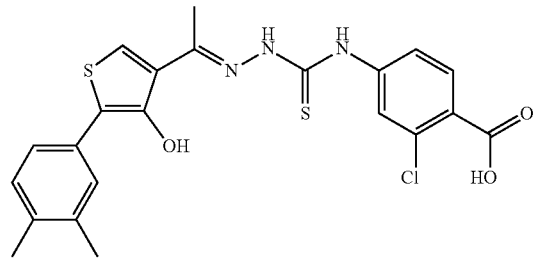
SYNTHETIC EX. 214
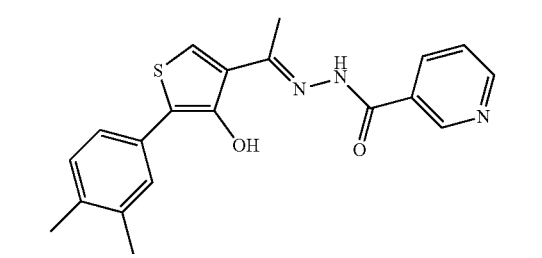
SYNTHETIC EX. 215
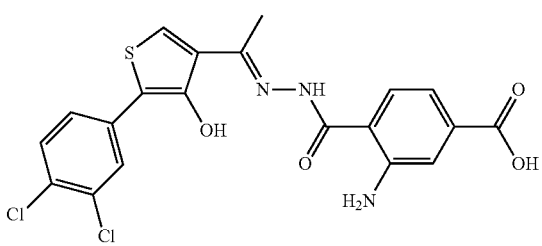
SYNTHETIC EX. 216
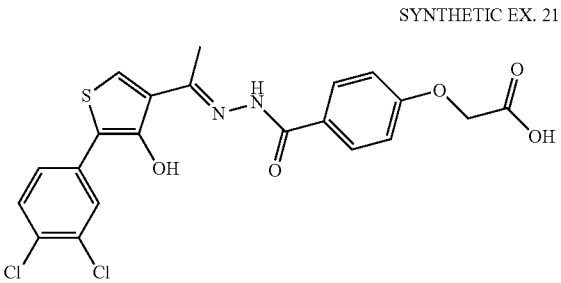
SYNTHETIC EX. 217
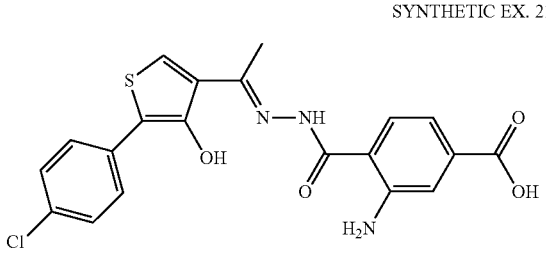

591
-continued
SYNTHETIC EX. 218
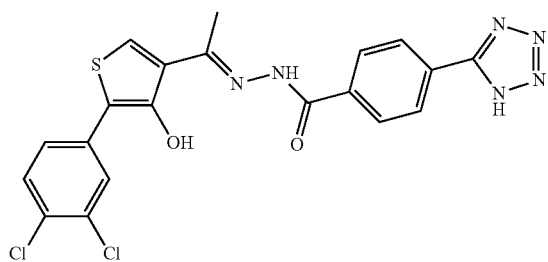
SYNTHETIC EX. 219
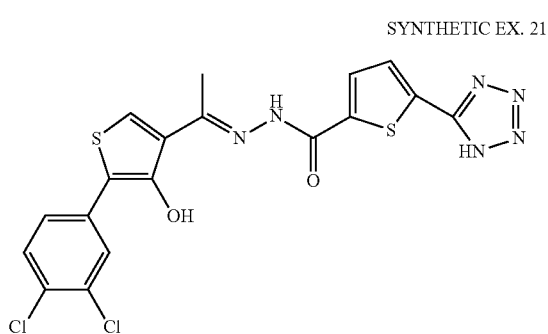
SYNTHETIC EX. 220
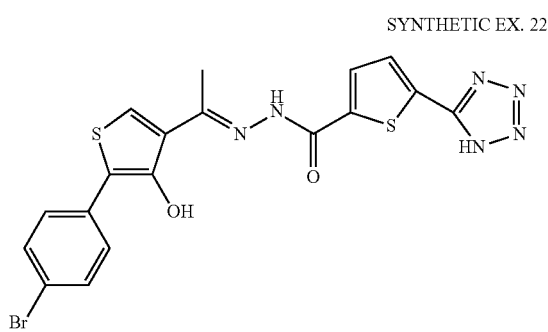
SYNTHETIC EX. 221
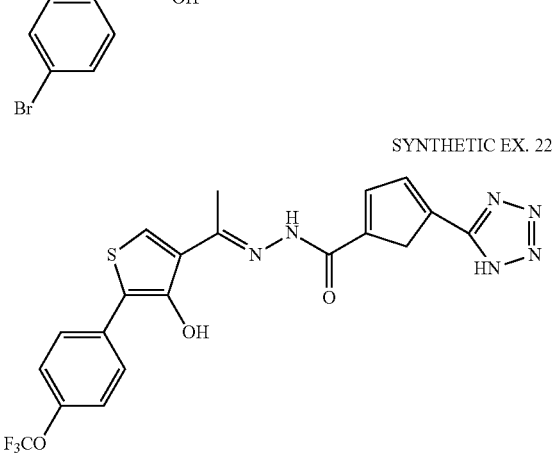
SYNTHETIC EX. 222
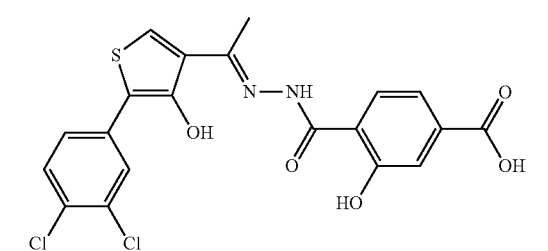
592
-continued
SYNTHETIC EX. 223
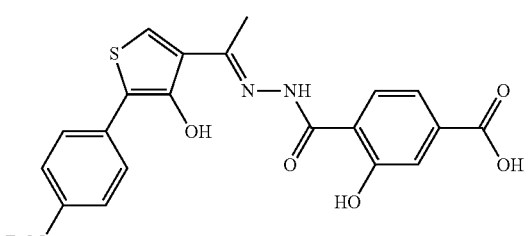
SYNTHETIC EX. 224
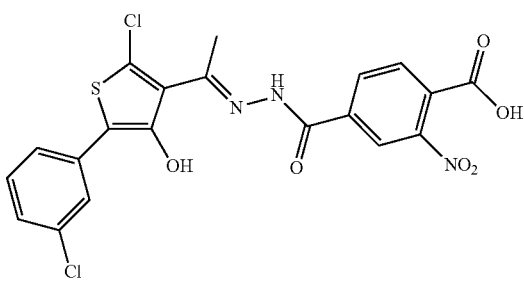
SYNTHETIC EX. 225
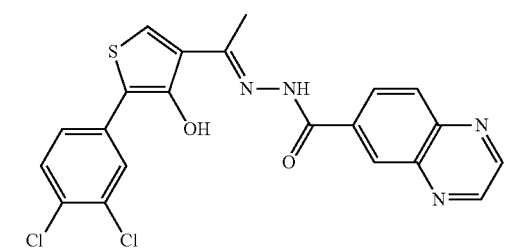
SYNTHETIC EX. 226
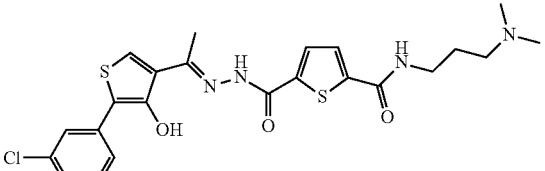
SYNTHETIC EX. 227
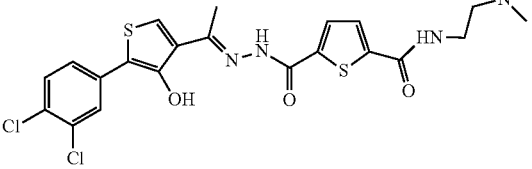
SYNTHETIC EX. 228
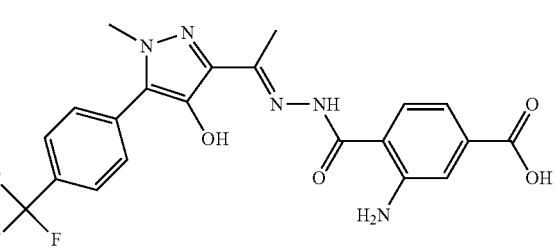

SYNTHETIC EX. 229
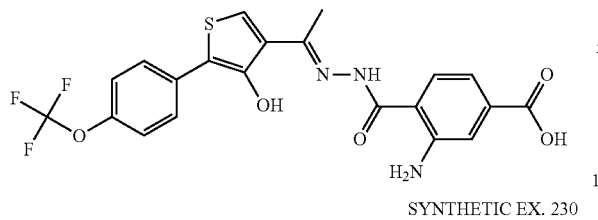
SYNTHETIC EX. 230
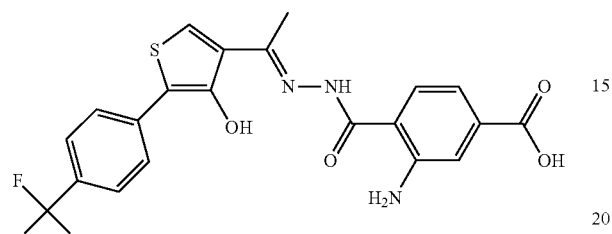
SYNTHETIC EX. 231
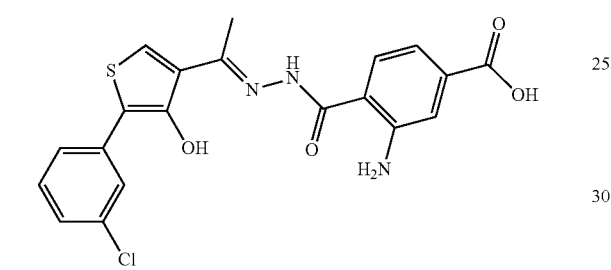
SYNTHETIC EX. 232
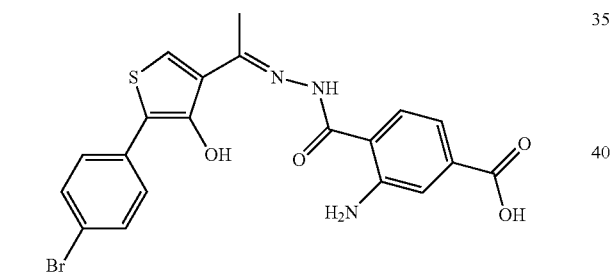
SYNTHETIC EX. 233
SYNTHETIC EX. 234
SYNTHETIC EX. 235
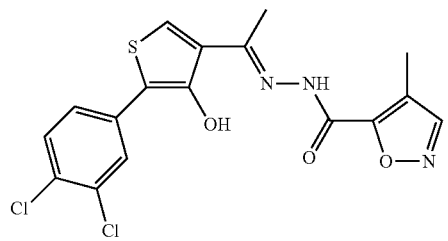
SYNTHETIC EX. 236
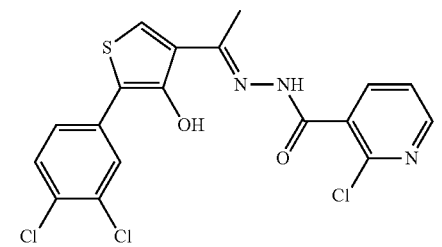
SYNTHETIC EX. 237
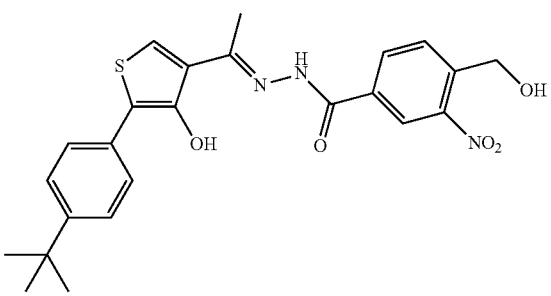
SYNTHETIC EX. 238
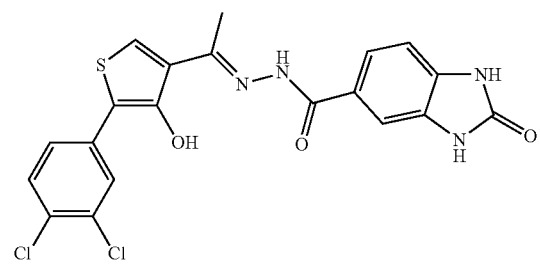
SYNTHETIC EX. 239
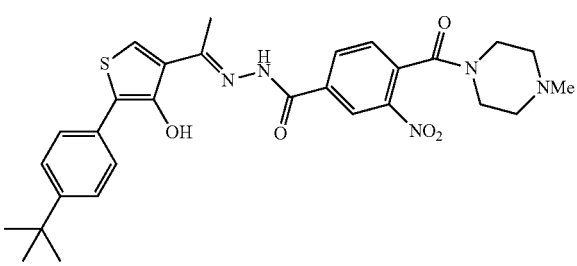

-continued

SYNTHETIC EX. 240

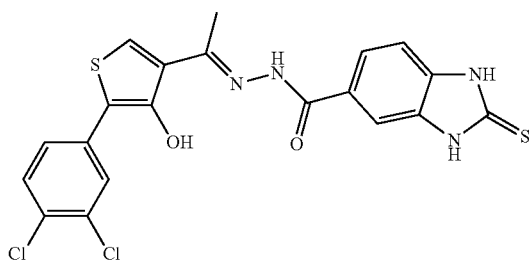

Assay Example 1

Stimulation of Proliferation of a Thrombopoietin (TPO)-Dependent Cell Line (1)

The reactivity of the compound of Synthetic Example 3 of the present invention with thrombopoietin (TPO) receptor was assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human TPO receptor (c-mpl) under control of a cytomegaloviral promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in Iscove's modified Dulbecco's medium (IMDM; GIBCO) containing 10% fetal bovine serum (FBS; TRACE SCIENTIFIC, Thermo Electron or Bio-West) using a $CO_2$ incubator (5% $CO_2$, 37° C.)

(2) Cell Proliferation Assay

Figure 2:
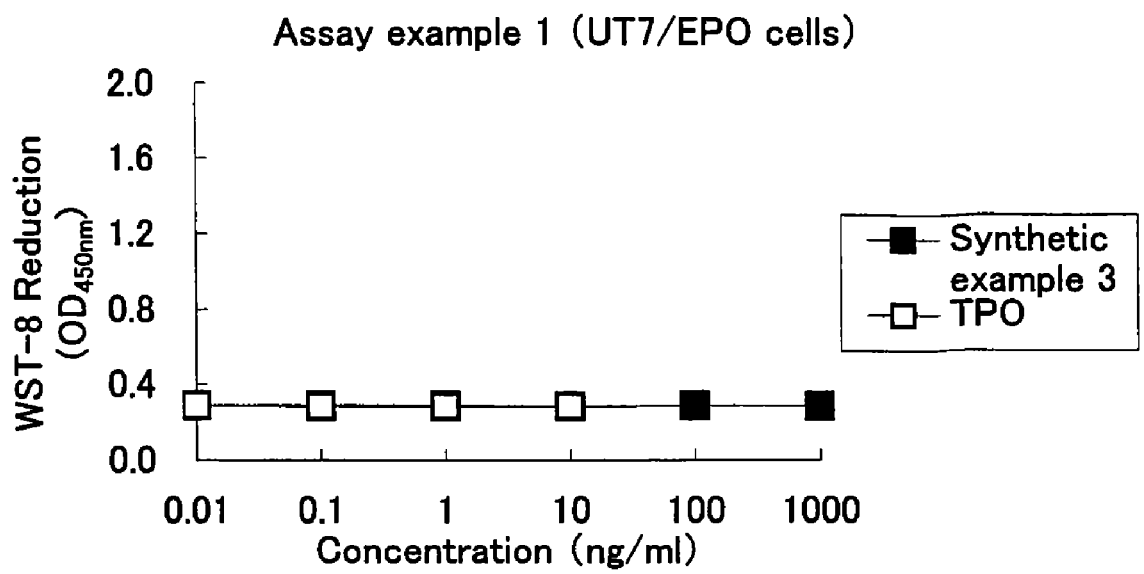
FIG. 2 shows the proliferation of UT7/EPO cells when stimulated by the compound of the present invention (Synthetic Example 3).

The subcultured cells described above were washed twice with phosphate buffered saline (PBS) and suspended in IMDM containing 10% FBS at a cell density of $6 \times 10^4$ cells/ml. The cell suspension was transferred to a 96-well tissue culture plate (CORNING) in 100-μl aliquots. Then either TPO (PeproTech EC) or the compound of Synthetic Example 3 dissolved in dimethyl sulfoxide (DMSO) was diluted 83-fold with IMDM containing 10% FBS and added to the aforementioned cell suspension in 20-μl aliquots. The suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-μl aliquot of 5 mM WST-8 reagent solution was added to each well of the tissue culture plate, and the plate was incubated at 37° C. for 4 h. The formazan pigment generated was detected by measuring the absorbance at 450 nm with a 96-well microplate reader (Nihon Molecular Devices, Spectramax 190). FIG. 1 shows the results with UT7/EPO-mpl cells, while FIG. 2 shows data obtained with UT7/EPO cells expressing no TPO receptor.

Assay Example 2

Activity of Signal Transduction Mediated by TPO Receptor

The signal-transducing activity of the compound of Synthetic Example 3 of the present invention mediated by TPO receptor was assayed according to the method of Komatsu et al. (Blood, 87:4552-4560 (1996)). Human leukemic cell line UT7/EPO-mpl was washed three times with PBS and suspended in IMDM containing 10% FBS at a cell density of $9 \times 10^5$ cells/ml. The cell suspension was incubated in a $CO_2$ incubator (5% $CO_2$, 37° C.) for 18 h. To 2 ml of this cell suspension ($7 \times 10^6$ cells/ml), either TPO (final concentration, 30 ng/ml) or a DMSO solution of the compound of Synthetic Example 3 (final concentration, 1 μg/ml) was added. After incubating the mixture at 37° C. for 1-15 min, the cells were lysed in 1.4 ml of THE buffer (20 mM Tris-HCl buffer (pH 7.4) containing 150 mM NaCl, 1 mM EDTA, 1% Triton X-100, 1 mM PMSF, 1 mM $Na_3VO_4$, and 1/400-diluted Protease Inhibitor Cocktail (SIGMA)). The cell lysate was centrifuged to collect the supernatant for immunoprecipitation with antibodies against proteins involved in signal transduction (anti-STAT3 (SANTA CRUZ BIOTECHNOLOGY) and anti-STAT5A (UPSTATE BIOTECHNOLOGY)) and protein G Sepharose (PHARMACIA). The immunoprecipitated protein fraction was collected and denatured in a sample buffer for separation by SDS-polyacrylamide gel electrophoresis (7.5%). The separated proteins were transferred onto polyvinylidene difluoride (PVDF) membrane (Atto Corporation, 0.2 μm pore size) at 100 V for 1 h for detection of tyrosine phosphorylation using an alkaline phosphatase-labelled antibody against phosphorylated tyrosine (RC20, TRANSDUCTION LABORATORIES). The antigen-antibody complex formed on the PVDF membrane was visualized with 150 μg/ml NBT (BIO-RAD) and 300 μg/ml BCIP (BIO-RAD). The results are summarized in Table 22.

TABLE 22

| | DMSO | SYNTHETIC EXAMPLE 3 | TPO |
|---|---|---|---|
| STAT 3 | − | + | + |
| STAT 5A | − | + | + |

FIG. 1 demonstrated that proliferation of TPO-responsive UT7/EPO-mpl cells was stimulated by the compound of Synthetic Example 3 in a concentration-dependent manner, while no effect of this compound on proliferation was observed with UT7/EPO, the mother cell line, as shown in FIG. 2. These results indicate that the compound of Synthetic Example 3 of the present invention acts on the TPO receptor selectively as an activator.

Table 22 shows that the compound of Synthetic Example 3 stimulates phosphorylation of STAT3 and STAT5A in the same manner as TPO does. The results demonstrate that the compound of the present invention shows agonistic action through the same signal transduction as that caused by TPO.

Assay Example 3

The compounds of the following Synthetic Examples were tested according to the method of Assay Example 1 to determine the concentration of each compound that yields a growth rate corresponding to 50% of the growth of human leukemic cell line UT-7/EPO-mpl observed in the presence of 10 ng/ml TPO ($EC_{50}$). The results are summarized in Table 23.

TABLE 23

| Synthetic Example No. | $EC_{50}$ (ng/ml) |
|---|---|
| 1 | 3.5 |
| 2 | 4.5 |
| 3 | 2.7 |

TABLE 23-continued

| Synthetic Example No. | EC$_{50}$ (ng/ml) |
|---|---|
| 4 | 10.5 |
| 5 | 45.0 |
| 6 | 3.5 |
| 7 | 3.8 |
| 8 | 3.7 |
| 9 | 5.9 |
| 10 | 21.3 |
| 11 | 2.9 |
| 13 | 7.8 |
| 32 | 4.3 |
| 49 | 14 |
| 76 | 5.8 |
| 89 | 3.2 |
| 97 | 4.7 |
| 107 | 3.3 |
| 113 | 4.7 |
| 124 | 2.9 |
| 126 | 3.4 |
| 127 | 3.5 |
| 136 | 3.1 |
| 154 | 2.8 |
| 155 | 5.3 |
| 157 | 3.1 |
| 161 | 3.9 |
| 164 | 3.0 |
| 167 | 3.9 |
| 169 | 3.7 |
| 176 | 16 |
| 178 | 3.4 |
| 179 | 3.0 |
| 181 | 2.8 |
| 212 | 0.24 |
| 218 | 2.2 |
| 221 | 2.9 |
| 226 | 2.2 |
| 228 | 0.72 |
| 235 | 13 |
| 239 | 4.2 |
| 240 | 6.0 |

Assay Example 4

Megakaryocyte Colony Stimulating Activity

The action of the compound of Synthetic Example 2 of the present invention on the proliferation, differentiation and maturation of megakaryocyte cells was measured by the megakaryocyte colony forming method using human bone marrow cells. Human bone marrow CD34$^+$ cells (Cambrex Bio Science Walkersville) were incubated on 2-well chamber slide for 11 days in a CO$_2$ incubator (5% CO$_2$, 37° C.) using MegaCult™-C (StemCell Technologies) containing 0.1% (v/v) of the compound of Synthetic Example 2 dissolved in DMSO. After dehydration and fixation, the cells were stained with an anti-glycoprotein IIb/IIIa antibody in accordance with the instruction by the manufacturer. The colonies consisting of at least 8 stained megakaryocyte cells in each well was counted under a microscope. The megakaryocyte colony counts of duplicate or more assays were averaged.

The results demonstrate that the compound of the present invention has excellent megakaryocyte colony stimulating activity and increases platelets through the activity.

The results are shown in Table 24.

TABLE 24

| | Synthetic Example 2 | |
|---|---|---|
| Concentration (μg/ml) | 0.3 | 1 |
| Megakaryocyte colony Count | 25 | 48 |

Formulation Example 1

A granule preparation containing the following ingredients is prepared.

| Ingredients | |
|---|---|
| Compound represented by the formula (1) | 10 mg |
| Lactose | 700 mg |
| Corn Starch | 274 mg |
| HPC-L | 16 mg |
| | 1000 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (1) | 10 mg |
| Lactose | 79 mg |
| Corn Starch | 10 mg |
| Magnesium Stearate | 1 mg |
| | 100 mg |

A compound represented by the formula (1) and lactose are sifted through a 60-mesh sieve. Corn starch is sifted though a 120-mesh sieve. They are mixed with magnesium stearate in a V-type blender. The 10% powder is put in hard capsules No. 5, 100 mg each.

Formulation Example 3

A granule preparation for capsulation containing the following ingredients is prepared.

| Ingredients | |
|---|---|
| Compound represented by the formula (1) | 15 mg |
| Lactose | 90 mg |

-continued

| Ingredients | |
|---|---|
| Corn Starch | 42 mg |
| HPC-L | 3 mg |
| | 150 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (1) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (1), lactose, microcrystalline cellulose and CMC—Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| Compound represented by the formula (1) | 100 mg |
|---|---|
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

What is claimed is:
1. A compound represented by the formula (1)

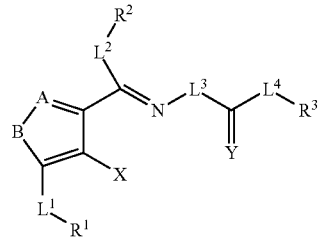

wherein
A is a CH, and
B is sulfur;
$R^1$ is a phenyl, wherein the phenyl is substituted with one or more substituents selected from the group consisting of chlorine, trifluoromethyl, and t-butyl,
$L^1$ is a bond,
X is OH,
$R^2$ is methyl,
$L^2$ is a bond,
$L^3$ is NH,
$L^4$ is NH,
Y is sulfur, and
$R^3$ is phenyl substituted with a carboxy group,
a tautomer, prodrug or pharmaceutically acceptable salt of the compound.

2. 4-{[(2-[1-[5-(4-t-butylphenyl)-4-hydroxy-3-thienyl] ethylidene]hydrazine)cabonothioyl]amino}benzoic acid, a tautomer thereof or a pharmaceutically acceptable salt thereof.

3. 4-([(2-(1-[5-(3,4-dichlorophenyl)-4-hydroxy-3-thienyl] ethyliden)hydrazine)carbonothioyl]amino)benzoic acid, a tautomer thereof or a pharmaceutically acceptable salt thereof.

4. 4-[(2-{1-[5-(4-trifluoromethylphenyl)-4-hydroxy-3-thienyl]ethylidene}hydrazino)carbonyl]benzoic acid, a tautomer thereof or a pharmaceutically acceptable salt thereof.

5. 4-{[(2-{1-[5-(3-trifluoromethylphenyl)-4-hydroxy-3-thienyl]ethylidene}hydrazino)-carbonothioyl] amino}benzoic acid, a tautomer thereof or a pharmaceutically acceptable salt thereof.

6. 3-{[(2-(1-[5-(3,4-dichlorophenyl)-4-hydroxy-3-thienyl]ethylidene)hydrazine)-carbonothioyl]amino}benzoic acid, a tautomer thereof or a pharmaceutically acceptable salt thereof.

7. 3-([(2-(1-[5-(4-t-butylphenyl)-4-hydroxy-3-thienyl] ethylidene)hydrazine)-carbonothioyl]amino)benzoic acid, a tautomer thereof or a pharmaceutically acceptable salt thereof.

8. 3-([[(2-(1-[5-(4-chlorophenyl)-4-hydroxy-3-thienyl]ethylidene)hydrazine)-carbonothioyl]amino)benzoic acid, a tautomer thereof or a pharmaceutically acceptable salt thereof.

9. 3-([[(2-(1-[5-(3-chlorophenyl)-4-hydroxy-3-thienyl]ethylidene)hydrazine)-carbonothioyl]amino)benzoic acid, a tautomer thereof or a pharmaceutically acceptable salt thereof.

10. A composition comprising at least one compound of claim 1, a tautomer thereof, a prodrug thereof, or a pharmaceutically acceptable salt thereof; and at least one carrier.

11. A composition comprising the compound of claim 2, a tautomer thereof, or a pharmaceutically acceptable salt thereof; and at least one carrier.

12. A composition comprising the compound of claim 3, a tautomer thereof, or a pharmaceutically acceptable salt thereof; and at least one carrier.

13. A composition comprising the compound of claim 4, a tautomer thereof, or a pharmaceutically acceptable salt thereof; and at least one carrier.

14. A composition comprising the compound of claim 5, a tautomer thereof, or a pharmaceutically acceptable salt thereof; and at least one carrier.

15. A composition comprising the compound of claim 6, a tautomer thereof, or a pharmaceutically acceptable salt thereof; and at least one carrier.

16. A composition comprising the compound of claim 7, a tautomer thereof, or a pharmaceutically acceptable salt thereof; and at least one carrier.

17. A composition comprising the compound of claim 8, a tautomer thereof, or a pharmaceutically acceptable salt thereof; and at least one carrier.

18. A composition comprising the compound of claim 9, a tautomer thereof or a pharmaceutically acceptable salt thereof; and at least one carrier.

19. A method of treating thrombocytopenia in a patient in need thereof, the method comprising administering to the patient an effective amount of at least one compound of claim 1, a tautomer thereof, a prodrug thereof, or a pharmaceutically acceptable salt thereof to treat the thrombocytopenia.

20. A method of treating thrombocytopenia in a patient in need thereof, the method comprising administering to the patient an effective amount of at least one compound of claim 2, a tautomer thereof, or a pharmaceutically acceptable salt thereof to treat the thrombocytopenia.

21. A method of treating thrombocytopenia in a patient in need thereof, the method comprising administering to the patient an effective amount of at least one compound of claim 3, a tautomer thereof, or a pharmaceutically acceptable salt thereof to treat the thrombocytopenia.

22. A method of treating thrombocytopenia in a patient in need thereof, the method comprising administering to the patient an effective amount of at least one compound of claim 4, a tautomer thereof, or a pharmaceutically acceptable salt thereof to treat the thrombocytopenia.

23. A method of treating thrombocytopenia in a patient in need thereof, the method comprising administering to the patient an effective amount of at least one compound of claim 5, a tautomer thereof, or a pharmaceutically acceptable salt thereof to treat the thrombocytopenia.

24. A method of treating thrombocytopenia in a patient in need thereof, the method comprising administering to the patient an effective amount of at least one compound of claim 6, a tautomer thereof, or a pharmaceutically acceptable salt thereof to treat the thrombocytopenia.

25. A method of treating thrombocytopenia in a patient in need thereof, the method comprising administering to the patient an effective amount of at least one compound of claim 7, a tautomer thereof, or a pharmaceutically acceptable salt thereof to treat the thrombocytopenia.

26. A method of treating thrombocytopenia in a patient in need thereof, the method comprising administering to the patient an effective amount of at least one compound of claim 8, a tautomer thereof, or a pharmaceutically acceptable salt thereof to treat the thrombocytopenia.

27. A method of treating thrombocytopenia in a patient in need thereof, the method comprising administering to the patient an effective amount of at least one compound of claim 9, a tautomer thereof, or a pharmaceutically acceptable salt thereof to treat the thrombocytopenia.

28. A method of increasing platelets, vascular endothelial cells and/or endothelial progenitor cells, the method comprising administering to the patient an effective amount of at least one compound of claim 1, a tautomer thereof, a prodrug thereof, or a pharmaceutically acceptable salt thereof to increase platelets, vascular endothelial cells and/or endothelial progenitor cells.

29. A method of increasing platelets, vascular endothelial cells and/or endothelial progenitor cells, the method comprising administering to the patient an effective amount of at least one compound of claim 2, a tautomer thereof or a pharmaceutically acceptable salt thereof to increase platelets, vascular endothelial cells and/or endothelial progenitor cells.

30. A method of increasing platelets, vascular endothelial cells and/or endothelial progenitor cells, the method comprising administering to the patient an effective amount of at least one compound of claim 3, a tautomer thereof or a pharmaceutically acceptable salt thereof to increase platelets, vascular endothelial cells and/or endothelial progenitor cells.

31. A method of increasing platelets, vascular endothelial cells and/or endothelial progenitor cells, the method comprising administering to the patient an effective amount of at least one compound of claim 4, a tautomer thereof or a pharmaceutically acceptable salt thereof to increase platelets, vascular endothelial cells and/or endothelial progenitor cells.

32. A method of increasing platelets, vascular endothelial cells and/or endothelial progenitor cells, the method comprising administering to the patient an effective amount of at least one compound of claim 5, a tautomer thereof or a pharmaceutically acceptable salt thereof to increase platelets, vascular endothelial cells and/or endothelial progenitor cells.

33. A method of increasing platelets, vascular endothelial cells and/or endothelial progenitor cells, the method comprising administering to the patient an effective amount of at least one compound of claim 6, a tautomer thereof or a pharmaceutically acceptable salt thereof to increase platelets, vascular endothelial cells and/or endothelial progenitor cells.

34. A method of increasing platelets, vascular endothelial cells and/or endothelial progenitor cells, the method comprising administering to the patient an effective amount of at least one compound of claim 7, a tautomer thereof or a pharmaceutically acceptable salt thereof to increase platelets, vascular endothelial cells and/or endothelial progenitor cells.

35. A method of increasing platelets, vascular endothelial cells and/or endothelial progenitor cells, the method comprising administering to the patient an effective amount of at least one compound of claim 8, a tautomer thereof or a pharmaceutically acceptable salt thereof to increase platelets, vascular endothelial cells and/or endothelial progenitor cells.

36. A method of increasing platelets, vascular endothelial cells and/or endothelial progenitor cells, the method comprising administering to the patient an effective amount of at least one compound of claim 9, a tautomer thereof or a pharmaceutically acceptable salt thereof to increase platelets, vascular endothelial cells and/or endothelial progenitor cells.

* * * * *